US010246462B2

(12) United States Patent
Beck et al.

(10) Patent No.: US 10,246,462 B2
(45) Date of Patent: Apr. 2, 2019

(54) CHEMOKINE RECEPTOR MODULATORS AND USES THEREOF

(71) Applicant: FLX Bio, Inc., South San Francisco, CA (US)

(72) Inventors: Hilary Plake Beck, Emerald Hills, CA (US); Berenger Biannic, San Mateo, CA (US); Minna Hue Thanh Bui, Oakland, CA (US); Dennis X. Hu, San Mateo, CA (US); Jeffrey J. Jackson, San Bruno, CA (US); John Michael Ketcham, San Mateo, CA (US); Jay Patrick Powers, Pacifica, CA (US); Maureen Kay Reilly, San Francisco, CA (US); Omar Robles-Resendiz, Redwood City, CA (US); Hunter Paul Shunatona, San Francisco, CA (US); James Ross Walker, Verona, WI (US); David Juergen Wustrow, Los Gatos, CA (US); Ashkaan Younai, San Francisco, CA (US); Mikhail Zibinsky, Redwood City, CA (US)

(73) Assignee: FLX BIO, INC., South San Francisco, CA (US)

( * ) Notice: Subject to any disclaimer, the term of this patent is extended or adjusted under 35 U.S.C. 154(b) by 0 days.

(21) Appl. No.: 15/700,040

(22) Filed: Sep. 8, 2017

(65) Prior Publication Data

US 2018/0072743 A1   Mar. 15, 2018

Related U.S. Application Data

(60) Provisional application No. 62/545,194, filed on Aug. 14, 2017, provisional application No. 62/426,102, filed on Nov. 23, 2016, provisional application No. 62/385,802, filed on Sep. 9, 2016.

(51) Int. Cl.
*C07D 487/04* (2006.01)

(52) U.S. Cl.
CPC .................. *C07D 487/04* (2013.01)

(58) Field of Classification Search
CPC .................................................. C07D 487/04
USPC .................................................... 514/210.21
See application file for complete search history.

(56) References Cited

U.S. PATENT DOCUMENTS

| | | |
|---|---|---|
| 2010/0292196 A1 | 11/2010 | Rudra et al. |
| 2011/0130406 A1 | 6/2011 | Demeese et al. |
| 2012/0015932 A1 | 1/2012 | Hobbs et al. |
| 2013/0165423 A1 | 6/2013 | Leleti et al. |
| 2015/0190394 A1 | 7/2015 | Sokoloff et al. |

FOREIGN PATENT DOCUMENTS

| | | |
|---|---|---|
| WO | WO-2011/115943 A1 | 9/2011 |
| WO | WO-2013/082490 A1 | 6/2013 |
| WO | WO-2018/049271 A1 | 3/2018 |

OTHER PUBLICATIONS

Chiang, M.J. et al. (Mar. 5, 2014, e-published Feb. 24, 2014). "An Fc domain protein-small molecule conjugate as an enhanced immunomodulator," *J Am Chem Soc* 136(9):3370-3373.
Comerford, I. et al. (Feb. 2011). "Mini-review series: focus on chemokines," *Immunol Cell Biol* 89(2):183-184.
Gadhe, C.G. et al. (Feb. 2015, e-published Dec. 4, 2014). "Insights into the binding modes of CC chemokine receptor 4 (CCR4) inhibitors: a combined approach involving homology modelling, docking, and molecular dynamics simulation studies," *Mol Biosyst* 11(2):618-634.
Horuk, R. et al. (May 1994). "Molecular properties of the chemokine receptor family," *Trends Pharmacol Sci* 15(5):159-165.
Le, Y. et al. (Apr. 2004). "Chemokines and chemokine receptors: their manifold roles in homeostasis and disease," *Cell Mol Immunol* 1(2):95-104.
Li, W. et al. (2013). "Current drug research on PEGylation with small molecular agents," *Progress in Polymer Science* 38:421-444.
Ness, T.L. et al. (Dec. 2006). "CCR4 is a key modulator of innate immune responses," *J Immunol* 177(11):7531-7539.
Power, C.A. et al. (Aug. 18, 1995). "Molecular cloning and functional expression of a novel CC chemokine receptor cDNA from a human basophilic cell line," *J Biol Chem* 270(33):19495-19500.
Ramirez-Montagut, T. et al. (May 19, 2003). "Immunity to melanoma: unraveling the relation of tumor immunity and autoimmunity," *Oncogene* 22(20):3180-3187.
Sawaya, G.F. et al. (Oct. 2003). "Risk of cervical cancer associated with extending the interval between cervical-cancer screenings," *N Engl J Med* 349(16):1501-1509.
International Search Report dated Jan. 4, 2018, for PCT Application No. PCT/US2017/050834, filed Sep. 8, 2017, 4 pages.
Written Opinion dated Jan. 4, 2018, for PCT Application No. PCT/US2017/050834, filed Sep. 8, 2017, 6 pages.

*Primary Examiner* — Kahsay Habte
(74) *Attorney, Agent, or Firm* — Mintz

(57) ABSTRACT

Disclosed herein, inter alia, are compounds and methods of use thereof for the modulation of chemokine receptor activity.

77 Claims, No Drawings

CHEMOKINE RECEPTOR MODULATORS AND USES THEREOF

CROSS-REFERENCES TO RELATED APPLICATIONS

This application claims the benefit of priority under 35 U.S.C. § 119(e) of U.S. Provisional Application No. 62/385,802, filed Sep. 9, 2016, U.S. Provisional Application No. 62/426,102, filed Nov. 23, 2016, and U.S. Provisional Application No. 62/545,194, filed Aug. 14, 2017. The disclosure of each of the prior applications is considered part of, and is incorporated by reference, in the disclosure of this application.

BACKGROUND

The successful operation of the host defense system is the result of several processes that work together to eliminate foreign pathogens. Coordinated innate and acquired immune responses are required, and many secreted and cell-associated factors have been identified as important mediators coordinating and regulating these two arms of host defense. Chemokines are a family of cytokines that act as chemoattractants to guide leukocyte migration. They are secreted by a wide variety of cells and can be functionally divided into two groups, hemostatic chemokines and inflammatory chemokines. Hemostatic chemokines are constitutively produced in certain tissues and control cells of the immune system during processes of immune surveillance, such as directing lymphocytes to the lymph nodes to allow them to screen for invasion of pathogens. Inflammatory chemokines are released from cells in response to a pathological event (e.g., pro-inflammatory stimuli such as IL-1 or viruses). They function primarily as chemoattractants as part of the inflammatory response and serve to guide cells of both the innate and adaptive immune systems to the site of inflammation. The C—C chemokine receptor type 4 (CCR4), plays a role in the progression of a number of inflammation-related and other disorders. The identification of compounds that modulate CCR4 function is an ongoing challenge.

BRIEF SUMMARY

Disclosed herein are compounds that modulate CCR4 function and methods of using same. In a first aspect, there is provided a compound having structural Formula (I):

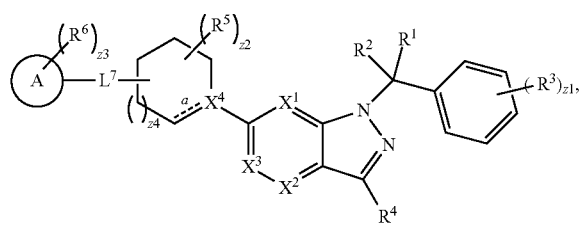

or a pharmaceutically acceptable salt thereof. In the compound of Formula (I), A is a substituted or unsubstituted heterocycloalkyl. $X^1$ is $CR^8$ or N. $X^2$ is $CR^9$ or N. $X^3$ is $CR^{10}$ or N. $X^4$ is C, $CR^{11}$ or N. The symbol "$\doteq$" is a single bond or double bond, wherein if $\doteq$ is a single bond, then $X^4$ is $CR^{11}$ or N, and if $\doteq$ is a double bond, then $X^4$ is C. $L^7$ is a bond, —O—, —S—, —$NR^{7B}$—, —C(O)—, —C(O)O—, —S(O)—, —$S(O)_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, —$CX^{2.1}_3$, —$CHX^{2.1}_2$, —$CH_2X^{2.1}$, —CN, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, —$CX^{3.1}_3$, —$CHX^{3.1}_2$, —$CH_2X^{3.1}$, —CN, —$SO_{n3}R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^4$ is hydrogen, halogen, —$CX^{4.1}_3$, —$CHX^{4.1}_2$, —$CH_2X^{4.1}$, —CN, —$SO_{n4}R^{4A}$, —$SO_{v4}NR^{4B}R^{4C}$, —$NHNR^{4B}R^{4C}$, —$ONR^{4B}R^{4C}$, —$NHC(O)NHNR^{4B}R^{4C}$, —$NHC(O)NR^{4B}R^{4C}$, —$N(O)_{m4}$, —$NR^{4B}R^{4C}$, —$C(O)R^{4D}$, —$C(O)OR^{4D}$, —$C(O)NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^5$ is hydrogen, halogen, oxo, —$CX^{5.1}_3$, —$CHX^{5.1}_2$, —$CH_2X^{5.1}$, —CN, —$SO_{n5}R^{5A}$, —$SO_{v5}NR^{5B}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^6$ is hydrogen, halogen, oxo, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —$NHC(O)NHNR^{6B}R^{6C}$, —$NHC(O)NR^{6B}R^{6C}$, —$N(O)_{m6}$, —$NR^{6B}R^{6C}$, —$C(O)R^{6D}$, —$C(O)OR^{6D}$, —$C(O)NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^8$ is hydrogen, halogen, —$CX^{8.1}_3$, —$CHX^{8.1}_2$, —$CH_2X^{8.1}$, —CN, —$SO_{n8}R^{8A}$, —$SO_{v8}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m8}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, —$CX^{9.1}_3$, —$CHX^{9.1}_2$, —$CH_2X^{9.1}$, —CN, —$SO_{n9}R^{9A}$, —$SO_{v9}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m9}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, —$CX^{10.1}_3$, —$CHX^{10.1}_2$, —$CH_2X^{10.1}$, —CN, —$SO_{n10}R^{10A}$, —$SO_{v10}NR^{10B}R^{10C}$, —$NHNR^{10B}R^{10C}$, —$ONR^{10B}R^{10C}$, —$NHC(O)NHNR^{10B}R^{10C}$, —$NHC(O)NR^{10B}R^{10C}$, —$N(O)_{m10}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$ is hydrogen, halogen, —$CX^{11.1}_3$, —$CHX^{11.1}_2$, —$CH_2X^{11.1}$, —CN, —$SO_{n11}R^{11A}$, —$SO_{v11}NR^{11B}R^{11C}$, —$NHNR^{11B}R^{11C}$, —$ONR^{11B}R^{11C}$, —$NHC(O)NHNR^{11B}R^{11C}$, —$NHC(O)NR^{11B}R^{11C}$, —$N(O)_{m11}$, —$NR^{11B}R^{11C}$, —$C(O)R^{11D}$, —$C(O)OR^{11D}$, —$C(O)NR^{11B}R^{11C}$, —$OR^{11A}$, —$NR^{11B}SO_2R^{11A}$, —$NR^{11B}C(O)R^{11D}$, —$NR^{11B}C(O)OR^{11D}$, —$NR^{11B}OR^{11D}$, —$OCX^{11.1}_3$, —$OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7B}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, and $R^{11D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{8B}$ and $R^{8C}$, $R^{9B}$ and $R^{9C}$, $R^{10B}$ and $R^{10C}$, $R^{11B}$ and $R^{11C}$ substituents bonded to the same nitrogen atom may optionally be joined to form a substituted or unsubstituted heterocycloalkyl or substituted or unsubstituted heteroaryl. $X^{1.1}$, $X^{2.1}$, $X^{3.1}$, $X^{4.1}$, $X^{5.1}$, $X^{6.1}$, $X^{8.1}$, $X^{9.1}$, $X^{10.1}$, $X^{11.1}$ are independently —Cl, —Br, —I or —F. The symbols n1, n2, n3, n4, n5, n6, n8, n9, n10, and n11 are independently an integer from 0 to 4. The symbols m1, m2, m3, m4, m5, m6, m8, m9, m10, m11, v1, v2, v3, v4, v5, v6, v8, v9, v10, and v11 are independently 1 or 2. The symbol z1 is an integer from 0 to 5. The symbol z2 is an integer from 0 to 13. The symbol z3 is an integer from 0 to 12. The symbol z4 is an integer from 0 to 3.

In an aspect is provided a pharmaceutical composition, including a compound as described herein, including embodiments (e.g., structural Formula (I), (Ia), (II), (III), (IIIa), (IIIb), (IV), (V), (Va), (Vb), (VI), (VII), (VIIa), (VIIb), (VIII), (VIIIa), (VIIIb), (IX), (IXa), (IXb), (IXc), (IXd) or (X), and a pharmaceutically acceptable excipient).

In another aspect is provided a method of inhibiting C—C chemokine receptor type 4 (CCR4), the method including contacting CCR4 with a compound as described herein, including embodiments (e.g, structural Formula (I), (Ia), (II), (III), (IIIa), (IIIb), (IV), (V), (Va), (Vb), (VI), (VII), (VIIa), (VIIb), (VIII), (VIIIa), (VIIIb), (IX), (IXa), (IXb), (IXc), (IXd) or (X), or a pharmaceutically acceptable salt thereof).

In an aspect, is provided a method of treating or preventing a disease or disorder mediated by CCR4, including administering to a subject in need thereof a therapeutically effective amount of a compound as described herein, including embodiments (e.g., structural Formula (I), (Ia), (II), (III), (IIIa), (IIIb), (IV), (V), (Va), (Vb), (VI), (VII), (VIIa), (VIIb), (VIII), (VIIIa), (VIIIb), (IX), (IXa), (IXb), (IXc), (IXd) or (X), or a pharmaceutically acceptable salt thereof).

In another aspect, provided herein is a kit including a compound described herein (e.g., a CCR4 inhibitor) or pharmaceutical compositions thereof. The kits are generally in the form of a physical structure housing various components, as described below, and may be utilized, for example, in practicing the methods described above.

DETAILED DESCRIPTION

Provided herein are, for example, compounds and compositions for inhibition of C—C chemokine receptor type 4, and pharmaceutical compositions including same. Also provided herein are, for example, methods of treating or preventing a disease, disorder or condition, or a symptom thereof, mediated by modulation (e.g., inhibition) of CCR4.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to eight optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. "Cycloalkyl" is also meant to refer to bicyclic and polycyclic hydrocarbon rings such as, for example, bicyclo[2.2.1]heptane, bicyclo[2.2.2]octane, etc.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " ~~~ " denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

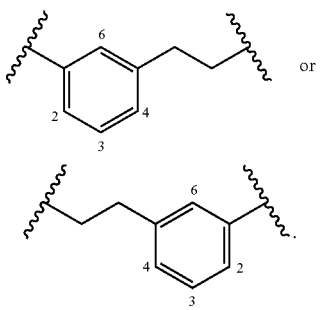

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$ SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:
(i) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(ii) alkyl, heteroalkyl, cycloalkyl, heterocycloalkyl, aryl, heteroaryl, substituted with at least one substituent selected from:
(a) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds disclosed herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)-for amino acids, and individual isomers are encompassed within the scope of the present disclosure. The compounds of the present disclosure do not include those that are known in art to be too unstable to synthesize and/or isolate. The presently disclosed compounds include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds may exist in tautomeric forms, all such tautomeric forms of the compounds being within the scope hereof.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope hereof.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope hereof.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In embodiments, compounds of the present disclosure contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of a compound to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "CCR4 inhibitor" refers to a compound (e.g., compounds described herein) that reduces the activity of CCR4 when compared to a control, such as absence of the compound or a compound with known inactivity. In embodiments, a CCR4 inhibitor contacts a CCR4 protein and thereby inhibits the activity of the contacted CCR4 protein. In embodiments, a CCR4 inhibitor inhibits one or more functions of the CCR4 protein. In embodiments, a CCR4 inhibitor is a CCR4 antagonist. In embodiments, a CCR4 inhibitor reduces the level of CCR4 protein or mRNA in a cell. As used herein, the terms "CCR4 inhibitor," "CCR4 antagonist," "C—C chemokine receptor type 4 inhibitor" and "C—C chemokine receptor type 4 antagonist" and all other related art-accepted terms, many of which are set forth below, refer to a compound capable of inhibiting, either directly or indirectly, the CCR4 receptor in an in vitro assay, an in vivo model, and/or other means indicative of therapeutic efficacy. The terms also refer to a compound that exhibits at least some therapeutic benefit in a human subject.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. In embodiments, the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences, with or without N-terminus methionine residues; immunologically tagged proteins; and the like.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments, contacting includes allowing a compound described herein to interact with a protein or enzyme that is involved in a signaling pathway (e.g., MAP kinase pathway).

As defined herein, the term "activation", "activate", "activating" and the like in reference to a protein refers to conversion of a protein into a biologically active derivative from an initial inactive or deactivated state or otherwise increasing (e.g., detectably) the activity of the protein or level of the protein. The terms reference activation, or activating, sensitizing, or up-regulating signal transduction or enzymatic activity or the amount of a protein decreased in a disease. The activating can increase protein activity 10%, 20%, 30%, 40%, 50%, 60%, 70%, 80%, 90% or more in comparison to a control in the absence of the activator (e.g., agonist). In certain instances, expression or activity is 1.5-fold, 2-fold, 3-fold, 4-fold, 5-fold, 10-fold or higher than the activity in the absence of the activator.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments, inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g., an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist. An antagonist prevents, reduces, inhibits, or neutralizes the activity of an agonist, and an antagonist can also prevent, inhibit, or reduce constitutive activity of a target, e.g., a target receptor, even where there is no identified agonist. In embodiments, inhibitors are molecules that decrease, block, prevent, delay activation, inactivate, desensitize, or down-regulate, e.g., a gene, protein, ligand, receptor, or cell. An inhibitor may also be defined as a molecule that reduces, blocks, or inactivates a constitutive activity. An "antagonist" is a molecule that opposes the action(s) of an agonist.

The terms "C—C chemokine receptor type 4" and "CCR4" refer to a protein (including homologs, isoforms, and functional fragments thereof) and is a high affinity receptor for the C—C-type chemokines (e.g., CCL2 (MCP-1), CCL4 (MIP-1), CCL5 (RANTES), CCL17 (TARC), and CCL22 (MDC)). It is referred to by a number of different names in the scientific literature, including "CC-CKR-4", "C—C CKR-4", "K5-5", "CD194", "CMKBR4", "ChemR13", "HGCN", and "14099". The term includes any recombinant or naturally-occurring form of CCR4 variants thereof that maintain CCR4 activity (e.g. within at least 30%, 40%, 50%, 60%, 70%, 80%, 90%, 95%, or 100% activity compared to wildtype CCR4). The term includes any mutant form of CCR4 variants (e.g., frameshift mutations) thereof that maintain CCR4 activity (e.g. within at least 30%, 40%, 50%, 60%, 70%, 80%, 90%, 95%, or 100% activity compared to wildtype CCR4). In embodiments, the CCR4 protein encoded by the CCR4 gene has the amino acid sequence set forth in or corresponding to Entrez 1233, UniProt P51679, or RefSeq (protein) NP_005499.1. In embodiments, the CCR4 gene has the nucleic acid sequence set forth in RefSeq (mRNA) NM_005508. In embodiments, the amino acid sequence or nucleic acid sequence is the sequence known at the time of filing of the present application. In embodiments, the sequence corresponds to GI:5031627. In embodiments, the sequence corresponds to NP_005499.1. In embodiments, the sequence corresponds to NM_005508.4. In embodiments, the sequence corresponds to GI:48762930. In embodiments, the CCR4 is a human CCR4, such as a human cancer causing CCR4. Though frequently found on dendritic cells, macrophages, NK cells, platelets, and basophils, CCR4 is predominantly associated with T cells. It plays a role in the progression of multiple inflammation-related disorders, and, as described herein, has also been implicated in a number of other conditions. The genomic sequence of CCR4 is present on chromosome 3 (NC_000003.12), and the CCR4 gene is conserved in a number of species, including chimpanzee, Rhesus monkey, dog, cow, mouse, rat, chicken, and zebrafish. In embodiments, the CCR4 polypeptide includes 360 amino acid residues (NP_005499.1), and, like other chemokine receptors, CCR4 is a G protein-coupled receptor found on the surface of leukocytes (see Horuk (1994) Trends Pharm. Sci. 15:159-165).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including MDS, AML, ALL, ATLL and CML), or multiple myeloma.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis. Such conditions are frequently inextricably intertwined with other diseases, disorders and conditions. A non-limiting list of inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders, which may be associated with chronic inflammation include Alzheimer's disease, congestive heart failure, stroke, aortic valve stenosis, arteriosclerosis, osteoporosis, Parkinson's disease, infections, inflammatory bowel disease (IBD), allergic contact dermatitis and other eczemas, systemic sclerosis, transplantation and multiple sclerosis. Some of the aforementioned diseases, disorders and conditions for which a compound (e.g., CCR4 inhibitor) of the present disclosure may be particularly efficacious (due to, for example, limitations of current therapies) are described in more detail hereafter.

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a CCR4 inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, chemotherapeutic, or treatment for a neurodegenerative disease). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g. colon cancer), cardiovascular disease, metabolic disease, immune or inflammatory disease or disorder.

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g. colon cancer), cardiovascular disease, metabolic disease, immune or inflammatory disease or disorder.

"Cardiovascular agent" is used in accordance with its plain ordinary meaning and refers to a composition (e.g. compound, drug, antagonist, inhibitor, modulator) used in any way to treat conditions of the heart or the circulatory or vascular system. In some embodiments, a cardiovascular agent is an agent identified herein having utility in methods of treating cardiovascular disease or disorder. In some embodiments, a cardiovascular agent is an agent approved by the FDA or similar regulatory agency of a country other than the USA, for treating cardiovascular disease or disorder.

"Anti-inflammatory agent" is used in accordance with its plain ordinary meaning and refers to a composition (e.g. compound, drug, antagonist, inhibitor, modulator) used in any way to reduce inflammation or swelling. In some embodiments, an anti-inflammatory agent is an agent identified herein having utility in methods of treating an inflammatory disease or disorder. In some embodiments, an anti-inflammatory agent is an agent approved by the FDA or similar regulatory agency of a country other than the USA, for reducing swelling and inflammation.

The compounds described herein can be administered to treat an immune or inflammatory disease or disorder, a cardiovascular or metabolic disease or disorder and/or cancer. In this regard, the compounds disclosed herein may be administered either alone to treat such diseases or disorders or may be co-administered with another therapeutic agent to treat such diseases or disorders.

The compounds disclosed herein may be co-administered with a cytokine or agonist or antagonist of cytokine function, (including agents which act on cytokine signaling pathways such as modulators of the SOCS system) including alpha-, beta-, and gamma-interferons; insulin-like growth factor type I (IGF-1); interleukins (IL) including IL1 to 17, and interleukin antagonists or inhibitors such as analcinra; tumour necrosis factor alpha (TNF-.alpha.) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

The compounds disclosed herein may be co-administered with an anti-inflammatory agent, such as thalidomide or a derivative thereof, a retinoid, dithranol or calcipotriol, a non-steroidal anti-inflammatory agent (hereinafter NSAID) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The compounds disclosed herein may be co-administered with a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Carib-aeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (-)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Gudrin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., Bacillus Calmette-Gudrin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

The compounds disclosed herein may be co-administered with an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin); (ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5.alpha.-reductase such as finasteride; (iii) an agent which inhibits cancer cell invasion (for example a metalloproteinase inhibitor like marimastat or an inhibitor of urokinase plasminogen activator receptor function); (iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazoli-n-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazoli-n-4-amine (CI 1033)), an inhibitor of the platelet-derived growth factor family, or an inhibitor of the hepatocyte growth factor family; (v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin .alpha.v.beta.3 function or an angiostatin); (vi) a vascular damaging agent such as combretastatin A4, or a compound disclosed in WO 99/02166, WO 00/40529, WO 00/41669, WO 01/92224, WO 02/04434 or WO 02/08213; (vii) an agent used in antisense therapy, for example one directed to one of the targets listed above, such as ISIS 2503, an anti-ras antisense; (viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In embodiments, the compounds disclosed herein can be co-administered with an antibody, such as a monoclonal antibody targeting B-Lymphocytes (such as CD20 (rituximab), MRA-aIL16R and T-Lymphocytes, CTLA4-Ig, HuMax I1-15) or antibody modulating Ig function such as anti-IgE (for example omalizumab).

In embodiments, treatment of cancer includes administration of an effective amount of at least two of the following: a CCR4 inhibitor, an inhibitor of the PD-L1/PD-1 pathway, an inhibitor of CTLA-4, an agonistic antibody of CD137 (4-1BB). In some embodiments, the method may comprise the use of two or more combinations.

In embodiments, treatment of cancer includes an effective amount of at least two or more of the following: a CCR4 inhibitor and any combination of agent that may be an immune modulator such as, but not limited to, those listed in Table 1. These immune modulators can be depleting antibodies, neutralizing antibodies, blocking antibodies, agonistic antibodies, small molecule modulators (inhibitors or stimulators), or small molecule analogs.

TABLE 1

| Target or Therapy | Examples of Agents | Regulatory Mechanism |
|---|---|---|
| TIM-3 | TSR-022, MGB453 | Checkpoint-receptor |
| LAG-3 | BMS-986016, IMP321 | Checkpoint-receptor |
| B7-H3 | MGA271, MGD-009 | Checkpoint-receptor |
| TIGIT | RG-6058 | Checkpoint-receptor |
| BTLA | | Checkpoint-receptor |
| CD28 | AMG 557, | Checkpoint-receptor |
| CD40 | SEA-CD40, dacetuzumab, CP-870,893, Chi Lob 7/4, lucatumumab | Checkpoint-receptor |
| CD80 | Galiximab | Checkpoint-receptor |
| GITR | INCAGN1876, TRX518, | Checkpoint-receptor |
| ICOS | MEDI-570 | Checkpoint-receptor |
| OX40 (CD134) | MEDI-6469, INCAGN1949, huMab OX40L, | Checkpoint-receptor |
| NKG2A | Monalizumab | Checkpoint-receptor |
| TGF-beta | Galunisertib, luspatercept, YH-14618, dalantercept, BG-00011, trabedersen, isth-0036,, ace-083, | Cytokines |
| IL2 | NKTR-214, recombinant IL2, aldesleukin | Cytokines |
| IL12 | EGEN-001, NHS-IL12 | Cytokines |
| IL7 | Recombinant IL-7, | Cytokines |
| IL15 | NIZ-985, ALT-803, | Cytokines |
| IL21 | Recombinant IL-21, anti-CD20.IL21, | Cytokines |
| IL13 | Tralokinumab, dupilumab | |
| CSF1R | Cabiralizumab | Cytokine |
| PI3K delta | INCB50465, idealisib, TGR-1202, AMG319, | Kinase |
| PI3K gamma | IPI-549 | Kinase |
| DNMT (DNA methyl transferase inhibitor) | Azacytidine, decitabine, guadecitabine, | Epigenetic Regulator |
| HDAC (histone deacetylase) | Vorinostat, Panobinostat, belinostat, entinostat, mocetinostat, givinostat, chidamide, quisinostat, abexinostat, chr-3996, ar-42, | Epigenetic Regulator |
| Brd4 | INCN54329, INCB57643, birabresib, apabetalone, alvocidib, PLX-51107, FT-1101, RG-6146, AZD-8186, CPI-0610, JQ1 | Transcription regulator |
| HMT (histone methyl transferases) | | Epigenetic Regulator |
| LSD1 | INCB59872, IMG-7289, RG-6016, CC-90011, GSK-2879552, ORY-2001, 4SC-202, ORY-3001, | Epigenetic Regulator |
| TNFa | Recombinant TNFa, MEDI-1873, FPA-154, LKZ-145 | Cytokine |
| IL1 | Recombinant IL1 | Cytokine |
| IFNa | Recombinant interferon alpha-n1, Recombinant interferon alpha-2b, Recombinant interferon alpha-n3 | Cytokine |
| IFNb | Recombinant IFN beta-1a, | Cytokine |
| IFNg | actimmune | Cytokine |
| STING | Cyclic di-nucleotides | Signaling Molecule |

TABLE 1-continued

| Target or Therapy | Examples of Agents | Regulatory Mechanism |
|---|---|---|
| TLR | Poly I:C, IMO-2055, TMX-101, imiquimod, CpG, MGN1703, glucopyranosyl lipid A, CBLB502, BCG, HILTONOL, AMPLIGEN, MOTOLIMOD, DUK-CPG-001, AS15 | Pathogen Recognition Receptor |
| IL10 | Recombinant IL-10 | Cytokine |
| CCR2 | CCX140, CCX872, BMS-813160, CENICRIVIROC, CNTX-6970. PF-4136309, plozalizumab, INCB-9471, PF-04634817 | Chemokine |
| CCR5 | Maraviroc, PRO-140, BMS-813160, NIFEVIROC, OHR-118 | Chemokine |
| CXCR4 | Ulocuplumab, plerixafor, x4p-001, usl-311, ly-2510924, APH-0812, BL-8040, BURIXAFOR, BALIXAFORTIDE, PTX-9908, GMI-1359, F-50067 | Chemokine |
| LFA1 | | Adhesion Molecule |
| MICA/B | IPH-4301 | Immune Receptor Ligand |
| VISTA | CA-170 | Checkpoint-Ligand |
| Adenosine | ISTRADEFYLLINE, TOZADENANT, PBF-509, PBF-999, CPI-444 | Nucleoside |
| CD39 | OREG-103. Anti-CD39 antibodies, | Ecto-enzyme |
| CD73 | Oleclumab, PBF-1662, anti-CD73 antibodies | Ecto-Enzyme |
| PD1 | Pembrolizumab, nivolumab, INCSHR1210, CT-011, AMP224 | Checkpoint-receptor |
| PD-L1 | Atezolizumab, avelumab | Checkpoint-Ligand |
| PD-L2 | | Checkpoint-Ligand |
| CTLA4 | Tremelimumab | Checkpoint-receptor |
| CD137 | Urelumab, utomilumab, BMS-663513, PF-05082566 | |
| AXL | BGB-324, BPI-9016M, S-49076 | Kinase |
| MERTK | BGB-324, BPI-9016M, S-49076 | Kinase |
| TYRO | BGB-324, BPI-9016M, S-49076 | |
| BTK | ibrutinib | Kinase |
| ITK | ibrutinib | Kinase |
| LCK | | Kinase |
| TET2 | | Enzyme |
| Arginase | Cb-1158 | Endo/ecto enzyme |
| GCN2 | | Kinase |
| B7-H4 | MDX-1140, AMP-110 | Checkpoint-receptor |
| HIF1alpha | PT2385 | Transcription Factor |
| LIGHT (TNFSF14) | | TNF Superfamily |
| FLT3 | CDX-301, FLX925, quizartinib, gilteritinib, PKC412, midostaurin, crenolanib | Kinase |
| CD158 | Lirlumab,. IPH-2101 | |
| CD47 | Anti-CD47, TTI-621, NI-1701, SRF-231, Effi-DEM, RCT-1938 | |
| IDO | Epacadostat, F287, BMS983205, GDC-0919, indoximod, | |
| RORgamma | | |

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In addition, a CCR4 inhibitor may be combined with the therapeutic administration of immune cells, sometimes referred to as adoptive cell transfer. These cells may be cells from the patient, a genetically related or unrelated donor, they may be genetically modified (e.g. CAR-T cells, NK cells, etc), cell lines, genetically modified cell lines and live or dead versions of the above. CCR4 inhibitors may also be combined with vaccines of any kind (e.g. protein/peptide, viral, bacterial, cellular) to stimulate immune responses to cancer.

In embodiments, treatment is administration of an effective amount of a CCR4 inhibitor in combination with an inhibitor of the PD-L1/PD-1 pathway, an inhibitor of CTLA-4, an agonistic antibody of CD137 (4-1BB) or in combination with another immune modulator as listed in Table 1.

In embodiments, treatment is therapeutic administration of an effective amount of a CCR4 inhibitor in combination with an inhibitor of the PD-L1/PD-1 pathway, an inhibitor of CTLA-4, an agonistic antibody of CD137 (4-1BB) or in combination with another immune modulator as listed in Table 1. Here, treatment starts when tumors reach a size of 40-70 mm$^3$.

The CCR4 inhibitors disclosed herein can be administered by any acceptable route, such oral, intraadiposal, intraarterial, intraarticular, intracranial, intradermal, intralesional, intramusculay, intranasal, intraocularal, intrapericardial, intraperitoneal, intrapleural, intraprostatical, intrarectal, intrathecal, intratracheal, intratumoral, intraumbilical, intravaginal, intravenousl, intravesicullar, intravitreal, liposomal, local, mucosal, parenteral, rectal, subconjunctival, subcutaneous, sublingual, topical, transbuccal, transdermal, vaginal, in cremes, in lipid compositions, via a catheter, via a lavage, via continuous infusion, via infusion, via inhalation, via injection, via local delivery, via localized perfusion, bathing target cells directly, or any combination thereof.

The immune modulators disclosed herein can be administered by any acceptable route, such oral, intraadiposal, intraarterial, intraarticular, intracranial, intradermal, intralesional, intramusculay, intranasal, intraocularal, intrapericardial, intraperitoneal, intrapleural, intraprostatical, intrarectal, intrathecal, intratracheal, intratumoral, intraumbilical, intravaginal, intravenousl, intravesicullar, intravitreal, liposomal, local, mucosal, parenteral, rectal, subconjunctival, subcutaneous, sublingual, topical, transbuccal, transdermal, vaginal, in cremes, in lipid compositions, via a catheter, via a lavage, via continuous infusion, via infusion, via inhalation, via injection, via local delivery, via localized perfusion, bathing target cells directly, or any combination thereof.

The CCR4 inhibitors disclosed herein may be administered once daily until study reached endpoint. The immune modulator disclosed herein may be administered at least three times but in some studies four or more times depending on the length of the study and/or the design of the study.

The methods disclosed herein may be used in combination with additional cancer therapy. In some embodiments, the distinct cancer therapy comprises surgery, radiotherapy, chemotherapy, toxin therapy, immunotherapy, cryotherapy or gene therapy. In some embodiments, the cancer is a chemotherapy-resistant or radio-resistant cancer.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, a CCR4 associated disease modulator is a compound that reduces the severity of one or more symptoms of a disease associated with CCR4 (e.g. cancer, inflammatory disease, autoimmune disease, or infectious disease). A CCR4 modulator is a compound that increases or decreases the activity or function or level of activity or level of function of CCR4. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an activator The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule. In embodiments, the terms "modulate," "modulation" and the like refer to the ability of a molecule (e.g., an activator or an inhibitor) to increase or decrease the function or activity of CCR4, either directly or indirectly, relative to the absence of the molecule.

The term "associated" or "associated with" or "mediated" or "mediated by" in the context of a substance or substance activity or function associated with a disease (e.g., a protein associated disease, a cancer associated with CCR4 activity, CCR4 associated cancer, CCR4 associated disease (e.g., cancer, inflammatory disease, autoimmune disease, or infectious disease)) or a disease mediated by a substance or substance activity or function. means that the disease (e.g., cancer, inflammatory disease, autoimmune disease, or infectious disease) is caused by (in whole or in part), or a symptom of the disease is caused by (in whole or in part) the substance or substance activity or function. For example, a cancer associated with CCR4 activity or function may be a cancer that results (entirely or partially) from aberrant CCR4 function (e.g. enzyme activity, protein-protein interaction, signaling pathway) or a cancer wherein a particular symptom of the disease is caused (entirely or partially) by aberrant CCR4 activity or function. As used herein, what is described as being associated with a disease, if a causative agent, could be a target for treatment of the disease. For example, a cancer associated with CCR4 activity or function or a CCR4 associated disease (e.g., cancer, inflammatory disease, autoimmune disease, or infectious disease), may be treated with a compound described herein (e.g., CCR4 modulator or CCR4 inhibitor), in the instance where increased CCR4 activity or function (e.g. signaling pathway activity) causes the disease (e.g., cancer, inflammatory disease, autoimmune disease, or infectious disease). For example, an inflammatory disease associated with CCR4 activity or function or a CCR4 associated inflammatory disease, may be treated with a CCR4 modulator or CCR4 inhibitor, in the instance where increased CCR4 activity or function (e.g. signaling pathway activity) causes the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extra-cellular components (e.g., proteins, nucleic acids, small molecules, ions, lipids) that conveys a change in one component to one or more other components, which in turn may convey a change to additional components, which is optionally propagated to other signaling pathway components. For example, binding of a CCR4 with a compound as described herein may reduce the level of a product of the CCR4 catalyzed reaction or the level of a downstream derivative of the product or binding may reduce the interactions between the CCR4 or a reaction product and downstream effectors or signaling pathway components (e.g., MAP kinase pathway), resulting in changes in cell growth, proliferation, or survival.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the component will make up greater than about 90%, or greater than about 95% of the total content of the composition (percentage in a weight per weight basis).

The terms "specifically binds" and "selectively binds," when referring to a ligand/receptor, antibody/antigen, or other binding pair, indicates a binding reaction which is determinative of the presence of the component of the binding pair in question (e.g., the protein in a heterogeneous population of proteins and other biologics). Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least 10-times greater, at least 20-times greater, or at least 100-times greater than the affinity of any other antibody, or binding composition derived therefrom. In embodiments, the antibody will have an affinity that is greater than about $10^9$ liters/mol, as determined by, e.g., Scatchard analysis (Munsen, et al. (1980) Analyt. Biochem. 107:220-239).

The terms "nucleic acid," "nucleic acid molecule," "polynucleotide" and the like are used interchangeably herein to refer to a polymeric form of nucleotides of any length (e.g., either deoxyribonucleotides or ribonucleotides, or analogs thereof). Non-limiting examples of polynucleotides include linear and circular nucleic acids, messenger RNA (mRNA), complementary DNA (cDNA), recombinant polynucleotides, vectors, probes, primers and the like.

As used herein, the terms "variants" and "homologs" are used interchangeably to refer to amino acid or nucleic acid sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring amino acid and nucleic acid sequences encoded thereby and their isoforms, as well as splice variants of a protein or gene. The terms also encompass nucleic acid sequences that vary in one or more bases from a naturally-occurring nucleic acid sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

II. Compounds

In aspects provided herein, there are compounds having structural Formula (I):

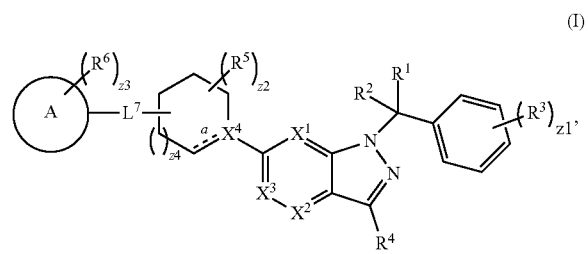

or a pharmaceutically acceptable salt thereof. A is a substituted or unsubstituted heterocycloalkyl. $X^1$ is $CR^8$ or N. $X^2$ is $CR^9$ or N. $X^3$ is $CR^{10}$ or N. In embodiments, at least one of $X^1$, $X^2$ and $X^3$ is N. $X^4$ is C, $CR^{11}$ or N. $L^7$ is a bond, —O—, —S—, —$NR^{7B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}_3$, $-OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-CX^{2.1}_3$, $-CHX^{2.1}_2$, $-CH_2X^{2.1}$, $-CN$, $-SO_{n2}R^{2A}$, $-SO_{v2}NR^{2B}R^{2C}$, $-NHNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m2}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^{2B}C(O)R^{2D}$, $-NR^{2B}C(O)OR^{2D}$, $-NR^{2B}OR^{2D}$, $-OCX^{2.1}_3$, $-OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, $-CX^{3.1}_3$, $-CHX^{3.1}_2$, $-CH_2X^{3.1}$, $-CN$, $-SO_{n3}R^{3A}$, $-SO_{v3}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m3}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^{3.1}_3$, $-OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^4$ is hydrogen, halogen, $-CX^{4.1}_3$, $-CHX^{4.1}_2$, $-CH_2X^{4.1}$, $-CN$, $-SO_{n4}R^{4A}$, $-SO_{v4}NR^{4B}R^{4C}$, $-NHNR^{4B}R^{4C}$, $-ONR^{4B}R^{4C}$, $-NHC(O)NHNR^{4B}R^{4C}$, $-NHC(O)NR^{4B}R^{4C}$, $-N(O)_{m4}$, $-NR^{4B}R^{4C}$, $-C(O)R^{4D}$, $-C(O)OR^{4D}$, $-C(O)NR^{4B}R^{4C}$, $-OR^{4A}$, $-NR^{4B}SO_2R^{4A}$, $-NR^{4B}C(O)R^{4D}$, $-NR^{4B}C(O)OR^{4D}$, $-NR^{4B}OR^{4D}$, $-OCX^{4.1}_3$, $-OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^5$ is hydrogen, halogen, oxo, $-CX^{5.1}_3$, $-CHX^{5.1}_2$, $-CH_2X^{5.1}$, $-CN$, $-SO_{n5}R^{5A}$, $-SO_{v5}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^{5.1}_3$, $-OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^6$ is hydrogen, halogen, oxo, $-CX^{6.1}_3$, $-CHX^{6.1}_2$, $-CH_2X^{6.1}$, $-CN$, $-SO_{n6}R^{6A}$, $-SO_{v6}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m6}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^8$ is hydrogen, halogen, $-CX^{8.1}_3$, $-CHX^{8.1}_2$, $-CH_2X^{8.1}$, $-CN$, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, $-CX^{9.1}_3$, $-CHX^{9.1}_2$, $-CH_2X^{9.1}$, $-CN$, $-SO_{n9}R^{9A}$, $-SO_{v9}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is hydrogen, halogen, $-CX^{10.1}_3$, $-CHX^{10.1}_2$, $-CH_2X^{10.1}$, $-CN$, $-SO_{n10}R^{10A}$, $-SO_{v10}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m10}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$ is hydrogen, halogen, $-CX^{11.1}_3$, $-CHX^{11.1}_2$, $-CH_2X^{11.1}$, $-CN$, $-SO_{n11}R^{11A}$, $-SO_{v11}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m11}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7B}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$ and $R^{11D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{8B}$ and $R^{8C}$, $R^{9B}$ and $R^{9C}$, $R^{10B}$ and $R^{10C}$, $R^{11B}$ and $R^{11C}$ substituents bonded to the same nitrogen atom may optionally be joined to form a substituted or unsubstituted heterocycloalkyl or substituted or unsubstituted heteroaryl. $X^{1.1}$, $X^{2.1}$, $X^{3.1}$, $X^{4.1}$, $X^{5.1}$, $X^{6.1}$, $X^{8.1}$, $X^{9.1}$, $X^{10.1}$, $X^{11.1}$ are independently $-Cl$, $-Br$, $-I$ or $-F$. The symbols n1, n2, n3, n4, n5, n6, n8, n9, n10, and n11 are independently an integer from 0 to 4. The symbols m1, m2, m3, m4, m5, m6, m8, m9, m10, m11, v1, v2, v3, v4, v5, v6, v8, v9, v10, and v11 are independently 1 or 2. The symbol z1 is an integer from 0 to 5. The symbol z2 is an integer from 0 to 13. The symbol z3 is an integer from 0 to 12. The symbol z4 is an integer from 0 to 3. The symbol ═ is a single bond or double bond, wherein if ⸗ is a single bond, then $X^4$ is $CR^{11}$ or N, and if ⸗ is a double bond, then $X^4$ is C.

For clarity, when A is a substituted heterocycloalkyl, it will be understood that A is substituted with one or more non-hydrogen $R^6$ substituents, as shown in Formula (I). For clarity, when A is an unsubstituted heterocycloalkyl, it will be understood that A is not substituted with one or more non-hydrogen $R^6$ substituents, as shown in Formula (I).

In embodiments, A is a substituted or unsubstituted heterocycloalkyl. In embodiments, A is a 4-membered to 8-membered heterocycloalkyl. In embodiments, A is a 4-membered heterocycloalkyl. In embodiments, A is a 5-membered heterocycloalkyl. In embodiments, A is a 6-membered heterocycloalkyl. In embodiments, A is a 7-membered heterocycloalkyl. In embodiments, A is an 8-membered heterocycloalkyl. In embodiments, A is a substituted 4-membered to 8-membered heterocycloalkyl. In embodiments, A is a substituted 4-membered heterocycloalkyl. In embodiments, A is a substituted 5-membered heterocycloalkyl. In embodiments, A is a substituted 6-membered heterocycloalkyl. In embodiments, A is a substituted 7-membered heterocycloalkyl. In embodiments, A is a substituted 8-membered heterocycloalkyl. In embodiments, A is an unsubstituted 4-membered to 8-membered heterocycloalkyl. In embodiments, A is an unsubstituted 4-membered heterocycloalkyl. In embodiments, A is an unsubstituted 5-membered heterocycloalkyl. In embodiments, A is an unsubstituted 6-membered heterocycloalkyl. In embodiments, A is an unsubstituted 7-membered heterocycloalkyl. In embodiments, A is an unsubstituted 8-membered heterocycloalkyl. In embodiments, A is an unsubstituted oxetanyl. In embodiments, A is a substituted oxetanyl. In embodiments, A is an unsubstituted azetidinyl. In embodiments, A is a substituted azetidinyl. In embodiments, A is an unsubstituted thietanyl. In embodiments, A is a substituted thietanyl. In embodiments, A is an unsubstituted azocanyl. In embodiments, A is a substituted azocanyl. In embodiments, A is an unsubstituted piperdinyl. In embodiments, A is a substituted piperdinyl. In embodiments, A is an unsubstituted pyrrolidinyl. In embodiments, A is a substituted pyrrolidinyl. In embodiments, A is an unsubstituted azepanyl. In embodiments, A is a substituted azepanyl. In embodiments, A is an unsubstituted 2,5-dihydro-1H-pyrrolyl. In embodiments, A is a substituted 2,5-dihydro-1H-pyrrolyl.

In embodiments, $X^1$ is $CR^8$ or N. In embodiments, $X^1$ is $CR^8$. In embodiments, $X^1$ is N.

In embodiments, $X^2$ is $CR^9$ or N. In embodiments, $X^2$ is $CR^9$. In embodiments, $X^2$ is N.

In embodiments, $X^3$ is $CR^{10}$ or N. In embodiments, $X^3$ is $CR^{10}$. In embodiments, $X^3$ is N.

In embodiments, $X^4$ is C, $CR^{11}$ or N. In embodiments, $X^4$ is C. In embodiments, $X^4$ is $CR^{11}$. In embodiments, $X^4$ is N.

In embodiments, at least one of $X^1$, $X^2$ and $X^3$ is N. In embodiments, $X^1$ is N. In embodiments, $X^2$ is N. In embodiments, $X^3$ is N. In embodiments, $X^1$ and $X^2$ are independently N. In embodiments, $X^1$ and $X^3$ are independently N. In embodiments, $X^2$ and $X^3$ are independently N.

In embodiments, the symbol "⸗" is a single bond or double bond, wherein if ⸗ is a single bond, then $X^4$ is $CR^{11}$ or N, and if ⸗ is a double bond, then $X^4$ is C. In embodiments, ⸗ is a single bond and $X^4$ is $CR^{11}$ or N. In embodiments, ⸗ is a single bond and $X^4$ is $CR^{11}$. In embodiments, ⸗ is a single bond and $X^4$ is N. In embodiments, ⸗ is a double bond and $X^4$ is C.

In embodiments, $L^7$ is a bond, —O—, —S—, —$NR^{7B}$—, —C(O)—, —C(O)O—, —S(O), —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^7$ is a bond, —O—, —S—, —$NR^{7B}$—, —C(O)—, —C(O)O—, —S(O), —S(O)$_2$—, substituted or unsubstituted alkylene (e.g., $C_1$-$C_8$ alkylene, $C_1$-$C_6$ alkylene, or $C_1$-$C_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., $C_3$-$C_8$ cycloalkylene, $C_3$-$C_6$ cycloalkylene, or $C_5$-$C_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., $C_6$-$C_{10}$ arylene, $C_{10}$ arylene, or phenylene), or substituted or unsubstituted heteroarylene (e.g., 5 to 10 membered heteroarylene, 5 to 9 membered heteroarylene, or 5 to 6 membered heteroarylene).

In embodiments, $L^7$ is a bond, —O—, —S—, —$NR^{7B}$—, —C(O)—, —C(O)O—, —S(O)—, —S(O)$_2$—, $R^{58}$-substituted or unsubstituted alkylene (e.g., $C_1$-$C_8$ alkylene, $C_1$-$C_6$ alkylene, or $C_1$-$C_4$ alkylene), $R^{58}$-substituted or unsubstituted heteroalkylene (e.g., 2 to 8 membered heteroalkylene, 2 to 6 membered heteroalkylene, or 2 to 4 membered heteroalkylene), $R^{58}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{58}$-substituted or unsubstituted heterocycloalkylene (e.g., 3 to 8 membered heterocycloalkylene, 3 to 6 membered heterocycloalkylene, or 5 to 6 membered heterocycloalkylene), $R^{58}$-substituted or unsubstituted arylene (e.g., $C_6$-$C_{10}$ arylene, $C_{10}$ arylene, or phenylene), or $R^{58}$-substituted or unsubstituted heteroarylene (e.g., 5 to 10 membered heteroarylene, 5 to 9 membered heteroarylene, or 5 to 6 membered heteroarylene). In embodiments, $L^7$ is a bond. In embodiments, $L^7$ is —N(CH$_2$CH$_3$)CH$_2$—. In embodiments, $L^7$ is —NHCH$_2$—. In embodiments, $L^7$ is —CH$_2$NHCH$_2$—. In embodiments, $L^7$ is —NH—. In embodiments, $L^7$ is —CH$_2$—. In embodiments, $L^7$ is —CH$_2$CH$_2$—. In embodiments, $L^7$ is —(CH$_2$)$_3$—. In embodiments, $L^7$ is —O—. In embodiments, $L^7$ is —S—. In embodiments, $L^7$ is —$NR^{7B}$—. In embodiments, $L^7$ is —C(O)—. In embodiments, $L^7$ is —C(O)O—. In embodiments, $L^7$ is —S(O)—. In embodiments, $L^7$ is —S(O)$_2$—. In embodiments, $L^7$ is C(O)NH. In embodiments, $R^{7B}$ is hydrogen. In embodiments, $R^{7B}$ is halogen. In embodiments, $R^{7B}$ is CH$_3$. In embodiments, $R^{7B}$ is CH$_2$CH$_3$.

In embodiments, $L^7$ is $R^{58}$-substituted or unsubstituted alkylene (e.g., $C_1$-$C_8$ alkylene, $C_1$-$C_6$ alkylene, or $C_1$-$C_4$ alkylene). In embodiments, $L^7$ is $R^{58}$-substituted alkylene (e.g., $C_1$-$C_8$ alkylene, $C_1$-$C_6$ alkylene, or $C_1$-$C_4$ alkylene). In embodiments, $L^7$ is an unsubstituted alkylene (e.g., $C_1$-$C_8$ alkylene, $C_1$-$C_6$ alkylene, or $C_1$-$C_4$ alkylene).

In embodiments, $L^7$ is $R^{58}$-substituted or unsubstituted heteroalkylene (e.g., 2 to 8 membered heteroalkylene, 2 to 6 membered heteroalkylene, or 2 to 4 membered heteroalkylene). In embodiments, $L^7$ is $R^{58}$-substituted heteroalkylene (e.g., 2 to 8 membered heteroalkylene, 2 to 6 membered heteroalkylene, or 2 to 4 membered heteroalkylene). In embodiments, $L^7$ is an unsubstituted heteroalkylene (e.g., 2 to 8 membered heteroalkylene, 2 to 6 membered heteroalkylene, or 2 to 4 membered heteroalkylene).

In embodiments, $L^7$ is $R^{58}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^7$ is $R^{58}$- substituted cycloalkylene (e.g., $C_3$-$C_8$ cycloalkylene, $C_3$-$C_6$ cycloalkylene, or $C_5$-$C_6$ cycloalkylene). In embodiments, $L^7$ is an unsubstituted cycloalkylene (e.g., $C_3$-$C_8$ cycloalkylene, $C_3$-$C_6$ cycloalkylene, or $C_5$-$C_6$ cycloalkylene).

In embodiments, $L^7$ is $R^{58}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^7$ is $R^{58}$-substituted heterocycloalkylene (e.g., 3 to 8 membered heterocycloalkylene, 3 to 6 membered heterocycloalkylene, or 5 to 6 membered heterocycloalkylene). In embodiments, $L^7$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^7$ is $R^{58}$-substituted or unsubstituted arylene (e.g., $C_6$-$C_{10}$ arylene, $C_{10}$ arylene, or phenylene). In embodiments, $L^7$ is $R^{58}$-substituted arylene (e.g., $C_6$-$C_{10}$ arylene, $C_{10}$ arylene, or phenylene). In embodiments, $L^7$ is an unsubstituted arylene (e.g., $C_6$-$C_{10}$ arylene, $C_{10}$ arylene, or phenylene).

In embodiments, $L^7$ is $R^{58}$-substituted or unsubstituted heteroarylene (e.g., 5 to 10 membered heteroarylene, 5 to 9 membered heteroarylene, or 5 to 6 membered heteroarylene). In embodiments, $L^7$ is $R^{58}$-substituted heteroarylene (e.g., 5 to 10 membered heteroarylene, 5 to 9 membered heteroarylene, or 5 to 6 membered heteroarylene). In embodiments, $L^7$ is an unsubstituted heteroarylene (e.g., 5 to 10 membered heteroarylene, 5 to 9 membered heteroarylene, or 5 to 6 membered heteroarylene).

In embodiments, $R^1$ is hydrogen, halogen, —$CX^{1.1}{}_3$, —$CHX^{1.1}{}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —NHC(O)NHNR$^{1B}R^{1C}$, —NHC(O)NR$^{1B}R^{1C}$, —N(O)$_{m1}$, —NR$^{1B}R^{1C}$, —C(O)R$^{1D}$, —C(O)OR$^{1D}$, —C(O)NR$^{1B}R^{1C}$, —OR$^{1A}$, —NR$^{1B}SO_2R^{1A}$, —NR$^{1B}C(O)R^{1D}$, —NR$^{1B}C(O)OR^{1D}$, —NR$^{1B}OR^{1D}$, —OCX$^{1.1}{}_3$, —OCHX$^{1.1}{}_2$, $R^{16}$-substituted or unsubstituted alkyl (e.g., $C_1$-$C_8$ alkyl, $C_1$-$C_6$ alkyl, or $C_1$-$C_4$ alkyl), $R^{16}$-substituted or unsubstituted heteroalkyl (e.g., 2 to 8 membered heteroalkyl, 2 to 6 membered heteroalkyl, or 2 to 4 membered heteroalkyl), $R^{16}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{16}$-substituted or unsubstituted heterocycloalkyl (e.g., 3 to 8 membered heterocycloalkyl, 3 to 6 membered heterocycloalkyl, or 5 to 6 membered heterocycloalkyl), $R^{16}$-substituted or unsubstituted aryl (e.g., $C_6$-$C_{10}$ aryl, $C_{10}$ aryl, or phenyl), or $R^{16}$-substituted or unsubstituted heteroaryl (e.g., 5 to 10 membered heteroaryl, 5 to 9 membered heteroaryl, or 5 to 6 membered heteroaryl).

In embodiments, $R^1$ is $R^{16}$-substituted or unsubstituted alkyl (e.g., $C_1$-$C_8$ alkyl, $C_1$-$C_6$ alkyl, or $C_1$-$C_4$ alkyl). In embodiments, $R^1$ is $R^{16}$-substituted alkyl (e.g., $C_1$-$C_8$ alkyl, $C_1$-$C_6$ alkyl, or $C_1$-$C_4$ alkyl). In embodiments, $R^1$ is an unsubstituted alkyl (e.g., $C_1$-$C_8$ alkyl, $C_1$-$C_6$ alkyl, or $C_1$-$C_4$ alkyl).

In embodiments, $R^1$ is $R^{16}$-substituted or unsubstituted heteroalkyl (e.g., 2 to 8 membered heteroalkyl, 2 to 6 membered heteroalkyl, or 2 to 4 membered heteroalkyl). In embodiments, $R^1$ is $R^{16}$-substituted heteroalkyl (e.g., 2 to 8 membered heteroalkyl, 2 to 6 membered heteroalkyl, or 2 to 4 membered heteroalkyl). In embodiments, $R^1$ is an unsubstituted heteroalkyl (e.g., 2 to 8 membered heteroalkyl, 2 to 6 membered heteroalkyl, or 2 to 4 membered heteroalkyl).

In embodiments, $R^1$ is $R^{16}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^1$ is $R^{16}$-substituted cycloalkyl (e.g., $C_3$-$C_8$ cycloalkyl, $C_3$-$C_6$ cycloalkyl, or $C_5$-$C_6$ cycloalkyl). In embodiments, $R^1$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^1$ is $R^{16}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is $R^{16}$-substituted heterocycloalkyl (e.g., 3 to 8 membered heterocycloalkyl, 3 to 6 membered heterocycloalkyl, or 5 to 6 membered heterocycloalkyl). In embodiments, $R^1$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^1$ is $R^{16}$-substituted or unsubstituted aryl (e.g., $C_6$-$C_{10}$ aryl, $C_{10}$ aryl, or phenyl). In embodiments, $R^1$ is $R^{16}$-substituted aryl (e.g., $C_6$-$C_{10}$ aryl, $C_{10}$ aryl, or phenyl). In embodiments, $R^1$ is an unsubstituted aryl (e.g., $C_6$-$C_{10}$ aryl, $C_{10}$ aryl, or phenyl).

In embodiments, $R^1$ is $R^{16}$-substituted or unsubstituted heteroaryl (e.g., 5 to 10 membered heteroaryl, 5 to 9 membered heteroaryl, or 5 to 6 membered heteroaryl). In embodiments, $R^1$ is $R^{16}$-substituted heteroaryl (e.g., 5 to 10 membered heteroaryl, 5 to 9 membered heteroaryl, or 5 to 6 membered heteroaryl). In embodiments, $R^1$ is an unsubstituted heteroaryl (e.g., 5 to 10 membered heteroaryl, 5 to 9 membered heteroaryl, or 5 to 6 membered heteroaryl).

In embodiments, $R^1$ is hydrogen. In embodiments, $R^1$ is substituted or unsubstituted alkyl. In embodiments, $R^1$ is substituted or unsubstituted heteroalkyl. In embodiments, $R^1$ is unsubstituted alkyl. In embodiments, $R^1$ is —$CH_3$ or —$CH_2CH_3$. In embodiments, $R^1$ is —$CH_3$. In embodiments, $R^1$ is —$CH_2CH_3$.

In embodiments, $R^2$ is hydrogen, halogen, —$CX^{2.1}{}_3$, —$CHX^{2.1}{}_2$, —$CH_2X^{2.1}$, —CN, —$SO_{n2}R^{2A}$, —$SO_{v2}NR^{2B}R^{2C}$, —$NHNR^{2B}R^{2C}$, —$ONR^{2B}R^{2C}$, —NHC(O)NHNR$^{2B}R^{2C}$, —NHC(O)NR$^{2B}R^{2C}$, —N(O)$_{m2}$, —NR$^{2B}R^{2C}$, —C(O)R$^{2D}$, —C(O)OR$^{2D}$, —C(O)NR$^{2B}R^{2C}$, —OR$^{2A}$, —NR$^{2B}SO_2R^{2A}$, —NR$^{2B}C(O)R^{2D}$, —NR$^{2B}C(O)OR^{2D}$, —NR$^{2B}OR^{2D}$, —OCX$^{2.1}{}_3$, —OCHX$^{2.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is hydrogen, halogen, —$CX^{2.1}{}_3$, —$CHX^{2.1}{}_2$, —$CH_2X^{2.1}$, —CN, —$SO_{n2}R^{2A}$, —$SO_{v2}NR^{2B}R^{2C}$, —$NHNR^{2B}R^{2C}$, —$ONR^{2B}R^{2C}$, —NHC(O)NHNR$^{2B}R^{2C}$, —NHC(O)NR$^{2B}R^{2C}$, —N(O)$_{m2}$, —NR$^{2B}R^{2C}$, —C(O)R$^{2D}$, —C(O)OR$^{2D}$, —C(O)NR$^{2B}R^{2C}$, —OR$^{2A}$, —NR$^{2B}SO_2R^{2A}$, —NR$^{2B}C(O)R^{2D}$, —NR$^{2B}C(O)OR^{2D}$, —NR$^{2B}OR^{2D}$, —OCX$^{2.1}{}_3$, —OCHX$^{2.1}{}_2$, $R^{19}$-substituted or unsubstituted alkyl (e.g., $C_1$-$C_8$ alkyl, $C_1$-$C_6$ alkyl, or $C_1$-$C_4$ alkyl), $R^{19}$-substituted or unsubstituted heteroalkyl (e.g., 2 to 8 membered heteroalkyl, 2 to 6 membered heteroalkyl, or 2 to 4 membered heteroalkyl), $R^{19}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{19}$-substituted or unsubstituted heterocycloalkyl (e.g., 3 to 8 membered heterocycloalkyl, 3 to 6 membered heterocycloalkyl, or 5 to 6 membered heterocycloalkyl), $R^{19}$-substituted or unsubstituted aryl (e.g., $C_6$-$C_{10}$ aryl, $C_{10}$ aryl, or phenyl), or $R^{19}$-substituted or unsubstituted heteroaryl (e.g., 5 to 10 membered heteroaryl, 5 to 9 membered heteroaryl, or 5 to 6 membered heteroaryl).

In embodiments, $R^2$ is $R^{19}$-substituted or unsubstituted alkyl (e.g., $C_1$-$C_8$ alkyl, $C_1$-$C_6$ alkyl, or $C_1$-$C_4$ alkyl). In embodiments, $R^2$ is $R^{19}$-substituted alkyl (e.g., $C_1$-$C_8$ alkyl, $C_1$-$C_6$ alkyl, or $C_1$-$C_4$ alkyl). In embodiments, $R^2$ is an unsubstituted alkyl (e.g., $C_1$-$C_8$ alkyl, $C_1$-$C_6$ alkyl, or $C_1$-$C_4$ alkyl). In embodiments, $R^2$ is an unsubstituted ethyl. In embodiments, $R^2$ is an unsubstituted $C_3$ alkyl. In embodiments, $R^2$ is an unsubstituted $C_4$ alkyl.

In embodiments, $R^2$ is $R^{19}$-substituted or unsubstituted heteroalkyl (e.g., 2 to 8 membered heteroalkyl, 2 to 6 membered heteroalkyl, or 2 to 4 membered heteroalkyl). In embodiments, $R^2$ is $R^{19}$-substituted heteroalkyl (e.g., 2 to 8 membered heteroalkyl, 2 to 6 membered heteroalkyl, or 2 to 4 membered heteroalkyl). In embodiments, $R^2$ is an unsubstituted heteroalkyl (e.g., 2 to 8 membered heteroalkyl, 2 to 6 membered heteroalkyl, or 2 to 4 membered heteroalkyl).

In embodiments, $R^2$ is $R^{19}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is $R^{19}$-substituted cycloalkyl (e.g., $C_3$-$C_8$ cycloalkyl, $C_3$-$C_6$ cycloalkyl, or $C_5$-$C_6$ cycloalkyl). In embodiments, $R^2$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^2$ is $R^{19}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^2$ is $R^{19}$-substituted heterocycloalkyl (e.g., 3 to 8 membered heterocycloalkyl, 3 to 6 membered heterocycloalkyl, or 5 to 6 membered heterocycloalkyl). In embodiments, $R^2$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^2$ is $R^{19}$-substituted or unsubstituted aryl (e.g., $C_6$-$C_{10}$ aryl, $C_{10}$ aryl, or phenyl). In embodiments, $R^2$ is $R^{19}$-substituted aryl (e.g., $C_6$-$C_{10}$ aryl, $C_{10}$ aryl, or phenyl). In embodiments, $R^2$ is an unsubstituted aryl (e.g., $C_6$-$C_{10}$ aryl, $C_{10}$ aryl, or phenyl).

In embodiments, $R^2$ is $R^{19}$-substituted or unsubstituted heteroaryl (e.g., 5 to 10 membered heteroaryl, 5 to 9 membered heteroaryl, or 5 to 6 membered heteroaryl). In embodiments, $R^2$ is $R^{19}$-substituted heteroaryl (e.g., 5 to 10 membered heteroaryl, 5 to 9 membered heteroaryl, or 5 to 6 membered heteroaryl). In embodiments, $R^2$ is an unsubstituted heteroaryl (e.g., 5 to 10 membered heteroaryl, 5 to 9 membered heteroaryl, or 5 to 6 membered heteroaryl).

In embodiments, $R^2$ is hydrogen. In embodiments, $R^2$ is substituted or unsubstituted alkyl. In embodiments, $R^2$ is substituted or unsubstituted heteroalkyl. In embodiments, $R^2$ is unsubstituted alkyl. In embodiments, $R^2$ is —$CH_3$ or —$CH_2CH_3$. In embodiments, $R^2$ is —$CH_3$. In embodiments, $R^2$ is —$CH_2CH_3$.

In embodiments, $R^1$ and $R^2$ are independently hydrogen, substituted or unsubstituted alkyl or substituted or unsubstituted heteroalkyl. In embodiments, $R^1$ and $R^2$ are independently hydrogen or unsubstituted alkyl.

In embodiments, $R^3$ is hydrogen, halogen, —$CX^{3.1}_3$, —$CHX^{3.1}_2$, —$CH_2X^{3.1}$, —CN, —$SO_{n3}R^{3A}$, —$SO_{v3}NR^{3B}R^{3C}$, —$NHNR^{3B}R^{3C}$, —$ONR^{3B}R^{3C}$, —NHC(O)NHNR^{3B}R^{3C}$, —NHC(O)NR^{3B}R^{3C}$, —$N(O)_{m3}$, —$NR^{3B}R^{3C}$, —C(O)R^{3D}$, —C(O)OR^{3D}$, —C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^3$ is halogen, —$CX^{3.1}_3$, —$CHX^{3.1}_2$, —$CH_2X^{3.1}$, —CN, —$SO_{n3}R^{3A}$, —$SO_{v3}NR^{3B}R^{3C}$, —$NHNR^{3B}R^{3C}$, —$ONR^{3B}R^{3C}$, —NHC(O)NHNR^{3B}R^{3C}$, —NHC(O)NR^{3B}R^{3C}$, —$N(O)_{m3}$, —$NR^{3B}R^{3C}$, —C(O)R^{3D}$, —C(O)OR^{3D}$, —C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.1}_2$, $R^{22}$-substituted or unsubstituted alkyl (e.g., $C_1$-$C_8$ alkyl, $C_1$-$C_6$ alkyl, or $C_1$-$C_4$ alkyl), $R^{22}$-substituted or unsubstituted heteroalkyl (e.g., 2 to 8 membered heteroalkyl, 2 to 6 membered heteroalkyl, or 2 to 4 membered heteroalkyl), $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22}$-substituted or unsubstituted aryl (e.g., $C_6$-$C_{10}$ aryl, $C_{10}$ aryl, or phenyl), or $R^{22}$-substituted or unsubstituted heteroaryl (e.g., 5 to 10 membered heteroaryl, 5 to 9 membered heteroaryl, or 5 to 6 membered heteroaryl).

In embodiments, $R^3$ is $R^{22}$-substituted or unsubstituted alkyl (e.g., $C_1$-$C_8$ alkyl, $C_1$-$C_6$ alkyl, or $C_1$-$C_4$ alkyl). In embodiments, $R^3$ is $R^{22}$-substituted alkyl (e.g., $C_1$-$C_8$ alkyl, $C_1$-$C_6$ alkyl, or $C_1$-$C_4$ alkyl). In embodiments, $R^3$ is an unsubstituted alkyl (e.g., $C_1$-$C_8$ alkyl, $C_1$-$C_6$ alkyl, or $C_1$-$C_4$ alkyl).

In embodiments, $R^3$ is $R^{22}$-substituted or unsubstituted heteroalkyl (e.g., 2 to 8 membered heteroalkyl, 2 to 6 membered heteroalkyl, or 2 to 4 membered heteroalkyl). In embodiments, $R^3$ is $R^{22}$-substituted heteroalkyl (e.g., 2 to 8 membered heteroalkyl, 2 to 6 membered heteroalkyl, or 2 to 4 membered heteroalkyl). In embodiments, $R^3$ is an unsubstituted heteroalkyl (e.g., 2 to 8 membered heteroalkyl, 2 to 6 membered heteroalkyl, or 2 to 4 membered heteroalkyl).

In embodiments, $R^3$ is $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is $R^{22}$-substituted cycloalkyl (e.g., $C_3$-$C_8$ cycloalkyl, $C_3$-$C_6$ cycloalkyl, or $C_5$-$C_6$ cycloalkyl). In embodiments, $R^3$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^3$ is $R^{22}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^{22}$-substituted heterocycloalkyl (e.g., 3 to 8 membered heterocycloalkyl, 3 to 6 membered heterocycloalkyl, or 5 to 6 membered heterocycloalkyl). In embodiments, $R^3$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^3$ is $R^{22}$-substituted or unsubstituted aryl (e.g., $C_6$-$C_{10}$ aryl, $C_{10}$ aryl, or phenyl). In embodiments, $R^3$ is $R^{22}$-substituted aryl (e.g., $C_6$-$C_{10}$ aryl, $C_{10}$ aryl, or phenyl). In embodiments, $R^3$ is an unsubstituted aryl (e.g., $C_6$-$C_{10}$ aryl, $C_{10}$ aryl, or phenyl).

In embodiments, $R^3$ is $R^{22}$-substituted or unsubstituted heteroaryl (e.g., 5 to 10 membered heteroaryl, 5 to 9 membered heteroaryl, or 5 to 6 membered heteroaryl). In embodiments, $R^3$ is $R^{22}$-substituted heteroaryl (e.g., 5 to 10 membered heteroaryl, 5 to 9 membered heteroaryl, or 5 to 6 membered heteroaryl). In embodiments, $R^3$ is an unsubstituted heteroaryl (e.g., 5 to 10 membered heteroaryl, 5 to 9 membered heteroaryl, or 5 to 6 membered heteroaryl).

In embodiments, $R^3$ is halogen, —Cl, or —F. In embodiments, $R^3$ is halogen. In embodiments, $R^3$ is —Cl. In embodiments, $R^3$ is —F. In embodiments, $R^3$ is $CH_3$.

In embodiments, $R^3$ is $CF_3$, $CHF_2$, $CH_2F$, $CCl_3$, $CHCl_2$, $CCl_3$, $CH_2CH_3$, unsubstituted propyl. In embodiments, $R^3$ is $CF_3$. In embodiments, $R^3$ is $CHF_2$. In embodiments, $R^3$ is $CH_2F$. In embodiments, $R^3$ is $CH_2Cl$. In embodiments, $R^3$ is $CHCl_2$. In embodiments, $R^3$ is $CCl_3$. In embodiments, $R^3$ is $CH_2CH_3$. In embodiments, $R^3$ is unsubstituted propyl.

In embodiments, the definition of $R^3$ is assumed by $R^{3.2}$ and $R^{3.3}$.

In embodiments, $R^4$ is hydrogen, halogen, —$CX^{4.1}{}_3$, —$CHX^{4.1}{}_2$, —$CH_2X^{4.1}$, —CN, —$SO_{n4}R^{4A}$, —$SO_{v4}NR^{4B}R^{4C}$, —$NHNR^{4B}R^{4C}$, —$ONR^{4B}R^{4C}$, —NHC(O)$NHNR^{4B}R^{4C}$, —NHC(O)$NR^{4B}R^{4C}$, —$N(O)_{m4}$, —$NR^{4B}R^{4C}$, —C(O)$R^{4D}$, —C(O)$OR^{4D}$, —C(O)$NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}{}_3$, —$OCHX^{4.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^4$ is hydrogen, halogen, —$CX^{4.1}{}_3$, —$CHX^{4.1}{}_2$, —$CH_2X^{4.1}$, —CN, —$SO_{n4}R^{4A}$, —$SO_{v4}NR^{4B}R^{4C}$, —$NHNR^{4B}R^{4C}$, —$ONR^{4B}R^{4C}$, —NHC(O)$NHNR^{4B}R^{4C}$, —NHC(O)$NR^{4B}R^{4C}$, —$N(O)_{m4}$, —$NR^{4B}R^{4C}$, —C(O)$R^{4D}$, —C(O)$OR^{4D}$, —C(O)$NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}{}_3$, —$OCHX^{4.1}{}_2$, $R^{25}$-substituted or unsubstituted alkyl (e.g., $C_1$-$C_8$ alkyl, $C_1$-$C_6$ alkyl, or $C_1$-$C_4$ alkyl), $R^{25}$-substituted or unsubstituted heteroalkyl (e.g., 2 to 8 membered heteroalkyl, 2 to 6 membered heteroalkyl, or 2 to 4 membered heteroalkyl), $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25}$-substituted or unsubstituted aryl (e.g., $C_6$-$C_{10}$ aryl, $C_{10}$ aryl, or phenyl), or $R^{25}$-substituted or unsubstituted heteroaryl (e.g., 5 to 10 membered heteroaryl, 5 to 9 membered heteroaryl, or 5 to 6 membered heteroaryl).

In embodiments, $R^4$ is hydrogen, —CN, —C(O)$NH_2$, —$CF_3$, —$CH_3$, —C($CH_3$)$_2$OH, or —C(O)$OCH_2CH_3$. In embodiments, $R^4$ is —CN. In embodiments, $R^4$ is hydrogen. In embodiments, $R^4$ is —C(O)$NH_2$. In embodiments, $R^4$ is —$CF_3$. In embodiments, $R^4$ is —$CH_3$. In embodiments, $R^4$ is —C(O)$OCH_2CH_3$. In embodiments, $R^4$ is C(O)$OR^{4D}$.

In embodiments, $R^4$ is halogen, $CHF_2$, $CH_2F$, $CH_2Cl$, $CHCl_2$, $CCl_3$, $CH_2CH_3$, unsubstituted propyl, —C(O)$OR^{4D}$, —C(O)$R^{4D}$, or —C(O)$NR^{4B}R^{4C}$. In embodiments, $R^4$ is halogen. In embodiments, $R^4$ is $CHF_2$. In embodiments, $R^4$ is $CH_2F$. In embodiments, $R^4$ is $CH_2Cl$. In embodiments, $R^4$ is $CHCl_2$. In embodiments, $R^4$ is $CCl_3$. In embodiments, $R^4$ is $CH_2CH_3$. In embodiments, $R^4$ is unsubstituted propyl. In embodiments, $R^4$ is C(O)$OR^{4D}$. In embodiments, $R^4$ is —C(O)$R^{4D}$. In embodiments, $R^4$ is —C(O)$NR^{4B}R^{4C}$. In embodiments, $R^{4B}$ is $CH_3$. In embodiments, $R^{4B}$ is $CF_3$. In embodiments, $R^{4B}$ is $CHF_2$. In embodiments, $R^{4B}$ is $CH_2F$. In embodiments, $R^{4B}$ is —$CH_2Cl$. In embodiments, $R^{4B}$ is $CHCl_2$. In embodiments, $R^{4B}$ is $CCl_3$. In embodiments, $R^{4B}$ is —$CH_2CH_3$. In embodiments, $R^{4B}$ is unsubstituted propyl. In embodiments, $R^{4B}$ is hydrogen. In embodiments, $R^{4C}$ is $CH_3$. In embodiments, $R^{4C}$ is $CF_3$. In embodiments, $R^{4C}$ is $CHF_2$. In embodiments, $R^{4C}$ is $CH_2F$. In embodiments, $R^{4C}$ is $CH_2Cl$. In embodiments, $R^{4C}$ is $CHCl_2$. In embodiments, $R^{4C}$ is $CCl_3$. In embodiments, $R^{4C}$ is $CH_2CH_3$. In embodiments, $R^{4C}$ is unsubstituted propyl. In embodiments, $R^{4C}$ is hydrogen. In embodiments, $R^{4D}$ is $CH_3$. In embodiments, $R^{4D}$ is —$CF_3$. In embodiments, $R^{4D}$ is $CHF_2$. In embodiments, $R^{4D}$ is $CH_2F$. In embodiments, $R^{4D}$ is $CH_2Cl$. In embodiments, $R^{4D}$ is $CHCl_2$. In embodiments, $R^{4D}$ is $CCl_3$. In embodiments, $R^{4D}$ is $CH_2CH_3$. In embodiments, $R^{4D}$ is unsubstituted propyl. In embodiments, $R^{4D}$ is hydrogen.

In embodiments, $R^4$ is $R^{25}$-substituted or unsubstituted alkyl (e.g., $C_1$-$C_8$ alkyl, $C_1$-$C_6$ alkyl, or $C_1$-$C_4$ alkyl). In embodiments, $R^4$ is $R^{25}$-substituted alkyl (e.g., $C_1$-$C_8$ alkyl, $C_1$-$C_6$ alkyl, or $C_1$-$C_4$ alkyl). In embodiments, $R^4$ is an unsubstituted alkyl (e.g., $C_1$-$C_8$ alkyl, $C_1$-$C_6$ alkyl, or $C_1$-$C_4$ alkyl). In embodiments, $R^4$ is an unsubstituted ethyl. In embodiments, $R^4$ is an unsubstituted $C_3$ alkyl. In embodiments, $R^4$ is an unsubstituted $C_4$ alkyl.

In embodiments, $R^4$ is $R^{25}$-substituted or unsubstituted heteroalkyl (e.g., 2 to 8 membered heteroalkyl, 2 to 6 membered heteroalkyl, or 2 to 4 membered heteroalkyl). In embodiments, $R^4$ is $R^{25}$-substituted heteroalkyl (e.g., 2 to 8 membered heteroalkyl, 2 to 6 membered heteroalkyl, or 2 to 4 membered heteroalkyl). In embodiments, $R^4$ is an unsubstituted heteroalkyl (e.g., 2 to 8 membered heteroalkyl, 2 to 6 membered heteroalkyl, or 2 to 4 membered heteroalkyl).

In embodiments, $R^4$ is $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^4$ is $R^{25}$-substituted cycloalkyl (e.g., $C_3$-$C_8$ cycloalkyl, $C_3$-$C_6$ cycloalkyl, or $C_5$-$C_6$ cycloalkyl). In embodiments, $R^4$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^4$ is $R^{25}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^4$ is $R^{25}$-substituted heterocycloalkyl (e.g., 3 to 8 membered heterocycloalkyl, 3 to 6 membered heterocycloalkyl, or 5 to 6 membered heterocycloalkyl). In embodiments, $R^4$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^4$ is $R^{25}$-substituted or unsubstituted aryl (e.g., $C_6$-$C_{10}$ aryl, $C_{10}$ aryl, or phenyl). In embodiments, $R^4$ is $R^{25}$-substituted aryl (e.g., $C_6$-$C_{10}$ aryl, $C_{10}$ aryl, or phenyl). In embodiments, $R^4$ is an unsubstituted aryl (e.g., $C_6$-$C_{10}$ aryl, $C_{10}$ aryl, or phenyl).

In embodiments, $R^4$ is $R^{25}$-substituted or unsubstituted heteroaryl (e.g., 5 to 10 membered heteroaryl, 5 to 9 membered heteroaryl, or 5 to 6 membered heteroaryl). In embodiments, $R^4$ is $R^{25}$-substituted heteroaryl (e.g., 5 to 10 membered heteroaryl, 5 to 9 membered heteroaryl, or 5 to 6 membered heteroaryl). In embodiments, $R^4$ is an unsubstituted heteroaryl (e.g., 5 to 10 membered heteroaryl, 5 to 9 membered heteroaryl, or 5 to 6 membered heteroaryl).

In embodiments, $R^4$ is hydrogen, —CN, —$CX^{4.1}{}_3$, —C(O)$R^{4D}$, —C(O)$OR^{4D}$, —C(O)$NR^{4B}R^{4C}$, substituted or unsubstituted alkyl or substituted or unsubstituted heteroalkyl.

In embodiments, $R^4$ is hydrogen, —OH, —CN, —$CX^{4.1}{}_3$, —C(O)$NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^4$ is —CN, —$CF_3$, —C(O)$NH_2$, —$CH_3$ or —C($CH_3$)$_2$OH.

In embodiments, $R^5$ is hydrogen, halogen, oxo, —$CX^{5.1}_3$, —$CHX^{5.1}_2$, —$CH_2X^{5.1}$, —CN, —$SO_{n5}R^{5A}$, —$SO_{v5}NR^{5B}R^{5C}$, —$NHNR^{5B}R^{5C}$, —$ONR^{5B}R^{5C}$, —NHC(O)$NHNR^{5B}R^{5C}$, —NHC(O)$NR^{5B}R^{5C}$, —N(O)$_{m5}$, —$NR^{5B}R^{5C}$, —C(O)$R^{5D}$, —C(O)O$R^{5D}$, —C(O)$NR^{5B}R^{5C}$, —O$R^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^5$ is halogen, oxo, —$CX^{5.1}_3$, —$CHX^{5.1}_2$, —$CH_2X^{5.1}$, —CN, —$SO_{n5}R^{5A}$, —$SO_{v5}NR^{5B}R^{5C}$, —$NHNR^{5B}R^{5C}$, —$ONR^{5B}R^{5C}$, —NHC(O)$NHNR^{5B}R^{5C}$, —NHC(O)$NR^{5B}R^{5C}$, —N(O)$_{m5}$, —$NR^{5B}R^{5C}$, —C(O)$R^{5D}$, —C(O)O$R^{5D}$, —C(O)$NR^{5B}R^{5C}$, —O$R^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^5$ is halogen, —$CX^{5.1}_3$, —$CHX^{5.1}_2$, —$CH_2X^{5.1}$, —CN, —$SO_{n5}R^{5A}$, —$SO_{v5}NR^{5B}R^{5C}$, —$NHNR^{5B}R^{5C}$, —$ONR^{5B}R^{5C}$, —NHC(O)$NHNR^{5B}R^{5C}$, —NHC(O)$NR^{5B}R^{5C}$, —N(O)$_{m5}$, —$NR^{5B}R^{5C}$, —C(O)$R^{5D}$, —C(O)O$R^{5D}$, —C(O)$NR^{5B}R^{5C}$, —O$R^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, $R^2$-substituted or unsubstituted alkyl (e.g., $C_1$-$C_8$ alkyl, $C_1$-$C_6$ alkyl, or $C_1$-$C_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^2$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl).

In embodiments, $R^5$ is $R^{28}$-substituted or unsubstituted alkyl (e.g., $C_1$-$C_8$ alkyl, $C_1$-$C_6$ alkyl, or $C_1$-$C_4$ alkyl). In embodiments, $R^5$ is $R^{28}$-substituted alkyl (e.g., $C_1$-$C_8$ alkyl, $C_1$-$C_6$ alkyl, or $C_1$-$C_4$ alkyl). In embodiments, $R^5$ is an unsubstituted alkyl (e.g., $C_1$-$C_8$ alkyl, $C_1$-$C_6$ alkyl, or $C_1$-$C_4$ alkyl).

In embodiments, $R^5$ is $R^{28}$-substituted or unsubstituted heteroalkyl (e.g., 2 to 8 membered heteroalkyl, 2 to 6 membered heteroalkyl, or 2 to 4 membered heteroalkyl). In embodiments, $R^5$ is $R^2$-substituted heteroalkyl (e.g., 2 to 8 membered heteroalkyl, 2 to 6 membered heteroalkyl, or 2 to 4 membered heteroalkyl). In embodiments, $R^5$ is an unsubstituted heteroalkyl (e.g., 2 to 8 membered heteroalkyl, 2 to 6 membered heteroalkyl, or 2 to 4 membered heteroalkyl).

In embodiments, $R^5$ is $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is $R^{28}$-substituted cycloalkyl (e.g., $C_3$-$C_8$ cycloalkyl, $C_3$-$C_6$ cycloalkyl, or $C_5$-$C_6$ cycloalkyl). In embodiments, $R^5$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^5$ is $R^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is $R^{28}$-substituted heterocycloalkyl (e.g., 3 to 8 membered heterocycloalkyl, 3 to 6 membered heterocycloalkyl, or 5 to 6 membered heterocycloalkyl). In embodiments, $R^5$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^5$ is $R^{28}$-substituted or unsubstituted aryl (e.g., $C_6$-$C_{10}$ aryl, $C_{10}$ aryl, or phenyl). In embodiments, $R^5$ is $R^{28}$-substituted aryl (e.g., $C_6$-$C_{10}$ aryl, $C_{10}$ aryl, or phenyl). In embodiments, $R^5$ is an unsubstituted aryl (e.g., $C_6$-$C_{10}$ aryl, $C_{10}$ aryl, or phenyl).

In embodiments, $R^5$ is $R^{28}$-substituted or unsubstituted heteroaryl (e.g., 5 to 10 membered heteroaryl, 5 to 9 membered heteroaryl, or 5 to 6 membered heteroaryl). In embodiments, $R^5$ is $R^{28}$-substituted heteroaryl (e.g., 5 to 10 membered heteroaryl, 5 to 9 membered heteroaryl, or 5 to 6 membered heteroaryl). In embodiments, $R^5$ is an unsubstituted heteroaryl (e.g., 5 to 10 membered heteroaryl, 5 to 9 membered heteroaryl, or 5 to 6 membered heteroaryl).

In embodiments, $R^5$ is hydrogen, fluorine, —CN, —$CH_3$, —$CF_3$, —$CH_2CH_3$, $CH_2OH$, C(O)OH, C($CH_3$)$_2$OH, —($CH_2$)$_2$OH, —CO$_2NH_2$, or —CO$_2CH_2CH_3$. In embodiments, $R^5$ is fluorine, —CN, —$CH_3$, —$CF_3$, —$CH_2CH_3$, $CH_2OH$, C(O)OH, —($CH_2$)$_2$OH, —CO$_2NH_2$, or —CO$_2CH_2CH_3$. In embodiments, $R^5$ is hydrogen. In embodiments, $R^5$ is fluorine. In embodiments, $R^5$ is —CN. In embodiments, $R^5$ is —$CH_3$. In embodiments, $R^5$ is —$CF_3$. In embodiments, $R^5$ is —$CH_2CH_3$. In embodiments, $R^5$ is $CH_2OH$. In embodiments, $R^5$ is C(O)OH. In embodiments, $R^5$ is C($CH_3$)$_2$OH. In embodiments, $R^5$ is —($CH_2$)$_2$OH. In embodiments, $R^5$ is —CO$_2NH_2$. In embodiments, $R^5$ is —CO$_2CH_2CH_3$.

In embodiments, $R^5$ is halogen, $CHF_2$, $CH_2F$, $CCl_3$, $CHCl_2$, $CH_2Cl$, —C(O)$R^{5D}$, —C(O)O$R^{5D}$, —CO$_2NR^{5B}R^{5C}$, or —O$R^{5A}$. In embodiments, $R^5$ is halogen, $CHF_2$, $CH_2F$, $CCl_3$, $CHCl_2$, $CH_2Cl$, —C(O)$R^{5D}$, —C(O)O$R^{5D}$, or —O$R^{5A}$. In embodiments, $R^5$ is halogen. In embodiments, $R^5$ is $CHF_2$. In embodiments, $R^5$ is $CH_2F$. In embodiments, $R^5$ is $CCl_3$. In embodiments, $R^5$ is $CHCl_2$. In embodiments, $R^5$ is $CH_2Cl$. In embodiments, $R^5$ is —C(O)$R^{5D}$. In embodiments, $R^5$ is —C(O)O$R^{5D}$. In embodiments, $R^5$ is —O$R^{5A}$. In embodiments, $R^5$ is —CO$_2NR^{5B}R^{5C}$. In embodiments, $R^{5B}$ is $CH_3$. In embodiments, $R^{5B}$ is $CF_3$. In embodiments, $R^{5B}$ is $CHF_2$. In embodiments, $R^{5B}$ is $CH_2F$. In embodiments, $R^{5B}$ is $CH_2Cl$. In embodiments, $R^{5B}$ is $CHCl_2$. In embodiments, $R^{5B}$ is $CCl_3$. In embodiments, $R^{5B}$ is $CH_2CH_3$. In embodiments, $R^{5B}$ is unsubstituted propyl. In embodiments, $R^{5B}$ is hydrogen. In embodiments, $R^{5C}$ is $CH_3$. In embodiments, $R^{5C}$ is $CF_3$. In embodiments, $R^{5C}$ is $CHF_2$. In embodiments, $R^{5C}$ is $CH_2F$. In embodiments, $R^{5C}$ is $CH_2Cl$. In embodiments, $R^{5C}$ is $CHCl_2$. In embodiments, $R^{5C}$ is $CCl_3$. In embodiments, $R^{5C}$ is $CH_2CH_3$. In embodiments, $R^{5C}$ is unsubstituted propyl. In embodiments, $R^{5C}$ is hydrogen. In embodiments, $R^{5D}$ is $CH_3$. In embodiments, $R^{5D}$ is $CF_3$. In embodiments, $R^{5D}$ is $CHF_2$. In embodiments, $R^{5D}$ is $CH_2F$. In embodiments, $R^{5D}$ is $CH_2Cl$. In embodiments, $R^{5D}$ is $CHCl_2$. In embodiments, $R^{5D}$ is $CCl_3$. In embodiments, $R^{5D}$ is $CH_2CH_3$. In embodiments, $R^{5D}$ is unsubstituted propyl. In embodiments, $R^{5D}$ is hydrogen.

In embodiments, the definition of $R^5$ is assumed by $R^{5.2}$, $R^{5.3}$, $R^{5.4}$ and $R^{5.5}$.

In embodiments, $R^6$ is hydrogen, halogen, oxo, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —NHC(O)$NHNR^{6B}R^{6C}$, —NHC(O)$NR^{6B}R^{6C}$, —N(O)$_{m6}$, —$NR^{6B}R^{6C}$, —C(O)$R^{6D}$, —C(O)O$R^{6D}$, —C(O)$NR^{6B}R^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}$$_3$, —OCHX$^{6.1}$$_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, R$^6$ is halogen, oxo, —CX$^{6.1}$$_3$, —CHX$^{6.1}$$_2$, —CH$_2$X$^{6.1}$, —CN, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}$$_3$, —OCHX$^{6.1}$$_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, R$^6$ is halogen, oxo, —CX$^{6.1}$$_3$, —CHX$^{6.1}$$_2$, —CH$_2$X$^{6.1}$, —CN, —SO$_{n6}$R$^{6A}$, —SO$_{v6}$NR$^{6B}$R$^{6C}$, —NHNR$^{6B}$R$^{6C}$, —ONR$^{6B}$R$^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}$$_3$, —OCHX$^{6.1}$$_2$, R$^{31}$-substituted or unsubstituted alkyl (e.g., C$_1$-C$_8$ alkyl, C$_1$-C$_6$ alkyl, or C$_1$-C$_4$ alkyl), R$^{31}$-substituted or unsubstituted heteroalkyl (e.g., 2 to 8 membered heteroalkyl, 2 to 6 membered heteroalkyl, or 2 to 4 membered heteroalkyl), R$^{31}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{31}$-substituted or unsubstituted heterocycloalkyl (e.g., 3 to 8 membered heterocycloalkyl, 3 to 6 membered heterocycloalkyl, or 5 to 6 membered heterocycloalkyl), R$^{31}$-substituted or unsubstituted aryl (e.g., C$_6$-C$_{10}$ aryl, C$_{10}$ aryl, or phenyl), or R$^{31}$-substituted or unsubstituted heteroaryl (e.g., 5 to 10 membered heteroaryl, 5 to 9 membered heteroaryl, or 5 to 6 membered heteroaryl).

In embodiments, R$^6$ is R$^{31}$-substituted or unsubstituted alkyl (e.g., C$_1$-C$_8$ alkyl, C$_1$-C$_6$ alkyl, or C$_1$-C$_4$ alkyl). In embodiments, R$^6$ is R$^{31}$-substituted alkyl (e.g., C$_1$-C$_8$ alkyl, C$_1$-C$_6$ alkyl, or C$_1$-C$_4$ alkyl). In embodiments, R$^6$ is an unsubstituted alkyl (e.g., C$_1$-C$_8$ alkyl, C$_1$-C$_6$ alkyl, or C$_1$-C$_4$ alkyl).

In embodiments, R$^6$ is R$^{31}$-substituted or unsubstituted heteroalkyl (e.g., 2 to 8 membered heteroalkyl, 2 to 6 membered heteroalkyl, or 2 to 4 membered heteroalkyl). In embodiments, R$^6$ is R$^{31}$-substituted heteroalkyl (e.g., 2 to 8 membered heteroalkyl, 2 to 6 membered heteroalkyl, or 2 to 4 membered heteroalkyl). In embodiments, R$^6$ is an unsubstituted heteroalkyl (e.g., 2 to 8 membered heteroalkyl, 2 to 6 membered heteroalkyl, or 2 to 4 membered heteroalkyl).

In embodiments, R$^6$ is R$^{31}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^6$ is R$^{31}$-substituted cycloalkyl (e.g., C$_3$-C$_8$ cycloalkyl, C$_3$-C$_6$ cycloalkyl, or C$_5$-C$_6$ cycloalkyl). In embodiments, R$^6$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^6$ is R$^{31}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^6$ is R$^{31}$-substituted heterocycloalkyl (e.g., 3 to 8 membered heterocycloalkyl, 3 to 6 membered heterocycloalkyl, or 5 to 6 membered heterocycloalkyl). In embodiments, R$^6$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^6$ is R$^{31}$-substituted or unsubstituted aryl (e.g., C$_6$-C$_{10}$ aryl, C$_{10}$ aryl, or phenyl). In embodiments, R$^6$ is R$^{31}$-substituted aryl (e.g., C$_6$-C$_{10}$ aryl, C$_{10}$ aryl, or phenyl). In embodiments, R$^6$ is an unsubstituted aryl (e.g., C$_6$-C$_{10}$ aryl, C$_{10}$ aryl, or phenyl).

In embodiments, R$^6$ is R$^{31}$-substituted or unsubstituted heteroaryl (e.g., 5 to 10 membered heteroaryl, 5 to 9 membered heteroaryl, or 5 to 6 membered heteroaryl). In embodiments, R$^6$ is R$^{31}$-substituted heteroaryl (e.g., 5 to 10 membered heteroaryl, 5 to 9 membered heteroaryl, or 5 to 6 membered heteroaryl). In embodiments, R$^6$ is an unsubstituted heteroaryl (e.g., 5 to 10 membered heteroaryl, 5 to 9 membered heteroaryl, or 5 to 6 membered heteroaryl).

In embodiments, R$^6$ is halogen, substituted or unsubstituted alkyl or substituted or unsubstituted heteroalkyl.

In embodiments, R$^6$ is hydrogen, —OH, —CH$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —CH$_2$CO$_2$NH$_2$, —(CH$_2$)$_2$CONH$_2$, —(CH$_2$)$_3$CO$_2$NH$_2$, —CH$_2$CHFCO$_2$H, —(CH$_2$)$_2$CHFCO$_2$H, —CH$_2$CF$_2$CO$_2$H, —(CH$_2$)$_2$CF$_2$CO$_2$H,

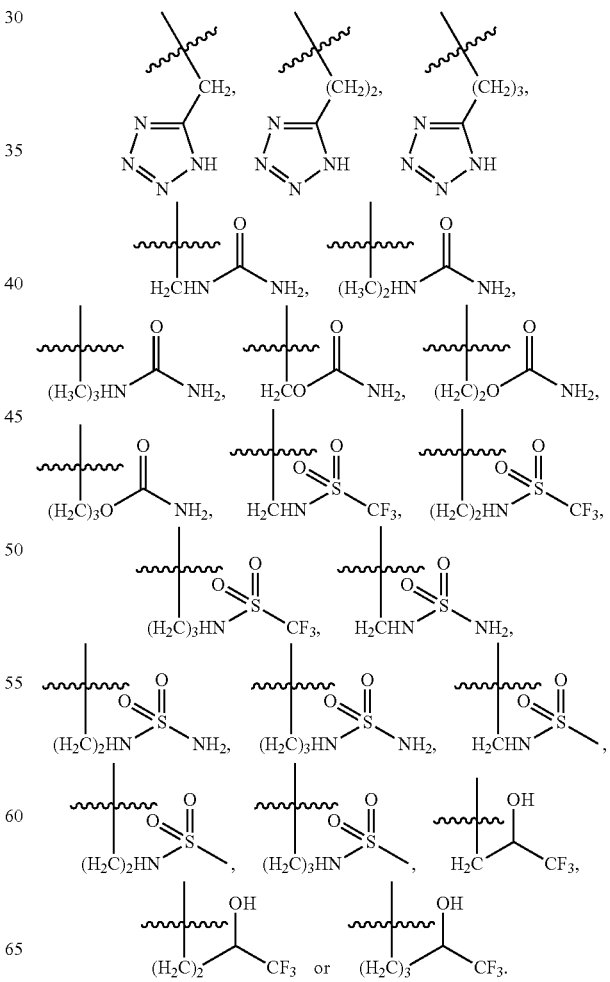

In embodiments, $R^6$ is F, —OH, —CH$_3$, —CH$_2$OH, C(CH$_3$)$_2$OH, —(CH$_2$)$_2$OH, —(CH$_2$)$_3$OH, C(O)OH, —CH$_2$NH$_2$, —C(O)NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —CH$_2$CO$_2$NH$_2$, —(CH$_2$)$_2$CONH$_2$, —(CH$_2$)$_3$CO$_2$NH$_2$, —CH$_2$CHFCO$_2$H, —(CH$_2$)$_2$CHFCO$_2$H, —CH$_2$CF$_2$CO$_2$H, —(CH$_2$)$_2$CF$_2$CO$_2$H, —(CH$_2$)$_2$SO$_2$NH$_2$, C(O)OH-substituted cyclopropyl, CH$_2$CH(OCH$_3$)CO$_2$H, —CH$_2$CH(OH)CO$_2$H, CH$_2$NHS(O$_2$)CH$_3$, CH(CH$_3$)CH$_2$CO$_2$H, CH$_2$OCH$_3$, C(O)NHCH$_3$, CH(OH)CH$_2$S(O$_2$)CH$_3$, —(CH$_2$)$_2$CH(OH)(CF$_3$),

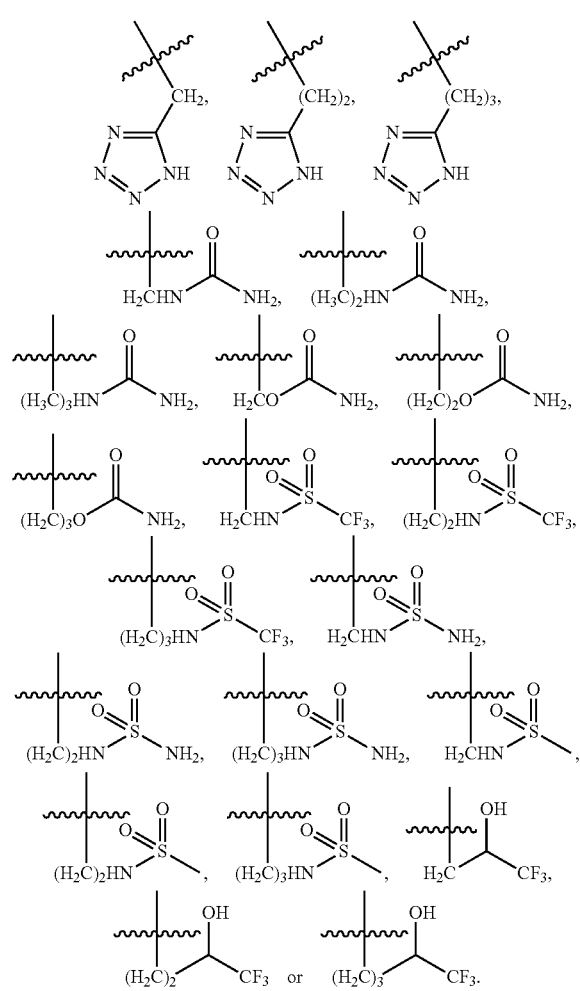

In embodiments, $R^6$ is F. In embodiments, $R^6$ is —OH. In embodiments, $R^6$ is —CH$_3$. In embodiments, $R^6$ is —CH$_2$OH. In embodiments, $R^6$ is C(CH$_3$)$_2$OH. In embodiments, $R^6$ is —(CH$_2$)$_2$OH. In embodiments, $R^6$ is —(CH$_2$)$_3$OH. In embodiments, $R^6$ is C(O)OH. In embodiments, $R^6$ is —CH$_2$NH$_2$. In embodiments, $R^6$ is —(CH$_2$)$_2$NH$_2$. In embodiments, $R^6$ is —(CH$_2$)$_3$NH$_2$. In embodiments, $R^6$ is —CH$_2$CO$_2$CH$_2$CH$_3$. In embodiments, $R^6$ is —(CH$_2$)$_2$CO$_2$CH$_2$CH$_3$. In embodiments, $R^6$ is —(CH$_2$)$_3$CO$_2$CH$_2$CH$_3$. In embodiments, $R^6$ is —CH$_2$CO$_2$H. In embodiments, $R^6$ is —(CH$_2$)$_2$CO$_2$H. In embodiments, $R^6$ is —(CH$_2$)$_3$CO$_2$H. In embodiments, $R^6$ is —CH$_2$CO$_2$NH$_2$. In embodiments, $R^6$ is —CH$_2$CONH$_2$. In embodiments, $R^6$ is —(CH$_2$)$_2$CONH$_2$. In embodiments, $R^6$ is —(CH$_2$)$_3$CO$_2$NH$_2$. In embodiments, $R^6$ is —(CH$_2$)$_3$CONH$_2$. In embodiments, $R^6$ is —CH$_2$CHFCO$_2$H. In embodiments, $R^6$ is —(CH$_2$)$_2$CHFCO$_2$H. In embodiments, $R^6$ is —CH$_2$CF$_2$CO$_2$H. In embodiments, $R^6$ is —(CH$_2$)$_2$CF$_2$CO$_2$H. In embodiments, $R^6$ is (CH$_2$)$_2$SO$_2$NH$_2$. In embodiments, $R^6$ is C(O)OH substituted cyclopropyl. In embodiments, $R^6$ is CH$_2$CH(OCH$_3$)CO$_2$H. In embodiments, $R^6$ is CH$_2$CH(OH)CO$_2$H. In embodiments, $R^6$ is CH(CH$_3$)CH$_2$CO$_2$H. In embodiments, $R^6$ is CH$_2$OCH$_3$. In embodiments, $R^6$ is C(O)NHCH$_3$. In embodiments, $R^6$ is CH(OH)CH$_2$S(O$_2$)CH$_3$. In embodiments, $R^6$ is

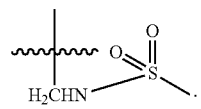

In embodiments, $R^6$ is —C(O)NH$_2$. In embodiments, $R^6$ is —(CH$_2$)$_2$SO$_2$NH$_2$. In embodiments, $R^6$ is C(O)OH-substituted cyclopropyl. In embodiments, $R^6$ is CH$_2$CH(OCH$_3$)CO$_2$H. In embodiments, $R^6$ is —CH$_2$CH(OH)CO$_2$H. In embodiments, $R^6$ is CH$_2$NHS(O$_2$)CH$_3$. In embodiments, $R^6$ is CH(CH$_3$)CH$_2$CO$_2$H. In embodiments, $R^6$ is CH$_2$OCH$_3$. In embodiments, $R^6$ is C(O)NHCH$_3$. In embodiments, $R^6$ is CH(OH)CH$_2$S(O$_2$)CH$_3$. In embodiments, $R^6$ is —(CH$_2$)$_2$CH(OH)(CF$_3$).

In embodiments, $R^6$ is halogen. In embodiments, $R^6$ is —OR$^{6A}$. In embodiments, $R^6$ is —C(O)OR$^{6D}$. In embodiments, $R^6$ is —CH$_2$NR$^{6B}$R$^{6C}$. In embodiments, $R^6$ is —(CH$_2$)$_2$NR$^{6B}$R$^{6C}$. In embodiments, $R^6$ is —(CH$_2$)$_3$NR$^{6B}$R$^{6C}$. In embodiments, $R^6$ is —CH$_2$C(O)OR$^{6D}$. In embodiments, $R^6$ is —(CH$_2$)$_2$C(O)OR$^{6D}$. In embodiments, $R^6$ is —(CH$_2$)$_3$C(O)OR$^{6D}$. In embodiments, $R^6$ is —CH$_2$C(O)OR$^{6D}$. In embodiments, $R^6$ is —CH$_2$CONR$^{6B}$R$^{6C}$. In embodiments, $R^6$ is —(CH$_2$)$_2$CO NR$^{6B}$R$^{6C}$. In embodiments, $R^6$ is —(CH$_2$)$_3$CONR$^{6B}$R$^{6C}$. In embodiments, $R^6$ is (CH$_2$)$_2$SO$_2$NR$^{6B}$R$^{6C}$. In embodiments, $R^6$ is —C(O)NR$^{6B}$R$^{6C}$. In embodiments, $R^6$ is CH$_2$NHSO$_2$R$^{6A}$. In embodiments, $R^{6A}$ is CH$_3$. In embodiments, $R^{6A}$ is CF$_3$. In embodiments, $R^{6A}$ is CHF$_2$. In embodiments, $R^{6A}$ is CH$_2$F. In embodiments, $R^{6A}$ is CH$_2$Cl. In embodiments, $R^{6A}$ is CHCl$_2$. In embodiments, $R^{6A}$ is CCl$_3$. In embodiments, $R^{6A}$ is CH$_2$CH$_3$. In embodiments, $R^{6A}$ is unsubstituted propyl. In embodiments, $R^{6A}$ is hydrogen. In embodiments, $R^{6B}$ is CH$_3$. In embodiments, $R^{6B}$ is CF$_3$. In embodiments, $R^{6B}$ is CHF$_2$. In embodiments, $R^{6B}$ is CH$_2$F. In embodiments, $R^{6B}$ is CH$_2$Cl. In embodiments, $R^{6B}$ is CHCl$_2$. In embodiments, $R^{6B}$ is CCl$_3$. In embodiments, $R^{6B}$ is CH$_2$CH$_3$. In embodiments, $R^{6B}$ is unsubstituted propyl. In embodiments, $R^{6B}$ is hydrogen. In embodiments, $R^{6C}$ is CH$_3$. In embodiments, $R^{6C}$ is CF$_3$. In embodiments, $R^{6C}$ is CHF$_2$. In embodiments, $R^{6C}$ is CH$_2$F. In embodiments, $R^{6C}$ is CH$_2$Cl. In embodiments, $R^{6C}$ is CHCl$_2$. In embodiments, $R^{6C}$ is CCl$_3$. In embodiments, $R^{6C}$ is CH$_2$CH$_3$. In embodiments, $R^{6C}$ is unsubstituted propyl. In embodiments, $R^{6C}$ is hydrogen. In embodiments, $R^{6D}$ is CH$_3$. In embodiments, $R^{6D}$ is CF$_3$. In embodiments, $R^{6D}$ is —CHF$_2$. In embodiments, $R^{6D}$ is CH$_2$F. In embodiments, $R^{6D}$ is CH$_2$Cl. In embodiments, $R^{6D}$ is —CHCl$_2$. In embodiments, $R^{6D}$ is CCl$_3$. In embodiments, $R^{6D}$ is CH$_2$CH$_3$. In embodiments, $R^{6D}$ is unsubstituted propyl. In embodiments, $R^{6D}$ is hydrogen.

In embodiments, the definition of $R^6$ is assumed by $R^{6.2}$, $R^{6.3}$, $R^{6.4}$, and $R^{6.5}$.

In embodiments, $R^8$ is hydrogen, halogen, —CX$^{8.1}_3$, —CHX$^{8.1}_2$, —CH$_2$X$^{8.1}$, —CN, —SO$_{n8}$R$^{8A}$, —$SO_{v8}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m8}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^8$ is hydrogen, halogen, —$CX^{8.1}_3$, —$CHX^{8.1}_2$, —$CH_2X^{8.1}$, —$CN$, —$SO_nR^{8A}$, —$SO_{v8}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m8}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, $R^{34}$-substituted or unsubstituted alkyl (e.g., $C_1$-$C_8$ alkyl, $C_1$-$C_6$ alkyl, or $C_1$-$C_4$ alkyl), $R^{34}$-substituted or unsubstituted heteroalkyl (e.g., 2 to 8 membered heteroalkyl, 2 to 6 membered heteroalkyl, or 2 to 4 membered heteroalkyl), $R^{34}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{34}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34}$-substituted or unsubstituted aryl (e.g., $C_6$-$C_{10}$ aryl, $C_{10}$ aryl, or phenyl), or $R^{34}$-substituted or unsubstituted heteroaryl (e.g., 5 to 10 membered heteroaryl, 5 to 9 membered heteroaryl, or 5 to 6 membered heteroaryl).

In embodiments, $R^8$ is $R^{34}$-substituted or unsubstituted alkyl (e.g., $C_1$-$C_8$ alkyl, $C_1$-$C_6$ alkyl, or $C_1$-$C_4$ alkyl). In embodiments, $R^8$ is $R^{34}$-substituted alkyl (e.g., $C_1$-$C_8$ alkyl, $C_1$-$C_6$ alkyl, or $C_1$-$C_4$ alkyl). In embodiments, $R^8$ is an unsubstituted alkyl (e.g., $C_1$-$C_8$ alkyl, $C_1$-$C_6$ alkyl, or $C_1$-$C_4$ alkyl).

In embodiments, $R^8$ is $R^{34}$-substituted or unsubstituted heteroalkyl (e.g., 2 to 8 membered heteroalkyl, 2 to 6 membered heteroalkyl, or 2 to 4 membered heteroalkyl). In embodiments, $R^8$ is $R^{34}$-substituted heteroalkyl (e.g., 2 to 8 membered heteroalkyl, 2 to 6 membered heteroalkyl, or 2 to 4 membered heteroalkyl). In embodiments, $R^8$ is an unsubstituted heteroalkyl (e.g., 2 to 8 membered heteroalkyl, 2 to 6 membered heteroalkyl, or 2 to 4 membered heteroalkyl).

In embodiments, $R^8$ is $R^{34}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^8$ is $R^{34}$-substituted cycloalkyl (e.g., $C_3$-$C_8$ cycloalkyl, $C_3$-$C_6$ cycloalkyl, or $C_5$-$C_6$ cycloalkyl). In embodiments, $R^8$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^8$ is $R^{34}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^8$ is $R^{34}$-substituted heterocycloalkyl (e.g., 3 to 8 membered heterocycloalkyl, 3 to 6 membered heterocycloalkyl, or 5 to 6 membered heterocycloalkyl). In embodiments, $R^8$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^8$ is $R^{34}$-substituted or unsubstituted aryl (e.g., $C_6$-$C_{10}$ aryl, $C_{10}$ aryl, or phenyl). In embodiments, $R^8$ is $R^{34}$-substituted aryl (e.g., $C_6$-$C_{10}$ aryl, $C_{10}$ aryl, or phenyl). In embodiments, $R^8$ is an unsubstituted aryl (e.g., $C_6$-$C_{10}$ aryl, $C_{10}$ aryl, or phenyl).

In embodiments, $R^8$ is $R^{34}$-substituted or unsubstituted heteroaryl (e.g., 5 to 10 membered heteroaryl, 5 to 9 membered heteroaryl, or 5 to 6 membered heteroaryl). In embodiments, $R^8$ is $R^{34}$-substituted heteroaryl (e.g., 5 to 10 membered heteroaryl, 5 to 9 membered heteroaryl, or 5 to 6 membered heteroaryl). In embodiments, $R^8$ is an unsubstituted heteroaryl (e.g., 5 to 10 membered heteroaryl, 5 to 9 membered heteroaryl, or 5 to 6 membered heteroaryl).

In embodiments, $R^9$ is hydrogen, halogen, —$CX^{9.1}_3$, —$CHX^{9.1}_2$, —$CH_2X^{9.1}$, —$CN$, —$SO_nR^{9A}$, —$SO_{v9}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m9}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^9$ is hydrogen, halogen, —$CX^{9.1}_3$, —$CHX^{9.1}_2$, —$CH_2X^{9.1}$, —$CN$, —$SO_nR^{9A}$, —$SO_{v9}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m9}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, $R^{37}$-substituted or unsubstituted alkyl (e.g., $C_1$-$C_8$ alkyl, $C_1$-$C_6$ alkyl, or $C_1$-$C_4$ alkyl), $R^{37}$-substituted or unsubstituted heteroalkyl (e.g., 2 to 8 membered heteroalkyl, 2 to 6 membered heteroalkyl, or 2 to 4 membered heteroalkyl), $R^{37}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37}$-substituted or unsubstituted aryl (e.g., $C_6$-$C_{10}$ aryl, $C_{10}$ aryl, or phenyl), or $R^{37}$-substituted or unsubstituted heteroaryl (e.g., 5 to 10 membered heteroaryl, 5 to 9 membered heteroaryl, or 5 to 6 membered heteroaryl).

In embodiments, $R^9$ is $R^{37}$-substituted or unsubstituted alkyl (e.g., $C_1$-$C_8$ alkyl, $C_1$-$C_6$ alkyl, or $C_1$-$C_4$ alkyl). In embodiments, $R^9$ is $R^{37}$-substituted alkyl (e.g., $C_1$-$C_8$ alkyl, $C_1$-$C_6$ alkyl, or $C_1$-$C_4$ alkyl). In embodiments, $R^9$ is an unsubstituted alkyl (e.g., $C_1$-$C_8$ alkyl, $C_1$-$C_6$ alkyl, or $C_1$-$C_4$ alkyl).

In embodiments, $R^9$ is $R^{37}$-substituted or unsubstituted heteroalkyl (e.g., 2 to 8 membered heteroalkyl, 2 to 6 membered heteroalkyl, or 2 to 4 membered heteroalkyl). In embodiments, $R^9$ is $R^{37}$-substituted heteroalkyl (e.g., 2 to 8 membered heteroalkyl, 2 to 6 membered heteroalkyl, or 2 to 4 membered heteroalkyl). In embodiments, $R^9$ is an unsubstituted heteroalkyl (e.g., 2 to 8 membered heteroalkyl, 2 to 6 membered heteroalkyl, or 2 to 4 membered heteroalkyl).

In embodiments, $R^9$ is $R^{37}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^9$ is $R^{37}$-substituted cycloalkyl (e.g., $C_3$-$C_8$ cycloalkyl, $C_3$-$C_6$ cycloalkyl, or $C_5$-$C_6$ cycloalkyl). In embodiments, $R^9$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^9$ is $R^{37}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^9$ is $R^{37}$-substituted heterocycloalkyl (e.g., 3 to 8 membered heterocycloalkyl, 3 to 6 membered heterocycloalkyl, or 5 to 6 membered heterocycloalkyl). In embodiments, $R^9$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^9$ is $R^{37}$-substituted or unsubstituted aryl (e.g., $C_6$-$C_{10}$ aryl, $C_{10}$ aryl, or phenyl). In embodiments, $R^9$ is $R^{37}$-substituted aryl (e.g., $C_6$-$C_{10}$ aryl, $C_{10}$ aryl, or phenyl). In embodiments, $R^9$ is an unsubstituted aryl (e.g., $C_6$-$C_{10}$ aryl, $C_{10}$ aryl, or phenyl).

In embodiments, $R^9$ is $R^{37}$-substituted or unsubstituted heteroaryl (e.g., 5 to 10 membered heteroaryl, 5 to 9 membered heteroaryl, or 5 to 6 membered heteroaryl). In embodiments, $R^9$ is $R^{37}$-substituted heteroaryl (e.g., 5 to 10 membered heteroaryl, 5 to 9 membered heteroaryl, or 5 to 6 membered heteroaryl). In embodiments, $R^9$ is an unsubstituted heteroaryl (e.g., 5 to 10 membered heteroaryl, 5 to 9 membered heteroaryl, or 5 to 6 membered heteroaryl).

In embodiments, $R^{10}$ is hydrogen, halogen, $-CX^{10.1}_3$, $-CHX^{10.1}_2$, $-CH_2X^{10.1}$, $-CN$, $-SO_{n10}R^{10A}$, $-SO_{v10}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m10}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{10}$ is hydrogen, halogen, $-CX^{10.1}_3$, $-CHX^{10.1}_2$, $-CH_2X^{10.1}$, $-CN$, $-SO_{n10}R^{10A}$, $-SO_{v10}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m10}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, $R^{40}$-substituted or unsubstituted alkyl (e.g., $C_1$-$C_8$ alkyl, $C_1$-$C_6$ alkyl, or $C_1$-$C_4$ alkyl), $R^{40}$-substituted or unsubstituted heteroalkyl (e.g., 2 to 8 membered heteroalkyl, 2 to 6 membered heteroalkyl, or 2 to 4 membered heteroalkyl), $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40}$-substituted or unsubstituted aryl (e.g., $C_6$-$C_{10}$ aryl, $C_{10}$ aryl, or phenyl), or $R^{40}$-substituted or unsubstituted heteroaryl (e.g., 5 to 10 membered heteroaryl, 5 to 9 membered heteroaryl, or 5 to 6 membered heteroaryl).

In embodiments, $R^{10}$ is $R^{40}$-substituted or unsubstituted alkyl (e.g., $C_1$-$C_8$ alkyl, $C_1$-$C_6$ alkyl, or $C_1$-$C_4$ alkyl). In embodiments, $R^{10}$ is $R^{40}$-substituted alkyl (e.g., $C_1$-$C_8$ alkyl, $C_1$-$C_6$ alkyl, or $C_1$-$C_4$ alkyl). In embodiments, $R^{10}$ is an unsubstituted alkyl (e.g., $C_1$-$C_8$ alkyl, $C_1$-$C_6$ alkyl, or $C_1$-$C_4$ alkyl).

In embodiments, $R^{10}$ is $R^{40}$-substituted or unsubstituted heteroalkyl (e.g., 2 to 8 membered heteroalkyl, 2 to 6 membered heteroalkyl, or 2 to 4 membered heteroalkyl). In embodiments, $R^{10}$ is $R^{40}$-substituted heteroalkyl (e.g., 2 to 8 membered heteroalkyl, 2 to 6 membered heteroalkyl, or 2 to 4 membered heteroalkyl). In embodiments, $R^{10}$ is an unsubstituted heteroalkyl (e.g., 2 to 8 membered heteroalkyl, 2 to 6 membered heteroalkyl, or 2 to 4 membered heteroalkyl).

In embodiments, $R^{10}$ is $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is $R^{40}$-substituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{10}$ is $R^{40}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{10}$ is $R^{40}$-substituted heterocycloalkyl (e.g., 3 to 8 membered heterocycloalkyl, 3 to 6 membered heterocycloalkyl, or 5 to 6 membered heterocycloalkyl). In embodiments, $R^{10}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{10}$ is $R^{40}$-substituted or unsubstituted aryl (e.g., $C_6$-$C_{10}$ aryl, $C_{10}$ aryl, or phenyl). In embodiments, $R^{10}$ is $R^{40}$-substituted aryl (e.g., $C_6$-$C_{10}$ aryl, $C_{10}$ aryl, or phenyl). In embodiments, $R^{10}$ is an unsubstituted aryl (e.g., $C_6$-$C_{10}$ aryl, $C_{10}$ aryl, or phenyl).

In embodiments, $R^{10}$ is $R^{40}$-substituted or unsubstituted heteroaryl (e.g., 5 to 10 membered heteroaryl, 5 to 9 membered heteroaryl, or 5 to 6 membered heteroaryl). In embodiments, $R^{10}$ is $R^{40}$-substituted heteroaryl (e.g., 5 to 10 membered heteroaryl, 5 to 9 membered heteroaryl, or 5 to 6 membered heteroaryl). In embodiments, $R^{10}$ is an unsubstituted heteroaryl (e.g., 5 to 10 membered heteroaryl, 5 to 9 membered heteroaryl, or 5 to 6 membered heteroaryl).

In embodiments, $R^{11}$ is hydrogen, halogen, $-CX^{11.1}_3$, $-CHX^{11.1}_2$, $-CH_2X^{11.1}$, $-CN$, $-SO_{n11}R^{11A}$, $-SO_{v11}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m11}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{11}$ is hydrogen, halogen, $-CX^{11.1}_3$, $-CHX^{11.1}_2$, $-CH_2X^{11.1}$, $-CN$, $-SO_{n11}R^{11A}$, $-SO_{v11}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m11}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, $R^{43}$-substituted or unsubstituted alkyl (e.g., $C_1$-$C_8$ alkyl, $C_1$-$C_6$ alkyl, or $C_1$-$C_4$ alkyl), $R^{43}$-substituted or unsubstituted heteroalkyl (e.g., 2 to 8 membered heteroalkyl, 2 to 6 membered heteroalkyl, or 2 to 4 membered heteroalkyl), $R^{43}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{43}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43}$-substituted or unsubstituted aryl (e.g., $C_6$-$C_{10}$ aryl, $C_{10}$ aryl, or phenyl), or $R^{43}$-substituted or unsubstituted heteroaryl (e.g., 5 to 10 membered heteroaryl, 5 to 9 membered heteroaryl, or 5 to 6 membered heteroaryl).

In embodiments, $R^{11}$ is $R^{43}$-substituted or unsubstituted alkyl (e.g., $C_1$-$C_8$ alkyl, $C_1$-$C_6$ alkyl, or $C_1$-$C_4$ alkyl). In embodiments, $R^{11}$ is $R^{43}$-substituted alkyl (e.g., $C_1$-$C_8$ alkyl, $C_1$-$C_6$ alkyl, or $C_1$-$C_4$ alkyl). In embodiments, $R^{11}$ is an unsubstituted alkyl (e.g., $C_1$-$C_8$ alkyl, $C_1$-$C_6$ alkyl, or $C_1$-$C_4$ alkyl).

In embodiments, $R^{11}$ is $R^{43}$-substituted or unsubstituted heteroalkyl (e.g., 2 to 8 membered heteroalkyl, 2 to 6 membered heteroalkyl, or 2 to 4 membered heteroalkyl). In embodiments, $R^{11}$ is $R^{43}$-substituted heteroalkyl (e.g., 2 to 8 membered heteroalkyl, 2 to 6 membered heteroalkyl, or 2 to 4 membered heteroalkyl). In embodiments, $R^{11}$ is an unsubstituted heteroalkyl (e.g., 2 to 8 membered heteroalkyl, 2 to 6 membered heteroalkyl, or 2 to 4 membered heteroalkyl).

In embodiments, $R^{11}$ is $R^{43}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{11}$ is $R^{43}$-substituted cycloalkyl (e.g., $C_3$-$C_8$ cycloalkyl, $C_3$-$C_6$ cycloalkyl, or $C_5$-$C_6$ cycloalkyl). In embodiments, $R^{11}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{11}$ is $R^{43}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{11}$ is $R^{43}$-substituted heterocycloalkyl (e.g., 3 to 8 membered heterocycloalkyl, 3 to 6 membered heterocycloalkyl, or 5 to 6 membered heterocycloalkyl). In embodiments, $R^{11}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{11}$ is $R^{43}$-substituted or unsubstituted aryl (e.g., $C_6$-$C_{10}$ aryl, $C_{10}$ aryl, or phenyl). In embodiments, $R^{11}$ is $R^{43}$-substituted aryl (e.g., $C_6$-$C_{10}$ aryl, $C_{10}$ aryl, or phenyl). In embodiments, $R^{11}$ is an unsubstituted aryl (e.g., $C_6$-$C_{10}$ aryl, $C_{10}$ aryl, or phenyl).

In embodiments, $R^{11}$ is $R^{43}$-substituted or unsubstituted heteroaryl (e.g., 5 to 10 membered heteroaryl, 5 to 9 membered heteroaryl, or 5 to 6 membered heteroaryl). In embodiments, $R^{11}$ is $R^{43}$-substituted heteroaryl (e.g., 5 to 10 membered heteroaryl, 5 to 9 membered heteroaryl, or 5 to 6 membered heteroaryl). In embodiments, $R^{11}$ is an unsubstituted heteroaryl (e.g., 5 to 10 membered heteroaryl, 5 to 9 membered heteroaryl, or 5 to 6 membered heteroaryl).

In embodiments, $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7B}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$ and $R^{11D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{8B}$ and $R^{8C}$, $R^{9B}$ and $R^{9C}$, $R^{10B}$ and $R^{10C}$, $R^{11B}$ and $R^{11C}$ substituents bonded to the same nitrogen atom may optionally be joined to form a substituted or unsubstituted heterocycloalkyl or substituted or unsubstituted heteroaryl.

In embodiments, $R^{1A}$ is hydrogen, halogen, —$CF_3$, —$CCl_3$, —$CBr_3$, —$CI_3$, —COOH, —$CONH_2$, $R^{16A}$-substituted or unsubstituted alkyl (e.g., $C_1$-$C_8$ alkyl, $C_1$-$C_6$ alkyl, or $C_1$-$C_4$ alkyl), $R^{16A}$-substituted or unsubstituted heteroalkyl (e.g., 2 to 8 membered heteroalkyl, 2 to 6 membered heteroalkyl, or 2 to 4 membered heteroalkyl), $R^{16A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{16A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{16A}$-substituted or unsubstituted aryl (e.g., $C_6$-$C_{10}$ aryl, $C_{10}$ aryl, or phenyl), or $R^{16A}$-substituted or unsubstituted heteroaryl (e.g., 5 to 10 membered heteroaryl, 5 to 9 membered heteroaryl, or 5 to 6 membered heteroaryl).

In embodiments, $R^{2A}$ is hydrogen, halogen, —$CF_3$, —$CCl_3$, —$CBr_3$, —$CI_3$, —COOH, —$CONH_2$, $R^{19A}$-substituted or unsubstituted alkyl (e.g., $C_1$-$C_8$ alkyl, $C_1$-$C_6$ alkyl, or $C_1$-$C_4$ alkyl), $R^{19A}$-substituted or unsubstituted heteroalkyl (e.g., 2 to 8 membered heteroalkyl, 2 to 6 membered heteroalkyl, or 2 to 4 membered heteroalkyl), $R^{19A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{19A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{19A}$-substituted or unsubstituted aryl (e.g., $C_6$-$C_{10}$ aryl, $C_{10}$ aryl, or phenyl), or $R^{19A}$-substituted or unsubstituted heteroaryl (e.g., 5 to 10 membered heteroaryl, 5 to 9 membered heteroaryl, or 5 to 6 membered heteroaryl).

In embodiments, $R^{3A}$ is hydrogen, halogen, —$CF_3$, —$CCl_3$, —$CBr_3$, —$CI_3$, —COOH, —$CONH_2$, $R^{22A}$-substituted or unsubstituted alkyl (e.g., $C_1$-$C_8$ alkyl, $C_1$-$C_6$ alkyl, or $C_1$-$C_4$ alkyl), $R^{22A}$-substituted or unsubstituted heteroalkyl (e.g., 2 to 8 membered heteroalkyl, 2 to 6 membered heteroalkyl, or 2 to 4 membered heteroalkyl), $R^{22A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22A}$-substituted or unsubstituted aryl (e.g., $C_6$-$C_{10}$ aryl, $C_{10}$ aryl, or phenyl), or $R^{22A}$-substituted or unsubstituted heteroaryl (e.g., 5 to 10 membered heteroaryl, 5 to 9 membered heteroaryl, or 5 to 6 membered heteroaryl).

In embodiments, $R^{4A}$ is hydrogen, halogen, —$CF_3$, —$CCl_3$, —$CBr_3$, —$CI_3$, —COOH, —$CONH_2$, $R^{25A}$-substituted or unsubstituted alkyl (e.g., $C_1$-$C_8$ alkyl, $C_1$-$C_6$ alkyl, or $C_1$-$C_4$ alkyl), $R^{25A}$-substituted or unsubstituted heteroalkyl (e.g., 2 to 8 membered heteroalkyl, 2 to 6 membered heteroalkyl, or 2 to 4 membered heteroalkyl), $R^{25A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25A}$-substituted or unsubstituted aryl (e.g., $C_6$-$C_{10}$ aryl, $C_{10}$ aryl, or phenyl), or $R^{25A}$-substituted or unsubstituted heteroaryl (e.g., 5 to 10 membered heteroaryl, 5 to 9 membered heteroaryl, or 5 to 6 membered heteroaryl).

In embodiments, $R^{5A}$ is hydrogen, halogen, —$CF_3$, —$CCl_3$, —$CBr_3$, —$CI_3$, —COOH, —$CONH_2$, $R^{28A}$-substituted or unsubstituted alkyl (e.g., $C_1$-$C_8$ alkyl, $C_1$-$C_6$ alkyl, or $C_1$-$C_4$ alkyl), $R^{28A}$-substituted or unsubstituted heteroalkyl (e.g., 2 to 8 membered heteroalkyl, 2 to 6 membered heteroalkyl, or 2 to 4 membered heteroalkyl), $R^{28A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28A}$-substituted or unsubstituted aryl (e.g., $C_6$-$C_{10}$ aryl, $C_{10}$ aryl, or phenyl), or $R^{28A}$-substituted or unsubstituted heteroaryl (e.g., 5 to 10 membered heteroaryl, 5 to 9 membered heteroaryl, or 5 to 6 membered heteroaryl).

In embodiments, $R^{6A}$ is hydrogen, halogen, —$CF_3$, —$CCl_3$, —$CBr_3$, —$CI_3$, —COOH, —$CONH_2$, $R^{31A}$-substituted or unsubstituted alkyl (e.g., $C_1$-$C_8$ alkyl, $C_1$-$C_6$ alkyl, or $C_1$-$C_4$ alkyl), $R^{31A}$-substituted or unsubstituted heteroalkyl (e.g., 2 to 8 membered heteroalkyl, 2 to 6 membered heteroalkyl, or 2 to 4 membered heteroalkyl), $R^{31A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31A}$-substituted or unsubstituted aryl (e.g., $C_6$-$C_{10}$ aryl, $C_{10}$ aryl, or phenyl), or $R^{31A}$-substituted or unsubstituted heteroaryl (e.g., 5 to 10 membered heteroaryl, 5 to 9 membered heteroaryl, or 5 to 6 membered heteroaryl).

In embodiments, $R^{8A}$ is hydrogen, halogen, —$CF_3$, —$CCl_3$, —$CBr_3$, —$CI_3$, —COOH, —$CONH_2$, $R^{34A}$-substituted or unsubstituted alkyl (e.g., $C_1$-$C_8$ alkyl, $C_1$-$C_6$ alkyl, or $C_1$-$C_4$ alkyl), $R^{34A}$-substituted or unsubstituted heteroalkyl (e.g., 2 to 8 membered heteroalkyl, 2 to 6 membered heteroalkyl, or 2 to 4 membered heteroalkyl), $R^{34A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{34A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34A}$-substituted or unsubstituted aryl (e.g., $C_6$-$C_{10}$ aryl, $C_{10}$ aryl, or phenyl), or $R^{34A}$-substituted or unsubstituted heteroaryl (e.g., 5 to 10 membered heteroaryl, 5 to 9 membered heteroaryl, or 5 to 6 membered heteroaryl).

In embodiments, $R^{9A}$ is hydrogen, halogen, —$CF_3$, —$CCl_3$, —$CBr_3$, —$CI_3$, —COOH, —$CONH_2$, $R^{37A}$-substituted or unsubstituted alkyl (e.g., $C_1$-$C_8$ alkyl, $C_1$-$C_6$ alkyl, or $C_1$-$C_4$ alkyl), $R^{37A}$-substituted or unsubstituted heteroalkyl (e.g., 2 to 8 membered heteroalkyl, 2 to 6 membered heteroalkyl, or 2 to 4 membered heteroalkyl), $R^{37A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37A}$-substituted or unsubstituted aryl (e.g., $C_6$-$C_{10}$ aryl, $C_{10}$ aryl, or phenyl), or $R^{37A}$-substituted or unsubstituted heteroaryl (e.g., 5 to 10 membered heteroaryl, 5 to 9 membered heteroaryl, or 5 to 6 membered heteroaryl).

In embodiments, $R^{10A}$ is hydrogen, halogen, —$CF_3$, —$CCl_3$, —$CBr_3$, —$CI_3$, —COOH, —$CONH_2$, $R^{40A}$-substituted or unsubstituted alkyl (e.g., $C_1$-$C_8$ alkyl, $C_1$-$C_6$ alkyl, or $C_1$-$C_4$ alkyl), $R^{40A}$-substituted or unsubstituted heteroalkyl (e.g., 2 to 8 membered heteroalkyl, 2 to 6 membered heteroalkyl, or 2 to 4 membered heteroalkyl), $R^{40A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40A}$-substituted or unsubstituted aryl (e.g., $C_6$-$C_{10}$ aryl, $C_{10}$ aryl, or phenyl), or $R^{40A}$-substituted or unsubstituted heteroaryl (e.g., 5 to 10 membered heteroaryl, 5 to 9 membered heteroaryl, or 5 to 6 membered heteroaryl).

In embodiments, $R^{11A}$ is hydrogen, halogen, —$CF_3$, —$CCl_3$, —$CBr_3$, —$CI_3$, —COOH, —$CONH_2$, $R^{43A}$-substituted or unsubstituted alkyl (e.g., $C_1$-$C_8$ alkyl, $C_1$-$C_6$ alkyl, or $C_1$-$C_4$ alkyl), $R^{43A}$-substituted or unsubstituted heteroalkyl (e.g., 2 to 8 membered heteroalkyl, 2 to 6 membered heteroalkyl, or 2 to 4 membered heteroalkyl), $R^{43A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{43A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43A}$-substituted or unsubstituted aryl (e.g., $C_6$-$C_{10}$ aryl, $C_{10}$ aryl, or phenyl), or $R^{43A}$-substituted or unsubstituted heteroaryl (e.g., 5 to 10 membered heteroaryl, 5 to 9 membered heteroaryl, or 5 to 6 membered heteroaryl).

In embodiments, $R^{1B}$ is hydrogen, halogen, —$CF_3$, —$CCl_3$, —$CBr_3$, —$CI_3$, —COOH, —$CONH_2$, $R^{16B}$-substituted or unsubstituted alkyl (e.g., $C_1$-$C_8$ alkyl, $C_1$-$C_6$ alkyl, or $C_1$-$C_4$ alkyl), $R^{16B}$-substituted or unsubstituted heteroalkyl (e.g., 2 to 8 membered heteroalkyl, 2 to 6 membered heteroalkyl, or 2 to 4 membered heteroalkyl), $R^{16B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{16B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{16B}$-substituted or unsubstituted aryl (e.g., $C_6$-$C_{10}$ aryl, $C_{10}$ aryl, or phenyl), or $R^{16B}$-substituted or unsubstituted heteroaryl (e.g., 5 to 10 membered heteroaryl, 5 to 9 membered heteroaryl, or 5 to 6 membered heteroaryl). In embodiments, $R^{1B}$ and $R^{1C}$ substituents bonded to the same nitrogen atom may optionally be joined to form a $R^{16B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{16B}$-substituted or unsubstituted heteroaryl (e.g., 5 to 10 membered heteroaryl, 5 to 9 membered heteroaryl, or 5 to 6 membered heteroaryl).

In embodiments, $R^{2B}$ is hydrogen, halogen, —$CF_3$, —$CCl_3$, —$CBr_3$, —$CI_3$, —COOH, —$CONH_2$, $R^{19B}$-substituted or unsubstituted alkyl (e.g., $C_1$-$C_8$ alkyl, $C_1$-$C_6$ alkyl, or $C_1$-$C_4$ alkyl), $R^{19B}$-substituted or unsubstituted heteroalkyl (e.g., 2 to 8 membered heteroalkyl, 2 to 6 membered heteroalkyl, or 2 to 4 membered heteroalkyl), $R^{19B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{19B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{19B}$-substituted or unsubstituted aryl (e.g., $C_6$-$C_{10}$ aryl, $C_{10}$ aryl, or phenyl), or $R^{19B}$-substituted or unsubstituted heteroaryl (e.g., 5 to 10 membered heteroaryl, 5 to 9 membered heteroaryl, or 5 to 6 membered heteroaryl). In embodiments, $R^{2B}$ and $R^{2C}$ substituents bonded to the same nitrogen atom may optionally be joined to form a $R^{19B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{19B}$-substituted or unsubstituted heteroaryl (e.g., 5 to 10 membered heteroaryl, 5 to 9 membered heteroaryl, or 5 to 6 membered heteroaryl).

In embodiments, $R^{3B}$ is hydrogen, halogen, —$CF_3$, —$CCl_3$, —$CBr_3$, —$CI_3$, —COOH, —$CONH_2$, $R^{22B}$-substituted or unsubstituted alkyl (e.g., $C_1$-$C_8$ alkyl, $C_1$-$C_6$ alkyl, or $C_1$-$C_4$ alkyl), $R^{22B}$-substituted or unsubstituted heteroalkyl (e.g., 2 to 8 membered heteroalkyl, 2 to 6 membered heteroalkyl, or 2 to 4 membered heteroalkyl), $R^{22B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22B}$-substituted or unsubstituted aryl (e.g., $C_6$-$C_{10}$ aryl, $C_{10}$ aryl, or phenyl), or $R^{22B}$-substituted or unsubstituted heteroaryl (e.g., 5 to 10 membered heteroaryl, 5 to 9 membered heteroaryl, or 5 to 6 membered heteroaryl). In embodiments, $R^{3B}$ and $R^{3C}$ substituents bonded to the same nitrogen atom may optionally be joined to form a $R^{22B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{22B}$-substituted or unsubstituted heteroaryl (e.g., 5 to 10 membered heteroaryl, 5 to 9 membered heteroaryl, or 5 to 6 membered heteroaryl).

In embodiments, $R^{4B}$ is hydrogen, halogen, $-CF_3$, $-CCl_3$, $-CBr_3$, $-CI_3$, $-COOH$, $-CONH_2$, $R^{25B}$-substituted or unsubstituted alkyl (e.g., $C_1$-$C_8$ alkyl, $C_1$-$C_6$ alkyl, or $C_1$-$C_4$ alkyl), $R^{25B}$-substituted or unsubstituted heteroalkyl (e.g., 2 to 8 membered heteroalkyl, 2 to 6 membered heteroalkyl, or 2 to 4 membered heteroalkyl), $R^{25B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25B}$-substituted or unsubstituted aryl (e.g., $C_6$-$C_{10}$ aryl, $C_{10}$ aryl, or phenyl), or $R^{25B}$-substituted or unsubstituted heteroaryl (e.g., 5 to 10 membered heteroaryl, 5 to 9 membered heteroaryl, or 5 to 6 membered heteroaryl). In embodiments, $R^{4B}$ and $R^{4C}$ substituents bonded to the same nitrogen atom may optionally be joined to form a $R^{25B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{25B}$-substituted or unsubstituted heteroaryl (e.g., 5 to 10 membered heteroaryl, 5 to 9 membered heteroaryl, or 5 to 6 membered heteroaryl).

In embodiments, $R^{5B}$ is hydrogen, halogen, $-CF_3$, $-CCl_3$, $-CBr_3$, $-CI_3$, $-COOH$, $-CONH_2$, $R^{28B}$-substituted or unsubstituted alkyl (e.g., $C_1$-$C_8$ alkyl, $C_1$-$C_6$ alkyl, or $C_1$-$C_4$ alkyl), $R^{28B}$-substituted or unsubstituted heteroalkyl (e.g., 2 to 8 membered heteroalkyl, 2 to 6 membered heteroalkyl, or 2 to 4 membered heteroalkyl), $R^{28B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28B}$-substituted or unsubstituted aryl (e.g., $C_6$-$C_{10}$ aryl, $C_{10}$ aryl, or phenyl), or $R^{28B}$-substituted or unsubstituted heteroaryl (e.g., 5 to 10 membered heteroaryl, 5 to 9 membered heteroaryl, or 5 to 6 membered heteroaryl). In embodiments, $R^{5B}$ and $R^{5C}$ substituents bonded to the same nitrogen atom may optionally be joined to form a $R^{28B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{28B}$-substituted or unsubstituted heteroaryl (e.g., 5 to 10 membered heteroaryl, 5 to 9 membered heteroaryl, or 5 to 6 membered heteroaryl).

In embodiments, $R^{6B}$ is hydrogen, halogen, $-CF_3$, $-CCl_3$, $-CBr_3$, $-CI_3$, $-COOH$, $-CONH_2$, $R^{31B}$-substituted or unsubstituted alkyl (e.g., $C_1$-$C_8$ alkyl, $C_1$-$C_6$ alkyl, or $C_1$-$C_4$ alkyl), $R^{31B}$-substituted or unsubstituted heteroalkyl (e.g., 2 to 8 membered heteroalkyl, 2 to 6 membered heteroalkyl, or 2 to 4 membered heteroalkyl), $R^{31B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31B}$-substituted or unsubstituted aryl (e.g., $C_6$-$C_{10}$ aryl, $C_{10}$ aryl, or phenyl), or $R^{31B}$-substituted or unsubstituted heteroaryl (e.g., 5 to 10 membered heteroaryl, 5 to 9 membered heteroaryl, or 5 to 6 membered heteroaryl). In embodiments, $R^{6B}$ and $R^{6C}$ substituents bonded to the same nitrogen atom may optionally be joined to form a $R^{31B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{31B}$-substituted or unsubstituted heteroaryl (e.g., 5 to 10 membered heteroaryl, 5 to 9 membered heteroaryl, or 5 to 6 membered heteroaryl).

In embodiments, $R^{7B}$ is hydrogen, halogen, $-CF_3$, $-CCl_3$, $-CBr_3$, $-CI_3$, $-COOH$, $-CONH_2$, $R^{58B}$-substituted or unsubstituted alkyl (e.g., $C_1$-$C_8$ alkyl, $C_1$-$C_6$ alkyl, or $C_1$-$C_4$ alkyl), $R^{58B}$-substituted or unsubstituted heteroalkyl (e.g., 2 to 8 membered heteroalkyl, 2 to 6 membered heteroalkyl, or 2 to 4 membered heteroalkyl), $R^{58B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{58B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{58B}$-substituted or unsubstituted aryl (e.g., $C_6$-$C_{10}$ aryl, $C_{10}$ aryl, or phenyl), or $R^{58B}$-substituted or unsubstituted heteroaryl (e.g., 5 to 10 membered heteroaryl, 5 to 9 membered heteroaryl, or 5 to 6 membered heteroaryl). In embodiments, $R^{7B}$ and $R^{7C}$ substituents bonded to the same nitrogen atom may optionally be joined to form a $R^{58B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{58B}$-substituted or unsubstituted heteroaryl (e.g., 5 to 10 membered heteroaryl, 5 to 9 membered heteroaryl, or 5 to 6 membered heteroaryl).

In embodiments, $R^{8B}$ is hydrogen, halogen, $-CF_3$, $-CCl_3$, $-CBr_3$, $-CI_3$, $-COOH$, $-CONH_2$, $R^{34B}$-substituted or unsubstituted alkyl (e.g., $C_1$-$C_8$ alkyl, $C_1$-$C_6$ alkyl, or $C_1$-$C_4$ alkyl), $R^{34B}$-substituted or unsubstituted heteroalkyl (e.g., 2 to 8 membered heteroalkyl, 2 to 6 membered heteroalkyl, or 2 to 4 membered heteroalkyl), $R^{34B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{34B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34B}$-substituted or unsubstituted aryl (e.g., $C_6$-$C_{10}$ aryl, $C_{10}$ aryl, or phenyl), or $R^{34B}$-substituted or unsubstituted heteroaryl (e.g., 5 to 10 membered heteroaryl, 5 to 9 membered heteroaryl, or 5 to 6 membered heteroaryl). In embodiments, $R^{8B}$ and $R^{8C}$ substituents bonded to the same nitrogen atom may optionally be joined to form a $R^{34B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{34B}$-substituted or unsubstituted heteroaryl (e.g., 5 to 10 membered heteroaryl, 5 to 9 membered heteroaryl, or 5 to 6 membered heteroaryl).

In embodiments, $R^{9B}$ is hydrogen, halogen, $-CF_3$, $-CCl_3$, $-CBr_3$, $-CI_3$, $-COOH$, $-CONH_2$, $R^{37B}$-substituted or unsubstituted alkyl (e.g., $C_1$-$C_8$ alkyl, $C_1$-$C_6$ alkyl, or $C_1$-$C_4$ alkyl), $R^{37B}$-substituted or unsubstituted heteroalkyl (e.g., 2 to 8 membered heteroalkyl, 2 to 6 membered heteroalkyl, or 2 to 4 membered heteroalkyl), $R^{37B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37B}$-substituted or unsubstituted aryl (e.g., $C_6$-$C_{10}$ aryl, $C_{10}$ aryl, or phenyl), or $R^{37B}$-substituted or unsubstituted heteroaryl (e.g., 5 to 10 membered heteroaryl, 5 to 9 membered heteroaryl, or 5 to 6 membered heteroaryl). In embodiments, $R^{9B}$ and $R^{9C}$ substituents bonded to the same nitrogen atom may optionally be joined to form a $R^{37B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{37B}$-substituted or unsubstituted heteroaryl (e.g., 5 to 10 membered heteroaryl, 5 to 9 membered heteroaryl, or 5 to 6 membered heteroaryl).

In embodiments, $R^{10B}$ is hydrogen, halogen, $-CF_3$, $-CCl_3$, $-CBr_3$, $-CI_3$, $-COOH$, $-CONH_2$, $R^{40B}$-substituted or unsubstituted alkyl (e.g., $C_1$-$C_8$ alkyl, $C_1$-$C_6$ alkyl, or $C_1$-$C_4$ alkyl), $R^{40B}$-substituted or unsubstituted heteroalkyl (e.g., 2 to 8 membered heteroalkyl, 2 to 6 membered heteroalkyl, or 2 to 4 membered heteroalkyl), $R^{40B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40B}$-substituted or unsubstituted aryl (e.g., $C_6$-$C_{10}$ aryl, $C_{10}$ aryl, or phenyl), or $R^{40B}$-substituted or unsubstituted heteroaryl (e.g., 5 to 10 membered heteroaryl, 5 to 9 membered heteroaryl, or 5 to 6 membered heteroaryl). In embodiments, $R^{10B}$ and $R^{10C}$ substituents bonded to the same nitrogen atom may optionally be joined to form a $R^{40B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{40B}$-substituted or unsubstituted heteroaryl (e.g., 5 to 10 membered heteroaryl, 5 to 9 membered heteroaryl, or 5 to 6 membered heteroaryl).

In embodiments, $R^{11B}$ is hydrogen, halogen, $-CF_3$, $-CCl_3$, $-CBr_3$, $-CI_3$, $-COOH$, $-CONH_2$, $R^{43B}$-substituted or unsubstituted alkyl (e.g., $C_1$-$C_8$ alkyl, $C_1$-$C_6$ alkyl, or $C_1$-$C_4$ alkyl), $R^{43B}$-substituted or unsubstituted heteroalkyl (e.g., 2 to 8 membered heteroalkyl, 2 to 6 membered heteroalkyl, or 2 to 4 membered heteroalkyl), $R^{43B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{43B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43B}$-substituted or unsubstituted aryl (e.g., $C_6$-$C_{10}$ aryl, $C_{10}$ aryl, or phenyl), or $R^{43B}$-substituted or unsubstituted heteroaryl (e.g., 5 to 10 membered heteroaryl, 5 to 9 membered heteroaryl, or 5 to 6 membered heteroaryl). In embodiments, $R^{11B}$ and $R^{11C}$ substituents bonded to the same nitrogen atom may optionally be joined to form a $R^{43B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{43B}$-substituted or unsubstituted heteroaryl (e.g., 5 to 10 membered heteroaryl, 5 to 9 membered heteroaryl, or 5 to 6 membered heteroaryl).

In embodiments, $R^{1C}$ is hydrogen, halogen, $-CF_3$, $-CCl_3$, $-CBr_3$, $-CI_3$, $-COOH$, $-CONH_2$, $R^{16C}$-substituted or unsubstituted alkyl (e.g., $C_1$-$C_8$ alkyl, $C_1$-$C_6$ alkyl, or $C_1$-$C_4$ alkyl), $R^{16C}$-substituted or unsubstituted heteroalkyl (e.g., 2 to 8 membered heteroalkyl, 2 to 6 membered heteroalkyl, or 2 to 4 membered heteroalkyl), $R^{16C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{16C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{16C}$-substituted or unsubstituted aryl (e.g., $C_6$-$C_{10}$ aryl, $C_{10}$ aryl, or phenyl), or $R^{16C}$-substituted or unsubstituted heteroaryl (e.g., 5 to 10 membered heteroaryl, 5 to 9 membered heteroaryl, or 5 to 6 membered heteroaryl). In embodiments, $R^{1B}$ and $R^{1C}$ substituents bonded to the same nitrogen atom may optionally be joined to form a $R^{16C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{16C}$-substituted or unsubstituted heteroaryl (e.g., 5 to 10 membered heteroaryl, 5 to 9 membered heteroaryl, or 5 to 6 membered heteroaryl).

In embodiments, $R^{2C}$ is hydrogen, halogen, $-CF_3$, $-CCl_3$, $-CBr_3$, $-CI_3$, $-COOH$, $-CONH_2$, $R^{19C}$-substituted or unsubstituted alkyl (e.g., $C_1$-$C_8$ alkyl, $C_1$-$C_6$ alkyl, or $C_1$-$C_4$ alkyl), $R^{19C}$-substituted or unsubstituted heteroalkyl (e.g., 2 to 8 membered heteroalkyl, 2 to 6 membered heteroalkyl, or 2 to 4 membered heteroalkyl), $R^{19C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{19C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{19C}$-substituted or unsubstituted aryl (e.g., $C_6$-$C_{10}$ aryl, $C_{10}$ aryl, or phenyl), or $R^{19C}$-substituted or unsubstituted heteroaryl (e.g., 5 to 10 membered heteroaryl, 5 to 9 membered heteroaryl, or 5 to 6 membered heteroaryl). In embodiments, $R^{2B}$ and $R^{2C}$ substituents bonded to the same nitrogen atom may optionally be joined to form a $R^{19C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{19C}$-substituted or unsubstituted heteroaryl (e.g., 5 to 10 membered heteroaryl, 5 to 9 membered heteroaryl, or 5 to 6 membered heteroaryl).

In embodiments, $R^{3C}$ is hydrogen, halogen, $-CF_3$, $-CCl_3$, $-CBr_3$, $-CI_3$, $-COOH$, $-CONH_2$, $R^{22C}$-substituted or unsubstituted alkyl (e.g., $C_1$-$C_8$ alkyl, $C_1$-$C_6$ alkyl, or $C_1$-$C_4$ alkyl), $R^{22C}$-substituted or unsubstituted heteroalkyl (e.g., 2 to 8 membered heteroalkyl, 2 to 6 membered heteroalkyl, or 2 to 4 membered heteroalkyl), $R^{22C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22C}$-substituted or unsubstituted aryl (e.g., $C_6$-$C_{10}$ aryl, $C_{10}$ aryl, or phenyl), or $R^{22C}$-substituted or unsubstituted heteroaryl (e.g., 5 to 10 membered heteroaryl, 5 to 9 membered heteroaryl, or 5 to 6 membered heteroaryl). In embodiments, $R^{3B}$ and $R^{3C}$ substituents bonded to the same nitrogen atom may optionally be joined to form a $R^{22C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{22C}$-substituted or unsubstituted heteroaryl (e.g., 5 to 10 membered heteroaryl, 5 to 9 membered heteroaryl, or 5 to 6 membered heteroaryl).

In embodiments, $R^{4C}$ is hydrogen, halogen, $-CF_3$, $-CCl_3$, $-CBr_3$, $-CI_3$, $-COOH$, $-CONH_2$, $R^{25C}$-substituted or unsubstituted alkyl (e.g., $C_1$-$C_8$ alkyl, $C_1$-$C_6$ alkyl, or $C_1$-$C_4$ alkyl), $R^{25C}$-substituted or unsubstituted heteroalkyl (e.g., 2 to 8 membered heteroalkyl, 2 to 6 membered heteroalkyl, or 2 to 4 membered heteroalkyl), $R^{25C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25C}$-substituted or unsubstituted aryl (e.g., $C_6$-$C_{10}$ aryl, $C_{10}$ aryl, or phenyl), or $R^{25C}$-substituted or unsubstituted heteroaryl (e.g., 5 to 10 membered heteroaryl, 5 to 9 membered heteroaryl, or 5 to 6 membered heteroaryl). In embodiments, $R^{4B}$ and $R^{4C}$ substituents bonded to the same nitrogen atom may optionally be joined to form a $R^{25C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{25C}$-substituted or unsubstituted heteroaryl (e.g., 5 to 10 membered heteroaryl, 5 to 9 membered heteroaryl, or 5 to 6 membered heteroaryl).

In embodiments, $R^{5C}$ is hydrogen, halogen, $-CF_3$, $-CCl_3$, $-CBr_3$, $-CI_3$, $-COOH$, $-CONH_2$, $R^{28C}$-substituted or unsubstituted alkyl (e.g., $C_1$-$C_8$ alkyl, $C_1$-$C_6$ alkyl, or $C_1$-$C_4$ alkyl), $R^{28C}$-substituted or unsubstituted heteroalkyl (e.g., 2 to 8 membered heteroalkyl, 2 to 6 membered heteroalkyl, or 2 to 4 membered heteroalkyl), $R^{28C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28C}$-substituted or unsubstituted aryl (e.g., $C_6$-$C_{10}$ aryl, $C_{10}$ aryl, or phenyl), or $R^{28C}$-substituted or unsubstituted heteroaryl (e.g., 5 to 10 membered heteroaryl, 5 to 9 membered heteroaryl, or 5 to 6 membered heteroaryl). In embodiments, $R^{5B}$ and $R^{5C}$ substituents bonded to the same nitrogen atom may optionally be joined to form a $R^{28C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{28C}$-substituted or unsubstituted heteroaryl (e.g., 5 to 10 membered heteroaryl, 5 to 9 membered heteroaryl, or 5 to 6 membered heteroaryl).

In embodiments, $R^{6C}$ is hydrogen, halogen, $-CF_3$, $-CCl_3$, $-CBr_3$, $-CI_3$, $-COOH$, $-CONH_2$, $R^{31C}$-substituted or unsubstituted alkyl (e.g., $C_1$-$C_8$ alkyl, $C_1$-$C_6$ alkyl, or $C_1$-$C_4$ alkyl), $R^{31C}$-substituted or unsubstituted heteroalkyl (e.g., 2 to 8 membered heteroalkyl, 2 to 6 membered heteroalkyl, or 2 to 4 membered heteroalkyl), $R^{31C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31C}$-substituted or unsubstituted aryl (e.g., $C_6$-$C_{10}$ aryl, $C_{10}$ aryl, or phenyl), or $R^{31C}$-substituted or unsubstituted heteroaryl (e.g., 5 to 10 membered heteroaryl, 5 to 9 membered heteroaryl, or 5 to 6 membered heteroaryl). In embodiments, $R^{6B}$ and $R^{6C}$ substituents bonded to the same nitrogen atom may optionally be joined to form a $R^{31C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{31C}$-substituted or unsubstituted heteroaryl (e.g., 5 to 10 membered heteroaryl, 5 to 9 membered heteroaryl, or 5 to 6 membered heteroaryl).

In embodiments, $R^{8C}$ is hydrogen, halogen, $-CF_3$, $-CCl_3$, $-CBr_3$, $-CI_3$, $-COOH$, $-CONH_2$, $R^{34C}$-substituted or unsubstituted alkyl (e.g., $C_1$-$C_8$ alkyl, $C_1$-$C_6$ alkyl, or $C_1$-$C_4$ alkyl), $R^{34C}$-substituted or unsubstituted heteroalkyl (e.g., 2 to 8 membered heteroalkyl, 2 to 6 membered heteroalkyl, or 2 to 4 membered heteroalkyl), $R^{34C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{34C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34C}$-substituted or unsubstituted aryl (e.g., $C_6$-$C_{10}$ aryl, $C_{10}$ aryl, or phenyl), or $R^{34C}$-substituted or unsubstituted heteroaryl (e.g., 5 to 10 membered heteroaryl, 5 to 9 membered heteroaryl, or 5 to 6 membered heteroaryl). In embodiments, $R^{8B}$ and $R^{8C}$ substituents bonded to the same nitrogen atom may optionally be joined to form a $R^{34C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{34C}$-substituted or unsubstituted heteroaryl (e.g., 5 to 10 membered heteroaryl, 5 to 9 membered heteroaryl, or 5 to 6 membered heteroaryl).

In embodiments, $R^{9C}$ is hydrogen, halogen, $-CF_3$, $-CCl_3$, $-CBr_3$, $-CI_3$, $-COOH$, $-CONH_2$, $R^{37C}$-substituted or unsubstituted alkyl (e.g., $C_1$-$C_8$ alkyl, $C_1$-$C_6$ alkyl, or $C_1$-$C_4$ alkyl), $R^{37C}$-substituted or unsubstituted heteroalkyl (e.g., 2 to 8 membered heteroalkyl, 2 to 6 membered heteroalkyl, or 2 to 4 membered heteroalkyl), $R^{37C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37C}$-substituted or unsubstituted aryl (e.g., $C_6$-$C_{10}$ aryl, $C_{10}$ aryl, or phenyl), or $R^{37C}$-substituted or unsubstituted heteroaryl (e.g., 5 to 10 membered heteroaryl, 5 to 9 membered heteroaryl, or 5 to 6 membered heteroaryl). In embodiments, $R^{9B}$ and $R^{9C}$ substituents bonded to the same nitrogen atom may optionally be joined to form a $R^{37C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{37C}$-substituted or unsubstituted heteroaryl (e.g., 5 to 10 membered heteroaryl, 5 to 9 membered heteroaryl, or 5 to 6 membered heteroaryl).

In embodiments, $R^{10C}$ is hydrogen, halogen, $-CF_3$, $-CCl_3$, $-CBr_3$, $-CI_3$, $-COOH$, $-CONH_2$, $R^{40C}$-substituted or unsubstituted alkyl (e.g., $C_1$-$C_8$ alkyl, $C_1$-$C_6$ alkyl, or $C_1$-$C_4$ alkyl), $R^{40C}$-substituted or unsubstituted heteroalkyl (e.g., 2 to 8 membered heteroalkyl, 2 to 6 membered heteroalkyl, or 2 to 4 membered heteroalkyl), $R^{40C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40C}$-substituted or unsubstituted aryl (e.g., $C_6$-$C_{10}$ aryl, $C_{10}$ aryl, or phenyl), or $R^{40C}$-substituted or unsubstituted heteroaryl (e.g., 5 to 10 membered heteroaryl, 5 to 9 membered heteroaryl, or 5 to 6 membered heteroaryl). In embodiments, $R^{10B}$ and $R^{10C}$ substituents bonded to the same nitrogen atom may optionally be joined to form a $R^{40B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{40B}$-substituted or unsubstituted heteroaryl (e.g., 5 to 10 membered heteroaryl, 5 to 9 membered heteroaryl, or 5 to 6 membered heteroaryl).

In embodiments, $R^{11C}$ is hydrogen, halogen, $-CF_3$, $-CCl_3$, $-CBr_3$, $-CI_3$, $-COOH$, $-CONH_2$, $R^{43C}$-substituted or unsubstituted alkyl (e.g., $C_1$-$C_8$ alkyl, $C_1$-$C_6$ alkyl, or $C_1$-$C_4$ alkyl), $R^{43C}$-substituted or unsubstituted heteroalkyl (e.g., 2 to 8 membered heteroalkyl, 2 to 6 membered heteroalkyl, or 2 to 4 membered heteroalkyl), $R^{43C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{43C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43C}$-substituted or unsubstituted aryl (e.g., $C_6$-$C_{10}$ aryl, $C_{10}$ aryl, or phenyl), or $R^{43C}$-substituted or unsubstituted heteroaryl (e.g., 5 to 10 membered heteroaryl, 5 to 9 membered heteroaryl, or 5 to 6 membered heteroaryl). In embodiments, $R^{11B}$ and $R^{11C}$ substituents bonded to the same nitrogen atom may optionally be joined to form a $R^{43C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{43C}$-substituted or unsub- In embodiments, $R^{1D}$ is hydrogen, halogen, —$CF_3$, —$CCl_3$, —$CBr_3$, —$CI_3$, —COOH, —$CONH_2$, $R^{16D}$-substituted or unsubstituted alkyl (e.g., $C_1$-$C_8$ alkyl, $C_1$-$C_6$ alkyl, or $C_1$-$C_4$ alkyl), $R^{16D}$-substituted or unsubstituted heteroalkyl (e.g., 2 to 8 membered heteroalkyl, 2 to 6 membered heteroalkyl, or 2 to 4 membered heteroalkyl), $R^{16D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{16D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{16D}$-substituted or unsubstituted aryl (e.g., $C_6$-$C_{10}$ aryl, $C_{10}$ aryl, or phenyl), or $R^{16D}$-substituted or unsubstituted heteroaryl (e.g., 5 to 10 membered heteroaryl, 5 to 9 membered heteroaryl, or 5 to 6 membered heteroaryl).

In embodiments, $R^{2D}$ is hydrogen, halogen, —$CF_3$, —$CCl_3$, —$CBr_3$, —$CI_3$, —COOH, —$CONH_2$, $R^{19D}$-substituted or unsubstituted alkyl (e.g., $C_1$-$C_8$ alkyl, $C_1$-$C_6$ alkyl, or $C_1$-$C_4$ alkyl), $R^{19D}$-substituted or unsubstituted heteroalkyl (e.g., 2 to 8 membered heteroalkyl, 2 to 6 membered heteroalkyl, or 2 to 4 membered heteroalkyl), $R^{19D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{19D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{19D}$-substituted or unsubstituted aryl (e.g., $C_6$-$C_{10}$ aryl, $C_{10}$ aryl, or phenyl), or $R^{19D}$-substituted or unsubstituted heteroaryl (e.g., 5 to 10 membered heteroaryl, 5 to 9 membered heteroaryl, or 5 to 6 membered heteroaryl).

In embodiments, $R^{3D}$ is hydrogen, halogen, —$CF_3$, —$CCl_3$, —$CBr_3$, —$CI_3$, —COOH, —$CONH_2$, $R^{22D}$-substituted or unsubstituted alkyl (e.g., $C_1$-$C_8$ alkyl, $C_1$-$C_6$ alkyl, or $C_1$-$C_4$ alkyl), $R^{22D}$-substituted or unsubstituted heteroalkyl (e.g., 2 to 8 membered heteroalkyl, 2 to 6 membered heteroalkyl, or 2 to 4 membered heteroalkyl), $R^{22D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22D}$-substituted or unsubstituted aryl (e.g., $C_6$-$C_{10}$ aryl, $C_{10}$ aryl, or phenyl), or $R^{22D}$-substituted or unsubstituted heteroaryl (e.g., 5 to 10 membered heteroaryl, 5 to 9 membered heteroaryl, or 5 to 6 membered heteroaryl).

In embodiments, $R^{4D}$ is hydrogen, halogen, —$CF_3$, —$CCl_3$, —$CBr_3$, —$CI_3$, —COOH, —$CONH_2$, $R^{25D}$-substituted or unsubstituted alkyl (e.g., $C_1$-$C_8$ alkyl, $C_1$-$C_6$ alkyl, or $C_1$-$C_4$ alkyl), $R^{25D}$-substituted or unsubstituted heteroalkyl (e.g., 2 to 8 membered heteroalkyl, 2 to 6 membered heteroalkyl, or 2 to 4 membered heteroalkyl), $R^{25D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25D}$-substituted or unsubstituted aryl (e.g., $C_6$-$C_{10}$ aryl, $C_{10}$ aryl, or phenyl), or $R^{25D}$-substituted or unsubstituted heteroaryl (e.g., 5 to 10 membered heteroaryl, 5 to 9 membered heteroaryl, or 5 to 6 membered heteroaryl).

In embodiments, $R^{5D}$ is hydrogen, halogen, —$CF_3$, —$CCl_3$, —$CBr_3$, —$CI_3$, —COOH, —$CONH_2$, $R^{28D}$-substituted or unsubstituted alkyl (e.g., $C_1$-$C_8$ alkyl, $C_1$-$C_6$ alkyl, or $C_1$-$C_4$ alkyl), $R^{28D}$-substituted or unsubstituted heteroalkyl (e.g., 2 to 8 membered heteroalkyl, or 2 to 4 membered heteroalkyl), $R^{28D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28D}$-substituted or unsubstituted aryl (e.g., $C_6$-$C_{10}$ aryl, $C_{10}$ aryl, or phenyl), or $R^{28D}$-substituted or unsubstituted heteroaryl (e.g., 5 to 10 membered heteroaryl, 5 to 9 membered heteroaryl, or 5 to 6 membered heteroaryl).

In embodiments, $R^{6D}$ is hydrogen, halogen, —$CF_3$, —$CCl_3$, —$CBr_3$, —$CI_3$, —COOH, —$CONH_2$, $R^{31D}$-substituted or unsubstituted alkyl (e.g., $C_1$-$C_8$ alkyl, $C_1$-$C_6$ alkyl, or $C_1$-$C_4$ alkyl), $R^{31D}$-substituted or unsubstituted heteroalkyl (e.g., 2 to 8 membered heteroalkyl, 2 to 6 membered heteroalkyl, or 2 to 4 membered heteroalkyl), $R^{31D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31D}$-substituted or unsubstituted aryl (e.g., $C_6$-$C_{10}$ aryl, $C_{10}$ aryl, or phenyl), or $R^{31D}$-substituted or unsubstituted heteroaryl (e.g., 5 to 10 membered heteroaryl, 5 to 9 membered heteroaryl, or 5 to 6 membered heteroaryl).

In embodiments, $R^{8D}$ is hydrogen, halogen, —$CF_3$, —$CCl_3$, —$CBr_3$, —$CI_3$, —COOH, —$CONH_2$, $R^{34D}$-substituted or unsubstituted alkyl (e.g., $C_1$-$C_8$ alkyl, $C_1$-$C_6$ alkyl, or $C_1$-$C_4$ alkyl), $R^{34D}$-substituted or unsubstituted heteroalkyl (e.g., 2 to 8 membered heteroalkyl, 2 to 6 membered heteroalkyl, or 2 to 4 membered heteroalkyl), $R^{34D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{34D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34D}$-substituted or unsubstituted aryl (e.g., $C_6$-$C_{10}$ aryl, $C_{10}$ aryl, or phenyl), or $R^{34D}$-substituted or unsubstituted heteroaryl (e.g., 5 to 10 membered heteroaryl, 5 to 9 membered heteroaryl, or 5 to 6 membered heteroaryl).

In embodiments, $R^{9D}$ is hydrogen, halogen, —$CF_3$, —$CCl_3$, —$CBr_3$, —$CI_3$, —COOH, —$CONH_2$, $R^{37D}$-substituted or unsubstituted alkyl (e.g., $C_1$-$C_8$ alkyl, $C_1$-$C_6$ alkyl, or $C_1$-$C_4$ alkyl), $R^{37D}$-substituted or unsubstituted heteroalkyl (e.g., 2 to 8 membered heteroalkyl, 2 to 6 membered heteroalkyl, or 2 to 4 membered heteroalkyl), $R^{37D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37D}$-substituted or unsubstituted aryl (e.g., $C_6$-$C_{10}$ aryl, $C_{10}$ aryl, or phenyl), or $R^{37D}$-substituted or unsubstituted heteroaryl (e.g., 5 to 10 membered heteroaryl, 5 to 9 membered heteroaryl, or 5 to 6 membered heteroaryl).

In embodiments, $R^{10D}$ is hydrogen, halogen, —$CF_3$, —$CCl_3$, —$CBr_3$, —$CI_3$, —COOH, —$CONH_2$, $R^{40D}$-substituted or unsubstituted alkyl (e.g., $C_1$-$C_8$ alkyl, $C_1$-$C_6$ alkyl, or $C_1$-$C_4$ alkyl), $R^{40D}$-substituted or unsubstituted heteroalkyl (e.g., 2 to 8 membered heteroalkyl, 2 to 6 membered heteroalkyl, or 2 to 4 membered heteroalkyl), $R^{40D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40D}$-substituted or unsubstituted aryl (e.g., $C_6$-$C_{10}$ aryl, $C_{10}$ aryl, or phenyl), or $R^{40D}$-substituted or unsubstituted heteroaryl (e.g., 5 to 10 membered heteroaryl, 5 to 9 membered heteroaryl, or 5 to 6 membered heteroaryl).

In embodiments, $R^{11D}$ is hydrogen, halogen, —CF$_3$, —CCl$_3$, —CBr$_3$, —CI$_3$, —COOH, —CONH$_2$, $R^{43D}$-substituted or unsubstituted alkyl (e.g., C$_1$-C$_8$ alkyl, C$_1$-C$_6$ alkyl, or C$_1$-C$_4$ alkyl), $R^{43D}$-substituted or unsubstituted heteroalkyl (e.g., 2 to 8 membered heteroalkyl, 2 to 6 membered heteroalkyl, or 2 to 4 membered heteroalkyl), $R^{43D}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{43D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43D}$-substituted or unsubstituted aryl (e.g., C$_6$-C$_{10}$ aryl, C$_{10}$ aryl, or phenyl), or $R^{43D}$-substituted or unsubstituted heteroaryl (e.g., 5 to 10 membered heteroaryl, 5 to 9 membered heteroaryl, or 5 to 6 membered heteroaryl).

$R^{16}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{17}$-substituted or unsubstituted alkyl (e.g., C$_1$-C$_8$ alkyl, C$_1$-C$_6$ alkyl, or C$_1$-C$_4$ alkyl), $R^{17}$-substituted or unsubstituted heteroalkyl (e.g., 2 to 8 membered heteroalkyl, 2 to 6 membered heteroalkyl, or 2 to 4 membered heteroalkyl), $R^{17}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{17}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17}$-substituted or unsubstituted aryl (e.g., C$_6$-C$_{10}$ aryl, C$_{10}$ aryl, or phenyl), or $R^{17}$-substituted or unsubstituted heteroaryl (e.g., 5 to 10 membered heteroaryl, 5 to 9 membered heteroaryl, or 5 to 6 membered heteroaryl).

In embodiments, $R^{16}$ is $R^{17}$-substituted or unsubstituted alkyl (e.g., C$_1$-C$_8$ alkyl, C$_1$-C$_6$ alkyl, or C$_1$-C$_4$ alkyl). In embodiments, $R^{16}$ is $R^{17}$-substituted alkyl (e.g., C$_1$-C$_8$ alkyl, C$_1$-C$_6$ alkyl, or C$_1$-C$_4$ alkyl). In embodiments, $R^{16}$ is an unsubstituted alkyl (e.g., C$_1$-C$_8$ alkyl, C$_1$-C$_6$ alkyl, or C$_1$-C$_4$ alkyl).

In embodiments, $R^{16}$ is $R^{17}$-substituted or unsubstituted heteroalkyl (e.g., 2 to 8 membered heteroalkyl, 2 to 6 membered heteroalkyl, or 2 to 4 membered heteroalkyl). In embodiments, $R^{16}$ is $R^{17}$-substituted heteroalkyl (e.g., 2 to 8 membered heteroalkyl, 2 to 6 membered heteroalkyl, or 2 to 4 membered heteroalkyl). In embodiments, $R^{16}$ is an unsubstituted heteroalkyl (e.g., 2 to 8 membered heteroalkyl, 2 to 6 membered heteroalkyl, or 2 to 4 membered heteroalkyl).

In embodiments, $R^{16}$ is $R^{17}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{16}$ is $R^{17}$-substituted cycloalkyl (e.g., C$_3$-C$_8$ cycloalkyl, C$_3$-C$_6$ cycloalkyl, or C$_5$-C$_6$ cycloalkyl). In embodiments, $R^{16}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{16}$ is $R^{17}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{16}$ is $R^{17}$-substituted heterocycloalkyl (e.g., 3 to 8 membered heterocycloalkyl, 3 to 6 membered heterocycloalkyl, or 5 to 6 membered heterocycloalkyl). In embodiments, $R^{16}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{16}$ is $R^{17}$-substituted or unsubstituted aryl (e.g., C$_6$-C$_{10}$ aryl, C$_{10}$ aryl, or phenyl). In embodiments, $R^{16}$ is $R^{17}$-substituted aryl (e.g., C$_6$-C$_{10}$ aryl, C$_{10}$ aryl, or phenyl). In embodiments, $R^{16}$ is an unsubstituted aryl (e.g., C$_6$-C$_{10}$ aryl, C$_{10}$ aryl, or phenyl).

In embodiments, $R^{16}$ is $R^{17}$-substituted or unsubstituted heteroaryl (e.g., 5 to 10 membered heteroaryl, 5 to 9 membered heteroaryl, or 5 to 6 membered heteroaryl). In embodiments, $R^{16}$ is $R^{17}$-substituted heteroaryl (e.g., 5 to 10 membered heteroaryl, 5 to 9 membered heteroaryl, or 5 to 6 membered heteroaryl). In embodiments, $R^{16}$ is an unsubstituted heteroaryl (e.g., 5 to 10 membered heteroaryl, 5 to 9 membered heteroaryl, or 5 to 6 membered heteroaryl).

$R^{17}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OC HCl$_2$, —OCHBr$_2$, —OCHI$_2$, —OCHF$_2$, $R^{18}$-substituted or unsubstituted alkyl (e.g., C$_1$-C$_8$ alkyl, C$_1$-C$_6$ alkyl, or C$_1$-C$_4$ alkyl), $R^{18}$-substituted or unsubstituted heteroalkyl (e.g., 2 to 8 membered heteroalkyl, 2 to 6 membered heteroalkyl, or 2 to 4 membered heteroalkyl), $R^{18}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{18}$-substituted or unsubstituted heterocycloalkyl (e.g., 3 to 8 membered heterocycloalkyl, 3 to 6 membered heterocycloalkyl, or 5 to 6 membered heterocycloalkyl), $R^{18}$-substituted or unsubstituted aryl (e.g., C$_6$-C$_{10}$ aryl, C$_{10}$ aryl, or phenyl), or $R^{18}$-substituted or unsubstituted heteroaryl (e.g., 5 to 10 membered heteroaryl, 5 to 9 membered heteroaryl, or 5 to 6 membered heteroaryl).

In embodiments, $R^{17}$ is $R^{18}$-substituted or unsubstituted alkyl (e.g., C$_1$-C$_8$ alkyl, C$_1$-C$_6$ alkyl, or C$_1$-C$_4$ alkyl). In embodiments, $R^{17}$ is $R^{18}$-substituted alkyl (e.g., C$_1$-C$_8$ alkyl, C$_1$-C$_6$ alkyl, or C$_1$-C$_4$ alkyl). In embodiments, $R^{17}$ is an unsubstituted alkyl (e.g., C$_1$-C$_8$ alkyl, C$_1$-C$_6$ alkyl, or C$_1$-C$_4$ alkyl).

In embodiments, $R^{17}$ is $R^{18}$-substituted or unsubstituted heteroalkyl (e.g., 2 to 8 membered heteroalkyl, 2 to 6 membered heteroalkyl, or 2 to 4 membered heteroalkyl). In embodiments, $R^{17}$ is $R^{18}$-substituted heteroalkyl (e.g., 2 to 8 membered heteroalkyl, 2 to 6 membered heteroalkyl, or 2 to 4 membered heteroalkyl). In embodiments, $R^{17}$ is an unsubstituted heteroalkyl (e.g., 2 to 8 membered heteroalkyl, 2 to 6 membered heteroalkyl, or 2 to 4 membered heteroalkyl).

In embodiments, $R^{17}$ is $R^{18}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{17}$ is $R^{18}$-substituted cycloalkyl (e.g., C$_3$-C$_8$ cycloalkyl, C$_3$-C$_6$ cycloalkyl, or C$_5$-C$_6$ cycloalkyl). In embodiments, $R^{17}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{17}$ is $R^{18}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{17}$ is $R^{18}$-substituted heterocycloalkyl (e.g., 3 to 8 membered heterocycloalkyl, 3 to 6 membered heterocycloalkyl, or 5 to 6 membered heterocycloalkyl). In embodiments, $R^{17}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{17}$ is $R^{18}$-substituted or unsubstituted aryl (e.g., $C_6$-$C_{10}$ aryl, $C_{10}$ aryl, or phenyl). In embodiments, $R^{17}$ is $R^{18}$-substituted aryl (e.g., $C_6$-$C_{10}$ aryl, $C_{10}$ aryl, or phenyl). In embodiments, $R^{17}$ is an unsubstituted aryl (e.g., $C_6$-$C_{10}$ aryl, $C_{10}$ aryl, or phenyl).

In embodiments, $R^{17}$ is $R^{18}$-substituted or unsubstituted heteroaryl (e.g., 5 to 10 membered heteroaryl, 5 to 9 membered heteroaryl, or 5 to 6 membered heteroaryl). In embodiments, $R^{17}$ is $R^{18}$-substituted heteroaryl (e.g., 5 to 10 membered heteroaryl, 5 to 9 membered heteroaryl, or 5 to 6 membered heteroaryl). In embodiments, $R^{17}$ is an unsubstituted heteroaryl (e.g., 5 to 10 membered heteroaryl, 5 to 9 membered heteroaryl, or 5 to 6 membered heteroaryl).

$R^{19}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{20}$-substituted or unsubstituted alkyl (e.g., $C_1$-$C_8$ alkyl, $C_1$-$C_6$ alkyl, or $C_1$-$C_4$ alkyl), $R^{20}$-substituted or unsubstituted heteroalkyl (e.g., 2 to 8 membered heteroalkyl, 2 to 6 membered heteroalkyl, or 2 to 4 membered heteroalkyl), $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20}$-substituted or unsubstituted aryl (e.g., $C_6$-$C_{10}$ aryl, $C_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl).

In embodiments, $R^{19}$ is $R^{20}$-substituted or unsubstituted alkyl (e.g., $C_1$-$C_8$ alkyl, $C_1$-$C_6$ alkyl, or $C_1$-$C_4$ alkyl). In embodiments, $R^{19}$ is $R^{20}$-substituted alkyl (e.g., $C_1$-$C_8$ alkyl, $C_1$-$C_6$ alkyl, or $C_1$-$C_4$ alkyl). In embodiments, $R^{19}$ is an unsubstituted alkyl (e.g., $C_1$-$C_8$ alkyl, $C_1$-$C_6$ alkyl, or $C_1$-$C_4$ alkyl).

In embodiments, $R^{19}$ is $R^{20}$-substituted or unsubstituted heteroalkyl (e.g., 2 to 8 membered heteroalkyl, 2 to 6 membered heteroalkyl, or 2 to 4 membered heteroalkyl). In embodiments, $R^{19}$ is $R^{20}$-substituted heteroalkyl (e.g., 2 to 8 membered heteroalkyl, 2 to 6 membered heteroalkyl, or 2 to 4 membered heteroalkyl). In embodiments, $R^{19}$ is an unsubstituted heteroalkyl (e.g., 2 to 8 membered heteroalkyl, 2 to 6 membered heteroalkyl, or 2 to 4 membered heteroalkyl).

In embodiments, $R^{19}$ is $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{19}$ is $R^{20}$-substituted cycloalkyl (e.g., $C_3$-$C_8$ cycloalkyl, $C_3$-$C_6$ cycloalkyl, or $C_5$-$C_6$ cycloalkyl). In embodiments, $R^{19}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{19}$ is $R^{20}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{19}$ is $R^{20}$-substituted heterocycloalkyl (e.g., 3 to 8 membered heterocycloalkyl, 3 to 6 membered heterocycloalkyl, or 5 to 6 membered heterocycloalkyl). In embodiments, $R^{19}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{19}$ is $R^{20}$-substituted or unsubstituted aryl (e.g., $C_6$-$C_{10}$ aryl, $C_{10}$ aryl, or phenyl). In embodiments, $R^{19}$ is $R^{20}$-substituted aryl (e.g., $C_6$-$C_{10}$ aryl, $C_{10}$ aryl, or phenyl). In embodiments, $R^{19}$ is an unsubstituted aryl (e.g., $C_6$-$C_{10}$ aryl, $C_{10}$ aryl, or phenyl).

In embodiments, $R^{19}$ is $R^{20}$-substituted or unsubstituted heteroaryl (e.g., 5 to 10 membered heteroaryl, 5 to 9 membered heteroaryl, or 5 to 6 membered heteroaryl). In embodiments, $R^{19}$ is $R^{20}$-substituted heteroaryl (e.g., 5 to 10 membered heteroaryl, 5 to 9 membered heteroaryl, or 5 to 6 membered heteroaryl). In embodiments, $R^{19}$ is an unsubstituted heteroaryl (e.g., 5 to 10 membered heteroaryl, 5 to 9 membered heteroaryl, or 5 to 6 membered heteroaryl).

$R^{20}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{21}$-substituted or unsubstituted alkyl (e.g., $C_1$-$C_8$ alkyl, $C_1$-$C_6$ alkyl, or $C_1$-$C_4$ alkyl), $R^{21}$-substituted or unsubstituted heteroalkyl (e.g., 2 to 8 membered heteroalkyl, 2 to 6 membered heteroalkyl, or 2 to 4 membered heteroalkyl), $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{21}$-substituted or unsubstituted heterocycloalkyl (e.g., 3 to 8 membered heterocycloalkyl, 3 to 6 membered heterocycloalkyl, or 5 to 6 membered heterocycloalkyl), $R^{21}$-substituted or unsubstituted aryl (e.g., $C_6$-$C_{10}$ aryl, $C_{10}$ aryl, or phenyl), or $R^{21}$-substituted or unsubstituted heteroaryl (e.g., 5 to 10 membered heteroaryl, 5 to 9 membered heteroaryl, or 5 to 6 membered heteroaryl).

In embodiments, $R^{20}$ is $R^{21}$-substituted or unsubstituted alkyl (e.g., $C_1$-$C_8$ alkyl, $C_1$-$C_6$ alkyl, or $C_1$-$C_4$ alkyl). In embodiments, $R^{20}$ is $R^{21}$-substituted alkyl (e.g., $C_1$-$C_8$ alkyl, $C_1$-$C_6$ alkyl, or $C_1$-$C_4$ alkyl). In embodiments, $R^{20}$ is an unsubstituted alkyl (e.g., $C_1$-$C_8$ alkyl, $C_1$-$C_6$ alkyl, or $C_1$-$C_4$ alkyl).

In embodiments, $R^{20}$ is $R^{21}$-substituted or unsubstituted heteroalkyl (e.g., 2 to 8 membered heteroalkyl, 2 to 6 membered heteroalkyl, or 2 to 4 membered heteroalkyl). In embodiments, $R^{20}$ is $R^{21}$-substituted heteroalkyl (e.g., 2 to 8 membered heteroalkyl, 2 to 6 membered heteroalkyl, or 2 to 4 membered heteroalkyl). In embodiments, $R^{20}$ is an unsubstituted heteroalkyl (e.g., 2 to 8 membered heteroalkyl, 2 to 6 membered heteroalkyl, or 2 to 4 membered heteroalkyl).

In embodiments, $R^{20}$ is $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{20}$ is $R^{21}$-substituted cycloalkyl (e.g., $C_3$-$C_8$ cycloalkyl, $C_3$-$C_6$ cycloalkyl, or $C_5$-$C_6$ cycloalkyl). In embodiments, $R^{20}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{20}$ is $R^{21}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{20}$ is $R^{21}$-substituted heterocycloalkyl (e.g., 3 to 8 membered heterocycloalkyl, 3 to 6 membered heterocycloalkyl, or 5 to 6 membered heterocycloalkyl). In embodiments, $R^{20}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{20}$ is $R^{21}$-substituted or unsubstituted aryl (e.g., $C_6$-$C_{10}$ aryl, $C_{10}$ aryl, or phenyl). In embodiments, $R^{20}$ is $R^{21}$-substituted aryl (e.g., $C_6$-$C_{10}$ aryl, $C_{10}$ aryl, or phenyl). In embodiments, $R^{20}$ is an unsubstituted aryl (e.g., $C_6$-$C_{10}$ aryl, $C_{10}$ aryl, or phenyl).

In embodiments, $R^{20}$ is $R^{21}$-substituted or unsubstituted heteroaryl (e.g., 5 to 10 membered heteroaryl, 5 to 9 membered heteroaryl, or 5 to 6 membered heteroaryl). In embodiments, $R^{20}$ is $R^{21}$-substituted heteroaryl (e.g., 5 to 10 membered heteroaryl, 5 to 9 membered heteroaryl, or 5 to 6 membered heteroaryl). In embodiments, $R^{20}$ is an unsubstituted heteroaryl (e.g., 5 to 10 membered heteroaryl, 5 to 9 membered heteroaryl, or 5 to 6 membered heteroaryl).

$R^{22}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OC HCl$_2$, —OCHBr$_2$, —OCHI$_2$, —OCHF$_2$, $R^{23}$-substituted or unsubstituted alkyl (e.g., C$_1$-C$_8$ alkyl, C$_1$-C$_6$ alkyl, or C$_1$-C$_4$ alkyl), $R^{23}$-substituted or unsubstituted heteroalkyl (e.g., 2 to 8 membered heteroalkyl, 2 to 6 membered heteroalkyl, or 2 to 4 membered heteroalkyl), $R^{23}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{23}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23}$-substituted or unsubstituted aryl (e.g., C$_6$-C$_{10}$ aryl, C$_{10}$ aryl, or phenyl), or $R^{23}$-substituted or unsubstituted heteroaryl (e.g., 5 to 10 membered heteroaryl, 5 to 9 membered heteroaryl, or 5 to 6 membered heteroaryl).

In embodiments, $R^{22}$ is $R^{23}$-substituted or unsubstituted alkyl (e.g., C$_1$-C$_8$ alkyl, C$_1$-C$_6$ alkyl, or C$_1$-C$_4$ alkyl). In embodiments, $R^{22}$ is $R^{23}$-substituted alkyl (e.g., C$_1$-C$_8$ alkyl, C$_1$-C$_6$ alkyl, or C$_1$-C$_4$ alkyl). In embodiments, $R^{22}$ is an unsubstituted alkyl (e.g., C$_1$-C$_8$ alkyl, C$_1$-C$_6$ alkyl, or C$_1$-C$_4$ alkyl).

In embodiments, $R^{22}$ is $R^{23}$-substituted or unsubstituted heteroalkyl (e.g., 2 to 8 membered heteroalkyl, 2 to 6 membered heteroalkyl, or 2 to 4 membered heteroalkyl). In embodiments, $R^{22}$ is $R^{23}$-substituted heteroalkyl (e.g., 2 to 8 membered heteroalkyl, 2 to 6 membered heteroalkyl, or 2 to 4 membered heteroalkyl). In embodiments, $R^{22}$ is an unsubstituted heteroalkyl (e.g., 2 to 8 membered heteroalkyl, 2 to 6 membered heteroalkyl, or 2 to 4 membered heteroalkyl).

In embodiments, $R^{22}$ is $R^{23}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{22}$ is $R^{23}$-substituted cycloalkyl (e.g., C$_3$-C$_8$ cycloalkyl, C$_3$-C$_6$ cycloalkyl, or C$_5$-C$_6$ cycloalkyl). In embodiments, $R^{22}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{22}$ is $R^{23}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{22}$ is $R^{23}$-substituted heterocycloalkyl (e.g., 3 to 8 membered heterocycloalkyl, 3 to 6 membered heterocycloalkyl, or 5 to 6 membered heterocycloalkyl). In embodiments, $R^{22}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{22}$ is $R^{23}$-substituted or unsubstituted aryl (e.g., C$_6$-C$_{10}$ aryl, C$_{10}$ aryl, or phenyl). In embodiments, $R^{22}$ is $R^{23}$-substituted aryl (e.g., C$_6$-C$_{10}$ aryl, C$_{10}$ aryl, or phenyl). In embodiments, $R^{22}$ is an unsubstituted aryl (e.g., C$_6$-C$_{10}$ aryl, C$_{10}$ aryl, or phenyl).

In embodiments, $R^{22}$ is $R^{23}$-substituted or unsubstituted heteroaryl (e.g., 5 to 10 membered heteroaryl, 5 to 9 membered heteroaryl, or 5 to 6 membered heteroaryl). In embodiments, $R^{22}$ is $R^{23}$-substituted heteroaryl (e.g., 5 to 10 membered heteroaryl, 5 to 9 membered heteroaryl, or 5 to 6 membered heteroaryl). In embodiments, $R^{22}$ is an unsubstituted heteroaryl (e.g., 5 to 10 membered heteroaryl, 5 to 9 membered heteroaryl, or 5 to 6 membered heteroaryl).

$R^{23}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OC HCl$_2$, —OCHBr$_2$, —OCHI$_2$, —OCHF$_2$, $R^{24}$-substituted or unsubstituted alkyl (e.g., C$_1$-C$_8$ alkyl, C$_1$-C$_6$ alkyl, or C$_1$-C$_4$ alkyl), $R^{24}$-substituted or unsubstituted heteroalkyl (e.g., 2 to 8 membered heteroalkyl, 2 to 6 membered heteroalkyl, or 2 to 4 membered heteroalkyl), $R^{24}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{24}$-substituted or unsubstituted heterocycloalkyl (e.g., 3 to 8 membered heterocycloalkyl, 3 to 6 membered heterocycloalkyl, or 5 to 6 membered heterocycloalkyl), $R^{24}$-substituted or unsubstituted aryl (e.g., C$_6$-C$_{10}$ aryl, C$_{10}$ aryl, or phenyl), or $R^{24}$-substituted or unsubstituted heteroaryl (e.g., 5 to 10 membered heteroaryl, 5 to 9 membered heteroaryl, or 5 to 6 membered heteroaryl).

In embodiments, $R^{23}$ is $R^{24}$-substituted or unsubstituted alkyl (e.g., C$_1$-C$_8$ alkyl, C$_1$-C$_6$ alkyl, or C$_1$-C$_4$ alkyl). In embodiments, $R^{23}$ is $R^{24}$-substituted alkyl (e.g., C$_1$-C$_8$ alkyl, C$_1$-C$_6$ alkyl, or C$_1$-C$_4$ alkyl). In embodiments, $R^{23}$ is an unsubstituted alkyl (e.g., C$_1$-C$_8$ alkyl, C$_1$-C$_6$ alkyl, or C$_1$-C$_4$ alkyl).

In embodiments, $R^{23}$ is $R^{24}$-substituted or unsubstituted heteroalkyl (e.g., 2 to 8 membered heteroalkyl, 2 to 6 membered heteroalkyl, or 2 to 4 membered heteroalkyl). In embodiments, $R^{23}$ is $R^{24}$-substituted heteroalkyl (e.g., 2 to 8 membered heteroalkyl, 2 to 6 membered heteroalkyl, or 2 to 4 membered heteroalkyl). In embodiments, $R^{23}$ is an unsubstituted heteroalkyl (e.g., 2 to 8 membered heteroalkyl, 2 to 6 membered heteroalkyl, or 2 to 4 membered heteroalkyl).

In embodiments, $R^{23}$ is $R^{24}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{23}$ is $R^{24}$-substituted cycloalkyl (e.g., C$_3$-C$_8$ cycloalkyl, C$_3$-C$_6$ cycloalkyl, or C$_5$-C$_6$ cycloalkyl). In embodiments, $R^{23}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{23}$ is $R^{24}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{23}$ is $R^{24}$-substituted heterocycloalkyl (e.g., 3 to 8 membered heterocycloalkyl, 3 to 6 membered heterocycloalkyl, or 5 to 6 membered heterocycloalkyl). In embodiments, $R^{23}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{23}$ is $R^{24}$-substituted or unsubstituted aryl (e.g., C$_6$-C$_{10}$ aryl, C$_{10}$ aryl, or phenyl). In embodiments, $R^{23}$ is $R^{24}$-substituted aryl (e.g., C$_6$-C$_{10}$ aryl, C$_{10}$ aryl, or phenyl). In embodiments, $R^{23}$ is an unsubstituted aryl (e.g., C$_6$-C$_{10}$ aryl, C$_{10}$ aryl, or phenyl).

In embodiments, $R^{23}$ is $R^{24}$-substituted or unsubstituted heteroaryl (e.g., 5 to 10 membered heteroaryl, 5 to 9 membered heteroaryl, or 5 to 6 membered heteroaryl). In embodiments, $R^{23}$ is $R^{24}$-substituted heteroaryl (e.g., 5 to 10 membered heteroaryl, 5 to 9 membered heteroaryl, or 5 to 6 membered heteroaryl). In embodiments, $R^{23}$ is an unsubstituted heteroaryl (e.g., 5 to 10 membered heteroaryl, 5 to 9 membered heteroaryl, or 5 to 6 membered heteroaryl).

$R^{25}$ is independently oxo, halogen, —CCl$_3$, —CBr$_3$, —CF$_3$, —CI$_3$, —CN, —OH, —NH$_2$, —COOH —CONH$_2$, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, $R^{26}$-substituted or unsubstituted alkyl (e.g., $C_1$-$C_8$ alkyl, $C_1$-$C_6$ alkyl, or $C_1$-$C_4$ alkyl), $R^{26}$-substituted or unsubstituted heteroalkyl (e.g., 2 to 8 membered heteroalkyl, 2 to 6 membered heteroalkyl, or 2 to 4 membered heteroalkyl), $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26}$-substituted or unsubstituted aryl (e.g., $C_6$-$C_{10}$ aryl, $C_{10}$ aryl, or phenyl), or $R^{26}$-substituted or unsubstituted heteroaryl (e.g., 5 to 10 membered heteroaryl, 5 to 9 membered heteroaryl, or 5 to 6 membered heteroaryl).

In embodiments, $R^{25}$ is $R^{26}$-substituted or unsubstituted alkyl (e.g., $C_1$-$C_8$ alkyl, $C_1$-$C_6$ alkyl, or $C_1$-$C_4$ alkyl). In embodiments, $R^{25}$ is $R^{26}$-substituted alkyl (e.g., $C_1$-$C_8$ alkyl, $C_1$-$C_6$ alkyl, or $C_1$-$C_4$ alkyl). In embodiments, $R^{25}$ is an unsubstituted alkyl (e.g., $C_1$-$C_8$ alkyl, $C_1$-$C_6$ alkyl, or $C_1$-$C_4$ alkyl).

In embodiments, $R^{25}$ is $R^{26}$-substituted or unsubstituted heteroalkyl (e.g., 2 to 8 membered heteroalkyl, 2 to 6 membered heteroalkyl, or 2 to 4 membered heteroalkyl). In embodiments, $R^{25}$ is $R^{26}$-substituted heteroalkyl (e.g., 2 to 8 membered heteroalkyl, 2 to 6 membered heteroalkyl, or 2 to 4 membered heteroalkyl). In embodiments, $R^{25}$ is an unsubstituted heteroalkyl (e.g., 2 to 8 membered heteroalkyl, 2 to 6 membered heteroalkyl, or 2 to 4 membered heteroalkyl).

In embodiments, $R^{25}$ is $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{25}$ is $R^{26}$-substituted cycloalkyl (e.g., $C_3$-$C_8$ cycloalkyl, $C_3$-$C_6$ cycloalkyl, or $C_5$-$C_6$ cycloalkyl). In embodiments, $R^{25}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{25}$ is $R^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{25}$ is $R^{26}$-substituted heterocycloalkyl (e.g., 3 to 8 membered heterocycloalkyl, 3 to 6 membered heterocycloalkyl, or 5 to 6 membered heterocycloalkyl). In embodiments, $R^{25}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{25}$ is $R^{26}$-substituted or unsubstituted aryl (e.g., $C_6$-$C_{10}$ aryl, $C_{10}$ aryl, or phenyl). In embodiments, $R^{25}$ is $R^{26}$-substituted aryl (e.g., $C_6$-$C_{10}$ aryl, $C_{10}$ aryl, or phenyl). In embodiments, $R^{25}$ is an unsubstituted aryl (e.g., $C_6$-$C_{10}$ aryl, $C_{10}$ aryl, or phenyl).

In embodiments, $R^{25}$ is $R^{26}$-substituted or unsubstituted heteroaryl (e.g., 5 to 10 membered heteroaryl, 5 to 9 membered heteroaryl, or 5 to 6 membered heteroaryl). In embodiments, $R^{25}$ is $R^{26}$-substituted heteroaryl (e.g., 5 to 10 membered heteroaryl, 5 to 9 membered heteroaryl, or 5 to 6 membered heteroaryl). In embodiments, $R^{25}$ is an unsubstituted heteroaryl (e.g., 5 to 10 membered heteroaryl, 5 to 9 membered heteroaryl, or 5 to 6 membered heteroaryl).

$R^{26}$ is independently oxo, halogen, —CCl₃, —CBr₃, —CF₃, —CI₃, —CN, —OH, —NH₂—COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OC HCl₂, —OCHBr₂, —OCHI₂, —OCHF₂, $R^{27}$-substituted or unsubstituted alkyl (e.g., $C_1$-$C_8$ alkyl, $C_1$-$C_6$ alkyl, or $C_1$-$C_4$ alkyl), $R^{27}$-substituted or unsubstituted heteroalkyl (e.g., 2 to 8 membered heteroalkyl, 2 to 6 membered heteroalkyl, or 2 to 4 membered heteroalkyl), $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27}$-substituted or unsubstituted aryl (e.g., $C_6$-$C_{10}$ aryl, $C_{10}$ aryl, or phenyl), or $R^{27}$-substituted or unsubstituted heteroaryl (e.g., 5 to 10 membered heteroaryl, 5 to 9 membered heteroaryl, or 5 to 6 membered heteroaryl).

In embodiments, $R^{26}$ is $R^{27}$-substituted or unsubstituted alkyl (e.g., $C_1$-$C_8$ alkyl, $C_1$-$C_6$ alkyl, or $C_1$-$C_4$ alkyl). In embodiments, $R^{26}$ is $R^{27}$-substituted alkyl (e.g., $C_1$-$C_8$ alkyl, $C_1$-$C_6$ alkyl, or $C_1$-$C_4$ alkyl). In embodiments, $R^{26}$ is an unsubstituted alkyl (e.g., $C_1$-$C_8$ alkyl, $C_1$-$C_6$ alkyl, or $C_1$-$C_4$ alkyl).

In embodiments, $R^{26}$ is $R^{27}$-substituted or unsubstituted heteroalkyl (e.g., 2 to 8 membered heteroalkyl, 2 to 6 membered heteroalkyl, or 2 to 4 membered heteroalkyl). In embodiments, $R^{26}$ is $R^{27}$-substituted heteroalkyl (e.g., 2 to 8 membered heteroalkyl, 2 to 6 membered heteroalkyl, or 2 to 4 membered heteroalkyl). In embodiments, $R^{26}$ is an unsubstituted heteroalkyl (e.g., 2 to 8 membered heteroalkyl, 2 to 6 membered heteroalkyl, or 2 to 4 membered heteroalkyl).

In embodiments, $R^{26}$ is $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{26}$ is $R^{27}$-substituted cycloalkyl (e.g., $C_3$-$C_8$ cycloalkyl, $C_3$-$C_6$ cycloalkyl, or $C_5$-$C_6$ cycloalkyl). In embodiments, $R^{26}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{26}$ is $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{26}$ is $R^{27}$-substituted heterocycloalkyl (e.g., 3 to 8 membered heterocycloalkyl, 3 to 6 membered heterocycloalkyl, or 5 to 6 membered heterocycloalkyl). In embodiments, $R^{26}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{26}$ is $R^{27}$-substituted or unsubstituted aryl (e.g., $C_6$-$C_{10}$ aryl, $C_{10}$ aryl, or phenyl). In embodiments, $R^{26}$ is $R^{27}$-substituted aryl (e.g., $C_6$-$C_{10}$ aryl, $C_{10}$ aryl, or phenyl). In embodiments, $R^{26}$ is an unsubstituted aryl (e.g., $C_6$-$C_{10}$ aryl, $C_{10}$ aryl, or phenyl).

In embodiments, $R^{26}$ is $R^{27}$-substituted or unsubstituted heteroaryl (e.g., 5 to 10 membered heteroaryl, 5 to 9 membered heteroaryl, or 5 to 6 membered heteroaryl). In embodiments, $R^{26}$ is $R^{27}$-substituted heteroaryl (e.g., 5 to 10 membered heteroaryl, 5 to 9 membered heteroaryl, or 5 to 6 membered heteroaryl). In embodiments, $R^{21}$ is an unsubstituted heteroaryl (e.g., 5 to 10 membered heteroaryl, 5 to 9 membered heteroaryl, or 5 to 6 membered heteroaryl).

$R^{28}$ is independently oxo, halogen, —CCl₃, —CBr₃, —CF₃, —CI₃, —CN, —OH, —NH₂—COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, $R^{29}$-substituted or unsubstituted alkyl (e.g., $C_1$-$C_8$ alkyl, $C_1$-$C_6$ alkyl, or $C_1$-$C_4$ alkyl), $R^{29}$-substituted or unsubstituted heteroalkyl (e.g., 2 to 8 membered heteroalkyl, 2 to 6 membered heteroalkyl, or 2 to 4 membered heteroalkyl), $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29}$-substituted or unsubstituted aryl (e.g., $C_6$-$C_{10}$ aryl, $C_{10}$ aryl, or phenyl), or $R^{29}$-substituted or unsubstituted heteroaryl (e.g., 5 to 10 membered heteroaryl, 5 to 9 membered heteroaryl, or 5 to 6 membered heteroaryl).

In embodiments, $R^{28}$ is $R^{29}$-substituted or unsubstituted alkyl (e.g., $C_1$-$C_8$ alkyl, $C_1$-$C_6$ alkyl, or $C_1$-$C_4$ alkyl). In embodiments, $R^{28}$ is $R^{29}$-substituted alkyl (e.g., $C_1$-$C_8$ alkyl, $C_1$-$C_6$ alkyl, or $C_1$-$C_4$ alkyl). In embodiments, $R^{28}$ is an unsubstituted alkyl (e.g., $C_1$-$C_8$ alkyl, $C_1$-$C_6$ alkyl, or $C_1$-$C_4$ alkyl).

In embodiments, $R^{28}$ is $R^{29}$-substituted or unsubstituted heteroalkyl (e.g., 2 to 8 membered heteroalkyl, 2 to 6 membered heteroalkyl, or 2 to 4 membered heteroalkyl). In embodiments, $R^{28}$ is $R^{29}$-substituted heteroalkyl (e.g., 2 to 8 membered heteroalkyl, 2 to 6 membered heteroalkyl, or 2 to 4 membered heteroalkyl). In embodiments, $R^{28}$ is an unsubstituted heteroalkyl (e.g., 2 to 8 membered heteroalkyl, 2 to 6 membered heteroalkyl, or 2 to 4 membered heteroalkyl).

In embodiments, $R^{28}$ is $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{28}$ is $R^{29}$-substituted cycloalkyl (e.g., $C_3$-$C_8$ cycloalkyl, $C_3$-$C_6$ cycloalkyl, or $C_5$-$C_6$ cycloalkyl). In embodiments, $R^{28}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{28}$ is $R^{29}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{28}$ is $R^{29}$-substituted heterocycloalkyl (e.g., 3 to 8 membered heterocycloalkyl, 3 to 6 membered heterocycloalkyl, or 5 to 6 membered heterocycloalkyl). In embodiments, $R^{28}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{28}$ is $R^{29}$-substituted or unsubstituted aryl (e.g., $C_6$-$C_{10}$ aryl, $C_{10}$ aryl, or phenyl). In embodiments, $R^{28}$ is $R^{29}$-substituted aryl (e.g., $C_6$-$C_{10}$ aryl, $C_{10}$ aryl, or phenyl). In embodiments, $R^{28}$ is an unsubstituted aryl (e.g., $C_6$-$C_{10}$ aryl, $C_{10}$ aryl, or phenyl).

In embodiments, $R^{28}$ is $R^{29}$-substituted or unsubstituted heteroaryl (e.g., 5 to 10 membered heteroaryl, 5 to 9 membered heteroaryl, or 5 to 6 membered heteroaryl). In embodiments, $R^{28}$ is $R^{29}$-substituted heteroaryl (e.g., 5 to 10 membered heteroaryl, 5 to 9 membered heteroaryl, or 5 to 6 membered heteroaryl). In embodiments, $R^{28}$ is an unsubstituted heteroaryl (e.g., 5 to 10 membered heteroaryl, 5 to 9 membered heteroaryl, or 5 to 6 membered heteroaryl).

$R^{29}$ is independently oxo, halogen, —$CCl_3$, —$CBr_3$, —$CF_3$, —$CI_3$, —CN, —OH, —$NH_2$—COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{30}$-substituted or unsubstituted alkyl (e.g., $C_1$-$C_8$ alkyl, $C_1$-$C_6$ alkyl, or $C_1$-$C_4$ alkyl), $R^{30}$-substituted or unsubstituted heteroalkyl (e.g., 2 to 8 membered heteroalkyl, 2 to 6 membered heteroalkyl, or 2 to 4 membered heteroalkyl), $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{30}$-substituted or unsubstituted heterocycloalkyl (e.g., 3 to 8 membered heterocycloalkyl, 3 to 6 membered heterocycloalkyl, or 5 to 6 membered heterocycloalkyl), $R^{30}$-substituted or unsubstituted aryl (e.g., $C_6$-$C_{10}$ aryl, $C_{10}$ aryl, or phenyl), or $R^{30}$-substituted or unsubstituted heteroaryl (e.g., 5 to 10 membered heteroaryl, 5 to 9 membered heteroaryl, or 5 to 6 membered heteroaryl).

In embodiments, $R^{29}$ is $R^{30}$-substituted or unsubstituted alkyl (e.g., $C_1$-$C_8$ alkyl, $C_1$-$C_6$ alkyl, or $C_1$-$C_4$ alkyl). In embodiments, $R^{29}$ is $R^{30}$-substituted alkyl (e.g., $C_1$-$C_8$ alkyl, $C_1$-$C_6$ alkyl, or $C_1$-$C_4$ alkyl). In embodiments, $R^{29}$ is an unsubstituted alkyl (e.g., $C_1$-$C_8$ alkyl, $C_1$-$C_6$ alkyl, or $C_1$-$C_4$ alkyl).

In embodiments, $R^{29}$ is $R^{30}$-substituted or unsubstituted heteroalkyl (e.g., 2 to 8 membered heteroalkyl, 2 to 6 membered heteroalkyl, or 2 to 4 membered heteroalkyl). In embodiments, $R^{29}$ is $R^{30}$-substituted heteroalkyl (e.g., 2 to 8 membered heteroalkyl, 2 to 6 membered heteroalkyl, or 2 to 4 membered heteroalkyl). In embodiments, $R^{29}$ is an unsubstituted heteroalkyl (e.g., 2 to 8 membered heteroalkyl, 2 to 6 membered heteroalkyl, or 2 to 4 membered heteroalkyl).

In embodiments, $R^{29}$ is $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{29}$ is $R^{30}$-substituted cycloalkyl (e.g., $C_3$-$C_8$ cycloalkyl, $C_3$-$C_6$ cycloalkyl, or $C_5$-$C_6$ cycloalkyl). In embodiments, $R^{29}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{29}$ is $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{29}$ is $R^{30}$-substituted heterocycloalkyl (e.g., 3 to 8 membered heterocycloalkyl, 3 to 6 membered heterocycloalkyl, or 5 to 6 membered heterocycloalkyl). In embodiments, $R^{29}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{29}$ is $R^{30}$-substituted or unsubstituted aryl (e.g., $C_6$-$C_{10}$ aryl, $C_{10}$ aryl, or phenyl). In embodiments, $R^{29}$ is $R^{30}$-substituted aryl (e.g., $C_6$-$C_{10}$ aryl, $C_{10}$ aryl, or phenyl). In embodiments, $R^{29}$ is an unsubstituted aryl (e.g., $C_6$-$C_{10}$ aryl, $C_{10}$ aryl, or phenyl).

In embodiments, $R^{29}$ is $R^{30}$-substituted or unsubstituted heteroaryl (e.g., 5 to 10 membered heteroaryl, 5 to 9 membered heteroaryl, or 5 to 6 membered heteroaryl). In embodiments, $R^{29}$ is $R^{30}$-substituted heteroaryl (e.g., 5 to 10 membered heteroaryl, 5 to 9 membered heteroaryl, or 5 to 6 membered heteroaryl). In embodiments, $R^{29}$ is an unsubstituted heteroaryl (e.g., 5 to 10 membered heteroaryl, 5 to 9 membered heteroaryl, or 5 to 6 membered heteroaryl).

$R^{31}$ is independently oxo, halogen, —$CCl_3$, —$CBr_3$, —$CF_3$, —$CI_3$, —CN, —OH, —$NH_2$—COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{32}$-substituted or unsubstituted alkyl (e.g., $C_1$-$C_8$ alkyl, $C_1$-$C_6$ alkyl, or $C_1$-$C_4$ alkyl), $R^{32}$-substituted or unsubstituted heteroalkyl (e.g., 2 to 8 membered heteroalkyl, 2 to 6 membered heteroalkyl, or 2 to 4 membered heteroalkyl), $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32}$-substituted or unsubstituted aryl (e.g., $C_6$-$C_{10}$ aryl, $C_{10}$ aryl, or phenyl), or $R^{32}$-substituted or unsubstituted heteroaryl (e.g., 5 to 10 membered heteroaryl, 5 to 9 membered heteroaryl, or 5 to 6 membered heteroaryl).

In embodiments, $R^{31}$ is $R^{32}$-substituted or unsubstituted alkyl (e.g., $C_1$-$C_8$ alkyl, $C_1$-$C_6$ alkyl, or $C_1$-$C_4$ alkyl). In embodiments, $R^{31}$ is $R^{32}$-substituted alkyl (e.g., $C_1$-$C_8$ alkyl, $C_1$-$C_6$ alkyl, or $C_1$-$C_4$ alkyl). In embodiments, $R^{31}$ is an unsubstituted alkyl (e.g., $C_1$-$C_8$ alkyl, $C_1$-$C_6$ alkyl, or $C_1$-$C_4$ alkyl).

In embodiments, $R^{31}$ is $R^{32}$-substituted or unsubstituted heteroalkyl (e.g., 2 to 8 membered heteroalkyl, 2 to 6 membered heteroalkyl, or 2 to 4 membered heteroalkyl). In embodiments, $R^{31}$ is $R^{32}$-substituted heteroalkyl (e.g., 2 to 8 membered heteroalkyl, 2 to 6 membered heteroalkyl, or 2 to 4 membered heteroalkyl). In embodiments, $R^{31}$ is an unsubstituted heteroalkyl (e.g., 2 to 8 membered heteroalkyl, 2 to 6 membered heteroalkyl, or 2 to 4 membered heteroalkyl).

In embodiments, $R^{31}$ is $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{31}$ is $R^{32}$-substituted cycloalkyl (e.g., $C_3$-$C_8$ cycloalkyl, $C_3$-$C_6$ cycloalkyl, or $C_5$-$C_6$ cycloalkyl). In embodiments, $R^{31}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{31}$ is $R^{32}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{31}$ is $R^{32}$-substituted heterocycloalkyl (e.g., 3 to 8 membered heterocycloalkyl, 3 to 6 membered heterocycloalkyl, or 5 to 6 membered heterocycloalkyl). In embodiments, $R^{31}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{31}$ is $R^{32}$-substituted or unsubstituted aryl (e.g., $C_6$-$C_{10}$ aryl, $C_{10}$ aryl, or phenyl). In embodiments, $R^{31}$ is $R^{32}$-substituted aryl (e.g., $C_6$-$C_{10}$ aryl, $C_{10}$ aryl, or phenyl). In embodiments, $R^{31}$ is an unsubstituted aryl (e.g., $C_6$-$C_{10}$ aryl, $C_{10}$ aryl, or phenyl).

In embodiments, $R^{31}$ is $R^{32}$-substituted or unsubstituted heteroaryl (e.g., 5 to 10 membered heteroaryl, 5 to 9 membered heteroaryl, or 5 to 6 membered heteroaryl). In embodiments, $R^{31}$ is $R^{32}$-substituted heteroaryl (e.g., 5 to 10 membered heteroaryl, 5 to 9 membered heteroaryl, or 5 to 6 membered heteroaryl). In embodiments, $R^{31}$ is an unsubstituted heteroaryl (e.g., 5 to 10 membered heteroaryl, 5 to 9 membered heteroaryl, or 5 to 6 membered heteroaryl).

$R^{32}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{33}$-substituted or unsubstituted alkyl (e.g., $C_1$-$C_8$ alkyl, $C_1$-$C_6$ alkyl, or $C_1$-$C_4$ alkyl), $R^{33}$-substituted or unsubstituted heteroalkyl (e.g., 2 to 8 membered heteroalkyl, 2 to 6 membered heteroalkyl, or 2 to 4 membered heteroalkyl), $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{33}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33}$-substituted or unsubstituted aryl (e.g., $C_6$-$C_{10}$ aryl, $C_{10}$ aryl, or phenyl), or $R^{33}$-substituted or unsubstituted heteroaryl (e.g., 5 to 10 membered heteroaryl, 5 to 9 membered heteroaryl, or 5 to 6 membered heteroaryl).

In embodiments, $R^{32}$ is $R^{33}$-substituted or unsubstituted alkyl (e.g., $C_1$-$C_8$ alkyl, $C_1$-$C_6$ alkyl, or $C_1$-$C_4$ alkyl). In embodiments, $R^{32}$ is $R^{33}$-substituted alkyl (e.g., $C_1$-$C_8$ alkyl, $C_1$-$C_6$ alkyl, or $C_1$-$C_4$ alkyl). In embodiments, $R^{32}$ is an unsubstituted alkyl (e.g., $C_1$-$C_8$ alkyl, $C_1$-$C_6$ alkyl, or $C_1$-$C_4$ alkyl).

In embodiments, $R^{32}$ is $R^{33}$-substituted or unsubstituted heteroalkyl (e.g., 2 to 8 membered heteroalkyl, 2 to 6 membered heteroalkyl, or 2 to 4 membered heteroalkyl). In embodiments, $R^{32}$ is $R^{33}$-substituted heteroalkyl (e.g., 2 to 8 membered heteroalkyl, 2 to 6 membered heteroalkyl, or 2 to 4 membered heteroalkyl). In embodiments, $R^{32}$ is an unsubstituted heteroalkyl (e.g., 2 to 8 membered heteroalkyl, 2 to 6 membered heteroalkyl, or 2 to 4 membered heteroalkyl).

In embodiments, $R^{32}$ is $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{32}$ is $R^{33}$-substituted cycloalkyl (e.g., $C_3$-$C_8$ cycloalkyl, $C_3$-$C_6$ cycloalkyl, or $C_5$-$C_6$ cycloalkyl). In embodiments, $R^{32}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{32}$ is $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{32}$ is $R^{33}$-substituted heterocycloalkyl (e.g., 3 to 8 membered heterocycloalkyl, 3 to 6 membered heterocycloalkyl, or 5 to 6 membered heterocycloalkyl). In embodiments, $R^{32}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{32}$ is $R^{33}$-substituted or unsubstituted aryl (e.g., $C_6$-$C_{10}$ aryl, $C_{10}$ aryl, or phenyl). In embodiments, $R^{32}$ is $R^{33}$-substituted aryl (e.g., $C_6$-$C_{10}$ aryl, $C_{10}$ aryl, or phenyl). In embodiments, $R^{32}$ is an unsubstituted aryl (e.g., $C_6$-$C_{10}$ aryl, $C_{10}$ aryl, or phenyl).

In embodiments, $R^{32}$ is $R^{33}$-substituted or unsubstituted heteroaryl (e.g., 5 to 10 membered heteroaryl, 5 to 9 membered heteroaryl, or 5 to 6 membered heteroaryl). In embodiments, $R^{32}$ is $R^{33}$-substituted heteroaryl (e.g., 5 to 10 membered heteroaryl, 5 to 9 membered heteroaryl, or 5 to 6 membered heteroaryl). In embodiments, $R^{32}$ is an unsubstituted heteroaryl (e.g., 5 to 10 membered heteroaryl, 5 to 9 membered heteroaryl, or 5 to 6 membered heteroaryl).

$R^{34}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{35}$-substituted or unsubstituted alkyl (e.g., $C_1$-$C_8$ alkyl, $C_1$-$C_6$ alkyl, or $C_1$-$C_4$ alkyl), $R^{35}$-substituted or unsubstituted heteroalkyl (e.g., 2 to 8 membered heteroalkyl, 2 to 6 membered heteroalkyl, or 2 to 4 membered heteroalkyl), $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted or unsubstituted aryl (e.g., $C_6$-$C_{10}$ aryl, $C_{10}$ aryl, or phenyl), or $R^{35}$-substituted or unsubstituted heteroaryl (e.g., 5 to 10 membered heteroaryl, 5 to 9 membered heteroaryl, or 5 to 6 membered heteroaryl).

In embodiments, $R^{34}$ is $R^{35}$-substituted or unsubstituted alkyl (e.g., $C_1$-$C_8$ alkyl, $C_1$-$C_6$ alkyl, or $C_1$-$C_4$ alkyl). In embodiments, $R^{34}$ is $R^{35}$-substituted alkyl (e.g., $C_1$-$C_8$ alkyl, $C_1$-$C_6$ alkyl, or $C_1$-$C_4$ alkyl). In embodiments, $R^{34}$ is an unsubstituted alkyl (e.g., $C_1$-$C_8$ alkyl, $C_1$-$C_6$ alkyl, or $C_1$-$C_4$ alkyl).

In embodiments, $R^{34}$ is $R^{35}$-substituted or unsubstituted heteroalkyl (e.g., 2 to 8 membered heteroalkyl, 2 to 6 membered heteroalkyl, or 2 to 4 membered heteroalkyl). In embodiments, $R^{34}$ is $R^{35}$-substituted heteroalkyl (e.g., 2 to 8 membered heteroalkyl, 2 to 6 membered heteroalkyl, or 2 to 4 membered heteroalkyl). In embodiments, $R^{34}$ is an unsubstituted heteroalkyl (e.g., 2 to 8 membered heteroalkyl, 2 to 6 membered heteroalkyl, or 2 to 4 membered heteroalkyl).

In embodiments, $R^{34}$ is $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{34}$ is $R^{35}$-substituted cycloalkyl (e.g., $C_3$-$C_8$ cycloalkyl, $C_3$-$C_6$ cycloalkyl, or $C_5$-$C_6$ cycloalkyl). In embodiments, $R^{34}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{34}$ is $R^{35}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{34}$ is $R^{35}$-substituted heterocycloalkyl (e.g., 3 to 8 membered heterocycloalkyl, 3 to 6 membered heterocycloalkyl, or 5 to 6 membered heterocycloalkyl). In embodiments, $R^{34}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{34}$ is $R^{35}$-substituted or unsubstituted aryl (e.g., $C_6$-$C_{10}$ aryl, $C_{10}$ aryl, or phenyl). In embodiments, $R^{34}$ is $R^{35}$-substituted aryl (e.g., $C_6$-$C_{10}$ aryl, $C_{10}$ aryl, or phenyl). In embodiments, $R^{34}$ is an unsubstituted aryl (e.g., $C_6$-$C_{10}$ aryl, $C_{10}$ aryl, or phenyl).

In embodiments, $R^{34}$ is $R^{35}$-substituted or unsubstituted heteroaryl (e.g., 5 to 10 membered heteroaryl, 5 to 9 membered heteroaryl, or 5 to 6 membered heteroaryl). In embodiments, $R^{34}$ is $R^{35}$-substituted heteroaryl (e.g., 5 to 10 membered heteroaryl, 5 to 9 membered heteroaryl, or 5 to 6 membered heteroaryl). In embodiments, $R^{34}$ is an unsubstituted heteroaryl (e.g., 5 to 10 membered heteroaryl, 5 to 9 membered heteroaryl, or 5 to 6 membered heteroaryl).

$R^{35}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{36}$-substituted or unsubstituted alkyl (e.g., $C_1$-$C_8$ alkyl, $C_1$-$C_6$ alkyl, or $C_1$-$C_4$ alkyl), $R^{36}$-substituted or unsubstituted heteroalkyl (e.g., 2 to 8 membered heteroalkyl, 2 to 6 membered heteroalkyl, or 2 to 4 membered heteroalkyl), $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36}$-substituted or unsubstituted aryl (e.g., $C_6$-$C_{10}$ aryl, $C_{10}$ aryl, or phenyl), or $R^{36}$-substituted or unsubstituted heteroaryl (e.g., 5 to 10 membered heteroaryl, 5 to 9 membered heteroaryl, or 5 to 6 membered heteroaryl).

In embodiments, $R^{35}$ is $R^{36}$-substituted or unsubstituted alkyl (e.g., $C_1$-$C_8$ alkyl, $C_1$-$C_6$ alkyl, or $C_1$-$C_4$ alkyl). In embodiments, $R^{35}$ is $R^{36}$-substituted alkyl (e.g., $C_1$-$C_8$ alkyl, $C_1$-$C_6$ alkyl, or $C_1$-$C_4$ alkyl). In embodiments, $R^{35}$ is an unsubstituted alkyl (e.g., $C_1$-$C_8$ alkyl, $C_1$-$C_6$ alkyl, or $C_1$-$C_4$ alkyl).

In embodiments, $R^{35}$ is $R^{36}$-substituted or unsubstituted heteroalkyl (e.g., 2 to 8 membered heteroalkyl, 2 to 6 membered heteroalkyl, or 2 to 4 membered heteroalkyl). In embodiments, $R^{35}$ is $R^{36}$-substituted heteroalkyl (e.g., 2 to 8 membered heteroalkyl, 2 to 6 membered heteroalkyl, or 2 to 4 membered heteroalkyl). In embodiments, $R^{35}$ is an unsubstituted heteroalkyl (e.g., 2 to 8 membered heteroalkyl, 2 to 6 membered heteroalkyl, or 2 to 4 membered heteroalkyl).

In embodiments, $R^{35}$ is $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{35}$ is $R^{36}$-substituted cycloalkyl (e.g., $C_3$-$C_8$ cycloalkyl, $C_3$-$C_6$ cycloalkyl, or $C_5$-$C_6$ cycloalkyl). In embodiments, $R^{35}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{35}$ is $R^{36}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{35}$ is $R^{36}$-substituted heterocycloalkyl (e.g., 3 to 8 membered heterocycloalkyl, 3 to 6 membered heterocycloalkyl, or 5 to 6 membered heterocycloalkyl). In embodiments, $R^{35}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{35}$ is $R^{36}$-substituted or unsubstituted aryl (e.g., $C_6$-$C_{10}$ aryl, $C_{10}$ aryl, or phenyl). In embodiments, $R^{35}$ is $R^{36}$-substituted aryl (e.g., $C_6$-$C_{10}$ aryl, $C_{10}$ aryl, or phenyl). In embodiments, $R^{35}$ is an unsubstituted aryl (e.g., $C_6$-$C_{10}$ aryl, $C_{10}$ aryl, or phenyl).

In embodiments, $R^{35}$ is $R^{36}$-substituted or unsubstituted heteroaryl (e.g., 5 to 10 membered heteroaryl, 5 to 9 membered heteroaryl, or 5 to 6 membered heteroaryl). In embodiments, $R^{35}$ is $R^{36}$-substituted heteroaryl (e.g., 5 to 10 membered heteroaryl, 5 to 9 membered heteroaryl, or 5 to 6 membered heteroaryl). In embodiments, $R^{35}$ is an unsubstituted heteroaryl (e.g., 5 to 10 membered heteroaryl, 5 to 9 membered heteroaryl, or 5 to 6 membered heteroaryl).

$R^{37}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{38}$-substituted or unsubstituted alkyl (e.g., $C_1$-$C_8$ alkyl, $C_1$-$C_6$ alkyl, or $C_1$-$C_4$ alkyl), $R^{38}$-substituted or unsubstituted heteroalkyl (e.g., 2 to 8 membered heteroalkyl, 2 to 6 membered heteroalkyl, or 2 to 4 membered heteroalkyl), $R^{38}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted or unsubstituted aryl (e.g., $C_6$-$C_{10}$ aryl, $C_{10}$ aryl, or phenyl), or $R^{38}$-substituted or unsubstituted heteroaryl (e.g., 5 to 10 membered heteroaryl, 5 to 9 membered heteroaryl, or 5 to 6 membered heteroaryl).

In embodiments, $R^{37}$ is $R^{38}$-substituted or unsubstituted alkyl (e.g., $C_1$-$C_8$ alkyl, $C_1$-$C_6$ alkyl, or $C_1$-$C_4$ alkyl). In embodiments, $R^{37}$ is $R^{38}$-substituted alkyl (e.g., $C_1$-$C_8$ alkyl, $C_1$-$C_6$ alkyl, or $C_1$-$C_4$ alkyl). In embodiments, $R^{37}$ is an unsubstituted alkyl (e.g., $C_1$-$C_8$ alkyl, $C_1$-$C_6$ alkyl, or $C_1$-$C_4$ alkyl).

In embodiments, $R^{37}$ is $R^{38}$-substituted or unsubstituted heteroalkyl (e.g., 2 to 8 membered heteroalkyl, 2 to 6 membered heteroalkyl, or 2 to 4 membered heteroalkyl). In embodiments, $R^{37}$ is $R^{38}$-substituted heteroalkyl (e.g., 2 to 8 membered heteroalkyl, 2 to 6 membered heteroalkyl, or 2 to 4 membered heteroalkyl). In embodiments, $R^{37}$ is an unsubstituted heteroalkyl (e.g., 2 to 8 membered heteroalkyl, 2 to 6 membered heteroalkyl, or 2 to 4 membered heteroalkyl).

In embodiments, $R^{37}$ is $R^{38}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{37}$ is $R^{38}$-substituted cycloalkyl (e.g., $C_3$-$C_8$ cycloalkyl, $C_3$-$C_6$ cycloalkyl, or $C_5$-$C_6$ cycloalkyl). In embodiments, $R^{37}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{37}$ is $R^{38}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{37}$ is $R^{38}$-substituted heterocycloalkyl (e.g., 3 to 8 membered heterocycloalkyl, 3 to 6 membered heterocycloalkyl, or 5 to 6 membered heterocycloalkyl). In embodiments, $R^{37}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{37}$ is $R^{38}$-substituted or unsubstituted aryl (e.g., $C_6$-$C_{10}$ aryl, $C_{10}$ aryl, or phenyl). In embodiments, $R^{37}$ is $R^{38}$-substituted aryl (e.g., $C_6$-$C_{10}$ aryl, $C_{10}$ aryl, or phenyl). In embodiments, $R^{37}$ is an unsubstituted aryl (e.g., $C_6$-$C_{10}$ aryl, $C_{10}$ aryl, or phenyl).

In embodiments, $R^{37}$ is $R^{38}$-substituted or unsubstituted heteroaryl (e.g., 5 to 10 membered heteroaryl, 5 to 9 membered heteroaryl, or 5 to 6 membered heteroaryl). In embodiments, $R^{37}$ is $R^{38}$-substituted heteroaryl (e.g., 5 to 10 membered heteroaryl, 5 to 9 membered heteroaryl, or 5 to 6 membered heteroaryl). In embodiments, $R^{37}$ is an unsubstituted heteroaryl (e.g., 5 to 10 membered heteroaryl, 5 to 9 membered heteroaryl, or 5 to 6 membered heteroaryl).

$R^{38}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{39}$-substituted or unsubstituted alkyl (e.g., $C_1$-$C_8$ alkyl, $C_1$-$C_6$ alkyl, or $C_1$-$C_4$ alkyl), $R^{39}$-substituted or unsubstituted heteroalkyl (e.g., 2 to 8 membered heteroalkyl, 2 to 6 membered heteroalkyl, or 2 to 4 membered heteroalkyl), $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{39}$-substituted or unsubstituted heterocycloalkyl (e.g., 3 to 8 membered heterocycloalkyl, 3 to 6 membered heterocycloalkyl, or 5 to 6 membered heterocycloalkyl), $R^{39}$-substituted or unsubstituted aryl (e.g., $C_6$-$C_{10}$ aryl, $C_{10}$ aryl, or phenyl), or $R^{39}$-substituted or unsubstituted heteroaryl (e.g., 5 to 10 membered heteroaryl, 5 to 9 membered heteroaryl, or 5 to 6 membered heteroaryl).

In embodiments, $R^{38}$ is $R^{39}$-substituted or unsubstituted alkyl (e.g., $C_1$-$C_8$ alkyl, $C_1$-$C_6$ alkyl, or $C_1$-$C_4$ alkyl). In embodiments, $R^{38}$ is $R^{39}$-substituted alkyl (e.g., $C_1$-$C_8$ alkyl, $C_1$-$C_6$ alkyl, or $C_1$-$C_4$ alkyl). In embodiments, $R^{38}$ is an unsubstituted alkyl (e.g., $C_1$-$C_8$ alkyl, $C_1$-$C_6$ alkyl, or $C_1$-$C_4$ alkyl).

In embodiments, $R^{38}$ is $R^{39}$-substituted or unsubstituted heteroalkyl (e.g., 2 to 8 membered heteroalkyl, 2 to 6 membered heteroalkyl, or 2 to 4 membered heteroalkyl). In embodiments, $R^{38}$ is $R^{39}$-substituted heteroalkyl (e.g., 2 to 8 membered heteroalkyl, 2 to 6 membered heteroalkyl, or 2 to 4 membered heteroalkyl). In embodiments, $R^{38}$ is an unsubstituted heteroalkyl (e.g., 2 to 8 membered heteroalkyl, 2 to 6 membered heteroalkyl, or 2 to 4 membered heteroalkyl).

In embodiments, $R^{38}$ is $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{38}$ is $R^{39}$-substituted cycloalkyl (e.g., $C_3$-$C_8$ cycloalkyl, $C_3$-$C_6$ cycloalkyl, or $C_5$-$C_6$ cycloalkyl). In embodiments, $R^{38}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{38}$ is $R^{39}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{38}$ is $R^{39}$-substituted heterocycloalkyl (e.g., 3 to 8 membered heterocycloalkyl, 3 to 6 membered heterocycloalkyl, or 5 to 6 membered heterocycloalkyl). In embodiments, $R^{38}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{38}$ is $R^{39}$-substituted or unsubstituted aryl (e.g., $C_6$-$C_{10}$ aryl, $C_{10}$ aryl, or phenyl). In embodiments, $R^{38}$ is $R^{39}$-substituted aryl (e.g., $C_6$-$C_{10}$ aryl, $C_{10}$ aryl, or phenyl). In embodiments, $R^{38}$ is an unsubstituted aryl (e.g., $C_6$-$C_{10}$ aryl, $C_{10}$ aryl, or phenyl).

In embodiments, $R^{38}$ is $R^{39}$-substituted or unsubstituted heteroaryl (e.g., 5 to 10 membered heteroaryl, 5 to 9 membered heteroaryl, or 5 to 6 membered heteroaryl). In embodiments, $R^{38}$ is $R^{39}$-substituted heteroaryl (e.g., 5 to 10 membered heteroaryl, 5 to 9 membered heteroaryl, or 5 to 6 membered heteroaryl). In embodiments, $R^{38}$ is an unsubstituted heteroaryl (e.g., 5 to 10 membered heteroaryl, 5 to 9 membered heteroaryl, or 5 to 6 membered heteroaryl).

$R^{40}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{41}$-substituted or unsubstituted alkyl (e.g., $C_1$-$C_8$ alkyl, $C_1$-$C_6$ alkyl, or $C_1$-$C_4$ alkyl), $R^{41}$-substituted or unsubstituted heteroalkyl (e.g., 2 to 8 membered heteroalkyl, 2 to 6 membered heteroalkyl, or 2 to 4 membered heteroalkyl), $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{41}$-substituted or unsubstituted heterocycloalkyl (e.g., 3 to 8 membered heterocycloalkyl, 3 to 6 membered heterocycloalkyl, or 5 to 6 membered heterocycloalkyl), $R^{41}$-substituted or unsubstituted aryl (e.g., $C_6$-$C_{10}$ aryl, $C_{10}$ aryl, or phenyl), or $R^{41}$-substituted or unsubstituted heteroaryl (e.g., 5 to 10 membered heteroaryl, 5 to 9 membered heteroaryl, or 5 to 6 membered heteroaryl).

In embodiments, $R^{40}$ is $R^{41}$-substituted or unsubstituted alkyl (e.g., $C_1$-$C_8$ alkyl, $C_1$-$C_6$ alkyl, or $C_1$-$C_4$ alkyl). In embodiments, $R^{40}$ is $R^{41}$-substituted alkyl (e.g., $C_1$-$C_8$ alkyl, $C_1$-$C_6$ alkyl, or $C_1$-$C_4$ alkyl). In embodiments, $R^{40}$ is an unsubstituted alkyl (e.g., $C_1$-$C_8$ alkyl, $C_1$-$C_6$ alkyl, or $C_1$-$C_4$ alkyl).

In embodiments, $R^{40}$ is $R^{41}$-substituted or unsubstituted heteroalkyl (e.g., 2 to 8 membered heteroalkyl, 2 to 6 membered heteroalkyl, or 2 to 4 membered heteroalkyl). In embodiments, $R^{40}$ is $R^{41}$-substituted heteroalkyl (e.g., 2 to 8 membered heteroalkyl, 2 to 6 membered heteroalkyl, or 2 to 4 membered heteroalkyl). In embodiments, $R^{40}$ is an unsubstituted heteroalkyl (e.g., 2 to 8 membered heteroalkyl, 2 to 6 membered heteroalkyl, or 2 to 4 membered heteroalkyl).

In embodiments, $R^{40}$ is $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{40}$ is $R^{41}$-substituted cycloalkyl (e.g., $C_3$-$C_8$ cycloalkyl, $C_3$-$C_6$ cycloalkyl, or $C_5$-$C_6$ cycloalkyl). In embodiments, $R^{40}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{40}$ is $R^{41}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{40}$ is $R^{41}$-substituted heterocycloalkyl (e.g., 3 to 8 membered heterocycloalkyl, 3 to 6 membered heterocycloalkyl, or 5 to 6 membered heterocycloalkyl). In embodiments, $R^{40}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{40}$ is $R^{41}$-substituted or unsubstituted aryl (e.g., $C_6$-$C_{10}$ aryl, $C_{10}$ aryl, or phenyl). In embodiments, $R^{40}$ is $R^{41}$-substituted aryl (e.g., $C_6$-$C_{10}$ aryl, $C_{10}$ aryl, or phenyl). In embodiments, $R^{40}$ is an unsubstituted aryl (e.g., $C_6$-$C_{10}$ aryl, $C_{10}$ aryl, or phenyl).

In embodiments, $R^{40}$ is $R^{41}$-substituted or unsubstituted heteroaryl (e.g., 5 to 10 membered heteroaryl, 5 to 9 membered heteroaryl, or 5 to 6 membered heteroaryl). In embodiments, $R^{40}$ is $R^{41}$-substituted heteroaryl (e.g., 5 to 10 membered heteroaryl, 5 to 9 membered heteroaryl, or 5 to 6 membered heteroaryl). In embodiments, $R^{40}$ is an unsubstituted heteroaryl (e.g., 5 to 10 membered heteroaryl, 5 to 9 membered heteroaryl, or 5 to 6 membered heteroaryl).

$R^{41}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{42}$-substituted or unsubstituted alkyl (e.g., $C_1$-$C_8$ alkyl, $C_1$-$C_6$ alkyl, or $C_1$-$C_4$ alkyl), $R^{42}$-substituted or unsubstituted heteroalkyl (e.g., 2 to 8 membered heteroalkyl, 2 to 6 membered heteroalkyl, or 2 to 4 membered heteroalkyl), $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{42}$-substituted or unsubstituted heterocycloalkyl (e.g., 3 to 8 membered heterocycloalkyl, 3 to 6 membered heterocycloalkyl, or 5 to 6 membered heterocycloalkyl), $R^{42}$-substituted or unsubstituted aryl (e.g., $C_6$-$C_{10}$ aryl, $C_{10}$ aryl, or phenyl), or $R^{42}$-substituted or unsubstituted heteroaryl (e.g., 5 to 10 membered heteroaryl, 5 to 9 membered heteroaryl, or 5 to 6 membered heteroaryl).

In embodiments, $R^{41}$ is $R^{42}$-substituted or unsubstituted alkyl (e.g., $C_1$-$C_8$ alkyl, $C_1$-$C_6$ alkyl, or $C_1$-$C_4$ alkyl). In embodiments, $R^{41}$ is $R^{42}$-substituted alkyl (e.g., $C_1$-$C_8$ alkyl, $C_1$-$C_6$ alkyl, or $C_1$-$C_4$ alkyl). In embodiments, $R^{41}$ is an unsubstituted alkyl (e.g., $C_1$-$C_8$ alkyl, $C_1$-$C_6$ alkyl, or $C_1$-$C_4$ alkyl).

In embodiments, $R^{41}$ is $R^{42}$-substituted or unsubstituted heteroalkyl (e.g., 2 to 8 membered heteroalkyl, 2 to 6 membered heteroalkyl, or 2 to 4 membered heteroalkyl). In embodiments, $R^{41}$ is $R^{42}$-substituted heteroalkyl (e.g., 2 to 8 membered heteroalkyl, 2 to 6 membered heteroalkyl, or 2 to 4 membered heteroalkyl). In embodiments, $R^{41}$ is an unsubstituted heteroalkyl (e.g., 2 to 8 membered heteroalkyl, 2 to 6 membered heteroalkyl, or 2 to 4 membered heteroalkyl).

In embodiments, $R^{41}$ is $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{41}$ is $R^{42}$-substituted cycloalkyl (e.g., $C_3$-$C_8$ cycloalkyl, $C_3$-$C_6$ cycloalkyl, or $C_5$-$C_6$ cycloalkyl). In embodiments, $R^{41}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{41}$ is $R^{42}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{41}$ is $R^{42}$-substituted heterocycloalkyl (e.g., 3 to 8 membered heterocycloalkyl, 3 to 6 membered heterocycloalkyl, or 5 to 6 membered heterocycloalkyl). In embodiments, $R^{41}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{41}$ is $R^{42}$-substituted or unsubstituted aryl (e.g., $C_6$-$C_{10}$ aryl, $C_{10}$ aryl, or phenyl). In embodiments, $R^{41}$ is $R^{42}$-substituted aryl (e.g., $C_6$-$C_{10}$ aryl, $C_{10}$ aryl, or phenyl). In embodiments, $R^{41}$ is an unsubstituted aryl (e.g., $C_6$-$C_{10}$ aryl, $C_{10}$ aryl, or phenyl).

In embodiments, $R^{41}$ is $R^{42}$-substituted or unsubstituted heteroaryl (e.g., 5 to 10 membered heteroaryl, 5 to 9 membered heteroaryl, or 5 to 6 membered heteroaryl). In embodiments, $R^{41}$ is $R^{42}$-substituted heteroaryl (e.g., 5 to 10 membered heteroaryl, 5 to 9 membered heteroaryl, or 5 to 6 membered heteroaryl). In embodiments, $R^{41}$ is an unsubstituted heteroaryl (e.g., 5 to 10 membered heteroaryl, 5 to 9 membered heteroaryl, or 5 to 6 membered heteroaryl).

$R^{43}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{44}$-substituted or unsubstituted alkyl (e.g., $C_1$-$C_8$ alkyl, $C_1$-$C_6$ alkyl, or $C_1$-$C_4$ alkyl), $R^{44}$-substituted or unsubstituted heteroalkyl (e.g., 2 to 8 membered heteroalkyl, 2 to 6 membered heteroalkyl, or 2 to 4 membered heteroalkyl), $R^{44}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{44}$-substituted or unsubstituted heterocycloalkyl (e.g., 3 to 8 membered heterocycloalkyl, 3 to 6 membered heterocycloalkyl, or 5 to 6 membered heterocycloalkyl), $R^{44}$-substituted or unsubstituted aryl (e.g., $C_6$-$C_{10}$ aryl, $C_{10}$ aryl, or phenyl), or $R^{44}$-substituted or unsubstituted heteroaryl (e.g., 5 to 10 membered heteroaryl, 5 to 9 membered heteroaryl, or 5 to 6 membered heteroaryl).

In embodiments, $R^{43}$ is $R^{44}$-substituted or unsubstituted alkyl (e.g., $C_1$-$C_8$ alkyl, $C_1$-$C_6$ alkyl, or $C_1$-$C_4$ alkyl). In embodiments, $R^{43}$ is $R^{44}$-substituted alkyl (e.g., $C_1$-$C_8$ alkyl, $C_1$-$C_6$ alkyl, or $C_1$-$C_4$ alkyl). In embodiments, $R^{43}$ is an unsubstituted alkyl (e.g., $C_1$-$C_8$ alkyl, $C_1$-$C_6$ alkyl, or $C_1$-$C_4$ alkyl).

In embodiments, $R^{43}$ is $R^{44}$-substituted or unsubstituted heteroalkyl (e.g., 2 to 8 membered heteroalkyl, 2 to 6 membered heteroalkyl, or 2 to 4 membered heteroalkyl). In embodiments, $R^{43}$ is $R^{44}$-substituted heteroalkyl (e.g., 2 to 8 membered heteroalkyl, 2 to 6 membered heteroalkyl, or 2 to 4 membered heteroalkyl). In embodiments, $R^{43}$ is an unsubstituted heteroalkyl (e.g., 2 to 8 membered heteroalkyl, 2 to 6 membered heteroalkyl, or 2 to 4 membered heteroalkyl).

In embodiments, $R^{43}$ is $R^{44}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{43}$ is $R^{44}$-substituted cycloalkyl (e.g., $C_3$-$C_8$ cycloalkyl, $C_3$-$C_6$ cycloalkyl, or $C_5$-$C_6$ cycloalkyl). In embodiments, $R^{43}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{43}$ is $R^{44}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{43}$ is $R^{44}$-substituted heterocycloalkyl (e.g., 3 to 8 membered heterocycloalkyl, 3 to 6 membered heterocycloalkyl, or 5 to 6 membered heterocycloalkyl). In embodiments, $R^{43}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{43}$ is $R^{44}$-substituted or unsubstituted aryl (e.g., $C_6$-$C_{10}$ aryl, $C_{10}$ aryl, or phenyl). In embodiments, $R^{43}$ is $R^{44}$-substituted aryl (e.g., $C_6$-$C_{10}$ aryl, $C_{10}$ aryl, or phenyl). In embodiments, $R^{43}$ is an unsubstituted aryl (e.g., $C_6$-$C_{10}$ aryl, $C_{10}$ aryl, or phenyl).

In embodiments, $R^{43}$ is $R^{44}$-substituted or unsubstituted heteroaryl (e.g., 5 to 10 membered heteroaryl, 5 to 9 membered heteroaryl, or 5 to 6 membered heteroaryl). In embodiments, $R^{43}$ is $R^{44}$-substituted heteroaryl (e.g., 5 to 10 membered heteroaryl, 5 to 9 membered heteroaryl, or 5 to 6 membered heteroaryl). In embodiments, $R^{43}$ is an unsubstituted heteroaryl (e.g., 5 to 10 membered heteroaryl, 5 to 9 membered heteroaryl, or 5 to 6 membered heteroaryl).

$R^{44}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{45}$-substituted or unsubstituted alkyl (e.g., $C_1$-$C_8$ alkyl, $C_1$-$C_6$ alkyl, or $C_1$-$C_4$ alkyl), $R^{45}$-substituted or unsubstituted heteroalkyl (e.g., 2 to 8 membered heteroalkyl, 2 to 6 membered heteroalkyl, or 2 to 4 membered heteroalkyl), $R^{45}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45}$-substituted or unsubstituted aryl (e.g., $C_6$-$C_{10}$ aryl, $C_{10}$ aryl, or phenyl), or $R^{45}$-substituted or unsubstituted heteroaryl (e.g., 5 to 10 membered heteroaryl, 5 to 9 membered heteroaryl, or 5 to 6 membered heteroaryl).

In embodiments, $R^{44}$ is $R^{45}$-substituted or unsubstituted alkyl (e.g., $C_1$-$C_8$ alkyl, $C_1$-$C_6$ alkyl, or $C_1$-$C_4$ alkyl). In embodiments, $R^{44}$ is $R^{45}$-substituted alkyl (e.g., $C_1$-$C_8$ alkyl, $C_1$-$C_6$ alkyl, or $C_1$-$C_4$ alkyl). In embodiments, $R^{44}$ is an unsubstituted alkyl (e.g., $C_1$-$C_8$ alkyl, $C_1$-$C_6$ alkyl, or $C_1$-$C_4$ alkyl).

In embodiments, $R^{44}$ is $R^{45}$-substituted or unsubstituted heteroalkyl (e.g., 2 to 8 membered heteroalkyl, 2 to 6 membered heteroalkyl, or 2 to 4 membered heteroalkyl). In embodiments, $R^{44}$ is $R^{45}$-substituted heteroalkyl (e.g., 2 to 8 membered heteroalkyl, 2 to 6 membered heteroalkyl, or 2 to 4 membered heteroalkyl). In embodiments, $R^{44}$ is an unsubstituted heteroalkyl (e.g., 2 to 8 membered heteroalkyl, 2 to 6 membered heteroalkyl, or 2 to 4 membered heteroalkyl).

In embodiments, $R^{44}$ is $R^{45}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{44}$ is $R^{45}$-substituted cycloalkyl (e.g., $C_3$-$C_8$ cycloalkyl, $C_3$-$C_6$ cycloalkyl, or $C_5$-$C_6$ cycloalkyl). In embodiments, $R^{44}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{44}$ is $R^{45}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{44}$ is $R^{45}$-substituted heterocycloalkyl (e.g., 3 to 8 membered heterocycloalkyl, 3 to 6 membered heterocycloalkyl, or 5 to 6 membered heterocycloalkyl). In embodiments, $R^{44}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{44}$ is $R^{45}$-substituted or unsubstituted aryl (e.g., $C_6$-$C_{10}$ aryl, $C_{10}$ aryl, or phenyl). In embodiments, $R^{44}$ is $R^{45}$-substituted aryl (e.g., $C_6$-$C_{10}$ aryl, $C_{10}$ aryl, or phenyl). In embodiments, $R^{44}$ is an unsubstituted aryl (e.g., $C_6$-$C_{10}$ aryl, $C_{10}$ aryl, or phenyl).

In embodiments, $R^{44}$ is $R^{45}$-substituted or unsubstituted heteroaryl (e.g., 5 to 10 membered heteroaryl, 5 to 9 membered heteroaryl, or 5 to 6 membered heteroaryl). In embodiments, $R^{44}$ is $R^{45}$-substituted heteroaryl (e.g., 5 to 10 membered heteroaryl, 5 to 9 membered heteroaryl, or 5 to 6 membered heteroaryl). In embodiments, $R^{44}$ is an unsubstituted heteroaryl (e.g., 5 to 10 membered heteroaryl, 5 to 9 membered heteroaryl, or 5 to 6 membered heteroaryl).

$R^{58}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{59}$-substituted or unsubstituted alkyl (e.g., $C_1$-$C_8$ alkyl, $C_1$-$C_6$ alkyl, or $C_1$-$C_4$ alkyl), $R^{59}$-substituted or unsubstituted heteroalkyl (e.g., 2 to 8 membered heteroalkyl, 2 to 6 membered heteroalkyl, or 2 to 4 membered heteroalkyl), $R^{59}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{59}$-substituted or unsubstituted heterocycloalkyl (e.g., 3 to 8 membered heterocycloalkyl, 3 to 6 membered heterocycloalkyl, or 5 to 6 membered heterocycloalkyl), $R^{59}$-substituted or unsubstituted aryl (e.g., $C_6$-$C_{10}$ aryl, $C_{10}$ aryl, or phenyl), or $R^{59}$-substituted or unsubstituted heteroaryl (e.g., 5 to 10 membered heteroaryl, 5 to 9 membered heteroaryl, or 5 to 6 membered heteroaryl).

In embodiments, $R^{58}$ is $R^{59}$-substituted or unsubstituted alkyl (e.g., $C_1$-$C_8$ alkyl, $C_1$-$C_6$ alkyl, or $C_1$-$C_4$ alkyl). In embodiments, $R^{58}$ is $R^{59}$-substituted alkyl (e.g., $C_1$-$C_8$ alkyl, $C_1$-$C_6$ alkyl, or $C_1$-$C_4$ alkyl). In embodiments, $R^{58}$ is an unsubstituted alkyl (e.g., $C_1$-$C_8$ alkyl, $C_1$-$C_6$ alkyl, or $C_1$-$C_4$ alkyl).

In embodiments, $R^{58}$ is $R^{59}$-substituted or unsubstituted heteroalkyl (e.g., 2 to 8 membered heteroalkyl, 2 to 6 membered heteroalkyl, or 2 to 4 membered heteroalkyl). In embodiments, $R^{58}$ is $R^{59}$-substituted heteroalkyl (e.g., 2 to 8 membered heteroalkyl, 2 to 6 membered heteroalkyl, or 2 to 4 membered heteroalkyl). In embodiments, $R^{58}$ is an unsubstituted heteroalkyl (e.g., 2 to 8 membered heteroalkyl, 2 to 6 membered heteroalkyl, or 2 to 4 membered heteroalkyl).

In embodiments, $R^{58}$ is $R^{59}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{58}$ is $R^{59}$-substituted cycloalkyl (e.g., $C_3$-$C_8$ cycloalkyl, $C_3$-$C_6$ cycloalkyl, or $C_5$-$C_6$ cycloalkyl). In embodiments, $R^{58}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{58}$ is $R^{59}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{58}$ is $R^{59}$-substituted heterocycloalkyl (e.g., 3 to 8 membered heterocycloalkyl, 3 to 6 membered heterocycloalkyl, or 5 to 6 membered heterocycloalkyl). In embodiments, $R^{58}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{58}$ is $R^{59}$-substituted or unsubstituted aryl (e.g., $C_6$-$C_{10}$ aryl, $C_{10}$ aryl, or phenyl). In embodiments, $R^{58}$ is $R^{59}$-substituted aryl (e.g., $C_6$-$C_{10}$ aryl, $C_{10}$ aryl, or phenyl). In embodiments, $R^{58}$ is an unsubstituted aryl (e.g., $C_6$-$C_{10}$ aryl, $C_{10}$ aryl, or phenyl).

In embodiments, $R^{58}$ is $R^{59}$-substituted or unsubstituted heteroaryl (e.g., 5 to 10 membered heteroaryl, 5 to 9 membered heteroaryl, or 5 to 6 membered heteroaryl). In embodiments, $R^{58}$ is $R^{59}$-substituted heteroaryl (e.g., 5 to 10 membered heteroaryl, 5 to 9 membered heteroaryl, or 5 to 6 membered heteroaryl). In embodiments, $R^{58}$ is an unsubstituted heteroaryl (e.g., 5 to 10 membered heteroaryl, 5 to 9 membered heteroaryl, or 5 to 6 membered heteroaryl).

$R^{59}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OC HCl$_2$, —OCHBr$_2$, —OCHI$_2$, —OCHF$_2$, $R^{60}$-substituted or unsubstituted alkyl (e.g., $C_1$-$C_8$ alkyl, $C_1$-$C_6$ alkyl, or $C_1$-$C_4$ alkyl), $R^{60}$-substituted or unsubstituted heteroalkyl (e.g., 2 to 8 membered heteroalkyl, 2 to 6 membered heteroalkyl, or 2 to 4 membered heteroalkyl), $R^{60}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{60}$-substituted or unsubstituted heterocycloalkyl (e.g., 3 to 8 membered heterocycloalkyl, 3 to 6 membered heterocycloalkyl, or 5 to 6 membered heterocycloalkyl), $R^{60}$-substituted or unsubstituted aryl (e.g., $C_6$-$C_{10}$ aryl, $C_{10}$ aryl, or phenyl), or $R^{60}$-substituted or unsubstituted heteroaryl (e.g., 5 to 10 membered heteroaryl, 5 to 9 membered heteroaryl, or 5 to 6 membered heteroaryl).

In embodiments, $R^{59}$ is $R^{60}$-substituted or unsubstituted alkyl (e.g., $C_1$-$C_8$ alkyl, $C_1$-$C_6$ alkyl, or $C_1$-$C_4$ alkyl). In embodiments, $R^{59}$ is $R^{60}$-substituted alkyl (e.g., $C_1$-$C_8$ alkyl, $C_1$-$C_6$ alkyl, or $C_1$-$C_4$ alkyl). In embodiments, $R^{59}$ is an unsubstituted alkyl (e.g., $C_1$-$C_8$ alkyl, $C_1$-$C_6$ alkyl, or $C_1$-$C_4$ alkyl).

In embodiments, $R^{59}$ is $R^{60}$-substituted or unsubstituted heteroalkyl (e.g., 2 to 8 membered heteroalkyl, 2 to 6 membered heteroalkyl, or 2 to 4 membered heteroalkyl). In embodiments, $R^{59}$ is $R^{60}$-substituted heteroalkyl (e.g., 2 to 8 membered heteroalkyl, 2 to 6 membered heteroalkyl, or 2 to 4 membered heteroalkyl). In embodiments, $R^{59}$ is an unsubstituted heteroalkyl (e.g., 2 to 8 membered heteroalkyl, 2 to 6 membered heteroalkyl, or 2 to 4 membered heteroalkyl).

In embodiments, $R^{59}$ is $R^{60}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{59}$ is $R^{60}$-substituted cycloalkyl (e.g., $C_3$-$C_8$ cycloalkyl, $C_3$-$C_6$ cycloalkyl, or $C_5$-$C_6$ cycloalkyl). In embodiments, $R^{59}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{59}$ is $R^{60}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{59}$ is $R^{60}$-substituted heterocycloalkyl (e.g., 3 to 8 membered heterocycloalkyl, 3 to 6 membered heterocycloalkyl, or 5 to 6 membered heterocycloalkyl). In embodiments, $R^{59}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{59}$ is $R^{60}$-substituted or unsubstituted aryl (e.g., $C_6$-$C_{10}$ aryl, $C_{10}$ aryl, or phenyl). In embodiments, $R^{59}$ is $R^{60}$-substituted aryl (e.g., $C_6$-$C_{10}$ aryl, $C_{10}$ aryl, or phenyl). In embodiments, $R^{59}$ is an unsubstituted aryl (e.g., $C_6$-$C_{10}$ aryl, $C_{10}$ aryl, or phenyl).

In embodiments, $R^{59}$ is $R^{60}$-substituted or unsubstituted heteroaryl (e.g., 5 to 10 membered heteroaryl, or 5 to 6 membered heteroaryl). In embodiments, $R^{59}$ is $R^{60}$-substituted heteroaryl (e.g., 5 to 10 membered heteroaryl, 5 to 9 membered heteroaryl, or 5 to 6 membered heteroaryl). In embodiments, $R^{59}$ is an unsubstituted heteroaryl (e.g., 5 to 10 membered heteroaryl, 5 to 9 membered heteroaryl, or 5 to 6 membered heteroaryl).

$R^{16A}$, $R^{16B}$, $R^{16C}$, $R^{16D}$, $R^{18}$, $R^{19A}$, $R^{19B}$, $R^{19C}$, $R^{19D}$, $R^{21}$, $R^{22A}$, $R^{22B}$, $R^{22C}$, $R^{22D}$, $R^{24}$, $R^{25A}$, $R^{25B}$, $R^{25C}$, $R^{25D}$, $R^{27}$, $R^{28A}$, $R^{28B}$, $R^{28C}$, $R^{28D}$, $R^{30}$, $R^{31A}$, $R^{31B}$, $R^{31C}$, $R^{31D}$, $R^{33}$, $R^{34A}$, $R^{34B}$, $R^{34C}$, $R^{34D}$, $R^{36}$, $R^{37A}$, $R^{37B}$, $R^{37C}$, $R^{37D}$, $R^{39}$, $R^{40A}$, $R^{40B}$, $R^{40C}$, $R^{40D}$, $R^{42}$, $R^{43A}$, $R^{43B}$, $R^{43C}$, $R^{43D}$, $R^{45}$, $R^{58B}$ and $R^{60}$ are independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OC HCl$_2$, —OCHBr$_2$, —OCHI$_2$, —OCHF$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $R^{16A}$, $R^{16B}$, $R^{16C}$, $R^{16D}$, $R^{18}$, $R^{19A}$, $R^{19B}$, $R^{19C}$, $R^{19D}$, $R^{21}$, $R^{22A}$, $R^{22B}$, $R^{22C}$, $R^{22D}$, $R^{24}$, $R^{25A}$, $R^{25B}$, $R^{25C}$, $R^{25D}$, $R^{27}$, $R^{28A}$, $R^{28B}$, $R^{28C}$, $R^{28D}$, $R^{30}$, $R^{31A}$, $R^{31B}$, $R^{31C}$, $R^{31D}$, $R^{33}$, $R^{34A}$, $R^{34B}$, $R^{34C}$, $R^{34D}$, $R^{36}$, $R^{37A}$, $R^{37B}$, $R^{37C}$, $R^{37D}$, $R^{39}$, $R^{40A}$, $R^{40B}$, $R^{40C}$, $R^{40D}$, $R^{42}$, $R^{43A}$, $R^{43B}$, $R^{43C}$, $R^{43D}$, $R^{45}$, $R^{58B}$ and $R^{60}$ are independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $X^{1.1}$, $X^{2.1}$, $X^{3.1}$, $X^{4.1}$, $X^{5.1}$, $X^{6.1}$, $X^{8.1}$, $X^{9.1}$, $X^{10.1}$, $X^{11.1}$ are independently —Cl, —Br, —I or —F.

In embodiments, $X^{1.1}$ is —Cl. In embodiments, $X^{1.1}$ is —F. In embodiments, $X^{1.1}$ is —Br. In embodiments, $X^{1.1}$ is —I. In embodiments, $X^{2.1}$ is —Cl. In embodiments, $X^{2.1}$ is —F. In embodiments, $X^{2.1}$ is —Br. In embodiments, $X^{2.1}$ is —I. In embodiments, $X^{3.1}$ is —Cl. In embodiments, $X^{3.1}$ is —F. In embodiments, $X^{3.1}$ is —Br. In embodiments, $X^{3.1}$ is —I. In embodiments, $X^{4.1}$ is —Cl. In embodiments, $X^{4.1}$ is —F. In embodiments, $X^{4.1}$ is —Br. In embodiments, $X^{4.1}$ is —I. In embodiments, $X^{5.1}$ is —Cl. In embodiments, $X^{5.1}$ is —F. In embodiments, $X^{5.1}$ is —Br. In embodiments, $X^{5.1}$ is —I. In embodiments, $X^{6.1}$ is —Cl. In embodiments, $X^{6.1}$ is —F. In embodiments, $X^{6.1}$ is —Br. In embodiments, $X^{6.1}$ is —I. In embodiments, $X^{8.1}$ is —Cl. In embodiments, $X^{8.1}$ is —F. In embodiments, $X^{8.1}$ is —Br. In embodiments, $X^{8.1}$ is —I. In embodiments, $X^{9.1}$ is —Cl. In embodiments, $X^{9.1}$ is —F. In embodiments, $X^{9.1}$ is —Br. In embodiments, $X^{9.1}$ is —I. In embodiments, $X^{10.1}$ is —Cl. In embodiments, $X^{10.1}$ is —F. In embodiments, $X^{10.1}$ is —Br. In embodiments, $X^{10.1}$ is —I. In embodiments, $X^{11.1}$ is —Cl. In embodiments, $X^{11.1}$ is —F. In embodiments, $X^{11.1}$ is —Br. In embodiments, $X^{11.1}$ is —I.

In embodiments, $X^{1.1}$ is —Cl, and $X^1$ is N. In embodiments, $X^{1.1}$ is —F, and $X^1$ is N. In embodiments, $X^{1.1}$ is —Br, and $X^1$ is N. In embodiments, $X^{1.1}$ is —I, and $X^1$ is N. In embodiments, $X^{2.1}$ is —Cl, and $X^1$ is N. In embodiments, $X^{2.1}$ is —F, and $X^1$ is N. In embodiments, $X^{2.1}$ is —Br, and $X^1$ is N. In embodiments, $X^{2.1}$ is —I, and $X^1$ is N. In embodiments, $X^{3.1}$ is —Cl, and $X^1$ is N. In embodiments, $X^{3.1}$ is —F, and $X^1$ is N. In embodiments, $X^{3.1}$ is —Br, and $X^1$ is N. In embodiments, $X^{3.1}$ is —I, and $X^1$ is N. In embodiments, $X^{4.1}$ is —Cl, and $X^1$ is N. In embodiments, $X^{4.1}$ is —F, and $X^1$ is N. In embodiments, $X^{4.1}$ is —Br, and $X^1$ is N. In embodiments, $X^{4.1}$ is —I, and $X^1$ is N. In embodiments, $X^{5.1}$ is —Cl, and $X^1$ is N. In embodiments, $X^{5.1}$ is —F, and $X^1$ is N. In embodiments, $X^{5.1}$ is —Br, and $X^1$ is N. In embodiments, $X^{5.1}$ is —I, and $X^1$ is N. In embodiments, $X^{6.1}$ is —Cl, and $X^1$ is N. In embodiments, $X^{6.1}$ is —F, and $X^1$ is N. In embodiments, $X^{6.1}$ is —Br, and $X^1$ is N. In embodiments, $X^{6.1}$ is —I, and $X^1$ is N. In embodiments, $X^{7.1}$ is —Cl, and $X^1$ is N. In embodiments, $X^{7.1}$ is —F, and $X^1$ is N. In embodiments, $X^{7.1}$ is —Br, and $X^1$ is N. In embodiments, $X^{7.1}$ is —I, and $X^1$ is N. In embodiments, $X^{8.1}$ is —Cl, and $X^1$ is N. In embodiments, $X^{8.1}$ is —F, and $X^1$ is N. In embodiments, $X^{8.1}$ is —Br, and $X^1$ is N. In embodiments, $X^{8.1}$ is —I, and $X^1$ is N. In embodiments, $X^{9.1}$ is —Cl, and $X^1$ is N. In embodiments, $X^{9.1}$ is —F, and $X^1$ is N. In embodiments, $X^{9.1}$ is —Br, and $X^1$ is N. In embodiments, $X^{9.1}$ is —I, and $X^1$ is N. In embodiments, $X^{10.1}$ is —Cl, and $X^1$ is N. In embodiments, $X^{10.1}$ is —F, and $X^1$ is N. In embodiments, $X^{10.1}$ is —Br, and $X^1$ is N. In embodiments, $X^{10.1}$ is —I, and $X^1$ is N. In embodiments, $X^{11.1}$ is —Cl, and $X^1$ is N. In embodiments, $X^{11.1}$ is —F, and $X^1$ is N. In embodiments, $X^{11.1}$ is —Br, and $X^1$ is N. In embodiments, $X^{11.1}$ is —I, and $X^1$ is N.

In embodiments, $X^{1.1}$ is —Cl, and $X^2$ is N. In embodiments, $X^{1.1}$ is —F, and $X^2$ is N. In embodiments, $X^{1.1}$ is —Br, and $X^2$ is N. In embodiments, $X^{1.1}$ is —I, and $X^2$ is N. In embodiments, $X^{2.1}$ is —Cl, and $X^2$ is N. In embodiments, $X^{2.1}$ is —F, and $X^2$ is N. In embodiments, $X^{2.1}$ is —Br, and $X^2$ is N. In embodiments, $X^{2.1}$ is —I, and $X^2$ is N. In embodiments, $X^{3.1}$ is —Cl, and $X^2$ is N. In embodiments, $X^{3.1}$ is —F, and $X^2$ is N. In embodiments, $X^{3.1}$ is —Br, and $X^2$ is N. In embodiments, $X^{3.1}$ is —I, and $X^2$ is N. In embodiments, $X^{4.1}$ is —Cl, and $X^2$ is N. In embodiments, $X^{4.1}$ is —F, and $X^2$ is N. In embodiments, $X^{4.1}$ is —Br, and $X^2$ is N. In embodiments, $X^{4.1}$ is —I, and $X^2$ is N. In embodiments, $X^{5.1}$ is —Cl, and $X^2$ is N. In embodiments, $X^{5.1}$ is —F, and $X^2$ is N. In embodiments, $X^{5.1}$ is —Br, and $X^2$ is N. In embodiments, $X^{5.1}$ is —I, and $X^2$ is N. In embodiments, $X^{6.1}$ is —Cl, and $X^2$ is N. In embodiments, $X^{6.1}$ is —F, and $X^2$ is N. In embodiments, $X^{6.1}$ is —Br, and $X^2$ is N. In embodiments, $X^{6.1}$ is —I, and $X^2$ is N. In embodiments, $X^{7.1}$ is —Cl, and $X^2$ is N. In embodiments, $X^{7.1}$ is —F, and $X^2$ is N. In embodiments, $X^{7.1}$ is —Br, and $X^2$ is N. In embodiments, $X^{7.1}$ is —I, and $X^2$ is N. In embodiments, $X^{8.1}$ is —Cl, and $X^2$ is N. In embodiments, $X^{8.1}$ is —F, and $X^2$ is N. In embodiments, $X^{8.1}$ is —Br, and $X^2$ is N. In embodiments, $X^{8.1}$ is —I, and $X^2$ is N. In embodiments, $X^{9.1}$ is —Cl, and $X^2$ is N. In embodiments, $X^{9.1}$ is —F, and $X^2$ is N. In embodiments, $X^{9.1}$ is —Br, and $X^2$ is N. In embodiments, $X^{9.1}$ is —I, and $X^2$ is N. In embodiments, $X^{10.1}$ is —Cl, and $X^2$ is N. In embodiments, $X^{10.1}$ is —F, and $X^2$ is N. In embodiments, $X^{10.1}$ is —Br, and $X^2$ is N. In embodiments, $X^{10.1}$ is —I, and $X^2$ is N. In embodiments, $X^{11.1}$ is —Cl, and $X^2$ is N. In embodiments, $X^{11.1}$ is —F, and $X^2$ is N. In embodiments, $X^{11.1}$ is —Br, and $X^2$ is N. In embodiments, $X^{11.1}$ is —I, and $X^2$ is N.

In embodiments, $X^{1.1}$ is —Cl, and $X^3$ is N. In embodiments, $X^{1.1}$ is —F, and $X^3$ is N. In embodiments, $X^{1.1}$ is —Br, and $X^3$ is N. In embodiments, $X^{1.1}$ is —I, and $X^3$ is N. In embodiments, $X^{2.1}$ is —Cl, and $X^3$ is N. In embodiments, $X^{2.1}$ is —F, and $X^3$ is N. In embodiments, $X^{2.1}$ is —Br, and $X^3$ is N. In embodiments, $X^{2.1}$ is —I, and $X^3$ is N. In embodiments, $X^{3.1}$ is —Cl, and $X^3$ is N. In embodiments, $X^{3.1}$ is —F, and $X^3$ is N. In embodiments, $X^{3.1}$ is —Br, and $X^3$ is N. In embodiments, $X^{3.1}$ is —I, and $X^3$ is N. In embodiments, $X^{4.1}$ is —Cl, and $X^3$ is N. In embodiments, $X^{4.1}$ is —F, and $X^3$ is N. In embodiments, $X^{4.1}$ is —Br, and $X^3$ is N. In embodiments, $X^{4.1}$ is —I, and $X^3$ is N. In embodiments, $X^{5.1}$ is —Cl, and $X^3$ is N. In embodiments, $X^{5.1}$ is —F, and $X^3$ is N. In embodiments, $X^{51}$ is —Br, and $X^3$ is N. In embodiments, $X^{5.1}$ is —I, and $X^3$ is N. In embodiments, $X^{6.1}$ is —Cl, and $X^3$ is N. In embodiments, $X^{6.1}$ is —F, and $X^3$ is N. In embodiments, $X^{6.1}$ is —Br, and $X^3$ is N. In embodiments, $X^{6.1}$ is —I, and $X^3$ is N. In embodiments, $X^{7.1}$ is —Cl, and $X^3$ is N. In embodiments, $X^{7.1}$ is —F, and $X^3$ is N. In embodiments, $X^{7.1}$ is —Br, and $X^3$ is N. In embodiments, $X^{7.1}$ is —I, and $X^3$ is N. In embodiments, $X^{8.1}$ is —Cl, and $X^3$ is N. In embodiments, $X^{8.1}$ is —F, and $X^3$ is N. In embodiments, $X^{8.1}$ is —Br, and $X^3$ is N. In embodiments, $X^{8.1}$ is —I, and $X^3$ is N. In embodiments, $X^{9.1}$ is —Cl, and $X^3$ is N. In embodiments, $X^{9.1}$ is —F, and $X^3$ is N. In embodiments, $X^{9.1}$ is —Br, and $X^3$ is N. In embodiments, $X^{9.1}$ is —I, and $X^3$ is N. In embodiments, $X^{10.1}$ is —Cl, and $X^3$ is N. In embodiments, $X^{10.1}$ is —F, and $X^3$ is N. In embodiments, $X^{10.1}$ is —Br, and $X^3$ is N. In embodiments, $X^{10.1}$ is —I, and $X^3$ is N. In embodiments, $X^{11.1}$ is —Cl, and $X^3$ is N. In embodiments, $X^{11.1}$ is —F, and $X^3$ is N. In embodiments, $X^{11.1}$ is —Br, and $X^3$ is N. In embodiments, $X^{11.1}$ is —I, and $X^3$ is N.

In embodiments, the symbol n1 is an integer from 0 to 4. In embodiments, n1 is 0. In embodiments, n1 is 1. In embodiments, n1 is 2. In embodiments, n1 is 3. In embodiments, n1 is 4.

In embodiments, the symbol n2 is an integer from 0 to 4. In embodiments, n2 is 0. In embodiments, n2 is 1. In embodiments, n2 is 2. In embodiments, n2 is 3. In embodiments, n2 is 4.

In embodiments, the symbol n3 is an integer from 0 to 4. In embodiments, n3 is 0. In embodiments, n3 is 1. In embodiments, n3 is 2. In embodiments, n3 is 3. In embodiments, n3 is 4.

In embodiments, the symbol n4 is an integer from 0 to 4. In embodiments, n4 is 0. In embodiments, n4 is 1. In embodiments, n4 is 2. In embodiments, n4 is 3. In embodiments, n4 is 4.

In embodiments, the symbol n5 is an integer from 0 to 4. In embodiments, n5 is 0. In embodiments, n5 is 1. In embodiments, n5 is 2. In embodiments, n5 is 3. In embodiments, n5 is 4.

In embodiments, the symbol n6 is an integer from 0 to 4. In embodiments, n6 is 0. In embodiments, n6 is 1. In embodiments, n6 is 2. In embodiments, n6 is 3. In embodiments, n6 is 4.

In embodiments, the symbol n8 is an integer from 0 to 4. In embodiments, n8 is 0. In embodiments, n8 is 1. In embodiments, n8 is 2. In embodiments, n8 is 3. In embodiments, n8 is 4.

In embodiments, the symbol n9 is an integer from 0 to 4. In embodiments, n9 is 0. In embodiments, n9 is 1. In embodiments, n9 is 2. In embodiments, n9 is 3. In embodiments, n9 is 4.

In embodiments, the symbol n10 is an integer from 0 to 4. In embodiments, n10 is 0. In embodiments, n10 is 1. In embodiments, n10 is 2. In embodiments, n10 is 3. In embodiments, n10 is 4.

In embodiments, the symbol n11 is an integer from 0 to 4. In embodiments, n11 is 0. In embodiments, n11 is 1. In embodiments, n11 is 2. In embodiments, n11 is 3. In embodiments, n11 is 4.

In embodiments, the symbols m1 and v1 are independently 1 or 2. In embodiments, m1 is 1. In embodiments, m1 is 2. In embodiments, v1 is 1. In embodiments, v1 is 2.

In embodiments, the symbols m2 and v2 are independently 1 or 2. In embodiments, m2 is 1. In embodiments, m2 is 2. In embodiments, v2 is 1. In embodiments, v2 is 2.

In embodiments, the symbols m3 and v3 are independently 1 or 2. In embodiments, m3 is 1. In embodiments, m3 is 2. In embodiments, v3 is 1. In embodiments, v3 is 2.

In embodiments, the symbols m4 and v4 are independently 1 or 2. In embodiments, m4 is 1. In embodiments, m4 is 2. In embodiments, v4 is 1. In embodiments, v4 is 2.

In embodiments, the symbols m5 and v5 are independently 1 or 2. In embodiments, m5 is 1. In embodiments, m5 is 2. In embodiments, v5 is 1. In embodiments, v5 is 2.

In embodiments, the symbols m6 and v6 are independently 1 or 2. In embodiments, m6 is 1. In embodiments, m6 is 2. In embodiments, v6 is 1. In embodiments, v6 is 2.

In embodiments, the symbols m8 and v8 are independently 1 or 2. In embodiments, m8 is 1. In embodiments, m8 is 2. In embodiments, v8 is 1. In embodiments, v8 is 2.

In embodiments, the symbols m9 and v9 are independently 1 or 2. In embodiments, m9 is 1. In embodiments, m9 is 2. In embodiments, v9 is 1. In embodiments, v9 is 2.

In embodiments, the symbols m10 and v10 are independently 1 or 2. In embodiments, m10 is 1. In embodiments, m10 is 2. In embodiments, v10 is 1. In embodiments, v10 is 2.

In embodiments, the symbols m11 and v11 are independently 1 or 2. In embodiments, m11 is 1. In embodiments, m11 is 2. In embodiments, v11 is 1. In embodiments, v11 is 2.

In embodiments, the symbol z1 is an integer from 0 to 5. In embodiments, z1 is 0. In embodiments, z1 is 1. In embodiments, z1 is 2. In embodiments, z1 is 3. In embodiments, z1 is 4. In embodiments, z1 is 5.

In embodiments, the symbol z2 is an integer from 0 to 13. In embodiments, z2 is 0. In embodiments, z2 is 1. In embodiments, z2 is 2. In embodiments, z2 is 3. In embodiments, z2 is 4. In embodiments, z2 is 5. In embodiments, z2 is 6. In embodiments, z2 is 7. In embodiments, z2 is 8. In embodiments, z2 is 9. In embodiments, z2 is 10. In embodiments, z2 is 11. In embodiments, z2 is 12. In embodiments, z2 is 13.

The symbol z3 is an integer from 0 to 12. In embodiments, z3 is an integer from 0 to 2. In embodiments, z3 is 0. In embodiments, z3 is 1. In embodiments, z3 is 2. In embodiments, z3 is 3. In embodiments, z3 is 4. In embodiments, z3 is 5. In embodiments, z3 is 6. In embodiments, z3 is 7. In embodiments, z3 is 8. In embodiments, z3 is 9. In embodiments, z3 is 10. In embodiments, z3 is 11. In embodiments, z3 is 12.

In embodiments, z2 and z3 are independently an integer from 0 to 2. In embodiments, z3 and z5 are independently 1.

In embodiments, the symbol z4 is an integer from 0 to 3. In embodiments, z4 is 0. In embodiments, z4 is 1. In embodiments, z4 is 2. In embodiments, z4 is 3. In embodiments, z1 is 2 and z4 is 1.

In embodiments, the compounds provided herein have structural Formula (Ia):

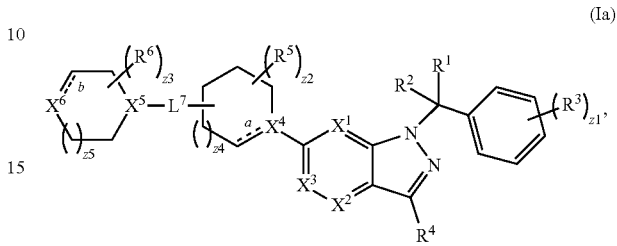

or a pharmaceutically acceptable salt thereof. $X^5$ is $CR^{12}$ or N. $X^6$ is $CR^{13}$, $CR^{13}R^{14}$, N or $NR^{15}$. $R^{12}$ is hydrogen, halogen, $-CX^{12.1}_3$, $-CHX^{12.1}_2$, $-CH_2X^{12.1}$, $-CN$, $-SO_{n12}R^{12A}$, $-SO_{v12}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m12}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{13}$ is hydrogen, halogen, $-CX^{13.1}_3$, $-CHX^{13.1}_2$, $-CH_2X^{13.1}$, $-CN$, $-SO_{n13}R^{13A}$, $-SO_{v13}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m13}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{14}$ is hydrogen, halogen, $-CX^{14.1}_3$, $-CHX^{14.1}_2$, $-CH_2X^{14.1}$, $-CN$, $-SO_{n14}R^{14A}$, $-SO_{v14}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m14}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{15}$ is hydrogen, halogen, $-CX^{15.1}_3$, $-CHX^{15.1}_2$, $-CH_2X^{15.1}$, $-CN$, $-SO_{n15}R^{15A}$, $-SO_{v15}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m15}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted aryl, or substituted or unsubstituted heteroaryl. $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$ and $R^{15D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{12B}$ and $R^{12C}$, $R^{13B}$ and $R^{13C}$, $R^{14B}$ and $R^{14C}$ and $R^{15B}$ and $R^{15C}$ substituents bonded to the same nitrogen atom may optionally be joined to form a substituted or unsubstituted heterocycloalkyl or substituted or unsubstituted heteroaryl. The symbol ⹀ is a single bond or double bond, wherein if ⹀ is a single bond, then $X^6$ is $CR^{13}R^{14}$ or $NR^{15}$, and if ⹀ is a double bond, then $X^6$ is N or $CR^{13}$. The symbol z3 is an integer from 0 to 12. The symbol z5 is an integer from 0 to 3. $X^{12.1}$, $X^{13.1}$, $X^{14.1}$ and $X^{15.1}$ are independently —Cl, —Br, —I or —F.

z1, z2, z3, z4, ⹀, $X^1$, $X^2$, $X^3$, $X^4$, $L^7$, $R^1$, $R^2$, $R^3$, $R^4$, $R^5$ and $R^6$ are as described herein, including embodiments.

In embodiments, $X^5$ is $CR^{12}$ or N. In embodiments, $X^5$ is $CR^{12}$. In embodiments, $X^5$ is N.

In embodiments, $X^6$ is $CR^{13}$, $CR^{13}R^{14}$, N or $NR^{15}$. In embodiments, $X^6$ is $CR^{13}$. In embodiments, $X^6$ is $CR^{13}R^{14}$. In embodiments, $X^6$ is N. In embodiments, $X^6$ is $NR^{15}$.

In embodiments, the symbol z5 is an integer from 0 to 3. In embodiments, z5 is 0. In embodiments, z5 is 1. In embodiments, z5 is 2. In embodiments, z5 is 3.

In embodiments, the symbol ⹀ is a single bond or double bond, wherein if ⹀ is a single bond, then $X^6$ is $CR^{13}R^{14}$ or $NR^{15}$, and if ⹀ is a double bond, then $X^6$ is N or $CR^{13}$.

In embodiments, $R^{12}$ is hydrogen, halogen, —$CX^{12.1}_3$, —$CHX^{12.1}_2$, —$CH_2X^{12.1}$, —CN, —$SO_{n12}R^{12A}$, —$SO_{v12}NR^{12B}R^{12C}$, —$NHNR^{12B}R^{12C}$, —$ONR^{12B}R^{12C}$, —$NHC(O)NHNR^{12B}R^{12C}$, —$NHC(O)NR^{12B}R^{12C}$, —$N(O)_{m12}$, —$NR^{12B}R^{12C}$, —$C(O)R^{12D}$, —$C(O)OR^{12D}$, —$C(O)NR^{12B}R^{12C}$, —$OR^{12A}$, —$NR^{12B}SO_2R^{12A}$, —$NR^{12B}C(O)R^{12D}$, —$NR^{12B}C(O)OR^{12D}$, —$NR^{12B}OR^{12D}$, —$OCX^{12.1}_3$, —$OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{12}$ is hydrogen, halogen, —$CX^{12.1}_3$, —$CHX^{12.1}_2$, —$CH_2X^{12.1}$, —CN, —$SO_{n12}R^{12A}$, —$SO_{v12}NR^{12B}R^{12C}$, —$NHNR^{12B}R^{12C}$, —$ONR^{12B}R^{12C}$, —$NHC(O)NHNR^{12B}R^{12C}$, —$NHC(O)NR^{12B}R^{12C}$, —$N(O)_{m12}$, —$NR^{12B}R^{12C}$, —$C(O)R^{12D}$, —$C(O)OR^{12D}$, —$C(O)NR^{12B}R^{12C}$, —$OR^{12A}$, —$NR^{12B}SO_2R^{12A}$, —$NR^{12B}C(O)R^{12D}$, —$NR^{12B}C(O)OR^{12D}$, —$NR^{12B}OR^{12D}$, —$OCX^{12.1}_3$, —$OCHX^{12.1}_2$, $R^{46}$-substituted or unsubstituted alkyl (e.g., $C_1$-$C_8$ alkyl, $C_1$-$C_6$ alkyl, or $C_1$-$C_4$ alkyl), $R^{46}$-substituted or unsubstituted heteroalkyl (e.g., 2 to 8 membered heteroalkyl, 2 to 6 membered heteroalkyl, or 2 to 4 membered heteroalkyl), $R^{46}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46}$-substituted or unsubstituted aryl (e.g., $C_6$-$C_{10}$ aryl, $C_{10}$ aryl, or phenyl), or $R^{46}$-substituted or unsubstituted heteroaryl (e.g., 5 to 10 membered heteroaryl, 5 to 9 membered heteroaryl, or 5 to 6 membered heteroaryl).

In embodiments, $R^{12}$ is $R^{46}$-substituted or unsubstituted alkyl (e.g., $C_1$-$C_8$ alkyl, $C_1$-$C_6$ alkyl, or $C_1$-$C_4$ alkyl). In embodiments, $R^{12}$ is $R^{46}$-substituted alkyl (e.g., $C_1$-$C_8$ alkyl, $C_1$-$C_6$ alkyl, or $C_1$-$C_4$ alkyl). In embodiments, $R^{12}$ is an unsubstituted alkyl (e.g., $C_1$-$C_8$ alkyl, $C_1$-$C_6$ alkyl, or $C_1$-$C_4$ alkyl).

In embodiments, $R^{12}$ is $R^{46}$-substituted or unsubstituted heteroalkyl (e.g., 2 to 8 membered heteroalkyl, 2 to 6 membered heteroalkyl, or 2 to 4 membered heteroalkyl). In embodiments, $R^{12}$ is $R^{46}$-substituted heteroalkyl (e.g., 2 to 8 membered heteroalkyl, 2 to 6 membered heteroalkyl, or 2 to 4 membered heteroalkyl). In embodiments, $R^{12}$ is an unsubstituted heteroalkyl (e.g., 2 to 8 membered heteroalkyl, 2 to 6 membered heteroalkyl, or 2 to 4 membered heteroalkyl).

In embodiments, $R^{12}$ is $R^{46}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{12}$ is $R^{46}$-substituted cycloalkyl (e.g., $C_3$-$C_8$ cycloalkyl, $C_3$-$C_6$ cycloalkyl, or $C_5$-$C_6$ cycloalkyl). In embodiments, $R^{12}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{12}$ is $R^{46}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{12}$ is $R^{46}$-substituted heterocycloalkyl (e.g., 3 to 8 membered heterocycloalkyl, 3 to 6 membered heterocycloalkyl, or 5 to 6 membered heterocycloalkyl). In embodiments, $R^{12}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{12}$ is $R^{46}$-substituted or unsubstituted aryl (e.g., $C_6$-$C_{10}$ aryl, $C_{10}$ aryl, or phenyl). In embodiments, $R^{12}$ is $R^{46}$-substituted aryl (e.g., $C_6$-$C_{10}$ aryl, $C_{10}$ aryl, or phenyl). In embodiments, $R^{12}$ is an unsubstituted aryl (e.g., $C_6$-$C_{10}$ aryl, $C_{10}$ aryl, or phenyl).

In embodiments, $R^{12}$ is $R^{46}$-substituted or unsubstituted heteroaryl (e.g., 5 to 10 membered heteroaryl, 5 to 9 membered heteroaryl, or 5 to 6 membered heteroaryl). In embodiments, $R^{12}$ is $R^{46}$-substituted heteroaryl (e.g., 5 to 10 membered heteroaryl, 5 to 9 membered heteroaryl, or 5 to 6 membered heteroaryl). In embodiments, $R^{12}$ is an unsubstituted heteroaryl (e.g., 5 to 10 membered heteroaryl, 5 to 9 membered heteroaryl, or 5 to 6 membered heteroaryl).

In embodiments, $R^{13}$ is hydrogen, halogen, —$CX^{13.1}_3$, —$CHX^{13.1}_2$, —$CH_2X^{13.1}$, —CN, —$SO_{n13}R^{13A}$, —$SO_{v13}NR^{13B}R^{13C}$, —$NHNR^{13B}R^{13C}$, —$ONR^{13B}R^{13C}$, —$NHC(O)NHNR^{13B}R^{13C}$, —$NHC(O)NR^{13B}R^{13C}$, —$N(O)_{m13}$, —$NR^{13B}R^{13C}$, —$C(O)R^{13D}$, —$C(O)OR^{13D}$, —$C(O)NR^{13B}R^{13C}$, —$OR^{13A}$, —$NR^{13B}SO_2R^{13A}$, —$NR^{13B}C(O)R^{13D}$, —$NR^{13B}C(O)OR^{13D}$, —$NR^{13B}OR^{13D}$, —$OCX^{13.1}_3$, —$OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{13}$ is hydrogen, halogen, —$CX^{13.1}_3$, —$CHX^{13.1}_2$, —$CH_2X^{13.1}$, —CN, —$SO_{n13}R^{13A}$, —$SO_{v13}NR^{13B}R^{13C}$, —$NHNR^{13B}R^{13C}$, —$ONR^{13B}R^{13C}$, —$NHC(O)NHNR^{13B}R^{13C}$, —$NHC(O)NR^{13B}R^{13C}$, —$N(O)_{m13}$, —$NR^{13B}R^{13C}$, —$C(O)R^{13D}$, —$C(O)OR^{13D}$, —$C(O)NR^{13B}R^{13C}$, —$OR^{13A}$, —$NR^{13B}SO_2R^{13A}$, —$NR^{13B}C(O)R^{13D}$, —$NR^{13B}C(O)OR^{13D}$, —$NR^{13B}OR^{13D}$, —$OCX^{13.1}_3$, —$OCHX^{13.1}_2$, $R^{49}$-substituted or unsubstituted alkyl (e.g., $C_1$-$C_8$ alkyl, $C_1$-$C_6$ alkyl, or $C_1$-$C_4$ alkyl), $R^{49}$-substituted or unsubstituted heteroalkyl (e.g., 2 to 8 membered heteroalkyl, 2 to 6 membered heteroalkyl, or 2 to 4 membered heteroalkyl), $R^{49}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{49}$-substituted or unsubstituted heterocycloalkyl (e.g., 3 to 8 membered heterocycloalkyl, 3 to 6 membered heterocycloalkyl, or 5 to 6 membered heterocycloalkyl), $R^{49}$-substituted or unsubstituted aryl (e.g., $C_6$-$C_{10}$ aryl, $C_{10}$ aryl, or phenyl), or $R^{49}$-substituted or unsubstituted heteroaryl (e.g., 5 to 10 membered heteroaryl, 5 to 9 membered heteroaryl, or 5 to 6 membered heteroaryl).

In embodiments, $R^{13}$ is $R^{49}$-substituted or unsubstituted alkyl (e.g., $C_1$-$C_8$ alkyl, $C_1$-$C_6$ alkyl, or $C_1$-$C_4$ alkyl). In embodiments, $R^{13}$ is $R^{49}$-substituted alkyl (e.g., $C_1$-$C_8$ alkyl, $C_1$-$C_6$ alkyl, or $C_1$-$C_4$ alkyl). In embodiments, $R^{13}$ is an unsubstituted alkyl (e.g., $C_1$-$C_8$ alkyl, $C_1$-$C_6$ alkyl, or $C_1$-$C_4$ alkyl).

In embodiments, $R^{13}$ is $R^{49}$-substituted or unsubstituted heteroalkyl (e.g., 2 to 8 membered heteroalkyl, 2 to 6 membered heteroalkyl, or 2 to 4 membered heteroalkyl). In embodiments, $R^{13}$ is $R^{49}$-substituted heteroalkyl (e.g., 2 to 8 membered heteroalkyl, 2 to 6 membered heteroalkyl, or 2 to 4 membered heteroalkyl). In embodiments, $R^{13}$ is an unsubstituted heteroalkyl (e.g., 2 to 8 membered heteroalkyl, 2 to 6 membered heteroalkyl, or 2 to 4 membered heteroalkyl).

In embodiments, $R^{13}$ is $R^{49}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{13}$ is $R^{49}$-substituted cycloalkyl (e.g., $C_3$-$C_8$ cycloalkyl, $C_3$-$C_6$ cycloalkyl, or $C_5$-$C_6$ cycloalkyl). In embodiments, $R^{13}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{13}$ is $R^{49}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{13}$ is $R^{49}$-substituted heterocycloalkyl (e.g., 3 to 8 membered heterocycloalkyl, 3 to 6 membered heterocycloalkyl, or 5 to 6 membered heterocycloalkyl). In embodiments, $R^{13}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{13}$ is $R^{49}$-substituted or unsubstituted aryl (e.g., $C_6$-$C_{10}$ aryl, $C_{10}$ aryl, or phenyl). In embodiments, $R^{13}$ is $R^{49}$-substituted aryl (e.g., $C_6$-$C_{10}$ aryl, $C_{10}$ aryl, or phenyl). In embodiments, $R^{13}$ is an unsubstituted aryl (e.g., $C_6$-$C_{10}$ aryl, $C_{10}$ aryl, or phenyl).

In embodiments, $R^{13}$ is $R^{49}$-substituted or unsubstituted heteroaryl (e.g., 5 to 10 membered heteroaryl, 5 to 9 membered heteroaryl, or 5 to 6 membered heteroaryl). In embodiments, $R^{13}$ is $R^{49}$-substituted heteroaryl (e.g., 5 to 10 membered heteroaryl, 5 to 9 membered heteroaryl, or 5 to 6 membered heteroaryl). In embodiments, $R^{13}$ is an unsubstituted heteroaryl (e.g., 5 to 10 membered heteroaryl, 5 to 9 membered heteroaryl, or 5 to 6 membered heteroaryl).

In embodiments, $R^{14}$ is hydrogen, halogen, $-CX^{14.1}_3$, $-CHX^{14.1}_2$, $-CH_2X^{14.1}$, $-CN$, $-SO_{n14}R^{14A}$, $-SO_{v14}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m14}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{14}$ is hydrogen, halogen, $-CX^{14.14}$, $-CHX^{14.1}_2$, $-CH_2X^{14.1}$, $-CN$, $-SO_{n14}R^{14A}$, $-SO_{v14}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m14}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.14}$, $-OCHX^{14.1}_2$, $R^{52}$-substituted or unsubstituted alkyl (e.g., $C_1$-$C_8$ alkyl, $C_1$-$C_6$ alkyl, or $C_1$-$C_4$ alkyl), $R^{52}$-substituted or unsubstituted heteroalkyl (e.g., 2 to 8 membered heteroalkyl, 2 to 6 membered heteroalkyl, or 2 to 4 membered heteroalkyl), $R^{52}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{52}$-substituted or unsubstituted heterocycloalkyl (e.g., 3 to 8 membered heterocycloalkyl, 3 to 6 membered heterocycloalkyl, or 5 to 6 membered heterocycloalkyl), $R^{52}$-substituted or unsubstituted aryl (e.g., $C_6$-$C_{10}$ aryl, $C_{10}$ aryl, or phenyl), or $R^{52}$-substituted or unsubstituted heteroaryl (e.g., 5 to 10 membered heteroaryl, 5 to 9 membered heteroaryl, or 5 to 6 membered heteroaryl).

In embodiments, $R^{14}$ is $R^{52}$-substituted or unsubstituted alkyl (e.g., $C_1$-$C_8$ alkyl, $C_1$-$C_6$ alkyl, or $C_1$-$C_4$ alkyl). In embodiments, $R^{14}$ is $R^{52}$-substituted alkyl (e.g., $C_1$-$C_8$ alkyl, $C_1$-$C_6$ alkyl, or $C_1$-$C_4$ alkyl). In embodiments, $R^{14}$ is an unsubstituted alkyl (e.g., $C_1$-$C_8$ alkyl, $C_1$-$C_6$ alkyl, or $C_1$-$C_4$ alkyl).

In embodiments, $R^{14}$ is $R^{52}$-substituted or unsubstituted heteroalkyl (e.g., 2 to 8 membered heteroalkyl, 2 to 6 membered heteroalkyl, or 2 to 4 membered heteroalkyl). In embodiments, $R^{14}$ is $R^{52}$-substituted heteroalkyl (e.g., 2 to 8 membered heteroalkyl, 2 to 6 membered heteroalkyl, or 2 to 4 membered heteroalkyl). In embodiments, $R^{14}$ is an unsubstituted heteroalkyl (e.g., 2 to 8 membered heteroalkyl, 2 to 6 membered heteroalkyl, or 2 to 4 membered heteroalkyl).

In embodiments, $R^{14}$ is $R^{52}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{14}$ is $R^{52}$-substituted cycloalkyl (e.g., $C_3$-$C_8$ cycloalkyl, $C_3$-$C_6$ cycloalkyl, or $C_5$-$C_6$ cycloalkyl). In embodiments, $R^{14}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{14}$ is $R^{52}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{14}$ is $R^{52}$-substituted heterocycloalkyl (e.g., 3 to 8 membered heterocycloalkyl, 3 to 6 membered heterocycloalkyl, or 5 to 6 membered heterocycloalkyl). In embodiments, $R^{14}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{14}$ is $R^{52}$-substituted or unsubstituted aryl (e.g., $C_6$-$C_{10}$ aryl, $C_{10}$ aryl, or phenyl). In embodiments, $R^{14}$ is $R^{52}$-substituted aryl (e.g., $C_6$-$C_{10}$ aryl, $C_{10}$ aryl, or phenyl). In embodiments, $R^{14}$ is an unsubstituted aryl (e.g., $C_6$-$C_{10}$ aryl, $C_{10}$ aryl, or phenyl).

In embodiments, $R^{14}$ is $R^{52}$-substituted or unsubstituted heteroaryl (e.g., 5 to 10 membered heteroaryl, 5 to 9 membered heteroaryl, or 5 to 6 membered heteroaryl). In embodiments, $R^{14}$ is $R^{52}$-substituted heteroaryl (e.g., 5 to 10 membered heteroaryl, 5 to 9 membered heteroaryl, or 5 to 6 membered heteroaryl). In embodiments, $R^{14}$ is an unsubstituted heteroaryl (e.g., 5 to 10 membered heteroaryl, 5 to 9 membered heteroaryl, or 5 to 6 membered heteroaryl).

In embodiments, $R^{15}$ is hydrogen, halogen, $-CX^{15.1}_3$, $-CHX^{15.1}_2$, $-CH_2X^{15.1}$, $-CN$, $-SO_{n15}R^{15A}$, $-SO_{v15}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m15}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{15}$ is hydrogen, halogen, —$CX^{15.15}_3$, —$CHX^{15.1}_2$, —$CH_2X^{15.1}$, —CN, —$SO_{n15}R^{15A}$, —$SO_{v15}NR^{15B}R^{15C}$, —$NHNR^{15B}R^{15C}$, —$ONR^{15B}R^{15C}$, —$NHC(O)NHNR^{15B}R^{15C}$, —$NHC(O)NR^{15B}R^{15C}$, —$N(O)_{m15}$, —$NR^{15B}R^{15C}$, —$C(O)R^{15D}$, —$C(O)OR^{15D}$, —$C(O)NR^{15B}R^{15C}$, —$OR^{15A}$, —$NR^{15B}SO_2R^{15A}$, —$NR^{15B}C(O)R^{15D}$, —$NR^{15B}C(O)OR^{15D}$, —$NR^{15B}OR^{15D}$, —$OCX^{15.15}_3$, —$OCHX^{15.1}_2$, $R^{55}$-substituted or unsubstituted alkyl (e.g., $C_1$-$C_8$ alkyl, $C_1$-$C_6$ alkyl, or $C_1$-$C_4$ alkyl), $R^{55}$-substituted or unsubstituted heteroalkyl (e.g., 2 to 8 membered heteroalkyl, 2 to 6 membered heteroalkyl, or 2 to 4 membered heteroalkyl), $R^{55}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{55}$-substituted or unsubstituted heterocycloalkyl (e.g., 3 to 8 membered heterocycloalkyl, 3 to 6 membered heterocycloalkyl, or 5 to 6 membered heterocycloalkyl), $R^{55}$-substituted or unsubstituted aryl (e.g., $C_6$-$C_{10}$ aryl, $C_{10}$ aryl, or phenyl), or $R^{55}$-substituted or unsubstituted heteroaryl (e.g., 5 to 10 membered heteroaryl, 5 to 9 membered heteroaryl, or 5 to 6 membered heteroaryl).

In embodiments, $R^{15}$ is $R^{55}$-substituted or unsubstituted alkyl (e.g., $C_1$-$C_8$ alkyl, $C_1$-$C_6$ alkyl, or $C_1$-$C_4$ alkyl). In embodiments, $R^{15}$ is $R^{55}$-substituted alkyl (e.g., $C_1$-$C_8$ alkyl, $C_1$-$C_6$ alkyl, or $C_1$-$C_4$ alkyl). In embodiments, $R^{15}$ is an unsubstituted alkyl (e.g., $C_1$-$C_8$ alkyl, $C_1$-$C_6$ alkyl, or $C_1$-$C_4$ alkyl).

In embodiments, $R^{15}$ is $R^{55}$-substituted or unsubstituted heteroalkyl (e.g., 2 to 8 membered heteroalkyl, 2 to 6 membered heteroalkyl, or 2 to 4 membered heteroalkyl). In embodiments, $R^{15}$ is $R^{55}$-substituted heteroalkyl (e.g., 2 to 8 membered heteroalkyl, 2 to 6 membered heteroalkyl, or 2 to 4 membered heteroalkyl). In embodiments, $R^{15}$ is an unsubstituted heteroalkyl (e.g., 2 to 8 membered heteroalkyl, 2 to 6 membered heteroalkyl, or 2 to 4 membered heteroalkyl).

In embodiments, $R^{15}$ is $R^{55}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is $R^{55}$-substituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{15}$ is $R^{55}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15}$ is $R^{55}$-substituted heterocycloalkyl (e.g., 3 to 8 membered heterocycloalkyl, 3 to 6 membered heterocycloalkyl, or 5 to 6 membered heterocycloalkyl). In embodiments, $R^{15}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{15}$ is $R^{55}$-substituted or unsubstituted aryl (e.g., $C_6$-$C_{10}$ aryl, $C_{10}$ aryl, or phenyl). In embodiments, $R^{15}$ is $R^{55}$-substituted aryl (e.g., $C_6$-$C_{10}$ aryl, $C_{10}$ aryl, or phenyl). In embodiments, $R^{15}$ is an unsubstituted aryl (e.g., $C_6$-$C_{10}$ aryl, $C_{10}$ aryl, or phenyl).

In embodiments, $R^{15}$ is $R^{55}$-substituted or unsubstituted heteroaryl (e.g., 5 to 10 membered heteroaryl, 5 to 9 membered heteroaryl, or 5 to 6 membered heteroaryl). In embodiments, $R^{15}$ is $R^{55}$-substituted heteroaryl (e.g., 5 to 10 membered heteroaryl, 5 to 9 membered heteroaryl, or 5 to 6 membered heteroaryl). In embodiments, $R^{15}$ is an unsubstituted heteroaryl (e.g., 5 to 10 membered heteroaryl, 5 to 9 membered heteroaryl, or 5 to 6 membered heteroaryl).

In embodiments, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$ and $R^{15D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$ and $R^{15D}$ are independently halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{12B}$ and $R^{12C}$, $R^{13B}$ and $R^{13C}$, $R^{14B}$ and $R^{14C}$, and $R^{15B}$ and $R^{15C}$ substituents bonded to the same nitrogen atom may optionally be joined to form a substituted or unsubstituted heterocycloalkyl or substituted or unsubstituted heteroaryl.

In embodiments, $R^{12A}$ is hydrogen, halogen, —$CF_3$, —$CCl_3$, —$CBr_3$, —$CI_3$, —COOH, —$CONH_2$, $R^{46A}$-substituted or unsubstituted alkyl (e.g., $C_1$-$C_8$ alkyl, $C_1$-$C_6$ alkyl, or $C_1$-$C_4$ alkyl), $R^{46A}$-substituted or unsubstituted heteroalkyl (e.g., 2 to 8 membered heteroalkyl, 2 to 6 membered heteroalkyl, or 2 to 4 membered heteroalkyl), $R^{46A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46A}$-substituted or unsubstituted aryl (e.g., $C_6$-$C_{10}$ aryl, $C_{10}$ aryl, or phenyl), or $R^{46A}$-substituted or unsubstituted heteroaryl (e.g., 5 to 10 membered heteroaryl, 5 to 9 membered heteroaryl, or 5 to 6 membered heteroaryl).

In embodiments, $R^{13A}$ is hydrogen, halogen, —$CF_3$, —$CCl_3$, —$CBr_3$, —$CI_3$, —COOH, —$CONH_2$, $R^{49A}$-substituted or unsubstituted alkyl (e.g., $C_1$-$C_8$ alkyl, $C_1$-$C_6$ alkyl, or $C_1$-$C_4$ alkyl), $R^{49A}$-substituted or unsubstituted heteroalkyl (e.g., 2 to 8 membered heteroalkyl, 2 to 6 membered heteroalkyl, or 2 to 4 membered heteroalkyl), $R^{49A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{49A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{49A}$-substituted or unsubstituted aryl (e.g., $C_6$-$C_{10}$ aryl, $C_{10}$ aryl, or phenyl), or $R^{49A}$-substituted or unsubstituted heteroaryl (e.g., 5 to 10 membered heteroaryl, 5 to 9 membered heteroaryl, or 5 to 6 membered heteroaryl).

In embodiments, $R^{14A}$ is hydrogen, halogen, —$CF_3$, —$CCl_3$, —$CBr_3$, —$CI_3$, —COOH, —$CONH_2$, $R^{52A}$-substituted or unsubstituted alkyl (e.g., $C_1$-$C_8$ alkyl, $C_1$-$C_6$ alkyl, or $C_1$-$C_4$ alkyl), $R^{52A}$-substituted or unsubstituted heteroalkyl (e.g., 2 to 8 membered heteroalkyl, 2 to 6 membered heteroalkyl, or 2 to 4 membered heteroalkyl), $R^{52A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{52A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{52A}$-substituted or unsubstituted aryl (e.g., $C_6$-$C_{10}$ aryl, $C_{10}$ aryl, or phenyl), or $R^{52A}$-substituted or unsubstituted heteroaryl (e.g., 5 to 10 membered heteroaryl, 5 to 9 membered heteroaryl, or 5 to 6 membered heteroaryl).

In embodiments, $R^{15A}$ is hydrogen, halogen, —$CF_3$, —$CCl_3$, —$CBr_3$, —$CI_3$, —COOH, —$CONH_2$, $R^{55A}$-substituted or unsubstituted alkyl (e.g., $C_1$-$C_8$ alkyl, $C_1$-$C_6$ alkyl, or $C_1$-$C_4$ alkyl), $R^{55A}$-substituted or unsubstituted heteroalkyl (e.g., 2 to 8 membered heteroalkyl, 2 to 6 membered heteroalkyl, or 2 to 4 membered heteroalkyl), $R^{55A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{55A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{55A}$-substituted or unsubstituted aryl (e.g., $C_6$-$C_{10}$ aryl, $C_{10}$ aryl, or phenyl), or $R^{55A}$-substituted or unsubstituted heteroaryl (e.g., 5 to 10 membered heteroaryl, 5 to 9 membered heteroaryl, or 5 to 6 membered heteroaryl).

In embodiments, $R^{12B}$ is hydrogen, halogen, —$CF_3$, —$CCl_3$, —$CBr_3$, —$CI_3$, —COOH, —$CONH_2$, $R^{46B}$-substituted or unsubstituted alkyl (e.g., $C_1$-$C_8$ alkyl, $C_1$-$C_6$ alkyl, or $C_1$-$C_4$ alkyl), $R^{46B}$-substituted or unsubstituted heteroalkyl (e.g., 2 to 8 membered heteroalkyl, 2 to 6 membered heteroalkyl, or 2 to 4 membered heteroalkyl), $R^{46B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46B}$-substituted or unsubstituted aryl (e.g., $C_6$-$C_{10}$ aryl, $C_{10}$ aryl, or phenyl), or $R^{46B}$-substituted or unsubstituted heteroaryl (e.g., 5 to 10 membered heteroaryl, 5 to 9 membered heteroaryl, or 5 to 6 membered heteroaryl). In embodiments, $R^{12B}$ and $R^{12C}$ substituents bonded to the same nitrogen atom may optionally be joined to form a $R^{46B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{46B}$-substituted or unsubstituted heteroaryl (e.g., 5 to 10 membered heteroaryl, 5 to 9 membered heteroaryl, or 5 to 6 membered heteroaryl).

In embodiments, $R^{13B}$ is hydrogen, halogen, —$CF_3$, —$CCl_3$, —$CBr_3$, —$CI_3$, —COOH, —$CONH_2$, $R^{49B}$-substituted or unsubstituted alkyl (e.g., $C_1$-$C_8$ alkyl, $C_1$-$C_6$ alkyl, or $C_1$-$C_4$ alkyl), $R^{49B}$-substituted or unsubstituted heteroalkyl (e.g., 2 to 8 membered heteroalkyl, 2 to 6 membered heteroalkyl, or 2 to 4 membered heteroalkyl), $R^{49B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{49B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{49B}$-substituted or unsubstituted aryl (e.g., $C_6$-$C_{10}$ aryl, $C_{10}$ aryl, or phenyl), or $R^{49B}$-substituted or unsubstituted heteroaryl (e.g., 5 to 10 membered heteroaryl, 5 to 9 membered heteroaryl, or 5 to 6 membered heteroaryl). In embodiments, $R^{13B}$ and $R^{13C}$ substituents bonded to the same nitrogen atom may optionally be joined to form a $R^{49B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{49B}$-substituted or unsubstituted heteroaryl (e.g., 5 to 10 membered heteroaryl, 5 to 9 membered heteroaryl, or 5 to 6 membered heteroaryl).

In embodiments, $R^{14B}$ is hydrogen, halogen, —$CF_3$, —$CCl_3$, —$CBr_3$, —$CI_3$, —COOH, —$CONH_2$, $R^{52B}$-substituted or unsubstituted alkyl (e.g., $C_1$-$C_8$ alkyl, $C_1$-$C_6$ alkyl, or $C_1$-$C_4$ alkyl), $R^{52B}$-substituted or unsubstituted heteroalkyl (e.g., 2 to 8 membered heteroalkyl, 2 to 6 membered heteroalkyl, or 2 to 4 membered heteroalkyl), $R^{52B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{52B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{52B}$-substituted or unsubstituted aryl (e.g., $C_6$-$C_{10}$ aryl, $C_{10}$ aryl, or phenyl), or $R^{52B}$-substituted or unsubstituted heteroaryl (e.g., 5 to 10 membered heteroaryl, 5 to 9 membered heteroaryl, or 5 to 6 membered heteroaryl). In embodiments, $R^{14B}$ and $R^{14C}$ substituents bonded to the same nitrogen atom may optionally be joined to form a $R^{52B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{52B}$-substituted or unsubstituted heteroaryl (e.g., 5 to 10 membered heteroaryl, 5 to 9 membered heteroaryl, or 5 to 6 membered heteroaryl).

In embodiments, $R^{15B}$ is hydrogen, halogen, —$CF_3$, —$CCl_3$, —$CBr_3$, —$CI_3$, —COOH, —$CONH_2$, $R^{55B}$-substituted or unsubstituted alkyl (e.g., $C_1$-$C_8$ alkyl, $C_1$-$C_6$ alkyl, or $C_1$-$C_4$ alkyl), $R^{55B}$-substituted or unsubstituted heteroalkyl (e.g., 2 to 8 membered heteroalkyl, 2 to 6 membered heteroalkyl, or 2 to 4 membered heteroalkyl), $R^{55B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{55B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{55B}$-substituted or unsubstituted aryl (e.g., $C_6$-$C_{10}$ aryl, $C_{10}$ aryl, or phenyl), or $R^{55B}$-substituted or unsubstituted heteroaryl (e.g., 5 to 10 membered heteroaryl, 5 to 9 membered heteroaryl, or 5 to 6 membered heteroaryl). In embodiments, $R^{15B}$ and $R^{15C}$ substituents bonded to the same nitrogen atom may optionally be joined to form a $R^{55B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{55B}$-substituted or unsubstituted heteroaryl (e.g., 5 to 10 membered heteroaryl, 5 to 9 membered heteroaryl, or 5 to 6 membered heteroaryl).

In embodiments, $R^{12C}$ is hydrogen, halogen, —$CF_3$, —$CCl_3$, —$CBr_3$, —$CI_3$, —COOH, —$CONH_2$, $R^{46C}$-substituted or unsubstituted alkyl (e.g., $C_1$-$C_8$ alkyl, $C_1$-$C_6$ alkyl, or $C_1$-$C_4$ alkyl), $R^{46C}$-substituted or unsubstituted heteroalkyl (e.g., 2 to 8 membered heteroalkyl, 2 to 6 membered heteroalkyl, or 2 to 4 membered heteroalkyl), $R^{46C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46C}$-substituted or unsubstituted aryl (e.g., $C_6$-$C_{10}$ aryl, $C_{10}$ aryl, or phenyl), or $R^{46C}$-substituted or unsubstituted heteroaryl (e.g., 5 to 10 membered heteroaryl, 5 to 9 membered heteroaryl, or 5 to 6 membered heteroaryl). In embodiments, $R^{12B}$ and $R^{12C}$ substituents bonded to the same nitrogen atom may optionally be joined to form a $R^{46C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{46C}$-substituted or unsubstituted heteroaryl (e.g., 5 to 10 membered heteroaryl, 5 to 9 membered heteroaryl, or 5 to 6 membered heteroaryl).

In embodiments, $R^{13C}$ is hydrogen, halogen, —$CF_3$, —$CCl_3$, —$CBr_3$, —$CI_3$, —COOH, —$CONH_2$, $R^{49C}$-substituted or unsubstituted alkyl (e.g., $C_1$-$C_8$ alkyl, $C_1$-$C_6$ alkyl, or $C_1$-$C_4$ alkyl), $R^{49C}$-substituted or unsubstituted heteroalkyl (e.g., 2 to 8 membered heteroalkyl, 2 to 6 membered heteroalkyl, or 2 to 4 membered heteroalkyl), $R^{49C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{49C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{49C}$-substituted or unsubstituted aryl (e.g., $C_6$-$C_{10}$ aryl, $C_{10}$ aryl, or phenyl), or $R^{49C}$-substituted or unsubstituted heteroaryl (e.g., 5 to 10 membered heteroaryl, 5 to 9 membered heteroaryl, or 5 to 6 membered heteroaryl). In embodiments, $R^{13B}$ and $R^{13C}$ substituents bonded to the same nitrogen atom may optionally be joined to form a $R^{49C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{49C}$-substituted or unsubstituted heteroaryl (e.g., 5 to 10 membered heteroaryl, 5 to 9 membered heteroaryl, or 5 to 6 membered heteroaryl).

In embodiments, $R^{14C}$ is hydrogen, halogen, —$CF_3$, —$CCl_3$, —$CBr_3$, —$CI_3$, —COOH, —$CONH_2$, $R^{52C}$-substituted or unsubstituted alkyl (e.g., $C_1$-$C_8$ alkyl, $C_1$-$C_6$ alkyl, or $C_1$-$C_4$ alkyl), $R^{52C}$-substituted or unsubstituted heteroalkyl (e.g., 2 to 8 membered heteroalkyl, 2 to 6 membered heteroalkyl, or 2 to 4 membered heteroalkyl), $R^{52C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{52C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{52C}$-substituted or unsubstituted aryl (e.g., $C_6$-$C_{10}$ aryl, $C_{10}$ aryl, or phenyl), or $R^{52C}$-substituted or unsubstituted heteroaryl (e.g., 5 to 10 membered heteroaryl, 5 to 9 membered heteroaryl, or 5 to 6 membered heteroaryl). In embodiments, $R^{14B}$ and $R^{14C}$ substituents bonded to the same nitrogen atom may optionally be joined to form a $R^{52C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{52C}$-substituted or unsubstituted heteroaryl (e.g., 5 to 10 membered heteroaryl, 5 to 9 membered heteroaryl, or 5 to 6 membered heteroaryl).

In embodiments, $R^{15C}$ is hydrogen, halogen, —$CF_3$, —$CCl_3$, —$CBr_3$, —$CI_3$, —COOH, —$CONH_2$, $R^{55C}$-substituted or unsubstituted alkyl (e.g., $C_1$-$C_8$ alkyl, $C_1$-$C_6$ alkyl, or $C_1$-$C_4$ alkyl), $R^{55C}$-substituted or unsubstituted heteroalkyl (e.g., 2 to 8 membered heteroalkyl, 2 to 6 membered heteroalkyl, or 2 to 4 membered heteroalkyl), $R^{55C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{55C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{55C}$-substituted or unsubstituted aryl (e.g., $C_6$-$C_{10}$ aryl, $C_{10}$ aryl, or phenyl), or $R^{55C}$-substituted or unsubstituted heteroaryl (e.g., 5 to 10 membered heteroaryl, 5 to 9 membered heteroaryl, or 5 to 6 membered heteroaryl). In embodiments, $R^{15B}$ and $R^{15C}$ substituents bonded to the same nitrogen atom may optionally be joined to form a $R^{55C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{55C}$-substituted or unsubstituted heteroaryl (e.g., 5 to 10 membered heteroaryl, 5 to 9 membered heteroaryl, or 5 to 6 membered heteroaryl).

In embodiments, $R^{12D}$ is hydrogen, halogen, —$CF_3$, —$CCl_3$, —$CBr_3$, —$CI_3$, —COOH, —$CONH_2$, $R^{46D}$-substituted or unsubstituted alkyl (e.g., $C_1$-$C_8$ alkyl, $C_1$-$C_6$ alkyl, or $C_1$-$C_4$ alkyl), $R^{46D}$-substituted or unsubstituted heteroalkyl (e.g., 2 to 8 membered heteroalkyl, 2 to 6 membered heteroalkyl, or 2 to 4 membered heteroalkyl), $R^{46D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46D}$-substituted or unsubstituted aryl (e.g., $C_6$-$C_{10}$ aryl, $C_{10}$ aryl, or phenyl), or $R^{46D}$-substituted or unsubstituted heteroaryl (e.g., 5 to 10 membered heteroaryl, 5 to 9 membered heteroaryl, or 5 to 6 membered heteroaryl).

In embodiments, $R^{13D}$ is hydrogen, halogen, —$CF_3$, —$CCl_3$, —$CBr_3$, —$CI_3$, —COOH, —$CONH_2$, $R^{49D}$-substituted or unsubstituted alkyl (e.g., $C_1$-$C_8$ alkyl, $C_1$-$C_6$ alkyl, or $C_1$-$C_4$ alkyl), $R^{49D}$-substituted or unsubstituted heteroalkyl (e.g., 2 to 8 membered heteroalkyl, 2 to 6 membered heteroalkyl, or 2 to 4 membered heteroalkyl), $R^{49D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{49D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{49D}$-substituted or unsubstituted aryl (e.g., $C_6$-$C_{10}$ aryl, $C_{10}$ aryl, or phenyl), or $R^{49D}$-substituted or unsubstituted heteroaryl (e.g., 5 to 10 membered heteroaryl, 5 to 9 membered heteroaryl, or 5 to 6 membered heteroaryl).

In embodiments, $R^{14D}$ is hydrogen, halogen, —$CF_3$, —$CCl_3$, —$CBr_3$, —$CI_3$, —COOH, —$CONH_2$, $R^{52D}$-substituted or unsubstituted alkyl (e.g., $C_1$-$C_8$ alkyl, $C_1$-$C_6$ alkyl, or $C_1$-$C_4$ alkyl), $R^{52D}$-substituted or unsubstituted heteroalkyl (e.g., 2 to 8 membered heteroalkyl, 2 to 6 membered heteroalkyl, or 2 to 4 membered heteroalkyl), $R^{52D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{52D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{52D}$-substituted or unsubstituted aryl (e.g., $C_6$-$C_{10}$ aryl, $C_{10}$ aryl, or phenyl), or $R^{52D}$-substituted or unsubstituted heteroaryl (e.g., 5 to 10 membered heteroaryl, 5 to 9 membered heteroaryl, or 5 to 6 membered heteroaryl).

In embodiments, $R^{15D}$ is hydrogen, halogen, —$CF_3$, —$CCl_3$, —$CBr_3$, —$CI_3$, —COOH, —$CONH_2$, $R^{55D}$-substituted or unsubstituted alkyl (e.g., $C_1$-$C_8$ alkyl, $C_1$-$C_6$ alkyl, or $C_1$-$C_4$ alkyl), $R^{55D}$-substituted or unsubstituted heteroalkyl (e.g., 2 to 8 membered heteroalkyl, 2 to 6 membered heteroalkyl, or 2 to 4 membered heteroalkyl), $R^{55D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{55D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{55D}$-substituted or unsubstituted aryl (e.g., $C_6$-$C_{10}$ aryl, $C_{10}$ aryl, or phenyl), or $R^{55D}$-substituted or unsubstituted heteroaryl (e.g., 5 to 10 membered heteroaryl, 5 to 9 membered heteroaryl, or 5 to 6 membered heteroaryl).

$R^{46}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{47}$-substituted or unsubstituted alkyl (e.g., $C_1$-$C_8$ alkyl, $C_1$-$C_6$ alkyl, or $C_1$-$C_4$ alkyl), $R^{47}$-substituted or unsubstituted heteroalkyl (e.g., 2 to 8 membered heteroalkyl, 2 to 6 membered heteroalkyl, or 2 to 4 membered heteroalkyl), $R^{47}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{47}$-substituted or unsubstituted heterocycloalkyl (e.g., 3 to 8 membered heterocycloalkyl, 3 to 6 membered heterocycloalkyl, or 5 to 6 membered heterocycloalkyl), $R^{47}$-substituted or unsubstituted aryl (e.g., $C_6$-$C_{10}$ aryl, $C_{10}$ aryl, or phenyl), or $R^{47}$-substituted or unsubstituted heteroaryl (e.g., 5 to 10 membered heteroaryl, 5 to 9 membered heteroaryl, or 5 to 6 membered heteroaryl).

In embodiments, $R^{46}$ is $R^{47}$-substituted or unsubstituted alkyl (e.g., $C_1$-$C_8$ alkyl, $C_1$-$C_6$ alkyl, or $C_1$-$C_4$ alkyl). In embodiments, $R^{46}$ is $R^{47}$-substituted alkyl (e.g., $C_1$-$C_8$ alkyl, $C_1$-$C_6$ alkyl, or $C_1$-$C_4$ alkyl). In embodiments, $R^{46}$ is an unsubstituted alkyl (e.g., $C_1$-$C_8$ alkyl, $C_1$-$C_6$ alkyl, or $C_1$-$C_4$ alkyl).

In embodiments, $R^{46}$ is $R^{47}$-substituted or unsubstituted heteroalkyl (e.g., 2 to 8 membered heteroalkyl, 2 to 6 membered heteroalkyl, or 2 to 4 membered heteroalkyl). In embodiments, $R^{46}$ is $R^{47}$-substituted heteroalkyl (e.g., 2 to 8 membered heteroalkyl, 2 to 6 membered heteroalkyl, or 2 to 4 membered heteroalkyl). In embodiments, $R^{46}$ is an unsubstituted heteroalkyl (e.g., 2 to 8 membered heteroalkyl, 2 to 6 membered heteroalkyl, or 2 to 4 membered heteroalkyl).

In embodiments, $R^{46}$ is $R^{47}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{46}$ is $R^{47}$-substituted cycloalkyl (e.g., $C_3$-$C_8$ cycloalkyl, $C_3$-$C_6$ cycloalkyl, or $C_5$-$C_6$ cycloalkyl). In embodiments, $R^{46}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{46}$ is $R^{47}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{46}$ is $R^{47}$-substituted heterocycloalkyl (e.g., 3 to 8 membered heterocycloalkyl, 3 to 6 membered heterocycloalkyl, or 5 to 6 membered heterocycloalkyl). In embodiments, $R^{46}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{46}$ is $R^{47}$-substituted or unsubstituted aryl (e.g., $C_6$-$C_{10}$ aryl, $C_{10}$ aryl, or phenyl). In embodiments, $R^{46}$ is $R^{47}$-substituted aryl (e.g., $C_6$-$C_{10}$ aryl, $C_{10}$ aryl, or phenyl). In embodiments, $R^{46}$ is an unsubstituted aryl (e.g., $C_6$-$C_{10}$ aryl, $C_{10}$ aryl, or phenyl).

In embodiments, $R^{46}$ is $R^{47}$-substituted or unsubstituted heteroaryl (e.g., 5 to 10 membered heteroaryl, 5 to 9 membered heteroaryl, or 5 to 6 membered heteroaryl). In embodiments, $R^{46}$ is $R^{47}$-substituted heteroaryl (e.g., 5 to 10 membered heteroaryl, 5 to 9 membered heteroaryl, or 5 to 6 membered heteroaryl). In embodiments, $R^{46}$ is an unsubstituted heteroaryl (e.g., 5 to 10 membered heteroaryl, 5 to 9 membered heteroaryl, or 5 to 6 membered heteroaryl).

$R^{47}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{48}$-substituted or unsubstituted alkyl (e.g., $C_1$-$C_8$ alkyl, $C_1$-$C_6$ alkyl, or $C_1$-$C_4$ alkyl), $R^{48}$-substituted or unsubstituted heteroalkyl (e.g., 2 to 8 membered heteroalkyl, 2 to 6 membered heteroalkyl, or 2 to 4 membered heteroalkyl), $R^{48}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{48}$-substituted or unsubstituted heterocycloalkyl (e.g., 3 to 8 membered heterocycloalkyl, 3 to 6 membered heterocycloalkyl, or 5 to 6 membered heterocycloalkyl), $R^{48}$-substituted or unsubstituted aryl (e.g., $C_6$-$C_{10}$ aryl, $C_{10}$ aryl, or phenyl), or $R^{48}$-substituted or unsubstituted heteroaryl (e.g., 5 to 10 membered heteroaryl, 5 to 9 membered heteroaryl, or 5 to 6 membered heteroaryl).

In embodiments, $R^{47}$ is $R^{48}$-substituted or unsubstituted alkyl (e.g., $C_1$-$C_8$ alkyl, $C_1$-$C_6$ alkyl, or $C_1$-$C_4$ alkyl). In embodiments, $R^{47}$ is $R^{48}$-substituted alkyl (e.g., $C_1$-$C_8$ alkyl, $C_1$-$C_6$ alkyl, or $C_1$-$C_4$ alkyl). In embodiments, $R^{47}$ is an unsubstituted alkyl (e.g., $C_1$-$C_8$ alkyl, $C_1$-$C_6$ alkyl, or $C_1$-$C_4$ alkyl).

In embodiments, $R^{47}$ is $R^{48}$-substituted or unsubstituted heteroalkyl (e.g., 2 to 8 membered heteroalkyl, 2 to 6 membered heteroalkyl, or 2 to 4 membered heteroalkyl). In embodiments, $R^{47}$ is $R^{48}$-substituted heteroalkyl (e.g., 2 to 8 membered heteroalkyl, 2 to 6 membered heteroalkyl, or 2 to 4 membered heteroalkyl). In embodiments, $R^{47}$ is an unsubstituted heteroalkyl (e.g., 2 to 8 membered heteroalkyl, 2 to 6 membered heteroalkyl, or 2 to 4 membered heteroalkyl).

In embodiments, $R^{47}$ is $R^{48}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{47}$ is $R^{48}$-substituted cycloalkyl (e.g., $C_3$-$C_8$ cycloalkyl, $C_3$-$C_6$ cycloalkyl, or $C_5$-$C_6$ cycloalkyl). In embodiments, $R^{47}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{47}$ is $R^{48}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{47}$ is $R^{48}$-substituted heterocycloalkyl (e.g., 3 to 8 membered heterocycloalkyl, 3 to 6 membered heterocycloalkyl, or 5 to 6 membered heterocycloalkyl). In embodiments, $R^{47}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{47}$ is $R^{48}$-substituted or unsubstituted aryl (e.g., $C_6$-$C_{10}$ aryl, $C_{10}$ aryl, or phenyl). In embodiments, $R^{47}$ is $R^{48}$-substituted aryl (e.g., $C_6$-$C_{10}$ aryl, $C_{10}$ aryl, or phenyl). In embodiments, $R^{47}$ is an unsubstituted aryl (e.g., $C_6$-$C_{10}$ aryl, $C_{10}$ aryl, or phenyl).

In embodiments, $R^{47}$ is $R^{48}$-substituted or unsubstituted heteroaryl (e.g., 5 to 10 membered heteroaryl, 5 to 9 membered heteroaryl, or 5 to 6 membered heteroaryl). In embodiments, $R^{47}$ is $R^{48}$-substituted heteroaryl (e.g., 5 to 10 membered heteroaryl, 5 to 9 membered heteroaryl, or 5 to 6 membered heteroaryl). In embodiments, $R^{47}$ is an unsubstituted heteroaryl (e.g., 5 to 10 membered heteroaryl, 5 to 9 membered heteroaryl, or 5 to 6 membered heteroaryl).

$R^{49}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{50}$-substituted or unsubstituted alkyl (e.g., $C_1$-$C_8$ alkyl, $C_1$-$C_6$ alkyl, or $C_1$-$C_4$ alkyl), $R^{50}$-substituted or unsubstituted heteroalkyl (e.g., 2 to 8 membered heteroalkyl, 2 to 6 membered heteroalkyl, or 2 to 4 membered heteroalkyl), $R^{50}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{50}$-substituted or unsubstituted heterocycloalkyl (e.g., 3 to 8 membered heterocycloalkyl, 3 to 6 membered heterocycloalkyl, or 5 to 6 membered heterocycloalkyl), $R^{50}$-substituted or unsubstituted aryl (e.g., $C_6$-$C_{10}$ aryl, $C_{10}$ aryl, or phenyl), or $R^{50}$-substituted or unsubstituted heteroaryl (e.g., 5 to 10 membered heteroaryl, 5 to 9 membered heteroaryl, or 5 to 6 membered heteroaryl).

In embodiments, $R^{49}$ is $R^{50}$-substituted or unsubstituted alkyl (e.g., $C_1$-$C_8$ alkyl, $C_1$-$C_6$ alkyl, or $C_1$-$C_4$ alkyl). In embodiments, $R^{49}$ is $R^{50}$-substituted alkyl (e.g., $C_1$-$C_8$ alkyl, $C_1$-$C_6$ alkyl, or $C_1$-$C_4$ alkyl). In embodiments, $R^{49}$ is an unsubstituted alkyl (e.g., $C_1$-$C_8$ alkyl, $C_1$-$C_6$ alkyl, or $C_1$-$C_4$ alkyl).

In embodiments, $R^{49}$ is $R^{50}$-substituted or unsubstituted heteroalkyl (e.g., 2 to 8 membered heteroalkyl, 2 to 6 membered heteroalkyl, or 2 to 4 membered heteroalkyl). In embodiments, $R^{49}$ is $R^{50}$-substituted heteroalkyl (e.g., 2 to 8 membered heteroalkyl, 2 to 6 membered heteroalkyl, or 2 to 4 membered heteroalkyl). In embodiments, $R^{49}$ is an unsubstituted heteroalkyl (e.g., 2 to 8 membered heteroalkyl, 2 to 6 membered heteroalkyl, or 2 to 4 membered heteroalkyl).

In embodiments, $R^{49}$ is $R^{50}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{49}$ is $R^{50}$-substituted cycloalkyl (e.g., $C_3$-$C_8$ cycloalkyl, $C_3$-$C_6$ cycloalkyl, or $C_5$-$C_6$ cycloalkyl). In embodiments, $R^{49}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{49}$ is $R^{50}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{49}$ is $R^{50}$-substituted heterocycloalkyl (e.g., 3 to 8 membered heterocycloalkyl, 3 to 6 membered heterocycloalkyl, or 5 to 6 membered heterocycloalkyl). In embodiments, $R^{49}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{49}$ is $R^{50}$-substituted or unsubstituted aryl (e.g., $C_6$-$C_{10}$ aryl, $C_{10}$ aryl, or phenyl). In embodiments, $R^{49}$ is $R^{50}$-substituted aryl (e.g., $C_6$-$C_{10}$ aryl, $C_{10}$ aryl, or phenyl). In embodiments, $R^{49}$ is an unsubstituted aryl (e.g., $C_6$-$C_{10}$ aryl, $C_{10}$ aryl, or phenyl).

In embodiments, $R^{49}$ is $R^{50}$-substituted or unsubstituted heteroaryl (e.g., 5 to 10 membered heteroaryl, 5 to 9 membered heteroaryl, or 5 to 6 membered heteroaryl). In embodiments, $R^{49}$ is $R^{50}$-substituted heteroaryl (e.g., 5 to 10 membered heteroaryl, 5 to 9 membered heteroaryl, or 5 to 6 membered heteroaryl). In embodiments, $R^{49}$ is an unsubstituted heteroaryl (e.g., 5 to 10 membered heteroaryl, 5 to 9 membered heteroaryl, or 5 to 6 membered heteroaryl).

$R^{50}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{51}$-substituted or unsubstituted alkyl (e.g., $C_1$-$C_8$ alkyl, $C_1$-$C_6$ alkyl, or $C_1$-$C_4$ alkyl), $R^{51}$-substituted or unsubstituted heteroalkyl (e.g., 2 to 8 membered heteroalkyl, 2 to 6 membered heteroalkyl, or 2 to 4 membered heteroalkyl), $R^{51}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{51}$-substituted or unsubstituted heterocycloalkyl (e.g., 3 to 8 membered heterocycloalkyl, 3 to 6 membered heterocycloalkyl, or 5 to 6 membered heterocycloalkyl), $R^{51}$-substituted or unsubstituted aryl (e.g., $C_6$-$C_{10}$ aryl, $C_{10}$ aryl, or phenyl), or $R^{51}$-substituted or unsubstituted heteroaryl (e.g., 5 to 10 membered heteroaryl, 5 to 9 membered heteroaryl, or 5 to 6 membered heteroaryl).

In embodiments, $R^{50}$ is $R^{51}$-substituted or unsubstituted alkyl (e.g., $C_1$-$C_8$ alkyl, $C_1$-$C_6$ alkyl, or $C_1$-$C_4$ alkyl). In embodiments, $R^{50}$ is $R^{51}$-substituted alkyl (e.g., $C_1$-$C_8$ alkyl, $C_1$-$C_6$ alkyl, or $C_1$-$C_4$ alkyl). In embodiments, $R^{50}$ is an unsubstituted alkyl (e.g., $C_1$-$C_8$ alkyl, $C_1$-$C_6$ alkyl, or $C_1$-$C_4$ alkyl).

In embodiments, $R^{50}$ is $R^{51}$-substituted or unsubstituted heteroalkyl (e.g., 2 to 8 membered heteroalkyl, 2 to 6 membered heteroalkyl, or 2 to 4 membered heteroalkyl). In embodiments, $R^{50}$ is $R^{51}$-substituted heteroalkyl (e.g., 2 to 8 membered heteroalkyl, 2 to 6 membered heteroalkyl, or 2 to 4 membered heteroalkyl). In embodiments, $R^{50}$ is an unsubstituted heteroalkyl (e.g., 2 to 8 membered heteroalkyl, 2 to 6 membered heteroalkyl, or 2 to 4 membered heteroalkyl).

In embodiments, $R^{50}$ is $R^{51}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{50}$ is $R^{51}$-substituted cycloalkyl (e.g., $C_3$-$C_8$ cycloalkyl, $C_3$-$C_6$ cycloalkyl, or $C_5$-$C_6$ cycloalkyl). In embodiments, $R^{50}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{50}$ is $R^{51}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{50}$ is $R^{51}$-substituted heterocycloalkyl (e.g., 3 to 8 membered heterocycloalkyl, 3 to 6 membered heterocycloalkyl, or 5 to 6 membered heterocycloalkyl). In embodiments, $R^{50}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{50}$ is $R^{51}$-substituted or unsubstituted aryl (e.g., $C_6$-$C_{10}$ aryl, $C_{10}$ aryl, or phenyl). In embodiments, $R^{50}$ is $R^{51}$-substituted aryl (e.g., $C_6$-$C_{10}$ aryl, $C_{10}$ aryl, or phenyl). In embodiments, $R^{50}$ is an unsubstituted aryl (e.g., $C_6$-$C_{10}$ aryl, $C_{10}$ aryl, or phenyl).

In embodiments, $R^{50}$ is $R^{51}$-substituted or unsubstituted heteroaryl (e.g., 5 to 10 membered heteroaryl, 5 to 9 membered heteroaryl, or 5 to 6 membered heteroaryl). In embodiments, $R^{50}$ is $R^{51}$-substituted heteroaryl (e.g., 5 to 10 membered heteroaryl, 5 to 9 membered heteroaryl, or 5 to 6 membered heteroaryl). In embodiments, $R^{50}$ is an unsubstituted heteroaryl (e.g., 5 to 10 membered heteroaryl, 5 to 9 membered heteroaryl, or 5 to 6 membered heteroaryl).

$R^{52}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{53}$-substituted or unsubstituted alkyl (e.g., $C_1$-$C_8$ alkyl, $C_1$-$C_6$ alkyl, or $C_1$-$C_4$ alkyl), $R^{53}$-substituted or unsubstituted heteroalkyl (e.g., 2 to 8 membered heteroalkyl, 2 to 6 membered heteroalkyl, or 2 to 4 membered heteroalkyl), $R^{53}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{53}$-substituted or unsubstituted heterocycloalkyl (e.g., 3 to 8 membered heterocycloalkyl, 3 to 6 membered heterocycloalkyl, or 5 to 6 membered heterocycloalkyl), $R^{53}$-substituted or unsubstituted aryl (e.g., $C_6$-$C_{10}$ aryl, $C_{10}$ aryl, or phenyl), or $R^{53}$-substituted or unsubstituted heteroaryl (e.g., 5 to 10 membered heteroaryl, 5 to 9 membered heteroaryl, or 5 to 6 membered heteroaryl).

In embodiments, $R^{52}$ is $R^{53}$-substituted or unsubstituted alkyl (e.g., $C_1$-$C_8$ alkyl, $C_1$-$C_6$ alkyl, or $C_1$-$C_4$ alkyl). In embodiments, $R^{52}$ is $R^{53}$-substituted alkyl (e.g., $C_1$-$C_8$ alkyl, $C_1$-$C_6$ alkyl, or $C_1$-$C_4$ alkyl). In embodiments, $R^{52}$ is an unsubstituted alkyl (e.g., $C_1$-$C_8$ alkyl, $C_1$-$C_6$ alkyl, or $C_1$-$C_4$ alkyl).

In embodiments, $R^{52}$ is $R^{53}$-substituted or unsubstituted heteroalkyl (e.g., 2 to 8 membered heteroalkyl, 2 to 6 membered heteroalkyl, or 2 to 4 membered heteroalkyl). In embodiments, $R^{52}$ is $R^{53}$-substituted heteroalkyl (e.g., 2 to 8 membered heteroalkyl, 2 to 6 membered heteroalkyl, or 2 to 4 membered heteroalkyl). In embodiments, $R^{52}$ is an unsubstituted heteroalkyl (e.g., 2 to 8 membered heteroalkyl, 2 to 6 membered heteroalkyl, or 2 to 4 membered heteroalkyl).

In embodiments, $R^{52}$ is $R^{53}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{52}$ is $R^{53}$-substituted cycloalkyl (e.g., $C_3$-$C_8$ cycloalkyl, $C_3$-$C_6$ cycloalkyl, or $C_5$-$C_6$ cycloalkyl). In embodiments, $R^{52}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{52}$ is $R^{53}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{52}$ is $R^{53}$-substituted heterocycloalkyl (e.g., 3 to 8 membered heterocycloalkyl, 3 to 6 membered heterocycloalkyl, or 5 to 6 membered heterocycloalkyl). In embodiments, $R^{52}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{52}$ is $R^{53}$-substituted or unsubstituted aryl (e.g., $C_6$-$C_{10}$ aryl, $C_{10}$ aryl, or phenyl). In embodiments, $R^{52}$ is $R^{53}$-substituted aryl (e.g., $C_6$-$C_{10}$ aryl, $C_{10}$ aryl, or phenyl). In embodiments, $R^{52}$ is an unsubstituted aryl (e.g., $C_6$-$C_{10}$ aryl, $C_{10}$ aryl, or phenyl).

In embodiments, $R^{52}$ is $R^{53}$-substituted or unsubstituted heteroaryl (e.g., 5 to 10 membered heteroaryl, 5 to 9 membered heteroaryl, or 5 to 6 membered heteroaryl). In embodiments, $R^{52}$ is $R^{53}$-substituted heteroaryl (e.g., 5 to 10 membered heteroaryl, 5 to 9 membered heteroaryl, or 5 to 6 membered heteroaryl). In embodiments, $R^{52}$ is an unsubstituted heteroaryl (e.g., 5 to 10 membered heteroaryl, 5 to 9 membered heteroaryl, or 5 to 6 membered heteroaryl).

$R^{53}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{54}$-substituted or unsubstituted alkyl (e.g., $C_1$-$C_8$ alkyl, $C_1$-$C_6$ alkyl, or $C_1$-$C_4$ alkyl), $R^{54}$-substituted or unsubstituted heteroalkyl (e.g., 2 to 8 membered heteroalkyl, 2 to 6 membered heteroalkyl, or 2 to 4 membered heteroalkyl), $R^{54}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{54}$-substituted or unsubstituted heterocycloalkyl (e.g., 3 to 8 membered heterocycloalkyl, 3 to 6 membered heterocycloalkyl, or 5 to 6 membered heterocycloalkyl), $R^{54}$-substituted or unsubstituted aryl (e.g., $C_6$-$C_{10}$ aryl, $C_{10}$ aryl, or phenyl), or $R^{54}$-substituted or unsubstituted heteroaryl (e.g., 5 to 10 membered heteroaryl, 5 to 9 membered heteroaryl, or 5 to 6 membered heteroaryl).

In embodiments, $R^{53}$ is $R^{54}$-substituted or unsubstituted alkyl (e.g., $C_1$-$C_8$ alkyl, $C_1$-$C_6$ alkyl, or $C_1$-$C_4$ alkyl). In embodiments, $R^{53}$ is $R^{54}$-substituted alkyl (e.g., $C_1$-$C_8$ alkyl, $C_1$-$C_6$ alkyl, or $C_1$-$C_4$ alkyl). In embodiments, $R^{53}$ is an unsubstituted alkyl (e.g., $C_1$-$C_8$ alkyl, $C_1$-$C_6$ alkyl, or $C_1$-$C_4$ alkyl).

In embodiments, $R^{53}$ is $R^{54}$-substituted or unsubstituted heteroalkyl (e.g., 2 to 8 membered heteroalkyl, 2 to 6 membered heteroalkyl, or 2 to 4 membered heteroalkyl). In embodiments, $R^{53}$ is $R^{54}$-substituted heteroalkyl (e.g., 2 to 8 membered heteroalkyl, 2 to 6 membered heteroalkyl, or 2 to 4 membered heteroalkyl). In embodiments, $R^{53}$ is an unsubstituted heteroalkyl (e.g., 2 to 8 membered heteroalkyl, 2 to 6 membered heteroalkyl, or 2 to 4 membered heteroalkyl).

In embodiments, $R^{53}$ is $R^{54}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{53}$ is $R^{54}$-substituted cycloalkyl (e.g., $C_3$-$C_8$ cycloalkyl, $C_3$-$C_6$ cycloalkyl, or $C_5$-$C_6$ cycloalkyl). In embodiments, $R^{53}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{53}$ is $R^{54}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{53}$ is $R^{54}$-substituted heterocycloalkyl (e.g., 3 to 8 membered heterocycloalkyl, 3 to 6 membered heterocycloalkyl, or 5 to 6 membered heterocycloalkyl). In embodiments, $R^{53}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{53}$ is $R^{54}$-substituted or unsubstituted aryl (e.g., $C_6$-$C_{10}$ aryl, $C_{10}$ aryl, or phenyl). In embodiments, $R^{53}$ is $R^{54}$-substituted aryl (e.g., $C_6$-$C_{10}$ aryl, $C_{10}$ aryl, or phenyl). In embodiments, $R^{53}$ is an unsubstituted aryl (e.g., $C_6$-$C_{10}$ aryl, $C_{10}$ aryl, or phenyl).

In embodiments, $R^{53}$ is $R^{54}$-substituted or unsubstituted heteroaryl (e.g., 5 to 10 membered heteroaryl, 5 to 9 membered heteroaryl, or 5 to 6 membered heteroaryl). In embodiments, $R^{53}$ is $R^{54}$-substituted heteroaryl (e.g., 5 to 10 membered heteroaryl, 5 to 9 membered heteroaryl, or 5 to 6 membered heteroaryl). In embodiments, $R^{53}$ is an unsubstituted heteroaryl (e.g., 5 to 10 membered heteroaryl, 5 to 9 membered heteroaryl, or 5 to 6 membered heteroaryl).

$R^{55}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{56}$-substituted or unsubstituted alkyl (e.g., $C_1$-$C_8$ alkyl, $C_1$-$C_6$ alkyl, or $C_1$-$C_4$ alkyl), $R^{56}$-substituted or unsubstituted heteroalkyl (e.g., 2 to 8 membered heteroalkyl, 2 to 6 membered heteroalkyl, or 2 to 4 membered heteroalkyl), $R^{56}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{56}$-substituted or unsubstituted heterocycloalkyl (e.g., 3 to 8 membered heterocycloalkyl, 3 to 6 membered heterocycloalkyl, or 5 to 6 membered heterocycloalkyl), $R^{56}$-substituted or unsubstituted aryl (e.g., $C_6$-$C_{10}$ aryl, $C_{10}$ aryl, or phenyl), or $R^{56}$-substituted or unsubstituted heteroaryl (e.g., 5 to 10 membered heteroaryl, 5 to 9 membered heteroaryl, or 5 to 6 membered heteroaryl).

In embodiments, $R^{55}$ is $R^{56}$-substituted or unsubstituted alkyl (e.g., $C_1$-$C_8$ alkyl, $C_1$-$C_6$ alkyl, or $C_1$-$C_4$ alkyl). In embodiments, $R^{55}$ is $R^{56}$-substituted alkyl (e.g., $C_1$-$C_8$ alkyl, $C_1$-$C_6$ alkyl, or $C_1$-$C_4$ alkyl). In embodiments, $R^{55}$ is an unsubstituted alkyl (e.g., $C_1$-$C_8$ alkyl, $C_1$-$C_6$ alkyl, or $C_1$-$C_4$ alkyl).

In embodiments, $R^{55}$ is $R^{56}$-substituted or unsubstituted heteroalkyl (e.g., 2 to 8 membered heteroalkyl, 2 to 6 membered heteroalkyl, or 2 to 4 membered heteroalkyl). In embodiments, $R^{55}$ is $R^{56}$-substituted heteroalkyl (e.g., 2 to 8 membered heteroalkyl, 2 to 6 membered heteroalkyl, or 2 to 4 membered heteroalkyl). In embodiments, $R^{55}$ is an unsubstituted heteroalkyl (e.g., 2 to 8 membered heteroalkyl, 2 to 6 membered heteroalkyl, or 2 to 4 membered heteroalkyl).

In embodiments, $R^{55}$ is $R^{56}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{55}$ is $R^{56}$-substituted cycloalkyl (e.g., $C_3$-$C_8$ cycloalkyl, $C_3$-$C_6$ cycloalkyl, or $C_5$-$C_6$ cycloalkyl). In embodiments, $R^{55}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{55}$ is $R^{56}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{55}$ is $R^{56}$-substituted heterocycloalkyl (e.g., 3 to 8 membered heterocycloalkyl, 3 to 6 membered heterocycloalkyl, or 5 to 6 membered heterocycloalkyl). In embodiments, $R^{55}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{55}$ is $R^{56}$-substituted or unsubstituted aryl (e.g., $C_6$-$C_{10}$ aryl, $C_{10}$ aryl, or phenyl). In embodiments, $R^{55}$ is $R^{56}$-substituted aryl (e.g., $C_6$-$C_{10}$ aryl, $C_{10}$ aryl, or phenyl). In embodiments, $R^{55}$ is an unsubstituted aryl (e.g., $C_6$-$C_{10}$ aryl, $C_{10}$ aryl, or phenyl).

In embodiments, $R^{55}$ is $R^{56}$-substituted or unsubstituted heteroaryl (e.g., 5 to 10 membered heteroaryl, 5 to 9 membered heteroaryl, or 5 to 6 membered heteroaryl). In embodiments, $R^{55}$ is $R^{56}$-substituted heteroaryl (e.g., 5 to 10 membered heteroaryl, 5 to 9 membered heteroaryl, or 5 to 6 membered heteroaryl). In embodiments, $R^{55}$ is an unsubstituted heteroaryl (e.g., 5 to 10 membered heteroaryl, 5 to 9 membered heteroaryl, or 5 to 6 membered heteroaryl).

$R^{56}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{57}$-substituted or unsubstituted alkyl (e.g., $C_1$-$C_8$ alkyl, $C_1$-$C_6$ alkyl, or $C_1$-$C_4$ alkyl), $R^{57}$-substituted or unsubstituted heteroalkyl (e.g., 2 to 8 membered heteroalkyl, 2 to 6 membered heteroalkyl, or 2 to 4 membered heteroalkyl), $R^{57}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{57}$-substituted or unsubstituted heterocycloalkyl (e.g., 3 to 8 membered heterocycloalkyl, 3 to 6 membered heterocycloalkyl, or 5 to 6 membered heterocycloalkyl), $R^{57}$-substituted or unsubstituted aryl (e.g., $C_6$-$C_{10}$ aryl, $C_{10}$ aryl, or phenyl), or $R^{57}$-substituted or unsubstituted heteroaryl (e.g., 5 to 10 membered heteroaryl, 5 to 9 membered heteroaryl, or 5 to 6 membered heteroaryl).

In embodiments, $R^{56}$ is $R^{57}$-substituted or unsubstituted alkyl (e.g., $C_1$-$C_8$ alkyl, $C_1$-$C_6$ alkyl, or $C_1$-$C_4$ alkyl). In embodiments, $R^{56}$ is $R^{57}$-substituted alkyl (e.g., $C_1$-$C_8$ alkyl, $C_1$-$C_6$ alkyl, or $C_1$-$C_4$ alkyl). In embodiments, $R^{56}$ is an unsubstituted alkyl (e.g., $C_1$-$C_8$ alkyl, $C_1$-$C_6$ alkyl, or $C_1$-$C_4$ alkyl).

In embodiments, $R^{56}$ is $R^{57}$-substituted or unsubstituted heteroalkyl (e.g., 2 to 8 membered heteroalkyl, 2 to 6 membered heteroalkyl, or 2 to 4 membered heteroalkyl). In embodiments, $R^{56}$ is $R^{57}$-substituted heteroalkyl (e.g., 2 to 8 membered heteroalkyl, 2 to 6 membered heteroalkyl, or 2 to 4 membered heteroalkyl). In embodiments, $R^{56}$ is an unsubstituted heteroalkyl (e.g., 2 to 8 membered heteroalkyl, 2 to 6 membered heteroalkyl, or 2 to 4 membered heteroalkyl).

In embodiments, $R^{56}$ is $R^{57}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{56}$ is $R^{57}$-substituted cycloalkyl (e.g., $C_3$-$C_8$ cycloalkyl, $C_3$-$C_6$ cycloalkyl, or $C_5$-$C_6$ cycloalkyl). In embodiments, $R^{56}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{56}$ is $R^{57}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{56}$ is $R^{57}$-substituted heterocycloalkyl (e.g., 3 to 8 membered heterocycloalkyl, 3 to 6 membered heterocycloalkyl, or 5 to 6 membered heterocycloalkyl). In embodiments, $R^{56}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{56}$ is $R^{57}$-substituted or unsubstituted aryl (e.g., $C_6$-$C_{10}$ aryl, $C_{10}$ aryl, or phenyl). In embodiments, $R^{56}$ is $R^{57}$-substituted aryl (e.g., $C_6$-$C_{10}$ aryl, $C_{10}$ aryl, or phenyl). In embodiments, $R^{56}$ is an unsubstituted aryl (e.g., $C_6$-$C_{10}$ aryl, $C_{10}$ aryl, or phenyl).

In embodiments, $R^{56}$ is $R^{57}$-substituted or unsubstituted heteroaryl (e.g., 5 to 10 membered heteroaryl, 5 to 9 membered heteroaryl, or 5 to 6 membered heteroaryl). In embodiments, $R^{56}$ is $R^{57}$-substituted heteroaryl (e.g., 5 to 10 membered heteroaryl, 5 to 9 membered heteroaryl, or 5 to 6 membered heteroaryl). In embodiments, $R^{56}$ is an unsubstituted heteroaryl (e.g., 5 to 10 membered heteroaryl, 5 to 9 membered heteroaryl, or 5 to 6 membered heteroaryl).

$R^{46A}$, $R^{46B}$, $R^{46C}$, $R^{46D}$, $R^{48}$, $R^{49A}$, $R^{49B}$, $R^{49C}$, $R^{49D}$, $R^{51}$, $R^{52A}$, $R^{52B}$, $R^{52C}$, $R^{52D}$, $R^{54}$, $R^{55A}$, $R^{55B}$, $R^{55C}$, $R^{55D}$ and $R^{57}$ are independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $R^{46A}$, $R^{46B}$, $R^{46C}$, $R^{46D}$, $R^{48}$, $R^{49A}$, $R^{49B}$, $R^{49C}$, $R^{49D}$, $R^{51}$, $R^{52A}$, $R^{52B}$, $R^{52C}$, $R^{52D}$, $R^{54}$, $R^{55A}$, $R^{55B}$, $R^{55C}$, $R^{55D}$ and $R^{57}$ are independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $X^{12.1}$, $X^{13.1}$, $X^{14.1}$ and $X^{15.1}$ are independently —Cl, —Br, —I or —F. The symbols n12, n13, n14, n15 are independently an integer from 0 to 4. The symbols m12, m13, m14, m15, v12, v13, v14, and v15 are independently 1 or 2.

In embodiments, $X^{12.1}$ is —Cl. In embodiments, $X^{12.1}$ is —F. In embodiments, $X^{12.1}$ is —Br. In embodiments, $X^{12.1}$ is —I. In embodiments, $X^{13.1}$ is —Cl. In embodiments, $X^{13.1}$ is —F. In embodiments, $X^{13.1}$ is —Br. In embodiments, $X^{13.1}$ is —I. In embodiments, $X^{14.1}$ is —Cl. In embodiments, $X^{14.1}$ is —F. In embodiments, $X^{14.1}$ is —Br. In embodiments, $X^{14.1}$ is —I. In embodiments, $X^{15.1}$ is —Cl. In embodiments, $X^{15.1}$ is —F. In embodiments, $X^{15.1}$ is —Br. In embodiments, $X^{15.1}$ is —I.

In embodiments, $X^{12.1}$ is —Cl, and $X^1$ is N. In embodiments, $X^{12.1}$ is —F, and $X^1$ is N. In embodiments, $X^{12.1}$ is —Br, and $X^1$ is N. In embodiments, $X^{12.1}$ is —I, and $X^1$ is N. In embodiments, $X^{13.1}$ is —Cl, and $X^1$ is N. In embodiments, $X^{13.1}$ is —F, and $X^1$ is N. In embodiments, $X^{13.1}$ is —Br, and $X^1$ is N. In embodiments, $X^{13.1}$ is —I, and $X^1$ is N. In embodiments, $X^{14.1}$ is —Cl, and $X^1$ is N. In embodiments, $X^{14.1}$ is —F, and $X^1$ is N. In embodiments, $X^{14.1}$ is —Br, and $X^1$ is N. In embodiments, $X^{14.1}$ is —I, and $X^1$ is N. In embodiments, $X^{15.1}$ is —Cl, and $X^1$ is N. In embodiments, $X^{15.1}$ is —F, and $X^1$ is N. In embodiments, $X^{15.1}$ is —Br, and $X^1$ is N. In embodiments, $X^{15.1}$ is —I, and $X^1$ is N.

In embodiments, $X^{12.1}$ is —Cl, and $X^2$ is N. In embodiments, $X^{12.1}$ is —F, and $X^2$ is N. In embodiments, $X^{12.1}$ is —Br, and $X^2$ is N. In embodiments, $X^{12.1}$ is —I, and $X^2$ is N. In embodiments, $X^{13.1}$ is —Cl, and $X^2$ is N. In embodiments, $X^{13.1}$ is —F, and $X^2$ is N. In embodiments, $X^{13.1}$ is —Br, and $X^2$ is N. In embodiments, $X^{13.1}$ is —I, and $X^2$ is N. In embodiments, $X^{14.1}$ is —Cl, and $X^2$ is N. In embodiments, $X^{14.1}$ is —F, and $X^2$ is N. In embodiments, $X^{14.1}$ is —Br, and $X^2$ is N. In embodiments, $X^{14.1}$ is —I, and $X^2$ is N. In embodiments, $X^{15.1}$ is —Cl, and $X^2$ is N. In embodiments, $X^{15.1}$ is —F, and $X^2$ is N. In embodiments, $X^{15.1}$ is —Br, and $X^2$ is N. In embodiments, $X^{15.1}$ is —I, and $X^2$ is N.

In embodiments, $X^{12.1}$ is —Cl, and $X^3$ is N. In embodiments, $X^{12.1}$ is —F, and $X^3$ is N. In embodiments, $X^{12.1}$ is —Br, and $X^3$ is N. In embodiments, $X^{12.1}$ is —I, and $X^3$ is N. In embodiments, $X^{13.1}$ is —Cl, and $X^3$ is N. In embodiments, $X^{13.1}$ is —F, and $X^3$ is N. In embodiments, $X^{13.1}$ is —Br, and $X^3$ is N. In embodiments, $X^{13.1}$ is —I, and $X^3$ is N. In embodiments, $X^{14.1}$ is —Cl, and $X^3$ is N. In embodiments, $X^{14.1}$ is —F, and $X^3$ is N. In embodiments, $X^{14.1}$ is —Br, and $X^3$ is N. In embodiments, $X^{14.1}$ is —I, and $X^3$ is N. In embodiments, $X^{15.1}$ is —Cl, and $X^3$ is N. In embodiments, $X^{15.1}$ is —F, and $X^3$ is N. In embodiments, $X^{15.1}$ is —Br, and $X^3$ is N. In embodiments, $X^{15.1}$ is —I, and $X^3$ is N.

In embodiments, the symbol n12 is an integer from 0 to 4. In embodiments, n12 is 0. In embodiments, n12 is 1. In embodiments, n12 is 2. In embodiments, n12 is 3. In embodiments, n12 is 4.

In embodiments, the symbol n13 is an integer from 0 to 4. In embodiments, n13 is 0. In embodiments, n13 is 1. In embodiments, n13 is 2. In embodiments, n13 is 3. In embodiments, n13 is 4.

In embodiments, the symbol n14 is an integer from 0 to 4. In embodiments, n14 is 0. In embodiments, n14 is 1. In embodiments, n14 is 2. In embodiments, n14 is 3. In embodiments, n14 is 4.

In embodiments, the symbol n15 is an integer from 0 to 4. In embodiments, n15 is 0. In embodiments, n15 is 1. In embodiments, n15 is 2. In embodiments, n15 is 3. In embodiments, n15 is 4.

In embodiments, the symbols m12 and v12 are independently 1 or 2. In embodiments, m12 is 1. In embodiments, m12 is 2. In embodiments, v12 is 1. In embodiments, v12 is 2.

In embodiments, the symbols m13 and v13 are independently 1 or 2. In embodiments, m13 is 1. In embodiments, m13 is 2. In embodiments, v13 is 1. In embodiments, v13 is 2.

In embodiments, the symbols m14 and v14 are independently 1 or 2. In embodiments, m14 is 1. In embodiments, m14 is 2. In embodiments, v14 is 1. In embodiments, v14 is 2.

In embodiments, the symbols m15 and v15 are independently 1 or 2. In embodiments, m15 is 1. In embodiments, m15 is 2. In embodiments, v15 is 1. In embodiments, v15 is 2.

In embodiments, the compounds provided herein have structural Formula (II):

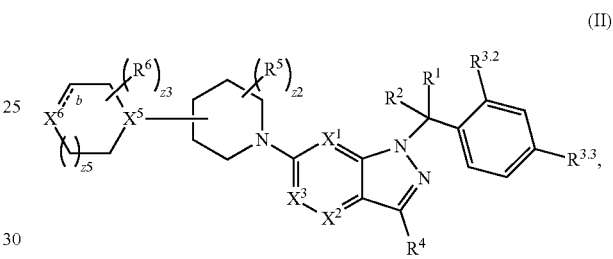

(II)

or a pharmaceutically acceptable salt thereof. $R^{3.2}$ is hydrogen, halogen, $-CX^{3.2}_3$, $-CHX^{3.2}_2$, $-CH_2X^{3.2}$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3.3}$ is hydrogen, halogen, $-CX^{3.3}_3$, $-CHX^{3.3}_2$, $-CH_2X^{3.3}$, $-CN$, $-SO_{n3.3}R^{3.3A}$, $-SO_{v3.3}NR^{3.3B}R^{3.3C}$, $-NHNR^{3.3B}R^{3.3C}$, $-ONR^{3.3B}R^{3.3C}$, $-NHC(O)NHNR^{3.3B}R^{3.3C}$, $-NHC(O)NR^{3.3B}R^{3.3C}$, $-N(O)_{m3.3}$, $-NR^{3.3B}R^{3.3C}$, $-C(O)R^{3.3D}$, $-C(O)OR^{3.3D}$, $-C(O)NR^{3.3B}R^{3.3C}$, $-OR^{3.3A}$, $-NR^{3.3B}SO_2R^{3.3A}$, $-NR^{3.3B}C(O)R^{3.3D}$, $-NR^{3.3B}C(O)OR^{3.3D}$, $-NR^{3.3B}OR^{3.3D}$, $-OCX^{3.3}_3$, $-OCHX^{3.3}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3.2A}$, $R^{3.2B}$, $R^{3.2C}$, $R^{3.2D}$, $R^{3.3A}$, $R^{3.3B}$, $R^{3.3C}$ and $R^{3.3D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.2B}$ and $R^{3.2C}$ or $R^{3.3B}$ and $R^{3.3C}$ substituents bonded to the same nitrogen atom may optionally be joined to form a substituted or unsubstituted heterocycloalkyl or substituted or unsubstituted heteroaryl. $X^{3.2}$ and $X^{3.3}$ are independently —Cl, —Br, —I or —F.

z2, z3, z5, ≠, $X^1$, $X^2$, $X^3$, $X^5$, $X^6$, $R^1$, $R^2$, $R^4$, $R^5$ and $R^6$ are as described herein, including embodiments.

In embodiments, $R^{3.2}$ is hydrogen, halogen, $-CX^{3.2}_3$, $-CHX^{3.2}_2$, $-CH_2X^{3.2}$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{3.2}$ is hydrogen, halogen, $-CX^{3.2}_3$, $-CHX^{3.2}_2$, $-CH_2X^{3.2}$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, $R^{22.2}$-substituted or unsubstituted alkyl (e.g., $C_1$-$C_8$ alkyl, $C_1$-$C_6$ alkyl, or $C_1$-$C_4$ alkyl), $R^{22.2}$-substituted or unsubstituted heteroalkyl (e.g., 2 to 8 membered heteroalkyl, 2 to 6 membered heteroalkyl, or 2 to 4 membered heteroalkyl), $R^{2.2}_2$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22.2}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22.2}$-substituted or unsubstituted aryl (e.g., $C_6$-$C_{10}$ aryl, $C_{10}$ aryl, or phenyl), or $R^{22.2}$-substituted or unsubstituted heteroaryl (e.g., 5 to 10 membered heteroaryl, 5 to 9 membered heteroaryl, or 5 to 6 membered heteroaryl).

In embodiments, $R^{3.2}$ is $R^{22.2}$-substituted or unsubstituted alkyl (e.g., $C_1$-$C_8$ alkyl, $C_1$-$C_6$ alkyl, or $C_1$-$C_4$ alkyl). In embodiments, $R^{3.2}$ is $R^{22.2}$-substituted alkyl (e.g., $C_1$-$C_8$ alkyl, $C_1$-$C_6$ alkyl, or $C_1$-$C_4$ alkyl). In embodiments, $R^{3.2}$ is an unsubstituted alkyl (e.g., $C_1$-$C_8$ alkyl, $C_1$-$C_6$ alkyl, or $C_1$-$C_4$ alkyl).

In embodiments, $R^{3.2}$ is $R^{22.2}$-substituted or unsubstituted heteroalkyl (e.g., 2 to 8 membered heteroalkyl, 2 to 6 membered heteroalkyl, or 2 to 4 membered heteroalkyl). In embodiments, $R^{3.2}$ is $R^{22.2}$-substituted heteroalkyl (e.g., 2 to 8 membered heteroalkyl, 2 to 6 membered heteroalkyl, or 2 to 4 membered heteroalkyl). In embodiments, $R^{3.2}$ is an unsubstituted heteroalkyl (e.g., 2 to 8 membered heteroalkyl, 2 to 6 membered heteroalkyl, or 2 to 4 membered heteroalkyl).

In embodiments, $R^{3.2}$ is $R^{22.2}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3.2}$ is $R^{22.2}$-substituted cycloalkyl (e.g., $C_3$-$C_8$ cycloalkyl, $C_3$-$C_6$ cycloalkyl, or $C_5$-$C_6$ cycloalkyl). In embodiments, $R^{3.2}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{3.2}$ is $R^{22.2}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3.2}$ is $R^{22.2}$-substituted heterocycloalkyl (e.g., 3 to 8 membered heterocycloalkyl, 3 to 6 membered heterocycloalkyl, or 5 to 6 membered heterocycloalkyl). In embodiments, $R^{3.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{3.2}$ is $R^{22.2}$-substituted or unsubstituted aryl (e.g., $C_6$-$C_{10}$ aryl, $C_{10}$ aryl, or phenyl). In embodiments, $R^{3.2}$ is $R^{22.2}$-substituted aryl (e.g., $C_6$-$C_{10}$ aryl, $C_{10}$ aryl, or phenyl). In embodiments, $R^{3.2}$ is an unsubstituted aryl (e.g., $C_6$-$C_{10}$ aryl, $C_{10}$ aryl, or phenyl).

In embodiments, $R^{3.2}$ is $R^{22.2}$-substituted or unsubstituted heteroaryl (e.g., 5 to 10 membered heteroaryl, 5 to 9 membered heteroaryl, or 5 to 6 membered heteroaryl). In embodiments, $R^{3.2}$ is $R^{22.2}$-substituted heteroaryl (e.g., 5 to 10 membered heteroaryl, 5 to 9 membered heteroaryl, or 5 to 6 membered heteroaryl). In embodiments, $R^{3.2}$ is an unsubstituted heteroaryl (e.g., 5 to 10 membered heteroaryl, 5 to 9 membered heteroaryl, or 5 to 6 membered heteroaryl).

In embodiments, $R^{3.2}$ is hydrogen, halogen, $-CN$, $CF_3$ or unsubstituted alkyl. In embodiments, $R^{3.2}$ is chlorine. In embodiments, $R^{3.2}$ is fluorine. In embodiments, $R^{3.2}$ is $-CH_3$. In embodiments, $R^{3.2}$ is hydrogen. In embodiments, $R^{3.2}$ is halogen. In embodiments, $R^{3.2}$ is $-CN$. In embodiments, $R^{3.2}$ is $CF_3$. In embodiments, $R^{3.2}$ is unsubstituted alkyl.

In embodiments, $R^{3.2}$ is $CHF_2$, $CH_2F$. $CCl_3$, $CHCl_2$, $CH_2Cl$, $-CH_3$, $-CH_2CH_3$. In embodiments, $R^{3.2}$ is $CHF_2$. In embodiments, $R^{3.2}$ is $CH_2F$. In embodiments, $R^{3.2}$ is $CCl_3$. In embodiments, $R^{3.2}$ is $CHCl_2$. In embodiments, $R^{3.2}$ is $CH_2Cl$. In embodiments, $R^{3.2}$ is $-CH_3$. In embodiments, $R^{3.2}$ is $-CH_2CH_3$. In embodiments, $R^{3.2}$ is Cl. In embodiments, $R^{3.2}$ is F.

In embodiments, $R^{3.3}$ is hydrogen, halogen, $-CX^{3.3}_3$, $-CHX^{3.3}_2$, $-CH_2X^{3.3}$, $-CN$, $-SO_{n3.3}R^{3.3A}$, $-SO_{v3.3}NR^{33B}R^{3.3C}$, $-NHNR^{3.3B}R^{3.3C}$, $-ONR^{3.3B}R^{3.3C}$, $-NHC(O)NHNR^{3.3B}R^{3.3C}$, $-NHC(O)NR^{3.3B}R^{3.3C}$, $-N(O)_{m3.3}$, $-NR^{3.3B}R^{3.3C}$, $-C(O)R^{3.3D}$, $-C(O)OR^{3.3D}$, $-C(O)NR^{3.3B}R^{3.3C}$, $-OR^{3.3A}$, $-NR^{3.3B}SO_2R^{3.3A}$, $-NR^{3.3B}C(O)R^{3.3D}$, $-NR^{3.3B}C(O)OR^{3.3D}$, $-NR^{3.3B}OR^{3.3D}$, $-OCX^{3.3}_3$, $-OCHX^{3.3}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{3.3}$ is hydrogen, halogen, $-CX^{3.3}_3$, $-CHX^{3.3}_2$, $-CH_2X^{3.3}$, $-CN$, $-SO_{n3.3}R^{3.3A}$, $-SO_{v3.3}NR^{3.3B}R^{3.3C}$, $-NHNR^{3.3B}R^{3.3C}$, $-ONR^{3.3B}R^{3.3C}$, $-NHC(O)NHNR^{3.3B}R^{3.3C}$, $-NHC(O)NR^{3.3B}R^{3.3C}$, $-N(O)_{m3.3}$, $-NR^{3.3B}R^{3.3C}$, $-C(O)R^{3.3D}$, $-C(O)OR^{3.3D}$, $-C(O)NR^{3.3B}R^{3.3C}$, $-OR^{3.3A}$, $-NR^{3.3B}SO_2R^{3.3A}$, $-NR^{3.3B}C(O)R^{3.3D}$, $-NR^{3.3B}C(O)OR^{3.3D}$, $-NR^{3.3B}OR^{3.3D}$, $-OCX^{3.3}_3$, $-OCHX^{3.3}_2$, $R^{22.3}$-substituted or unsubstituted alkyl (e.g., $C_1$-$C_8$ alkyl, $C_1$-$C_6$ alkyl, or $C_1$-$C_4$ alkyl), $R^{22.3}$-substituted or unsubstituted heteroalkyl (e.g., 2 to 8 membered heteroalkyl, 2 to 6 membered heteroalkyl, or 2 to 4 membered heteroalkyl), $R^{22.3}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22.3}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22.3}$-substituted or unsubstituted aryl (e.g., $C_6$-$C_{10}$ aryl, $C_{10}$ aryl, or phenyl), or $R^{22.3}$-substituted or unsubstituted heteroaryl (e.g., 5 to 10 membered heteroaryl, 5 to 9 membered heteroaryl, or 5 to 6 membered heteroaryl).

In embodiments, $R^{3.3}$ is $R^{22.3}$-substituted or unsubstituted alkyl (e.g., $C_1$-$C_8$ alkyl, $C_1$-$C_6$ alkyl, or $C_1$-$C_4$ alkyl). In embodiments, $R^{3.3}$ is $R^{22.3}$-substituted alkyl (e.g., $C_1$-$C_8$ alkyl, $C_1$-$C_6$ alkyl, or $C_1$-$C_4$ alkyl). In embodiments, $R^{3.3}$ is an unsubstituted alkyl (e.g., $C_1$-$C_8$ alkyl, $C_1$-$C_6$ alkyl, or $C_1$-$C_4$ alkyl).

In embodiments, $R^{3.3}$ is $R^{22.3}$-substituted or unsubstituted heteroalkyl (e.g., 2 to 8 membered heteroalkyl, 2 to 6 membered heteroalkyl, or 2 to 4 membered heteroalkyl). In embodiments, $R^{3.3}$ is $R^{22.3}$-substituted heteroalkyl (e.g., 2 to 8 membered heteroalkyl, 2 to 6 membered heteroalkyl, or 2 to 4 membered heteroalkyl). In embodiments, $R^{3.3}$ is an unsubstituted heteroalkyl (e.g., 2 to 8 membered heteroalkyl, 2 to 6 membered heteroalkyl, or 2 to 4 membered heteroalkyl).

In embodiments, $R^{3.3}$ is $R^{22.3}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3.3}$ is $R^{22.3}$-substituted cycloalkyl (e.g., $C_3$-$C_8$ cycloalkyl, $C_3$-$C_6$ cycloalkyl, or $C_5$-$C_6$ cycloalkyl). In embodiments, $R^{3.3}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{3.3}$ is $R^{22.3}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3.3}$ is $R^{22.3}$-substituted heterocycloalkyl (e.g., 3 to 8 membered heterocycloalkyl, 3 to 6 membered heterocycloalkyl, or 5 to 6 membered heterocycloalkyl). In embodiments, $R^{3.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{3.3}$ is $R^{22.3}$-substituted or unsubstituted aryl (e.g., $C_6$-$C_{10}$ aryl, $C_{10}$ aryl, or phenyl). In embodiments, $R^{3.3}$ is $R^{22.3}$-substituted aryl (e.g., $C_6$-$C_{10}$ aryl, $C_{10}$ aryl, or phenyl). In embodiments, $R^{3.3}$ is an unsubstituted aryl (e.g., $C_6$-$C_{10}$ aryl, $C_{10}$ aryl, or phenyl).

In embodiments, $R^{3.3}$ is $R^{22.3}$-substituted or unsubstituted heteroaryl (e.g., 5 to 10 membered heteroaryl, 5 to 9 membered heteroaryl, or 5 to 6 membered heteroaryl). In embodiments, $R^{3.3}$ is $R^{22.3}$-substituted heteroaryl (e.g., 5 to 10 membered heteroaryl, 5 to 9 membered heteroaryl, or 5 to 6 membered heteroaryl). In embodiments, $R^{3.3}$ is an unsubstituted heteroaryl (e.g., 5 to 10 membered heteroaryl, 5 to 9 membered heteroaryl, or 5 to 6 membered heteroaryl).

In embodiments, $R^{3.2}$ and $R^{3.3}$ are independently halogen, —CN, $CF_3$ or unsubstituted alkyl. In embodiments, $R^{3.2}$ and $R^{3.3}$ are independently chlorine or fluorine. In embodiments, $R^{3.2}$ and $R^{3.3}$ are independently —$CH_3$.

In embodiments, $R^{3.2A}$, $R^{3.2B}$, $R^{3.2C}$, $R^{3.2D}$, $R^{3.3A}$, $R^{3.3B}$, $R^{3.3C}$ and $R^{3.3D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{3.2A}$, $R^{3.2B}$, $R^{3.2C}$, $R^{3.2D}$, $R^{3.3A}$, $R^{3.3B}$, $R^{3.3C}$ and $R^{3.3D}$ are independently halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{3.2B}$ and $R^{3.2C}$ or $R^{3.3B}$ and $R^{3.3C}$ substituents bonded to the same nitrogen atom may optionally be joined to form a substituted or unsubstituted heterocycloalkyl or substituted or unsubstituted heteroaryl.

In embodiments, $R^{3.2A}$ is hydrogen, halogen, —$CF_3$, —$CCl_3$, —$CBr_3$, —$CI_3$, —COOH, —$CONH_2$, $R^{22A}$-substituted or unsubstituted alkyl (e.g., $C_1$-$C_8$ alkyl, $C_1$-$C_6$ alkyl, or $C_1$-$C_4$ alkyl), $R^{22A}$-substituted or unsubstituted heteroalkyl (e.g., 2 to 8 membered heteroalkyl, 2 to 6 membered heteroalkyl, or 2 to 4 membered heteroalkyl), $R^{22A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22A}$-substituted or unsubstituted aryl (e.g., $C_6$-$C_{10}$ aryl, $C_{10}$ aryl, or phenyl), or $R^{22A}$-substituted or unsubstituted heteroaryl (e.g., 5 to 10 membered heteroaryl, 5 to 9 membered heteroaryl, or 5 to 6 membered heteroaryl).

In embodiments, $R^{3.3A}$ is hydrogen, halogen, —$CF_3$, —$CCl_3$, —$CBr_3$, —$CI_3$, —COOH, —$CONH_2$, $R^{22A}$-substituted or unsubstituted alkyl (e.g., $C_1$-$C_8$ alkyl, $C_1$-$C_6$ alkyl, or $C_1$-$C_4$ alkyl), $R^{22A}$-substituted or unsubstituted heteroalkyl (e.g., 2 to 8 membered heteroalkyl, 2 to 6 membered heteroalkyl, or 2 to 4 membered heteroalkyl), $R^{22A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22A}$-substituted or unsubstituted aryl (e.g., $C_6$-$C_{10}$ aryl, $C_{10}$ aryl, or phenyl), or $R^{22A}$-substituted or unsubstituted heteroaryl (e.g., 5 to 10 membered heteroaryl, 5 to 9 membered heteroaryl, or 5 to 6 membered heteroaryl).

In embodiments, $R^{3.2B}$ is hydrogen, halogen, —$CF_3$, —$CCl_3$, —$CBr_3$, —$CI_3$, —COOH, —$CONH_2$, $R^{22B}$-substituted or unsubstituted alkyl (e.g., $C_1$-$C_8$ alkyl, $C_1$-$C_6$ alkyl, or $C_1$-$C_4$ alkyl), $R^{22B}$-substituted or unsubstituted heteroalkyl (e.g., 2 to 8 membered heteroalkyl, 2 to 6 membered heteroalkyl, or 2 to 4 membered heteroalkyl), $R^{22B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22B}$-substituted or unsubstituted aryl (e.g., $C_6$-$C_{10}$ aryl, $C_{10}$ aryl, or phenyl), or $R^{22B}$-substituted or unsubstituted heteroaryl (e.g., 5 to 10 membered heteroaryl, 5 to 9 membered heteroaryl, or 5 to 6 membered heteroaryl). In embodiments, $R^{3.2B}$ and $R^{3.2C}$ substituents bonded to the same nitrogen atom may optionally be joined to form a $R^{22B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{22B}$-substituted or unsubstituted heteroaryl (e.g., 5 to 10 membered heteroaryl, 5 to 9 membered heteroaryl, or 5 to 6 membered heteroaryl).

In embodiments, $R^{3.3B}$ is hydrogen, halogen, —$CF_3$, —$CCl_3$, —$CBr_3$, —$CI_3$, —COOH, —$CONH_2$, $R^{22B}$-substituted or unsubstituted alkyl (e.g., $C_1$-$C_8$ alkyl, $C_1$-$C_6$ alkyl, or $C_1$-$C_4$ alkyl), $R^{22B}$-substituted or unsubstituted heteroalkyl (e.g., 2 to 8 membered heteroalkyl, 2 to 6 membered heteroalkyl, or 2 to 4 membered heteroalkyl), $R^{22B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22B}$-substituted or unsubstituted aryl (e.g., $C_6$-$C_{10}$ aryl, $C_{10}$ aryl, or phenyl), or $R^{22B}$-substituted or unsubstituted heteroaryl (e.g., 5 to 10 membered heteroaryl, 5 to 9 membered heteroaryl, or 5 to 6 membered heteroaryl). In embodiments, $R^{3.3B}$ and $R^{3.3C}$ substituents bonded to the same nitrogen atom may optionally be joined to form a $R^{22B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{22B}$-substituted or unsubstituted heteroaryl (e.g., 5 to 10 membered heteroaryl, 5 to 9 membered heteroaryl, or 5 to 6 membered heteroaryl).

In embodiments, $R^{3.2C}$ is hydrogen, halogen, —$CF_3$, —$CCl_3$, —$CBr_3$, —$CI_3$, —COOH, —$CONH_2$, $R^{22C}$-substituted or unsubstituted alkyl (e.g., $C_1$-$C_8$ alkyl, $C_1$-$C_6$ alkyl, or $C_1$-$C_4$ alkyl), $R^{22C}$-substituted or unsubstituted heteroalkyl (e.g., 2 to 8 membered heteroalkyl, 2 to 6 membered heteroalkyl, or 2 to 4 membered heteroalkyl), $R^{22C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22C}$-substituted or unsubstituted aryl (e.g., $C_6$-$C_{10}$ aryl, $C_{10}$ aryl, or phenyl), or $R^{22C}$-substituted or unsubstituted heteroaryl (e.g., 5 to 10 membered heteroaryl, 5 to 9 membered heteroaryl, or 5 to 6 membered heteroaryl). In embodiments, $R^{3.2B}$ and $R^{3.2C}$ substituents bonded to the same nitrogen atom may optionally be joined to form a $R^{22C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{22C}$-substituted or unsubstituted heteroaryl (e.g., 5 to 10 membered heteroaryl, 5 to 9 membered heteroaryl, or 5 to 6 membered heteroaryl).

In embodiments, $R^{3.3C}$ is hydrogen, halogen, —$CF_3$, —$CCl_3$, —$CBr_3$, —$CI_3$, —COOH, —$CONH_2$, $R^{22C}$-substituted or unsubstituted alkyl (e.g., $C_1$-$C_8$ alkyl, $C_1$-$C_6$ alkyl, or $C_1$-$C_4$ alkyl), $R^{22C}$-substituted or unsubstituted heteroalkyl (e.g., 2 to 8 membered heteroalkyl, 2 to 6 membered heteroalkyl, or 2 to 4 membered heteroalkyl), $R^{22C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22C}$-substituted or unsubstituted aryl (e.g., $C_6$-$C_{10}$ aryl, $C_{10}$ aryl, or phenyl), or $R^{22C}$-substituted or unsubstituted heteroaryl (e.g., 5 to 10 membered heteroaryl, 5 to 9 membered heteroaryl, or 5 to 6 membered heteroaryl). In embodiments, $R^{3.3B}$ and $R^{3.3C}$ substituents bonded to the same nitrogen atom may optionally be joined to form a $R^{22C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{22C}$-substituted or unsubstituted heteroaryl (e.g., 5 to 10 membered heteroaryl, 5 to 9 membered heteroaryl, or 5 to 6 membered heteroaryl).

In embodiments, $R^{3.2D}$ is hydrogen, halogen, —$CF_3$, —$CCl_3$, —$CBr_3$, —$CI_3$, —COOH, —$CONH_2$, $R^{22D}$-substituted or unsubstituted alkyl (e.g., $C_1$-$C_8$ alkyl, $C_1$-$C_6$ alkyl, or $C_1$-$C_4$ alkyl), $R^{22D}$-substituted or unsubstituted heteroalkyl (e.g., 2 to 8 membered heteroalkyl, 2 to 6 membered heteroalkyl, or 2 to 4 membered heteroalkyl), $R^{22D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22D}$-substituted or unsubstituted aryl (e.g., $C_6$-$C_{10}$ aryl, $C_{10}$ aryl, or phenyl), or $R^{22D}$-substituted or unsubstituted heteroaryl (e.g., 5 to 10 membered heteroaryl, 5 to 9 membered heteroaryl, or 5 to 6 membered heteroaryl).

In embodiments, $R^{3.3D}$ is hydrogen, halogen, —$CF_3$, —$CCl_3$, —$CBr_3$, —$CI_3$, —COOH, —$CONH_2$, $R^{22D}$-substituted or unsubstituted alkyl (e.g., $C_1$-$C_8$ alkyl, $C_1$-$C_6$ alkyl, or $C_1$-$C_4$ alkyl), $R^{22D}$-substituted or unsubstituted heteroalkyl (e.g., 2 to 8 membered heteroalkyl, 2 to 6 membered heteroalkyl, or 2 to 4 membered heteroalkyl), $R^{22D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22D}$-substituted or unsubstituted aryl (e.g., $C_6$-$C_{10}$ aryl, $C_{10}$ aryl, or phenyl), or $R^{22D}$-substituted or unsubstituted heteroaryl (e.g., 5 to 10 membered heteroaryl, 5 to 9 membered heteroaryl, or 5 to 6 membered heteroaryl).

$R^{22.2}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC$HCl_2$, —$OCHBr_2$, —$OCHI_2$, —$OCHF_2$, $R^{23.2}$-substituted or unsubstituted alkyl (e.g., $C_1$-$C_8$ alkyl, $C_1$-$C_6$ alkyl, or $C_1$-$C_4$ alkyl), $R^{23.2}$-substituted or unsubstituted heteroalkyl (e.g., 2 to 8 membered heteroalkyl, 2 to 6 membered heteroalkyl, or 2 to 4 membered heteroalkyl), $R^{23.2}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{23.2}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23.2}$-substituted or unsubstituted aryl (e.g., $C_6$-$C_{10}$ aryl, $C_{10}$ aryl, or phenyl), or $R^{23.2}$-substituted or unsubstituted heteroaryl (e.g., 5 to 10 membered heteroaryl, 5 to 9 membered heteroaryl, or 5 to 6 membered heteroaryl).

In embodiments, $R^{22.2}$ is $R^{23.2}$-substituted or unsubstituted alkyl (e.g., $C_1$-$C_8$ alkyl, $C_1$-$C_6$ alkyl, or $C_1$-$C_4$ alkyl). In embodiments, $R^{22.2}$ is $R^{23.2}$-substituted alkyl (e.g., $C_1$-$C_8$ alkyl, $C_1$-$C_6$ alkyl, or $C_1$-$C_4$ alkyl). In embodiments, $R^{22.2}$ is an unsubstituted alkyl (e.g., $C_1$-$C_8$ alkyl, $C_1$-$C_6$ alkyl, or $C_1$-$C_4$ alkyl).

In embodiments, $R^{22.2}$ is $R^{23.2}$-substituted or unsubstituted heteroalkyl (e.g., 2 to 8 membered heteroalkyl, 2 to 6 membered heteroalkyl, or 2 to 4 membered heteroalkyl). In embodiments, $R^{22.2}$ is $R^{23.2}$-substituted heteroalkyl (e.g., 2 to 8 membered heteroalkyl, 2 to 6 membered heteroalkyl, or 2 to 4 membered heteroalkyl). In embodiments, $R^{22.2}$ is an unsubstituted heteroalkyl (e.g., 2 to 8 membered heteroalkyl, 2 to 6 membered heteroalkyl, or 2 to 4 membered heteroalkyl).

In embodiments, $R^{22.2}$ is $R^{23.2}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{22.2}$ is $R^{23.2}$-substituted cycloalkyl (e.g., $C_3$-$C_8$ cycloalkyl, $C_3$-$C_6$ cycloalkyl, or $C_5$-$C_6$ cycloalkyl). In embodiments, $R^{22.2}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{22.2}$ is $R^{23.2}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{22.2}$ is $R^{23.2}$-substituted heterocycloalkyl (e.g., 3 to 8 membered heterocycloalkyl, 3 to 6 membered heterocycloalkyl, or 5 to 6 membered heterocycloalkyl). In embodiments, $R^{22.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{22.2}$ is $R^{23.2}$-substituted or unsubstituted aryl (e.g., $C_6$-$C_{10}$ aryl, $C_{10}$ aryl, or phenyl). In embodiments, $R^{22.2}$ is $R^{23.2}$-substituted aryl (e.g., $C_6$-$C_{10}$ aryl, $C_{10}$ aryl, or phenyl). In embodiments, $R^{22.2}$ is an unsubstituted aryl (e.g., $C_6$-$C_{10}$ aryl, $C_{10}$ aryl, or phenyl).

In embodiments, $R^{22.2}$ is $R^{23.2}$-substituted or unsubstituted heteroaryl (e.g., 5 to 10 membered heteroaryl, 5 to 9 membered heteroaryl, or 5 to 6 membered heteroaryl). In embodiments, $R^{22.2}$ is $R^{23.2}$-substituted heteroaryl (e.g., 5 to 10 membered heteroaryl, 5 to 9 membered heteroaryl, or 5 to 6 membered heteroaryl). In embodiments, $R^{22.2}$ is an unsubstituted heteroaryl (e.g., 5 to 10 membered heteroaryl, 5 to 9 membered heteroaryl, or 5 to 6 membered heteroaryl).

$R^{23.2}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OC HCl$_2$, —OCHBr$_2$, —OCHI$_2$, —OCHF$_2$, $R^{24.2}$-substituted or unsubstituted alkyl (e.g., C$_1$-C$_8$ alkyl, C$_1$-C$_6$ alkyl, or C$_1$-C$_4$ alkyl), $R^{24.2}$-substituted or unsubstituted heteroalkyl (e.g., 2 to 8 membered heteroalkyl, 2 to 6 membered heteroalkyl, or 2 to 4 membered heteroalkyl), $R^{24.2}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{24.2}$-substituted or unsubstituted heterocycloalkyl (e.g., 3 to 8 membered heterocycloalkyl, 3 to 6 membered heterocycloalkyl, or 5 to 6 membered heterocycloalkyl), $R^{24.2}$-substituted or unsubstituted aryl (e.g., C$_6$-C$_{10}$ aryl, C$_{10}$ aryl, or phenyl), or $R^{24.2}$-substituted or unsubstituted heteroaryl (e.g., 5 to 10 membered heteroaryl, 5 to 9 membered heteroaryl, or 5 to 6 membered heteroaryl).

In embodiments, $R^{23.2}$ is $R^{24.2}$-substituted or unsubstituted alkyl (e.g., C$_1$-C$_8$ alkyl, C$_1$-C$_6$ alkyl, or C$_1$-C$_4$ alkyl). In embodiments, $R^{23.2}$ is $R^{24.2}$-substituted alkyl (e.g., C$_1$-C$_8$ alkyl, C$_1$-C$_6$ alkyl, or C$_1$-C$_4$ alkyl). In embodiments, $R^{23.2}$ is an unsubstituted alkyl (e.g., C$_1$-C$_8$ alkyl, C$_1$-C$_6$ alkyl, or C$_1$-C$_4$ alkyl).

In embodiments, $R^{23.2}$ is $R^{24.2}$-substituted or unsubstituted heteroalkyl (e.g., 2 to 8 membered heteroalkyl, 2 to 6 membered heteroalkyl, or 2 to 4 membered heteroalkyl). In embodiments, $R^{23.2}$ is $R^{24.2}$-substituted heteroalkyl (e.g., 2 to 8 membered heteroalkyl, 2 to 6 membered heteroalkyl, or 2 to 4 membered heteroalkyl). In embodiments, $R^{23.2}$ is an unsubstituted heteroalkyl (e.g., 2 to 8 membered heteroalkyl, 2 to 6 membered heteroalkyl, or 2 to 4 membered heteroalkyl).

In embodiments, $R^{23.2}$ is $R^{24.2}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{23.2}$ is $R^{24.2}$-substituted cycloalkyl (e.g., C$_3$-C$_8$ cycloalkyl, C$_3$-C$_6$ cycloalkyl, or C$_5$-C$_6$ cycloalkyl). In embodiments, $R^{23.2}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{23.2}$ is $R^{24.2}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{23.2}$ is $R^{24.2}$-substituted heterocycloalkyl (e.g., 3 to 8 membered heterocycloalkyl, 3 to 6 membered heterocycloalkyl, or 5 to 6 membered heterocycloalkyl). In embodiments, $R^{23.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{23.2}$ is $R^{24.2}$-substituted or unsubstituted aryl (e.g., C$_6$-C$_{10}$ aryl, C$_{10}$ aryl, or phenyl). In embodiments, $R^{23.2}$ is $R^{24.2}$-substituted aryl (e.g., C$_6$-C$_{10}$ aryl, C$_{10}$ aryl, or phenyl). In embodiments, $R^{23.2}$ is an unsubstituted aryl (e.g., C$_6$-C$_{10}$ aryl, C$_{10}$ aryl, or phenyl).

In embodiments, $R^{23.2}$ is $R^{24.2}$-substituted or unsubstituted heteroaryl (e.g., 5 to 10 membered heteroaryl, 5 to 9 membered heteroaryl, or 5 to 6 membered heteroaryl). In embodiments, $R^{23.2}$ is $R^{24.2}$-substituted heteroaryl (e.g., 5 to 10 membered heteroaryl, 5 to 9 membered heteroaryl, or 5 to 6 membered heteroaryl). In embodiments, $R^{23.2}$ is an unsubstituted heteroaryl (e.g., 5 to 10 membered heteroaryl, 5 to 9 membered heteroaryl, or 5 to 6 membered heteroaryl).

In embodiments, $R^{3.3}$ is hydrogen, halogen, —CN, —CF$_3$ or unsubstituted alkyl. In embodiments, $R^{3.3}$ is hydrogen. In embodiments, $R^{3.3}$ halogen. In embodiments, $R^{3.3}$ —CN. In embodiments, $R^{3.3}$ —CF$_3$. In embodiments, $R^{3.3}$ unsubstituted alkyl. In embodiments, $R^{3.3}$ is chlorine or fluorine. In embodiments, $R^{3.3}$ is —CH$_3$.

In embodiments, $R^{3.3}$ is CHF$_2$, CH$_2$F. CCl$_3$, CHCl$_2$, CH$_2$Cl, —CH$_3$, —CH$_2$CH$_3$. In embodiments, $R^{3.3}$ is CHF$_2$. In embodiments, $R^{3.3}$ is CH$_2$F. In embodiments, $R^{3.3}$ is CCl$_3$. In embodiments, $R^{3.3}$ is CHCl$_2$. In embodiments, $R^{3.3}$ is CH$_2$Cl. In embodiments, $R^{3.3}$ is —CH$_3$. In embodiments, $R^{3.3}$ is —CH$_2$CH$_3$. In embodiments, $R^{3.3}$ is —Cl. In embodiments, $R^{3.3}$ is —F.

$R^{22.3}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OC HCl$_2$, —OCHBr$_2$, —OCHI$_2$, —OCHF$_2$, $R^{23.3}$-substituted or unsubstituted alkyl (e.g., C$_1$-C$_8$ alkyl, C$_1$-C$_6$ alkyl, or C$_1$-C$_4$ alkyl), $R^{23.3}$-substituted or unsubstituted heteroalkyl (e.g., 2 to 8 membered heteroalkyl, 2 to 6 membered heteroalkyl, or 2 to 4 membered heteroalkyl), $R^{23.3}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{23.3}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23.3}$-substituted or unsubstituted aryl (e.g., C$_6$-C$_{10}$ aryl, C$_{10}$ aryl, or phenyl), or $R^{23.3}$-substituted or unsubstituted heteroaryl (e.g., 5 to 10 membered heteroaryl, 5 to 9 membered heteroaryl, or 5 to 6 membered heteroaryl).

In embodiments, $R^{22.3}$ is $R^{23.3}$-substituted or unsubstituted alkyl (e.g., C$_1$-C$_8$ alkyl, C$_1$-C$_6$ alkyl, or C$_1$-C$_4$ alkyl). In embodiments, $R^{22.3}$ is $R^{23.3}$-substituted alkyl (e.g., C$_1$-C$_8$ alkyl, C$_1$-C$_6$ alkyl, or C$_1$-C$_4$ alkyl). In embodiments, $R^{22.3}$ is an unsubstituted alkyl (e.g., C$_1$-C$_8$ alkyl, C$_1$-C$_6$ alkyl, or C$_1$-C$_4$ alkyl).

In embodiments, $R^{22.3}$ is $R^{23.3}$-substituted or unsubstituted heteroalkyl (e.g., 2 to 8 membered heteroalkyl, 2 to 6 membered heteroalkyl, or 2 to 4 membered heteroalkyl). In embodiments, $R^{22.3}$ is $R^{23.3}$-substituted heteroalkyl (e.g., 2 to 8 membered heteroalkyl, 2 to 6 membered heteroalkyl, or 2 to 4 membered heteroalkyl). In embodiments, $R^{22.3}$ is an unsubstituted heteroalkyl (e.g., 2 to 8 membered heteroalkyl, 2 to 6 membered heteroalkyl, or 2 to 4 membered heteroalkyl).

In embodiments, $R^{22.3}$ is $R^{23.3}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{22.3}$ is $R^{23.3}$-substituted cycloalkyl (e.g., C$_3$-C$_8$ cycloalkyl, C$_3$-C$_6$ cycloalkyl, or C$_5$-C$_6$ cycloalkyl). In embodiments, $R^{22.3}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{22.3}$ is $R^{23.3}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{22.3}$ is $R^{23.3}$-substituted heterocycloalkyl (e.g., 3 to 8 membered heterocycloalkyl, 3 to 6 membered heterocycloalkyl, or 5 to 6 membered heterocycloalkyl). In embodiments, $R^{22.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{22.3}$ is $R^{23.3}$-substituted or unsubstituted aryl (e.g., $C_6$-$C_{10}$ aryl, $C_{10}$ aryl, or phenyl). In embodiments, $R^{22.3}$ is $R^{23.3}$-substituted aryl (e.g., $C_6$-$C_{10}$ aryl, $C_{10}$ aryl, or phenyl). In embodiments, $R^{22.3}$ is an unsubstituted aryl (e.g., $C_6$-$C_{10}$ aryl, $C_{10}$ aryl, or phenyl).

In embodiments, $R^{22.3}$ is $R^{23.3}$-substituted or unsubstituted heteroaryl (e.g., 5 to 10 membered heteroaryl, 5 to 9 membered heteroaryl, or 5 to 6 membered heteroaryl). In embodiments, $R^{22.3}$ is $R^{23.3}$-substituted heteroaryl (e.g., 5 to 10 membered heteroaryl, 5 to 9 membered heteroaryl, or 5 to 6 membered heteroaryl). In embodiments, $R^{22.3}$ is an unsubstituted heteroaryl (e.g., 5 to 10 membered heteroaryl, 5 to 9 membered heteroaryl, or 5 to 6 membered heteroaryl).

$R^{23.3}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $R^{24.3}$-substituted or unsubstituted alkyl (e.g., $C_1$-$C_8$ alkyl, $C_1$-$C_6$ alkyl, or $C_1$-$C_4$ alkyl), $R^{24.3}$-substituted or unsubstituted heteroalkyl (e.g., 2 to 8 membered heteroalkyl, 2 to 6 membered heteroalkyl, or 2 to 4 membered heteroalkyl), $R^{24.3}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{24.3}$-substituted or unsubstituted heterocycloalkyl (e.g., 3 to 8 membered heterocycloalkyl, 3 to 6 membered heterocycloalkyl, or 5 to 6 membered heterocycloalkyl), $R^{24.3}$-substituted or unsubstituted aryl (e.g., $C_6$-$C_{10}$ aryl, $C_{10}$ aryl, or phenyl), or $R^{24.3}$-substituted or unsubstituted heteroaryl (e.g., 5 to 10 membered heteroaryl, 5 to 9 membered heteroaryl, or 5 to 6 membered heteroaryl).

In embodiments, $R^{23.3}$ is $R^{24.3}$-substituted or unsubstituted alkyl (e.g., $C_1$-$C_8$ alkyl, $C_1$-$C_6$ alkyl, or $C_1$-$C_4$ alkyl). In embodiments, $R^{23.3}$ is $R^{24.3}$-substituted alkyl (e.g., $C_1$-$C_8$ alkyl, $C_1$-$C_6$ alkyl, or $C_1$-$C_4$ alkyl). In embodiments, $R^{23.3}$ is an unsubstituted alkyl (e.g., $C_1$-$C_8$ alkyl, $C_1$-$C_6$ alkyl, or $C_1$-$C_4$ alkyl).

In embodiments, $R^{23.3}$ is $R^{24.3}$-substituted or unsubstituted heteroalkyl (e.g., 2 to 8 membered heteroalkyl, 2 to 6 membered heteroalkyl, or 2 to 4 membered heteroalkyl). In embodiments, $R^{23.3}$ is $R^{24.3}$-substituted heteroalkyl (e.g., 2 to 8 membered heteroalkyl, 2 to 6 membered heteroalkyl, or 2 to 4 membered heteroalkyl). In embodiments, $R^{23.3}$ is an unsubstituted heteroalkyl (e.g., 2 to 8 membered heteroalkyl, 2 to 6 membered heteroalkyl, or 2 to 4 membered heteroalkyl).

In embodiments, $R^{23.3}$ is $R^{24.3}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{23.3}$ is $R^{24.3}$-substituted cycloalkyl (e.g., $C_3$-$C_8$ cycloalkyl, $C_3$-$C_6$ cycloalkyl, or $C_5$-$C_6$ cycloalkyl). In embodiments, $R^{23.3}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{23.3}$ is $R^{24.3}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{23.3}$ is $R^{24.3}$-substituted heterocycloalkyl (e.g., 3 to 8 membered heterocycloalkyl, 3 to 6 membered heterocycloalkyl, or 5 to 6 membered heterocycloalkyl). In embodiments, $R^{23.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{23.3}$ is $R^{24.3}$-substituted or unsubstituted aryl (e.g., $C_6$-$C_{10}$ aryl, $C_{10}$ aryl, or phenyl). In embodiments, $R^{23.3}$ is $R^{24.3}$-substituted aryl (e.g., $C_6$-$C_{10}$ aryl, $C_{10}$ aryl, or phenyl). In embodiments, $R^{23.3}$ is an unsubstituted aryl (e.g., $C_6$-$C_{10}$ aryl, $C_{10}$ aryl, or phenyl).

In embodiments, $R^{23.3}$ is $R^{24.3}$-substituted or unsubstituted heteroaryl (e.g., 5 to 10 membered heteroaryl, 5 to 9 membered heteroaryl, or 5 to 6 membered heteroaryl). In embodiments, $R^{23.3}$ is $R^{24.3}$-substituted heteroaryl (e.g., 5 to 10 membered heteroaryl, 5 to 9 membered heteroaryl, or 5 to 6 membered heteroaryl). In embodiments, $R^{23.3}$ is an unsubstituted heteroaryl (e.g., 5 to 10 membered heteroaryl, 5 to 9 membered heteroaryl, or 5 to 6 membered heteroaryl).

$R^{3.2A}$, $R^{3.2B}$, $R^{3.2C}$, $R^{3.2D}$, $R^{24.2}$, $R^{3.3A}$, $R^{3.3B}$, $R^{3.3C}$, $R^{3.3D}$ and $R^{24.3}$ are independently hydrogen, oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $R^{3.2A}$, $R^{3.2B}$, $R^{3.2C}$, $R^{3.2D}$, $R^{24.2}$, $R^{3.3A}$, $R^{3.3B}$, $R^{3.3C}$, $R^{3.3D}$ and $R^{24.3}$ are independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $X^{3.2}$ and $X^{3.3}$ are independently —Cl, —Br, —I or —F. The symbols n3.2 and n3.3 are independently an integer from 0 to 4. The symbols m3.2, m3.3, v3.2, and v3.3 are independently 1 or 2.

In embodiments, $X^{3.2}$ is —Cl, and $X^1$ is N. In embodiments, $X^{3.2}$ is —F, and $X^1$ is N. In embodiments, $X^{3.2}$ is —Br, and $X^1$ is N. In embodiments, $X^{3.2}$ is —I, and $X^1$ is N. In embodiments, $X^{3.3}$ is —Cl, and $X^1$ is N. In embodiments, $X^{3.3}$ is —F, and $X^1$ is N. In embodiments, $X^{3.3}$ is —Br, and $X^1$ is N. In embodiments, $X^{3.3}$ is —I, and $X^1$ is N.

In embodiments, $X^{3.2}$ is —Cl, and $X^2$ is N. In embodiments, $X^{3.2}$ is —F, and $X^2$ is N. In embodiments, $X^{3.2}$ is —Br, and $X^2$ is N. In embodiments, $X^{3.2}$ is —I, and $X^2$ is N. In embodiments, $X^{3.3}$ is —Cl, and $X^2$ is N. In embodiments, $X^{3.3}$ is —F, and $X^2$ is N. In embodiments, $X^{3.3}$ is —Br, and $X^2$ is N. In embodiments, $X^{3.3}$ is —I, and $X^2$ is N.

In embodiments, $X^{3.2}$ is —Cl, and $X^3$ is N. In embodiments, $X^{3.2}$ is —F, and $X^3$ is N. In embodiments, $X^{3.2}$ is —Br, and $X^3$ is N. In embodiments, $X^{3.2}$ is —I, and $X^3$ is N. In embodiments, $X^{3.3}$ is —Cl, and $X^3$ is N. In embodiments, $X^{3.3}$ is —F, and $X^3$ is N. In embodiments, $X^{3.3}$ is —Br, and $X^3$ is N. In embodiments, $X^{3.3}$ is —I, and $X^3$ is N.

In embodiments, the symbol n3.2 is an integer from 0 to 4. In embodiments, n3.2 is 0. In embodiments, n3.2 is 1. In embodiments, n3.2 is 2. In embodiments, n3.2 is 3. In embodiments, n3.2 is 4.

In embodiments, the symbol n3.3 is an integer from 0 to 4. In embodiments, n3.3 is 0. In embodiments, n3.3 is 1. In embodiments, n3.3 is 2. In embodiments, n3.3 is 3. In embodiments, n3.3 is 4.

In embodiments, the symbols m3.2 and v3.2 are independently 1 or 2. In embodiments, m3.2 is 1. In embodiments, m3.2 is 2. In embodiments, v3.2 is 1. In embodiments, v3.2 is 2.

In embodiments, the symbols m3.3 and v3.3 are independently 1 or 2. In embodiments, m3.3 is 1. In embodiments, m3.3 is 2. In embodiments, v3.3 is 1. In embodiments, v3.3 is 2.

In embodiments, the compounds provided herein have structural Formula (III):

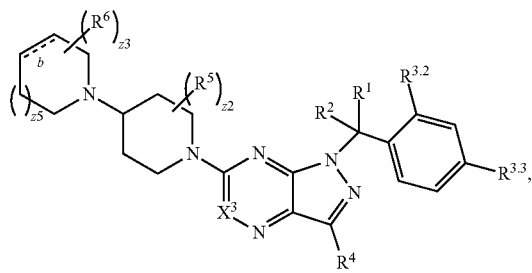

(III)

or a pharmaceutically acceptable salt thereof.

z2, z3, z5, ⎓, $X^3$, $R^1$, $R^2$, $R^4$, $R^{3.2}$, $R^{3.3}$, $R^5$ and $R^6$ are as described herein, including embodiments.

In embodiments, the compounds provided herein have structural Formula (IIIa):

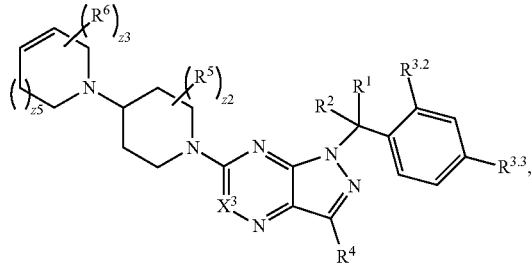

(IIIa)

or a pharmaceutically acceptable salt thereof.

z2, z3, z5, $X^3$, $R^1$, $R^2$, $R^4$, $R^{3.2}$, $R^{3.3}$, $R^5$ and $R^6$ are as described herein, including embodiments.

In embodiments, the compounds provided herein have structural Formula (IIIb):

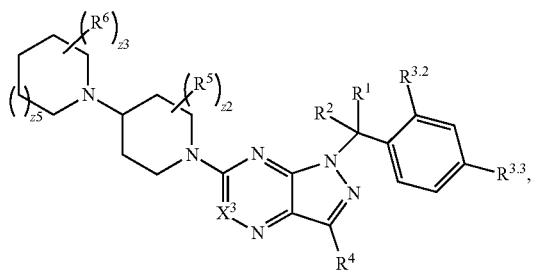

(IIIb)

or a pharmaceutically acceptable salt thereof.

z2, z3, z5, $X^3$, $R^1$, $R^2$, $R^4$, $R^{3.2}$, $R^{3.3}$, $R^5$ and $R^6$ are as described herein, including embodiments.

In embodiments, the compounds provided herein have structural (IV):

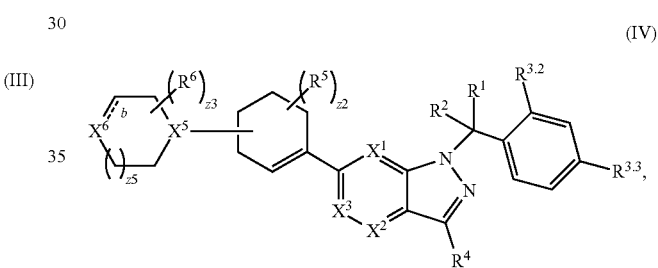

(IV)

or a pharmaceutically acceptable salt thereof.

z2, z3, z5, ⎓, $X^1$, $X^2$, $X^3$, $X^5$, $X^6$, $R^1$, $R^2$, $R^{3.2}$, $R^{3.3}$, $R^4$, $R^5$ and $R^6$ are as described herein, including embodiments.

In embodiments, the compounds provided herein have structural Formula (V):

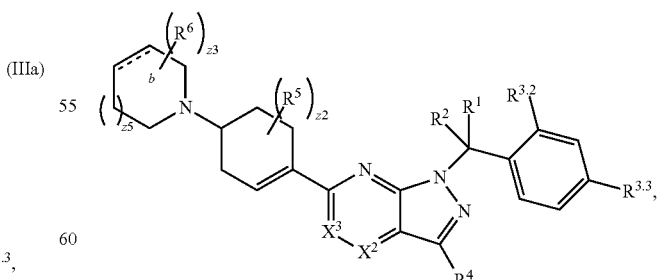

(V)

or a pharmaceutically acceptable salt thereof.

z2, z3, z5, ⎓, $X^2$, $X^3$, $R^1$, $R^2$, $R^{3.2}$, $R^{3.3}$, $R^4$, $R^5$ and $R^6$ are as described herein, including embodiments.

In embodiments, the compounds provided herein have structural Formula (Va):

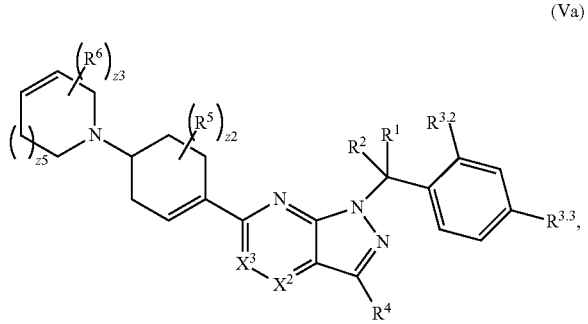

(Va)

or a pharmaceutically acceptable salt thereof.

z2, z3, z5, $X^2$, $X^3$, $R^1$, $R^2$, $R^{3.2}$, $R^{3.3}$, $R^4$, $R^5$ and $R^6$ are as described herein, including embodiments.

In embodiments, the compounds provided herein have structural Formula (Vb):

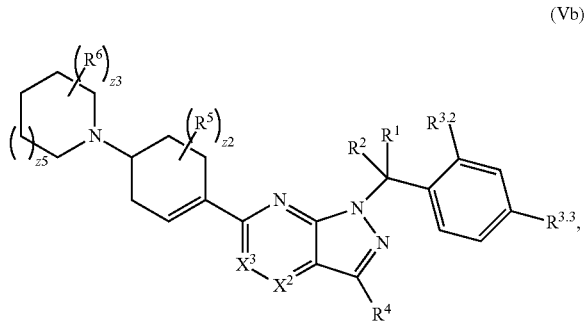

(Vb)

or a pharmaceutically acceptable salt thereof.

z2, z3, z5, $X^2$, $X^3$, $R^1$, $R^2$, $R^{3.2}$, $R^{3.3}$, $R^4$, $R^5$ and $R^6$ are as described herein, including embodiments.

In embodiments, the compounds provided herein have structural Formula (VI):

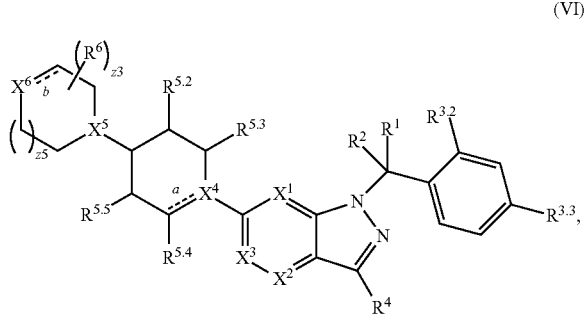

(VI)

or a pharmaceutically acceptable salt thereof. $R^{5.2}$ is hydrogen, halogen, $-CX^{5.6}_3$, $-CHX^{5.6}_2$, $-CH_2X^{5.6}$, $-CN$, $-SO_{n5.2}R^{5.6A}$, $-SO_{v5.2}NR^{5.6B}R^{5.6C}$, $-NHNR^{5.6B}R^{5.6C}$, $-ONR^{5.6B}R^{5.6C}$, $-NHC(O)NHNR^{5.6B}R^{5.6C}$, $-NHC(O)NR^{5.6B}R^{5.6C}$, $-N(O)_{m5.2}$, $-NR^{5.6B}R^{5.6C}$, $-C(O)R^{5.6D}$, $-C(O)OR^{5.6D}$, $-C(O)NR^{5.6B}R^{5.6C}$, $-OR^{5.6A}$, $-NR^{5.6B}SO_2R^{5.6A}$, $-NR^{5.6B}C(O)R^{5.6D}$, $-NR^{5.6B}C(O)OR^{5.6D}$, $-NR^{5.6B}OR^{5.6D}$, $-OCX^{5.6}_3$, $-OCHX^{5.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{5.3}$ is hydrogen, halogen, $-CX^{5.7}_3$, $-CHX^{5.7}_2$, $-CH_2X^{5.7}$, $-CN$, $-SO_{n5.3}R^{5.7A}$, $-SO_{v5.3}NR^{5.7B}R^{5.7C}$, $-NHNR^{5.7B}R^{5.7C}$, $-ONR^{5.7B}R^{5.7C}$, $-NHC(O)NHNR^{5.7B}R^{5.7C}$, $-NHC(O)NR^{5.7B}R^{5.7C}$, $-N(O)_{m5.3}$, $-NR^{5.7B}R^{5.7C}$, $-C(O)R^{5.7D}$, $-C(O)OR^{5.7D}$, $-C(O)NR^{5.7B}R^{5.7C}$, $-OR^{5.7A}$, $-NR^{5.7B}SO_2R^{5.7A}$, $-NR^{5.7B}C(O)R^{5.7D}$, $-NR^{5.7B}C(O)OR^{5.7D}$, $-NR^{5.7B}OR^{5.7D}$, $-OCX^{5.7}_3$, $-OCHX^{5.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{5.4}$ is hydrogen, halogen, $-CX^{5.8}_3$, $-CHX^{5.8}_2$, $-CH_2X^{5.8}$, $-CN$, $-SO_{n5.4}R^{5.8A}$, $-SO_{v5.4}NR^{5.8B}R^{5.8C}$, $-NHNR^{5.8B}R^{5.8C}$, $-ONR^{5.8B}R^{5.8C}$, $-NHC(O)NHNR^{5.8B}R^{5.8C}$, $NHC(O)NR^{5.8B}R^{5.8C}$, $-N(O)_{m5.4}$, $-NR^{5.8B}R^{5.8C}$, $-C(O)R^{5.8D}$, $-C(O)OR^{5.8D}$, $-C(O)NR^{5.8B}R^{5.8C}$, $-OR^{5.8A}$, $-NR^{5.8B}SO_2R^{5.8A}$, $-NR^{5.8B}C(O)R^{5.8D}$, $-NR^{5.8B}C(O)OR^{5.8D}$, $-NR^{5.8B}OR^{5.8D}$, $-OCX^{5.8}_3$, $-OCHX^{5.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{5.5}$ is hydrogen, halogen, $-CX^{5.9}_3$, $-CHX^{5.9}_2$, $-CH_2X^{5.9}$, $-CN$, $-SO_{n5.5}R^{5.9A}$, $-SO_{v5.5}NR^{5.9B}R^{5.9C}$, $NHNR^{5.9B}R^{5.9C}$, $-ONR^{5.9B}R^{5.9C}$, $-NHC(O)NHNR^{5.9B}R^{5.9C}$, $-NHC(O)NR^{5.9B}R^{5.9C}$, $-N(O)_{m5.5}$, $-NR^{5.9B}R^{5.9C}$, $-C(O)R^{5.9D}$, $-C(O)OR^{5.9D}$, $-C(O)NR^{5.9B}R^{5.9C}$, $-OR^{5.9A}$, $-NR^{5.9B}SO_2R^{5.9A}$, $-NR^{5.9B}C(O)R^{5.9D}$, $-NR^{5.9B}C(O)OR^{5.9D}$, $-NR^{5.9B}OR^{5.9D}$, $-OCX^{5.9}_3$, $-OCHX^{5.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{5.6A}$, $R^{5.6B}$, $R^{5.6C}$, $R^{5.6D}$, $R^{5.7A}$, $R^{5.7B}R^{5.7C}$, $R^{5.7D}$, $R^{5.8A}$, $R^{5.8B}$, $R^{5.8C}$, $R^{5.8D}$, $R^{5.9A}$, $R^{5.9B}$, $R^{5.9C}$ and $R^{5.9D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5.6B}$ and $R^{5.6C}$, $R^{5.7B}$ and $R^{5.7C}$, $R^{5.8B}$ and $R^{5.8C}$, $R^{5.9B}$ and $R^{5.9C}$ substituents bonded to the same nitrogen atom may optionally be joined to form a substituted or unsubstituted heterocycloalkyl or substituted or unsubstituted heteroaryl. $X^{5.6}$, $X^{5.7}$, $X^{5.8}$ and $X^{5.9}$ are independently $-Cl$, $-Br$, $-I$ or $-F$.

The symbols n5.2, n5.3, n5.4, and n5.5 are independently an integer from 0 to 4. The symbols m5.2, m5.3, m5.4, m5.5, v5.2, v5.3, v5.4, and v5.5 are independently 1 or 2.

In embodiments, the symbol n5.2 is an integer from 0 to 4. In embodiments, n5.2 is 0. In embodiments, n5.2 is 1. In embodiments, n5.2 is 2. In embodiments, n5.2 is 3. In embodiments, n5.2 is 4.

In embodiments, the symbol n5.3 is an integer from 0 to 4. In embodiments, n5.3 is 0. In embodiments, n5.3 is 1. In embodiments, n5.3 is 2. In embodiments, n5.3 is 3. In embodiments, n5.3 is 4.

In embodiments, the symbol n5.4 is an integer from 0 to 4. In embodiments, n5.4 is 0. In embodiments, n5.4 is 1. In embodiments, n5.4 is 2. In embodiments, n5.4 is 3. In embodiments, n5.4 is 4.

In embodiments, the symbol n5.5 is an integer from 0 to 4. In embodiments, n5.5 is 0. In embodiments, n5.5 is 1. In embodiments, n5.5 is 2. In embodiments, n5.5 is 3. In embodiments, n5.5 is 4.

In embodiments, the symbols m5.2 and v5.2 are independently 1 or 2. In embodiments, m5.2 is 1. In embodiments, m5.2 is 2. In embodiments, v5.2 is 1. In embodiments, v5.2 is 2.

In embodiments, the symbols m5.3 and v5.3 are independently 1 or 2. In embodiments, m5.3 is 1. In embodiments, m5.3 is 2. In embodiments, v5.3 is 1. In embodiments, v5.3 is 2.

In embodiments, the symbols m5.4 and v5.4 are independently 1 or 2. In embodiments, m5.4 is 1. In embodiments, m5.4 is 2. In embodiments, v5.4 is 1. In embodiments, v5.4 is 2.

In embodiments, the symbols m5.5 and v5.5 are independently 1 or 2. In embodiments, m5.5 is 1. In embodiments, m5.5 is 2. In embodiments, v5.5 is 1. In embodiments, v5.5 is 2.

$z3$, $z5$, ⇌, ⇌, $X^1$, $X^2$, $X^3$, $X^4$, $X^5$, $X^6$, $R^1$, $R^2$, $R^{3.2}$, $R^{3.3}$, $R^4$ and $R^6$ are as described herein, including embodiments.

In embodiments, $R^{5.2}$ is hydrogen, halogen, $-CX^{5.6}_3$, $-CHX^{5.6}_2$, $-CH_2X^{5.6}$, $-CN$, $-SO_{n5.2}R^{5.6A}$, $-SO_{v5.2}NR^{5.6B}R^{5.6C}$, $-NHNR^{5.6B}R^{5.6C}$, $-ONR^{5.6B}R^{5.6C}$, $-NHC(O)NHNR^{5.6B}R^{5.6C}$, $-NHC(O)NR^{5.6B}R^{5.6C}$, $-N(O)_{m5.2}$, $-NR^{5.6B}R^{5.6C}$, $-C(O)R^{5.6D}$, $-C(O)OR^{5.6D}$, $-C(O)NR^{5.6B}R^{5.6C}$, $-OR^{5.6A}$, $-NR^{5.6B}SO_2R^{5.6A}$, $-NR^{5.6B}C(O)R^{5.6D}$, $-NR^{5.6B}C(O)OR^{5.6D}$, $-NR^{5.6B}OR^{5.6D}$, $-OCX^{5.6}_3$, $-OCHX^{5.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{5.2}$ is hydrogen, halogen, $-CX^{5.6}_3$, $-CHX^{5.6}_2$, $-CH_2X^{5.6}$, $-CN$, $-SO_{n5.2}R^{5.6A}$, $-SO_{v5.2}NR^{5.6B}R^{5.6C}$, $NHNR^{5.6B}R^{5.6C}$, $-ONR^{5.6B}R^{5.6C}$, $NHC(O)NHNR^{5.6B}R^{5.6C}$, $-NHC(O)NR^{5.6B}R^{5.6C}$, $-N(O)_{m5.2}$, $-NR^{5.6B}R^{5.6C}$, $-C(O)R^{5.6D}$, $-C(O)OR^{5.6D}$, $-C(O)NR^{5.6B}R^{5.6C}$, $-OR^{5.6A}$, $-NR^{5.6B}SO_2R^{5.6A}$, $-NR^{5.6B}C(O)R^{5.6D}$, $-NR^{5.6B}C(O)OR^{5.6D}$, $-NR^{5.6B}OR^{5.6D}$, $-OCX^{5.6}_3$, $-OCHX^{5.6}_2$, $R^{28.6}$-substituted or unsubstituted alkyl (e.g., $C_1$-$C_8$ alkyl, $C_1$-$C_6$ alkyl, or $C_1$-$C_4$ alkyl), $R^{28.6}$-substituted or unsubstituted heteroalkyl (e.g., 2 to 8 membered heteroalkyl, 2 to 6 membered heteroalkyl, or 2 to 4 membered heteroalkyl), $R^{28.6}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.6}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.6}$-substituted or unsubstituted aryl (e.g., $C_6$-$C_{10}$ aryl, $C_{10}$ aryl, or phenyl), or $R^{28.6}$-substituted or unsubstituted heteroaryl (e.g., 5 to 10 membered heteroaryl, 5 to 9 membered heteroaryl, or 5 to 6 membered heteroaryl).

In embodiments, $R^{5.2}$ is $R^{28.6}$-substituted or unsubstituted alkyl (e.g., $C_1$-$C_8$ alkyl, $C_1$-$C_6$ alkyl, or $C_1$-$C_4$ alkyl). In embodiments, $R^{5.2}$ is $R^{28.6}$-substituted alkyl (e.g., $C_1$-$C_8$ alkyl, $C_1$-$C_6$ alkyl, or $C_1$-$C_4$ alkyl). In embodiments, $R^{5.2}$ is an unsubstituted alkyl (e.g., $C_1$-$C_8$ alkyl, $C_1$-$C_6$ alkyl, or $C_1$-$C_4$ alkyl).

In embodiments, $R^{5.2}$ is $R^{28.6}$-substituted or unsubstituted heteroalkyl (e.g., 2 to 8 membered heteroalkyl, 2 to 6 membered heteroalkyl, or 2 to 4 membered heteroalkyl). In embodiments, $R^{5.2}$ is $R^{28.6}$-substituted heteroalkyl (e.g., 2 to 8 membered heteroalkyl, 2 to 6 membered heteroalkyl, or 2 to 4 membered heteroalkyl). In embodiments, $R^{5.2}$ is an unsubstituted heteroalkyl (e.g., 2 to 8 membered heteroalkyl, 2 to 6 membered heteroalkyl, or 2 to 4 membered heteroalkyl).

In embodiments, $R^{5.2}$ is $R^{28.6}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5.2}$ is $R^{28.6}$-substituted cycloalkyl (e.g., $C_3$-$C_8$ cycloalkyl, $C_3$-$C_6$ cycloalkyl, or $C_5$-$C_6$ cycloalkyl). In embodiments, $R^{5.2}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{5.2}$ is $R^{28.6}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{5.2}$ is $R^{28.6}$-substituted heterocycloalkyl (e.g., 3 to 8 membered heterocycloalkyl, 3 to 6 membered heterocycloalkyl, or 5 to 6 membered heterocycloalkyl). In embodiments, $R^{5.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{5.2}$ is $R^{28.6}$-substituted or unsubstituted aryl (e.g., $C_6$-$C_{10}$ aryl, $C_{10}$ aryl, or phenyl). In embodiments, $R^{5.2}$ is $R^{28.6}$-substituted aryl (e.g., $C_6$-$C_{10}$ aryl, $C_{10}$ aryl, or phenyl). In embodiments, $R^{5.2}$ is an unsubstituted aryl (e.g., $C_6$-$C_{10}$ aryl, $C_{10}$ aryl, or phenyl).

In embodiments, $R^{5.2}$ is $R^{28.6}$-substituted or unsubstituted heteroaryl (e.g., 5 to 10 membered heteroaryl, 5 to 9 membered heteroaryl, or 5 to 6 membered heteroaryl). In embodiments, $R^{5.2}$ is $R^{28.6}$-substituted heteroaryl (e.g., 5 to 10 membered heteroaryl, 5 to 9 membered heteroaryl, or 5 to 6 membered heteroaryl). In embodiments, $R^{5.2}$ is an unsubstituted heteroaryl (e.g., 5 to 10 membered heteroaryl, 5 to 9 membered heteroaryl, or 5 to 6 membered heteroaryl).

In embodiments, $R^{5.2}$ is hydrogen, fluorine, $-OH$, $-CN$, $-CH_3$, $-CH_2CH_3$, $-CF_3$, $-(CH_2)OH$, $-(CH_2)_2OH$, $-(CH_3)_2OH$, $-CO_2H$, $-CO_2NH_2$ or $-CO_2CH_2CH_3$. In embodiments, $R^{5.2}$ is hydrogen. In embodiments, $R^{5.2}$ is fluorine. In embodiments, $R^{5.2}$ is $-OH$. In embodiments, $R^{5.2}$ is $-CN$. In embodiments, $R^{5.2}$ is $-CH_3$. In embodiments, $R^{5.2}$ is $-CH_2CH_3$. In embodiments, $R^{5.2}$ is $-CF_3$. In embodiments, $R^{5.2}$ is $-(CH_2)OH$. In embodiments, $R^{5.2}$ is $-(CH_2)_2OH$. In embodiments, $R^{5.2}$ is $-(CH_3)_2OH$. In embodiments, $R^{5.2}$ is $-CO_2H$. In embodiments, $R^{5.2}$ is $-CO_2NH_2$. In embodiments, $R^{5.2}$ is $-CO_2CH_2CH_3$.

In embodiments, $R^{5.2}$ is halogen, $CCl$, $CCl_2$, $CCl_3$, $-CF_2$, $-CF$. In embodiments, $R^{5.2}$ is halogen. In embodiments, $R^{5.2}$ is $CCl$. In embodiments, $R^{5.2}$ is $CCl_2$. In embodiments, $R^{5.2}$ is $CCl_3$. In embodiments, $R^{5.2}$ is $-CF_2$. In embodiments, $R^{5.2}$ is $-CF$.

In embodiments, $R^{5.2}$ is hydrogen, fluorine, $-CN$, $-CH_3$, $-CF_3$, $-CH_2CH_3$, $CH_2OH$, $C(O)OH$, $C(CH_3)_2OH$, $-(CH_2)_2OH$, $-CO_2NH_2$, or $-CO_2CH_2CH_3$. In embodiments, $R^{5.2}$ is fluorine, $-CN$, $-CH_3$, $-CF_3$, $-CH_2CH_3$, $CH_2OH$, $C(O)OH$, $-(CH_2)_2OH$, $-CO_2NH_2$, or $-CO_2CH_2CH_3$. In embodiments, $R^{5.2}$ is hydrogen. In embodiments, $R^{5.2}$ is $-OH$. In embodiments, $R^{5.2}$ is fluorine. In embodiments, $R^{5.2}$ is $-CN$. In embodiments, $R^{5.2}$ is $-CH_3$. In embodiments, $R^{5.2}$ is $-CF_3$. In embodiments, $R^{5.2}$ $-CH_2CH_3$. In embodiments, $R^{5.2}$ is $CH_2OH$. In embodiments, $R^{5.2}$ is $C(O)OH$. In embodiments, $R^{5.2}$ is $C(CH_3)_2OH$. In embodiments, $R^{5.2}$ is $-(CH_2)_2OH$. In embodiments, $R^{5.2}$ is $-CO_2NH_2$. In embodiments, $R^{5.2}$ is $-CO_2CH_2CH_3$.

In embodiments, $R^{5.2}$ is halogen, $CHF_2$, $CH_2F$, $CCl_3$, $CHCl_2$, $CH_2Cl$, $-C(O)R^{5.6D}$, $-C(O)OR^{5.6D}$, —CO$_2$NR$^{5.6B}$R$^{5.6C}$, or —OR$^{5.2A}$. In embodiments, R$^{5.2}$ is halogen, CHF$_2$, CH$_2$F, CCl$_3$, CHCl$_2$, CH$_2$Cl, —C(O)R$^{5.6D}$, —C(O)OR$^{5.6D}$, or —OR$^{5.2A}$. In embodiments, R$^{5.2}$ is halogen. In embodiments, R$^{5.2}$ is CHF$_2$. In embodiments, R$^{5.2}$ is CH$_2$F. In embodiments, R$^{5.2}$ is CCl$_3$. In embodiments, R$^{5.2}$ is CHCl$_2$. In embodiments, R$^{5.2}$ is CH$_2$Cl. In embodiments, R$^{5.2}$ is —C(O)R$^{5.6D}$. In embodiments, R$^{5.2}$ is —C(O)OR$^{56D}$. In embodiments, R$^{5.2}$ is —OR$^{5.2A}$. In embodiments, R$^{5.2}$ is —CO$_2$NR$^{5.6B}$R$^{5.6C}$. In embodiments, R$^{5.6B}$ is CH$_3$. In embodiments, R$^{5.6B}$ is CF$_3$. In embodiments, R$^{5.6B}$ is CHF$_2$. In embodiments, R$^{5.6B}$ is CH$_2$F. In embodiments, R$^{5.6B}$ is CH$_2$Cl. In embodiments, R$^{5.6B}$ is CHCl$_2$. In embodiments, R$^{5.6B}$ is CCl$_3$. In embodiments, R$^{5.6B}$ is CH$_2$CH$_3$. In embodiments, R$^{5.6B}$ is unsubstituted propyl. In embodiments, R$^{5.6B}$ is hydrogen. In embodiments, R$^{5.6C}$ is CH$_3$. In embodiments, R$^{5.6C}$ is CF$_3$. In embodiments, R$^{5.6C}$ is CHF$_2$. In embodiments, R$^{5.6C}$ is CH$_2$F. In embodiments, R$^{5.6C}$ is CH$_2$Cl. In embodiments, R$^{5.6C}$ is CHCl$_2$. In embodiments, R$^{5.6C}$ is CCl$_3$. In embodiments, R$^{5.6C}$ is CH$_2$CH$_3$. In embodiments, R$^{5.6C}$ is unsubstituted propyl. In embodiments, R$^{5.6C}$ is hydrogen. In embodiments, R$^{5.6D}$ is CH$_3$. In embodiments, R$^{5.6D}$ is CF$_3$. In embodiments, R$^{5.6D}$ is CHF$_2$. In embodiments, R$^{5.6D}$ is CH$_2$F. In embodiments, R$^{5.6D}$ is CH$_2$Cl. In embodiments, R$^{5.6D}$ is CHCl$_2$. In embodiments, R$^{5.6D}$ is CCl$_3$. In embodiments, R$^{5.6D}$ is CH$_2$CH$_3$. In embodiments, R$^{5.6D}$ is unsubstituted propyl. In embodiments, R$^{5.6D}$ is hydrogen.

In embodiments, R$^{5.3}$ is hydrogen, halogen, —CX$^{5.7}_3$, —CHX$^{5.7}_2$, —CH$_2$X$^{5.7}$, —CN, —SO$_{n5.3}$R$^{5.7A}$, —SO$_{v5.3}$NR$^{5.7B}$R$^{5.7C}$, NHNR$^{5.7B}$R$^{5.7C}$, ONR$^{5.7B}$R$^{5.7C}$, NHC(O)NHNR$^{5.7B}$R$^{5.7C}$, —NHC(O)NR$^{5.7B}$R$^{5.7C}$, —N(O)$_{m5.3}$, —NR$^{5.7B}$R$^{5.7C}$, —C(O)R$^{5.7D}$, —C(O)OR$^{5.7D}$, —C(O)NR$^{5.7B}$R$^{5.7C}$, —OR$^{5.7A}$, —NR$^{5.7B}$SO$_2$R$^{5.7A}$, —NR$^{5.7B}$C(O)R$^{5.7D}$, —NR$^{5.7B}$C(O)OR$^{5.7D}$, —NR$^{5.7B}$OR$^{5.7D}$, —OCX$^{5.7}_3$, —OCHX$^{5.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^{5.3}$ is hydrogen, halogen, —CX$^{5.7}_3$, —CHX$^{5.7}_2$, —CH$_2$X$^{5.7}$, —CN, —SO$_{n5.3}$R$^{5.7A}$, —SO$_{v5.3}$NR$^{5.7B}$R$^{5.7C}$, NHNR$^{5.7B}$R$^{5.7C}$, ONR$^{5.7B}$R$^{5.7C}$, NHC(O)NHNR$^{5.7B}$R$^{5.7C}$, —NHC(O)NR$^{5.7B}$R$^{5.7C}$, —N(O)$_{m5.3}$, —NR$^{5.7B}$R$^{5.7C}$, —C(O)R$^{5.7D}$, —C(O)OR$^{5.7D}$, —C(O)NR$^{5.7B}$R$^{5.7C}$, —OR$^{5.7A}$, —NR$^{5.7B}$SO$_2$R$^{5.7A}$, —NR$^{5.7B}$C(O)R$^{5.7D}$, —NR$^{5.7B}$C(O)OR$^{5.7D}$, —NR$^{5.7B}$OR$^{5.7D}$, —OCX$^{5.7}_3$, —OCHX$^{5.7}_2$, R$^{28.7}$-substituted or unsubstituted alkyl (e.g., C$_1$-C$_8$ alkyl, C$_1$-C$_6$ alkyl, or C$_1$-C$_4$ alkyl), R$^{28.7}$-substituted or unsubstituted heteroalkyl (e.g., 2 to 8 membered heteroalkyl, 2 to 6 membered heteroalkyl, or 2 to 4 membered heteroalkyl), R$^{28.7}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{28.7}$-substituted or unsubstituted heterocycloalkyl (e.g., 3 to 8 membered heterocycloalkyl, 3 to 6 membered heterocycloalkyl, or 5 to 6 membered heterocycloalkyl), R$^{28.7}$-substituted or unsubstituted aryl (e.g., C$_6$-C$_{10}$ aryl, C$_{10}$ aryl, or phenyl), or R$^{28.7}$-substituted or unsubstituted heteroaryl (e.g., 5 to 10 membered heteroaryl, 5 to 9 membered heteroaryl, or 5 to 6 membered heteroaryl).

In embodiments, R$^{5.3}$ is R$^{28.7}$-substituted or unsubstituted alkyl (e.g., C$_1$-C$_8$ alkyl, C$_1$-C$_6$ alkyl, or C$_1$-C$_4$ alkyl). In embodiments, R$^{5.3}$ is R$^{28.7}$-substituted alkyl (e.g., C$_1$-C$_8$ alkyl, C$_1$-C$_6$ alkyl, or C$_1$-C$_4$ alkyl). In embodiments, R$^{5.3}$ is an unsubstituted alkyl (e.g., C$_1$-C$_8$ alkyl, C$_1$-C$_6$ alkyl, or C$_1$-C$_4$ alkyl).

In embodiments, R$^{5.3}$ is R$^{28.7}$-substituted or unsubstituted heteroalkyl (e.g., 2 to 8 membered heteroalkyl, 2 to 6 membered heteroalkyl, or 2 to 4 membered heteroalkyl). In embodiments, R$^{5.3}$ is R$^{28.7}$-substituted heteroalkyl (e.g., 2 to 8 membered heteroalkyl, 2 to 6 membered heteroalkyl, or 2 to 4 membered heteroalkyl). In embodiments, R$^{5.3}$ is an unsubstituted heteroalkyl (e.g., 2 to 8 membered heteroalkyl, 2 to 6 membered heteroalkyl, or 2 to 4 membered heteroalkyl).

In embodiments, R$^{5.3}$ is R$^{28.7}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{5.3}$ is R$^{28.7}$-substituted cycloalkyl (e.g., C$_3$-C$_8$ cycloalkyl, C$_3$-C$_6$ cycloalkyl, or C$_5$-C$_6$ cycloalkyl). In embodiments, R$^{5.3}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^{5.3}$ is R$^{28.7}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{5.3}$ is R$^{28.7}$-substituted heterocycloalkyl (e.g., 3 to 8 membered heterocycloalkyl, 3 to 6 membered heterocycloalkyl, or 5 to 6 membered heterocycloalkyl). In embodiments, R$^{5.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^{5.3}$ is R$^{28.7}$-substituted or unsubstituted aryl (e.g., C$_6$-C$_{10}$ aryl, C$_{10}$ aryl, or phenyl). In embodiments, R$^{5.3}$ is R$^{28.7}$-substituted aryl (e.g., C$_6$-C$_{10}$ aryl, C$_{10}$ aryl, or phenyl). In embodiments, R$^{5.3}$ is an unsubstituted aryl (e.g., C$_6$-C$_{10}$ aryl, C$_{10}$ aryl, or phenyl).

In embodiments, R$^{5.3}$ is R$^{28.7}$-substituted or unsubstituted heteroaryl (e.g., 5 to 10 membered heteroaryl, 5 to 9 membered heteroaryl, or 5 to 6 membered heteroaryl). In embodiments, R$^{5.3}$ is R$^{28.7}$-substituted heteroaryl (e.g., 5 to 10 membered heteroaryl, 5 to 9 membered heteroaryl, or 5 to 6 membered heteroaryl). In embodiments, R$^{5.3}$ is an unsubstituted heteroaryl (e.g., 5 to 10 membered heteroaryl, 5 to 9 membered heteroaryl, or 5 to 6 membered heteroaryl).

In embodiments, R$^{5.3}$ is hydrogen, fluorine, —OH, —CN, —CH$_3$, —CH$_2$CH$_3$, —CF$_3$, —(CH$_2$)OH, —(CH$_2$)$_2$OH, —(CH$_3$)$_2$OH, —CO$_2$H, —CO$_2$NH$_2$ or —CO$_2$CH$_2$CH$_3$. In embodiments, R$^{5.3}$ is hydrogen. In embodiments, R$^{5.3}$ is fluorine. In embodiments, R$^{5.3}$ is —OH. In embodiments, R$^{5.3}$ is —CN. In embodiments, R$^{5.3}$ is —CH$_3$. In embodiments, R$^{5.3}$ is —CH$_2$CH$_3$. In embodiments, R$^{5.3}$ is —CF$_3$. In embodiments, R$^{5.3}$ is —(CH$_2$)OH. In embodiments, R$^{5.3}$ is —(CH$_2$)$_2$OH. In embodiments, R$^{5.3}$ is —(CH$_3$)$_2$OH. In embodiments, R$^{5.3}$ is —CO$_2$H. In embodiments, R$^{5.3}$ is —CO$_2$NH$_2$. In embodiments, R$^{5.3}$ is —CO$_2$CH$_2$CH$_3$.

In embodiments, R$^{5.3}$ is halogen, CCl, CCl$_2$, CCl$_3$, —CF$_2$, —CF. In embodiments, R$^{5.3}$ is halogen. In embodiments, R$^{5.3}$ is CCl. In embodiments, R$^{5.3}$ is CCl$_2$. In embodiments, R$^{5.3}$ is CCl$_3$. In embodiments, R$^{5.3}$ is —CF$_2$. In embodiments, R$^{5.3}$ is —CF.

In embodiments, R$^{5.3}$ is hydrogen, fluorine, —CN, —CH$_3$, —CF$_3$, —CH$_2$CH$_3$, CH$_2$OH, C(O)OH, C(CH$_3$)$_2$OH, —(CH$_2$)$_2$OH, —CO$_2$NH$_2$, or —CO$_2$CH$_2$CH$_3$. In embodiments, R$^{5.3}$ is fluorine, —CN, —CH$_3$, —CF$_3$, —CH$_2$CH$_3$, CH$_2$OH, C(O)OH, —(CH$_2$)$_2$OH, —CO$_2$NH$_2$, or —CO$_2$CH$_2$CH$_3$. In embodiments, R$^{5.3}$ is hydrogen. In embodiments, R$^{5.3}$ is —OH. In embodiments, R$^{5.3}$ is fluorine. In embodiments, R$^{5.3}$ is —CN. In embodiments, R$^{5.3}$ is —CH$_3$. In embodiments, R$^{5.3}$ is —CF$_3$. In embodiments, R$^{5.3}$ —CH$_2$CH$_3$. In embodiments, R$^{5.3}$ is CH$_2$OH. In embodiments, R$^{5.3}$ is C(O)OH. In embodiments, R$^{5.3}$ is $C(CH_3)_2OH$. In embodiments, $R^{5.3}$ is —$(CH_2)_2OH$. In embodiments, $R^{5.3}$ is —$CO_2NH_2$. In embodiments, $R^{5.3}$ is —$CO_2CH_2CH_3$.

In embodiments, $R^{5.3}$ is halogen, $CHF_2$, $CH_2F$, $CCl_3$, $CHCl_2$, $CH_2Cl$, —$C(O)R^{5.7D}$, —$C(O)OR^{5.7D}$, —$CO_2NR^{5.7B}R^{5.7C}$, or —$OR^{5.3A}$. In embodiments, $R^{5.3}$ is halogen, $CHF_2$, $CH_2F$, $CCl_3$, $CHCl_2$, $CH_2Cl$, —$C(O)R^{5.7D}$, —$C(O)OR^{5.7D}$, or —$OR^{5.3A}$. In embodiments, $R^{5.3}$ is halogen. In embodiments, $R^{5.3}$ is $CHF_2$. In embodiments, $R^{5.3}$ is $CH_2F$. In embodiments, $R^{5.3}$ is $CCl_3$. In embodiments, $R^{5.3}$ is $CHCl_2$. In embodiments, $R^{5.3}$ is $CH_2Cl$. In embodiments, $R^{5.3}$ is —$C(O)R^{5.7D}$. In embodiments, $R^{5.3}$ is —$C(O)OR^{5.7D}$. In embodiments, $R^{5.3}$ is —$OR^{5.3A}$. In embodiments, $R^{5.3}$ is —$CO_2NR^{5.7B}R^{5.7C}$. In embodiments, $R^{5.7B}$ is $CH_3$. In embodiments, $R^{5.7B}$ is $CF_3$. In embodiments, $R^{5.7B}$ is $CHF_2$. In embodiments, $R^{5.7B}$ is $CH_2F$. In embodiments, $R^{5.7B}$ is $CH_2Cl$. In embodiments, $R^{5.7B}$ is $CHCl_2$. In embodiments, $R^{5.7B}$ is $CCl_3$. In embodiments, $R^{5.7B}$ is $CH_2CH_3$. In embodiments, $R^{5.7B}$ is unsubstituted propyl. In embodiments, $R^{5.7B}$ is hydrogen. In embodiments, $R^{5.7C}$ is $CH_3$. In embodiments, $R^{5.7C}$ is $CF_3$. In embodiments, $R^{5.7C}$ is $CHF_2$. In embodiments, $R^{5.7C}$ is $CH_2F$. In embodiments, $R^{5.7C}$ is $CH_2Cl$. In embodiments, $R^{5.7C}$ is $CHCl_2$. In embodiments, $R^{5.7C}$ is $CCl_3$. In embodiments, $R^{5.7C}$ is $CH_2CH_3$. In embodiments, $R^{5.7C}$ is unsubstituted propyl. In embodiments, $R^{5.7C}$ is hydrogen. In embodiments, $R^{5.7D}$ is $CH_3$. In embodiments, $R^{5.7D}$ is $CF_3$. In embodiments, $R^{5.7D}$ is $CHF_2$. In embodiments, $R^{5.7D}$ is $CH_2F$. In embodiments, $R^{5.7D}$ is $CH_2Cl$. In embodiments, $R^{5.7D}$ is $CHCl_2$. In embodiments, $R^{5.7D}$ is $CCl_3$. In embodiments, $R^{5.7D}$ is $CH_2CH_3$. In embodiments, $R^{5.7D}$ is unsubstituted propyl. In embodiments, $R^{5.7D}$ is hydrogen.

In embodiments, $R^{5.4}$ is hydrogen, halogen, —$CX^{5.8}_3$, —$CHX^{5.8}_2$, —$CH_2X^{5.8}$, —$CN$, —$SO_{n5.4}R^{5.8A}$, —$SO_{v5.4}NR^{5.8B}R^{5.8C}$, —$NHNR^{5.8B}R^{5.8C}$, —$ONR^{5.8B}R^{5.8C}$, —$NHC(O)NHNR^{5.8B}R^{5.8C}$, —$NHC(O)NR^{5.8B}R^{5.8C}$, —$N(O)_{m5.4}$, —$NR^{5.8B}R^{5.8C}$, —$C(O)R^{5.8D}$, —$C(O)OR^{5.8D}$, —$C(O)NR^{5.8B}R^{5.8C}$, —$OR^{5.8A}$, —$NR^{5.8B}SO_2R^{5.8A}$, —$NR^{5.8B}C(O)R^{5.8D}$, —$NR^{5.8B}C(O)OR^{5.8D}$, —$NR^{5.8B}OR^{5.8D}$, —$OCX^{5.8}_3$, —$OCHX^{5.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{5.4}$ is hydrogen, fluorine, —$OH$, —$CN$, —$CH_3$, —$CH_2CH_3$, —$CF_3$, —$(CH_2)OH$, —$(CH_2)_2OH$, —$(CH_3)_2OH$, —$CO_2H$, —$CO_2NH_2$ or —$CO_2CH_2CH_3$. In embodiments, $R^{5.4}$ is hydrogen. In embodiments, $R^{5.4}$ is fluorine. In embodiments, $R^{5.4}$ is —$OH$. In embodiments, $R^{5.4}$ is —$CN$. In embodiments, $R^{5.4}$ is —$CH_3$. In embodiments, $R^{5.4}$ is —$CH_2CH_3$. In embodiments, $R^{5.4}$ is —$CF_3$. In embodiments, $R^{5.4}$ is —$(CH_2)OH$. In embodiments, $R^{5.4}$ is —$(CH_2)_2OH$. In embodiments, $R^{5.4}$ is —$(CH_3)_2OH$. In embodiments, $R^{5.4}$ is —$CO_2H$. In embodiments, $R^{5.4}$ is —$CO_2NH_2$. In embodiments, $R^{5.4}$ is —$CO_2CH_2CH_3$.

In embodiments, $R^{5.4}$ is halogen, $CCl$, $CCl_2$, $CCl_3$, —$CF_2$, —$CF$. In embodiments, $R^{5.4}$ is halogen. In embodiments, $R^{5.4}$ is $CCl$. In embodiments, $R^{5.4}$ is $CCl_2$. In embodiments, $R^{5.4}$ is $CCl_3$. In embodiments, $R^{5.4}$ is —$CF_2$. In embodiments, $R^{5.4}$ is —$CF$.

In embodiments, $R^{5.4}$ is hydrogen, fluorine, —$CN$, —$CH_3$, —$CF_3$, —$CH_2CH_3$, $CH_2OH$, $C(O)OH$, $C(CH_3)_2OH$, —$(CH_2)_2OH$, —$CO_2NH_2$, or —$CO_2CH_2CH_3$. In embodiments, $R^{5.4}$ is fluorine. In embodiments, $R^{5.4}$ is —$CN$, —$CH_3$, —$CF_3$, —$CH_2CH_3$, $CH_2OH$, $C(O)OH$, —$(CH_2)_2OH$, —$CO_2NH_2$, or —$CO_2CH_2CH_3$. In embodiments, $R^{5.4}$ is hydrogen. In embodiments, $R^{5.4}$ is —$OH$. In embodiments, $R^{5.4}$ is fluorine. In embodiments, $R^{5.4}$ is —$CN$. In embodiments, $R^{5.4}$ is —$CH_3$. In embodiments, $R^{5.4}$ is —$CF_3$. In embodiments, $R^{5.4}$ —$CH_2CH_3$. In embodiments, $R^{5.4}$ is $CH_2OH$. In embodiments, $R^{5.4}$ is $C(O)OH$. In embodiments, $R^{5.4}$ is $C(CH_3)_2OH$. In embodiments, $R^{5.4}$ is —$(CH_2)_2OH$. In embodiments, $R^{5.4}$ is —$CO_2NH_2$. In embodiments, $R^{5.4}$ is —$CO_2CH_2CH_3$.

In embodiments, $R^{5.4}$ is halogen, $CHF_2$, $CH_2F$, $CCl_3$, $CHCl_2$, $CH_2Cl$, —$C(O)R^{5.8D}$, —$C(O)OR^{5.8D}$, —$CO_2NR^{5.8B}R^{5.8C}$, or —$OR^{5.4A}$. In embodiments, $R^{5.4}$ is halogen, $CHF_2$, $CH_2F$, $CCl_3$, $CHCl_2$, $CH_2Cl$, —$C(O)R^{5.8D}$, —$C(O)OR^{5.8D}$, or —$OR^{5.4A}$. In embodiments, $R^{5.4}$ is halogen. In embodiments, $R^{5.4}$ is $CHF_2$. In embodiments, $R^{5.4}$ is $CH_2F$. In embodiments, $R^{5.4}$ is $CCl_3$. In embodiments, $R^{5.4}$ is $CHCl_2$. In embodiments, $R^{5.4}$ is $CH_2Cl$. In embodiments, $R^{5.4}$ is —$C(O)R^{5.8D}$. In embodiments, $R^{5.4}$ is —$C(O)OR^{5.8D}$. In embodiments, $R^{5.4}$ is —$OR^{5.4A}$. In embodiments, $R^{5.4}$ is —$CO_2NR^{5.8B}R^{5.8C}$. In embodiments, $R^{5.8B}$ is $CH_3$. In embodiments, $R^{5.8B}$ is $CF_3$. In embodiments, $R^{5.8B}$ is $CHF_2$. In embodiments, $R^{5.8B}$ is $CH_2F$. In embodiments, $R^{5.8B}$ is $CH_2Cl$. In embodiments, $R^{5.8B}$ is $CHCl_2$. In embodiments, $R^{5.8B}$ is $CCl_3$. In embodiments, $R^{5.8B}$ is $CH_2CH_3$. In embodiments, $R^{5.8B}$ is unsubstituted propyl. In embodiments, $R^{5.8B}$ is hydrogen. In embodiments, $R^{5.8C}$ is $CH_3$. In embodiments, $R^{5.8C}$ is $CF_3$. In embodiments, $R^{5.8C}$ is $CHF_2$. In embodiments, $R^{5.8C}$ is $CH_2F$. In embodiments, $R^{5.8C}$ is $CH_2Cl$. In embodiments, $R^{5.8C}$ is $CHCl_2$. In embodiments, $R^{5.8C}$ is $CCl_3$. In embodiments, $R^{5.8C}$ is $CH_2CH_3$. In embodiments, $R^{5.8C}$ is unsubstituted propyl. In embodiments, $R^{5.8C}$ is hydrogen. In embodiments, $R^{5.8D}$ is $CH_3$. In embodiments, $R^{5.8D}$ is $CF_3$. In embodiments, $R^{5.8D}$ is $CHF_2$. In embodiments, $R^{5.8D}$ is $CH_2F$. In embodiments, $R^{5.8D}$ is $CH_2Cl$. In embodiments, $R^{5.8D}$ is $CHCl_2$. In embodiments, $R^{5.8D}$ is $CCl_3$. In embodiments, $R^{5.8D}$ is $CH_2CH_3$. In embodiments, $R^{5.8D}$ is unsubstituted propyl. In embodiments, $R^{5.8D}$ is hydrogen.

In embodiments, $R^{5.4}$ is hydrogen, halogen, —$CX^{5.8}_3$, —$CHX^{5.8}_2$, —$CH_2X^{5.8}$, —$CN$, —$SO_{n5.4}R^{5.8A}$, —$SO_{v5.4}NR^{5.8B}R^{5.8C}$, —$NHNR^{5.8B}R^{5.8C}$, —$ONR^{5.8B}R^{5.8C}$, —$NHC(O)NHNR^{5.8B}R^{5.8C}$, —$NHC(O)NR^{5.8B}R^{5.8C}$, —$N(O)_{m5.4}$, —$NR^{5.8B}R^{5.8C}$, —$C(O)R^{5.8D}$, —$C(O)OR^{5.8D}$, —$C(O)NR^{5.8B}R^{5.8C}$, —$OR^{5.8A}$, —$NR^{5.8B}SO_2R^{5.8A}$, —$NR^{5.8B}C(O)R^{5.8D}$, —$NR^{5.8B}C(O)OR^{5.8D}$, —$NR^{5.8B}OR^{5.8D}$, —$OCX^{5.8}_3$, —$OCHX^{5.8}_2$, $R^{28.8}$-substituted or unsubstituted alkyl (e.g., $C_1$-$C_8$ alkyl, $C_1$-$C_6$ alkyl, or $C_1$-$C_4$ alkyl), $R^{28.8}$-substituted or unsubstituted heteroalkyl (e.g., 2 to 8 membered heteroalkyl, 2 to 6 membered heteroalkyl, or 2 to 4 membered heteroalkyl), $R^{28.8}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.8}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.8}$-substituted or unsubstituted aryl (e.g., $C_6$-$C_{10}$ aryl, $C_{10}$ aryl, or phenyl), or $R^{28.8}$-substituted or unsubstituted heteroaryl (e.g., 5 to 10 membered heteroaryl, 5 to 9 membered heteroaryl, or 5 to 6 membered heteroaryl).

In embodiments, $R^{5.4}$ is $R^{28.8}$-substituted or unsubstituted alkyl (e.g., $C_1$-$C_8$ alkyl, $C_1$-$C_6$ alkyl, or $C_1$-$C_4$ alkyl). In embodiments, $R^{5.4}$ is $R^{28.8}$-substituted alkyl (e.g., $C_1$-$C_8$ alkyl, $C_1$-$C_6$ alkyl, or $C_1$-$C_4$ alkyl). In embodiments, $R^{5.4}$ is an unsubstituted alkyl (e.g., $C_1$-$C_8$ alkyl, $C_1$-$C_6$ alkyl, or $C_1$-$C_4$ alkyl).

In embodiments, $R^{5.4}$ is $R^{28.8}$-substituted or unsubstituted heteroalkyl (e.g., 2 to 8 membered heteroalkyl, 2 to 6 membered heteroalkyl, or 2 to 4 membered heteroalkyl). In embodiments, $R^{5.4}$ is $R^{28.8}$-substituted heteroalkyl (e.g., 2 to 8 membered heteroalkyl, 2 to 6 membered heteroalkyl, or 2 to 4 membered heteroalkyl). In embodiments, $R^{5.4}$ is an unsubstituted heteroalkyl (e.g., 2 to 8 membered heteroalkyl, 2 to 6 membered heteroalkyl, or 2 to 4 membered heteroalkyl).

In embodiments, $R^{5.4}$ is $R^{28.8}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5.4}$ is $R^{28.8}$-substituted cycloalkyl (e.g., $C_3$-$C_8$ cycloalkyl, $C_3$-$C_6$ cycloalkyl, or $C_5$-$C_6$ cycloalkyl). In embodiments, $R^{5.4}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{5.4}$ is $R^{28.8}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{5.4}$ is $R^{28.8}$-substituted heterocycloalkyl (e.g., 3 to 8 membered heterocycloalkyl, 3 to 6 membered heterocycloalkyl, or 5 to 6 membered heterocycloalkyl). In embodiments, $R^{5.4}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{5.4}$ is $R^{28.8}$-substituted or unsubstituted aryl (e.g., $C_6$-$C_{10}$ aryl, $C_{10}$ aryl, or phenyl). In embodiments, $R^{5.4}$ is $R^{28.8}$-substituted aryl (e.g., $C_6$-$C_{10}$ aryl, $C_{10}$ aryl, or phenyl). In embodiments, $R^{5.4}$ is an unsubstituted aryl (e.g., $C_6$-$C_{10}$ aryl, $C_{10}$ aryl, or phenyl).

In embodiments, $R^{5.4}$ is $R^{28.8}$-substituted or unsubstituted heteroaryl (e.g., 5 to 10 membered heteroaryl, 5 to 9 membered heteroaryl, or 5 to 6 membered heteroaryl). In embodiments, $R^{5.4}$ is $R^{28.8}$-substituted heteroaryl (e.g., 5 to 10 membered heteroaryl, 5 to 9 membered heteroaryl, or 5 to 6 membered heteroaryl). In embodiments, $R^{5.4}$ is an unsubstituted heteroaryl (e.g., 5 to 10 membered heteroaryl, 5 to 9 membered heteroaryl, or 5 to 6 membered heteroaryl).

In embodiments, $R^{5.5}$ is hydrogen, halogen, —$CX^{5.9}_3$, —$CHX^{5.9}_2$, —$CH_2X^{5.9}$, —CN, —$SO_{n5.5}R^{5.9A}$, —$SO_{v5.5}NR^{5.9B}R^{5.9C}$, —$NHNR^{5.9B}R^{5.9C}$, —$ONR^{5.9B}R^{5.9C}$, —$NHC(O)NHNR^{5.9B}R^{5.9C}$, —$NHC(O)NR^{5.9B}R^{5.9C}$, —$N(O)_{m5.5}$, —$NR^{5.9B}R^{5.9C}$, —$C(O)R^{5.9D}$, —$C(O)OR^{5.9D}$, —$C(O)NR^{5.9B}R^{5.9C}$, —$OR^{5.9A}$, —$NR^{5.9B}SO_2R^{5.9A}$, —$NR^{5.9B}C(O)R^{5.9D}$, —$NR^{5.9B}C(O)OR^{5.9D}$, —$NR^{5.9B}OR^{5.9D}$, —$OCX^{5.9}_3$, —$OCHX^{5.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{5.5}$ is hydrogen, fluorine, —OH, —CN, —$CH_3$, —$CH_2CH_3$, —$CF_3$, $C(CH_3)_2OH$, —$(CH_2)OH$, —$(CH_2)_2OH$, —$(CH_3)_2OH$, —$CO_2H$, —$C(O)NH_2$, —$CO_2NH_2$ or —$CO_2CH_2CH_3$. In embodiments, $R^{5.5}$ is hydrogen. In embodiments, $R^{5.5}$ is fluorine. In embodiments, $R^{5.5}$ is —OH. In embodiments, $R^{5.5}$ is —CN. In embodiments, $R^{5.5}$ is —$CH_3$. In embodiments, $R^{5.5}$ is —$CH_2CH_3$. In embodiments, $R^{5.5}$ is —$CF_3$. In embodiments, $R^{5.5}$ is $C(CH_3)_2OH$. In embodiments, $R^{5.5}$ is —$(CH_2)OH$. In embodiments, $R^{5.5}$ is —$(CH_2)_2OH$. In embodiments, $R^{5.5}$ is —$(CH_3)_2OH$. In embodiments, $R^{5.5}$ is —$CO_2H$. In embodiments, $R^{5.5}$ is —$C(O)NH_2$. In embodiments, $R^{5.5}$ is —$CO_2NH_2$. In embodiments, $R^{55}$ is —$CO_2CH_2CH_3$.

In embodiments, $R^{5.5}$ is halogen, CCl, $CCl_2$, $CCl_3$, —$CF_2$, —CF. In embodiments, $R^{5.5}$ is halogen. In embodiments, $R^{5.5}$ is CCl. In embodiments, $R^{5.5}$ is $CCl_2$. In embodiments, $R^{5.5}$ is $CCl_3$. In embodiments, $R^{5.5}$ is —$CF_2$. In embodiments, $R^{5.5}$ is —CF.

In embodiments, $R^{5.5}$ is hydrogen, fluorine, —CN, —$CH_3$, —$CF_3$, —$CH_2CH_3$, $CH_2OH$, $C(O)OH$, $C(CH_3)_2$ OH, —$(CH_2)_2OH$, —$CO_2NH_2$, or —$CO_2CH_2CH_3$. In embodiments, $R^{5.5}$ is fluorine, —CN, —$CH_3$, —$CF_3$, —$CH_2CH_3$, $CH_2OH$, $C(O)OH$, —$(CH_2)_2OH$, —$CO_2NH_2$, or —$CO_2CH_2CH_3$. In embodiments, $R^{5.5}$ is hydrogen. In embodiments, $R^{5.5}$ is —OH. In embodiments, $R^{5.5}$ is fluorine. In embodiments, $R^{5.5}$ is —CN. In embodiments, $R^{5.5}$ is —$CH_3$. In embodiments, $R^{5.5}$ is —$CF_3$. In embodiments, $R^{5.5}$ —$CH_2CH_3$. In embodiments, $R^{5.5}$ is $CH_2OH$. In embodiments, $R^{5.5}$ is $C(O)OH$. In embodiments, $R^{5.5}$ is $C(CH_3)_2OH$. In embodiments, $R^{5.5}$ is —$(CH_2)_2OH$. In embodiments, $R^{5.5}$ is —$CO_2NH_2$. In embodiments, $R^{5.5}$ is —$CO_2CH_2CH_3$.

In embodiments, $R^{5.5}$ is halogen, $CHF_2$, $CH_2F$, $CCl_3$, $CHCl_2$, $CH_2Cl$, —$C(O)R^{5.9D}$, —$C(O)OR^{5.9D}$, —$CO_2NR^{5.9B}R^{5.9C}$, or —$OR^{5.5A}$. In embodiments, $R^{5.5}$ is halogen, $CHF_2$, $CH_2F$, $CCl_3$, $CHCl_2$, $CH_2Cl$, —$C(O)R^{5.9D}$, —$C(O)OR^{5.9D}$, or —$OR^{5.5A}$. In embodiments, $R^{5.5}$ is halogen. In embodiments, $R^{5.5}$ is $CHF_2$. In embodiments, $R^{5.5}$ is $CH_2F$. In embodiments, $R^{5.5}$ is $CCl_3$. In embodiments, $R^{5.5}$ is $CHCl_2$. In embodiments, $R^{5.5}$ is $CH_2Cl$. In embodiments, $R^{5.5}$ is —$C(O)R^{5.9D}$ In embodiments, $R^{5.5}$ is —$C(O)OR^{5.9D}$. In embodiments, $R^{5.5}$ is —$OR^{5.5A}$. In embodiments, $R^{5.5}$ is —$CO_2NR^{5.9B}R^{5.9C}$. In embodiments, $R^{5.9B}$ is $CH_3$. In embodiments, $R^{5.9B}$ is $CF_3$. In embodiments, $R^{5.9B}$ is $CHF_2$. In embodiments, $R^{5.9B}$ is $CH_2F$. In embodiments, $R^{5.9B}$ is $CH_2Cl$. In embodiments, $R^{5.9B}$ is $CHCl_2$. In embodiments, $R^{5.9B}$ is $CCl_3$. In embodiments, $R^{5.9B}$ is $CH_2CH_3$. In embodiments, $R^{5.9B}$ is unsubstituted propyl. In embodiments, $R^{5.9B}$ is hydrogen. In embodiments, $R^{5.9C}$ is $CH_3$. In embodiments, $R^{5.9C}$ is $CF_3$. In embodiments, $R^{5.9C}$ is $CHF_2$. In embodiments, $R^{5.9C}$ is $CH_2F$. In embodiments, $R^{5.9C}$ is $CH_2Cl$. In embodiments, $R^{5.9C}$ is $CHCl_2$. In embodiments, $R^{5.9C}$ is $CCl_3$. In embodiments, $R^{5.9C}$ is $CH_2CH_3$. In embodiments, $R^{5.9C}$ is unsubstituted propyl. In embodiments, $R^{5.9C}$ is hydrogen. In embodiments, $R^{5.9D}$ is $CH_3$. In embodiments, $R^{5.9D}$ is $CF_3$. In embodiments, $R^{5.9D}$ is $CHF_2$. In embodiments, $R^{5.9D}$ is $CH_2F$. In embodiments, $R^{5.9D}$ is $CH_2Cl$. In embodiments, $R^{5.9D}$ is $CHCl_2$. In embodiments, $R^{5.9D}$ is $CCl_3$. In embodiments, $R^{5.9D}$ is $CH_2CH_3$. In embodiments, $R^{5.9D}$ is unsubstituted propyl. In embodiments, $R^{5.9D}$ is hydrogen.

In embodiments, $R^{5.4}$ and $R^{5.5}$ are independently hydrogen, fluorine, —CN, —$CH_3$, —$CH_2CH_3$, —$CF_3$, —$(CH_2)$ OH, —$(CH_2)_2OH$, —$(CH_3)_2OH$, —$CO_2H$, —$CO_2NH_2$ or —$CO_2CH_2CH_3$.

In embodiments, $R^{5.5}$ is hydrogen, halogen, —$CX^{5.9}_3$, —$CHX^{5.9}_2$, —$CH_2X^{5.9}$, —CN, —$SO_{n5.5}R^{5.9A}$, —$SO_{v5.5}NR^{5.9B}R^{5.9C}$, —$NHNR^{5.9B}R^{5.9C}$, —$ONR^{5.9B}R^{5.9C}$, —$NHC(O)NHNR^{5.9B}R^{5.9C}$, —$NHC(O)NR^{5.9B}R^{5.9C}$, —$N(O)_{m5.5}$, —$NR^{5.9B}R^{5.9C}$, —$C(O)R^{5.9D}$, —$C(O)OR^{5.9D}$, —$C(O)NR^{5.9B}R^{5.9C}$, —$OR^{5.9A}$, —$NR^{5.9B}SO_2R^{5.9A}$, —$NR^{5.9B}C(O)R^{5.9D}$, —$NR^{5.9B}C(O)OR^{5.9D}$, —$NR^{5.9B}OR^{5.9D}$, —$OCX^{5.9}_3$, —$OCHX^{5.9}_2$, $R^{28.9}$-substituted or unsubstituted alkyl (e.g., $C_1$-$C_8$ alkyl, $C_1$-$C_6$ alkyl, or $C_1$-$C_4$ alkyl), $R^{28.9}$-substituted or unsubstituted heteroalkyl (e.g., 2 to 8 membered heteroalkyl, 2 to 6 membered heteroalkyl, or 2 to 4 membered heteroalkyl), $R^{28.9}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.9}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.9}$-substituted or unsubstituted aryl (e.g., $C_6$-$C_{10}$ aryl, $C_{10}$ aryl, or phenyl), or $R^{28.9}$-substituted or unsubstituted heteroaryl (e.g., 5 to 10 membered heteroaryl, 5 to 9 membered heteroaryl, or 5 to 6 membered heteroaryl).

In embodiments, $R^{5.5}$ is $R^{28.9}$-substituted or unsubstituted alkyl (e.g., $C_1$-$C_8$ alkyl, $C_1$-$C_6$ alkyl, or $C_1$-$C_4$ alkyl). In embodiments, $R^{5.5}$ is $R^{28.9}$-substituted alkyl (e.g., $C_1$-$C_8$ alkyl, $C_1$-$C_6$ alkyl, or $C_1$-$C_4$ alkyl). In embodiments, $R^{5.5}$ is an unsubstituted alkyl (e.g., $C_1$-$C_8$ alkyl, $C_1$-$C_6$ alkyl, or $C_1$-$C_4$ alkyl).

In embodiments, $R^{5.5}$ is $R^{28.9}$-substituted or unsubstituted heteroalkyl (e.g., 2 to 8 membered heteroalkyl, 2 to 6 membered heteroalkyl, or 2 to 4 membered heteroalkyl). In embodiments, $R^{5.5}$ is $R^{28.9}$-substituted heteroalkyl (e.g., 2 to 8 membered heteroalkyl, 2 to 6 membered heteroalkyl, or 2 to 4 membered heteroalkyl). In embodiments, $R^{5.5}$ is an unsubstituted heteroalkyl (e.g., 2 to 8 membered heteroalkyl, 2 to 6 membered heteroalkyl, or 2 to 4 membered heteroalkyl).

In embodiments, $R^{5.5}$ is $R^{28.9}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5.5}$ is $R^{28.9}$-substituted cycloalkyl (e.g., $C_3$-$C_8$ cycloalkyl, $C_3$-$C_6$ cycloalkyl, or $C_5$-$C_6$ cycloalkyl). In embodiments, $R^{5.5}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{5.5}$ is $R^{28.9}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{5.5}$ is $R^{28.9}$-substituted heterocycloalkyl (e.g., 3 to 8 membered heterocycloalkyl, 3 to 6 membered heterocycloalkyl, or 5 to 6 membered heterocycloalkyl). In embodiments, $R^{5.5}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{5.5}$ is $R^{28.9}$-substituted or unsubstituted aryl (e.g., $C_6$-$C_{10}$ aryl, $C_{10}$ aryl, or phenyl). In embodiments, $R^{5.5}$ is $R^{28.9}$-substituted aryl (e.g., $C_6$-$C_{10}$ aryl, $C_{10}$ aryl, or phenyl). In embodiments, $R^{5.5}$ is an unsubstituted aryl (e.g., $C_6$-$C_{10}$ aryl, $C_{10}$ aryl, or phenyl).

In embodiments, $R^{5.5}$ is $R^{28.9}$-substituted or unsubstituted heteroaryl (e.g., 5 to 10 membered heteroaryl, 5 to 9 membered heteroaryl, or 5 to 6 membered heteroaryl). In embodiments, $R^{5.5}$ is $R^{28.9}$-substituted heteroaryl (e.g., 5 to 10 membered heteroaryl, 5 to 9 membered heteroaryl, or 5 to 6 membered heteroaryl). In embodiments, $R^{5.5}$ is an unsubstituted heteroaryl (e.g., 5 to 10 membered heteroaryl, 5 to 9 membered heteroaryl, or 5 to 6 membered heteroaryl).

In embodiments, $R^{5.6A}$, $R^{5.6B}$, $R^{5.6C}$, $R^{5.6D}$, $R^{5.7A}$, $R^{5.7B}$, $R^{5.7C}$, $R^{5.7D}$, $R^{5.8A}$, $R^{5.8B}$, $R^{5.9C}$, $R^{5.8D}$ $R^{5.9A}$, $R^{5.9B}$, $R^{5.9C}$ and $R^{5.9D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{5.6B}$ and $R^{5.6C}$, $R^{5.7B}$ and $R^{5.7C}$, $R^{5.8B}$ and $R^{5.8C}$, $R^{5.9B}$ and $R^{5.9C}$ substituents bonded to the same nitrogen atom may optionally be joined to form a substituted or unsubstituted heterocycloalkyl or substituted or unsubstituted heteroaryl.

In embodiments, $R^{5.6A}$ is hydrogen, halogen, —$CF_3$, —$CCl_3$, —$CBr_3$, —$CI_3$, —COOH, —$CONH_2$, $R^{28.6A}$-substituted or unsubstituted alkyl (e.g., $C_1$-$C_8$ alkyl, $C_1$-$C_6$ alkyl, or $C_1$-$C_4$ alkyl), $R^{28.6A}$-substituted or unsubstituted heteroalkyl (e.g., 2 to 8 membered heteroalkyl, 2 to 6 membered heteroalkyl, or 2 to 4 membered heteroalkyl), $R^{28.6A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.6A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.6A}$-substituted or unsubstituted aryl (e.g., $C_6$-$C_{10}$ aryl, $C_{10}$ aryl, or phenyl), or $R^{28.6A}$-substituted or unsubstituted heteroaryl (e.g., 5 to 10 membered heteroaryl, 5 to 9 membered heteroaryl, or 5 to 6 membered heteroaryl).

In embodiments, $R^{5.7A}$ is hydrogen, halogen, —$CF_3$, —$CCl_3$, —$CBr_3$, —$CI_3$, —COOH, —$CONH_2$, $R^{28.7A}$-substituted or unsubstituted alkyl (e.g., $C_1$-$C_8$ alkyl, $C_1$-$C_6$ alkyl, or $C_1$-$C_4$ alkyl), $R^{28.7A}$-substituted or unsubstituted heteroalkyl (e.g., 2 to 8 membered heteroalkyl, 2 to 6 membered heteroalkyl, or 2 to 4 membered heteroalkyl), $R^{28.7A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.7A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.7A}$-substituted or unsubstituted aryl (e.g., $C_6$-$C_{10}$ aryl, $C_{10}$ aryl, or phenyl), or $R^{28.7A}$-substituted or unsubstituted heteroaryl (e.g., 5 to 10 membered heteroaryl, 5 to 9 membered heteroaryl, or 5 to 6 membered heteroaryl).

In embodiments, $R^{5.8A}$ is hydrogen, halogen, —$CF_3$, —$CCl_3$, —$CBr_3$, —$CI_3$, —COOH, —$CONH_2$, $R^{28.8A}$-substituted or unsubstituted alkyl (e.g., $C_1$-$C_8$ alkyl, $C_1$-$C_6$ alkyl, or $C_1$-$C_4$ alkyl), $R^{28.8A}$-substituted or unsubstituted heteroalkyl (e.g., 2 to 8 membered heteroalkyl, 2 to 6 membered heteroalkyl, or 2 to 4 membered heteroalkyl), $R^{28.8A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.8A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.8A}$-substituted or unsubstituted aryl (e.g., $C_6$-$C_{10}$ aryl, $C_{10}$ aryl, or phenyl), or $R^{28.8A}$-substituted or unsubstituted heteroaryl (e.g., 5 to 10 membered heteroaryl, 5 to 9 membered heteroaryl, or 5 to 6 membered heteroaryl).

In embodiments, $R^{5.9A}$ is hydrogen, halogen, —$CF_3$, —$CCl_3$, —$CBr_3$, —$CI_3$, —COOH, —$CONH_2$, $R^{28.9A}$-substituted or unsubstituted alkyl (e.g., $C_1$-$C_8$ alkyl, $C_1$-$C_6$ alkyl, or $C_1$-$C_4$ alkyl), $R^{28.9A}$-substituted or unsubstituted heteroalkyl (e.g., 2 to 8 membered heteroalkyl, 2 to 6 membered heteroalkyl, or 2 to 4 membered heteroalkyl), $R^{28.9A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.9A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.9A}$-substituted or unsubstituted aryl (e.g., $C_6$-$C_{10}$ aryl, $C_{10}$ aryl, or phenyl), or $R^{28.9A}$-substituted or unsubstituted heteroaryl (e.g., 5 to 10 membered heteroaryl, 5 to 9 membered heteroaryl, or 5 to 6 membered heteroaryl).

In embodiments, $R^{5.6B}$ is hydrogen, halogen, —$CF_3$, —$CCl_3$, —$CBr_3$, —$CI_3$, —COOH, —$CONH_2$, $R^{28.6B}$-substituted or unsubstituted alkyl (e.g., $C_1$-$C_8$ alkyl, $C_1$-$C_6$ alkyl, or $C_1$-$C_4$ alkyl), $R^{28.6B}$-substituted or unsubstituted heteroalkyl (e.g., 2 to 8 membered heteroalkyl, 2 to 6 membered heteroalkyl, or 2 to 4 membered heteroalkyl), $R^{28.6B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.6B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.6B}$-substituted or unsubstituted aryl (e.g., $C_6$-$C_{10}$ aryl, $C_{10}$ aryl, or phenyl), or $R^{28.6B}$-substituted or unsubstituted heteroaryl (e.g., 5 to 10 membered heteroaryl, 5 to 9 membered heteroaryl, or 5 to 6 membered heteroaryl). In embodiments, $R^{5.6B}$ and $R^{5.6C}$ substituents bonded to the same nitrogen atom may optionally be joined to form a $R^{28.6B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{28.6B}$-substituted or unsubstituted heteroaryl (e.g., 5 to 10 membered heteroaryl, 5 to 9 membered heteroaryl, or 5 to 6 membered heteroaryl).

In embodiments, $R^{5.7B}$ is hydrogen, halogen, $-CF_3$, $-CCl_3$, $-CBr_3$, $-CI_3$, $-COOH$, $-CONH_2$, $R^{28.7B}$-substituted or unsubstituted alkyl (e.g., $C_1$-$C_8$ alkyl, $C_1$-$C_6$ alkyl, or $C_1$-$C_4$ alkyl), $R^{28.7B}$-substituted or unsubstituted heteroalkyl (e.g., 2 to 8 membered heteroalkyl, 2 to 6 membered heteroalkyl, or 2 to 4 membered heteroalkyl), $R^{28.7B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.7B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.7B}$-substituted or unsubstituted aryl (e.g., $C_6$-$C_{10}$ aryl, $C_{10}$ aryl, or phenyl), or $R^{28.8B}$-substituted or unsubstituted heteroaryl (e.g., 5 to 10 membered heteroaryl, 5 to 9 membered heteroaryl, or 5 to 6 membered heteroaryl). In embodiments, $R^{5.7B}$ and $R^{5.7C}$ substituents bonded to the same nitrogen atom may optionally be joined to form a $R^{28.7B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{28.7B}$-substituted or unsubstituted heteroaryl (e.g., 5 to 10 membered heteroaryl, 5 to 9 membered heteroaryl, or 5 to 6 membered heteroaryl).

In embodiments, $R^{5.8B}$ is hydrogen, halogen, $-CF_3$, $-CCl_3$, $-CBr_3$, $-CI_3$, $-COOH$, $-CONH_2$, $R^{28.8B}$-substituted or unsubstituted alkyl (e.g., $C_1$-$C_8$ alkyl, $C_1$-$C_6$ alkyl, or $C_1$-$C_4$ alkyl), $R^{28.8B}$ substituted or unsubstituted heteroalkyl (e.g., 2 to 8 membered heteroalkyl, 2 to 6 membered heteroalkyl, or 2 to 4 membered heteroalkyl), $R^{28.8B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.8B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.8B}$-substituted or unsubstituted aryl (e.g., $C_6$-$C_{10}$ aryl, $C_{10}$ aryl, or phenyl), or $R^{28.8B}$-substituted or unsubstituted heteroaryl (e.g., 5 to 10 membered heteroaryl, 5 to 9 membered heteroaryl, or 5 to 6 membered heteroaryl). In embodiments, $R^{5.8B}$ and $R^{5.8C}$ substituents bonded to the same nitrogen atom may optionally be joined to form a $R^{28.8B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{28.8B}$-substituted or unsubstituted heteroaryl (e.g., 5 to 10 membered heteroaryl, 5 to 9 membered heteroaryl, or 5 to 6 membered heteroaryl).

In embodiments, $R^{5.9B}$ is hydrogen, halogen, $-CF_3$, $-CCl_3$, $-CBr_3$, $-CI_3$, $-COOH$, $-CONH_2$, $R^{28.9B}$-substituted or unsubstituted alkyl (e.g., $C_1$-$C_8$ alkyl, $C_1$-$C_6$ alkyl, or $C_1$-$C_4$ alkyl), $R^{28.9B}$-substituted or unsubstituted heteroalkyl (e.g., 2 to 8 membered heteroalkyl, 2 to 6 membered heteroalkyl, or 2 to 4 membered heteroalkyl), $R^{28.9B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.9B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.9B}$-substituted or unsubstituted aryl (e.g., $C_6$-$C_{10}$ aryl, $C_{10}$ aryl, or phenyl), or $R^{28.9B}$-substituted or unsubstituted heteroaryl (e.g., 5 to 10 membered heteroaryl, 5 to 9 membered heteroaryl, or 5 to 6 membered heteroaryl). In embodiments, $R^{5.9B}$ and $R^{5.9C}$ substituents bonded to the same nitrogen atom may optionally be joined to form a $R^{28.9B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{28.9B}$-substituted or unsubstituted heteroaryl (e.g., 5 to 10 membered heteroaryl, 5 to 9 membered heteroaryl, or 5 to 6 membered heteroaryl).

In embodiments, $R^{5.6C}$ is hydrogen, halogen, $-CF_3$, $-CCl_3$, $-CBr_3$, $-CI_3$, $-COOH$, $-CONH_2$, $R^{28.6C}$-substituted or unsubstituted alkyl (e.g., $C_1$-$C_8$ alkyl, $C_1$-$C_6$ alkyl, or $C_1$-$C_4$ alkyl), $R^{28.6C}$-substituted or unsubstituted heteroalkyl (e.g., 2 to 8 membered heteroalkyl, 2 to 6 membered heteroalkyl, or 2 to 4 membered heteroalkyl), $R^{28.6C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.6C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.6C}$-substituted or unsubstituted aryl (e.g., $C_6$-$C_{10}$ aryl, $C_{10}$ aryl, or phenyl), or $R^{28.6C}$-substituted or unsubstituted heteroaryl (e.g., 5 to 10 membered heteroaryl, 5 to 9 membered heteroaryl, or 5 to 6 membered heteroaryl). In embodiments, $R^{5.6C}$ and $R^{5.6C}$ substituents bonded to the same nitrogen atom may optionally be joined to form a $R^{28.6C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{28.6C}$-substituted or unsubstituted heteroaryl (e.g., 5 to 10 membered heteroaryl, 5 to 9 membered heteroaryl, or 5 to 6 membered heteroaryl).

In embodiments, $R^{5.7C}$ is hydrogen, halogen, $-CF_3$, $-CCl_3$, $-CBr_3$, $-CI_3$, $-COOH$, $-CONH_2$, $R^{28.7C}$-substituted or unsubstituted alkyl (e.g., $C_1$-$C_8$ alkyl, $C_1$-$C_6$ alkyl, or $C_1$-$C_4$ alkyl), $R^{28.7C}$-substituted or unsubstituted heteroalkyl (e.g., 2 to 8 membered heteroalkyl, 2 to 6 membered heteroalkyl, or 2 to 4 membered heteroalkyl), $R^{28.7C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.7C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.7C}$-substituted or unsubstituted aryl (e.g., $C_6$-$C_{10}$ aryl, $C_{10}$ aryl, or phenyl), or $R^{28.8C}$-substituted or unsubstituted heteroaryl (e.g., 5 to 10 membered heteroaryl, 5 to 9 membered heteroaryl, or 5 to 6 membered heteroaryl). In embodiments, $R^{5.7C}$ and $R^{5.7C}$ substituents bonded to the same nitrogen atom may optionally be joined to form a $R^{28.7C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{28.7C}$-substituted or unsubstituted heteroaryl (e.g., 5 to 10 membered heteroaryl, 5 to 9 membered heteroaryl, or 5 to 6 membered heteroaryl).

In embodiments, $R^{5.8C}$ is hydrogen, halogen, $-CF_3$, $-CCl_3$, $-CBr_3$, $-CI_3$, $-COOH$, $-CONH_2$, $R^{28.8C}$-substituted or unsubstituted alkyl (e.g., $C_1$-$C_8$ alkyl, $C_1$-$C_6$ alkyl, or $C_1$-$C_4$ alkyl), $R^{28.8C}$-substituted or unsubstituted heteroalkyl (e.g., 2 to 8 membered heteroalkyl, 2 to 6 membered heteroalkyl, or 2 to 4 membered heteroalkyl), $R^{28.8C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.8C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.8C}$-substituted or unsubstituted aryl (e.g., $C_6$-$C_{10}$ aryl, $C_{10}$ aryl, or phenyl), or $R^{28.8C}$-substituted or unsubstituted heteroaryl (e.g., 5 to 10 membered heteroaryl, 5 to 9 membered heteroaryl, or 5 to 6 membered heteroaryl). In embodiments, $R^{5.8C}$ and $R^{5.8C}$ substituents bonded to the same nitrogen atom may optionally be joined to form a $R^{28.8C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{28.8C}$-substituted or unsubstituted heteroaryl (e.g., 5 to 10 membered heteroaryl, 5 to 9 membered heteroaryl, or 5 to 6 membered heteroaryl).

In embodiments, $R^{5.9C}$ is hydrogen, halogen, —$CF_3$, —$CCl_3$, —$CBr_3$, —$CI_3$, —COOH, —$CONH_2$, $R^{28.9C}$-substituted or unsubstituted alkyl (e.g., $C_1$-$C_8$ alkyl, $C_1$-$C_6$ alkyl, or $C_1$-$C_4$ alkyl), $R^{28.9C}$-substituted or unsubstituted heteroalkyl (e.g., 2 to 8 membered heteroalkyl, 2 to 6 membered heteroalkyl, or 2 to 4 membered heteroalkyl), $R^{28.9C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.9C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.9C}$-substituted or unsubstituted aryl (e.g., $C_6$-$C_{10}$ aryl, $C_{10}$ aryl, or phenyl), or $R^{28.9C}$-substituted or unsubstituted heteroaryl (e.g., 5 to 10 membered heteroaryl, 5 to 9 membered heteroaryl, or 5 to 6 membered heteroaryl). In embodiments, $R^{5.9C}$ and $R^{5.9C}$ substituents bonded to the same nitrogen atom may optionally be joined to form a $R^{28.9C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{28.9C}$-substituted or unsubstituted heteroaryl (e.g., 5 to 10 membered heteroaryl, 5 to 9 membered heteroaryl, or 5 to 6 membered heteroaryl).

In embodiments, $R^{5.6D}$ is hydrogen, halogen, —$CF_3$, —$CCl_3$, —$CBr_3$, —$CI_3$, —COOH, —$CONH_2$, $R^{28.6D}$-substituted or unsubstituted alkyl (e.g., $C_1$-$C_8$ alkyl, $C_1$-$C_6$ alkyl, or $C_1$-$C_4$ alkyl), $R^{28.6D}$-substituted or unsubstituted heteroalkyl (e.g., 2 to 8 membered heteroalkyl, 2 to 6 membered heteroalkyl, or 2 to 4 membered heteroalkyl), $R^{28.6D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.6D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.6D}$-substituted or unsubstituted aryl (e.g., $C_6$-$C_{10}$ aryl, $C_{10}$ aryl, or phenyl), or $R^{28.6D}$-substituted or unsubstituted heteroaryl (e.g., 5 to 10 membered heteroaryl, 5 to 9 membered heteroaryl, or 5 to 6 membered heteroaryl).

In embodiments, $R^{5.7D}$ is hydrogen, halogen, —$CF_3$, —$CCl_3$, —$CBr_3$, —$CI_3$, —COOH, —$CONH_2$, $R^{28.7D}$-substituted or unsubstituted alkyl (e.g., $C_1$-$C_8$ alkyl, $C_1$-$C_6$ alkyl, or $C_1$-$C_4$ alkyl), $R^{28.7D}$-substituted or unsubstituted heteroalkyl (e.g., 2 to 8 membered heteroalkyl, 2 to 6 membered heteroalkyl, or 2 to 4 membered heteroalkyl), $R^{28.7D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.7D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.7D}$-substituted or unsubstituted aryl (e.g., $C_6$-$C_{10}$ aryl, $C_{10}$ aryl, or phenyl), or $R^{28.7D}$-substituted or unsubstituted heteroaryl (e.g., 5 to 10 membered heteroaryl, 5 to 9 membered heteroaryl, or 5 to 6 membered heteroaryl).

In embodiments, $R^{5.8D}$ is hydrogen, halogen, —$CF_3$, —$CCl_3$, —$CBr_3$, —$CI_3$, —COOH, —$CONH_2$, $R^{28.8D}$-substituted or unsubstituted alkyl (e.g., $C_1$-$C_8$ alkyl, $C_1$-$C_6$ alkyl, or $C_1$-$C_4$ alkyl), $R^{28.8D}$-substituted or unsubstituted heteroalkyl (e.g., 2 to 8 membered heteroalkyl, 2 to 6 membered heteroalkyl, or 2 to 4 membered heteroalkyl), $R^{28.8D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.8D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.8D}$-substituted or unsubstituted aryl (e.g., $C_6$-$C_{10}$ aryl, $C_{10}$ aryl, or phenyl), or $R^{28.8D}$-substituted or unsubstituted heteroaryl (e.g., 5 to 10 membered heteroaryl, 5 to 9 membered heteroaryl, or 5 to 6 membered heteroaryl).

In embodiments, $R^{5.9D}$ is hydrogen, halogen, —$CF_3$, —$CCl_3$, —$CBr_3$, —$CI_3$, —COOH, —$CONH_2$, $R^{28.9D}$-substituted or unsubstituted alkyl (e.g., $C_1$-$C_8$ alkyl, $C_1$-$C_6$ alkyl, or $C_1$-$C_4$ alkyl), $R^{28.9D}$-substituted or unsubstituted heteroalkyl (e.g., 2 to 8 membered heteroalkyl, 2 to 6 membered heteroalkyl, or 2 to 4 membered heteroalkyl), $R^{28.9D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28.9D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28.9D}$-substituted or unsubstituted aryl (e.g., $C_6$-$C_{10}$ aryl, $C_{10}$ aryl, or phenyl), or $R^{28.9D}$-substituted or unsubstituted heteroaryl (e.g., 5 to 10 membered heteroaryl, 5 to 9 membered heteroaryl, or 5 to 6 membered heteroaryl).

$R^{28.6}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{29.6}$-substituted or unsubstituted alkyl (e.g., $C_1$-$C_8$ alkyl, $C_1$-$C_6$ alkyl, or $C_1$-$C_4$ alkyl), $R^{29.6}$-substituted or unsubstituted heteroalkyl (e.g., 2 to 8 membered heteroalkyl, 2 to 6 membered heteroalkyl, or 2 to 4 membered heteroalkyl), $R^{29.6}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29.6}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29.6}$-substituted or unsubstituted aryl (e.g., $C_6$-$C_{10}$ aryl, $C_{10}$ aryl, or phenyl), or $R^{29.6}$-substituted or unsubstituted heteroaryl (e.g., 5 to 10 membered heteroaryl, 5 to 9 membered heteroaryl, or 5 to 6 membered heteroaryl).

In embodiments, $R^{28.6}$ is $R^{29.6}$-substituted or unsubstituted alkyl (e.g., $C_1$-$C_8$ alkyl, $C_1$-$C_6$ alkyl, or $C_1$-$C_4$ alkyl). In embodiments, $R^{28.6}$ is $R^{29.6}$-substituted alkyl (e.g., $C_1$-$C_8$ alkyl, $C_1$-$C_6$ alkyl, or $C_1$-$C_4$ alkyl). In embodiments, $R^{28.6}$ is an unsubstituted alkyl (e.g., $C_1$-$C_8$ alkyl, $C_1$-$C_6$ alkyl, or $C_1$-$C_4$ alkyl).

In embodiments, $R^{28.6}$ is $R^{29.6}$-substituted or unsubstituted heteroalkyl (e.g., 2 to 8 membered heteroalkyl, 2 to 6 membered heteroalkyl, or 2 to 4 membered heteroalkyl). In embodiments, $R^{28.6}$ is $R^{29.6}$-substituted heteroalkyl (e.g., 2 to 8 membered heteroalkyl, 2 to 6 membered heteroalkyl, or 2 to 4 membered heteroalkyl). In embodiments, $R^{28.6}$ is an unsubstituted heteroalkyl (e.g., 2 to 8 membered heteroalkyl, 2 to 6 membered heteroalkyl, or 2 to 4 membered heteroalkyl).

In embodiments, $R^{28.6}$ is $R^{29.6}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{28.6}$ is $R^{29.6}$-substituted cycloalkyl (e.g., $C_3$-$C_8$ cycloalkyl, $C_3$-$C_6$ cycloalkyl, or $C_5$-$C_6$ cycloalkyl). In embodiments, $R^{28.6}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{28.6}$ is $R^{29.6}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{28.6}$ is $R^{29.6}$-substituted heterocycloalkyl (e.g., 3 to 8 membered heterocycloalkyl, 3 to 6 membered heterocycloalkyl, or 5 to 6 membered heterocycloalkyl). In embodiments, $R^{28.6}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{28.6}$ is $R^{29.6}$-substituted or unsubstituted aryl (e.g., $C_6$-$C_{10}$ aryl, $C_{10}$ aryl, or phenyl). In embodiments, $R^{28.6}$ is $R^{29.6}$-substituted aryl (e.g., $C_6$-$C_{10}$ aryl, $C_{10}$ aryl, or phenyl). In embodiments, $R^{28.6}$ is an unsubstituted aryl (e.g., $C_6$-$C_{10}$ aryl, $C_{10}$ aryl, or phenyl).

In embodiments, $R^{28.6}$ is $R^{29.6}$-substituted or unsubstituted heteroaryl (e.g., 5 to 10 membered heteroaryl, 5 to 9 membered heteroaryl, or 5 to 6 membered heteroaryl). In embodiments, $R^{28.6}$ is $R^{29.6}$-substituted heteroaryl (e.g., 5 to 10 membered heteroaryl, 5 to 9 membered heteroaryl, or 5 to 6 membered heteroaryl). In embodiments, $R^{28.6}$ is an unsubstituted heteroaryl (e.g., 5 to 10 membered heteroaryl, 5 to 9 membered heteroaryl, or 5 to 6 membered heteroaryl).

$R^{29.6}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{30.6}$-substituted or unsubstituted alkyl (e.g., $C_1$-$C_8$ alkyl, $C_1$-$C_6$ alkyl, or $C_1$-$C_4$ alkyl), $R^{30.6}$-substituted or unsubstituted heteroalkyl (e.g., 2 to 8 membered heteroalkyl, 2 to 6 membered heteroalkyl, or 2 to 4 membered heteroalkyl), $R^{30.6}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{30.6}$-substituted or unsubstituted heterocycloalkyl (e.g., 3 to 8 membered heterocycloalkyl, 3 to 6 membered heterocycloalkyl, or 5 to 6 membered heterocycloalkyl), $R^{30.6}$-substituted or unsubstituted aryl (e.g., $C_6$-$C_{10}$ aryl, $C_{10}$ aryl, or phenyl), or $R^{30.6}$-substituted or unsubstituted heteroaryl (e.g., 5 to 10 membered heteroaryl, 5 to 9 membered heteroaryl, or 5 to 6 membered heteroaryl).

In embodiments, $R^{29.6}$ is $R^{30.6}$-substituted or unsubstituted alkyl (e.g., $C_1$-$C_8$ alkyl, $C_1$-$C_6$ alkyl, or $C_1$-$C_4$ alkyl). In embodiments, $R^{29.6}$ is $R^{30.6}$-substituted alkyl (e.g., $C_1$-$C_8$ alkyl, $C_1$-$C_6$ alkyl, or $C_1$-$C_4$ alkyl). In embodiments, $R^{29.6}$ is an unsubstituted alkyl (e.g., $C_1$-$C_8$ alkyl, $C_1$-$C_6$ alkyl, or $C_1$-$C_4$ alkyl).

In embodiments, $R^{29.6}$ is $R^{30.6}$-substituted or unsubstituted heteroalkyl (e.g., 2 to 8 membered heteroalkyl, 2 to 6 membered heteroalkyl, or 2 to 4 membered heteroalkyl). In embodiments, $R^{29.6}$ is $R^{30.6}$-substituted heteroalkyl (e.g., 2 to 8 membered heteroalkyl, 2 to 6 membered heteroalkyl, or 2 to 4 membered heteroalkyl). In embodiments, $R^{29.6}$ is an unsubstituted heteroalkyl (e.g., 2 to 8 membered heteroalkyl, 2 to 6 membered heteroalkyl, or 2 to 4 membered heteroalkyl).

In embodiments, $R^{29.6}$ is $R^{30.6}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{29.6}$ is $R^{30.6}$-substituted cycloalkyl (e.g., $C_3$-$C_8$ cycloalkyl, $C_3$-$C_6$ cycloalkyl, or $C_5$-$C_6$ cycloalkyl). In embodiments, $R^{29.6}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{29.6}$ is $R^{30.6}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{29.6}$ is $R^{30.6}$-substituted heterocycloalkyl (e.g., 3 to 8 membered heterocycloalkyl, 3 to 6 membered heterocycloalkyl, or 5 to 6 membered heterocycloalkyl). In embodiments, $R^{29.6}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{29.6}$ is $R^{30.6}$-substituted or unsubstituted aryl (e.g., $C_6$-$C_{10}$ aryl, $C_{10}$ aryl, or phenyl). In embodiments, $R^{29.6}$ is $R^{30.6}$-substituted aryl (e.g., $C_6$-$C_{10}$ aryl, $C_{10}$ aryl, or phenyl). In embodiments, $R^{29.6}$ is an unsubstituted aryl (e.g., $C_6$-$C_{10}$ aryl, $C_{10}$ aryl, or phenyl).

In embodiments, $R^{29.6}$ is $R^{30.6}$-substituted or unsubstituted heteroaryl (e.g., 5 to 10 membered heteroaryl, 5 to 9 membered heteroaryl, or 5 to 6 membered heteroaryl). In embodiments, $R^{29.6}$ is $R^{30.6}$-substituted heteroaryl (e.g., 5 to 10 membered heteroaryl, 5 to 9 membered heteroaryl, or 5 to 6 membered heteroaryl). In embodiments, $R^{29.6}$ is an unsubstituted heteroaryl (e.g., 5 to 10 membered heteroaryl, 5 to 9 membered heteroaryl, or 5 to 6 membered heteroaryl).

$R^{28.7}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{29.7}$-substituted or unsubstituted alkyl (e.g., $C_1$-$C_8$ alkyl, $C_1$-$C_6$ alkyl, or $C_1$-$C_4$ alkyl), $R^{29.7}$-substituted or unsubstituted heteroalkyl (e.g., 2 to 8 membered heteroalkyl, 2 to 6 membered heteroalkyl, or 2 to 4 membered heteroalkyl), $R^{29.7}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29.7}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29.7}$-substituted or unsubstituted aryl (e.g., $C_6$-$C_{10}$ aryl, $C_{10}$ aryl, or phenyl), or $R^{29.7}$-substituted or unsubstituted heteroaryl (e.g., 5 to 10 membered heteroaryl, 5 to 9 membered heteroaryl, or 5 to 6 membered heteroaryl).

In embodiments, $R^{28.7}$ is $R^{29.7}$-substituted or unsubstituted alkyl (e.g., $C_1$-$C_8$ alkyl, $C_1$-$C_6$ alkyl, or $C_1$-$C_4$ alkyl). In embodiments, $R^{28.7}$ is $R^{29.7}$-substituted alkyl (e.g., $C_1$-$C_8$ alkyl, $C_1$-$C_6$ alkyl, or $C_1$-$C_4$ alkyl). In embodiments, $R^{28.7}$ is an unsubstituted alkyl (e.g., $C_1$-$C_8$ alkyl, $C_1$-$C_6$ alkyl, or $C_1$-$C_4$ alkyl).

In embodiments, $R^{28.7}$ is $R^{29.7}$-substituted or unsubstituted heteroalkyl (e.g., 2 to 8 membered heteroalkyl, 2 to 6 membered heteroalkyl, or 2 to 4 membered heteroalkyl). In embodiments, $R^{28.7}$ is $R^{29.7}$-substituted heteroalkyl (e.g., 2 to 8 membered heteroalkyl, 2 to 6 membered heteroalkyl, or 2 to 4 membered heteroalkyl). In embodiments, $R^{28.7}$ is an unsubstituted heteroalkyl (e.g., 2 to 8 membered heteroalkyl, 2 to 6 membered heteroalkyl, or 2 to 4 membered heteroalkyl).

In embodiments, $R^{28.7}$ is $R^{29.7}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{28.7}$ is $R^{29.7}$-substituted cycloalkyl (e.g., $C_3$-$C_8$ cycloalkyl, $C_3$-$C_6$ cycloalkyl, or $C_5$-$C_6$ cycloalkyl). In embodiments, $R^{28.7}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{28.7}$ is $R^{29.7}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{28.7}$ is $R^{29.7}$-substituted heterocycloalkyl (e.g., 3 to 8 membered heterocycloalkyl, 3 to 6 membered heterocycloalkyl, or 5 to 6 membered heterocycloalkyl). In embodiments, $R^{28.7}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{28.7}$ is $R^{29.7}$-substituted or unsubstituted aryl (e.g., $C_6$-$C_{10}$ aryl, $C_{10}$ aryl, or phenyl). In embodiments, $R^{28.7}$ is $R^{29.7}$-substituted aryl (e.g., $C_6$-$C_{10}$ aryl, $C_{10}$ aryl, or phenyl). In embodiments, $R^{28.7}$ is an unsubstituted aryl (e.g., $C_6$-$C_{10}$ aryl, $C_{10}$ aryl, or phenyl).

In embodiments, $R^{28.7}$ is $R^{29.7}$-substituted or unsubstituted heteroaryl (e.g., 5 to 10 membered heteroaryl, 5 to 9 membered heteroaryl, or 5 to 6 membered heteroaryl). In embodiments, $R^{28.7}$ is $R^{29.7}$-substituted heteroaryl (e.g., 5 to 10 membered heteroaryl, 5 to 9 membered heteroaryl, or 5 to 6 membered heteroaryl). In embodiments, $R^{28.7}$ is an unsubstituted heteroaryl (e.g., 5 to 10 membered heteroaryl, 5 to 9 membered heteroaryl, or 5 to 6 membered heteroaryl).

$R^{29.7}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{30.7}$-substituted or unsubstituted alkyl (e.g., $C_1$-$C_8$ alkyl, $C_1$-$C_6$ alkyl, or $C_1$-$C_4$ alkyl), $R^{30.7}$-substituted or unsubstituted heteroalkyl (e.g., 2 to 8 membered heteroalkyl, 2 to 6 membered heteroalkyl, or 2 to 4 membered heteroalkyl), $R^{30.7}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{30.7}$-substituted or unsubstituted heterocycloalkyl (e.g., 3 to 8 membered heterocycloalkyl, 3 to 6 membered heterocycloalkyl, or 5 to 6 membered heterocycloalkyl), $R^{30.7}$-substituted or unsubstituted aryl (e.g., $C_6$-$C_{10}$ aryl, $C_{10}$ aryl, or phenyl), or $R^{30.7}$-substituted or unsubstituted heteroaryl (e.g., 5 to 10 membered heteroaryl, 5 to 9 membered heteroaryl, or 5 to 6 membered heteroaryl).

In embodiments, $R^{29.7}$ is $R^{30.7}$-substituted or unsubstituted alkyl (e.g., $C_1$-$C_8$ alkyl, $C_1$-$C_6$ alkyl, or $C_1$-$C_4$ alkyl). In embodiments, $R^{29.7}$ is $R^{30.7}$-substituted alkyl (e.g., $C_1$-$C_8$ alkyl, $C_1$-$C_6$ alkyl, or $C_1$-$C_4$ alkyl). In embodiments, $R^{29.7}$ is an unsubstituted alkyl (e.g., $C_1$-$C_8$ alkyl, $C_1$-$C_6$ alkyl, or $C_1$-$C_4$ alkyl).

In embodiments, $R^{29.7}$ is $R^{30.7}$-substituted or unsubstituted heteroalkyl (e.g., 2 to 8 membered heteroalkyl, 2 to 6 membered heteroalkyl, or 2 to 4 membered heteroalkyl). In embodiments, $R^{29.7}$ is $R^{30.7}$-substituted heteroalkyl (e.g., 2 to 8 membered heteroalkyl, 2 to 6 membered heteroalkyl, or 2 to 4 membered heteroalkyl). In embodiments, $R^{29.7}$ is an unsubstituted heteroalkyl (e.g., 2 to 8 membered heteroalkyl, 2 to 6 membered heteroalkyl, or 2 to 4 membered heteroalkyl).

In embodiments, $R^{29.7}$ is $R^{30.7}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{29.7}$ is $R^{30.7}$-substituted cycloalkyl (e.g., $C_3$-$C_8$ cycloalkyl, $C_3$-$C_6$ cycloalkyl, or $C_5$-$C_6$ cycloalkyl). In embodiments, $R^{29.7}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{29.7}$ is $R^{30.7}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{29.7}$ is $R^{30.7}$-substituted heterocycloalkyl (e.g., 3 to 8 membered heterocycloalkyl, 3 to 6 membered heterocycloalkyl, or 5 to 6 membered heterocycloalkyl). In embodiments, $R^{29.7}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{29.7}$ is $R^{30.7}$-substituted or unsubstituted aryl (e.g., $C_6$-$C_{10}$ aryl, $C_{10}$ aryl, or phenyl). In embodiments, $R^{29.7}$ is $R^{30.7}$-substituted aryl (e.g., $C_6$-$C_{10}$ aryl, $C_{10}$ aryl, or phenyl). In embodiments, $R^{29.7}$ is an unsubstituted aryl (e.g., $C_6$-$C_{10}$ aryl, $C_{10}$ aryl, or phenyl).

In embodiments, $R^{29.7}$ is $R^{30.7}$-substituted or unsubstituted heteroaryl (e.g., 5 to 10 membered heteroaryl, 5 to 9 membered heteroaryl, or 5 to 6 membered heteroaryl). In embodiments, $R^{29.7}$ is $R^{30.7}$-substituted heteroaryl (e.g., 5 to 10 membered heteroaryl, 5 to 9 membered heteroaryl, or 5 to 6 membered heteroaryl). In embodiments, $R^{29.7}$ is an unsubstituted heteroaryl (e.g., 5 to 10 membered heteroaryl, 5 to 9 membered heteroaryl, or 5 to 6 membered heteroaryl).

$R^{28.8}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —OC $HCl_2$, —$OCHBr_2$, —$OCHI_2$, —$OCHF_2$, $R^{29.8}$-substituted or unsubstituted alkyl (e.g., $C_1$-$C_8$ alkyl, $C_1$-$C_6$ alkyl, or $C_1$-$C_4$ alkyl), $R^{29.8}$-substituted or unsubstituted heteroalkyl (e.g., 2 to 8 membered heteroalkyl, 2 to 6 membered heteroalkyl, or 2 to 4 membered heteroalkyl), $R^{29.8}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29.8}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29.8}$-substituted or unsubstituted aryl (e.g., $C_6$-$C_{10}$ aryl, $C_{10}$ aryl, or phenyl), or $R^{29.8}$-substituted or unsubstituted heteroaryl (e.g., 5 to 10 membered heteroaryl, 5 to 9 membered heteroaryl, or 5 to 6 membered heteroaryl).

In embodiments, $R^{28.8}$ is $R^{29.8}$-substituted or unsubstituted alkyl (e.g., $C_1$-$C_8$ alkyl, $C_1$-$C_6$ alkyl, or $C_1$-$C_4$ alkyl). In embodiments, $R^{28.8}$ is $R^{29.8}$-substituted alkyl (e.g., $C_1$-$C_8$ alkyl, $C_1$-$C_6$ alkyl, or $C_1$-$C_4$ alkyl). In embodiments, $R^{28.8}$ is an unsubstituted alkyl (e.g., $C_1$-$C_8$ alkyl, $C_1$-$C_6$ alkyl, or $C_1$-$C_4$ alkyl).

In embodiments, $R^{28.8}$ is $R^{29.8}$-substituted or unsubstituted heteroalkyl (e.g., 2 to 8 membered heteroalkyl, 2 to 6 membered heteroalkyl, or 2 to 4 membered heteroalkyl). In embodiments, $R^{28.8}$ is $R^{29.8}$-substituted heteroalkyl (e.g., 2 to 8 membered heteroalkyl, 2 to 6 membered heteroalkyl, or 2 to 4 membered heteroalkyl). In embodiments, $R^{28.8}$ is an unsubstituted heteroalkyl (e.g., 2 to 8 membered heteroalkyl, 2 to 6 membered heteroalkyl, or 2 to 4 membered heteroalkyl).

In embodiments, $R^{28.8}$ is $R^{29.8}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{28.8}$ is $R^{29.8}$-substituted cycloalkyl (e.g., $C_3$-$C_8$ cycloalkyl, $C_3$-$C_6$ cycloalkyl, or $C_5$-$C_6$ cycloalkyl). In embodiments, $R^{28.8}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{28.8}$ is $R^{29.8}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{28.8}$ is $R^{29.8}$-substituted heterocycloalkyl (e.g., 3 to 8 membered heterocycloalkyl, 3 to 6 membered heterocycloalkyl, or 5 to 6 membered heterocycloalkyl). In embodiments, $R^{28.8}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{28.8}$ is $R^{29.8}$-substituted or unsubstituted aryl (e.g., $C_6$-$C_{10}$ aryl, $C_{10}$ aryl, or phenyl). In embodiments, $R^{28.8}$ is $R^{29.8}$-substituted aryl (e.g., $C_6$-$C_{10}$ aryl, $C_{10}$ aryl, or phenyl). In embodiments, $R^{28.8}$ is an unsubstituted aryl (e.g., $C_6$-$C_{10}$ aryl, $C_{10}$ aryl, or phenyl).

In embodiments, $R^{28.8}$ is $R^{29.8}$-substituted or unsubstituted heteroaryl (e.g., 5 to 10 membered heteroaryl, 5 to 9 membered heteroaryl, or 5 to 6 membered heteroaryl). In embodiments, $R^{28.8}$ is $R^{29.8}$-substituted heteroaryl (e.g., 5 to 10 membered heteroaryl, 5 to 9 membered heteroaryl, or 5 to 6 membered heteroaryl). In embodiments, $R^{28.8}$ is an unsubstituted heteroaryl (e.g., 5 to 10 membered heteroaryl, 5 to 9 membered heteroaryl, or 5 to 6 membered heteroaryl).

$R^{29.8}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OC HCl$_2$, —OCHBr$_2$, —OCHI$_2$, —OCHF$_2$, $R^{30.8}$-substituted or unsubstituted alkyl (e.g., C$_1$-C$_8$ alkyl, C$_1$-C$_6$ alkyl, or C$_1$-C$_4$ alkyl), $R^{30.8}$-substituted or unsubstituted heteroalkyl (e.g., 2 to 8 membered heteroalkyl, 2 to 6 membered heteroalkyl, or 2 to 4 membered heteroalkyl), $R^{30.8}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{30.8}$-substituted or unsubstituted heterocycloalkyl (e.g., 3 to 8 membered heterocycloalkyl, 3 to 6 membered heterocycloalkyl, or 5 to 6 membered heterocycloalkyl), $R^{30.8}$-substituted or unsubstituted aryl (e.g., C$_6$-C$_{10}$ aryl, C$_{10}$ aryl, or phenyl), or $R^{30.8}$-substituted or unsubstituted heteroaryl (e.g., 5 to 10 membered heteroaryl, 5 to 9 membered heteroaryl, or 5 to 6 membered heteroaryl).

In embodiments, $R^{29.8}$ is $R^{30.8}$-substituted or unsubstituted alkyl (e.g., C$_1$-C$_8$ alkyl, C$_1$-C$_6$ alkyl, or C$_1$-C$_4$ alkyl). In embodiments, $R^{29.8}$ is $R^{30.8}$-substituted alkyl (e.g., C$_1$-C$_8$ alkyl, C$_1$-C$_6$ alkyl, or C$_1$-C$_4$ alkyl). In embodiments, $R^{29.8}$ is an unsubstituted alkyl (e.g., C$_1$-C$_8$ alkyl, C$_1$-C$_6$ alkyl, or C$_1$-C$_4$ alkyl).

In embodiments, $R^{29.8}$ is $R^{30.8}$-substituted or unsubstituted heteroalkyl (e.g., 2 to 8 membered heteroalkyl, 2 to 6 membered heteroalkyl, or 2 to 4 membered heteroalkyl). In embodiments, $R^{29.8}$ is $R^{30.8}$-substituted heteroalkyl (e.g., 2 to 8 membered heteroalkyl, 2 to 6 membered heteroalkyl, or 2 to 4 membered heteroalkyl). In embodiments, $R^{29.8}$ is an unsubstituted heteroalkyl (e.g., 2 to 8 membered heteroalkyl, 2 to 6 membered heteroalkyl, or 2 to 4 membered heteroalkyl).

In embodiments, $R^{29.8}$ is $R^{30.8}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{29.8}$ is $R^{30.8}$-substituted cycloalkyl (e.g., C$_3$-C$_8$ cycloalkyl, C$_3$-C$_6$ cycloalkyl, or C$_5$-C$_6$ cycloalkyl). In embodiments, $R^{29.8}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{29.8}$ is $R^{30.8}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{29.8}$ is $R^{30.8}$-substituted heterocycloalkyl (e.g., 3 to 8 membered heterocycloalkyl, 3 to 6 membered heterocycloalkyl, or 5 to 6 membered heterocycloalkyl). In embodiments, $R^{29.8}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{29.8}$ is $R^{30.8}$-substituted or unsubstituted aryl (e.g., C$_6$-C$_{10}$ aryl, C$_{10}$ aryl, or phenyl). In embodiments, $R^{29.8}$ is $R^{30.8}$-substituted aryl (e.g., C$_6$-C$_{10}$ aryl, C$_{10}$ aryl, or phenyl). In embodiments, $R^{29.8}$ is an unsubstituted aryl (e.g., C$_6$-C$_{10}$ aryl, C$_{10}$ aryl, or phenyl).

In embodiments, $R^{29.8}$ is $R^{30.8}$-substituted or unsubstituted heteroaryl (e.g., 5 to 10 membered heteroaryl, 5 to 9 membered heteroaryl, or 5 to 6 membered heteroaryl). In embodiments, $R^{29.8}$ is $R^{30.8}$-substituted heteroaryl (e.g., 5 to 10 membered heteroaryl, 5 to 9 membered heteroaryl, or 5 to 6 membered heteroaryl). In embodiments, $R^{29.8}$ is an unsubstituted heteroaryl (e.g., 5 to 10 membered heteroaryl, 5 to 9 membered heteroaryl, or 5 to 6 membered heteroaryl).

$R^{28.9}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OC HCl$_2$, —OCHBr$_2$, —OCHI$_2$, —OCHF$_2$, $R^{29.9}$-substituted or unsubstituted alkyl (e.g., C$_1$-C$_8$ alkyl, C$_1$-C$_6$ alkyl, or C$_1$-C$_4$ alkyl), $R^{29.9}$-substituted or unsubstituted heteroalkyl (e.g., 2 to 8 membered heteroalkyl, 2 to 6 membered heteroalkyl, or 2 to 4 membered heteroalkyl), $R^{29.9}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{29.9}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29.9}$-substituted or unsubstituted aryl (e.g., C$_6$-C$_{10}$ aryl, C$_{10}$ aryl, or phenyl), or $R^{29.9}$-substituted or unsubstituted heteroaryl (e.g., 5 to 10 membered heteroaryl, 5 to 9 membered heteroaryl, or 5 to 6 membered heteroaryl).

In embodiments, $R^{28.9}$ is $R^{29.9}$-substituted or unsubstituted alkyl (e.g., C$_1$-C$_8$ alkyl, C$_1$-C$_6$ alkyl, or C$_1$-C$_4$ alkyl). In embodiments, $R^{28.9}$ is $R^{29.9}$-substituted alkyl (e.g., C$_1$-C$_8$ alkyl, C$_1$-C$_6$ alkyl, or C$_1$-C$_4$ alkyl). In embodiments, $R^{28.9}$ is an unsubstituted alkyl (e.g., C$_1$-C$_8$ alkyl, C$_1$-C$_6$ alkyl, or C$_1$-C$_4$ alkyl).

In embodiments, $R^{28.9}$ is $R^{29.9}$-substituted or unsubstituted heteroalkyl (e.g., 2 to 8 membered heteroalkyl, 2 to 6 membered heteroalkyl, or 2 to 4 membered heteroalkyl). In embodiments, $R^{28.9}$ is $R^{29.9}$-substituted heteroalkyl (e.g., 2 to 8 membered heteroalkyl, 2 to 6 membered heteroalkyl, or 2 to 4 membered heteroalkyl). In embodiments, $R^{28.9}$ is an unsubstituted heteroalkyl (e.g., 2 to 8 membered heteroalkyl, 2 to 6 membered heteroalkyl, or 2 to 4 membered heteroalkyl).

In embodiments, $R^{28.9}$ is $R^{29.9}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{28.9}$ is $R^{29.9}$-substituted cycloalkyl (e.g., C$_3$-C$_8$ cycloalkyl, C$_3$-C$_6$ cycloalkyl, or C$_5$-C$_6$ cycloalkyl). In embodiments, $R^{28.9}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{28.9}$ is $R^{29.9}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{28.9}$ is $R^{29.9}$-substituted heterocycloalkyl (e.g., 3 to 8 membered heterocycloalkyl, 3 to 6 membered heterocycloalkyl, or 5 to 6 membered heterocycloalkyl). In embodiments, $R^{28.9}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{28.9}$ is $R^{29.9}$-substituted or unsubstituted aryl (e.g., C$_6$-C$_{10}$ aryl, C$_{10}$ aryl, or phenyl). In embodiments, $R^{28.9}$ is $R^{29.9}$-substituted aryl (e.g., C$_6$-C$_{10}$ aryl, C$_{10}$ aryl, or phenyl). In embodiments, $R^{28.9}$ is an unsubstituted aryl (e.g., C$_6$-C$_{10}$ aryl, C$_{10}$ aryl, or phenyl).

In embodiments, $R^{28.9}$ is $R^{29.9}$-substituted or unsubstituted heteroaryl (e.g., 5 to 10 membered heteroaryl, 5 to 9 membered heteroaryl, or 5 to 6 membered heteroaryl). In embodiments, $R^{28.9}$ is $R^{29.9}$-substituted heteroaryl (e.g., 5 to 10 membered heteroaryl, 5 to 9 membered heteroaryl, or 5 to 6 membered heteroaryl). In embodiments, $R^{28.9}$ is an unsubstituted heteroaryl (e.g., 5 to 10 membered heteroaryl, 5 to 9 membered heteroaryl, or 5 to 6 membered heteroaryl).

$R^{29.9}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OC HCl$_2$, —OCHBr$_2$, —OCHI$_2$, —OCHF$_2$, $R^{30.9}$-substituted or unsubstituted alkyl (e.g., C$_1$-C$_8$ alkyl, C$_1$-C$_6$ alkyl, or C$_1$-C$_4$ alkyl), $R^{30.9}$-substituted or unsubstituted heteroalkyl (e.g., 2 to 8 membered heteroalkyl, 2 to 6 membered heteroalkyl, or 2 to 4 membered heteroalkyl), $R^{30.9}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{30.9}$-substituted or unsubstituted heterocycloalkyl (e.g., 3 to 8 membered heterocycloalkyl, 3 to 6 membered heterocycloalkyl, or 5 to 6 membered heterocycloalkyl), $R^{30.9}$-substituted or unsubstituted aryl (e.g., C$_6$-C$_{10}$ aryl, C$_{10}$ aryl, or phenyl), or $R^{30.9}$-substituted or unsubstituted heteroaryl (e.g., 5 to 10 membered heteroaryl, 5 to 9 membered heteroaryl, or 5 to 6 membered heteroaryl).

In embodiments, $R^{29.9}$ is $R^{30.9}$-substituted or unsubstituted alkyl (e.g., C$_1$-C$_8$ alkyl, C$_1$-C$_6$ alkyl, or C$_1$-C$_4$ alkyl). In embodiments, $R^{29.9}$ is $R^{30.9}$-substituted alkyl (e.g., C$_1$-C$_8$ alkyl, C$_1$-C$_6$ alkyl, or C$_1$-C$_4$ alkyl). In embodiments, $R^{29.9}$ is an unsubstituted alkyl (e.g., C$_1$-C$_8$ alkyl, C$_1$-C$_6$ alkyl, or C$_1$-C$_4$ alkyl).

In embodiments, $R^{29.9}$ is $R^{30.9}$-substituted or unsubstituted heteroalkyl (e.g., 2 to 8 membered heteroalkyl, 2 to 6 membered heteroalkyl, or 2 to 4 membered heteroalkyl). In embodiments, $R^{29.9}$ is $R^{30.9}$-substituted heteroalkyl (e.g., 2 to 8 membered heteroalkyl, 2 to 6 membered heteroalkyl, or 2 to 4 membered heteroalkyl). In embodiments, $R^{29.9}$ is an unsubstituted heteroalkyl (e.g., 2 to 8 membered heteroalkyl, 2 to 6 membered heteroalkyl, or 2 to 4 membered heteroalkyl).

In embodiments, $R^{29.9}$ is $R^{30.9}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{29.9}$ is $R^{30.9}$-substituted cycloalkyl (e.g., C$_3$-C$_8$ cycloalkyl, C$_3$-C$_6$ cycloalkyl, or C$_5$-C$_6$ cycloalkyl). In embodiments, $R^{29.9}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{29.9}$ is $R^{30.9}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{29.9}$ is $R^{30.9}$-substituted heterocycloalkyl (e.g., 3 to 8 membered heterocycloalkyl, 3 to 6 membered heterocycloalkyl, or 5 to 6 membered heterocycloalkyl). In embodiments, $R^{29.9}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{29.9}$ is $R^{30.9}$-substituted or unsubstituted aryl (e.g., C$_6$-C$_{10}$ aryl, C$_{10}$ aryl, or phenyl). In embodiments, $R^{29.9}$ is $R^{30.9}$-substituted aryl (e.g., C$_6$-C$_{10}$ aryl, C$_{10}$ aryl, or phenyl). In embodiments, $R^{29.9}$ is an unsubstituted aryl (e.g., C$_6$-C$_{10}$ aryl, C$_{10}$ aryl, or phenyl).

In embodiments, $R^{29.9}$ is $R^{30.9}$-substituted or unsubstituted heteroaryl (e.g., 5 to 10 membered heteroaryl, 5 to 9 membered heteroaryl, or 5 to 6 membered heteroaryl). In embodiments, $R^{29.9}$ is $R^{30.9}$-substituted heteroaryl (e.g., 5 to 10 membered heteroaryl, 5 to 9 membered heteroaryl, or 5 to 6 membered heteroaryl). In embodiments, $R^{29.9}$ is an unsubstituted heteroaryl (e.g., 5 to 10 membered heteroaryl, 5 to 9 membered heteroaryl, or 5 to 6 membered heteroaryl).

$R^{28.6A}$, $R^{28.6B}$, $R^{28.6C}$, $R^{28.6D}$, $R^{28.7A}$, $R^{28.7B}$, $R^{28.7C}$, $R^{28.7D}$, $R^{28.8A}$, $R^{28.8B}$, $R^{28.8C}$, $R^{28.8D}$, $R^{28.9A}$, $R^{28.9B}$, $R^{28.9C}$, $R^{28.9D}$, $R^{3.6}$, $R^{3.7}$, $R^{3.8}$ and $R^{3.9}$ are independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{5.6A}$, $R^{5.6B}$, $R^{5.6C}$, $R^{5.6D}$, $R^{5.7A}$, $R^{5.7B}$, $R^{5.7C}$, $R^{5.7D}$, $R^{5.8A}$, $R^{5.8B}$, $R^{5.8C}$, $R^{5.8D}$, $R^{5.9A}$, $R^{5.9B}$, $R^{5.9C}$, and $R^{5.9D}$ are independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $X^{5.6}$, $X^{5.7}$, $X^{5.8}$ and $X^{5.9}$ are independently —Cl, —Br, —I or —F.

In embodiments, $X^{5.6}$ is —Cl. In embodiments, $X^{5.6}$ is —F. In embodiments, $X^{5.6}$ is —Br. In embodiments, $X^{5.6}$ is —I. In embodiments, $X^{5.7}$ is —Cl. In embodiments, $X^{5.7}$ is —F. In embodiments, $X^{5.7}$ is —Br. In embodiments, $X^{5.7}$ is —I. In embodiments, $X^{5.8}$ is —Cl. In embodiments, $X^{5.8}$ is —F. In embodiments, $X^{5.8}$ is —Br. In embodiments, $X^{5.8}$ is —I. In embodiments, $X^{5.9}$ is —Cl. In embodiments, $X^{5.9}$ is —F. In embodiments, $X^{5.9}$ is —Br. In embodiments, $X^{5.9}$ is —I.

In embodiments, $X^{5.6}$ is —Cl, and $X^1$ is N. In embodiments, $X^{5.6}$ is —F, and $X^1$ is N. In embodiments, $X^{5.6}$ is —Br, and $X^1$ is N. In embodiments, $X^{5.6}$ is —I, and $X^1$ is N. In embodiments, $X^{5.7}$ is —Cl, and $X^1$ is N. In embodiments, $X^{5.7}$ is —F, and $X^1$ is N. In embodiments, $X^{5.7}$ is —Br, and $X^1$ is N. In embodiments, $X^{5.7}$ is —I, and $X^1$ is N. In embodiments, $X^{5.8}$ is —Cl, and $X^1$ is N. In embodiments, $X^{5.8}$ is —F, and $X^1$ is N. In embodiments, $X^{5.8}$ is —Br, and $X^1$ is N. In embodiments, $X^{5.8}$ is —I, and $X^1$ is N. In embodiments, $X^{5.9}$ is —Cl, and $X^1$ is N. In embodiments, $X^{5.9}$ is —F, and $X^1$ is N. In embodiments, $X^{5.9}$ is —Br, and $X^1$ is N. In embodiments, $X^{5.9}$ is —I, and $X^1$ is N.

In embodiments, $X^{5.6}$ is —Cl, and $X^2$ is N. In embodiments, $X^{5.6}$ is —F, and $X^2$ is N. In embodiments, $X^{5.6}$ is —Br, and $X^2$ is N. In embodiments, $X^{5.6}$ is —I, and $X^2$ is N. In embodiments, $X^{5.7}$ is —Cl, and $X^2$ is N. In embodiments, $X^{5.7}$ is —F, and $X^2$ is N. In embodiments, $X^{5.7}$ is —Br, and $X^2$ is N. In embodiments, $X^{5.7}$ is —I, and $X^2$ is N. In embodiments, $X^{5.8}$ is —Cl, and $X^2$ is N. In embodiments, $X^{5.8}$ is —F, and $X^2$ is N. In embodiments, $X^{5.8}$ is —Br, and $X^2$ is N. In embodiments, $X^{5.8}$ is —I, and $X^2$ is N. In embodiments, $X^{5.9}$ is —Cl, and $X^2$ is N. In embodiments, $X^{5.9}$ is —F, and $X^2$ is N. In embodiments, $X^{5.9}$ is —Br, and $X^2$ is N. In embodiments, $X^{5.9}$ is —I, and $X^2$ is N.

In embodiments, $X^{5.6}$ is —Cl, and $X^3$ is N. In embodiments, $X^{5.6}$ is —F, and $X^3$ is N. In embodiments, $X^{5.6}$ is —Br, and $X^3$ is N. In embodiments, $X^{5.6}$ is —I, and $X^3$ is N. In embodiments, $X^{5.7}$ is —Cl, and $X^3$ is N. In embodiments, $X^{5.7}$ is —F, and $X^3$ is N. In embodiments, $X^{5.7}$ is —Br, and $X^3$ is N. In embodiments, $X^{5.7}$ is —I, and $X^3$ is N. In embodiments, $X^{5.8}$ is —Cl, and $X^3$ is N. In embodiments, $X^{5.8}$ is —F, and $X^3$ is N. In embodiments, $X^{5.8}$ is —Br, and $X^3$ is N. In embodiments, $X^{5.8}$ is —I, and $X^3$ is N. In embodiments, $X^{5.9}$ is —Cl, and $X^3$ is N. In embodiments, $X^{5.9}$ is —F, and $X^3$ is N. In embodiments, $X^{5.9}$ is —Br, and $X^3$ is N. In embodiments, $X^{5.9}$ is —I, and $X^3$ is N.

In embodiments, the compounds provided herein have structural Formula (VII):

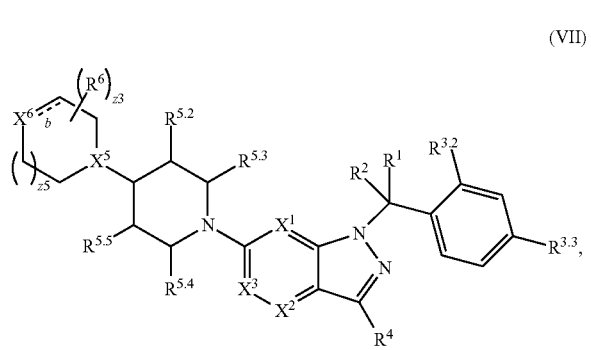

(VII)

or a pharmaceutically acceptable salt thereof.

z3, z5, ⁓, $X^1$, $X^2$, $X^3$, $X^5$, $X^6$, $R^1$, $R^2$, $R^{3.2}$, $R^{3.3}$, $R^4$, $R^{5.2}$, $R^{5.3}$, $R^{5.4}$, $R^{5.5}$ and $R^6$ are as described herein, including embodiments.

In embodiments, the compounds provided herein have structural Formula (VIIa):

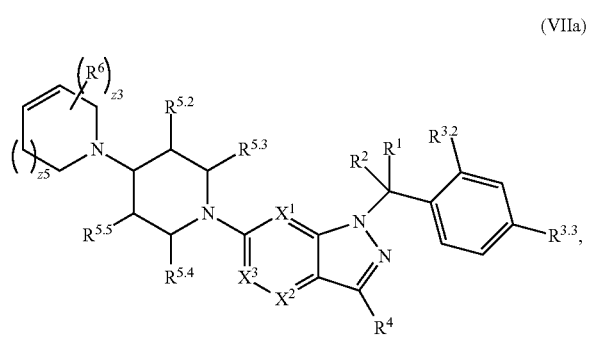

(VIIa)

or a pharmaceutically acceptable salt thereof.

z3, z5, $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$ and $R^6$ are as described herein, including embodiments.

In embodiments, the compounds provided herein have structural Formula (VIIb):

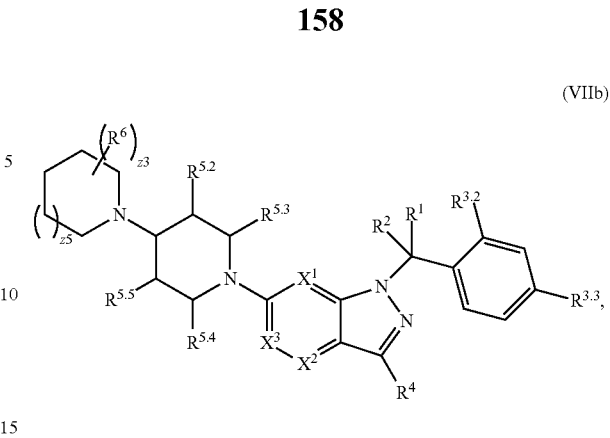

(VIIb)

or a pharmaceutically acceptable salt thereof.

z3, z5, $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$ and $R^6$ are as described herein, including embodiments.

In embodiments, the compounds provided herein have structural Formula (VIII):

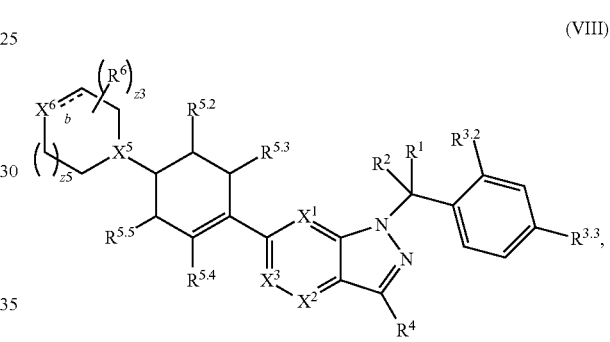

(VIII)

or a pharmaceutically acceptable salt thereof.

z3, z5, ⁓, $X^1$, $X^2$, $X^3$, $X^5$, $X^6$, $R^1$, $R^2$, $R^{3.2}$, $R^{3.3}$, $R^4$, $R^{5.2}$, $R^{5.3}$, $R^{5.4}$, $R^{5.5}$ and $R^6$ are as described herein, including embodiments.

In embodiments, the compounds provided herein have structural Formula (VIIIa):

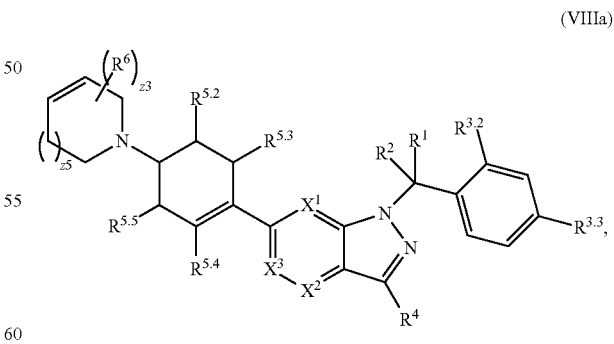

(VIIIa)

or a pharmaceutically acceptable salt thereof.

z3, z5, $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$ and $R^6$ are as described herein, including embodiments.

In embodiments, the compounds provided herein have structural Formula (VIIIb):

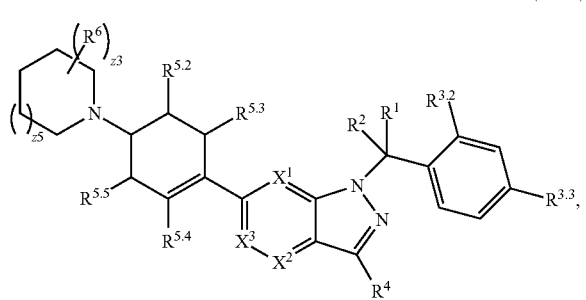

(VIIIb)

or a pharmaceutically acceptable salt thereof.

z3, z5, $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$ and $R^6$ are as described herein, including embodiments.

In embodiments, the compounds provided herein have structural Formula (IX):

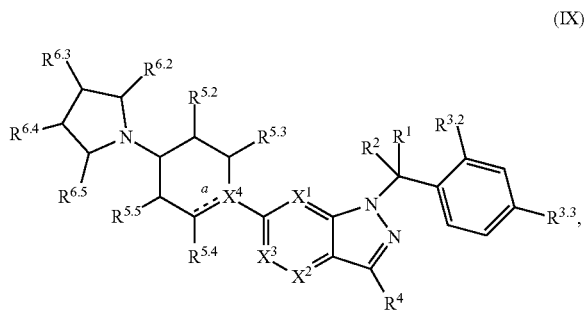

(IX)

or a pharmaceutically acceptable salt thereof. $R^{6.2}$ is hydrogen, halogen, $-CX^{6.6}_3$, $-CHX^{6.6}_2$, $-CH_2X^{6.6}$, $-CN$, $-SO_{n6.2}R^{6.6A}$, $-SO_{v6.2}NR^{6.6B}R^{6.6C}$, $-NHNR^{6.6B}R^{6.6C}$, $-ONR^{6.6B}R^{6.6C}$, $-NHC(O)NHNR^{6.6B}R^{6.6C}$, $-NHC(O)NR^{6.6B}R^{6.6C}$, $-N(O)_{m6.2}$, $-NR^{6.6B}R^{6.6C}$, $-C(O)R^{6.6D}$, $-C(O)OR^{6.6D}$, $-C(O)NR^{6.6B}R^{6.6C}$, $-OR^{6.6A}$, $-NR^{6.6B}SO_2R^{6.6A}$, $-NR^{6.6B}C(O)R^{6.6D}$, $-NR^{6.6B}C(O)OR^{6.6D}$, $-NR^{6.6B}OR^{6.6D}$, $-OCX^{6.6}_3$, $-OCHX^{6.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{6.3}$ is hydrogen, halogen, $-CX^{6.7}_3$, $-CHX^{6.7}_2$, $-CH_2X^{6.7}$, $-CN$, $-SO_{n6.3}R^{6.7A}$, $-SO_{v6.3}NR^{6.7B}R^{6.7C}$, $-NHNR^{6.7B}R^{6.7C}$, $-ONR^{6.7B}R^{6.7C}$, $-NHC(O)NHNR^{6.7B}R^{6.7C}$, $-NHC(O)NR^{6.7B}R^{6.7C}$, $-N(O)_{m6.3}$, $-NR^{6.7B}R^{6.7C}$, $-C(O)R^{6.7D}$, $-C(O)OR^{6.7D}$, $-C(O)NR^{6.7B}R^{6.7C}$, $-OR^{6.7A}$, $-NR^{6.7B}SO_2R^{6.7A}$, $-NR^{6.7B}C(O)R^{6.7D}$, $-NR^{6.7B}C(O)OR^{6.7D}$, $-NR^{6.7B}OR^{6.7D}$, $-OCX^{6.7}_3$, $-OCHX^{6.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{6.4}$ is hydrogen, halogen, $-CX^{6.8}_3$, $-CHX^{6.8}_2$, $-CH_2X^{6.8}$, $-CN$, $-SO_{n6.4}R^{6.8A}$, $-SO_{v6.4}NR^{6.8B}R^{6.8C}$, $-NHNR^{6.8B}R^{6.8C}$, $-ONR^{6.8B}R^{6.8C}$, $-NHC(O)NHNR^{6.8B}R^{6.8C}$, $-NHC(O)NR^{6.8B}R^{6.8C}$, $-N(O)_{m6.4}$, $-NR^{6.8B}R^{6.8C}$, $-C(O)R^{6.8D}$, $-C(O)OR^{6.8D}$, $-C(O)NR^{6.8B}R^{6.8C}$, $-OR^{6.8A}$, $-NR^{6.8B}SO_2R^{6.8A}$, $-NR^{6.8B}C(O)R^{6.8D}$, $-NR^{6.8B}C(O)OR^{6.8D}$, $-NR^{6.8B}OR^{6.8D}$, $-OCX^{6.8}_3$, $-OCHX^{6.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{6.5}$ is hydrogen, halogen, $-CX^{6.9}_3$, $-CHX^{6.9}_2$, $-CH_2X^{6.9}$, $-CN$, $-SO_{n6.5}R^{6.9A}$, $-SO_{v6.5}NR^{6.9B}R^{6.9C}$, $-NHNR^{6.9B}R^{6.9C}$, $-ONR^{6.9B}R^{6.9C}$, $-NHC(O)NHNR^{6.9B}R^{6.9C}$, $-NHC(O)NR^{6.9B}R^{6.9C}$, $-N(O)_{m6.5}$, $-NR^{6.9B}R^{6.9C}$, $-C(O)R^{6.9D}$, $-C(O)OR^{6.9D}$, $-C(O)NR^{6.9B}R^{6.9C}$, $-OR^{6.9A}$, $-NR^{6.9B}SO_2R^{6.9A}$, $-NR^{6.9B}C(O)R^{6.9D}$, $-NR^{6.9B}C(O)OR^{6.9D}$, $-NR^{6.9B}OR^{6.9D}$, $-OCX^{6.9}_3$, $-OCHX^{6.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{6.6A}$, $R^{6.6B}$, $R^{6.6C}$, $R^{6.6D}$, $R^{6.7A}$, $R^{6.7B}$, $R^{6.7C}$, $R^{6.7D}$, $R^{6.8A}$, $R^{6.8B}$, $R^{6.8C}$, $R^{6.8D}$, $R^{6.9A}$, $R^{6.9B}$, $R^{6.9C}$ and $R^{6.9D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6.6B}$ and $R^{6.6C}$, $R^{6.7B}$ and $R^{6.7C}$, $R^{6.8B}$ and $R^{6.8C}$, $R^{6.9B}$ and $R^{6.9C}$ substituents bonded to the same nitrogen atom may optionally be joined to form a substituted or unsubstituted heterocycloalkyl or substituted or unsubstituted heteroaryl. $X^{6.6}$, $X^{6.7}$, $X^{6.8}$ and $X^{6.9}$ are independently $-Cl$, $-Br$, $-I$ or $-F$.

The symbols n6.2, n6.3, n6.4, and n6.5 are independently an integer from 0 to 4. The symbols m6.2, m6.3, m6.4, m6.5, v6.2, v6.3, v6.4, and v6.5 are independently 1 or 2.

In embodiments, the symbol n6.2 is an integer from 0 to 4. In embodiments, n6.2 is 0. In embodiments, n6.2 is 1. In embodiments, n6.2 is 2. In embodiments, n6.2 is 3. In embodiments, n6.2 is 4.

In embodiments, the symbol n6.3 is an integer from 0 to 4. In embodiments, n6.3 is 0. In embodiments, n6.3 is 1. In embodiments, n6.3 is 2. In embodiments, n6.3 is 3. In embodiments, n6.3 is 4.

In embodiments, the symbol n6.4 is an integer from 0 to 4. In embodiments, n6.4 is 0. In embodiments, n6.4 is 1. In embodiments, n6.4 is 2. In embodiments, n6.4 is 3. In embodiments, n6.4 is 4.

In embodiments, the symbol n6.5 is an integer from 0 to 4. In embodiments, n6.5 is 0. In embodiments, n6.5 is 1. In embodiments, n6.5 is 2. In embodiments, n6.5 is 3. In embodiments, n6.5 is 4.

In embodiments, the symbols m6.2 and v6.2 are independently 1 or 2. In embodiments, m6.2 is 1. In embodiments, m6.2 is 2. In embodiments, v6.2 is 1. In embodiments, v6.2 is 2.

In embodiments, the symbols m6.3 and v6.3 are independently 1 or 2. In embodiments, m6.3 is 1. In embodiments, m6.3 is 2. In embodiments, v6.3 is 1. In embodiments, v6.3 is 2.

In embodiments, the symbols m6.4 and v6.4 are independently 1 or 2. In embodiments, m6.4 is 1. In embodiments, m6.4 is 2. In embodiments, v6.4 is 1. In embodiments, v6.4 is 2.

In embodiments, the symbols m6.5 and v6.5 are independently 1 or 2. In embodiments, m6.5 is 1. In embodiments, m6.5 is 2. In embodiments, v6.5 is 1. In embodiments, v6.5 is 2.

$X^1$, $X^2$, $X^3$, $X^4$, $R^1$, $R^2$, $R^{3.2}$, $R^{3.3}$, $R^4$, $R^{5.2}$, $R^{5.3}$, $R^{5.4}$, and $R^{5.5}$ are as described herein, including embodiments.

In embodiments, $R^{6.2}$ is hydrogen, halogen, $-CX^{6.6}_3$, $-CHX^{6.6}_2$, $-CH_2X^{6.6}$, $-CN$, $-SO_{n6.2}R^{6.6A}$, $-SO_{v6.2}NR^{6.6B}R^{6.6C}$, $-NHNR^{6.6B}R^{6.6C}$, $-ONR^{6.6B}R^{6.6C}$, —NHC(O)NHNR$^{6.6B}$R$^{6.6C}$, —NHC(O)NR$^{6.6B}$R$^{6.6C}$, —N(O)$_{m6.2}$, —NR$^{6.6B}$R$^{6.6C}$, —C(O)R$^{6.6D}$, —C(O)OR$^{6.6D}$, —C(O)NR$^{6.6B}$R$^{6.6C}$, —OR$^{6.6A}$, —NR$^{6.6B}$SO$_2$R$^{6.6A}$, —NR$^{6.6B}$C(O)R$^{6.6D}$, —NR$^{6.6B}$C(O)OR$^{6.6D}$, —NR$^{6.6B}$OR$^{6.6D}$, —OCX$^{6.6}_3$, —OCHX$^{6.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^{6.2}$ is hydrogen, F, —OH, —CH$_3$, —CH$_2$OH, C(CH$_3$)$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H, (CH$_2$)$_2$SO$_2$NH$_2$, C(O)OH substituted cyclopropyl, CH$_2$CH(OCH$_3$)CO$_2$H, CH$_2$CH(OH)CO$_2$H, CH(CH$_3$)CH$_2$CO$_2$H, CH$_2$OCH$_3$, C(O)NHCH$_3$, CH(OH)CH$_2$S(O$_2$)CH$_3$,

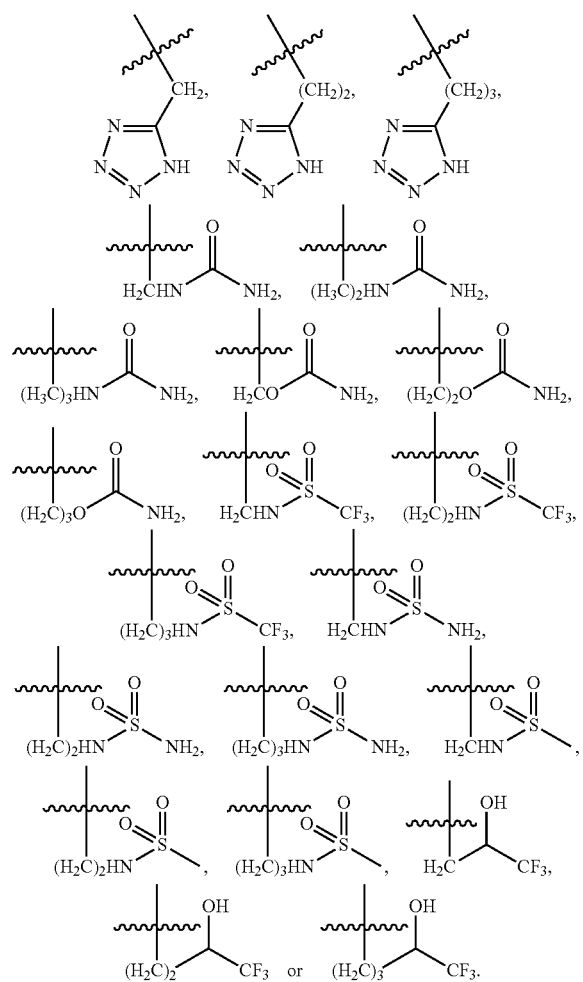

In embodiments, R$^{6.2}$ is F. In embodiments, R$^{6.2}$ is —OH. In embodiments, R$^{6.2}$ is —CH$_3$. In embodiments, R$^{6.2}$ is —CH$_2$OH. In embodiments, R$^{6.2}$ is C(CH$_3$)$_2$OH. In embodiments, R$^{6.2}$ is —(CH$_2$)$_2$OH. In embodiments, R$^{6.2}$ is —(CH$_2$)$_3$OH. In embodiments, R$^{6.2}$ is C(O)OH. In embodiments, R$^{6.2}$ is —CH$_2$NH$_2$. In embodiments, R$^{6.2}$ is —(CH$_2$)$_2$NH$_2$. In embodiments, R$^{6.2}$ is —(CH$_2$)$_3$NH$_2$. In embodiments, R$^{6.2}$ is —CH$_2$CO$_2$CH$_2$CH$_3$. In embodiments, R$^{6.2}$ is —(CH$_2$)$_2$CO$_2$CH$_2$CH$_3$. In embodiments, R$^{6.2}$ is —(CH$_2$)$_3$CO$_2$CH$_2$CH$_3$. In embodiments, R$^{6.2}$ is —CH$_2$CO$_2$H. In embodiments, R$^{6.2}$ is —(CH$_2$)$_2$CO$_2$H. In embodiments, R$^{6.2}$ is —(CH$_2$)$_3$CO$_2$H. In embodiments, R$^{6.2}$ is —CH$_2$CO$_2$NH$_2$. In embodiments, R$^{6.2}$ is —(CH$_2$)$_2$CONH$_2$. In embodiments, R$^{6.2}$ is —(CH$_2$)$_3$CO$_2$NH$_2$. In embodiments, R$^{6.2}$ is —CH$_2$CHFCO$_2$H. In embodiments, R$^{6.2}$ is —(CH$_2$)$_2$CHFCO$_2$H. In embodiments, R$^{6.2}$ is —CH$_2$CF$_2$CO$_2$H. In embodiments, R$^{6.2}$ is —(CH$_2$)$_2$CF$_2$CO$_2$H. In embodiments, R$^{6.2}$ is (CH$_2$)$_2$SO$_2$NH$_2$. In embodiments, R$^{6.2}$ is C(O)OH substituted cyclopropyl. In embodiments, R$^{6.2}$ is CH$_2$CH(OCH$_3$)CO$_2$H. In embodiments, R$^{6.2}$ is CH$_2$CH(OH)CO$_2$H. In embodiments, R$^{6.2}$ is CH(CH$_3$)CH$_2$CO$_2$H. In embodiments, R$^{6.2}$ is —CH$_2$OCH$_3$. In embodiments, R$^{6.2}$ is C(O)NHCH$_3$. In embodiments, R$^{6.2}$ is CH(OH)CH$_2$S(O$_2$)CH$_3$. In embodiments, R$^{6.2}$ is

In embodiments, R$^{6.2}$ is F, —OH, —CH$_3$, —CH$_2$OH, —C(CH$_3$)$_2$OH, —(CH$_2$)$_2$OH, —(CH$_2$)$_3$OH, C(O)OH, —CH$_2$NH$_2$, —C(O)NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —CH$_2$CO$_2$NH$_2$, —(CH$_2$)$_2$CONH$_2$, —(CH$_2$)$_3$CO$_2$NH$_2$, —CH$_2$CHFCO$_2$H, —(CH$_2$)$_2$CHFCO$_2$H, —CH$_2$CF$_2$CO$_2$H, —(CH$_2$)$_2$CF$_2$CO$_2$H, —(CH$_2$)$_2$SO$_2$NH$_2$, C(O)OH-substituted cyclopropyl, —CH$_2$CH(OCH$_3$)CO$_2$H, —CH$_2$CH(OH)CO$_2$H, CH$_2$NHS(O$_2$)CH$_3$, CH(CH$_3$)CH$_2$CO$_2$H, CH$_2$OCH$_3$, —C(O)NHCH$_3$, CH(OH)CH$_2$S(O$_2$)CH$_3$, —(CH$_2$)$_2$CH(OH)(CF$_3$),

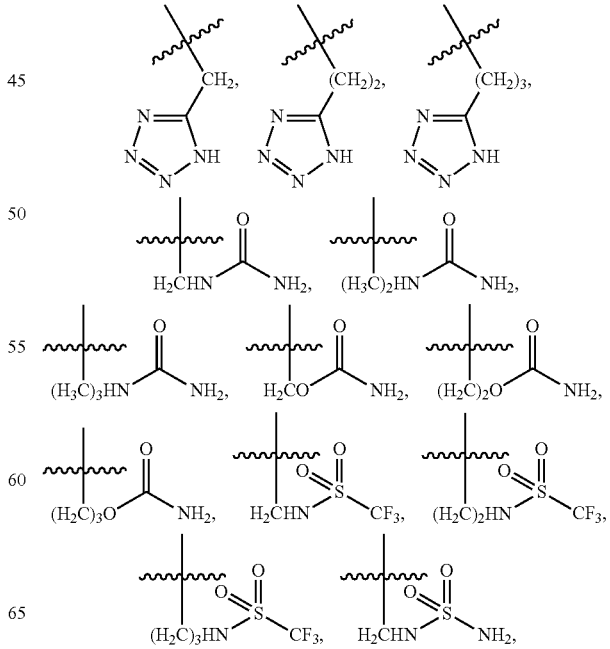

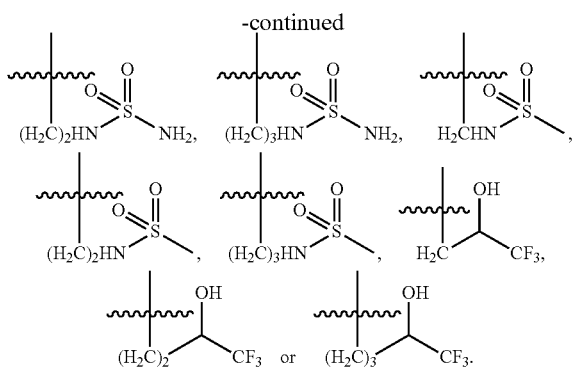

In embodiments, $R^{6.2}$ is F. In embodiments, $R^{6.2}$ is —OH. In embodiments, $R^{6.2}$ is —CH$_3$. In embodiments, $R^{6.2}$ is —CH$_2$OH. In embodiments, $R^{6.2}$ is C(CH$_3$)$_2$OH. In embodiments, $R^{6.2}$ is —(CH$_2$)$_2$OH. In embodiments, $R^{6.2}$ is —(CH$_2$)$_3$OH. In embodiments, $R^{6.2}$ is C(O)OH. In embodiments, $R^{6.2}$ is —CH$_2$NH$_2$. In embodiments, $R^{6.2}$ is —(CH$_2$)$_2$NH$_2$. In embodiments, $R^{6.2}$ is —(CH$_2$)$_3$NH$_2$. In embodiments, $R^{6.2}$ is —CH$_2$CO$_2$CH$_2$CH$_3$. In embodiments, $R^{6.2}$ is —(CH$_2$)$_2$CO$_2$CH$_2$CH$_3$. In embodiments, $R^{6.2}$ is —(CH$_2$)$_3$CO$_2$CH$_2$CH$_3$. In embodiments, $R^{6.2}$ is —CH$_2$CO$_2$H. In embodiments, $R^{6.2}$ is —(CH$_2$)$_2$CO$_2$H. In embodiments, $R^{6.2}$ is —(CH$_2$)$_3$CO$_2$H. In embodiments, $R^{6.2}$ is —CH$_2$CO$_2$NH$_2$. In embodiments, $R^{6.2}$ is —CH$_2$CONH$_2$. In embodiments, $R^{6.2}$ is —(CH$_2$)$_2$CONH$_2$. In embodiments, $R^{6.2}$ is —(CH$_2$)$_3$CO$_2$NH$_2$. In embodiments, $R^{6.2}$ is —(CH$_2$)$_3$CONH$_2$. In embodiments, $R^{6.2}$ is —CH$_2$CHFCO$_2$H. In embodiments, $R^{6.2}$ is —(CH$_2$)$_2$CHFCO$_2$H. In embodiments, $R^{6.2}$ is —CH$_2$CF$_2$CO$_2$H. In embodiments, $R^{6.2}$ is —(CH$_2$)$_2$CF$_2$CO$_2$H. In embodiments, $R^{6.2}$ is (CH$_2$)$_2$SO$_2$NH$_2$. In embodiments, $R^{6.2}$ is C(O)OH substituted cyclopropyl. In embodiments, $R^{6.2}$ is CH$_2$CH(OCH$_3$)CO$_2$H. In embodiments, $R^{6.2}$ is CH$_2$CH(OH)CO$_2$H. In embodiments, $R^{6.2}$ is CH(CH$_3$)CH$_2$CO$_2$H. In embodiments, $R^{6.2}$ is CH$_2$OCH$_3$. In embodiments, $R^{6.2}$ is C(O)NHCH$_3$. In embodiments, $R^{6.2}$ is CH(OH)CH$_2$S(O$_2$)CH$_3$. In embodiments, $R^{6.2}$ is

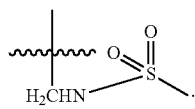

In embodiments, $R^{6.2}$ is —C(O)NH$_2$. In embodiments, $R^{6.2}$ is —(CH$_2$)$_2$SO$_2$NH$_2$. In embodiments, $R^{6.2}$ is C(O)OH-substituted cyclopropyl. In embodiments, $R^{6.2}$ is CH$_2$CH(OCH$_3$)CO$_2$H. In embodiments, $R^{6.2}$ is —CH$_2$CH(OH)CO$_2$H. In embodiments, $R^{6.2}$ is CH$_2$NHS(O$_2$)CH$_3$. In embodiments, $R^{6.2}$ is CH(CH$_3$)CH$_2$CO$_2$H. In embodiments, $R^{6.2}$ is CH$_2$OCH$_3$. In embodiments, $R^{6.2}$ is C(O)NHCH$_3$. In embodiments, $R^{6.2}$ is CH(OH)CH$_2$S(O$_2$)CH$_3$. In embodiments, $R^{6.2}$ is —(CH$_2$)$_2$CH(OH)(CF$_3$). In embodiments, $R^{6.2}$ is hydrogen.

In embodiments, $R^{6.2}$ is halogen. In embodiments, $R^{6.2}$ is —OR$^{6.6A}$. In embodiments, $R^{6.2}$ is —C(O)OR$^{6.6D}$. In embodiments, $R^{6.2}$ is —CH$_2$NR$^{6.6B}$R$^{6.6C}$. In embodiments, $R^{6.2}$ is —(CH$_2$)$_2$NR$^{6.6B}$R$^{6.6C}$. In embodiments, $R^{6.2}$ is —(CH$_2$)$_3$NR$^{6.6B}$R$^{6.6C}$. In embodiments, $R^{6.2}$ is —CH$_2$C(O)OR$^{6.6D}$. In embodiments, $R^{6.2}$ is —(CH$_2$)$_2$C(O)OR$^{6.6D}$. In embodiments, $R^{6.2}$ is —(CH$_2$)$_3$C(O)OR$^{6.6D}$. In embodiments, $R^{6.2}$ is —CH$_2$C(O)OR$^{6.6D}$. In embodiments, $R^{6.2}$ is —CH$_2$CONR$^{6.6B}$R$^{6.6C}$. In embodiments, $R^{6.2}$ is —(CH$_2$)$_2$CONR$^{6.6B}$R$^{6.6C}$. In embodiments, $R^{6.2}$ is —(CH$_2$)$_3$CONR$^{6.6B}$R$^{6.6C}$. In embodiments, $R^{6.2}$ is (CH$_2$)$_2$SO$_2$NR$^{6.6B}$R$^{6.6C}$. In embodiments, $R^{6.2}$ is —C(O)NR$^{6.6B}$R$^{6.6C}$. In embodiments, $R^{6.2}$ is CH$_2$NHSO$_2$R$^{6.6A}$. In embodiments, $R^{6.6A}$ is CH$_3$. In embodiments, $R^{6.6A}$ is CF$_3$. In embodiments, $R^{6.6A}$ is CHF$_2$. In embodiments, $R^{6.6A}$ is CH$_2$F. In embodiments, $R^{6.6A}$ is CH$_2$Cl. In embodiments, $R^{6.6A}$ is CHCl$_2$. In embodiments, $R^{6.6A}$ is CCl$_3$. In embodiments, $R^{6.6A}$ is CH$_2$CH$_3$. In embodiments, $R^{6.6A}$ is unsubstituted propyl. In embodiments, $R^{6.6A}$ is hydrogen. In embodiments, $R^{6.6B}$ is CH$_3$. In embodiments, $R^{6.6B}$ is CF$_3$. In embodiments, $R^{6.6B}$ is CHF$_2$. In embodiments, $R^{6.6B}$ is CH$_2$F. In embodiments, $R^{6.6B}$ is CH$_2$Cl. In embodiments, $R^{6.6B}$ is CHCl$_2$. In embodiments, $R^{6.6B}$ is CCl$_3$. In embodiments, $R^{6.6B}$ is CH$_2$CH$_3$. In embodiments, $R^{6.6B}$ is unsubstituted propyl. In embodiments, $R^{6.6B}$ is hydrogen. In embodiments, $R^{6.6C}$ is CH$_3$. In embodiments, $R^{6.6C}$ is CF$_3$. In embodiments, $R^{6.6C}$ is CHF$_2$. In embodiments, $R^{6.6C}$ is CH$_2$F. In embodiments, $R^{6.6C}$ is CH$_2$Cl. In embodiments, $R^{6.6C}$ is CHCl$_2$. In embodiments, $R^{6.6C}$ is CCl$_3$. In embodiments, $R^{6.6C}$ is CH$_2$CH$_3$. In embodiments, $R^{6.6C}$ is unsubstituted propyl. In embodiments, $R^{6.6C}$ is hydrogen. In embodiments, $R^{6.6D}$ is CH$_3$. In embodiments, $R^{6.6D}$ is CF$_3$. In embodiments, $R^{6.6D}$ is CHF$_2$. In embodiments, $R^{6.6D}$ is CH$_2$F. In embodiments, $R^{6.6D}$ is CH$_2$Cl. In embodiments, $R^{6.6D}$ is CHCl$_2$. In embodiments, $R^{6.6D}$ is CCl$_3$. In embodiments, $R^{6.6D}$ is CH$_2$CH$_3$. In embodiments, $R^{6.6D}$ is unsubstituted propyl. In embodiments, $R^{6.6D}$ is hydrogen.

In embodiments, $R^{6.2}$ is hydrogen, halogen, —CX$^{6.6}_3$, —CHX$^{6.6}_2$, —CH$_2$X$^{6.6}$, —CN, —SO$_{n6.2}$R$^{6.6A}$, —SO$_{v6.2}$NR$^{6.6B}$R$^{6.6C}$, —NHNR$^{6.6B}$R$^{6.6C}$, —ONR$^{6.6B}$R$^{6.6C}$, —NHC(O)NHNR$^{6.6B}$R$^{6.6C}$, —NHC(O)NR$^{6.6B}$R$^{6.6C}$, —N(O)$_{m6.2}$, —NR$^{6.6B}$R$^{6.6C}$, —C(O)R$^{6.6D}$, —C(O)OR$^{6.6D}$, —C(O)NR$^{6.6B}$R$^{6.6C}$, —OR$^{6.6A}$, —NR$^{6.6B}$SO$_2$R$^{6.6A}$, —NR$^{6.6B}$C(O)R$^{6.6D}$, —NR$^{6.6B}$C(O)OR$^{6.6D}$, —NR$^{6.6B}$OR$^{6.6D}$, —OCX$^{6.6}_3$, —OCHX$^{6.6}_2$, R$^{31.6}$-substituted or unsubstituted alkyl (e.g., $C_1$-$C_8$ alkyl, $C_1$-$C_6$ alkyl, or $C_1$-$C_4$ alkyl), R$^{31.6}$-substituted or unsubstituted heteroalkyl (e.g., 2 to 8 membered heteroalkyl, 2 to 6 membered heteroalkyl, or 2 to 4 membered heteroalkyl), R$^{31.6}$-substituted or unsubstituted cycloalkyl (e.g., $C_3$-$C_8$ cycloalkyl, $C_3$-$C_6$ cycloalkyl, or $C_5$-$C_6$ cycloalkyl), R$^{31.6}$-substituted or unsubstituted heterocycloalkyl (e.g., 3 to 8 membered heterocycloalkyl, 3 to 6 membered heterocycloalkyl, or 5 to 6 membered heterocycloalkyl), R$^{31.6}$-substituted or unsubstituted aryl (e.g., $C_6$-$C_{10}$ aryl, $C_{10}$ aryl, or phenyl), or R$^{31.6}$-substituted or unsubstituted heteroaryl (e.g., 5 to 10 membered heteroaryl, 5 to 9 membered heteroaryl, or 5 to 6 membered heteroaryl).

In embodiments, $R^{6.2}$ is R$^{31.6}$-substituted or unsubstituted alkyl (e.g., $C_1$-$C_8$ alkyl, $C_1$-$C_6$ alkyl, or $C_1$-$C_4$ alkyl). In embodiments, $R^{6.2}$ is R$^{31.6}$-substituted alkyl (e.g., $C_1$-$C_8$ alkyl, $C_1$-$C_6$ alkyl, or $C_1$-$C_4$ alkyl). In embodiments, $R^{6.2}$ is an unsubstituted alkyl (e.g., $C_1$-$C_8$ alkyl, $C_1$-$C_6$ alkyl, or $C_1$-$C_4$ alkyl).

In embodiments, $R^{6.2}$ is R$^{31.6}$-substituted or unsubstituted heteroalkyl (e.g., 2 to 8 membered heteroalkyl, 2 to 6 membered heteroalkyl, or 2 to 4 membered heteroalkyl). In embodiments, $R^{6.2}$ is R$^{31.6}$-substituted heteroalkyl (e.g., 2 to 8 membered heteroalkyl, 2 to 6 membered heteroalkyl, or 2 to 4 membered heteroalkyl). In embodiments, $R^{6.2}$ is an unsubstituted heteroalkyl (e.g., 2 to 8 membered heteroalkyl, 2 to 6 membered heteroalkyl, or 2 to 4 membered heteroalkyl).

In embodiments, $R^{6.2}$ is R$^{31.6}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{6.2}$ is R$^{31.6}$-substituted In embodiments, $R^{6.2}$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{6.2}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{6.2}$ is $R^{31.6}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6.2}$ is $R^{31.6}$-substituted heterocycloalkyl (e.g., 3 to 8 membered heterocycloalkyl, 3 to 6 membered heterocycloalkyl, or 5 to 6 membered heterocycloalkyl). In embodiments, $R^{6.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{6.2}$ is $R^{31.6}$-substituted or unsubstituted aryl (e.g., $C_6$-$C_{10}$ aryl, $C_{10}$ aryl, or phenyl). In embodiments, $R^{6.2}$ is $R^{31.6}$-substituted aryl (e.g., $C_6$-$C_{10}$ aryl, $C_{10}$ aryl, or phenyl). In embodiments, $R^{6.2}$ is an unsubstituted aryl (e.g., $C_6$-$C_{10}$ aryl, $C_{10}$ aryl, or phenyl).

In embodiments, $R^{6.2}$ is $R^{31.6}$-substituted or unsubstituted heteroaryl (e.g., 5 to 10 membered heteroaryl, 5 to 9 membered heteroaryl, or 5 to 6 membered heteroaryl). In embodiments, $R^{6.2}$ is $R^{31.6}$-substituted heteroaryl (e.g., 5 to 10 membered heteroaryl, 5 to 9 membered heteroaryl, or 5 to 6 membered heteroaryl). In embodiments, $R^{6.2}$ is an unsubstituted heteroaryl (e.g., 5 to 10 membered heteroaryl, 5 to 9 membered heteroaryl, or 5 to 6 membered heteroaryl).

In embodiments, $R^{6.3}$ is hydrogen, halogen, $-CX^{6.7}_3$, $-CHX^{6.7}_2$, $-CH_2X^{6.7}$, $-CN$, $-SO_{n6.3}R^{6.7A}$, $-SO_{v6.3}NR^{6.7B}R^{6.7C}$, $-NHNR^{6.7B}R^{6.7C}$, $-ONR^{6.7B}R^{6.7C}$, $-NHC(O)NHNR^{6.7B}R^{6.7C}$, $-NHC(O)NR^{6.7B}R^{6.7C}$, $-N(O)_{m6.3}$, $-NR^{6.7B}R^{6.7C}$, $-C(O)R^{6.7D}$, $-C(O)OR^{6.7D}$, $-C(O)NR^{6.7B}R^{6.7C}$, $-OR^{6.7A}$, $-NR^{6.7B}SO_2R^{6.7A}$, $-NR^{6.7B}C(O)R^{6.7D}$, $-NR^{6.7B}C(O)OR^{6.7D}$, $-NR^{6.7B}OR^{6.7D}$, $-OCX^{6.7}_3$, $-OCHX^{6.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{6.3}$ is hydrogen, halogen, $-CX^{6.7}_3$, $-CHX^{6.7}_2$, $-CH_2X^{6.7}$, $-CN$, $-SO_{n6.3}R^{6.7A}$, $-SO_{v6.3}NR^{6.7B}R^{6.7C}$, $-NHNR^{6.7B}R^{6.7C}$, $-ONR^{6.7B}R^{6.7C}$, $-NHC(O)NHNR^{6.7B}R^{6.7C}$, $-NHC(O)NR^{6.7B}R^{6.7C}$, $-N(O)_{m6.3}$, $-NR^{6.7B}R^{6.7C}$, $-C(O)R^{6.7D}$, $-C(O)OR^{6.7D}$, $-C(O)NR^{6.7B}R^{6.7C}$, $-OR^{6.7A}$, $-NR^{6.7B}SO_2R^{6.7A}$, $-NR^{6.7B}C(O)R^{6.7D}$, $-NR^{6.7B}C(O)OR^{6.7D}$, $-NR^{6.7B}OR^{6.7D}$, $-OCX^{6.7}_3$, $-OCHX^{6.7}_2$, $R^{31.7}$-substituted or unsubstituted alkyl (e.g., $C_1$-$C_8$ alkyl, $C_1$-$C_6$ alkyl, or $C_1$-$C_4$ alkyl), $R^{31.7}$-substituted or unsubstituted heteroalkyl (e.g., 2 to 8 membered heteroalkyl, 2 to 6 membered heteroalkyl, or 2 to 4 membered heteroalkyl), $R^{31.7}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.7}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.7}$-substituted or unsubstituted aryl (e.g., $C_6$-$C_{10}$ aryl, $C_{10}$ aryl, or phenyl), or $R^{31.7}$-substituted or unsubstituted heteroaryl (e.g., 5 to 10 membered heteroaryl, 5 to 9 membered heteroaryl, or 5 to 6 membered heteroaryl).

In embodiments, $R^{6.3}$ is $R^{31.7}$-substituted or unsubstituted alkyl (e.g., $C_1$-$C_8$ alkyl, $C_1$-$C_6$ alkyl, or $C_1$-$C_4$ alkyl). In embodiments, $R^{6.3}$ is $R^{31.7}$-substituted alkyl (e.g., $C_1$-$C_8$ alkyl, $C_1$-$C_6$ alkyl, or $C_1$-$C_4$ alkyl). In embodiments, $R^{6.3}$ is an unsubstituted alkyl (e.g., $C_1$-$C_8$ alkyl, $C_1$-$C_6$ alkyl, or $C_1$-$C_4$ alkyl).

In embodiments, $R^{6.3}$ is $R^{31.7}$-substituted or unsubstituted heteroalkyl (e.g., 2 to 8 membered heteroalkyl, 2 to 6 membered heteroalkyl, or 2 to 4 membered heteroalkyl). In embodiments, $R^{6.3}$ is $R^{31.7}$-substituted heteroalkyl (e.g., 2 to 8 membered heteroalkyl, 2 to 6 membered heteroalkyl, or 2 to 4 membered heteroalkyl). In embodiments, $R^{6.3}$ is an unsubstituted heteroalkyl (e.g., 2 to 8 membered heteroalkyl, 2 to 6 membered heteroalkyl, or 2 to 4 membered heteroalkyl).

In embodiments, $R^{6.3}$ is $R^{31.7}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{6.3}$ is $R^{31.7}$-substituted cycloalkyl (e.g., $C_3$-$C_8$ cycloalkyl, $C_3$-$C_6$ cycloalkyl, or $C_5$-$C_6$ cycloalkyl). In embodiments, $R^{6.3}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{6.3}$ is $R^{31.7}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6.3}$ is $R^{31.7}$-substituted heterocycloalkyl (e.g., 3 to 8 membered heterocycloalkyl, 3 to 6 membered heterocycloalkyl, or 5 to 6 membered heterocycloalkyl). In embodiments, $R^{6.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{6.3}$ is $R^{31.7}$-substituted or unsubstituted aryl (e.g., $C_6$-$C_{10}$ aryl, $C_{10}$ aryl, or phenyl). In embodiments, $R^{6.3}$ is $R^{31.7}$-substituted aryl (e.g., $C_6$-$C_{10}$ aryl, $C_{10}$ aryl, or phenyl). In embodiments, $R^{6.3}$ is an unsubstituted aryl (e.g., $C_6$-$C_{10}$ aryl, $C_{10}$ aryl, or phenyl).

In embodiments, $R^{6.3}$ is $R^{31.7}$-substituted or unsubstituted heteroaryl (e.g., 5 to 10 membered heteroaryl, 5 to 9 membered heteroaryl, or 5 to 6 membered heteroaryl). In embodiments, $R^{6.3}$ is $R^{31.7}$-substituted heteroaryl (e.g., 5 to 10 membered heteroaryl, 5 to 9 membered heteroaryl, or 5 to 6 membered heteroaryl). In embodiments, $R^{6.3}$ is an unsubstituted heteroaryl (e.g., 5 to 10 membered heteroaryl, 5 to 9 membered heteroaryl, or 5 to 6 membered heteroaryl).

In embodiments, $R^{6.3}$ is hydrogen or $CH_3$. In embodiments, $R^{6.3}$ is hydrogen. In embodiments, $R^{6.3}$ is $CH_3$.

In embodiments, $R^{6.3}$ is $CH_2CH_3$, OH, $-CH_2OH$, $C(CH_3)_2OH$, $-(CH_2)_2OH$, $-(CH_2)_3OH$, $CO_2H$, $CH_2CH(OCH_3)CO_2H$, $CH_2CH(OH)CO_2H$, $CH(CH_3)CH_2CO_2H$, $CH_2OCH_3$. In embodiments, $R^{6.3}$ is $CH_2CH_3$. In embodiments, $R^{6.3}$ is OH. In embodiments, $R^{6.3}$ is $-CH_2OH$. In embodiments, $R^{6.3}$ is $C(CH_3)_2OH$. In embodiments, $R^{6.3}$ is $-(CH_2)_2OH$. In embodiments, $R^{6.3}$ is $-(CH_2)_3OH$. In embodiments, $R^{6.3}$ is $CO_2H$. In embodiments, $R^{6.3}$ is $CH_2CH(OCH_3)CO_2H$. In embodiments, $R^{6.3}$ is $CH_2CH(OH)CO_2H$. In embodiments, $R^{6.3}$ is $CH(CH_3)CH_2CO_2H$. In embodiments, $R^{6.3}$ is $-CH_2OCH_3$.

In embodiments, $R^{6.3}$ is F, $-OH$, $-CH_3$, $-CH_2OH$, $-C(CH_3)_2OH$, $-(CH_2)_2OH$, $-(CH_2)_3OH$, $C(O)OH$, $-CH_2NH_2$, $-C(O)NH_2$, $-(CH_2)_2NH_2$, $-(CH_2)_3NH_2$, $-CH_2CO_2CH_2CH_3$, $-(CH_2)_2CO_2CH_2CH_3$, $-(CH_2)_3CO_2CH_2CH_3$, $-CH_2CO_2H$, $-(CH_2)_2CO_2H$, $-(CH_2)_3CO_2H$, $-CH_2CO_2NH_2$, $-(CH_2)_2CONH_2$, $-(CH_2)_3CO_2NH_2$, $-CH_2CHFCO_2H$, $-(CH_2)_2CHFCO_2H$, $-CH_2CF_2CO_2H$, $-(CH_2)_2CF_2CO_2H$, $-(CH_2)_2SO_2NH_2$, $C(O)OH$-substituted cyclopropyl, $CH_2CH(OCH_3)CO_2H$, $-CH_2CH(OH)CO_2H$, $CH_2NHS(O_2)CH_3$, $CH(CH_3)CH_2CO_2H$, $CH_2OCH_3$, $C(O)NHCH_3$, $CH(OH)CH_2S(O_2)CH_3$, $-(CH_2)_2CH(OH)(CF_3)$,

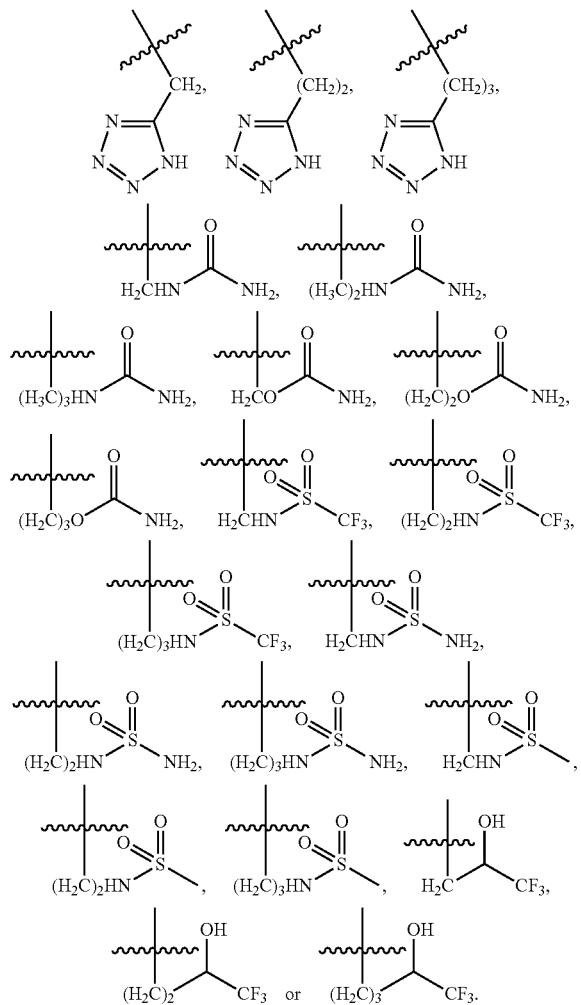

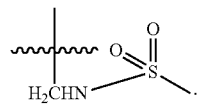

In embodiments, $R^{6.3}$ is —C(O)NH$_2$. In embodiments, $R^{6.3}$ is —(CH$_2$)$_2$SO$_2$NH$_2$. In embodiments, $R^{6.3}$ is C(O)OH-substituted cyclopropyl. In embodiments, $R^{6.3}$ is CH$_2$CH(OCH$_3$)CO$_2$H. In embodiments, $R^{6.3}$ is —CH$_2$CH(OH)CO$_2$H. In embodiments, $R^{6.3}$ is CH$_2$NHS(O$_2$)CH$_3$. In embodiments, $R^{6.3}$ is CH(CH$_3$)CH$_2$CO$_2$H. In embodiments, $R^{6.3}$ is CH$_2$OCH$_3$. In embodiments, $R^{6.3}$ is C(O)NHCH$_3$. In embodiments, $R^{6.3}$ is CH(OH)CH$_2$S(O$_2$)CH$_3$. In embodiments, $R^{6.3}$ is —(CH$_2$)$_2$CH(OH)(CF$_3$). In embodiments, $R^{6.3}$ is hydrogen.

In embodiments, $R^{6.3}$ is halogen. In embodiments, $R^{6.3}$ is —OR$^{6.7A}$. In embodiments, $R^{6.3}$ is —C(O)OR$^{6.7D}$. In embodiments, $R^{6.3}$ is —CH$_2$NR$^{6.7B}$R$^{6.7C}$. In embodiments, $R^{6.3}$ is —(CH$_2$)$_2$NR$^{6.7B}$R$^{6.7C}$. In embodiments, $R^{6.3}$ is —(CH$_2$)$_3$NR$^{6.7B}$R$^{6.7C}$. In embodiments, $R^{6.3}$ is —CH$_2$C(O)OR$^{6.7D}$. In embodiments, $R^{6.3}$ is —(CH$_2$)$_2$C(O)OR$^{6.7D}$. In embodiments, $R^{6.3}$ is —(CH$_2$)$_3$C(O)OR$^{6.7D}$. In embodiments, $R^{6.3}$ is —CH$_2$C(O)OR$^{6.7D}$. In embodiments, $R^{6.3}$ is —CH$_2$CONR$^{6.7B}$R$^{6.7C}$. In embodiments, $R^{6.3}$ is —(CH$_2$)$_2$CONR$^{6.7B}$R$^{6.7C}$. In embodiments, $R^{6.3}$ is —(CH$_2$)$_3$CONR$^{6.7B}$R$^{6.7C}$. In embodiments, $R^{6.3}$ is (CH$_2$)$_2$SO$_2$NR$^{6.7B}$R$^{6.7C}$. In embodiments, $R^{6.3}$ is —C(O)NR$^{6.7B}$R$^{6.7C}$. In embodiments, $R^{6.3}$ is CH$_2$NHSO$_2$R$^{6.7A}$. In embodiments, $R^{6.7A}$ is CH$_3$. In embodiments, $R^{6.7A}$ is CF$_3$. In embodiments, $R^{6.7A}$ is CHF$_2$. In embodiments, $R^{6.7A}$ is CH$_2$F. In embodiments, $R^{6.7A}$ is CH$_2$Cl. In embodiments, $R^{6.7A}$ is CHCl$_2$. In embodiments, $R^{6.7A}$ is CCl$_3$. In embodiments, $R^{6.7A}$ is CH$_2$CH$_3$. In embodiments, $R^{6.7A}$ is unsubstituted propyl. In embodiments, $R^{6.7A}$ is hydrogen. In embodiments, $R^{6.7B}$ is CH$_3$. In embodiments, $R^{6.7B}$ is CF$_3$. In embodiments, $R^{6.7B}$ is CHF$_2$. In embodiments, $R^{6.7B}$ is CH$_2$F. In embodiments, $R^{6.7B}$ is CH$_2$Cl. In embodiments, $R^{6.7B}$ is CHCl$_2$. In embodiments, $R^{6.7B}$ is CCl$_3$. In embodiments, $R^{6.7B}$ is CH$_2$CH$_3$. In embodiments, $R^{6.7B}$ is unsubstituted propyl. In embodiments, $R^{6.7B}$ is hydrogen. In embodiments, $R^{6.7C}$ is CH$_3$. In embodiments, $R^{6.7C}$ is CF$_3$. In embodiments, $R^{6.7C}$ is CHF$_2$. In embodiments, $R^{6.7C}$ is CH$_2$F. In embodiments, $R^{6.7C}$ is CH$_2$Cl. In embodiments, $R^{6.7C}$ is CHCl$_2$. In embodiments, $R^{6.7C}$ is CCl$_3$. In embodiments, $R^{6.7C}$ is CH$_2$CH$_3$. In embodiments, $R^{6.7C}$ is unsubstituted propyl. In embodiments, $R^{6.7C}$ is hydrogen. In embodiments, $R^{6.7D}$ is CH$_3$. In embodiments, $R^{6.7D}$ is CF$_3$. In embodiments, $R^{6.7D}$ is CHF$_2$. In embodiments, $R^{6.7D}$ is CH$_2$F. In embodiments, $R^{6.7D}$ is CH$_2$Cl. In embodiments, $R^{6.7D}$ is CHCl$_2$. In embodiments, $R^{6.7D}$ is CCl$_3$. In embodiments, $R^{6.7D}$ is CH$_2$CH$_3$. In embodiments, $R^{6.7D}$ is unsubstituted propyl. In embodiments, $R^{6.7D}$ is hydrogen.

In embodiments, $R^{6.4}$ is hydrogen, halogen, —CX$^{6.8}_3$, —CHX$^{6.8}_2$, —CH$_2$X$^{6.8}$, —CN, —SO$_{n6.4}$R$^{6.8A}$, —SO$_{v6.4}$NR$^{6.8B}$R$^{6.8C}$, —NHNR$^{6.8B}$R$^{6.8C}$, —ONR$^{6.8B}$R$^{6.8C}$, —NHC(O)NHNR$^{6.8B}$R$^{6.8C}$, —NHC(O)NR$^{6.8B}$R$^{6.8C}$, —N(O)$_{m6.4}$, —NR$^{6.8B}$R$^{6.8C}$, —C(O)R$^{6.8D}$, —C(O)OR$^{6.8D}$, —C(O)NR$^{6.8B}$R$^{6.8C}$, —OR$^{6.8A}$, —NR$^{6.8B}$SO$_2$R$^{6.8A}$, —NR$^{6.8B}$C(O)R$^{6.8D}$, —NR$^{6.8B}$C(O)OR$^{6.8D}$, —NR$^{6.8B}$OR$^{6.8D}$, —OCX$^{6.8}_3$, —OCHX$^{6.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{6.4}$ is hydrogen, halogen, $-CX^{6.8}_3$, $-CHX^{6.8}_2$, $-CH_2X^{6.8}$, $-CN$, $-SO_{n6.4}R^{6.8A}$, $-SO_{v6.4}NR^{6.8B}R^{6.8C}$, $-NHNR^{6.8B}R^{6.8C}$, $-ONR^{6.8B}R^{6.8C}$, $-NHC(O)NHNR^{6.8B}R^{6.8C}$, $-NHC(O)NR^{6.8B}R^{6.8C}$, $-N(O)_{m6.4}$, $-NR^{6.8B}R^{6.8C}$, $-C(O)R^{6.8D}$, $-C(O)OR^{6.8D}$, $-C(O)NR^{6.8B}R^{6.8C}$, $-OR^{6.8A}$, $-NR^{6.8B}SO_2R^{6.8A}$, $-NR^{6.8B}C(O)R^{6.8D}$, $-NR^{6.8B}C(O)OR^{6.8D}$, $-NR^{6.8B}OR^{6.8D}$, $-OCX^{6.8}_3$, $-OCHX^{6.8}_2$, $R^{31.8}$-substituted or unsubstituted alkyl (e.g., $C_1$-$C_8$ alkyl, $C_1$-$C_6$ alkyl, or $C_1$-$C_4$ alkyl), $R^{31.8}$-substituted or unsubstituted heteroalkyl (e.g., 2 to 8 membered heteroalkyl, 2 to 6 membered heteroalkyl, or 2 to 4 membered heteroalkyl), $R^{31.8}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.8}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.8}$-substituted or unsubstituted aryl (e.g., $C_6$-$C_{10}$ aryl, $C_{10}$ aryl, or phenyl), or $R^{31.8}$-substituted or unsubstituted heteroaryl (e.g., 5 to 10 membered heteroaryl, 5 to 9 membered heteroaryl, or 5 to 6 membered heteroaryl).

In embodiments, $R^{64}$ is $R^{31.8}$-substituted or unsubstituted alkyl (e.g., $C_1$-$C_8$ alkyl, $C_1$-$C_6$ alkyl, or $C_1$-$C_4$ alkyl). In embodiments, $R^{6.4}$ is $R^{31.8}$-substituted alkyl (e.g., $C_1$-$C_8$ alkyl, $C_1$-$C_6$ alkyl, or $C_1$-$C_4$ alkyl). In embodiments, $R^{6.4}$ is an unsubstituted alkyl (e.g., $C_1$-$C_8$ alkyl, $C_1$-$C_6$ alkyl, or $C_1$-$C_4$ alkyl).

In embodiments, $R^{6.4}$ is $R^{31.8}$-substituted or unsubstituted heteroalkyl (e.g., 2 to 8 membered heteroalkyl, 2 to 6 membered heteroalkyl, or 2 to 4 membered heteroalkyl). In embodiments, $R^{6.4}$ is $R^{31.8}$-substituted heteroalkyl (e.g., 2 to 8 membered heteroalkyl, 2 to 6 membered heteroalkyl, or 2 to 4 membered heteroalkyl). In embodiments, $R^{6.4}$ is an unsubstituted heteroalkyl (e.g., 2 to 8 membered heteroalkyl, 2 to 6 membered heteroalkyl, or 2 to 4 membered heteroalkyl).

In embodiments, $R^{6.4}$ is $R^{31.8}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{6.4}$ is $R^{31.8}$-substituted cycloalkyl (e.g., $C_3$-$C_8$ cycloalkyl, $C_3$-$C_6$ cycloalkyl, or $C_5$-$C_6$ cycloalkyl). In embodiments, $R^{6.4}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{6.4}$ is $R^{31.8}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6.4}$ is $R^{31.8}$-substituted heterocycloalkyl (e.g., 3 to 8 membered heterocycloalkyl, 3 to 6 membered heterocycloalkyl, or 5 to 6 membered heterocycloalkyl). In embodiments, $R^{6.4}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{6.4}$ is $R^{31.8}$-substituted or unsubstituted aryl (e.g., $C_6$-$C_{10}$ aryl, $C_{10}$ aryl, or phenyl). In embodiments, $R^{6.4}$ is $R^{31.8}$-substituted aryl (e.g., $C_6$-$C_{10}$ aryl, $C_{10}$ aryl, or phenyl). In embodiments, $R^{6.4}$ is an unsubstituted aryl (e.g., $C_6$-$C_{10}$ aryl, $C_{10}$ aryl, or phenyl).

In embodiments, $R^{6.4}$ is $R^{31.8}$-substituted or unsubstituted heteroaryl (e.g., 5 to 10 membered heteroaryl, 5 to 9 membered heteroaryl, or 5 to 6 membered heteroaryl). In embodiments, $R^{6.4}$ is $R^{31.8}$-substituted heteroaryl (e.g., 5 to 10 membered heteroaryl, 5 to 9 membered heteroaryl, or 5 to 6 membered heteroaryl). In embodiments, $R^{6.4}$ is an unsubstituted heteroaryl (e.g., 5 to 10 membered heteroaryl, 5 to 9 membered heteroaryl, or 5 to 6 membered heteroaryl).

In embodiments, $R^{64}$ is hydrogen, OH, or $CH_3$. In embodiments, $R^{64}$ is hydrogen. In embodiments, $R^{6.4}$ is $CH_3$. In embodiments, $R^{6.4}$ is OH.

In embodiments, $R^{6.4}$ is $CH_2CH_3$, $-CH_2OH$, $C(CH_3)_2OH$, $-(CH_2)_2OH$, $-(CH_2)_3OH$, $CO_2H$, $CH_2CH(OCH_3)CO_2H$, $CH_2CH(OH)CO_2H$, $CH(CH_3)CH_2CO_2H$, $CH_2OCH_3$. In embodiments, $R^{6.4}$ is $CH_2CH_3$. In embodiments, $R^{6.4}$ is $-CH_2OH$. In embodiments, $R^{6.4}$ is $C(CH_3)_2OH$. In embodiments, $R^{6.4}$ is $-(CH_2)_2OH$. In embodiments, $R^{6.4}$ is $-(CH_2)_3OH$. In embodiments, $R^{6.4}$ is $CO_2H$. In embodiments, $R^{6.4}$ is $CH_2CH(OCH_3)CO_2H$. In embodiments, $R^{6.4}$ is $CH_2CH(OH)CO_2H$. In embodiments, $R^{6.4}$ is $CH(CH_3)CH_2CO_2H$. In embodiments, $R^{6.4}$ is $CH_2OCH_3$.

In embodiments, $R^{6.4}$ is F, $-OH$, $-CH_3$, $-CH_2OH$, $-C(CH_3)_2OH$, $-(CH_2)_2OH$, $-(CH_2)_3OH$, $C(O)OH$, $-CH_2NH_2$, $-C(O)NH_2$, $-(CH_2)_2NH_2$, $-(CH_2)_3NH_2$, $-CH_2CO_2CH_2CH_3$, $-(CH_2)_2CO_2CH_2CH_3$, $-(CH_2)_3CO_2CH_2CH_3$, $-CH_2CO_2H$, $-(CH_2)_2CO_2H$, $-(CH_2)_3CO_2H$, $-CH_2CO_2NH_2$, $-(CH_2)_2CONH_2$, $-(CH_2)_3CO_2NH_2$, $-CH_2CHFCO_2H$, $-(CH_2)_2CHFCO_2H$, $-CH_2CF_2CO_2H$, $-(CH_2)_2CF_2CO_2H$, $-(CH_2)_2SO_2NH_2$, $C(O)OH$-substituted cyclopropyl, $CH_2CH(OCH_3)CO_2H$, $-CH_2CH(OH)CO_2H$, $CH_2NHS(O_2)CH_3$, $CH(CH_3)CH_2CO_2H$, $CH_2OCH_3$, $C(O)NHCH_3$, $CH(OH)CH_2S(O_2)CH_3$, $-(CH_2)_2CH(OH)(CF_3)$,

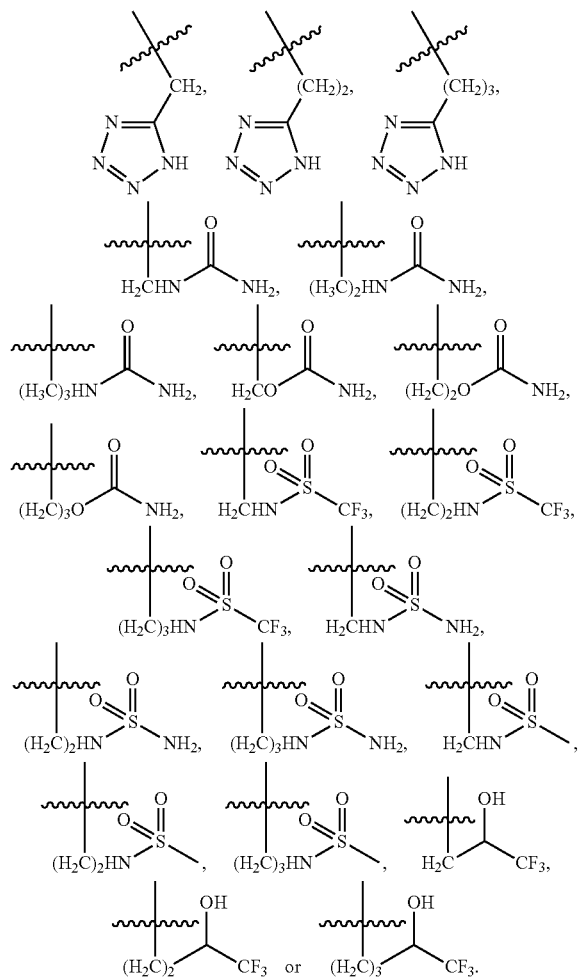

In embodiments, $R^{6.4}$ is F. In embodiments, $R^{6.4}$ is $-OH$. In embodiments, $R^{6.4}$ is $-CH_3$. In embodiments, $R^{6.4}$ is —CH$_2$OH. In embodiments, R$^{6.4}$ is C(CH$_3$)$_2$OH. In embodiments, R$^{6.4}$ is —(CH$_2$)$_2$OH. In embodiments, R$^{6.4}$ is —(CH$_2$)$_3$OH. In embodiments, R$^{6.4}$ is C(O)OH. In embodiments, R$^{6.4}$ is —CH$_2$NH$_2$. In embodiments, R$^{6.4}$ is —(CH$_2$)$_2$NH$_2$. In embodiments, R$^{6.4}$ is —(CH$_2$)$_3$NH$_2$. In embodiments, R$^{6.4}$ is —CH$_2$CO$_2$CH$_2$CH$_3$. In embodiments, R$^{6.4}$ is —(CH$_2$)$_2$CO$_2$CH$_2$CH$_3$. In embodiments, R$^{64}$ is —(CH$_2$)$_3$CO$_2$CH$_2$CH$_3$. In embodiments, R$^{6.4}$ is —CH$_2$CO$_2$H. In embodiments, R$^{6.4}$ is —(CH$_2$)$_2$CO$_2$H. In embodiments, R$^{6.4}$ is —(CH$_2$)$_3$CO$_2$H. In embodiments, R$^{6.4}$ is —CH$_2$CO$_2$NH$_2$. In embodiments, R$^{6.4}$ is —CH$_2$CONH$_2$. In embodiments, R$^{6.4}$ is —(CH$_2$)$_2$CONH$_2$. In embodiments, R$^{6.4}$ is —(CH$_2$)$_3$CO$_2$NH$_2$. In embodiments, R$^{6.4}$ is —(CH$_2$)$_3$CONH$_2$. In embodiments, R$^{6.4}$ is —CH$_2$CHFCO$_2$H. In embodiments, R$^{6.4}$ is —(CH$_2$)$_2$CHFCO$_2$H. In embodiments, R$^{6.4}$ is —CH$_2$CF$_2$CO$_2$H. In embodiments, R$^{6.4}$ is —(CH$_2$)$_2$CF$_2$CO$_2$H. In embodiments, R$^{6.4}$ is (CH$_2$)$_2$SO$_2$NH$_2$. In embodiments, R$^{6.4}$ is C(O)OH substituted cyclopropyl. In embodiments, R$^{6.4}$ is CH$_2$CH(OCH$_3$)CO$_2$H. In embodiments, R$^{6.4}$ is CH$_2$CH(OH)CO$_2$H. In embodiments, R$^{6.4}$ is CH(CH$_3$)CH$_2$CO$_2$H. In embodiments, R$^{6.4}$ is CH$_2$OCH$_3$. In embodiments, R$^{6.4}$ is C(O)NHCH$_3$. In embodiments, R$^{6.4}$ is CH(OH)CH$_2$S(O$_2$)CH$_3$. In embodiments, R$^{6.4}$ is

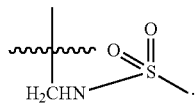

In embodiments, R$^{6.4}$ is —C(O)NH$_2$. In embodiments, R$^{6.4}$ is —(CH$_2$)$_2$SO$_2$NH$_2$. In embodiments, R$^{6.4}$ is C(O)OH-substituted cyclopropyl. In embodiments, R$^{6.4}$ is CH$_2$CH(OCH$_3$)CO$_2$H. In embodiments, R$^{6.4}$ is —CH$_2$CH(OH)CO$_2$H. In embodiments, R$^{6.4}$ is CH$_2$NHS(O$_2$)CH$_3$. In embodiments, R$^{6.4}$ is CH(CH$_3$)CH$_2$CO$_2$H. In embodiments, R$^{6.4}$ is CH$_2$OCH$_3$. In embodiments, R$^{6.4}$ is C(O)NHCH$_3$. In embodiments, R$^{6.4}$ is CH(OH)CH$_2$S(O$_2$)CH$_3$. In embodiments, R$^{6.4}$ is —(CH$_2$)$_2$CH(OH)(CF$_3$). In embodiments, R$^{6.4}$ is hydrogen.

In embodiments, R$^{6.4}$ is halogen. In embodiments, R$^{6.4}$ is —OR$^{6.8A}$. In embodiments, R$^{6.4}$ is —C(O)OR$^{68D}$. In embodiments, R$^{6.4}$ is —CH$_2$NR$^{6.8B}$R$^{6.8C}$. In embodiments, R$^{6.4}$ is —(CH$_2$)$_2$NR$^{6.8B}$R$^{6.8C}$. In embodiments, R$^{6.4}$ is —(CH$_2$)$_3$NR$^{6.8B}$R$^{6.8C}$. In embodiments, R$^{6.4}$ is —CH$_2$C(O)OR$^{6.8D}$. In embodiments, R$^{6.4}$ is —(CH$_2$)$_2$C(O)OR$^{6.8D}$. In embodiments, R$^{6.4}$ is —(CH$_2$)$_3$C(O)OR$^{6.8D}$. In embodiments, R$^{6.4}$ is —CH$_2$C(O)OR$^{6.8D}$. In embodiments, R$^{6.4}$ is —CH$_2$CONR$^{6.8B}$R$^{6.8C}$. In embodiments, R$^{6.4}$ is —(CH$_2$)$_2$CONR$^{6.8B}$R$^{6.8C}$. In embodiments, R$^{6.4}$ is —(CH$_2$)$_3$CONR$^{6.8B}$R$^{6.8C}$. In embodiments, R$^{6.4}$ is (CH$_2$)$_2$SO$_2$NR$^{6.8B}$R$^{6.8C}$. In embodiments, R$^{6.4}$ is —C(O)NR$^{6.8B}$R$^{6.8C}$. In embodiments, R$^{6.4}$ is CH$_2$NHSO$_2$R$^{6.8A}$. In embodiments, R$^{6.8A}$ is CH$_3$. In embodiments, R$^{6.8A}$ is CF$_3$. In embodiments, R$^{6.8A}$ is CHF$_2$. In embodiments, R$^{6.8A}$ is CH$_2$F. In embodiments, R$^{6.8A}$ is CH$_2$Cl. In embodiments, R$^{6.8A}$ is CHCl$_2$. In embodiments, R$^{6.8A}$ is CCl$_3$. In embodiments, R$^{6.8A}$ is CH$_2$CH$_3$. In embodiments, R$^{6.8A}$ is unsubstituted propyl. In embodiments, R$^{6.8A}$ is hydrogen. In embodiments, R$^{6.8B}$ is CH$_3$. In embodiments, R$^{6.8B}$ is CF$_3$. In embodiments, R$^{6.8B}$ is CHF$_2$. In embodiments, R$^{6.8B}$ is CH$_2$F. In embodiments, R$^{6.8B}$ is CH$_2$Cl. In embodiments, R$^{6.8B}$ is CHCl$_2$. In embodiments, R$^{6.8B}$ is CCl$_3$. In embodiments, R$^{6.8B}$ is CH$_2$CH$_3$. In embodiments, R$^{6.8B}$ is unsubstituted propyl. In embodiments, R$^{6.8B}$ is hydrogen. In embodiments, R$^{6.8C}$ is CH$_3$. In embodiments, R$^{6.8C}$ is CF$_3$. In embodiments, R$^{6.8C}$ is CHF$_2$. In embodiments, R$^{6.8C}$ is CH$_2$F. In embodiments, R$^{6.8C}$ is CH$_2$Cl. In embodiments, R$^{6.8C}$ is CHCl$_2$. In embodiments, R$^{6.8C}$ is CCl$_3$. In embodiments, R$^{6.8C}$ is CH$_2$CH$_3$. In embodiments, R$^{6.8C}$ is unsubstituted propyl. In embodiments, R$^{6.8C}$ is hydrogen. In embodiments, R$^{6.8D}$ is CH$_3$. In embodiments, R$^{6.8D}$ is CF$_3$. In embodiments, R$^{6.8D}$ is CHF$_2$. In embodiments, R$^{6.8D}$ is CH$_2$F. In embodiments, R$^{6.8D}$ is CH$_2$Cl. In embodiments, R$^{6.8D}$ is CHCl$_2$. In embodiments, R$^{6.8D}$ is CCl$_3$. In embodiments, R$^{6.8D}$ is CH$_2$CH$_3$. In embodiments, R$^{6.8D}$ is unsubstituted propyl. In embodiments, R$^{6.8D}$ is hydrogen.

In embodiments, R$^{6.5}$ is hydrogen, halogen, —CX$^{6.9}_3$, —CHX$^{6.9}_2$, —CH$_2$X$^{6.9}$, —CN, —SO$_{n6.5}$R$^{6.9A}$, —SO$_{v6.5}$NR$^{6.9B}$R$^{6.9C}$, —NHNR$^{6.9B}$R$^{6.9C}$, —ONR$^{6.9B}$R$^{6.9C}$, —NHC(O)NHNR$^{6.9B}$R$^{6.9C}$, —NHC(O)NR$^{6.9B}$R$^{6.9C}$, —N(O)$_{m6.5}$, —NR$^{6.9B}$R$^{6.9C}$, —C(O)R$^{6.9D}$, —C(O)OR$^{69D}$, —C(O)NR$^{6.9B}$R$^{6.9C}$, —OR$^{6.9A}$, —NR$^{6.9B}$SO$_2$R$^{6.9A}$, —NR$^{6.9B}$C(O)R$^{6.9D}$, —NR$^{6.9B}$C(O)OR$^{6.9D}$, —NR$^{6.9B}$OR$^{6.9D}$, —OCX$^{6.9}_3$, —OCHX$^{6.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^{6.5}$ is hydrogen, halogen, —CX$^{6.9}_3$, —CHX$^{6.9}_2$, —CH$_2$X$^{6.9}$, —CN, —SO$_{n6.5}$R$^{6.9A}$, —SO$_{v6.5}$NR$^{6.9B}$R$^{6.9C}$, —NHNR$^{6.9B}$R$^{6.9C}$, —ONR$^{6.9B}$R$^{6.9C}$, —NHC(O)NHNR$^{6.9B}$R$^{6.9C}$, —NHC(O)NR$^{6.9B}$R$^{6.9C}$, —N(O)$_{m6.5}$, —NR$^{6.9B}$R$^{6.9C}$, —C(O)R$^{6.9D}$, —C(O)OR$^{6.9D}$, —C(O)NR$^{6.9B}$R$^{6.9C}$, —OR$^{6.9A}$, —NR$^{6.9B}$SO$_2$R$^{6.9A}$, —NR$^{6.9B}$C(O)R$^{6.9D}$, —NR$^{6.9B}$C(O)OR$^{6.9D}$, —NR$^{6.9B}$OR$^{6.9D}$, —OCX$^{6.9}_3$, —OCHX$^{6.9}_2$, R$^{31.9}$-substituted or unsubstituted alkyl (e.g., C$_1$-C$_8$ alkyl, C$_1$-C$_6$ alkyl, or C$_1$-C$_4$ alkyl), R$^{31.9}$-substituted or unsubstituted heteroalkyl (e.g., 2 to 8 membered heteroalkyl, 2 to 6 membered heteroalkyl, or 2 to 4 membered heteroalkyl), R$^{31.9}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{31.9}$-substituted or unsubstituted heterocycloalkyl (e.g., 3 to 8 membered heterocycloalkyl, 3 to 6 membered heterocycloalkyl, or 5 to 6 membered heterocycloalkyl), R$^{31.9}$-substituted or unsubstituted aryl (e.g., C$_6$-C$_{10}$ aryl, C$_{10}$ aryl, or phenyl), or R$^{31.9}$-substituted or unsubstituted heteroaryl (e.g., 5 to 10 membered heteroaryl, 5 to 9 membered heteroaryl, or 5 to 6 membered heteroaryl).

In embodiments, R$^{6.5}$ is R$^{31.9}$-substituted or unsubstituted alkyl (e.g., C$_1$-C$_8$ alkyl, C$_1$-C$_6$ alkyl, or C$_1$-C$_4$ alkyl). In embodiments, R$^{6.5}$ is R$^{31.9}$-substituted alkyl (e.g., C$_1$-C$_8$ alkyl, C$_1$-C$_6$ alkyl, or C$_1$-C$_4$ alkyl). In embodiments, R$^{6.5}$ is an unsubstituted alkyl (e.g., C$_1$-C$_8$ alkyl, C$_1$-C$_6$ alkyl, or C$_1$-C$_4$ alkyl).

In embodiments, R$^{6.5}$ is R$^{31.9}$-substituted or unsubstituted heteroalkyl (e.g., 2 to 8 membered heteroalkyl, 2 to 6 membered heteroalkyl, or 2 to 4 membered heteroalkyl). In embodiments, R$^{6.5}$ is R$^{31.9}$-substituted heteroalkyl (e.g., 2 to 8 membered heteroalkyl, 2 to 6 membered heteroalkyl, or 2 to 4 membered heteroalkyl). In embodiments, R$^{6.5}$ is an unsubstituted heteroalkyl (e.g., 2 to 8 membered heteroalkyl, 2 to 6 membered heteroalkyl, or 2 to 4 membered heteroalkyl).

In embodiments, R$^{6.5}$ is R$^{31.9}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{6.5}$ is R$^{31.9}$-substituted cycloalkyl (e.g., C$_3$-C$_8$ cycloalkyl, C$_3$-C$_6$ cycloalkyl, or C$_5$-C$_6$ cycloalkyl). In embodiments, R$^{6.5}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{6.5}$ is $R^{31.9}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6.5}$ is $R^{31.9}$-substituted heterocycloalkyl (e.g., 3 to 8 membered heterocycloalkyl, 3 to 6 membered heterocycloalkyl, or 5 to 6 membered heterocycloalkyl). In embodiments, $R^{6.5}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{6.5}$ is $R^{31.9}$-substituted or unsubstituted aryl (e.g., $C_6$-$C_{10}$ aryl, $C_{10}$ aryl, or phenyl). In embodiments, $R^{6.5}$ is $R^{31.9}$-substituted aryl (e.g., $C_6$-$C_{10}$ aryl, $C_{10}$ aryl, or phenyl). In embodiments, $R^{6.5}$ is an unsubstituted aryl (e.g., $C_6$-$C_{10}$ aryl, $C_{10}$ aryl, or phenyl).

In embodiments, $R^{6.5}$ is $R^{31.9}$-substituted or unsubstituted heteroaryl (e.g., 5 to 10 membered heteroaryl, 5 to 9 membered heteroaryl, or 5 to 6 membered heteroaryl). In embodiments, $R^{6.5}$ is $R^{31.9}$-substituted heteroaryl (e.g., 5 to 10 membered heteroaryl, 5 to 9 membered heteroaryl, or 5 to 6 membered heteroaryl). In embodiments, $R^{6.5}$ is an unsubstituted heteroaryl (e.g., 5 to 10 membered heteroaryl, 5 to 9 membered heteroaryl, or 5 to 6 membered heteroaryl).

In embodiments, $R^{6.6A}$, $R^{6.6B}$, $R^{6.6C}$, $R^{6.6D}$, $R^{6.7A}$, $R^{6.7B}$, $R^{6.7C}$, $R^{6.7D}$, $R^{6.8A}$, $R^{6.8B}$, $R^{6.8C}$, $R^{6.8D}$, $R^{6.9A}$, $R^{6.9B}$, $R^{6.9C}$ and $R^{6.9D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{6.5}$ is hydrogen or $CH_3$. In embodiments, $R^{6.5}$ is hydrogen. In embodiments, $R^{6.5}$ is $CH_3$.

In embodiments, $R^{6.5}$ is $CH_2CH_3$, OH, —$CH_2$OH, $C(CH_3)_2$OH, —$(CH_2)_2$OH, —$(CH_2)_3$OH, $CO_2$H, $CH_2$CH$(OCH_3)CO_2$H, $CH_2$CH(OH)$CO_2$H, CH$(CH_3)CH_2CO_2$H, $CH_2OCH_3$. In embodiments, $R^{6.4}$ is $CH_2CH_3$. In embodiments, $R^{6.5}$ is —$CH_2$OH. In embodiments, $R^{6.5}$ is $C(CH_3)_2$OH. In embodiments, $R^{6.5}$ is —$(CH_2)_2$OH. In embodiments, $R^{6.5}$ is —$(CH_2)_3$OH. In embodiments, $R^{6.5}$ is $CO_2$H. In embodiments, $R^{6.5}$ is $CH_2$CH$(OCH_3)CO_2$H. In embodiments, $R^{6.5}$ is $CH_2$CH(OH)$CO_2$H. In embodiments, $R^{6.5}$ is CH$(CH_3)CH_2CO_2$H. In embodiments, $R^{6.5}$ is $CH_2OCH_3$.

In embodiments, $R^{6.5}$ is F, —OH, —$CH_3$, —$CH_2$OH, —$C(CH_3)_2$OH, —$(CH_2)_2$OH, —$(CH_2)_3$OH, C(O)OH, —$CH_2NH_2$, —C(O)$NH_2$, —$(CH_2)_2NH_2$, —$(CH_2)_3NH_2$, —$CH_2CO_2CH_2CH_3$, —$(CH_2)_2CO_2CH_2CH_3$, —$(CH_2)_3CO_2CH_2CH_3$, —$CH_2CO_2$H, —$(CH_2)_2CO_2$H, —$(CH_2)_3CO_2$H, —$CH_2CO_2NH_2$, —$(CH_2)_2CONH_2$, —$(CH_2)_3CO_2NH_2$, —$CH_2CHFCO_2$H, —$(CH_2)_2CHFCO_2$H, —$CH_2CF_2CO_2$H, —$(CH_2)_2CF_2CO_2$H, —$(CH_2)_2SO_2NH_2$, C(O)OH-substituted cyclopropyl, $CH_2$CH$(OCH_3)CO_2$H, —$CH_2$CH(OH)$CO_2$H, $CH_2$NHS$(O_2)CH_3$, CH$(CH_3)CH_2CO_2$H, $CH_2OCH_3$, C(O)NHCH$_3$, CH(OH)$CH_2$S$(O_2)$CH$_3$, —$(CH_2)_2$CH(OH)(CF$_3$),

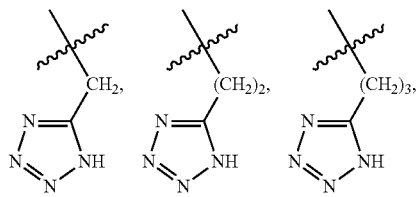

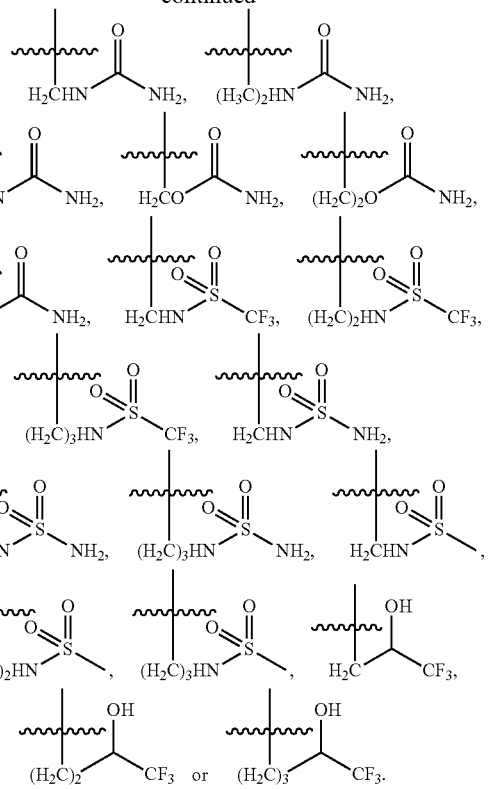

In embodiments, $R^{6.5}$ is F. In embodiments, $R^{6.5}$ is —OH. In embodiments, $R^{6.5}$ is —$CH_3$. In embodiments, $R^{6.5}$ is —$CH_2$OH. In embodiments, $R^{6.5}$ is $C(CH_3)_2$OH. In embodiments, $R^{6.5}$ is —$(CH_2)_2$OH. In embodiments, $R^{6.5}$ is —$(CH_2)_3$OH. In embodiments, $R^{6.5}$ is C(O)OH. In embodiments, $R^{6.5}$ is —$CH_2NH_2$. In embodiments, $R^{6.5}$ is —$(CH_2)_2NH_2$. In embodiments, $R^{6.5}$ is —$(CH_2)_3NH_2$. In embodiments, $R^{6.5}$ is —$CH_2CO_2CH_2CH_3$. In embodiments, $R^{6.5}$ is —$(CH_2)_2CO_2CH_2CH_3$. In embodiments, $R^{6.5}$ is —$(CH_2)_3CO_2CH_2CH_3$. In embodiments, $R^{6.5}$ is —$CH_2CO_2$H. In embodiments, $R^{6.5}$ is —$(CH_2)_2CO_2$H. In embodiments, $R^{6.5}$ is —$(CH_2)_3CO_2$H. In embodiments, $R^{6.5}$ is —$CH_2CO_2NH_2$. In embodiments, $R^{6.5}$ is —$CH_2CONH_2$. In embodiments, $R^{6.5}$ is —$(CH_2)_2CONH_2$. In embodiments, $R^{6.5}$ is —$(CH_2)_3CO_2NH_2$. In embodiments, $R^{6.5}$ is —$(CH_2)_3CONH_2$. In embodiments, $R^{6.5}$ is —$CH_2CHFCO_2$H. In embodiments, $R^{6.5}$ is —$(CH_2)_2CHFCO_2$H. In embodiments, $R^{6.5}$ is —$CH_2CF_2CO_2$H. In embodiments, $R^{6.5}$ is —$(CH_2)_2CF_2CO_2$H. In embodiments, $R^{6.5}$ is $(CH_2)_2SO_2NH_2$. In embodiments, $R^{6.5}$ is C(O)OH substituted cyclopropyl. In embodiments, $R^{6.5}$ is $CH_2$CH$(OCH_3)CO_2$H. In embodiments, $R^{6.5}$ is $CH_2$CH(OH)$CO_2$H. In embodiments, $R^{6.5}$ is CH$(CH_3)CH_2CO_2$H. In embodiments, $R^{6.5}$ is $CH_2OCH_3$. In embodiments, $R^{6.5}$ is C(O)NHCH$_3$. In embodiments, $R^{6.5}$ is CH(OH)$CH_2$S$(O_2)$CH$_3$. In embodiments, $R^{6.5}$ is

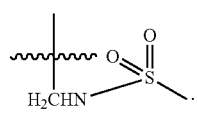

In embodiments, $R^{6.5}$ is —C(O)$NH_2$. In embodiments, $R^{6.5}$ is —$(CH_2)_2SO_2NH_2$. In embodiments, $R^{6.5}$ is C(O)OH-substituted cyclopropyl. In embodiments, $R^{6.5}$ is $CH_2CH(OCH_3)CO_2H$. In embodiments, $R^{6.5}$ is $—CH_2CH(OH)CO_2H$. In embodiments, $R^{6.5}$ is $CH_2NHS(O_2)CH_3$. In embodiments, $R^{6.5}$ is $CH(CH_3)CH_2CO_2H$. In embodiments, $R^{6.5}$ is $CH_2OCH_3$. In embodiments, $R^{6.5}$ is $C(O)NHCH_3$. In embodiments, $R^{6.5}$ is $CH(OH)CH_2S(O_2)CH_3$. In embodiments, $R^{6.5}$ is $—(CH_2)_2CH(OH)(CF_3)$. In embodiments, $R^{6.5}$ is hydrogen.

In embodiments, $R^{6.5}$ is halogen. In embodiments, $R^{6.5}$ is $—OR^{6.9A}$. In embodiments, $R^{6.5}$ is $—C(O)OR^{6.9D}$. In embodiments, $R^{6.5}$ is $—CH_2NR^{6.9B}R^{6.9C}$. In embodiments, $R^{6.5}$ is $—(CH_2)_2NR^{6.9B}R^{6.9C}$. In embodiments, $R^{6.5}$ is $—(CH_2)_3NR^{6.9B}R^{6.9C}$. In embodiments, $R^{6.5}$ is $—CH_2C(O)OR^{6.9D}$. In embodiments, $R^{6.5}$ is $—(CH_2)_2C(O)OR^{6.9D}$. In embodiments, $R^{6.5}$ is $—(CH_2)_3C(O)OR^{6.9D}$. In embodiments, $R^{6.5}$ is $—CH_2C(O)OR^{6.9D}$. In embodiments, $R^{6.5}$ is $—CH_2CONR^{6.9B}R^{6.9C}$. In embodiments, $R^{6.5}$ is $—(CH_2)_2CONR^{6.9B}R^{6.9C}$. In embodiments, $R^{6.5}$ is $—(CH_2)_3CONR^{6.9B}R^{6.9C}$. In embodiments, $R^{6.5}$ is $(CH_2)_2SO_2NR^{6.9B}R^{6.9C}$. In embodiments, $R^{6.5}$ is $—C(O)NR^{6.9B}R^{6.9C}$. In embodiments, $R^{6.5}$ is $CH_2NHSO_2R^{6.9A}$. In embodiments, $R^{6.9A}$ is $CH_3$. In embodiments, $R^{6.9A}$ is $CF_3$. In embodiments, $R^{6.9A}$ is $CHF_2$. In embodiments, $R^{6.9A}$ is $CH_2F$. In embodiments, $R^{6.9A}$ is $CH_2Cl$. In embodiments, $R^{6.9A}$ is $CHCl_2$. In embodiments, $R^{6.9A}$ is $CCl_3$. In embodiments, $R^{6.9A}$ is $CH_2CH_3$. In embodiments, $R^{6.9A}$ is unsubstituted propyl. In embodiments, $R^{6.9A}$ is hydrogen. In embodiments, $R^{6.9B}$ is $CH_3$. In embodiments, $R^{6.9B}$ is $CF_3$. In embodiments, $R^{6.9B}$ is $CHF_2$. In embodiments, $R^{6.9B}$ is $CH_2F$. In embodiments, $R^{6.9B}$ is $CH_2Cl$. In embodiments, $R^{6.9B}$ is $CHCl_2$. In embodiments, $R^{6.9B}$ is $CCl_3$. In embodiments, $R^{6.9B}$ is $CH_2CH_3$. In embodiments, $R^{6.9B}$ is unsubstituted propyl. In embodiments, $R^{6.9B}$ is hydrogen. In embodiments, $R^{6.9C}$ is $CH_3$. In embodiments, $R^{6.9C}$ is $CF_3$. In embodiments, $R^{6.9C}$ is $CHF_2$. In embodiments, $R^{6.9C}$ is $CH_2F$. In embodiments, $R^{6.9C}$ is $CH_2Cl$. In embodiments, $R^{6.9C}$ is $CHCl_2$. In embodiments, $R^{6.9C}$ is $CCl_3$. In embodiments, $R^{6.9C}$ is $CH_2CH_3$. In embodiments, $R^{6.9C}$ is unsubstituted propyl. In embodiments, $R^{6.9C}$ is hydrogen. In embodiments, $R^{6.9D}$ is $CH_3$. In embodiments, $R^{6.9D}$ is $CF_3$. In embodiments, $R^{6.9D}$ is $CHF_2$. In embodiments, $R^{6.9D}$ is $CH_2F$. In embodiments, $R^{6.9D}$ is $CH_2Cl$. In embodiments, $R^{6.9D}$ is $CHCl_2$. In embodiments, $R^{6.9D}$ is $CCl_3$. In embodiments, $R^{6.9D}$ is $CH_2CH_3$. In embodiments, $R^{6.9D}$ is unsubstituted propyl. In embodiments, $R^{6.9D}$ is hydrogen.

In embodiments, $R^{6.6B}$ and $R^{6.6C}$, $R^{6.7B}$ and $R^{6.7C}$, $R^{6.8B}$ and $R^{6.8C}$, $R^{6.9B}$ and $R^{6.9C}$ substituents bonded to the same nitrogen atom may optionally be joined to form a substituted or unsubstituted heterocycloalkyl or substituted or unsubstituted heteroaryl.

In embodiments, $R^{6.6A}$ is hydrogen, halogen, $—CF_3$, $—CCl_3$, $—CBr_3$, $—CI_3$, $—COOH$, $—CONH_2$, $R^{31.6A}$-substituted or unsubstituted alkyl (e.g., $C_1$-$C_8$ alkyl, $C_1$-$C_6$ alkyl, or $C_1$-$C_4$ alkyl), $R^{31.6A}$-substituted or unsubstituted heteroalkyl (e.g., 2 to 8 membered heteroalkyl, 2 to 6 membered heteroalkyl, or 2 to 4 membered heteroalkyl), $R^{31.6A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.6A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.6A}$-substituted or unsubstituted aryl (e.g., $C_6$-$C_{10}$ aryl, $C_{10}$ aryl, or phenyl), or $R^{31.6A}$-substituted or unsubstituted heteroaryl (e.g., 5 to 10 membered heteroaryl, 5 to 9 membered heteroaryl, or 5 to 6 membered heteroaryl).

In embodiments, $R^{6.7A}$ is hydrogen, halogen, $—CF_3$, $—CCl_3$, $—CBr_3$, $—CI_3$, $—COOH$, $—CONH_2$, $R^{31.7A}$-substituted or unsubstituted alkyl (e.g., $C_1$-$C_8$ alkyl, $C_1$-$C_6$ alkyl, or $C_1$-$C_4$ alkyl), $R^{31.7A}$-substituted or unsubstituted heteroalkyl (e.g., 2 to 8 membered heteroalkyl, 2 to 6 membered heteroalkyl, or 2 to 4 membered heteroalkyl), $R^{31.7A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.7A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.7A}$-substituted or unsubstituted aryl (e.g., $C_6$-$C_{10}$ aryl, $C_{10}$ aryl, or phenyl), or $R^{31.7A}$-substituted or unsubstituted heteroaryl (e.g., 5 to 10 membered heteroaryl, 5 to 9 membered heteroaryl, or 5 to 6 membered heteroaryl).

In embodiments, $R^{6.8A}$ is hydrogen, halogen, $—CF_3$, $—CCl_3$, $—CBr_3$, $—CI_3$, $—COOH$, $—CONH_2$, $R^{31.8A}$-substituted or unsubstituted alkyl (e.g., $C_1$-$C_8$ alkyl, $C_1$-$C_6$ alkyl, or $C_1$-$C_4$ alkyl), $R^{31.8A}$-substituted or unsubstituted heteroalkyl (e.g., 2 to 8 membered heteroalkyl, 2 to 6 membered heteroalkyl, or 2 to 4 membered heteroalkyl), $R^{31.8A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.8A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.8A}$-substituted or unsubstituted aryl (e.g., $C_6$-$C_{10}$ aryl, $C_{10}$ aryl, or phenyl), or $R^{31.8A}$-substituted or unsubstituted heteroaryl (e.g., 5 to 10 membered heteroaryl, 5 to 9 membered heteroaryl, or 5 to 6 membered heteroaryl).

In embodiments, $R^{6.9A}$ is hydrogen, halogen, $—CF_3$, $—CCl_3$, $—CBr_3$, $—CI_3$, $—COOH$, $—CONH_2$, $R^{31.9A}$-substituted or unsubstituted alkyl (e.g., $C_1$-$C_8$ alkyl, $C_1$-$C_6$ alkyl, or $C_1$-$C_4$ alkyl), $R^{31.9A}$-substituted or unsubstituted heteroalkyl (e.g., 2 to 8 membered heteroalkyl, 2 to 6 membered heteroalkyl, or 2 to 4 membered heteroalkyl), $R^{31.9A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.9A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.9A}$-substituted or unsubstituted aryl (e.g., $C_6$-$C_{10}$ aryl, $C_{10}$ aryl, or phenyl), or $R^{31.9A}$-substituted or unsubstituted heteroaryl (e.g., 5 to 10 membered heteroaryl, 5 to 9 membered heteroaryl, or 5 to 6 membered heteroaryl).

In embodiments, $R^{6.6B}$ is hydrogen, halogen, $—CF_3$, $—CCl_3$, $—CBr_3$, $—CI_3$, $—COOH$, $—CONH_2$, $R^{31.6B}$-substituted or unsubstituted alkyl (e.g., $C_1$-$C_8$ alkyl, $C_1$-$C_6$ alkyl, or $C_1$-$C_4$ alkyl), $R^{31.6B}$-substituted or unsubstituted heteroalkyl (e.g., 2 to 8 membered heteroalkyl, 2 to 6 membered heteroalkyl, or 2 to 4 membered heteroalkyl), $R^{31.6B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.6B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.6B}$-substituted or unsubstituted aryl (e.g., $C_6$-$C_{10}$ aryl, $C_{10}$ aryl, or phenyl), or $R^{31.6B}$-substituted or unsubstituted heteroaryl (e.g., 5 to 10 membered heteroaryl, 5 to 9 membered heteroaryl, or 5 to 6 membered heteroaryl). In embodiments, $R^{6.6B}$ and $R^{6.6C}$ substituents bonded to the same nitrogen atom may optionally be joined to form a $R^{31.6B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{31.6B}$-substituted or unsubstituted heteroaryl (e.g., 5 to 10 membered heteroaryl, 5 to 9 membered heteroaryl, or 5 to 6 membered heteroaryl).

In embodiments, $R^{6.7B}$ is hydrogen, halogen, $—CF_3$, $—CCl_3$, $—CBr_3$, $—CI_3$, $—COOH$, $—CONH_2$, $R^{31.7B}$-substituted or unsubstituted alkyl (e.g., $C_1$-$C_8$ alkyl, $C_1$-$C_6$ alkyl, or $C_1$-$C_4$ alkyl), $R^{31.7B}$-substituted or unsubstituted heteroalkyl (e.g., 2 to 8 membered heteroalkyl, 2 to 6 membered heteroalkyl, or 2 to 4 membered heteroalkyl), $R^{31.7B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.7B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.7B}$-substituted or unsubstituted aryl (e.g., $C_6$-$C_{10}$ aryl, $C_{10}$ aryl, or phenyl), or $R^{31.8B}$-substituted or unsubstituted heteroaryl (e.g., 5 to 10 membered heteroaryl, 5 to 9 membered heteroaryl, or 5 to 6 membered heteroaryl). In embodiments, $R^{6.7B}$ and $R^{6.7C}$ substituents bonded to the same nitrogen atom may optionally be joined to form a $R^{31.7B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{31.7B}$-substituted or unsubstituted heteroaryl (e.g., 5 to 10 membered heteroaryl, 5 to 9 membered heteroaryl, or 5 to 6 membered heteroaryl).

In embodiments, $R^{6.8B}$ is hydrogen, halogen, —$CF_3$, —$CCl_3$, —$CBr_3$, —$CI_3$, —COOH, —$CONH_2$, $R^{31.8B}$-substituted or unsubstituted alkyl (e.g., $C_1$-$C_8$ alkyl, $C_1$-$C_6$ alkyl, or $C_1$-$C_4$ alkyl), $R^{31.8B}$-substituted or unsubstituted heteroalkyl (e.g., 2 to 8 membered heteroalkyl, 2 to 6 membered heteroalkyl, or 2 to 4 membered heteroalkyl), $R^{31.8B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.8B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.8B}$-substituted or unsubstituted aryl (e.g., $C_6$-$C_{10}$ aryl, $C_{10}$ aryl, or phenyl), or $R^{31.8B}$-substituted or unsubstituted heteroaryl (e.g., 5 to 10 membered heteroaryl, 5 to 9 membered heteroaryl, or 5 to 6 membered heteroaryl). In embodiments, $R^{6.8B}$ and $R^{6.8C}$ substituents bonded to the same nitrogen atom may optionally be joined to form a $R^{31.8B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{31.8B}$-substituted or unsubstituted heteroaryl (e.g., 5 to 10 membered heteroaryl, 5 to 9 membered heteroaryl, or 5 to 6 membered heteroaryl).

In embodiments, $R^{6.9B}$ is hydrogen, halogen, —$CF_3$, —$CCl_3$, —$CBr_3$, —$CI_3$, —COOH, —$CONH_2$, $R^{31.9B}$-substituted or unsubstituted alkyl (e.g., $C_1$-$C_8$ alkyl, $C_1$-$C_6$ alkyl, or $C_1$-$C_4$ alkyl), $R^{31.9B}$-substituted or unsubstituted heteroalkyl (e.g., 2 to 8 membered heteroalkyl, 2 to 6 membered heteroalkyl, or 2 to 4 membered heteroalkyl), $R^{31.9B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.9B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.9B}$-substituted or unsubstituted aryl (e.g., $C_6$-$C_{10}$ aryl, $C_{10}$ aryl, or phenyl), or $R^{31.9B}$-substituted or unsubstituted heteroaryl (e.g., 5 to 10 membered heteroaryl, 5 to 9 membered heteroaryl, or 5 to 6 membered heteroaryl). In embodiments, $R^{6.9B}$ and $R^{6.9C}$ substituents bonded to the same nitrogen atom may optionally be joined to form a $R^{31.9B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{31.9B}$-substituted or unsubstituted heteroaryl (e.g., 5 to 10 membered heteroaryl, 5 to 9 membered heteroaryl, or 5 to 6 membered heteroaryl).

In embodiments, $R^{6.6C}$ is hydrogen, halogen, —$CF_3$, —$CCl_3$, —$CBr_3$, —$CI_3$, —COOH, —$CONH_2$, $R^{31.6C}$-substituted or unsubstituted alkyl (e.g., $C_1$-$C_8$ alkyl, $C_1$-$C_6$ alkyl, or $C_1$-$C_4$ alkyl), $R^{31.6C}$-substituted or unsubstituted heteroalkyl (e.g., 2 to 8 membered heteroalkyl, 2 to 6 membered heteroalkyl, or 2 to 4 membered heteroalkyl), $R^{31.6C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.6C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.6C}$-substituted or unsubstituted aryl (e.g., $C_6$-$C_{10}$ aryl, $C_{10}$ aryl, or phenyl), or $R^{31.6C}$-substituted or unsubstituted heteroaryl (e.g., 5 to 10 membered heteroaryl, 5 to 9 membered heteroaryl, or 5 to 6 membered heteroaryl). In embodiments, $R^{6.6C}$ and $R^{6.6B}$ substituents bonded to the same nitrogen atom may optionally be joined to form a $R^{31.6C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{31.6C}$-substituted or unsubstituted heteroaryl (e.g., 5 to 10 membered heteroaryl, 5 to 9 membered heteroaryl, or 5 to 6 membered heteroaryl).

In embodiments, $R^{6.7C}$ is hydrogen, halogen, —$CF_3$, —$CCl_3$, —$CBr_3$, —$CI_3$, —COOH, —$CONH_2$, $R^{31.7C}$-substituted or unsubstituted alkyl (e.g., $C_1$-$C_8$ alkyl, $C_1$-$C_6$ alkyl, or $C_1$-$C_4$ alkyl), $R^{31.7C}$-substituted or unsubstituted heteroalkyl (e.g., 2 to 8 membered heteroalkyl, 2 to 6 membered heteroalkyl, or 2 to 4 membered heteroalkyl), $R^{31.7C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.7C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.7C}$-substituted or unsubstituted aryl (e.g., $C_6$-$C_{10}$ aryl, $C_{10}$ aryl, or phenyl), or $R^{31.8C}$-substituted or unsubstituted heteroaryl (e.g., 5 to 10 membered heteroaryl, 5 to 9 membered heteroaryl, or 5 to 6 membered heteroaryl). In embodiments, $R^{6.7C}$ and $R^{6.7B}$ substituents bonded to the same nitrogen atom may optionally be joined to form a $R^{31.7C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{31.7C}$-substituted or unsubstituted heteroaryl (e.g., 5 to 10 membered heteroaryl, 5 to 9 membered heteroaryl, or 5 to 6 membered heteroaryl).

In embodiments, $R^{6.8C}$ is hydrogen, halogen, —$CF_3$, —$CCl_3$, —$CBr_3$, —$CI_3$, —COOH, —$CONH_2$, $R^{31.8C}$-substituted or unsubstituted alkyl (e.g., $C_1$-$C_8$ alkyl, $C_1$-$C_6$ alkyl, or $C_1$-$C_4$ alkyl), $R^{31.8C}$-substituted or unsubstituted heteroalkyl (e.g., 2 to 8 membered heteroalkyl, 2 to 6 membered heteroalkyl, or 2 to 4 membered heteroalkyl), $R^{31.8C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.8C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.8C}$-substituted or unsubstituted aryl (e.g., $C_6$-$C_{10}$ aryl, $C_{10}$ aryl, or phenyl), or $R^{31.8C}$-substituted or unsubstituted heteroaryl (e.g., 5 to 10 membered heteroaryl, 5 to 9 membered heteroaryl, or 5 to 6 membered heteroaryl). In embodiments, $R^{6.8C}$ and $R^{6.8B}$ substituents bonded to the same nitrogen atom may optionally be joined to form a $R^{31.8C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{31.8C}$-substituted or unsubstituted heteroaryl (e.g., 5 to 10 membered heteroaryl, 5 to 9 membered heteroaryl, or 5 to 6 membered heteroaryl).

In embodiments, $R^{6.9C}$ is hydrogen, halogen, —$CF_3$, —$CCl_3$, —$CBr_3$, —$CI_3$, —COOH, —$CONH_2$, $R^{31.9C}$-substituted or unsubstituted alkyl (e.g., $C_1$-$C_8$ alkyl, $C_1$-$C_4$ alkyl), $R^{31.9C}$-substituted or unsubstituted heteroalkyl (e.g., 2 to 8 membered heteroalkyl, 2 to 6 membered heteroalkyl, or 2 to 4 membered heteroalkyl), $R^{31.9C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.9C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.9C}$-substituted or unsubstituted aryl (e.g., $C_6$-$C_{10}$ aryl, $C_{10}$ aryl, or phenyl), or $R^{31.9C}$-substituted or unsubstituted heteroaryl (e.g., 5 to 10 membered heteroaryl, 5 to 9 membered heteroaryl, or 5 to 6 membered heteroaryl). In embodiments, $R^{6.9C}$ and $R^{6.9B}$ substituents bonded to the same nitrogen atom may optionally be joined to form a $R^{31.9C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{31.9C}$-substituted or unsubstituted heteroaryl (e.g., 5 to 10 membered heteroaryl, 5 to 9 membered heteroaryl, or 5 to 6 membered heteroaryl).

In embodiments, $R^{6.6D}$ is hydrogen, halogen, —$CF_3$, —$CCl_3$, —$CBr_3$, —$CI_3$, —COOH, —$CONH_2$, $R^{31.6D}$-substituted or unsubstituted alkyl (e.g., $C_1$-$C_8$ alkyl, $C_1$-$C_6$ alkyl, or $C_1$-$C_4$ alkyl), $R^{31.6D}$-substituted or unsubstituted heteroalkyl (e.g., 2 to 8 membered heteroalkyl, 2 to 6 membered heteroalkyl, or 2 to 4 membered heteroalkyl), $R^{31.6D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.6D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.6D}$-substituted or unsubstituted aryl (e.g., $C_6$-$C_{10}$ aryl, $C_{10}$ aryl, or phenyl), or $R^{31.6D}$-substituted or unsubstituted heteroaryl (e.g., 5 to 10 membered heteroaryl, 5 to 9 membered heteroaryl, or 5 to 6 membered heteroaryl).

In embodiments, $R^{6.7D}$ is hydrogen, halogen, —$CF_3$, —$CCl_3$, —$CBr_3$, —$CI_3$, —COOH, —$CONH_2$, $R^{31.7D}$-substituted or unsubstituted alkyl (e.g., $C_1$-$C_8$ alkyl, $C_1$-$C_6$ alkyl, or $C_1$-$C_4$ alkyl), $R^{31.7D}$-substituted or unsubstituted heteroalkyl (e.g., 2 to 8 membered heteroalkyl, 2 to 6 membered heteroalkyl, or 2 to 4 membered heteroalkyl), $R^{31.7D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.7D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.7D}$-substituted or unsubstituted aryl (e.g., $C_6$-$C_{10}$ aryl, $C_{10}$ aryl, or phenyl), or $R^{31.7D}$-substituted or unsubstituted heteroaryl (e.g., 5 to 10 membered heteroaryl, 5 to 9 membered heteroaryl, or 5 to 6 membered heteroaryl).

In embodiments, $R^{6.8D}$ is hydrogen, halogen, —$CF_3$, —$CCl_3$, —$CBr_3$, —$CI_3$, —COOH, —$CONH_2$, $R^{31.8D}$-substituted or unsubstituted alkyl (e.g., $C_1$-$C_8$ alkyl, $C_1$-$C_6$ alkyl, or $C_1$-$C_4$ alkyl), $R^{31.8D}$-substituted or unsubstituted heteroalkyl (e.g., 2 to 8 membered heteroalkyl, 2 to 6 membered heteroalkyl, or 2 to 4 membered heteroalkyl), $R^{31.8D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.8D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.8D}$-substituted or unsubstituted aryl (e.g., $C_6$-$C_{10}$ aryl, $C_{10}$ aryl, or phenyl), or $R^{31.8D}$-substituted or unsubstituted heteroaryl (e.g., 5 to 10 membered heteroaryl, 5 to 9 membered heteroaryl, or 5 to 6 membered heteroaryl).

In embodiments, $R^{6.9D}$ is hydrogen, halogen, —$CF_3$, —$CCl_3$, —$CBr_3$, —$CI_3$, —COOH, —$CONH_2$, $R^{31.9D}$-substituted or unsubstituted alkyl (e.g., $C_1$-$C_8$ alkyl, $C_1$-$C_6$ alkyl, or $C_1$-$C_4$ alkyl), $R^{31.9D}$-substituted or unsubstituted heteroalkyl (e.g., 2 to 8 membered heteroalkyl, 2 to 6 membered heteroalkyl, or 2 to 4 membered heteroalkyl), $R^{31.9D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{31.9D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31.9D}$-substituted or unsubstituted aryl (e.g., $C_6$-$C_{10}$ aryl, $C_{10}$ aryl, or phenyl), or $R^{31.9D}$-substituted or unsubstituted heteroaryl (e.g., 5 to 10 membered heteroaryl, 5 to 9 membered heteroaryl, or 5 to 6 membered heteroaryl).

$R^{31.6}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{32.6}$-substituted or unsubstituted alkyl (e.g., $C_1$-$C_8$ alkyl, $C_1$-$C_6$ alkyl, or $C_1$-$C_4$ alkyl), $R^{32.6}$-substituted or unsubstituted heteroalkyl (e.g., 2 to 8 membered heteroalkyl, 2 to 6 membered heteroalkyl, or 2 to 4 membered heteroalkyl), $R^{32.6}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32.6}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32.6}$-substituted or unsubstituted aryl (e.g., $C_6$-$C_{10}$ aryl, $C_{10}$ aryl, or phenyl), or $R^{32.6}$-substituted or unsubstituted heteroaryl (e.g., 5 to 10 membered heteroaryl, 5 to 9 membered heteroaryl, or 5 to 6 membered heteroaryl).

In embodiments, $R^{31.6}$ is $R^{32.6}$-substituted or unsubstituted alkyl (e.g., $C_1$-$C_8$ alkyl, $C_1$-$C_6$ alkyl, or $C_1$-$C_4$ alkyl). In embodiments, $R^{31.6}$ is $R^{32.6}$-substituted alkyl (e.g., $C_1$-$C_8$ alkyl, $C_1$-$C_6$ alkyl, or $C_1$-$C_4$ alkyl). In embodiments, $R^{31.6}$ is an unsubstituted alkyl (e.g., $C_1$-$C_8$ alkyl, $C_1$-$C_6$ alkyl, or $C_1$-$C_4$ alkyl).

In embodiments, $R^{31.6}$ is $R^{32.6}$-substituted or unsubstituted heteroalkyl (e.g., 2 to 8 membered heteroalkyl, 2 to 6 membered heteroalkyl, or 2 to 4 membered heteroalkyl). In embodiments, $R^{31.6}$ is $R^{32.6}$-substituted heteroalkyl (e.g., 2 to 8 membered heteroalkyl, 2 to 6 membered heteroalkyl, or 2 to 4 membered heteroalkyl). In embodiments, $R^{31.6}$ is an unsubstituted heteroalkyl (e.g., 2 to 8 membered heteroalkyl, 2 to 6 membered heteroalkyl, or 2 to 4 membered heteroalkyl).

In embodiments, $R^{31.6}$ is $R^{32.6}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{31.6}$ is $R^{32.6}$-substituted cycloalkyl (e.g., $C_3$-$C_8$ cycloalkyl, $C_3$-$C_6$ cycloalkyl, or $C_5$-$C_6$ cycloalkyl). In embodiments, $R^{31.6}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{31.6}$ is $R^{32.6}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{31.6}$ is $R^{32.6}$-substituted heterocycloalkyl (e.g., 3 to 8 membered heterocycloalkyl, 3 to 6 membered heterocycloalkyl, or 5 to 6 membered heterocycloalkyl). In embodiments, $R^{31.6}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{31.6}$ is $R^{32.6}$-substituted or unsubstituted aryl (e.g., $C_6$-$C_{10}$ aryl, $C_{10}$ aryl, or phenyl). In embodiments, $R^{31.6}$ is $R^{32.6}$-substituted aryl (e.g., $C_6$-$C_{10}$ aryl, $C_{10}$ aryl, or phenyl). In embodiments, $R^{31.6}$ is an unsubstituted aryl (e.g., $C_6$-$C_{10}$ aryl, $C_{10}$ aryl, or phenyl).

In embodiments, $R^{31.6}$ is $R^{32.6}$-substituted or unsubstituted heteroaryl (e.g., 5 to 10 membered heteroaryl, 5 to 9 membered heteroaryl, or 5 to 6 membered heteroaryl). In embodiments, $R^{31.6}$ is $R^{32.6}$-substituted heteroaryl (e.g., 5 to 10 membered heteroaryl, 5 to 9 membered heteroaryl, or 5 to 6 membered heteroaryl). In embodiments, $R^{31.6}$ is an unsubstituted heteroaryl (e.g., 5 to 10 membered heteroaryl, 5 to 9 membered heteroaryl, or 5 to 6 membered heteroaryl).

$R^{32.6}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{33.6}$-substituted or unsubstituted alkyl (e.g., $C_1$-$C_8$ alkyl, $C_1$-$C_6$ alkyl, or $C_1$-$C_4$ alkyl), $R^{33.6}$-substituted or unsubstituted heteroalkyl (e.g., 2 to 8 membered heteroalkyl, 2 to 6 membered heteroalkyl, or 2 to 4 membered heteroalkyl), $R^{33.6}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{33.6}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33.6}$-substituted or unsubstituted aryl (e.g., $C_6$-$C_{10}$ aryl, $C_{10}$ aryl, or phenyl), or $R^{33.6}$-substituted or unsubstituted heteroaryl (e.g., 5 to 10 membered heteroaryl, 5 to 9 membered heteroaryl, or 5 to 6 membered heteroaryl).

In embodiments, $R^{32.6}$ is $R^{33.6}$-substituted or unsubstituted alkyl (e.g., $C_1$-$C_8$ alkyl, $C_1$-$C_6$ alkyl, or $C_1$-$C_4$ alkyl). In embodiments, $R^{32.6}$ is $R^{33.6}$-substituted alkyl (e.g., $C_1$-$C_8$ alkyl, $C_1$-$C_6$ alkyl, or $C_1$-$C_4$ alkyl). In embodiments, $R^{32.6}$ is an unsubstituted alkyl (e.g., $C_1$-$C_8$ alkyl, $C_1$-$C_6$ alkyl, or $C_1$-$C_4$ alkyl).

In embodiments, $R^{32.6}$ is $R^{33.6}$-substituted or unsubstituted heteroalkyl (e.g., 2 to 8 membered heteroalkyl, 2 to 6 membered heteroalkyl, or 2 to 4 membered heteroalkyl). In embodiments, $R^{32.6}$ is $R^{33.6}$-substituted heteroalkyl (e.g., 2 to 8 membered heteroalkyl, 2 to 6 membered heteroalkyl, or 2 to 4 membered heteroalkyl). In embodiments, $R^{32.6}$ is an unsubstituted heteroalkyl (e.g., 2 to 8 membered heteroalkyl, 2 to 6 membered heteroalkyl, or 2 to 4 membered heteroalkyl).

In embodiments, $R^{32.6}$ is $R^{33.6}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{32.6}$ is $R^{33.6}$-substituted cycloalkyl (e.g., $C_3$-$C_8$ cycloalkyl, $C_3$-$C_6$ cycloalkyl, or $C_5$-$C_6$ cycloalkyl). In embodiments, $R^{32.6}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{32.6}$ is $R^{33.6}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{32.6}$ is $R^{33.6}$-substituted heterocycloalkyl (e.g., 3 to 8 membered heterocycloalkyl, 3 to 6 membered heterocycloalkyl, or 5 to 6 membered heterocycloalkyl). In embodiments, $R^{32.6}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{32.6}$ is $R^{33.6}$-substituted or unsubstituted aryl (e.g., $C_6$-$C_{10}$ aryl, $C_{10}$ aryl, or phenyl). In embodiments, $R^{32.6}$ is $R^{33.6}$-substituted aryl (e.g., $C_6$-$C_{10}$ aryl, $C_{10}$ aryl, or phenyl). In embodiments, $R^{32.6}$ is an unsubstituted aryl (e.g., $C_6$-$C_{10}$ aryl, $C_{10}$ aryl, or phenyl).

In embodiments, $R^{32.6}$ is $R^{33.6}$-substituted or unsubstituted heteroaryl (e.g., 5 to 10 membered heteroaryl, 5 to 9 membered heteroaryl, or 5 to 6 membered heteroaryl). In embodiments, $R^{32.6}$ is $R^{33.6}$-substituted heteroaryl (e.g., 5 to 10 membered heteroaryl, 5 to 9 membered heteroaryl, or 5 to 6 membered heteroaryl). In embodiments, $R^{32.6}$ is an unsubstituted heteroaryl (e.g., 5 to 10 membered heteroaryl, 5 to 9 membered heteroaryl, or 5 to 6 membered heteroaryl).

$R^{31.7}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^{32.7}$-substituted or unsubstituted alkyl (e.g., $C_1$-$C_8$ alkyl, $C_1$-$C_6$ alkyl, or $C_1$-$C_4$ alkyl), $R^{32.7}$-substituted or unsubstituted heteroalkyl (e.g., 2 to 8 membered heteroalkyl, 2 to 6 membered heteroalkyl, or 2 to 4 membered heteroalkyl), $R^{32.7}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32.7}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32.7}$-substituted or unsubstituted aryl (e.g., $C_6$-$C_{10}$ aryl, $C_{10}$ aryl, or phenyl), or $R^{32.7}$-substituted or unsubstituted heteroaryl (e.g., 5 to 10 membered heteroaryl, 5 to 9 membered heteroaryl, or 5 to 6 membered heteroaryl).

In embodiments, $R^{31.7}$ is $R^{32.7}$-substituted or unsubstituted alkyl (e.g., $C_1$-$C_8$ alkyl, $C_1$-$C_6$ alkyl, or $C_1$-$C_4$ alkyl). In embodiments, $R^{31.7}$ is $R^{32.7}$-substituted alkyl (e.g., $C_1$-$C_8$ alkyl, $C_1$-$C_6$ alkyl, or $C_1$-$C_4$ alkyl). In embodiments, $R^{31.7}$ is an unsubstituted alkyl (e.g., $C_1$-$C_8$ alkyl, $C_1$-$C_6$ alkyl, or $C_1$-$C_4$ alkyl).

In embodiments, $R^{31.7}$ is $R^{32.7}$-substituted or unsubstituted heteroalkyl (e.g., 2 to 8 membered heteroalkyl, 2 to 6 membered heteroalkyl, or 2 to 4 membered heteroalkyl). In embodiments, $R^{31.7}$ is $R^{32.7}$-substituted heteroalkyl (e.g., 2 to 8 membered heteroalkyl, 2 to 6 membered heteroalkyl, or 2 to 4 membered heteroalkyl). In embodiments, $R^{31.7}$ is an unsubstituted heteroalkyl (e.g., 2 to 8 membered heteroalkyl, 2 to 6 membered heteroalkyl, or 2 to 4 membered heteroalkyl).

In embodiments, $R^{31.7}$ is $R^{32.7}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{31.7}$ is $R^{32.7}$-substituted cycloalkyl (e.g., $C_3$-$C_8$ cycloalkyl, $C_3$-$C_6$ cycloalkyl, or $C_5$-$C_6$ cycloalkyl). In embodiments, $R^{31.7}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{31.7}$ is $R^{32.7}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{31.7}$ is $R^{32.7}$-substituted heterocycloalkyl (e.g., 3 to 8 membered heterocycloalkyl, 3 to 6 membered heterocycloalkyl, or 5 to 6 membered heterocycloalkyl). In embodiments, $R^{31.7}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{31.7}$ is $R^{32.7}$-substituted or unsubstituted aryl (e.g., $C_6$-$C_{10}$ aryl, $C_{10}$ aryl, or phenyl). In embodiments, $R^{31.7}$ is $R^{32.7}$-substituted aryl (e.g., $C_6$-$C_{10}$ aryl, $C_{10}$ aryl, or phenyl). In embodiments, $R^{31.7}$ is an unsubstituted aryl (e.g., $C_6$-$C_{10}$ aryl, $C_{10}$ aryl, or phenyl).

In embodiments, $R^{31.7}$ is $R^{32.7}$-substituted or unsubstituted heteroaryl (e.g., 5 to 10 membered heteroaryl, 5 to 9 membered heteroaryl, or 5 to 6 membered heteroaryl). In embodiments, $R^{31.7}$ is $R^{32.7}$-substituted heteroaryl (e.g., 5 to 10 membered heteroaryl, 5 to 9 membered heteroaryl, or 5 to 6 membered heteroaryl). In embodiments, $R^{31.7}$ is an unsubstituted heteroaryl (e.g., 5 to 10 membered heteroaryl, 5 to 9 membered heteroaryl, or 5 to 6 membered heteroaryl).

$R^{32.7}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{33.7}$-substituted or unsubstituted alkyl (e.g., $C_1$-$C_8$ alkyl, $C_1$-$C_6$ alkyl, or $C_1$-$C_4$ alkyl), $R^{33.7}$-substituted or unsubstituted heteroalkyl (e.g., 2 to 8 membered heteroalkyl, 2 to 6 membered heteroalkyl, or 2 to 4 membered heteroalkyl), $R^{33.7}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{33.7}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33.7}$-substituted or unsubstituted aryl (e.g., $C_6$-$C_{10}$ aryl, $C_{10}$ aryl, or phenyl), or $R^{33.7}$-substituted or unsubstituted heteroaryl (e.g., 5 to 10 membered heteroaryl, 5 to 9 membered heteroaryl, or 5 to 6 membered heteroaryl).

In embodiments, $R^{32.7}$ is $R^{33.7}$-substituted or unsubstituted alkyl (e.g., $C_1$-$C_8$ alkyl, $C_1$-$C_6$ alkyl, or $C_1$-$C_4$ alkyl). In embodiments, $R^{32.7}$ is $R^{33.7}$-substituted alkyl (e.g., $C_1$-$C_8$ alkyl, $C_1$-$C_6$ alkyl, or $C_1$-$C_4$ alkyl). In embodiments, $R^{32.7}$ is an unsubstituted alkyl (e.g., $C_1$-$C_8$ alkyl, $C_1$-$C_6$ alkyl, or $C_1$-$C_4$ alkyl).

In embodiments, $R^{32.7}$ is $R^{33.7}$-substituted or unsubstituted heteroalkyl (e.g., 2 to 8 membered heteroalkyl, 2 to 6 membered heteroalkyl, or 2 to 4 membered heteroalkyl). In embodiments, $R^{32.7}$ is $R^{33.7}$-substituted heteroalkyl (e.g., 2 to 8 membered heteroalkyl, 2 to 6 membered heteroalkyl, or 2 to 4 membered heteroalkyl). In embodiments, $R^{32.7}$ is an unsubstituted heteroalkyl (e.g., 2 to 8 membered heteroalkyl, 2 to 6 membered heteroalkyl, or 2 to 4 membered heteroalkyl).

In embodiments, $R^{32.7}$ is $R^{33.7}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{32.7}$ is $R^{33.7}$-substituted cycloalkyl (e.g., $C_3$-$C_8$ cycloalkyl, $C_3$-$C_6$ cycloalkyl, or $C_5$-$C_6$ cycloalkyl). In embodiments, $R^{32.7}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{32.7}$ is $R^{33.7}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{32.7}$ is $R^{33.7}$-substituted heterocycloalkyl (e.g., 3 to 8 membered heterocycloalkyl, 3 to 6 membered heterocycloalkyl, or 5 to 6 membered heterocycloalkyl). In embodiments, $R^{32.7}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{32.7}$ is $R^{33.7}$-substituted or unsubstituted aryl (e.g., $C_6$-$C_{10}$ aryl, $C_{10}$ aryl, or phenyl). In embodiments, $R^{32.7}$ is $R^{33.7}$-substituted aryl (e.g., $C_6$-$C_{10}$ aryl, $C_{10}$ aryl, or phenyl). In embodiments, $R^{32.7}$ is an unsubstituted aryl (e.g., $C_6$-$C_{10}$ aryl, $C_{10}$ aryl, or phenyl).

In embodiments, $R^{32.7}$ is $R^{33.7}$-substituted or unsubstituted heteroaryl (e.g., 5 to 10 membered heteroaryl, 5 to 9 membered heteroaryl, or 5 to 6 membered heteroaryl). In embodiments, $R^{32.7}$ is $R^{33.7}$-substituted heteroaryl (e.g., 5 to 10 membered heteroaryl, 5 to 9 membered heteroaryl, or 5 to 6 membered heteroaryl). In embodiments, $R^{32.7}$ is an unsubstituted heteroaryl (e.g., 5 to 10 membered heteroaryl, 5 to 9 membered heteroaryl, or 5 to 6 membered heteroaryl).

$R^{31.8}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, $R^{32.8}$-substituted or unsubstituted alkyl (e.g., $C_1$-$C_8$ alkyl, $C_1$-$C_6$ alkyl, or $C_1$-$C_4$ alkyl), $R^{32.8}$-substituted or unsubstituted heteroalkyl (e.g., 2 to 8 membered heteroalkyl, 2 to 6 membered heteroalkyl, or 2 to 4 membered heteroalkyl), $R^{32.8}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32.8}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32.8}$-substituted or unsubstituted aryl (e.g., $C_6$-$C_{10}$ aryl, $C_{10}$ aryl, or phenyl), or $R^{32.8}$-substituted or unsubstituted heteroaryl (e.g., 5 to 10 membered heteroaryl, 5 to 9 membered heteroaryl, or 5 to 6 membered heteroaryl).

In embodiments, $R^{31.8}$ is $R^{32.8}$-substituted or unsubstituted alkyl (e.g., $C_1$-$C_8$ alkyl, $C_1$-$C_6$ alkyl, or $C_1$-$C_4$ alkyl). In embodiments, $R^{31.8}$ is $R^{32.8}$-substituted alkyl (e.g., $C_1$-$C_8$ alkyl, $C_1$-$C_6$ alkyl, or $C_1$-$C_4$ alkyl). In embodiments, $R^{31.8}$ is an unsubstituted alkyl (e.g., $C_1$-$C_8$ alkyl, $C_1$-$C_6$ alkyl, or $C_1$-$C_4$ alkyl).

In embodiments, $R^{31.8}$ is $R^{32.8}$-substituted or unsubstituted heteroalkyl (e.g., 2 to 8 membered heteroalkyl, 2 to 6 membered heteroalkyl, or 2 to 4 membered heteroalkyl). In embodiments, $R^{31.8}$ is $R^{32.8}$-substituted heteroalkyl (e.g., 2 to 8 membered heteroalkyl, 2 to 6 membered heteroalkyl, or 2 to 4 membered heteroalkyl). In embodiments, $R^{31.8}$ is an unsubstituted heteroalkyl (e.g., 2 to 8 membered heteroalkyl, 2 to 6 membered heteroalkyl, or 2 to 4 membered heteroalkyl).

In embodiments, $R^{31.8}$ is $R^{32.8}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{31.8}$ is $R^{32.8}$-substituted cycloalkyl (e.g., $C_3$-$C_8$ cycloalkyl, $C_3$-$C_6$ cycloalkyl, or $C_5$-$C_6$ cycloalkyl). In embodiments, $R^{31.8}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{31.8}$ is $R^{32.8}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{31.8}$ is $R^{32.8}$-substituted heterocycloalkyl (e.g., 3 to 8 membered heterocycloalkyl, 3 to 6 membered heterocycloalkyl, or 5 to 6 membered heterocycloalkyl). In embodiments, $R^{31.8}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{31.8}$ is $R^{32.8}$-substituted or unsubstituted aryl (e.g., $C_6$-$C_{10}$ aryl, $C_{10}$ aryl, or phenyl). In embodiments, $R^{31.8}$ is $R^{32.8}$-substituted aryl (e.g., $C_6$-$C_{10}$ aryl, $C_{10}$ aryl, or phenyl). In embodiments, $R^{31.8}$ is an unsubstituted aryl (e.g., $C_6$-$C_{10}$ aryl, $C_{10}$ aryl, or phenyl).

In embodiments, $R^{31.8}$ is $R^{32.8}$-substituted or unsubstituted heteroaryl (e.g., 5 to 10 membered heteroaryl, 5 to 9 membered heteroaryl, or 5 to 6 membered heteroaryl). In embodiments, $R^{31.8}$ is $R^{32.8}$-substituted heteroaryl (e.g., 5 to 10 membered heteroaryl, 5 to 9 membered heteroaryl, or 5 to 6 membered heteroaryl). In embodiments, $R^{31.8}$ is an unsubstituted heteroaryl (e.g., 5 to 10 membered heteroaryl, 5 to 9 membered heteroaryl, or 5 to 6 membered heteroaryl).

$R^{32.8}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, R$^{33.8}$-substituted or unsubstituted alkyl (e.g., C$_1$-C$_8$ alkyl, C$_1$-C$_6$ alkyl, or C$_1$-C$_4$ alkyl), R$^{33.8}$-substituted or unsubstituted heteroalkyl (e.g., 2 to 8 membered heteroalkyl, 2 to 6 membered heteroalkyl, or 2 to 4 membered heteroalkyl), R$^{33.8}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{33.8}$-substituted or unsubstituted heterocycloalkyl (e.g., 3 to 8 membered heterocycloalkyl, 3 to 6 membered heterocycloalkyl, or 5 to 6 membered heterocycloalkyl), R$^{33.8}$-substituted or unsubstituted aryl (e.g., C$_6$-C$_{10}$ aryl, C$_{10}$ aryl, or phenyl), or R$^{33.8}$-substituted or unsubstituted heteroaryl (e.g., 5 to 10 membered heteroaryl, 5 to 9 membered heteroaryl, or 5 to 6 membered heteroaryl).

In embodiments, R$^{32.8}$ is R$^{33.8}$-substituted or unsubstituted alkyl (e.g., C$_1$-C$_8$ alkyl, C$_1$-C$_6$ alkyl, or C$_1$-C$_4$ alkyl). In embodiments, R$^{32.8}$ is R$^{33.8}$-substituted alkyl (e.g., C$_1$-C$_8$ alkyl, C$_1$-C$_6$ alkyl, or C$_1$-C$_4$ alkyl). In embodiments, R$^{32.8}$ is an unsubstituted alkyl (e.g., C$_1$-C$_8$ alkyl, C$_1$-C$_6$ alkyl, or C$_1$-C$_4$ alkyl).

In embodiments, R$^{32.8}$ is R$^{33.8}$-substituted or unsubstituted heteroalkyl (e.g., 2 to 8 membered heteroalkyl, 2 to 6 membered heteroalkyl, or 2 to 4 membered heteroalkyl). In embodiments, R$^{32.8}$ is R$^{33.8}$-substituted heteroalkyl (e.g., 2 to 8 membered heteroalkyl, 2 to 6 membered heteroalkyl, or 2 to 4 membered heteroalkyl). In embodiments, R$^{32.8}$ is an unsubstituted heteroalkyl (e.g., 2 to 8 membered heteroalkyl, 2 to 6 membered heteroalkyl, or 2 to 4 membered heteroalkyl).

In embodiments, R$^{32.8}$ is R$^{33.8}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{32.8}$ is R$^{33.8}$-substituted cycloalkyl (e.g., C$_3$-C$_8$ cycloalkyl, C$_3$-C$_6$ cycloalkyl, or C$_5$-C$_6$ cycloalkyl). In embodiments, R$^{32.8}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^{32.8}$ is R$^{33.8}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{32.8}$ is R$^{33.8}$-substituted heterocycloalkyl (e.g., 3 to 8 membered heterocycloalkyl, 3 to 6 membered heterocycloalkyl, or 5 to 6 membered heterocycloalkyl). In embodiments, R$^{32.8}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^{32.8}$ is R$^{33.8}$-substituted or unsubstituted aryl (e.g., C$_6$-C$_{10}$ aryl, C$_{10}$ aryl, or phenyl). In embodiments, R$^{32.8}$ is R$^{33.8}$-substituted aryl (e.g., C$_6$-C$_{10}$ aryl, C$_{10}$ aryl, or phenyl). In embodiments, R$^{32.8}$ is an unsubstituted aryl (e.g., C$_6$-C$_{10}$ aryl, C$_{10}$ aryl, or phenyl).

In embodiments, R$^{32.8}$ is R$^{33.8}$-substituted or unsubstituted heteroaryl (e.g., 5 to 10 membered heteroaryl, 5 to 9 membered heteroaryl, or 5 to 6 membered heteroaryl). In embodiments, R$^{32.8}$ is R$^{33.8}$-substituted heteroaryl (e.g., 5 to 10 membered heteroaryl, 5 to 9 membered heteroaryl, or 5 to 6 membered heteroaryl). In embodiments, R$^{32.8}$ is an unsubstituted heteroaryl (e.g., 5 to 10 membered heteroaryl, 5 to 9 membered heteroaryl, or 5 to 6 membered heteroaryl).

R$^{31.9}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, R$^{32.9}$-substituted or unsubstituted alkyl (e.g., C$_1$-C$_8$ alkyl, C$_1$-C$_6$ alkyl, or C$_1$-C$_4$ alkyl), R$^{32.9}$-substituted or unsubstituted heteroalkyl (e.g., 2 to 8 membered heteroalkyl, 2 to 6 membered heteroalkyl, or 2 to 4 membered heteroalkyl), R$^{32.9}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{32.9}$-substituted or unsubstituted heterocycloalkyl (e.g., 3 to 8 membered heterocycloalkyl, 3 to 6 membered heterocycloalkyl, or 5 to 6 membered heterocycloalkyl), R$^{32.9}$-substituted or unsubstituted aryl (e.g., C$_6$-C$_{10}$ aryl, C$_{10}$ aryl, or phenyl), or R$^{32.9}$-substituted or unsubstituted heteroaryl (e.g., 5 to 10 membered heteroaryl, 5 to 9 membered heteroaryl, or 5 to 6 membered heteroaryl).

In embodiments, R$^{31.9}$ is R$^{32.9}$-substituted or unsubstituted alkyl (e.g., C$_1$-C$_8$ alkyl, C$_1$-C$_6$ alkyl, or C$_1$-C$_4$ alkyl). In embodiments, R$^{31.9}$ is R$^{32.9}$-substituted alkyl (e.g., C$_1$-C$_8$ alkyl, C$_1$-C$_6$ alkyl, or C$_1$-C$_4$ alkyl). In embodiments, R$^{31.9}$ is an unsubstituted alkyl (e.g., C$_1$-C$_8$ alkyl, C$_1$-C$_6$ alkyl, or C$_1$-C$_4$ alkyl).

In embodiments, R$^{31.9}$ is R$^{32.9}$-substituted or unsubstituted heteroalkyl (e.g., 2 to 8 membered heteroalkyl, 2 to 6 membered heteroalkyl, or 2 to 4 membered heteroalkyl). In embodiments, R$^{31.9}$ is R$^{32.9}$-substituted heteroalkyl (e.g., 2 to 8 membered heteroalkyl, 2 to 6 membered heteroalkyl, or 2 to 4 membered heteroalkyl). In embodiments, R$^{31.9}$ is an unsubstituted heteroalkyl (e.g., 2 to 8 membered heteroalkyl, 2 to 6 membered heteroalkyl, or 2 to 4 membered heteroalkyl).

In embodiments, R$^{31.9}$ is R$^{32.9}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{31.9}$ is R$^{32.9}$-substituted cycloalkyl (e.g., C$_3$-C$_8$ cycloalkyl, C$_3$-C$_6$ cycloalkyl, or C$_5$-C$_6$ cycloalkyl). In embodiments, R$^{31.9}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^{31.9}$ is R$^{32.9}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{31.9}$ is R$^{32.9}$-substituted heterocycloalkyl (e.g., 3 to 8 membered heterocycloalkyl, 3 to 6 membered heterocycloalkyl, or 5 to 6 membered heterocycloalkyl). In embodiments, R$^{31.9}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^{31.9}$ is R$^{32.9}$-substituted or unsubstituted aryl (e.g., C$_6$-C$_{10}$ aryl, C$_{10}$ aryl, or phenyl). In embodiments, R$^{31.9}$ is R$^{32.9}$-substituted aryl (e.g., C$_6$-C$_{10}$ aryl, C$_{10}$ aryl, or phenyl). In embodiments, R$^{31.9}$ is an unsubstituted aryl (e.g., C$_6$-C$_{10}$ aryl, C$_{10}$ aryl, or phenyl).

In embodiments, R$^{31.9}$ is R$^{32.9}$-substituted or unsubstituted heteroaryl (e.g., 5 to 10 membered heteroaryl, 5 to 9 membered heteroaryl, or 5 to 6 membered heteroaryl). In embodiments, R$^{31.9}$ is R$^{32.9}$-substituted heteroaryl (e.g., 5 to 10 membered heteroaryl, 5 to 9 membered heteroaryl, or 5 to 6 membered heteroaryl). In embodiments, R$^{31.9}$ is an unsubstituted heteroaryl (e.g., 5 to 10 membered heteroaryl, 5 to 9 membered heteroaryl, or 5 to 6 membered heteroaryl).

R$^{32.9}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, R$^{33.9}$-substituted or unsubstituted alkyl (e.g., C$_1$-C$_8$ alkyl, C$_1$-C$_6$ alkyl, or C$_1$-C$_4$ alkyl), R$^{33.9}$-substituted or unsubstituted heteroalkyl (e.g., 2 to 8 membered heteroalkyl, 2 to 6 membered heteroalkyl, or 2 to 4 membered heteroalkyl), $R^{33.9}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{33.9}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33.9}$-substituted or unsubstituted aryl (e.g., $C_6$-$C_{10}$ aryl, $C_{10}$ aryl, or phenyl), or $R^{33.9}$-substituted or unsubstituted heteroaryl (e.g., 5 to 10 membered heteroaryl, 5 to 9 membered heteroaryl, or 5 to 6 membered heteroaryl).

In embodiments, $R^{32.9}$ is $R^{33.9}$-substituted or unsubstituted alkyl (e.g., $C_1$-$C_8$ alkyl, $C_1$-$C_6$ alkyl, or $C_1$-$C_4$ alkyl). In embodiments, $R^{32.9}$ is $R^{33.9}$-substituted alkyl (e.g., $C_1$-$C_8$ alkyl, $C_1$-$C_6$ alkyl, or $C_1$-$C_4$ alkyl). In embodiments, $R^{32.9}$ is an unsubstituted alkyl (e.g., $C_1$-$C_8$ alkyl, $C_1$-$C_6$ alkyl, or $C_1$-$C_4$ alkyl).

In embodiments, $R^{32.9}$ is $R^{33.9}$-substituted or unsubstituted heteroalkyl (e.g., 2 to 8 membered heteroalkyl, 2 to 6 membered heteroalkyl, or 2 to 4 membered heteroalkyl). In embodiments, $R^{32.9}$ is $R^{33.9}$-substituted heteroalkyl (e.g., 2 to 8 membered heteroalkyl, 2 to 6 membered heteroalkyl, or 2 to 4 membered heteroalkyl). In embodiments, $R^{32.9}$ is an unsubstituted heteroalkyl (e.g., 2 to 8 membered heteroalkyl, 2 to 6 membered heteroalkyl, or 2 to 4 membered heteroalkyl).

In embodiments, $R^{32.9}$ is $R^{33.9}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{32.9}$ is $R^{33.9}$-substituted cycloalkyl (e.g., $C_3$-$C_8$ cycloalkyl, $C_3$-$C_6$ cycloalkyl, or $C_5$-$C_6$ cycloalkyl). In embodiments, $R^{32.9}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{32.9}$ is $R^{33.9}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{32.9}$ is $R^{33.9}$-substituted heterocycloalkyl (e.g., 3 to 8 membered heterocycloalkyl, 3 to 6 membered heterocycloalkyl, or 5 to 6 membered heterocycloalkyl). In embodiments, $R^{32.9}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{32.9}$ is $R^{33.9}$-substituted or unsubstituted aryl (e.g., $C_6$-$C_{10}$ aryl, $C_{10}$ aryl, or phenyl). In embodiments, $R^{32.9}$ is $R^{33.9}$-substituted aryl (e.g., $C_6$-$C_{10}$ aryl, $C_{10}$ aryl, or phenyl). In embodiments, $R^{32.9}$ is an unsubstituted aryl (e.g., $C_6$-$C_{10}$ aryl, $C_{10}$ aryl, or phenyl).

In embodiments, $R^{32.9}$ is $R^{33.9}$-substituted or unsubstituted heteroaryl (e.g., 5 to 10 membered heteroaryl, 5 to 9 membered heteroaryl, or 5 to 6 membered heteroaryl). In embodiments, $R^{32.9}$ is $R^{33.9}$-substituted heteroaryl (e.g., 5 to 10 membered heteroaryl, 5 to 9 membered heteroaryl, or 5 to 6 membered heteroaryl). In embodiments, $R^{32.9}$ is an unsubstituted heteroaryl (e.g., 5 to 10 membered heteroaryl, 5 to 9 membered heteroaryl, or 5 to 6 membered heteroaryl).

$R^{31.6A}$, $R^{31.6B}$, $R^{31.6C}$, $R^{31.6D}$, $R^{31.7A}$, $R^{31.7B}$, $R^{31.7C}$, $R^{31.7D}$, $R^{31.8A}$, $R^{31.8B}$, $R^{31.8C}$, $R^{31.8D}$, $R^{31.9A}$, $R^{31.9B}$, $R^{31.9C}$, $R^{31.9D}$, $R^{33.6}$, $R^{33.7}$, $R^{33.8}$ and $R^{33.9}$ are independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{31.6A}$, $R^{31.6B}$, $R^{31.6C}$, $R^{31.6D}$, $R^{31.7A}$, $R^{31.7B}$, $R^{31.7C}$, $R^{31.7D}$, $R^{31.8A}$, $R^{31.8B}$, $R^{31.8C}$, $R^{31.8D}$, $R^{31.9A}$, $R^{31.9B}$, $R^{31.9C}$, $R^{31.9D}$, $R^{33.6}$, $R^{33.7}$, $R^{33.8}$ and $R^{33.9}$ are independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{6.6A}$, $R^{6.6B}$, $R^{6.6C}$, $R^{6.6D}$, $R^{6.7A}$, $R^{6.7B}$ $R^{6.7C}$, $R^{6.7D}$, $R^{6.8A}$, $R^{6.8B}$, $R^{6.8C}$, $R^{6.8D}$, $R^{6.9A}$, $R^{6.9B}$, $R^{6.9C}$, and $R^{6.9D}$ are independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{6.6A}$, $R^{6.6B}$, $R^{6.6C}$, $R^{6.6D}$, $R^{6.7A}$, $R^{6.7B}$ $R^{6.7C}$, $R^{6.7D}$, $R^{6.8A}$, $R^{6.8B}$, $R^{6.8C}$, $R^{6.8D}$, $R^{6.9A}$, $R^{6.9B}$, $R^{6.9C}$, and $R^{6.9D}$ are independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $X^{6.6}$, $X^{6.7}$, $X^{6.8}$ and $X^{6.9}$ are independently —Cl, —Br, —I or —F.

In embodiments, $X^{6.6}$ is —Cl. In embodiments, $X^{6.6}$ is —F. In embodiments, $X^{6.6}$ is —Br. In embodiments, $X^{6.6}$ is —I. In embodiments, $X^{6.7}$ is —Cl. In embodiments, $X^{6.7}$ is —F. In embodiments, $X^{6.7}$ is —Br. In embodiments, $X^{6.7}$ is —I. In embodiments, $X^{6.8}$ is —Cl. In embodiments, $X^{6.8}$ is —F. In embodiments, $X^{6.8}$ is —Br. In embodiments, $X^{6.8}$ is —I. In embodiments, $X^{6.9}$ is —Cl. In embodiments, $X^{6.9}$ is —F. In embodiments, $X^{6.9}$ is —Br. In embodiments, $X^{6.9}$ is —I.

In embodiments, $X^{6.6}$ is —Cl, and $X^1$ is N. In embodiments, $X^{6.6}$ is —F, and $X^1$ is N. In embodiments, $X^{6.6}$ is —Br, and $X^1$ is N. In embodiments, $X^{6.6}$ is —I, and $X^1$ is N. In embodiments, $X^{6.7}$ is —Cl, and $X^1$ is N. In embodiments, $X^{6.7}$ is —F, and $X^1$ is N. In embodiments, $X^{6.7}$ is —Br, and $X^1$ is N. In embodiments, $X^{6.7}$ is —I, and $X^1$ is N. In embodiments, $X^{6.8}$ is —Cl, and $X^1$ is N. In embodiments, $X^{6.8}$ is —F, and $X^1$ is N. In embodiments, $X^{6.8}$ is —Br, and $X^1$ is N. In embodiments, $X^{6.8}$ is —I, and $X^1$ is N. In embodiments, $X^{6.9}$ is —Cl, and $X^1$ is N. In embodiments, $X^{6.9}$ is —F, and $X^1$ is N. In embodiments, $X^{6.9}$ is —Br, and $X^1$ is N. In embodiments, $X^{6.9}$ is —I, and $X^1$ is N.

In embodiments, $X^{6.6}$ is —Cl, and $X^2$ is N. In embodiments, $X^{6.6}$ is —F, and $X^2$ is N. In embodiments, $X^{6.6}$ is —Br, and $X^2$ is N. In embodiments, $X^{6.6}$ is —I, and $X^2$ is N. In embodiments, $X^{6.7}$ is —Cl, and $X^2$ is N. In embodiments, $X^{6.7}$ is —F, and $X^2$ is N. In embodiments, $X^{6.7}$ is —Br, and $X^2$ is N. In embodiments, $X^{6.7}$ is —I, and $X^2$ is N. In embodiments, $X^{6.8}$ is —Cl, and $X^2$ is N. In embodiments, $X^{6.8}$ is —F, and $X^2$ is N. In embodiments, $X^{6.8}$ is —Br, and $X^2$ is N. In embodiments, $X^{6.8}$ is —I, and $X^2$ is N. In embodiments, $X^{6.9}$ is —Cl, and $X^2$ is N. In embodiments, $X^{6.9}$ is —F, and $X^2$ is N. In embodiments, $X^{6.9}$ is —Br, and $X^2$ is N. In embodiments, $X^{6.9}$ is —I, and $X^2$ is N.

In embodiments, $X^{6.6}$ is —Cl, and $X^3$ is N. In embodiments, $X^{6.6}$ is —F, and $X^3$ is N. In embodiments, $X^{6.6}$ is —Br, and $X^3$ is N. In embodiments, $X^{6.6}$ is —I, and $X^3$ is N. In embodiments, $X^{6.7}$ is —Cl, and $X^3$ is N. In embodiments, $X^{6.7}$ is —F, and $X^3$ is N. In embodiments, $X^{6.7}$ is —Br, and $X^3$ is N. In embodiments, $X^{6.7}$ is —I, and $X^3$ is N. In embodiments, $X^{6.8}$ is —Cl, and $X^3$ is N. In embodiments, $X^{6.8}$ is —F, and $X^3$ is N. In embodiments, $X^{6.8}$ is —Br, and $X^3$ is N. In embodiments, $X^{6.8}$ is —I, and $X^3$ is N. In embodiments, $X^{6.9}$ is —Cl, and $X^3$ is N. In embodiments, $X^{6.9}$ is —F, and $X^3$ is N. In embodiments, $X^{6.9}$ is —Br, and $X^3$ is N. In embodiments, $X^{6.9}$ is —I, and $X^3$ is N.

In embodiments, the compounds provided herein have structural Formula (IXa):

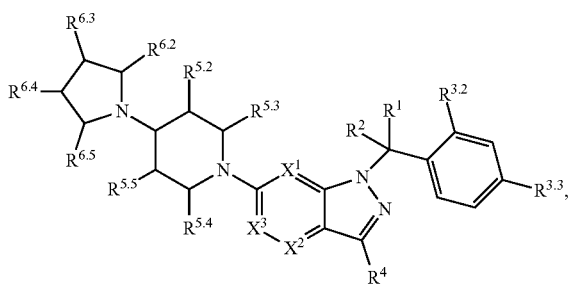

(IXa)

or a pharmaceutically acceptable salt thereof.

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments.

In embodiments, the compounds provided herein have structural Formula (IXb):

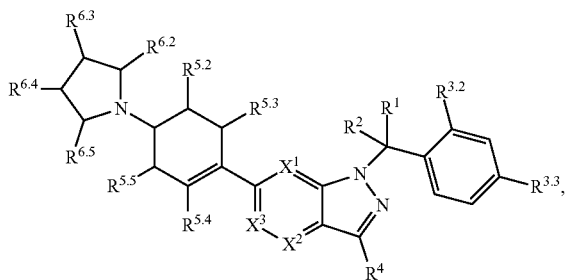

(IXb)

or a pharmaceutically acceptable salt thereof.

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments.

In embodiments, the compounds provided herein have structural Formula:

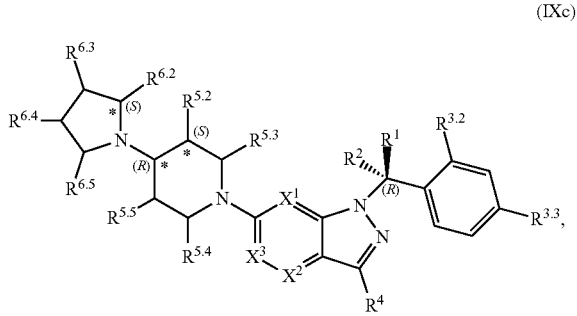

(IXc)

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments.

In embodiments, the compounds provided herein have structural Formula:

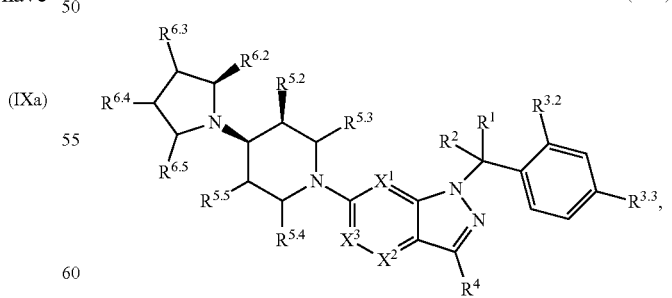

(IXci)

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula:

(IXcii)

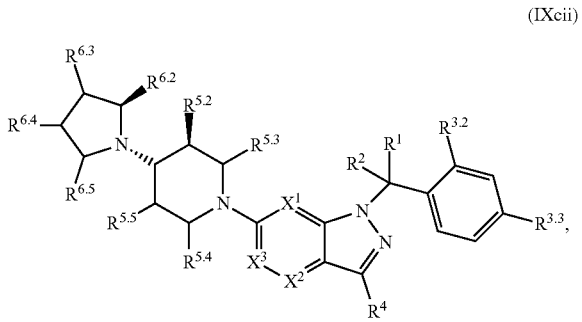

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula:

(IXciii)

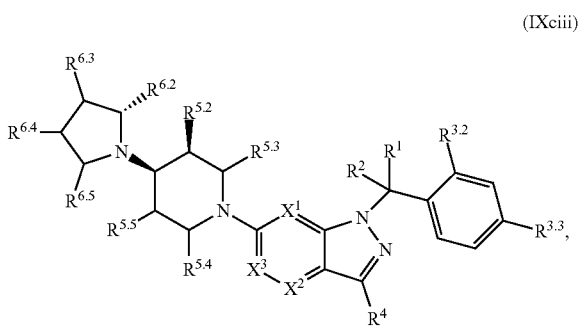

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula:

(IXciv)

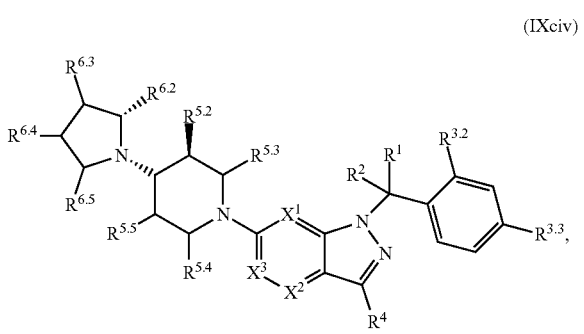

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula:

(IXcv)

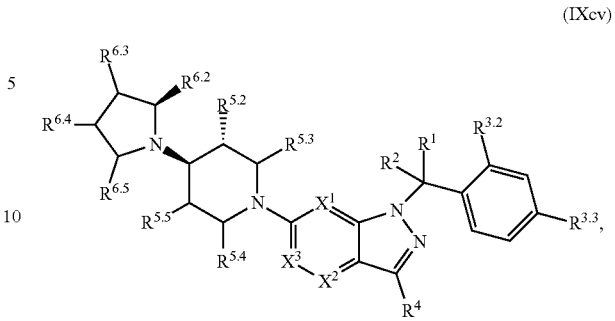

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula:

(IXcvi)

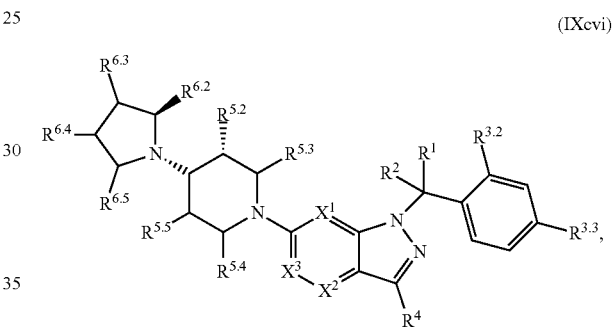

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula:

(IXcvii)

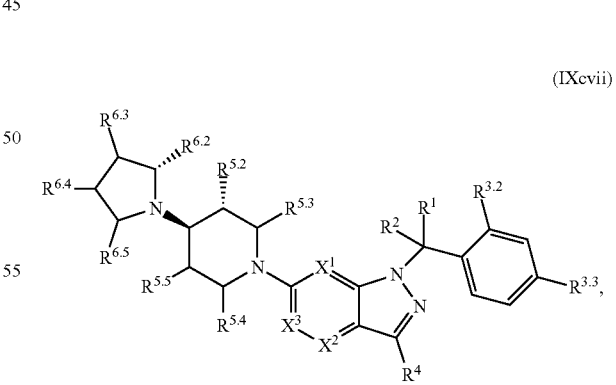

or a pharmaceutically acceptable salt thereof. $X^1$, $X^2$, $X^3$, R, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula:

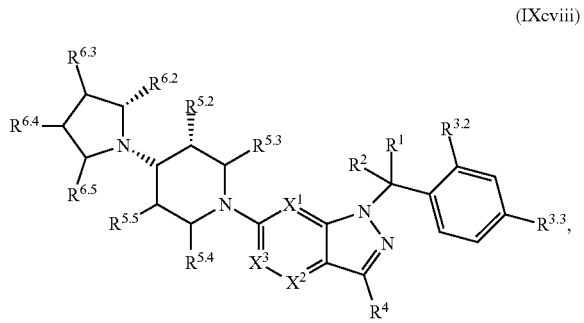

(IXcviii)

or a pharmaceutically acceptable salt thereof.

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments.

In embodiments, $R^1$ in structural Formula (IXc) is hydrogen.

In embodiments, the compounds provided herein have structural Formula:

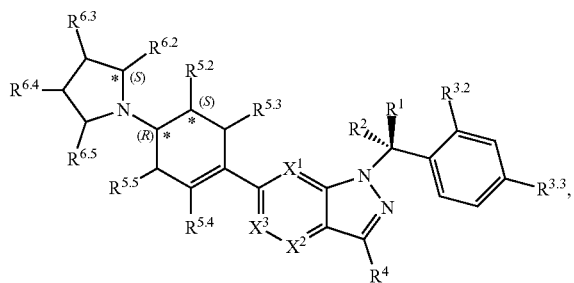

(IXd)

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments.

In embodiments, the compounds provided herein have structural Formula

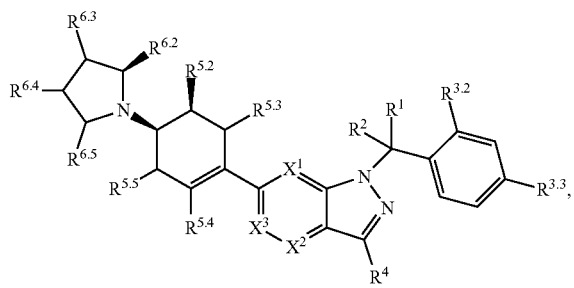

(IXdi)

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula

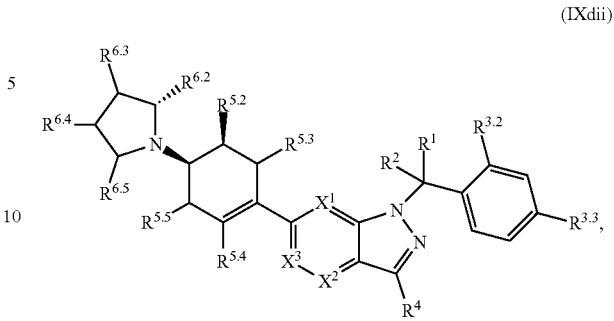

(IXdii)

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula

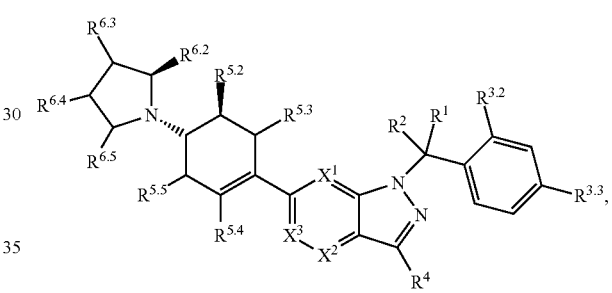

(IXdiii)

or a pharmaceutically acceptable salt thereof. $X^1$, $X^2$, $X^3$, R, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula

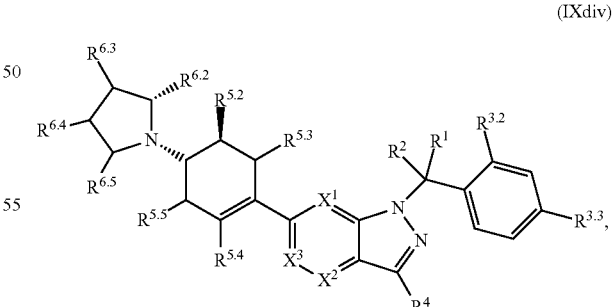

(IXdiv)

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula (IXdv)

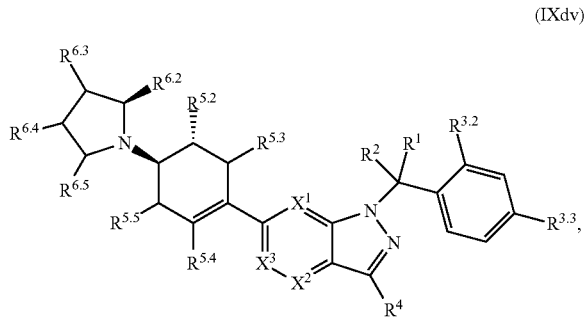

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{65}$ are as described herein, including embodiments. In embodiments, the compounds provided herein have structural Formula (IXdvi)

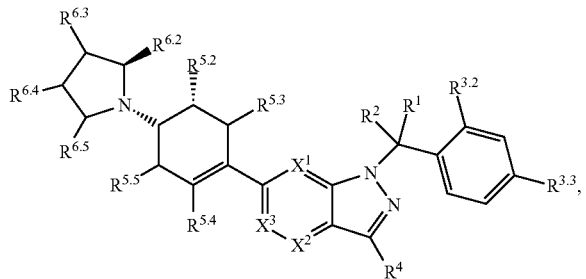

or a pharmaceutically acceptable salt thereof. $X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural (IXdvii)

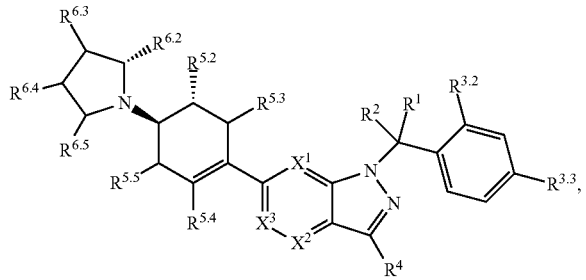

or a pharmaceutically acceptable salt thereof. $X^1$, $X^2$, $X^3$, R, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compounds provided herein have structural Formula (IXdviii)

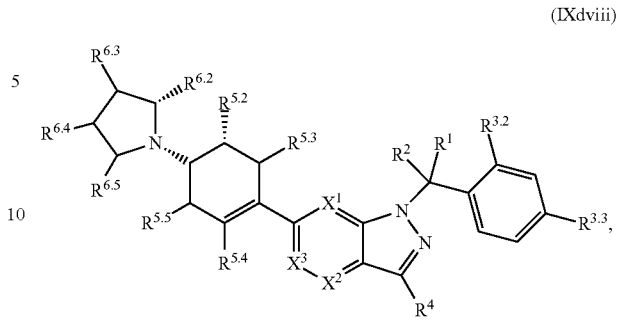

or a pharmaceutically acceptable salt thereof.

In embodiments, $R^1$ in structural Formula (IXd) is hydrogen.

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments.

In embodiments, the compound has formula:

(IXcia)

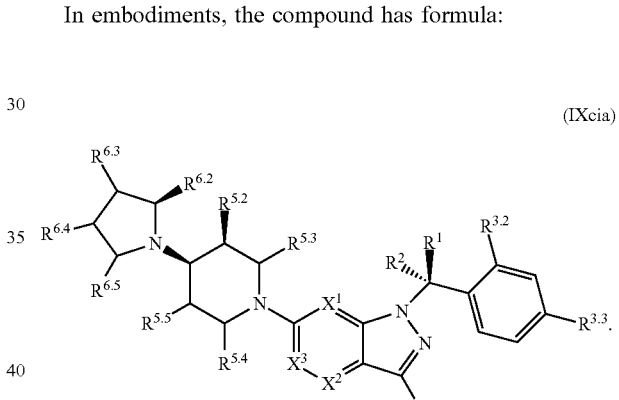

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXciia)

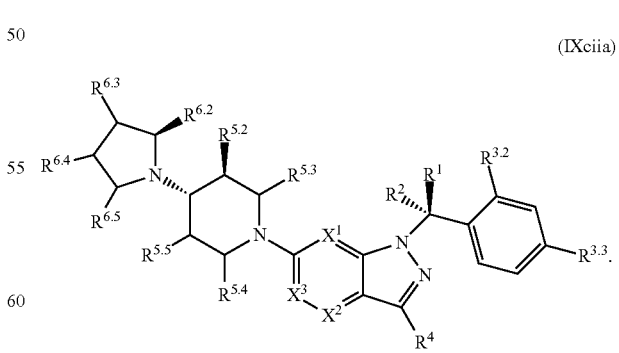

$X^1$, $X^2$, $X^3$, R, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXciiia)

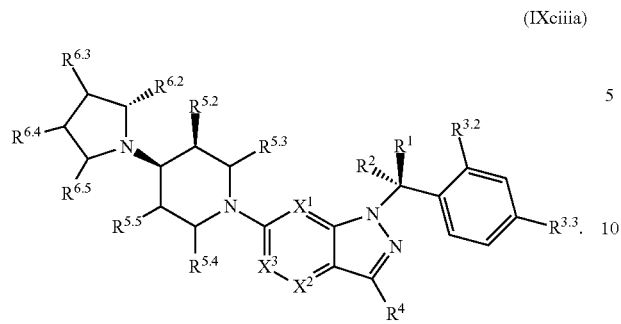

X¹, X², X³, R, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXciva)

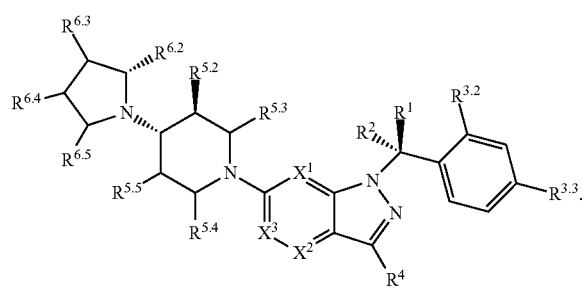

X¹, X², X³, R¹, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcva)

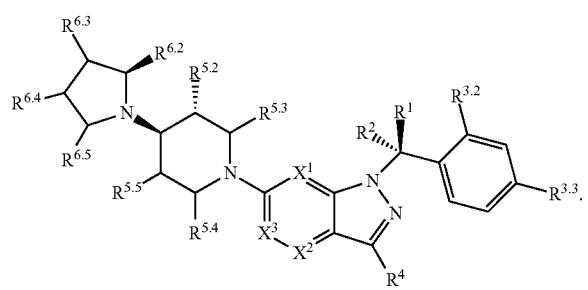

X¹, X², X³, R¹, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcvia)

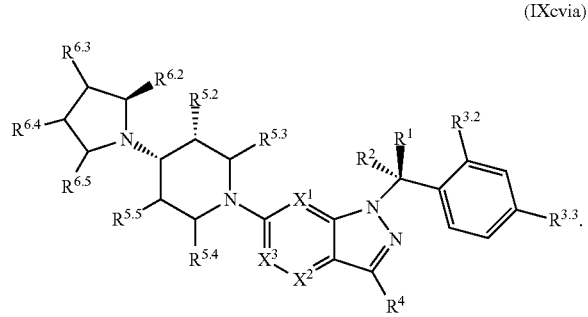

X¹, X², X³, R, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcviia)

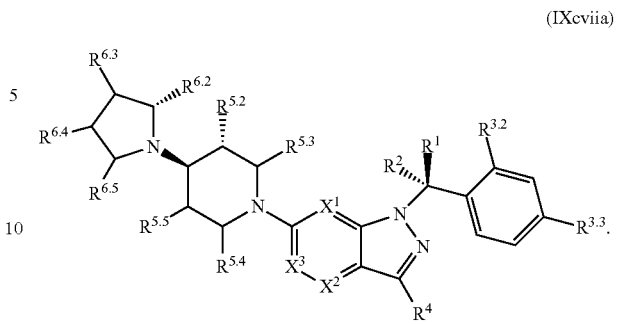

X¹, X², X³, R¹, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcviiia)

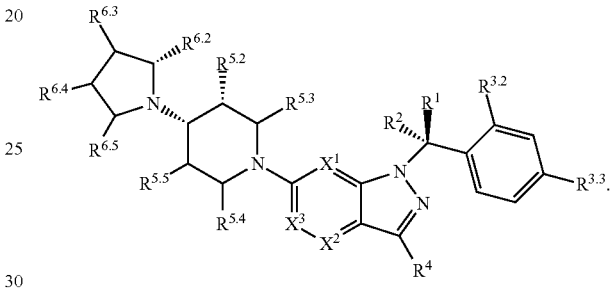

X¹, X², X³, R¹, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{65}$ are as described herein, including embodiments. In embodiments, the compound has formula:

(IXcxa)

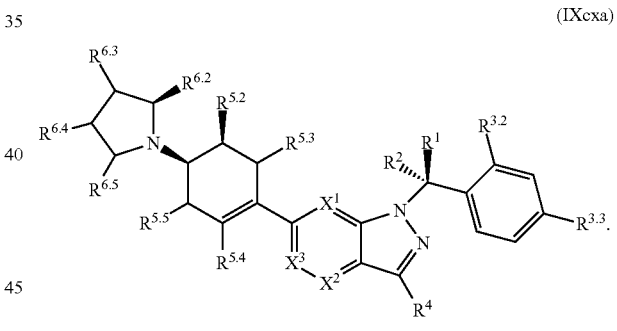

X¹, X², X³, R¹, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcxia)

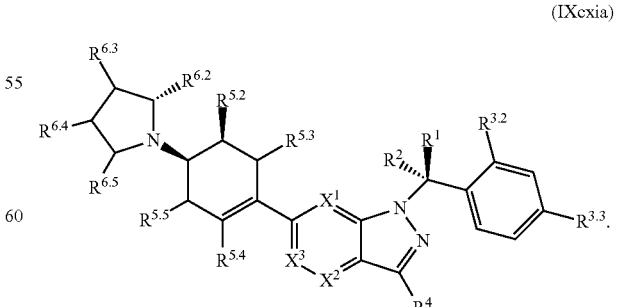

X¹, X², X³, R, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcxiia)

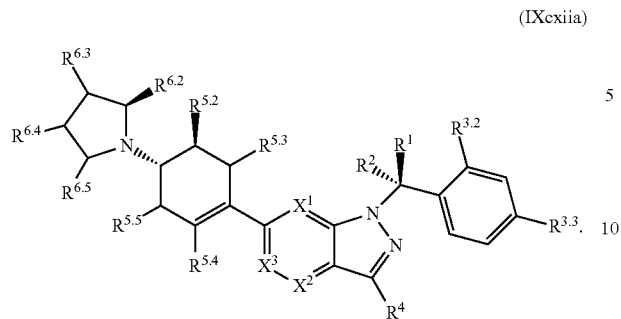

X¹, X², X³, R, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcxiiia)

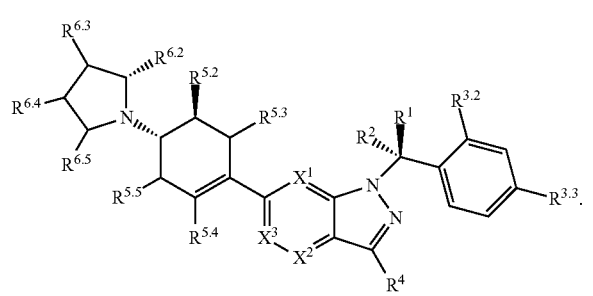

X¹, X², X³, R, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcxiva)

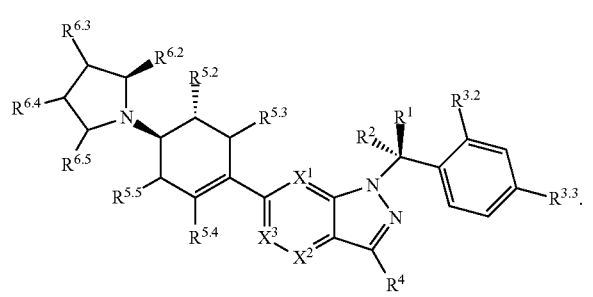

X¹, X², X³, R, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcxva)

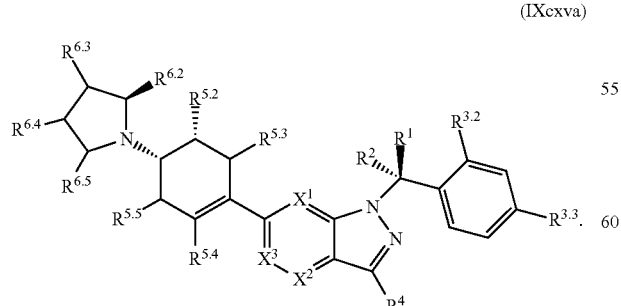

X¹, X², X³, R, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcxvia)

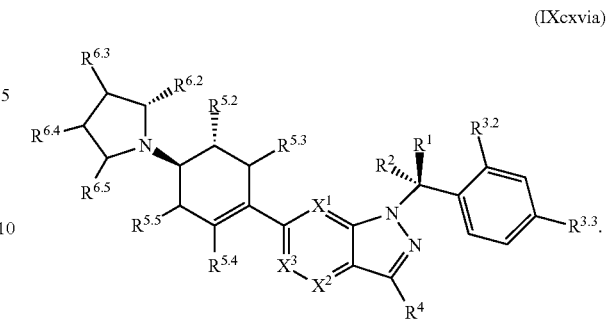

X¹, X², X³, R, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcxviia)


X¹, X², X³, R¹, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments.

In embodiments, the compound has formula:

(IXcib)


X¹, X², X³, R¹, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXciib)

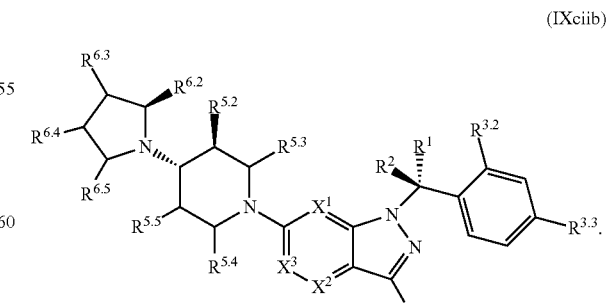

X¹, X², X³, R¹, R², $R^{3.2}$, $R^{3.3}$, R⁴, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXciiib)

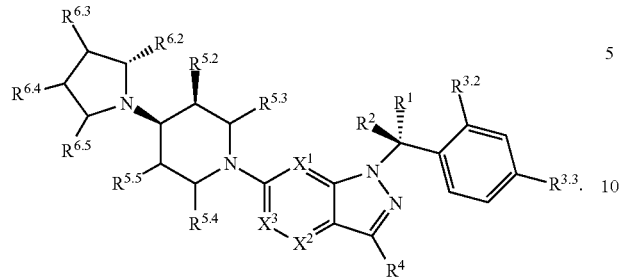

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcivb)

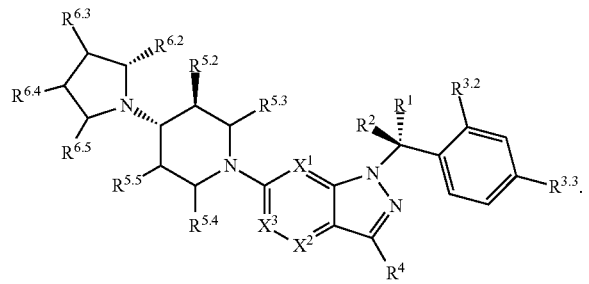

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcvb)

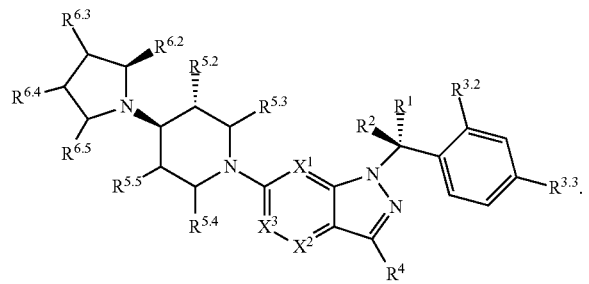

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcvib)

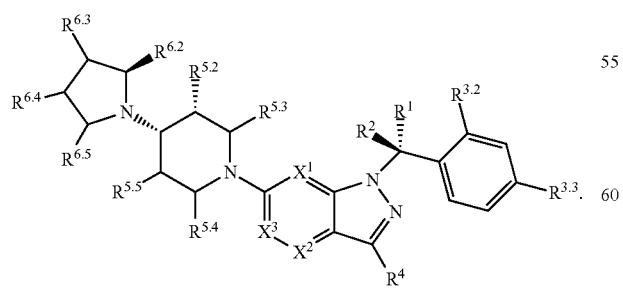

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcviib)

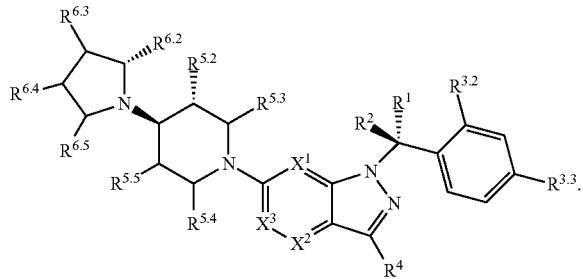

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcviiib)

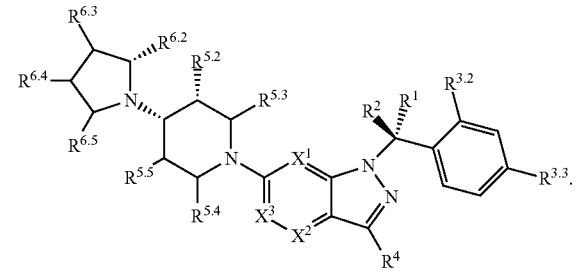

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcxb)

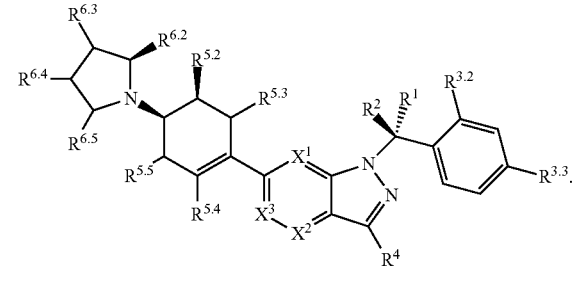

$X^1$, $X^2$, $X^3$, R, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

(IXcxib)

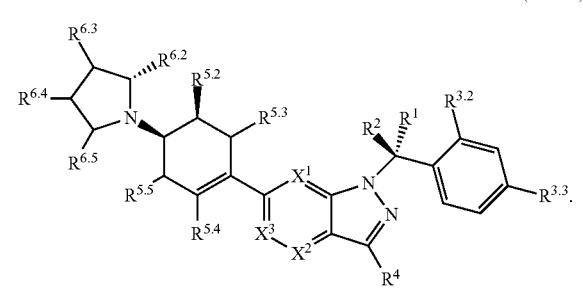

$X^1$, $X^2$, $X^3$, $R^1$, $R^2$, $R^{32}$, $R^{33}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

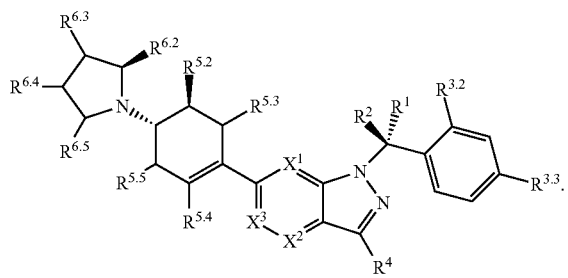

(IXcxiib)

$X^1$, $X^2$, $X^3$, R, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

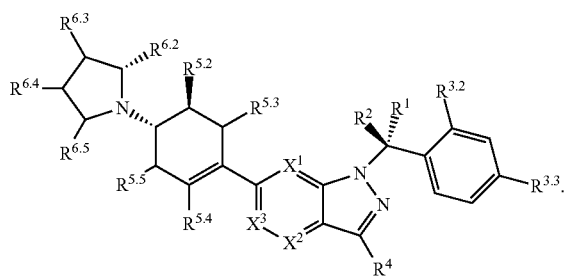

(IXcxiiib)

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

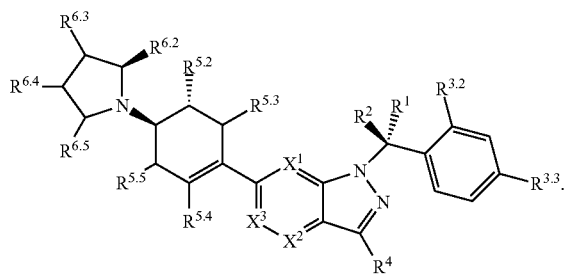

(IXcxivb)

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

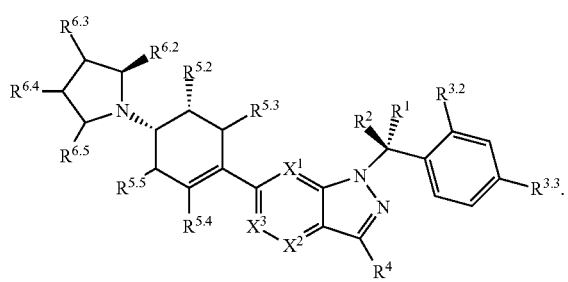

(IXcxvb)

$X^1$, $X^2$, $X^3$, R, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

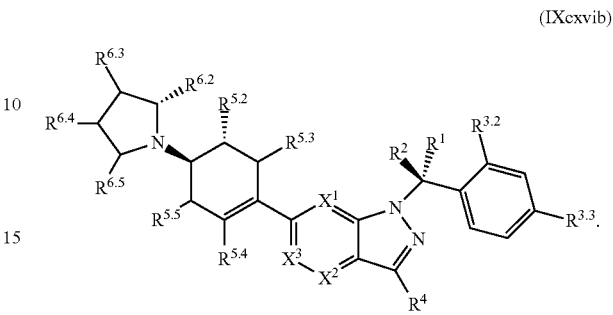

(IXcxvib)

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments. In embodiments, the compound has formula:

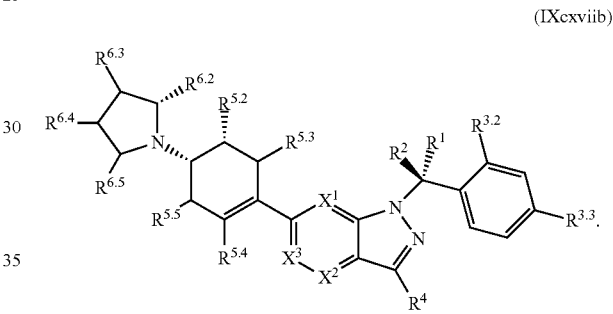

(IXcxviib)

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments.

$X^1$, $X^2$, $X^3$, $R^1$, $R^2$, $R^{3.2}$, $R^{3.3}$, $R^4$, $R^{5.2}$, $R^{5.3}$, $R^{5.4}$, $R^{5.5}$, $R^{6.2}$, $R^{6.3}$, $R^{6.4}$ and $R^{6.5}$ are as described herein, including embodiments.

In embodiments, the compounds provided herein have structural Formula (X):

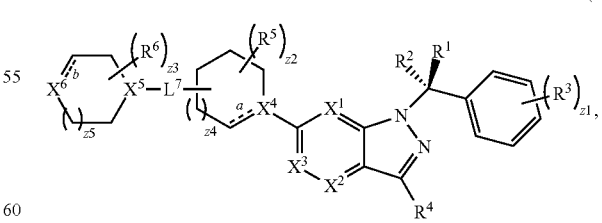

(X)

or a pharmaceutically acceptable salt thereof.

z1, z2, z3, z4, z5, ⁻⁻⁻, ⁻⁻⁻, $X^1$, $X^2$, $X^3$, $X^4$, $X^5$, $X^6$, $L^7$, $R^1$, $R^2$, $R^3$, $R^4$, $R^5$ and $R^6$ are as described herein, including embodiments.

In embodiments, the following are compounds provided herein:
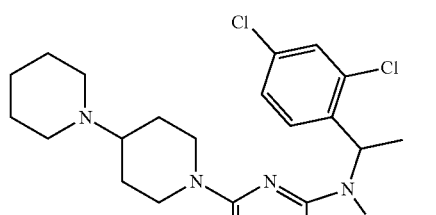
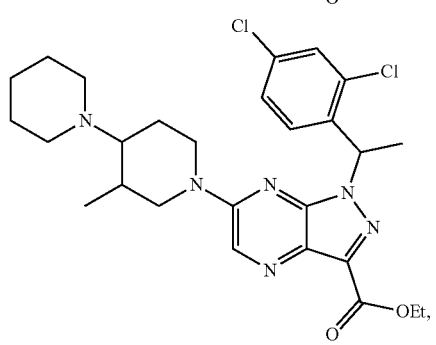
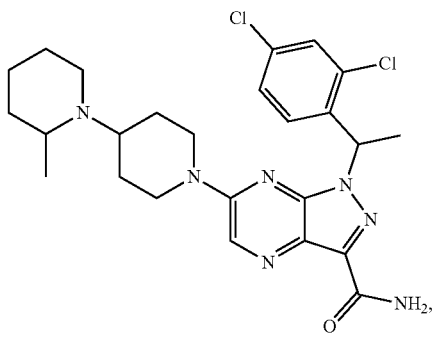
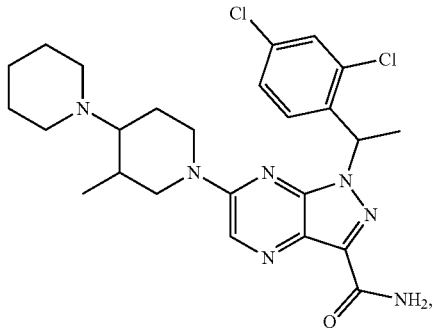
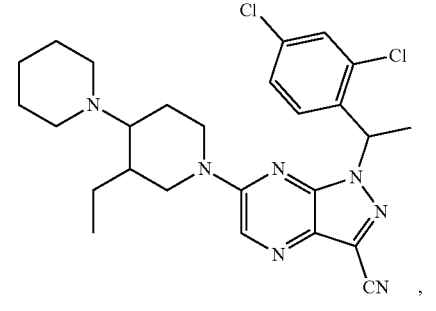
-continued
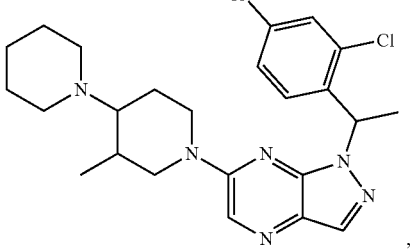
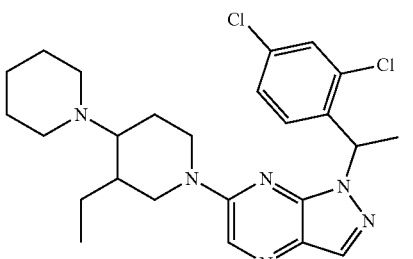
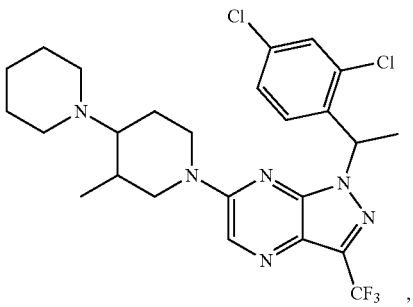
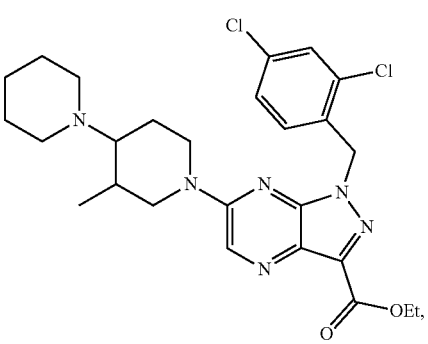
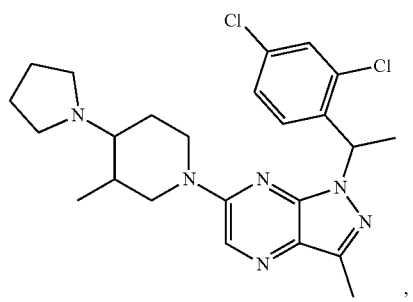

207
-continued
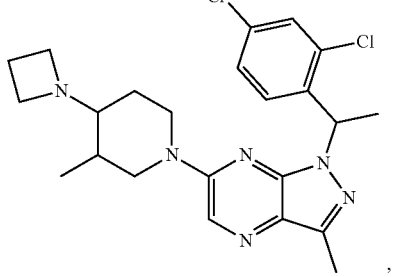
,
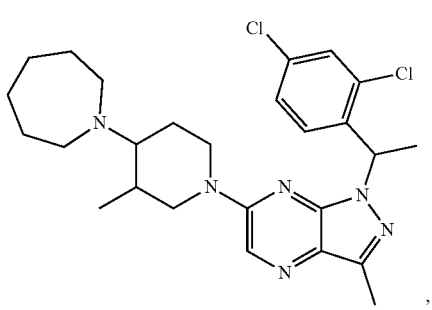
,
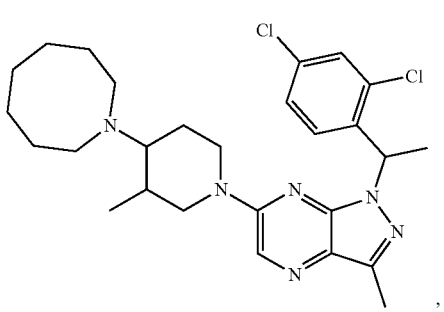
,
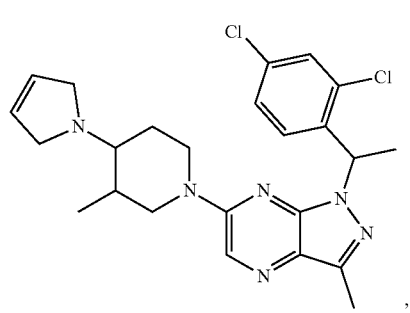
,
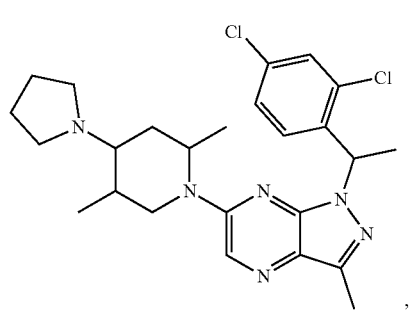
,
208
-continued
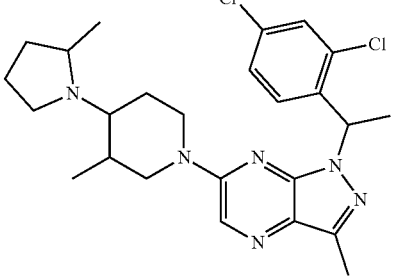
,
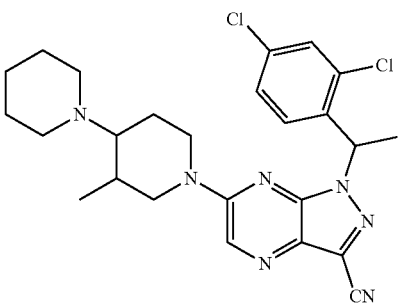
,
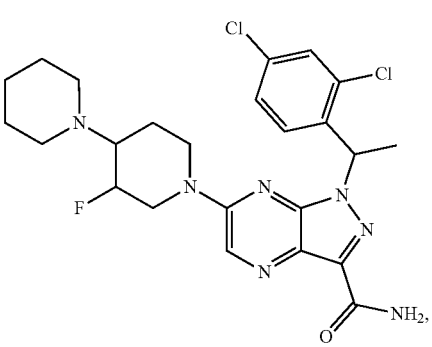
,
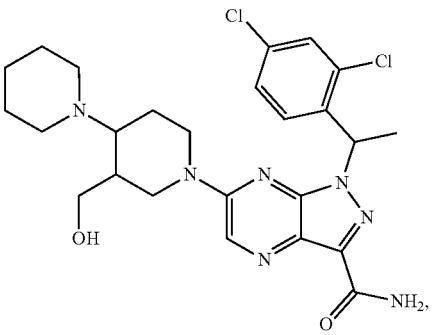
,
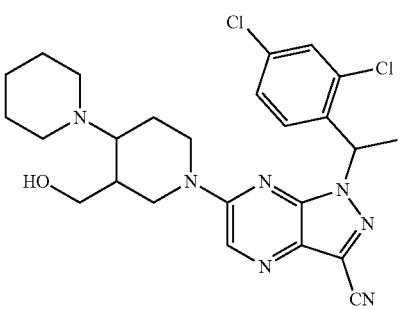
,

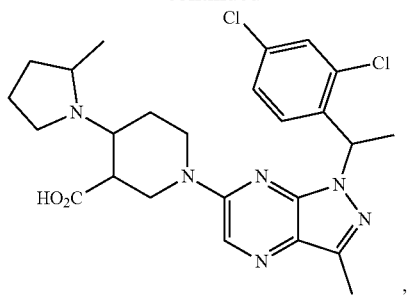
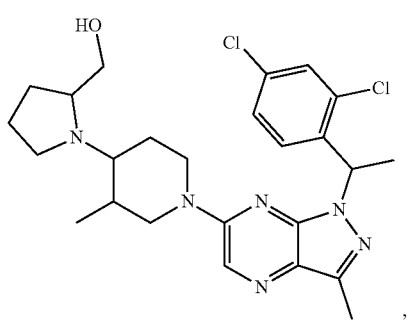
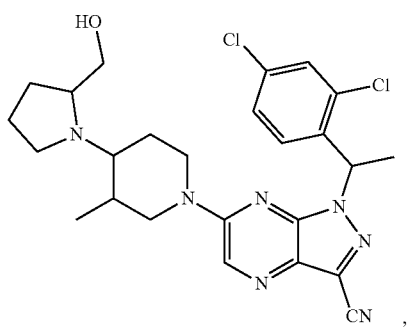
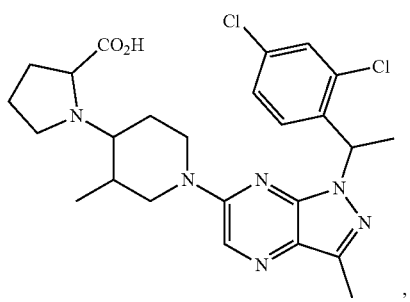
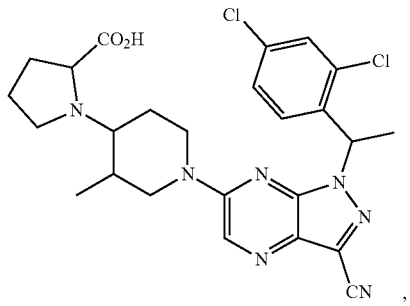
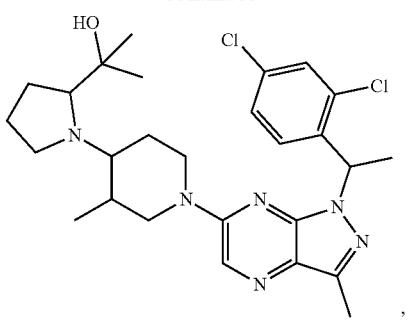
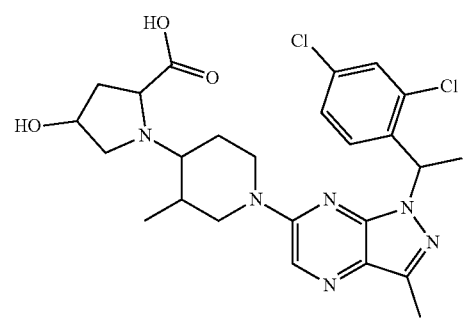
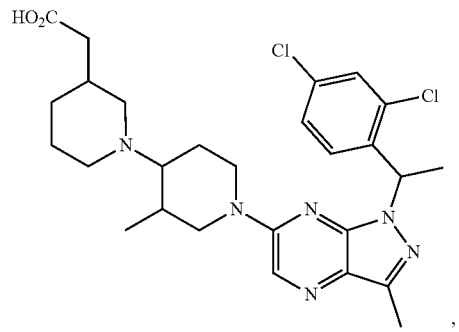
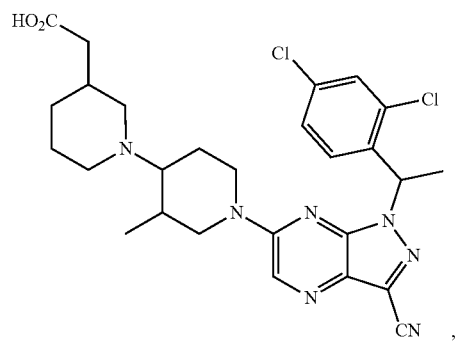
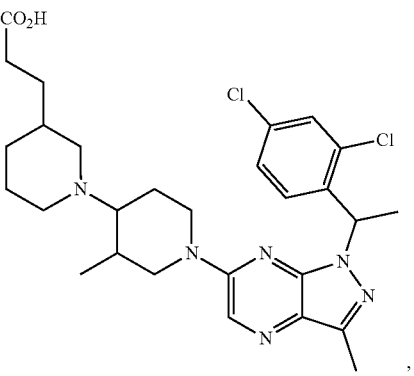

211
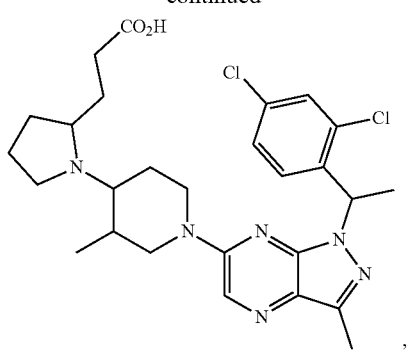
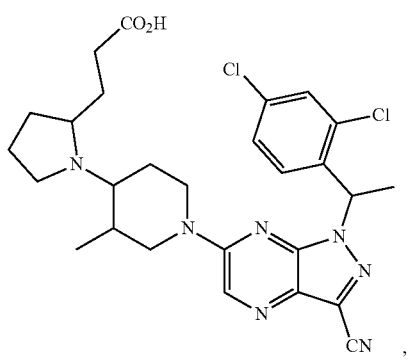
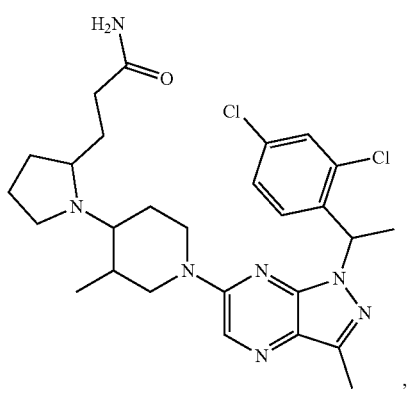
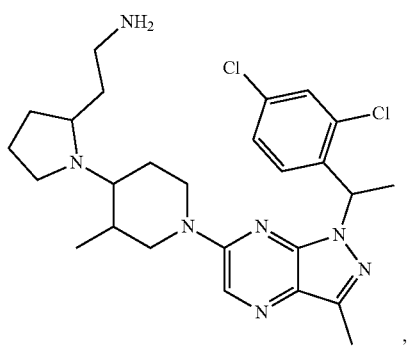
212
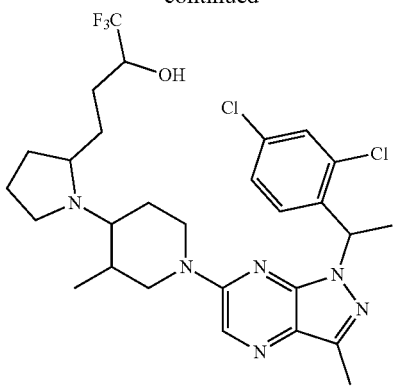
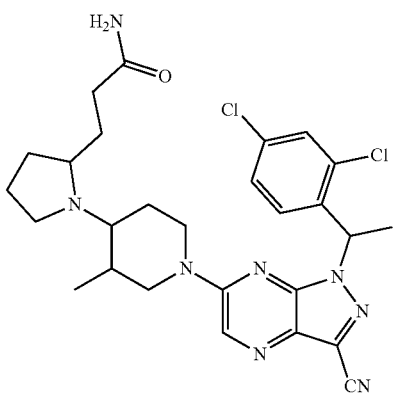
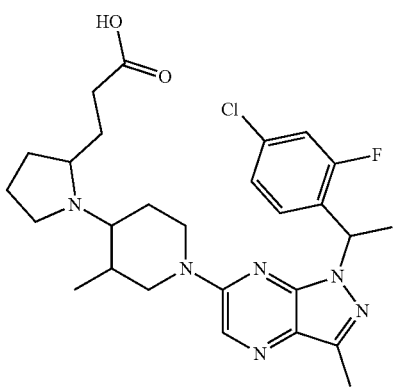
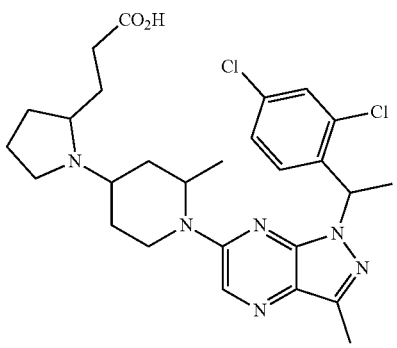

213
-continued
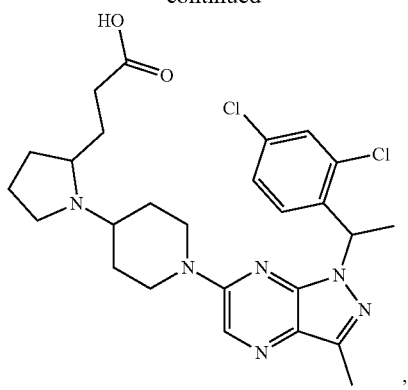
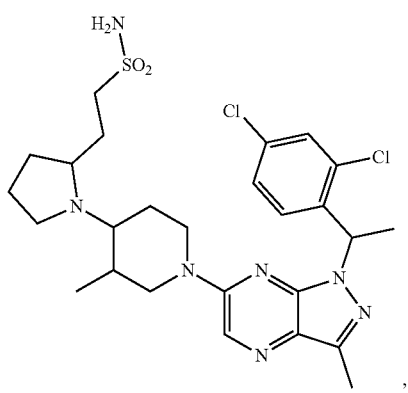
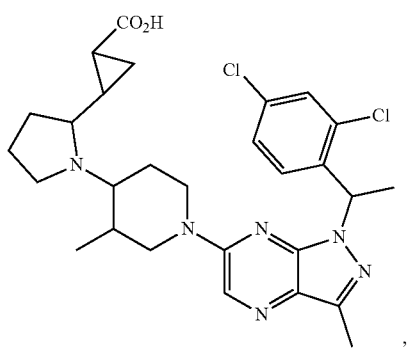
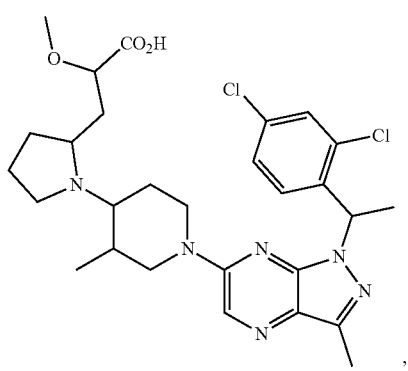
214
-continued
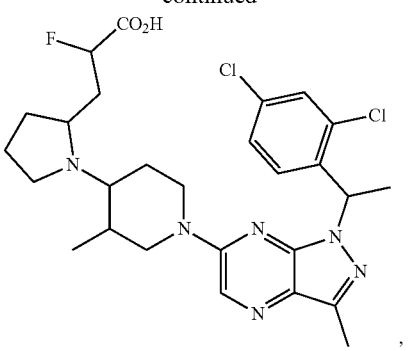
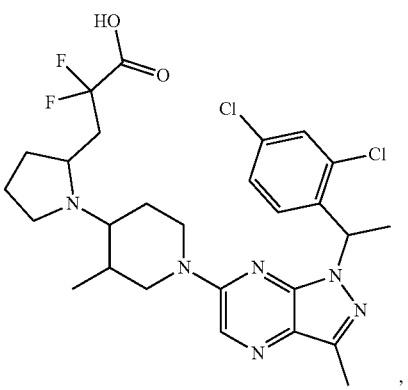
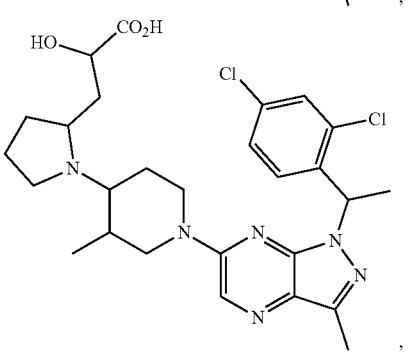
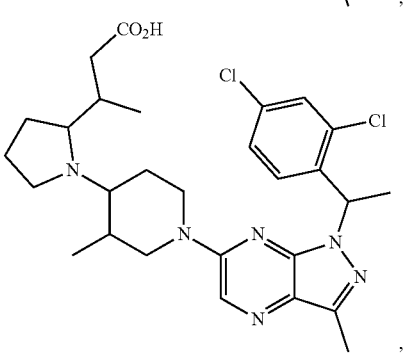
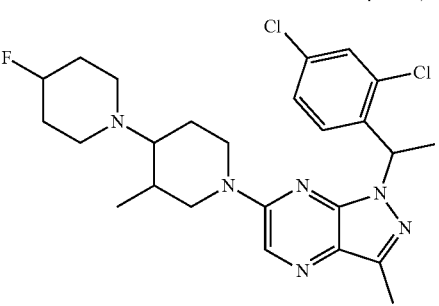

215
-continued
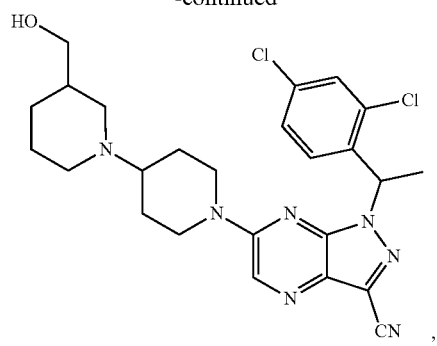
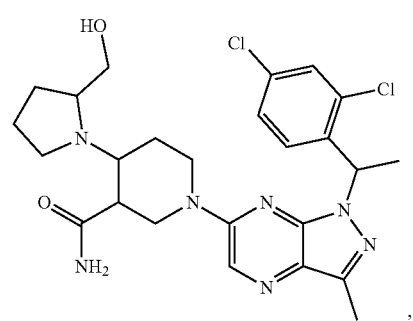
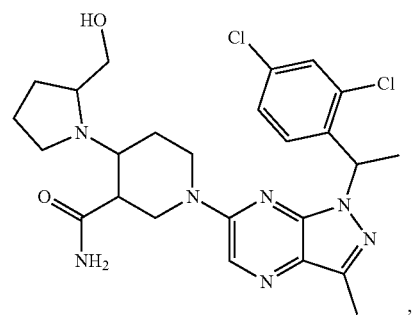
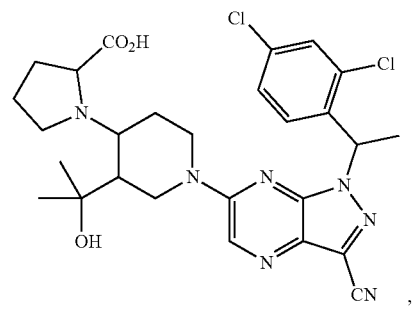
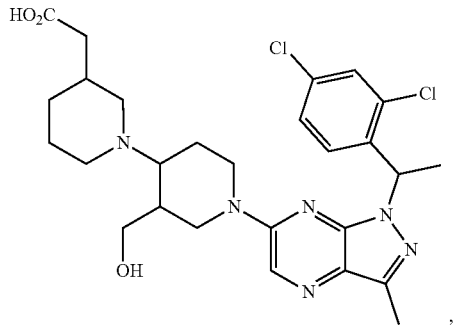
216
-continued
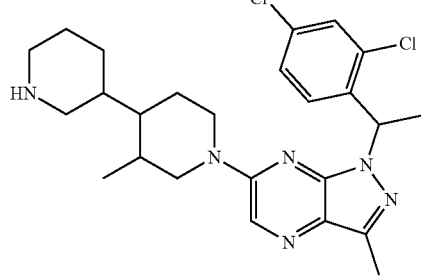
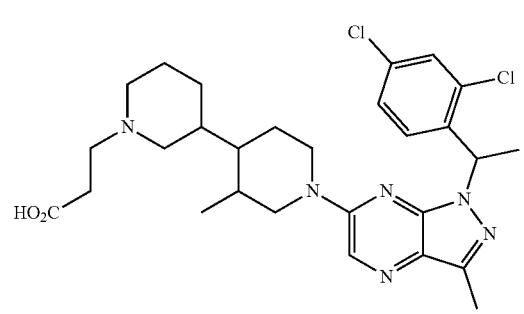
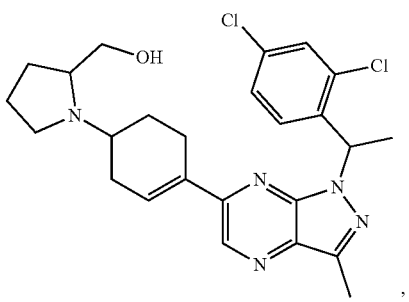
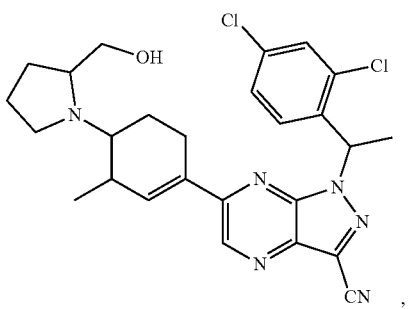
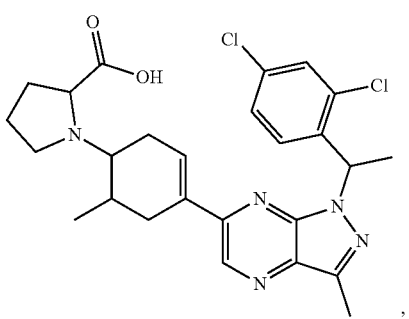

217
-continued
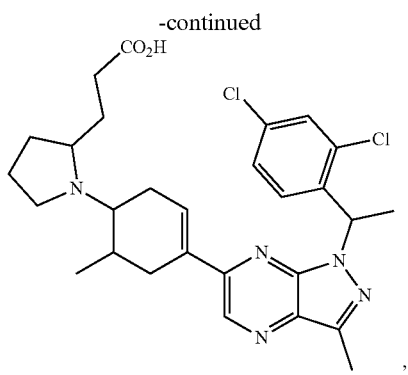
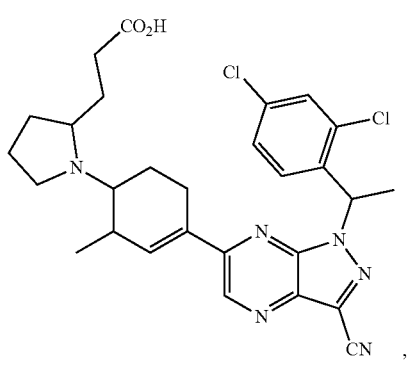
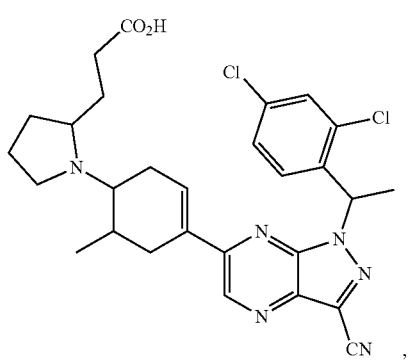
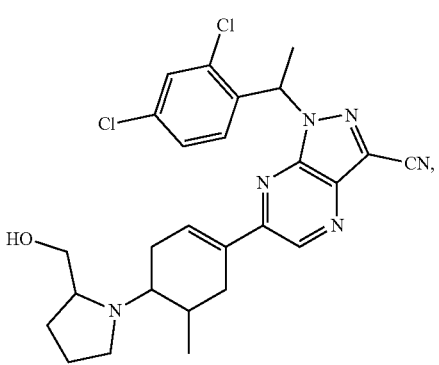
218
-continued
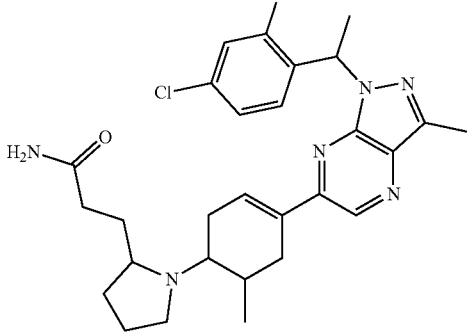
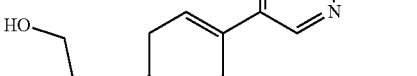
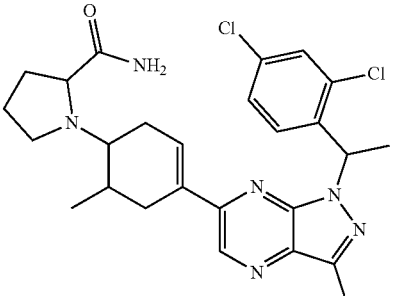
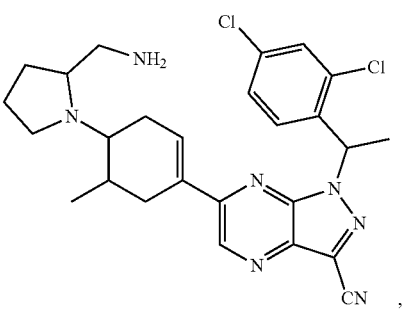
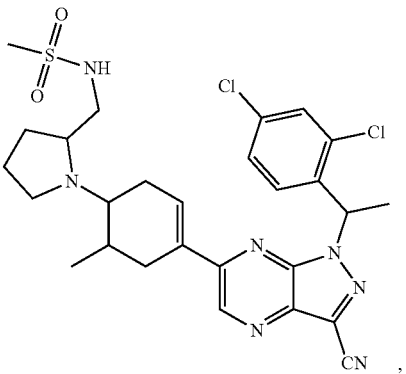

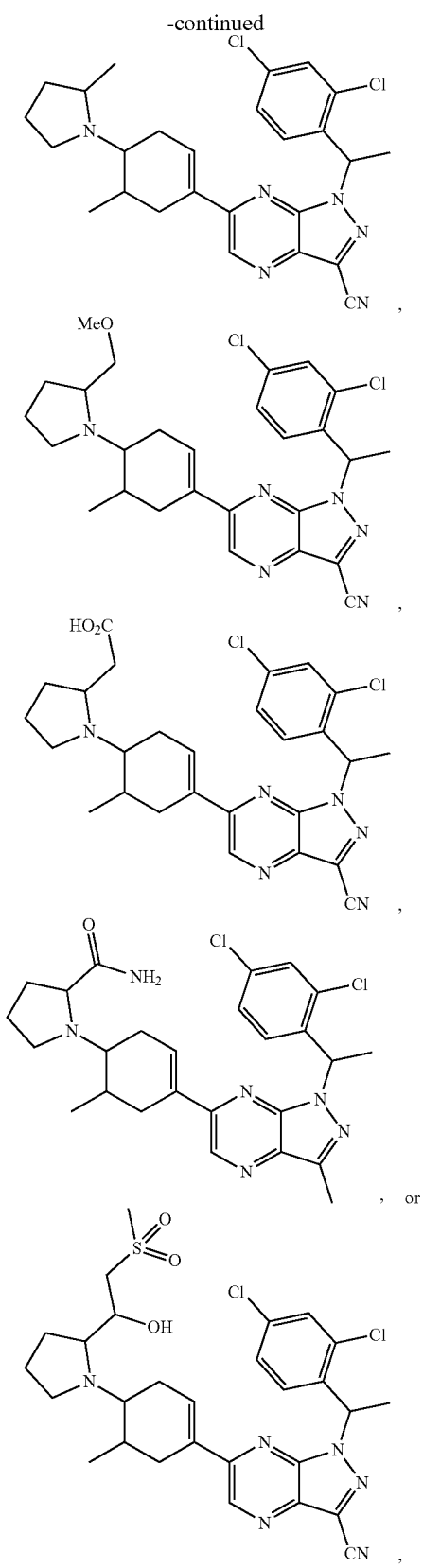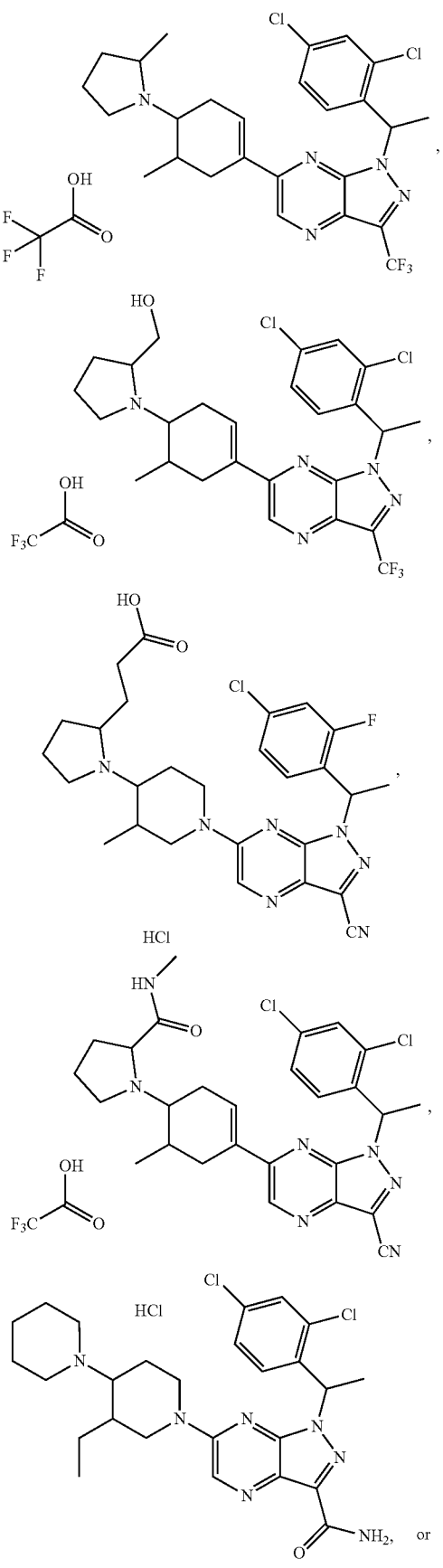
or a pharmaceutically acceptable salt thereof.
In embodiments, the pharmaceutically acceptable salt of the compound is:

-continued
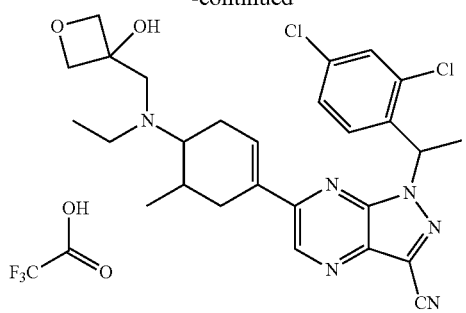
In embodiments, the pharmaceutically acceptable salt of the compound is:
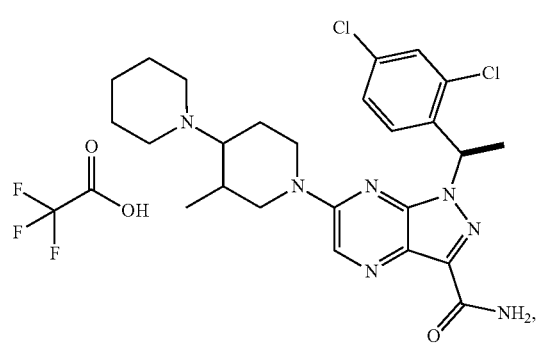
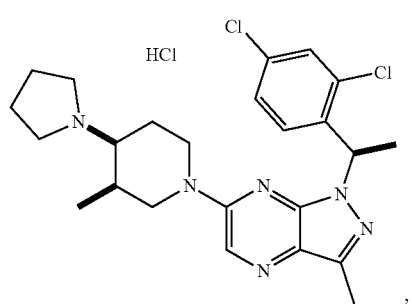
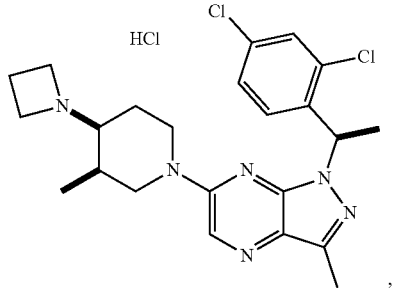
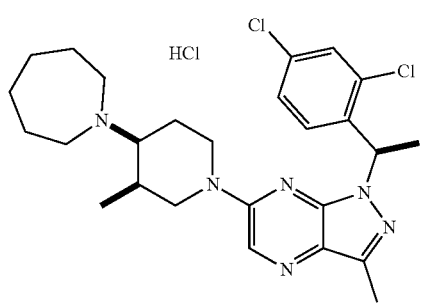
-continued
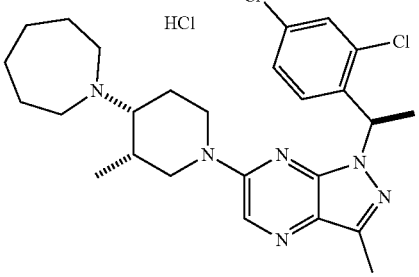
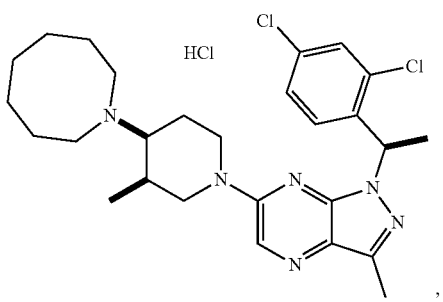
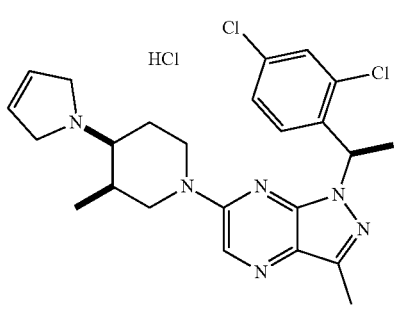
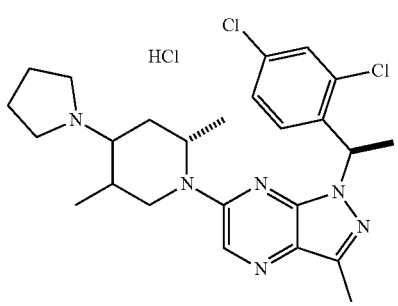
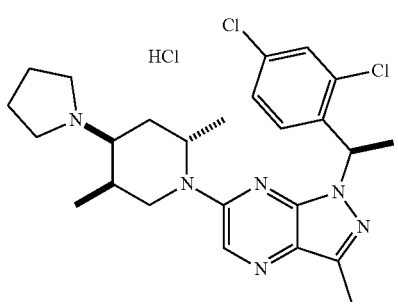

223
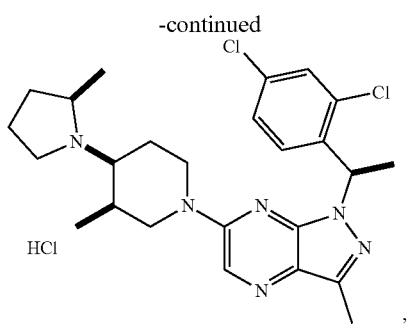
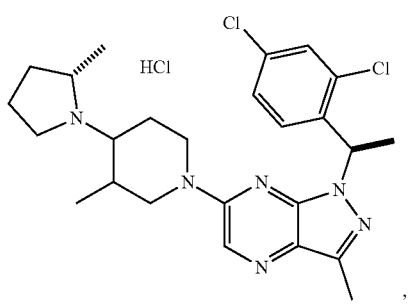
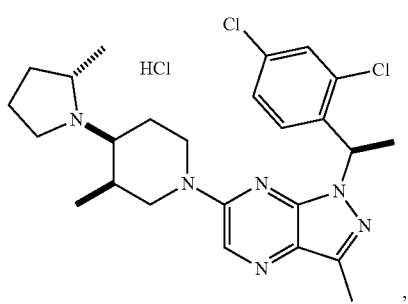
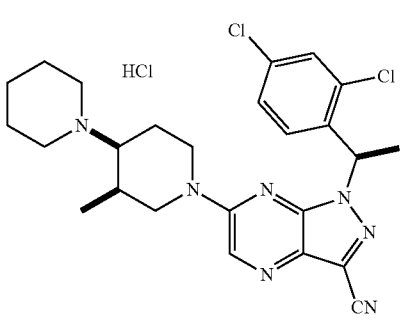
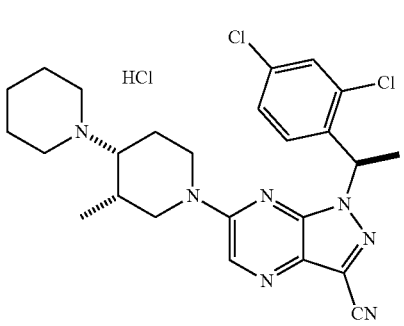
224

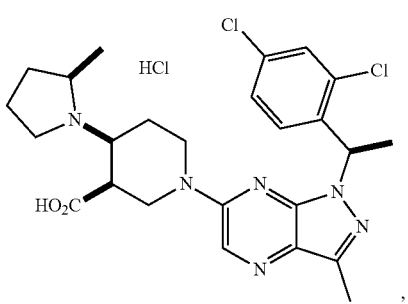
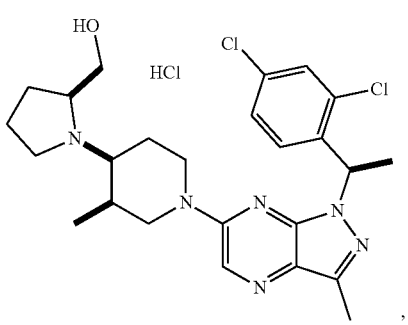
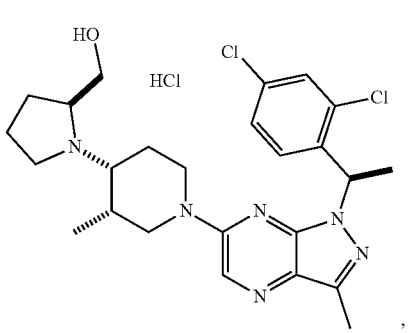

225
-continued
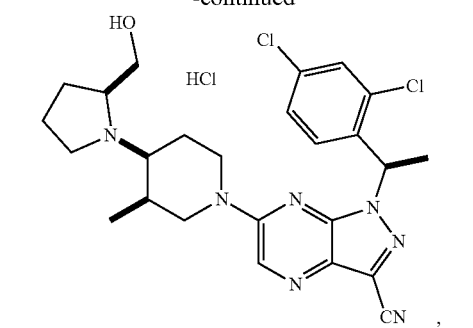
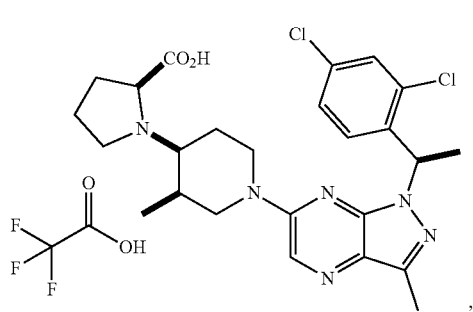
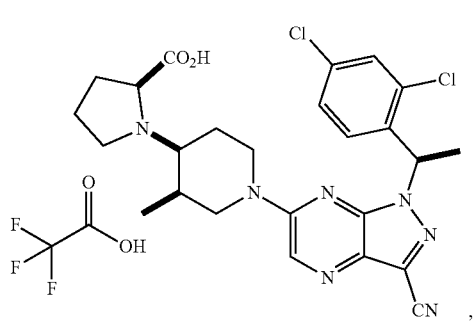
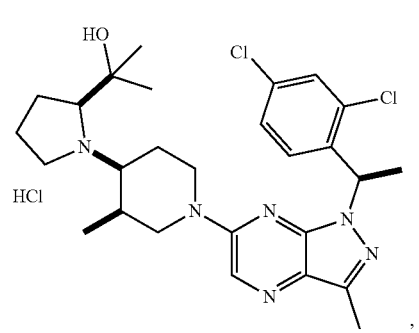
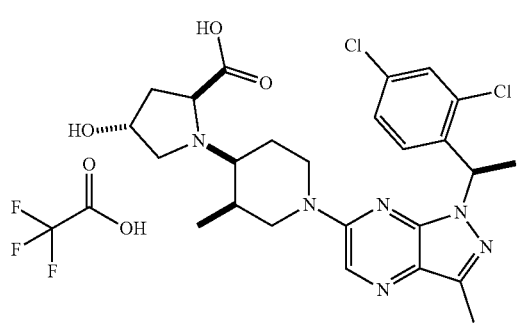
226
-continued
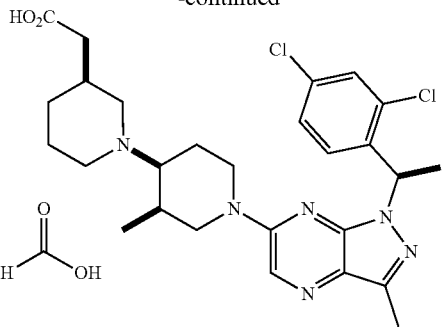
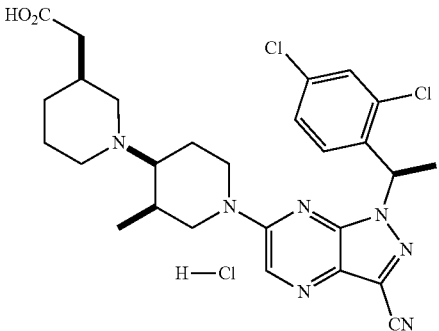
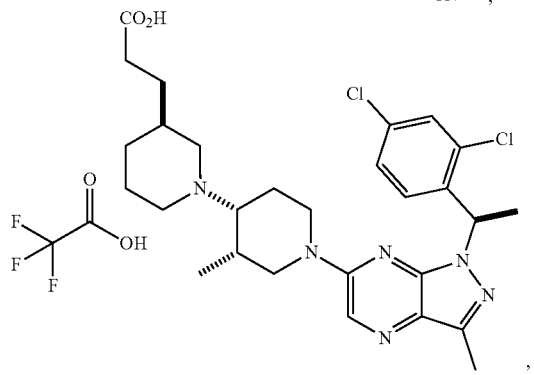
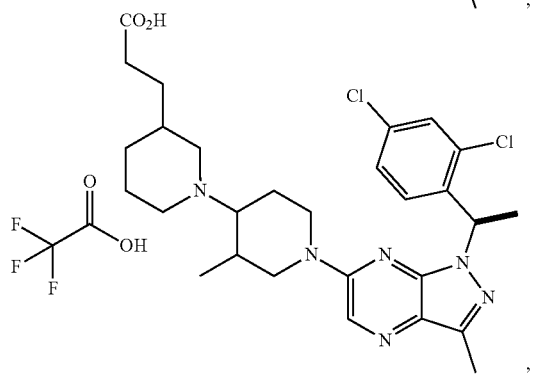
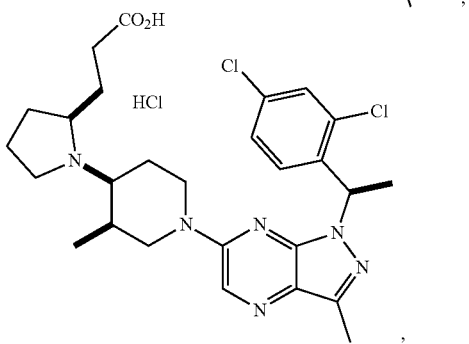

227
-continued
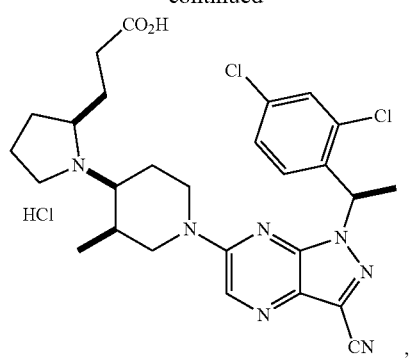
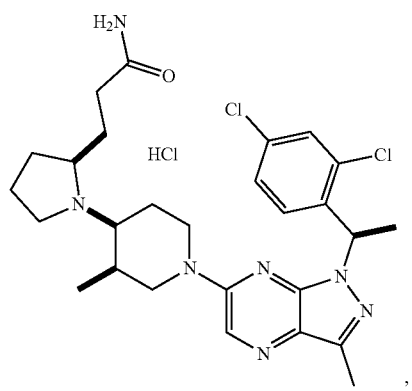
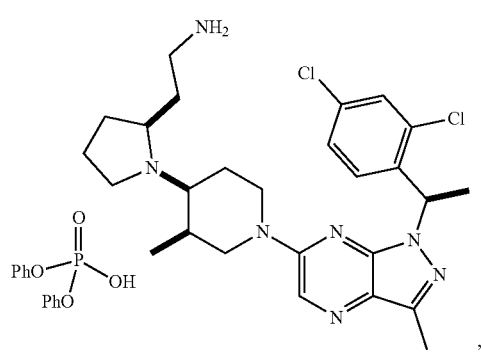
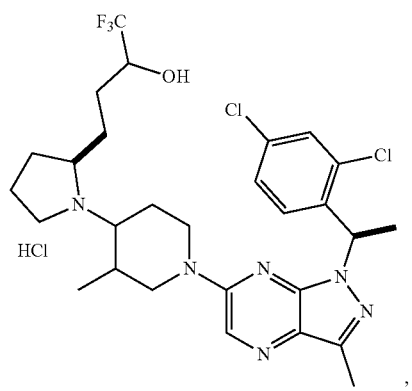
228
-continued
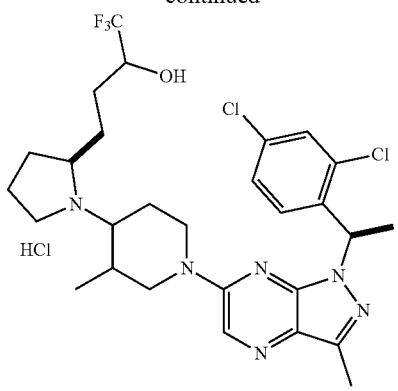
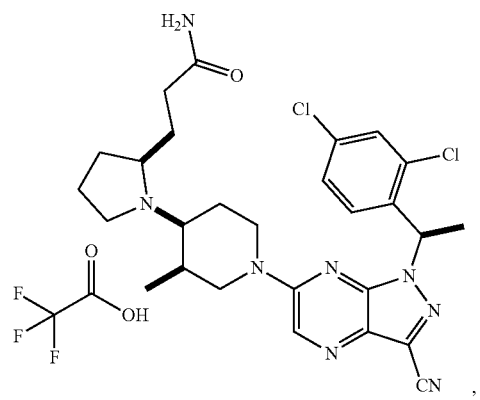
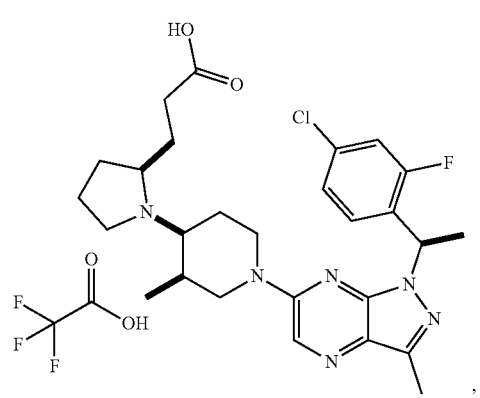
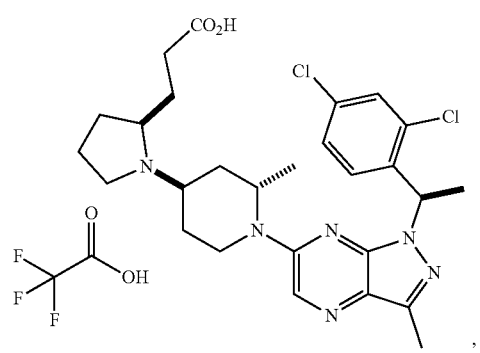

229 -continued 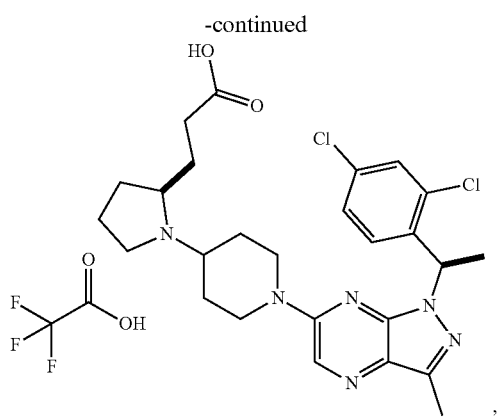
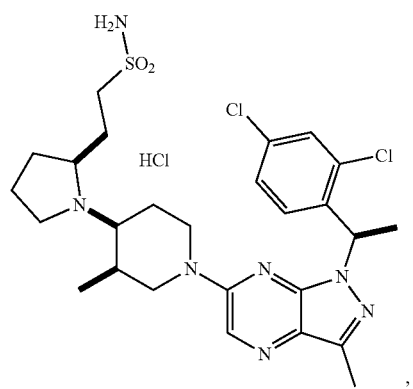
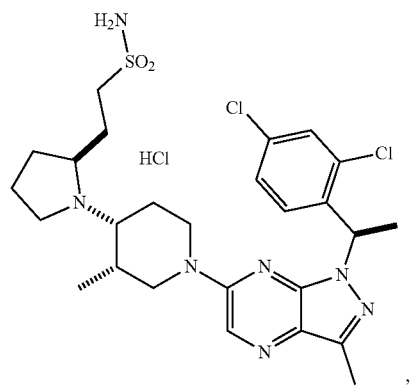
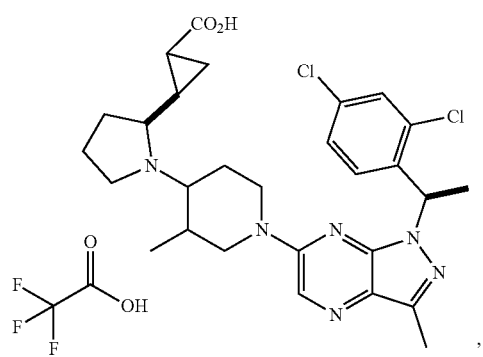
230 -continued 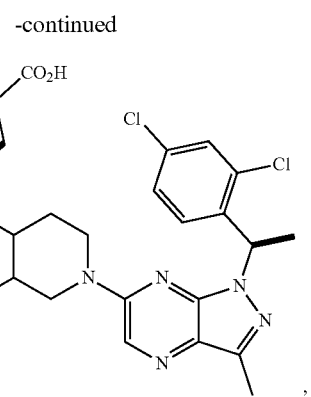
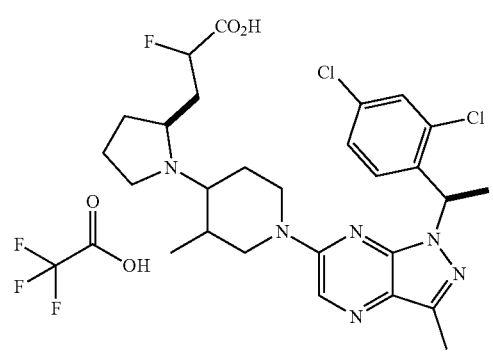
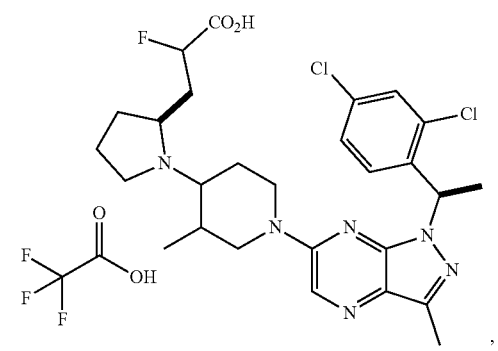
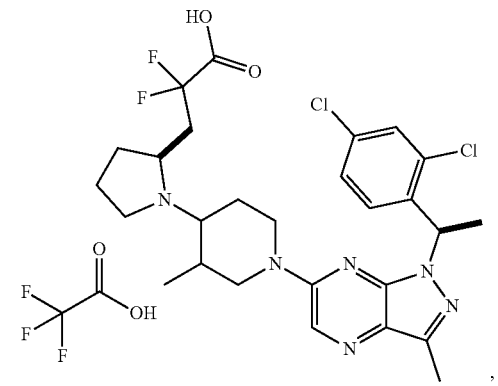

231
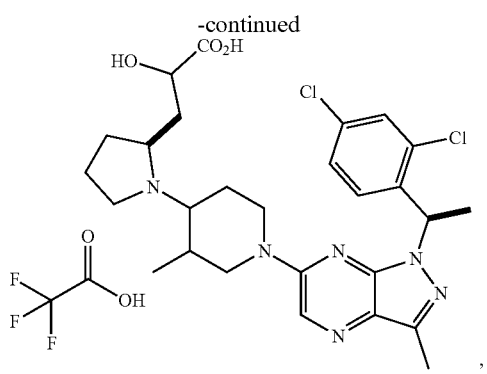
,
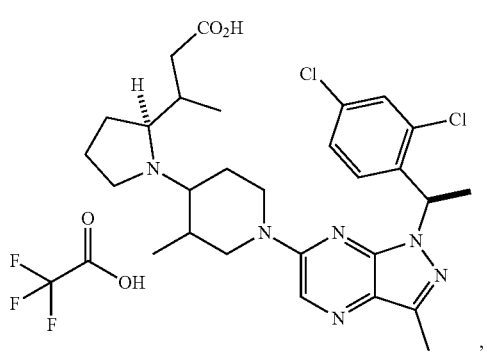
,
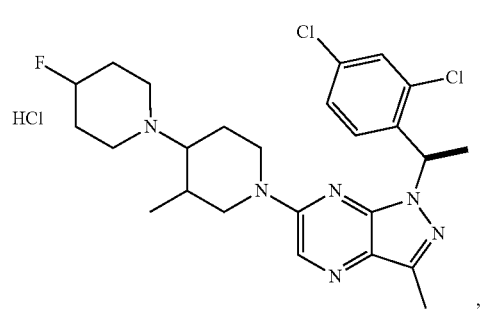
,
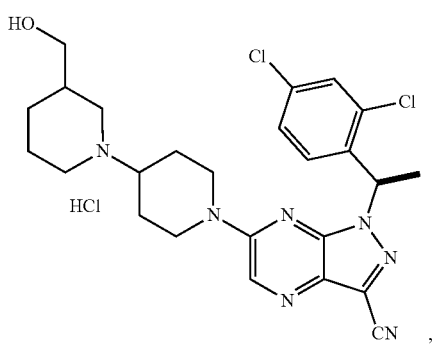
,
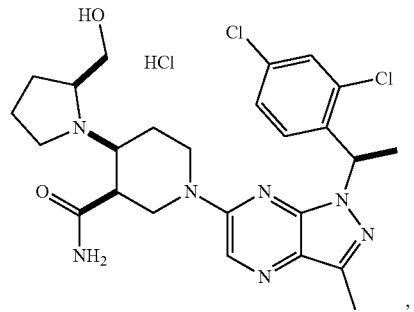
,
232
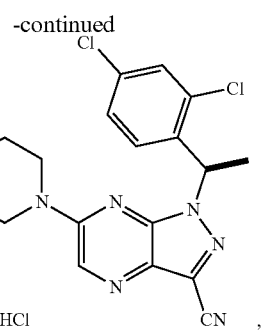
,
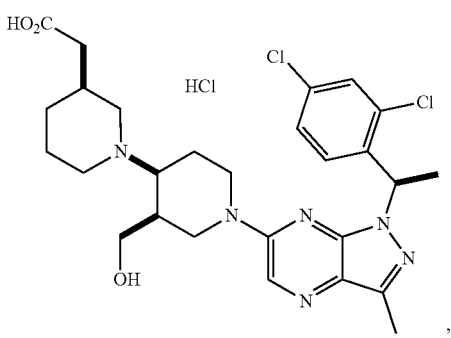
,
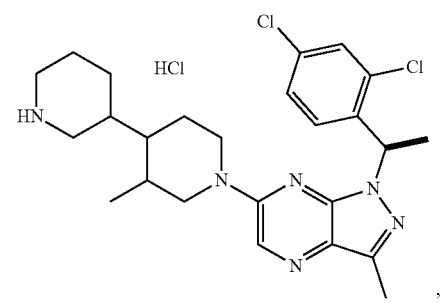
,
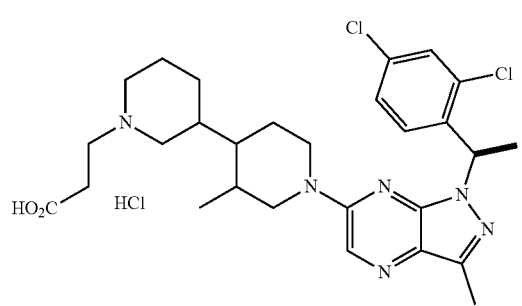
,
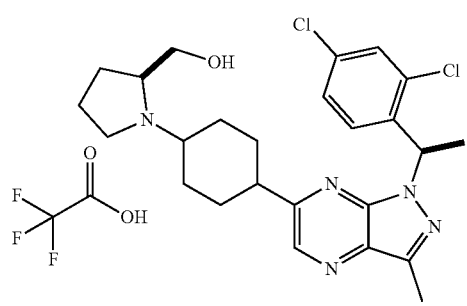
, 233
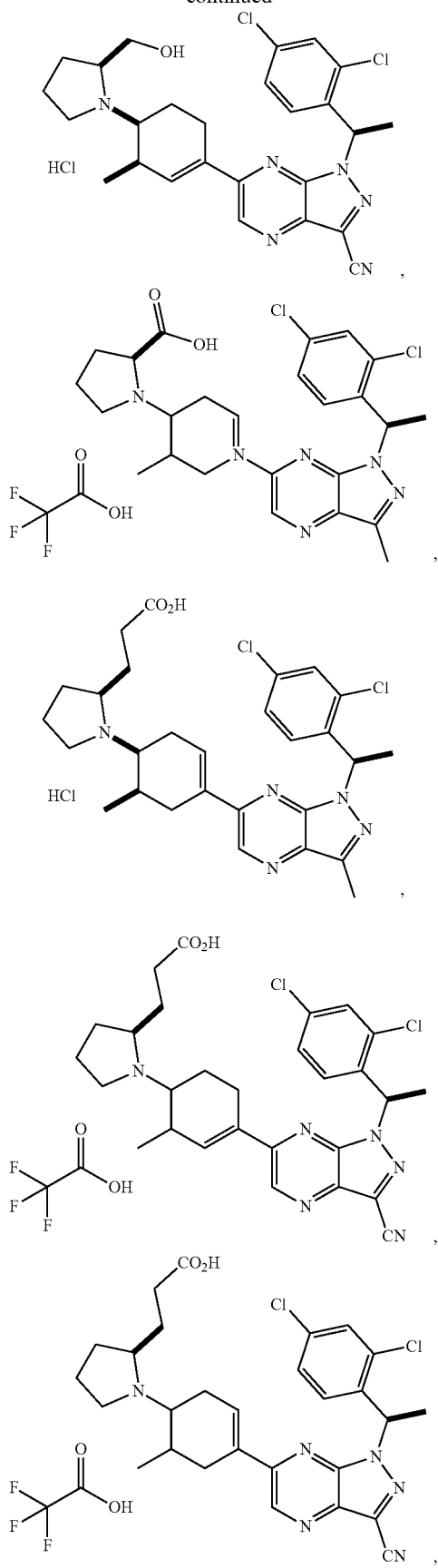
234
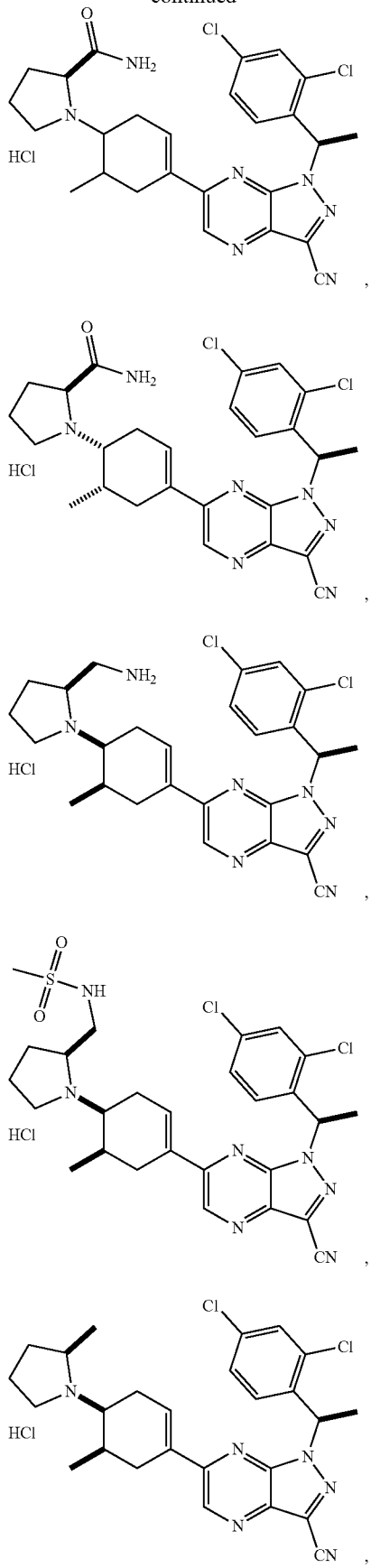

235
-continued
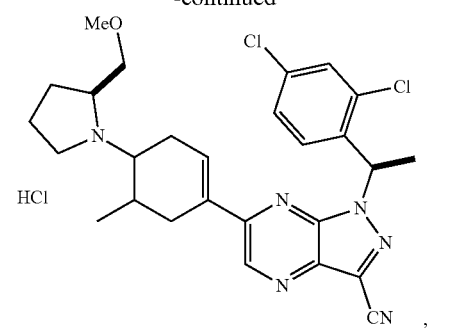
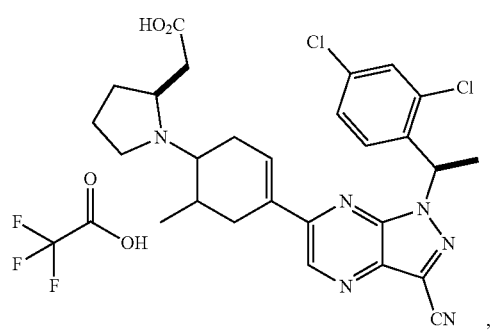
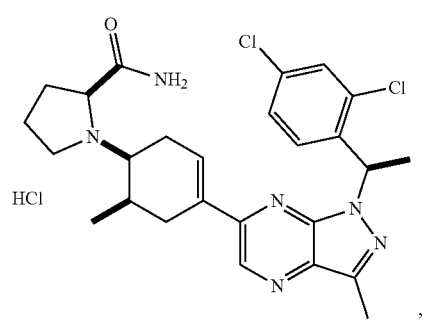
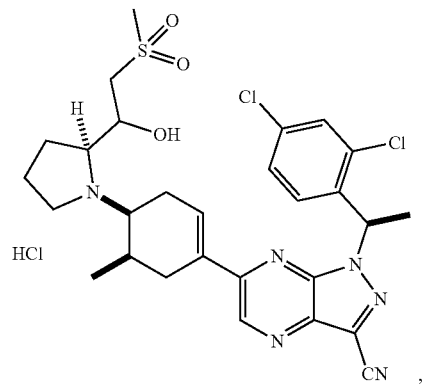
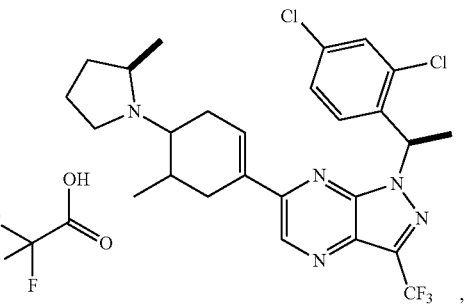
236
-continued
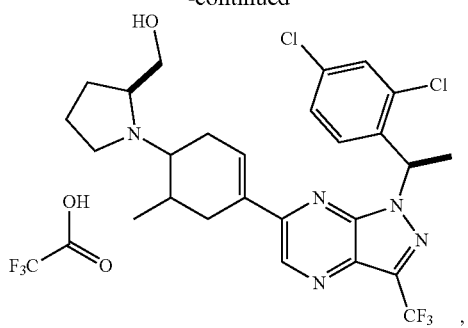
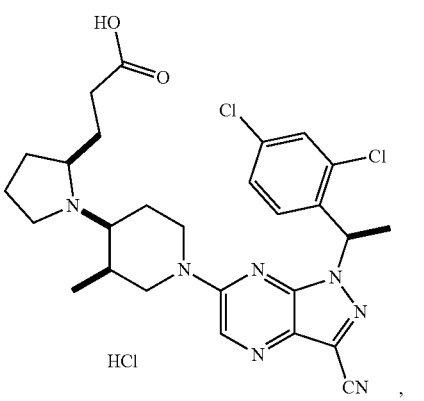
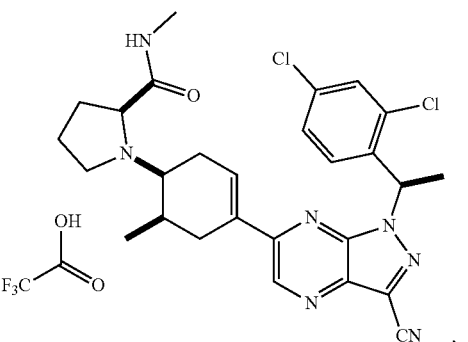, or
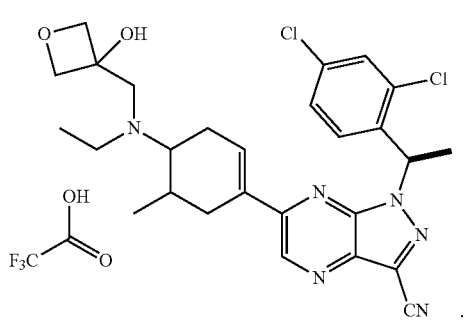.

In embodiments, the compound has structure:
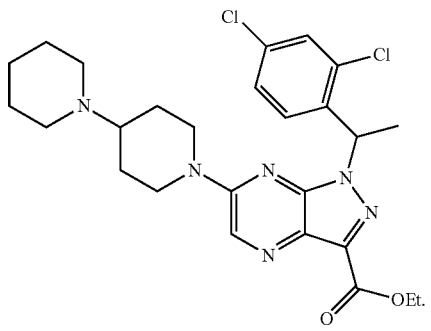 [SMILES: CCOC(=O)c1nn(C(C)c2ccc(Cl)cc2Cl)c2nc(N3CCC(N4CCCCC4)CC3)cnc12]
In embodiments, the compound has structure:
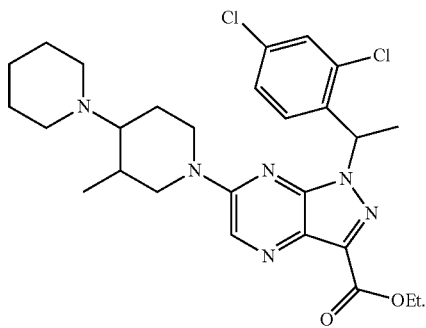 [SMILES: CCOC(=O)c1nn(C(C)c2ccc(Cl)cc2Cl)c2nc(N3CCC(N4CCCCC4)C(C)C3)cnc12]
In embodiments, the compound has structure:
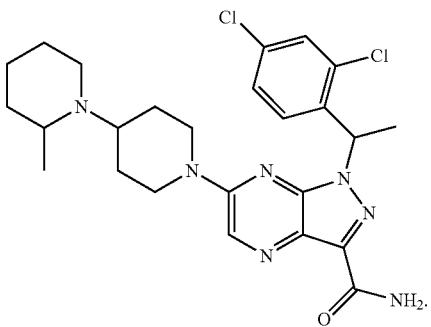 [SMILES: CC1CCCCN1C1CCN(c2cnc3c(C(N)=O)nn(C(C)c4ccc(Cl)cc4Cl)c3n2)CC1]
In embodiments, the compound has structure:
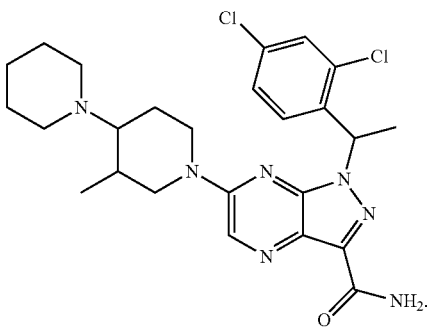 [SMILES: CC1CN(c2cnc3c(C(N)=O)nn(C(C)c4ccc(Cl)cc4Cl)c3n2)CCC1N1CCCCC1]
In embodiments, the compound has structure:
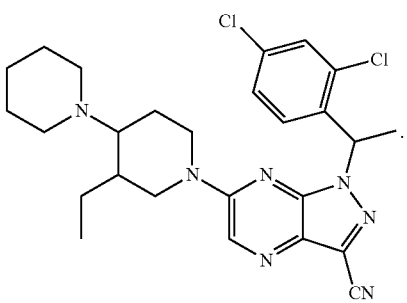
In embodiments, the compound has structure:
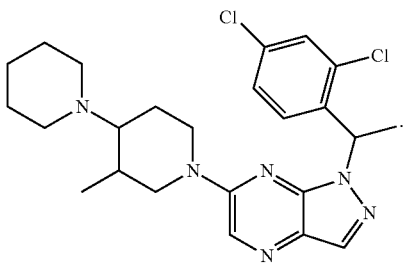 [SMILES: CC1CN(c2cnc3cnn(C(C)c4ccc(Cl)cc4Cl)c3n2)CCC1N1CCCCC1]
In embodiments, the compound has structure:
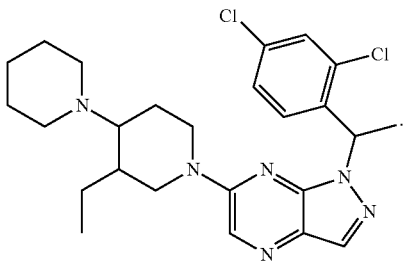 [SMILES: CCC1CN(c2cnc3cnn(C(C)c4ccc(Cl)cc4Cl)c3n2)CCC1N1CCCCC1]
In embodiments, the compound has structure:
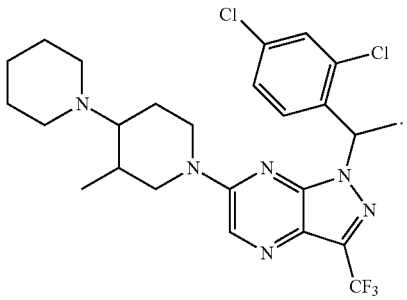 [SMILES: CC1CN(c2cnc3c(C(F)(F)F)nn(C(C)c4ccc(Cl)cc4Cl)c3n2)CCC1N1CCCCC1]

In embodiments, the compound has structure:
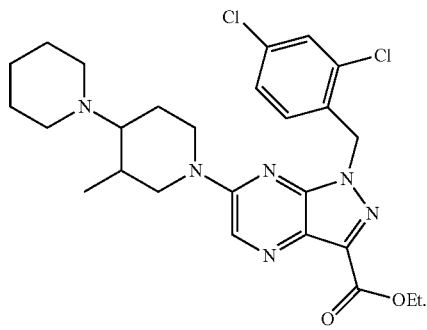 [SMILES: CCOC(=O)c1nn(Cc2ccc(Cl)cc2Cl)c2nc(N3CCC(N4CCCCC4)C(C)C3)cnc12]
In embodiments, the compound has structure:
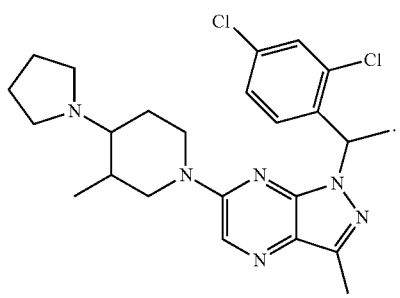 [SMILES: Cc1nn(C(C)c2ccc(Cl)cc2Cl)c2nc(N3CCC(N4CCCC4)C(C)C3)cnc12]
In embodiments, the compound has structure:
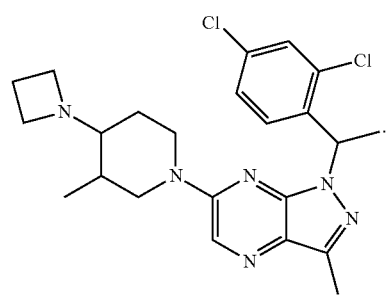 [SMILES: Cc1nn(C(C)c2ccc(Cl)cc2Cl)c2nc(N3CCC(N4CCC4)C(C)C3)cnc12]
In embodiments, the compound has structure:
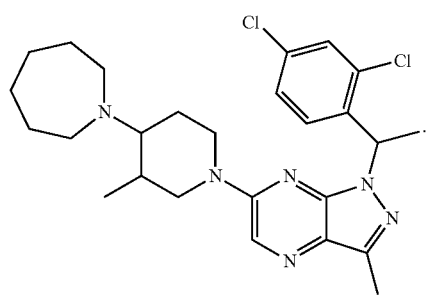 [SMILES: Cc1nn(C(C)c2ccc(Cl)cc2Cl)c2nc(N3CCC(N4CCCCCC4)C(C)C3)cnc12]
In embodiments, the compound has structure:
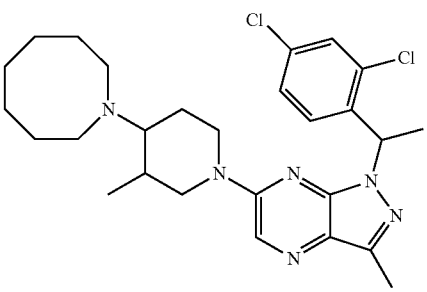
In embodiments, the compound has structure:
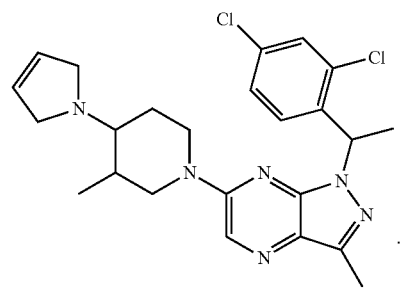 [SMILES: Cc1nn(C(C)c2ccc(Cl)cc2Cl)c2nc(N3CCC(N4CC=CC4)C(C)C3)cnc12]
In embodiments, the compound has structure:
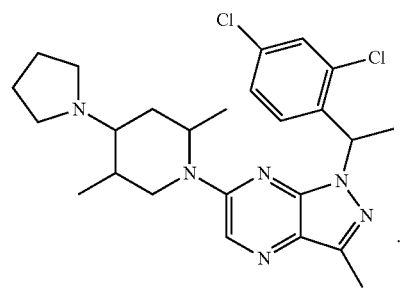 [SMILES: Cc1nn(C(C)c2ccc(Cl)cc2Cl)c2nc(N3CC(C)C(N4CCCC4)CC3C)cnc12]
In embodiments, the compound has structure:
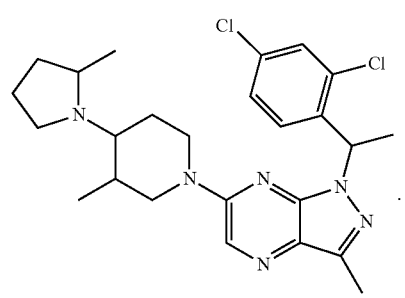 [SMILES: Cc1nn(C(C)c2ccc(Cl)cc2Cl)c2nc(N3CCC(N4CCCC4C)C(C)C3)cnc12]

In embodiments, the compound has structure:
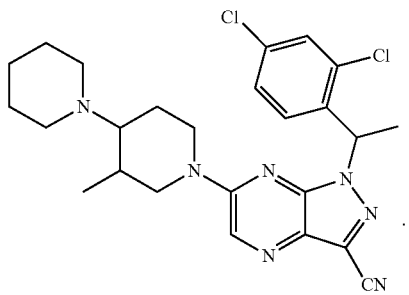 [SMILES: CC1CN(c2cnc3c(C#N)nn(C(C)c4ccc(Cl)cc4Cl)c3n2)CCC1N1CCCCC1]
In embodiments, the compound has structure:
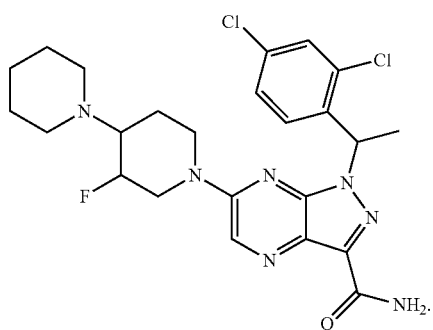
In embodiments, the compound has structure:
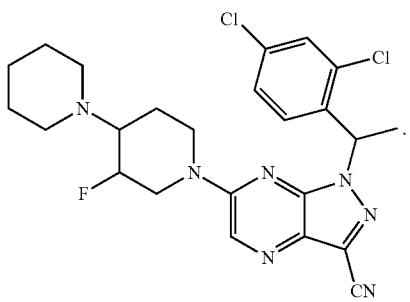
In embodiments, the compound has structure:
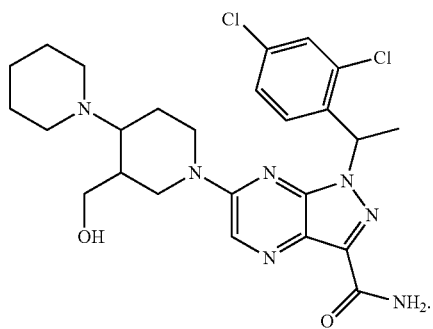 [SMILES: CC(c1ccc(Cl)cc1Cl)n1nc(C(N)=O)c2ncc(N3CCC(N4CCCCC4)C(CO)C3)nc21]
In embodiments, the compound has structure:
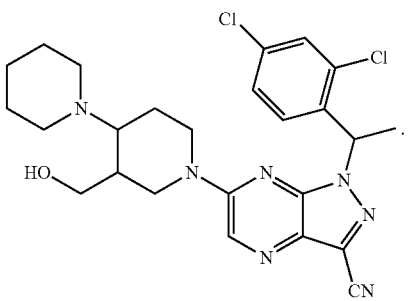 [SMILES: CC(c1ccc(Cl)cc1Cl)n1nc(C#N)c2ncc(N3CCC(N4CCCCC4)C(CO)C3)nc21]
In embodiments, the compound has structure:
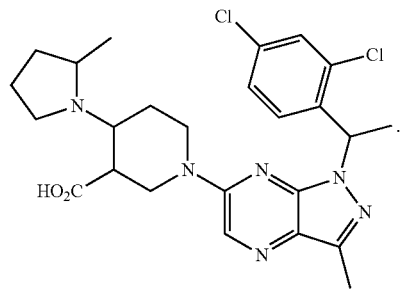 [SMILES: Cc1nn(C(C)c2ccc(Cl)cc2Cl)c2nc(N3CCC(N4CCCC4C)C(C(=O)O)C3)cnc12]
In embodiments, the compound has structure:
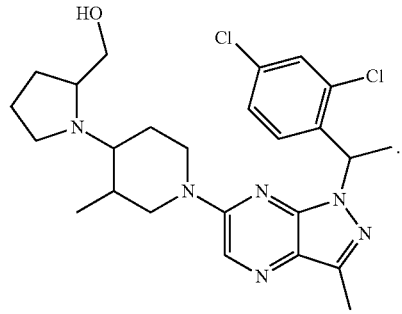 [SMILES: Cc1nn(C(C)c2ccc(Cl)cc2Cl)c2nc(N3CCC(N4CCCC4CO)C(C)C3)cnc12]
In embodiments, the compound has structure:
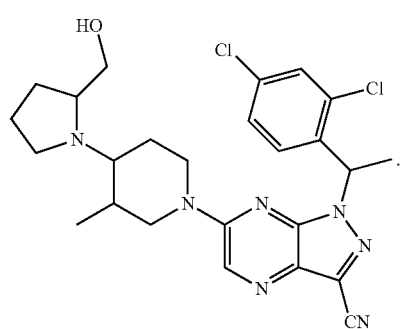 [SMILES: CC1CN(c2cnc3c(C#N)nn(C(C)c4ccc(Cl)cc4Cl)c3n2)CCC1N1CCCC1CO]

In embodiments, the compound has structure:
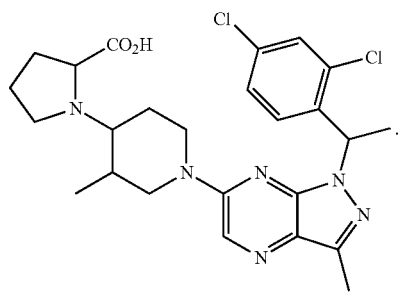 [SMILES: Cc1nn(C(C)c2ccc(Cl)cc2Cl)c2nc(N3CCC(N4CCCC4C(=O)O)C(C)C3)cnc12]
In embodiments, the compound has structure:
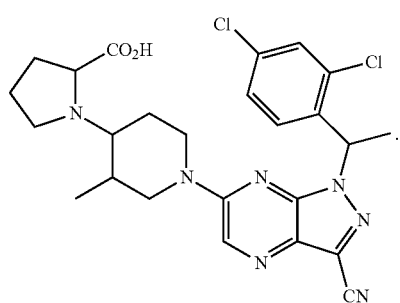 [SMILES: CC1CN(c2cnc3c(C#N)nn(C(C)c4ccc(Cl)cc4Cl)c3n2)CCC1N1CCCC1C(=O)O]
In embodiments, the compound has structure:
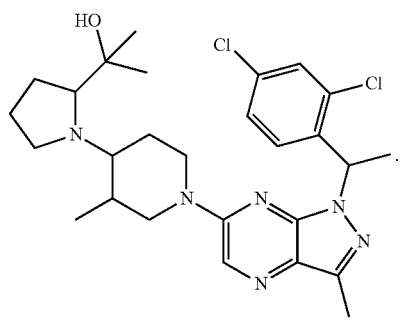 [SMILES: Cc1nn(C(C)c2ccc(Cl)cc2Cl)c2nc(N3CCC(N4CCCC4C(C)(C)O)C(C)C3)cnc12]
In embodiments, the compound has structure:
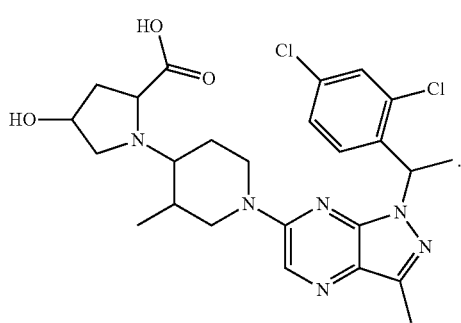 [SMILES: Cc1nn(C(C)c2ccc(Cl)cc2Cl)c2nc(N3CCC(N4CC(O)CC4C(=O)O)C(C)C3)cnc12]
In embodiments, the compound has structure:
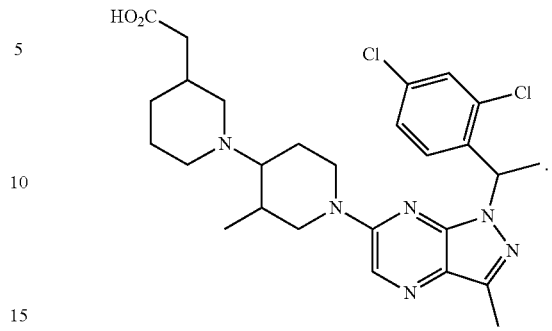
In embodiments, the compound has structure:
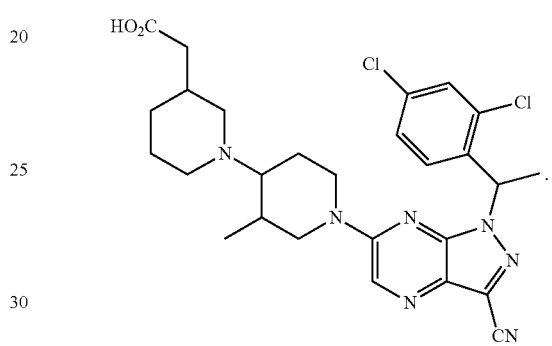
In embodiments, the compound has structure:
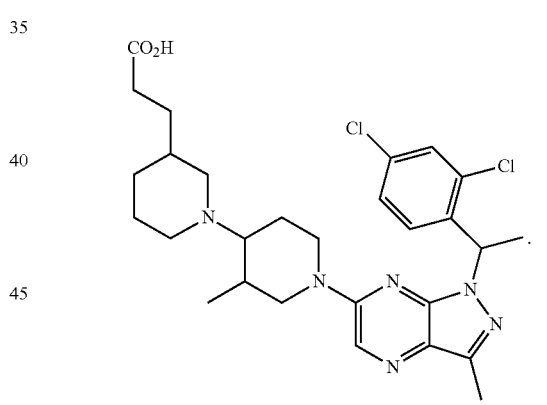
In embodiments, the compound has structure:
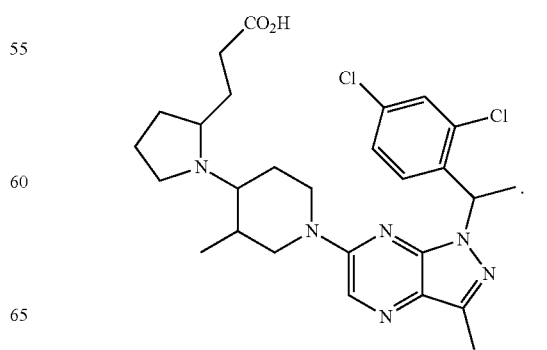

In embodiments, the compound has structure:
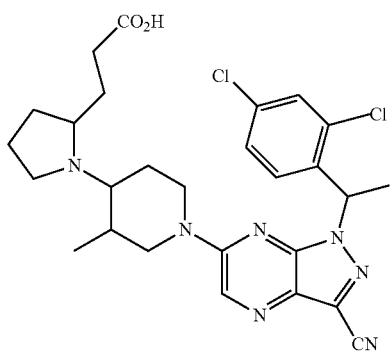
In embodiments, the compound has structure:
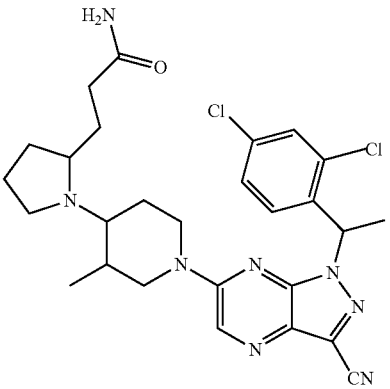
In embodiments, the compound has structure:
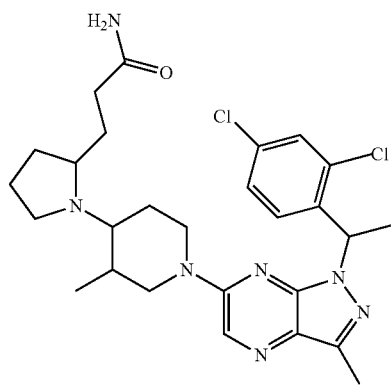
In embodiments, the compound has structure:
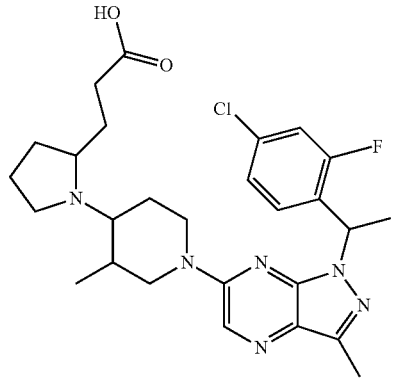
In embodiments, the compound has structure:
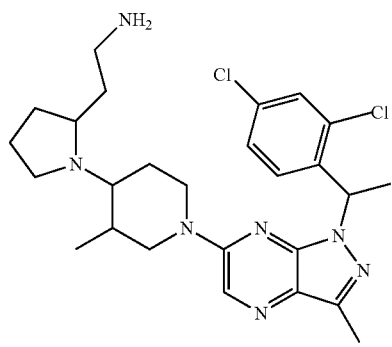
In embodiments, the compound has structure:
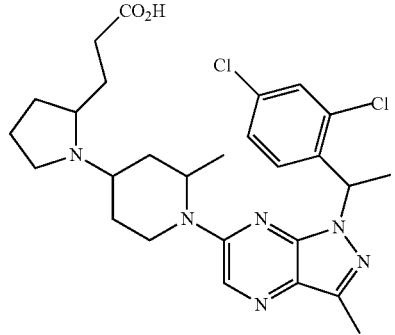
In embodiments, the compound has structure:
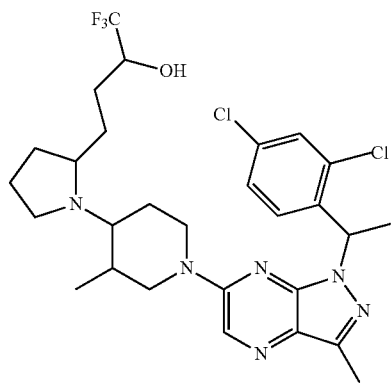
In embodiments, the compound has structure:
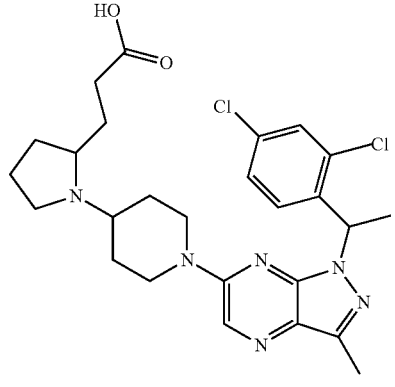

In embodiments, the compound has structure:
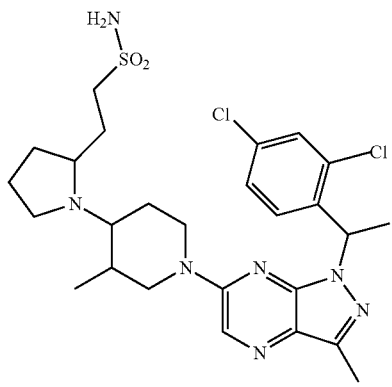
In embodiments, the compound has structure:
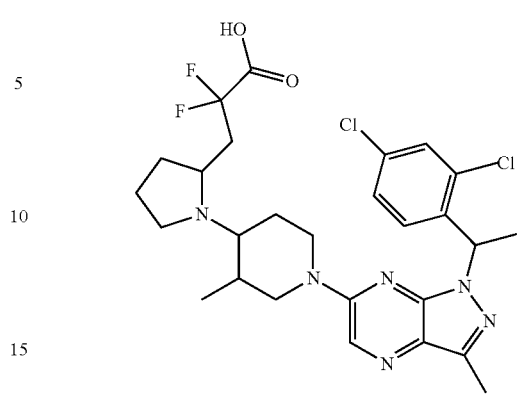
In embodiments, the compound has structure:
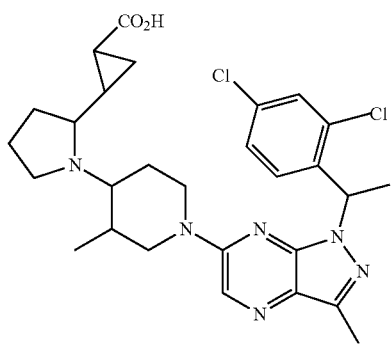
In embodiments, the compound has structure:
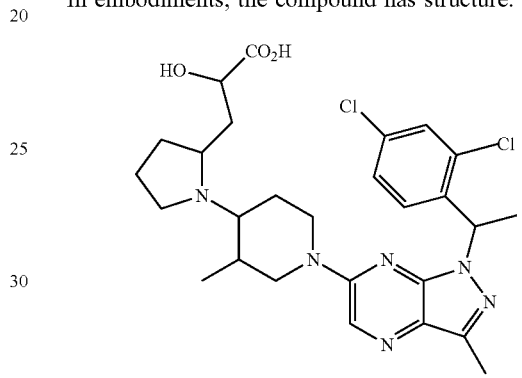
In embodiments, the compound has structure:
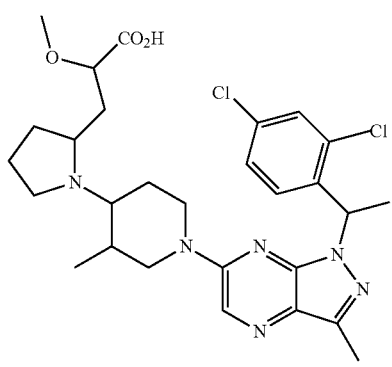
In embodiments, the compound has structure:
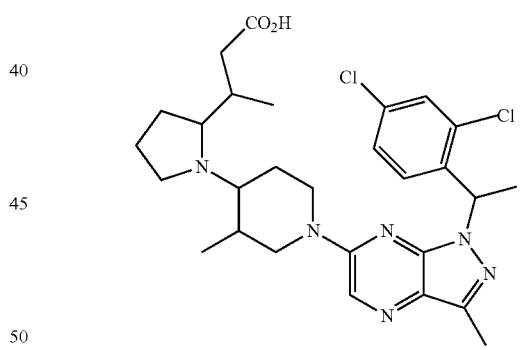
In embodiments, the compound has structure:
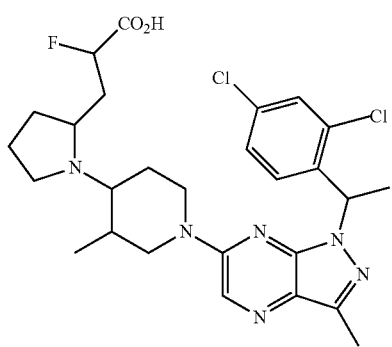
In embodiments, the compound has structure:
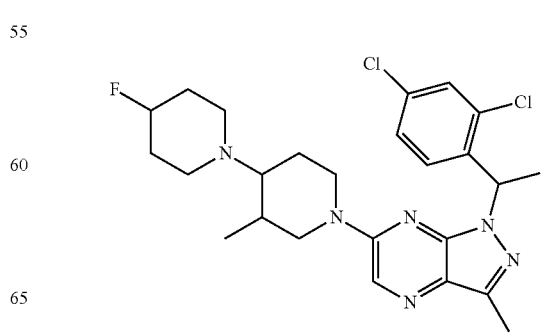

In embodiments, the compound has structure:
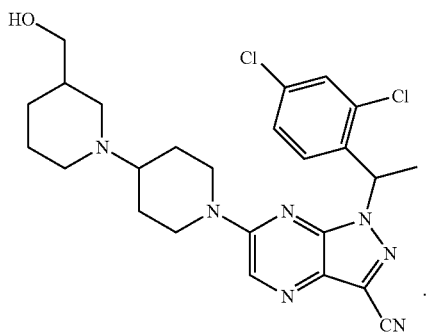 [SMILES: CC(c1ccc(Cl)cc1Cl)n1nc(C#N)c2ncc(N3CCC(N4CCCC(CO)C4)CC3)nc21]
In embodiments, the compound has structure:
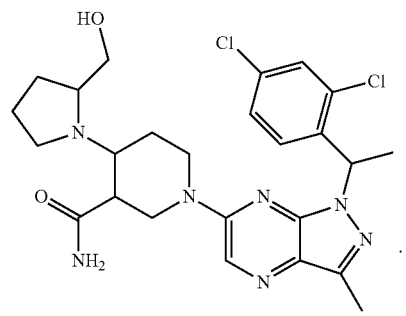 [SMILES: Cc1nn(C(C)c2ccc(Cl)cc2Cl)c2nc(N3CCC(N4CCCC4CO)C(C(N)=O)C3)cnc12]
In embodiments, the compound has structure:
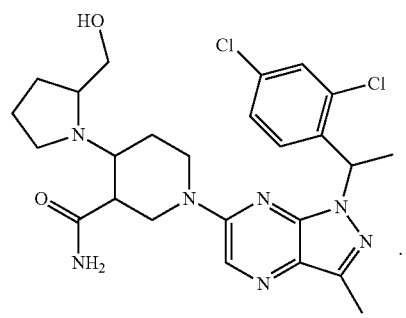 [SMILES: Cc1nn(C(C)c2ccc(Cl)cc2Cl)c2nc(N3CCC(N4CCCC4CO)C(C(N)=O)C3)cnc12]
In embodiments, the compound has structure:
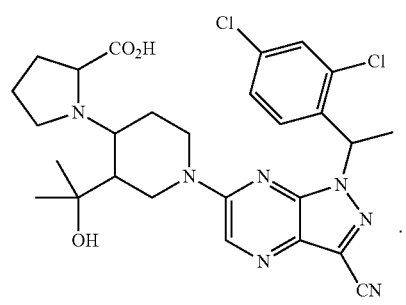 [SMILES: CC(c1ccc(Cl)cc1Cl)n1nc(C#N)c2ncc(N3CCC(N4CCCC4C(=O)O)C(C(C)(C)O)C3)nc21]
In embodiments, the compound has structure:
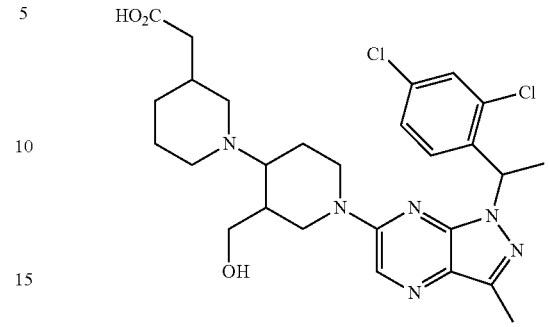
In embodiments, the compound has structure:
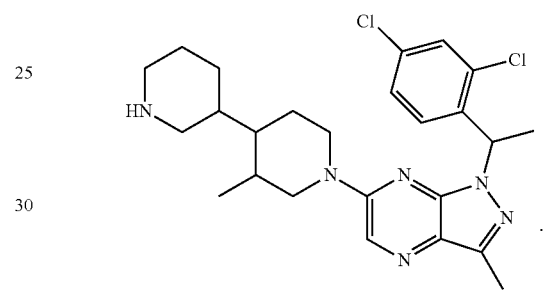
In embodiments, the compound has structure:
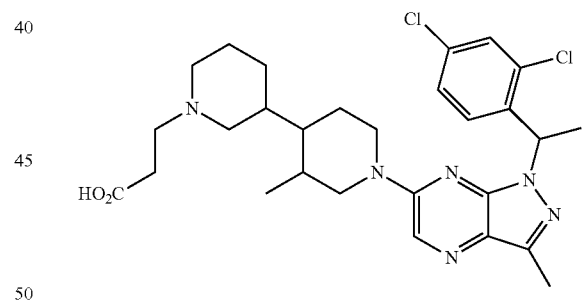
In embodiments, the compound has structure:
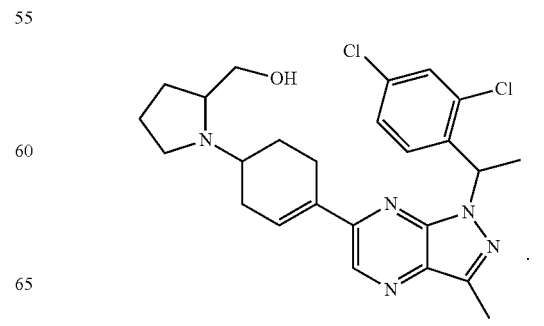

251
In embodiments, the compound has structure:
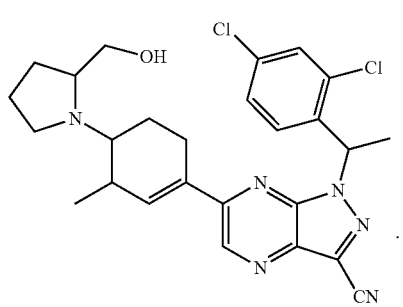 [SMILES: CC1C=C(c2cnc3c(C#N)nn(C(C)c4ccc(Cl)cc4Cl)c3n2)CCC1N1CCCC1CO]
In embodiments, the compound has structure:
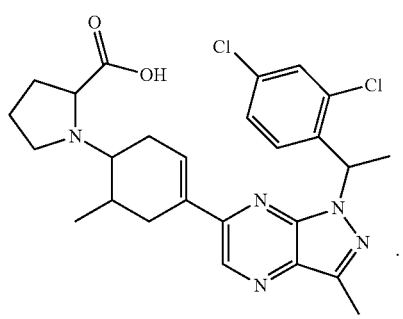 [SMILES: Cc1nn(C(C)c2ccc(Cl)cc2Cl)c2nc(C3=CCC(N4CCCC4C(=O)O)C(C)C3)cnc12]
In embodiments, the compound has structure:
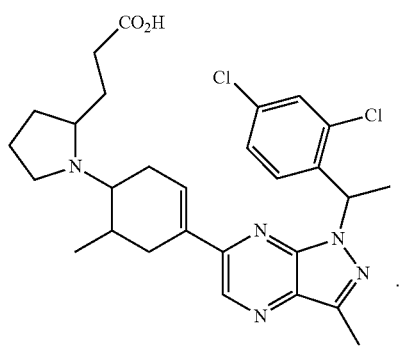 [SMILES: Cc1nn(C(C)c2ccc(Cl)cc2Cl)c2nc(C3=CCC(N4CCCC4CCC(=O)O)C(C)C3)cnc12]
In embodiments, the compound has structure:
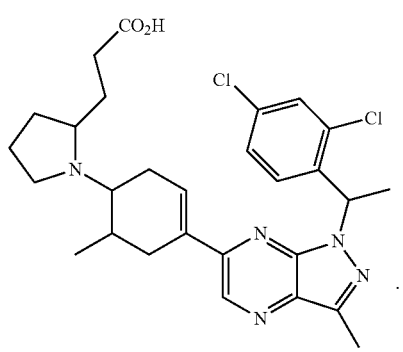 [SMILES: Cc1nn(C(C)c2ccc(Cl)cc2Cl)c2nc(C3=CCC(N4CCCC4CCC(=O)O)C(C)C3)cnc12]
252
In embodiments, the compound has structure:
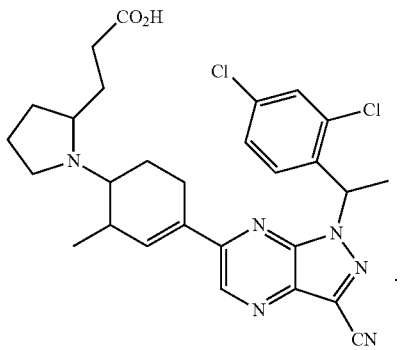 [SMILES: CC1C=C(c2cnc3c(C#N)nn(C(C)c4ccc(Cl)cc4Cl)c3n2)CCC1N1CCCC1CCC(=O)O]
In embodiments, the compound has structure:
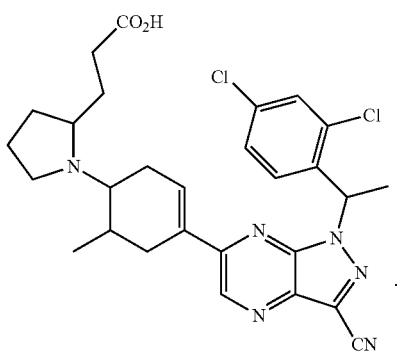 [SMILES: CC1CC(c2cnc3c(C#N)nn(C(C)c4ccc(Cl)cc4Cl)c3n2)=CCC1N1CCCC1CCC(=O)O]
In embodiments, the compound has structure:
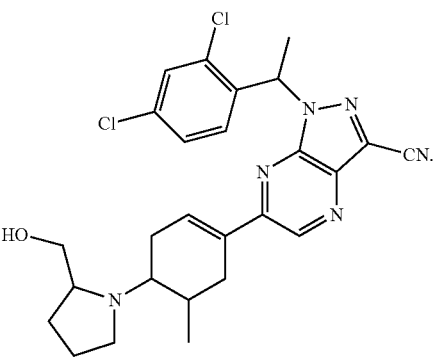 [SMILES: CC1CC(c2cnc3c(C#N)nn(C(C)c4ccc(Cl)cc4Cl)c3n2)=CCC1N1CCCC1CO]
In embodiments, the compound has structure:
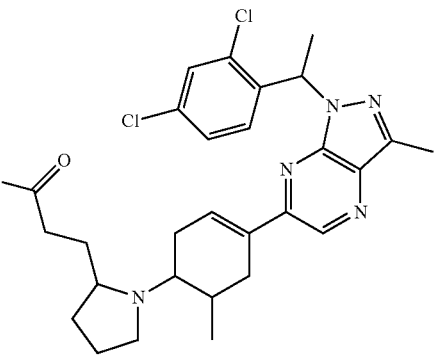

In embodiments, the compound has structure:
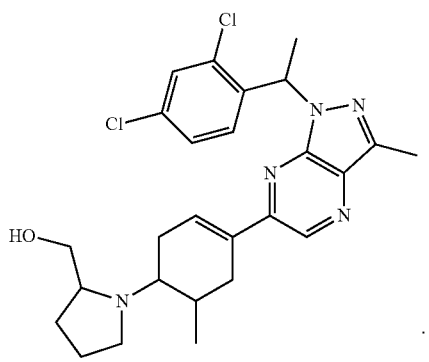 [SMILES: Cc1nn(C(C)c2ccc(Cl)cc2Cl)c2nc(C3=CCC(N4CCCC4CO)C(C)C3)cnc12]
In embodiments, the compound has structure:
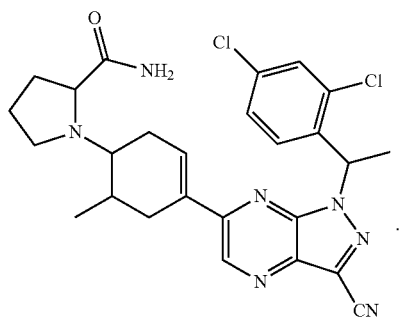 [SMILES: CC1CC(c2cnc3c(C#N)nn(C(C)c4ccc(Cl)cc4Cl)c3n2)=CCC1N1CCCC1C(N)=O]
In embodiments, the compound has structure:
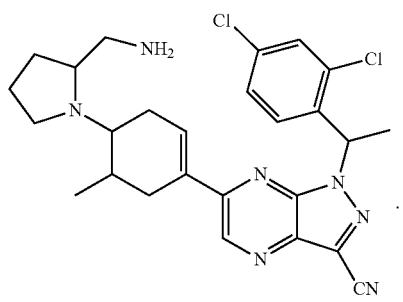 [SMILES: CC1CC(c2cnc3c(C#N)nn(C(C)c4ccc(Cl)cc4Cl)c3n2)=CCC1N1CCCC1CN]
In embodiments, the compound has structure:
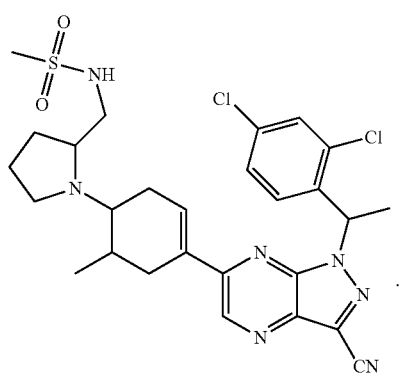 [SMILES: CC1CC(c2cnc3c(C#N)nn(C(C)c4ccc(Cl)cc4Cl)c3n2)=CCC1N1CCCC1CNS(C)(=O)=O]
In embodiments, the compound has structure:
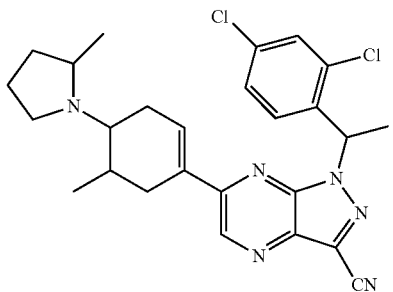
In embodiments, the compound has structure:
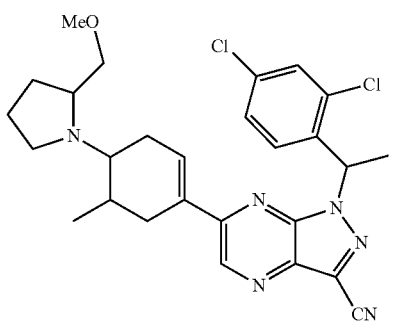
In embodiments, the compound has structure:
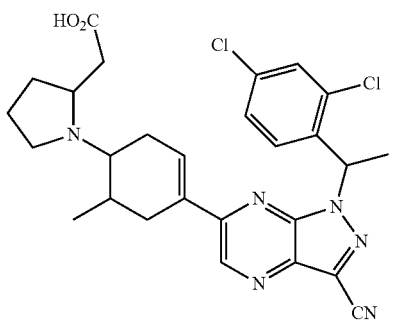
In embodiments, the compound has structure:
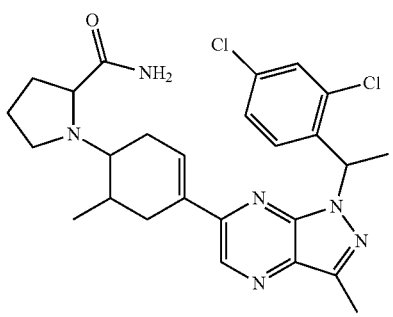

In embodiments, the compound has structure:
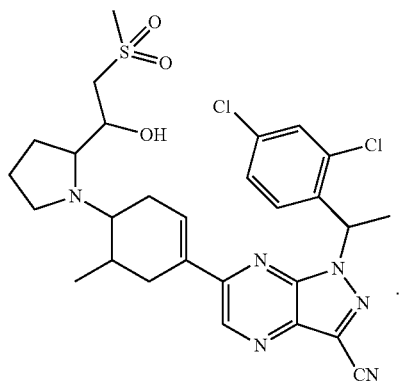 [SMILES: CC1CC(c2cnc3c(C#N)nn(C(C)c4ccc(Cl)cc4Cl)c3n2)=CCC1N1CCCC1C(O)CS(C)(=O)=O]
In embodiments, the compound has structure:
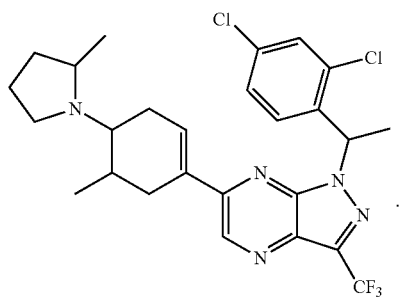 [SMILES: CC1CC(c2cnc3c(C(F)(F)F)nn(C(C)c4ccc(Cl)cc4Cl)c3n2)=CCC1N1CCCC1C]
In embodiments, the compound has structure:
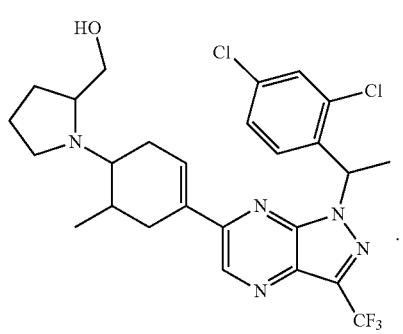 [SMILES: CC1CC(c2cnc3c(C(F)(F)F)nn(C(C)c4ccc(Cl)cc4Cl)c3n2)=CCC1N1CCCC1CO]
In embodiments, the compound has structure:
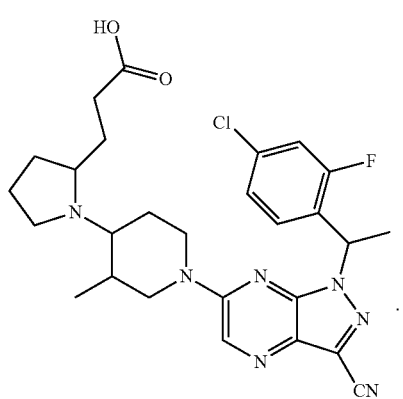 [SMILES: CC1CN(c2cnc3c(C#N)nn(C(C)c4ccc(Cl)cc4F)c3n2)CCC1N1CCCC1CCC(=O)O]
In embodiments, the compound has structure:
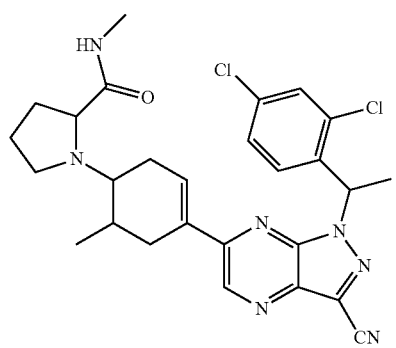
In embodiments, the compound has structure:
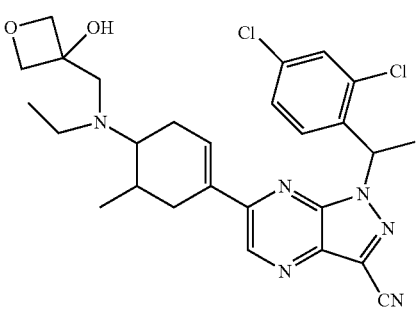
In embodiments, the compound has structure:
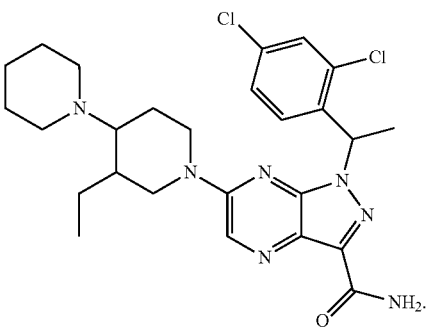 [SMILES: CCC1CN(c2cnc3c(C(N)=O)nn(C(C)c4ccc(Cl)cc4Cl)c3n2)CCC1N1CCCCC1]
In embodiments, the compound has structure:
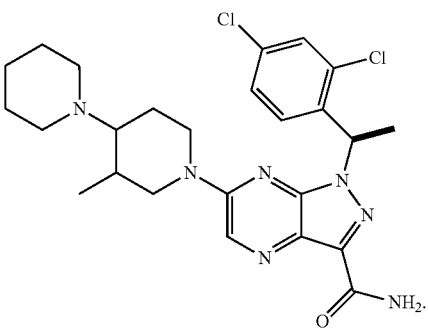 [SMILES: CC1CN(c2cnc3c(C(N)=O)nn([C@H](C)c4ccc(Cl)cc4Cl)c3n2)CCC1N1CCCCC1]

In embodiments, the compound has structure:

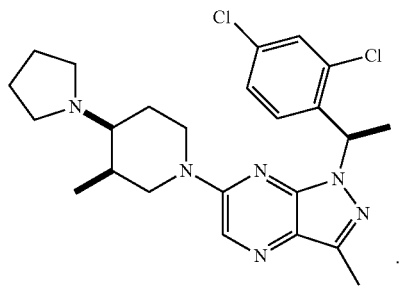

In embodiments, the compound has structure:

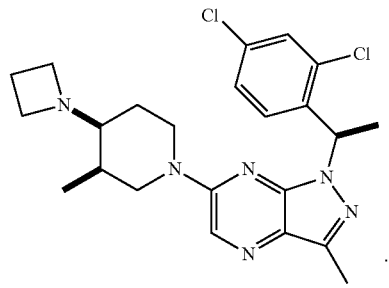 [SMILES: Cc1nn([C@H](C)c2ccc(Cl)cc2Cl)c2nc(N3CC[C@H](N4CCC4)[C@H](C)C3)cnc12]

In embodiments, the compound has structure:

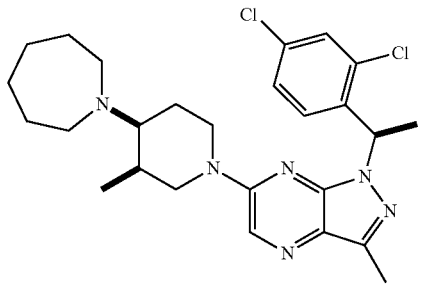

In embodiments, the compound has structure:

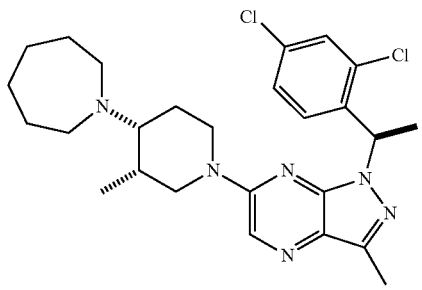

In embodiments, the compound has structure:

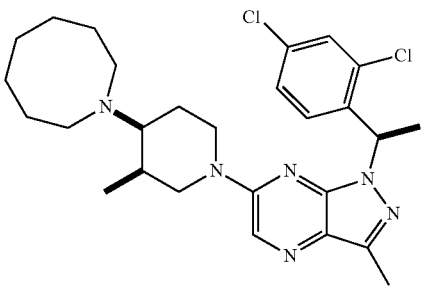

In embodiments, the compound has structure:

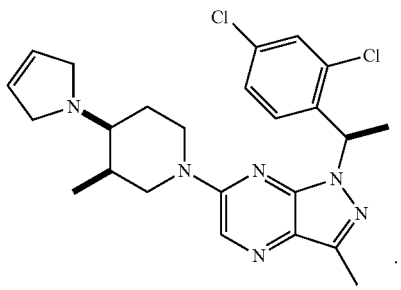 [SMILES: Cc1nn([C@H](C)c2ccc(Cl)cc2Cl)c2nc(N3CC[C@H](N4CC=CC4)[C@H](C)C3)cnc12]

In embodiments, the compound has structure:

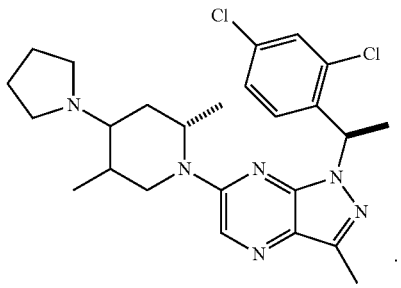 [SMILES: Cc1nn([C@H](C)c2ccc(Cl)cc2Cl)c2nc(N3CC(C)C(N4CCCC4)C[C@@H]3C)cnc12]

In embodiments, the compound has structure:

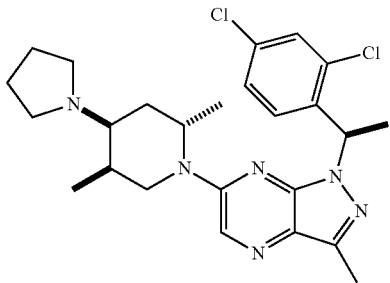

In embodiments, the compound has structure:

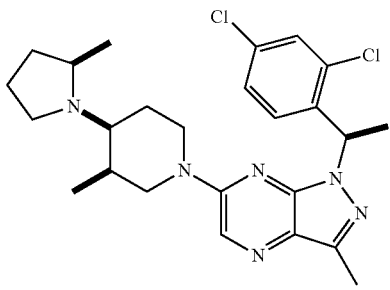

In embodiments, the compound has structure:

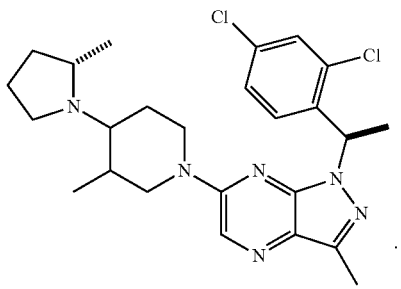 [SMILES: Cc1nn([C@H](C)c2ccc(Cl)cc2Cl)c2nc(N3CCC(N4CCC[C@@H]4C)C(C)C3)cnc12]

In embodiments, the compound has structure:

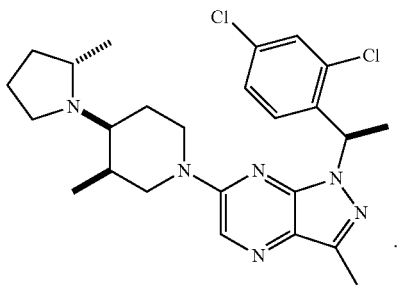 [SMILES: Cc1nn([C@H](C)c2ccc(Cl)cc2Cl)c2nc(N3CC[C@H](N4CCC[C@@H]4C)[C@H](C)C3)cnc12]

In embodiments, the compound has structure:

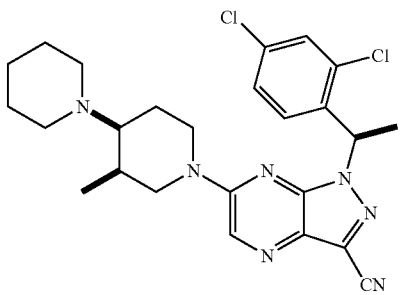

In embodiments, the compound has structure:

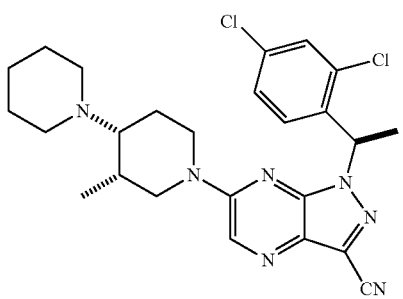

In embodiments, the compound has structure:

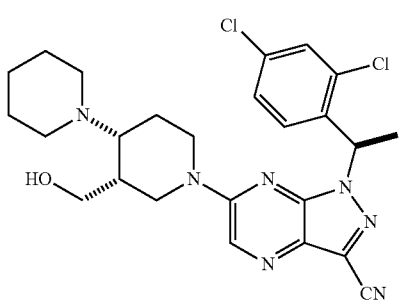

In embodiments, the compound has structure:

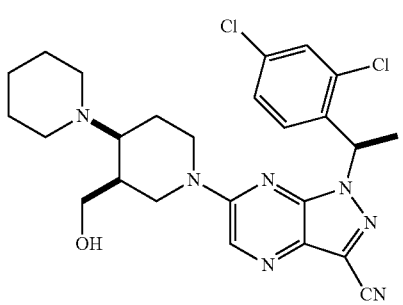

In embodiments, the compound has structure:

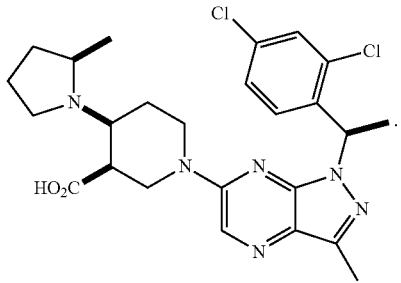

In embodiments, the compound has structure:

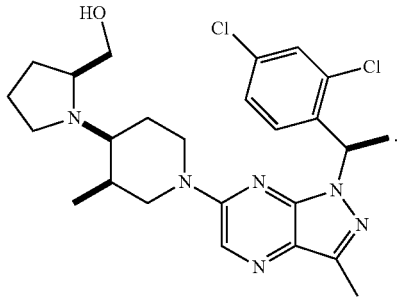

In embodiments, the compound has structure:

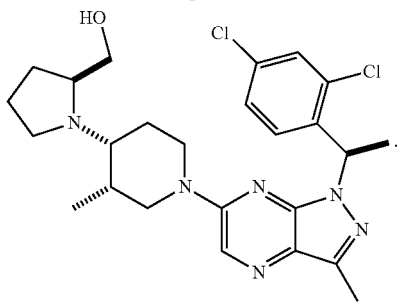

In embodiments, the compound has structure:

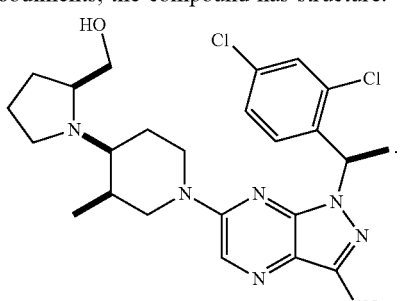

In embodiments, the compound has structure:

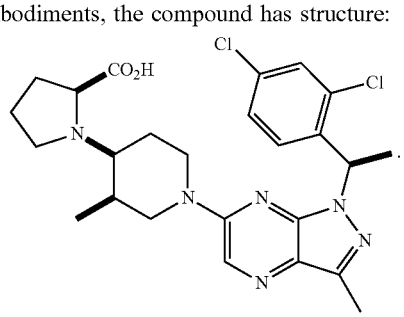

In embodiments, the compound has structure:
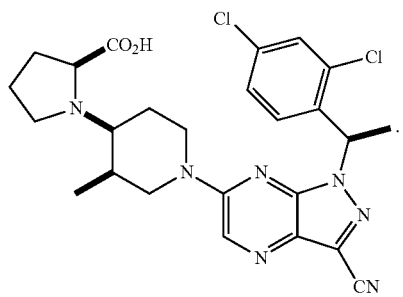
In embodiments, the compound has structure:
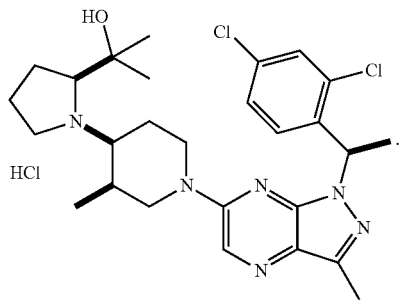
In embodiments, the compound has structure:
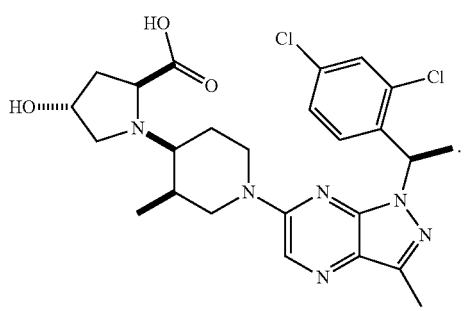
In embodiments, the compound has structure:
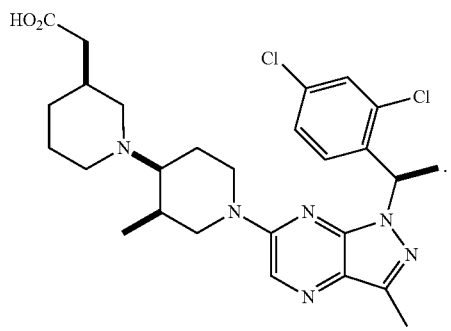
In embodiments, the compound has structure:
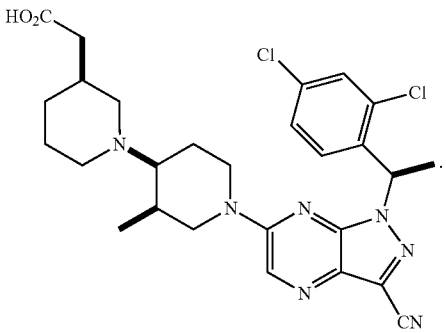
In embodiments, the compound has structure:
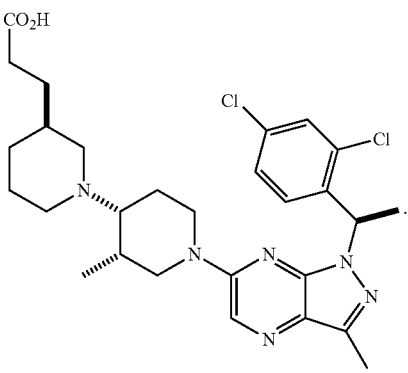
In embodiments, the compound has structure:
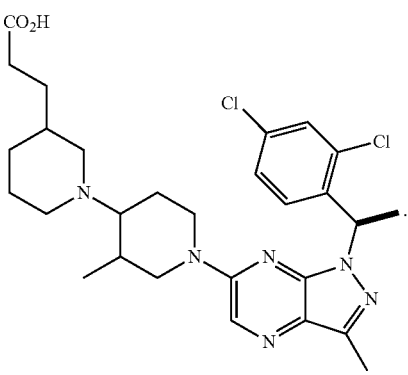 [SMILES: Cc1nn([C@H](C)c2ccc(Cl)cc2Cl)c2nc(N3CCC(N4CCCC(CCC(=O)O)C4)C(C)C3)cnc12]
In embodiments, the compound has structure:
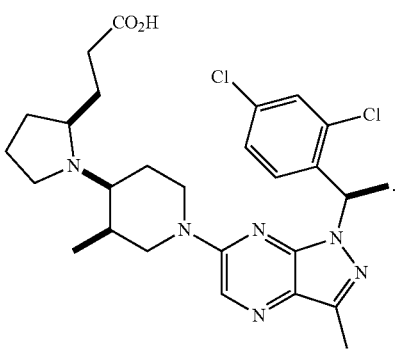 [SMILES: Cc1nn([C@H](C)c2ccc(Cl)cc2Cl)c2nc(N3CC[C@H](N4CCC[C@H]4CCC(=O)O)[C@H](C)C3)cnc12]

In embodiments, the compound has structure:
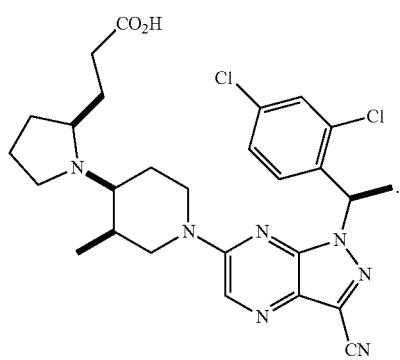 [SMILES: C[C@@H]1CN(c2cnc3c(C#N)nn([C@H](C)c4ccc(Cl)cc4Cl)c3n2)CC[C@@H]1N1CCC[C@H]1CCC(=O)O]
In embodiments, the compound has structure:
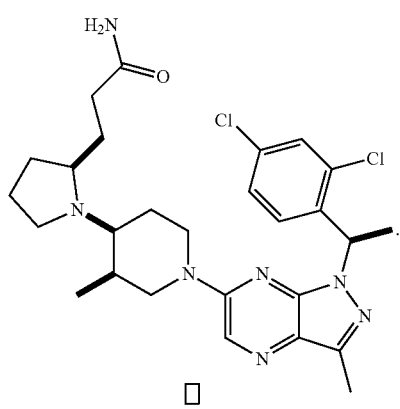 [SMILES: Cc1nn([C@H](C)c2ccc(Cl)cc2Cl)c2nc(N3CC[C@H](N4CCC[C@H]4CCC(N)=O)[C@H](C)C3)cnc12]
☐
In embodiments, the compound has structure:
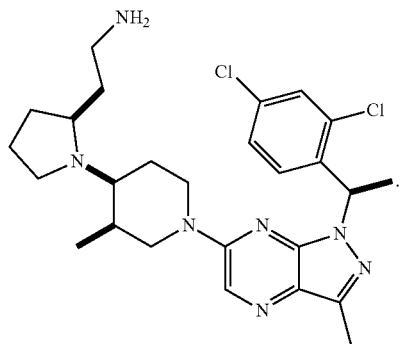 [SMILES: Cc1nn([C@H](C)c2ccc(Cl)cc2Cl)c2nc(N3CC[C@H](N4CCC[C@H]4CCN)[C@H](C)C3)cnc12]
In embodiments, the compound has structure:
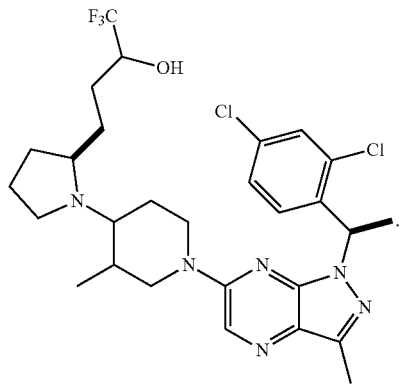 [SMILES: Cc1nn([C@H](C)c2ccc(Cl)cc2Cl)c2nc(N3CCC(N4CCC[C@H]4CCC(O)C(F)(F)F)C(C)C3)cnc12]
In embodiments, the compound has structure:
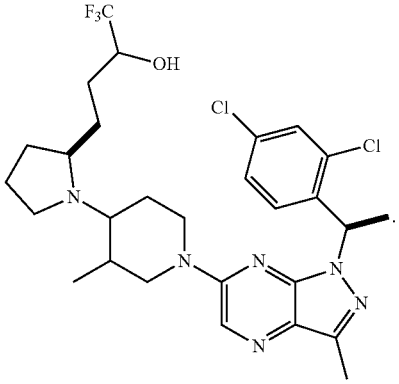 [SMILES: Cc1nn([C@H](C)c2ccc(Cl)cc2Cl)c2nc(N3CCC(N4CCC[C@H]4CCC(O)C(F)(F)F)C(C)C3)cnc12]
In embodiments, the compound has structure:
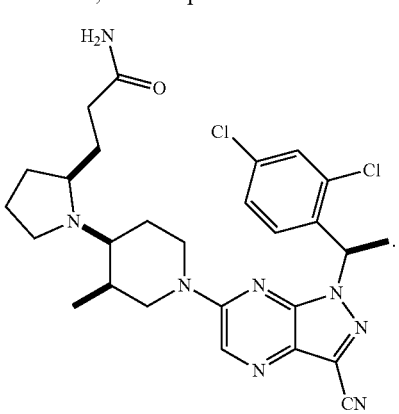
In embodiments, the compound has structure:
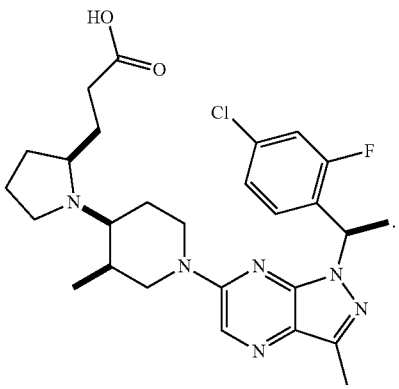 [SMILES: Cc1nn([C@H](C)c2ccc(Cl)cc2F)c2nc(N3CC[C@H](N4CCC[C@H]4CCC(=O)O)[C@H](C)C3)cnc12]
In embodiments, the compound has structure:
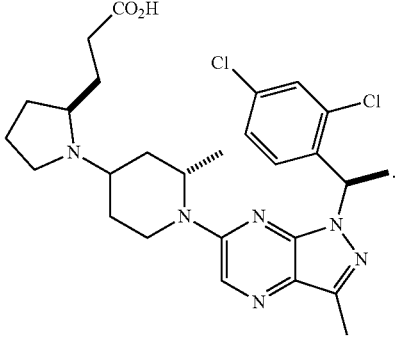 [SMILES: Cc1nn([C@H](C)c2ccc(Cl)cc2Cl)c2nc(N3CCC(N4CCC[C@H]4CCC(=O)O)C[C@@H]3C)cnc12]

In embodiments, the compound has structure:
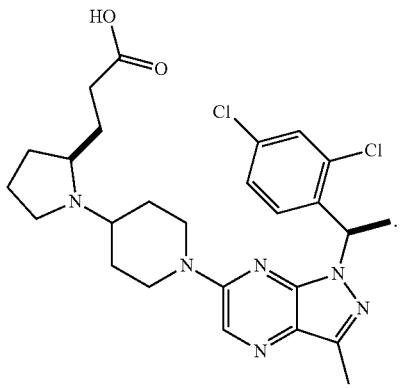 [SMILES: Cc1nn([C@H](C)c2ccc(Cl)cc2Cl)c2nc(N3CCC(N4CCC[C@H]4CCC(=O)O)CC3)cnc12]
In embodiments, the compound has structure:
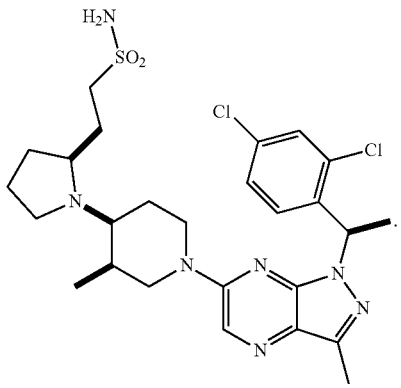 [SMILES: Cc1nn([C@H](C)c2ccc(Cl)cc2Cl)c2nc(N3CC[C@H](N4CCC[C@H]4CCS(N)(=O)=O)[C@H](C)C3)cnc12]
In embodiments, the compound has structure:
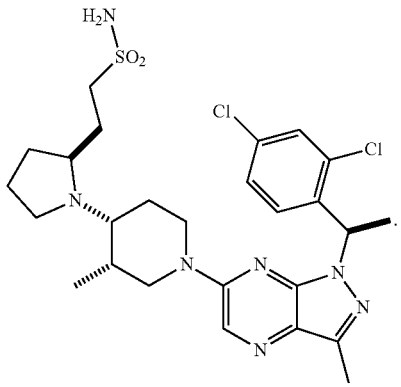 [SMILES: Cc1nn([C@H](C)c2ccc(Cl)cc2Cl)c2nc(N3CC[C@@H](N4CCC[C@H]4CCS(N)(=O)=O)[C@@H](C)C3)cnc12]
In embodiments, the compound has structure:
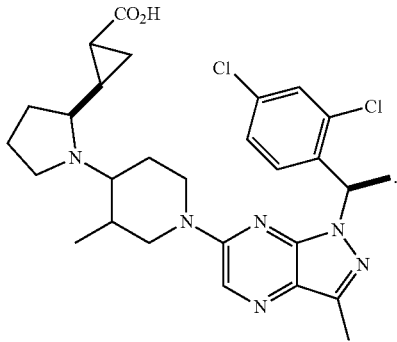 [SMILES: Cc1nn([C@H](C)c2ccc(Cl)cc2Cl)c2nc(N3CCC(N4CCC[C@H]4C4CC4C(=O)O)C(C)C3)cnc12]
In embodiments, the compound has structure:
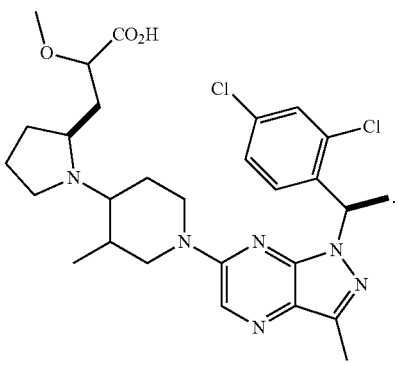 [SMILES: COC(C[C@@H]1CCCN1C1CCN(c2cnc3c(C)nn([C@H](C)c4ccc(Cl)cc4Cl)c3n2)CC1C)C(=O)O]
In embodiments, the compound has structure:
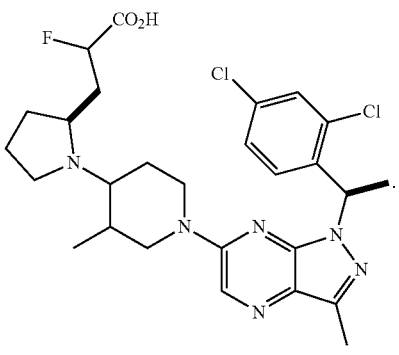 [SMILES: Cc1nn([C@H](C)c2ccc(Cl)cc2Cl)c2nc(N3CCC(N4CCC[C@H]4CC(F)C(=O)O)C(C)C3)cnc12]
In embodiments, the compound has structure:
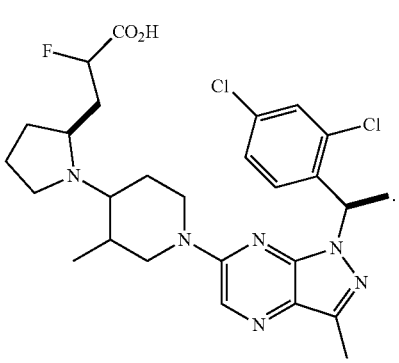 [SMILES: Cc1nn([C@H](C)c2ccc(Cl)cc2Cl)c2nc(N3CCC(N4CCC[C@H]4CC(F)C(=O)O)C(C)C3)cnc12]
In embodiments, the compound has structure:
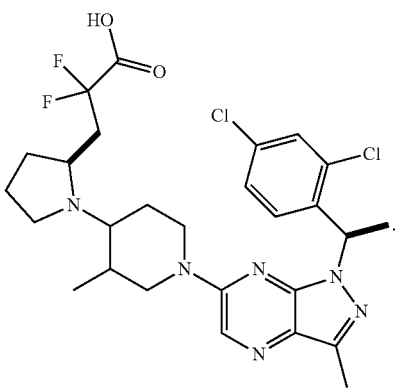 [SMILES: Cc1nn([C@H](C)c2ccc(Cl)cc2Cl)c2nc(N3CCC(N4CCC[C@H]4CC(F)(F)C(=O)O)C(C)C3)cnc12]

In embodiments, the compound has structure:
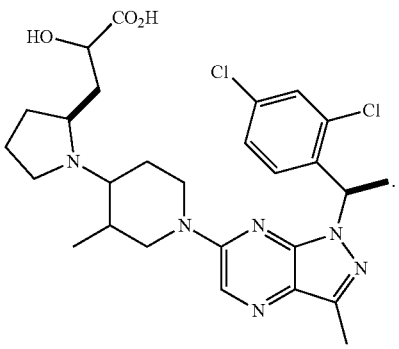 [SMILES: Cc1nn([C@H](C)c2ccc(Cl)cc2Cl)c2nc(N3CCC(N4CCC[C@H]4CC(O)C(=O)O)C(C)C3)cnc12]
In embodiments, the compound has structure:
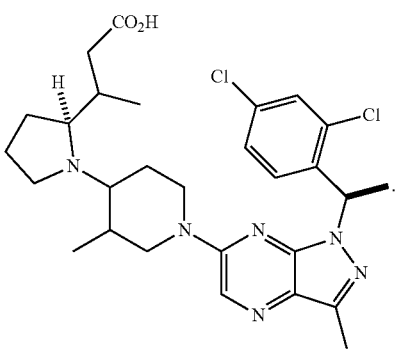 [SMILES: Cc1nn([C@H](C)c2ccc(Cl)cc2Cl)c2nc(N3CCC(N4CCC[C@H]4C(C)CC(=O)O)C(C)C3)cnc12]
In embodiments, the compound has structure:
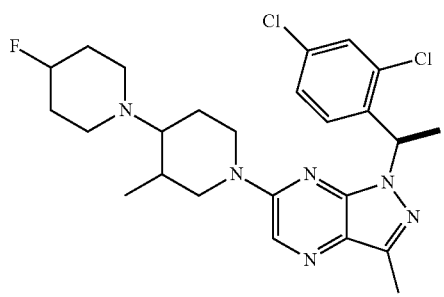
In embodiments, the compound has structure:
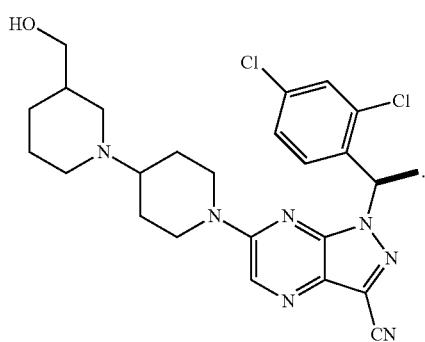 [SMILES: C[C@H](c1ccc(Cl)cc1Cl)n1nc(C#N)c2ncc(N3CCC(N4CCCC(CO)C4)CC3)nc21]
In embodiments, the compound has structure:
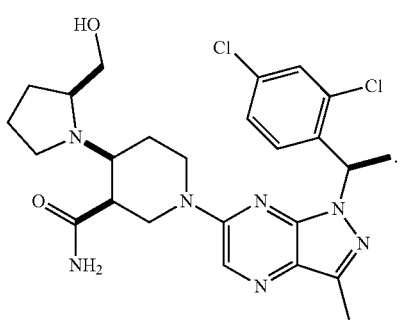 [SMILES: Cc1nn([C@H](C)c2ccc(Cl)cc2Cl)c2nc(N3CC[C@H](N4CCC[C@H]4CO)[C@H](C(N)=O)C3)cnc12]
In embodiments, the compound has structure:
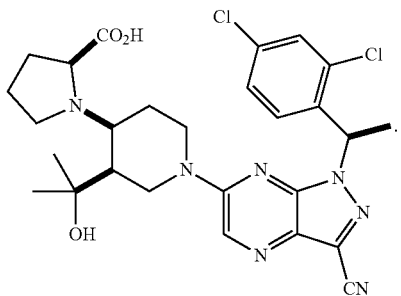 [SMILES: C[C@H](c1ccc(Cl)cc1Cl)n1nc(C#N)c2ncc(N3CC[C@H](N4CCC[C@H]4C(=O)O)[C@H](C(C)(C)O)C3)nc21]
In embodiments, the compound has structure:
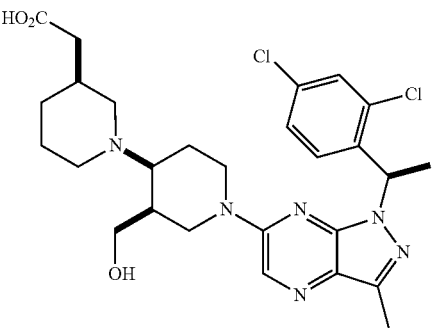
In embodiments, the compound has structure:
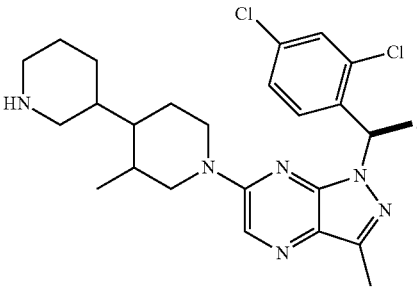

269
In embodiments, the compound has structure:
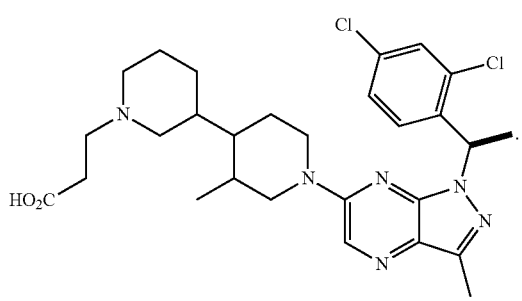 [SMILES: Cc1nn([C@H](C)c2ccc(Cl)cc2Cl)c2nc(N3CCC(C4CCCN(CCC(=O)O)C4)C(C)C3)cnc12]
In embodiments, the compound has structure:
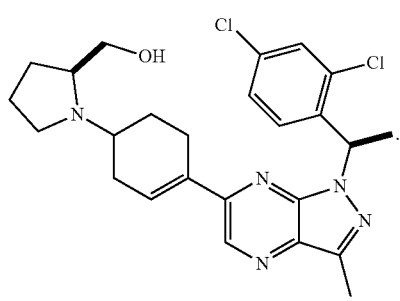 [SMILES: Cc1nn([C@H](C)c2ccc(Cl)cc2Cl)c2nc(C3=CCC(N4CCC[C@H]4CO)CC3)cnc12]
In embodiments, the compound has structure:
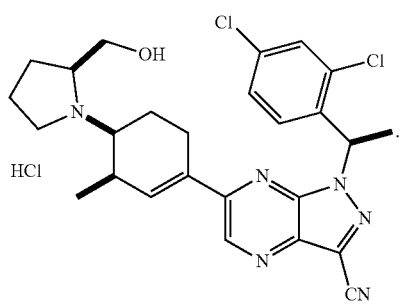 [SMILES: C[C@@H]1C=C(c2cnc3c(C#N)nn([C@H](C)c4ccc(Cl)cc4Cl)c3n2)CC[C@@H]1N1CCC[C@H]1CO ; Cl]
In embodiments, the compound has structure:
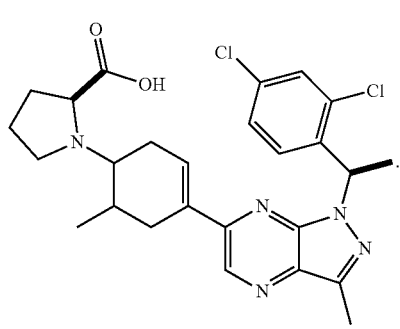 [SMILES: Cc1nn([C@H](C)c2ccc(Cl)cc2Cl)c2nc(C3=CCC(N4CCC[C@H]4C(=O)O)C(C)C3)cnc12]
270
In embodiments, the compound has structure:
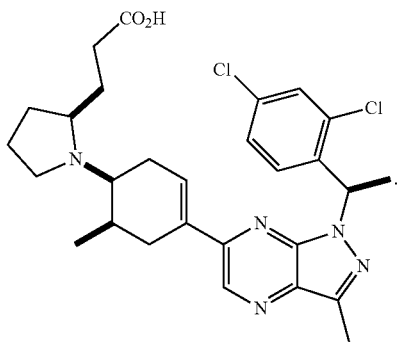 [SMILES: Cc1nn([C@H](C)c2ccc(Cl)cc2Cl)c2nc(C3=CC[C@H](N4CCC[C@H]4CCC(=O)O)[C@H](C)C3)cnc12]
In embodiments, the compound has structure:
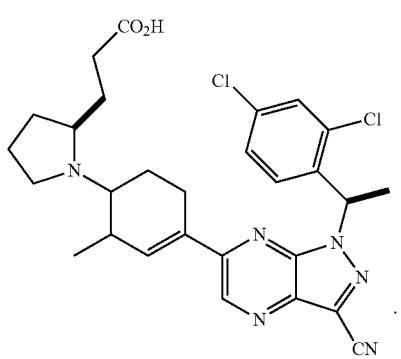 [SMILES: CC1C=C(c2cnc3c(C#N)nn([C@H](C)c4ccc(Cl)cc4Cl)c3n2)CCC1N1CCC[C@H]1CCC(=O)O]
In embodiments, the compound has structure:
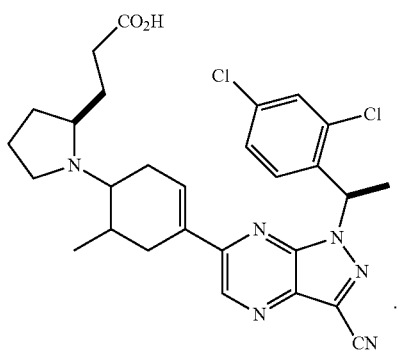 [SMILES: CC1CC(c2cnc3c(C#N)nn([C@H](C)c4ccc(Cl)cc4Cl)c3n2)=CCC1N1CCC[C@H]1CCC(=O)O]
In embodiments, the compound has structure:
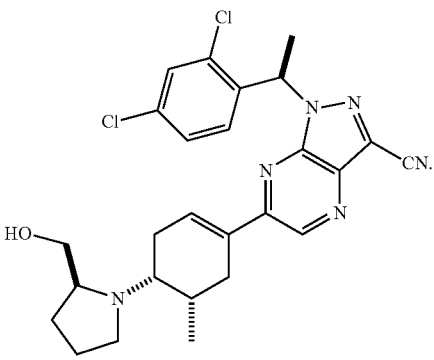

In embodiments, the compound has structure:
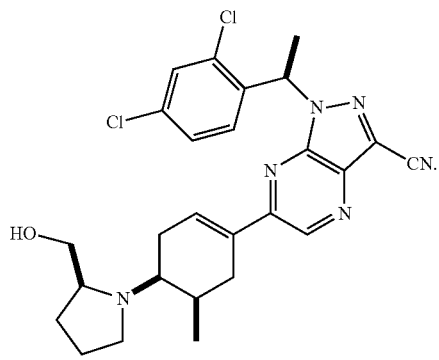 [SMILES: C[C@@H]1CC(c2cnc3c(C#N)nn([C@H](C)c4ccc(Cl)cc4Cl)c3n2)=CC[C@@H]1N1CCC[C@H]1CO]
In embodiments, the compound has structure:
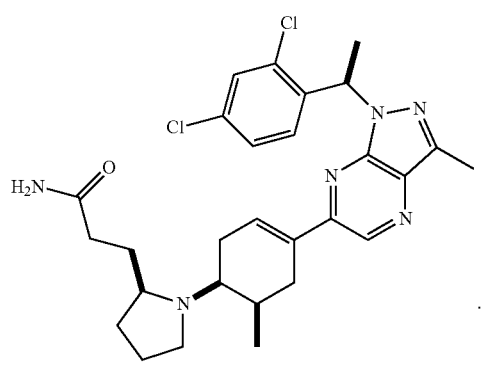 [SMILES: Cc1nn([C@H](C)c2ccc(Cl)cc2Cl)c2nc(C3=CC[C@H](N4CCC[C@H]4CCC(N)=O)[C@H](C)C3)cnc12]
In embodiments, the compound has structure:
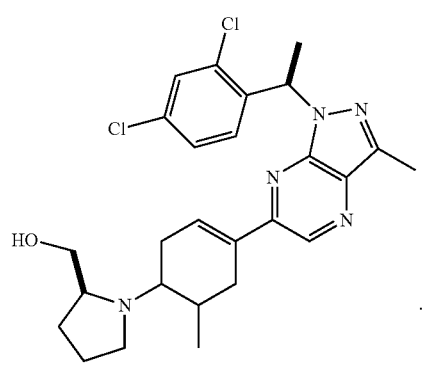 [SMILES: Cc1nn([C@H](C)c2ccc(Cl)cc2Cl)c2nc(C3=CCC(N4CCC[C@H]4CO)C(C)C3)cnc12]
In embodiments, the compound has structure:
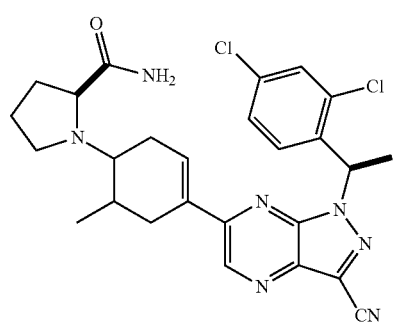
In embodiments, the compound has structure:
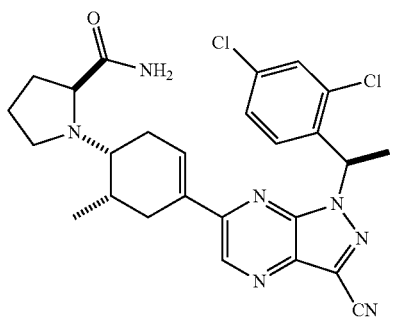
In embodiments, the compound has structure:
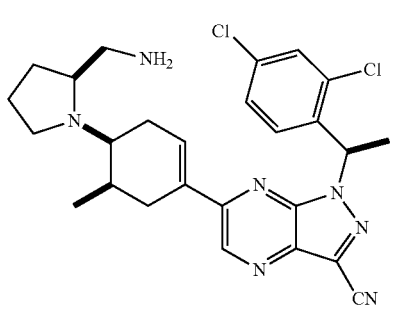
In embodiments, the compound has structure:
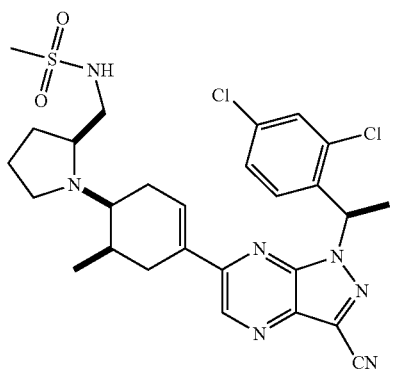
In embodiments, the compound has structure:
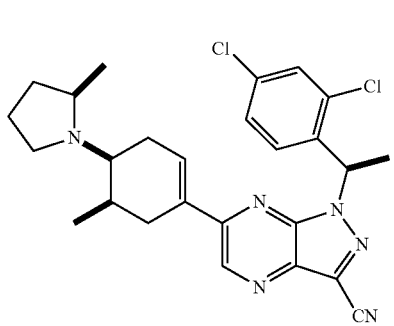

In embodiments, the compound has structure:
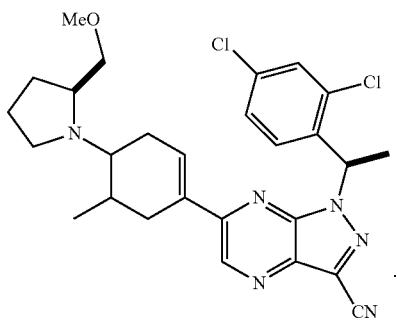 [SMILES: COC[C@@H]1CCCN1C1CC=C(c2cnc3c(C#N)nn([C@H](C)c4ccc(Cl)cc4Cl)c3n2)CC1C]
In embodiments, the compound has structure:
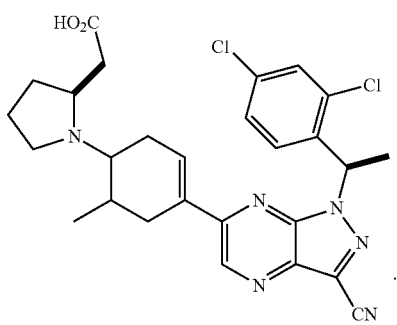
In embodiments, the compound has structure:
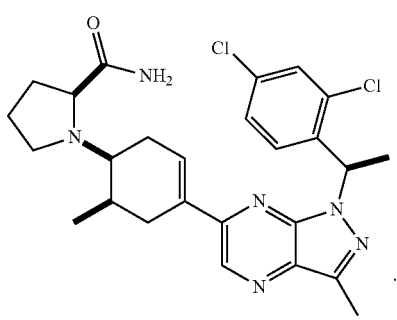 [SMILES: Cc1nn([C@H](C)c2ccc(Cl)cc2Cl)c2nc(C3=CC[C@H](N4CCC[C@H]4C(N)=O)[C@H](C)C3)cnc12]
In embodiments, the compound has structure:
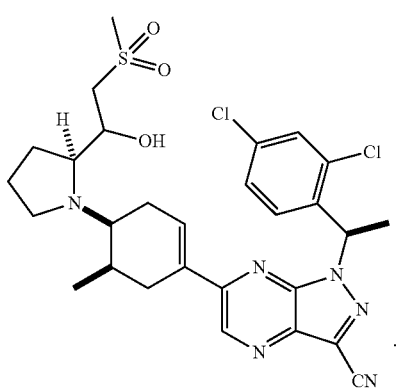 [SMILES: C[C@@H]1CC(c2cnc3c(C#N)nn([C@H](C)c4ccc(Cl)cc4Cl)c3n2)=CC[C@@H]1N1CCC[C@H]1C(O)CS(C)(=O)=O]
In embodiments, the compound has structure:
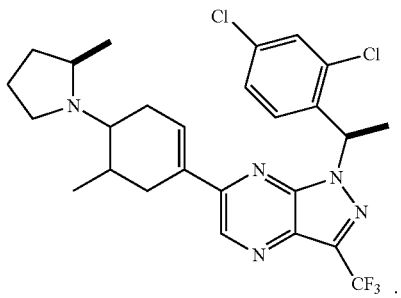 [SMILES: CC1CC(c2cnc3c(C(F)(F)F)nn([C@H](C)c4ccc(Cl)cc4Cl)c3n2)=CCC1N1CCC[C@H]1C]
In embodiments, the compound has structure:
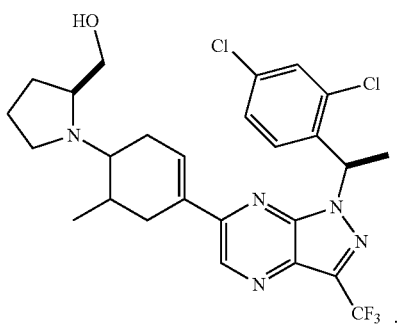 [SMILES: CC1CC(c2cnc3c(C(F)(F)F)nn([C@H](C)c4ccc(Cl)cc4Cl)c3n2)=CCC1N1CCC[C@H]1CO]
In embodiments, the compound has structure:
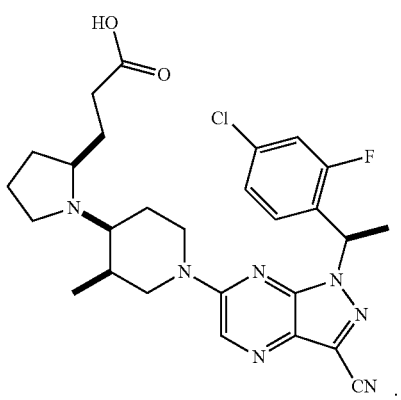 [SMILES: C[C@@H]1CN(c2cnc3c(C#N)nn([C@H](C)c4ccc(Cl)cc4F)c3n2)CC[C@@H]1N1CCC[C@H]1CCC(=O)O]
In embodiments, the compound has structure:
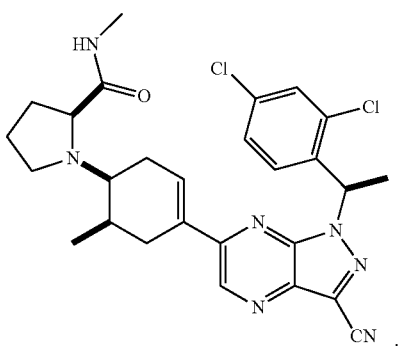 [SMILES: CNC(=O)[C@@H]1CCCN1[C@H]1CC=C(c2cnc3c(C#N)nn([C@H](C)c4ccc(Cl)cc4Cl)c3n2)C[C@H]1C]

In embodiments, the compound has structure:

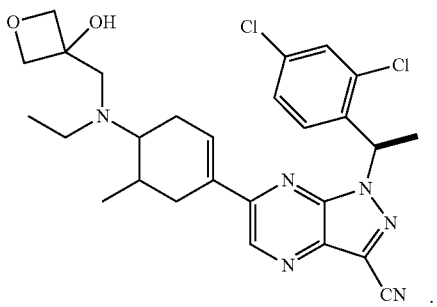 [SMILES: CCN(CC1(O)COC1)C1CC=C(c2cnc3c(C#N)nn([C@H](C)c4ccc(Cl)cc4Cl)c3n2)CC1C]

In embodiments, the compound is a compound described herein (e.g., in an aspect, embodiment, example, claim, or scheme).

Pharmaceutical Compositions

In an aspect, there is provided a pharmaceutical composition, including a compound as described herein, including embodiments (e.g., the structural Formula (I), (Ia), (II), (III), (IIIa), (IIIb), (IV), (V), (Va), (Vb), (VI), (VII), (VIIa), (VIIb), (VIII), (VIIIa), (VIIIb), (IX), (IXa), (IXb), (IXc), (IXd) or (X), and a pharmaceutically acceptable excipient).

The compounds (e.g., CCR4 inhibitors) of the present disclosure may be in the form of compositions suitable for administration to a subject. In general, such compositions are "pharmaceutical compositions" comprising a compound (e.g., CCR4 inhibitor(s)) and one or more pharmaceutically acceptable or physiologically acceptable diluents, carriers or excipients. In certain embodiments, the compound (e.g., CCR4 inhibitor) is present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein.

The pharmaceutical compositions containing the active ingredient (e.g., an inhibitor of CCR4 function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known in the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a CCR4 inhibitor contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a CCR4 inhibitor, including implants (e.g., implantable pumps) and catheter systems, slow injection pumps and devices, all of which are well known to the skilled artisan.

Depot injections, which are generally administered subcutaneously or intramuscularly, may also be utilized to release the compound (e.g., CCR4 inhibitor) disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, N.J.) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

The present disclosure contemplates the administration of the compound (e.g., CCR4 inhibitor) in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The compound (e.g., CCR4 inhibitor) contemplated by the present disclosure may be in the form of any other suitable pharmaceutical composition (e.g., sprays for nasal or inhalation use) currently known or developed in the future.

III. Methods of Use

In another aspect, there is provided a method of inhibiting C—C chemokine receptor type 4 (CCR4), the method including contacting CCR4 with a compound as described herein, including embodiments (e.g., structural Formula (I), (Ia), (II), (III), (IIIa), (IIIb), (IV), (V), (Va), (Vb), (VI), (VII), (VIIa), (VIIb), (VIII), (VIIIa), (VIIIb), (IX), (IXa), (IXb), (IXc), (IXd) or (X), or a pharmaceutically acceptable salt thereof).

In an aspect, there is provided a method of treating or preventing a disease or disorder mediated by CCR4, the method including administering to a subject in need thereof a therapeutically effective amount of a compound as described herein, including embodiments (e.g., Formula (I), (Ia), (II), (III), (IIIa), (IIIb), (IV), (V), (Va), (Vb), (VI), (VII), (VIIa), (VIIb), (VIII), (VIIIa), (VIIIb), (IX), (IXa), (IXb), (IXc), (IXd) or (X), or a pharmaceutically acceptable salt thereof).

In embodiments, the disease or disorder is an immune or inflammatory disease or disorder. In embodiments, the methods of treating an immune or inflammatory disease or disorder disclosed herein further include co-administering an anti-inflammatory agent in combination with a compound of structural Formula (I), (Ia), (II), (III), (IIIa), (IIIb), (IV), (V), (Va), (Vb), (VI), (VII), (VIIa), (VIIb), (VIII), (VIIIa), (VIIIb), (IX), (IXa), (IXb), (IXc), (IXd) or (X), or a pharmaceutically acceptable salt thereof. In embodiments, the anti-inflammatory agent is thalidomide or a derivative thereof, a retinoid, dithranol or calcipotriol, a non-steroidal anti-inflammatory agent (NSAID), cyclo-oxygenase inhibiting nitric oxide donors (CINODs), glucocorticosteroids, methotrexate, leflunomide, hydroxychloroquine, d-penicillamine, auranofin, analgesics; diacerein, hyaluronic acid derivatives or nutritional supplements.

In embodiments, the disease or disorder is a cardiovascular or metabolic disease or disorder. In embodiments, the methods of treating a cardiovascular or metabolic disease or disorder disclosed herein further include co-administering a cardiovascular agent or a metabolic disorder agent in combination with a compound of structural Formula (I), (Ia), (II), (III), (IIIa), (IIIb), (IV), (V), (Va), (Vb), (VI), (VII), (VIIa), (VIIb), (VIII), (VIIIa), (VIIIb), (IX), (IXa), (IXb), (IXc), (IXd) or (X), or a pharmaceutically acceptable salt thereof. In embodiments, the cardiovascular agent is a calcium channel blocker, a beta-adrenoceptor blocker, an angiotensin-converting enzyme (ACE) inhibitor, an angiotensin-2 receptor antagonist, a lipid lowering agent, a modulator of blood cell morphology, a thrombolytic or an anticoagulant.

In embodiments, the disease or disorder is cancer. In embodiments, the disease or disorder is inflammatory bowel disease. In embodiments, the disease or disorder is rheumatoid arthritis. In embodiments, the disease or disorder is psoriasis. In embodiments, the disease or disorder is an allergy-related disorder (e.g., hypersensitivity and anaphylactic responses); a gastrointestinal disorder (e.g., Crohn's disease, ulcerative colitis, ileitis and enteritis); psoriasis or other inflammatory dermatosis (e.g., dermatitis, eczema, atopic dermatitis, allergic contact dermatitis, dermatomyositis, urticaria and pruritus); vasculitis; scleroderma; asthma, COPD, or other respiratory allergic disease (e.g., allergic rhinitis and hypersensitivity lung diseases); an autoimmune disease, such as arthritis (e.g., rheumatoid and psoriatic), multiple sclerosis, systemic lupus erythematosus, type I diabetes or glomerulonephritis; graft rejection (e.g., allograft rejection); transplant rejection (e.g., solid organ); cancers, such as leukemias, lymphomas and metastatic cancers, particularly solid tumors (e.g., gastric cancers); or other disease in which inhibition of undesired inflammatory and/or immune responses is desired, such as atherosclerosis, neurodegenerative diseases (e.g., Alzheimer's disease), encephalitis, meningitis, hepatitis, nephritis, sepsis, sarcoidosis, allergic conjunctivitis, otitis, or sinusitis. In particular embodiments, the CCR4-mediated disease, disorder or condition is asthma, COPD, rhinitis, idiopathic pulmonary fibrosis, psoriasis or contact dermatitis. In embodiments the disease or disorder is pulmonary fibrosis, hepatic inflammation, asthma, atopic dermatitis, cancer (e.g., thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma), or granuloma development.

It is frequently beneficial to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity. Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

In embodiments, compounds of the present disclosure are effective in the treatment and prevention of IBD (e.g., Crohn's disease and ulcerative colitis, both of which are chronic idiopathic diseases that can affect any part of the gastrointestinal tract, and are associated with many untoward effects, and patients with prolonged ulcerative colitis are at an increased risk of developing colon cancer). Current IBD treatments are aimed at controlling inflammatory symptoms, and while certain agents (e.g., corticosteroids, aminosalicylates and standard immunosuppressive agents (e.g., cyclosporine, azathioprine, and methotrexate)) have met with limited success, long-term therapy may cause liver damage (e.g., fibrosis or cirrhosis) and bone marrow suppression, and patients often become refractory to such treatments.

The compounds of the present disclosure can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The compounds described herein can also be used to stimulate the immune system of patients suffering from iatrogenically-induced immune suppression, including those who have undergone bone marrow transplants, chemotherapy, or radiotherapy.

Oncology-related Disorders. In accordance with the present disclosure, a compound or pharmaceutical salt thereof can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, or angiogenesis. The disclosure contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In some embodiments, the tumor or cancer is colon cancer, ovarian cancer, breast cancer, melanoma, lung cancer, glioblastoma, or leukemia. In particular embodiments, the cancer is gastric cancer. The use of the term(s) cancer-related diseases, disorders and conditions is meant to refer broadly to conditions that are associated, directly or indirectly, with cancer, and includes, e.g., angiogenesis and precancerous conditions such as dysplasia. In embodiments, the cancer is thyroid carcinoma, cholangiocarcinoma, pancreatic cancer pancreatic adenocarcinoma, skin cutaneous melanoma, colon cancer, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma.

In embodiments, a cancer be metastatic or at risk of becoming metastatic, or may occur in a diffuse tissue, including cancers of the blood or bone marrow (e.g., leukemia). In some further embodiments, the compounds of the disclosure can be used to overcome T-cell tolerance.

In some embodiments, the present disclosure provides methods for treating a proliferative condition, cancer, tumor, or precancerous condition with a compound described herein and at least one additional therapeutic or diagnostic agent, examples of which are set forth elsewhere herein.

The present disclosure provides methods for treating and/or preventing a proliferative condition, cancer, tumor, or precancerous disease, disorder or condition with a compound described herein.

In embodiments drawn to methods of treating cancer, the administration of a therapeutically effective amount of a compound described herein results in a cancer survival rate greater than the cancer survival rate observed in the absence of administration of the compound. In further embodiments drawn to methods of treating cancer, the administration of a therapeutically effective amount of a compound described herein (e.g., CCR4 inhibitor) results in a reduction of tumor size or a slowing of tumor growth greater than reduction of tumor size or tumor growth observed in the absence of administration of the compound. In embodiments, the methods of treating cancer disclosed herein further include administering a chemotherapeutic agent or anticancer agent in combination with a compound of structural Formula (I), (Ia), (II), (III), (IIIa), (IIIb), (IV), (V), (Va), (Vb), (VI), (VII), (VIIa), (VIIb), (VIII), (VIIIa), (VIIIb), (IX), (IXa), (IXb), (IXc), (IXd) or (X), or a pharmaceutically acceptable salt thereof. In embodiments, the chemotherapeutic agent or anticancer agent is an antiproliferative/antineoplastic drug, an antimetabolite, an antitumour antibiotic, an antimitotic agent, a topoisomerase inhibitor, a cytostatic agent, an oestrogen receptor down regulator, an antiandrogen, a LHRH antagonist or LHRH agonist, a progestogen, an aromatase inhibitor, an inhibitor of 5.alpha.-reductase, an agent which inhibits cancer cell invasion, an inhibitor of growth factor function, a farnesyl transferase inhibitor, a tyrosine kinase inhibitor, a serine/threonine kinase inhibitor, an inhibitor of the epidermal growth factor family, an inhibitor of the platelet-derived growth factor family, an inhibitor of the hepatocyte growth factor family; an antiangiogenic agent, a vascular damaging agent, an agent used in antisense therapy, an anti-ras antisense, an agent used in a gene therapy, an immunotherapeutic agent, or an antibody. In embodiments, the methods of treating cancer disclosed herein further include co-administering a therapeutically effective amount of at least two of: a CCR4 inhibitor, an inhibitor of the PD-L1/PD-1 pathway, an inhibitor of CTLA-4 or an agonistic antibody of CD137 (4-1BB). In embodiments, the methods of treating cancer disclosed herein further include co-administering a therapeutically effective amount of at least two of: a CCR4 inhibitor, an agent that may be an immune modulator or an agent from Table 1.

CNS-related and Neurological Disorders. Inhibition of CCR4 activity may also represent an important strategy for the treatment or prevention of neurological, neuropsychiatric, neurodegenerative or other diseases, disorders and conditions having some association with the central nervous system, including disorders associated with impairment of cognitive function and/or motor function. Many of these diseases, disorders and conditions comprise an immune and/or inflammatory component. In embodiments, the disease or disorder is Parkinson's disease, extra pyramidal syndrome (EPS), dystonia, akathisia, tardive dyskinesia, restless leg syndrome, epilepsy, periodic limb movement in sleep, attention deficit disorders, depression, anxiety, dementia, Alzheimer's disease, Huntington's disease, multiple sclerosis, cerebral ischemia, hemorrhagic stroke, subarachnoid hemorrhage, or traumatic brain injury.

Other Disorders. Embodiments of the present disclosure contemplate the administration of the compounds described herein to a subject for the treatment or prevention of any other disorder that may benefit from at least some level of CCR4 modulation. Such diseases, disorders and conditions may include, for example, asthma, chronic obstructive pulmonary disease (COPD) including chronic bronchitis and emphysema, idiopathic pulmonary fibrosis, atopic or contact dermatitis, urticaria, allergic rhinitis, nasal polyps, allergic conjunctivitis, thrombosis, reperfusion injury of the myocardium and brain, chronic glomerulonephritis, sepsis, adult respiratory distress syndrome, and pain. Additional diseases, disorders and conditions include allergic bronchopulmonary aspergillosis, allergic fungal sinusitis, severe asthma with fungal sensitization and diseases involving a pathogenic role for fungi including invasion or colonization (such as invasive aspergillosis, aspergilloma or candidiasis).

In embodiments, the disease or disorder is a cardiovascular (e.g., cardiac ischemia), metabolic (e.g., development of insulititis diabetes), hepatic (e.g., hepatic fibrosis, NASH, and NAFLD), ophthalmologic (e.g., diabetic retinopathy), or renal (e.g., renal failure) disorder.

The present disclosure contemplates the administration of the compounds described herein, and compositions (e.g., pharmaceutical salts, pharmaceutical composition) thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the compounds disclosed herein over a defined period of time. In embodiments, the administration is oral administration.

Metabolic and Cardiovascular Diseases. The present disclosure provides methods for treating and/or preventing certain cardiovascular- and/or metabolic-related diseases, disorders and conditions, as well as disorders associated therewith, with a compound described herein.

The compounds of the present disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the compounds of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In embodiments, the compounds contemplated by the present disclosure may be administered (e.g., orally) at dosage levels of about 0.01 mg/kg to about 50 mg/kg, or about 1 mg/kg to about 25 mg/kg, of subject body weight per day, one, two, three, four or more times a day, to obtain the desired therapeutic effect. For administration of an oral agent, the compositions can be provided in the form of tablets, capsules and the like containing from 0.05 to 1000 milligrams of the active ingredient, particularly 0.05, 0.1, 0.25, 0.5, 0.75, 1.0, 1.25, 1.5, 1.75, 2.0, 2.5, 5.0, 7.5, 10.0, 15.0, 20.0, 25.0, 50.0, 75.0, 100.0, 125.0, 150.0, 175.0, 200.0, 250.0, 300.0, 400.0, 500.0, 600.0, 750.0, 800.0, 900.0, and 1000.0 milligrams of the active ingredient. A pharmaceutically acceptable carrier(s), diluent(s) and/or excipient(s) may be present in an amount of from about 0.1 g to about 2.0 g.

In embodiments, the dosage of the desired compound is contained in a "unit dosage form". The phrase "unit dosage form" refers to physically discrete units, each unit including a predetermined amount of the compound (e.g., CCR4 inhibitor), sufficient to produce the desired effect. It will be appreciated that the parameters of a unit dosage form will depend on the particular agent and the effect to be achieved.

IV. Kits

In another aspect, provided herein is a kit including a compound described herein (e.g., a CCR4 inhibitor) or pharmaceutical compositions thereof. The kits are generally in the form of a physical structure housing various components, as described below, and may be utilized, for example, in practicing the methods described above.

A kit may include one or more of the compounds disclosed herein (e.g., provided in a sterile container), which may be in the form of a pharmaceutical composition suitable for administration to a subject. In embodiments, the compound has the structure of Formulae (I), (Ia), (II), (III), (IIIa), (IIIb), (IV), (V), (Va), (Vb), (VI), (VII), (VIIa), (VIIb), (VIII), (VIIIa), (VIIIb), (IX), (IXa), (IXb), (IXc), (IXd) or (X), or a pharmaceutically acceptable salt thereof. The compounds described herein (e.g., CCR4 inhibitors) can be provided in a form that is ready for use (e.g., a tablet or capsule) or in a form requiring, for example, reconstitution or dilution (e.g., a powder) prior to administration. When the compound (e.g., CCR4 inhibitor) is in a form that needs to be reconstituted or diluted by a user, the kit may also include diluents (e.g., sterile water), buffers, pharmaceutically acceptable excipients, and the like, packaged with, or separately from, the compound. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes.

EXAMPLES

The successful operation of the host defense system is the result of several processes that work together to eliminate foreign pathogens. Coordinated innate and acquired immune responses are required, and many secreted and cell-associated factors have been identified as important mediators coordinating and regulating these two arms of host defense (see, e.g., Ness, T. et al. (2006) J Immunol 177:7531-39).

Chemokines are a family of cytokines that act as chemoattractants to guide leukocyte migration. They are secreted by a wide variety of cells and can be functionally divided into two groups, hemostatic chemokines and inflammatory chemokines. Hemostatic chemokines are constituently produced in certain tissues and control cells of the immune system during processes of immune surveillance, such as directing lymphocytes to the lymph nodes to allow them to screen for invasion of pathogens. Inflammatory chemokines are released from cells in response to a pathological event (e.g., pro-inflammatory stimuli such as IL-1 or viruses). They function primarily as chemoattractants as part of the inflammatory response and serve to guide cells of both the innate and adaptive immune systems to the site of inflammation. [See, e.g., Le, Y. et al. (2004) Cellular & Molec Immuno 1(2):95-104.]

Structurally, there are four subgroups of chemokines, classified according to the spacing of the first two cysteine residues: i) CC chemokines (β-chemokines) have adjacent cysteines; ii) CXC chemokines (α-chemokines) having a single amino acid residue between the first two cysteines; iii) C chemokines (γ-chemokines) have only a single N-terminal cysteine residue; and iv) $CX_3C$ chemokines (δ-chemokines) having three amino acid residues between the first two cysteines. CC chemokines, examples of which include monocyte chemoattractant protein-1 (MCP-1 or CCL2) and CCL5 (RANTES), induce the migration of monocytes and other cell types; at least 27 members have been identified. CXC chemokines (some 17 in number) can be subdivided into two groups, both of which have unique structural and functional features; the CXC chemokines bind to CXC chemokine receptors, of which 7 are known (designated CXCR1-7). Only two members of the C chemokine subgroup have been identified, XCL1 and XCL2 (lymphotactin-α and β, respectively). Finally, the $CX_3C$ chemokine subgroup has only one member, $CX_3CL1$, which is both secreted and associated with the surface of the cells that express it, resulting in both chemoattractant and adhesion properties. [See Sokol, C. and Luster, A. (2015) Cold Spring Harb Prospect Biol doi: 10.1101/cshperspect.a016303.]

Chemokines bind to specific G protein-coupled receptors ("chemokine receptors"), which are characterized by containing seven transmembrane domains, found on the surface of leukocytes (see Horuk (1994) Trends Pharm. Sci. 15:159-165). Approximately 20 human chemokine receptors have been identified, which are divided into four subgroups depending on the type of chemokine they bind: CXCR bind CXC chemokines; CCR bind CC chemokines; CX3CR1 binds CX3CL1, the sole CXC3 chemokine; and XCR1 binds XCL1 and XCL2, the two XC chemokines. Binding of a chemokine ligand to its cognate receptor triggers the receptor, resulting in dissociation of an intracellular heterotrimeric G-protein complex into Gα and Gβγ subunits. These second messengers play an integral role in the activation of several signaling cascades (e.g., the MAP kinase pathway), resulting in responses that include chemotaxis, inflammatory mediator release, degranulation, and changes in cell shape. Chemokine receptors have been implicated as being important mediators of inflammatory and immunoregulatory disorders and diseases, including asthma and allergic diseases, as well as autoimmune pathologies such as rheumatoid arthritis and atherosclerosis. [See, e.g., Comerford, I. and McColl, S. (2011) Immunol Cell Biol 89:183-84.]

The C—C chemokine receptor type 4 (CCR4), first identified by Power et al. (J. Biol. Chem. 270:19495-500 (1995)), plays a vital role in the progression of a number of inflammation-related and other disorders (Gadhe, C G (February 2015) Mol Biosyst 11(2):618-34). CCR4 is a high affinity receptor for the C—C-type chemokines CCL2 (MCP-1), CCL4 (MIP-1), CCL5 (RANTES), CCL17 (TARC), and CCL22 (MDC). Increased expression of CCR4 and its ligands is associated with the pathogenesis of a diverse array of diseases, including pulmonary fibrosis, hepatic inflammation, granuloma development, certain cancers and diabetes, each of which is characterized by the infiltration of $CCR4^+$ T cells into affected sites. The identification of compounds that modulate CCR4 function provides an opportunity for the development of therapeutic agents for the treatment of a diverse array of diseases and disorders associated with CCR4 activation.

The present disclosure relates to compounds that inhibit C—C chemokine receptor type 4 (CCR4) activity, and compositions (e.g., pharmaceutical compositions) comprising the compounds. Such compounds, including methods of their synthesis, and compositions are described in detail herein. The present disclosure also relates to the use of such compounds and compositions for the treatment and/or prevention of diseases, disorders and conditions mediated, in whole or in part, by CCR4.

Many subjects suffer from the debilitating effects of inflammatory- and/or immune-related disorders such as asthma and rheumatoid arthritis. Recently generated data support the role of inhibitors of CCR4 function to modulate such inflammatory- and/or immune-related activity in a therapeutically beneficial manner. In addition, subjects diagnosed with cancer and the number of deaths attributable to cancer continue to rise, both in the US and abroad. Traditional treatment approaches comprising chemotherapy and radiotherapy are generally difficult for the patient to tolerate and become less effective as cancers (e.g., tumors) evolve to circumvent such treatments.

Identification of CCR4 Inhibitors

In embodiments, compounds described herein possess at least one property or characteristic that is of therapeutic relevance. Candidate inhibitors may be identified by using, for example, an art-accepted assay or model. The Example section describes assay(s) that were used to determine the CCR4 inhibitory activity of the compounds described herein, as well as assays that are being used to evaluate one or more characteristics of the compounds.

After identification, candidate inhibitors can be further evaluated by using techniques that provide data regarding characteristics of the inhibitors (e.g., pharmacokinetic parameters). Comparisons of the candidate inhibitors to a reference standard (which may the "best-of-class" of current inhibitors) are indicative of the potential viability of such candidates. CCR4 inhibitors that can serve as reference or benchmark compounds include those shown to demonstrate desired activity and characteristics as described in, for example, US Patent Publn 2012/0015932 and PCT Publn 2013/082490. Other means of analyzing candidate inhibitors will be apparent to the skilled artisan.

Synthesis Details

The R group substituents as described in the Examples below are intended to be applied only to the Examples below and do not necessarily correspond with the R group substituents used in other sections of the present application (e.g., Definitions, Compounds, Methods of use, Kits, or Claims). For example an $R^1$ substituent in the Examples below does not necessarily correspond to an $R^1$ substituent in the Compound section above or the Claims below.

The following general schemes represent synthetic methods that may be used in the preparation of the compounds of the present disclosure, as well as common chemical intermediates generated in the preparation thereof. The skilled artisan will recognize that these schemes are representative only, and that in many instances alternative synthetic means may be employed.

The following examples are put forth so as to provide those of ordinary skill in the art with a complete disclosure and description of how to make and use the compounds disclosed herein, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for. Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; µg=microgram; mg=milligram; g=gram; kg=kilogram; dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; psi=pounds per square inch; HPLC=high performance liquid chromatography; BW=body weight; U=unit; ns=not statistically significant; MBTE=methyl t-butyl ether; DCM=dichloromethane; PBS=phosphate-buffered saline; IHC=immunohistochemistry; DMEM=Dulbeco's Modification of Eagle's Medium; EDTA=ethylenediaminetetraacetic acid.

General Preparation of the Hydrazine Starting Material

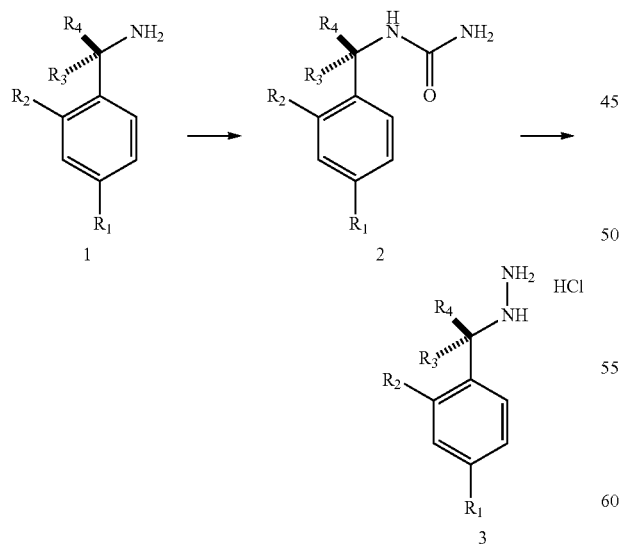

A substituted aminomethyl benzene of general structure 1 can be reacted with an alkaline metal cyanate such as potassium cyanate in an acidified solvent such as concentrated HCl. The resulting urea of general structure 2 can be isolated by standard methods such as filtration. After suitable purification the urea of general structure 2 can be dissolved in a mixture organic solvents such as toluene and tert-butanol and treated with tert-butyl hypochlorite under a nitrogen atmosphere and the mixture is cooled to a temperature between −40 and 0° C. preferably around −20° C. The mixture is then warmed to 0° C., and the resulting solution is transferred to a flask containing a solution of an alkoxide base such a potassium tert-butoxide in a mixture of organic solvents such as toluene and tert-butanol, which is being maintained at a temperature between −40 and 0° C., preferably at −20° C. After the addition, the reaction is stirred for 15 min at a temperature of 0° C. and then poured onto ice water. The mixture is allowed to warm to room temperature over 20 min and is then extracted with an organic solvent such as ethyl acetate. The organic extract is washed with water, an aqueous solution of sodium thiosulfate, and brine. The mixture was then concentrated to give the desired tert-butyl hydrazine carboxylate intermediate, which can be immediately hydrolyzed in an acidic organic mixture such as HCl in 1,4-dioxane for 8-24 h. Concentration of the solution followed by trituration of the resulting residue with an organic solvent such as ethyl acetate affords the desired hydrazine hydrochloride 3.

General Synthesis of Pyrazolopyrazine and Pyridines

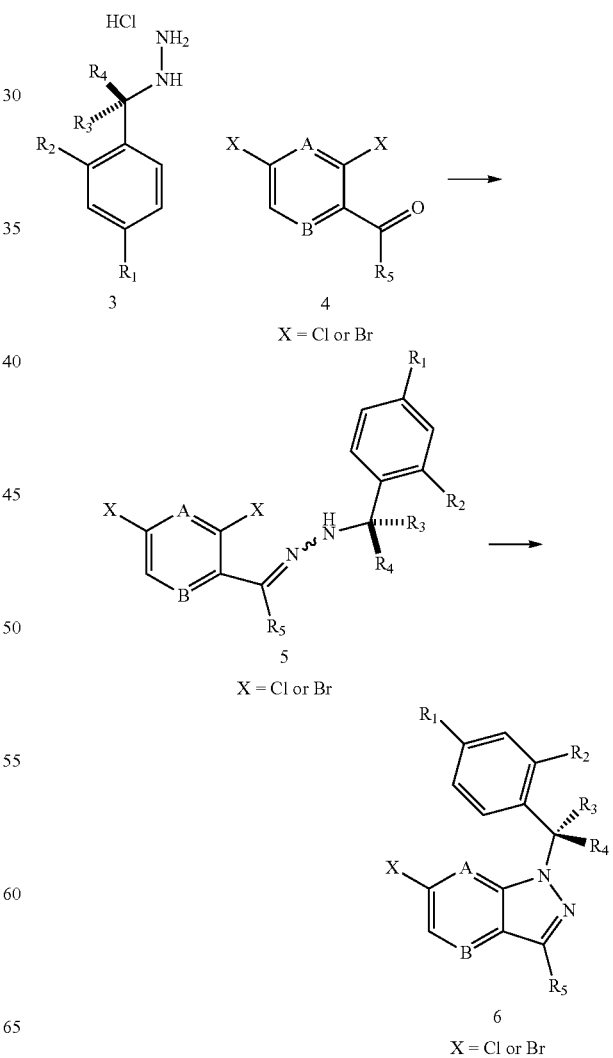

A solution of hydrazine hydrochloride of general structure 3 in a protic organic solvent such as ethanol is treated with the ketone of general structure 4. The mixture is stirred for 8 h at room temperature. The reaction is concentrated under reduced pressure to give a residue. The residue is suspended in the mixed organic solvents such as ethyl acetate and hexanes and then filtered through a silica gel plug and eluted with a similar solvent mixture. The filtrate is concentrated to give the crude hydrazone of the general structure 5 as a mixture of E and Z isomers. The mixture of E and Z hydrazine isomers of general structure 5 is dissolved in a polar aprotic solvent such as N-methyl-2-pyrrolidinone and treated with excess of a Lewis base, for example 2,6-lutidine. The mixture is degassed with nitrogen and stirred under a nitrogen atmosphere at an elevated temperature, for example 100° C., for 8 h. The reaction mixture is cooled to room temperature and then poured into an acidic aqueous solution such as 1 M HCl, and the resulting mixture is extracted with an organic solvent such as ethyl acetate. The layers were separated, and the organic layer was washed with an acidic aqueous solution such as 1 M HCl, dried over a drying agent such as magnesium sulfate, and concentrated under reduced pressure. The resulting residue could be optionally purified by recrystallization or silica gel chromatography using a mixture of organic solvents for example a mixture of MTBE and dichloromethane to give compounds of the general formula 6. In certain instances, where ketone 4 is not commercially available, it can be prepared in the following way

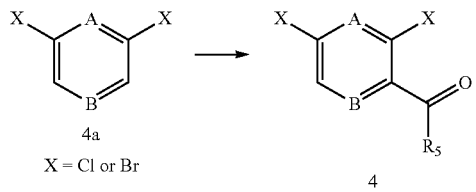

4a
X = Cl or Br

4

A solution of halide of general structure 4a and a source of acetate in polar aprotic solvent such as THF is treated with a strong alkali complex base such as LiTMP at low temperature −78° C. to afford 4, which is used right away in the next step described in the previous procedure to afford compounds of the general formula 6.

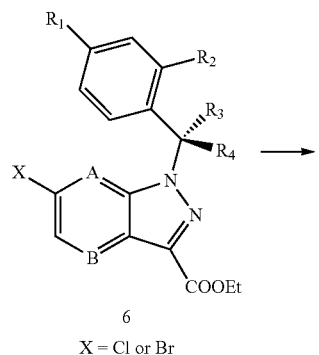

6
X = Cl or Br

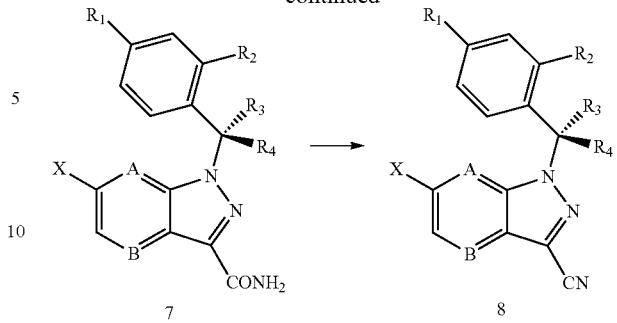

7

8

A solution of halide of general structure 6 in an organic solvent such as 1,4-dioxane is treated with ammonia source such as ammonium hydroxide (29% in water). The mixture is stirred at room temperature for 3 d. The reaction is diluted with a solvent such as ethyl acetate and washed with a weak aqueous base such as aqueous sodium carbonate. The organic layer is separated and dried over a drying agent such as magnesium sulfate. The organic layer is concentrated under reduced pressure to give compounds of general formula 7. A solution of primary amide of general structure 7 in a polar aprotic organic solvent such as dichloromethane at room temperature under inert atmosphere is added dehydration agent such as Burgess' reagent. The mixture is stirred at room temperature for about 2 d. The resulting mixture can be purified by silica gel chromatography using a mixture of organic solvents for example a mixture of ethyl acetate and hexanes to give compounds of the general formula 8.

General Synthesis of 1,4'-bipiperidine

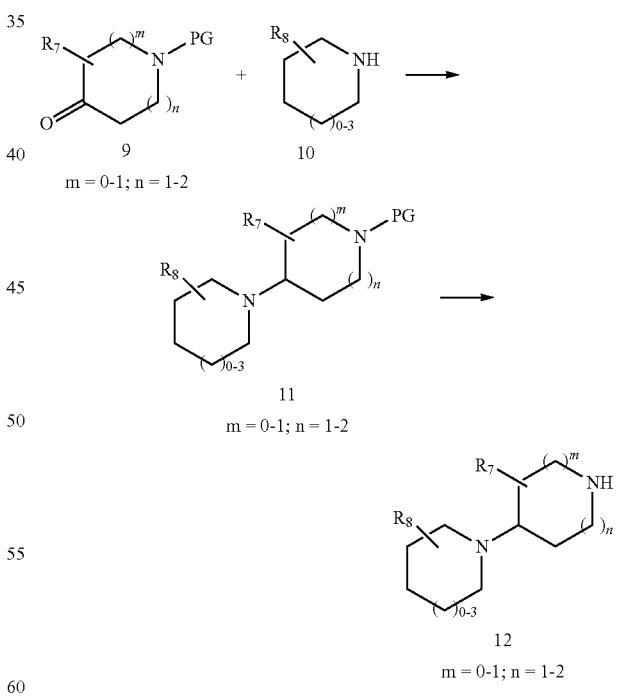

9
m = 0-1; n = 1-2

10

11
m = 0-1; n = 1-2

12
m = 0-1; n = 1-2

To a solution of the protected ketone of general structure 9 in an organic solvent such as 1,2-dichloroethane is added amine 10 and an imine reducing agent such as sodium triacetoxyborohydride. The mixture is stirred for between 4 and 18 h. The reaction is treated with a weak aqueous base such as aqueous sodium carbonate, and the mixture is extracted with an organic solvent such as ethyl acetate. The organic solvent is separated, treated with a drying agent such as sodium sulfate, and the dried solution is evaporated to give amine of general structure 11. The protective group on compound of general structure 11 can be exposed to an acidic organic solution, for example HCl in 1,4-dioxane or trifluoroacetic acid in dichloromethane or can be removed using catalytic Pd. The mixture is stirred at room temperature for a time between 1 and 16 h. The reaction mixture can be concentrated or filtered through a Celite pad and then concentrated under reduced pressure to give an amine salt of the general structure 12 that can be used in subsequent reactions without further purification.

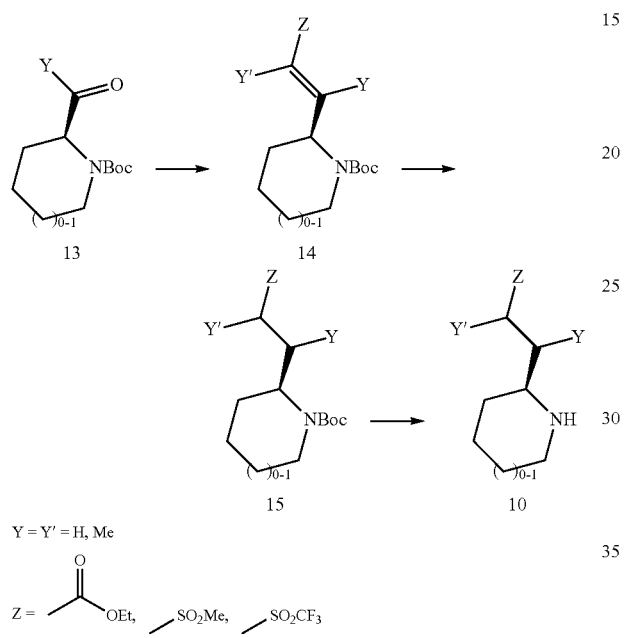

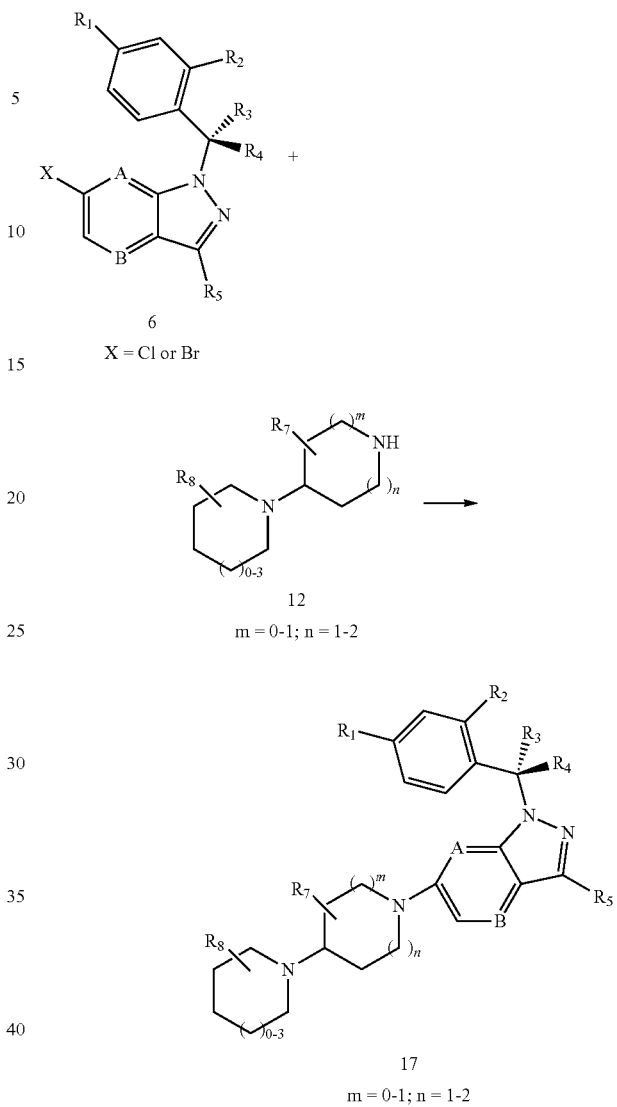

In a certain instances compounds of general structure 10 can be made from aldehydes or ketone of general structure 13 that undergo an HWE reaction. To a solution of the aldehyde or ketone of general structure 13 in an organic solvent such as THF is cannulated a mixture of phosphonate carbanions such as ethyl 2-(diethoxyphosphoryl)acetate and a strong base such as sodium tert-butoxide in THF at cold temperature like 5° C. for 30 min. The reaction is stirred at room temperature for 1-2 h. The reaction is treated with a weak aqueous base such as aqueous sodium carbonate, and the mixture is extracted with an organic solvent such as ethyl acetate. The organic solvent is separated, treated with a drying agent such as sodium sulfate, and the dried solution is evaporated to give the title compound of general structure 14. The compound of general structure 14 is undergo double bond reduction using catalytic amount of $PtO_2$ under hydrogen for 30 min. The reaction is filtered through a celite pad and purified by silica gel chromatography using a mixture of organic solvents for example a mixture of ethyl acetate and Hexanes to give compounds of the general formula 15. The compound of general structure 15 can be exposed to an acidic organic solution, for example HCl in 1,4-dioxane or trifluoroacetic acid in dichloromethane. The mixture is stirred at room temperature for a time between 1 and 16 h. The reaction mixture can be concentrated under reduced pressure to give an amine salt of the general structure 10 that can be used in previously described reactions without further purification.

Compounds of general formulas 6 and 12 in an organic solvent such as DMF are heated in the presence of a base such as di-isopropyl ethyl amine at a temperature ranging between 70 and 100° C. for 1 hour. The reaction mixture can be partitioned between ethyl acetate and water containing trifluoroacetic acid. The aqueous layer is evaporated and the resulting residue can be purified by reversed phase preparative HPLC using a stationary phase such as C-18 and a solvent system such as varying amounts of water and acetonitrile containing 0.1% trifluoroacetic acid. The resulting mixture of stereoisomers could be converted to the free base by passing through amyberlyst resin and the basified amines purified using a chiral HPLC column such as Chiracel OZ-H and the like using a mixture of organic solvents such as ethanol and heptanes containing 0.1% diethyl amine. The purified stereoisomers could be dissolved in ethanol and treated with HCl in diethyl ether, and the solvents were removed under reduced pressure to give the desired compound 17 as an HCl salt.

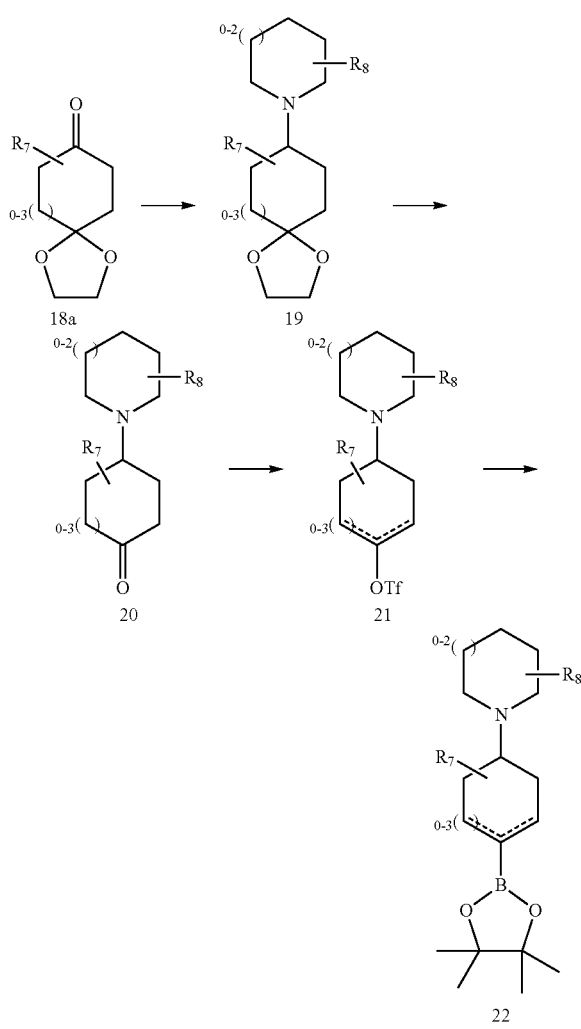

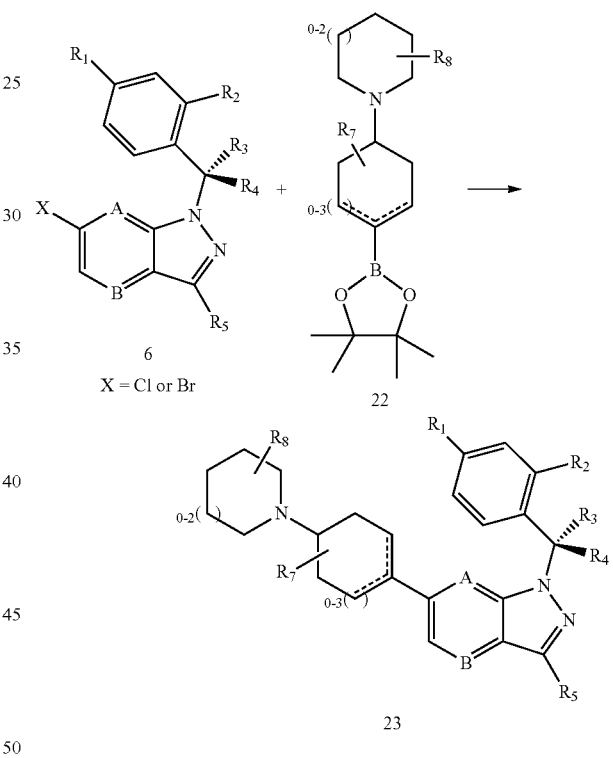

X = Cl or Br as LDA dropwise at low temperature such as −78° C. After 2 h at −78° C., a triflate source such as N-phenyl-bis-trifluoromethanesulfonimide is added, and the reaction mixture is warmed up slowly to around 0° C. over a 2 h period time. The reaction is quenched with a weak aqueous base such as aqueous sodium carbonate, and the mixture is extracted with an organic solvent such as ethyl acetate. The organic solvent is separated, treated with a drying agent such as sodium sulfate, and the dried solution is evaporated to give a title compound of general formula 21.

To a solution of a title compound of general formula 21 in a polar solvent such as 1,4-dioxane is added bis(pinacolato)diboron, followed by excess KOAc, KBr, and a catalytic Pd source such as Pd(dppf)Cl$_2$. The mixture is heated at 95° C. for 2 h. The mixture is concentrated under reduced pressure. The residue is purified by silica gel chromatography using a mixture of organic solvents for example a mixture of MeOH and dichloromethane to give the title compound of general formula 22.

To a solution of the protected ketone of general structure 18a in an organic solvent such as dichloroethane is added amine and an imine reducing agent such as sodium triacetoxyborohydride and followed by acetic acid. The mixture is heated to 70° C. and stirred for 5 h. The reaction is treated with a weak aqueous base such as aqueous sodium carbonate, and the mixture is extracted with an organic solvent such as ethyl acetate. The organic solvent is separated, treated with a drying agent such as sodium sulfate, and the dried solution is evaporated to give a title compound of general structure 19.

The protective group on compound of general structure 19 can be exposed to an acidic organic solution, for example HCl in 1,4-dioxane under reflux at 70° C. for 16 h. The reaction mixture is concentrated and diluted with dichloromethane. The solution is treated with a weak aqueous base such as aqueous sodium carbonate, and the mixture is extracted with an organic solvent such as ethyl acetate. The organic solvent is separated, treated with a drying agent such as sodium sulfate, and the dried solution is evaporated. The residue is purified by silica gel chromatography using a mixture of organic solvents for example a mixture of MeOH and dichloromethane to give the title compound of general formula 20.

The title compound of general formula 20 in an aprotic polar solvent such as THF is treated with a strong base such To a solution of compound with general structure 6 and 22 in a 1,4-dioxane/water mixture (5:1) are added potassium carbonate and catalytic Pd such as Pd(dppf)Cl$_2$. The mixture is heated to 95° C. for 2 h. The mixture is concentrated under reduced pressure. The residue is purified by silica gel chromatography using a mixture of organic solvents for example a mixture of MeOH and dichloromethane and further purified by using a chiral HPLC column such as Chiracel OZ-H and the like using a mixture of organic solvents such as ethanol and heptanes containing 0.1% diethyl amine as the solvent. The purified stereoisomers can be converted to the free base by passing through amyberlyst resin. The freebase compound can be dissolved in ethanol and treated with HCl in diethyl ether, and the solvents are removed under reduced pressure to give the desired compound 23 as an HCl salt.

A more divergent route to get to the compound of general formula 23 can be achieved as follows

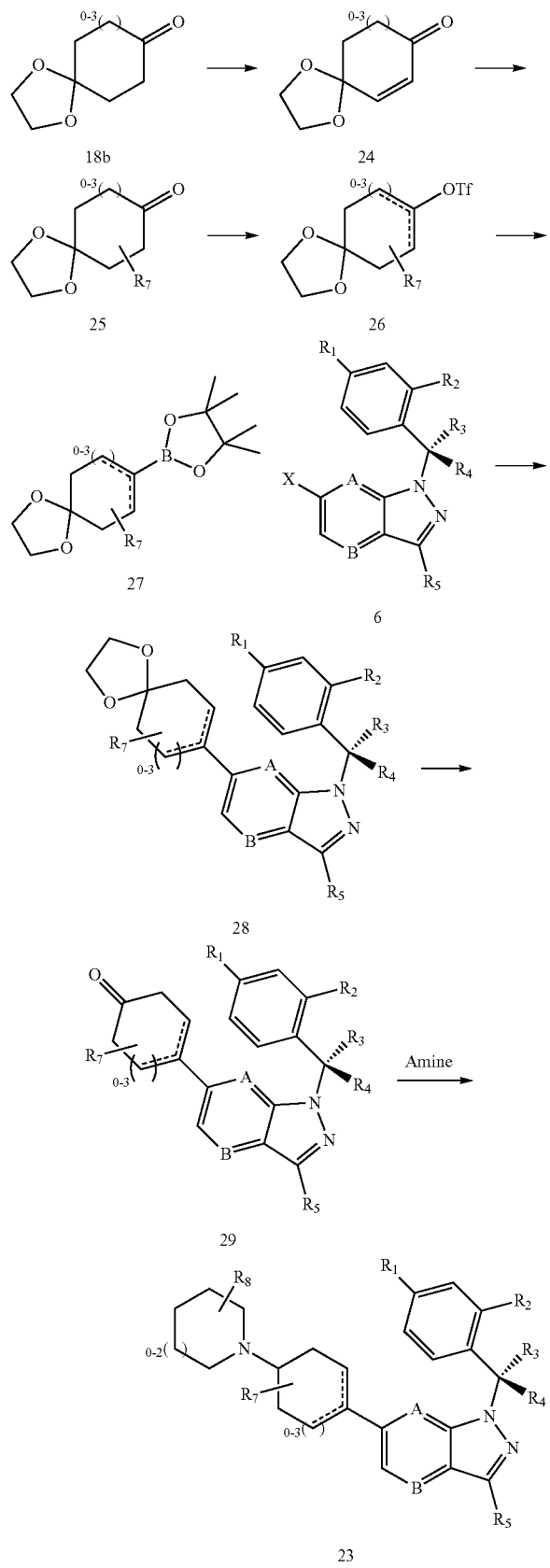

To a solution of ketone 18b in organic solvent such as DCM is added a base such as triethylamine. The resulting solution was cooled to 0° C. before adding trimethylsilyl trifluoromethanesulfonate. The resulting solution was stirred at −2 to −5° C. for 2.5 h before quenching with an aqueous base such as saturated sodium carbonate. The organic solvent is separated, treated with a drying agent such as sodium sulfate, and the dried solution is evaporated. The residue is diluted with an organic solvent such as ethyl acetate and passed through a Celite plug, and solvent is removed. The crude residue is diluted in acetonitrile, and Pd(OAc)$_2$ is added. The resulting mixture is stirred overnight. The mixture is filtered thought a silica/Celite plug. The solvent is removed. The residue is purified by silica gel chromatography using a mixture of organic solvents for example a mixture of ethyl acetate and hexanes to give the title compound of general formula 24.

To a solution of compound of general formula 24 and trimethylsilylchloride in a mixture organic solvent such as diethyl ether/THF at low temperature such as −30° C. is added the cuprate solution, which is prepared from copper cyanide and methyl lithium in diethyl ether at −30° C. The resulting mixture is continued stirring at −30° C. for 80 min. The reaction mixture is quenched with a mixture aqueous solution of ammonium chloride and ammonium hydroxide. The mixture is stirred at room for 30 min. The mixture is extracted with an organic solvent such as ethyl acetate. The organic solvent is separated, treated with a drying agent such as sodium sulfate, and the dried solution is evaporated to give the title compound of general formula 25.

To a solution of compound of general formula 25 in an organic solvent such as THF at low temperature such as −78° C. is added a triflate source such as N-phenyl-bis-trifluoromethanesulfonimide. The reaction is stirred at −78° C. and gradually warmed to room temperature. After stirring at room temperature for 14 h, it is diluted with a mild aqueous base such as aqueous sodium bicarbonate. The organic solvent is separated, treated with a drying agent such as sodium sulfate and the dried solution is evaporated. The residue is purified by silica gel chromatography using a mixture of organic solvents for example a mixture of ethyl acetate and hexanes to give the title compound of general formula 26.

To a solution of a title compound of general formula 26 in a polar solvent such as 1,4-dioxane is added bis(pinacolato)diboron, followed by excess KOAc, KBr, and a catalytic Pd source such as Pd(dppf)Cl$_2$. The mixture is heated to 100° C. for 20 h. The mixture is filtered through a Celite pad and concentrated under reduced pressure. The residue is purified by silica gel chromatography using a mixture of organic solvents for example a mixture of ethyl acetate and hexanes to give the title compound of general formula 27.

To a solution of the title compound of general formula 27 and 6 in organic solvent such as 1,4-dioxane was added an aqueous base such as sodium carbonate. The resulting mixture was heated to 95° C. for 75 min under inert gas such as nitrogen. The reaction was diluted with ethyl acetate, and a mild base such as saturated aqueous sodium bicarbonate is added. The organic solvent is separated and treated with a drying agent such as sodium sulfate, and the dried solution is evaporated. The residue is purified by silica gel chromatography using a mixture of organic solvents for example a mixture of ethyl acetate and hexanes to give the title compound of general formula 28.

The protective group on compound of general structure 28 can be exposed to an acidic organic solution, for example trifluoroacetic acid in dichloromethane at room temperature for 20 h. The reaction mixture is treated with a weak aqueous base such as aqueous sodium carbonate, and the mixture is extracted with an organic solvent such as dichloromethane. The organic solvent is separated and treated with a drying agent such as sodium sulfate, and the dried solution is evaporated to give the title compound of general formula 29.

To a solution of the ketone of general formula 29 in an organic solvent such as 1,2-dichloroethane is added amine and an imine reducing agent such as sodium triacetoxyborohydride and followed by acetic acid. The mixture is stirred at room temperature for 16 h. The reaction is treated with a weak aqueous base such as aqueous sodium carbonate, and the mixture is extracted with an organic solvent such as ethyl acetate. The organic solvent is separated and treated with a drying agent such as sodium sulfate. The mixture is concentrated under reduced pressure, and the resulting residue is purified by reversed phase preparative HPLC using a stationary phase such as C-18 and a solvent system such as varying amounts of water and acetonitrile containing 0.1% trifluoroacetic acid to give a compound of general structure 23.

In certain instances where $R^8$=—$(CH_2)_nCO_2Et$ in compound 17 or 23 is dissolved in an organic solvent such as 1,4-dioxane and then treated with an alkali metal hydroxide such as LiOH, and the resulting mixture is stirred for 3 h. An aqueous acid such as 3 M HCl is then added to the reaction. The mixture is concentrated under reduced pressure, and the resulting residue is purified by reversed phase preparative HPLC using a stationary phase such as C-18 and a solvent system such as varying amounts of water and acetonitrile containing 0.1% trifluoroacetic acid to give a compound of general structure 30 or 31.

Example 1

Ethyl 6-([1,4'-bipiperidin]-1'-yl)-1-(1-(2,4-dichlorophenyl)ethyl)-1H-pyrazolo[3,4-b]pyrazine-3-carboxylate hydrochloride

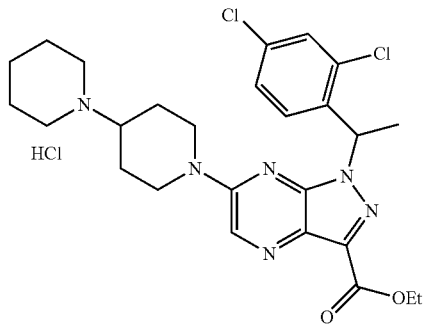 [SMILES: CCOC(=O)c1nn(C(C)c2ccc(Cl)cc2Cl)c2nc(N3CCC(N4CCCCC4)CC3)cnc12 ; Cl]

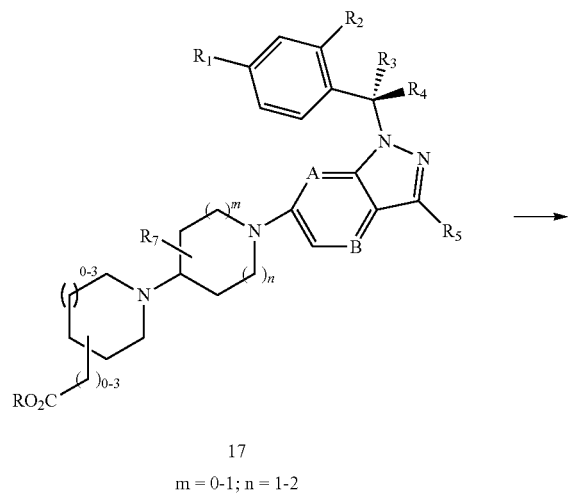

17
m = 0-1; n = 1-2 or

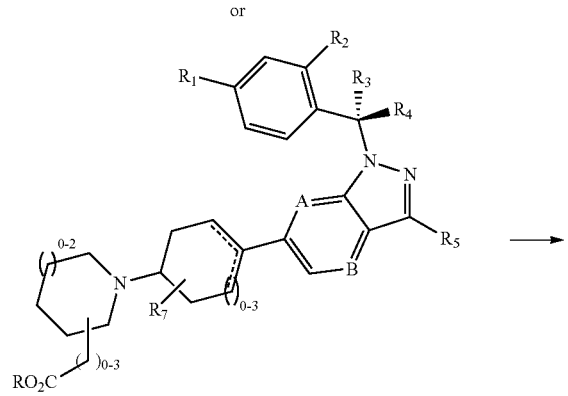

23

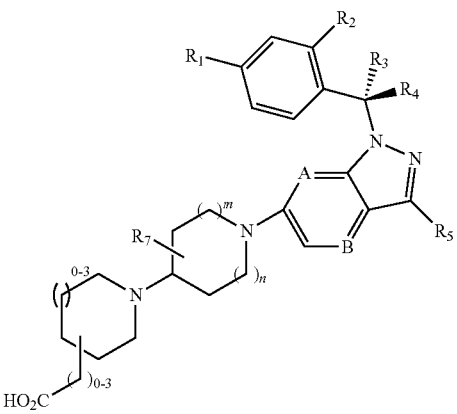

30
m = 0-1; n = 1-2 or

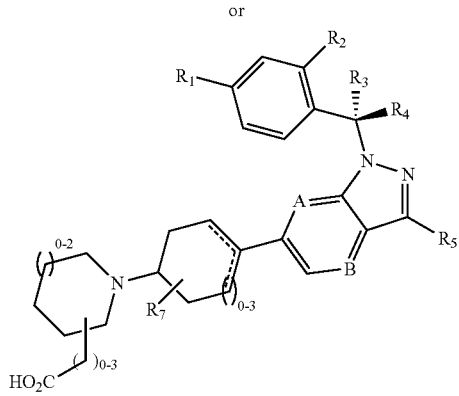

31

Step 1. (1-(2,4-Dichlorophenyl)ethyl)hydrazine hydrochloride

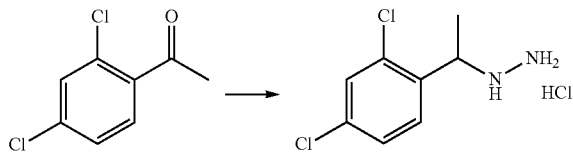

To a solution 2,4-dichloroacetophenone (10.3 g, 54.4 mmol) in ethanol (50 mL) at room temperature was added tert-butyl carbazate (21.6 g, 163 mmol). The mixture was stirred at room temperature for 2 d. Then the mixture was stirred at 50° C. for 1 h. Next, the mixture was cooled to 0° C. and filtered. The filtrate was concentrated, and the residue was precipitated from ethanol. The solids were combined and purified using silica gel chromatography (0 to 25% ethyl acetate in hexanes) to give a residue. The residue was dissolved in ethanol (125 mL), and one crystal of bromocresol green was added. Then NaCNBH$_3$ (11.8 g, 188 mmol) was added, and AcOH was added dropwise to maintain yellow color. The mixture was stirred at 60° C. for 2 d, and AcOH was added dropwise to maintain a yellow color. The mixture was cooled to room temperature and purified using silica gel chromatography (10 to 20% MTBE in hexanes) to give a residue. The residue was dissolved in 1,4-dioxane (0.17 M) and HCl in 1,4-dioxane (4 M, 10 equiv.) was added. The mixture was stirred at 50° C. for 16 h, and a white precipitate formed. The mixture was cooled to room temperature and concentrated under reduced pressure to give the title compound as a white solid.

Step 2. Ethyl (E)-2-(2-(1-(2,4-dichlorophenyl)ethyl)hydrazono)-2-(3,5-dichloropyrazin-2-yl)acetate and ethyl (Z)-2-(2-(1-(2,4-dichlorophenyl)ethyl)hydrazono)-2-(3,5-dichloropyrazin-2-yl)acetate

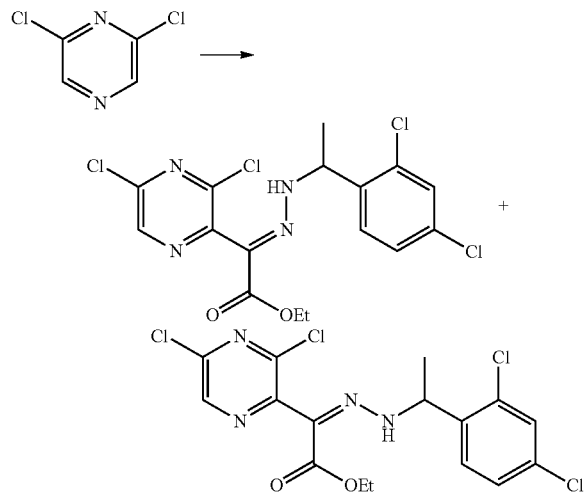

To a solution of n-BuLi (2.5 M in hexanes, 132 mL, 0.329 mol) was added 2,2,6,6-tetramethylpiperidine (56.0 mL, 0.329 mol) in THF (200 mL) at −78° C. over 15 min. The yellow slurry was stirred at −78° C. for 15 min. In a separate flask, diethyl oxalate (41.0 mL, 0.302 mol) and 2,6-dichloropyrazine (40.0 g, 0.274 mol) were dissolved in THF (685 mL) and cooled to −78° C. The lithium 2,2,6,6-tetramethylpiperidine solution was added to the 2,6-dichloropyrazine solution via cannula over 15 min at −78° C. The mixture was stirred at −78° C. for 30 min before the addition of AcOH (20 mL). The mixture was warmed to room temperature, and saturated ammonium chloride was added. The mixture was diluted with ethyl acetate and the layers were separated. The aqueous layer was extracted with ethyl acetate (2×). The combined organic layers were washed with saturated ammonium chloride, dried over MgSO$_4$ and concentrated under reduced pressure. This residue was dissolved in ethanol (50 mL) and (1-(2,4-dichlorophenyl)ethyl)hydrazine hydrochloride (Example 1, Step 1, 9.83 g, 40.7 mmol) was added. The mixture was stirred at room temperature for 16 h. and saturated sodium bicarbonate was added. The mixture was concentrated under reduced pressure to removed ethanol. The aqueous layer was extracted with dichloromethane (3×). The combined organic layers were dried over sodium sulfate and concentrated under reduced pressure. The residue was purified by silica gel chromatograph (0 to 20% ethyl acetate in hexanes) to give the title compounds and a mixture of E- and Z-isomers.

Step 3. Ethyl 6-chloro-1-(1-(2,4-dichlorophenyl)ethyl)-1H-pyrazolo[3,4-b]pyrazine-3-carboxylate

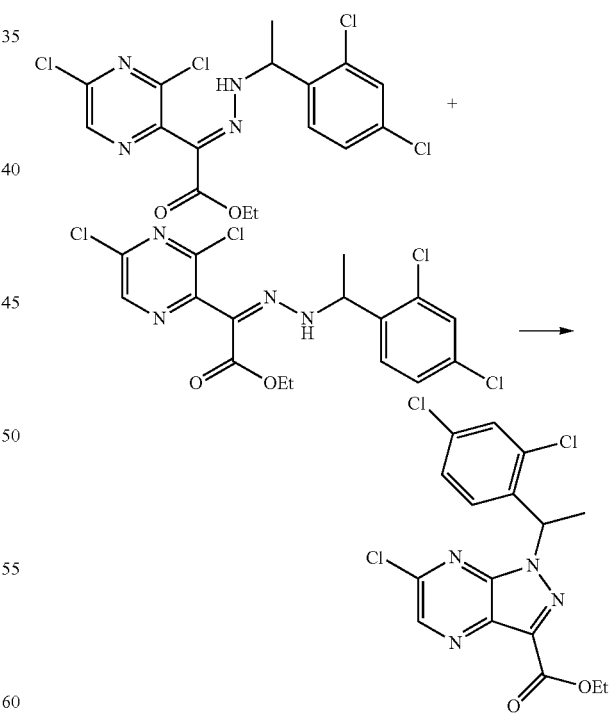

A mixture of ethyl (E)-2-(2-(1-(2,4-dichlorophenyl)ethyl)hydrazono)-2-(3,5-dichloropyrazin-2-yl)acetate and ethyl (Z)-2-(2-(1-(2,4-dichlorophenyl)ethyl)hydrazono)-2-(3,5-dichloropyrazin-2-yl)acetate (Example 1, Step 2, 54.0 g, 126 mmol) was dissolved in THF (500 mL) and cooled to 5° C.

Then NaH (60% dispersion in oil, 5.56 g, 139 mmol) was added portion wise. The mixture was warmed to room temperature and stirred at room temperature for 1 h before the portion-wise addition of more NaH (60% dispersion in oil, 5.00 g, 126 mmol). The mixture was stirred at room temperature for 2 h. Then 5 drops of tert-BuOH was added, and the mixture was allowed to stir at room temperature for 10.5 d. The mixture was diluted with saturated ammonium chloride and ethyl acetate. The layers were separated and organic layer was dried over MgSO₄ and concentrated under reduced pressure. The residue was recrystallized from dichloromethane and hexanes to give the title compound as a tan solid.

Step 4. Ethyl 6-([1,4'-bipiperidin]-1'-yl)-1-(1-(2,4-dichlorophenyl)ethyl)-1H-pyrazolo[3,4-b]pyrazine-3-carboxylate hydrochloride

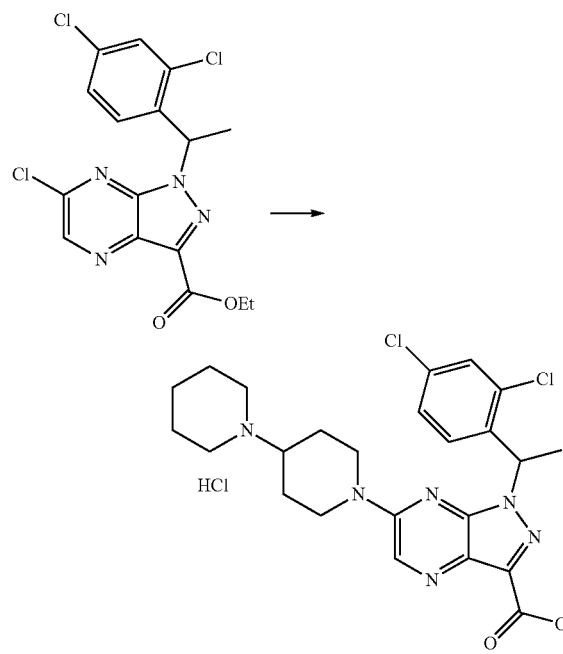

To a solution of ethyl 6-chloro-1-(1-(2,4-dichlorophenyl)ethyl)-1H-pyrazolo[3,4-b]pyrazine-3-carboxylate (Example 1, Step 3, 155 mg, 0.338 mmol) in DMSO (1 mL) was added 1-(4-piperidyl)piperidine (65.0 mg, 0.338 mmol) and N,N-diisopropylethylamine (0.12 mL, 0.69 mmol). The mixture was stirred at 44° C. for 16 h. The mixture was diluted with dichloromethane and washed with NaOH (1 M). The layers were separated, and the organic layer was dried over sodium sulfate and preabsorbed onto silica. The mixture was purified by silica gel chromatography (60-100% ethyl acetate in hexanes). The residue was diluted with dichloromethane (0.7 mL) and HCl in Et₂O (1 M, 0.34 mL) was added dropwise. The volatiles were removed to give the title compounds as a mixture of enantiomers at the benzylic position. 1H NMR (400 MHz, CDCl₃; HCl salt) δ 8.34 (s, 1H), 7.37-7.33 (m, 2H), 7.19-7.09 (m, 1H), 6.46 (q, J=7.1 Hz, 1H), 4.63-4.52 (m, 2H), 4.48 (d, J=13.2 Hz, 2H), 2.96 (t, J=11.8 Hz, 2H), 2.51 (m, 4H), 1.97 (t, J=6.3 Hz, 6H), 1.67-1.50 (m, 8H), 1.47 (t, J=7.1 Hz, 3H); m/z 531.2 (M+H⁺).

Example 2

Ethyl 1-(1-(2,4-dichlorophenyl)ethyl)-6-(3'-methyl-[1,4'-bipiperidin]-1'-yl)-1H-pyrazolo[3,4-b]pyrazine-3-carboxylate hydrochloride

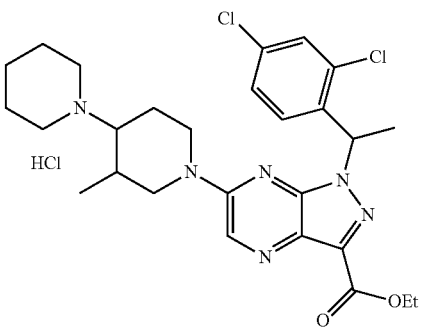 [SMILES: CCOC(=O)c1nn(C(C)c2ccc(Cl)cc2Cl)c2nc(N3CCC(N4CCCCC4)C(C)C3)cnc12 ; Cl]

Step 1. t-Butyl 3'-methyl-[1,4'-bipiperidine]-1'-carboxylate

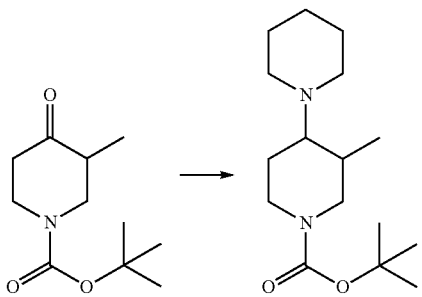 [SMILES: CC1CN(C(=O)OC(C)(C)C)CCC1=O ; CC1CN(C(=O)OC(C)(C)C)CCC1N1CCCCC1]

To a solution of 1-t-Butoxycarbonyl-3-methyl-4-piperidone (2.83 g, 13.3 mmol) in dichloroethane (30 mL) at room temperature was added piperidine (1.58 mL, 16 mmol), AcOH (1.14 mL, 20 mmol), and sodium triacetoxyborohydride (4.24 g, 20 mmol). The mixture was stirred at room temperature for 16 h. The mixture was poured onto saturated sodium bicarbonate and extracted with dichloromethane. The organic layer was dried over sodium sulfate and concentrated under reduced pressure. The residue was purified by silica gel chromatography (0 to 100% ethyl acetate in hexanes) to give the title compound as a mixture of diastereomers.

Step 2. 3'-Methyl-1,4'-bipiperidine 2,2,2-trifluoroacetate

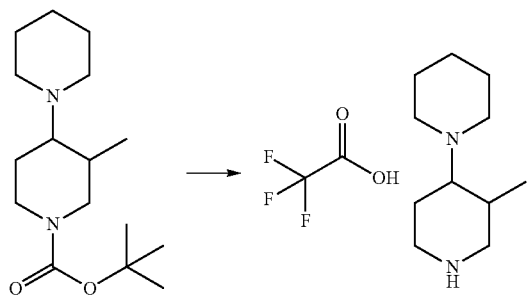

To tert-butyl 3'-methyl-[1,4'-bipiperidine]-1'-carboxylate (Example 2, Step 1) was added a mixture of 25% trifluoroacetic acid in dichloromethane (0.25 M). The mixture was stirred at room temperature for 16 h and then concentrated under reduced pressure to give the title compound.

Step 3. Ethyl 1-(1-(2,4-dichlorophenyl)ethyl)-6-(3'-methyl-[1,4'-bipiperidin]-1'-yl)-1H-pyrazolo[3,4-b]pyrazine-3-carboxylate hydrochloride

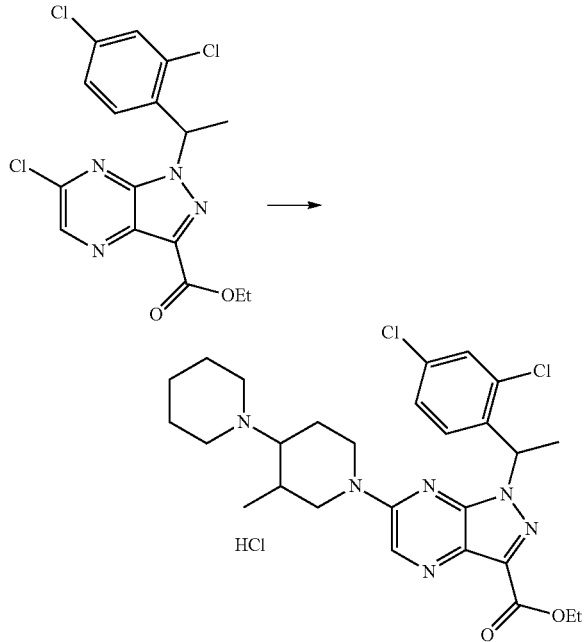

The title compound was prepared from ethyl 6-chloro-1-(1-(2,4-dichlorophenyl)ethyl)-1H-pyrazolo[3,4-b]pyrazine-3-carboxylate (Example 1, Step 3) by procedures similar to those described in Example 1, Step 4, replacing 1-(4-piperidyl)piperidine with 3'-methyl-1,4'-bipiperidine 2,2,2-trifluoroacetate (Example 2, Step 2) to yield the product as a mixture of diastereomers. $^1$H NMR (400 MHz, CDCl$_3$; HCl salt) δ 8.33-8.31 (m, 1H), 7.41-7.24 (m, 2H), 7.14-7.10 (m, 1H), 6.52-6.37 (m, 1H), 4.54 (q, J=7.1 Hz, 2H), 4.35 (t, J=12.5 Hz, 1H), 3.00 (dd, J=21.6, 6.4 Hz, 1H), 2.82 (dt, J=15.4, 11.5 Hz, 1H), 2.42 (s, 4H), 2.30-2.17 (m, 2H), 1.96 (d, J=7.1 Hz, 3H), 1.93-1.82 (m, 1H), 1.67-1.34 (m, 11H), 0.87 (d, J=6.9 Hz, 1.9H), 0.78 (d, J=6.9 Hz, 1.1H); m/z 545.2 (M+H$^+$).

Example 3

1-(1-(2,4-Dichlorophenyl)ethyl)-6-(2-methyl-[1,4'-bipiperidin]-1'-yl)-1H-pyrazolo[3,4-b]pyrazine-3-carboxamide hydrochloride

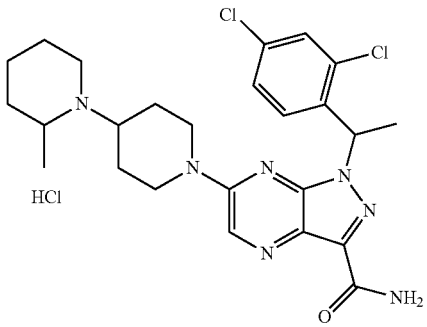 [SMILES: CC1CCCCN1C1CCN(c2cnc3c(C(N)=O)nn(C(C)c4ccc(Cl)cc4Cl)c3n2)CC1 ; Cl]

Step 1. t-Butyl 2-methyl-[1,4'-bipiperidine]-1'-carboxylate

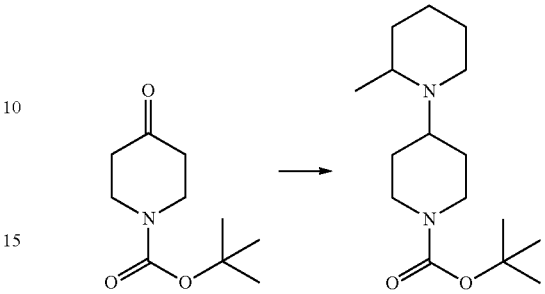

A white slurry mixture of 1-(tert-butoxycarbonyl)-4-piperidinone (10 g, 50 mmol) and 2-methylpiperidine (12 mL, 100 mmol) was heated to 100° C. All solids dissolved, and then p-toluenesulfonic acid monohydrate (1.4 g, 7.5 mmol) was added. The mixture was stirred at 100° C. for 4 h, and then a Dean Stark apparatus was attached. The mixture was diluted with toluene (50 mL) and more 2-methylpiperidine (11.8 mL, 100 mmol) was added. The mixture was refluxed with Dean-Stark apparatus for 16 h, and then cooled to room temperature. The mixture was concentrated under reduced pressure to afford a tan solid. This solid was dissolved in dichloroethane (50 mL) and AcOH (1.1 g, 50 mmol), and sodium triacetoxyborohydride (16 g, 75 mmol) were added. The mixture was stirred at room temperature for 24 h. The mixture was poured onto NaOH (1 M) and extracted with dichloromethane. The organic layer was dried over MgSO$_4$ and concentrated under reduced pressure. The residue was purified by silica gel chromatography (50% ethyl acetate in hexanes) to give the title compound.

Step 2. 2-Methyl-1,4'-bipiperidine

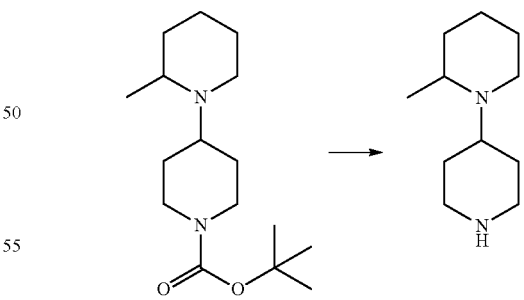

To a solution of tert-butyl 2-methyl-[1,4'-bipiperidine]-1'-carboxylate (Example 3, Step 1, 50 mmol) in MeOH (10 mL) was added HCl in 1,4-dioxanes (4 M, 11 mL). The mixture was stirred at room temperature for 16 h then basified to pH 12 with NaOH (1 M). The mixture was extracted with dichloromethane (2×100 mL). The combined organic layers were dried over MgSO$_4$ and concentrated under reduced pressure to give the title compound as an orange oil.

Step 3. 1-(1-(2,4-Dichlorophenyl)ethyl)-6-(2-methyl-[1,4'-bipiperidin]-1'-yl)-1H-pyrazolo[3,4-b]pyrazine-3-carboxamide hydrochloride

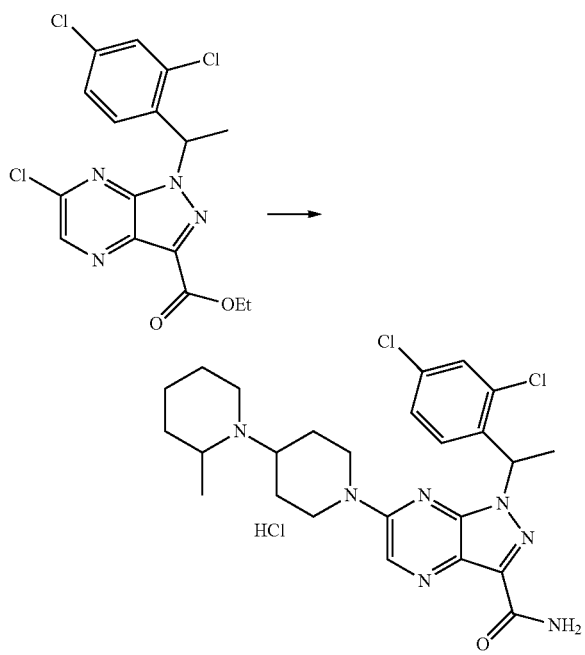

The title compounds were prepared from ethyl 6-chloro-1-(1-(2,4-dichlorophenyl)ethyl)-1H-pyrazolo[3,4-b]pyrazine-3-carboxylate (Example 1, Step 3) by procedures similar to those described in Example 1, Step 4, replacing 1-(4-piperidyl)piperidine with 2-methyl-1,4'-bipiperidine (Example 3, Step 2). To the crude mixture was added ammonia in methanol (7 M, 20 mL). The mixture was stirred at room temperature for 16 h and then ammonia gas was bubbled through the mixture for 3 min. The mixture was stirred at room temperature for 2 h and concentrated under reduced pressure. The residue was dissolved in dichloromethane and HCl in diethyl ether (1 M, 1 equiv) was added. The mixture was concentrated under reduced pressure to give the title compound as a mixture of diastereomers. $^1$H NMR (400 MHz, CD$_3$OD; HCl salt) δ 8.18 (s, 1H), 7.27-7.17 (m, 2H), 7.04 (dt, J=8.5, 1.9 Hz, 1H), 6.19 (q, J=7.1 Hz, 1H), 4.38 (d, J=13.3 Hz, 2H), 2.97-2.63 (m, 3H), 2.58-2.44 (m, 1H), 2.43-2.30 (m, 1H), 1.89 (d, J=10.9 Hz, 1H), 1.67 (d, J=7.1 Hz, 3H), 1.64-0.93 (m, 10H), 0.85 (d, J=6.2 Hz, 3H); m/z 516.2 (M+H$^+$).

Example 4

1-(1-(2,4-Dichlorophenyl)ethyl)-6-(3'-methyl-[1,4'-bipiperidin]-1'-yl)-1H-pyrazolo[3,4-b]pyrazine-3-carboxamide hydrochloride

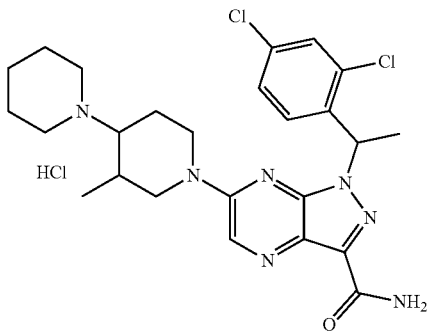 [SMILES: CC1CN(c2cnc3c(C(N)=O)nn(C(C)c4ccc(Cl)cc4Cl)c3n2)CCC1N1CCCCC1 ; Cl]

Step 1. 1-(1-(2,4-Dichlorophenyl)ethyl)-6-(3'-methyl-[1,4'-bipiperidin]-1'-yl)-1H-pyrazolo[3,4-b]pyrazine-3-carboxylic acid

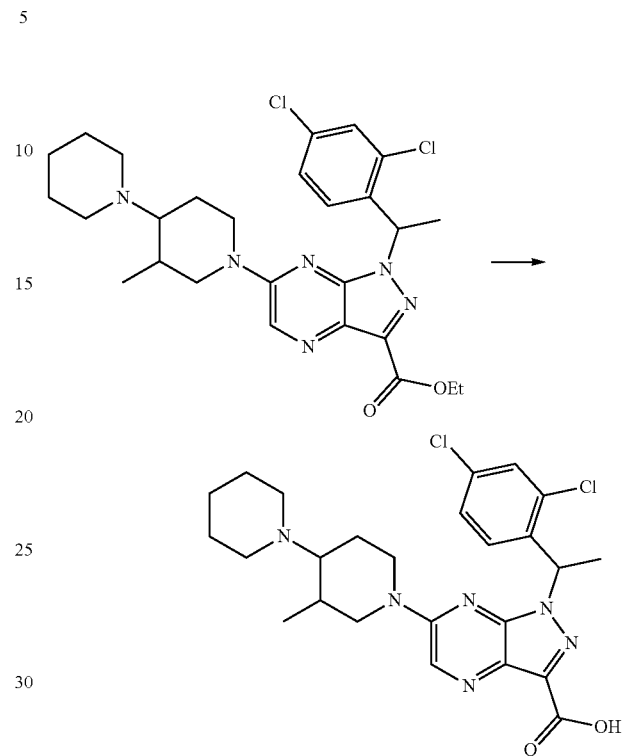

To a solution of ethyl 1-(1-(2,4-dichlorophenyl)ethyl)-6-(3'-methyl-[1,4'-bipiperidin]-1'-yl)-1H-pyrazolo[3,4-b]pyrazine-3-carboxylate hydrochloride (Example 2, Step 3, 35 mg, 0.064 mmol) in ethanol (0.26 mL), THF (0.26 mL) and water (0.13 mL) was added LiOH (12 mg, 0.52 mmol). The mixture was stirred at 60° C. for 16 h. The reaction was diluted with aqueous 0.5 M HCl (10 mL) and was filtered, rinsing with 5 mL aqueous 0.5 M HCl. The solid material was dried by vacuum filtration to afford the desired product as the HCl salt.

Step 2. 1-(1-(2,4-Dichlorophenyl)ethyl)-6-(3'-methyl-[1,4'-bipiperidin]-1'-yl)-1H-pyrazolo[3,4-b]pyrazine-3-carboxamide hydrochloride

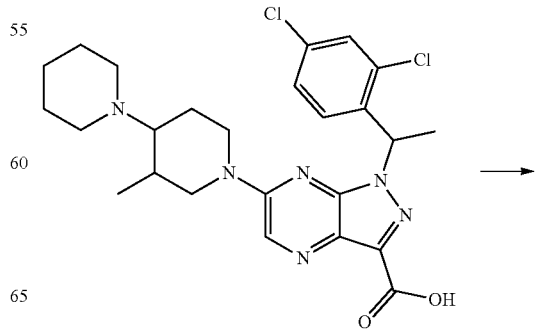

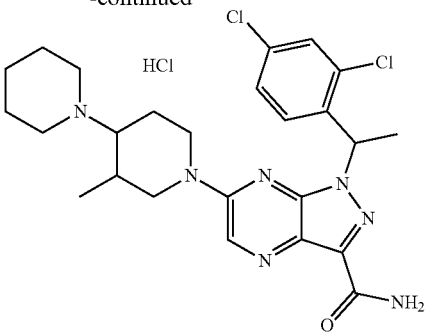

To a solution of 1-(1-(2,4-dichlorophenyl)ethyl)-6-(3'-methyl-[1,4'-bipiperidin]-1'-yl)-1H-pyrazolo[3,4-b]pyrazine-3-carboxylic acid (Example 3, Step 3, 13 mg, 0.025 mmol) in DMF (0.125 mL) was added N,N-diisopropylethylamine (0.009 mL, 0.05 mmol), HATU (12 mg, 0.030 mmol). Then ammonia gas was bubbled through the mixture for 2 min. The mixture was sealed and stirred at room temperature for 5 h. After this time, aqueous HCl (0.5 M, 10 mL) was added and a precipitate formed. The precipitate was isolated by filtration and washed with HCl (0.5 M) to give the title compounds. $^1$H NMR (400 MHz, CDCl$_3$, HCl salt) δ 8.29-8.28 (m, 1H), 7.75 (br s, 1H), 7.48-7.27 (m, 2H), 7.09-7.03 (m, 2H), 6.39 (q, J=7.1 Hz, 1H), 4.55-4.49 (m, 1H), 4.37-4.30 (m, 1H), 3.10-2.97 (m, 1H), 2.86-2.76 (m, 1H), 2.40-2.12 (m, 5H), 1.92 (d, J=7.1 Hz, 3H), 1.55-1.32 (m, 7H), 1.84 (d, J=6.2 Hz, 1.7H), 1.78 (d, J=6.2 Hz, 1.3H); m/z 516.2 (M+H$^+$).

Example 5

1-((R)-1-(2,4-Dichlorophenyl)ethyl)-6-(3'-methyl-[1,4'-bipiperidin]-1'-yl)-1H-pyrazolo[3,4-b]pyrazine-3-carboxamide 2,2,2-trifluoroacetate

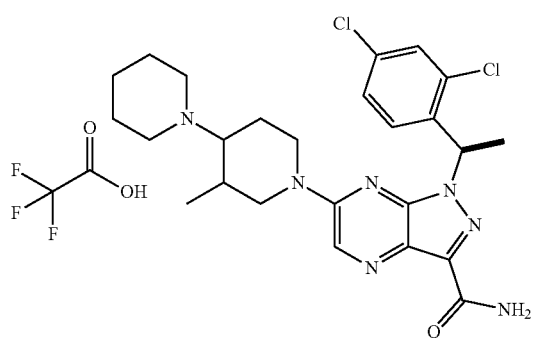

Step 1. (R)-1-(1-(2,4-dichlorophenyl)ethyl)urea

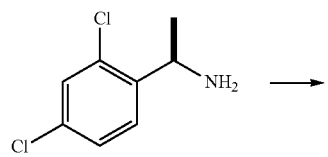

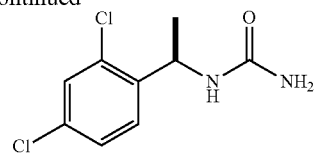

To a 6 L flask equipped with overhead stirrer was added (R)-1-(2,4-dichlorophenyl)ethan-1-amine (211 g, 1.11 mol) [reference WO 2013082490], water (3.4 L) and concentrated HCl (92.5 mL, 1.11 mol). The mixture was a slurry. Then solid KOCN (90 g, 1.11 mol) was added in one portion at room temperature. All solids went into solution and a white precipitate began to form after 1 h. The white precipitate was isolated by filtration. The filtrate was allowed to stand at room temperature and more precipitate formed. The precipitate was isolated by filtration. This was repeated several times until no more precipitate formed in the filtrate upon standing at room temperature for 1 d. All the solids were combined and dried under high vacuum.

Step 2. (R)-(1-(2,4-dichlorophenyl)ethyl)hydrazine hydrochloride

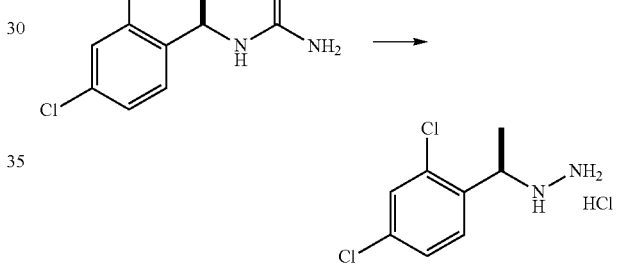

(R)-1-(1-(2,4-dichlorophenyl)ethyl)urea (Example 5, Step 1, 50 g, 214.6 mmol) was milled into a fine powder and placed into an oven dried 2 L flask. The 2 L flask was purged with nitrogen gas and a degassed mixture of 1 L of toluene and 375 mL of tert-BuOH added via cannula under nitrogen. Solid tert-BuOK (240.3 g, 2146 mmol) was milled into fine powder and added to a separate 5 L, 3 neck flask. The 5 L flask was purged with nitrogen, and a degassed mixture of 1 L of toluene and 650 mL of tert-BuOH was added via cannula under nitrogen gas. The 2 L and the 5 L mixtures were slurries and were cooled to −20° C. The lights inside the hood were turned off before tBuOCl (23.18 g, 24 mL, 214.6 mmol) was added to the 2 L flask at −20° C. Then the −20° C. bath was removed and the mixture was placed in a 0° C. bath. As soon as the slurry went all into solution, the mixture was transferred to the 5 L flask via cannula under nitrogen at −20° C. The lights in the hood were turned on. The −20° C. bath was removed, and the mixture was placed into 0° C. bath. The mixture was stirred at 0° C. for 10 min and then warmed to room temperature, at which time the mixture was poured onto ice. The mixture was extracted with ethyl acetate (2×) and the combined organic layers were washed with 1 L water, 500 mL saturated sodium thiosulfate, and 1 L brine. The solvents were concentrated under reduced pressure to give tert-butyl (R)-2-(1-(2,4-dichlorophenyl)ethyl)hydrazine-1-carboxylate with 98.9% enantiomeric excess. Enantiomeric excess was determined by HPLC using a Chiralpak® IF-3 column (Daicel, Corporation, West Chester, Pa.) and eluting with 5% IPA/heptanes at 20 mL/min, $R_t$=5.3 min.

Other enantiomer: tert-butyl (S)-2-(1-(2,4-dichlorophenyl)ethyl)hydrazine-1-carboxylate: $R_t$=4.5 min.

The residue was dissolved in 250 mL of 1,4-dioxane and HCl in 1,4-dioxane (4 M, 161 mL, 643.8 mmol) was added at room temperature. The mixture was stirred at room temperature overnight and then concentrated under reduced pressure. The residue was triturated from 25% ethyl acetate in hexanes (1 mL of solvent per 1 g of residue) to give (R)-(1-(2,4-dichlorophenyl)ethyl)hydrazine hydrochloride with 99.2% enantiomeric excess. Enantiomeric excess was determined by HPLC using a Chiralpak® IF-3 column (Daicel, Corporation, West Chester, Pa.) and eluting with 20% IPA/heptanes. $R_t$=4.7 min. Other enantiomer: (S)-(1-(2,4-dichlorophenyl)ethyl)hydrazine hydrochloride: $R_t$=6.9 min.

Step 3. Ethyl 2-(3,5-dichloropyrazin-2-yl)-2-oxoacetate

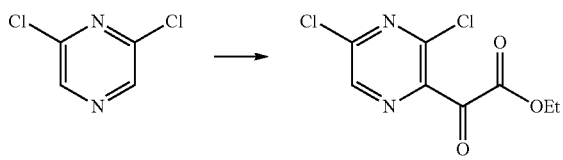 [SMILES: Clc1cncc(Cl)n1 ; CCOC(=O)C(=O)c1ncc(Cl)nc1Cl]

To a solution of 2,2,6,6-tetramethylpiperidine (67 mL, 0.4 moles) in THF (600 mL) at −78° C. was added n-BuLi (2.5 M in hexanes, 208 mL, 0.52 mol). The mixture was stirred at −78° C. for 20 min. and then warmed to 0° C. In a separate flask, diethyl oxalate (65 mL, 0.48 mol) and 2,6-dichloropyrazine (60 g, 0.4 mol) were dissolved in THF (600 mL) and cooled to −78° C. The lithium 2,2,6,6-tetramethylpiperidine solution was added to the 2,6-dichloropyrazine solution via cannula over 1 h at −78° C. The mixture was stirred at −78° C. for 20 min and then the mixture was poured into a mixture of saturated ammonium chloride (300 mL) and water (300 mL). The mixture was diluted with ethyl acetate (300 mL) and the layers were separated. The aqueous layer was extracted with ethyl acetate (300 mL) and the combined organic layers were dried over MgSO₄. The mixture was concentrated under reduced pressure. The residue was purified by silica gel chromatography (5 to 20% ethyl acetate in hexanes) to provide the title compound (32 g, 32% yield).

Step 4. Ethyl (R)-6-chloro-1-(1-(2,4-dichlorophenyl)ethyl)-1H-pyrazolo[3,4-b]pyrazine-3-carboxylate

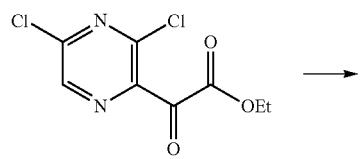

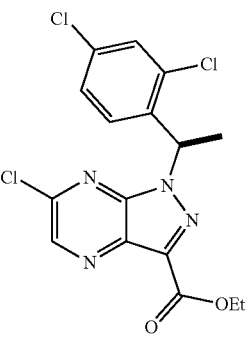

To a solution of ethyl 2-(3,5-dichloropyrazin-2-yl)-2-oxoacetate (Example 5, Step 3, 14.5 g, 58.4 mmol) in THF (97 mL) was added (R)-(1-(2,4-dichlorophenyl)ethyl)hydrazine hydrochloride (Example 5, Step 2, 11.7 g, 48.7 mmol). The mixture was warmed to 80° C. for 2 h and then cooled to room temperature. The mixture was allowed to stand at room temperature under argon for 12 h. The mixture was diluted with brine and the layers were separated. The aqueous layer was extracted with ethyl acetate (2×) and the combined organic layers were dried over MgSO₄ and concentrated under reduced pressure to give a red oil.

The red oil was dissolved in THF (240 mL) and cooled to 0° C. Sodium hydride (60% dispersion in mineral oil, 3.9 g, 97.4 mmol) was added and the mixture was stirred at room temperature for 15 h. The mixture was diluted with saturated ammonium chloride (200 mL), water (200 mL), and ethyl acetate (200 mL). The layers were separated and the aqueous layer was extracted with ethyl acetate (100 mL). The combined organic layers were dried over MgSO₄ and concentrated under reduced pressure. The residue was purified by silica gel chromatography (10 to 20% ethyl acetate in hexanes) to provide the title compound (9 g, 46% yield) with >99% enantiomeric excess. Enantiomeric excess was determined by HPLC using a Chiralpak® IF-3 column (Daicel, Corporation, West Chester, Pa.) and eluting with 5% IPA/heptanes, $R_t$=7.2 min. Other enantiomer: ethyl (S)-6-chloro-1-(1-(2,4-dichlorophenyl)ethyl)-1H-pyrazolo[3,4-b]pyrazine-3-carboxylate: $R_t$=3.9 min.

Step 5. 1-((R)-1-(2,4-Dichlorophenyl)ethyl)-6-(3'-methyl-[1,4'-bipiperidin]-1'-yl)-1H-pyrazolo[3,4-b]pyrazine-3-carboxamide 2,2,2-trifluoroacetate

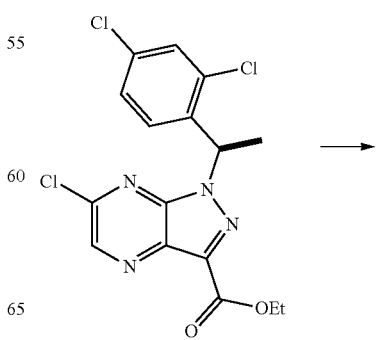

311
-continued

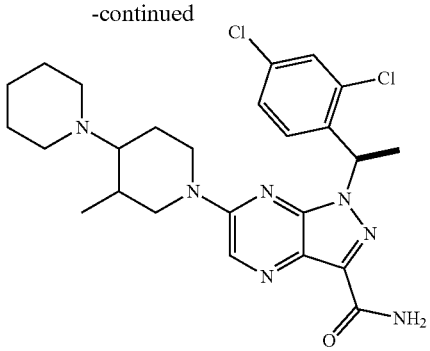

The title compounds were prepared from ethyl (R)-6-chloro-1-(1-(2,4-dichlorophenyl)ethyl)-1H-pyrazolo[3,4-b]pyrazine-3-carboxylate (Example 5, Step 4) by procedures similar to those described in Example 3, Step 3, replacing 2-methyl-1,4'-bipiperidine with 3'-methyl-1,4'-bipiperidine 2,2,2-trifluoroacetate (Example 2, Step 2). The residue was purified by reverse phase preparative HPLC (Phenomenex Gemini-NX, 10μ, C18, 110A, 250×30 mm (Phenomenex, Torrance, Calif.), eluent: 0 to 100% acetonitrile in water, both eluents containing 0.1% trifluoroacetic acid, gradient elution over 30 min) to give the title compounds as trifluoroacetic acid salts a mixture of cis-diastereomers (1:1). $^1$H-NMR (400 MHz; CD$_3$OD, trifluoroacetic acid-salt): δ 8.37 (s, 0.5H), 8.36 (s, 0.5H), 7.37 (m, 1H), 7.31-7.27 (m, J=8.5 Hz, 1H), 7.20-7.15 (m, 1H), 6.40-6.33 (m, J=7.1, 1.8 Hz, 1H), 3.69-3.61 (m, 1H), 3.60-3.51 (m, 1H), 3.43-3.37 (m, 1H), 3.10-3.00 (m, 1H), 2.97-2.78 (m, 3H), 2.55-2.48 (m, 1H), 2.18-2.11 (m, 1H), 1.95-1.87 (m, 3H), 1.85-1.80 (m, 3H), 1.75-1.40 (m, 6H), 0.91 (d, J=6.8 Hz, 1.5H), 0.83 (d, J=6.9 Hz, 1.5H); m/Z 516.2 (M+H$^+$).

Example 6

1-(1-(2,4-Dichlorophenyl)ethyl)-6-(3'-ethyl-[1,4'-bipiperidin]-1'-yl)-1H-pyrazolo[3,4-b]pyrazine-3-carboxamide hydrochloride

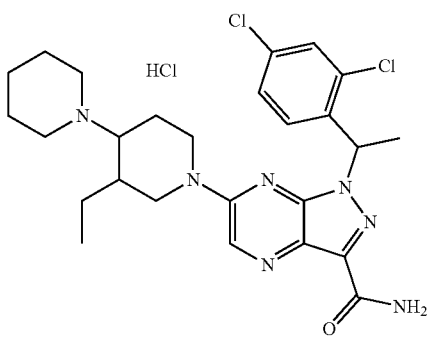 [SMILES: CCC1CN(c2cnc3c(C(N)=O)nn(C(C)c4ccc(Cl)cc4Cl)c3n2)CCC1N1CCCCC1 ; Cl]

312

Step 1. 1-Benzyl-3-ethylpiperidin-4-one hydrochloride

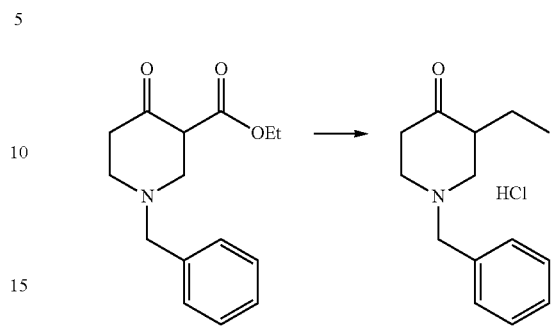

To a solution of ethyl 1-benzyl-4-oxopiperidine-3-carboxylate (5.09 g, 19.1 mmol) in THF (67 mL) at room temperature was added ethyl iodide (7.67 mL, 95.7 mmol) and potassium carbonate (7.92 g, 57.3 mmol). The mixture was stirred at reflux for 16 h and then cooled to room temperature. Water was added and the mixture was extracted with ethyl acetate. The organic layer was dried over sodium sulfate and concentrated under reduce pressure. The reside was diluted with HCl (6 M, 70 mL). The mixture was stirred at reflux for 24 h and the cooled to room temperature. The mixture was neutralized with NaOH (3 M) and extracted with dichloromethane (3×). The combined organic layers were concentrated under reduced pressure to give the title compound as an orange oil.

Step 2. 1'-Benzyl-3'-ethyl-1,4'-bipiperidine

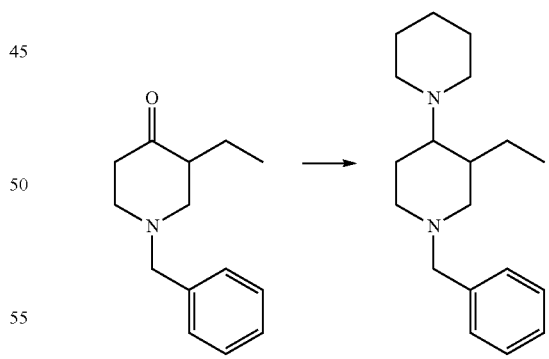

The title compound was prepared from 1-benzyl-3-ethylpiperidin-4-one hydrochloride (Example 6, Step 1) by procedures similar to those described in Example 3, Step 1, replacing 2-methylpiperidine with piperidine. The residue was purified by silica gel chromatography (1 to 10% [2 M ammonia in MeOH] in dichloromethane) to give the title compounds as a mixture of diastereomers.

Step 3. 3'-Ethyl-1,4'-bipiperidine

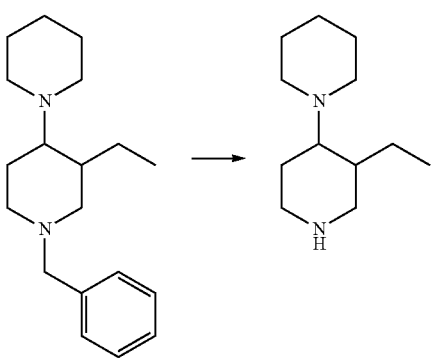 [SMILES: CCC1CN(Cc2ccccc2)CCC1N1CCCCC1 ; CCC1CNCCC1N1CCCCC1]

To a solution of 1'-benzyl-3'-ethyl-1,4'-bipiperidine (Example 6, Step 2, 1.7 g, 5.94 mmol) in MeOH (40 mL) was added Pd(OH)$_2$ (20% wet, 160 mg). Then H$_2$ (g) was bubble through the mixture for 3 h and the mixture was stirred under an atmosphere of H$_2$ (g) for an additional 16 h. The mixture was filtered through a pad of celite, washing with methanole, and the filtrate was concentrated under reduced pressure to give the title compound as a yellow oil.

Step 4. Ethyl 1-(1-(2,4-dichlorophenyl)ethyl)-6-(3'-ethyl-[1,4'-bipiperidin]-1'-yl)-1H-pyrazolo[3,4-b]pyrazine-3-carboxylate

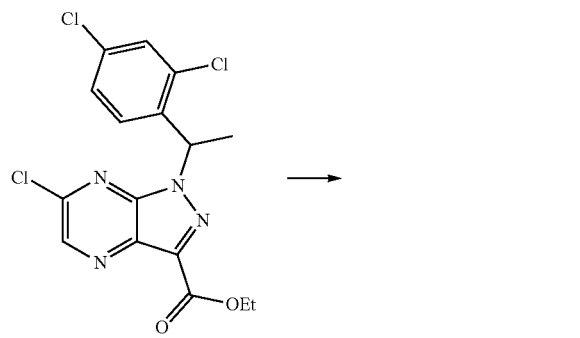

The title compounds were prepared from ethyl 6-chloro-1-(1-(2,4-dichlorophenyl)ethyl)-1H-pyrazolo[3,4-b]pyrazine-3-carboxylate (Example 1, Step 3) by procedures similar to those described in Example 1, Step 4, replacing 1-(4-piperidyl)piperidine with 3'-ethyl-1,4'-bipiperidine (Example 6, Step 3), DMSO with DMF and the mixture was stirred at room temperature instead of 44° C.

Step 5. 1-(1-(2,4-Dichlorophenyl)ethyl)-6-(3'-ethyl-[1,4'-bipiperidin]-1'-yl)-1H-pyrazolo[3,4-b]pyrazine-3-carboxylic acid

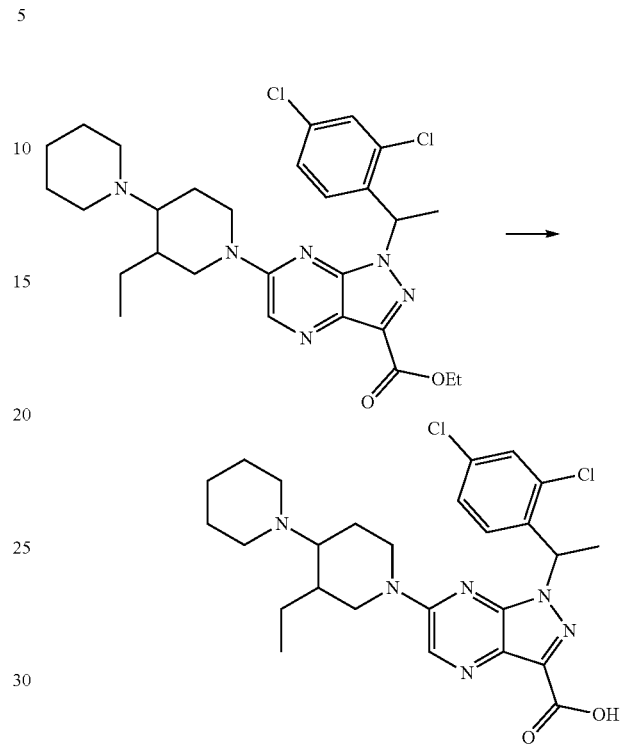

Ethyl 1-(1-(2,4-dichlorophenyl)ethyl)-6-(3'-ethyl-[1,4'-bipiperidin]-1'-yl)-1H-pyrazolo[3,4-b]pyrazine-3-carboxylate (Example 6, Step 4, 200 mg, 0.36 mmol) in THF (1.2 mL) and water (1.0 mL) at room temperature was added LiOH (10 mg, 0.43 mmol). The mixture was stirred at room temperature for 16 h. Then HCl in Et$_2$O (1 M, 0.86 mL, 0.86 mmol) was added and the mixture was concentrated under reduced pressure to give the title compounds which were used without further purification.

Step 6. 1-(1-(2,4-Dichlorophenyl)ethyl)-6-(3'-ethyl-[1,4'-bipiperidin]-1'-yl)-1H-pyrazolo[3,4-b]pyrazine-3-carboxamide hydrochloride

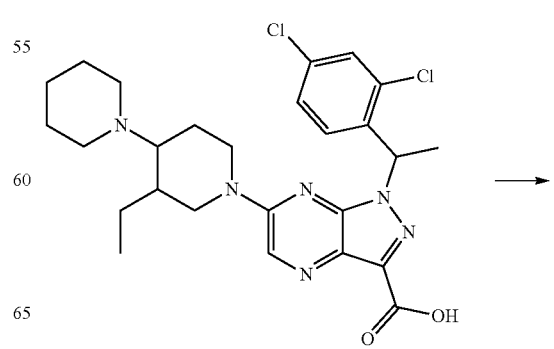

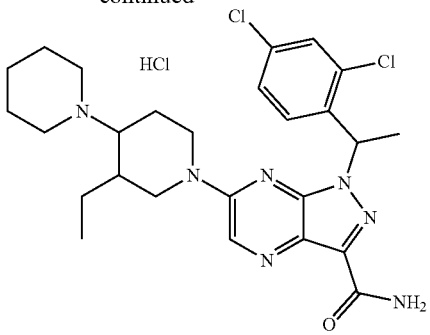

The title compounds were prepared from ethyl 6-chloro-1-(1-(2,4-dichlorophenyl)ethyl)-1H-pyrazolo[3,4-b]pyrazine-3-carboxylate (Example 6, Step 5) by procedures similar to those described in Example 4, Step 2. The residue was purified by silica gel chromatography (2 to 10% [2 M ammonia in MeOH] in dichloromethane) to give the product as a mixture of diastereomers. The residue was redissolved in dichloromethane (5 mL) and HCl in Et$_2$O (1 M, 0.4 mL) was added to yield the HCl salts. $^1$H NMR (400 MHz, CDCl$_3$; HCl salt): δ 8.24 (s, 0.4H), 8.23 (s, 0.6H), 7.69 (s, 1H), 7.40-7.31 (m, 2H), 7.27-7.26 (m, 1H), 7.16-7.09 (m, 1H), 6.46-6.39 (m, 1H), 5.95 (brs, 1H), 4.71 (d, J=13.4 Hz, 1H), 4.48 (d, J=12.7 Hz, 1H), 2.98-2.82 (m, 2H), 2.59-2.25 (m, 4H), 2.07-1.71 (m, 6H), 1.70-1.37 (m, 7H), 1.20-1.05 (m, 1H), 1.01 (t, J=7.3 Hz, 1.8H), 0.75 (t, J=7.4 Hz, 1.2H); m/z 530.2 (M+H$^+$).

Example 7

1-(1-(2,4-Dichlorophenyl)ethyl)-6-(3'-ethyl-[1,4'-bipiperidin]-1'-yl)-1H-pyrazolo[3,4-b]pyrazine-3-carbonitrile 2,2,2-trifluoroacetate

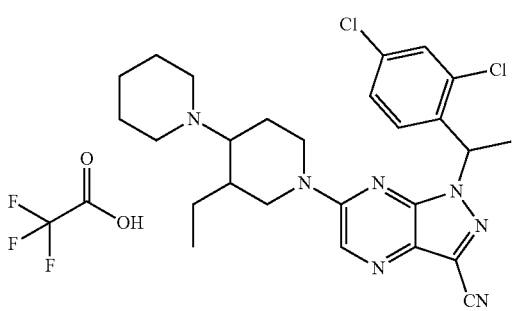

To a dichloromethane (1 mL) solution of diastereomeric mixture synthesized in Example 6, Step 6 (80 mg, 0.151 mmol) at room temperature was added Burgess Reagent (90 mg, 0.377 mmol). The mixture was stirred at room temperature for 16 h and then concentrated under reduced pressure. The residue was purified by silica gel chromatography (2 to 10% [2 M ammonia in methanol] in dichloromethane)) to give a mixture. The residue was purified by reverse phase preparative HPLC (Phenomenex Gemini-NX, 10μ, C18, 110A, 250×30 mm (Phenomenex, Torrance, Calif.)), eluent: 0 to 100% acetonitrile in water, both eluents containing 0.1% trifluoroacetic acid, gradient elution over 30 min) to give the title compounds as a mixture of diastereomers. $^1$H NMR (400 MHz, CDCl$_3$; trifluoroacetic acid Salt): δ 8.33 (s, 0.4H), 8.32 (s, 0.6H), 7.40-7.32 (m, 1.5H), 7.24-7.16 (m, 1.5H), 6.49-6.39 (m, 1H), 4.89 (dd, J=21.6, 14.4 Hz, 1H), 4.65 (dd, J=29.6, 12.6 Hz, 1H), 3.94 (s, 5H), 3.64 (t, J=11.4 Hz, 1H), 3.32-3.13 (m, 1H), 3.06-2.94 (m, 1H), 2.94-2.84 (m, 1H), 2.83-2.66 (m, 2H), 2.25-1.83 (m, 8H), 1.65-1.23 (m, 4H), 1.10 (t, J=7.2 Hz, 1.8H), 0.82 (t, J=7.2 Hz, 1.2H); m/z 512.2 (M+H$^+$).

Example 8

1-(1-(2,4-Dichlorophenyl)ethyl)-6-(3'-methyl-[1,4'-bipiperidin]-1'-yl)-1H-pyrazolo[3,4-b]pyrazine hydrochloride

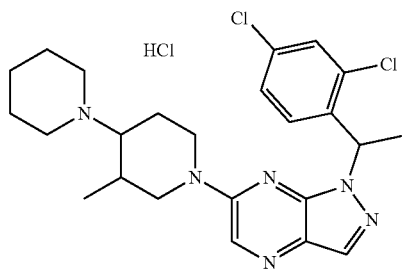 [SMILES: CC1CN(c2cnc3cnn(C(C)c4ccc(Cl)cc4Cl)c3n2)CCC1N1CCCCC1 ; Cl]

Step 1. (Z)-3,5-Dichloro-2-((2-(1-(2,4-dichlorophenyl)ethyl)hydrazono)methyl)pyrazine and (E)-3,5-dichloro-2-((2-(1-(2,4-dichlorophenyl)ethyl)hydrazono)methyl)pyrazine

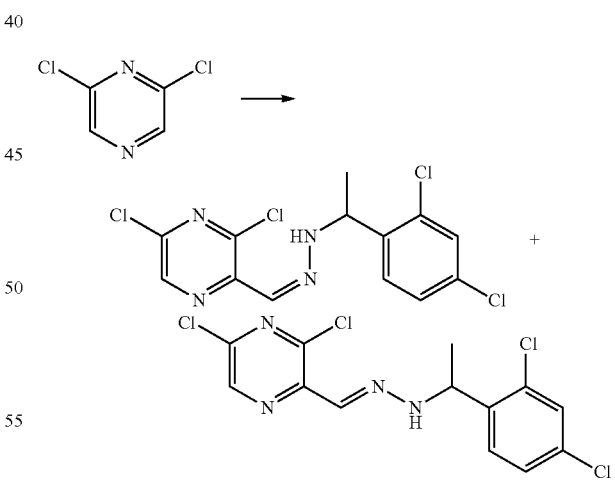

To a solution of 2,2,6,6-tetramethylpiperidine (22.85 mL, 134.25 mmol) in THF (200 mL) at −40° C. was added n-BuLi (2.5 M in hexanes, 56.39 mL, 140.96 mmol). The mixture was stirred at −40° C. for 30 min. In a separate flask, ethyl formate (10.85 mL, 134.25 mmol) and 2,6-dichloropyrazine (10 g, 67.13 mmol) were dissolved in THF (200 mL) and cooled to −90° C. The lithium 2,2,6,6-tetramethylpiperidine solution was added to the 2,6-dichloropyrazine solution via cannula over 30 min at −90° C. The mixture was stirred at −90° C. for 1 h and then acetic acid (7.68 mL, 134.25 mmol) was added, followed by (1-(2,4-dichlorophenyl)ethyl)hydrazine hydrochloride (Example 1, step 1, 8.11 g, 33.56 mmol). The mixture was allowed to warm up to room temperature and stirred at room temperature for 6 h. The mixture was filtered through a silica gel-celite plug, concentrated under reduced pressure and then the residue was purified by silica gel chromatography (20 to 100% ethyl acetate in hexanes) to provide the title compounds (6.2 g, 25% yield) as a viscous orange oil.

Step 2. 1-(1-(2,4-Dichlorophenyl)ethyl)-6-(3'-methyl-[1,4'-bipiperidin]-1'-yl)-1H-pyrazolo[3,4-b]pyrazine hydrochloride

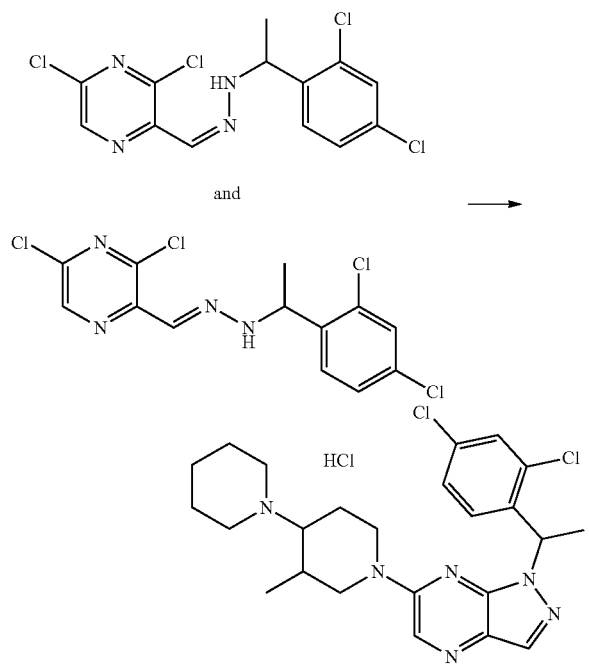

(Z)-3,5-dichloro-2-((2-(1-(2,4-dichlorophenyl)ethyl)hydrazono)methyl)pyrazine and (E)-3,5-dichloro-2-((2-(1-(2,4-dichlorophenyl)ethyl)hydrazono)methyl)pyrazine (Example 8, step 1, 100 mg, 0.275 mmol) were dissolved in DMF (5 mL) and then the solution was degassed. 1,8-Diazabicyclo[5.4.0]undec-7-ene (82 µL, 0.549 mmol) was added and then the mixture was heated to 140° C. and stirred for 2 h. 3'-methyl-1,4'-bipiperidine (Example 2, Step 2, 100 mg, 0.549 mmol) was then added and the mixture was further stirred at 140° C. for 2 h. The mixture was concentrated under reduced pressure and The residue was purified by reverse phase preparative HPLC (Gemini-NX, 10 µm, 250×30 mm, C18 column (Phenomenex, Torrance, Calif.), eluent: 0 to 100% acetonitrile in water, both eluents containing 0.1% trifluoroacetic acid, gradient elution over 30 min). The fractions containing the desired product were concentrated under reduced pressure. The residue was free-based by passing it through a basic column (Agilent) using dichloromethane and methanol (4:1) as eluent and concentrated under reduced pressure. Then, HCl (1N in diethyl ether, 1 mL) was added and then the mixture was concentrated under reduced pressure to give the title compounds as a mixture of diastereomers (8 mg, 6% yield). $^1$H NMR (400 MHz, CDCl$_3$; HCl Salt) δ 11.22 (bs, 1H), 8.21 (s, 0.66H), 8.20 (s, 0.34H), 8.09 (s, 0.66H), 8.09 (s, 0.34H), 7.40-7.35 (m, 2H), 7.17 (dd, J=8.5, 2.0 Hz, 1H), 6.39 (q, J=7.2 Hz, 1H), 4.86-4.63 (m, 3H), 4.57-4.47 (m, 1H), 3.88-3.78 (m, 1H), 3.73-3.64 (m, 1H), 3.34-3.23 (m, 1H), 3.13-3.04 (m, 1H), 2.98-2.88 (m, 1H), 2.83-2.69 (m, 2H), 2.64-2.54 (m, 1H), 2.26-2.00 (m, 3H), 1.93 (d, J=7.0 Hz, 3H), 1.91-1.88 (m, 2H), 1.52-1.40 (m, 1H), 1.21 (d, J=6.6 Hz, 2H), 1.13 (d, J=6.6 Hz, 1H). m/z 473.3 (M+H$^+$).

Example 9

1-(1-(2,4-Dichlorophenyl)ethyl)-6-(3'-ethyl-[1,4'-bipiperidin]-1'-yl)-1H-pyrazolo[3,4-b]pyrazine hydrochloride

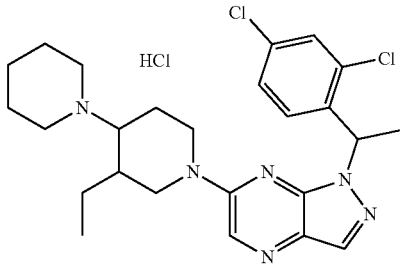 [SMILES: CCC1CN(c2cnc3cnn(C(C)c4ccc(Cl)cc4Cl)c3n2)CCC1N1CCCCC1 ; Cl]

The title compounds were prepared from (Z)-3,5-dichloro-2-((2-(1-(2,4-dichlorophenyl)ethyl)hydrazono)methyl)pyrazine and (E)-3,5-dichloro-2-((2-(1-(2,4-dichlorophenyl)ethyl)hydrazono)methyl)pyrazine (Example 8, Step 1, 100 mg, 0.275 mmol) by procedures similar to those described in Example 8, Step 2, replacing 3'-methyl-1,4'-bipiperidine 2,2,2-trifluoroacetate with 3'-ethyl-1,4'-bipiperidine (Example 6, Step 3, 107.9 mg, 0.549 mmol). The crude was purified by reverse phase preparative HPLC (Gemini-NX, 10 µm, 250×30 mm, C18 column (Phenomenex, Torrance, Calif.), eluent: 0 to 100% acetonitrile in water, both eluents containing 0.1% trifluoroacetic acid, gradient elution over 30 min). The fractions containing the desired product were concentrated under reduced pressure. The residue was free-based by passing it through a Agilent PL-HCO3 ion exchange column using dichloromethane and methanol (4:1) as eluent and concentrated under reduced pressure. HCl (1N in diethyl ether, 1 mL) was added and then the mixture was concentrated under reduced pressure to give the title compounds (42 mg, 31% yield, 3:2 dr). $^1$H NMR (400 MHz, CDCl$_3$; HCl Salt) δ 8.17 (s, 0.4H), 8.16 (s, 0.6H), 8.03 (s, 0.4H), 8.02 (s, 0.6H), 7.41-7.34 (m, 2H), 7.18-7.12 (m, 1H), 6.43-6.34 (m, 1H), 4.78-4.67 (m, 1H), 4.53-4.41 (m, 1H), 2.97-2.80 (m, 2H), 2.53-2.33 (m, 4H), 2.24-2.14 (m, 1H), 1.94 (s, 1H), 1.93 (d, J=7.0 Hz, 1.2H), 1.91 (d, J=7.0 Hz, 1.8H), 1.90-1.86 (m, 1H), 1.68-1.53 (m, 6H), 1.51-1.41 (m, 3H), 1.03 (t, J=7.3 Hz, 1.8H), 0.79 (t, J=7.5 Hz, 1.2H). m/z 487.2 (M+H$^+$).

Example 10

1-(1-(2,4-Dichlorophenyl)ethyl)-6-(3'-methyl-[1,4'-bipiperidin]-1'-yl)-3-(trifluoromethyl)-1H-pyrazolo[3,4-b]pyrazine hydrochloride

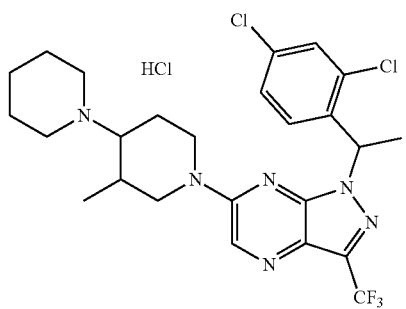 [SMILES: CC1CN(c2cnc3c(C(F)(F)F)nn(C(C)c4ccc(Cl)cc4Cl)c3n2)CCC1N1CCCCC1 ; Cl]

Step 1. (E)-3,5-Dichloro-2-(1-(2-(1-(2,4-dichlorophenyl)ethyl)hydrazono)-2,2,2-trifluoroethyl)pyrazine and (Z)-3,5-dichloro-2-(1-(2-(1-(2,4-dichlorophenyl)ethyl)hydrazono)-2,2,2-trifluoroethyl)pyrazine

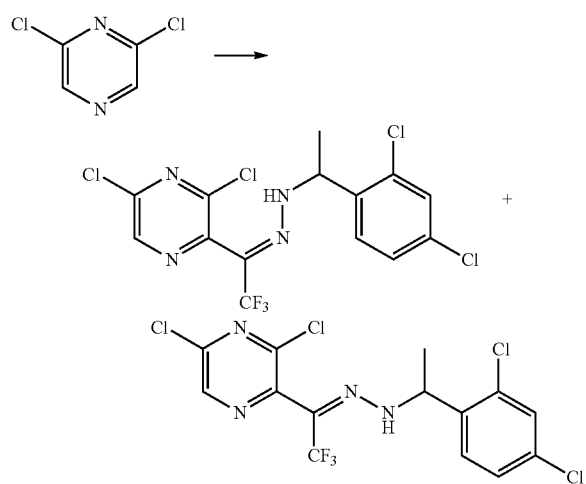

To a solution of 2,2,6,6-tetramethylpiperidine (13.71 mL, 80.55 mmol) in THF (200 mL) at −40° C. was added n-BuLi (2.5 M in hexanes, 34.91 mL, 87.26 mmol). The mixture was stirred at −40° C. for 30 min. In a separate flask, ethyl 2,2,2-trifluoroacetate (10.38 mL, 87.26 mmol) and 2,6-dichloropyrazine (10 g, 67.13 mmol) were dissolved in THF (200 mL) and cooled to −90° C. The lithium 2,2,6,6-tetramethylpiperidine solution was added to the 2,6-dichloropyrazine solution via cannula over 30 min at −90° C. The mixture was stirred at −90° C. for 30 min and then (1-(2,4-dichlorophenyl)ethyl)hydrazine hydrochloride (Example 1, step 1, 9.73 g, 40.28 mmol) was added, and then the mixture was allowed to warm up to room temperature. The mixture was concentrated under reduced pressure, then ethanol (200 mL) was added and the mixture was stirred at room temperature for 24 h. The mixture was concentrated under reduced pressure and then the residue was purified by silica gel chromatography (0 to 100% ethyl acetate in hexanes) to provide the title compounds (6.2 g, 21% yield) as a viscous orange oil.

Step 2. 6-Chloro-1-(1-(2,4-dichlorophenyl)ethyl)-3-(trifluoromethyl)-1H-pyrazolo[3,4-b]pyrazine

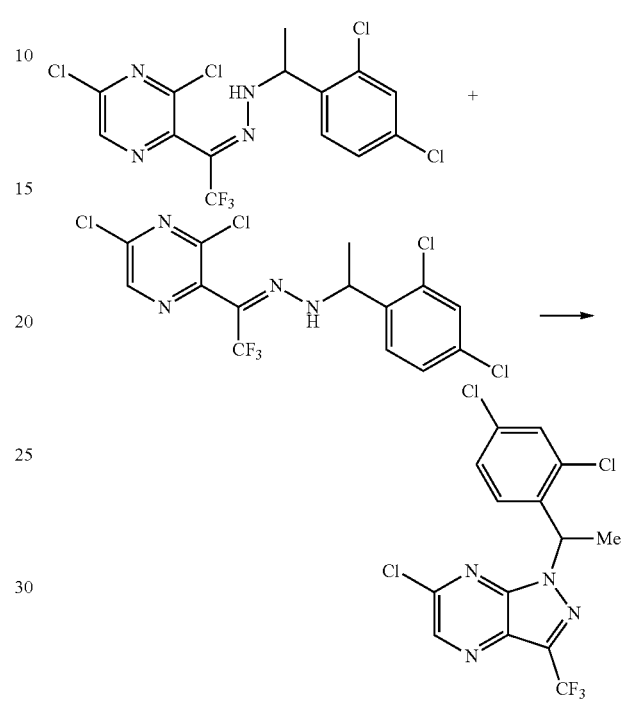

(E)-3,5-dichloro-2-(1-(2-(1-(2,4-dichlorophenyl)ethyl)hydrazono)-2,2,2-trifluoroethyl)pyrazine and (Z)-3,5-dichloro-2-(1-(2-(1-(2,4-dichlorophenyl)ethyl)hydrazono)-2,2,2-trifluoroethyl)pyrazine (Example 10, step 1, 2.5 g, 5.79 mmol) were dissolved in THF (58 mL) and then the solution was cooled to 0° C. Then, 1,8-Diazabicyclo[5.4.0]undec-7-ene (1.73 mL, 11.57 mmol) was then added dropwise. After the addition was completed, the mixture was allowed to warm up to room temperature and stirred for 10 h. The mixture was concentrated under reduced pressure and then the residue was purified by silica gel chromatography (0 to 20% ethyl acetate in hexanes) to provide the title compound (1.8 g, 79% yield) as a light orange oil.

Step 3. 1-(1-(2,4-Dichlorophenyl)ethyl)-6-(3'-methyl-[1,4'-bipiperidin]-1'-yl)-3-(trifluoromethyl)-1H-pyrazolo[3,4-b]pyrazine hydrochloride

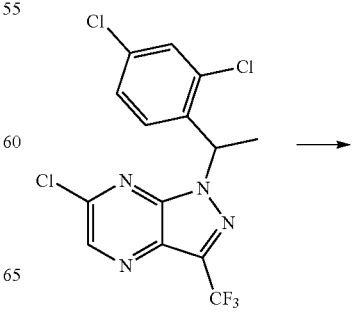

321

-continued

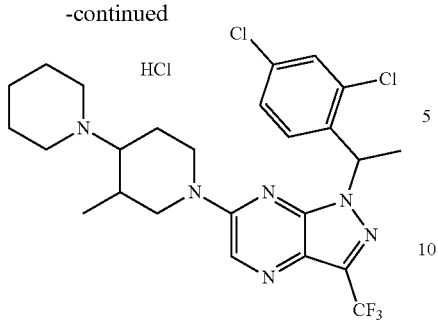

The title compound was synthesized using 6-Chloro-1-(1-(2,4-dichlorophenyl)ethyl)-3-(trifluoromethyl)-1H-pyrazolo[3,4-b]pyrazine (Example 10, step 2, 100 mg, 0.253 mmol) was dissolved in dichloromethane (5 mL) and then 3'-methyl-1,4'-bipiperidine (Example 2, Step 2, 50.7 mg, 0.278 mmol) was added, followed by N,N-diisopropylethylamine (88 μL, 0.506 mmol) and then the mixture was stirred at room temperature for 8 h. The mixture was concentrated under reduced pressure and then the residue was purified by silica gel chromatography (0 to 20% methanol in dichloromethane), the fractions containing the desired product were concentrated under reduced pressure. Then, HCl (1N in diethyl ether, 1 mL) was added and then the mixture was concentrated under reduced pressure to provide the title compounds as a mixture of diastereomers (114 mg, 78% yield) as a yellow solid. $^1$H NMR (400 MHz, CDCl$_3$; HCl Salt) δ 8.28 (s, 0.6H), 8.28 (s, 0.4H), 7.41-7.33 (m, 2H), 7.22-7.15 (m, 1H), 6.49-6.40 (m, 1H), 4.59 (d, J=13.2 Hz, 1H), 4.40 (t, J=13.1 Hz, 1H), 3.06 (d, J=12.9 Hz, 1H), 2.88 (t, J=13.1 Hz, 1H), 2.55-2.38 (m, 4H), 2.36-2.19 (m, 2H), 1.93 (d, J=7.1 Hz, 3H), 1.60 (m, 6H), 1.50-1.41 (m, 2H), 0.91 (d, J=6.9 Hz, 1.8H), 0.84 (d, J=6.8 Hz, 1.2H). m/z 541.2 (M+H$^+$).

Example 11

Ethyl 1-(2,4-dichlorobenzyl)-6-(3'-methyl-[1,4'-bipiperidin]-1'-yl)-1H-pyrazolo[3,4-b]pyrazine-3-carboxylate hydrochloride

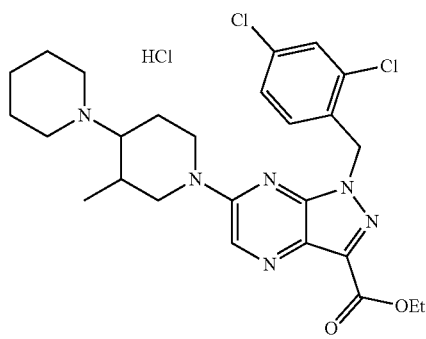 [SMILES: CCOC(=O)c1nn(Cc2ccc(Cl)cc2Cl)c2nc(N3CCC(N4CCCCC4)C(C)C3)cnc12 ; Cl]

322

Step 1. Ethyl 6-chloro-1-(2,4-dichlorobenzyl)-H-pyrazolo[3,4-b]pyrazine-3-carboxylate

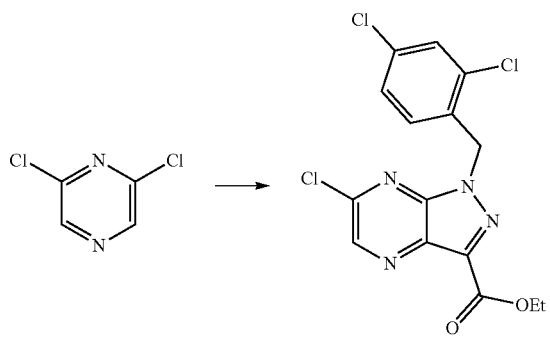 [SMILES: Clc1cncc(Cl)n1 ; CCOC(=O)c1nn(Cc2ccc(Cl)cc2Cl)c2nc(Cl)cnc12]

The title compound was prepared from 2,6-dichloropyrazine by procedures similar to those described in Example 1, Steps 2 and 3, replacing (1-(2,4-dichlorophenyl)ethyl)hydrazine hydrochloride in Step 2 with 2,4-dichlorobenzyl hydrazine hydrochloride.

Step 2. Ethyl 1-(2,4-dichlorobenzyl)-6-(3'-methyl-[1,4'-bipiperidin]-1'-yl)-1H-pyrazolo[3,4-b]pyrazine-3-carboxylate hydrochloride

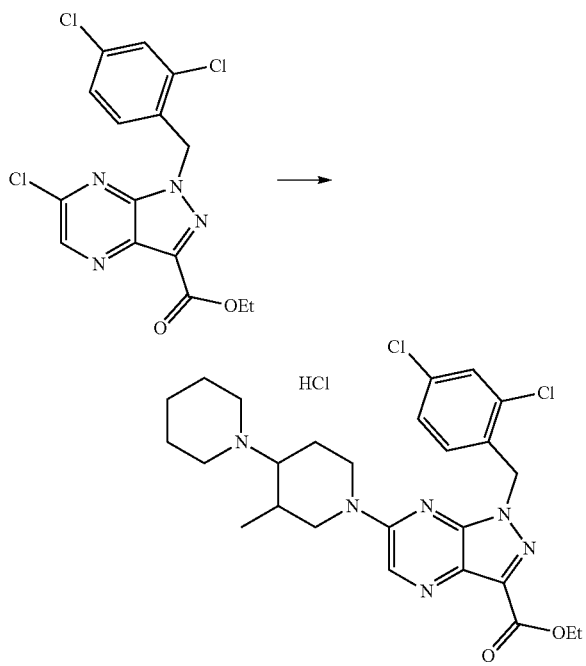

The title compounds were prepared from ethyl 6-chloro-1-(2,4-dichlorobenzyl)-1H-pyrazolo[3,4-b]pyrazine-3-carboxylate (Example 11, step 1) by procedures similar to those described in Example 1, Step 4, replacing 1-(4-piperidyl)piperidine with 3'-methyl-1,4'-bipiperidine (Example 2, Step 2), DMSO with DMF and the mixture was stirred at room temperature instead of 44° C. $^1$H-NMR (400 MHz; CDCl$_3$) δ 8.37 (s, 1H), 7.38 (d, J=2.1 Hz, 1H), 7.10 (d, J=8.4, 2.1 Hz, 1H), 6.85 (d, J=8.4 Hz, 1H), 5.64 (d, J=1.8 Hz, 2H), 4.63-4.54 (m, 1H), 4.52 (q, J=7.1 Hz, 2H), 4.40-4.34 (m, 1H), 3.05 (dd, J=13.4, 2.5 Hz, 1H), 2.85 (dt, J=13.2, 2.9 Hz, 1H), 2.47-2.35 (m, 4H), 2.33-2.24 (m, 1H), 2.21 (dt, J=11.8, 4.0 Hz, 1H), 1.93-1.84 (m, 1H), 1.62-1.49 (m, 5H), 1.44 (t, J=7.1 Hz, 3H), 1.43-1.38 (m, 2H), 0.85 (d, J=6.9 Hz, 3H); m/z 531.2 (M+H$^+$).

Example 12

1-((R)-1-(2,4-Dichlorophenyl)ethyl)-3-methyl-6-((3R,4S)-3-methyl-4-(pyrrolidin-1-yl)piperidin-1-yl)-1H-pyrazolo[3,4-b]pyrazine hydrochloride

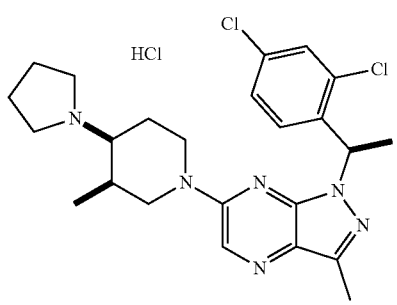

Step 1. 3,5-Dichloropyrazine-2-carboxamide

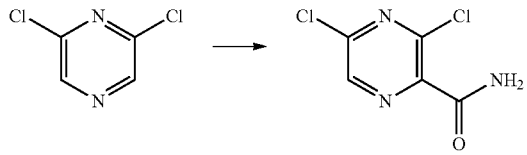 [SMILES: Clc1cncc(Cl)n1 ; NC(=O)c1ncc(Cl)nc1Cl]

2,6-Dichloropyrazine (55 g, 0.37 mol) and formamide (300 mL) were combined and heated to 90° C. Sodium persulfate (86.7 g, 0.36 mol) was added to the mixture at 90° C. in Ig portions at 20-30 seconds intervals. An exotherm was observed and the color of the mixture turned from yellow to dark red/brown. The mixture was stirred at 90° C. for 2 h and then cooled to room temperature. The mixture was diluted with water (500 mL) and filtered. The filtrate layers were separated. The aqueous layer was extracted with IPA:chloroform (1:3, 3×750 mL). The combined organic layers were dried over sodium sulfate and concentrated under vacuum to afford a viscous oil. The oil was purified by silica gel chromatography (0 to 100% ethyl acetate in hexanes) to provide the title product as a colorless solid (25 g, 36% yield). $^1$H NMR (400 MHz, DMSO-d6) δ ppm 8.87 (s, 1H), 8.18 (br. s., 1H), 8.01 (br. s., 1H).

Step 2. 3,5-Dichloropyrazine-2-carbonitrile

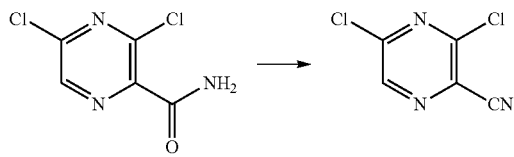 [SMILES: NC(=O)c1ncc(Cl)nc1Cl ; N#Cc1ncc(Cl)nc1Cl]

To a solution of 3,5-dichloropyrazine-2-carboxamide (Example 12, Step 2, 52 g, 0.27 mol) in acetonitrile (1 L) was added POCl$_3$ (146 g, 89 mL, 0.95 mol) at room temperature. The mixture was heated to 90-100° C. for 4 h. The mixture was cooled to room temperature and poured slowly into vigorously stirring solution of saturated aq. sodium bicarbonate. Evolution of gas was observed. The mixture was extracted with ethyl acetate (3×). The combined organic layers were dried over sodium sulfate then concentrated under reduced pressure to give a residue. The residue was purified by silica gel chromatography (0-30% ethyl acetate in hexanes) to give the title compound as a pale yellow solid. $^1$H NMR (400 MHz, CDCl$_3$) δ ppm 8.64 (s, 1H); $^{13}$C NMR (101 MHz, CDCl$_3$) δ ppm 150.8, 150.43, 143.24, 128.06, 113.06.

Step 3. 1-(3,5-Dichloropyrazin-2-yl)ethan-1-one

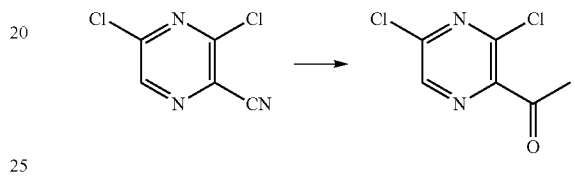

3,5-Dichloropyrazine-2-carbonitrile (Example 12, Step 2, 31.0 g, 178.18 mmol) was dissolved in anhydrous diethyl ether (890 mL, 0.2M) and cooled to −78° C. Then MeMgBr in diethyl ether (3.0 M, 65.33 mL, 190.0 mmol) was added slowly to maintain low temperature. After the addition was complete, the mixture was slowly warmed room temperature and stirred 1 h. The mixture was poured into a beaker containing a mixture of HCl in water (1.0 M, 1 L) and ice (1 kg). The mixture was stirred vigorously for 10 min. The mixture was extracted with diethyl ether (3×1 L), the combined organic layers were dried over sodium sulfate and concentrated under reduced pressure to afford the title compound as an orange oil (34 g, 99% yield). The mixture was used for the next reaction without further purification.

Step 4. (R,Z)-3,5-Dichloro-2-(1-(2-(1-(2,4-dichlorophenyl)ethyl)hydrazono)ethyl)pyrazine and (R,E)-3,5-dichloro-2-(1-(2-(1-(2,4-dichlorophenyl)ethyl)hydrazono)ethyl)pyrazine (9:1)

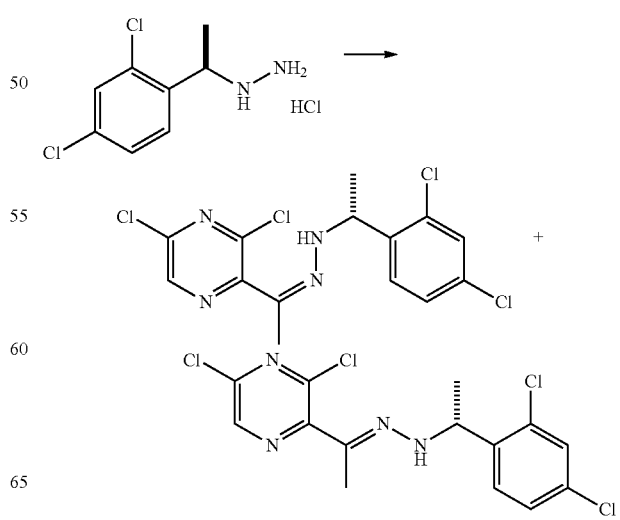

(R)-(1-(2,4-dichlorophenyl)ethyl)hydrazine hydrochloride (Example 5, Step 2, 47.29 g, 195.8 mmol) was dissolved in ethanol (356 mL, 0.5M) at room temperature, and then 1-(3,5-dichloropyrazin-2-yl)ethan-1-one (Example 12, Step 3, 34.0 g, 178.0 mmol) was added. The mixture was stirred at room temperature for 8 h. The mixture was concentrated under reduced pressure to give a residue. The residue was suspended in 20% ethyl acetate in hexanes (200 mL) and then filtered through a silica gel plug and eluted using a 20% ethyl acetate in hexanes. The filtrate was concentrated under reduced pressure to give the title products as a viscous orange oil.

Step 5. (R)-6-Chloro-1-(1-(2,4-dichlorophenyl)ethyl)-3-methyl-1H-pyrazolo[3,4-b]pyrazine

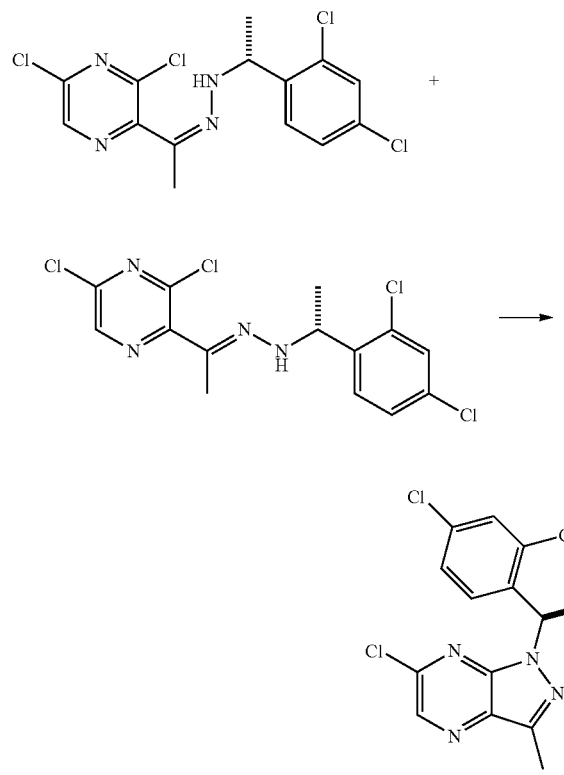

A mixture of (R,Z)-3,5-dichloro-2-(1-(2-(1-(2,4-dichlorophenyl)ethyl)hydrazono)ethyl)pyrazine and (R,E)-3,5-dichloro-2-(1-(2-(1-(2,4-dichlorophenyl)ethyl)hydrazono)ethyl)pyrazine (9:1) (Example 12, Step 5, 33 g, 87.28 mmol) was dissolved in N-methyl-2-pyrrolidone (218 mL) at room temperature then 2,6-lutidine (30.3 mL, 261.85 mmol) was added. The mixture was degassed with nitrogen and then heated to 100° C. under nitrogen for 8 h. The reaction mixture was cooled to room temperature and then poured into a separatory funnel containing 500 mL of 1M HCl in water and 500 mL of ethyl acetate. The layers were separated and the organic layer was washed with 500 mL of 1M HCl in water, dried over MgSO₄, and concentrated under reduced pressure. The residue was purified by silica gel chromatography (0 to 20% (1:1 MTBE:dichloromethane) in hexanes) to provide the title compounds as off-white solid (67% yield).

Step 6. tert-Butyl 3-methyl-4-(pyrrolidin-1-yl)piperidine-1-carboxylate


To a solution of 1-tert-butoxycarbonyl-3-methyl-4-piperidone (213 mg, 1.0 mmol) in 1,2 dichloroethane (2.5 mL) was added pyrrolidine (0.123 mL, 1.5 mmol) and sodium triacetoxyborohydride (316 mg, 1.5 mmol). The mixture was stirred at room temperature for 16 h.

Then 1 M sodium carbonate was added and the mixture was extracted with ethyl acetate (3×25 mL). The combined organic layers were dried over sodium sulfate and concentrated under reduced pressure to give the title compound which was used without further purification.

Step 7. 3-Methyl-4-(pyrrolidin-1-yl)piperidine hydrochloride

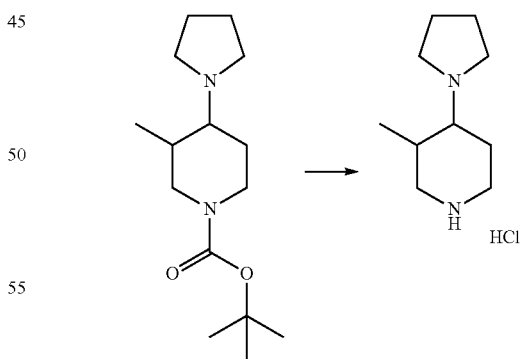

tert-butyl 3-methyl-4-(pyrrolidin-1-yl)piperidine-1-carboxylate (Example 12, Step 6, 268 mg, 1 mmol) was dissolved in HCl in 1,4-dioxane (4 M, 2 mL, 8 mmol) and methanol (0.5 mL). The mixture was stirred at room temperature for 1 h and then concentrated under reduced pressure to give the title compound which was used without further purification.

Step 8. 1-((R)-1-(2,4-Dichlorophenyl)ethyl)-3-methyl-6-((3R,4S)-3-methyl-4-(pyrrolidin-1-yl)piperidin-1-yl)-1H-pyrazolo[3,4-b]pyrazine hydrochloride

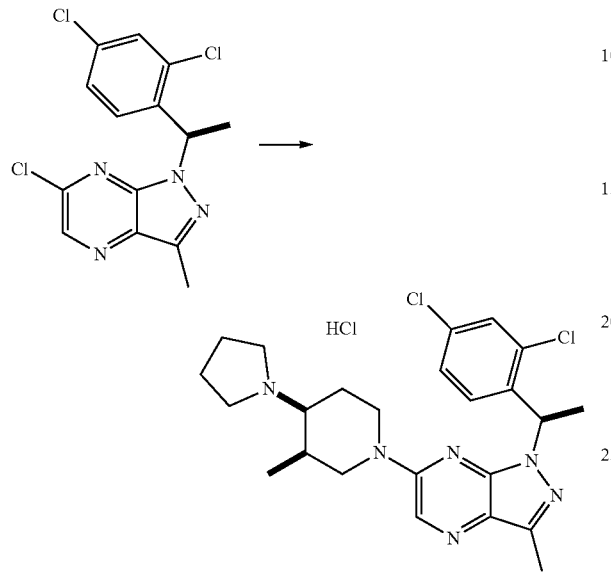

The product of Example 12, Step 7, 3-methyl-4-(pyrrolidin-1-yl)piperidine hydrochloride (41 mg, 0.2 mmol) was dissolved in DMF (0.5 mL). Then, (R)-6-Chloro-1-(1-(2,4-dichlorophenyl)ethyl)-3-methyl-1H-pyrazolo[3,4-b]pyrazine (Example 12, Step 5, 75 mg, 0.22 mmol) and N,N-diisopropylethylamine (0.150 mL, 0.861 mmol) were added. The mixture was heated to 80° C. for 1 h. A mixture of 10% ethyl acetate in hexanes (1.0 mL), water (1.5 mL), and trifluoroacetic acid (0.5 mL) were added. The aqueous layer was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give a mixture of stereoisomers. The mixture of stereoisomers was basified using Amberlyst and the filtrate was concentrated under reduced pressure. The residue was azeotroped with ethanol. The residue was further purified using chiral HPLC (OZ-H (Chiracel Daicel, Corporation, West Chester, Pa.), eluent: 20% ethanol in heptanes, with heptanes containing 0.1% diethylamine, 30 min) to give the free base of the title compound as the first eluting isomer. The free base was dissolved in ethanol, treated with 2M HCl in Et$_2$O (0.2 mL), and concentrated under reduced pressure to afford the title compound. $^1$H NMR (400 MHz, CD$_3$OD; HCl salt) δ 8.31 (s, 1H), 7.46 (d, J=2.1 Hz, 1H), 7.43 (d, J=8.5 Hz, 1H), 7.28 (dd, J=8.5, 2.1 Hz, 1H), 6.32 (q, J=6.9 Hz, 1H), 4.75 (dm, J=14.1 Hz, 1H), 4.60 (dm, J=13.8 Hz, 1H), 3.76-3.67 (m, 2H), 3.52-3.45 (m, 1H), 3.26-3.11 (m, 3H), 3.01 (td, J=13.6, 3.0 Hz, 1H), 2.57-2.50 (m, 1H), 2.52 (s, 3H), 2.24-2.16 (m, 2H), 2.14-1.98 (m, 3H), 1.96-1.83 (m, 1H), 1.89 (d, J=7.1 Hz, 3H), 1.05 (d, J=6.9 Hz, 3H); m/z 473.0 (M+H$^+$).

Example 13

6-((3R,4S)-4-(Azetidin-1-yl)-3-methylpiperidin-1-yl)-1-((R)-1-(2,4-dichlorophenyl)ethyl)-3-methyl-1H-pyrazolo[3,4-b]pyrazine hydrochloride

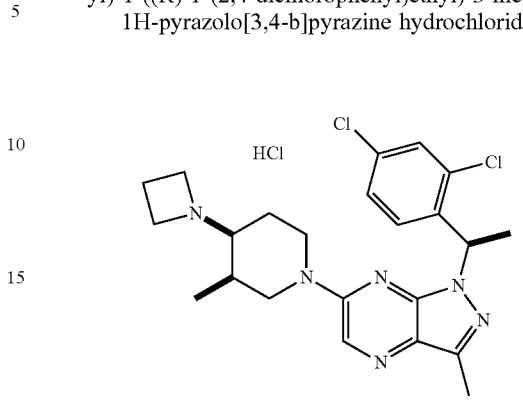

The title compound was prepared from (R)-6-Chloro-1-(1-(2,4-dichlorophenyl)ethyl)-3-methyl-1H-pyrazolo[3,4-b]pyrazine (Example 12, Step 5) by procedures similar to those described in Example 12, Steps 6-8, replacing pyrrolidine in Step 6 with azetidine hydrochloride. $^1$H NMR (400 MHz, CD$_3$OD; HCl salt) δ 8.32 (s, 1H), 7.46 (s, J=2.1 Hz, 1H), 7.44 (d, J=8.5 Hz, 1H), 7.29 (dd, J=8.5, 2.1 Hz, 1H), 6.31 (q, J=7.1 Hz, 1H), 4.70 (dm, J=13.5 Hz, 1H), 4.57 (dt, J=13.8, 2.4 Hz, 1H), 4.37-4.09 (m, 4H), 3.64 (dt, J=12.2, 4.3 Hz, 1H), 3.18 (dd, J=14.0, 2.6 Hz, 1H), 3.06-2.97 (m, 1H), 2.74-2.58 (m, 1H), 2.52 (s, 3H), 2.47-2.32 (m, 2H), 1.96-1.88 (m, 1H), 1.89 (d, J=7.1 Hz, 3H), 1.71-1.56 (m, 1H), 0.92 (d, J=7.0 Hz, 3H); m/z 459.1 (M+H$^+$).

Example 14

6-((3R,4S)-4-(Azepan-1-yl)-3-methylpiperidin-1-yl)-1-((R)-1-(2,4-dichlorophenyl)ethyl)-3-methyl-1H-pyrazolo[3,4-b]pyrazine hydrochloride

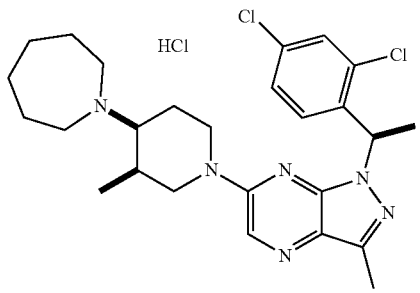 [SMILES: Cc1nn([C@H](C)c2ccc(Cl)cc2Cl)c2nc(N3CC[C@H](N4CCCCCC4)[C@H](C)C3)cnc12 ; Cl]

The title compound was prepared from (R)-6-Chloro-1-(1-(2,4-dichlorophenyl)ethyl)-3-methyl-1H-pyrazolo[3,4-b]pyrazine (Example 12, Step 5) by procedures similar to those described in Example 12, Steps 6-8, replacing pyrrolidine in Step 6 with azepane hydrochloride. $^1$H NMR (400 MHz, CD$_3$OD; HCl salt) δ 8.34 (s, 1H), 7.46 (d, J=2.1 Hz, 1H), 7.43 (d, J=8.5 Hz, 1H), 7.29 (dd, J=8.5, 2.2 Hz, 1H), 6.32 (q, J=7.1 Hz, 1H), 4.76 (dm, J=13.6 Hz, 1H), 4.61 (dt, J=13.8, 2.5 Hz, 1H), 3.66 (dt, J=12.3, 3.8 Hz, 1H), 3.58-3.32 (m, 3H), 3.20 (dd, J=13.8, 2.4 Hz, 1H), 3.09-3.00 (m, 2H), 2.65-2.60 (m, 1H), 2.53 (s, J=3.7 Hz, 3H), 2.19 (dm, J=11.9

Hz, 1H), 2.00-1.87 (m, 4H), 1.89 (d, J=7.1 Hz, 3H), 1.85-1.66 (m, 5H), 1.05 (d, J=6.9 Hz, 3H); m/z 501.1 (M+H$^+$).

Example 15

6-((3S,4R)-4-(Azepan-1-yl)-3-methylpiperidin-1-yl)-1-((R)-1-(2,4-dichlorophenyl)ethyl)-3-methyl-1H-pyrazolo[3,4-b]pyrazine hydrochloride

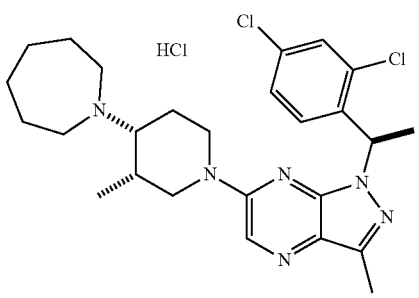 [SMILES: Cc1nn([C@H](C)c2ccc(Cl)cc2Cl)c2nc(N3CC[C@@H](N4CCCCCC4)[C@@H](C)C3)cnc12 ; Cl]

Further elution of the chiral column described in Example 14 provided the free base of title compound as the second (slower) eluting isomer. The free base was dissolved in ethanol, treated with 2M HCl in diethyl ether (0.2 mL), and concentrated under reduced pressure to afford the title compound. $^1$H NMR (400 MHz, CD$_3$OD; HCl salt) δ 8.11 (s, 1H), 7.21 (d, J=2.1 Hz, 1H), 7.14 (d, J=8.5 Hz, 1H), 7.04 (dd, J=8.5, 2.2 Hz, 1H), 6.09 (q, J=7.2 Hz, 1H), 4.56-4.38 (m, 2H), 3.42 (dt, J=7.0, 3.7 Hz, 1H), 3.35-3.07 (m, 4H), 2.95 (dd, J=14.0, 2.2 Hz, 1H), 2.87-2.78 (m, 1H), 2.37 (s, 1H), 2.33-2.27 (m, 1H), 2.29 (s, 3H), 1.94 (br d, J=11.0 Hz, 1H), 1.74 (d, J=25.2 Hz, 4H), 1.65 (d, J=7.1 Hz, 3H), 1.61-1.45 (m, 4H), 0.73 (d, J=6.9 Hz, 3H); m/z 501.1 (M+H$^+$).

Example 16

6-((3R,4S)-4-(Azocan-1-yl)-3-methylpiperidin-1-yl)-1-((R)-1-(2,4-dichlorophenyl)ethyl)-3-methyl-1H-pyrazolo[3,4-b]pyrazine hydrochloride

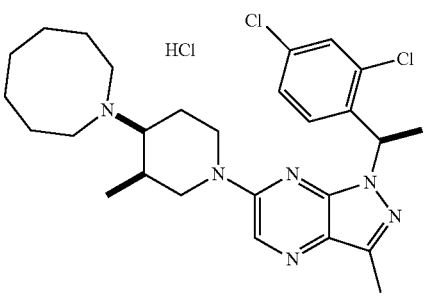 [SMILES: Cc1nn([C@H](C)c2ccc(Cl)cc2Cl)c2nc(N3CC[C@H](N4CCCCCCC4)[C@H](C)C3)cnc12 ; Cl]

The title compound was prepared from (R)-6-Chloro-1-(1-(2,4-dichlorophenyl)ethyl)-3-methyl-1H-pyrazolo[3,4-b]pyrazine (Example 12, Step 5) by procedures similar to those described in Example 12, Steps 6-8, replacing pyrrolidine in Step 6 with 1-azacyclooctane. $^1$H NMR (400 MHz, CD$_3$OD; HCl salt) δ 8.37 (s, 1H), 7.49-7.41 (m, 2H), 7.29 (d, J=7.6 Hz, 1H), 6.32 (q, J=6.2 Hz, 1H), 4.75 (br d, J=9.1 Hz, 1H), 4.62 (br d, J=10.9 Hz, 1H), 3.78-3.67 (m, 1H), 3.66-3.51 (m, 2H), 3.32-3.18 (m, 3H), 3.11-3.01 (m, 1H), 2.65-2.57 (m, 1H), 2.53 (s, 3H), 2.14 (d, J=31.5 Hz, 3H), 1.90 (d, J=6.8 Hz, 5H), 1.99-1.78 (m, 5H), 1.74-1.44 (m, 2H), 1.06 (br s, 3H); m/z 515.1 (M+H$^+$).

Example 17

1-((R)-1-(2,4-Dichlorophenyl)ethyl)-6-((3R,4S)-4-(2,5-dihydro-1H-pyrrol-1-yl)-3-methylpiperidin-1-yl)-3-methyl-1H-pyrazolo[3,4-b]pyrazine hydrochloride

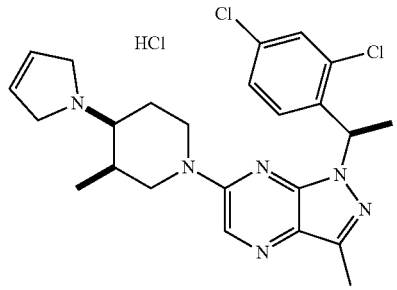 [SMILES: Cc1nn([C@H](C)c2ccc(Cl)cc2Cl)c2nc(N3CC[C@H](N4CC=CC4)[C@H](C)C3)cnc12 ; Cl]

The title compound was prepared from (R)-6-Chloro-1-(1-(2,4-dichlorophenyl)ethyl)-3-methyl-1H-pyrazolo[3,4-b]pyrazine (Example 12, Step 5) by procedures similar to those described in Example 12, Steps 6-8, replacing pyrrolidine in Step 6 with 2,5-dihydropyrrole. $^1$H NMR (400 MHz, CD$_3$OD; HCl salt) δ 8.34 (s, 1H), 7.46 (d, J=2.0 Hz, 1H), 7.44 (d, J=8.5 Hz, 1H), 7.29 (dd, J=8.4, 1.9 Hz, 1H), 6.32 (q, J=6.8 Hz, 1H), 6.04 (br s, 2H), 4.80-4.73 (m, J=11.6 Hz, 1H), 4.66-4.59 (m, J=13.0 Hz, 1H), 4.39-4.26 (m, 2H), 4.25-4.10 (m, 2H), 3.80-3.69 (m, 1H), 3.19 (br d, J=13.3 Hz, 1H), 3.10-2.97 (m, 1H), 2.61-2.53 (m, 1H), 2.52 (s, J=12.5 Hz, 3H), 2.14-2.06 (m, 1H), 1.98-1.91 (m, 1H), 1.89 (d, J=7.1 Hz, 3H), 1.06 (d, J=6.2 Hz, 3H); m/z 471.1 (M+H$^+$).

Example 18

1-((R)-1-(2,4-Dichlorophenyl)ethyl)-6-((2S)-2,5-dimethyl-4-(pyrrolidin-1-yl)piperidin-1-yl)-3-methyl-1H-pyrazolo[3,4-b]pyrazine hydrochloride

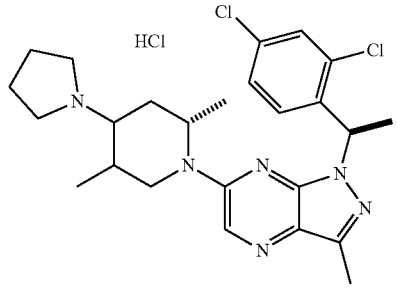 [SMILES: Cc1nn([C@H](C)c2ccc(Cl)cc2Cl)c2nc(N3CC(C)C(N4CCCC4)C[C@@H]3C)cnc12 ; Cl]

Step 1. tert-butyl (2S)-2,5-Dimethyl-4-oxopiperidine-1-carboxylate

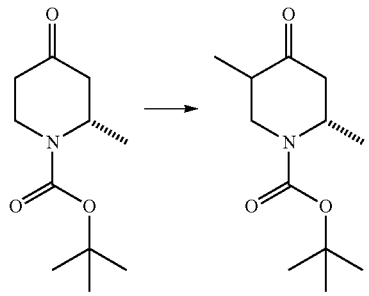

To (S)-2-methyl-4-piperidone (2.5 g, 11.7 mmol) in THF (59 mL) at −78° C. was added lithium diisopropylamide (12.9 mmol, 2.0 M in THF). The mixture was stirred at −78° C. for 2 h before the addition of methyl iodide (940 μL, 15.2 mmol, 1.3 eq). The mixture was allowed to warm gradually to room temperature overnight (16 h). The mixture was then quenched with saturated aqueous ammonium chloride and extracted with ethyl acetate (250 mL). The organic layer was dried over sodium sulfate and concentrated under reduced pressure. The residue was purified by silica gel chromatography (5 to 30% ethyl acetate in hexanes). The residue was further purified by silica gel chromatography (20 to 30% ethyl acetate in hexanes) to afford the title compound as a 1:1 mixture of isomers.

Step 2. 1-((R)-1-(2,4-dichlorophenyl)ethyl)-6-((2S,5R)-2,5-dimethyl-4-(pyrrolidin-1-yl)piperidin-1-yl)-3-methyl-1H-pyrazolo[3,4-b]pyrazine hydrochloride and 1-((R)-1-(2,4-dichlorophenyl)ethyl)-6-((2S,5S)-2,5-dimethyl-4-(pyrrolidin-1-yl)piperidin-1-yl)-3-methyl-1H-pyrazolo[3,4-b]pyrazine hydrochloride

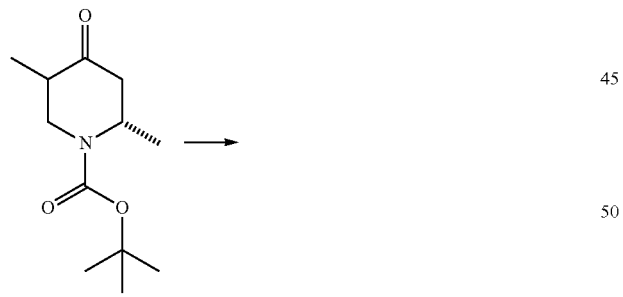

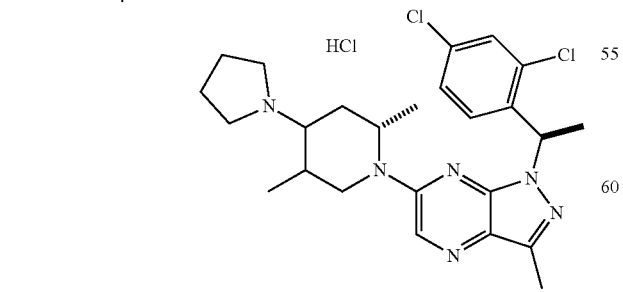

The title compound was prepared from (R)-6-chloro-1-(1-(2,4-dichlorophenyl)ethyl)-3-methyl-1H-pyrazolo[3,4-b]pyrazine (Example 12, Step 5) by procedures similar to those described in Example 12, Steps 6-8, replacing 1-tert-butoxycarbonyl-3-methyl-4-piperidone in Step 6 with tert-butyl (2S)-2,5-dimethyl-4-oxopiperidine-1-carboxylate (Example 18, Step 1) to give the product as a 2.8:1 mixture of diastereomers around the piperidine. $^1$H NMR (400 MHz, CD$_3$OD; HCl salt) δ 8.14 (s, 0.74H), 8.11 (s, 0.26H), 7.49-7.43 (m, 1H), 7.42-7.33 (m, 1H), 7.26 (dd, J=8.5, 2.1 Hz, 1H), 6.33-6.23 (m, 1H), 4.36-4.03 (m, 2H), 3.77-3.52 (m, 3H), 3.25-2.98 (m, 3H), 2.51 (s, 3H), 2.41-1.93 (m, 7H), 1.92-1.85 (m, 3H), 1.41 (d, J=6.7 Hz, 0.78H), 1.36 (d, J=6.0 Hz, 2.22H), 1.19 (d, J=6.8 Hz, 0.78H), 1.13 (d, J=6.9 Hz, 2.22H); m/z 487.1 (M+H$^+$).

Example 19

1-((R)-1-(2,4-Dichlorophenyl)ethyl)-6-((2S,4S,5R)-2,5-dimethyl-4-(pyrrolidin-1-yl)piperidin-1-yl)-3-methyl-1H-pyrazolo[3,4-b]pyrazine hydrochloride

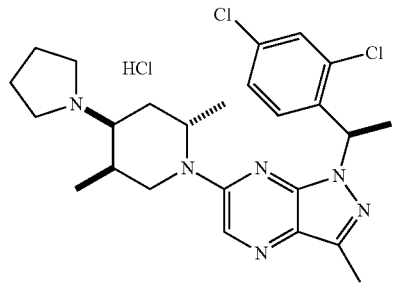 [SMILES: Cc1nn([C@H](C)c2ccc(Cl)cc2Cl)c2nc(N3C[C@@H](C)[C@@H](N4CCCC4)C[C@@H]3C)cnc12 ; Cl]

Further elution of the chiral column described in Example 18, Step 2 provided the free base of title compound as the second eluting isomer. The free base was dissolved in ethanol, treated with 2M HCl in Et$_2$O (0.2 mL), and concentrated under reduced pressure to afford the title compound. $^1$H NMR (400 MHz, CD$_3$OD; HCl salt) δ 8.28 (s, 1H), 7.46 (d, J=2.1 Hz, 1H), 7.44 (d, J=8.4 Hz, 1H), 7.29 (dd, J=8.5, 2.1 Hz, 1H), 6.30 (q, J=7.1 Hz, 1H), 5.07-4.97 (m, 1H), 4.44 (br d, J=13.9 Hz, 1H), 3.78-3.67 (m, 3H), 3.36 (dd, J=14.4, 2.2 Hz, 1H), 3.28-3.11 (m, 2H), 2.52 (s, 3H), 2.29-1.95 (m, 7H), 1.90 (d, J=7.1 Hz, 3H), 1.31 (d, J=7.0 Hz, 3H), 1.10 (d, J=6.9 Hz, 3H); m/z 487.1 (M+H$^+$).

Example 20

1-((R)-1-(2,4-Dichlorophenyl)ethyl)-3-methyl-6-((3R,4S)-3-methyl-4-((R)-2-methylpyrrolidin-1-yl)piperidin-1-yl)-1H-pyrazolo[3,4-b]pyrazine hydrochloride

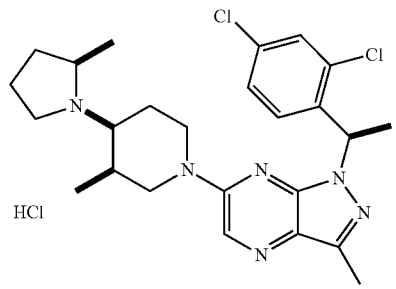 [SMILES: Cc1nn([C@H](C)c2ccc(Cl)cc2Cl)c2nc(N3CC[C@H](N4CCC[C@H]4C)[C@H](C)C3)cnc12 ; Cl]

The title compound was prepared from (R)-6-Chloro-1-(1-(2,4-dichlorophenyl)ethyl)-3-methyl-1H-pyrazolo[3,4-b]pyrazine (Example 12, Step 5) by procedures similar to those described in Example 12, Steps 6-8, replacing pyrrolidine in Step 6 with (R)-2-methylpyrrolidine (500 mg, 4.1 mmol). The mixture of isomers was purified via HPLC using a Chiralpak® ID column (Daicel, Corporation, West Chester, Pa.) and eluting with 15% IPA in heptanes to give the free base of the title compound as the first eluting isomer. The residue was dissolved in 1 mL of dichloromethane and 1M HCl in diethyl ether was added at room temperature. The mixture was then concentrated under reduced pressure to give the title as the HCl salt. $^1$H NMR (400 MHz, CDCl$_3$; HCl salt): δ 8.09 (s, 1H), 7.40 (d, J=8.5 Hz, 1H), 7.35 (d, J=2.1 Hz, 1H), 7.14 (dd, J=8.5, 2.2 Hz, 1H), 6.31 (q, J=7.1 Hz, 1H), 4.55-4.47 (m, 1H), 4.37-4.31 (m, 1H), 3.15-3.07 (m, 1H), 3.05-2.98 (m, 1H), 2.86 (td, J=12.8, 3.6 Hz, 1H), 2.79-2.72 (m, 1H), 2.68-2.60 (m, 1H), 2.58-2.53 (m, 4H), 2.18-2.11 (m, 1H), 1.90 (d, J=7.1 Hz, 3H), 1.83-1.63 (m, 5H), 1.50-1.42 (m, 1H), 0.99-0.93 (m, 6H); m/z 487.2 (M+H$^+$).

Example 21

1-((R)-1-(2,4-Dichlorophenyl)ethyl)-3-methyl-6-(3-methyl-4-((S)-2-methylpyrrolidin-1-yl)piperidin-1-yl)-1H-pyrazolo[3,4-b]pyrazine hydrochloride

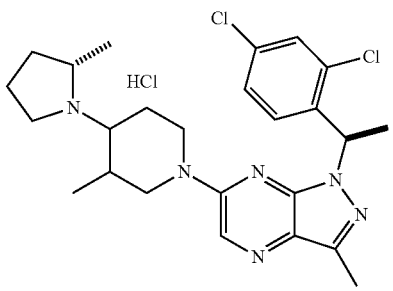 [SMILES: Cc1nn([C@H](C)c2ccc(Cl)cc2Cl)c2nc(N3CCC(N4CCC[C@@H]4C)C(C)C3)cnc12 ; Cl]

The title compound was prepared analogously to Example 20, replacing (R)-2-methylpyrrolidine with (S)-2-methylpyrrolidine (500 mg, 4.1 mmol). The mixture of isomers was purified via HPLC using a Chiralpak® ID column (Daicel, Corporation, West Chester, Pa.) and eluting with 5% IPA in heptanes to give the free base of the title compound as the first eluting isomer. The residue was dissolved in 1 mL of dichloromethane and 1M HCl in diethyl ether was added at room temperature. The mixture was then concentrated under reduced pressure to give the title compound as the HCl salt of one of the trans diastereomers about the piperdine. $^1$H NMR (400 MHz, CDCl$_3$; HCl-salt): δ 8.09 (s, 1H), 7.37 (d, J=8.5 Hz, 1H), 7.34 (d, J=2.0 Hz, 1H), 7.14-7.11 (m, 1H), 6.33 (q, J=7.2 Hz, 1H), 4.38-4.31 (m, 1H), 4.30-4.24 (m, 1H), 3.11-3.02 (m, 1H), 3.02-2.93 (m, 1H), 2.89-2.83 (m, 1H), 2.76-2.65 (m, 2H), 2.57 (s, 3H), 2.51-2.44 (m, 1H), 1.90 (d, J=7.1 Hz, 3H), 1.86-1.59 (m, 3H), 1.40-1.24 (m, 4H), 1.03 (d, J=6.6 Hz, 3H), 0.98 (d, J=6.1 Hz, 3H); m/z 487.1 (M+H$^+$).

Example 22

1-((R)-1-(2,4-Dichlorophenyl)ethyl)-3-methyl-6-((3R,4S)-3-methyl-4-((S)-2-methylpyrrolidin-1-yl)piperidin-1-yl)-1H-pyrazolo[3,4-b]pyrazine hydrochloride

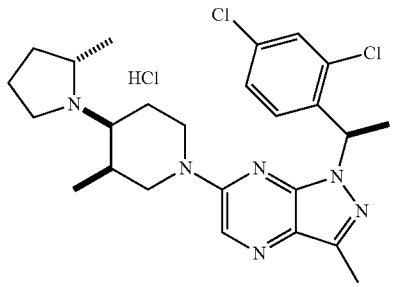 [SMILES: Cc1nn([C@H](C)c2ccc(Cl)cc2Cl)c2nc(N3CC[C@H](N4CCC[C@@H]4C)[C@H](C)C3)cnc12 ; Cl]

The title compound was prepared from Example 21, Step 1 and was obtained as the second eluting isomer from the chiral HPLC separation which was converted to the HCl salt as in Example 21, Step 1. $^1$H NMR (400 MHz, CDCl$_3$; HCl-salt): δ 8.08 (s, 1H), 7.37 (d, J=8.5 Hz, 1H), 7.34 (d, J=2.1 Hz, 1H), 7.15-7.11 (m, 1H), 6.35-6.29 (m, 1H), 4.58-4.51 (m, 1H), 4.38-4.33 (m, 1H), 3.18-2.98 (m, 2H), 2.92-2.61 (m, 3H), 2.56 (s, 3H), 2.19-2.10 (m, 1H), 1.90 (d, J=7.1 Hz, 4H), 1.83-1.60 (m, 2H), 1.49-1.42 (m, 1H), 1.32-1.23 (m, 3H), 0.95 (d, J=6.3 Hz, 3H), 0.87 (d, J=6.7 Hz, 3H); m/z 487.1 (M+H$^+$).

Example 23

1-((R)-1-(2,4-Dichlorophenyl)ethyl)-6-((3'R,4'S)-3'-methyl-[1,4'-bipiperidin]-1'-yl)-1H-pyrazolo[3,4-b]pyrazine-3-carbonitrile hydrochloride

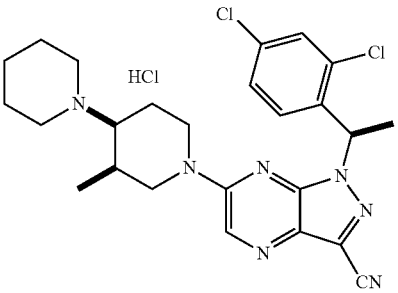 [SMILES: C[C@@H]1CN(c2cnc3c(C#N)nn([C@H](C)c4ccc(Cl)cc4Cl)c3n2)CC[C@@H]1N1CCCCC1 ; Cl]

Step 1. (R)-6-Chloro-1-(1-(2,4-dichlorophenyl)ethyl)-1H-pyrazolo[3,4-b]pyrazine-3-carboxamide

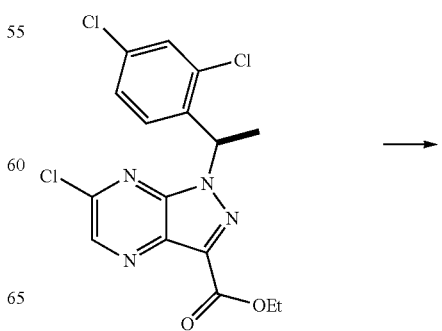

335
-continued

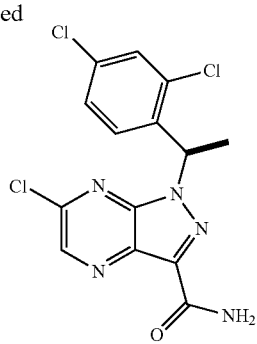

To a solution of ethyl (R)-6-chloro-1-(1-(2,4-dichlorophenyl)ethyl)-1H-pyrazolo[3,4-b]pyrazine-3-carboxylate (Example 5, Step 4, 4 g, 10 mmol) in 1,4-dioxane (40 mL) at room temperature was added ammonium hydroxide (29% in water, 40 mL). The mixture was stirred in a sealed tube at room temperature for 3 d. The mixture was diluted with saturated aqueous sodium bicarbonate. The mixture was extracted with ethyl acetate (2×). The combined organic layers were dried over MgSO$_4$ and concentrated under reduced pressure to give the title compound (3.4 g, 92% yield) as a light yellow solid.

Step 2. (R)-6-Chloro-1-(1-(2,4-dichlorophenyl)ethyl)-1H-pyrazolo[3,4-b]pyrazine-3-carbonitrile

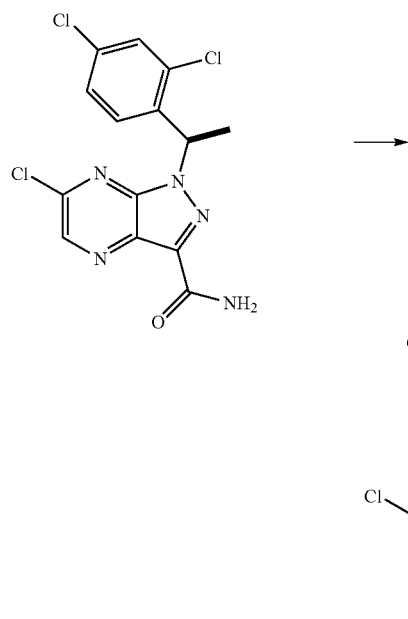

To a solution of (R)-6-chloro-1-(1-(2,4-dichlorophenyl)ethyl)-1H-pyrazolo[3,4-b]pyrazine-3-carboxamide (Example 23, step 1, 4.5 g, 12.2 mmol) in dichloromethane (30 mL) at room temperature under argon was added methyl N-(triethylammoniumsulfonyl)carbamate (Burgess reagent, 4.3 g, 18.1 mmol). The mixture was stirred at room temperature for 2 d. The mixture was absorbed onto silica gel and purified by column chromatography (5% to 20% ethyl acetate in hexanes) to give the title compound (3.68 g, 88% yield) as a sticky colorless solid.

336

Step 3. 1-((R)-1-(2,4-Dichlorophenyl)ethyl)-6-((3'R,4'S)-3'-methyl-[1,4'-bipiperidin]-1'-yl)-1H-pyrazolo[3,4-b]pyrazine-3-carbonitrile hydrochloride

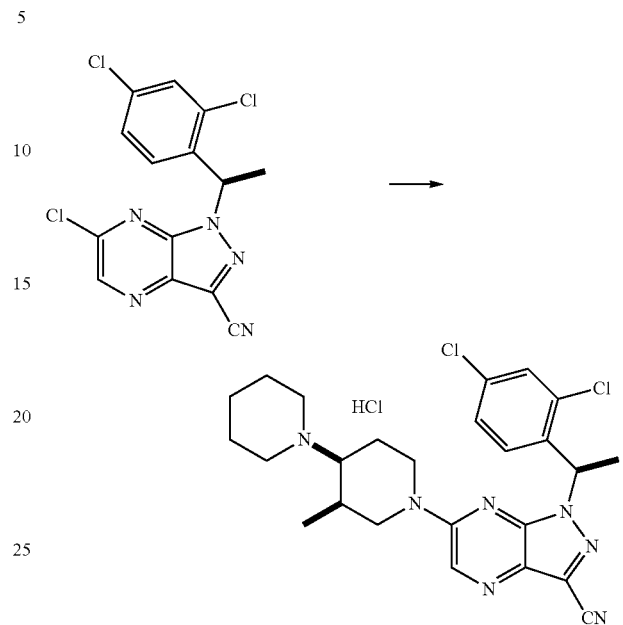

The title compound was prepared from (R)-6-chloro-1-(1-(2,4-dichlorophenyl)ethyl)-1H-pyrazolo[3,4-b]pyrazine-3-carbonitrile (Example 23, Step 2) and 3'-methyl-1,4'-bipiperidine 2,2,2-trifluoroacetate (Example 2, Step 2) by procedures similar to those described in Example 2, Step 3. The mixture of isomers was purified via HPLC using a Chiralpak® ID column (Daicel, Corporation, West Chester, Pa.) and eluting with 5% IPA in heptanes to give the free base of the title compound as the first eluting isomer. The residue was dissolved in 1 mL of dichloromethane and 1M HCl in diethyl ether was added at room temperature. The mixture was then concentrated under reduced pressure to give the title compound as the HCl salt. $^1$H NMR (400 MHz, CDCl$_3$; HCl salt): δ 8.28 (s, 1H), 7.41-7.36 (m, 2H), 7.20 (dd, J=8.5, 2.1 Hz, 1H), 6.45 (q, J=7.2 Hz, 1H), 4.61-4.54 (m, 1H), 4.43-4.35 (m, 1H), 3.10-3.04 (m, 1H), 2.93-2.85 (m, 1H), 2.49-2.18 (m, 6H), 1.91 (d, J=7.1 Hz, 3H), 1.64-1.40 (m, 8H), 0.90 (d, J=6.9 Hz, 3H); m/z 498.2 (M+H$^+$).

Example 24

1-((R)-1-(2,4-Dichlorophenyl)ethyl)-6-((3'S,4'R)-3'-methyl-[1,4'-bipiperidin]-1'-yl)-1H-pyrazolo[3,4-b]pyrazine-3-carbonitrile hydrochloride

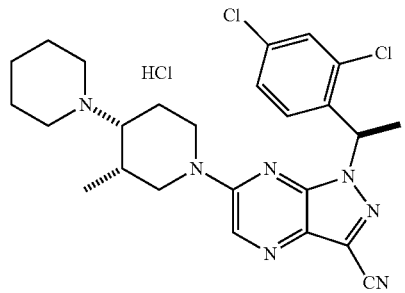

Further elution of chiral preparative HPLC conditions from Example 23, Step 3 gave the title product as the second eluting isomer. The residue was dissolved in 1 mL of dichloromethane and 1M HCl in diethyl ether was added at room temperature. The mixture was then concentrated under reduced pressure to give the title compound 1-((R)-1-(2,4-dichlorophenyl)ethyl)-6-((3'S,4'R)-3'-methyl-[1,4'-bipiperidin]-1'-yl)-1H-pyrazolo[3,4-b]pyrazine-3-carbonitrile hydrochloride as the HCl salt. ¹H-NMR (400 MHz, CDCl₃; HCl salt): δ 8.28 (s, 1H), 7.38-7.34 (m, 2H), 7.19 (dd, J=8.5, 2.1 Hz, 1H), 6.46 (q, J=7.2 Hz, 1H), 4.63-4.55 (m, 1H), 4.46-4.38 (m, 1H), 3.12-3.04 (m, 1H), 2.93-2.84 (m, 1H), 2.50-2.18 (m, 6H), 1.91 (d, J=7.1 Hz, 3H), 1.64-1.40 (m, 8H), 0.83 (d, J=7.0 Hz, 3H); m/z 498.2 (M+H⁺).

Example 25

1-(1-(2,4-Dichlorophenyl)ethyl)-6-(3'-fluoro-[1,4'-bipiperidin]-1'-yl)-1H-pyrazolo[3,4-b]pyrazine-3-carboxamide hydrochloride

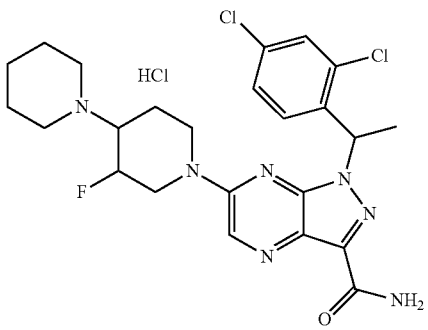 [SMILES: CC(c1ccc(Cl)cc1Cl)n1nc(C(N)=O)c2ncc(N3CCC(N4CCCCC4)C(F)C3)nc21 ; Cl]

The title compounds were prepared from ethyl 6-chloro-1-(1-(2,4-dichlorophenyl)ethyl)-1H-pyrazolo[3,4-b]pyrazine-3-carboxylate (Example 1, Step 3) by procedures similar to those described in Example 1, Step 4, replacing DMSO with DMF, and 1-(4-piperidyl)piperidine with 3'-fluoro-1,4'-bipiperidine 2,2,2-trifluoroacetate which was synthesized analogously to Example 2, Steps 2-3 substituting tert-butyl 3-fluoro-4-oxopiperidine-1-carboxylate for tert-butyl-3-methyl-4-oxopiperidine-1-carboxylate. The synthesis was finished analogously to Example 3, Step 3. The residue was purified using silica chromatography (2 to 6% methanol in dicholoromethane) to give the product as a mixture of diastereomers. ¹H-NMR (400 MHz, CDCl₃; HCl salt): δ 8.28 (s, 0.6H), 8.27 (s, 0.4H), 7.69 (brs, 1H), 7.47-7.32 (m, 2H), 7.14 (dd, J=8.5, 2.1 Hz, 1H), 6.47 (q, J=7.1 Hz, 1H), 6.10 (brs, 1H), 5.15 (d, J=48.8 Hz, 1H), 4.86-4.57 (m, 2H), 3.21-2.89 (m, 2H), 2.70-2.46 (m, 5H), 2.19-1.76 (m, 5H), 1.70-1.52 (m, 4H), 1.51-1.39 (m, 2H); m/z 520.2 (M+H⁺).

Example 26

1-(1-(2,4-Dichlorophenyl)ethyl)-6-(3'-fluoro-[1,4'-bipiperidin]-1'-yl)-1H-pyrazolo[3,4-b]pyrazine-3-carbonitrile 2,2,2-trifluoroacetate

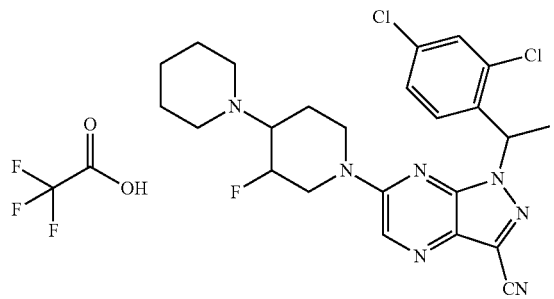 [SMILES: O=C(O)C(F)(F)F ; CC(c1ccc(Cl)cc1Cl)n1nc(C#N)c2ncc(N3CCC(N4CCCCC4)C(F)C3)nc21]

The title compound was synthesized as a mixture of diastereomers analogously to the procedure outlined in Example 7, substituting the compound generated in Example 25 for Example 6, Step 6. The residue was purified using silica chromatography (2 to 10% MeOH in dicholoromethane). The residue was further purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the product as a mixture of diastereomers. ¹H-NMR (400 MHz, CD₃OD; trifluoroacetic acid Salt): δ 8.56 (s, 0.6H), 8.55 (s, 0.4H), 7.49 (dd, J=11.1, 2.0 Hz, 1H), 7.41 (dd, J=11.0, 8.6 Hz, 1H), 7.32 (dd, J=8.5, 1.9 Hz, 1H), 6.55-6.43 (m, 1H), 5.46 (d, J=48.8 Hz, 1H), 5.14-5.01 (m, 1H), 4.91-4.79 (m, 1H), 3.84-3.58 (m, 3H), 3.45 (d, J=15.6 Hz, 0.6H), 3.39-3.29 (m, 1.4H), 3.20-3.00 (m, 3H), 2.27 (t, J=11.1 Hz, 1H), 2.13-1.89 (m, 6H), 1.89-1.70 (m, 3H).

Example 27

1-(1-(2,4-Dichlorophenyl)ethyl)-6-(3'-(hydroxymethyl)-[1,4'-bipiperidin]-1'-yl)-1H-pyrazolo[3,4-b]pyrazine-3-carboxamide hydrochloride

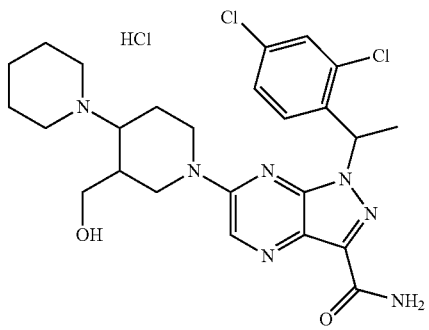 [SMILES: CC(c1ccc(Cl)cc1Cl)n1nc(C(N)=O)c2ncc(N3CCC(N4CCCCC4)C(CO)C3)nc21 ; Cl]

339

Step 1. 1'-(tert-butyl) 3'-Ethyl [1,4'-bipiperidine]-1', 3'-dicarboxylate

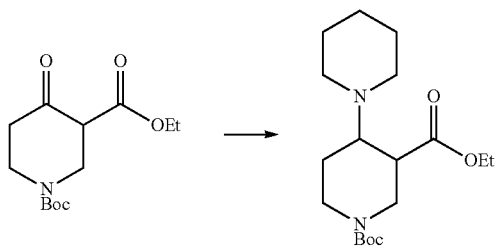 [SMILES: CCOC(=O)C1CN(C(=O)OC(C)(C)C)CCC1=O ; CCOC(=O)C1CN(C(=O)OC(C)(C)C)CCC1N1CCCCC1]

To a stirred solution of 1-(tert-butyl) 3-ethyl 4-oxopiperidine-1,3-dicarboxylate (1.0 g, 3.69 mmol) was added acetic acid (0.31 mL, 5.4 mmol), and piperidine (0.44 mL, 4.43 mmol) in 1,2-dichloroethane (7.5 mL). To the solution was added sodium triacetoxyborohydride (1.17 g, 5.54 mmol) and the mixture was stirred overnight at room temperature. The reaction was quenched by the addition of aqueous sodium bicarbonate, followed by extraction with dichloromethane (3×) and the combined organic layers were dried over sodium sulfate and concentrated to give the crude compound which was used without purification.

Step 2. [1,4'-Bipiperidin]-3'-ylmethanol

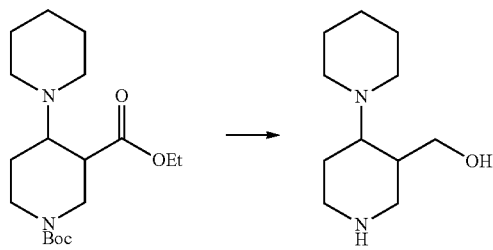 [SMILES: CCOC(=O)C1CN(C(=O)OC(C)(C)C)CCC1N1CCCCC1 ; OCC1CNCCC1N1CCCCC1]

The product from Example 27, Step 1 (380 mg, 1.05 mmol) was dissolved in a 4:1 mixture of THF to methanol (5 mL) and cooled to 0° C. before the addition of lithium borohydride (46 mg, 2.1 mmol). The reaction was slowly warmed to room temperature. After stirring for 12 h. additional lithium borohydride was added in 20 mg batches until consumption of starting material was observed. The reaction was quenched by the addition of aqueous sodium bicarbonate, followed by extraction with dichloromethane (3×) and the combined organic layers were dried over sodium sulfate and concentrated to give the crude compound which was used without purification.

The crude material was then dissolved in methanol (4 mL) and to it was added 4N HCl in 1,4-dioxane (1 mL) and the reaction was stirred for 16 h. After this time, the reaction was concentrated to give the HCl salt of the title compound.

Step 3. 1-(1-(2,4-Dichlorophenyl)ethyl)-6-(3'-(hydroxymethyl)-[1,4'-bipiperidin]-1'-yl)-1H-pyrazolo[3,4-b]pyrazine-3-carboxamide hydrochloride

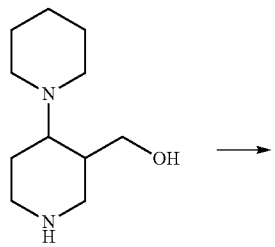

340

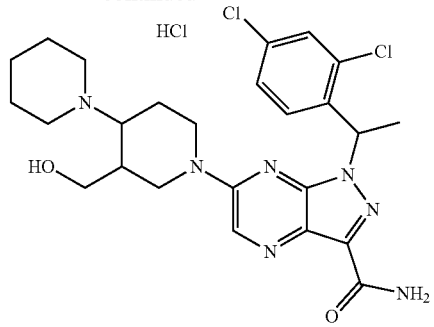

The title compound mixture was prepared from ethyl 6-chloro-1-(1-(2,4-dichlorophenyl)ethyl)-1H-pyrazolo[3,4-b]pyrazine-3-carboxylate (Example 1, Step 3) by procedures similar to those described in Example 1, Step 4, substituting 1-(4-piperidyl)piperidine with [1,4'-bipiperidin]-3'-ylmethanol hydrochloride (Example 27, Step 2). This intermediate was purified by silica chromatography (2 to 10% methanol in dichloromethane) and the HCl salt was not formed. The synthesis was finished analogously to Example 3, Step 3. The residue was purified using silica chromatography (2 to 10% methanol in dicholoromethane) and the fractions containing the product were collected and concentrated. The product was then dissolved in dichloromethane and made acidic (pH ~2) with 2M HCl in diethyl ether and volatiles removed under reduced pressure to give the product as a mixture of diastereomers. $^{1}$H-NMR (400 MHz, CD$_{3}$OD; HCl salt): δ 8.42 (s, 0.6H), 8.41 (s, 0.4H), 7.49-7.43 (m, 2H), 7.28 (t, J=2.2 Hz, 0.6H), 7.26 (t, J=2.2 Hz, 0.4H), 6.50-6.41 (m, 1H), 4.78-4.56 (m, 2H), 3.77 (ddd, J=10.6, 7.1, 3.3 Hz, 1H), 3.45 (dd, J=10.9, 8.1 Hz, 1H), 3.02 (dd, J=13.8, 2.6 Hz, 1H), 2.96-2.84 (m, 1H), 2.67-2.38 (m, 6H), 2.03-1.89 (m, 4H), 1.67-1.45 (m, 7H); m/z 532.2 (M+H$^{+}$).

Example 28

1-((R)-1-(2,4-Dichlorophenyl)ethyl)-6-((3'S,4'R)-3'-(hydroxymethyl)-[1,4'-bipiperidin]-1'-yl)-1H-pyrazolo[3,4-b]pyrazine-3-carbonitrile hydrochloride

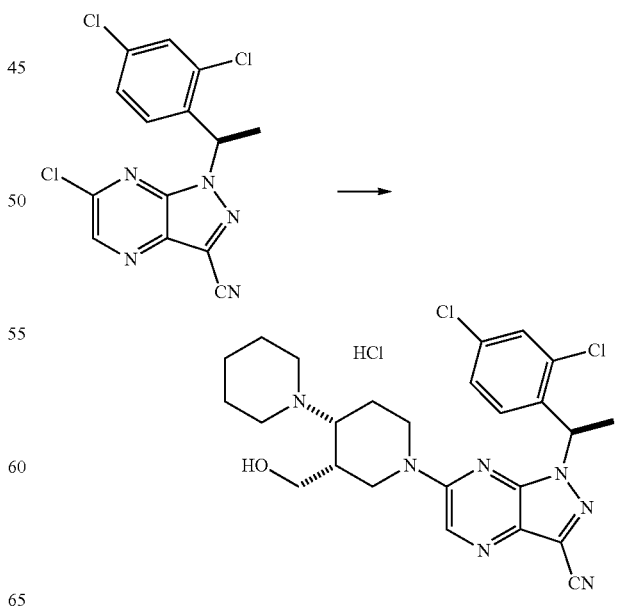

The title compound was synthesized analogously to the procedure outlined in Example 23, Step 3 substituting compounds generated in Example 27, Step 2 for 3'-methyl-1,4'-bipiperidine 2,2,2-trifluoroacetate. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the product as a mixture of diastereomers. These cis diastereomers were further separated using the Chiralpak® ID-3 column, (Daicel, Corporation, West Chester, Pa.) and eluting with 80% heptane, 20% ethanol at 20 mL/min. The title compound eluted as the first isomer (13.2 min) and was converted into the HCl salt using 2N HCl in diethyl ether. $^1$H NMR (400 MHz, CDCl$_3$; HCl salt): δ 8.26 (s, 1H), 7.39-7.34 (m, 2H), 7.20 (dd, J=8.5, 2.1 Hz, 1H), 6.45 (q, J=7.0 Hz, 1H), 4.60 (d, J=13.6 Hz, 1H), 4.46 (d, J=13.9 Hz, 1H), 3.87 (t, J=10.8 Hz, 1H), 3.53 (dd, J=10.9, 5.0 Hz, 1H), 3.02 (dd, J=13.9, 2.8 Hz, 1H), 2.93 (td, J=13.3, 3.1 Hz, 1H), 2.75-2.58 (m, 4H), 2.49 (br s, 2H), 2.05-1.96 (m, 1H), 1.95-1.82 (m, 4H), 1.59 (d, J=5.1 Hz, 4H), 1.47 (d, J=5.1 Hz, 2H); m/z 514.2 (M+H$^+$).

Example 29

1-((R)-1-(2,4-Dichlorophenyl)ethyl)-6-((3'R,4'S)-3'-(hydroxymethyl)-[1,4'-bipiperidin]-1'-yl)-1H-pyrazolo[3,4-b]pyrazine-3-carbonitrile hydrochloride

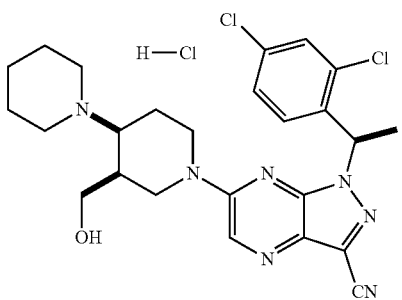

Further elution of the chiral preparative HPLC from Example 28 gave the title compound as the second eluting isomer (17.1 min) which was converted into the HCl salt using 2N HCl in diethyl ether. $^1$H NMR (400 MHz, CDCl$_3$; HCl salt): δ 8.27 (s, 1H), 7.37 (d, J=2.3 Hz, 1H), 7.34 (d, J=8.5 Hz, 1H), 7.20 (dd, J=8.5, 2.1 Hz, 1H), 6.44 (q, J=7.1 Hz, 1H), 4.56 (d, J=13.6 Hz, 1H), 4.46 (d, J=14.0 Hz, 1H), 3.98-3.86 (m, 1H), 3.69-3.60 (m, 1H), 3.06-2.89 (m, 2H), 2.65 (d, J=9.5 Hz, 4H), 2.47 (br s, 2H), 2.01-1.96 (m, 1H), 1.91 (d, J=7.1 Hz, 3H), 1.90-1.76 (m, 1H), 1.64-1.55 (m, 4H), 1.51-1.43 (m, 2H); m/z 514.2 (M+H$^+$).

Example 30

(3R,4S)-1-(1-((R)-1-(2,4-Dichlorophenyl)ethyl)-3-methyl-1H-pyrazolo[3,4-b]pyrazin-6-yl)-4-((R)-2-methylpyrrolidin-1-yl)piperidine-3-carboxylic acid hydrochloride

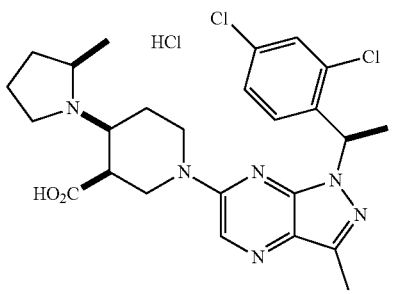 [SMILES: Cc1nn([C@H](C)c2ccc(Cl)cc2Cl)c2nc(N3CC[C@H](N4CCC[C@H]4C)[C@H](C(=O)O)C3)cnc12 ; Cl]

Step 1. Methyl 4-((R)-2-methylpyrrolidin-1-yl)piperidine-3-carboxylate

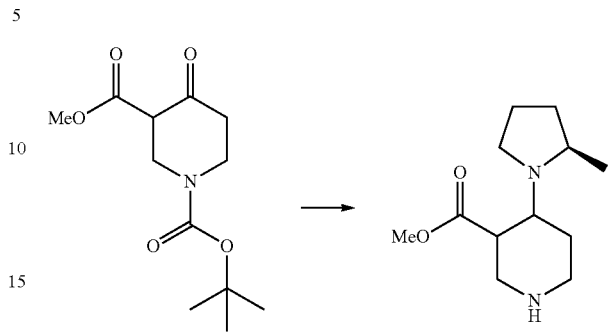

The title compound was synthesized analogously to Example 2, Step 1, substituting (R)-2-methylpyrrolidine hydrochloride for piperidine and heating the reaction to 70° C., then cooled to r.t. To the product of this reaction was added 4N HCl in 1,4-dioxane (10 mL) and this mixture was stirred for 16 h. at room temperature before removal of solvent under reduced pressure to give the hydrochloride salt of the title compound as a mixture of diastereomers.

Step 2. (3R,4S)-1-(1-((R)-1-(2,4-Dichlorophenyl)ethyl)-3-methyl-1H-pyrazolo[3,4-b]pyrazin-6-yl)-4-((R)-2-methylpyrrolidin-1-yl)piperidine-3-carboxylic acid hydrochloride

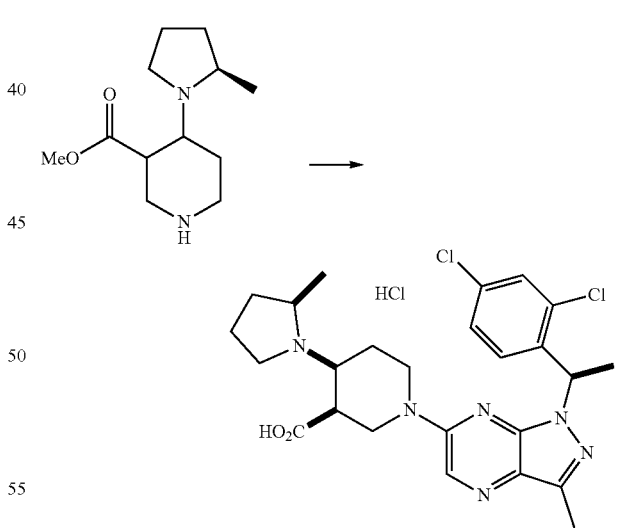

The title compound was synthesized according to the procedures outlined in Example 12, Step 8 substituting methyl 4-((R)-2-methylpyrrolidin-1-yl)piperidine-3-carboxylate for 3-methyl-4-(pyrrolidin-1-yl)piperidine hydrochloride and DMSO for DMF. The product of this reaction was then hydrolyzed according to the procedure outlined in Example 6, Step 5. The compound was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the product as the first eluting isomer. ¹H NMR (400 MHz, CD₃OD; HCl Salt): δ 8.32 (s, 1H), 7.44 (d, J=2.1 Hz, 1H), 7.41 (d, J=8.5 Hz, 1H), 7.27 (dd, J=8.5, 2.1 Hz, 1H), 6.36 (q, J=7.2 Hz, 1H), 5.07-4.99 (m, 1H), 4.86-4.74 (m, 1H), 4.66-4.57 (m, 1H), 4.12 (td, J=13.0, 3.8 Hz, 1H), 3.84-3.73 (m, 1H), 3.29-3.26 (m, 2H), 3.24 (d, J=2.1 Hz, 1H), 3.22-3.19 (m, 1H), 3.18-3.10 (m, 1H), 2.90 (td, J=10.8, 4.7 Hz, 1H), 2.66 (s, 1H), 2.27 (ddd, J=12.5, 6.1, 3.3 Hz, 1H), 2.21-2.12 (m, 1H), 2.09-1.92 (m, 3H), 1.90 (d, J=7.1 Hz, 3H), 1.84-1.73 (m, 2H), 1.54 (d, J=6.4 Hz, 3H); m/z 517.2 (M+H⁺).

Example 31

((S)-1-((3R,4S)-1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)methanol hydrochloride Step 1. ((2S)-1-(3-Methylpiperidin-4-yl)pyrrolidin-2-yl)methanol

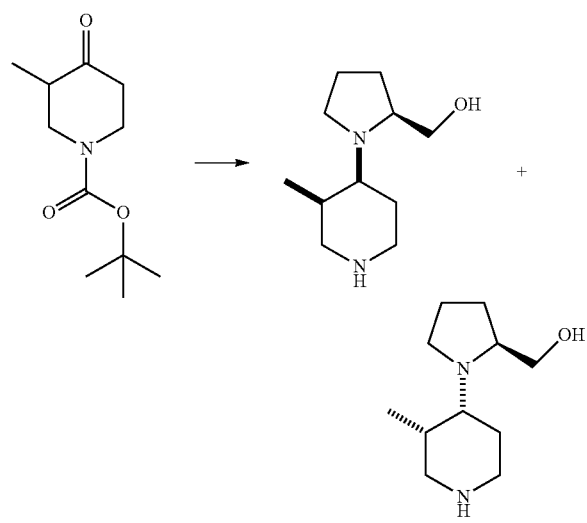

The title compound was synthesized analogously to the procedures outlined in Example 2, Step 1, substituting (S)-pyrrolidin-2-ylmethanol for piperidine. The product of this reaction was separated into its two cis-diastereomers via column chromatography (0 to 20% methanol in dichloromethane) before deprotection of the amines using the procedure from Example 2, Step 2 to yield the title compound as the 2,2,2-trifluoroacetate salts.

Step 2. ((S)-1-((3R,4S)-1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)methanol hydrochloride

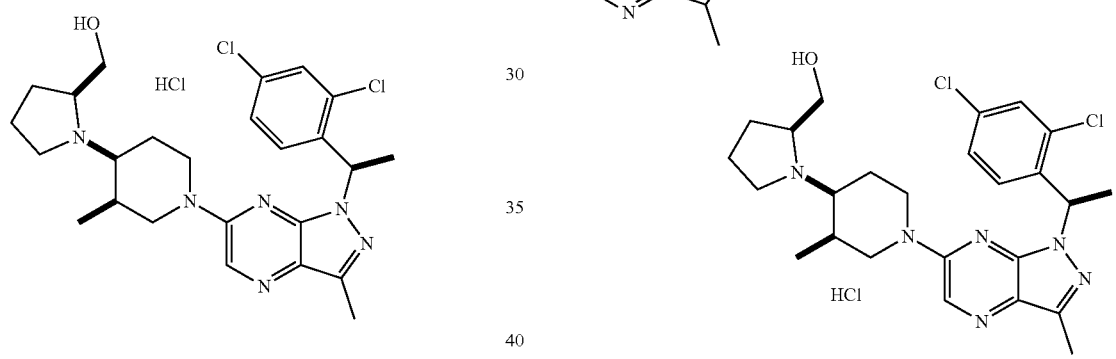

The title compound was synthesized according to the procedures in Example 12, Step 8, substituting the first eluting amine diastereomer from Example 31, Step 1 for 3-methyl-4-(pyrrolidin-1-yl)piperidine hydrochloride and DMSO for DMF. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the trifluoroacetate product. This material was then dissolved in dichloromethane and washed with saturated aqueous sodium bicarbonate. The organic layers were then made acidic (pH ~2) with 2N HCl in diethyl ether and the volatiles were removed to give the title compound. ¹H NMR (400 MHz, CD₃CN; HCl salt): δ 8.20 (s, 1H), 7.47-7.42 (m, 2H), 7.26 (dd, J=8.5, 2.2 Hz, 1H), 6.27 (q, J=7.1 Hz, 1H), 4.66-4.57 (m, 1H), 4.52 (dt, J=13.8, 2.5, 1H), 4.02-3.92 (m, 1H), 3.71 (dd, J=12.3, 4.2 Hz, 1H), 3.66-3.52 (m, 2H), 3.46-3.35 (m, 1H), 3.34-3.22 (m, 1H), 3.04 (dd, J=13.7, 2.4 Hz, 1H), 2.53-2.46 (m, 1H), 2.44 (s, 3H), 2.19-2.08 (m, 2H), 2.06-1.85 (m, 4H), 1.84 (d, J=7.1 Hz, 3H), 1.85-1.77 (m, 1H), 1.01 (d, J=6.9 Hz, 3H); m/z 503.2 (M+H⁺).

Example 32

((S)-1-((3S,4R)-1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)methanol hydrochloride

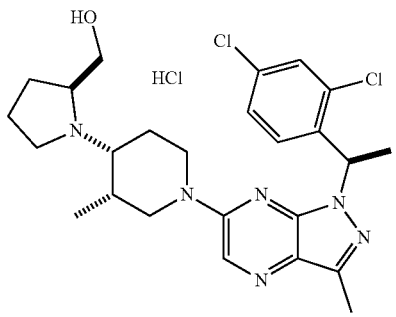 [SMILES: Cc1nn([C@H](C)c2ccc(Cl)cc2Cl)c2nc(N3CC[C@@H](N4CCC[C@H]4CO)[C@@H](C)C3)cnc12 ; Cl]

The title compound was synthesized according to the procedures in Example 12, Step 8, substituting the second eluting amine diastereomer from Example 31, Step 1 for 3-methyl-4-(pyrrolidin-1-yl)piperidine hydrochloride and DMSO for DMF. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the trifluoroacetate product. This material was then dissolved in dichloromethane and washed with aqueous sodium bicarbonate. The organic layers were then made acidic with 2N HCl in diethyl ether and the volatiles were removed to give the title compound. $^1$H NMR (400 MHz, CD$_3$CN; HCl salt): δ 8.22 (s, 1H), 7.48 (d, J=2.2 Hz, 1H), 7.43 (d, J=8.5 Hz, 1H), 7.28 (dd, J=8.5, 2.2 Hz, 1H), 6.30 (q, J=7.1 Hz, 1H), 4.70-4.53 (m, 1H), 3.97-3.88 (m, 1H), 3.86-3.77 (m, 1H), 3.75-3.67 (m, 1H), 3.62-3.48 (m, 2H), 3.37-3.24 (m, 1H), 3.10 (dt, J=13.8, 2.2 Hz, 1H), 3.02-2.90 (m, 1H), 2.60-2.51 (m, 1H), 2.48 (s, 3H), 2.25-2.12 (m, 2H), 2.10-1.94 (m, 4H), 1.93-1.85 (m, 1H), 1.87 (d, J=7.1 Hz, 3H), 0.99 (d, J=6.8 Hz, 3H); m/z 503.2 (M+H$^+$).

Example 33

1-((R)-1-(2,4-Dichlorophenyl)ethyl)-6-((3R,4S)-4-((S)-2-(hydroxymethyl)pyrrolidin-1-yl)-3-methylpiperidin-1-yl)-1H-pyrazolo[3,4-b]pyrazine-3-carbonitrile hydrochloride

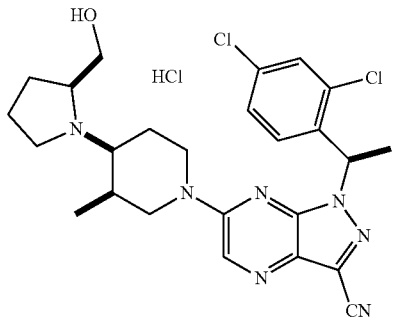 [SMILES: C[C@@H]1CN(c2cnc3c(C#N)nn([C@H](C)c4ccc(Cl)cc4Cl)c3n2)CC[C@@H]1N1CCC[C@H]1CO ; Cl]

The title compound was synthesized according to the procedures in Example 23, Step 3, substituting the first eluting amine diastereomer from Example 31, Step 1 for 3'-methyl-1,4'-bipiperidine 2,2,2-trifluoroacetate and DMSO for DMF. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the product as the trifluoroacetate salt. This material was then dissolved in dichloromethane and washed with aqueous sodium bicarbonate. The organic layers were then made acidic with 2N HCl in diethyl ether and the volatiles were removed to give the title compound. $^1$H NMR (400 MHz, CD$_3$CN; HCl salt): δ 8.43 (s, 1H), 7.52 (d, J=2.2 Hz, 1H), 7.46 (d, J=8.5 Hz, 1H), 7.33 (dd, J=8.5, 2.2 Hz, 1H), 6.45 (q, J=7.0 Hz, 1H), 4.72-4.54 (m, 2H), 4.02-3.90 (m, 1H), 3.74-3.68 (m, 2H), 3.65-3.55 (m, 1H), 3.46-3.36 (m, 1H), 3.35-3.25 (m, 1H), 3.09 (dd, J=13.7, 1.9 Hz, 1H), 2.99 (dt, J=13.4, 3.0 Hz, 1H), 2.59-2.50 (m, 1H), 2.28-2.20 (m, 1H), 2.19-1.93 (m, 4H), 1.91 (d, J=7.1 Hz, 3H), 1.88-1.78 (m, 1H), 1.06 (d, J=6.9 Hz, 3H); m/z 514.2 (M+H$^+$).

Example 34

((3R,4S)-1-(1-((R)-1-(2,4-Dichlorophenyl)ethyl)-3-methyl-1H-pyrazolo[3,4-b]pyrazin-6-yl)-3-methylpiperidin-4-yl)-L-proline 2,2,2-trifluoroacetate

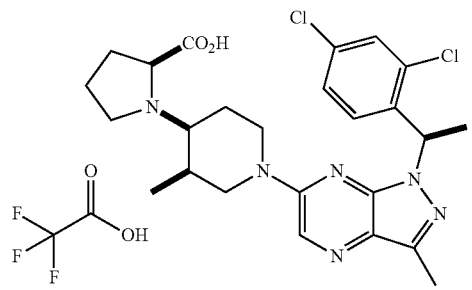

Step 1. (3-Methylpiperidin-4-yl)-L-proline

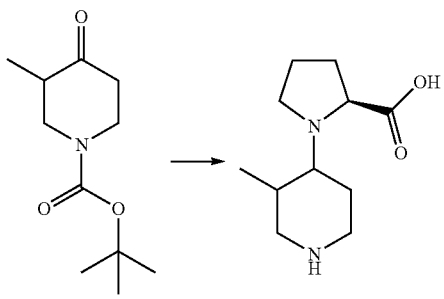

The title compound was synthesized analogously to the procedures outlined in Example 2, Step 1, substituting L-Proline tert-butyl ester for piperidine. The product of this reaction was separated away from the trans isomers into a mixture of the two cis-diastereomers via column chromatography (5 to 50% ethyl acetate in hexanes) before deprotection of the amine using the procedure from Example 2, Step 2 to yield the title compound as the 2,2,2-trifluoroacetate salt.

Step 2. ((3R,4S)-1-(1-((R)-1-(2,4-Dichlorophenyl)ethyl)-3-methyl-1H-pyrazolo[3,4-b]pyrazin-6-yl)-3-methylpiperidin-4-yl)-L-proline 2,2,2-trifluoroacetate

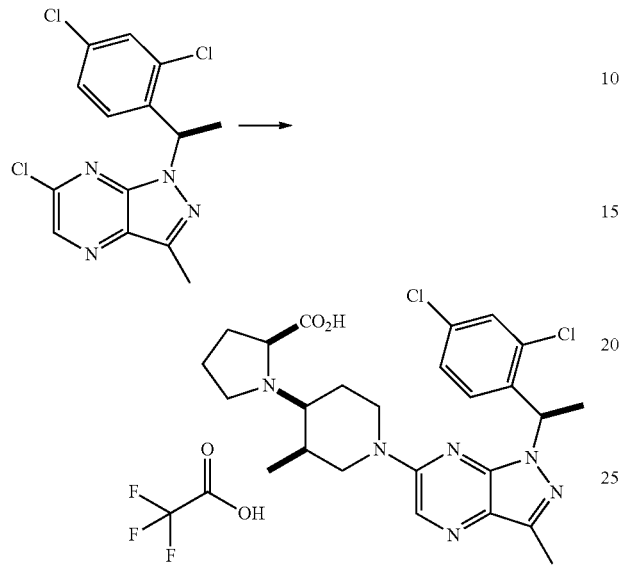

The title compound was synthesized according to the procedures in Example 12, Step 8, substituting (3-methylpiperidin-4-yl)-L-proline Example 34, Step 1 for 3-methyl-4-(pyrrolidin-1-yl)piperidine hydrochloride and DMSO for DMF. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the trifluoroacetate product as the second eluting isomer. $^1$H NMR (400 MHz, CD$_3$CN; trifluoroacetic acid salt): δ 8.20 (s, 1H), 7.48-7.43 (m, 2H), 7.27 (dd, J=8.5, 2.1 Hz, 1H), 6.29 (q, 1H), 4.66-4.51 (m, 2H), 4.47 (dd, J=10.2, 4.0 Hz, 1H), 3.90-3.80 (m, 1H), 3.63-3.50 (m, 1H), 3.32-3.17 (m, 1H), 3.07 (d, J=13.7 Hz, 1H), 2.97-2.85 (m, 1H), 2.56-2.46 (m, 2H), 2.46 (s, 3H), 2.35-2.24 (m, 1H), 2.20-2.09 (m, 1H), 2.06-1.95 (m, 1H), 1.93-1.87 (m, 2H), 1.85 (d, J=7.1 Hz, 3H), 1.09 (d, J=6.9 Hz, 3H); m/z 517.2 (M+H$^+$).

Example 35

((3R,4S)-1-(3-Cyano-1-((R)-1-(2,4-dichlorophenyl)ethyl)-1H-pyrazolo[3,4-b]pyrazin-6-yl)-3-methylpiperidin-4-yl)-L-proline 2,2,2-trifluoroacetate The title compound was synthesized according to the procedure in Example 23, Step 3, substituting (3-methylpiperidin-4-yl)-L-proline Example 34, Step 1 for 3'-methyl-1,4'-bipiperidine 2,2,2-trifluoroacetate and DMSO for DMF. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the product as the second eluting isomer. $^1$H-NMR (400 MHz, CD$_3$CN; trifluoroacetic acid salt): δ 8.38 (s, 1H), 7.47 (d, J=2.1 Hz, 1H), 7.43 (d, J=8.5 Hz, 1H), 7.28 (dd, J=8.4, 2.1 Hz, 1H), 6.41 (q, J=7.0 Hz, 1H), 4.59 (t, J=13.7 Hz, 2H), 4.45 (dd, J=10.2, 4.0, 1H), 3.89-3.77 (m, 1H), 3.63-3.50 (m, 1H), 3.30-3.16 (m, 1H), 3.09 (d, J=13.9 Hz, 1H), 3.01-2.90 (m, 1H), 2.57-2.37 (m, 2H), 2.33-2.22 (m, 1H), 2.18-2.06 (m, 1H), 2.04-1.92 (m, 1H), 1.90-1.80 (m, 2H), 1.86 (d, J=7.1 Hz, 3H), 1.06 (d, J=6.9 Hz, 3H); m/z 528.2 (M+H$^+$).

Example 36

2-((S)-1-((3R,4S)-1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)propan-2-ol hydrochloride

Step 1. tert-butyl 4-((S)-2-(Methoxycarbonyl)pyrrolidin-1-yl)-3-methylpiperidine-1-carboxylate The title compound was synthesized analogously to the procedures outlined in Example 2, Step 1, substituting L-Proline methyl ester for piperidine. The product of this reaction was purified via column chromatography (5 to 50% ethyl acetate in hexanes) to give the product as a mixture of diastereomers.

Step 2. 2-((2S)-1-(3-Methylpiperidin-4-yl)pyrrolidin-2-yl)propan-2-ol

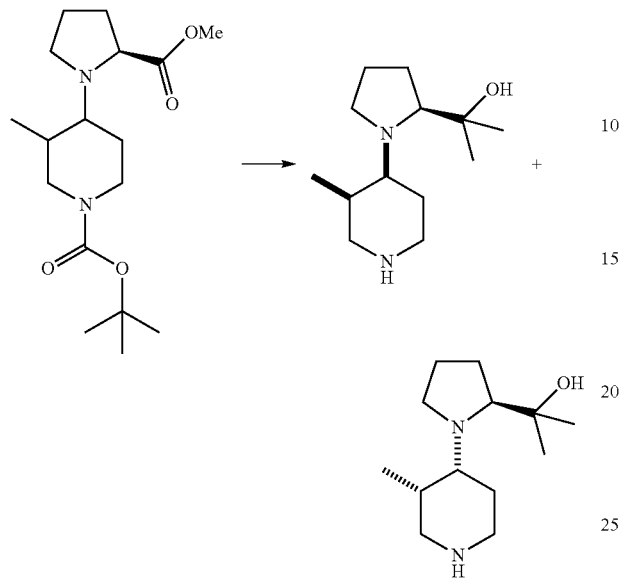

A solution of tert-butyl 4-((S)-2-(methoxycarbonyl)pyrrolidin-1-yl)-3-methylpiperidine-1-carboxylate (1.0 g, 3.06 mmol) in THF (15 mL) was cooled to 0° C. before the addition of methylmagnesium bromide (2.0M in diethyl ether, 6.12 mL, 12.25 mmol). The reaction was allowed to warm to room temperature for 30 min. before careful addition of aqueous sodium bicarbonate. The mixture was then extracted with ethyl acetate (3×) and the combined organic layers were dried over anhydrous sodium sulfate and concentrated. The crude residue was purified by silica chromatography (1 to 10% methanol in dichloromethane). The second eluting peak was a mixture of the two cis diastereomers. To this mixture was then added 4N HCl (5 mL) and stirred for 16 h. before removal of the solvent under reduced pressure to yield the title compounds as hydrochloride salts.

Step 3. 2-((S)-1-((3R,4S)-1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)propan-2-ol hydrochloride

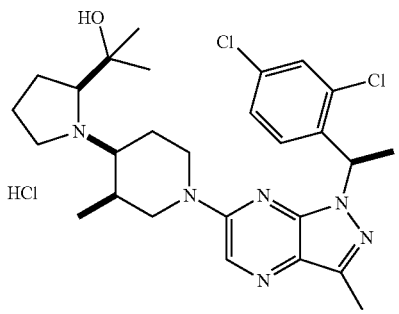 [SMILES: Cc1nn([C@H](C)c2ccc(Cl)cc2Cl)c2nc(N3CC[C@H](N4CCC[C@H]4C(C)(C)O)[C@H](C)C3)cnc12 ; Cl]

The title compound was synthesized according to the procedures in Example 12, Step 8, substituting 2-((2S)-1-(3-methylpiperidin-4-yl)pyrrolidin-2-yl)propan-2-ol hydrochloride (Example 36, Step 2) for 3-methyl-4-(pyrrolidin-1-yl)piperidine hydrochloride and DMSO for DMF. The reaction was quenched by the addition of water and subsequent extraction with dichloromethane (3×). The combined organics were dried over anhydrous sodium sulfate and concentrated. The residue was purified using silica chromatography (0 to 10% MeOH in dicholoromethane) to give the product as the first eluting isomer. $^1$H NMR (400 MHz, CDCl$_3$; HCl salt) δ 8.08 (s, 1H), 7.38 (d, J=8.5 Hz, 1H), 7.36 (d, J=2.1 Hz, 1H), 7.13 (dd, J=8.5, 2.2 Hz, 1H), 6.30 (q, J=7.1 Hz, 1H), 4.50 (d, J=13.5 Hz, 1H), 4.38 (d, J=13.2 Hz, 1H), 3.09-2.92 (m, 4H), 2.89-2.67 (m, 3H), 2.56 (s, 3H), 2.30-2.21 (m, 1H), 1.89 (d, J=7.1 Hz, 3H), 1.85-1.63 (m, 6H), 1.15 (s, 3H), 1.06 (s, 3H), 1.02 (d, J=6.9 Hz, 3H); m/z 531.2 (M+H$^+$).

Example 37

(2S,4R)-1-((3R,4S)-1-(1-((R)-1-(2,4-Dichlorophenyl)ethyl)-3-methyl-1H-pyrazolo[3,4-b]pyrazin-6-yl)-3-methylpiperidin-4-yl)-4-hydroxypyrrolidine-2-carboxylic acid 2,2,2-trifluoroacetate

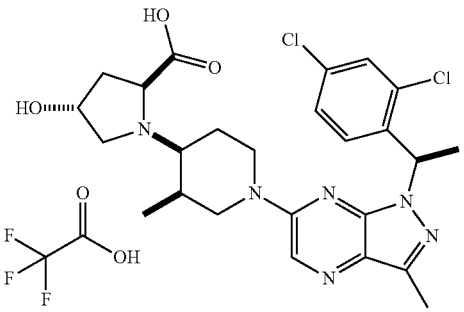

Step 1. tert-Butyl 4-((2S,4R)-4-hydroxy-2-(methoxycarbonyl)pyrrolidin-1-yl)-3-methylpiperidine-1-carboxylate

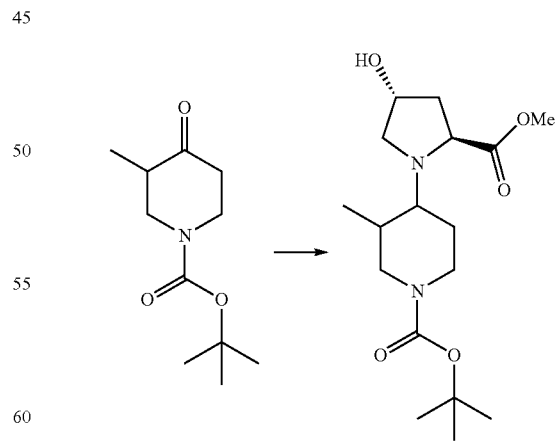

The title compound was synthesized analogously to the procedures outlined in Example 2, Step 1, substituting trans-4-Hydroxy-L-proline methyl ester hydrochloride for piperidine and the addition of N,N-diisopropylethylamine (0.3 equiv). The product of this reaction was purified via column chromatography (20 to 100% ethyl acetate in hexanes) to give the product as a mixture of diastereomers.

Step 2. (2S,4R)-4-Hydroxy-1-(3-methylpiperidin-4-yl)pyrrolidine-2-carboxylic acid hydrochloride

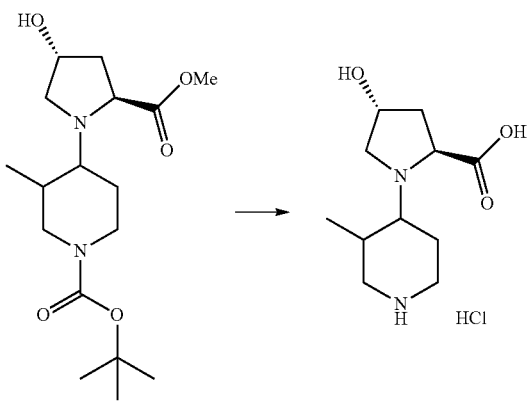 [SMILES: COC(=O)[C@@H]1C[C@@H](O)CN1C1CCN(C(=O)OC(C)(C)C)CC1C ; CC1CNCCC1N1C[C@H](O)C[C@H]1C(=O)O ; Cl]

A solution of tert-butyl 4-((2S,4R)-4-hydroxy-2-(methoxycarbonyl)pyrrolidin-1-yl)-3-methylpiperidine-1-carboxylate (870 mg, 2.54 mmol) from Example 37, Step 1 was dissolved in THF (17 mL) before the addition of lithium hydroxide (120 mg, 5.05 mmol, dissolved in 2.3 mL water). This reaction mixture was vigorously stirred at 50° C. for 16 h. before cooling to room temperature. After this time, 4N HCl in 1,4-dioxane (16 mL) was added and the reaction was stirred for an additional 12 h at room temperature before the removal of the solvent under reduced pressure to yield the HCl salt of the crude compound which was used without purification.

Step 3. (2S,4R)-1-((3R,4S)-1-(1-((R)-1-(2,4-Dichlorophenyl)ethyl)-3-methyl-1H-pyrazolo[3,4-b]pyrazin-6-yl)-3-methylpiperidin-4-yl)-4-hydroxypyrrolidine-2-carboxylic acid 2,2,2-trifluoroacetate

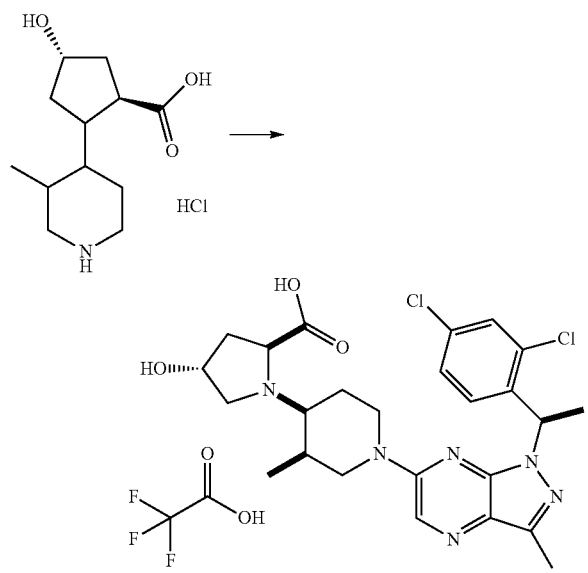

The title compound was synthesized according to the procedures in Example 12, Step 8, substituting (2S,4R)-4-hydroxy-1-(3-methylpiperidin-4-yl)pyrrolidine-2-carboxylic acid hydrochloride (Example 37, Step 2) for 3-methyl-4-(pyrrolidin-1-yl)piperidine hydrochloride and DMSO for DMF. The residue was purified by reverse phase preparative HPLC (Gemini-NX, 10 µm, 250×30 mm, C18 column (Phenomenex, Torrance, Calif.), eluent: 0 to 100% acetonitrile in water, both eluents containing 0.1% trifluoroacetic acid, gradient elution over 30 min) to give the product as the second eluting isomer. $^1$H NMR (400 MHz, CDCl$_3$; trifluoroacetic acid salt) δ 8.14 (s, 1H), 7.38 (d, J=8.5 Hz, 1H), 7.33 (d, J=2.1 Hz, 1H), 7.14 (dd, J=8.4, 2.1 Hz, 1H), 6.29 (q, J=7.1 Hz, 1H), 4.77-4.46 (m, 4H), 4.03 (d, J=10.5 Hz, 1H), 3.81-3.64 (m, 1H), 3.62-3.44 (m, 1H), 3.06 (d, J=12.9 Hz, 1H), 2.98-2.86 (m, 1H), 2.70-2.15 (m, 6H), 2.06-1.75 (m, 5H), 1.12 (d, J=6.4 Hz, 3H); m/z 533.2 (M+H$^+$).

Example 38

2-((3S,3'R,4'S)-1'-(1-((R)-1-(2,4-Dichlorophenyl)ethyl)-3-methyl-1H-pyrazolo[3,4-b]pyrazin-6-yl)-3'-methyl-[1,4'-bipiperidin]-3-yl)acetic acid formate

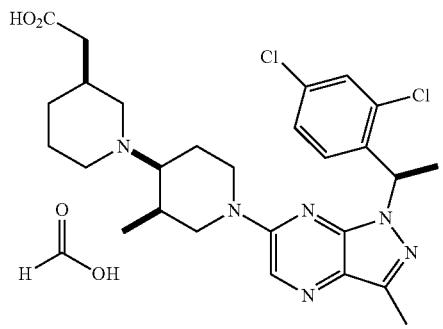

Step 1. Ethyl (S)-2-(piperidin-3-yl)acetate (D)-mandelate complex

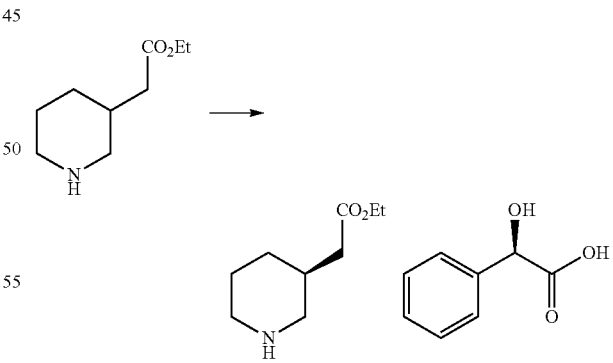

Following the procedure from patent WO2011115943A1, racemic piperidine 3-acetic acid ethyl ester (1.5 g, 8.76 mmol) was dissolved in ethyl acetate (13 mL) before the addition (D)-mandelic acid (1.33 g, 8.76 mmol). This solution was then heated to reflux for 4 h before being cooled to room temperature for 12 h. The flask containing the reaction was then incubated at 4° C. in a refrigerator for 1 h at which time solids had formed. The solids were filtered, washing with minimal ethyl acetate. These solids were subsequently recrystallized from boiling ethyl acetate twice more.

Step 2. tert-Butyl (3S)-3-(2-ethoxy-2-oxoethyl)-3'-methyl-[1,4'-bipiperidine]-1'-carboxylate

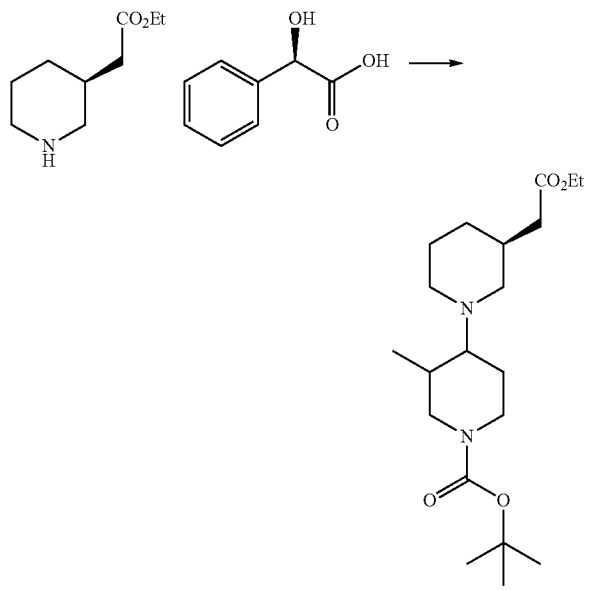

The product of Example 38, Step 1 (850 mg, 2.63 mmol) was dissolved in DMA (8.8 mL) before the addition of tert-butyl 3-methyl-4-oxopiperidine-1-carboxylate (560 mg, 2.63 mmol). The reaction was then heated to 35° C. and stirred for 1 h. at this temperature. Then sodium triacetoxyborohydride (696 mg, 3.29 mmol) was added and the mixture was stirred for 24 h. at 35° C. The reaction was cooled to room temperature before being quenched with aqueous sodium bicarbonate. The aqueous layer was extracted with dichloromethane (3×), and then concentrated. The residue was taken up in ethyl acetate and washed with 1M HCl. The aqueous layer was then made basic (pH ~9) with 1M aqueous sodium hydroxide and extracted with dichloromethane (3×), and the combine organics were dried over sodium sulfate and concentrated. The crude residue was purified by silica chromatography (40 to 60% ethyl acetate in hexanes) to yield the product as a mixture of diastereomers.

Step 3. 2-((3S)-3'-Methyl-[1,4'-bipiperidin]-3-yl)acetic acid

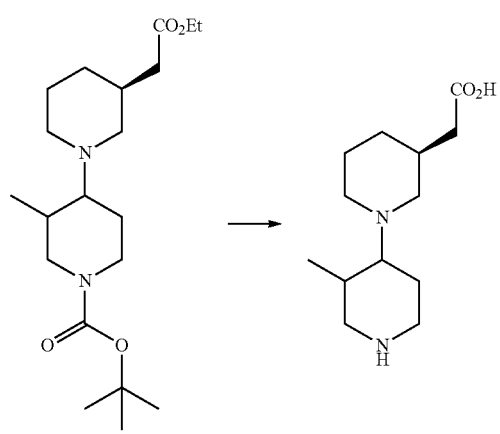 [SMILES: CCOC(=O)C[C@@H]1CCCN(C2CCN(C(=O)OC(C)(C)C)CC2C)C1 ; CC1CNCCC1N1CCC[C@@H](CC(=O)O)C1]

The title compound was synthesized analogously to Example 37, Step 2, substituting tert-butyl (3S)-3-(2-ethoxy-2-oxoethyl)-3'-methyl-[1,4'-bipiperidine]-1'-carboxylate for tert-butyl 4-((2S,4R)-4-hydroxy-2-(methoxycarbonyl)pyrrolidin-1-yl)-3-methylpiperidine-1-carboxylate to yield the product as a hydrochloride salt.

Step 4. 2-((3S,3'R,4'S)-1'-(1-((R)-1-(2,4-dichlorophenyl)ethyl)-3-methyl-1H-pyrazolo[3,4-b]pyrazin-6-yl)-3'-methyl-[1,4'-bipiperidin]-3-yl)acetic acid formate

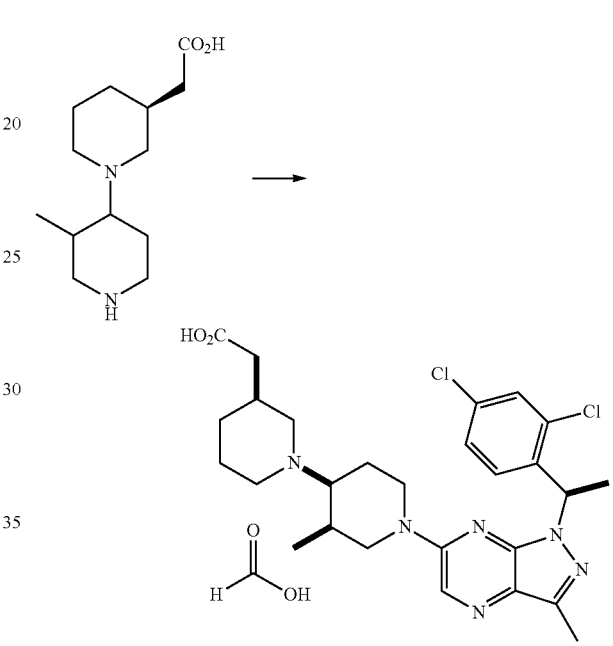

The title compound was synthesized according to the procedure in Example 12, Step 8, substituting 2-((3S)-3'-methyl-[1,4'-bipiperidin]-3-yl)acetic acid for 3-methyl-4-(pyrrolidin-1-yl)piperidine hydrochloride. The residue was purified by reverse phase preparative HPLC (Gemini-NX, 10 µm, 250×30 mm, C18 column (Phenomenex, Torrance, Calif.), eluent: 0 to 100% acetonitrile in water, both eluents containing 0.1% trifluoroacetic acid, gradient elution over 30 min). The residue was further purified by reverse phase preparative HPLC (Gemini-NX, 10 µm, 250×30 mm, C18 column (Phenomenex, Torrance, Calif.), eluent: 30 to 35% acetonitrile in water (containing 0.1% ammonium formate), gradient elution over 30 min) to give the product as the first eluting isomer. $^1$H NMR (400 MHz, CD$_3$CN; Formate salt) δ 8.21 (s, 1H), 8.17 (s, 1H), 7.45 (d, J=2.2 Hz, 1H), 7.42 (d, J=8.5 Hz, 1H), 7.25 (dd, J=8.5, 2.2 Hz, 1H), 6.25 (q, J=7.1 Hz, 1H), 4.62-4.51 (m, 1H), 4.42 (d, J=13.3 Hz, 1H), 3.16-2.96 (m, 3H), 2.90-2.70 (m, 3H), 2.52-2.35 (m, 5H), 2.25 (d, J=5.7 Hz, 3H), 2.15-2.05 (m, 1H), 1.83 (d, J=7.1 Hz, 3H), 1.80-1.60 (m, 4H), 1.28-1.14 (m, 1H), 0.90 (d, J=6.9 Hz, 3H); m/z 545.2 (M+H$^+$).

Example 39

2-((3S,3'R,4'S)-1'-(3-Cyano-1-((R)-1-(2,4-dichlorophenyl)ethyl)-1H-pyrazolo[3,4-b]pyrazin-6-yl)-3'-methyl-[1,4'-bipiperidin]-3-yl)acetic acid formate

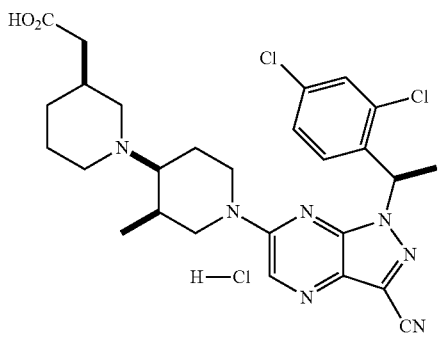

The title compound was synthesized according to the procedure outlined in Example 23, Step 3, substituting 2-((3S)-3'-methyl-[1,4'-bipiperidin]-3-yl)acetic acid (Example 38, Step 3) for 3'-methyl-1,4'-bipiperidine 2,2,2-trifluoroacetate (Example 2, Step 2) and DMSO for DMF. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min). The residue was further purified by reverse phase preparative HPLC (Gemini-NX, 10 μm, 250×30 mm, C18 column (Phenomenex, Torrance, Calif.), eluent: 35 to 40% acetonitrile in water (containing 0.1% ammonium formate), gradient elution over 20 min) to give the product as the second eluting isomer. This residue was then washed with saturated aqueous sodium bicarbonate and extracted with dichloromethane (3×). This was then concentrated, dissolved in 1 mL of dichloromethane and made acidic (pH-2) with HCl in diethyl ether. The volatiles were removed under reduced pressure to give the title compound. $^1$H NMR (400 MHz, CD$_3$CN; HCl salt) δ 8.40 (s, 1H), 7.48 (d, J=2.1 Hz, 1H), 7.44 (d, J=8.5 Hz, 1H), 7.30 (dd, J=8.5, 2.1 Hz, 1H), 6.41 (q, J=7.0 Hz, 1H), 4.66 (d, J=13.1 Hz, 1H), 4.55 (d, J=13.6 Hz, 1H), 3.72 (d, J=9.7 Hz, 1H), 3.54 (d, J=11.2 Hz, 1H), 3.39-2.88 (m, 3H), 2.83-2.61 (m, 2H), 2.55-1.99 (m, 8H), 1.87 (d, J=7.0 Hz, 4H), 1.32-1.16 (m, 1H), 1.12 (d, J=6.6 Hz, 3H).

Example 40

3-((3S,3'S,4'R)-1'-(1-((R)-1-(2,4-Dichlorophenyl)ethyl)-3-methyl-1H-pyrazolo[3,4-b]pyrazin-6-yl)-3'-methyl-[1,4'-bipiperidin]-3-yl)propanoic acid 2,2,2-trifluoroacetate

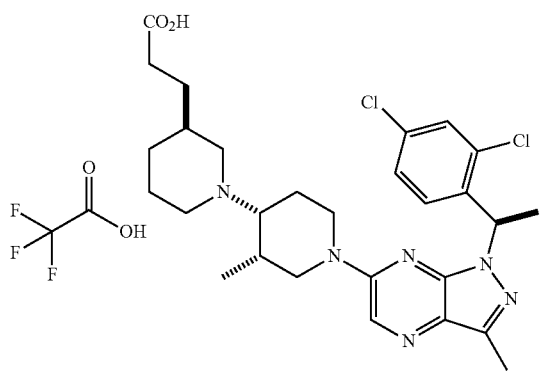

Step 1. Ethyl 3-(3'-methyl-[1,4'-bipiperidin]-3-yl)propanoate

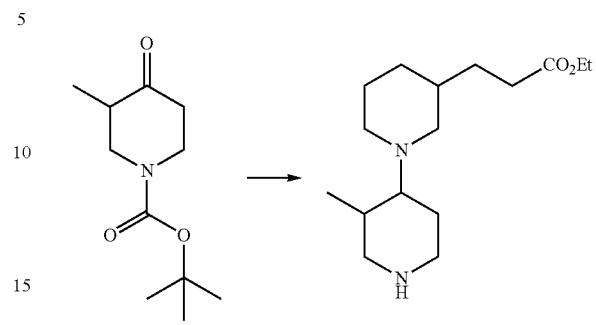

The title compound was synthesized analogously to the procedures outlined in Example 2, Step 1, substituting ethyl 3-(piperidin-3-yl)propanoate for piperidine. The product of this reaction was purified via column chromatography (20 to 100% ethyl acetate in hexanes) to give the product as a mixture of diastereomers. This mixture was then taken up in 4N HCl in 1,4-dioxane and stirred for 16 h. The solvent was then removed under reduced pressure to give the title compound as a hydrochloride salt.

Step 2. Ethyl 3-(1'-(1-((R)-1-(2,4-dichlorophenyl)ethyl)-3-methyl-1H-pyrazolo[3,4-b]pyrazin-6-yl)-3'-methyl-[1,4'-bipiperidin]-3-yl)propanoate

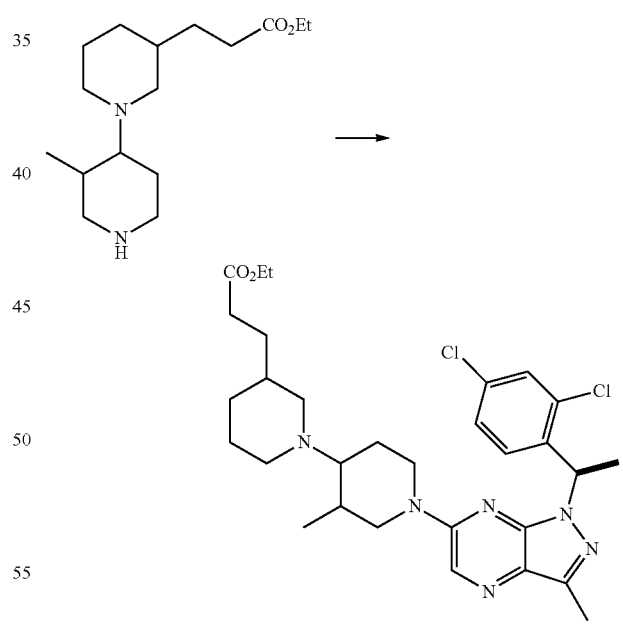

The title compound was synthesized by the procedure outlined in Example 12, Step 8, substituting ethyl 3-(3'-methyl-[1,4'-bipiperidin]-3-yl)propanoate hydrochloride for 3-methyl-4-(pyrrolidin-1-yl)piperidine hydrochloride. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the title compound as a mixture of diastereomers. The diastereomers were further separated using the Chiralpak® ID-3 column, (Daicel, Corporation, West Chester, Pa.) and eluting with 85% heptane, 15% isopropanol at 20 mL/min.

Step 3. 3-((3S,3'S,4'R)-1'-(1-((R)-1-(2,4-dichlorophenyl)ethyl)-3-methyl-1H-pyrazolo[3,4-b]pyrazin-6-yl)-3'-methyl-[1,4'-bipiperidin]-3-yl)propanoic acid

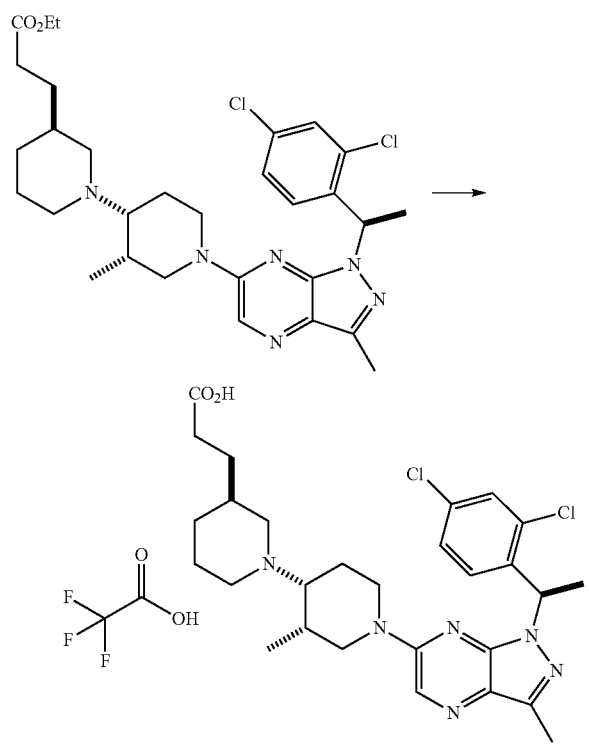

The first eluting isomer from Example 40, Step 2 (15 mg, 0.026 mmol) was then dissolved in THF (0.26 mL) before the addition of lithium hydroxide (1.2 mg, 0.052 mmol) in 0.1 mL of water. This reaction was then stirred at 55° C. overnight and quenched by the addition of trifluoroacetic acid before volatiles were removed. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the title compound as the trifluoroacetate salt. $^1$H NMR (400 MHz; CD$_3$CN; trifluoroacetic acid salt) δ 8.20 (s, 1H), 7.47 (d, J=2.1 Hz, 1H), 7.44 (d, J=8.5 Hz, 1H), 7.27 (dd, J=8.4, 2.2 Hz, 1H), 6.27 (q, J=7.1 Hz, 1H), 4.63 (d, J=13.3 Hz, 1H), 4.51 (d, J=13.8 Hz, 1H), 3.72 (d, J=12.2 Hz, 1H), 3.52 (d, J=11.9 Hz, 1H), 3.34-3.22 (m, 1H), 3.03 (dd, J=13.9, 2.3 Hz, 1H), 2.96-2.84 (m, 1H), 2.70-2.55 (m, 2H), 2.45 (s, 3H), 2.41-2.25 (m, 2H), 2.10-1.95 (m, 2H), 1.90-1.85 (m, 2H), 1.84 (d, J=7.1 Hz, 3H), 1.70-1.46 (m, 2H), 1.42-1.26 (m, 3H), 1.19-1.06 (m, 1H), 1.02 (d, J=6.8 Hz, 3H); m/z 559.3 (M+H$^+$).

Example 41

3-(1'-(1-((R)-1-(2,4-dichlorophenyl)ethyl)-3-methyl-1H-pyrazolo[3,4-b]pyrazin-6-yl)-3'-methyl-[1,4'-bipiperidin]-3-yl)propanoic acid

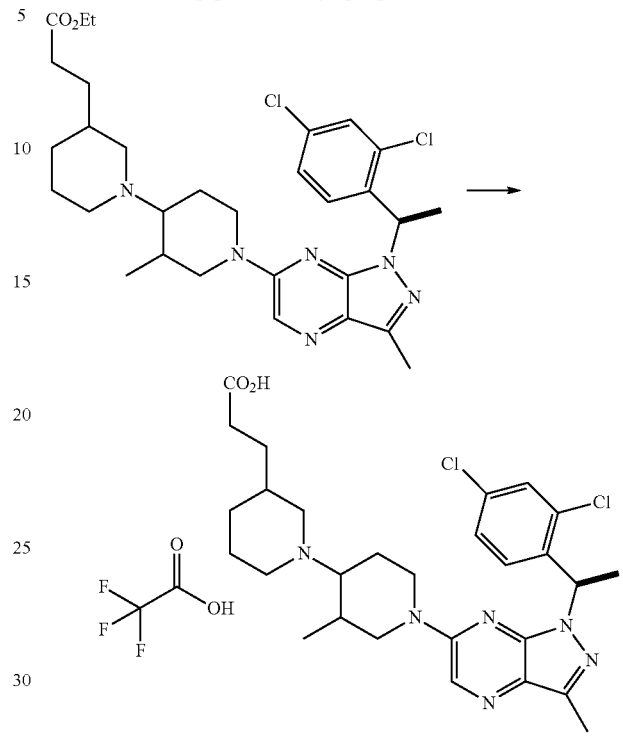

The second eluting peak from Example 40, Step 2 contained a mixture of at least 2 diastereomers. This mixture was then hydrolyzed according to the procedure outlined in Example 40, Step 3. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the title compound as a mixture of diastereomers of unknown stereochemistry. $^1$H NMR (400 MHz; CD$_3$CN; trifluoroacetic acid salt) δ 8.18 (br s, 1H), 7.39 (d, J=8.5 Hz, 1H), 7.36-7.32 (m, 1H), 7.15 (dd, J=8.5, 2.1 Hz, 1H), 6.37-6.27 (m, 1H), 4.78-4.39 (m, 2H), 3.97-3.76 (m, 1H), 3.70-3.60 (m, 1H), 3.36-3.18 (m, 1H), 3.14-2.85 (m, 2H), 2.68-2.26 (m, 8H), 2.23-1.92 (m, 6H), 1.89 (d, J=7.1 Hz, 3H), 1.73-1.60 (m, 1H), 1.60-1.49 (m, 1H), 1.16-1.00 (m, 4H); m/z 559.3 (M+H$^+$).

Example 42

3-((S)-1-((3R,4S)-1-(1-((R)-1-(2,4-dichlorophenyl)ethyl)-3-methyl-1H-pyrazolo[3,4-b]pyrazin-6-yl)-3-methylpiperidin-4-yl)pyrrolidin-2-yl)propanoic acid hydrochloride

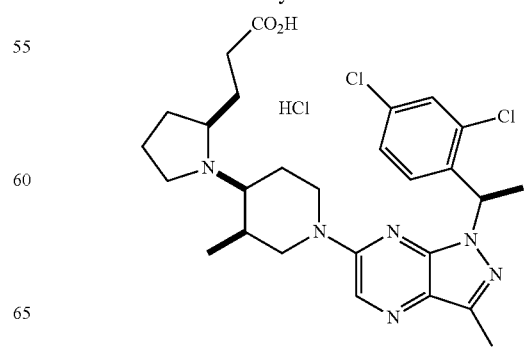

Step 1. tert-butyl (S,E)-2-(3-ethoxy-3-oxoprop-1-en-1-yl)pyrrolidine-1-carboxylate

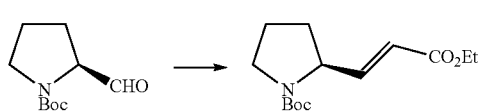 [SMILES: CC(C)(C)OC(=O)N1CCC[C@H]1C=O ; CCOC(=O)/C=C/[C@@H]1CCCN1C(=O)OC(C)(C)C]

To a cooled (0° C.) solution of triethylphosphonoacetate (11 mL, 55.2 mmol) in THF (500 mL) was added potassium tert-butoxide (5.63 g, 50.2 mmol, 0.91 equiv). After 30 min, N-Boc-L-prolinal (9.4 mL, 50.2 mmol, 0.91 equiv) was added and the mixture was allowed to warm to ambient temperature. After 1 h (progress monitored by TLC and LCMS), the reaction was quenched with water, and extracted (3×) with ethyl acetate, and the combined organics were dried over sodium sulfate and concentrated. The crude residue was purified by silica chromatography (30% ethyl acetate in hexanes) to yield the product (11.7 g, 87% yield).

Step 2. tert-butyl (S)-2-(3-ethoxy-3-oxopropyl)pyrrolidine-1-carboxylate

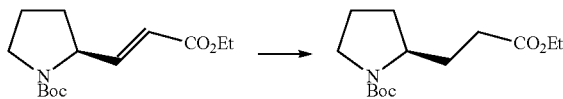 [SMILES: CCOC(=O)/C=C/[C@@H]1CCCN1C(=O)OC(C)(C)C ; CCOC(=O)CC[C@@H]1CCCN1C(=O)OC(C)(C)C]

A solution of tert-butyl (S,E)-2-(3-ethoxy-3-oxoprop-1-en-1-yl)pyrrolidine-1-carboxylate (Example 42, Step 1, 11.7 g, 43.5 mmol) and platinum (II) oxide (124 mg, 0.435 mmol, 0.01 equiv) in ethanol (145 mL, 0.3 M) was stirred under a hydrogen atmosphere for 6 h before being filtered through a pad of Celite and concentrated in vacuo. The crude residue was purified by silica chromatography (15% ethyl acetate in hexanes) to yield the title compound (10.3 g, 87% yield).

Step 3. Ethyl (S)-3-(pyrrolidin-2-yl)propanoate hydrochloride

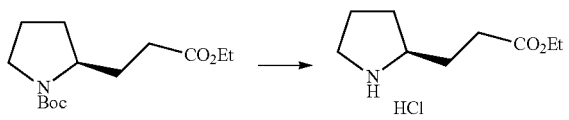 [SMILES: CCOC(=O)CC[C@@H]1CCCN1C(=O)OC(C)(C)C ; CCOC(=O)CC[C@@H]1CCCN1 ; Cl]

To a flask in an ice-bath containing tert-butyl (S)-2-(3-ethoxy-3-oxopropyl)pyrrolidine-1-carboxylate (Example 42, Step 2, 11.8 g, 43.3 mmol) and a stir bar was added HCl in 1,4-dioxane (4 N solution, 54 mL, 217 mmol, 5.0 equiv). The resulting mixture was allowed to warm to ambient temperature over the course of 16 h before the solvent was removed in vacuo to provide the title compound as the hydrochloride salt.

Step 4. tert-butyl 4-((S)-2-(3-ethoxy-3-oxopropyl)pyrrolidin-1-yl)-3-methylpiperidine-1-carboxylate

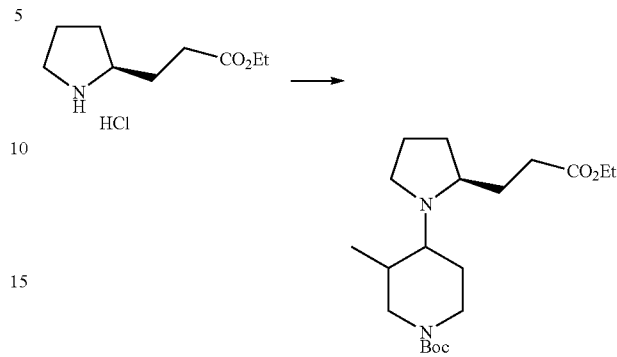

The title compound was synthesized as a mixture of diastereomers according to the procedures outlined in Example 12, Step 6, substituting ethyl (S)-3-(pyrrolidin-2-yl)propanoate hydrochloride (Example 42, Step 3) for pyrrolidine.

Step 5. 3-((2S)-1-(3-methylpiperidin-4-yl)pyrrolidin-2-yl)propanoic acid hydrochloride

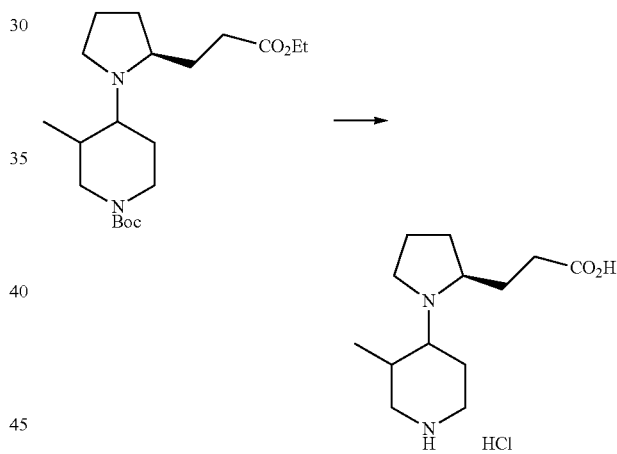

The title compound was synthesized analogously to the procedures outlined in Example 37, Step 2 to give the title compound as the HCl salt of a mixture of diastereomers.

Step 6. 3-((S)-1-((3R,4S)-1-(1-((R)-1-(2,4-dichlorophenyl)ethyl)-3-methyl-1H-pyrazolo[3,4-b]pyrazin-6-yl)-3-methylpiperidin-4-yl)pyrrolidin-2-yl)propanoic acid hydrochloride

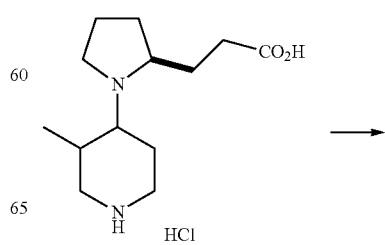

-continued

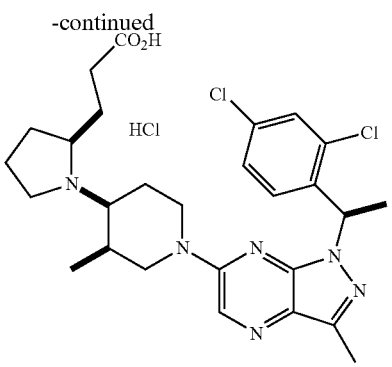

The title compound was synthesized according to the procedures in Example 12, Step 8, substituting 3-((2S)-1-(3-methylpiperidin-4-yl)pyrrolidin-2-yl)propanoic acid hydrochloride (Example 42, Step 5) for 3-methyl-4-(pyrrolidin-1-yl)piperidine hydrochloride and DMSO for DMF. The crude material was purified using reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the title compound as a mixture of diastereomers. These diastereomers were separated on reverse phase preparative HPLC (Gemini-NX, 10 μm, 250×30 mm, C18 column (Phenomenex, Torrance, Calif.), eluent: 35 to 40% acetonitrile in water (containing 0.1% ammonium formate), gradient over 20 min) to give the title compound as the second eluting isomer. The formate salt was washed with saturated aq. sodium bicarbonate and extracted (3×) with dichloromethane, then the combined organics were dried over sodium sulfate and concentrated. The residue was re-dissolved in dichloromethane, treated with 2M HCl in Et$_2$O (0.2 mL), and concentrated under reduced pressure to afford the title compound as the hydrochloride salt. $^1$H NMR (400 MHz, CD$_3$CN, HCl salt) δ 8.31 (s, 1H), 8.17 (s, 1H), 7.46 (d, J=2.2 Hz, 1H), 7.43 (d, J=8.5 Hz, 1H), 7.27-7.22 (m, 1H), 6.26 (q, J=7.1 Hz, 1H), 4.63-4.53 (m, 1H), 4.45 (dt, J=13.6, 2.6 Hz, 1H), 3.66-3.57 (m, J=5.9, 3.2 Hz, 1H), 3.31-3.20 (m, 1H), 3.06-2.80 (m, 4H), 2.49 (ddd, J=17.6, 9.9, 3.0 Hz, 1H), 2.43 (s, J=1.4 Hz, 3H), 2.41-2.33 (m, 2H), 2.15-1.96 (m, 3H), 1.93-1.85 (m, 2H), 1.83 (d, J=7.1 Hz, 3H), 1.81-1.68 (m, 3H), 0.98 (d, J=6.9 Hz, 3H); m/z 545.2 (M+H$^+$).

Example 43

3-((S)-1-((3R,4S)-1-(3-Cyano-1-((R)-1-(2,4-dichlorophenyl)ethyl)-1H-pyrazolo[3,4-b]pyrazin-6-yl)-3-methylpiperidin-4-yl)pyrrolidin-2-yl)propanoic acid hydrochloride

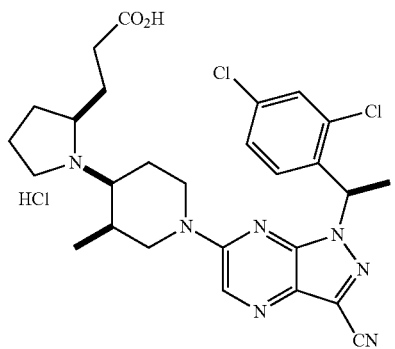

The title compound was synthesized according to the procedures in Example 23, Step 3, substituting 3-((2S)-1-(3-methylpiperidin-4-yl)pyrrolidin-2-yl)propanoic acid hydrochloride (Example 42, Step 5) for 3'-methyl-1,4'-bipiperidine 2,2,2-trifluoroacetate (Example 2, Step 2) and DMSO for DMF. The crude material was purified using reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to give the title compound as a mixture of diastereomers, which was further purified by chiral SFC to afford the desired compound. $^1$H NMR (400 MHz, CD$_3$CN, HCl salt) δ 8.41 (s, 1H), 7.50 (d, J=2.1 Hz, 1H), 7.44 (d, J=8.5 Hz, 1H), 7.31 (dd, J=8.5, 2.1 Hz, 1H), 6.42 (q, J=7.1 Hz, 1H), 4.66 (d, J=13.1 Hz, 1H), 4.54 (d, J=13.3 Hz, 1H), 3.72 (br s, 1H), 3.57-3.44 (m, J=12.5 Hz, 2H), 3.21-3.05 (m, J=13.2 Hz, 2H), 3.05-2.93 (m, J=14.5 Hz, 1H), 2.59-2.42 (m, 3H), 2.24-2.12 (m, 8H), 1.88 (d, J=7.0 Hz, 3H), 1.12 (d, J=6.0 Hz, 3H); m/z 556.2 (M+H$^+$).

Example 44

3-((S)-1-((3R,4S)-1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)propanamide hydrochloride

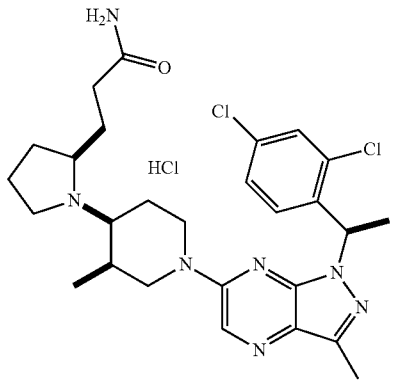

The product of Example 42, Step 6 was converted to the title compound analogously to the procedure described in Example 4, Step 2. $^1$H NMR (400 MHz, CD$_3$CN; HCl salt) δ 10.99-10.79 (m, 1H), 8.26 (s, 1H), 7.59-7.44 (m, 2H), 7.32 (d, J=8.7 Hz, 1H), 6.90 (dd, J=13.9, 10.2 Hz, 1H), 6.35 (d, J=6.9 Hz, 1H), 6.21 (d, J=1.1 Hz, 1H), 4.60 (ddd, J=17.8, 13.3, 8.5 Hz, 1H), 3.60-3.37 (m, 1H), 3.33-3.12 (m, 2H), 3.12-2.89 (m, 3H), 2.68-2.47 (m, 2H), 2.36-2.18 (m, 2H), 2.03 (dd, J=8.1, 4.7 Hz, 2H), 1.91 (dd, J=5.1, 2.0 Hz, 2H), 1.85-1.78 (m, 3H), 1.27 (d, J=16.9 Hz, 5H), 1.10-1.01 (m, 4H); m/z 544.2 (M+H$^+$).

Example 45

3-((R)-1-((3R,4S)-1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)ethan-1-amine

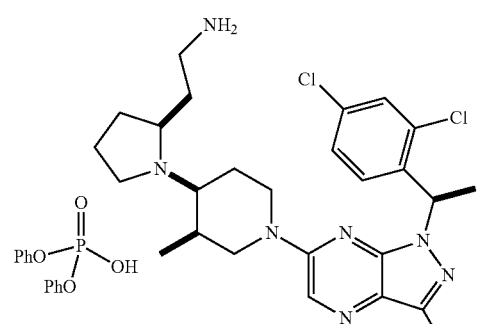

The product of Example 42, Step 6 (48 mg, 0.082 mmol) was converted to the title compound by first dissolving it in tert-butanol (0.4 mL). Then triethylamine (0.044 mL, 3 equiv) and diphenyl phosphoryl azide (0.026 mL, 1.5 equiv) were added. The mixture was heated to 80° C. in a sealed microwave vial until the starting material was completely consumed by LCMS (18 h). The mixture was concentrated in vacuo and treated with 4M HCl in 1,4-dioxane (2 mL) for 1 h. The residue was concentrated in vacuo and purified by HPLC (Gemini-NX, 10 µm, 250×30 mm, C18 column (Phenomenex, Torrance, Calif.), eluent: 0 to 100% acetonitrile in water, both eluents containing 0.1% trifluoroacetic acid, gradient elution over 30 min) to afford the title compound as the 1:1 diphenylphosphate salt. H NMR (400 MHz, CD$_3$OD; diphenylphosphate salt) δ 8.25 (s, 1H), 7.44 (d, J=2.1 Hz, 1H), 7.40 (d, J=8.6 Hz, 1H), 7.31-7.14 (m, 8H), 7.02 (t, J=7.2 Hz, 2H), 6.31 (q, J=7.1 Hz, 1H), 4.77-4.68 (m, 1H), 4.61-4.49 (m, 1H), 3.92-3.80 (m, 1H), 3.59-3.54 (m, 2H), 3.12-2.93 (m, 5H), 2.52 (s, 3H), 2.13 (s, 10H), 1.88 (d, J=7.1 Hz, 3H), 1.06 (d, J=6.9 Hz, 3H); m/z 258.6 (M+2H$^+$), 516.1 (M+H$^+$).

Example 46

4-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-1,1,1-trifluorobutan-2-ol hydrochloride

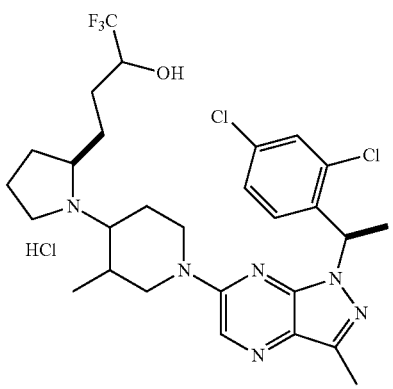 [SMILES: Cc1nn([C@H](C)c2ccc(Cl)cc2Cl)c2nc(N3CCC(N4CCC[C@H]4CCC(O)C(F)(F)F)C(C)C3)cnc12 ; Cl]

Step 1. Tert-butyl (S,E)-2-(3-methoxy-3-oxoprop-1-en-1-yl)pyrrolidine-1-carboxylate

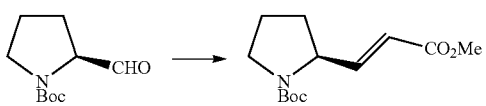 [SMILES: CC(C)(C)OC(=O)N1CCC[C@H]1C=O ; COC(=O)/C=C/[C@@H]1CCCN1C(=O)OC(C)(C)C]

To a solution of methyl 2-(dimethoxyphosphoryl)acetate (5.0 g, 28 mmol) in THF (100 mL) was added tert-BuONa (2.5 g, 25 1 mmol). The mixture was stirred at 0° C. for 1 h. A solution of the tert-butyl (S)-2-formylpyrrolidine-1-carboxylate (5.0 g, 25 mmol) in THF (50 mL) was added slowly, and the mixture was stirred at room temperature for 2 h, poured into saturated sodium bicarbonate (200 mL). The mixture was extracted with ethyl acetate (2×100 mL), dried over sodium sulfate, filtered, and concentrated to afford a crude tert-butyl (S)-2-(3-methoxy-3-oxoprop-1-en-1-yl)pyrrolidine-1-carboxylate (6.4 g) as a light yellow oil.

Step 2. Methyl (S)-3-(pyrrolidin-2-yl)propanoate

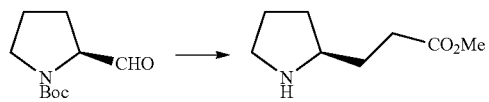 [SMILES: CC(C)(C)OC(=O)N1CCC[C@H]1C=O ; COC(=O)CC[C@@H]1CCCN1]

The title compound was synthesized according to the procedures described in Example 42, Steps 2 and 3, substituting tert-butyl (S,E)-2-(3-methoxy-3-oxoprop-1-en-1-yl)pyrrolidine-1-carboxylate (Example 46, Step 1) as the starting material.

Step 3. Tert-butyl 4-((S)-2-(3-methoxy-3-oxopropyl)pyrrolidin-1-yl)-3-methylpiperidine-1-carboxylate

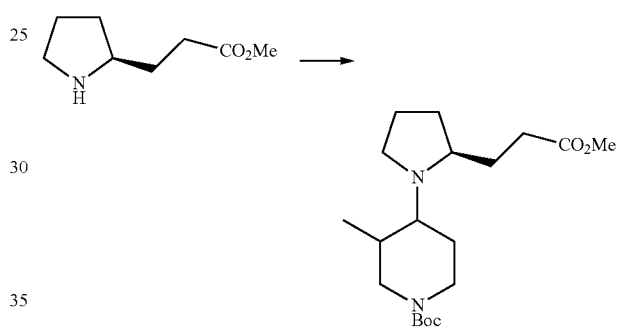

To a solution of the methyl (S)-3-(pyrrolidin-2-yl)propanoate (Example 46, Step 2, 3.7 g, 23.5 mmol) in 1,2-dichloroethane (60 mL) was added tert-butyl 3-methyl-4-oxopiperidine-1-carboxylate (5.0 g, 23.5 mmol). The mixture was stirred at room temperature for 30 min. Na(OAc)$_3$BH (15.0 g, 70.5 mmol, 3.0 equiv) was added, and the mixture was stirred at room temperature overnight. The reaction mixture was then poured onto saturated sodium bicarbonate, extracted with dichloromethane (3×100 mL), dried over sodium sulfate, filtered, and concentrated to afford the crude product, which was purified by flash column chromatography twice to provide 3.1 g (37%) of the tert-butyl 4-((S)-2-(3-methoxy-3-oxopropyl)pyrrolidin-1-yl)-3-methylpiperidine-1-carboxylate as a colorless oil.

Step 4. Tert-butyl 4-((S)-2-(3-hydroxypropyl)pyrrolidin-1-yl)-3-methylpiperidine-1-carboxylate

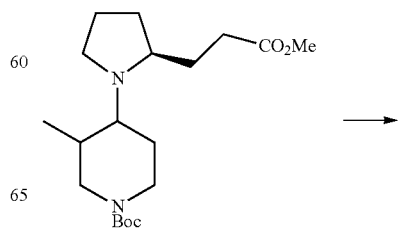

-continued

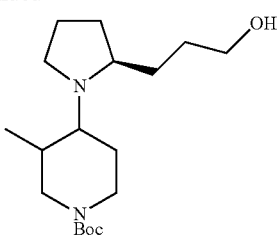

To a solution of tert-butyl 4-((S)-2-(3-methoxy-3-oxopropyl)pyrrolidin-1-yl)-3-methylpiperidine-1-carboxylate (Example 46, Step 3, 2.5 g, 7.1 mmol) in diethyl ether (50 mL) was added LiAlH$_4$ (2 M in THF, 5.3 mL, 10.6 mmol) at 0° C. The mixture was stirred at 0° C. for 4 h. Water (0.3 mL) was added to the reaction mixture followed by 15% aqueous NaOH (0.6 mL) then water (0.3 mL). The mixture was stirred at room temperature for 1 h and filtered. The filtrate was concentrated to afford tert-butyl 4-((S)-2-(3-hydroxypropyl)pyrrolidin-1-yl)-3-methylpiperidine-1-carboxylate (2.2 g, 79%) as a colorless oil.

Step 5. Tert-butyl 3-methyl-4-((S)-2-(3-oxopropyl)pyrrolidin-1-yl)piperidine-1-carboxylate

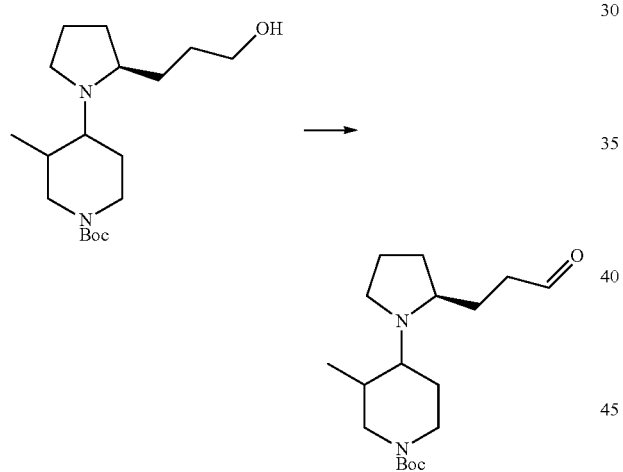

To a solution of oxalyl chloride (2 M in DCM, 4.0 mL) in DCM (26 mL) was added DMSO (1.2 mL, 3.0 mmol) at −78° C. The mixture was stirred at −78° C. for 10 min. A solution of tert-butyl 4-((S)-2-(3-methoxy-3-oxopropyl)pyrrolidin-1-yl)-3-methylpiperidine-1-carboxylate (Example 46, Step 4, 2.2 g, 6.8 mmol) in DCM (18 mL) was added slowly, and the resulting mixture was stirred for 30 min. Triethylamine (3.4 mL, 24 mmol) was added, and the mixture was stirred at −78° C. for 2 h and at room temperature for 12 h. The reaction was diluted with dichloromethane (50 mL), washed with water, dried over sodium sulfate, filtered, and concentrated to afford a crude product. The crude product was purified by silica gel chromatography, eluting with 50% ethyl acetate in hexanes to afford tert-butyl 3-methyl-4-((S)-2-(3-oxopropyl)pyrrolidin-1-yl)piperidine-1-carboxylate (1.3 g, 59%) as a colorless oil.

Step 6. Tert-butyl 3-methyl-4-((2S)-2-(4,4,4-trifluoro-3-hydroxybutyl)pyrrolidin-1-yl)piperidine-1-carboxylate

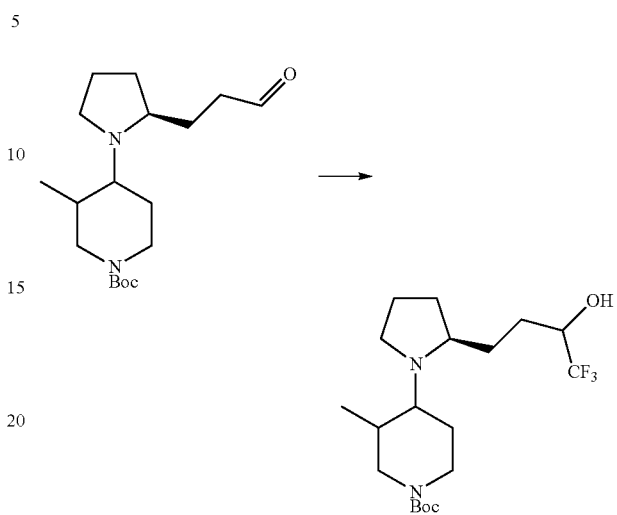

To a solution of tert-butyl 3-methyl-4-((S)-2-(3-oxopropyl)pyrrolidin-1-yl)piperidine-1-carboxylate (Example 46, Step 4, 1.3 g, 4.0 mmol) in THF (30 mL) at −60° C. was added trifluoromethyltrimethylsilane (1.2 g, 8.0 mmol) and TBAF (1 M in THF, 8.0 mL, 8.0 mmol). The mixture was warmed from −60° C. to 0° C. over 4 h before cooling back to −60° C. Trifluoromethyltrimethylsilane (1.2 g, 8.0 mmol) and then TBAF (1 M in THF, 8.0 mL, 8.0 mmol) was added. The mixture was warmed from −60° C. to room temperature over 14 h. The reaction mixture was concentrated and partitioned between diethyl ether (30 mL) and water (6 mL). The organic layer were separated, dried over sodium sulfate, and concentrated to afford tert-butyl 3-methyl-4-((2S)-2-(4,4,4-trifluoro-3-hydroxybutyl)pyrrolidin-1-yl)piperidine-1-carboxylate as a mixture of diastereomers.

Step 7. 1,1,1-Trifluoro-4-((2S)-1-(3-methylpiperidin-4-yl)pyrrolidin-2-yl)butan-2-ol

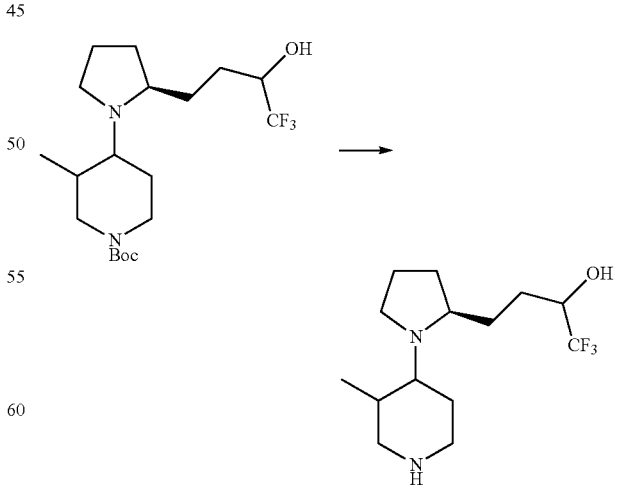

To a solution of tert-butyl 3-methyl-4-((2S)-2-(4,4,4-trifluoro-3-hydroxybutyl)pyrrolidin-1-yl)piperidine-1-carboxylate (Example 46, Step 6, 146 mg, 0.37 mmol) in dichloromethane (3.0 mL) was added trifluoroacetic acid (1.0 mL). The mixture was stirred at room temperature for 2 h and concentrated. The residue was co-evaporated with dichloromethane twice and dried under high vacuum to afford the 2,2,2-trifluoroacetate salt of the title compound, which was used directly in the next reaction.

Step 8. 4-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-1,1,1-trifluorobutan-2-ol hydrochloride

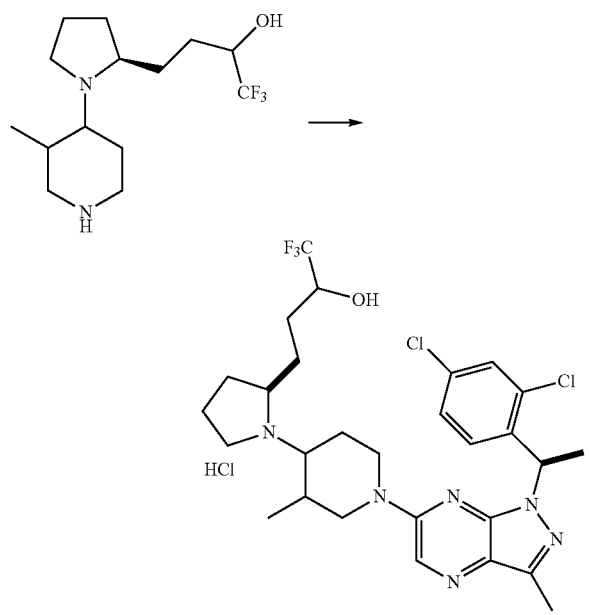

The title compound was synthesized according to the procedures in Example 12, Step 8, substituting 1,1,1-trifluoro-4-((2S)-1-(3-methylpiperidin-4-yl)pyrrolidin-2-yl)butan-2-ol (Example 46, Step 7) for 3-methyl-4-(pyrrolidin-1-yl)piperidine hydrochloride. The crude material was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the compound as a trifluoroacetic acid salt. The diastereomers were separated by preparative SFC (AD-H (2×25 cm), 15% methanol with 0.1% diethylamine and $CO_2$ at 100 bar, 70 mL/min) to afford 4 diastereomers. The third eluting diastereomer (9 mg) was converted to the HCl salt by diluting in dichloromethane (1 mL) and adding 1 M HCl in $Et_2O$ (0.05 mL). The resulting yellow solution was concentrated under reduced pressure to afford the title compound. $^1$H NMR (400 MHz, $CDCl_3$, HCl salt) δ 8.08 (s, 1H), 7.40 (d, J=8.5 Hz, 1H), 7.35 (d, J=2.1 Hz, 1H), 7.15 (dd, J=8.4, 2.2 Hz, 1H), 6.30 (q, J=7.0 Hz, 1H), 4.62-4.50 (m, 1H), 4.35 (dt, J=13.2, 2.3 Hz, 1H), 3.82 (s, 1H), 3.22-3.13 (m, 1H), 3.13-3.06 (m, 1H), 3.01 (dd, J=13.4, 2.4 Hz, 1H), 2.91-2.78 (m, 1H), 2.60 (dd, J=9.6, 4.8 Hz, 1H), 2.57 (s, 3H), 2.47 (td, J=9.9, 6.2 Hz, 1H), 2.23 (s, 1H), 2.08-1.93 (m, 2H), 1.90 (d, J=7.1 Hz, 4H), 1.87-1.67 (m, 6H), 1.66-1.56 (m, 2H), 1.02 (d, J=6.9 Hz, 3H); m/z 598.8 (M+H$^+$).

Example 47

4-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-1,1,1-trifluorobutan-2-ol hydrochloride

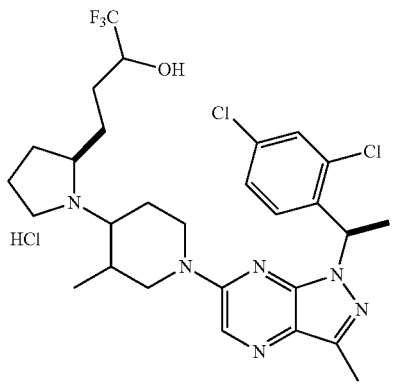 [SMILES: Cc1nn([C@H](C)c2ccc(Cl)cc2Cl)c2nc(N3CCC(N4CCC[C@H]4CCC(O)C(F)(F)F)C(C)C3)cnc12 ; Cl]

Further elution from the SFC purification described in Example 46, Step 8, gave the title compound as the fourth eluting isomer. This compound (10 mg) was converted to the HCl salt by diluting in dichloromethane (1 mL) and adding 1 M HCl in $Et_2O$ (0.05 mL). The resulting yellow solution was concentrated under reduced pressure to afford the title compound. $^1$H-NMR (400 MHz; $CDCl_3$, HCl salt): δ 8.09 (s, 1H), 7.41 (d, J=8.5 Hz, 1H), 7.35 (d, J=2.1 Hz, 1H), 7.14 (dd, J=8.5, 2.2 Hz, 1H), 6.30 (q, J=7.1 Hz, 1H), 4.51 (d, J=13.3 Hz, 1H), 4.40 (d, J=13.4 Hz, 1H), 3.84 (td, J=7.4, 3.8 Hz, 1H), 3.16-3.10 (m, 1H), 3.05-2.92 (m, 2H), 2.88-2.68 (m, 2H), 2.57 (s, 3H), 2.55-2.48 (m, 1H), 2.25-2.22 (m, 1H), 2.10-1.45 (m, 14H), 1.02 (d, J=6.9 Hz, 3H); m/z 598.8 (M+H$^+$).

Example 48

3-((S)-1-((3R,4S)-1-(3-Cyano-1-((R)-1-(2,4-dichlorophenyl)ethyl)-1H-pyrazolo[3,4-b]pyrazin-6-yl)-3-methylpiperidin-4-yl)pyrrolidin-2-yl)propanamide 2,2,2-trifluoroacetate

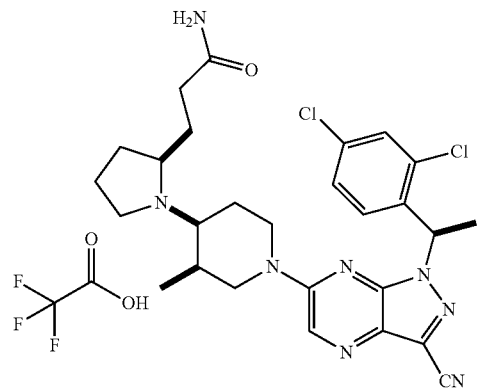

The product of Example 43 was converted to the title compound analogously to the procedure described in Example 4, Step 2. ¹H-NMR (400 MHz; CDCl₃, trifluoroacetic acid salt): δ 11.08 (s, 1H), 8.34 (s, 1H), 7.37 (dd, J=5.3, 3.2 Hz, 2H), 7.21 (dd, J=8.4, 2.1 Hz, 1H), 6.45 (q, J=7.1 Hz, 1H), 6.01 (s, 1H), 4.69-4.63 (m, 1H), 4.58 (d, J=13.7 Hz, 1H), 4.20-3.97 (m, 2H), 3.63 (br s, 1H), 3.47 (br s, 1H), 3.26-3.00 (m, 3H), 2.69 (br s, 2H), 2.53 (br s, 1H), 2.45-1.98 (m, 7H), 1.92 (d, J=7.1 Hz, 3H), 1.14 (d, J=6.9 Hz, 3H); m/z 555.2 (M+H⁺).

Example 49

3-((S)-1-((3R,4S)-1-(1-((R)-1-(4-Chloro-2-fluorophenyl)ethyl)-3-methyl-1H-pyrazolo[3,4-b]pyrazin-6-yl)-3-methylpiperidin-4-yl)pyrrolidin-2-yl)propanoic acid 2,2,2-trifluoroacetate

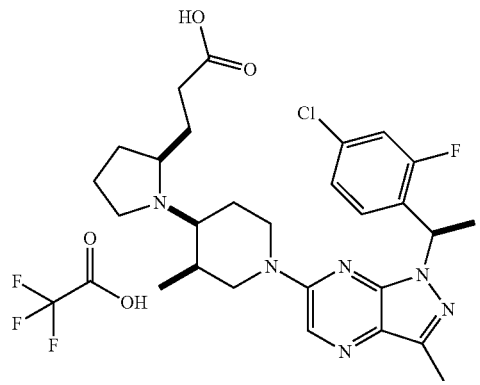

Step 1: (R)-1-(4-Chloro-2-fluorophenyl)ethan-1-ol

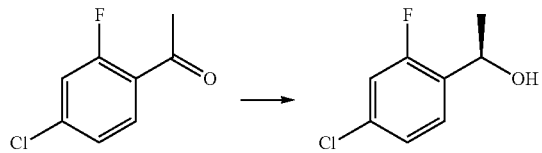

To a solution of 1-(4-chloro-2-fluorophenyl)ethan-1-one (10 g, 58 mmol) in THF (100 mL) at −78° C. under a nitrogen atmosphere was added (+)-DIP-Cl (50 to 60% wt in hexanes, 9.2 mL, 64 mmol), slowly. The resulting mixture was slowly warmed to −25° C. and stirred at this temperature for 2 h. 1-(4-Chloro-2-fluorophenyl)ethan-1-one was detected by LCMS and HPLC, and the mixture was cooled back to −78° C. Additional (+)-DIP-Cl (50 to 65% wt in hexanes, 5.4 mL, 38 mmol) was added to the mixture at −78° C. The resulting mixture was slowly warmed to −25° C. and stirred at this temperature for 5 h. Diethanolamine (18 mL, 191 mmol) was added to the reaction mixture, which was then stirred at room temperature for 3 d. The reaction was filtered, and the filtrate was concentrated and purified by silica gel chromatography (0 to 30% ethyl acetate in hexanes) to afford 18.8 g impure (R)-1-(chloro-2-fluorophenyl)ethan-1-ol.

Step 2: 4-Chloro-1-(1-chloroethyl)-2-fluorobenzene

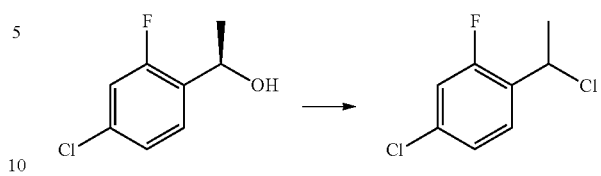

To a flask containing (R)-1-(4-chloro-2-fluorophenyl)ethan-1-ol (18.8 g, 108 mmol) in dichloromethane (1 L) was added PPh₃ (113 g, 432 mmol) and CCl₄ (41.7 mL, 432 mmol). The mixture was stirred at ambient temperature for 3 d, then silica gel (~400 g) was added to the mixture. The mixture was then concentrated under reduced pressure, and the residue was purified by silica gel column chromatography (100% hexanes) to afford 4-chloro-1-(1-chloroethyl)-2-fluorobenzene (8 g) as a colorless oil.

Step 3: (1-(4-Chloro-2-fluorophenyl)ethyl)hydrazine hydrochloride

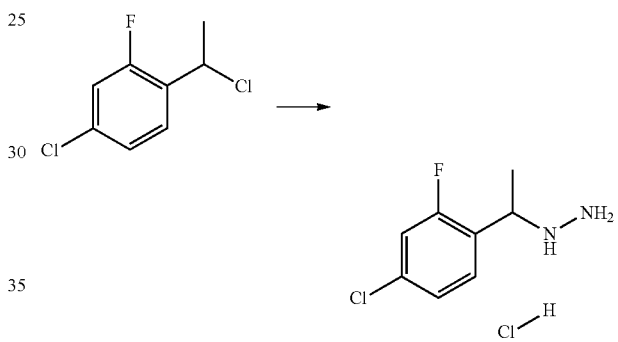

To a solution of 4-chloro-1-(1-chloroethyl)-2-fluorobenzene (4.0 g, 41 mmol) in ethanol (120 mL) was added hydrazine hydrate (excess). The mixture was stirred at 35° C. for 3 d. The reaction was concentrated, and diethyl was added to the mixture. The bottom hydrazine layer was removed, and about 5 mL of 4 M HCl in 1,4-dioxane was added to the mixture at 0° C. The mixture was kept at 0° C. until all of the hydrazine HCl salt precipitated. The mixture was filtered, washed with cold diethyl ether, and concentrated in vacuo to afford the title compound as the hydrochloride salt (3.95 g), which was used without further purification.

Step 4. (R)-6-chloro-1-(1-(4-chloro-2-fluorophenyl)ethyl)-3-methyl-1H-pyrazolo[3,4-b]pyrazine

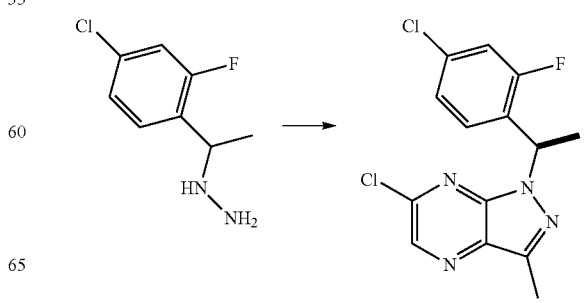

The title compound was synthesized according to the procedures outlined in Example 12, Steps 4 and 5. The crude product was purified using an alumina column (eluting with 25% to 50% dichloromethane in hexanes) to afford impure 6-chloro-1-(1-(4-chloro-2-fluorophenyl)ethyl)-3-methyl-1H-pyrazolo[3,4-b]pyrazine (2.2 g). This material was repurified by alumina column to afford the title compound (1.94 g) as a light yellow oil which was purified by SFC (Lux-amylose 4 (two 2×15 cm columns), eluting with 10% methanol with 0.1% DEA and $CO_2$ at 100 bar, 60 mL/min) to afford the pure product as a mixture of enantiomers. The enantiomers were separated by preparative chiral SFC (OJ-H (2×25 cm), eluting with 10% isopropanol with 0.1% DEA and $CO_2$ at 100 bar, 70 mL/min) to afford the desired enantiomer as the first eluting enantiomer (485 mg) at 2.67 min.

Step 6. 3-((S)-1-((3R,4S)-1-(1-((R)-1-(4-Chloro-2-fluorophenyl)ethyl)-3-methyl-1H-pyrazolo[3,4-b]pyrazin-6-yl)-3-methylpiperidin-4-yl)pyrrolidin-2-yl)propanoic acid 2,2,2-trifluoroacetate

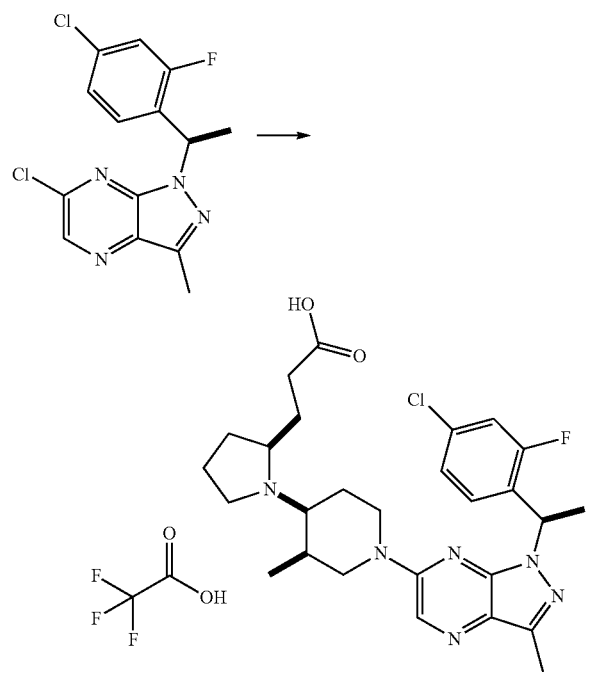

The title compound was synthesized according to the procedures outlined in Example 42, Step 6, replacing (R)-6-chloro-1-(1-(4-chloro-2-fluorophenyl)ethyl)-3-methyl-1H-pyrazolo[3,4-b]pyrazine (Example 49, Step 4) for (R)-6-chloro-1-(1-(2,4-dichlorophenyl)ethyl)-3-methyl-1H-pyrazolo[3,4-b]pyrazine (Example 12, Step 5). The crude material was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the title compound as the major diastereomer and trifluoroacetic acid salt. $^1$H NMR (400 MHz, $CD_3CN$, trifluoroacetic acid salt) δ 8.24 (s, 1H), 7.43 (t, J=8.2 Hz, 1H), 7.26-7.12 (m, 2H), 6.21 (q, J=7.0 Hz, 1H), 4.75-4.60 (m, 2H), 4.55 (dt, J=5.4, 2.9 Hz, 2H), 3.92 (dt, J=8.7, 4.0 Hz, 1H), 3.58 (dt, J=11.7, 5.8 Hz, 1H), 3.47 (td, J=8.6, 4.7 Hz, 1H), 3.25 (dq, J=12.1, 6.5 Hz, 1H), 3.09 (dd, J=13.8, 2.7 Hz, 1H), 3.00-2.91 (m, 1H), 2.69-2.47 (m, 3H), 2.46 (s, 4H), 2.31-1.99 (m, 5H), 1.89 (d, J=7.1 Hz, 3H), 1.04 (d, J=6.9 Hz, 3H); m/z 529.1 (M+H$^+$).

Example 50

3-((2S)-1-((2S)-1-(1-((R)-1-(2,4-Dichlorophenyl)ethyl)-3-methyl-1H-pyrazolo[3,4-b]pyrazin-6-yl)-2-methylpiperidin-4-yl)pyrrolidin-2-yl)propanoic acid 2,2,2-trifluoroacetate

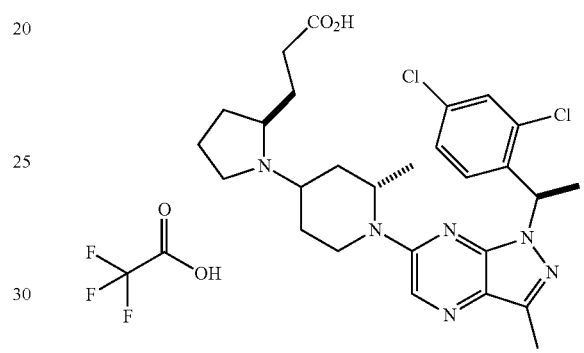

Step 1. (S)-1-(1-((R)-1-(2,4-Dichlorophenyl)ethyl)-3-methyl-1H-pyrazolo[3,4-b]pyrazin-6-yl)-2-methyl-piperidin-4-one

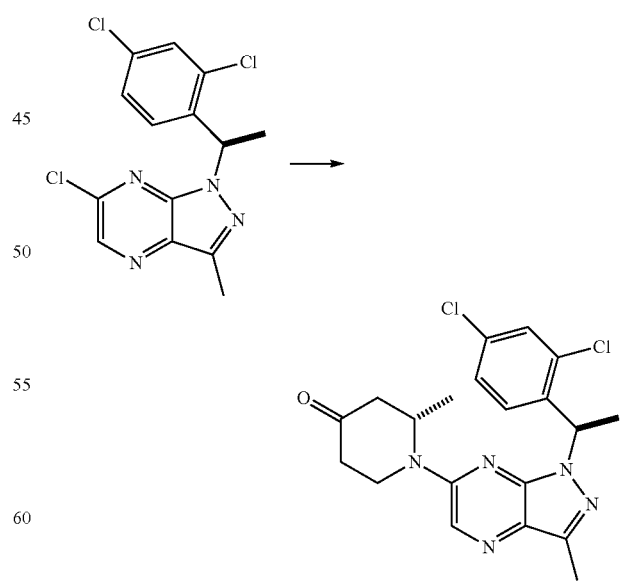

To (S)-2-methylpiperidin-4-one hydrochloride (250 mg, 1.67 mmol) and (R)-6-chloro-1-(1-(2,4-dichlorophenyl)ethyl)-3-methyl-1H-pyrazolo[3,4-b]pyrazine (627 mg, 1.84 mmol, 1.1 equiv) in DMSO (4.2 mL) was added N,N-diisopropylethylamine (1.0 mL, 3.5 equiv). The reaction mixture was heated to 120° C. for 4 h before being cooled to room temperature and poured into ethyl acetate (50 mL) and washed with water (50 mL). The aqueous layer was extracted with ethyl acetate (2×25 mL) and the combined organic layers were dried over sodium sulfate, filtered, and concentrated in vacuo. The residue was purified by flash column chromatography (silica gel, 0 to 20% methanol in dichloromethane) to afford the intermediate ketone as a 1.5:1 mixture of diastereomers (104 mg, 15% yield).

Step 2. Methyl 3-((2S)-1-((2S)-1-(1-((R)-1-(2,4-dichlorophenyl)ethyl)-3-methyl-1H-pyrazolo[3,4-b]pyrazin-6-yl)-2-methylpiperidin-4-yl)pyrrolidin-2-yl)propanoate

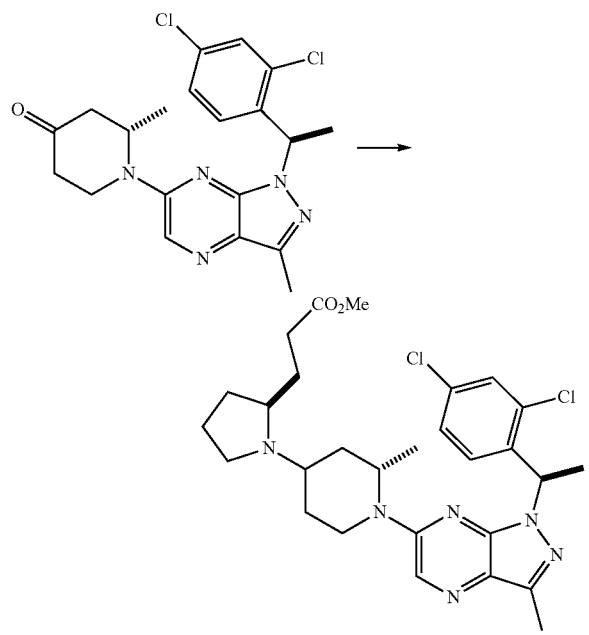

To the ketone intermediate (Example 50, Step 1, 104 mg, 0.25 mmol) in 1,2-dichloroethane (0.63 mL) was added methyl (S)-3-(pyrrolidin-2-yl)propanoate hydrochloride (110 mg, 0.57 mmol) followed by sodium triacetoxyborohydride (158 mg, 3.0 equiv). The reaction was allowed to stir overnight before being diluted with ethyl acetate (25 mL) and washed with 1 M aqueous sodium carbonate (10 mL). The aqueous layer was extracted with ethyl acetate (10 mL) and the combined organic layers were dried over sodium sulfate, filtered, and concentrated in vacuo. The residue was purified by flash column chromatography (silica gel, 0 to 20% methanol in dichloromethane gradient) to afford the amine as a mixture of diastereomers. The residue was azetroped with ethanol (5 mL). The residue was further purified using chiral HPLC using a Chiralpak® IF-3 column (Daicel, Corporation, West Chester, Pa., eluent: 30% ethanol in heptanes, both eluents containing 0.1% Et$_2$NH, 30 min., 20 mL/min) to give the title compound as a mixture of diastereomers as the third eluting peak.

Step 3. 3-((2S)-1-((2S)-1-(1-((R)-1-(2,4-Dichlorophenyl)ethyl)-3-methyl-1H-pyrazolo[3,4-b]pyrazin-6-yl)-2-methylpiperidin-4-yl)pyrrolidin-2-yl)propanoic acid 2,2,2-trifluoroacetate

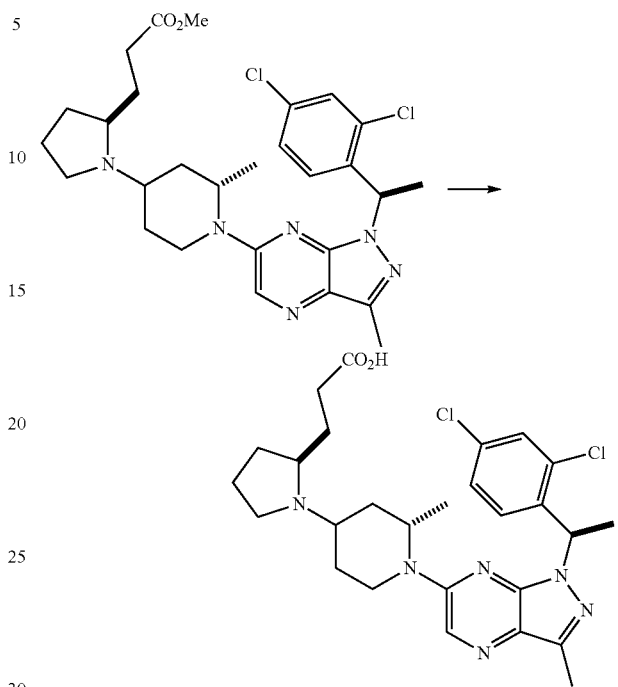

To the isolated isomers from Example 50, Step 2 (3 mg) was added 1,4-dioxane (1 mL) and 4 M aqueous LiOH (0.25 mL). The mixture was stirred until complete hydrolysis was observed by LCMS. The mixture was then acidified with 3 M HCl (1 mL) and purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the compound as a trifluoroacetic acid salt as a 2.7:1 mixture of two stereoisomers of unknown stereochemistry around the piperidine ring. $^1$H NMR (400 MHz, CD$_3$OD, trifluoroacetic acid salt) δ 8.25 (s, J=8.4 Hz, 0.73H), 8.12 (s, 0.27H), 7.49-7.33 (m, 2H), 7.33-7.23 (m, 1H), 6.39-6.24 (m, 1H), 5.18-5.03 (m, 1H), 4.62-4.21 (m, 1H), 3.95-3.45 (m, 3H), 3.28-3.18 (m, 2H), 2.51 (s, 3H), 2.67-1.68 (m, 12H), 1.90-1.87 (m, 3H), 1.32 (d, J=6.6 Hz, 0.81H), 1.26 (d, J=6.9 Hz, 2.19H); m/z 545.0 (M+H$^+$).

Example 51

3-((S)-1-(1-(1-((R)-1-(2,4-Dichlorophenyl)ethyl)-3-methyl-1H-pyrazolo[3,4-b]pyrazin-6-yl)piperidin-4-yl)pyrrolidin-2-yl)propanoic acid 2,2,2-trifluoroacetate

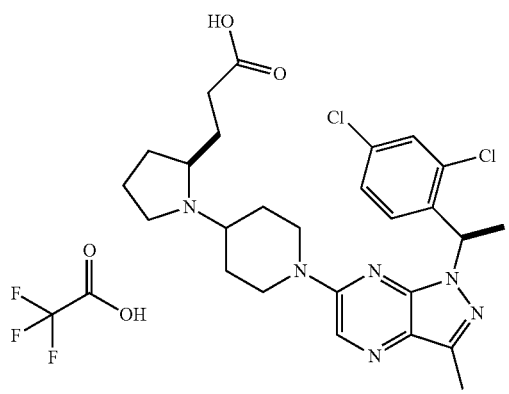 [SMILES: O=C(O)C(F)(F)F ; Cc1nn([C@H](C)c2ccc(Cl)cc2Cl)c2nc(N3CCC(N4CCC[C@H]4CCC(=O)O)CC3)cnc12]

Step 1. (S)-3-(1-(Piperidin-4-yl)pyrrolidin-2-yl)propanoic acid

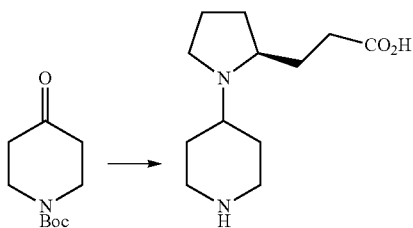 [SMILES: CC(C)(C)OC(=O)N1CCC(=O)CC1 ; O=C(O)CC[C@@H]1CCCN1C1CCNCC1]

The title compound was synthesized according to the general procedures outlined in Example 2, Steps 1, substituting ethyl (S)-3-(pyrrolidin-2-yl)propanoate (Example 42 Step 3), for piperidine and 4-Boc-piperidinone for 1-tert-butoxycarbonyl-3-methyl-4-piperidinone. The synthesis was finished according to the procedure described in Example 37, Step 2 to give the title compound as the hydrochloride salt.

Step 2. 3-((S)-1-(1-(1-((R)-1-(2,4-Dichlorophenyl)ethyl)-3-methyl-1H-pyrazolo[3,4-b]pyrazin-6-yl)piperidin-4-yl)pyrrolidin-2-yl)propanoic acid 2,2,2-trifluoroacetate

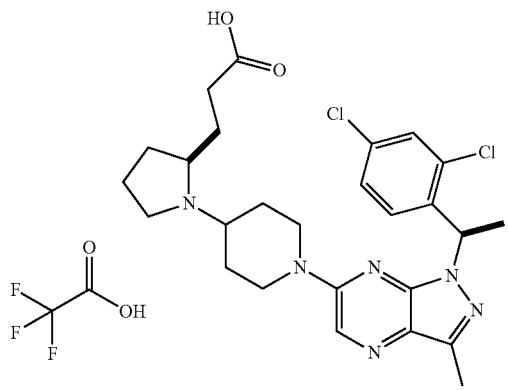 [SMILES: O=C(O)C(F)(F)F ; Cc1nn([C@H](C)c2ccc(Cl)cc2Cl)c2nc(N3CCC(N4CCC[C@H]4CCC(=O)O)CC3)cnc12]

The title compound was synthesized analogously to the procedures outlined in Example 12, Step 8, substituting (S)-3-(1-(piperidin-4-yl)pyrrolidin-2-yl)propanoic acid (Example 51, Step 1) for 3-methyl-4-(pyrrolidin-1-yl)piperidine hydrochloride (Example 12, Step 7), and DMSO for DMF. The aqueous layer was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the title compound as the 2,2,2-trifluoroacetate salt. $^1$H NMR (400 MHz, CD$_3$OD, trifluoroacetic acid salt) δ 8.28 (s, 1H), 7.46 (d, J=2.2 Hz, 1H), 7.40 (d, J=8.5 Hz, 1H), 7.27 (dd, J=8.5, 2.2 Hz, 1H), 6.33 (q, J=7.1 Hz, 1H), 4.71 (br t, J=15.9 Hz, 2H), 3.86-3.75 (m, 1H), 3.73-3.62 (m, 1H), 3.51-3.42 (m, 1H), 3.33-3.21 (m, 2H), 3.11-3.02 (m, 2H), 2.62-2.40 (m, 2H), 2.52 (s, 3H), 2.35-2.13 (m, 4H), 2.10-1.93 (m, 2H), 1.89 (d, J=7.1 Hz, 3H), 1.87-1.61 (m, 3H); m/z 531.0 (M+H$^+$).

Example 52

2-((S)-1-((3R,4S)-1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)ethane-1-sulfonamide hydrochloride

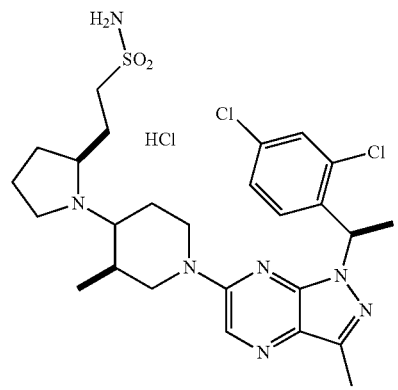 [SMILES: Cc1nn([C@H](C)c2ccc(Cl)cc2Cl)c2nc(N3CCC(N4CCC[C@H]4CCS(N)(=O)=O)[C@H](C)C3)cnc12 ; Cl]

Step 1. Tert-butyl (S)-2-(2-(acetylthio)ethyl)pyrrolidine-1-carboxylate

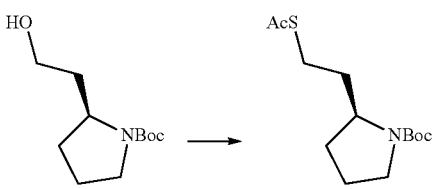

To tert-butyl (S)-2-(2-hydroxyethyl)pyrrolidine-1-carboxylate (800 mg, 3.7 mmol) in dichloromethane (10 mL) was added triethylamine (1.0 mL, 2.0 equiv). The mixture was cooled in an ice-water bath and methanesulfonyl chloride (0.35 mL, 1.2 equiv) was added. After 1.5 h, the reaction mixture was quenched with water (10 mL) and the organic layer was dried over sodium sulfate, filtered, and concentrated in vacuo to afford an oil which was used directly in the following step. To the intermediate mesylate (~3.7 mmol) in DMF (10 mL) was added potassium thioacetate (845 mg, 2.0 equiv). The mixture was heated to 50° C., upon which copious precipitate appears. An additional 10 mL of DMF was added to the mixture and the reaction was stirred for an additional 1 h. The reaction mixture was then partitioned between 50% ethyl acetate in hexanes (100 mL) and water (100 mL). The organic layer was washed with water (2×50 mL), dried over sodium sulfate, filtered, and concentrated in vacuo. The thioacetate product was purified by flash column chromatography (silica gel, 5 to 50% ethyl acetate in hexanes) to afford a white solid (678 mg, 68% over 2 steps).

Step 2. (S)-2-(Pyrrolidin-2-yl)ethane-1-sulfonamide

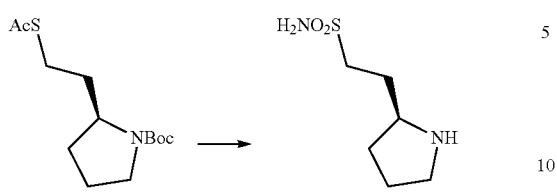

To a mixture of 2 M aqueous HCl (1.24 mL, 1.0 eq) in acetonitrile (16.5 mL) was added N-chlorosuccinimide (1.33 g, 4.0 equiv) at room temperature. The mixture was stirred for 10 min before being cooled to 0° C. The thioacetate intermediate (Example 52, Step 1, 678 mg, 2.5 mmol, 1.0 eq) was then added to the reaction mixture dropwise as a solution in acetonitrile (4 mL). The reaction mixture was warmed to room temperature and stirred for 10 min before being partitioned between ethyl acetate (100 mL) and water (100 mL). The organic layer was washed with brine (50 mL), dried over sodium sulfate, filtered, and concentrated in vacuo to afford the sulfonyl chloride intermediate as a white solid. To the sulfonyl chloride intermediate (~2.48 mmol) in acetonitrile (16.5 mL) was added concentrated aqueous ammonia (33%, 2.48 mL). The mixture was stirred for 15 min before being diluted with ethyl acetate (50 mL) and water (50 mL). The organic layer was dried over sodium sulfate, filtered, and concentrated in vacuo to afford the sulfonamide intermediate (642 mg, 93% yield over 2 steps). The sulfonamide intermediate (642 mg, 2.3 mmol) was treated with 4 M HCl in 1,4-dioxane (10 mL) and stirred overnight before being concentrated in vacuo. The solid was taken up in methanol (10 mL) and filtered over PL-HCO3 MP-Resin (~1.8 mmol/g, 3 g) to afford the free amine, which was used directly in the next step.

Step 3. 2-((2S)-1-(3-Methylpiperidin-4-yl)pyrrolidin-2-yl)ethane-1-sulfonamide

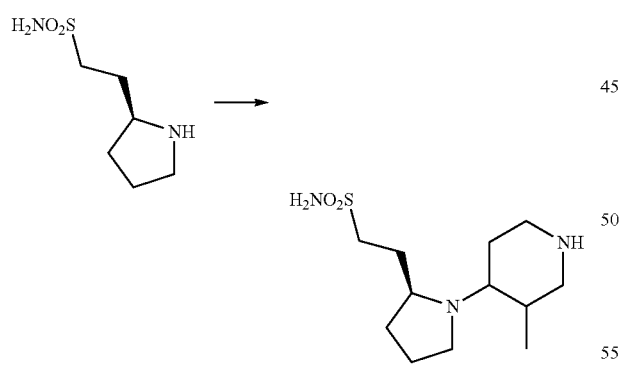

The title compound was synthesized according to the procedures outlined in Example 12, Step 6, substituting 2-((2S)-1-(3-methylpiperidin-4-yl)pyrrolidin-2-yl)ethane-1-sulfonamide for pyrrolidine. The crude residue was purified by flash column chromatography (silica gel, 0 to 30% methanol in dichloromethane) to afford diastereomer A (191 mg, 22% yield) as the first eluting fraction and a mixture of diastereomers (2:1) in a second fraction (95 mg, 11% yield). The title compound was obtained using the first eluting diastereomer in the procedure described in Example 2, Step 2.

Step 4. 2-((S)-1-((3R,4S)-1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)ethane-1-sulfonamide hydrochloride

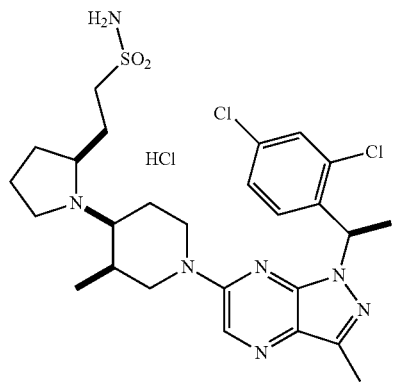

The title compound was synthesized analogously to the procedures outlined in Example 12, Step 8, substituting 2-((2S)-1-(3-methylpiperidin-4-yl)pyrrolidin-2-yl)ethane-1-sulfonamide (Example 52, Step 3) for 3-methyl-4-(pyrrolidin-1-yl)piperidine hydrochloride (Example 12, Step 7). The aqueous layer was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the 2,2,2-trifluoroacetate salt. The salt was dissolved in methanol, filtered over PL-HCO3 MP-Resin (~1.8 mmol/g, 0.5 g) and the filtrate was treated with 2 M HCl in diethyl ether (0.5 mL). The mixture was concentrated under reduced pressure to provide the title compound as the hydrochloride salt. δ 8.25 (s, 1H), 7.40 (d, J=2.1 Hz, 1H), 7.37 (d, J=8.5 Hz, 1H), 7.22 (dd, J=8.5, 2.1 Hz, 1H), 6.28 (q, J=7.1 Hz, 1H), 4.75 (dm, J=13.7 Hz, 1H), 4.59 (dm, J=13.8 Hz, 1H), 4.19-4.04 (m, 1H), 3.78-3.57 (m, 2H), 3.43-3.32 (m, 1H), 3.29-3.25 (m, 2H), 3.15 (br d, J=13.6 Hz, 1H), 3.02 (br t, J=11.9 Hz, 1H), 2.55 (br s, 1H), 2.49 (s, 3H), 2.39-1.91 (m, 10H), 1.85 (d, J=7.1 Hz, 3H), 1.07 (d, J=6.9 Hz, 3H); m/z 580.0 (M+H+).

Example 53

2-((S)-1-((3S,4R)-1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)ethane-1-sulfonamide hydrochloride

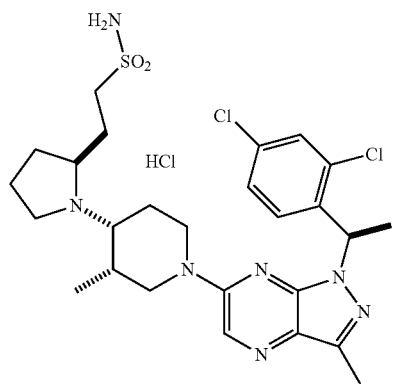

Obtained using the second eluting mixture of diastereomers from Example 52, Step 3. The title compound was obtained by reacting this mixture of diastereomers according to the procedures described in Example 2, Step 2 and to the procedures outlined in Example 12, Step 8, substituting 2-((2S)-1-(3-methylpiperidin-4-yl)pyrrolidin-2-yl)ethane-1-sulfonamide (Example 53) for 3-methyl-4-(pyrrolidin-1-yl)piperidine hydrochloride (Example 12, Step 7). $^1$H NMR (400 MHz, CD$_3$OD, HCl salt) δ 8.27 (s, 0.25H), 8.26 (s, 0.75H), 7.52-7.31 (m, 2H), 7.30-7.21 (m, 1H), 6.30 (q, J=7.0 Hz, 1H), 4.80-4.54 (m, 2H), 4.08 (s, 1H), 3.76-3.49 (m, 2H), 3.38 (dd, J=18.8, 8.0 Hz, 1H), 3.29-3.09 (m, 3H), 3.02 (t, J=10.9 Hz, 1H), 2.70-2.57 (m, 1H), 2.50 (s, 3H), 2.48-2.37 (m, 1H), 2.37-2.22 (m, 2H), 2.22-1.90 (m, 6H), 1.88 (d, J=7.1 Hz, 3H), 1.12-0.98 (m, 3H); m/z 580.1 (M+H$^+$).

Example 54

2-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)cyclopropane-1-carboxylic acid

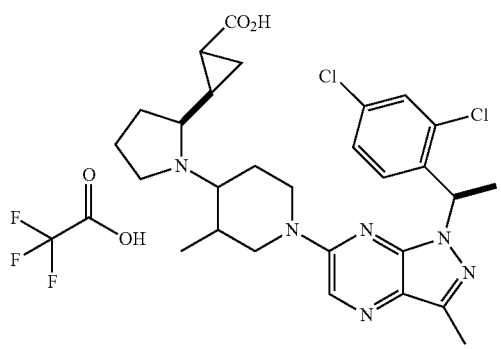

Step 1. Methyl (2R)-2-((S)-pyrrolidin-2-yl)cyclopropane-1-carboxylate

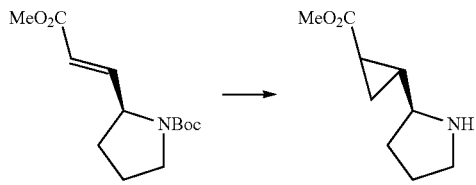 [SMILES: COC(=O)/C=C/[C@@H]1CCCN1C(=O)OC(C)(C)C ; COC(=O)C1CC1[C@@H]1CCCN1]

To NaH (60% dispersion in mineral oil, 220 mg, 1.4 eq) in DMSO (10 mL) was added trimethylsulfoxonium iodide (1.3 g, 5.9 mmol, 1.5 eq). The mixture was stirred for 1 h before tert-butyl (S,E)-2-(3-methoxy-3-oxoprop-1-en-1-yl)pyrrolidine-1-carboxylate (Example 42, Step 1; 1 g, 3.9 mmol) was added as a solution in 1:1 THF/DMSO (10 mL). The reaction mixture was allowed to stir overnight before being quenched with 1M HCl (50 mL) and extracted with ethyl acetate (100 mL). The organic layer was dried over sodium sulfate, filtered, and concentrated under reduced pressure. The residue was purified by flash column chromatography (silica gel, 20% ethyl acetate in hexanes) to afford a mixture of cyclopropane diastereomers (2:1 mixture, 106 mg, 10% yield). To the mixture of cyclopropane diastereomers (Example 54, Step 1, 106 mg, 0.39 mmol, 1.0 eq) was added 4M HCl in 1,4-dioxane (1 mL). The mixture was allowed to stir for 15 min before being concentrated under reduced pressure. The mixture was taken up in methanol (10 mL) and filtered over PL-HCO3 MP-Resin (~1.8 mmol/g, 0.5 g) and concentrated in vacuo to afford the free amine.

Step 2. Tert-butyl 4-((2S)-2-((1R)-2-(methoxycarbonyl)cyclopropyl)pyrrolidin-1-yl)-3-methylpiperidine-1-carboxylate

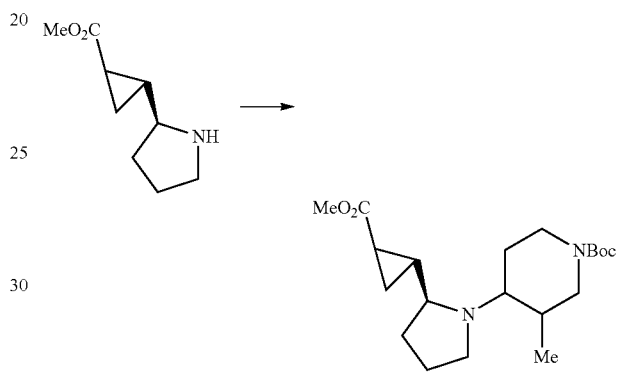

The synthesis accomplished according to the procedures outlined in Example 12, Step 6, substituting methyl (2R)-2-((S)-pyrrolidin-2-yl)cyclopropane-1-carboxylate for pyrrolidine.

The product was isolated by flash column chromatography (silica gel, 0 to 20% methanol in DCM gradient).

Step 3. (2R)-2-((2S)-1-(3-Methylpiperidin-4-yl)pyrrolidin-2-yl)cyclopropane-1-carboxylic acid

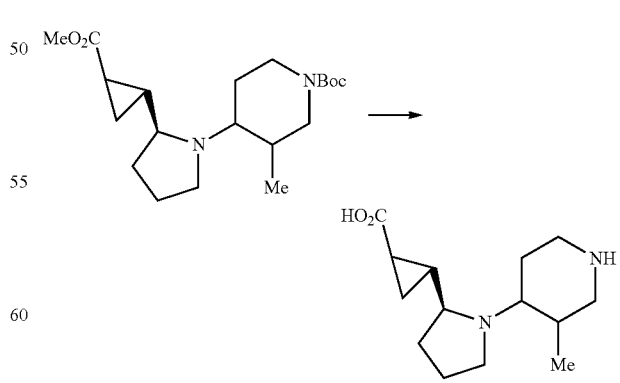

The title compound was synthesized according to the procedure outlined in Example 37, Step 2 to give the title compound as the HCl salt.

Step 4. (2R)-2-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)cyclopropane-1-carboxylic acid

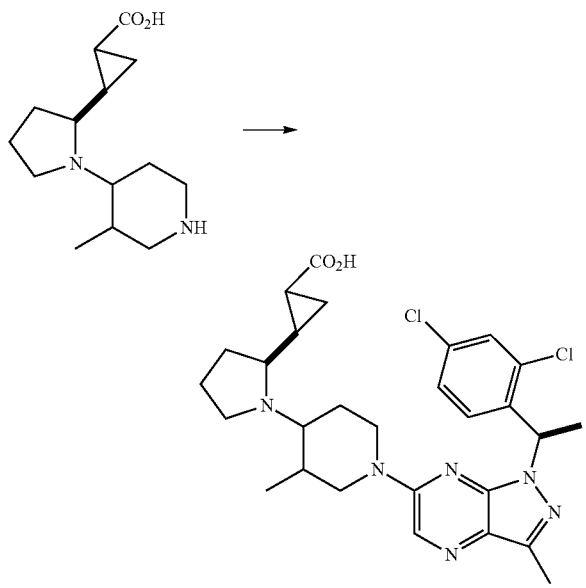

The title compound was synthesized analogously to the procedures outlined in Example 12, Step 8, substituting (2R)-2-((2S)-1-(3-methylpiperidin-4-yl)pyrrolidin-2-yl)cyclopropane-1-carboxylic acid (Example 54, Step 3) for 3-methyl-4-(pyrrolidin-1-yl)piperidine hydrochloride (Example 12, Step 7), and DMSO for DMF. The crude material was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the trifluoroacetate salt as the first eluting set of isomers as a 2:1 mixture of diastereomers. $^1$H NMR (400 MHz, CD$_3$OD, trifluoroacetic acid salt) δ 8.28 (s, 1H), 7.44 (dt, J=16.2, 5.3 Hz, 2H), 7.28 (dd, J=8.5, 2.2 Hz, 1H), 6.32 (q, J=7.1 Hz, 1H), 4.76 (s, 1H), 4.61 (d, J=13.9 Hz, 1H), 3.80-3.41 (m, 4H), 3.27-3.09 (m, 2H), 2.99 (s, 1H), 2.60 (d, J=41.8 Hz, 1H), 2.51 (s, 3H), 2.31 (s, 1H), 2.07 (dd, J=54.6, 22.8 Hz, 6H), 1.88 (d, J=7.1 Hz, 3H), 1.75 (s, 1H), 1.45-1.27 (m, 1H), 1.08 (d, J=7.2 Hz, 3H); m/z 557.1 (M+H$^+$).

Example 55

3-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-2-methoxypropanoic acid 2,2,2-trifluoroacetae

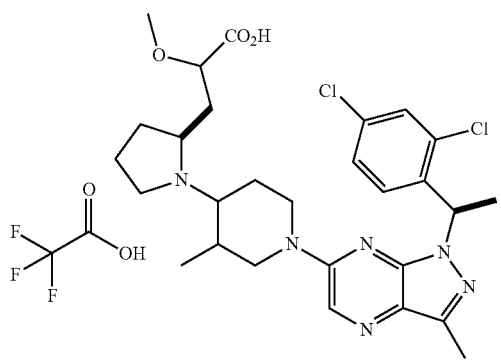

Step 1. Tert-butyl (2S)-2-(2-hydroxy-3-methoxy-3-oxopropyl)pyrrolidine-1-carboxylate

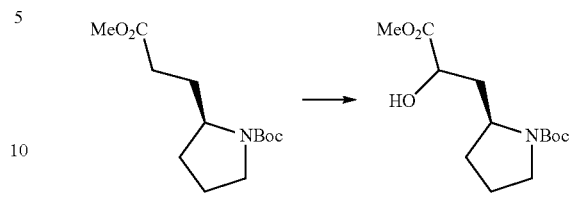

To tert-butyl (S)-2-(3-methoxy-3-oxopropyl)pyrrolidine-1-carboxylate (Example 46, Step 2, 514 mg, 2.0 mmol, 1.0 eq) in THF (12 mL) at −78° C. under inert atmosphere was added KHMDS (0.5 M in toluene, 4.8 mL, 1.2 eq). The mixture was stirred for 30 min, then 2-(phenylsulfonyl)-3-phenyl-oxaziridine (627 mg, 1.2 eq) was added as a solution in THF (4 mL). The reaction mixture was stirred for 2 h, maintaining the temperature at −78° C. before being quenched with saturated aq. ammonium chloride (25 mL). The mixture was allowed to warm to room temperature before being extracted with ethyl acetate (50 mL) and the organic layers were dried over sodium sulfate, filtered, and concentrated in vacuo. The residue was purified by flash column chromatography (silica gel, 0 to 20% methyl tert-butyl ether in dichloromethane gradient) to afford a major diastereomer (399 mg) and a minor diastereomer (102 mg) in separate fractions. The major diastereomer was used in the subsequent steps.

Step 2. Tert-butyl (2S)-2-(2,3-dimethoxy-3-oxopropyl)pyrrolidine-1-carboxylate

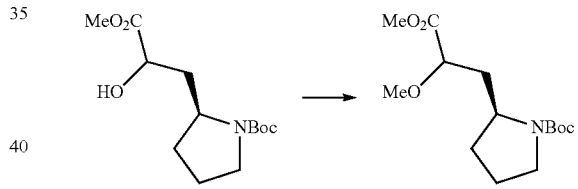

To the major diastereomer of alcohol from the previous step (Example 55, Step 1; 186 mg, 0.681 mmol, 1.0 eq) in acetonitrile (3.4 mL) was added silver(I) oxide (474 mg, 3.0 eq), methyl iodide (0.17 mL, 4.0 eq), and 4 Å molecular sieves (190 mg). The mixture was stirred for 24 h before being filtered over celite with ethyl acetate (50 mL) and concentrated in vacuo. The residue was purified by flash column chromatography (silica gel, 10 to 100% ethyl acetate in hexanes gradient) to afford the methyl ether (128 mg, 65% yield).

Step 3. Tert-butyl 4-((2S)-2-(2,3-dimethoxy-3-oxopropyl)pyrrolidin-1-yl)-3-methylpiperidine-1-carboxylate

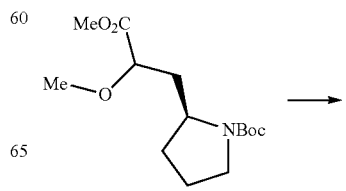

-continued

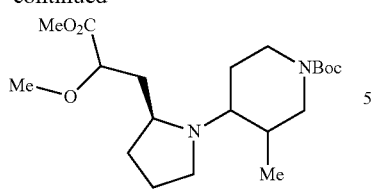

To the methyl ether (Example 55, Step 2, 128 mg, 0.45 mmol) was added 4M HCl in 1,4-dioxane (2 mL). The mixture was allowed to stir for 1 h before being concentrated in vacuo. The mixture was taken up in methanol (10 mL) and filtered through PL-HCO3 MP-Resin (~1.8 mmol/g, 0.5 g) and concentrated in vacuo to afford the free amine as a crystalline white solid. The synthesis of the title compound was finished according to the procedures outlined in Example 12, Step 6, substituting methyl 2-methoxy-3-((S)-pyrrolidin-2-yl)propanoate for pyrrolidine. The product was isolated by flash column chromatography (silica gel, 30 to 100% ethyl acetate in hexanes).

Step 4. 2-Methoxy-3-((2S)-1-(3-methylpiperidin-4-yl)pyrrolidin-2-yl)propanoic acid

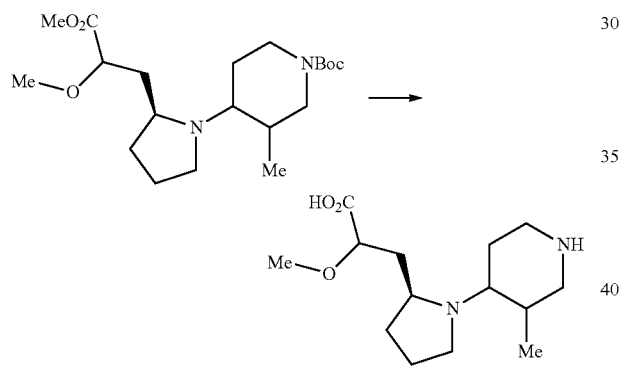

The title compound was synthesized according to the procedure outlined in Example 37, Step 2 to give the compound as the HCl salt.

Step 5. 3-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-2-methoxypropanoic acid 2,2,2-trifluoroacetae

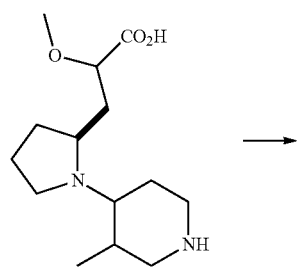

-continued

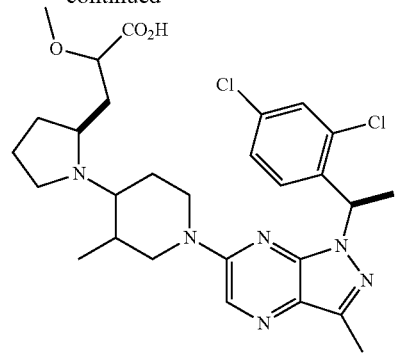

The title compound was synthesized analogously to the procedures outlined in Example 12, Step 8, substituting (2-methoxy-3-((2S)-1-(3-methylpiperidin-4-yl)pyrrolidin-2-yl)propanoic acid (Example 55, Step 4) for 3-methyl-4-(pyrrolidin-1-yl)piperidine hydrochloride (Example 12, Step 7), and DMSO for DMF. The crude material was purified by reverse phase preparative HPLC (Gemini-NX, 10 μm, 250× 30 mm, C18 column (Phenomenex, Torrance, Calif.), eluent: 0 to 100% acetonitrile in water, both eluents containing 0.1% trifluoroacetic acid, gradient elution over 30 min) to afford the trifluoroacetate salt as the first eluting set of isomers as a 10:1 mixture of diastereomers. $^1$H NMR (400 MHz, CD$_3$CN, trifluoroacetic acid salt) δ 8.24 (s, 1H), 8.14 (br s, 2H), 7.48 (dd, J=11.0, 5.3 Hz, 2H), 7.29 (dd, J=8.5, 2.1 Hz, 1H), 6.31 (q, J=6.9 Hz, 1H), 4.61 (dd, J=45.3, 12.6 Hz, 2H), 4.24-4.04 (m, 2H), 3.73-3.56 (m, 2H), 3.50-3.39 (m, 1H), 3.44 (s, 3H), 3.38-3.24 (m, 1H), 3.09 (br d, J=14.0 Hz, 1H), 2.95 (tm, J=12.9 Hz, 1H), 2.47 (s, 3H), 2.40-2.25 (m, 2H), 2.23-2.00 (m, 6H), 1.87 (d, J=7.1 Hz, 3H), 1.01 (d, J=6.9 Hz, 3H); m/z 575.1 (M+H$^+$).

Example 56

3-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-2-fluoropropanoic acid 2,2,2-trifluoroacetate (major diastereomer)

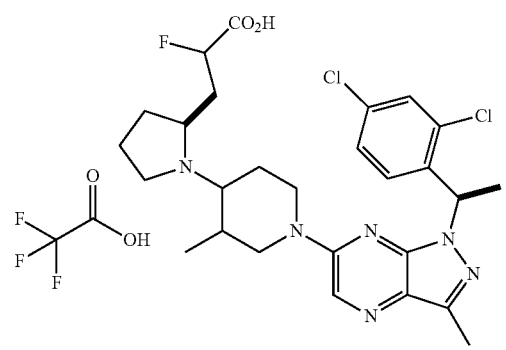

Step 1. Tert-butyl (2S)-2-(2-fluoro-3-methoxy-3-oxopropyl)pyrrolidine-1-carboxylate

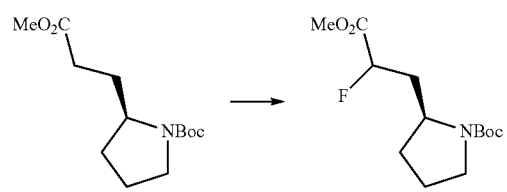 [SMILES: COC(=O)CC[C@@H]1CCCN1C(=O)OC(C)(C)C ; COC(=O)C(F)C[C@@H]1CCCN1C(=O)OC(C)(C)C]

To tert-butyl (S)-2-(3-methoxy-3-oxopropyl)pyrrolidine-1-carboxylate (Example 46, Step 2, 514 mg, 2.0 mmol, 1.0 equiv) in THF (12 mL) at −78° C. under inert atmosphere was added KHMDS (0.5 M in toluene, 4.8 mL, 1.2 equiv). The mixture was stirred for 30 min, then NFSI (757 mg, 1.2 equiv). The reaction mixture was stirred for 1 h before being raised to room temperature and stirred overnight. The reaction mixture was quenched with saturated aq. ammonium chloride (25 mL). The mixture was extracted with ethyl acetate (50 mL) and the organic layers were dried over sodium sulfate, filtered, and concentrated in vacuo. The residue was purified by flash column chromatography (silica gel, 5 to 10% methyl tert-butyl ether in dichloromethane) to afford a mixture of fluoroester diastereomers (250 mg, 3.9:1 dr). The diastereomers were separated by iterative preparatory chiral HPLC (Chiralpak® OZ-H column, Daicel, Corporation, West Chester, Pa., eluent: 3% ethanol in heptanes, 30 min, 20 mL/min) to afford the major (139 mg) and minor (22 mg) isomers, which were used independently in the following steps.

Step 2. Methyl 2-fluoro-3-((2S)-1-(3-methylpiperidin-4-yl)pyrrolidin-2-yl)propanoate

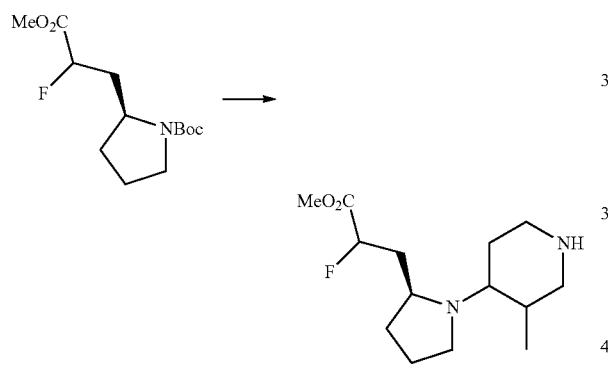

The major diastereomer from Example 56, Step 1 pyrrolidine (139 mg, 0.5 mmol) was treated with 4M HCl in 1,4-dioxane solution (1 mL) and stirred for 1.5 h. The mixture was concentrated in vacuo and the HCl salt. The title compound was then synthesized from this amine according to the procedures outlined in Example 12, Step 6, and Example 2, Step 2 to give the compound as the HCl salt.

Step 3. Methyl 3-((2S)-1-(1-(1-((R)-1-(2,4-dichlorophenyl)ethyl)-3-methyl-1H-pyrazolo[3,4-b]pyrazin-6-yl)-3-methylpiperidin-4-yl)pyrrolidin-2-yl)-2-fluoropropanoate

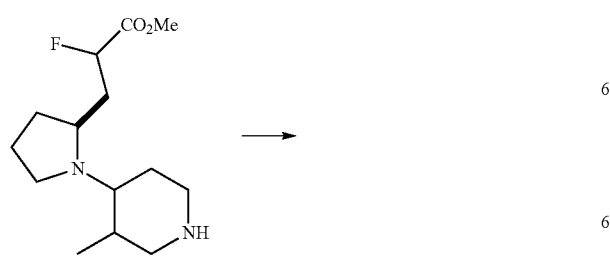

-continued

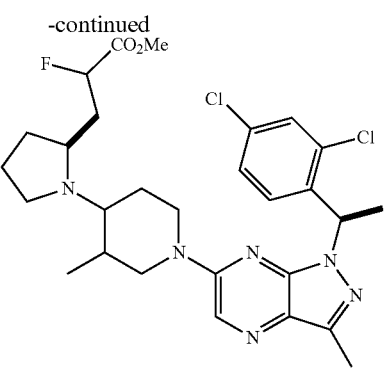

The title compound was synthesized analogously to the procedures outlined in Example 12, Step 8, substituting methyl 2-fluoro-3-((2S)-1-(3-methylpiperidin-4-yl)pyrrolidin-2-yl)propanoate (Example 56, Step 2) for 3-methyl-4-(pyrrolidin-1-yl)piperidine hydrochloride (Example 12, Step 7), and DMSO for DMF. The mixture was diluted with water (1.5 mL) and trifluoroacetic acid (0.5 mL) and extracted with 1 mL of 10% ethyl acetate in hexanes. The aqueous layer was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the ester as the trifluoroacetate salt. The mixture was basified by filtration over PL-HCO3 MP resin (1.8 mmol/g, 1 g) with ethanol and the filtrate was concentrated under reduced pressure. The residue was further purified using chiral HPLC sing Chiralpak® IF-3 column (Daicel, Corporation, West Chester, Pa., eluent: 5% ethanol in heptanes, both eluents containing 0.1% $Et_2NH$, 30 min, 20 mL/min) to give the desired ester as a single isomer (15 mg).

Step 4. 3-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-2-fluoropropanoic acid 2,2,2-trifluoroacetate

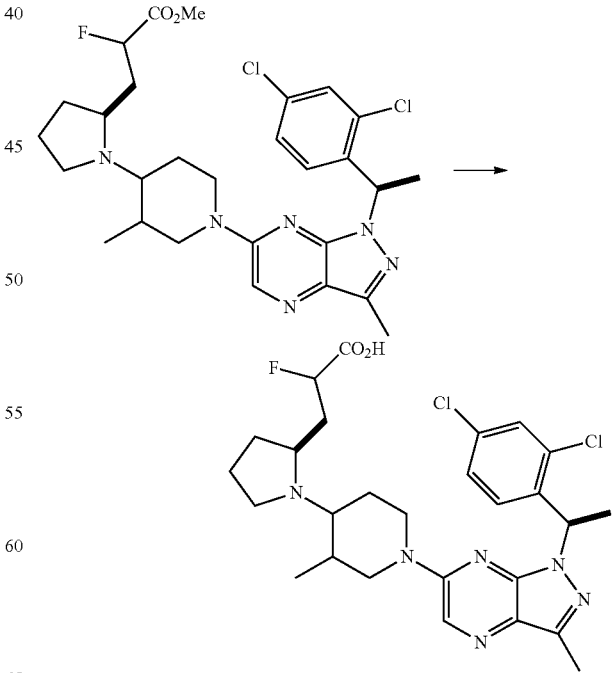

To methyl 3-((2S)-1-(1-(1-((R)-1-(2,4-dichlorophenyl)ethyl)-3-methyl-1H-pyrazolo[3,4-b]pyrazin-6-yl)-3-methylpiperidin-4-yl)pyrrolidin-2-yl)-2-fluoropropanoate (Example 56, Step 3) was dissolved in 1,4-dioxane (1 mL) and treated with 4M aq. LiOH (0.25 mL) for 1 h. The mixture was acidified with 3M aq. HCl (3 mL) and purified by reverse phase preparative HPLC (Gemini-NX, 10 μm, 250× 30 mm, C18 column (Phenomenex, Torrance, Calif.), eluent: 0 to 100% acetonitrile in water, both eluents containing 0.1% trifluoroacetic acid, gradient elution over 30 min) to afford the title compound as the trifluoroacetate salt. $^1$H NMR (400 MHz, CD$_3$OD, trifluoroacetic acid salt) δ 8.27 (s, 1H), 7.46 (d, J=2.1 Hz, 1H), 7.41 (d, J=8.5 Hz, 1H), 7.27 (dd, J=8.5, 2.1 Hz, 1H), 6.31 (q, J=7.4 Hz, 1H), 5.02 (br d, J=47.5 Hz, 1H), 4.80-4.70 (m, 1H), 4.65-4.56 (m, 1H), 4.24-4.11 (m, 1H), 3.60-3.49 (m, 1H), 3.46-3.23 (m, 3H), 3.07-2.92 (m, 1H), 2.51 (s, 3H), 2.59-2.48 (m, 1H), 2.44-1.92 (m, 8H), 1.88 (d, J=7.1 Hz, 3H), 1.05 (d, J=6.8 Hz, 3H); m/z 563.0 (M+H$^+$).

Example 57

3-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-2-fluoropropanoic acid 2,2,2-trifluoroacetate (minor diastereomer)

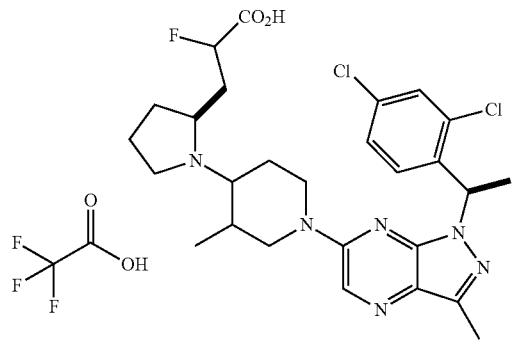 [SMILES: O=C(O)C(F)(F)F ; Cc1nn([C@H](C)c2ccc(Cl)cc2Cl)c2nc(N3CCC(N4CCC[C@H]4CC(F)C(=O)O)C(C)C3)cnc12]

The title compound was synthesized according to the procedures outlined in Example 56, Steps 2-4, starting with the minor diastereomer obtained from Example 56, Step 1. $^1$H NMR (400 MHz, CD$_3$OD, trifluoroacetic acid salt) δ 8.27 (s, 1H), 7.46 (d, J=2.0 Hz, 1H), 7.41 (d, J=8.3 Hz, 1H), 7.27 (dd, J=8.6, 2.3 Hz, 1H), 6.31 (q, J=7.2 Hz, 1H), 5.08-4.68 (m, 2H), 4.64-4.54 (m, 1H), 4.11-4.01 (m, 1H), 3.64-3.52 (m, 1H), 3.38-3.05 (m, 3H), 3.03-2.93 (m, 1H), 2.51 (s, 3H), 2.53-1.91 (m, 9H), 1.88 (d, J=7.4 Hz, 3H), 1.07 (d, J=6.9 Hz, 3H); m/z 563.0 (M+H$^+$).

Example 58

3-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-2,2-difluoropropanoic acid 2,2,2-trifluoroacetate

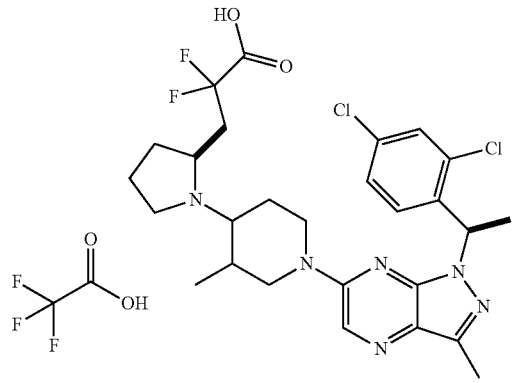 [SMILES: O=C(O)C(F)(F)F ; Cc1nn([C@H](C)c2ccc(Cl)cc2Cl)c2nc(N3CCC(N4CCC[C@H]4CC(F)(F)C(=O)O)C(C)C3)cnc12]

Step 1. Methyl 2,2-difluoro-3-((2S)-1-(3-methylpiperidin-4-yl)pyrrolidin-2-yl)propanoate

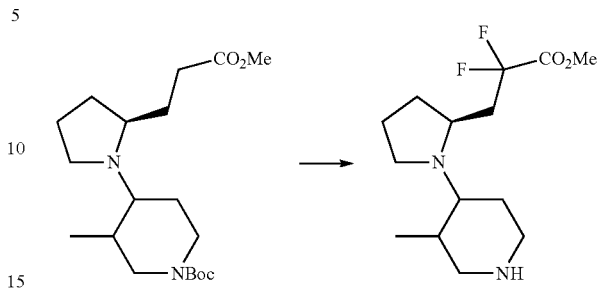

To tert-butyl 4-((S)-2-(3-methoxy-3-oxopropyl)pyrrolidin-1-yl)-3-methylpiperidine-1-carboxylate (Example 46, Step 3, 1.26 g, 4.9 mmol, 1.0 eq) in THF (25 mL) at −78° C. under inert atmosphere was added KHMDS (0.5 M, 10.8 mL, 1.1 eq). The mixture was stirred for 30 min, prior to the addition of NFSI (1.7 g, 1.1 eq). The reaction mixture was stirred for 1 h before being raised to room temperature and stirred overnight. The reaction mixture was quenched with saturated aq. ammonium chloride (50 mL). The mixture was extracted with ethyl acetate (100 mL) and the organic layers were dried over sodium sulfate, filtered, and concentrated in vacuo. The residue was purified by flash column chromatography (silica gel, 30 to 100% ethyl acetate in hexanes gradient) to afford a sample of difluoroester diastereomers as a minor product (61 mg). The product was treated with 4M HCl in 1,4-dioxane solution (1 mL) and stirred for 1.5 h. The mixture was concentrated in vacuo and the HCl salt was used in the following step without further purification.

Step 2. Methyl 3-((2S)-1-(1-(1-((R)-1-(2,4-dichlorophenyl)ethyl)-3-methyl-1H-pyrazolo[3,4-b]pyrazin-6-yl)-3-methylpiperidin-4-yl)pyrrolidin-2-yl)-2,2-difluoropropanoate

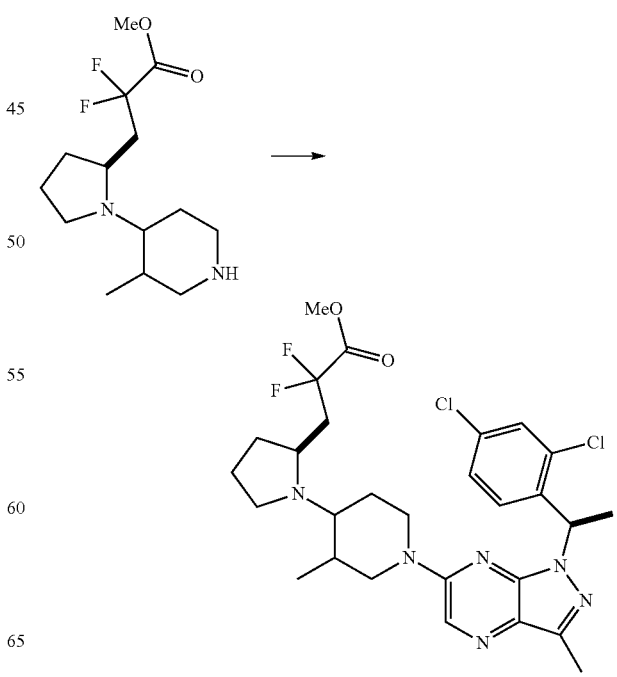

389

Then the title compound was synthesized analogously to the procedure outlined in Example 12, Step 8, substituting methyl 2,2-difluoro-3-((2S)-1-(3-methylpiperidin-4-yl)pyrrolidin-2-yl)propanoate (Example 58, Step 1) for 3-methyl-4-(pyrrolidin-1-yl)piperidine hydrochloride (Example 12, Step 7). The crude material was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the title compound as the trifluoroacetate salt.

Step 3. 3-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-2,2-difluoropropanoic acid 2,2,2-trifluoroacetate

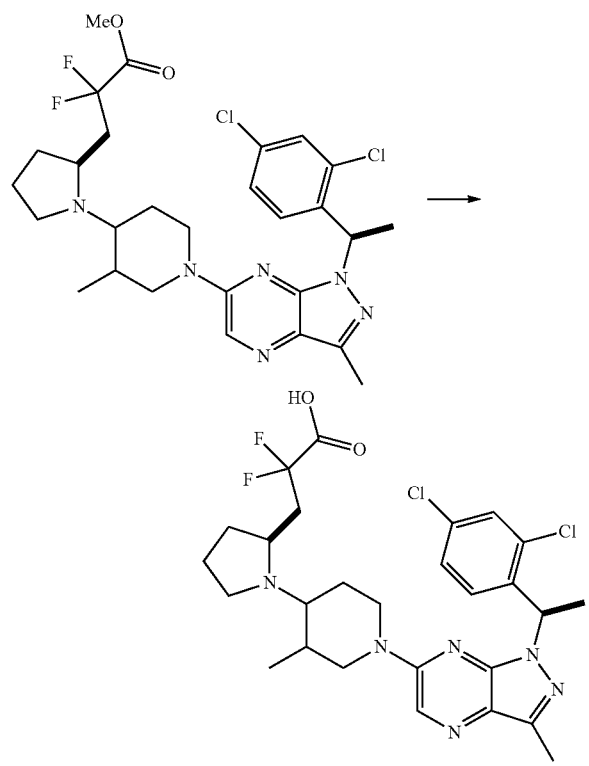

The title compound was synthesized from methyl 3-((2S)-1-(1-(1-((R)-1-(2,4-dichlorophenyl)ethyl)-3-methyl-1H-pyrazolo[3,4-b]pyrazin-6-yl)-3-methylpiperidin-4-yl)pyrrolidin-2-yl)-2,2-difluoropropanoate (Example 58, Step 2) using the procedure outlined in Example 56, Step 4 to give the product as a mixture of diastereomers. $^1$H NMR (400 MHz, CD$_3$OD, trifluoroacetic acid salt) δ 8.26 (s, 1H), 7.46 (d, J=2.1 Hz, 1H), 7.43 (d, J=8.6 Hz, 1H), 7.27 (q, J=8.4 Hz, 1H), 6.30 (q, J=7.0 Hz, 1H), 4.75-4.66 (m, 1H), 4.66-4.57 (m, 1H), 4.27-4.15 (m, 1H), 3.59-3.07 (m, 4H), 3.04-2.91 (m, 1H), 2.61-2.51 (m, 1H), 2.50 (s, 3H), 2.46-1.91 (m, 8H), 1.88 (d, J=7.0 Hz, 3H), 1.06 (d, J=7.1 Hz, 3H); m/z 581.1 (M+H$^+$).

Example 59

3-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-2-hydroxypropanoic acid 2,2,2-trifluoroacetate

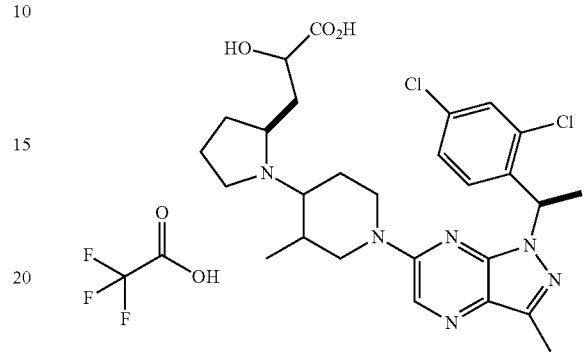

Step 1. Tert-butyl (2S)-2-(2-(benzyloxy)-3-methoxy-3-oxopropyl)pyrrolidine-1-carboxylate

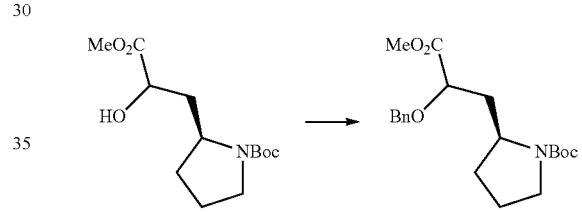

To the major diastereomer of tert-butyl (2S)-2-(2-hydroxy-3-methoxy-3-oxopropyl)pyrrolidine-1-carboxylate (Example 55, Step 1, 273 mg, 1.0 mmol) in dichloromethane (10 mL) was added benzyl 2,2,2-trichloroacetimidate (0.2 mL, 1.1 eq) and trifluoromethanesulfonic acid (1 drop). The mixture was allowed to stir for 2 h before being quenched with saturated aq. sodium bicarbonate solution (10 mL). The aqueous layer was extracted with ethyl acetate (25 mL) and the combined organic layers were dried over sodium sulfate, filtered, and concentrated in vacuo. The crude residue was purified by flash column chromatography (silica gel, 10 to 40% ethyl acetate in hexanes) to afford the title compound (169 mg, 47% yield).

Step 2. Tert-butyl 4-((2S)-2-(2-(benzyloxy)-3-methoxy-3-oxopropyl)pyrrolidin-1-yl)-3-methylpiperidine-1-carboxylate

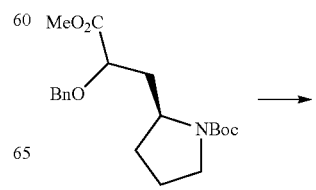

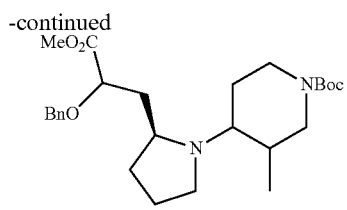

To the product of Example 59, Step 1, was added 4M HCl in 1,4-dioxane solution (2 mL) and stirred for 3 h. The mixture was concentrated in vacuo and the HCl salt was used in the following step. The title compound was obtained using the procedure outlined in Example 12, Step 6, substituting methyl 2-(benzyloxy)-3-((S)-pyrrolidin-2-yl)propanoate for pyrrolidine. The product was isolated as a mixture of diastereomers by flash column chromatography (silica gel, 30 to 100% ethyl acetate in hexanes).

Step 3. Methyl 2-hydroxy-3-((2S)-1-(3-methylpiperidin-4-yl)pyrrolidin-2-yl)propanoate

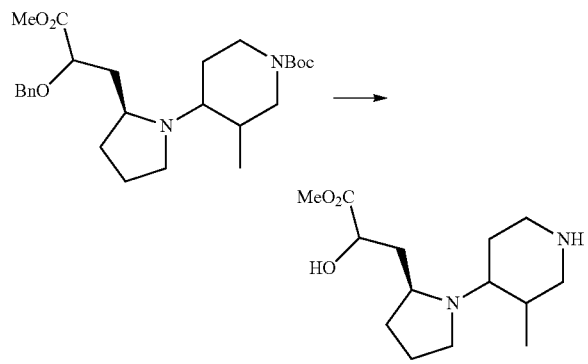

The product from Example 59, Step 2 (152 mg) was dissolved in methanol (3 mL) and 5% Pd/C (150 mg) was added. The mixture was stirred under hydrogen atmosphere overnight. Celite (1 g) was added, and the slurry was filtered over celite, washing with ethyl acetate. The filtrate was concentrated and the residue was used in the following step. This compound was then treated with 4M HCl in 1,4-dioxane solution (1 mL) and methanol (0.25 mL) and stirred for 0.5 h. The mixture was concentrated in vacuo and used in the following step without further purification.

Step 4. Methyl 3-((2S)-1-(1-(1-((R)-1-(2,4-dichlorophenyl)ethyl)-3-methyl-1H-pyrazolo[3,4-b]pyrazin-6-yl)-3-methylpiperidin-4-yl)pyrrolidin-2-yl)-2-hydroxypropanoate

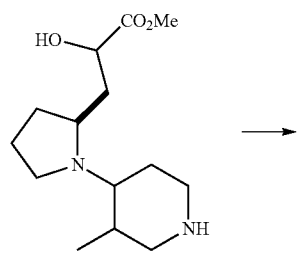

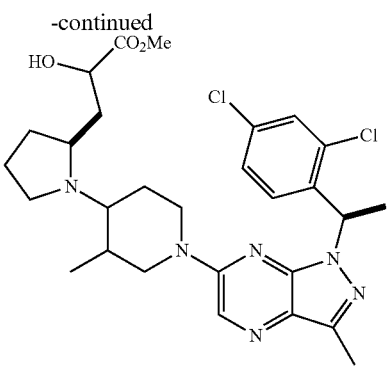

Then the title compound was synthesized analogously to the procedure outlined in Example 12, Step 8, substituting methyl 2-hydroxy-3-((2S)-1-(3-methylpiperidin-4-yl)pyrrolidin-2-yl)propanoate (Example 59, Step 3) for 3-methyl-4-(pyrrolidin-1-yl)piperidine hydrochloride (Example 12, Step 7). The crude material was purified by reverse phase preparative HPLC (Gemini-NX, 10 µm, 250×30 mm, C18 column (Phenomenex, Torrance, Calif.), eluent: 0 to 100% acetonitrile in water, both eluents containing 0.1% trifluoroacetic acid, gradient elution over 30 min) to afford the title compound as the trifluoroacetate salt.

Step 5. 3-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)-2-hydroxypropanoic acid 2,2,2-trifluoroacetate

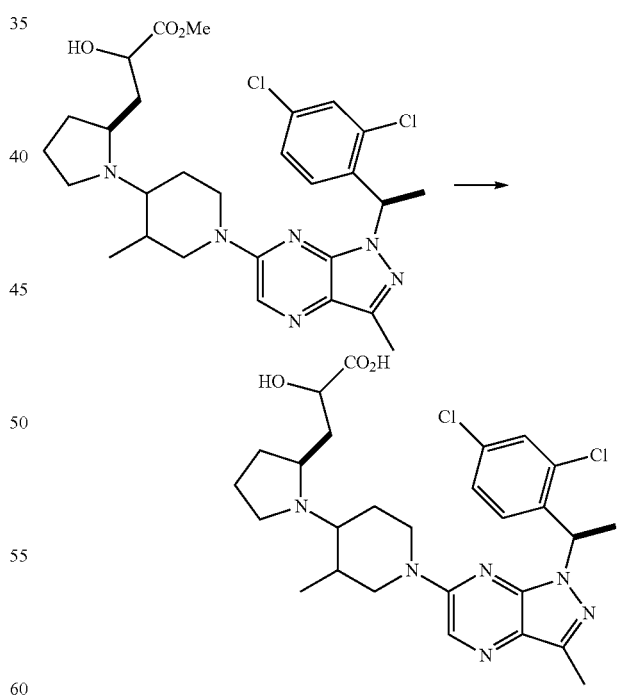

The title compound was synthesized from methyl 3-((2S)-1-(1-(1-((R)-1-(2,4-dichlorophenyl)ethyl)-3-methyl-1H-pyrazolo[3,4-b]pyrazin-6-yl)-3-methylpiperidin-4-yl)pyrrolidin-2-yl)-2-hydroxypropanoate (Example 59, Step 4) using the procedure outlined in Example 56, Step 4 to give the product as a mixture of diastereomers. ¹H NMR (400 MHz, CD$_3$CN, trifluoroacetic acid salt) δ 8.64 (br s, 1H), 8.23 (s, J=13.7 Hz, 1H), 7.52-7.44 (m, 2H), 7.29 (d, J=7.5 Hz, 1H), 6.31 (q, J=7.0 Hz, 1H), 4.64 (br d, J=11.8 Hz, 1H), 4.59-4.44 (m, 2H), 4.22-4.10 (m, 1H), 3.70-3.57 (m, 1H), 3.51-3.38 (m, 1H), 3.35-3.22 (m, 1H), 3.08 (d, J=13.6 Hz, 1H), 2.94 (t, J=13.1 Hz, 1H), 2.47 (s, 3H), 2.71-1.94 (m, 8H), 1.87 (d, J=7.0 Hz, 3H), 1.00 (d, J=6.3 Hz, 3H); m/z 561.1 (M+H$^+$).

Example 60

3-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)butanoic acid 2,2,2-trifluoroacetate

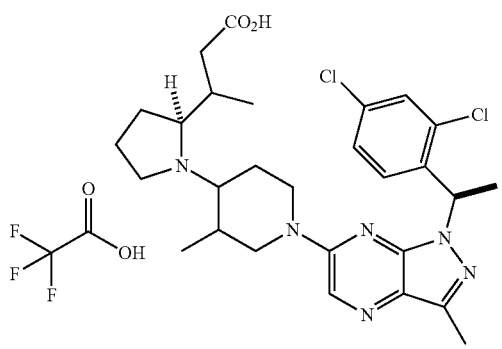

Step 1. Methyl 3-((S)-pyrrolidin-2-yl)butanoate

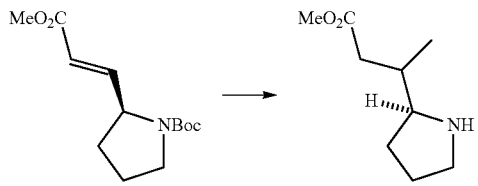 [SMILES: COC(=O)/C=C/[C@@H]1CCCN1C(=O)OC(C)(C)C ; COC(=O)CC(C)[C@@H]1CCCN1]

To CuI (822 mg, 4.3 mmol, 1.1 eq) in THF (13 mL) at −10° C. under inert atmosphere was added MeLi (3.1M in diglyme, 2.8 mL, 2.2 eq). The mixture was stirred for 15 min before being cooled to −78° C. Then, TMSCl (0.55 mL) was added, followed by dropwise addition of tert-butyl (S,E)-2-(3-methoxy-3-oxoprop-1-en-1-yl)pyrrolidine-1-carboxylate (Example 46, Step 1, 1.0 g, 3.9 mmol, 1.0 eq) in 3 mL THF over 15 min. After 1 h, the mixture was warmed to −40° C. and quenched with a 9:1 mixture of saturated aq. ammonium chloride to 30% aq. ammonia solutions (50 mL). The mixture was extracted with methyl tert-butyl ether (100 mL), filtered over celite, and washed with a 9:1 mixture of saturated aq. ammonium chloride and 30% aq. ammonia solutions (4×10 mL). The organic layer was dried over sodium sulfate, filtered, and concentrated in vacuo. The crude residue was purified by flash column chromatography (5 to 25% ethyl acetate in hexanes) to afford a mixture of diastereomers (370 mg). The mixture of diastereomers was purified by iterative preparatory chiral HPLC using a Chiralpak® IF-3 column (Daicel, Corporation, West Chester, Pa., eluent: 5% ethanol in heptanes, 30 min, 20 mL/min) to afford the major (245 mg) and minor (53 mg) isomers. The minor isomer was used in the following steps. The minor diastereomer (53 mg, 0.2 mmol) was treated with 4M HCl in 1,4-dioxane solution (1 mL) and stirred for 1 h. The mixture was concentrated in vacuo and the HCl salt was used in the following step without further purification.

Step 2. Methyl 3-((2S)-1-(3-methylpiperidin-4-yl)pyrrolidin-2-yl)butanoate

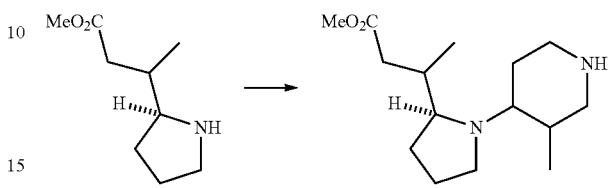

The title compound was synthesized according to the procedures outlined in Example 12, Step 6, and Example 2, Step 2 substituting methyl 3-((S)-pyrrolidin-2-yl)butanoate for pyrrolidine.

Step 3. Methyl 3-((2S)-1-(1-(1-((R)-1-(2,4-dichlorophenyl)ethyl)-3-methyl-1H-pyrazolo[3,4-b]pyrazin-6-yl)-3-methylpiperidin-4-yl)pyrrolidin-2-yl)butanoate

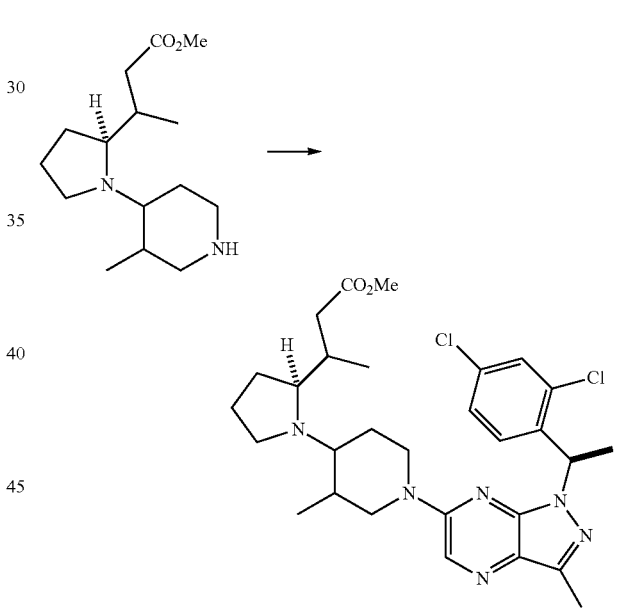

The title compound was synthesized according to the procedure outlined in Example 12, Step 8, substituting methyl 2-hydroxy-3-((2S)-1-(3-methylpiperidin-4-yl)pyrrolidin-2-yl)propanoate (Example 60, Step 2) for 3-methyl-4-(pyrrolidin-1-yl)piperidine hydrochloride (Example 12, Step 7). The aqueous layer was purified by reverse phase preparative HPLC (Gemini-NX, 10 µm, 250×30 mm, C18 column (Phenomenex, Torrance, Calif.), eluent: 0 to 100% acetonitrile in water, both eluents containing 0.1% trifluoroacetic acid, gradient elution over 30 min) to afford the ester as the trifluoroacetate salt. The mixture was basified by filtration over PL-HCO3 MP resin (1.8 mmol/g, 1 g) with ethanol and the filtrate was concentrated under reduced pressure. The residue was further purified using chiral using Chiralpak® OZ-H column (Daicel, Corporation, West Chester, Pa., eluent: 5% ethanol in heptanes, both eluents containing 0.1% Et$_2$NH 30 min, 20 mL/min) to give the title compound as a single isomer (15 mg).

Step 4. 3-((2S)-1-(1-(1-((R)-1-(2,4-Dichlorophenyl)ethyl)-3-methyl-1H-pyrazolo[3,4-b]pyrazin-6-yl)-3-methylpiperidin-4-yl)pyrrolidin-2-yl)butanoic acid 2,2,2-trifluoroacetate

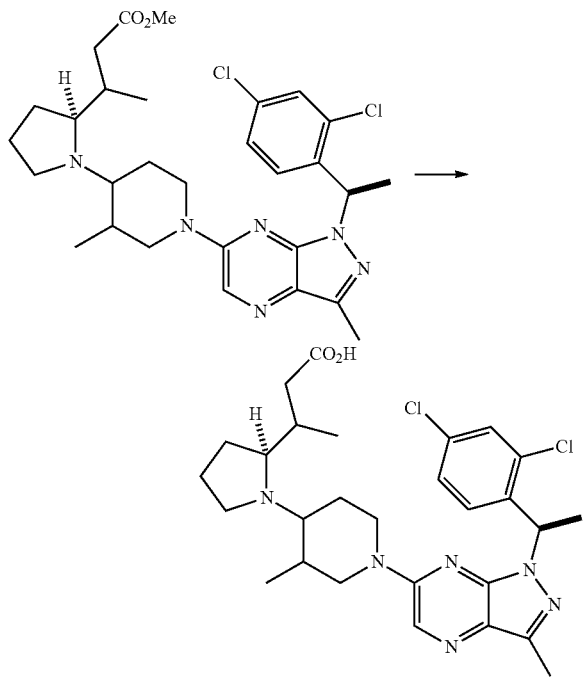

The title compound was synthesized from methyl 3-((2S)-1-(1-(1-((R)-1-(2,4-dichlorophenyl)ethyl)-3-methyl-1H-pyrazolo[3,4-b]pyrazin-6-yl)-3-methylpiperidin-4-yl)pyrrolidin-2-yl)butanoate (Example 60, Step 3) using the procedure outlined in Example 56, Step 4 to give the product. $^1$H NMR (400 MHz, CD$_3$OD, trifluoroacetic acid salt) δ 8.27 (s, 1H), 7.46 (d, J=2.2 Hz, 1H), 7.42 (d, J=8.5 Hz, 1H), 7.28 (dd, J=8.5, 2.1 Hz, 1H), 6.32 (q, J=7.1 Hz, 1H), 4.81-4.72 (m, 1H), 4.66-4.55 (m, 1H), 4.01-3.93 (m, 1H), 3.64-3.56 (m, 1H), 3.56-3.26 (m, 4H), 3.19-3.13 (m, 1H), 3.05-2.95 (m, 1H), 2.67-2.55 (m, 1H), 2.55-2.49 (m, 1H), 2.51 (s, 3H), 2.47-2.30 (m, 2H), 2.26-2.15 (m, 1H), 2.08 (s, 2H), 1.99-1.90 (m, 1H), 1.88 (d, J=7.1 Hz, 3H), 1.10 (d, J=6.7 Hz, 3H), 1.07 (d, J=7.0 Hz, 3H); m/z 559.1 (M+H$^+$).

Example 61

1-((R)-1-(2,4-Dichlorophenyl)ethyl)-6-(4-fluoro-3'-methyl-[1,4'-bipiperidin]-1'-yl)-3-methyl-1H-pyrazolo[3,4-b]pyrazine hydrochloride

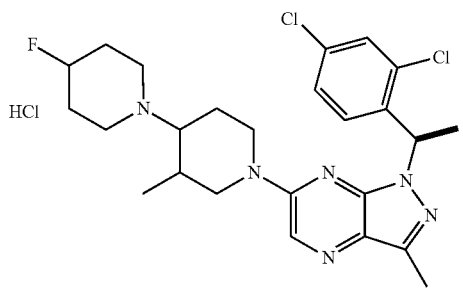 [SMILES: Cl ; Cc1nn([C@H](C)c2ccc(Cl)cc2Cl)c2nc(N3CCC(N4CCC(F)CC4)C(C)C3)cnc12]

Step 1. 4-Fluoro-3'-methyl-1,4'-bipiperidine

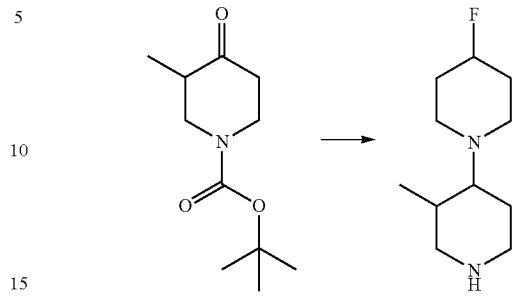

The title compound was synthesized analogously to the procedures outlined in Example 2, Step 1, substituting ethyl 3-(piperidin-3-yl)propanoate for piperidine. The product of this reaction was purified via column chromatography (20 to 100% ethyl acetate in hexanes) to give the product as a mixture of diastereomers. This mixture was then taken up in 4N HCl in 1,4-dioxane and stirred for 16 h. The solvent was then removed under reduced pressure to give the title compound as a hydrochloride salt.

Step 2. 1-((R)-1-(2,4-Dichlorophenyl)ethyl)-6-(4-fluoro-3'-methyl-[1,4'-bipiperidin]-1'-yl)-3-methyl-1H-pyrazolo[3,4-b]pyrazine hydrochloride

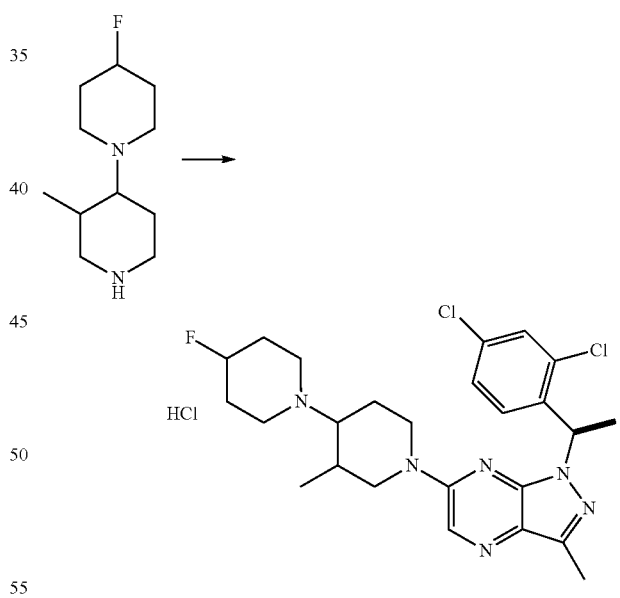

The title compound was synthesized by the procedure outlined in Example 12, Step 8, substituting 4-fluoro-3'-methyl-1,4'-bipiperidine hydrochloride for 3-methyl-4-(pyrrolidin-1-yl)piperidine hydrochloride. The residue was purified by silica gel chromatography (0 to 10% methanol in dichloromethane) to give the title compound as a mixture of diastereomers. The fractions containing the desired compound were collected and made acidic (pH ~2) with 2N HCl in diethyl ether. The volatiles were removed to yield the product as a mixture of diastereomers about the piperidine. $^1$H NMR (400 MHz, CD$_3$OD; HCl Salt): δ 8.41 (s, 1H), 7.57-7.10 (m, 3H), 6.43-6.15 (m, 1H), 5.12-4.65 (m, 1H), 3.93-3.49 (m, 3H), 3.43-3.10 (m, 4H), 2.89-2.43 (m, 5H), 2.42-1.75 (m, 10H), 1.20-1.00 (m, 3H); m/z 505.2 (M+H⁺).

Example 62

1-((R)-1-(2,4-Dichlorophenyl)ethyl)-6-(3-(hydroxymethyl)-[1,4'-bipiperidin]-1'-yl)-1H-pyrazolo[3,4-b]pyrazine-3-carbonitrile hydrochloride

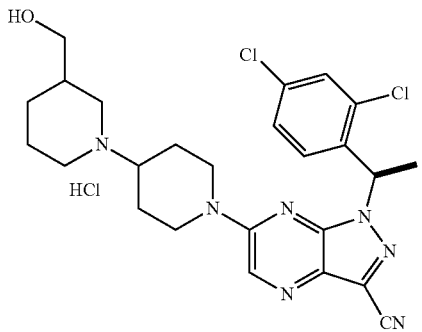 [SMILES: C[C@H](c1ccc(Cl)cc1Cl)n1nc(C#N)c2ncc(N3CCC(N4CCCC(CO)C4)CC3)nc21 ; Cl]

Step 1. [1,4'-Bipiperidin]-3-ylmethanol

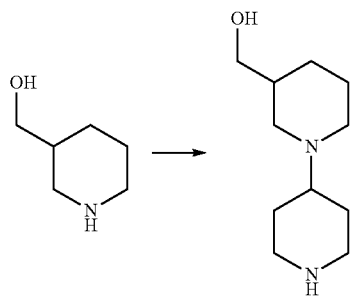 [SMILES: OCC1CCCNC1 ; OCC1CCCN(C2CCNCC2)C1]

The title compound was synthesized according to the procedures outlined in Example 2, Steps 1 and 2, substituting piperidin-3-ylmethanol for piperidine, and tert-butyl 4-oxopiperidine-1-carboxylate for tert-butyl 3-methyl-4-oxopiperidine-1-carboxylate.

Step 2. 1-((R)-1-(2,4-Dichlorophenyl)ethyl)-6-(3-(hydroxymethyl)-[1,4'-bipiperidin]-1'-yl)-1H-pyrazolo[3,4-b]pyrazine-3-carbonitrile hydrochloride

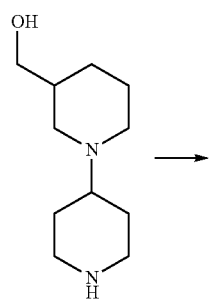

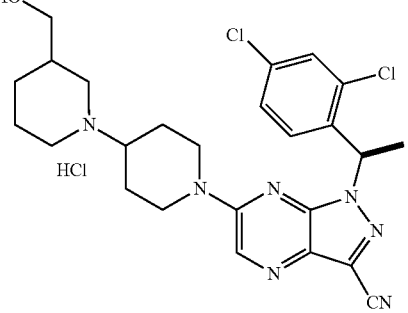

To a solution of [1,4'-bipiperidin]-3-ylmethanol trifluoroacetic acid salt (250 mg, 0.847 mmol) in DMSO (2.1 mL) was added diisopropylethylamine (0.295 mL, 1.69 mmol), and (R)-6-chloro-1-(1-(2,4-dichlorophenyl)ethyl)-1H-pyrazolo[3,4-b]pyrazine-3-carbonitrile (298 mg, 0.847 mmol). The reaction mixture was placed in a pre-heated block at 60° C. for 16 h. The reaction was diluted with saturated aq. sodium bicarbonate and ethyl acetate. The organic layer was separated, and the aqueous layer was extracted with ethyl acetate (2×). The combined organic layers were dried over magnesium sulfate, concentrated, and purified by silica gel chromatography, eluting with 5% to 10% methanol in dichloromethane to afford the title compound. The product was converted to the HCl salt by diluting with dichloromethane, treating with 1 M HCl in diethyl ether and concentrating to give the title compound as a mixture of diastereomers. ¹H-NMR (400 MHz; CD₃OD, HCl Salt): δ 8.50 (s, 1H), 7.48 (dd, J=2.1, 0.5 Hz, 1H), 7.39 (d, J=8.5 Hz, 1H), 7.31 (dd, J=8.5, 2.1 Hz, 1H), 6.47 (q, J=7.0 Hz, 1H), 4.86-4.67 (m, 2H), 3.53 (tdd, J=17.9, 12.1, 7.9 Hz, 5H), 3.11 (t, J=12.2 Hz, 2H), 2.99-2.85 (m, 1H), 2.78 (td, J=12.1, 6.4 Hz, 1H), 2.22 (d, J=10.8 Hz, 2H), 2.09-1.97 (m, 2H), 1.93 (d, J=7.1 Hz, 3H), 1.90-1.64 (m, 4H), 1.39-1.19 (m, 1H); m/z 514.2 (M+H⁺).

Example 63

(3R,4S)-1-(1-((R)-1-(2,4-Dichlorophenyl)ethyl)-3-methyl-1H-pyrazolo[3,4-b]pyrazin-6-yl)-4-((S)-2-(hydroxymethyl)pyrrolidin-1-yl)piperidine-3-carboxamide hydrochloride

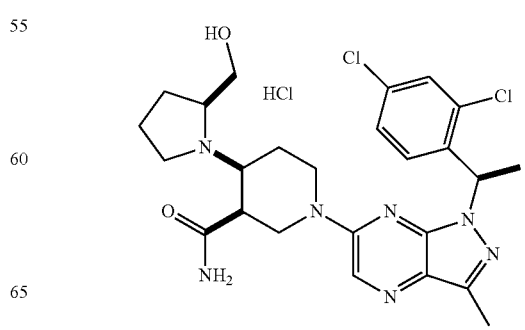

399

Step 1. Ethyl 4-((S)-2-(hydroxymethyl)pyrrolidin-1-yl)piperidine-3-carboxylate

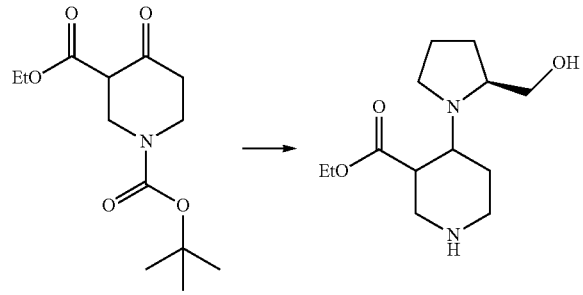 [SMILES: CCOC(=O)C1CN(C(=O)OC(C)(C)C)CCC1=O ; CCOC(=O)C1CNCCC1N1CCC[C@H]1CO]

The title compound was synthesized analogously to the procedures outlined in Example 2, Step 1, substituting 1-(tert-butyl) 3-ethyl 4-oxopiperidine-1,3-dicarboxylate for piperidine. The product of this reaction was purified via column chromatography (0 to 20% methanol in dichloromethane) to give the product as a mixture of diastereomers. This mixture was then taken up in 4N HCl in 1,4-dioxane and stirred for 16 h. The solvent was then removed under reduced pressure to give the title compound as a mixture of diastereomers as the hydrochloride salt.

Step 2. Ethyl 1-(1-((R)-1-(2,4-Dichlorophenyl)ethyl)-3-methyl-1H-pyrazolo[3,4-b]pyrazin-6-yl)-4-((S)-2-(hydroxymethyl)pyrrolidin-1-yl)piperidine-3-carboxylate

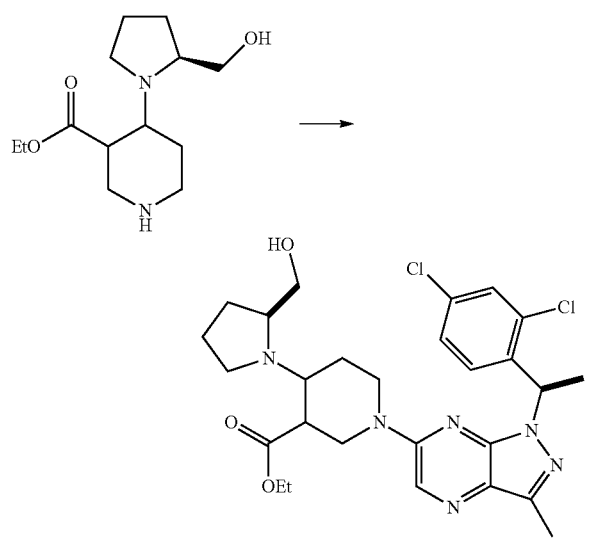

The title compound was synthesized by the procedure outlined in Example 12, Step 8, substituting ethyl 4-((S)-2-(hydroxymethyl)pyrrolidin-1-yl)piperidine-3-carboxylate hydrochloride for 3-methyl-4-(pyrrolidin-1-yl)piperidine hydrochloride.

400

Step 3. 1-(1-((R)-1-(2,4-Dichlorophenyl)ethyl)-3-methyl-1H-pyrazolo[3,4-b]pyrazin-6-yl)-4-((S)-2-(hydroxymethyl)pyrrolidin-1-yl)piperidine-3-carboxylic acid

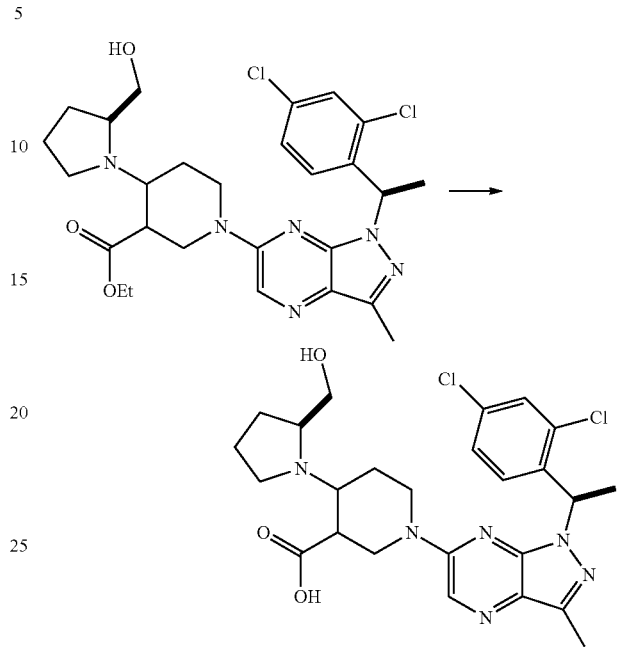

The title compound was synthesized by the procedure outlined in Example 40, Step 3. The residue was purified by reverse phase preparative HPLC (Gemini-NX, 10 μm, 250× 30 mm, C18 column (Phenomenex, Torrance, Calif.), eluent: 0 to 100% acetonitrile in water, both eluents containing 0.1% trifluoroacetic acid, gradient elution over 30 min).

Step 4. (3R,4S)-1-(1-((R)-1-(2,4-Dichlorophenyl)ethyl)-3-methyl-1H-pyrazolo[3,4-b]pyrazin-6-yl)-4-((S)-2-(hydroxymethyl)pyrrolidin-1-yl)piperidine-3-carboxamide hydrochloride

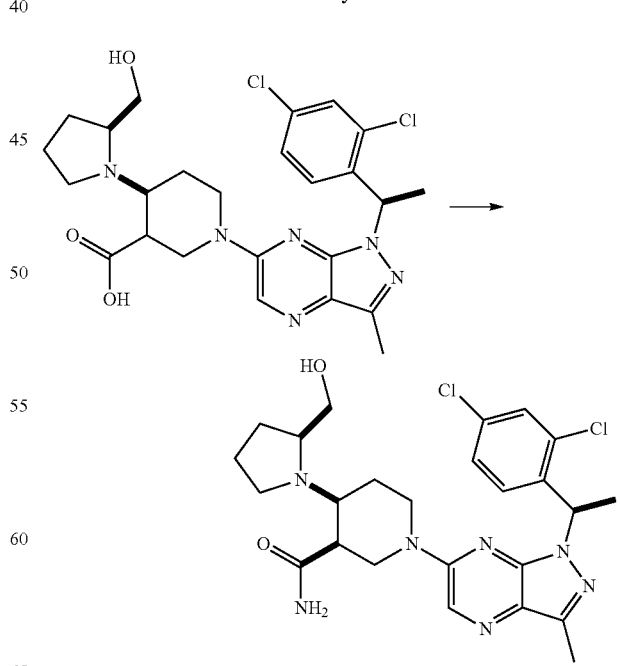

The title compound was synthesized analogously to the procedure outlined in Example 4, Step 2. After the reaction, the freebase residue was separated into its component diastereomers with reverse phase preparative HPLC (Gemini-NX, 10 μm, 250×30 mm, C18 column (Phenomenex, Torrance, Calif.), eluent: 35 to 40% acetonitrile in water (containing 0.1% ammonium formate), gradient over 20 min) to give the title compound as the second eluting isomer. The product was concentrated and then dissolved in dichloromethane before being wash twice with saturated aq. sodium bicarbonate. The organic layer was dried over sodium sulfate and removed. The residue was dissolved in dichloromethane before being made acidic with 2N HCl in diethyl ether to yield the title compound. $^1$H NMR (400 MHz, CD$_3$OD; HCl Salt): δ 8.29 (d, J=10.1 Hz, 1H), 7.48-7.31 (m, 2H), 7.24 (s, 1H), 6.29 (dd, J=8.1, 5.0 Hz, 1H), 5.20-4.95 (m, 4H), 3.85-3.59 (m, 2H), 3.52-3.34 (m, 2H), 2.45 (s, 3H), 2.37-2.19 (m, 4H), 2.15-1.93 (m, 4H), 1.83 (dd, J=5.8, 3.0 Hz, 2H), 1.22 (m, 5H); m/z 532.2 (M+H$^+$).

Example 64

((3R,4S)-1-(3-Cyano-1-((R)-1-(2,4-dichlorophenyl)ethyl)-1H-pyrazolo[3,4-b]pyrazin-6-yl)-3-(2-hydroxypropan-2-yl)piperidin-4-yl)-L-proline hydrochloride

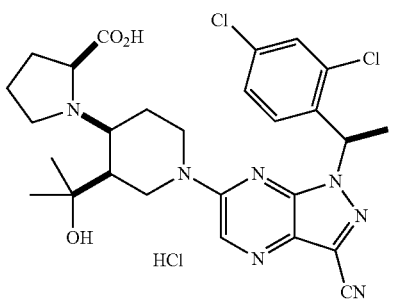

Step 1: (1-(t-Butoxycarbonyl)-3-(ethoxycarbonyl)piperidin-4-yl)-L-proline

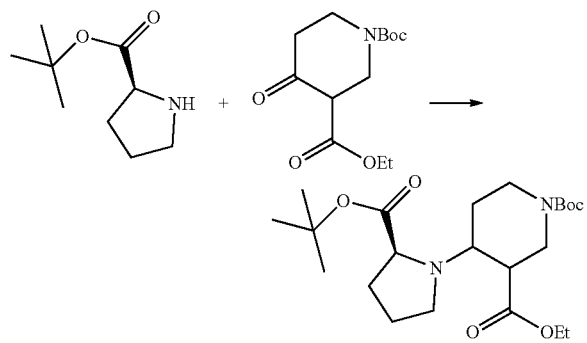

t-Butyl L-prolinate (3.79 g, 22.1 mmol), 1-(t-butyl) 3-ethyl 4-oxopiperidine-1,3-dicarboxylate (5.00 g, 18.4 mmol), acetic acid (1.58 mL, 27.7 mmol), and 1,2-dichloroethane (37 mL) were combined in a 250 mL round bottom flask. The reaction mixture was stirred at room temperature for 10 min before adding NaBH(OAc)$_3$ (5.87 g, 27.7 mmol). The reaction mixture was stirred at room temperature for 19 h before diluting with saturated aq. sodium bicarbonate and extracting with dichloromethane (3×). The combined organic layers were dried over sodium sulfate, filtered, and concentrated to afford the crude product, which was used directly in the next reaction.

Step 2: (3-(2-Hydroxypropan-2-yl)piperidin-4-yl)-L-proline

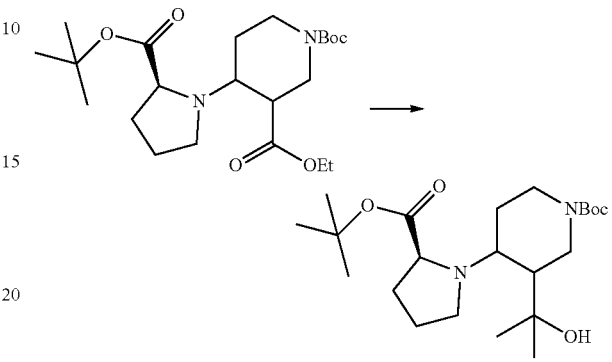

To a solution of (1-(t-butoxycarbonyl)-3-(ethoxycarbonyl)piperidin-4-yl)-L-proline (1.0 g, 2.3 mmol) in diethyl ether (23 mL) at 0° C. was added MeMgBr (3 M in diethyl ether, 4.0 mL, 12 mmol). After stirring for 2 h, the reaction was diluted with saturated aq. sodium bicarbonate. The reaction mixture was filtered, washing the solids with diethyl ether. The solution was partitioned, and the organic layer was separated. The aqueous layer was extracted with ethyl acetate (2×), and the combined organic layers were dried over sodium sulfate, filtered, and concentrated under reduced pressure to afford a crude mixture containing the title compound as a mixture of diastereomers.

Step 3: (3-(2-Hydroxypropan-2-yl)piperidin-4-yl)-L-proline

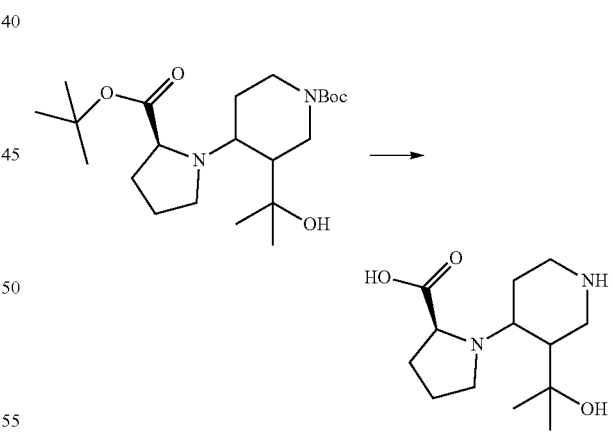

To a solution of (3-(2-hydroxypropan-2-yl)piperidin-4-yl)-L-proline in dichloromethane was added trifluoroacetic acid. The reaction solution was stirred at room temperature for 16 h before concentrating under reduced pressure. The crude residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford (3-(2-hydroxypropan-2-yl)piperidin-4-yl)-L-proline the title compound as the trifluoroacetic acid salt.

Step 4. ((3R,4S)-1-(3-Cyano-1-((R)-1-(2,4-dichlorophenyl)ethyl)-1H-pyrazolo[3,4-b]pyrazin-6-yl)-3-(2-hydroxypropan-2-yl)piperidin-4-yl)-L-proline hydrochloride

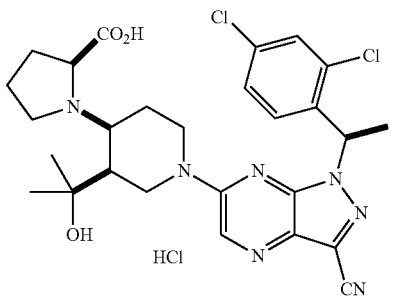

The title compound was synthesized according to the procedure described in Example 23, Step 3, substituting (3-(2-Hydroxypropan-2-yl)piperidin-4-yl)-L-proline (Example 64, Step 3) for 3'-methyl-1,4'-bipiperidine 2,2,2-trifluoroacetate (Example 2, Step 2) and DMSO for DMF. The cooled reaction was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the title compound as the major diastereomer and trifluoroacetic acid salt. The product was dissolved in 10% MeOH in dichloromethane and passed through a basifying column (PL-HCO₃ MP SPE, 0.5 g) to afford the free base, which was dissolved in dichloromethane, treated with 1 M HCl in diethyl ether, and concentrated to afford the HCl salt. ¹H-NMR (400 MHz; CD₃OD, HCl Salt): δ 8.49 (s, 1H), 7.46 (d, J=2.0 Hz, 1H), 7.35-7.23 (m, 2H), 6.46 (q, J=7.0 Hz, 1H), 4.90 (d, J=14.9 Hz, 1H), 4.67 (d, J=13.3 Hz, 1H), 4.60 (dd, J=9.6, 5.5 Hz, 1H), 4.24-4.12 (m, 1H), 3.73 (d, J=13.4 Hz, 1H), 3.47 (dd, J=17.3, 9.7 Hz, 1H), 3.17 (td, J=14.0, 4.1 Hz, 1H), 3.01 (dd, J=14.7, 3.9 Hz, 1H), 2.63-2.51 (m, 2H), 2.39 (qd, J=12.7, 4.8 Hz, 1H), 2.31-2.15 (m, 2H), 2.09 (d, J=12.8 Hz, 1H), 2.05-1.95 (m, 1H), 1.93 (d, J=7.1 Hz, 3H), 1.55 (s, 3H), 1.31 (s, 3H); m/z 572.3 (M+H⁺).

Example 65

2-((3S,3'R,4'S)-1'-(1-((R)-1-(2,4-Dichlorophenyl)ethyl)-3-methyl-1H-pyrazolo[3,4-b]pyrazin-6-yl)-3'-(hydroxymethyl)-[1,4'-bipiperidin]-3-yl)acetic acid hydrochloride

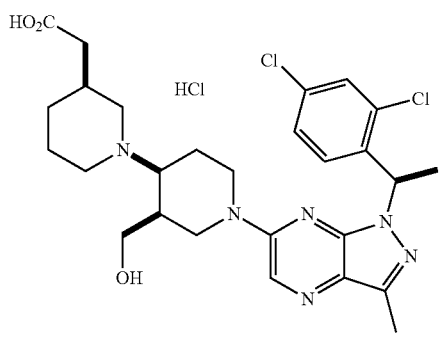

Step 1. Tert-butyl 4-hydroxy-3-(hydroxymethyl)piperidine-1-carboxylate

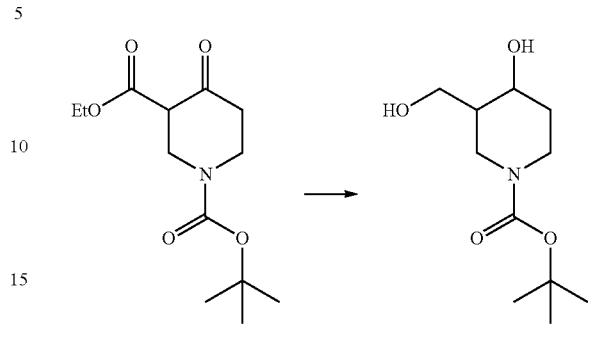

To a 0° C. solution of 1-(tert-butyl) 3-ethyl 4-oxopiperidine-1,3-dicarboxylate (10 g, 38.9 mmol) in ethanol (150 mL) was added sodium borohydride (14.7 g, 389 mmol) in 4 portions over 30 min. The reaction was then slowly warmed to room temperature and stirred for 16 h. at which point the reaction solidified. The reaction was carefully quenched with water and saturated aq. ammonium chloride until all solids dissolved. This mixture was then extracted with ethyl acetate (3×) and the combined organic layers were washed with water, brine, and then subsequently dried over magnesium sulfate. The volatiles were removed to give the compound as a clear oil.

Step 2. Tert-butyl 3-(((tert-butyldimethylsilyl)oxy)methyl)-4-hydroxypiperidine-1-carboxylate

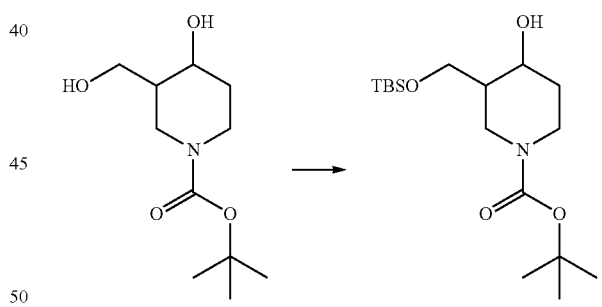

The product of Example 65, Step 1 (8.00 g, 34.6 mmol) was dissolved in dichloromethane (140 mL) and cooled to 0° C. before the addition of imidazole (2.59 g, 38.0 mmol). Once everything dissolved, tert-butyldimethylchlorosilane (5.48 g, 36.3 mmol) was added in portions and the reaction was stirred over night at room temperature. The reaction was carefully quenched with water and aqueous ammonium chloride until all solids dissolved. This mixture was then extracted with ethyl acetate (3×) and the combined organic layers were washed with water, brine, and then subsequently dried over magnesium sulfate. The volatiles were removed, and the crude residue was purified using silica gel chromatography (10 to 50% ethyl acetate in hexanes) to give the product as a mixture of diastereomers.

Step 3. Tert-butyl 3-(((tert-butyldimethylsilyl)oxy)methyl)-4-oxopiperidine-1-carboxylate

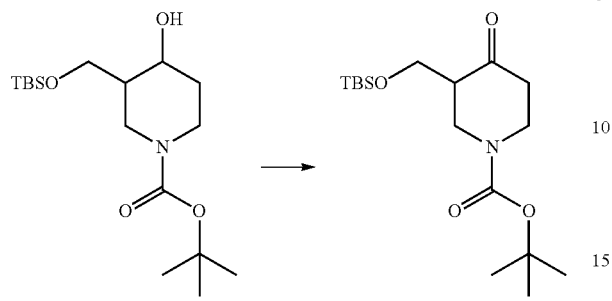

To a −78° C. solution of oxalyl chloride (3.20 mL, 37.6 mmol) in dichloromethane (100 mL) was added DMSO (5.34 mL, 75.2 mmol) in 20 mL of dichloromethane. The mixture was then stirred 15 min. before the product from Example 65, Step 2 (10.4 g, 30.1 mmol) in 30 mL dichloromethane was added. The reaction mixture was stirred an additional hour at −78° C., at which point triethylamine (21 mL, 150 mmol) was added. The mixture was stirred for 20 min at −78° C. and 30 min at 0° C. before being poured into water. The organic layer was separated, and the aqueous layer was extracted with dichloromethane (3×). The combined organics were washed with brine, dried over sodium sulfate, and concentrated. The crude residue was purified by silica gel chromatography (10 to 35% ethyl acetate in hexanes) to give the title compound.

Step 4. Tert-butyl (3S)-3'-(((tert-butyldimethylsilyl)oxy)methyl)-3-(2-ethoxy-2-oxoethyl)-[1,4'-bipiperidine]-1'-carboxylate

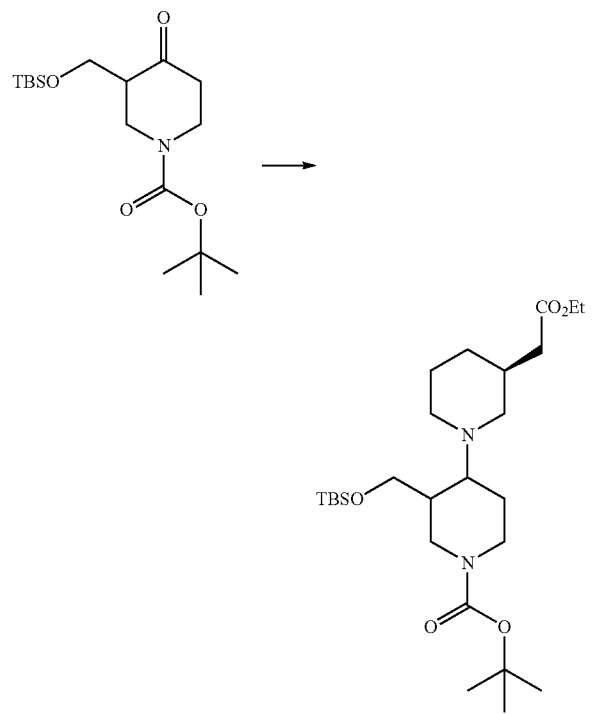

The title compound was synthesized analogously to the procedures outlined in Example 2, Step 1, substituting ethyl (S)-2-(piperidin-3-yl)acetate for piperidine, and tert-butyl 3-(((tert-butyldimethylsilyl)oxy)methyl)-4-hydroxypiperidine-1-carboxylate (Example 65, Step 3) for tert-butyl 3-methyl-4-oxopiperidine-1-carboxylate. The product of this reaction was purified via column chromatography (20 to 100% ethyl acetate in hexanes) to give the product as a mixture of diastereomers.

Step 5. 2-((3S)-3'-(Hydroxymethyl)-[1,4'-bipiperidin]-3-yl)acetic acid

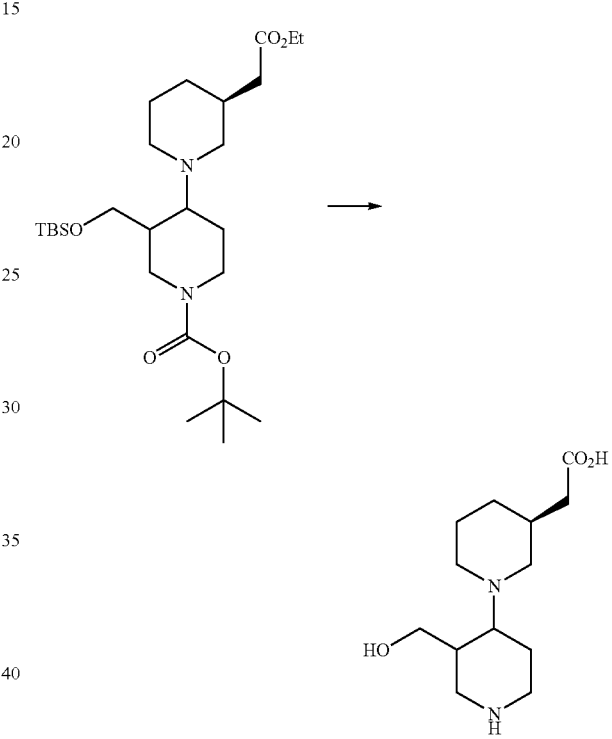

The title compound was prepared according to the procedures outlined in Example 37, Step 2, isolated as the HCl salt, and used without purification.

Step 6. 2-((3S,3'R,4'S)-1'-(1-((R)-1-(2,4-Dichlorophenyl)ethyl)-3-methyl-1H-pyrazolo[3,4-b]pyrazin-6-yl)-3'-(hydroxymethyl)-[1,4'-bipiperidin]-3-yl)acetic acid hydrochloride

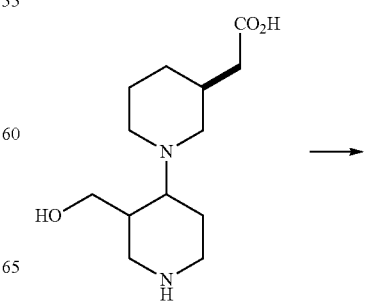

407

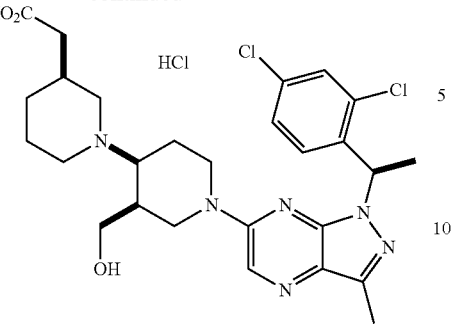

The title compound was synthesized analogously to the procedures outlined in Example 12, Step 8, substituting 2-((3S)-3'-(hydroxymethyl)-[1,4'-bipiperidin]-3-yl)acetic acid hydrochloride (Example 65, Step 5) for 3-methyl-4-(pyrrolidin-1-yl)piperidine hydrochloride (Example 12, Step 2), and DMSO for DMF. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min). The diastereomers were further separated by reverse phase preparative HPLC (Gemini-NX, 10 μm, 250×30 mm, C18 column (Phenomenex, Torrance, Calif.), eluent: 31% acetonitrile in water (containing 0.1% ammonium formate), over 30 min) to give the title compound as the first eluting isomer. The hydrochloride salt was obtained by dissolving the formate salt in dichloromethane and washing saturated aq. sodium bicarbonate. The aqueous layer was then extracted twice with dichloromethane and the combined organics were dried over sodium sulfate and concentrated under reduced pressure. The residue was then dissolved again in dichloromethane and this was made acidic (pH ~2) with 2N HCl in diethyl ether and the volatiles removed to give the product. $^1$H-NMR (400 MHz; CD$_3$CN; HCl Salt) δ 8.19 (s, 1H), 8.15 (s, 1H), 7.43 (d, J=2.2 Hz, 1H), 7.39 (d, J=8.5 Hz, 1H), 7.25 (dd, J=8.5, 2.2 Hz, 1H), 6.26 (q, J=7.0 Hz, 1H), 4.63-4.49 (m, 2H), 3.97-3.79 (m, 2H), 3.74-3.64 (m, 1H), 3.61 (dd, J=11.6, 4.7 Hz, 1H), 3.08-2.84 (m, 2H), 2.77-2.69 (m, 1H), 2.44 (s, 3H), 2.25-1.98 (m, 7H), 1.87-1.75 (m, 5H), 1.70 (d, J=10.0 Hz, 1H), 1.60 (d, J=13.3 Hz, 1H), 1.20-1.08 (m, 1H); m/z 561.2 (M+H$^+$).

Example 66

1-((R)-1-(2,4-Dichlorophenyl)ethyl)-3-methyl-6-(3'-methyl-[3,4'-bipiperidin]-1'-yl)-1H-pyrazolo[3,4-b]pyrazine hydrochloride

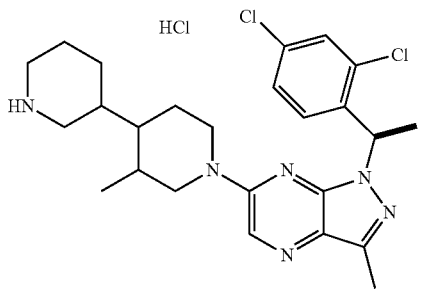 [SMILES: Cc1nn([C@H](C)c2ccc(Cl)cc2Cl)c2nc(N3CCC(C4CCCNC4)C(C)C3)cnc12 ; Cl]

408

Step 1: Tert-butyl 5-(((trifluoromethyl)sulfonyl)oxy)-3,6-dihydropyridine-1(2H)-carboxylate

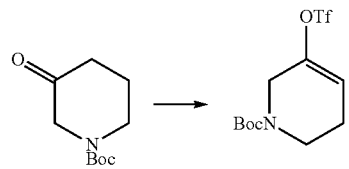 [SMILES: CC(C)(C)OC(=O)N1CCCC(=O)C1 ; CC(C)(C)OC(=O)N1CCC=C(OS(=O)(=O)C(F)(F)F)C1]

To a solution of diisopropylamine (12.2 mL, 86.2 mmol) in anhydrous THF (45 mL) at −78° C. was added n-BuLi (2.5 M in hexanes, 31.3 mL, 78.4 mmol), dropwise. The mixture was stirred at −20° C. for 30 min. In a separate flask, to a mixture of tert-butyl 3-oxopiperidine-1-carboxylate (10 g, 50.3 mmol) in anhydrous THF (60 mL) at −78° C. under nitrogen was slowly added the freshly-made LDA solution. The reaction was stirred at −20° C. for 30 min. The mixture was cooled back to −78° C., and a solution of N-phenyl-bis (trifluoromethanesulfonimide) (23.3 g, 65.3 mmol) in anhydrous THF (60 mL) was added, dropwise. The mixture was stirred at room temperature for 6 h. The reaction was quenched with saturated aq. ammonium chloride. The aqueous layer was extracted with ethyl acetate (2×60 mL). The combined organic layers were dried over sodium sulfate, filtered, and concentrated. The crude residue was purified by flash chromatography to afford tert-butyl 5-(((trifluoromethyl)sulfonyl)oxy)-3,6-dihydropyridine-1(2H)-carboxylate (6.7 g, 42%) as a yellow oil.

Step 2: Tert-butyl 5-(4,4,5,5-tetramethyl-1,3,2-dioxaborolan-2-yl)-3,6-dihydropyridine-1(2H)-carboxylate

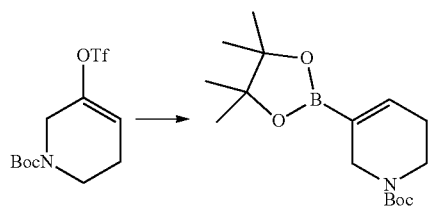 [SMILES: CC(C)(C)OC(=O)N1CCC=C(OS(=O)(=O)C(F)(F)F)C1 ; CC(C)(C)OC(=O)N1CCC=C(B2OC(C)(C)C(C)(C)O2)C1]

A mixture of tert-butyl 5-(((trifluoromethyl)sulfonyl)oxy)-3,6-dihydropyridine-1(2H)-carboxylate (3.5 g, 14.5 mmol), Pd(dppf)Cl$_2$ (0.38 g, 0.53 mmol), bis(pinacolato)diboron (3.9 g, 15.8 mmol), and KOAc (3.1 g, 31.5 mmol) in anhydrous DMF was degassed and purged with nitrogen three times. The mixture was heated at 85° C. for 4 h. After cooling down to room temperature, the reaction was diluted with ethyl acetate, filtered, and concentrated. The crude residue was purified by silica gel column chromatography to afford tert-butyl 5-(4,4,5,5-tetramethyl-1,3,2-dioxaborolan-2-yl)-3,6-dihydropyridine-1(2H)-carboxylate (1.4 g, 41%) as a colorless oil.

Step 3: Tert-butyl 3-(3-methylpyridin-4-yl)piperidine-1-carboxylate

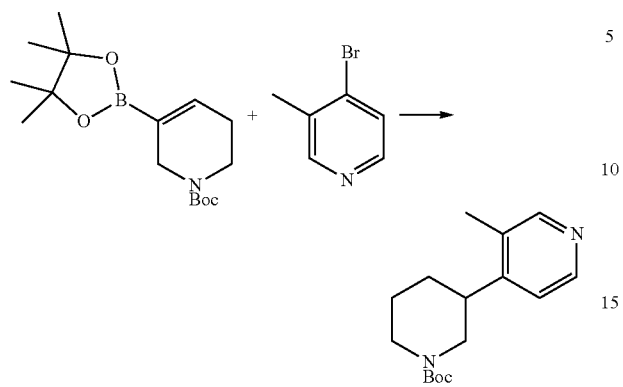

A mixture of tert-butyl 5-(4,4,5,5-tetramethyl-1,3,2-dioxaborolan-2-yl)-3,6-dihydropyridine-1(2H)-carboxylate (1.4 g, 4.5 mmol) and 4-bromo-3-methylpyridine hydrochloride (0.9 g, 4.3 mmol) in 1,4-dioxane (3 mL) and water (3 mL) was added $K_2CO_3$ (1.9 g, 14 mmol) and Pd(dppf)Cl$_2$ (0.16 g, 0.20 mmol). The mixture was degassed and purged with nitrogen three times. The reaction was heated at 80° C. for 4 h. After cooling down to room temperature, the reaction was diluted with ethyl acetate, filtered, and concentrated. The crude residue was purified by silica gel chromatography to afford tert-butyl 3-(3-methylpyridin-4-yl)piperidine-1-carboxylate (1.1 g, 92%) as a light brown oil.

Step 4: Tert-butyl 3'-methyl-[3,4'-bipiperidine]-1-carboxylate

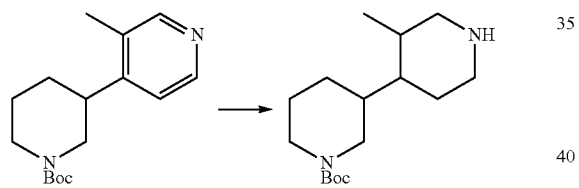

A mixture of tert-butyl 3-(3-methylpyridin-4-yl)piperidine-1-carboxylate (1.1 g, 4.0 mmol) and PtO$_2$ (5 mol %) in AcOH was hydrogenated at 60 psi in a Paar shaker flask for 48 h. The mixture was filtered and concentrated to afford tert-butyl 3'-methyl-[3,4'-bipiperidine]-1-carboxylate (0.75 g, 67%) as a colorless oil.

Step 5: Tert-butyl 1'-(1-((R)-1-(2,4-dichlorophenyl)ethyl)-3-methyl-1H-pyrazolo[3,4-b]pyrazin-6-yl)-3'-methyl-[3,4'-bipiperidine]-1-carboxylate

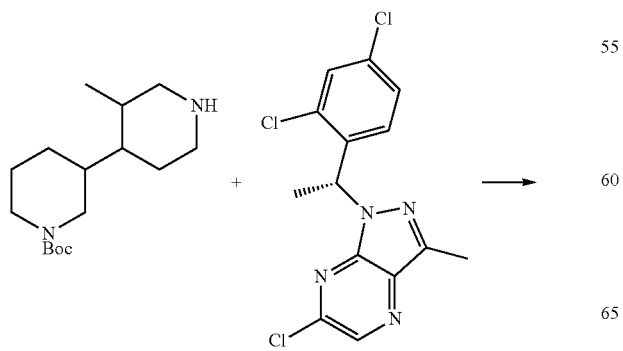

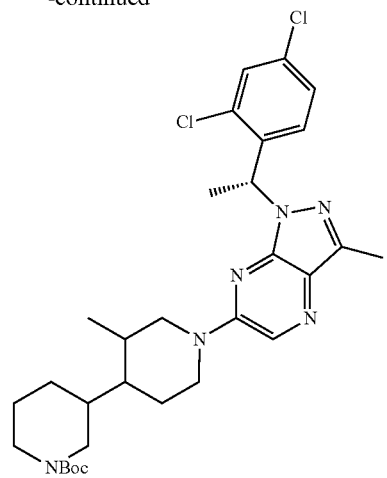

A mixture of tert-butyl 3'-methyl-[3,4'-bipiperidine]-1-carboxylate (105.9 mg, 0.37 mmol) and diisopropylethylamine (193.8 mg, 1.5 mmol) in DMF (2 mL) was added (R)-6-chloro-1-(1-(2,4-dichlorophenyl)ethyl)-3-methyl-1H-pyrazolo[3,4-b]pyrazine (120 mg, 0.35 mmol). The reaction was heated at 80° C. for 12 h. After cooling down to room temperature, the reaction was quenched with water and extracted with ethyl acetate. The organic phases were dried over sodium sulfate, filtered, and concentrated. The residue was purified by silica gel chromatography to afford tert-butyl 1'-(1-((R)-1-(2,4-dichlorophenyl)ethyl)-3-methyl-1H-pyrazolo[3,4-b]pyrazin-6-yl)-3'-methyl-[3,4'-bipiperidine]-1-carboxylate (86.6 mg, 42%).

Step 6: 1-((R)-1-(2,4-Dichlorophenyl)ethyl)-3-methyl-6-(3'-methyl-[3,4'-bipiperidin]-1'-yl)-1H-pyrazolo[3,4-b]pyrazine

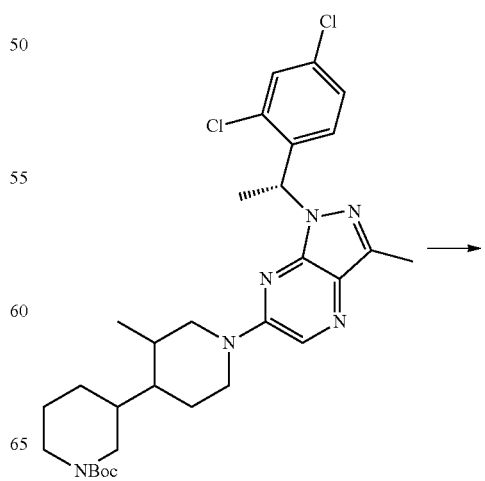

411
-continued

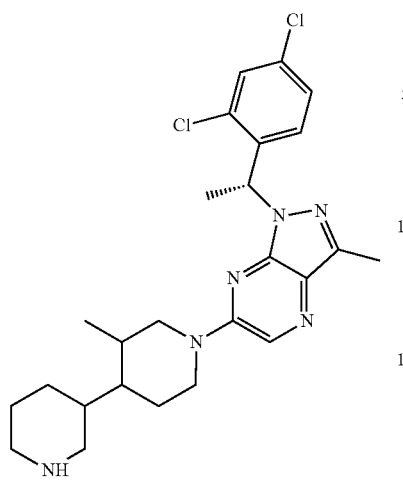

To a solution of tert-butyl 1'-(1-((R)-1-(2,4-dichlorophenyl)ethyl)-3-methyl-1H-pyrazolo[3,4-b]pyrazin-6-yl)-3'-methyl-[3,4'-bipiperidine]-1-carboxylate (74.5 mg, 0.13 mmol) in dichloromethane (1 mL) was added trifluoroacetic acid (0.13 mL, 1.7 mmol) at room temperature. The mixture was stirred for 1 h. The reaction was concentrated, diluted with dichloromethane, and neutralized with saturated aq. sodium bicarbonate. The organic layer was washed with brine, dried over sodium sulfate, filtered, and concentrated to afford 1-((R)-1-(2,4-dichlorophenyl)ethyl)-3-methyl-6-(3'-methyl-[3,4'-bipiperidin]-1'-yl)-1H-pyrazolo[3,4-b]pyrazine as a crude product (19.4 mg, 41%). $^1$H-NMR (400 MHz; CDCl$_3$): δ 8.18 (s, 1H), 7.45-7.34 (m, 2H), 7.18-7.13 (m, 1H), 6.37-6.29 (m, 1H), 4.59-4.34 (m, 2H), 3.27-2.73 (m, 4H), 2.56 (s, 3H), 2.34-2.24 (m, 1H), 2.17-2.02 (m, 1H), 2.00-1.91 (m, 9H), 1.90-0.78 (m, 7H); m/z 487.0 (M+H$^+$).

Example 67

3-(1'-(1-((R)-1-(2,4-Dichlorophenyl)ethyl)-3-methyl-1H-pyrazolo[3,4-b]pyrazin-6-yl)-3'-methyl-[3,4'-bipiperidin]-1-yl)propanoic acid hydrochloride

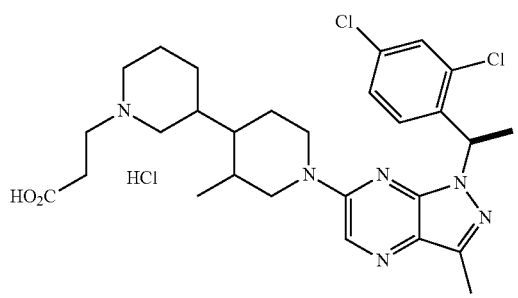 [SMILES: Cc1nn([C@H](C)c2ccc(Cl)cc2Cl)c2nc(N3CCC(C4CCCN(CCC(=O)O)C4)C(C)C3)cnc12 ; Cl]

412

Step 1: Methyl 3-(1'-(1-((R)-1-(2,4-dichlorophenyl)ethyl)-3-methyl-1H-pyrazolo[3,4-b]pyrazin-6-yl)-3'-methyl-[3,4'-bipiperidin]-1-yl)propanoate

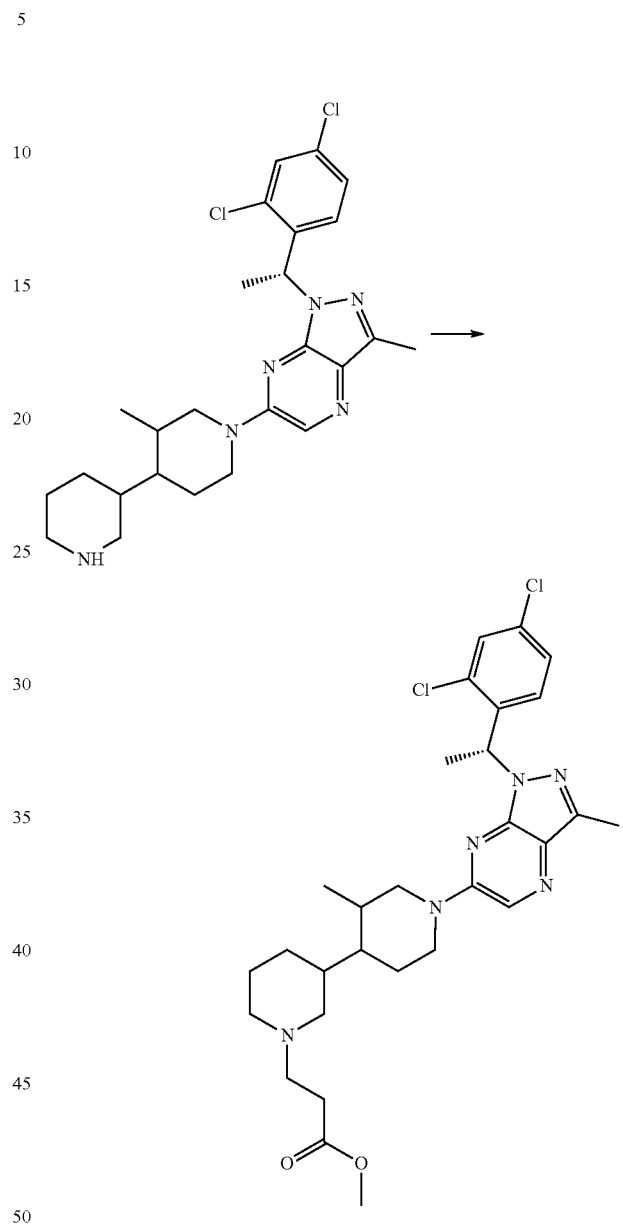

To a mixture of 1-((R)-1-(2,4-dichlorophenyl)ethyl)-3-methyl-6-(3'-methyl-[3,4'-bipiperidin]-1'-yl)-1H-pyrazolo[3,4-b]pyrazine (169 mg, 0.350 mmol) and K$_2$CO$_3$ (97 mg, 0.70 mmol) in N-methyl-2-pyrollidone (4 mL) was added methyl 3-bromopropionate (64 mg, 0.38 mmol) at room temperature. The reaction was stirred for 12 h. The reaction was diluted with ethyl acetate, washed with water and brine, dried over sodium sulfate, filtered, and concentrated. The residue was purified by silica gel column chromatography to afford methyl 3-(1'-(1-((R)-1-(2,4-dichlorophenyl)ethyl)-3-methyl-1H-pyrazolo[3,4-b]pyrazin-6-yl)-3'-methyl-[3,4'-bipiperidin]-1-yl)propanoate (200 mg, 100%).

Step 2: 3-(1'-(1-((R)-1-(2,4-Dichlorophenyl)ethyl)-3-methyl-1H-pyrazolo[3,4-b]pyrazin-6-yl)-3'-methyl-[3,4'-bipiperidin]-1-yl)propanoic acid

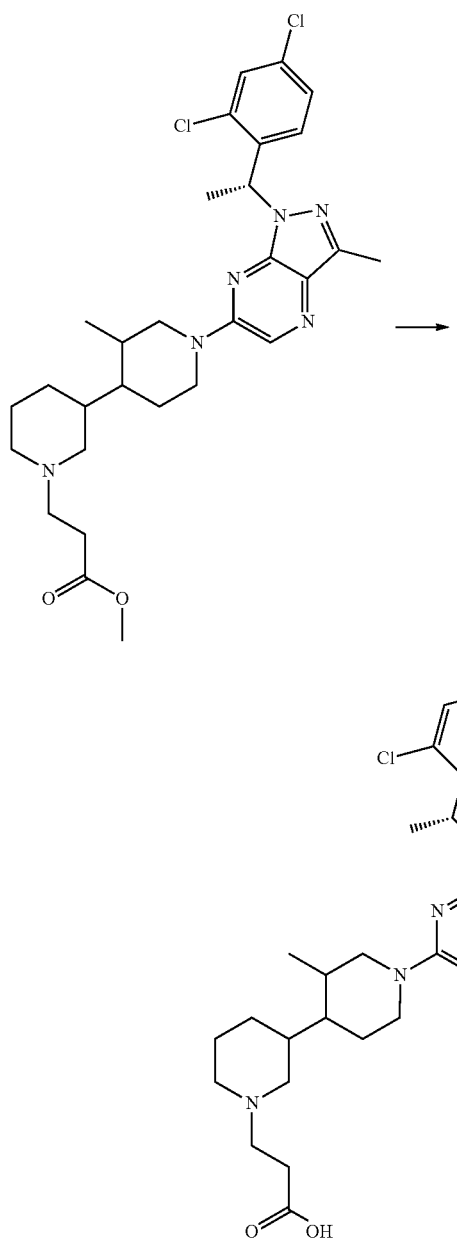

To a solution of methyl 3-(1'-(1-((R)-1-(2,4-dichlorophenyl)ethyl)-3-methyl-1H-pyrazolo[3,4-b]pyrazin-6-yl)-3'-methyl-[3,4'-bipiperidin]-1-yl)propanoate (200 mg, 0.35 mmol) in methanol (0.7 mL) and THF (2.1 mL) was added 1 N NaOH aqueous solution (0.7 mL, 0.35 mmol). The reaction was stirred at 50° C. for 1 h. The mixture was concentrated and the residue was purified by preparative reverse-phase HPLC (Phenomenex Luna, 10µm, C18, 250× 21.6 mm, 20 mL/min, eluting with 10% to 100% acetonitrile in water with 0.1% formic acid over first 20 min) to afford 3-(1'-(1-((R)-1-(2,4-dichlorophenyl)ethyl)-3-methyl-1H-pyrazolo[3,4-b]pyrazin-6-yl)-3'-methyl-[3,4'-bipiperidin]-1-yl)propanoic acid as a mixture of diastereomers. $^1$H-NMR (300 MHz; CDCl$_3$, formate salt): δ 9.91 (br s, 2H), 8.33 (br s, 1H), 8.06 (s, 1H), 7.42-7.34 (m, 2H), 7.17-7.12 (m, 1H), 6.32-6.24 (m, 1H), 4.54-4.31 (m, 2H), 3.60-3.43 (m, 2H), 3.21 (br s, 2H), 2.99-2.92 (m, 1H), 2.83-2.62 (m, 2H), 2.54 (s, 3H), 2.32 (br s, 1H), 2.11-0.74 (m, 14H); m/z 558.9 (M+H$^+$).

Example 68

((2S)-1-(4-(1-((R)-1-(2,4-Dichlorophenyl)ethyl)-3-methyl-1H-pyrazolo[3,4-b]pyrazin-6-yl)cyclohex-3-en-1-yl)pyrrolidin-2-yl)methanol

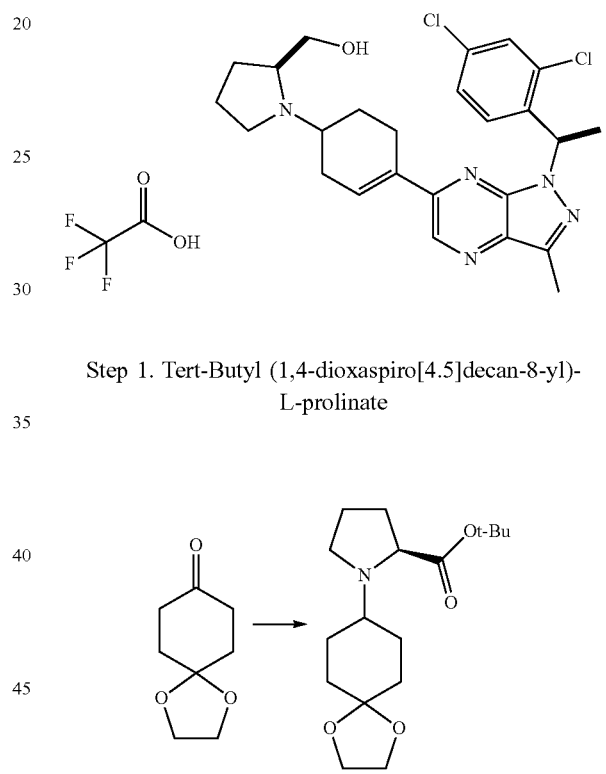

Step 1. Tert-Butyl (1,4-dioxaspiro[4.5]decan-8-yl)-L-prolinate 1,4-Dioxaspiro[4.5]decan-8-one (5.0 g, 32.01 mmol) was dissolved in 1,2-dichloroethane (35 mL) and then tert-butyl L-prolinate (6.58 g, 38.42 mmol) was added, followed by acetic acid (2.2 mL, 38.42 mmol). The mixture was heated to 70° C. and stirred for 5 h at 70° C. and then cooled to 22° C. Sodium triacetoxyborohydride (13.57 g, 64.03 mmol) was then added and the mixture was vigorously stirred for 2 h at 22° C. and then the reaction was quenched with saturated aq. sodium bicarbonate (20 ml). The mixture was extracted with dichloromethane (50 mL×3). The combined organic fractions were dried over sodium sulfate, filtered and concentrated under reduced pressure to provide the title compound as a viscous light yellow oil. The crude residue was used as was for the next reaction without any further purification.

Step 2. Methyl (4-oxocyclohexyl)-L-prolinate

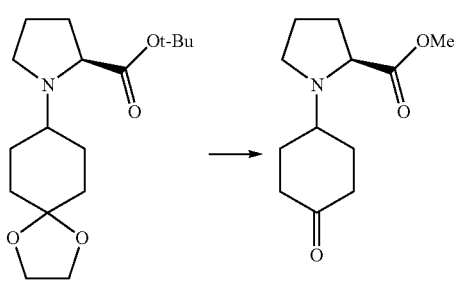 [SMILES: CC(C)(C)OC(=O)[C@@H]1CCCN1C1CCC2(CC1)OCCO2 ; COC(=O)[C@@H]1CCCN1C1CCC(=O)CC1]

Tert-butyl (1,4-dioxaspiro[4.5]decan-8-yl)-L-prolinate (Example 68, step 1, 9.97 g, 32.01 mmol) was dissolved in methanol (100 mL) and then water (20 mL) was added, followed by hydrochloric acid (26.68 mL, 320.14 mmol, 12 M in water). The flask was equipped with a reflux condenser and then mixture was heated to 80° C. and stirred for 16 h at 80° C. and then cooled to 22° C. The mixture was concentrated under reduced pressure and then the residue was diluted with dichloromethane (50 mL) and then washed with saturated aq. sodium bicarbonate (50 ml×2). The organic fraction was dried over sodium sulfate, filtered and concentrated under reduced pressure. The residue was purified by silica gel chromatography (0 to 20% methanol in dichloromethane), the fractions containing the desired product were concentrated under reduced pressure to provide the title compound (2.4 g, 33% yield) as a viscous light yellow oil.

Step 3. Methyl (4-(((trifluoromethyl)sulfonyl)oxy) cyclohex-3-en-1-yl)-L-prolinate

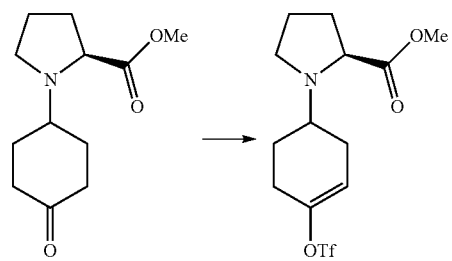 [SMILES: COC(=O)[C@@H]1CCCN1C1CCC(=O)CC1 ; COC(=O)[C@@H]1CCCN1C1CC=C(OS(=O)(=O)C(F)(F)F)CC1]

Methyl (4-oxocyclohexyl)-L-prolinate (Example 68, step 2, 1.0 g, 4.44 mmol) was dissolved in THF (20 mL) and then the solution was cooled to −78° C. Lithium diisopropylamide (4.88 mL, 4.88 mmol, 1 M in THF) was then added slowly dropwise. After the addition was completed, the mixture was stirred at −78° C. for 2 h. Next, N-phenyl-bis-trifluoromethanesulfonimide (1.74 g, 4.88 mmol) was then added (dissolved in 5 mL of THF), and then the mixture was allowed to warm to 0° C. slowly over a 2 h period. The reaction was quenched saturated aq. sodium bicarbonate (20 ml). The mixture was extracted with dichloromethane (50 mL×3). The combined organic fractions were dried over sodium sulfate, filtered, and concentrated under reduced pressure to provide the title compound as a mixture of diastereomers. The crude residue was used as was for the next reaction without any further purification.

Step 4. Methyl (4-(4,4,5,5-tetramethyl-1,3,2-dioxaborolan-2-yl)cyclohex-3-en-1-yl)-L-prolinate

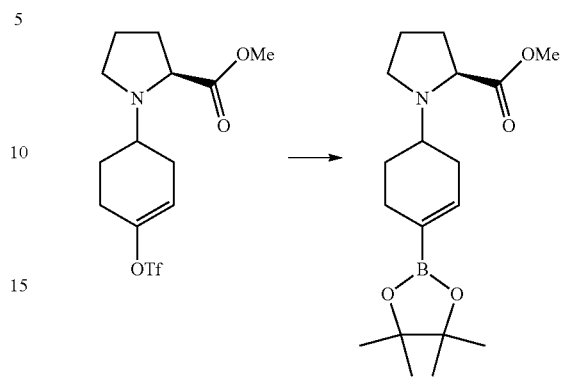

Methyl (4-(((trifluoromethyl)sulfonyl)oxy)cyclohex-3-en-1-yl)-L-prolinate (Example 68, step 3, 1.59 g, 4.44 mmol) was dissolved in 1,4-dioxane (10 mL), and then 4,4,4',4',5,5,5',5'-octamethyl-2,2'-bi(1,3,2-dioxaborolane) (1.36 g, 5.34 mmol) was added followed by potassium acetate (1.31 g, 13.3 mmol), potassium bromide (0.582 g, 4.89 mmol) and [1,1'-bis(diphenylphosphino)ferrocene]dichloropalladium(II) (0.162 g, 0.222 mmol). The mixture was degassed and then heated to 95° C. and stirred for 2 h at 95° C. The reaction was cooled to room temperature. The mixture was concentrated under reduced pressure, and the residue was purified by silica gel chromatography (0 to 20% methanol in dichloromethane) to afford the title compound as a diastereomeric mixture (0.92 g, 62% yield) and brown oil.

Step 5. Methyl (4-(1-((R)-1-(2,4-dichlorophenyl) ethyl)-3-methyl-1H-pyrazolo[3,4-b]pyrazin-6-yl) cyclohex-3-en-1-yl)-L-prolinate

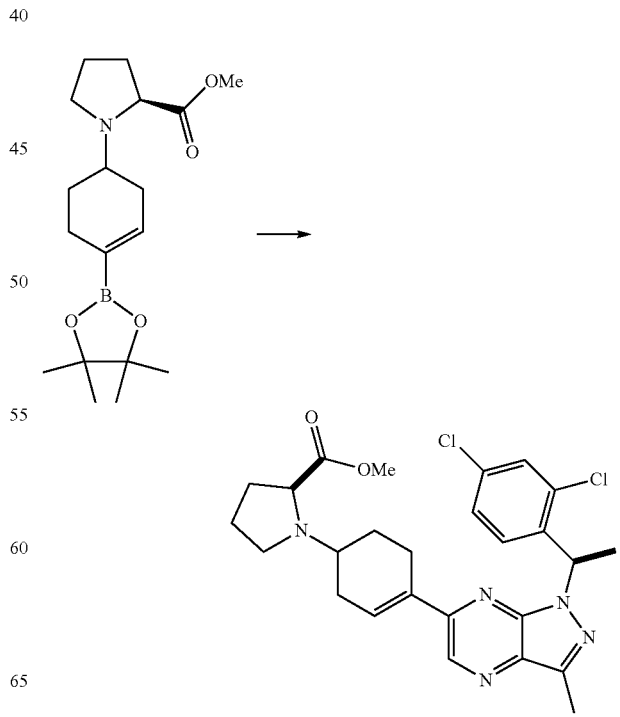

(R)-6-Chloro-1-(1-(2,4-dichlorophenyl)ethyl)-3-methyl-1H-pyrazolo[3,4-b]pyrazine (Example 12, Step 5, 350 mg, 1.02 mmol) was dissolved in a 1,4-dioxane/water mixture (5:1, 12 mL), and methyl (4-(4,4,5,5-tetramethyl-1,3,2-dioxaborolan-2-yl)cyclohex-3-en-1-yl)-L-prolinate (Example 68, step 4, 0.379 g, 1.13 mmol) were added followed by potassium carbonate (0.425 g, 13.3 mmol) and [1,1'-bis(diphenylphosphino)ferrocene]dichloropalladium(II) (37.4 mg, 0.0512 mmol). The mixture was degassed and then heated to 95° C. and stirred for 2 h at 95° C. The reaction was cooled to room temperature. The mixture was concentrated under reduced pressure, and the residue was purified by silica gel chromatography (0 to 20% methanol in dichloromethane) to afford a residue containing the product. The residue was further purified by reversed phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the product as the trifluoroacetic acid salt, which was dissolved in dichloromethane (20 mL) and washed with saturated aqueous sodium bicarbonate (20 ml×3). The organic layer was dried over sodium sulfate, filtered, and concentrated under reduced pressure to provide the title compound as a diastereomeric mixture (0.36 g, 69% yield) and brown oil.

Step 6. ((2S)-1-(4-(1-((R)-1-(2,4-Dichlorophenyl)ethyl)-3-methyl-1H-pyrazolo[3,4-b]pyrazin-6-yl)cyclohex-3-en-1-yl)pyrrolidin-2-yl)methanol

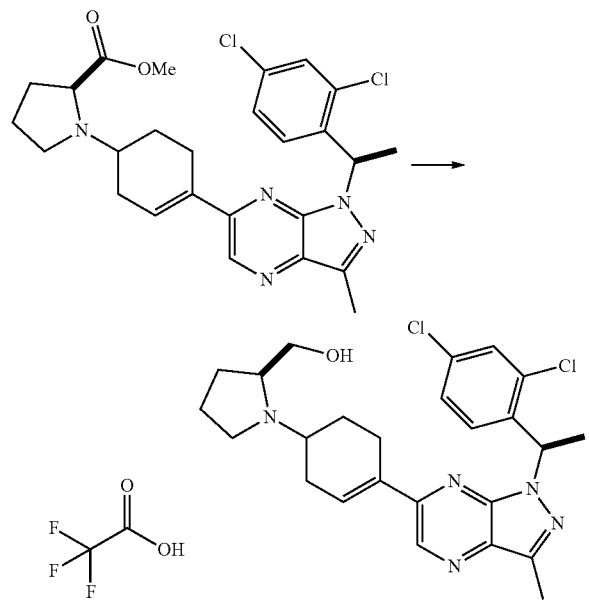

Methyl (4-(1-((R)-1-(2,4-dichlorophenyl)ethyl)-3-methyl-1H-pyrazolo[3,4-b]pyrazin-6-yl)cyclohex-3-en-1-yl)-L-prolinate (Example 68, step 5, 300 mg, 0.583 mmol) was dissolved in dichloromethane (5 mL), and the mixture was cooled to −78° C. Diisobutylaluminum hydride (0.486 mL, 0.583 mmol, 1.2 M in dichloromethane) was added dropwise to the reaction mixture. The mixture was stirred at −78° C. for 2 h. The mixture was warmed to 0° C., and the reaction was quenched with an aqueous saturated solution of potassium sodium tartrate (30 mL). The mixture was extracted with dichloromethane (3×30 mL), and the combined organic layers were dried over sodium sulfate, filtered, and concentrated under reduced pressure. The residue was purified by reversed phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the title compound as a mixture of diastereomers (73 mg, 26% yield) and light yellow oil. $^1$H NMR (400 MHz, CDCl$_3$, trifluoroacetic acid salt) 8.70 (s, 1H), 7.74 (bs, 2H), 7.42 (dd, J=8.5, 1.5 Hz, 1H), 7.37 (dd, J=2.1, 1.1 Hz, 1H), 7.17 (dd, J=8.5, 2.1 Hz, 1H), 6.71 (s, 1H), 6.56 (q, J=7.1 Hz, 1H), 3.96 (bs, 1H), 3.89-3.63 (m, 4H), 3.22-3.03 (m, 2H), 2.87 (dd, J=45.8, 20.7 Hz, 1H), 2.68 (s, 3H), 2.66-2.50 (m, 2H), 2.40-2.23 (m, 1H), 2.22-2.05 (m, 3H), 2.02-1.97 (m, 1H), 1.96 (d, J=7.1 Hz, 3H), 1.94-1.86 (m, 1H); m/z 486.0 (M+H$^+$).

Example 69

1-((R)-1-(2,4-Dichlorophenyl)ethyl)-6-((3R,4S)-4-((S)-2-(hydroxymethyl)pyrrolidin-1-yl)-3-methylcyclohex-1-en-1-yl)-1H-pyrazolo[3,4-b]pyrazine-3-carbonitrile hydrochloride

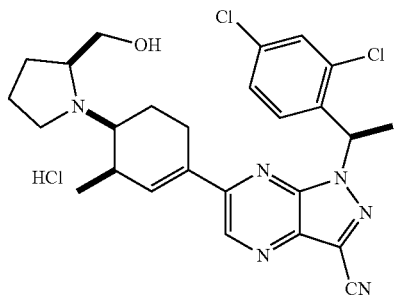 [SMILES: C[C@@H]1C=C(c2cnc3c(C#N)nn([C@H](C)c4ccc(Cl)cc4Cl)c3n2)CC[C@@H]1N1CCC[C@H]1CO ; Cl]

Step 1. 1,4-Dioxaspiro[4.5]dec-6-en-8-one

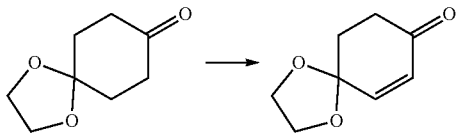 [SMILES: O=C1CCC2(CC1)OCCO2 ; O=C1C=CC2(CC1)OCCO2]

To a solution of 1,4-dioxaspiro[4.5]decan-8-one (20.0 g, 128 mmol) in dichloromethane (1.4 L) was added triethylamine (71.0 mL, 512 mmol). The resulting solution was cooled to 0° C. before adding trimethylsilyl trifluoromethanesulfonate (34.0 mL, 193 mmol), streamwise. The reaction turned light yellow. The resulting solution was stirred at −2 to −5° C. for 2.5 h before adding saturated aqueous sodium carbonate (1 L). The resulting solution was transferred to a separatory funnel, and the organic layer was separated. The organic layer was dried over sodium sulfate, decanted, and concentrated to afford an oil, which was diluted in 1:1 ethyl acetate/hexanes and filtered through a short silica gel plug. The plug was rinsed with 1:1 ethyl acetate/hexanes (1.4 L). The resulting solution was concentrated. The crude product was diluted with acetonitrile (1 L) before adding Pd(OAc)$_2$ (28.6 g, 128 mmol). The reaction was stirred overnight before concentrating the mixture to afford a black residue, which was diluted with ethyl acetate and passed through a silica/Celite plug. The resulting solution was concentrated and purified by silica gel chromatography (0% to 30% ethyl acetate in hexanes) to afford 1,4-dioxaspiro[4.5]dec-6-en-8-one as a light orange oil (14 g, 72% yield).

Step 2: 6-Methyl-1,4-dioxaspiro[4.5]decan-8-one

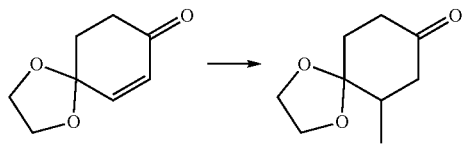

Copper cyanide (60.5 g, 675 mmol) was placed in 2 L flask and evacuated with nitrogen (2×). Diethyl ether (1.6 L) was added, and the solution was cooled to −30° C. to −40° C. Methyl lithium (200 mL 3.1 M in diethoxymethane and 35 mL 1.6 M in diethyl ether) was added streamwise over 30 min. The mixture turned from a cloudy sage color to a clear yellow solution with some bright yellow solids. In a separate 5 L flask, 1,4-dioxaspiro[4.5]dec-6-en-8-one (52.0 g, 337 mmol) was diluted in diethyl ether (0.64 L) and THF (0.64 L). Trimethylsilyl chloride (136 mL, 1070 mmol) was added to the solution, and the reaction solution was cooled to −30° C. The cuprate mixture was added to the enone solution via cannula transfer over ~10 min. Some bright yellow solids remained in the cuprate flask. The resulting reaction mixture contained some green and yellow solids and was stirred at −20° C. to −30° C. for about 80 min. The reaction was quenched by the slow addition of 3:1 saturated aqueous ammonium chloride and 30% aqueous NH$_4$OH (2 L). The reaction turned colorless with some grey solids. Then, the organic layer became cloudy and slightly yellow while the aqueous layer had some grey blue cloudiness. The reaction was allowed to stir at room temperature for 30 min. The organic layer was decanted from the 5 L flask into a 6 L separatory funnel. The aqueous layer was extracted with ethyl acetate (2×500 mL). The combined organic layers were washed with brine (2×500 mL) and dried over sodium sulfate. The solution was decanted, rinsing with ethyl acetate (400 mL) and concentrated by rotary evaporation to afford 6-methyl-1,4-dioxaspiro[4.5]decan-8-one as a light orange/brown oil (~57 g). The crude residue was characterized by LCMS and H NMR and was determined to contain about 4% of enone starting material.

Step 3: 10-Methyl-1,4-dioxaspiro[4.5]dec-7-en-8-yl trifluoromethanesulfonate and 6-methyl-1,4-dioxaspiro[4.5]dec-7-en-8-yl trifluoromethanesulfonate

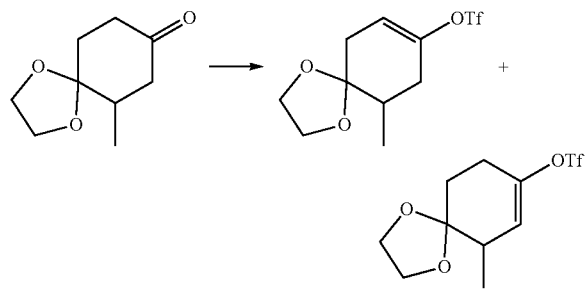

To a solution of 6-methyl-1,4-dioxaspiro[4.5]decan-8-one (14.0 g, 82.3 mmol) in THF (820 mL) cooled to −78° C. was added PhNTf$_2$ (35.2 g, 98.7 mmol) as a solution in THF (100 mL) via cannula transfer. The cold bath was removed after 1.5 h, and the reaction was allowed to warm to room temperature and stirred for 14 h. The resulting clear, red/brown solution was diluted with saturated aqueous sodium bicarbonate (1 L) and separated. The aqueous layer was extracted with ethyl acetate (1 L). The combined organic layers were dried over sodium sulfate and concentrated to afford the crude product. The crude residue was purified by silica gel chromatography (0% to 100% ethyl acetate in hexanes) to afford a 2:1 regioisomeric mixture of the desired triflates as a clear, colorless oil (17 g) containing some triflamide byproduct. This material was used directly in the next reaction.

Step 4: 4,4,5,5-Tetramethyl-2-(10-methyl-1,4-dioxaspiro[4.5]dec-7-en-8-yl)-1,3,2-dioxaborolane and 4,4,5,5-tetramethyl-2-(6-methyl-1,4-dioxaspiro[4.5]dec-7-en-8-yl)-1,3,2-dioxaborolane

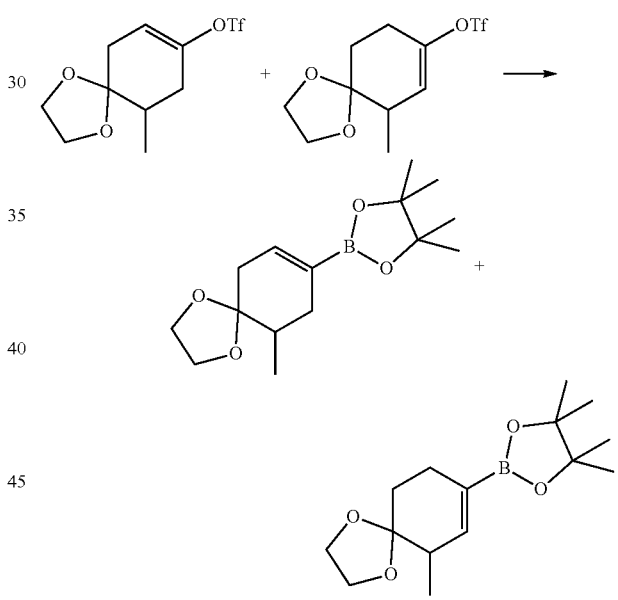

A solution of 10-methyl-1,4-dioxaspiro[4.5]dec-7-en-8-yl trifluoromethanesulfonate and 6-methyl-1,4-dioxaspiro[4.5]dec-7-en-8-yl trifluoromethanesulfonate in 1,4-dioxane (140 mL) was combined with bis(pinacolato)diboron (17 g, 68 mmol), Pd(dppf)Cl$_2$ (2.1 g, 2.8 mmol), KOAc (17 g, 170 mmol), and KBr (7.3 g, 62 mmol). Nitrogen gas was bubbled through the reaction mixture for 15 min before placing the cap on the sealed tube and heating the reaction vessel in a 100° C. oil bath for 20 h. The reaction mixture was filtered through a pad of Celite and silica gel, rinsing with ethyl acetate and concentrating to afford the crude product, which was purified by silica gel chromatography (10% to 15% ethyl acetate in hexanes). The product was isolated as an oil containing some triflamide and bis(pinacolato)diboron and was used directly in the next reaction.

Step 5: 1-((R)-1-(2,4-Dichlorophenyl)ethyl)-6-(10-(R,S) methyl-1,4-dioxaspiro[4.5]dec-7-en-8-yl)-1H-pyrazolo[3,4-b]pyrazine-3-carbonitrile and 1-((R)-1-(2,4-Dichlorophenyl)ethyl)-6-(6-(R,S)methyl-1,4-dioxaspiro[4.5]dec-7-en-8-yl)-1H-pyrazolo[3,4-b]pyrazine-3-carbonitrile

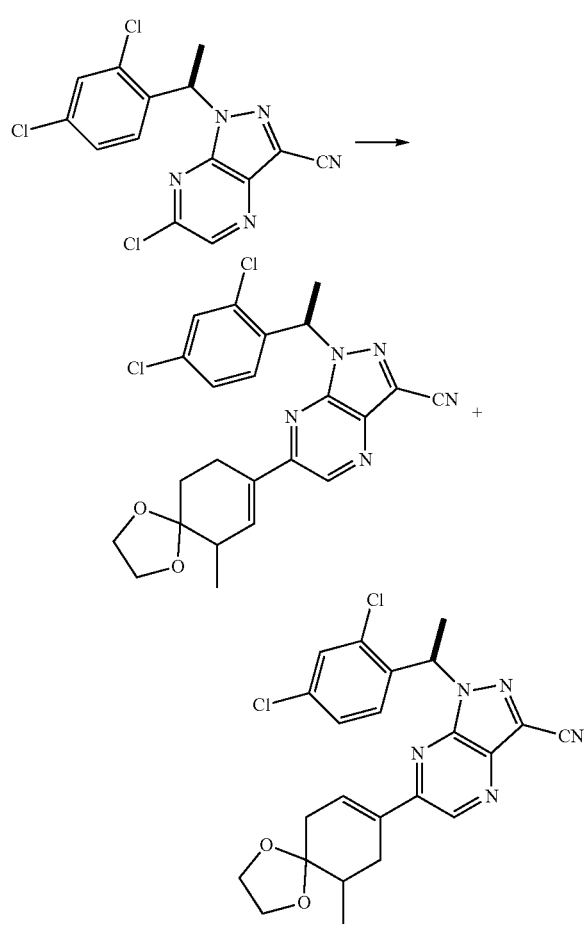

A round bottom flask was charged with 4,4,5,5-tetramethyl-2-(10-methyl-1,4-dioxaspiro[4.5]dec-7-en-8-yl)-1,3,2-dioxaborolane and 4,4,5,5-tetramethyl-2-(6-methyl-1,4-dioxaspiro[4.5]dec-7-en-8-yl)-1,3,2-dioxaborolane (Example 69, Step 4, 8.19 g, 23.4 mmol), (R)-6-chloro-1-(1-(2,4-dichlorophenyl)ethyl)-1H-pyrazolo[3,4-b]pyrazine-3-carbonitrile (Example 23, Step 2, 7.5 g, 21 mmol), PEPPSI-iPr (720 mg, 1.1 mmol), 1,4-dioxane (71 mL), and 1 M aqueous sodium carbonate (63.8 mL, 63.8 mmol). Nitrogen gas was bubbled through the reaction mixture for 15 min before placing the reaction vessel in a pre-heated oil bath at 95° C. for 75 min. The reaction mixture was cooled and diluted with ethyl acetate and saturated aqueous sodium bicarbonate. The organic layer was separated, and the aqueous layer was extracted with ethyl acetate (2×). The combined organic layers were washed with brine, dried over sodium sulfate, concentrated, and purified by silica gel chromatography (15% to 25% ethyl acetate in hexanes; $R_f$=0.15 in 20% ethyl acetate in hexanes) to afford 1-((R)-1-(2,4-dichlorophenyl)ethyl)-6-(6-methyl-1,4-dioxaspiro[4.5]dec-7-en-8-yl)-1H-pyrazolo[3,4-b]pyrazine-3-carbonitrile as the first eluting pair of diastereomers and 1-((R)-1-(2,4-dichlorophenyl)ethyl)-6-(10-methyl-1,4-dioxaspiro[4.5]dec-7-en-8-yl)-1H-pyrazolo[3,4-b]pyrazine-3-carbonitrile as the second eluting pair of diastereomers.

Step 6: 1-((R)-1-(2,4-Dichlorophenyl)ethyl)-6-(3-methyl-4-oxocyclohex-1-en-1-yl)-1H-pyrazolo[3,4-b]pyrazine-3-carbonitrile

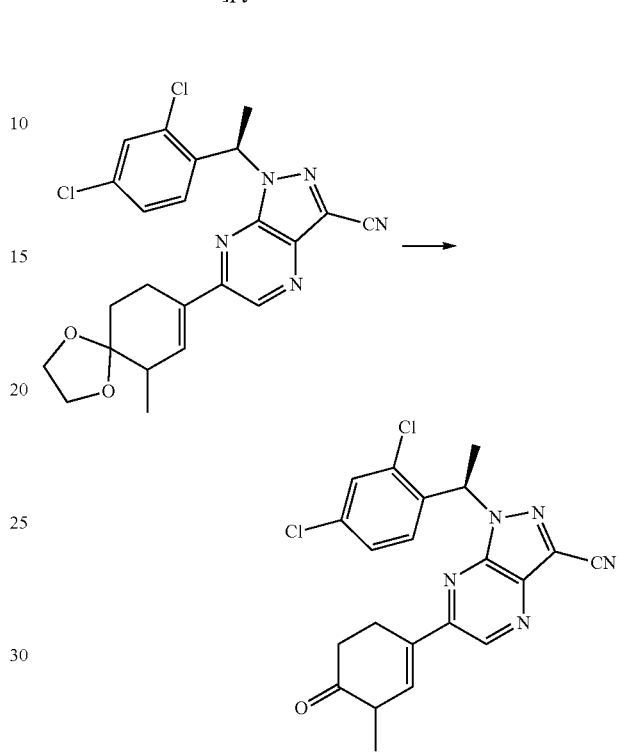

The first pair of diastereomers isolated from Example 69, Step 5, 1-((R)-1-(2,4-dichlorophenyl)ethyl)-6-(6-methyl-1,4-dioxaspiro[4.5]dec-7-en-8-yl)-1H-pyrazolo[3,4-b]pyrazine-3-carbonitrile (500 mg, 1.01 mmol) was diluted with dichloromethane (8 mL) and trifluoroacetic acid (1.6 mL). The resulting clear, red solution was stirred at room temperature for 20 h. The reaction was then carefully basified with saturated aqueous sodium bicarbonate and extracted with dichloromethane (3×). The combined organic layers were dried over sodium sulfate and concentrated to afford the title compound as a mixture of diastereomers (250 mg, 77% yield).

Step 7: 1-((R)-1-(2,4-Dichlorophenyl)ethyl)-6-((3R,4S)-4-((S)-2-(hydroxymethyl)pyrrolidin-1-yl)-3-methylcyclohex-1-en-1-yl)-1H-pyrazolo[3,4-b]pyrazine-3-carbonitrile hydrochloride

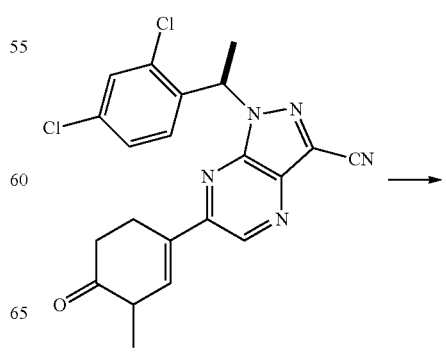

423

-continued

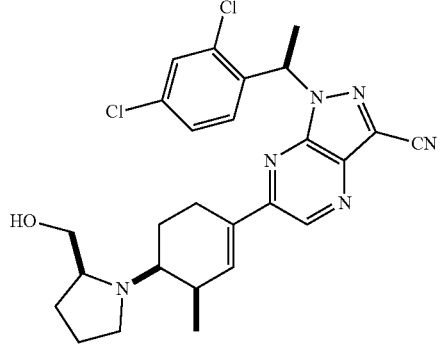

The title compound was synthesized according to the procedure outlined in Example 2, Step 1, substituting 1-((R)-1-(2,4-dichlorophenyl)ethyl)-6-(3-methyl-4-oxocyclohex-1-en-1-yl)-1H-pyrazolo[3,4-b]pyrazine-3-carbonitrile for 1-tert-butoxycarbonyl-3-methyl-4-piperidinone, and L-prolinol for piperidine. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min). The residue was further purified by reverse phase preparative HPLC (Gemini-NX, 10 μm, 250×30 mm, C18 column (Phenomenex, Torrance, Calif.), eluent: 52% acetonitrile in water (containing 0.1% ammonium formate), over 30 min) to give the title compound. The residue was diluted with dichloromethane and saturated aqueous sodium bicarbonate. The organic layer was separated, and the aqueous layer was extracted with dichloromethane (2×). The combined organic layers were dried over sodium sulfate and concentrated to afford the free base, which was converted to the HCl salt by diluting in dichloromethane (5 mL) and adding 1 M HCl in diethyl ether and concentrating under reduced pressure. 1H NMR (400 MHz; CDCl$_3$) δ 8.94 (s, 1H), 7.44-7.37 (m, 2H), 7.22 (dd, J=8.5, 2.1 Hz, 1H), 6.90 (dd, J=5.3, 1.9 Hz, 1H), 6.74 (q, J=7.0 Hz, 1H), 3.53 (dd, J=10.3, 4.6 Hz, 1H), 3.38 (dd, J=10.3, 3.0 Hz, 1H), 3.25-3.17 (m, 2H), 2.84 (dd, J=18.3, 4.5 Hz, 1H), 2.80-2.68 (m, 2H), 2.57-2.41 (m, 2H), 2.10-1.54 (m, 10H), 1.13 (d, J=6.7 Hz, 3H); m/z 511.1 (M+H$^+$).

Example 70

(4-(1-((R)-1-(2,4-Dichlorophenyl)ethyl)-3-methyl-1H-pyrazolo[3,4-b]pyrazin-6-yl)-6-methylcyclohex-3-en-1-yl)-L-proline trifluoroacetate

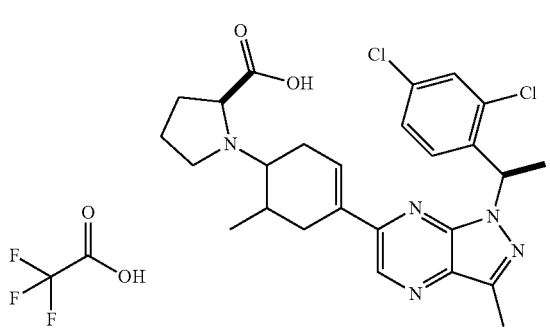 [SMILES: O=C(O)C(F)(F)F ; Cc1nn([C@H](C)c2ccc(Cl)cc2Cl)c2nc(C3=CCC(N4CCC[C@H]4C(=O)O)C(C)C3)cnc12]

424

Step 1. Tert-butyl (7-methyl-1,4-dioxaspiro[4.5]decan-8-yl)-L-prolinate

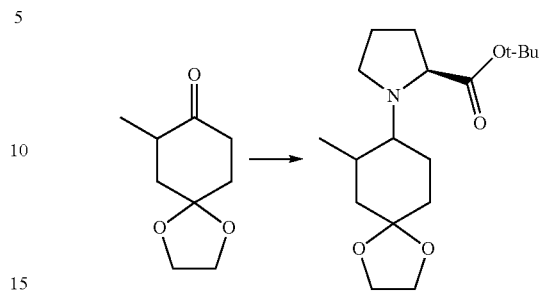

The title compound was isolated as a mixture of diastereomers according to the procedure outlined in Example 68, Step 1, substituting 7-methyl-1,4-dioxaspiro[4.5]decan-8-one for 1,4-dioxaspiro[4.5]decan-8-one. The crude residue was purified using silica gel chromatography (0 to 35% ethyl acetate in hexanes).

Step 2. Methyl (2-methyl-4-oxocyclohexyl)-L-prolinate

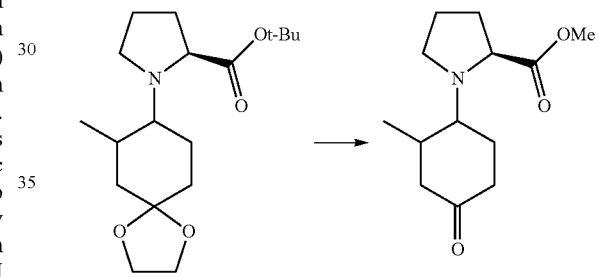

The title compound was isolated as a mixture of diastereomers according to the procedure outlined in Example 68, Step 2, substituting tert-butyl (7-methyl-1,4-dioxaspiro[4.5]decan-8-yl)-L-prolinate (Example 70, Step 1) for tert-butyl (1,4-dioxaspiro[4.5]decan-8-yl)-L-prolinate (Example 68, Step 1). The crude residue was purified using silica gel chromatography (10 to 50% ethyl acetate in hexanes. Rf=0.25 in 30% ethyl acetate in hexanes).

Step 3. Methyl (6-methyl-4-(((trifluoromethyl)sulfonyl)oxy)cyclohex-3-en-1-yl)-L-prolinate

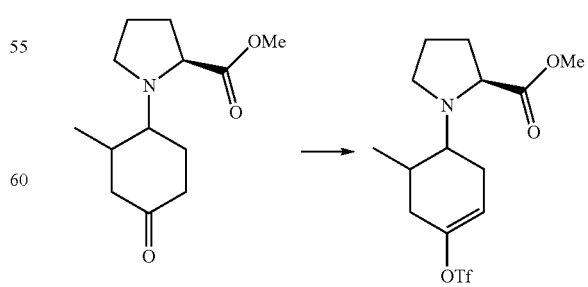

The title compound was isolated as a mixture of diastereomers according to the procedure outlined in Example 68, Step 3, substituting methyl (2-methyl-4-oxocyclohexyl)-L-prolinate (Example 70, Step 2) for Methyl (4-oxocyclohexyl)-L-prolinate (Example 68, Step 2). The crude residue was used without further purification.

Step 4. Methyl (6-methyl-4-(4,4,5,5-tetramethyl-1,3,2-dioxaborolan-2-yl)cyclohex-3-en-1-yl)-L-prolinate

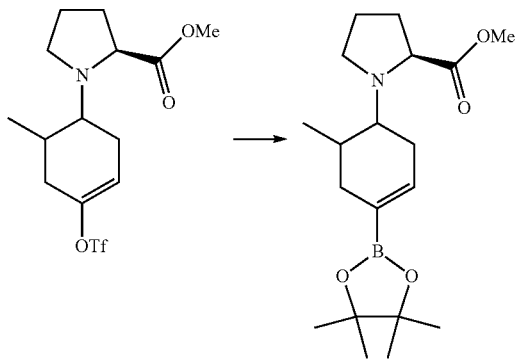 [SMILES: COC(=O)[C@@H]1CCCN1C1CC=C(OS(=O)(=O)C(F)(F)F)CC1C ; COC(=O)[C@@H]1CCCN1C1CC=C(B2OC(C)(C)C(C)(C)O2)CC1C]

The title compound was isolated as a mixture of diastereomers and olefin regioisomers according to the procedure outlined in Example 68, Step 4, substituting methyl (6-methyl-4-(((trifluoromethyl)sulfonyl)oxy)cyclohex-3-en-1-yl)-L-prolinate (Example 70, Step 3) for methyl (4-(((trifluoromethyl)sulfonyl)oxy)cyclohex-3-en-1-yl)-L-prolinate (Example 68, Step 3). The crude residue was purified using silica gel chromatography (5 to 10% ethyl acetate in hexanes. $R_f$=0.50 in 20% ethyl acetate in hexanes).

Step 5. Methyl (4-(1-((R)-1-(2,4-dichlorophenyl)ethyl)-3-methyl-1H-pyrazolo[3,4-b]pyrazin-6-yl)-6-methylcyclohex-3-en-1-yl)-L-prolinate

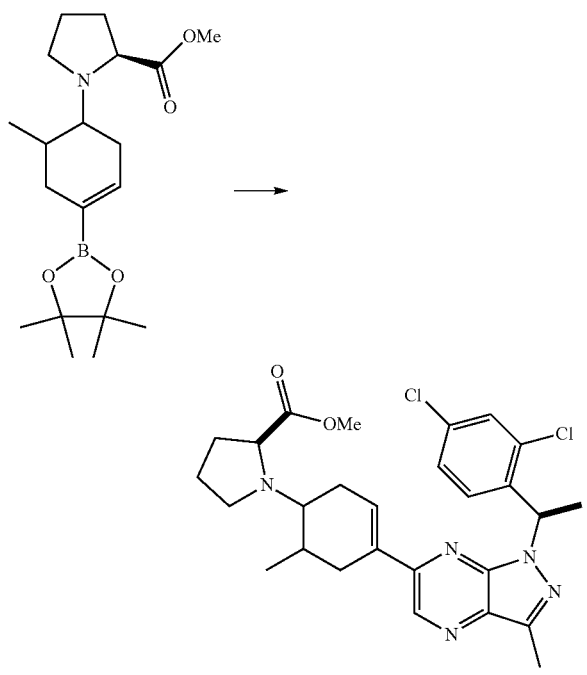

The title compound was isolated as a mixture of diastereomers and olefin regioisomers according to the procedure outlined in Example 68, Step 5, methyl (6-methyl-4-(4,4,5,5-tetramethyl-1,3,2-dioxaborolan-2-yl)cyclohex-3-en-1-yl)-L-prolinate (Example 70, Step 4) for methyl (4-(4,4,5,5-tetramethyl-1,3,2-dioxaborolan-2-yl)cyclohex-3-en-1-yl)-L-prolinate (Example 68, Step 4). The crude residue was purified using silica gel chromatography (10 to 100% ethyl acetate in hexanes). Some diastereomers were separated at this stage by reverse phase preparative HPLC (Gemini-NX, 10 μm, 250×30 mm, C18 column (Phenomenex, Torrance, Calif.), eluent: 80 to 100% acetonitrile in water containing 0.1% ammonium formate, gradient elution over 30 min). The last eluting peak containing the desired compound consisted of 3 diastereomers, which were taken through to the next step.

Step 6. (4-(1-((R)-1-(2,4-Dichlorophenyl)ethyl)-3-methyl-1H-pyrazolo[3,4-b]pyrazin-6-yl)-2-methyl-cyclohex-3-en-1-yl)-L-proline

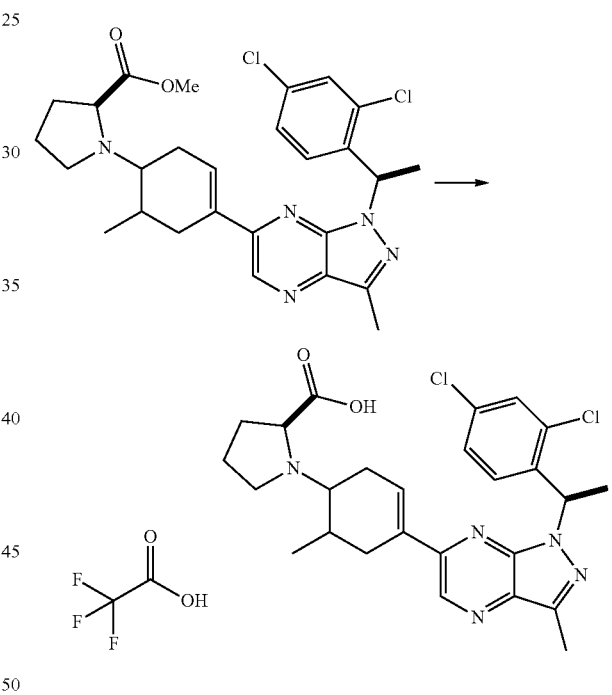

The title compound was isolated as a mixture of diastereomers following the procedure outlined in Example 40, Step 3. The residue was purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the product as a mixture of diastereomers. $^1$H NMR (400 MHz; CD$_3$CN; trifluoroacetic acid salt) δ 8.75 (s, 0.25H), 8.73 (s, 0.75H), 7.49-7.41 (m, 2H), 7.27 (dd, J=8.5, 2.2 Hz, 1H), 6.81-6.77 (m, 0.25H), 6.75-6.67 (m, 0.75H), 6.49 (q, J=7.0 Hz, 1H), 4.55 (dd, J=9.2, 4.2 Hz, 0.25H), 4.47 (dd, J=10.3, 3.7 Hz, 0.75H), 3.96-3.86 (m, 1H), 3.33-3.16 (m, 1H), 3.06-2.59 (m, 4H), 2.56 (s, 3H), 2.55-2.25 (m, 4H), 2.19-2.04 (m, 2H), 1.90 (d, J=7.1 Hz, 3H), 1.20 (d, J=6.9 Hz, 0.75H), 1.12 (d, J=6.8 Hz, 2.25H); m/z 514.2 (M+H$^+$).

Example 71

3-((S)-1-((1S,6R)-4-(1-((R)-1-(2,4-Dichlorophenyl)ethyl)-3-methyl-1H-pyrazolo[3,4-b]pyrazin-6-yl)-6-methylcyclohex-3-en-1-yl)pyrrolidin-2-yl)propanoic acid hydrochloride

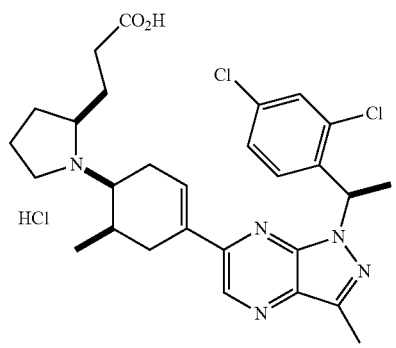

Step 1. Methyl 3-((S)-1-((1S,6R)-4-(1-((R)-1-(2,4-Dichlorophenyl)ethyl)-3-methyl-1H-pyrazolo[3,4-b]pyrazin-6-yl)-6-methylcyclohex-3-en-1-yl)pyrrolidin-2-yl)propanoate

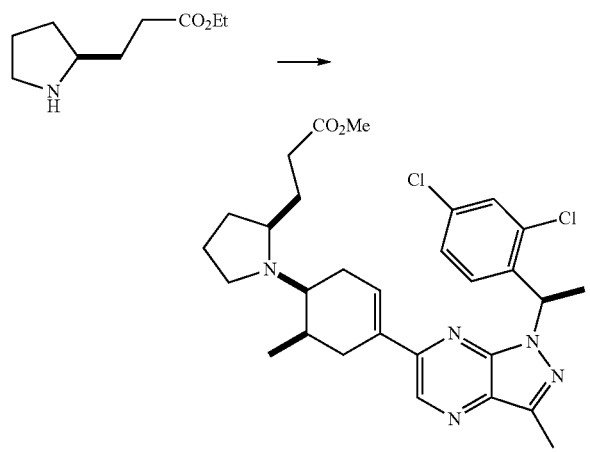

The title compound was synthesized according to the procedures outlined in Example 70, Steps 1-5, substituting ethyl (S)-3-(pyrrolidin-2-yl)propanoate (Example 42, Step 2) for tert-butyl L-prolinate in Step 1. The residue was purified by silica gel chromatography (1 to 10% methanol in dichloromethane), followed by reverse phase preparative HPLC (Gemini-NX, 10 μm, 250×30 mm, C18 column (Phenomenex, Torrance, Calif.), eluent: 70 to 85% acetonitrile in water (containing 0.1% ammonium formate), gradient elution over 20 min) to afford the product as a mixture of diastereomers. The first eluting set of diastereomers were further separated at this stage using SFC (AD-H column, 2×25 cm, 25% MeOH (with 0.1% diethylamine) in $CO_2$, 100 bar, 70 mL/min; 2.83 min).

Step 2. 3-((S)-1-((1S,6R)-4-(1-((R)-1-(2,4-Dichlorophenyl)ethyl)-3-methyl-1H-pyrazolo[3,4-b]pyrazin-6-yl)-6-methylcyclohex-3-en-1-yl)pyrrolidin-2-yl)propanoic acid hydrochloride

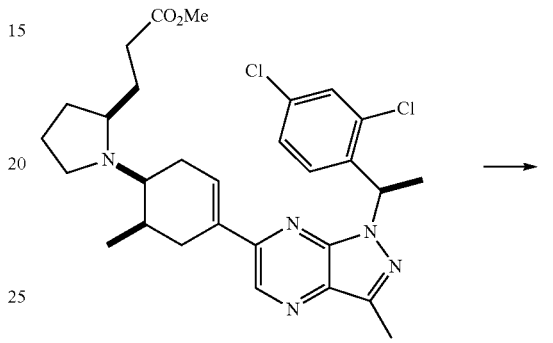

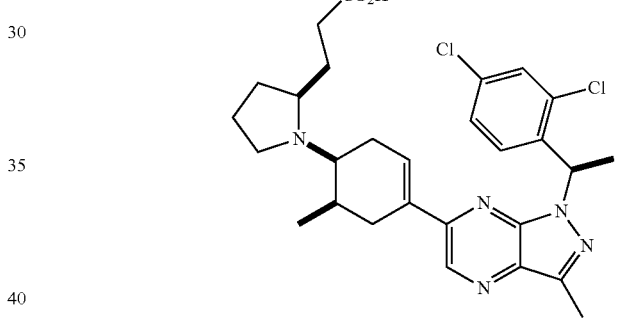

The title compound was prepared from (Example 71, Step 1) by procedures similar to those described in Example 40, Step 3. The residue was further purified by reverse phase preparative HPLC (Gemini-NX, 10 μm, 250×30 mm, C18 column (Phenomenex, Torrance, Calif.), eluent: 0 to 100% acetonitrile in water, both eluents containing 0.1% trifluoroacetic acid, gradient elution over 30 min) to afford the product. This compound was then dissolved in dichloromethane and washed with saturated aqueous sodium bicarbonate. The aqueous layer was extracted with dichloromethane (2×), and the combine organics were dried over sodium sulfate and concentrated. This residue was diluted in dichloromethane and made acidic (pH ~2) with 2 M HCl in diethyl ether to afford the title compound as the HCl salt. $^1$H NMR (400 MHz; $CD_3CN$; HCl salt) δ 8.77 (s, 1H), 7.52-7.40 (m, 2H), 7.29 (dd, J=8.5, 2.2 Hz, 1H), 6.83 (d, J=6.0 Hz, 1H), 6.54-6.48 (m, 1H), 3.94-3.49 (m, 4H), 3.39-2.91 (m, 3H), 2.75-2.34 (m, 7H), 2.35-2.00 (m, 6H), 1.92 (d, J=7.1 Hz, 3H), 1.90-1.76 (m, 1H), 1.31 (d, J=7.0 Hz, 3H); m/z 542.0 (M+H$^+$).

Example 72

3-((S)-1-((1R,6S)-4-(1-((R)-1-(2,4-Dichlorophenyl)ethyl)-3-methyl-1H-pyrazolo[3,4-b]pyrazin-6-yl)-6-methylcyclohex-3-en-1-yl)pyrrolidin-2-yl)propanoic acid hydrochloride

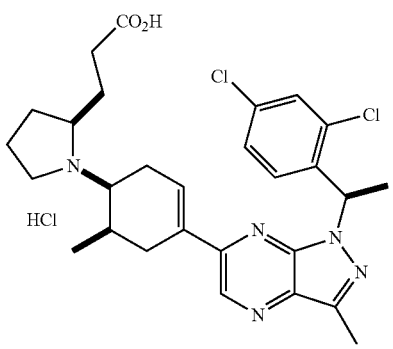

The title compound was synthesized using the other diastereomer obtained in Example 71, Step 1 (after the SFC purification) by procedures similar to those described in Example 40, Step 3. The residue was further purified by reverse phase preparative HPLC (Gemini-NX, 10 μm, 250× 30 mm, C18 column (Phenomenex, Torrance, Calif.), eluent: 0 to 100% acetonitrile in water, both eluents containing 0.1% trifluoroacetic acid, gradient elution over 30 min) to afford the product. This compound was then dissolved in dichloromethane and washed with saturated aqueous sodium bicarbonate. The aqueous layer was extracted with dichloromethane (2×), and the combine organics were dried over sodium sulfate and concentrated. This residue was diluted in dichloromethane and made acidic (pH ~2) with 2 M HCl in diethyl ether to afford the title compound as the HCl salt. $^1$H NMR (400 MHz; CD$_3$CN; HCl salt) δ 8.77 (s, 1H), 7.51-7.41 (m, 2H), 7.29 (dd, J=8.5, 2.2 Hz, 1H), 6.83 (dd, J=6.0, 1.9 Hz, 1H), 6.56-6.43 (m, 1H), 3.91-3.49 (m, 4H), 3.39-3.22 (m, 1H), 3.14-2.92 (m, 2H), 2.73-2.40 (m, 7H), 2.34-2.00 (m, 5H), 1.92 (d, J=7.1 Hz, 3H), 1.90-1.79 (m, 1H), 1.31 (d, J=7.0 Hz, 3H).

Example 73

3-((2S)-1-(4-(3-Cyano-1-((R)-1-(2,4-dichlorophenyl)ethyl)-1H-pyrazolo[3,4-b]pyrazin-6-yl)-2-methylcyclohex-3-en-1-yl)pyrrolidin-2-yl)propanoic acid 2,2,2-trifluoroacetate

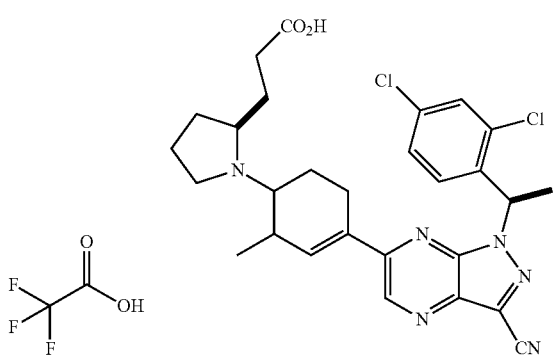 [SMILES: O=C(O)C(F)(F)F ; CC1C=C(c2cnc3c(C#N)nn([C@H](C)c4ccc(Cl)cc4Cl)c3n2)CCC1N1CCC[C@H]1CCC(=O)O]

Step 1. Methyl 3-((2S)-1-(2-methyl-4-(4,4,5,5-tetramethyl-1,3,2-dioxaborolan-2-yl)cyclohex-3-en-1-yl)pyrrolidin-2-yl)propanoate and methyl 3-((2S)-1-(6-methyl-4-(4,4,5,5-tetramethyl-1,3,2-dioxaborolan-2-yl)cyclohex-3-en-1-yl)pyrrolidin-2-yl)propanoate The title compounds were synthesized according to the procedures outlined in Example 70, Steps 3-4. The regioisomers of the compound were then separated by column chromatography (3 to 10% methanol in dichloromethane).

Step 2. Methyl 3-((2S)-1-(4-(3-Cyano-1-((R)-1-(2,4-dichlorophenyl)ethyl)-1H-pyrazolo[3,4-b]pyrazin-6-yl)-2-methylcyclohex-3-en-1-yl)pyrrolidin-2-yl)propanoate

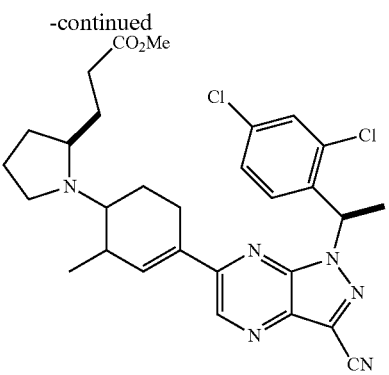

The title compound was prepared analogously to the procedures outlined in Example 68, Step 5.

The title compound was prepared analogously to Example 71, Step 1, substituting (R)-6-chloro-1-(1-(2,4-dichlorophenyl)ethyl)-1H-pyrazolo[3,4-b]pyrazine-3-carbonitrile (Example 23, Step 2) for (R)-6-chloro-1-(1-(2,4-dichlorophenyl)ethyl)-3-methyl-1H-pyrazolo[3,4-b]pyrazine (Example 12, Step 5), employing the first eluting peak from the silica gel column described in Example 73, Step 1. The crude material was purified by silica gel chromatography (1 to 5% methanol in dichloromethane) to afford the title compound as a mixture of diastereomers.

Step 3. 3-((2S)-1-(4-(3-Cyano-1-((R)-1-(2,4-dichlorophenyl)ethyl)-1H-pyrazolo[3,4-b]pyrazin-6-yl)-2-methylcyclohex-3-en-1-yl)pyrrolidin-2-yl)propanoic acid 2,2,2-trifluoroacetate

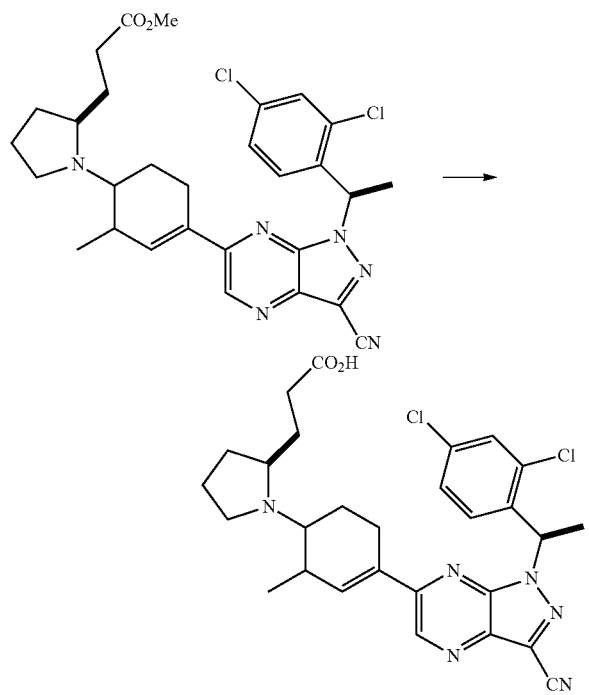

To a solution of methyl 3-((2S)-1-(4-(3-cyano-1-((R)-1-(2,4-dichlorophenyl)ethyl)-1H-pyrazolo[3,4-b]pyrazin-6-yl)-2-methylcyclohex-3-en-1-yl)pyrrolidin-2-yl)propanoate (70 mg, 0.12 mmol) in 1,2-dichloroethane (2.1 mL, 0.06 M) was added Me₃SnOH (67 mg, 0.37 mmol). The mixture was heated to 75° C. for 24 h before the addition of more Me₃SnOH (160 mg, 0.87 mmol). After another 48 h of heating, the reaction was cooled to room temperature and quenched with 1 N aqueous HCl. The mixture was extracted with dichloromethane (3×), and the combined organic layers were dried over sodium sulfate and concentrated under reduced pressure. The residue was purified by reverse phase preparative HPLC (Gemini-NX, 10 µm, 250×30 mm, C18 column (Phenomenex, Torrance, Calif.), eluent: 0 to 100% acetonitrile in water, both eluents containing 0.1% trifluoroacetic acid, gradient elution over 30 min) to yield a 1:1 mixture of title compound isomers. ¹H NMR (400 MHz, CD₃CN; trifluoroacetic acid salts) δ 9.03 (s, 0.5H), 9.03 (s, 0.5H), 8.41 (br s, 1H), 7.52 (t, J=2.3 Hz, 1H), 7.49 (dd, J=8.5, 1.4 Hz, 1H), 7.34 (dd, J=8.5, 2.1 Hz, 1H), 6.95-6.89 (m, 1H), 6.71-6.66 (m, 1H), 4.02-3.86 (m, 1H), 3.69-3.61 (m, 1H), 3.54-3.45 (m, 1H), 3.37-3.17 (m, 1H), 3.09-2.99 (m, 1H), 2.99-2.91 (m, 0.5H), 2.86-2.73 (m, 1H), 2.70-2.46 (m, 4H), 2.45-2.36 (m, 0.5H), 2.25-2.00 (m, 4H), 1.98 (d, J=0.7 Hz, 1.5H), 1.96 (d, J=0.7 Hz, 1.5H), 1.91-1.75 (m, 2H), 1.22 (d, J=7.0 Hz, 1.5H), 1.07 (d, J=6.9 Hz, 1.5H); m/z 553.0 (M+H⁺).

Example 74

3-((2S)-1-(4-(3-Cyano-1-((R)-1-(2,4-dichlorophenyl)ethyl)-1H-pyrazolo[3,4-b]pyrazin-6-yl)-6-methylcyclohex-3-en-1-yl)pyrrolidin-2-yl)propanoic acid 2,2,2-trifluoroacetate

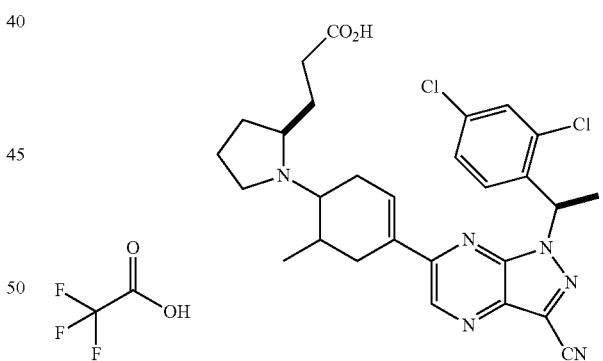

The title compound was isolated as a mixture of diastereomers following the procedures described in Example 73, Steps 4 and 5, substituting the second eluting mixture of isomers from Example 73, Step 1. ¹H NMR (400 MHz, CD₃CN; 2:1 mix of isomers as trifluoroacetic acid salts) δ 9.63 (s, 1H), 9.04 (d, J=1.0 Hz, 1H), 7.54-7.49 (m, 2H), 7.36 (dd, J=8.5, 2.2 Hz, 1H), 6.92 (s, 1H), 6.70 (q, J=7.0 Hz, 1H), 4.00-3.83 (m, 2H), 3.76-3.64 (m, 2H), 3.57-3.46 (m, 2H), 3.36-3.18 (m, 2H), 3.11-2.93 (m, 2H), 2.73-2.52 (m, 4H), 2.21-2.12 (m, 2H), 2.09-2.02 (m, 2H), 2.00-1.98 (m, 3H), 1.25 (d, J=6.9 Hz, 1H), 1.10 (d, J=6.7 Hz, 2H); m/z 553.1 (M+H⁺).

Example 75

1-((R)-1-(2,4-Dichlorophenyl)ethyl)-6-((4R,5S)-4-((S)-2-(hydroxymethyl)pyrrolidin-1-yl)-5-methylcyclohex-1-en-1-yl)-1H-pyrazolo[3,4-b]pyrazine-3-carbonitrile

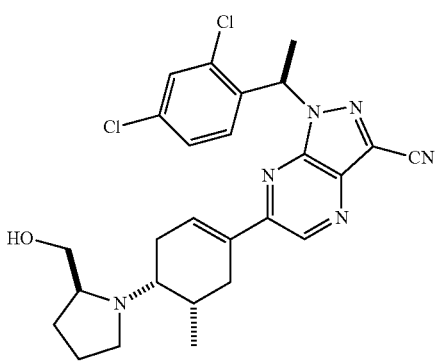

Step 1. 1-((R)-1-(2,4-Dichlorophenyl)ethyl)-6-(5-methyl-4-oxocyclohex-1-en-1-yl)-1H-pyrazolo[3,4-b]pyrazine-3-carbonitrile

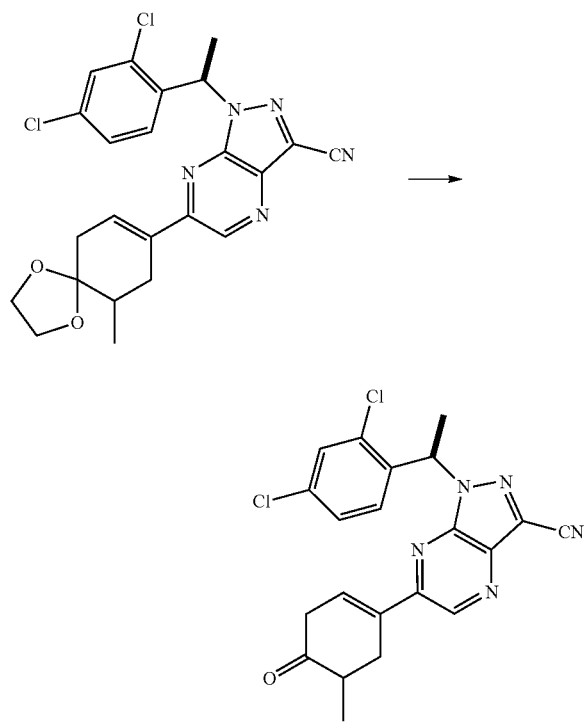 [SMILES: CC1CC(c2cnc3c(C#N)nn([C@H](C)c4ccc(Cl)cc4Cl)c3n2)=CCC12OCCO2 ; CC1CC(c2cnc3c(C#N)nn([C@H](C)c4ccc(Cl)cc4Cl)c3n2)=CCC1=O]

The title compound was synthesized according to the procedure outlined in Example 69, Step 6, replacing the substrate with the second eluting set of diastereomers from Example 69, Step 5.

Step 2. 1-((R)-1-(2,4-Dichlorophenyl)ethyl)-6-((4R,5S)-methyl-4-((S)-2-oxocyclohex-1-en-(hydroxymethyl)pyrrolidin-1-yl)-5-methylcyclohex-1-en-1-yl)-1H-pyrazolo[3,4-b]pyrazine-3-carbonitrile

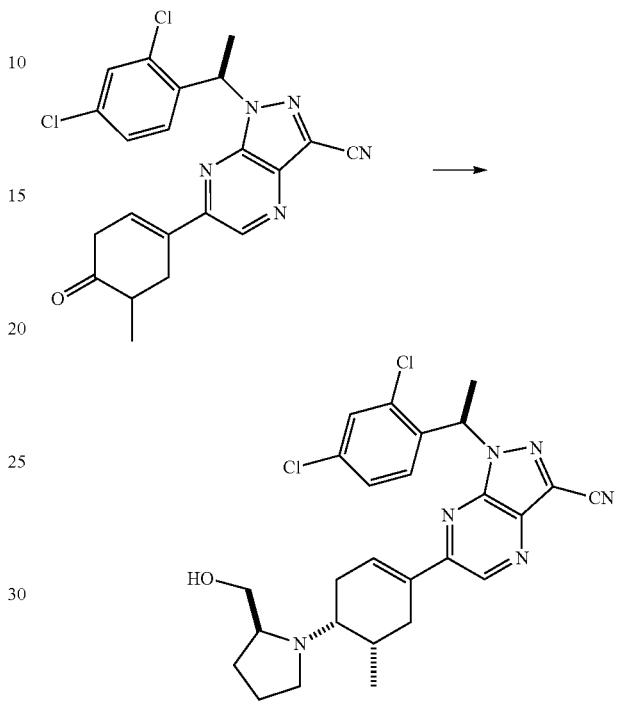

A solution of 1-((R)-1-(2,4-dichlorophenyl)ethyl)-6-(5-methyl-4-oxocyclohex-1-en-1-yl)-1H-pyrazolo[3,4-b]pyrazine-3-carbonitrile (Example 75, Step 1, 350 mg, 0.82 mmol) was made in 1,2-dichloroethane (1 mL) and toluene (2 mL). Then, L-prolinol (330 mg, 3.2 mmol) was added to the solution, which immediately turned a dark red/brown. To this mixture, NaBH$_3$CN (62 mg, 0.98 mmol) was added, followed by AcOH (0.046 mL). The reaction was stirred for 16 h at room temperature before adding more NaBH$_3$CN (68 mg, 1.0 mmol) and AcOH (0.10 mL). The reaction was stirred for another 16 h before diluting with ethyl acetate and saturated aqueous sodium bicarbonate. The organic layer was separated, and the aqueous layer was extracted with ethyl acetate (2×). The combined organic layers were dried over Mg$_2$SO$_4$ and concentrated under reduced pressure. The residue was purified by reverse phase preparative HPLC (Phenomenex Gemini-NX, 10µ, C18, 110A, 250×30 mm, eluent: 0 to 100% acetonitrile in water, both eluents containing 0.1% trifluoroacetic acid, gradient elution over 30 min) to afford a mixture of diastereomers, which were further purified by an additional reverse phase preparative HPLC (Phenomenex Gemini-NX, 10µ, C18, 110A, 250×30 mm, eluent: 45% to 75% acetonitrile in water, both eluents containing 0.1% trifluoroacetic acid, gradient elution over 30 min). The title compound eluted as the first isomer and was isolated as the 2,2,2-trifluoroacetate salt. $^1$H NMR (400 MHz, CDCl$_3$; trifluoroacetic acid salt) δ 10.55 (s, 1H), 8.92 (s, 1H), 7.43 (d, J=8.5 Hz, 1H), 7.40 (d, J=2.1 Hz, 1H), 7.23 (dd, J=8.5, 2.1 Hz, 1H), 6.80 (d, J=2.9 Hz, 1H), 6.73 (q, J=7.0 Hz, 1H), 4.90 (s, 3H), 3.92 (s, 3H), 3.45 (br d, J=7.6

Hz, 1H), 3.16 (br t, J=10.1 Hz, 1H), 2.94-2.63 (m, 5H), 2.28-2.02 (m, 4H), 1.99 (d, J=7.1 Hz, 3H), 1.17 (d, J=5.7 Hz, 3H); m/z 511.0 (M+H⁺).

Example 76

1-((R)-1-(2,4-Dichlorophenyl)ethyl)-6-((4S,5R)-4-((S)-2-(hydroxymethyl)pyrrolidin-1-yl)-5-methylcyclohex-1-en-1-yl)-1H-pyrazolo[3,4-b]pyrazine-3-carbonitrile

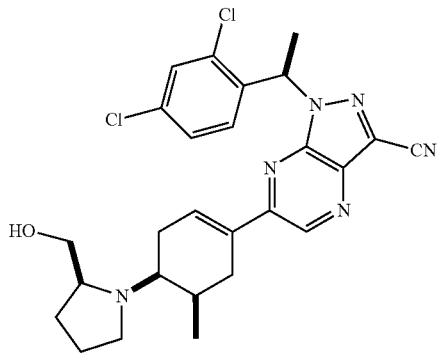

Further elution of the HPLC column described in Example 75, Step 2, afforded a 4:1:1 mixture of diastereomers, which was purified by preparative SFC (AD-H (2×25 cm), 40% isopropanol with 0.1% DEA and CO₂ at 100 bar, 50 mL/min). The title compound was isolated as the third eluting isomer from this purification. ¹H NMR (400 MHz, CD₃OD; trifluoroacetic acid salt) δ 9.08 (s, 1H), 7.46 (dd, J=6.7, 2.1 Hz, 1H), 7.43 (d, J=8.5 Hz, 1H), 7.31 (dd, J=8.5, 2.1 Hz, 1H), 7.02-6.92 (m, 1H), 6.72 (q, J=7.0 Hz, 1H), 4.01 (tt, J=8.7, 4.2 Hz, 1H), 3.81 (dd, J=12.0, 4.8 Hz, 1H), 3.71 (dd, J=12.0, 7.8 Hz, 2H), 3.65-3.57 (m, 1H), 3.44 (td, J=10.6, 6.4 Hz, 1H), 3.02 (dt, J=10.7, 3.8 Hz, 1H), 2.97-2.48 (m, 4H), 2.31-2.02 (m, 2H), 1.99 (d, J=7.0 Hz, 3H), 1.97-1.87 (m, 2H), 1.14 (d, J=6.7 Hz, 3H); m/z 511.1 (M+H⁺).

Example 77

3-((S)-1-((1S,6R)-4-(1-((R)-1-(2,4-Dichlorophenyl)ethyl)-3-methyl-1H-pyrazolo[3,4-b]pyrazin-6-yl)-6-methylcyclohex-3-en-1-yl)pyrrolidin-2-yl)propanamide 2,2,2-trifluoroacetae

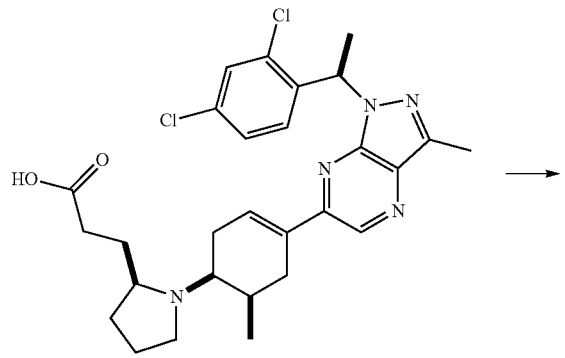

→

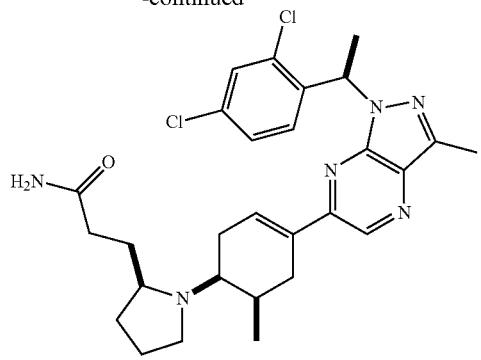

The title compound was synthesized from 3-((S)-1-((1S,6R)-4-(1-((R)-1-(2,4-dichlorophenyl)ethyl)-3-methyl-1H-pyrazolo[3,4-b]pyrazin-6-yl)-6-methylcyclohex-3-en-1-yl)pyrrolidin-2-yl)propanoic acid (Example 71, Step 2) according to the procedure outlined in Example 4, Step 2. Afterwards, the reaction was deposited on silica gel with dichloromethane and purified by silica gel chromatography, eluting with 5% to 20% methanol in dichloromethane. The product was then further purified by reverse phase preparative HPLC (Phenomenex Gemini-NX, 10μ, C18, 110A, 250×30 mm, eluent: 45% to 75% acetonitrile in water, both eluents containing 0.1% trifluoroacetic acid, gradient elution over 30 min) and isolated as the 2,2,2-trifluoroacetate salt. ¹H NMR (400 MHz, CDCl₃; trifluoroacetic acid salt) δ 11.30 (br s, 1H), 8.70 (s, 1H), 7.52 (s, 1H), 7.42 (d, J=8.4 Hz, 1H), 7.36 (d, J=1.5 Hz, 1H), 7.17 (dd, J=8.5, 1.5 Hz, 1H), 6.67 (br s, 1H), 6.55 (q, J=7.1 Hz, 1H), 5.86 (br s, 1H), 4.11-2.99 (m, 8H), 2.93 (d, J=17.2 Hz, 1H), 2.73 (d, J=19.8 Hz, 2H), 2.67 (s, 4H), 2.33-1.99 (m, 4H), 1.95 (d, J=7.0 Hz, 3H), 1.19 (d, J=6.1 Hz, 3H); m/z 541.1 (M+H⁺).

Example 78

((2S)-1-(4-(1-((R)-1-(2,4-Dichlorophenyl)ethyl)-3-methyl-1H-pyrazolo[3,4-b]pyrazin-6-yl)-6-methylcyclohex-3-en-1-yl)pyrrolidin-2-yl)methanol

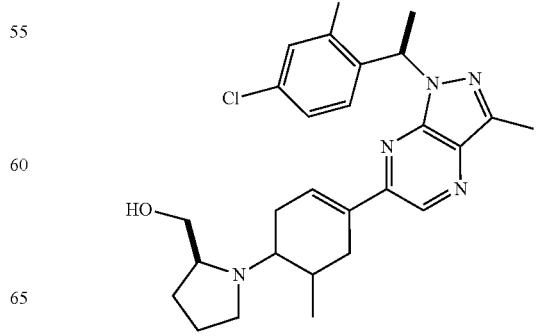

Step 1. 1-((R)-1-(2,4-Dichlorophenyl)ethyl)-3-methyl-6-(10-methyl-1,4-dioxaspiro[4.5]dec-7-en-8-yl)-1H-pyrazolo[3,4-b]pyrazine

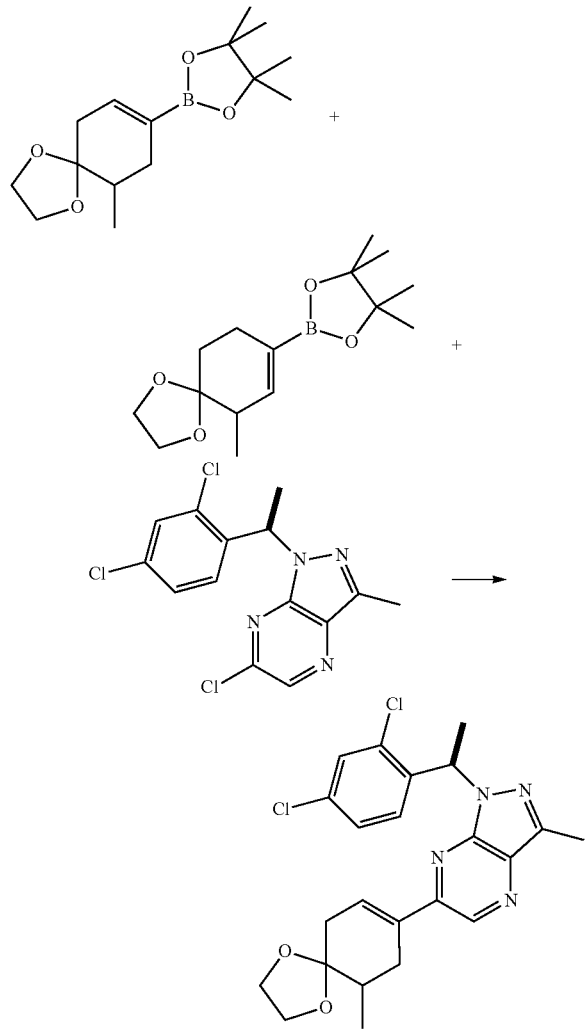

A 300 mL sealed tube was charged with a mixture of 4,4,5,5-tetramethyl-2-(10-methyl-1,4-dioxaspiro[4.5]dec-7-en-8-yl)-1,3,2-dioxaborolane and 4,4,5,5-tetramethyl-2-(6-methyl-1,4-dioxaspiro[4.5]dec-7-en-8-yl)-1,3,2-dioxaborolane (1.40 g, 5.00 mmol), (R)-6-chloro-1-(1-(2,4-dichlorophenyl)ethyl)-3-methyl-1H-pyrazolo[3,4-b]pyrazine (Example 12, Step 5, 1.14 g, 3.33 mmol), Pd(dppf)Cl$_2$ (183 mg, 0.250 mmol), 4:1 THF:H$_2$O (11.2 mL), and sodium carbonate (882 mg, 8.33 mmol). Nitrogen gas was bubbled through the reaction mixture for 35 min before placing the reaction vessel in a pre-heated oil bath at 90° C. for 4 h. The reaction mixture was cooled and diluted with ethyl acetate and saturated aqueous sodium bicarbonate. The organic layer was separated, and the aqueous layer was extracted with ethyl acetate (2×). The combined organic layers were washed with brine, dried over sodium sulfate, concentrated, and purified by silica gel chromatography (10% to 25% ethyl acetate in hexanes) to afford 1-((R)-1-(2,4-dichlorophenyl)ethyl)-3-methyl-6-(10-methyl-1,4-dioxaspiro[4.5]dec-7-en-8-yl)-1H-pyrazolo[3,4-b]pyrazine as the second eluting peak which contained a mixture of diastereomers (320 mg, 21% yield).

Step 2. 4-(1-((R)-1-(2,4-Dichlorophenyl)ethyl)-3-methyl-1H-pyrazolo[3,4-b]pyrazin-6-yl)-6-methylcyclohex-3-en-1-one

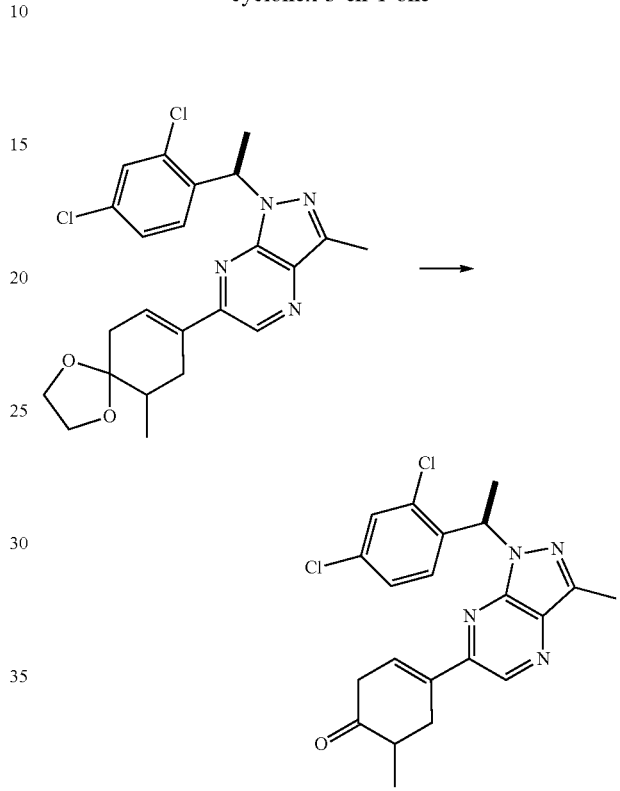

The title compound was synthesized according to the procedure outlined in Example 69, Step 6, replacing the substrate with the second eluting set of diastereomers from Example 78, Step 1.

Step 3. ((2S)-1-(4-(1-((R)-1-(2,4-Dichlorophenyl)ethyl)-3-methyl-1H-pyrazolo[3,4-b]pyrazin-6-yl)-6-methylcyclohex-3-en-1-yl)pyrrolidin-2-yl)methanol

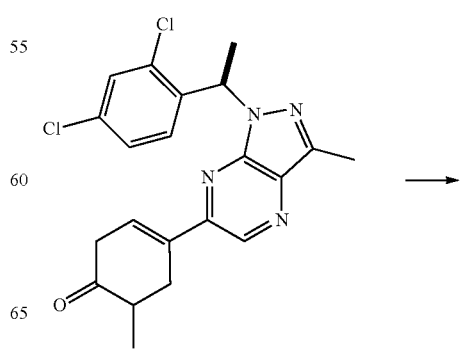

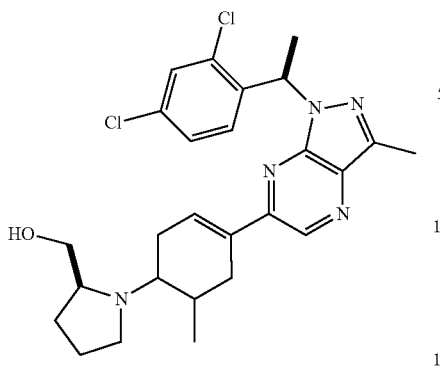

To a solution of 4-[1-[(1R)-1-(2,4-dichlorophenyl)ethyl]-3-methyl-pyrazolo[3,4-b]pyrazin-6-yl]-6-methyl-cyclohex-3-en-1-one (Example 78, Step 2, 287 mg, 0.690 mmol) in 1,2-dichloroethane (2 mL) at room temperature open to air was added [(2S)-pyrrolidin-2-yl]methanol (349 mg, 3.46 mmol), dropwise. The reaction immediately turned a deep red color. The reaction was allowed to stir at room temperature for 1 h. After this time, NaBH₃CN (87 mg, 1.4 mmol) and acetic acid (0.19 mL) were added, and the reaction was allowed to stir overnight at room temperature. The reaction was diluted with dichloromethane and saturated aqueous sodium bicarbonate. The aqueous layer was extracted with dichloromethane (2×10 mL), dried over sodium sulfate, and concentrated to afford a dark red crude mixture. The residue was dissolved in acetonitrile, DMF, and trifluoroacetic acid and purified by reverse phase preparative HPLC (Phenomenex Gemini-NX, 10µ, C18, 110A, 250×30 mm, eluent: 45% to 75% acetonitrile in water, both eluents containing 0.1% trifluoroacetic acid, gradient elution over 30 min). The desired product was isolated as an undefined mixture of diastereomers. $^1$H NMR (400 MHz, CD₃OD; trifluoroacetic acid salt) δ 8.81 (s, 0.5H), 8.80 (s, 0.5H), 7.54-7.40 (m, 2H), 7.27 (ddd, J=8.5, 3.7, 2.0 Hz, 1H), 6.88-6.75 (m, 1H), 6.54 (qd, J=7.1, 2.5 Hz, 1H), 4.15-3.35 (m, 6H), 3.13-2.73 (m, 3.5H), 2.73-2.50 (m, 4H), 2.38-1.99 (m, 3.5H), 1.99-1.84 (m, 4H), 1.22-1.01 (m, 3H); m/z 500.1 (M+H⁺).

Example 79

Step 1: (2S)-1-(4-(3-Cyano-1-((R)-1-(2,4-dichlorophenyl)ethyl)-1H-pyrazolo[3,4-b]pyrazin-6-yl)-6-methylcyclohex-3-en-1-yl)pyrrolidine-2-carboxamide hydrochloride

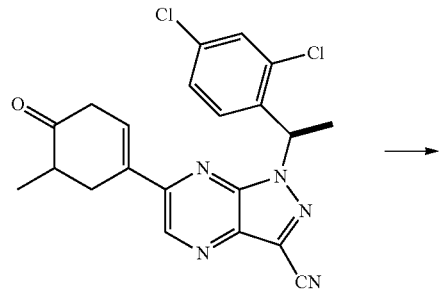

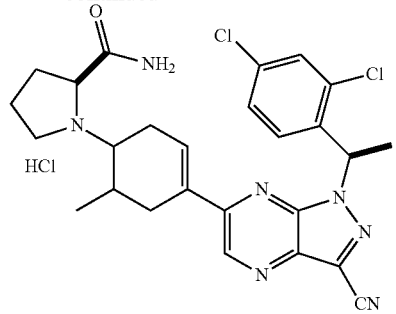

The title compound was synthesized by first combining L-prolinamide (46 .mg, 0.40 mmol) with 1-((R)-1-(2,4-dichlorophenyl)ethyl)-6-(5-methyl-4-oxocyclohex-1-en-1-yl)-1H-pyrazolo[3,4-b]pyrazine-3-carbonitrile (Example 75, Step 1, 120 mg, 0.28 mmol) in 1,2-dichloroethane (1.1 mL) at this point the reaction turns dark red. Then, sodium triacetoxyborohydride (119.31 mg, 0.56 mmol) was added and the color became a deep purple. The reaction was then stirred overnight. The reaction was quenched with the addition of saturated aqueous sodium bicarbonate, followed by extraction with dichloromethane (3×), washed with brine, and dried over anhydrous sodium sulfate. The organics were removed under reduced pressure and purified via reverse phase preparative HPLC (Phenomenex Gemini-NX, 10µ, C18, 110A, 250×30 mm, eluent: 0% to 100% acetonitrile in water, both eluents containing 0.1% trifluoroacetic acid, gradient elution over 30 min). The title compound eluted as the first peak as a mixture of diastereomers of unknown stereochemistry. The volatiles were removed and the trifluoroacetic acid salt was taken up in dichloromethane and washed with saturated aqueous sodium bicarbonate (2×), dried over sodium sulfate, and concentrated under reduced pressure. Then the free base was taken up in dichloromethane and 2 N HCl in diethyl ether was added until the pH was ~3. The volatiles were removed under reduced pressure to afford the title compound as the HCl salt. $^1$H NMR (400 MHz, CD₃CN; trifluoroacetic acid salt) δ 9.05-9.01 (m, 1H), 7.56-7.49 (m, 2H), 7.38-7.33 (m, 1H), 7.03 (s, 1H), 6.94-6.81 (m, 1H), 6.73-6.66 (m, 1H), 6.60 (s, 1H), 4.43 (dd, J=10.5, 2.9 Hz, 1H), 3.98-3.86 (m, 1H), 3.72-3.55 (m, 1H), 3.31-3.14 (m, 1H), 2.84-2.36 (m, 6H), 2.23-2.11 (m, 2.3H), 2.00-1.98 (m, 3H), 1.91-1.75 (m, 0.7H), 1.30 (d, J=6.8 Hz, 0.1H), 1.14 (d, J=6.9 Hz, 0.5H), 1.01 (d, J=6.8 Hz, 2.4H).

Example 80

(S)-1-((1R,6S)-4-(3-Cyano-1-((R)-1-(2,4-dichlorophenyl)ethyl)-1H-pyrazolo[3,4-b]pyrazin-6-yl)-6-methylcyclohex-3-en-1-yl)pyrrolidine-2-carboxamide hydrochloride

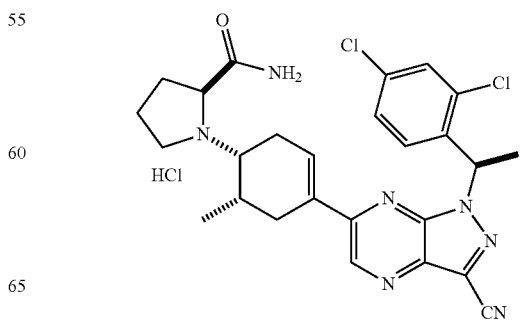

Further elution of the HPLC column in Example 79, gave the title compound as the second eluting peak from the HPLC as the first set of diastereomers with a diastereomeric ratio of ~5:1 of unknown stereochemistry. The volatiles were removed, and the trifluoroacetic acid salt was taken up in dichloromethane and washed with saturated aqueous sodium bicarbonate (2×), dried over sodium carbonate, and concentrated under reduced pressure. The free base was dissolved in dichloromethane, and 2 N HCl in diethyl ether was added until the pH was ~3. The volatiles were removed under reduced pressure to afford the title compound. $^1$H NMR (400 MHz, CD$_3$CN; trifluoroacetic acid salt) δ 9.02 (s, 1H), 7.55-7.48 (m, 2H), 7.36 (dd, J=8.5, 2.2 Hz, 1H), 7.08 (s, 1H), 6.92-6.78 (m, 1H), 6.77-6.63 (m, 2H), 4.43 (dd, J=10.4, 3.6 Hz, 1H), 4.02-3.89 (m, 1H), 3.69-3.61 (m, 1H), 2.89-2.35 (m, 8H), 2.25-2.13 (m, 2H), 1.99 (d, J=7.0 Hz, 3H), 1.14 (d, J=6.9 Hz, 3H); m/z 524.0 (M+H$^+$).

Example 81

6-((4S,5R)-4-((S)-2-(Aminomethyl)pyrrolidin-1-yl)-5-methylcyclohex-1-en-1-yl)-1-((R)-1-(2,4-dichlorophenyl)ethyl)-1H-pyrazolo[3,4-b]pyrazine-3-carbonitrile hydrochloride

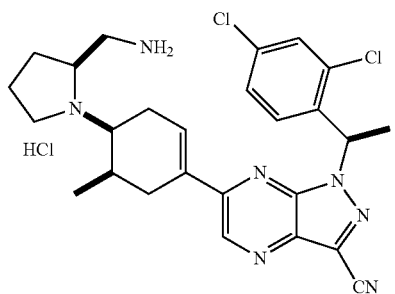

Step 1. (S)-1-Benzylpyrrolidine-2-carboxamide

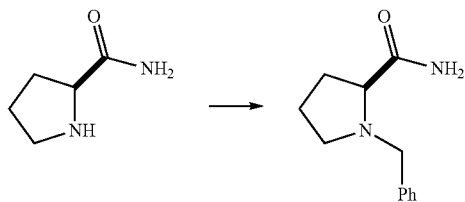 [SMILES: NC(=O)[C@@H]1CCCN1 ; NC(=O)[C@@H]1CCCN1Cc1ccccc1]

To a solution of L-prolinamide (11.4 g, 100 mmol) in dichloromethane-MeOH (4:1, 110 mL) was added benzyl bromide (12.5 mL, 105 mmol) at room temperature. The mixture was stirred under a nitrogen atmosphere overnight. After the starting material was consumed, the solvent was removed under reduced pressure, and the residue was diluted with dichloromethane (150 mL). The organic layer was then washed with saturated aqueous sodium bicarbonate (2×75 mL) and water (75 mL), dried over sodium sulfate, and concentrated under reduced pressure. The crude product was obtained as a white solid, which was used directly in the next step.

Step 2. (S)-(1-Benzylpyrrolidin-2-yl)methanamine

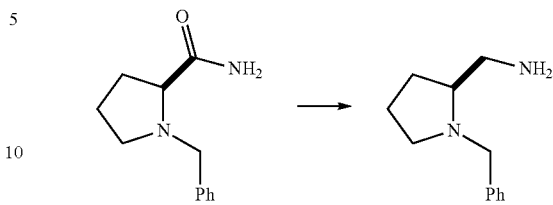

The product of Example 81, Step 1, (2S)-1-benzylpyrrolidine-2-carboxamide (19.9 g, 97.4 mmol) was dissolved in THF (390 mL) and added to lithium aluminum hydride (136 mL, 477 mmol, 4 M solution in THF, 136 mL), slowly. After the addition, the mixture was refluxed under a nitrogen atmosphere overnight. The mixture was cooled to −40° C., and the reaction was quenched by CAREFULLY adding water (19 mL), 15% aqueous NaOH (19 mL), and water (57 mL), sequentially. After the mixture was stirred at room temperature for 30 min, the solids were removed by filtering through Celite®. The Celite® was washed thoroughly with acetone. The solvent was removed under reduced pressure, and crude title compound was obtained as a slightly yellow oil.

Step 3. Tert-butyl (S)-((1-benzylpyrrolidin-2-yl)methyl)carbamate

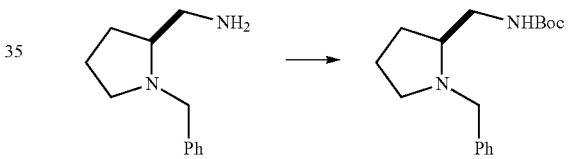

The product of Example 81, Step 2, (S)-(1-benzylpyrrolidin-2-yl)methanamine (19.9 g, 105 mmol) was dissolved in 1,4-dioxane (448 mL) and water (224 mL) and cooled to 0° C. before the addition of potassium carbonate (28.9 g, 209 mmol) and di-tert-butyl carbonate (27.4 g, 126 mmol). The reaction was then stirred at room temperature for 48 h. After this time, the organic solvent was removed under reduced pressure and water was added to dissolve the solids. The residue was extracted with dichloromethane (4×200 mL). The combined organic layers were washed with water, dried over anhydrous sodium sulfate, and concentrated to afford the crude compound.

Step 4. Tert-butyl (S)-(pyrrolidin-2-ylmethyl)carbamate

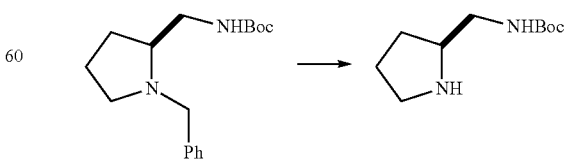

The product of Example 81, Step 3, tert-butyl (S)-((1-benzylpyrrolidin-2-yl)methyl)carbamate (5.0 g, 17 mmol) and 20% palladium hydroxide on carbon (500 mg, 0.70 mmol) were diluted with a solution of ethanol (35 mL) and acetic acid (15 mL). Hydrogen gas was then bubbled through the solution for 2 h before the reaction mixture was stirred under a hydrogen atmosphere overnight. The reaction was filtered through Celite, and the product was used directly in the next step.

Step 5. 6-((4S,5R)-4-((S)-2-(Aminomethyl)pyrrolidin-1-yl)-5-methylcyclohex-1-en-1-yl)-1-((R)-1-(2,4-dichlorophenyl)ethyl)-1H-pyrazolo[3,4-b]pyrazine-3-carbonitrile hydrochloride

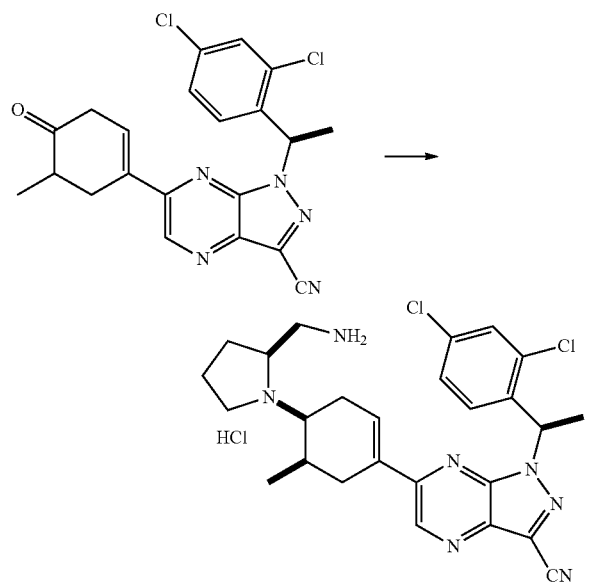

The title compound was synthesized by combining tert-butyl (S)-(pyrrolidin-2-ylmethyl)carbamate (Example 81, Step 4, 62 mg, 0.31 mmol) with 1-((R)-1-(2,4-dichlorophenyl)ethyl)-6-(5-methyl-4-oxocyclohex-1-en-1-yl)-1H-pyrazolo[3,4-b]pyrazine-3-carbonitrile (Example 75, Step 1, 120 mg, 0.28 mmol) in 1,2-dichloroethane (1.1 mL). The reaction turned a dark red color. Then, NaBH(OAc)$_3$ (120 mg, 0.56 mmol) was added, and the reaction turned a deep purple color. The reaction was then stirred overnight at room temperature. The reaction was diluted with saturated aqueous sodium bicarbonate and was extracted with dichloromethane (3×), washing with brine and dried over anhydrous sodium sulfate. The organic solvent was removed under reduced pressure, and the crude residue was purified by reverse phase preparative HPLC (Phenomenex Gemini-NX, 10μ, C18, 110A, 250×30 mm, eluent: 0% to 100% acetonitrile in water, both eluents containing 0.1% trifluoroacetic acid, gradient elution over 30 min), which separated the diastereomers and afforded the title compound as the second eluting peak out of three UV peaks. The residue was then subjected to 4 N HCl in 1,4-dixoane and stirred for 3 h before being concentrated under reduced pressure. This oil was rinsed with acetonitrile to remove an impurity, leaving the title compound as the final product. $^1$H NMR (400 MHz; CD$_3$OD; HCl salt) δ 9.10 (s, 1H), 7.50 (d, J=2.1 Hz, 1H), 7.45 (d, J=8.5 Hz, 1H), 7.34 (dd, J=8.5, 2.1 Hz, 1H), 6.99-6.93 (m, 1H), 6.74 (q, J=7.0 Hz, 1H), 4.27-4.18 (m, 1H), 3.86-3.77 (m, 2H), 3.77-3.70 (m, 2H), 3.69-3.63 (m, 4H), 3.60-3.54 (m, 2H), 3.49-3.38 (m, 2H), 2.96-2.82 (m, 2H), 2.74-2.62 (m, 1H), 2.44-2.30 (m, 1H), 2.28-2.08 (m, 2H), 2.01 (d, J=7.1 Hz, 3H), 1.18 (d, J=6.0 Hz, 3H); m/z 510.1 (M+H$^+$).

Example 82

N—(((S)-1-((1S,6R)-4-(3-Cyano-1-((R)-1-(2,4-dichlorophenyl)ethyl)-1H-pyrazolo[3,4-b]pyrazin-6-yl)-6-methylcyclohex-3-en-1-yl)pyrrolidin-2-yl)methyl)methanesulfonamide hydrochloride

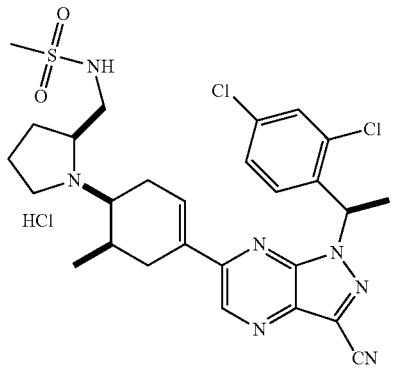

The title compound was synthesized by dissolving 6-((4S,5R)-4-((S)-2-(aminomethyl)pyrrolidin-1-yl)-5-methylcyclohex-1-en-1-yl)-1-((R)-1-(2,4-dichlorophenyl)ethyl)-1H-pyrazolo[3,4-b]pyrazine-3-carbonitrile hydrochloride (Example 81, Step 5, 15 mg, 0.030 mmol) in dichloromethane (0.3 mL) with triethylamine (12 μL, 0.090 mmol). Then, methanesulfonyl chloride (2.7 μL, 0.040 mmol) was added, and the reaction was stirred for 30 min before the addition of water. The aqueous layer was extracted with dichloromethane (3×), and the combined organics were dried over anhydrous sodium sulfate and purified by column chromatography (1 to 4% methanol in dichloromethane, Rf ~0.45 in 4% methanol in dichloromethane) to afford the product as the free base before. The product was then diluted with dichloromethane and acidified by the addition of 2 M HCl in diethyl ether until the pH was ~3. The solution was the concentrated to afford the title compound as the HCl salt. $^1$H NMR (400 MHz, CDCl$_3$) δ 8.94 (s, 1H), 7.43 (d, J=8.5 Hz, 1H), 7.39 (d, J=2.1 Hz, 1H), 7.23 (dd, J=8.5, 2.1 Hz, 1H), 6.86-6.81 (m, 1H), 6.75 (q, J=7.1 Hz, 1H), 4.98-4.75 (m, 1H), 3.24-3.02 (m, 3H), 2.98 (s, 3H), 2.76-2.24 (m, 7H), 2.01-1.90 (m, 4H), 1.86-1.69 (m, 3H), 0.95 (d, J=6.9 Hz, 3H); m/z 588.1 (M+H$^+$).

Example 83

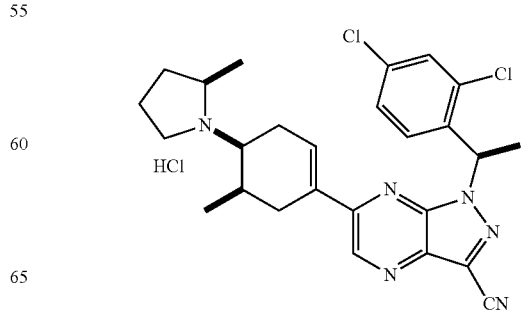

The title compound was synthesized according to the procedure outlined in Example 79, substituting (R)-2-methylpyrrolidine for L-prolinamide. The crude material was purified via reverse phase preparative HPLC (Phenomenex Gemini-NX, 10μ, C18, 110A, 250×30 mm, eluent: 0% to 100% acetonitrile in water, both eluents containing 0.1% trifluoroacetic acid, gradient elution over 30 min) to yield the title compound eluted as a mixture of diastereomers. These diastereomers were separated using chiral preparative SFC (OD-H (2×25 cm), 30% methanol with 0.1% diethylamine and $CO_2$ at 100 bar, 60 mL/min) to afford 3 diastereomers. The third eluting diastereomer ($t_r$=5.56 min, 39 mg) was converted to the HCl salt by diluting in dichloromethane (2 mL) and adding 1 M HCl in $Et_2O$ (0.5 mL) to yield the title compound. $^1$H NMR (400 MHz, $CDCl_3$) δ 8.94 (s, 1H), 7.43 (d, J=8.5 Hz, 1H), 7.39 (d, J=2.2 Hz, 1H), 7.22 (dd, J=8.5, 2.1 Hz, 1H), 6.90-6.84 (m, 1H), 6.74 (q, J=7.1 Hz, 1H), 3.34-3.07 (m, 1H), 2.86-2.24 (m, 8H), 1.99 (d, J=7.1 Hz, 4H), 1.90-1.71 (m, 2H), 1.55-1.42 (m, 1H), 0.99 (t, J=7.4 Hz, 6H); m/z 495.1 (M+H$^+$).

Example 84

1-((R)-1-(2,4-Dichlorophenyl)ethyl)-6-(4-((S)-2-(methoxymethyl)pyrrolidin-1-yl)-5-methylcyclohex-1-en-1-yl)-1H-pyrazolo[3,4-b]pyrazine-3-carbonitrile hydrochloride

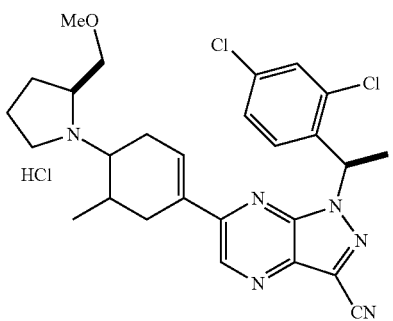 [SMILES: COC[C@@H]1CCCN1C1CC=C(c2cnc3c(C#N)nn([C@H](C)c4ccc(Cl)cc4Cl)c3n2)CC1C ; Cl]

Step 1. (S)-2-(Methoxymethyl)pyrrolidine

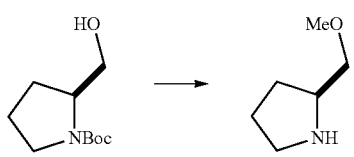 [SMILES: CC(C)(C)OC(=O)N1CCC[C@H]1CO ; COC[C@@H]1CCCN1]

To a solution of N-Boc-L-prolinol (2.0 g, 9.9 mmol) in THF (33 mL) cooled to 0° C. was added sodium hydride (0.75 g, 19 mmol). After 15 min, methyl iodide (0.74 mL, 12 mmol) was added, and the reaction was allowed to warm to room temperature and stirred 16 h. The reaction was quenched by the addition of saturated aqueous ammonium chloride, followed by extraction with ethyl acetate (3×), washed with brine, and dried over anhydrous sodium sulfate. The organics were removed under reduced pressure. The resulting yellow oil was diluted with 4 N HCl in 1,4-dioxane (17 mL) for 3 h before concentrating the solution under reduced pressure to afford the title compound as the HCl salt.

Step 2. 1-((R)-1-(2,4-Dichlorophenyl)ethyl)-6-(4-((S)-2-(methoxymethyl)pyrrolidin-1-yl)-5-methylcyclohex-1-en-1-yl)-1H-pyrazolo[3,4-b]pyrazine-3-carbonitrile hydrochloride

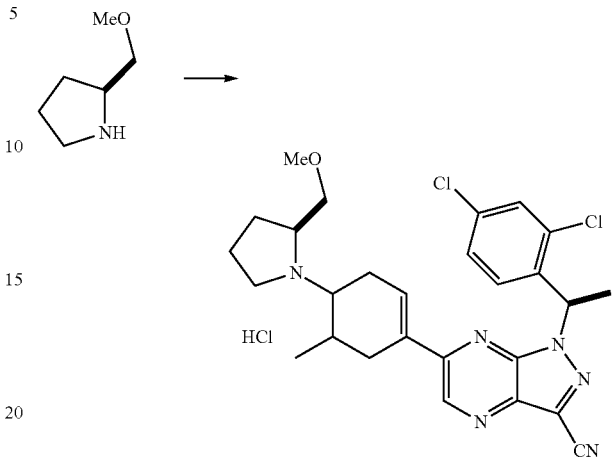

The title compound was synthesized according to the procedure outlined in Example 79, substituting (S)-2-(methoxymethyl)pyrrolidine (Example 79, Step 1) for L-Prolinamide. The crude material was purified via reverse phase preparative HPLC (Phenomenex Gemini-NX, 10μ, C18, 110A, 250×30 mm, eluent: 0% to 100% acetonitrile in water, both eluents containing 0.1% trifluoroacetic acid, gradient elution over 30 min) to yield the title compound eluted as a mixture of diastereomers of unknown stereochemistry. The fractions containing the product were combined and concentrated under reduced pressure. This residue was dissolved in dichloromethane and washed with sodium bicarbonate. The aqueous layer was extracted with dichloromethane (2×) and the combined organic layers were dried over sodium sulfate and concentrated under reduced pressure. The freebase was then dissolved in dichloromethane and the pH of the solution was adjusted to 2-3 with HCl in diethyl ether to provide the title compound as the HCl salt. $^1$H NMR (400 MHz, $CDCl_3$, trifluoroacetic acid salt) δ 8.94-8.86 (m, 1H), 7.47-7.36 (m, 2H), 7.23 (dt, J=8.3, 2.1 Hz, 1H), 6.80 (s, 1H), 6.74 (q, J=7.0 Hz, 1H), 6.34-5.85 (m, 1H), 4.39-3.89 (m, 1H), 3.86-3.73 (m, 1H), 3.68-3.33 (m, 5H), 3.27-3.09 (m, 1H), 3.07-2.57 (m, 5H), 2.50-1.88 (m, 7H), 1.31-1.10 (m, 3H); m/z 525.2 (M+H$^+$).

Example 85

2-((2S)-1-(4-(3-Cyano-1-((R)-1-(2,4-dichlorophenyl)ethyl)-1H-pyrazolo[3,4-b]pyrazin-6-yl)-6-methylcyclohex-3-en-1-yl)pyrrolidin-2-yl)acetic acid 2,2,2-trifluoroacetate

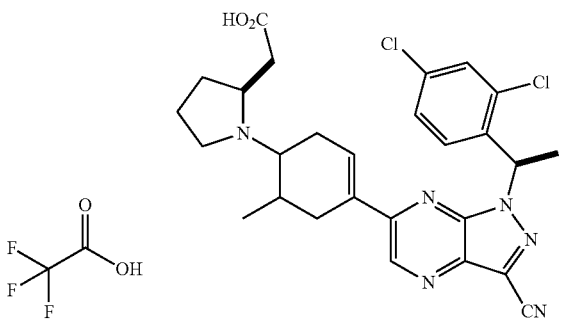 [SMILES: O=C(O)C(F)(F)F ; CC1CC(c2cnc3c(C#N)nn([C@H](C)c4ccc(Cl)cc4Cl)c3n2)=CCC1N1CCC[C@H]1CC(=O)O]

The title compound was synthesized according to the procedure outlined in Example 79, substituting (S)-2-(pyrrolidin-2-yl)acetic acid for L-prolinamide The crude mate-

Example 86

(S)-1-((1S,6R)-4-(1-((R)-1-(2,4-Dichlorophenyl) ethyl)-3-methyl-1H-pyrazolo[3,4-b]pyrazin-6-yl)-6-methylcyclohex-3-en-1-yl)pyrrolidine-2-carboxamide hydrochloride

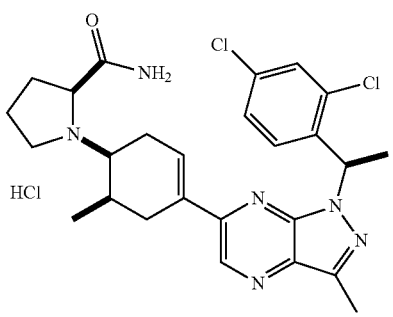

The following compound was made using similar methods as Example 79 replacing 1-((R)-1-(2,4-dichlorophenyl)ethyl)-6-(5-methyl-4-oxocyclohex-1-en-1-yl)-H-pyrazolo[3,4-b]pyrazine-3-carbonitrile (Example 75, Step 1) with 4-(1-((R)-1-(2,4-dichlorophenyl)ethyl)-3-methyl-1H-pyrazolo[3,4-b]pyrazin-6-yl)-6-methylcyclohex-3-en-1-one (Example 78, Step 3). The residue was purified by reverse phase preparative HPLC (Phenomenex Gemini-NX, 10μM, C18, 110A, 250×30 mm (Phenomenex, Torrance, Calif.), eluent: 0 to 100% acetonitrile in water, both eluents containing 0.1% trifluoroacetic acid, gradient elution over 30 min) to afford the title compound as a mixture of isomers as their trifluoroacetic acid salts. The product was diluted in a solution of 20% methanol in dichloromethane and passed through an Agilent StratoSphere plug (PL-HCO3 MP SPE, Flangeless) to afford the free base. The solvent was evaporated, and the oil was further purified by HPLC using a Chiralpak® OZ-H column (Daicel, Corporation, West Chester, Pa.), eluting with 30% IPA in heptanes containing 0.1% diethylamine to afford the free base of the title compound as the first eluting isomer. The residue was dissolved in dichloromethane (1 mL), and 1 M HCl in diethyl ether was added at room temperature. The mixture was then concentrated under reduced pressure to afford the title compound as the HCl salt. $^1$H NMR (400 MHz; CD$_3$CN; HCl salt): δ 8.69 (s, 1H), 7.47-7.41 (m, 2H), 7.28-7.23 (m, 1H), 7.10-7.03 (m, 1H), 6.75-6.71 (m, 1H), 6.48 (q, J=7.1 Hz, 1H), 5.89-5.81 (m, 1H), 3.26-3.20 (m, 1H), 3.15-3.10 (m, 1H), 2.66-2.53 (m, 6H), 2.42-2.25 (m, 4H), 1.89 (d, J=7.1 Hz, 3H), 1.85-1.70 (m, 4H), 0.95 (d, J=6.9 Hz, 3H); m/z 513.2 (M+H$^+$).

Example 87

1-((R)-1-(2,4-Dichlorophenyl)ethyl)-6-((4S,5R)-4-((2S)-2-(1-hydroxy-2-(methylsulfonyl)ethyl)pyrrolidin-1-yl)-5-methylcyclohex-1-en-1-yl)-1H-pyrazolo[3,4-b]pyrazine-3-carbonitrile hydrochloride

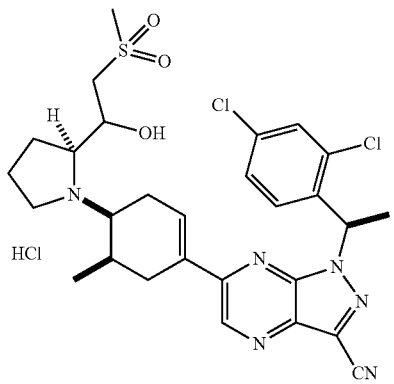

Step 1. Tert-butyl (2S)-2-(1-hydroxy-2-(methylsulfonyl)ethyl)pyrrolidine-1-carboxylate

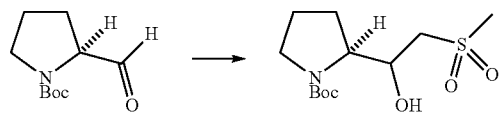 [SMILES: CC(C)(C)OC(=O)N1CCC[C@H]1C=O ; CC(C)(C)OC(=O)N1CCC[C@H]1C(O)CS(C)(=O)=O]

Dimethyl ((methylsulfonyl)methyl)phosphonate (3.65 g, 18.1 mmol) was dissolved in THF (150 mL), and the solution was cooled to 0° C. Sodium tert-butoxide (1.74 g, 18.1 mmol) was added, and the mixture was stirred for 30 min at 0° C. A solution of tert-butyl (S)-2-formylpyrrolidine-1-carboxylate (3.00 g, 15.1 mmol) in THF (10 mL) was added to the reaction mixture. The mixture was stirred vigorously for 30 min at 0° C. before warming to room temperature. The reaction mixture was stirred for 30 min at room temperature. The reaction was quenched by the addition of saturated aqueous sodium bicarbonate (150 mL), and the mixture was stirred vigorously for 30 min. The mixture was extracted with dichloromethane (3×200 mL). The combined organic layers were dried over sodium sulfate, filtered, and concentrated under reduced pressure. The residue was purified by silica gel chromatography (0 to 50% ethyl acetate in hexanes) to afford the title compounds as two distinct fractions, first eluting isomer (1.97 g, 45% yield, white solid) and second eluting isomer (2.06 g, 47% yield, white solid). The second eluting isomer was used in subsequent reactions.

Step 2. 2-(Methylsulfonyl)-1-((S)-pyrrolidin-2-yl)ethan-1-ol hydrochloride

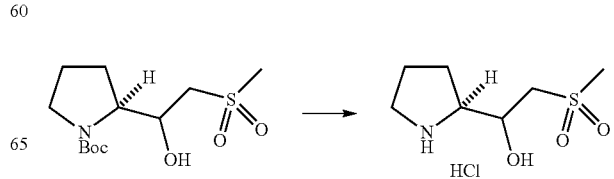

tert-Butyl (2S)-2-(1-hydroxy-2-(methylsulfonyl)ethyl) pyrrolidine-1-carboxylate (Example 87, step 1, second eluting isomer, 1.4 g, 4.8 mmol) was dissolved in dichloromethane (20 mL), and then HCl (4 N in 1,4-dioxane, 5.96 mL, 23.9 mmol) was added. The mixture was stirred for 1 h at room temperature before concentrating the mixture under reduced pressure to afford the title compound (1.08 g, 99% yield) as an off-white solid.

Step 3. 1-((S)-1-((1S,6R)-4-(1-((R)-1-(2,4-Dichlorophenyl)ethyl)-3-methyl-1H-pyrazolo[3,4-b]pyrazin-6-yl)-6-methylcyclohex-3-en-1-yl)pyrrolidin-2-yl)-2-(methylsulfonyl)ethan-1-ol hydrochloride

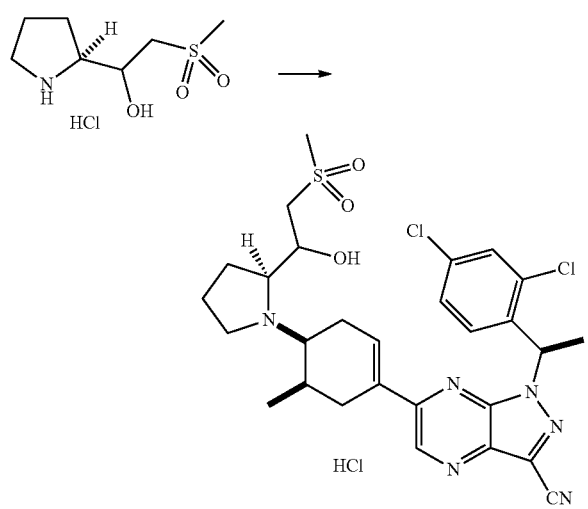

1-((R)-1-(2,4-Dichlorophenyl)ethyl)-6-(5-methyl-4-oxocyclohex-1-en-1-yl)-H-pyrazolo[3,4-b]pyrazine-3-carbonitrile (Example 75, Step 1, 100 mg, 0.235 mmol) was dissolved in 1,2-dichloroethane (3 mL) at room temperature. 2-(Methylsulfonyl)-1-((S)-pyrrolidin-2-yl)ethan-1-ol hydrochloride (Example 87, step 2, 160 mg, 0.70 mmol) was added to the reaction mixture, followed by NaBH(OAc)$_3$ (200 mg, 0.94 mmol). The mixture was stirred for 8 h at room temperature before adding acetic acid (0.5 mL) and by NaBH$_4$CN (59 mg, 0.94 mmol). The mixture was vigorously stirred for 30 min before the addition of saturated aqueous sodium bicarbonate (15 mL). The mixture was extracted with dichloromethane (3×15 mL). The combined organic fractions were dried over sodium sulfate, filtered, and concentrated under reduced pressure. The residue was purified by reversed phase preparative HPLC (Gemini-NX, 10 µm, 250×30 mm, C18 column (Phenomenex, Torrance, Calif.), eluent: 0 to 100% acetonitrile in water, both eluents containing 0.1% trifluoroacetic acid, gradient elution over 30 min) to afford the product as a mixture of diastereomers. The mixture of isomers was further purified by chiral HPLC using a Chiralpak® IF column (Daicel Corporation, West Chester, Pa.) eluting with 40% ethanol in heptanes (containing 0.1% diethylamine) to afford the free base of the title compound as the third eluting isomer. The residue was dissolved in dichloromethane (1 mL) before adding HCl (1 M in diethyl ether). The mixture was concentrated under reduced pressure to afford the title compound as a yellow solid (12 mg, 8.5% yield). $^1$H NMR (400 MHz, CDCl$_3$; free base) δ 8.94 (d, J=5.4 Hz, 1H), 7.44 (d, J=8.5 Hz, 1H), 7.40 (d, J=2.1 Hz, 1H), 7.24 (dd, J=8.5, 2.1 Hz, 1H), 6.86 (br s, 1H), 6.75 (q, J=7.1 Hz, 1H), 4.07-3.98 (m, 3H), 3.76-3.69 (m, 1H), 3.27-2.98 (m, 4H), 2.94 (s, 3H), 2.75-2.48 (m, 5H), 2.40 (s, 2H), 2.00 (d, J=7.1 Hz, 4H), 1.96-1.78 (m, 3H); m/z 603.1 (M+H$^+$).

Example 88

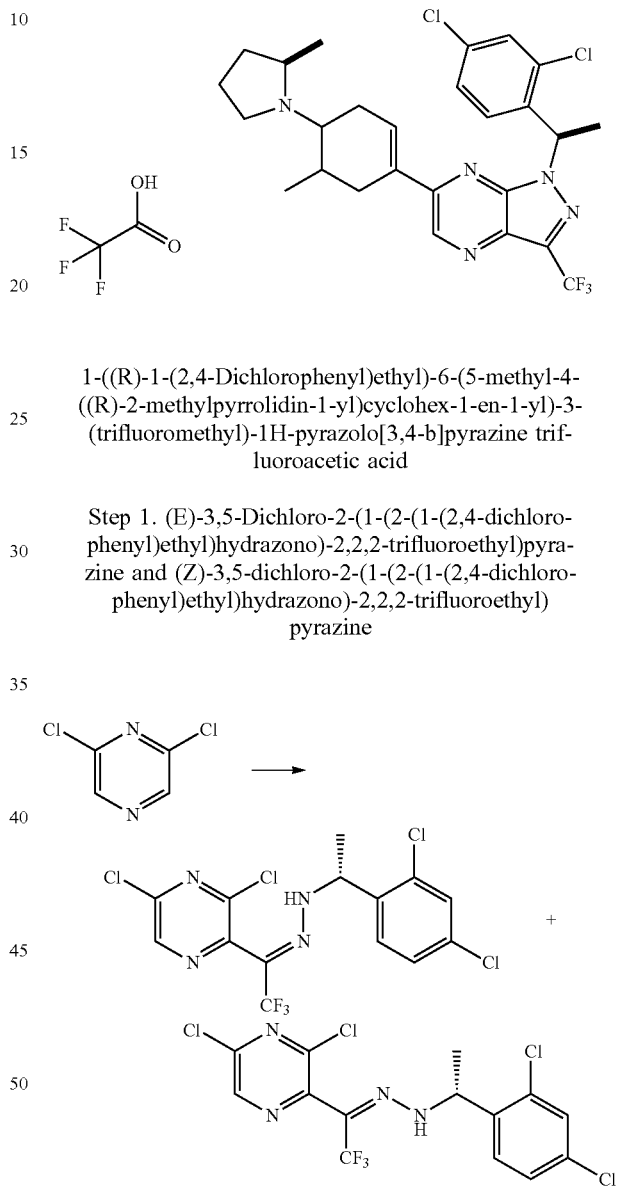

1-((R)-1-(2,4-Dichlorophenyl)ethyl)-6-(5-methyl-4-((R)-2-methylpyrrolidin-1-yl)cyclohex-1-en-1-yl)-3-(trifluoromethyl)-1H-pyrazolo[3,4-b]pyrazine trifluoroacetic acid Step 1. (E)-3,5-Dichloro-2-(1-(2-(1-(2,4-dichlorophenyl)ethyl)hydrazono)-2,2,2-trifluoroethyl)pyrazine and (Z)-3,5-dichloro-2-(1-(2-(1-(2,4-dichlorophenyl)ethyl)hydrazono)-2,2,2-trifluoroethyl)pyrazine To a solution of 2,2,6,6-tetramethylpiperidine (13.71 mL, 80.55 mmol) in THF (200 mL) at −40° C. was added n-BuLi (2.5 M in hexanes, 34.91 mL, 87.26 mmol). The mixture was stirred at −40° C. for 30 min. In a separate flask, ethyl 2,2,2-trifluoroacetate (10.38 mL, 87.26 mmol) and 2,6-dichloropyrazine (10.00 g, 67.13 mmol) were dissolved in THF (200 mL) and cooled to −90° C. The lithium 2,2,6,6-tetramethylpiperidine solution was added to the 2,6-dichloropyrazine solution via cannula over 30 min at −90° C. The mixture was stirred at −90° C. for 30 min and (R)-(1-(2,4-dichlorophenyl)ethyl)hydrazine hydrochloride (Example 5, Step 2, 11.7 g, 9.73 g, 40.28 mmol) was added, and then the mixture was allowed to warm up to room temperature. The mixture was concentrated under reduced pressure, then ethanol (200 mL) was added and the mixture was stirred at room temperature for 24 h. The mixture was concentrated under reduced pressure and then the residue was purified by silica gel chromatography (0 to 100% EtOAc in hexanes) to provide the step 1 title compounds as a viscous orange oil.

Step 2. (R)-6-Chloro-1-(1-(2,4-dichlorophenyl)ethyl)-3-(trifluoromethyl)-1H-pyrazolo[3,4-b]pyrazine

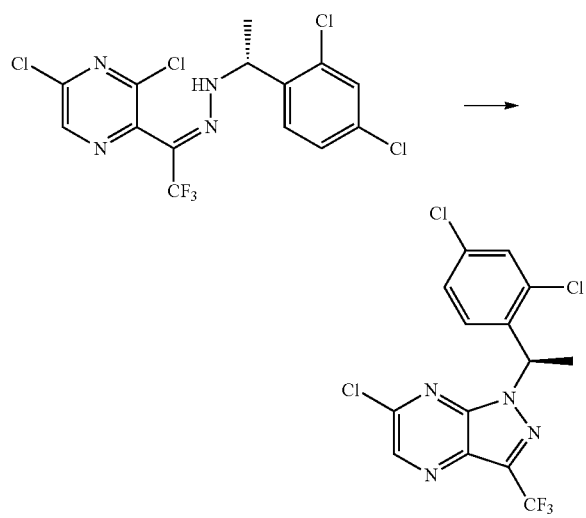

(Mixture of E/Z of (R))-3,5-Dichloro-2-(1-(2-(1-(2,4-dichlorophenyl)ethyl)hydrazono)-2,2,2-trifluoroethyl)pyrazine (2.5 g, 5.8 mmol) was dissolved in THF (58 mL) and then the solution was cooled to 0° C. Then, 1,8-diazabicyclo[5.4.0]undec-7-ene (1.73 mL, 11.8 mmol) was then added dropwise. After the addition was completed, the mixture was allowed to warm up to room temperature and stirred for 10 h. The mixture was concentrated under reduced pressure and then the residue was purified by silica gel chromatography (0 to 20% EtOAc in hexanes) to provide the step 2 title compound as a light orange oil.

Step 3. 1-((R)-1-(2,4-dichlorophenyl)ethyl)-6-(10-methyl-1,4-dioxaspiro[4.5]dec-7-en-8-yl)-3-(trifluoromethyl)-1H-pyrazolo[3,4-b]pyrazine

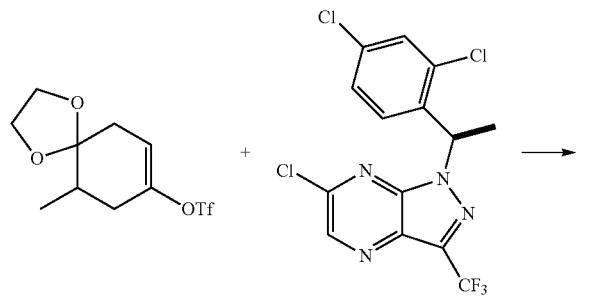

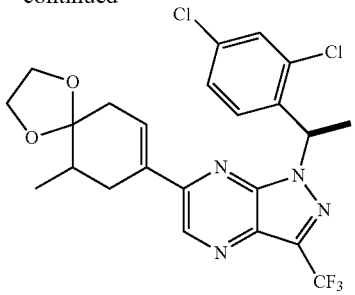

To a solution of 6-chloro-1-[(1R)-1-(2,4-dichlorophenyl)ethyl]-3-(trifluoromethyl)pyrazolo[3,4-b]pyrazine (800 mg, 2.02 mmol) in 5 mL 1,4-dioxane was added 4,4,5,5-tetramethyl-2-(6-methyl-1,4-dioxaspiro[4.5]dec-8-en-8-yl)-1,3,2-dioxaborolane (623 mg, 2.22 mmol). The resulting solution was sparged with argon by bubbling gas through the solution for about 10 min. Then, sodium carbonate (1M in water) (6.07 mL, 6.07 mmol) and PEPPSI-IPr catalyst (68 mg, 0.10 mmol) were added. The solution was heated at 90° C. for 16 h, upon which time the reaction was cooled to rt. The solution was diluted with water, extracted with EtOAc (3×) and then dried with sodium sulfate. The crude residue was purified by silica gel chromatography, eluting with 0-50% EtOAc in hexane to afford the product as a mixture of olefin isomers. The material was repurified by silica gel chromatography, eluting with 0-20% EtOAc in hexane to afford the step 3 title compound as an oil (385 mg, 0.750 mmol, 37% yield).

Step 4. 4-(1-((R)-1-(2,4-Dichlorophenyl)ethyl)-3-(trifluoromethyl)-1H-pyrazolo[3,4-b]pyrazin-6-yl)-6-methylcyclohex-3-en-1-one

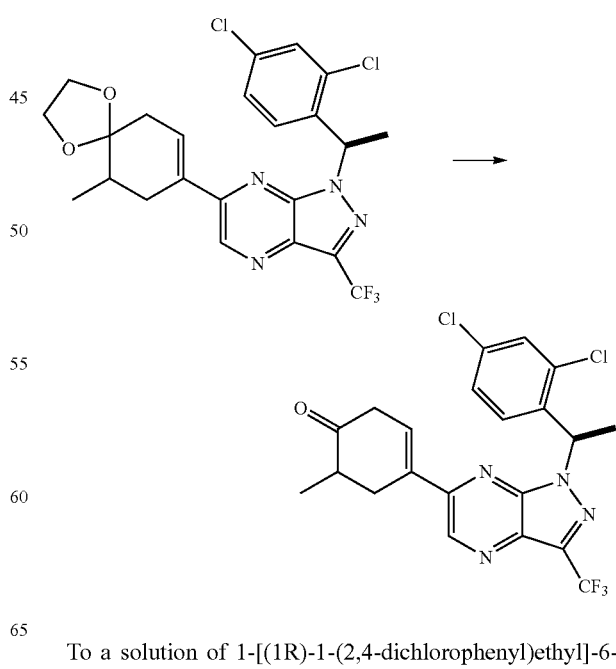

To a solution of 1-[(1R)-1-(2,4-dichlorophenyl)ethyl]-6-(6-methyl-1,4-dioxaspiro[4.5]dec-8-en-8-yl)-3-(trifluoromethyl)pyrazolo[3,4-b]pyrazine (233 mg, 0.460 mmol) in DCM (6.3 mL) was added TFA (1 mL, 10 mmol) at rt. The resulting purplish solution was allowed to stir overnight. The reaction solution was concentrated and then diluted with EtOAc (100 mL) and washed with sat. sodium bicarbonate solution (3×), dried over sodium sulfate, and concentrated. The crude residue was purified by silica gel chromatography, eluting with 0-100% EtOAc in hexane to afford the step 4 title compound as an orange oil (250 mg, 0.533 mmol, 117% by weight).

Step 5: 1-((R)-1-(2,4-dichlorophenyl)ethyl)-6-(5-methyl-4-((R)-2-methylpyrrolidin-1-yl)cyclohex-1-en-1-yl)-3-(trifluoromethyl)-1H-pyrazolo[3,4-b]pyrazine trifluoroacetate

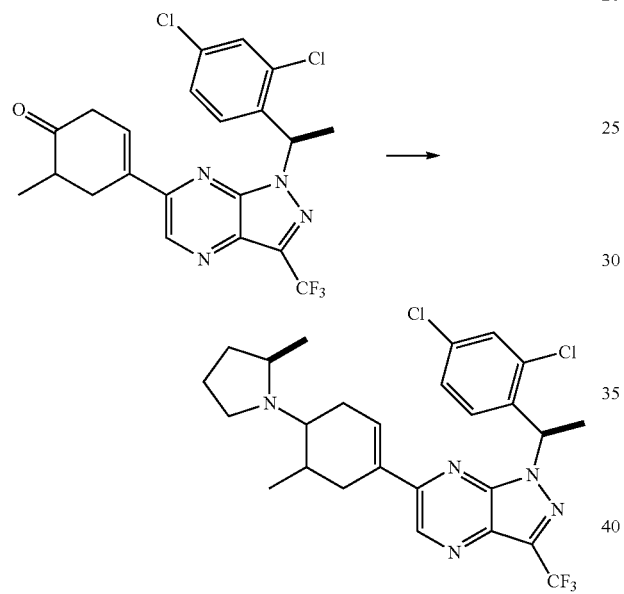

The title compound was synthesized by first combining (2R)-2-methylpyrrolidine hydrochloride (65 mg, 0.533 mmol) with 1-((R)-1-(2,4-dichlorophenyl)ethyl)-6-(5-methyl-4-oxocyclohex-1-en-1-yl)-1H-pyrazolo[3,4-b]pyrazine-3-carbonitrile (125 mg, 0.266 mmol) in 1,2-dichloroethane (2 mL) at this point the reaction turned dark red. Then, sodium triacetoxyborohydride (85 mg, 0.4 mmol) was added and the color became a deep purple. The reaction was then stirred overnight. The reaction was quenched with the addition of saturated aqueous sodium bicarbonate, followed by extraction with dichloromethane (3×), washed with brine, and dried over anhydrous Na₂SO₄. The organics were removed under reduced pressure and purified via reverse phase preparative HPLC (Phenomenex Gemini-NX, 10μ, C18, 110A, 250×30 mm, eluent: 0% to 100% acetonitrile in water, both eluents containing 0.1% TFA, gradient elution over 30 min). The title compound eluted as the first peak from a mixture with other diastereomers. 1H NMR (400 MHz, CD₃OD; TFA salt) δ 7.99 (d, J=1.0 Hz, 1H), 7.56-7.43 (m, 1H), 7.38-7.20 (m, 2H), 6.45 (qd, J=7.0, 3.6 Hz, 1H), 3.81-3.14 (m, 7H), 3.10-2.80 (m, 2H), 2.21-2.06 (m, 1H), 1.98-1.66 (m, 9H), 1.59-1.27 (m, 4H).

Example 89

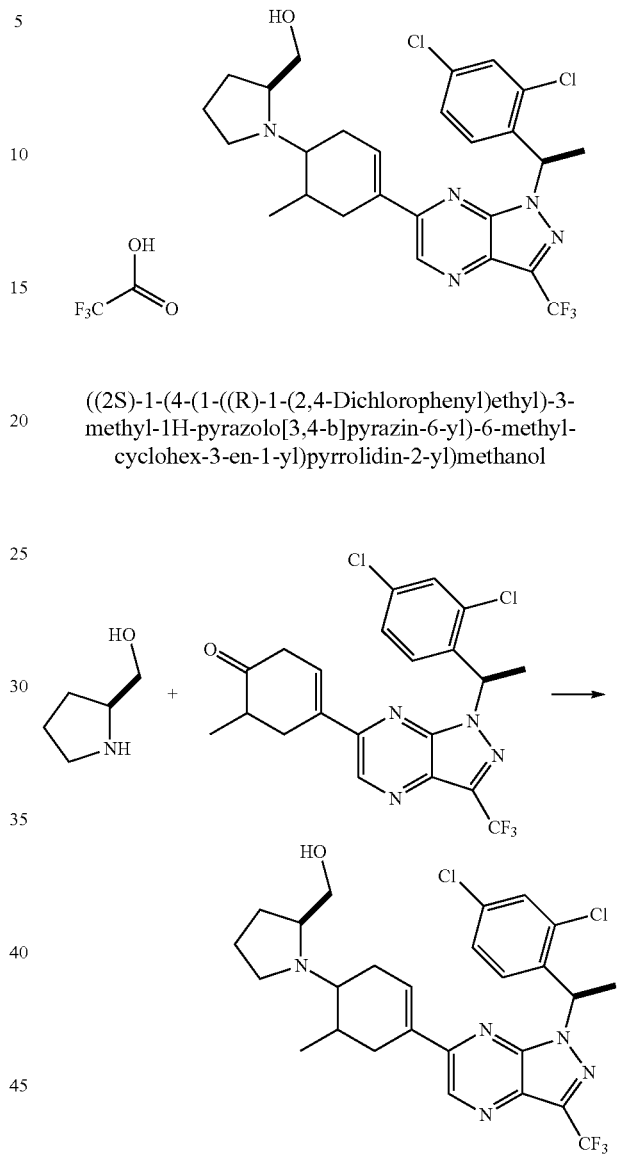

((2S)-1-(4-(1-((R)-1-(2,4-Dichlorophenyl)ethyl)-3-methyl-1H-pyrazolo[3,4-b]pyrazin-6-yl)-6-methyl-cyclohex-3-en-1-yl)pyrrolidin-2-yl)methanol A solution of 4-[1-[(1R)-1-(2,4-dichlorophenyl)ethyl]-3-(trifluoromethyl)pyrazolo[3,4-b]pyrazin-6-yl]-6-methyl-cyclohex-3-en-1-one (Example 88, Step 4, 125 mg, 0.270 mmol) and L-(+)-prolinol HCl (91 mg, 0.67 mmol) in DCE (2 mL) was stirred at 40° C. to dissolve the prolinol HCl. After 30 min, the reaction was charged with NaBH(OAc)₃ (85 mg, 0.40 mmol) was added at rt. The solution turned from yellow to a pinkish orange color. Over time, the solution turned a deep red color. After 16 h, the reaction was charged with additional NaBH(OAc)₃ (85 mg, 0.40 mmol). The reaction was allowed to stir for 3 d. The reaction was then diluted with sat. sodium bicarbonate, extracted with EtOAc (2×), dried over sodium sulfate, and concentrated. The crude residue was purified by reverse phase preparative HPLC to afford 1.0 mg of the title compound as a trifluoroacetic acid salt. 1H NMR (400 MHz, CD₃CN; TFA salt): δ 9.00-8.99 (m, 1H), 7.52-7.46 (m, 2H), 7.33 (dd, J=8.5, 2.2 Hz, 1H), 6.91-6.85 (m, 1H), 6.65 (q, J=7.1 Hz, 1H), 3.99-

3.92 (m, 2H), 3.89-3.77 (m, 2H), 3.77-3.62 (m, 4H), 3.59-3.40 (m, 1H), 3.39-3.21 (m, 2H), 2.98-2.61 (m, 4H), 1.97-1.96 (m, 3H), 1.11-1.05 (m, 3H); m/z 554.0 (M+H⁺).

Example 90

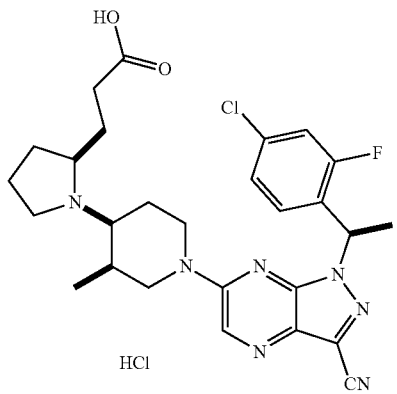 [SMILES: C[C@@H]1CN(c2cnc3c(C#N)nn([C@H](C)c4ccc(Cl)cc4F)c3n2)CC[C@@H]1N1CCC[C@H]1CCC(=O)O ; Cl]

3-((S)-1-((3R,4S)-1-(1-((R)-1-(4-chloro-2-fluorophenyl)ethyl)-3-cyano-1H-pyrazolo[3,4-b]pyrazin-6-yl)-3-methylpiperidin-4-yl)pyrrolidin-2-yl)propanoic acid hydrochloric acid Step 1. 4-Chloro-1-(1-chloroethyl)-2-fluorobenzene

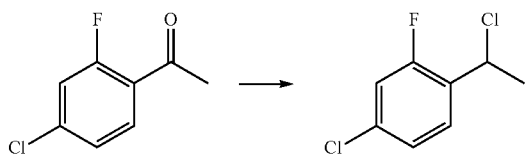

To a solution of 1-(4-chloro-2-fluorophenyl)ethan-1-one (25 g, 145 mmol) in MeOH (300 mL) at 0° C. was added NaBH₄ (8.0 g, 220 mmol) portion-wise. Then, the mixture was slowly warmed to room temperature and stirred for 1 h. The reaction was diluted with EtOAc and sat. sodium bicarbonate solution. The organic phase was separated, and the aqueous layer was extracted with EtOAc (2×). The combined organics were dried over sodium sulfate and concentrated to afford the crude product, which was purified by silica gel chromatography to afford 1-(4-chloro-2-fluorophenyl)ethan-1-ol (24.2 g). This material was dissolved in DCM (600 mL), and the solution was charged with triphenylphosphine (278 mmol, 72.9 g) and CCl₄ (556 mmol). The mixture was stirred for 3 d at room temperature. The mixture was concentrated to about 50 mL, and the mixture was filtered through a silica gel plug. The solution was concentrated, and the residue was suspended in DCM:hexanes 1:2 and stirred for 20 min. The material was filtered, and the residue was suspended in hexanes and filtered. The residue was purified by silica gel chromatography, eluting with hexanes, to afford 4-chloro-1-(1-chloroethyl)-2-fluorobenzene (24 g).

Step 2. (1-(4-Chloro-2-fluorophenyl)ethyl)hydrazine hydrochloride

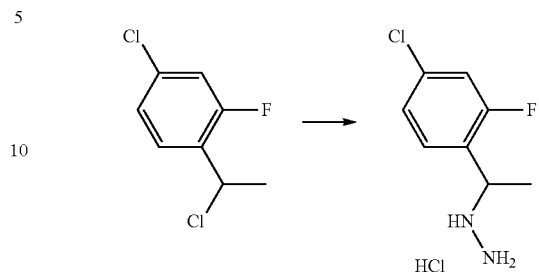

4-chloro-1-(1-chloroethyl)-2-fluorobenzene (2.0 g, 10.3 mmol) was treated with Boc-hydrazine (6.8 g, 51 mmol) and DIPEA (61 mmol) in DMF (10 mL) under N₂. The mixture was stirred at 100° C. for total of 60 h. The reaction mixture was diluted with EtOAc and water, extracting with EtOAc (2×), dried over sodium sulfate, and concentrated. The crude product was purified by silica gel chromatography twice (ethyl acetate:hexanes=1:8) to afford 2.2 g of the boc-protected (1-(4-chloro-2-fluorophenyl)ethyl)hydrazine. This material was treated directly with 4 M HCl in 1,4-dioxane at room temperature for 3 d. The reaction was then concentrated, and the resulting (1-(4-chloro-2-fluorophenyl)ethyl) hydrazine hydrochloride was used without purification in the next step.

Step 3. Ethyl 6-chloro-1-(1-(4-chloro-2-fluorophenyl)ethyl)-1H-pyrazolo[3,4-b]pyrazine-3-carboxylate

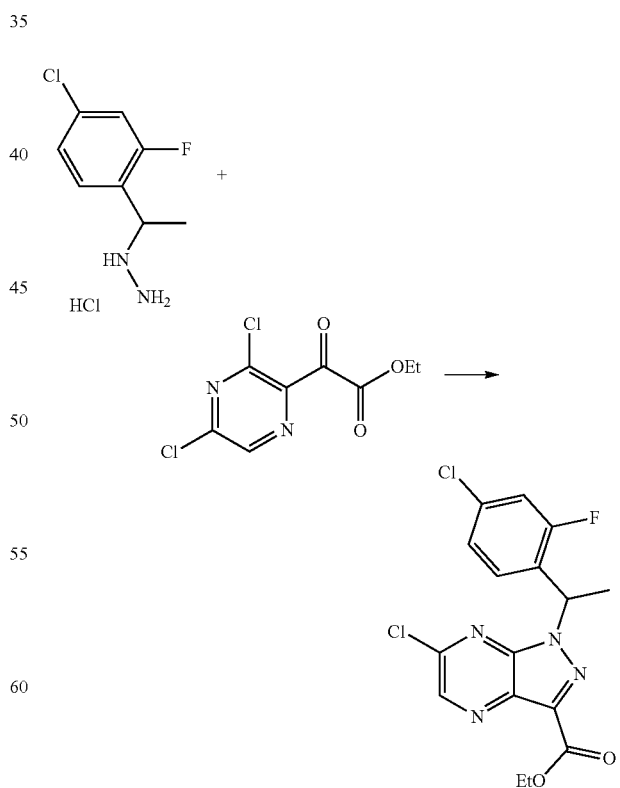

A mixture of the crude (1-(4-chloro-2-fluorophenyl)ethyl)hydrazine hydrochloride (2.2 g) and ethyl 2-(3,5-dichloropyrazin-2-yl)-2-oxoacetate (Example 5, Step 3, 1.05 eq) in THF (10 mL) was stirred at 80° C. for 2 h. The mixture was diluted with EtOAc and water, extracted with EtOAc (2×), dried over sodium sulfate, and concentrated. This material was diluted with 20 mL THF and cooled to 0° C. before adding Sodium hydride (60% in mineral oil, 1 equiv) was added portion-wise. The resulting mixture was slowly warmed to room temperature overnight. The reaction mixture was poured into an ice-cold saturated solution of ammonium chloride and extracted with ethyl acetate (2×). The crude was purified by silica gel chromatography, eluting with 10-25% EtOAc in hexanes to afford 16.3 g of ethyl 6-chloro-1-(1-(4-chloro-2-fluorophenyl)ethyl)-1H-pyrazolo[3,4-b]pyrazine-3-carboxylate.

Step 4. (R)-6-Chloro-1-(1-(4-chloro-2-fluorophenyl)ethyl)-1H-pyrazolo[3,4-b]pyrazine-3-carbonitrile

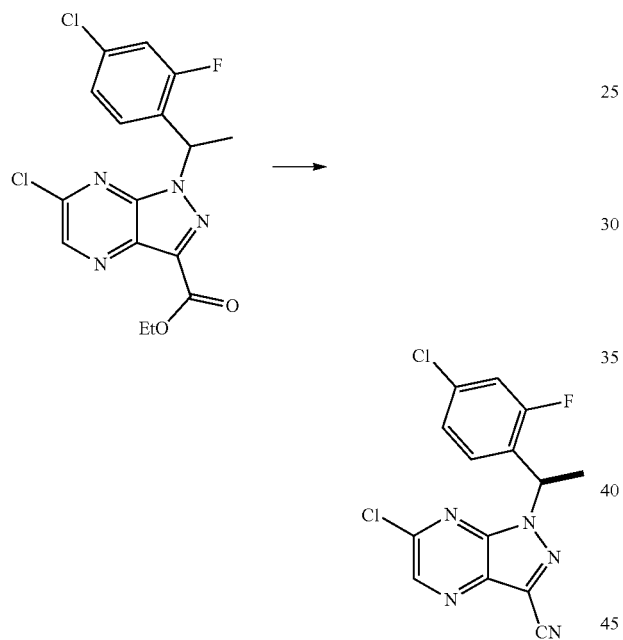

The amide formation was preformed analogously to the reaction in Example 23, Step 1, except (R)-6-Chloro-1-(1-(2,4-dichlorophenyl)ethyl)-1H-pyrazolo[3,4-b]pyrazine-3-carboxamide was replaced with ethyl 6-chloro-1-(1-(4-chloro-2-fluorophenyl)ethyl)-1H-pyrazolo[3,4-b]pyrazine-3-carboxylate. The dehydration of the amide was preformed analogously to the reaction in Example 23, Step 2, except (R)-6-chloro-1-(1-(2,4-dichlorophenyl)ethyl)-1H-pyrazolo[3,4-b]pyrazine-3-carboxamide was replaced with 6-chloro-1-(1-(2-fluoro-4-chlorophenyl)ethyl)-1H-pyrazolo[3,4-b]pyrazine-3-carboxamide. The enantiomers of the racemic material were separated by chiral supercritical fluid chromatography (SFC) using a Lux-4 (2×25 cm) column, eluting with 20% isopropanol/CO$_2$, 100 bar, 60 mL/min. These conditions were used to separate 2.95 g of racemic material and yielded 1.45 g of peak-1 (chemical purity >99%) and 1.45 g of peak-2 (chemical purity >99%). Peak 2 was assigned the (R)- configuration and was used for future reactions.

Step 5. 3-((S)-1-((3R,4S)-1-(1-((R)-1-(4-chloro-2-fluorophenyl)ethyl)-3-cyano-1H-pyrazolo[3,4-b]pyrazin-6-yl)-3-methylpiperidin-4-yl)pyrrolidin-2-yl)propanoic acid hydrochloric acid

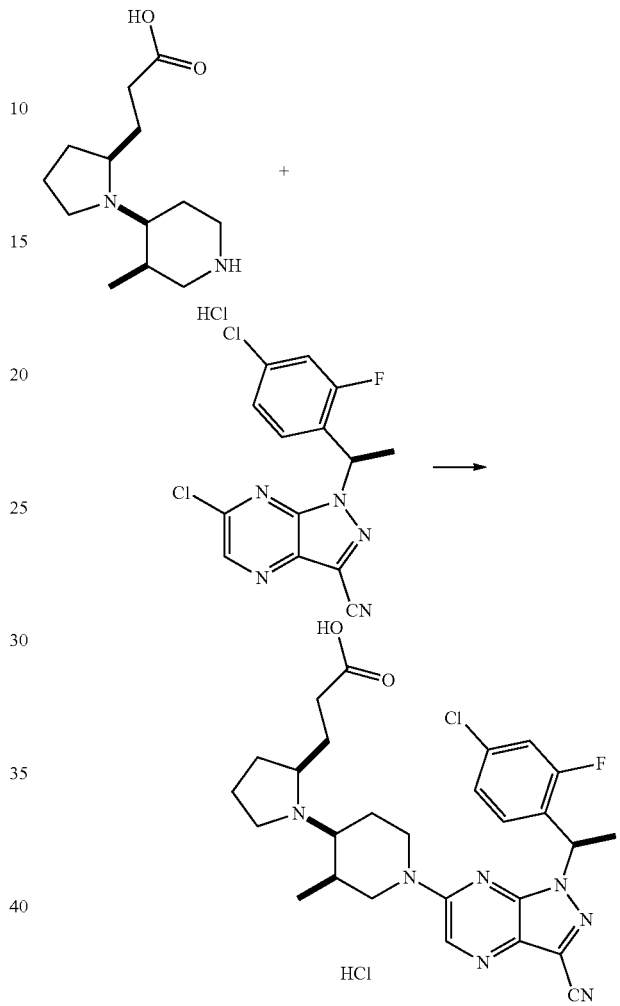

To a vial containing 6-chloro-1-[(1R)-1-[4-chloro-2-(trifluoromethyl)phenyl]ethyl]-3-methyl-pyrazolo[3,4-b]pyrazine (75 mg, 0.20 mmol) was added 3-[(2S)-1-[(3R,4S)-3-methyl-4-piperidyl]pyrrolidin-2-yl]propanoic acid (Example 42, Step 5, 96 mg, 0.40 mmol) as a solution in DMSO (~100 mg in 1.5 mL DMSO) followed by N,N-diisopropylethylamine (51 mg, 0.40 mmol). The reaction was placed in a 50° C. heating block for 20 h. The reaction was cooled to room temperature and diluted with TFA (0.5 mL) and ACN (1.0 mL) and purified by reverse phase preparatory HPLC. The product was identified in fractions 33 and 34 by LCMS (540.2 m/z) and was concentrated. The TFA salt was dissolved in 10:1 DCM:MeOH and passed through a basifying column to afford 22 mg of the free base as a light yellow oil. The free base was diluted in DCM (5 mL) and about 0.2 mL of a 1 M HCl solution in diethyl ether was added dropwise. The yellow mixture was concentrated to afford the title compound as a light yellow solid (23 mg). $^1$H NMR (400 MHz, CDCl$_3$, HCl salt) δ 8.32 (s, 1H), 7.39-7.33 (m, 1H), 7.15-7.04 (m, 2H), 6.32 (q, J=7.1 Hz, 1H), 4.65 (d, J=13.9 Hz, 1H), 4.47 (d, J=13.5 Hz, 1H), 3.47-3.37 (m, 1H), 3.34-3.22 (m, 1H), 3.09 (dd, J=13.6, 2.6 Hz, 1H), 2.94 (td, J=13.2, 3.3 Hz, 1H), 2.90-2.75 (m, 3H), 2.69-2.46 (m, 2H), 2.36 (s, 1H), 2.12 (dd, J=12.5, 8.3 Hz, 2H), 1.97-2.06 (m, 1H), 1.93 (d, J=7.1 Hz, 4H), 1.87-1.72 (m, 3H), 1.10 (d, J=6.9 Hz, 3H); m/z 540.2 (M+H⁺).

Example 91

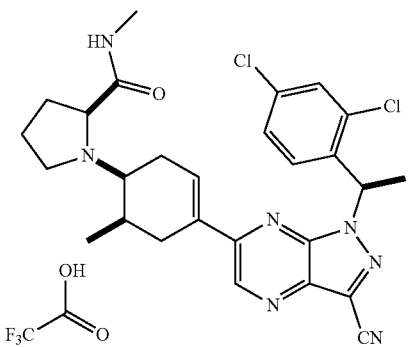

(S)-1-((1S,6R)-4-(3-Cyano-1-((R)-1-(2,4-dichlorophenyl)ethyl)-1H-pyrazolo[3,4-b]pyrazin-6-yl)-6-methylcyclohex-3-en-1-yl)-N-methylpyrrolidine-2-carboxamide trifluoroacetate

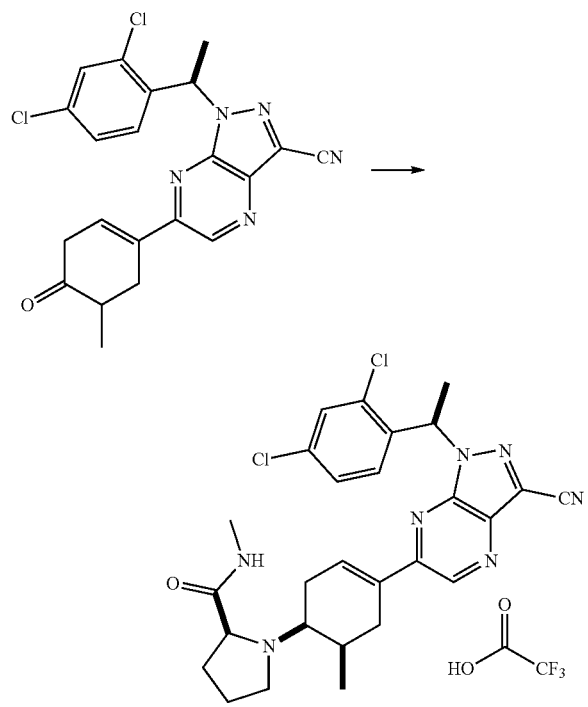

A solution of 1-((R)-1-(2,4-dichlorophenyl)ethyl)-6-(5-methyl-4-oxocyclohex-1-en-1-yl)-1H-pyrazolo[3,4-b]pyrazine-3-carbonitrile (Example 75, Step 1, 114 mg, 0.290 mmol) was made in 1,2-dichloroethane (1.4 mL). Then, (S)—N-methylpyrrolidine-2-carboxamide (111 mg, 0.87 mmol) was added to the solution, which immediately turned a dark red/brown. To this mixture, NaBH₃CN (93 mg, 0.44 mmol) was added. The reaction was stirred for 16 h at room temperature before diluting with DCM and sat. aqueous NaHCO₃. The organic layer was separated, and the aqueous layer was extracted with DCM (2×). The combined organic layers were dried over Mg₂SO₄ and concentrated under reduced pressure. The residue was purified by reverse phase preparative HPLC (Phenomenex Gemini-NX, 10μ, C18, 110A, 250×30 mm, eluent: 20 to 100% acetonitrile in water, both eluents containing 0.1% TFA, gradient elution over 30 min) to afford the title compound which eluted as the second isomer and was isolated as the 2,2,2-trifluoroacetate salt. ¹H NMR (400 MHz, CD₃OD; TFA salt) δ 9.07 (s, 1H), 8.57 (q, J=4.9 Hz, 1H), 7.48 (d, J=2.1 Hz, 1H), 7.44 (d, J=8.5 Hz, 1H), 7.33 (dd, J=8.5, 2.1 Hz, 1H), 6.89 (bs, 1H), 6.73 (q, J=7.0 Hz, 1H), 4.48-4.39 (m, 1H), 3.98 (bt, 1H), 3.71 (s, 1H), 3.40 (bq, 1H), 2.96-2.71 (m, 4 H), 2.87 (s, 3H), 2.70-2.45 (m, 3 H), 2.26-2.10 (m, 2 H), 2.00 (d, J=7.1 Hz, 3H), 1.19 (d, J=6.6 Hz, 3H); m/z 538.2 (M+H⁺).

Example 92

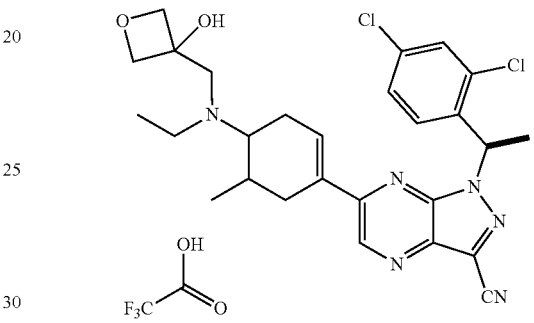

1-((R)-1-(2,4-dichlorophenyl)ethyl)-6-(4-(ethyl((3-hydroxyoxetan-3-yl)methyl)amino)-5-methylcyclohex-1-en-1-yl)-1H-pyrazolo[3,4-b]pyrazine-3-carbonitrile

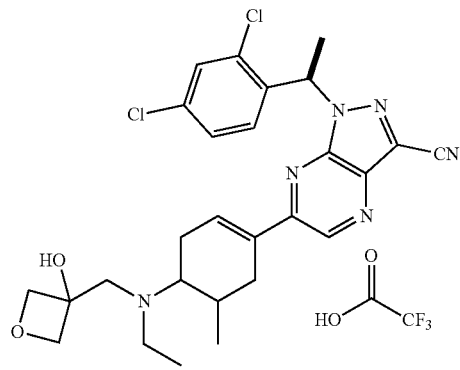

A solution of 1-((R)-1-(2,4-dichlorophenyl)ethyl)-6-(5-methyl-4-oxocyclohex-1-en-1-yl)-1H-pyrazolo[3,4-b]pyrazine-3-carbonitrile (Example 75, Step 1, 200 mg, 0.51 mmol) was made in 1,2-dichloroethane (1.7 mL). Then, 3-(aminomethyl)oxetan-3-ol (158 mg, 1.5 mmol) was added to the solution, which immediately turned a dark red/brown. To this mixture, NaBH$_3$CN (216 mg, 1.0 mmol) was added. The reaction was stirred for 16 h at room temperature before diluting with DCM and sat. aqueous NaHCO$_3$. The organic layer was separated, and the aqueous layer was extracted with DCM (2×). The combined organic layers were dried over Mg$_2$SO$_4$ and concentrated under reduced pressure. The crude residue was dissolved in 1,2-dichloroethane (1.7 mL) and acetaldehyde (90 mg, 2.0 mmol) was added to the solution followed by NaBH$_3$CN (216 mg, 1.0 mmol). The reaction was stirred for 16 h at room temperature before diluting with DCM and sat. aqueous NaHCO$_3$. The organic layer was separated, and the aqueous layer was extracted with DCM (2×). The combined organic layers were dried over Mg$_2$SO$_4$ and concentrated under reduced pressure. The residue was purified by reverse phase preparative HPLC (Phenomenex Gemini-NX, 10μ, C18, 110A, 250×30 mm, eluent: 20 to 100% acetonitrile in water, both eluents containing 0.1% TFA, gradient elution over 30 min) to afford the title compound which eluted as the second isomer and was isolated as the 2,2,2-trifluoroacetate salt. $^1$H NMR (400 MHz, CD$_3$OD; TFA salt) δ 9.10 (s, 1H), 7.50 (d, J=2.1 Hz, 1H), 7.48 (d, J=2.1 Hz, 1H), 7.46 (d, J=8.6 Hz, 1H), 7.35-7.31 (m, 1H), 6.95 (bs, 1H), 6.73 (q, J=6.9 Hz, 1H), 4.79-4.60 (m, 4H), 3.83-3.68 (m, 2H), 3.60-3.38 (m, 1H), 3.29-3.15 (m, 1H), 3.12-2.59 (m, 5H), 2.01 (d, J=7.0 Hz, 3H), 1.45-1.34 (m, 3H), 1.31-1.26 (m, 2H), 1.18-1.03 (m, 2H); m/z 541.2 (M+H$^+$).

Biological Examples

Activity for compounds described herein was provided in Table 1, wherein potency levels are provided as follows: (Potency: Ca Flux IC$_{50}$: A<0.1 μM; B=0.1-0.5 μM; C >0.5 μM)

TABLE 2

| Example no. | Ca Flux IC$_{50}$ |
| --- | --- |
| 1 | C |
| 2 | B |
| 3 | C |
| 4 | B |
| 5 | B |
| 6 | B |
| 7 | B |
| 8 | B |
| 9 | B |
| 10 | C |
| 11 | B |
| 12 | A |
| 13 | A |
| 14 | A |
| 15 | C |
| 16 | A |
| 17 | B |
| 18 | B |
| 19 | B |
| 20 | A |
| 21 | C |
| 22 | B |
| 23 | A |
| 24 | C |
| 25 | B |
| 26 | C |
| 27 | B |

TABLE 2-continued

| Example no. | Ca Flux IC$_{50}$ |
| --- | --- |
| 28 | B |
| 29 | A |
| 30 | B |
| 31 | A |
| 32 | C |
| 33 | A |
| 34 | C |
| 35 | B |
| 36 | B |
| 37 | C |
| 38 | B |
| 39 | B |
| 40 | C |
| 41 | C |
| 42 | B |
| 43 | A |
| 44 | A |
| 45 | B |
| 46 | B |
| 47 | B |
| 48 | A |
| 49 | B |
| 50 | C |
| 51 | B |
| 52 | A |
| 53 | B |
| 54 | C |
| 55 | C |
| 56 | B |
| 57 | C |
| 58 | C |
| 59 | B |
| 60 | B |
| 61 | B |
| 62 | B |
| 63 | B |
| 64 | C |
| 65 | B |
| 66 | B |
| 67 | B |
| 68 | B |
| 69 | B |
| 70 | B |
| 71 | A |
| 72 | C |
| 73 | B |
| 74 | A |
| 75 | B |
| 76 | A |
| 77 | A |
| 78 | A |
| 79 | A |
| 80 | B |
| 81 | B |
| 82 | B |
| 83 | A |
| 84 | B |
| 85 | B |
| 86 | B |
| 87 | A |
| 88 | B |
| 89 | B |
| 90 | A |
| 91 | B |
| 92 | B |

Potent and Selective C—C Motif Chemokine Receptor (CCR4) Antagonists Potentiate Anti-Tumor Immune Responses by Inhibiting Regulatory T Cells (T$_{reg}$)

Naturally occurring suppressive CD4$^+$Foxp3$^+$ T$_{reg}$ are essential for immune tolerance. Although T$_{reg}$-mediated suppression of effector cells is important to control inflammatory responses and prevent autoimmune diseases, the presence of T$_{reg}$ in the tumor microenvironment (TME) has been shown to dampen anti-tumor immune responses. Human T$_{reg}$ express CCR4, the receptor for the chemokines CCL17 and CCL22. These chemokines are produced by tumor cells or tumor-associated macrophages and dendritic cells, as well as by effector T cells ($T_{eff}$). Preclinical and clinical data in various cancer types supports a role for CCR4-mediated recruitment and accumulation of $T_{reg}$ in the TME which can be associated with poor prognosis. Further, recent longitudinal studies in patients receiving IO agents demonstrate an influx of $T_{reg}$ in responding patients which may dampen optimal anti-tumor responses. Therefore, CCR4 is an ideal target to selectively block $T_{reg}$ recruitment into the TME.

Multiple structurally unique series of selective small molecule antagonists of CCR4 have been developed. These antagonists have cellular potencies in multiple assays (including in a functional chemotaxis assay with primary human $T_{reg}$ in 100% serum) in the low double-digit nM range. Representative compounds are selective against other chemokine receptors, GPCRs and ion channels, including the hERG channel, and lack inhibition of common human CYP450 enzymes. Moreover, compounds have excellent in vitro and in vivo ADME properties, consistent with convenient oral dosing. In preclinical syngeneic tumor models, our CCR4 antagonists block $T_{reg}$ migration and support expansion of activated $T_{eff}$. In contrast to the non-selective approach of depleting anti-CCR4 antibodies, our compounds reduce $T_{reg}$ in the tumor, but not in peripheral tissues such as blood, spleen or skin. In preclinical efficacy studies, CCR4 antagonists potentiate the anti-tumor effects of various checkpoint inhibitors and immune stimulators such as anti-PD-L1 and anti-CD137 antibodies. Enhanced tumor growth inhibition and increases in the percentage of tumor free mice when these agents are combined with CCR4 antagonists, without any gross toxicity, was observed.

Chemotaxis Assays. Generally speaking, chemotaxis assays may be performed using 5 am filterplates (Neuroprobe) with the chemoattractant (MDC, TARC, or SDF) placed in the lower chamber, and a cell suspension of 100,000 CEM cells in the upper chamber. The assays may be incubated 1-2 h at 37° C., and the number of cells in the lower chamber quantified by the CyQUANT assay (Molecular Probes).

The following serum chemotaxis assay was used to determine the extent to which the compounds of the present disclosure block cellular migration mediated through CCR4. The assay was performed using the ChemoTX (Gaithersburg, Md.) migration system with a 5 am pore size polycarbonate trach-etch (PCTE) membrane. CCRF-CEM cells which express CCR4 were collected by centrifugation at 400×g at room temperature, then suspended at 2 million cells/mL in human serum. Compounds (or an equivalent volume of solvent (DMSO)) were then added to the cell/serum mixture at a final DMSO concentration of 0.25% (v/v), followed by a 30-minute compound pre-incubation period. Separately, recombinant human MDC was diluted to 0.9 nM in 1×HBSS with 0.1% BSA, and 29 µL of diluted MDC was placed in the lower wells of the ChemoTX plate. The polycarbonate (or PCTE) membrane (5 am pore size) was placed onto the plate, and 50 µL of the cell/compound mixture was transferred into each well of the membrane. The plates were incubated at 37° C. for 60 minutes, after which the polycarbonate membranes were removed, and 10 µL of the DNA-intercalating agent CyQUANT was added to the lower wells. The amount of fluorescence, corresponding to the number of migrated cells, was measured using an Envision plate reader (PerkinElmer; Waltham, Mass.).

Detection of radiolabeled TARC and/or MDC binding to CCR4—Protocol A. Source plates of chemical libraries may be obtained from commercial vendors and may contain individual compounds at 5 mg/mL in DMSO. From these, multiple compound plates containing 10 compounds in each well may be prepared and then diluted in 20% DMSO to a concentration of 50 µg/mL. An aliquot of 20 µL of each mixture may be put into the test plates and stored frozen until use.

A CCR4-expressing stable transfectant cell line may be prepared using current standard molecular biological methods. The CCR4 transfectants may be cultured in IMDM-5% FBS, and harvested when the concentration is between $0.5$-$1.0 \times 10^6$ cells/mL. The cells may be centrifuged and resuspended in assay buffer (20 mM HEPES, pH 7.1, 140 mM NaCl, 1 mM $CaCl_2$, 5 mM $MgCl_2$, and with 0.2% BSA) to a concentration of $5.6 \times 10^6$ cells/mL. To establish the screening assays, 0.09 mL of cells may be added to the assay plates containing the compounds (yielding a final compound concentration of 1-5 µg/mL each (~2-10 µM)), and then 0.09 mL of $^{125}$I-TARC or $^{125}$I-MDC diluted in assay buffer (final concentration ~50 pM, with ~30,000 cpm per well) may be added. The plates may then be sealed and incubated for approximately 3 hrs at 4° C. on a shaker platform. The assay plates may be harvested using Packard filter plates, pre-soaked in 0.3% PEI (polyethyleneimine) solution, on a Packard vacuum cell harvester. Scintillation fluid (50 µL) was added to all wells and the plates may be sealed and counted in a Top Count scintillation counter. Control wells containing either diluent only (for total counts) or excess MDC or TARC (1 µg/mL, for non-specific binding) may be used to calculate the percent of total inhibition for each set of compounds. $IC_{50}$ values are those concentrations required to reduce the binding of labeled MDC or TARC to the receptor by 50%.

Detection of radiolabeled TARC and/or MDC binding to CCR4—Protocol B. $^{125}$I-labelled TARC and MDC are available from commercial sources (e.g., Perkin Elmer Life Sciences). All buffers and materials are available from commercial sources (e.g., Sigma).

To measure binding of $^{125}$I-TARC or $^{125}$I-MDC to cells expressing CCR4 (e.g., CEM cells (e.g., ATCC HB-12624)), the $^{125}$I-TARC or $^{125}$I-MDC is diluted to a concentration of approximately 200 pM in a buffered saline solution (e.g., RPMI supplemented with 0.5% BSA), and added to an equal volume of a suspension of cells (e.g., CEM cells at $5 \times 10^6$ cells/mL). The resulting mixture is incubated for a period of time (e.g., 2 hrs), and the unbound $^{125}$I-TARC or $^{125}$I-MDC is separated from the cells by filtration, e.g., by passage through GF/B filter plate (Packard Biosciences) pre-treated with 0.3% polyethyleneimine (Sigma), using a Packard Filtermate 96 (Packard Biosciences). The amount of $^{125}$I-TARC or $^{125}$I-MDC retained with the cells on the filterplate is measured by adding a small amount of scintillation fluid (e.g., 50 µL of Microscint-20 Packard Biosciences)), and reading scintillation on appropriate detection equipment, e.g., a Packard TopCount 383 (Packard Biosciences).

Non-specific binding of $^{125}$I-TARC or $^{125}$I-MDC can be estimated by measuring the amount of $^{125}$I-TARC or $^{125}$I-MDC retained with the cells on the filterplate when the assay is performed in the presence of a large excess of unlabeled TARC or MDC. Inhibition of $^{125}$I-TARC or $^{125}$I-MDC binding to CCR4 is defined as a decrease in the retention of $^{125}$I-TARC or $^{125}$I-MDC to the cells on the filterplate.

Calcium Mobilization Assay. Calcium mobilization experiments may be performed by labeling the human T-cell line CEM with NDO-1 dye (45 min at room temperature), washing with PBS, and re-suspending into flux buffer (HBSS with 1% FBS). For each experiment, $1 \times 10^6$ cells may be incubated at 37° C. in the cuvette of a PTI spectrometer, and the ratio of 410/490 nm emission plotted over time (typically 2-3 minutes), with compounds added at 5 seconds, followed by MDC, TARC or other chemokines.

Production of TNFα. The present disclosure contemplates the use of a murine model of TNFα production by LPS stimulation. A CCR4 antagonistic compound(s) may be suspended in a medium, orally administered to a mouse (male, C57BL/6), and after 0.5 hour LPS (055:B5, Sigma) peritoneally administered to the mouse at a dose of 60 mg/kg. To the control groups, only the medium may be administered. Sixty min after LPS treatment, heparin-added blood collection may be conducted from the abdominal vena cava under ether anesthesia, and centrifuged (12,000 rpm) at 4° C. for 3 min to provide plasma (which may be stored at −80° C. before use). TNFα in the plasma may be quantified using an ELISA kit (R&D systems; Minneapolis, Minn.).

Efficacy of CCR4 Antagonists for Therapeutic Indications. A representative procedure for evaluating the efficacy of CCR4 antagonists for treatment of septic shock is described herein. An animal model of endotoxic shock may be induced by injecting mice with LPS. Three groups (15 mice per group) may be treated with an i.p. injection of an LPS dose that produces 90% mortality in mice. One group of mice may also receive PBS and Tween 0.5% i.p. 30 min before LPS administration. A second group of mice may also receive different doses of the CCR4 antagonist(s) given either i.p., IV, SC, IM, PO or via any other mode of administration 30 min before, or concurrently with, LPS administration. A third group of mice may serve as a positive control and consist of mice treated with either mouse IL-10 i.p. or anti-TNF antibodies i.p. 30 min before LPS administration. Mice are monitored for death for 72 h following the LPS injection.

Asthma. Representative procedures for evaluating the efficacy of CCR4 antagonists for treatment of asthma are as described herein. Procedure A: An animal model of asthma may be induced by sensitizing mice to an experimental antigen (e.g. OVA) by standard immunization techniques, and subsequently introducing that same antigen into the mice's lungs by aerosolization. Three groups of mice (10 mice per group) may be actively sensitized on Day 0 by a single i.p. injection with 100 µg OVA in PBS, along with an IgE-selective adjuvant (e.g. aluminum hydroxide). Eleven days' post-sensitization, at the peak of their IgE response, the mice may be placed in a Plexiglas chamber and challenged with aerosolized OVA (1%) for 30 min using the ultrasonic nebulizer (e.g., De Vilbliss; Ingersoll Rand; Dublin, I E). One group of mice may additionally receive PBS and Tween 0.5% i.p. at the initial sensitization, and at different dosing schedules thereafter, up until the aerosolized OVA challenge. A second group of mice may receive different doses of the CCR4 antagonist(s) given either i.p., IV, SC, IM, PO or via any other mode of administration at the initial sensitization, and at different dosing schedules thereafter, up until the aerosolized OVA challenge. A third group of mice, serving as a positive control, may be treated with either mouse IL-10 i.p., anti-IL-4 antibodies i.p., or anti-IL5 antibodies i.p. at the initial sensitization, and at different dosing schedules thereafter, up until the aerosolized OVA challenge.

Following the aerosolized OVA challenge, mice may be analyzed at different time points for pulmonary function, cellular infiltrates in bronchoalveolar lavage (BAL), histological examination of lungs, and measurement of serum OVA-specific IgE titers.

Procedure B. Ovalbumin (OVA, 0.2 mg/mL) and Alum (8 mg/mL) prepared in physiological saline may be intraperitoneally administered (500 µL) to mice (male, C57BL/6) on Day 1 (test starting day) and Day 8 (1 week thereafter), to sensitize the mice. On Days 15 to 21, mice may be placed in an inhalation chamber (W: 240 mm×L: 240 mm×H: 120 mm), and a 2% OVA solution may be sprayed with an ultrasonic wave-type nebulizer (NE-U12; Omron, San Ramon, Calif.) for 20 min to conduct induction. A CCR4 antagonist(s) may be suspended in a medium and administered orally at 30 min before OVA sensitization on Day 8 and at 30 min before OVA induction on Days 15 to 21. For a control group, only the medium may be administered. Three h post-OVA inhalation on Day 21, the mice may be exsanguinated, catheter tubes inserted into their trachea, and lungs washed with heparin-containing physiological saline (10 U/mL) to provide a bronchoalveolar lavage fluid (BALF). Leukocyte number in BALF may be counted using hemocyte counter (SF-3000; Sysmex, Kobe, J P).

Dermatitis. Representative procedures for evaluating the efficacy of CCR4 antagonists for treatment of dermatitis are as described herein. Mouse DTH Model. Mice (male, Balb/c) may be shaved on the abdomen with hair clippers, and to the abdomen may be applied ethanol solution (100 µL) of 7% (w/v) 2,4,6-trinitrochlorobenzene (TNCB), to sensitize the mice. Seven days' post-sensitization, a 1% (w/v) TNCB solution in olive oil (20 µL) may be applied to the auricle of the mice (both sides of the right ear), to conduct induction. A CCR4 antagonist(s) may be dissolved in a medium, applied to both sides of the right ear (20 µL) 2 h before applying TNCB. To the control groups, only the medium may be applied. Immediately following compound(s) administration and 24 h after TNCB application, the thickness of the mice auricles may be measured with Dialthickness gauge (Ozaki Seisakusho, JP), which may be used as indicator for efficacy in mouse DTH model.

Dermatitis Model to which Hapten is Applied. To the auricle (both sides of the right ear) of the mice (male, Balb/c), 1% (w/v) TNCB solution (acetone:olive oil=4:1) (20 µL) may be applied to conduct first sensitization. Seven days' post-sensitization, 1% (w/v) TNCB (acetone:olive oil=4:1) (20 µL) may be applied to the auricle of the mice, to conduct induction (Day 0); this procedure may be repeated on Days 2, 4, 6, 8, 10, 12, 14 and 16. A CCR4 antagonist(s) may be dissolved in a medium, and applied to both sides of the right ear (20 µL) two h before applying TNCB. To the control groups, medium only may be applied. Immediately following compound(s) administration and 24 h post-TNCB application, the thickness of the mice auricles may be measured with Dialthickness gauge, which may be used as an indicator of efficacy in mouse dermatitis model to which hapten is continuously applied.

Infection. A representative procedure for evaluating the efficacy of CCR4 antagonists for augmenting protective immunity against viruses, bacteria and parasites is as described herein. Protective immunity to microbial pathogens is frequently mediated by Th1 regulatory T cells. Because CCR4 antagonists are believed to be inhibitors of Th2 regulatory cells, they may alter the cross-regulation that normally exists between Th1 and Th2 cells and potentiate Th1 cells, thereby augmenting protection against infectious disease.

Three groups of mice (15 mice per group) may be infected with the intracellular parasite *Leishmania major* (*L. major*) by injecting *L. major* promastigotes SC into their left hind footpads. Four weeks after infection, the mice may be challenged with either *Leishmania* freeze-thawed antigen, or PBS as a negative control, in the contra-lateral footpad. One group of mice may also receive PBS and Tween 0.5% i.p. at the initial sensitization, and at different dosing schedules thereafter, up until the *Leishmania* antigen challenge. A second group of mice may receive different doses of the CCR4 antagonist(s) given either i.p., IV, SC, IM, PO or via any other mode of administration at the initial sensitization, and at different dosing schedules thereafter, up until the *Leishmania* antigen challenge. A third group of mice, serving as positive control, may consist of mice treated with either IL-12, anti-IL-4 antibodies i.p., or anti-IL-5 antibodies i.p. at the initial sensitization, and at different dosing schedules thereafter, up until the *Leishmania* antigen challenge.

Over the next 48 h, footpad swelling, caused by a Delayed-Type Hypersensitivity reaction to the *Leishmania* antigen challenge, may be monitored with a metric caliper. The response of draining lymph node T cells to *Leishmania* antigen stimulation in vitro may also be measured, both at the level of proliferation, cytokine production, and other phenotypic criteria.

Rheumatoid Arthritis. Rheumatoid Arthritis (RA), which is generally characterized by chronic inflammation in the membrane lining (the synovium) of the joints, affects approximately 1% of the U.S. population, or 2.1 million people in the U.S. Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL (etanercept), REMICADE (infliximab), HUMIRA (adalimumab) and KINERET (anakinra). Though some of these agents relieve symptoms, inhibit progression of structural damage, and improve physical function in particular patient populations, there is still a need for alternative agents with improved efficacy, complementary mechanisms of action, and fewer/less severe adverse effects.

A representative procedure for evaluating the efficacy of CCR4 antagonists for treatment of rheumatoid arthritis is as described herein. An animal model of rheumatoid arthritis may be induced in rodents by injecting them with type II collagen in selected adjuvants. Three rodent groups, each consisting of 15 genetically-susceptible mice or rats, may be injected SC or intra-dermally with type II collagen emulsified in Complete Freund's Adjuvant at days 0 and 21. One group of rodents may additionally receive PBS and Tween 0.5% i.p. at the initial sensitization, and at different dosing schedules thereafter. A second group of rodents may receive different doses of the CCR4 antagonist(s) given either i.p., IV, SC, IM, PO or via any other mode of administration at the initial sensitization, and at different dosing schedules thereafter. A third group, serving as positive control, may consist of rodents treated with either mouse IL-10 i.p., or anti-TNF antibodies i.p. at the initial sensitization, and at different dosing schedules thereafter.

Animals may be monitored from weeks 3 until 8 for the development of swollen joints or paws, and graded on a standard disease-severity scale. Disease severity may be confirmed by histological analysis of joints.

Systemic Lupus Erythematosus. A representative procedure for evaluating the efficacy of CCR4 antagonists for treatment of Systemic Lupus Erythematosus (SLE) is as described herein. Female NZB/W F1 mice spontaneously develop an SLE-like pathology commencing at 6 months of age that is characterized by proteinuria, serum autoantibodies, glomerulonephritis, and eventually death.

Three groups of NZB/W mice, each comprising 20 mice per group, may be evaluated. One group of mice may receive PBS and Tween 0.5% i.p. soon after weaning, and thereafter at varying dosing schedules. A second group of mice may receive different doses of the CCR4 antagonist(s) given either i.p., IV, SC, IM, PO or via any other mode of administration soon after weaning, and thereafter at varying dosing schedules. A third group of mice, serving as positive control, may comprise mice treated with anti-IL-10 antibodies given soon after weaning, and thereafter at varying dosing schedules. Disease development may be monitored in terms of eventual mortality, kidney histology, serum autoantibody levels, and proteinuria.

Cancer-related Malignancy. A representative procedure for evaluating the efficacy of CCR4 antagonists for treatment of cancer is as described herein. Mice homozygous for the severe combined immune deficiency spontaneous mutation Prkdc$^{scid}$ (SCID mice), are characterized by an absence of functional T cells and B cells, lymphopenia, hypogammaglobulinemia, and a normal hematopoietic microenvironment. Additional mouse genetic backgrounds can result in lack of natural killer cells (in NOD-SCID); while the addition of mutations in IL2 receptor gamma chain results in loss of much cytokine signaling resulting in highly immune-deficient mice (NSG). Immuno-deficient mice (SCID mice, NOD-SCID mice, NSG or other) can be engrafted with a human immune system following transplant of PBMCs, CD34+ hematopoietic stem cells, or isolated immune effector populations. These humanized mice may be transplanted cultured established human tumor cell lines (xenograft) or with primary human tumor cells to create a patient derived xenograft (PDX). Additionally, normal mouse strains may be transplanted with a variety of well-characterized mouse tumor lines, including the thymoma EL4 cell line, which have been transfected with OVA to allow easy evaluation of tumor-specific antigen responses following vaccination with OVA. Three groups of mice from any of these tumor models may be tested for CCR4 antagonist efficacy. One group receives PBS and Tween 0.5% i.p. soon after tumor transplant, and thereafter at varying dosing schedules. A second group receives different doses of the CCR4 antagonist(s) given either i.p., IV, SC, IM, PO or via any other mode of administration following tumor transplant, and thereafter at varying dosing schedules. A third group, serving as positive control, may comprise mice treated with either anti-IL-4 antibodies, anti-IFNγ antibodies, IL-4, or TNF, given i.p. soon after tumor transplant, and thereafter at varying dosing schedules. A second group receives different doses of the CCR4 antagonist(s) given either i.p., IV, SC, IM, PO or via any other mode of administration following tumor transplant, and thereafter at varying dosing schedules. A third group, serving as positive control, may comprise mice treated with either anti-IL -4 antibodies, anti-IFNγ antibodies, IL-4, or TNF, given i.p. soon after tumor transplant, and thereafter at varying dosing schedules.

Efficacy may be monitored via tumor growth versus regression. In the case of the OVA-transfected EL4 thymoma model, cytolytic OVA-specific responses may be measured by stimulating draining lymph node cells with OVA in vitro, and measuring antigen-specific cytotoxicity at various times, such as 72 h.

Allograft Transplantation Models. Allograft mouse tumor systems, also known as syngeneic models, may be used to evaluate the compounds of the present disclosure. In contrast to conventional xenograft models, which often lack relevance due to the animals' immunocompromised status, the host immune system is normal in syngeneic models, which may more closely represent the native tumor microenvironment. Because they retain intact immune systems, syngeneic mouse models are particularly relevant for studies of immunologically-based targeted therapies, that modulate the immune system's ability to seek out and destroy cancer cells. For example, the MC38 model of colorectal cancer can be used to explore the activity of treatment with a CCR4 inhibitor. Treatment with the CCR4 inhibitor and/or other agents may be initiated prior to, along with, or after MC38 cancer cells have been implanted or injected into recipient mice. Mice are then divided or randomized into treatment groups, each containing multiple mice, and the impact of treatment can be measured. Endpoints for anti-tumor responses include the absence or presence of a tumor, it's size, time to a size (including any detection at all) or time to regression, long term regression, or other accepted endpoints. Additional endpoints of activity include, for example, a characterization of the immune cell populations in and around the tumor or systemically or markers of immune cell responses (e.g. cytokine levels).

Syngeneic models consist of tumor tissues derived from the same genetic background as a given mouse strain. Cancerous cells or solid tumors may be transplanted into a host mouse. Because the cancer tissues and the recipient share ancestry, the transplant is not rejected by the host's immune system. Tissues may then be monitored for changes such as growth or shrinkage, metastasis, and survival rate. Therapeutic interventions may be performed and the results assessed to understand the treatment potentials.

A discussion of syngeneic models and other tumor models for efficacy determinations is set forth in Teicher, B A, (October 2006) Mol Cancer Ther 5:2435. Multiple syngeneic tumor models with well-characterized responses to known immune checkpoint inhibitors (e.g., anti-PDL-1, anti-PD -1 and anti-CTLA-4) are commercially available (e.g., GenScript (Piscataway, N.H.) and Charles River Labs (Wilmington, Mass.)).

Psoriasis. Psoriasis, a constellation of common immune-mediated chronic skin diseases, affects more than 4.5 million people in the U.S., of which 1.5 million are considered to have a moderate-to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL (etanercept), REMICADE (infliximab) and HUMIRA (adalimumab)), and T-cell inhibitors such as AMEVIVE (alefacept) and RAPTIVA (efalizumab). Though several of these agents are effective to some extent in certain patient populations, none have been shown to effectively treat all patients.

A representative procedure for evaluating the efficacy of CCR4 antagonists for treatment of psoriasis is as described herein. A rodent model of psoriasis may be generated by intravenously transferring a population of purified T cells (e.g., CD45Rbhi T cells) obtained from the spleens of BALB/c mice into immunodeficient recipient CB 17 scid/scid mice. Mice develop signs of redness, swelling, and skin lesions resembling those of human psoriasis in their ears, feet and tail by 8 weeks after transfer. Three groups of mice, each comprising 10-15 CB.17 scid/scid mice, may be injected with purified CD45Rbhi T cells. One group of mice may additionally receive PBS and Tween 0.5% i.p. at the initial cell transfer, and at different dosing schedules thereafter. A second group of mice may receive different doses of the CCR4 antagonist(s) given either i.p., IV, SC, IM, PO or via any other mode of administration at the initial cell transfer, and at different dosing schedules thereafter. A third group of mice, serving as positive control, may consist of mice treated with antibodies to either IL-12, IL-4, IFNγ, or TNF, or with cytokine IL-10 at the initial cell transfer, and at different dosing schedules thereafter. Animals may be monitored for development of psoriatic-like lesions for 3 months after cell transfer.

Inflammatory Bowel Disease. Several murine models of IBD (e.g., Crohn's disease and ulcerative colitis) have been developed. Some of the models occur in genetically engineered transgenic mice that have been depleted of certain cytokine genes (e.g., IL-10 or IL-2) by homologous recombination. A particular murine model of IBD is obtained by transferring highly purified populations of CD4+T lymphocytes bearing the surface marker phenotype cd45rb hi into SCID mice.

Representative procedures for evaluating the efficacy of CCR4 antagonists for treatment of inflammatory bowel disease comprise three groups of mice from any of the aforementioned models. One group of mice may receive PBS and Tween 0.5% i.p. soon after weaning in the case of the spontaneous models in transgenic mice, or at the time of cell transfer into SCID mice and varying dosings thereafter for the cell transfer model. A second group of mice may receive different doses of the CCR4 antagonist(s) given either i.p., IV, SC, IM, PO or via any other mode of administration soon after weaning in the case of the spontaneous models in transgenic mice, or at the time of cell transfer into SCID mice and varying dosings thereafter for the cell transfer model. A third group of mice, serving as positive control, may comprise mice treated with antibodies to either IFNγ or TNF, or with the cytokine IL-10 soon after weaning in the case of the spontaneous models in transgenic mice, or at the time of cell transfer into SCID mice and varying dosings thereafter for the cell transfer model. Mice may be evaluated for 6-8 weeks for disease development, monitored initially for weight loss and/or prolapsed rectum, and subsequently for histological evaluation of their colons and intestinal tracts.

Although the invention has been described with reference to the above example, it will be understood that modifications and variations are encompassed within the spirit and scope of the invention.

PI EMBODIMENTS

Embodiment PI1 A compound having structural Formula (I):

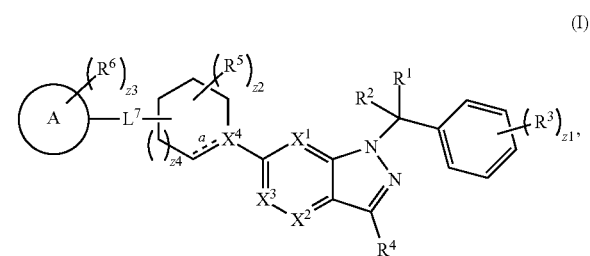

(I)

or a pharmaceutically acceptable salt thereof, wherein:
A is a substituted or unsubstituted heterocycloalkyl;

$X^1$ is $CR^8$ or N;
$X^2$ is $CR^9$ or N;
$X^3$ is $CR^{10}$ or N;
$X^4$ is C, $CR^{11}$ or N;
n1 is an integer from 0 to 4;
m1 and v1 are independently 1 or 2;
z1 is an integer from 0 to 5;
z2 is an integer from 0 to 13;
z3 is an integer from 0 to 12;
z4 is an integer from 0 to 3;
⁼ is a single bond or double bond, wherein if ⁼ is a single bond, then $X^4$ is $CR^{11}$ or N, and if ⁼ is a double bond, then $X^4$ is C;

$L^7$ is a bond, —O—, —S—, —$NR^{7B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^1$ is hydrogen, halogen, —$CX^{1.1}{}_3$, —$CHX^{1.1}{}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}{}_3$, —$OCHX^{1.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^{2.1}{}_3$, —$CHX^{2.1}{}_2$, —$CH_2X^{2.1}$, —CN, —$SO_{n1}R^{2A}$, —$SO_{v1}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m1}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}{}_3$, —$OCHX^{2.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^{3.1}{}_3$, —$CHX^{3.1}{}_2$, —$CH_2X^{3.1}$, —CN, —$SO_{n1}R^{3A}$, —$SO_{v1}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m1}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}{}_3$, —$OCHX^{3.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, —$CX^{4.1}{}_3$, —$CHX^{4.1}{}_2$, —$CH_2X^{4.1}$, —CN, —$SO_{n1}R^{4A}$, —$SO_{v1}NR^{4B}R^{4C}$, —$NHNR^{4B}R^{4C}$, —$ONR^{4B}R^{4C}$, —$NHC(O)NHNR^{4B}R^{4C}$, —$NHC(O)NR^{4B}R^{4C}$, —$N(O)_{m1}$, —$NR^{4B}R^{4C}$, —$C(O)R^{4D}$, —$C(O)OR^{4D}$, —$C(O)NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}{}_3$, —$OCHX^{4.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is hydrogen, halogen, oxo, —$CX^{5.1}{}_3$, —$CHX^{5.1}{}_2$, —$CH_2X^{5.1}$, —CN, —$SO_{n1}R^{5A}$, —$SO_{v1}NR^{5B}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, —$N(O)_{m1}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}{}_3$, —$OCHX^{5.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is hydrogen, halogen, oxo, —$CX^{6.1}{}_3$, —$CHX^{6.1}{}_2$, —$CH_2X^{6.1}$, —CN, —$SO_{n1}R^{6A}$, —$SO_{v1}NR^{6B}R^{6C}$, —$NHNR^{6B}R^{6C}$, —$ONR^{6B}R^{6C}$, —$NHC(O)NHNR^{6B}R^{6C}$, —$NHC(O)NR^{6B}R^{6C}$, —$N(O)_{m1}$, —$NR^{6B}R^{6C}$, —$C(O)R^{6D}$, —$C(O)OR^{6D}$, —$C(O)NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}{}_3$, —$OCHX^{6.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^8$ is hydrogen, halogen, —$CX^{8.1}{}_3$, —$CHX^{8.1}{}_2$, —$CH_2X^{8.1}$, —CN, —$SO_{n1}R^{8A}$, —$SO_{v1}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m1}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}{}_3$, —$OCHX^{8.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$CX^{9.1}{}_3$, —$CHX^{9.1}{}_2$, —$CH_2X^{9.1}$, —CN, —$SO_{n1}R^{9A}$, —$SO_{v1}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m1}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}{}_3$, —$OCHX^{9.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —$CX^{10.1}{}_3$, —$CHX^{10.1}{}_2$, —$CH_2X^{10.1}$, —CN, —$SO_{n1}R^{10A}$, —$SO_{v1}NR^{10B}R^{10C}$, —$NHNR^{10B}R^{10C}$, —$ONR^{10B}R^{10C}$, —NHC(O)$NHNR^{10B}R^{10C}$, —$NHC(O)NR^{10B}R^{10C}$, —$N(O)_{m1}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}{}_3$, —$OCHX^{10.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, —$CX^{11.1}{}_3$, —$CHX^{11.1}{}_2$, —$CH_2X^{11.1}$, —CN, —$SO_{n1}R_{11A}$, —$SO_{v1}NR^{11B}R^{11C}$, —$NHNR^{11B}R^{11C}$, —$ONR^{11B}R^{11C}$, —NHC(O)$NHNR^{11B}R^{11C}$, —$NHC(O)NR^{11B}R^{11C}$, —$N(O)_{m1}$, —$NR^{11B}R^{11C}$, —$C(O)R^{11D}$, —$C(O)OR^{11D}$, —$C(O)NR^{11B}R^{11C}$, —$OR^{11A}$, —$NR^{11B}SO_2R^{11A}$, —$NR^{11B}C(O)R^{11D}$, —$NR^{11B}C(O)OR^{11D}$, —$NR^{11B}OR^{11D}$, —$OCX^{11.1}{}_3$, —$OCHX^{11.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7B}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$ and $R^{11D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{8B}$ and $R^{8C}$, $R^{9B}$ and $R^{9C}$, $R^{10B}$ and $R^{10C}$, $R^{11B}$ and $R^{11C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$ are independently —Cl, —Br, —I or —F, wherein at least one of $X^1$, $X^2$ and $X^3$ is N.

Embodiment PI2 The compound of embodiment PI1, wherein the substituted or unsubstituted heterocycloalkyl is a 4-membered to 8-membered ring.

Embodiment PI3 The compound of embodiment PI1, wherein the compound has structural Formula (Ia):

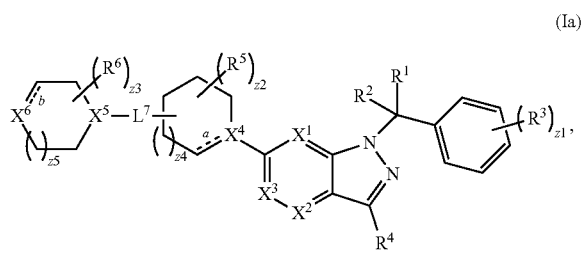

(Ia)

or a pharmaceutically acceptable salt thereof, wherein:
$X^5$ is $CR^{12}$ or N;
$X^6$ is $CR^{13}$, $CR^{13}R^{14}$, N or $NR^{15}$;
z3 is an integer from 0 to 12;
z5 is an integer from 0 to 3;

$R^{12}$ is hydrogen, halogen, —CX$^{12.1}_3$, —CHX$^{12.1}_2$, —CH$_2$X$^{12.1}$, —CN, —SO$_{n1}$R$^{12A}$, —SO$_{v1}$NR$^{12B}$R$^{12C}$, —NHNR$^{12B}$R$^{12C}$, —ONR$^{12B}$R$^{12C}$, —NHC(O)NHNR$^{12B}$R$^{12C}$, —NHC(O)NR$^{12B}$R$^{12C}$, —N(O)$_{m1}$, —NR$^{12B}$R$^{12C}$, —C(O)R$^{12D}$, —C(O)OR$^{12D}$, —C(O)NR$^{12B}$R$^{12C}$, —OR$^{12A}$, —NR$^{12B}$SO$_2$R$^{12A}$, —NR$^{12B}$C(O)R$^{12D}$, —NR$^{12B}$C(O)OR$^{12D}$, —NR$^{12B}$OR$^{12D}$, —OCX$^{12.1}_3$, —OCHX$^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, halogen, —CX$^{13.1}_3$, —CHX$^{13.1}_2$, —CH$_2$X$^{13.1}$, —CN, —SO$_{n1}$R$^{13A}$, —SO$_{v1}$NR$^{13B}$R$^{13C}$, —NHNR$^{13B}$R$^{13C}$, —ONR$^{13B}$R$^{13C}$, —NHC(O)NHNR$^{13B}$R$^{13C}$, —NHC(O)NR$^{13B}$R$^{13C}$, —N(O)$_{m1}$, —NR$^{13B}$R$^{13C}$, —C(O)R$^{13D}$, —C(O)OR$^{13D}$, —C(O)NR$^{13B}$R$^{13C}$, —OR$^{13A}$, —NR$^{13B}$SO$_2$R$^{13A}$, —NR$^{13B}$C(O)R$^{13D}$, —NR$^{13B}$C(O)OR$^{13D}$, —NR$^{13B}$OR$^{13D}$, —OCX$^{13.1}_3$, —OCHX$^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is hydrogen, halogen, —CX$^{14.1}_3$, —CHX$^{14.1}_2$, —CH$_2$X$^{14.1}$, —CN, —SO$_{n1}$R$^{14A}$, —SO$_{v1}$NR$^{14B}$R$^{14C}$, —NHNR$^{14B}$R$^{14C}$, —ONR$^{14B}$R$^{14C}$, —NHC(O)NHNR$^{14B}$R$^{14C}$, —NHC(O)NR$^{14B}$R$^{14C}$, —N(O)$_{m1}$, —NR$^{14B}$R$^{14C}$, —C(O)R$^{14D}$, —C(O)OR$^{14D}$, —C(O)NR$^{14B}$R$^{14C}$, —OR$^{14A}$, —NR$^{14B}$SO$_2$R$^{14A}$, —NR$^{14B}$C(O)R$^{14D}$, —NR$^{14B}$C(O)OR$^{14D}$, —NR$^{14B}$OR$^{14D}$, —OCX$^{14.1}_3$, —OCHX$^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, —CX$^{15.1}_3$, —CHX$^{15.1}_2$, —CH$_2$X$^{15.1}$, —CN, —SO$_{n1}$R$^{15A}$, —SO$_{v1}$NR$^{15B}$R$^{15C}$, —NHNR$^{15B}$R$^{15C}$, —ONR$^{15B}$R$^{15C}$, —NHC(O)NHNR$^{15B}$R$^{15C}$, —NHC(O)NR$^{15B}$R$^{15C}$, —N(O)$_{m1}$, —NR$^{15B}$R$^{15C}$, —C(O)R$^{15D}$, —C(O)OR$^{15D}$, —C(O)NR$^{15B}$R$^{15C}$, —OR$^{15A}$, —NR$^{15B}$SO$_2$R$^{15A}$, —NR$^{15B}$C(O)R$^{15D}$, —NR$^{15B}$C(O)OR$^{15D}$, —NR$^{15B}$OR$^{15D}$, —OCX$^{15.1}_3$, —OCHX$^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$ and $R^{15D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12B}$ and $R^{12C}$, $R^{13B}$ and $R^{13C}$, $R^{14B}$ and $R^{14C}$ and $R^{15B}$ and $R^{15C}$ substituents bonded to the same nitrogen atom may optionally be joined to form a substituted or unsubstituted heterocycloalkyl or substituted or unsubstituted heteroaryl;

⸻ is a single bond or double bond, wherein if ⸻ is a single bond, then $X^4$ is $CR^{13}R^{14}$ or $NR^{15}$, and if ⸻ is a double bond, then $X^4$ is N or $CR^{13}$; and $X^{12.1}$, $X^{13.1}$, $X^{14.1}$ and $X^{15.1}$ are independently —Cl, —Br, —I or —F.

Embodiment PI4 The compound of embodiment PI1, wherein: z1 is 2; and z4 is 1.

Embodiment PI5 The compound of Embodiment PI1, wherein $R^1$ and $R^2$ are independently hydrogen, substituted or unsubstituted alkyl or substituted or unsubstituted heteroalkyl.

Embodiment PI6 The compound of embodiment PI1, wherein $L^7$ is a bond.

Embodiment PI7 The compound of embodiment PI3, wherein the compound has structural Formula (II):

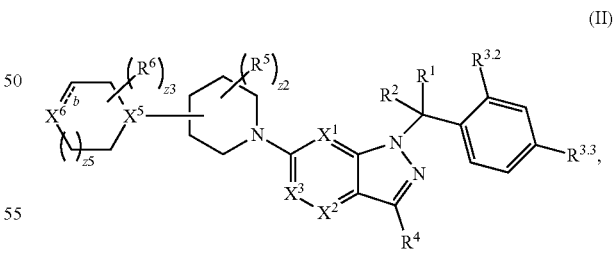

(II)

or a pharmaceutically acceptable salt thereof, wherein:
$R^4$ is hydrogen, —CX$^{4.1}_3$, —CN, —C(O)NR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.2}$ is hydrogen, halogen, —CX$^{3.2}_3$, —CHX$^{3.2}_2$, —CH$_2$X$^{3.2}$, —CN, —SO$_{n1}$R$^{3.2A}$, —SO$_{v1}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m1}$, —NR$^{3.2B}$R$^{3.2C}$, —C(O)R$^{3.2D}$, —C(O)OR$^{3.2D}$, —C(O) NR$^{3.2B}$R$^{3.2C}$, —OR$^{3.2A}$, —NR$^{3.2B}$SO$_2$R$^{3.2A}$, —NR$^{3.2B}$C(O) R$^{3.2D}$, —NR$^{3.2B}$C(O)OR$^{3.2D}$, —NR$^{3.2B}$OR$^{3.2D}$, —OCX$^{3.2}_3$, —OCHX$^{3.2}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{3.3}$ is hydrogen, halogen, —CX$^{3.3}_3$, —CHX$^{3.3}_2$, —CH$_2$X$^{3.3}$, —CN, —SO$_{n1}$R$^{3.3A}$, —SO$_{v1}$NR$^{3.3B}$R$^{3.3C}$, —NHNR$^{3.3B}$R$^{3.3C}$, —ONR$^{3.3B}$R$^{3.3C}$, —NHC(O) NHNR$^{3.3B}$R$^{3.3C}$, —NHC(O)NR$^{3.3B}$R$^{3.3C}$, —N(O)$_{m1}$, —NR$^{3.3B}$R$^{3.3C}$, —C(O)R$^{3.3D}$, —C(O)OR$^{3.3D}$, —C(O) NR$^{3.3B}$R$^{3.3C}$, —OR$^{3.3A}$, —NR$^{3.3B}$SO$_2$R$^{3.3A}$, —NR$^{3.3B}$C(O) R$^{3.3D}$, —NR$^{3.3B}$C(O)OR$^{3.3D}$, —NR$^{3.3B}$OR$^{3.3D}$, —OCX$^{3.3}_3$, —OCHX$^{3.3}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{3.2A}$, R$^{3.2B}$, R$^{3.2C}$, R$^{3.2D}$, R$^{3.3A}$, R$^{3.3B}$, R$^{3.3C}$ and R$^{3.3D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3.2B}$, R$^{3.2C}$, R$^{3.3B}$ and R$^{3.3C}$ substituents bonded to the same nitrogen atom may optionally be joined to form a substituted or unsubstituted heterocycloalkyl or substituted or unsubstituted heteroaryl; and X$^{3.2}$ and X$^{3.3}$ are independently —Cl, —Br, —I or —F.

Embodiment PI8 The compound of embodiment PI3, wherein the compound has structural Formula (III):

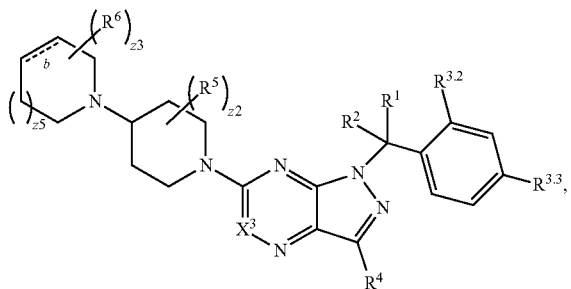

(III)

or a pharmaceutically acceptable salt thereof.

Embodiment PI9 The compound of embodiment PI3, wherein the compound has structural Formula (IIIa):

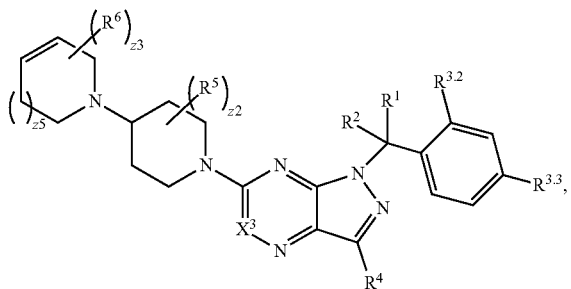

(IIIa)

or a pharmaceutically acceptable salt thereof.

Embodiment PI10 The compound of Embodiment PI3, wherein the compound has structural Formula (IIIb):

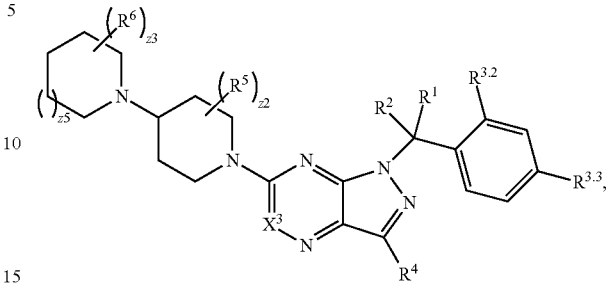

(IIIb)

or a pharmaceutically acceptable salt thereof.

Embodiment PI11 The compound of embodiment PI3, wherein the compound has structural Formula (IV):

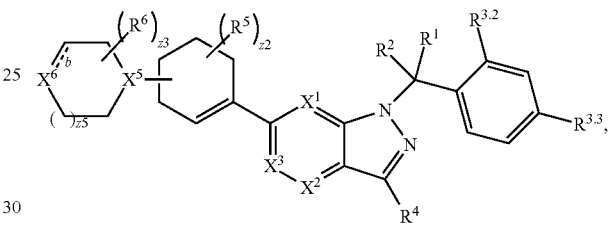

(IV)

or a pharmaceutically acceptable salt thereof.

Embodiment PI12 The compound of embodiment PI3, wherein the compound has structural Formula (V):

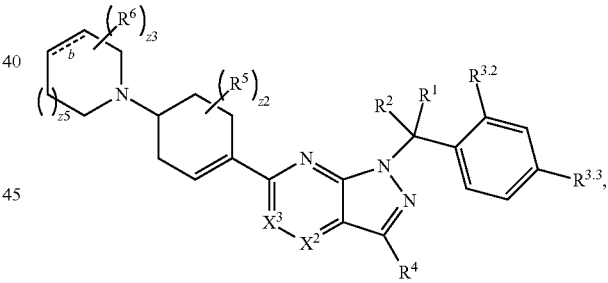

(V)

or a pharmaceutically acceptable salt thereof.

Embodiment PI13 The compound of embodiment PI3, wherein the compound has structural Formula (Va):

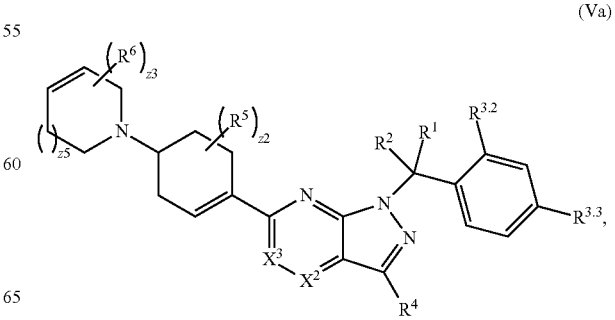

(Va)

or a pharmaceutically acceptable salt thereof.

Embodiment PI14 The compound of embodiment PI3, wherein the compound has structural Formula (Vb):

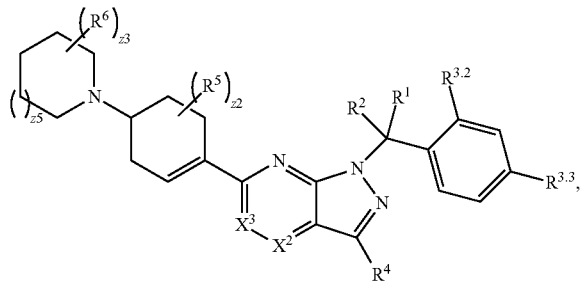

(Vb)

or a pharmaceutically acceptable salt thereof.

Embodiment PI15 The compound of any one of embodiments PI1 to PI14, wherein $R^4$ is hydrogen, —CN, —CX$^{4.1}_3$, —C(O)R$^{4D}$, —C(O)OR$^{4D}$, —C(O)NR$^{4B}$R$^{4C}$, substituted or unsubstituted alkyl or substituted or unsubstituted heteroalkyl.

Embodiment PI16 The compound of embodiment PI15, wherein $R^4$ is —CN, —CF$_3$, —C(O)NH$_2$, —CH$_3$ or —C(CH$_3$)$_2$OH.

Embodiment PI17 The compound of any one of embodiments PI7 to PI14, wherein $R^{3.2}$ and $R^{3.3}$ are independently halogen, —CN, CF$_3$ or unsubstituted alkyl.

Embodiment PI18 The compound of embodiment PI17, wherein the halogen is chlorine or fluorine.

Embodiment PI19 The compound of embodiment PI17, wherein the unsubstituted alkyl is —CH$_3$.

Embodiment PI20 The compound of any one of embodiments PI1 to PI14, wherein $R^1$ and $R^2$ are independently hydrogen or unsubstituted alkyl.

Embodiment PI21 The compound of embodiment PI20, wherein $R^1$ is —CH$_3$ or —CH$_2$CH$_3$.

Embodiment PI22 The compound of embodiment PI20, wherein $R^2$ is —CH$_3$ or —CH$_2$CH$_3$.

Embodiment PI23 The compound of any one of embodiments PI1 to PI14, wherein $R^1$ is hydrogen.

Embodiment PI24 The compound of any one of embodiments PI1 to PI14, wherein $R^2$ is hydrogen.

Embodiment PI25 The compound of any one of embodiments PI1 to PI14, wherein $X^2$ is N.

Embodiment PI26 The compound of any one of embodiments PI1 to PI14, wherein $X^3$ is N.

Embodiment PI27 The compound of any one of embodiments PI1 to PI14, wherein z2 and z3 are independently an integer from 0 to 2.

Embodiment PI28 The compound of any one of embodiments PI1 to PI14, wherein $R^5$ is hydrogen, fluorine, —CN, —CH$_3$, —CF$_3$, —(CH$_2$)$_2$OH, —CO$_2$NH$_2$ or —CO$_2$CH$_2$CH$_3$.

Embodiment PI29 The compound of any one of embodiments PI1 to PI14, wherein $R^6$ is hydrogen, —OH, —CH$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H,

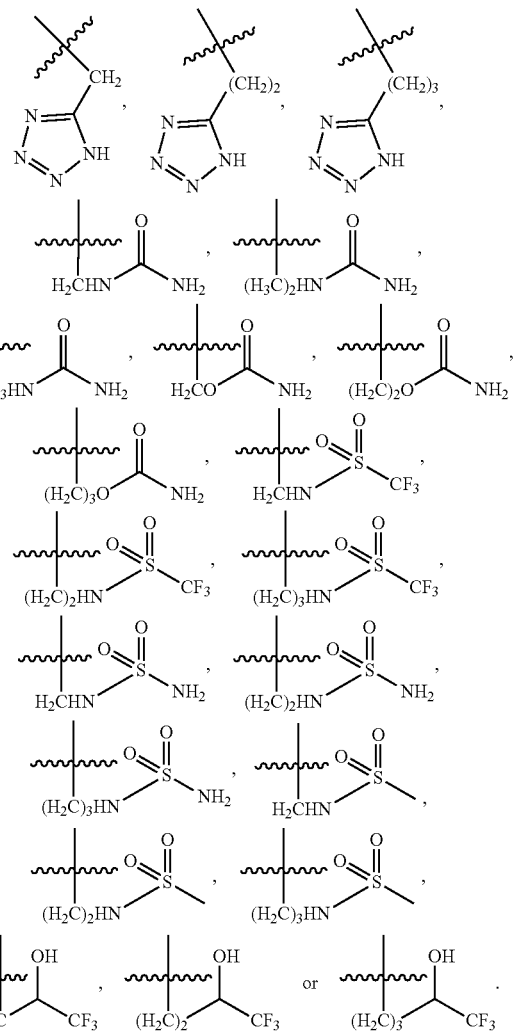

Embodiment PI30 The compound of embodiment PI3, wherein the compound has structural Formula (VI):

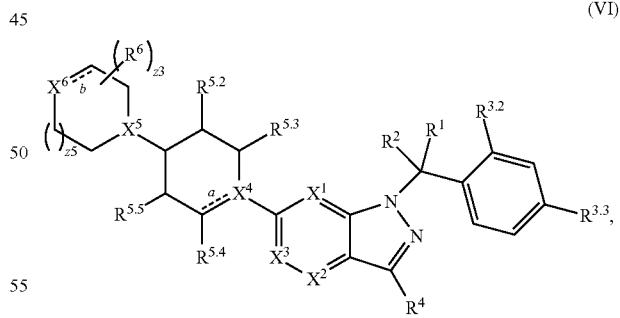

(VI)

or a pharmaceutically acceptable salt thereof, wherein:

$R^{5.2}$ is hydrogen, halogen, —CX$^{5.6}_3$, —CHX$^{5.6}_2$, —CH$_2$X$^{5.6}$, —CN, —SO$_{n1}$R$^{5.6A}$, —SO$_{v1}$NR$^{5.6B}$R$^{5.6C}$, —NHNR$^{5.6B}$R$^{5.6C}$, —ONR$^{5.6B}$R$^{5.6C}$, —NHC(O)NHNR$^{5.6B}$R$^{5.6C}$, —NHC(O)NR$^{5.6B}$R$^{5.6C}$, —N(O)$_{m1}$, —NR$^{5.6B}$R$^{5.6C}$, —C(O)R$^{5.6D}$, —C(O)OR$^{5.6D}$, —C(O)NR$^{5.6B}$R$^{5.6C}$, —OR$^{5.6A}$, —NR$^{5.6B}$SO$_2$R$^{5.6A}$, —NR$^{5.6B}$C(O)R$^{5.6D}$, —NR$^{5.6B}$C(O)OR$^{5.6D}$, —NR$^{5.6B}$OR$^{5.6D}$, —OCX$^{5.6}_3$, —OCHX$^{5.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5.3}$ is hydrogen, halogen, $-CX^{5.7}_3$, $-CHX^{5.7}_2$, $-CH_2X^{5.7}$, $-CN$, $-SO_{n1}R^{5.7A}$, $-SO_{v1}NR^{5.7B}R^{5.7C}$, $-NHNR^{5.7B}R^{5.7C}$, $-ONR^{5.7B}R^{5.7C}$, $-NHC(O)NHNR^{5.7B}R^{5.7C}$, $-NHC(O)NR^{5.7B}R^{5.7C}$, $-N(O)_{m1}$, $-NR^{5.7B}R^{5.7C}$, $-C(O)R^{5.7D}$, $-C(O)OR^{5.7D}$, $-C(O)NR^{5.7B}R^{5.7C}$, $-OR^{5.7A}$, $-NR^{5.7B}SO_2R^{5.7A}$, $-NR^{5.7B}C(O)R^{5.7D}$, $-NR^{5.7B}C(O)OR^{5.7D}$, $-NR^{5.7B}OR^{5.7D}$, $-OCX^{5.7}_3$, $-OCHX^{5.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5.4}$ is hydrogen, halogen, $-CX^{5.8}_3$, $-CHX^{5.8}_2$, $-CH_2X^{5.8}$, $-CN$, $-SO_{n1}R^{5.8A}$, $-SO_{v1}NR^{5.8B}R^{5.8C}$, $-NHNR^{5.8B}R^{5.8C}$, $-ONR^{5.8B}R^{5.8C}$, $-NHC(O)NHNR^{5.8B}R^{5.8C}$, $-NHC(O)NR^{5.8B}R^{5.8C}$, $-N(O)_{m1}$, $-NR^{5.8B}R^{5.8C}$, $-C(O)R^{5.8D}$, $-C(O)OR^{5.8D}$, $-C(O)NR^{5.8B}R^{5.8C}$, $-OR^{5.8A}$, $-NR^{5.8B}SO_2R^{5.8A}$, $-NR^{5.8B}C(O)R^{5.8D}$, $-NR^{5.8B}C(O)OR^{5.8D}$, $-NR^{5.8B}OR^{5.8D}$, $-OCX^{5.8}_3$, $-OCHX^{5.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5.5}$ is hydrogen, halogen, $-CX^{5.9}_3$, $-CHX^{5.9}_2$, $-CH_2X^{5.9}$, $-CN$, $-SO_{n1}R^{5.9A}$, $-SO_{v1}NR^{5.9B}R^{5.9C}$, $-NHNR^{5.9B}R^{5.9C}$, $-ONR^{5.9B}R^{5.9C}$, $-NHC(O)NHNR^{5.9B}R^{5.9C}$, $-NHC(O)NR^{5.9B}R^{5.9C}$, $-N(O)_{m1}$, $-NR^{5.9B}R^{5.9C}$, $-C(O)R^{5.9D}$, $-C(O)OR^{5.9D}$, $-C(O)NR^{5.9B}R^{5.9C}$, $-OR^{5.9A}$, $-NR^{5.9B}SO_2R^{5.9A}$, $-NR^{5.9B}C(O)R^{5.9D}$, $-NR^{5.9B}C(O)OR^{5.9D}$, $-NR^{5.9B}OR^{5.9D}$, $-OCX^{5.9}_3$, $-OCHX^{5.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5.6A}$, $R^{5.6B}$, $R^{5.6C}$, $R^{5.6D}$, $R^{5.7A}$, $R^{5.7B}$, $R^{5.7C}$, $R^{5.7D}$, $R^{5.8A}$, $R^{5.8B}$, $R^{5.8C}$, $R^{5.8D}$, $R^{5.9A}$, $R^{5.9B}$, $R^{5.9C}$ and $R^{5.9D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5.6B}$ and $R^{5.6C}$, $R^{5.7B}$ and $R^{5.7C}$, $R^{5.8B}$ and $R^{5.8C}$, $R^{5.9B}$ and $R^{5.9C}$ substituents bonded to the same nitrogen atom may optionally be joined to form a substituted or unsubstituted heterocycloalkyl or substituted or unsubstituted heteroaryl; and $X^{5.6}$, $X^{5.7}$, $X^{5.8}$ and $X^{5.9}$ are independently $-Cl$, $-Br$, $-I$ or $-F$.

Embodiment PI31 The compound of embodiment PI30, wherein the compound has structural Formula (VII):

(VII)

or a pharmaceutically acceptable salt thereof.

Embodiment PI32 The compound of embodiment PI30, wherein the compound has structural Formula (VIIa):

(VIIa)

or a pharmaceutically acceptable salt thereof.

Embodiment PI33 The compound of embodiment PI30, wherein the compound has structural Formula (VIIb):

(VIIb)

or a pharmaceutically acceptable salt thereof.

Embodiment PI34 The compound of embodiment PI30, wherein the compound has structural Formula (VIII):

(VIII)

or a pharmaceutically acceptable salt thereof.

Embodiment PI35 The compound of embodiment PI34, wherein the compound has structural Formula (VIIIa):

(VIIIa)

or a pharmaceutically acceptable salt thereof.

Embodiment PI36 The compound of embodiment PI34, wherein the compound has structural Formula (VIIIb):

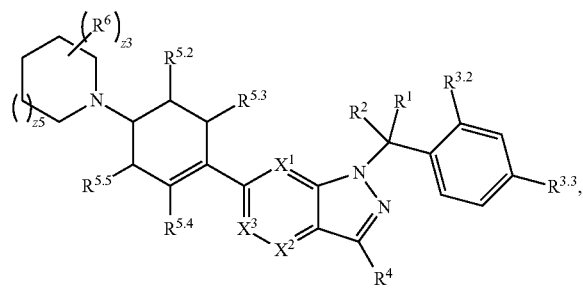

(VIIIb)

or a pharmaceutically acceptable salt thereof.

Embodiment PI37 The compound of any one of embodiments PI30 to PI36, wherein $X^1$ and $X^3$ are independently N.

Embodiment PI38 The compound of any one of embodiments PI30 to PI36, wherein $X^1$ and $X^2$ are independently N.

Embodiment PI39 The compound of any one of embodiments PI30 to PI36, wherein $R^4$ is —CN, —C(O)NH$_2$, —CF$_3$, —CH$_3$ or —C(CH$_3$)$_2$OH.

Embodiment PI40 The compound of any one of embodiments PI30 to PI36, wherein $R^{3.2}$ and $R^{3.3}$ are independently halogen, —CN, CF$_3$ or unsubstituted alkyl.

Embodiment PI41 The compound of embodiment PI40, wherein the halogen is chlorine or fluorine.

Embodiment PI42 The compound of embodiment PI40, wherein the unsubstituted alkyl is —CH$_3$.

Embodiment PI43 The compound of any one of embodiments PI30 to PI36, wherein $R^1$ and $R^2$ are independently hydrogen or unsubstituted alkyl.

Embodiment PI44 The compound of embodiment PI43, wherein $R^1$ is —CH$_3$ or —CH$_2$CH$_3$.

Embodiment PI45 The compound of embodiment PI43, wherein $R^2$ is —CH$_3$ or —CH$_2$CH$_3$.

Embodiment PI46 The compound of any one of embodiments PI30 to PI36, wherein $R^1$ is hydrogen.

Embodiment PI47 The compound of any one of embodiments PI30 to PI36, wherein $R^2$ is hydrogen.

Embodiment PI4 The compound of any one of embodiments PI30 to PI36, wherein z3 is an integer from 0 to 2.

Embodiment PI49 The compound of any one of embodiments PI30 to PI36, wherein $R^5$ is hydrogen, fluorine, —CN, —CH$_3$, —CF$_3$, —(CH$_2$)$_2$OH, —CO$_2$NH$_2$ or —CO$_2$CH$_2$CH$_3$.

Embodiment PI50 The compound of any one of embodiments PI30 to PI36, wherein $R^6$ is hydrogen, —OH, —CH$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H,

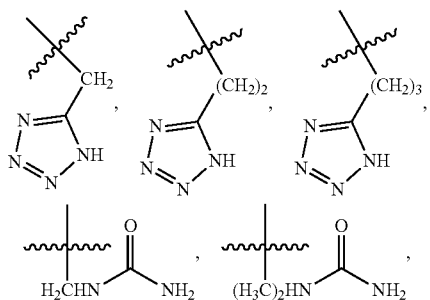

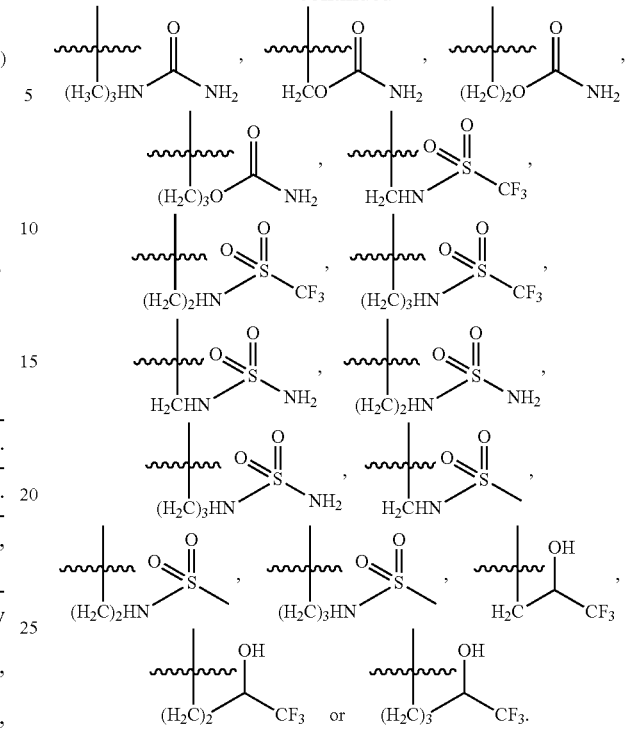

Embodiment PI51 The compound of any one of embodiments PI30 to P136, wherein z5 is 1.

Embodiment PI52 The compound of any one of embodiments PI30 to P136, wherein z5 is 0.

Embodiment PI53 The compound of embodiment PI36, wherein z3 and z5 are independently 1.

Embodiment PI54 The compound of embodiment PI36, wherein $R^6$ is halogen, substituted or unsubstituted alkyl or substituted or unsubstituted heteroalkyl.

Embodiment PI55 The compound of embodiment PI30, wherein the compound has structural Formula (IX):

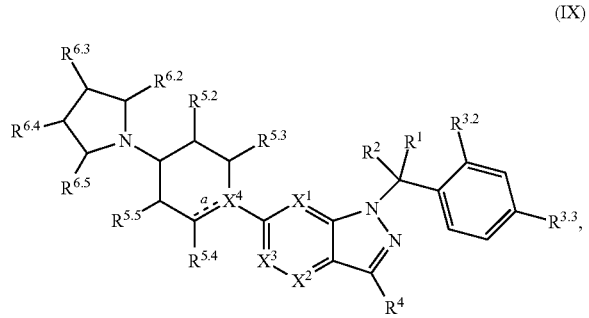

(IX)

or a pharmaceutically acceptable salt thereof, wherein:
$R^{6.2}$ is hydrogen, halogen, —CX$^{6.6}_3$, —CHX$^{6.6}_2$, —CH$_2$X$^{6.6}$, —CN, —SO$_{n1}$R$^{6.6A}$, —SO$_{v1}$NR$^{6.6B}$R$^{6.6C}$, —NHNR$^{6.6B}$R$^{6.6C}$, —ONR$^{6.6B}$R$^{6.6C}$, —NHC(O) NHNR$^{6.6B}$R$^{6.6C}$, —NHC(O)NR$^{6.6B}$R$^{6.6C}$, —N(O)$_{m1}$, —NR$^{6.6B}$R$^{6.6C}$, —C(O)R$^{6.6D}$, —C(O)OR$^{6.6D}$, —C(O) NR$^{6.6B}$R$^{6.6C}$, —OR$^{6.6A}$, —NR$^{6.6B}$SO$_2$R$^{6.6A}$, —NR$^{6.6B}$C(O) R$^{6.6D}$, —NR$^{6.6B}$C(O)OR$^{6.6D}$, —NR$^{6.6B}$OR$^{6.6D}$, —OCX$^{6.6}_3$, —OCHX$^{6.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6.3}$ is hydrogen, halogen, —$CX^{6.7}_3$, —$CHX^{6.7}_2$, —$CH_2X^{6.7}$, —CN, —$SO_{n1}R^{6.7A}$, —$SO_{v1}NR^{6.7B}R^{6.7C}$, —$NHNR^{6.7B}R^{6.7C}$, —$ONR^{6.7B}R^{6.7C}$, NHC(O)NHNR$^{6.7B}$R$^{6.7C}$, NHC(O)NR$^{6.7B}$R$^{6.7C}$, —N(O)$_{m1}$, —NR$^{6.7B}$R$^{6.7C}$, —C(O)R$^{6.7D}$, —C(O)OR$^{6.7D}$, —C(O)NR$^{6.7B}$R$^{6.7C}$, OR$^{6.7A}$, —NR$^{6.7B}$SO$_2$R$^{6.7A}$, —NR$^{6.7B}$C(O)R$^{6.7D}$, —NR$^{6.7B}$C(O)OR$^{6.7D}$, —NR$^{6.7B}$OR$^{6.7D}$, —OCX$^{6.7}_3$, —OCHX$^{6.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6.4}$ is hydrogen, halogen, —$CX^{6.8}_3$, —$CHX^{6.8}_2$, —$CH_2X^{6.8}$, —CN, —$SO_{n1}R^{6.8A}$, —$SO_{v1}NR^{6.8B}R^{6.8C}$, —$NHNR^{6.8B}R^{6.8C}$, —$ONR^{6.8B}R^{6.8C}$, —NHC(O)NHNR$^{6.8B}$R$^{6.8C}$, —NHC(O)NR$^{6.8B}$R$^{6.8C}$, —N(O)$_{m1}$, —NR$^{6.8B}$R$^{6.8C}$, —C(O)R$^{6.8D}$, —C(O)OR$^{6.8D}$, —C(O)NR$^{6.8B}$R$^{6.8C}$, OR$^{6.8A}$, —NR$^{6.8B}$SO$_2$R$^{6.8A}$, —NR$^{6.8B}$C(O)R$^{6.8D}$, —NR$^{6.8B}$C(O)OR$^{6.8D}$, —NR$^{6.8B}$OR$^{6.8D}$, —OCX$^{6.8}_3$, —OCHX$^{6.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6.5}$ is hydrogen, halogen, —$CX^{6.9}_3$, —$CHX^{6.9}_2$, —$CH_2X^{6.9}$, —CN, —$SO_{n1}R^{6.9A}$, —$SO_{v1}NR^{6.9B}R^{6.9C}$, —$NHNR^{6.9B}R^{6.9C}$, —$ONR^{6.9B}R^{6.9C}$, NHC(O)NHNR$^{6.9B}$R$^{6.9C}$, NHC(O)NR$^{6.9B}$R$^{6.9C}$, —N(O)$_{m1}$, —NR$^{6.9B}$R$^{6.9C}$, —C(O)R$^{6.9D}$, —C(O)OR$^{6.9D}$, —C(O)NR$^{6.9B}$R$^{6.9C}$, —OR$^{6.9A}$, —NR$^{6.9B}$SO$_2$R$^{6.9A}$, —NR$^{6.9B}$C(O)R$^{6.9D}$, —NR$^{6.9B}$C(O)OR$^{6.9D}$, —NR$^{6.9B}$OR$^{6.9D}$, —OCX$^{6.9}_3$, —OCHX$^{6.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6.6A}$, $R^{6.6B}$, $R^{6.6C}$, $R^{6.6D}$, $R^{6.7A}$, $R^{6.7B}$, $R^{6.7C}$, $R^{6.7D}$, $R^{6.8A}$, $R^{6.8B}$, $R^{6.8C}$, $R^{6.8D}$, $R^{6.9A}$, $R^{6.9B}$, $R^{6.9C}$ and $R^{6.9D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6.6B}$ and $R^{6.6C}$, $R^{6.7B}$ and $R^{6.7C}$, $R^{6.8B}$ and $R^{6.8C}$, $R^{6.9B}$ and $R^{6.9C}$ substituents bonded to the same nitrogen atom may optionally be joined to form a substituted or unsubstituted heterocycloalkyl or substituted or unsubstituted heteroaryl; and $X^{6.6}$, $X^{6.7}$, $X^{6.8}$ and $X^{6.9}$ are independently —Cl, —Br, —I or —F.

Embodiment PI56 The compound of embodiment PI55, wherein the compound has structural Formula (IXa):

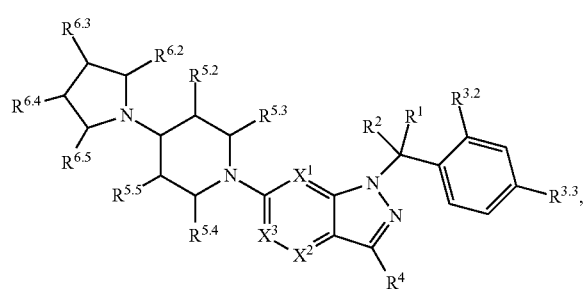

(IXa)

or a pharmaceutically acceptable salt thereof.

Embodiment PI57 The compound of embodiment PI56, wherein $X^1$ and $X^2$ are independently N.

Embodiment PI58 The compound of embodiment PI56, wherein $R^1$ and $R^2$ are independently hydrogen or unsubstituted alkyl.

Embodiment PI59 The compound of embodiment PI56, wherein $R^{3.2}$ and $R^{33}$ are independently halogen, —CN, $CF_3$ or unsubstituted alkyl.

Embodiment PI60 The compound of embodiment PI56, wherein $R^4$ is —CN, —C(O)NH$_2$, —CF$_3$, —CH$_3$ or —C(CH$_3$)$_2$OH.

Embodiment PI61 The compound of embodiment PI56, wherein $R^{5.4}$ and $R^{5.5}$ are independently hydrogen, fluorine, —CN, —CH$_3$, —CH$_2$CH$_3$, —CF$_3$, —(CH$_2$)OH, —(CH$_2$)$_2$OH, —(CH$_3$)$_2$OH, —CO$_2$H, —CO$_2$NH$_2$ or —CO$_2$CH$_2$CH$_3$.

Embodiment PI62 The compound of embodiment PI56, wherein $R^{6.2}$ is hydrogen, —CH$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H,

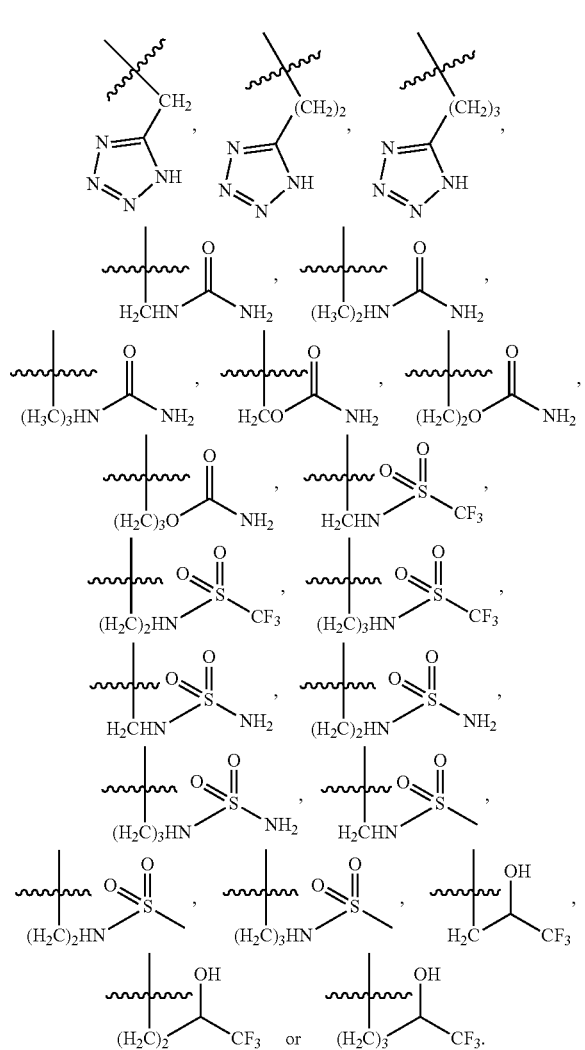

Embodiment PI63 The compound of embodiment PI55, wherein the compound has structural Formula (IXb):

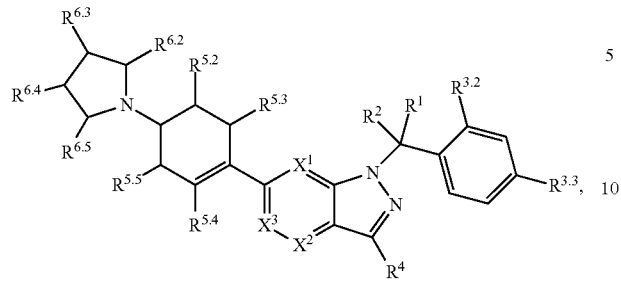

(IXb)

or a pharmaceutically acceptable salt thereof.

Embodiment PI64 The compound of embodiment PI63, wherein $X^1$ and $X^2$ are independently N.

Embodiment PI165 The compound of embodiment PI63, wherein $R^1$ and $R^2$ are independently hydrogen or unsubstituted alkyl.

Embodiment PI66 The compound of embodiment PI63, wherein $R^{3.2}$ and $R^{3.3}$ are independently halogen, —CN, $CF_3$ or unsubstituted alkyl.

Embodiment PI67 The compound of embodiment PI63, wherein $R^4$ is —CN, —C(O)$NH_2$, —$CF_3$, —$CH_3$ or —C($CH_3$)$_2$OH.

Embodiment PI68 The compound of embodiment PI63, wherein $R^{52}$ and $R^{55}$ are independently hydrogen, fluorine, —CN, —$CH_3$, —$CH_2CH_3$, —$CF_3$, —($CH_2$)OH, —($CH_2$)$_2$OH, —($CH_3$)$_2$OH, —$CO_2$H, —$CO_2NH_2$ or —$CO_2CH_2CH_3$.

Embodiment PI69 The compound of embodiment PI63, wherein $R^{6.2}$ is hydrogen, —OH, —$CH_3$, —$CH_2$OH, —($CH_2$)$_2$OH, —($CH_2$)$_3$OH, —$CH_2NH_2$, —($CH_2$)$_2NH_2$, —($CH_2$)$_3NH_2$, —$CH_2CO_2CH_2CH_3$, —($CH_2$)$_2$$CO_2CH_2CH_3$, —($CH_2$)$_3CO_2CH_2CH_3$, —$CH_2CO_2H$, —($CH_2$)$_2CO_2H$, —($CH_2$)$_3CO_2H$, —($CH_2$)$CO_2NH_2$, —($CH_2$)$_2CONH_2$, —($CH_2$)$_3CO_2NH_2$, —($CH_2$)CHF$CO_2H$, —($CH_2$)$_2$CHF$CO_2H$, —($CH_2$)$CF_2CO_2H$, —($CH_2$)$_2$$CF_2CO_2H$,

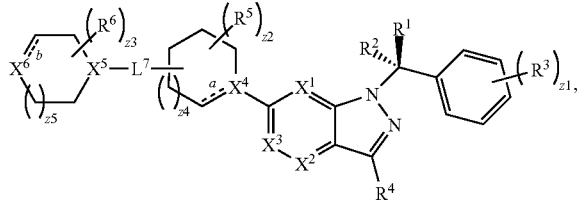

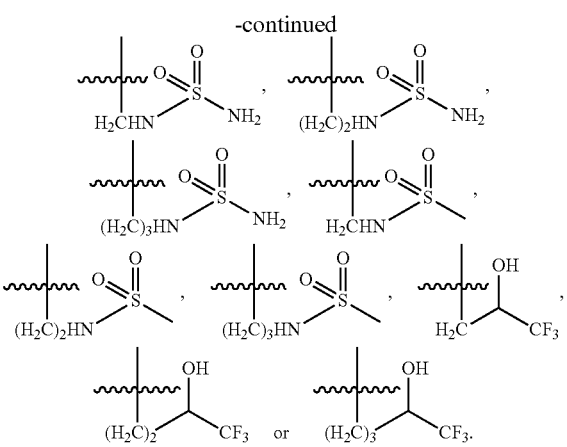

Embodiment PI70 The compound of embodiment PI3, wherein the compound has structural Formula (X):

(X)

[structure]

or a pharmaceutically acceptable salt thereof.

Embodiment PI71 The compound of embodiment PI70, wherein $R^1$ is hydrogen.

Embodiment PI72 The compound of embodiment PI70, wherein $R^2$ is hydrogen.

Embodiment PI73 The compound of embodiment PI1, wherein the compound is:

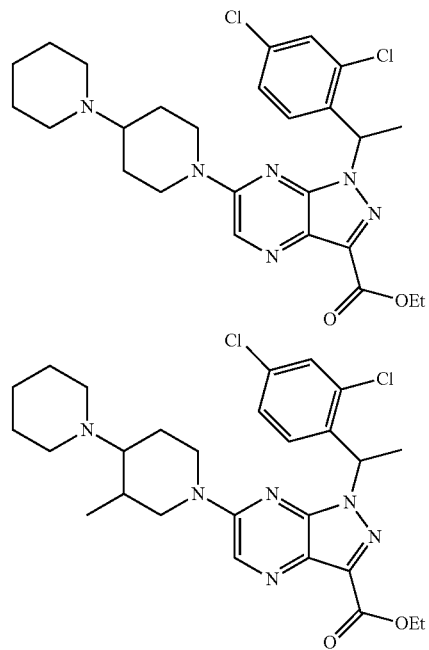

487
-continued
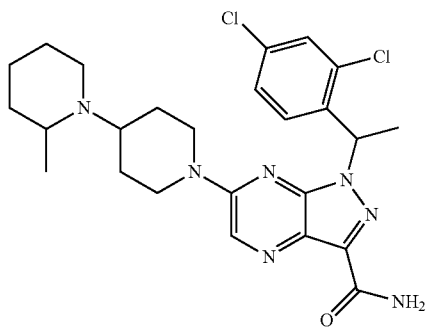
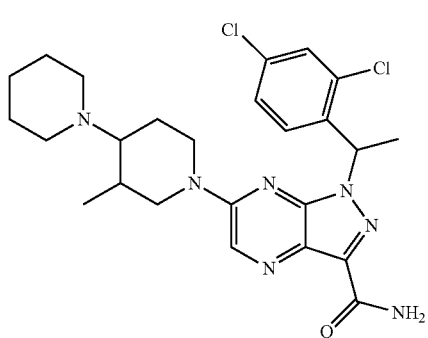
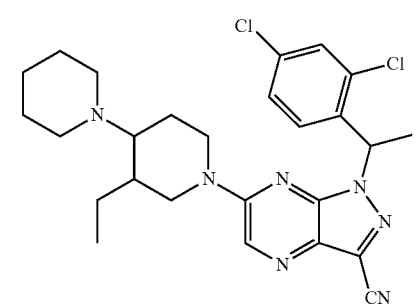
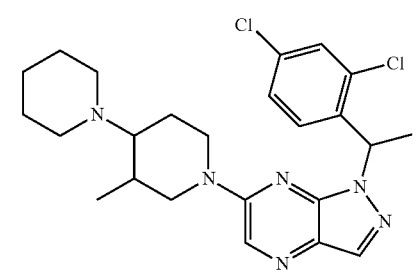
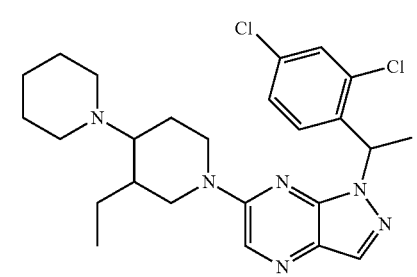
488
-continued
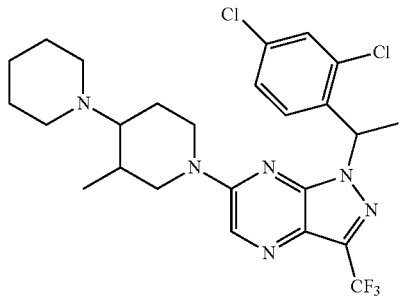
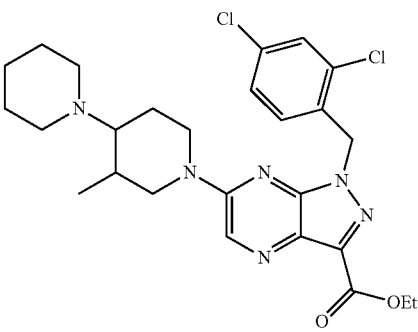
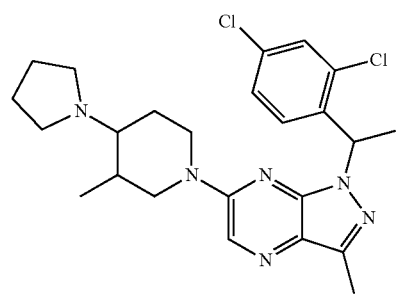
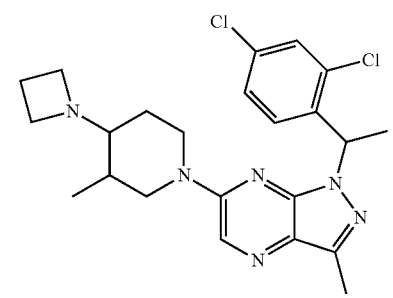
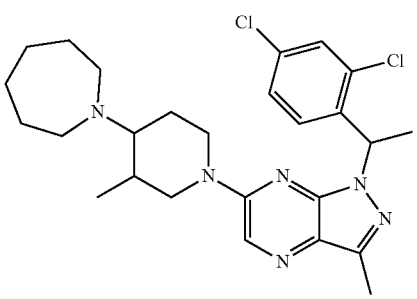

489
-continued
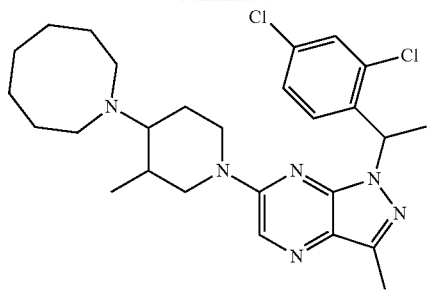
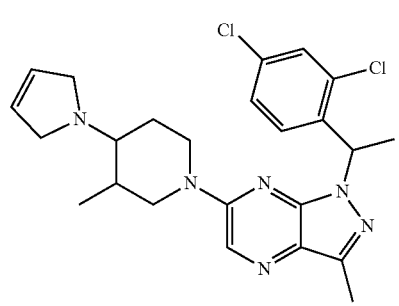
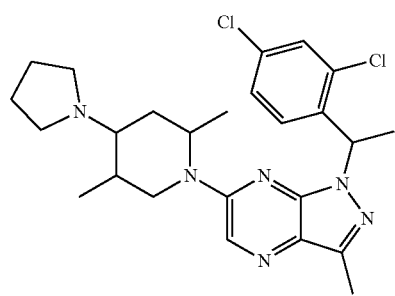
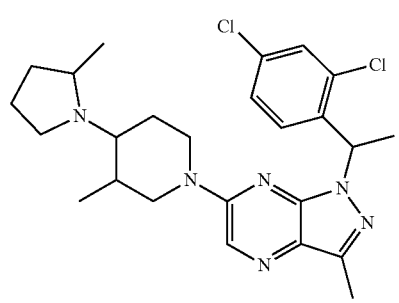
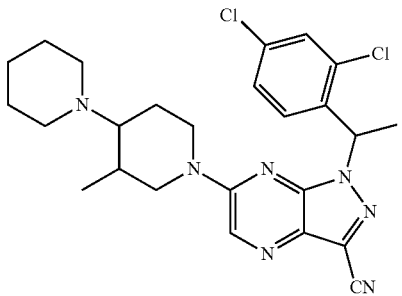
490
-continued
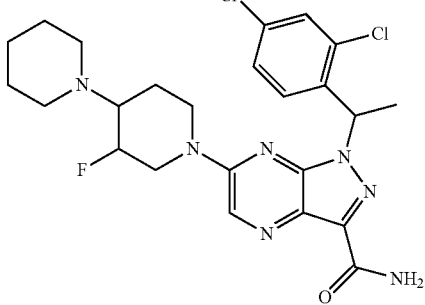
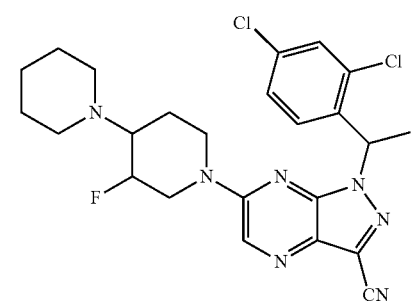
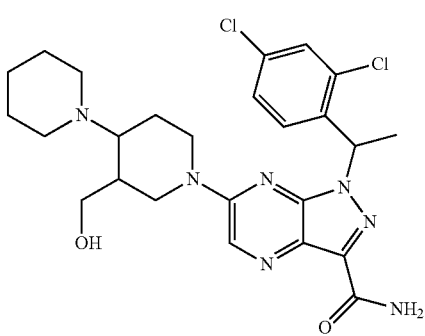
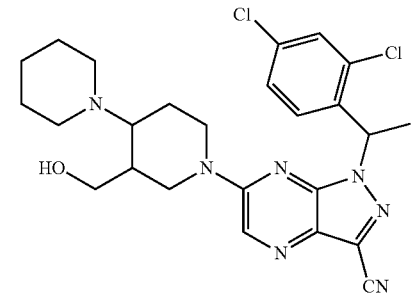
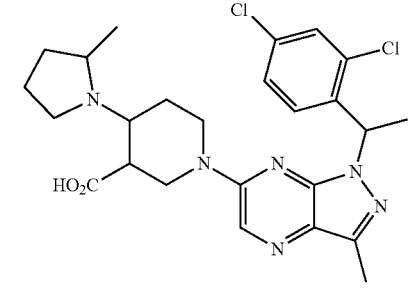

491
-continued
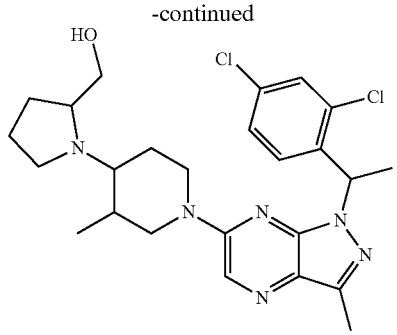
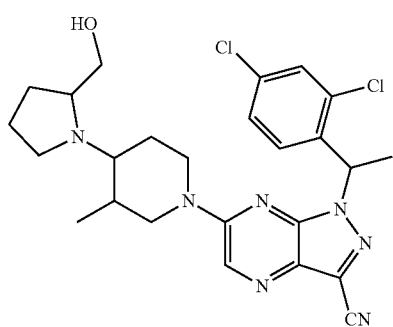
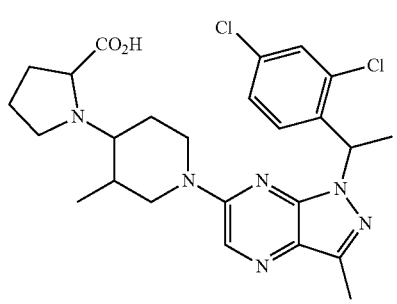
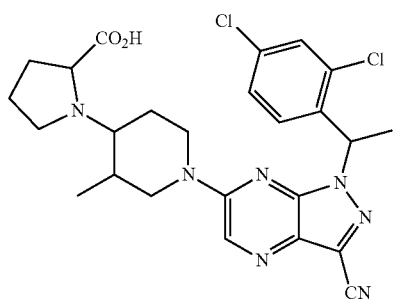
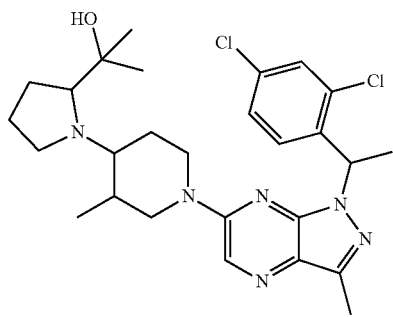
492
-continued
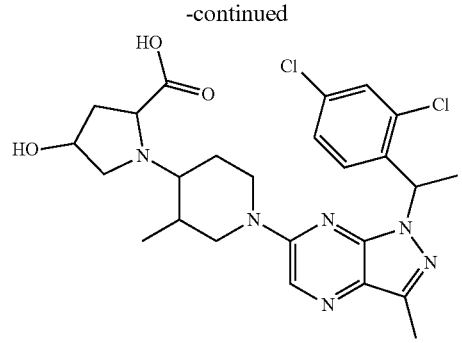
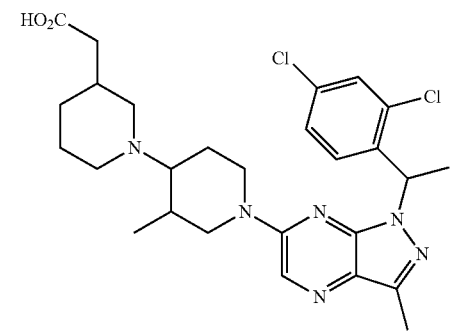
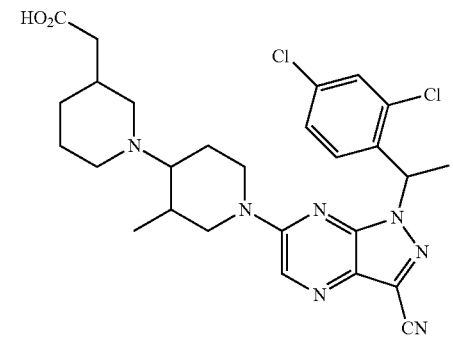
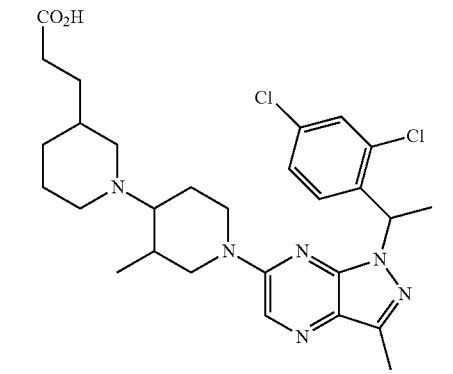
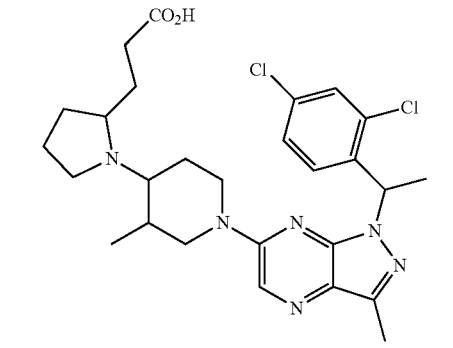

493
-continued
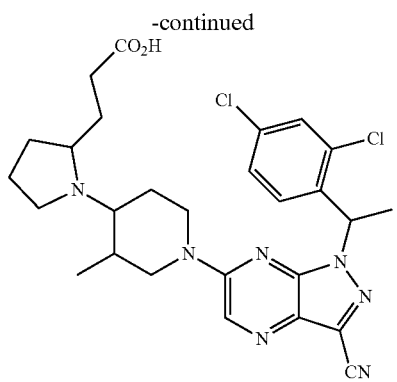
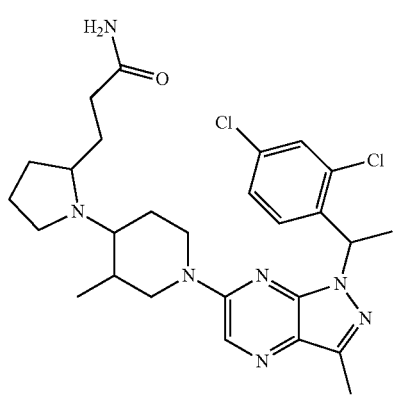
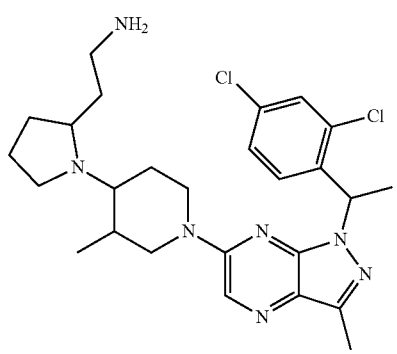
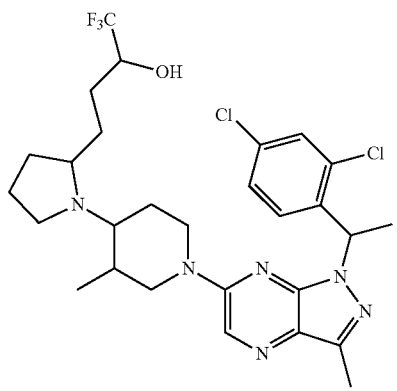
494
-continued
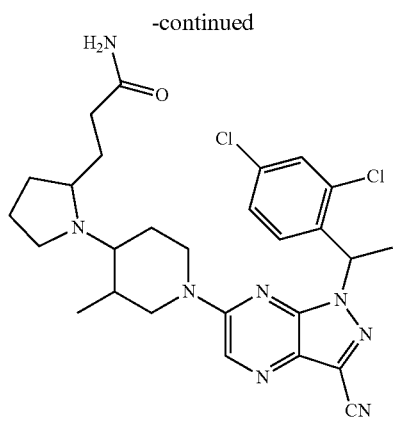
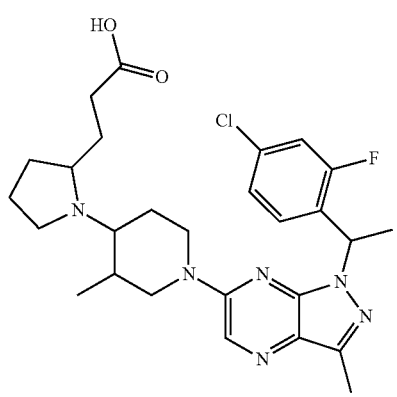
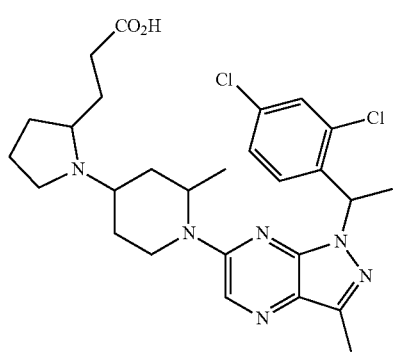
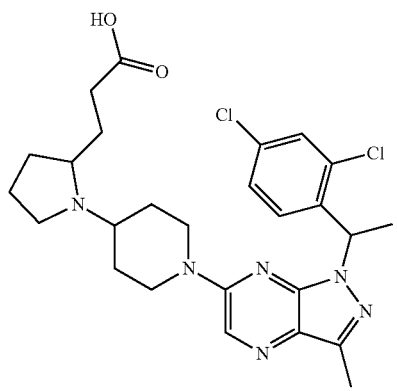

495
-continued
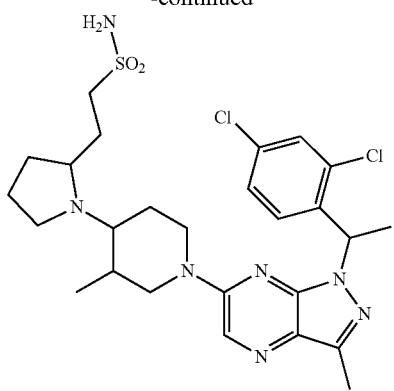
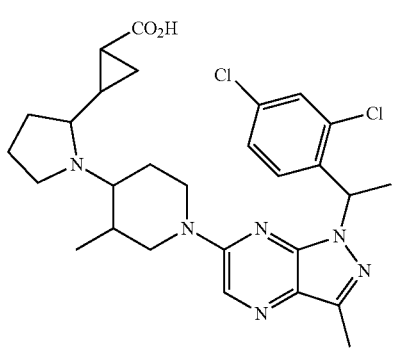
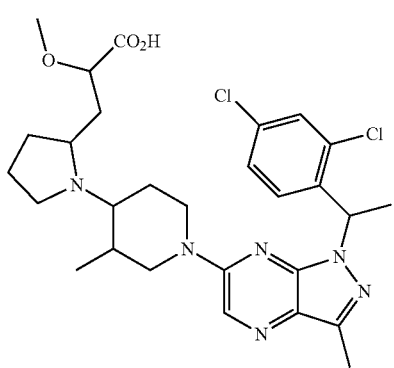
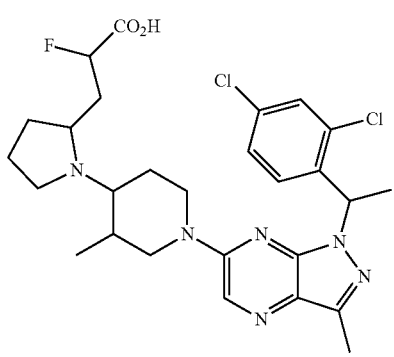
496
-continued
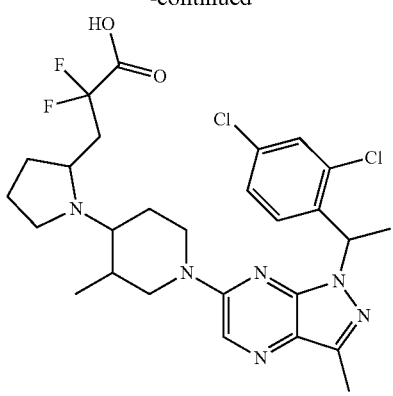
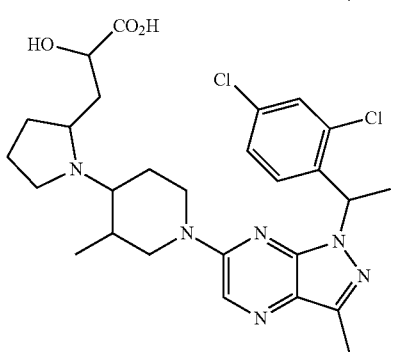
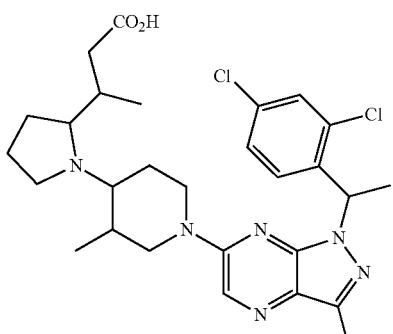
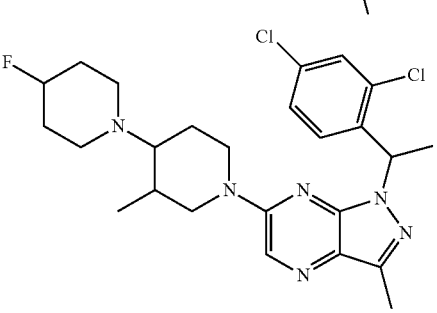
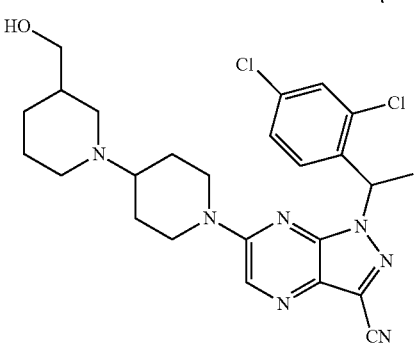

497
-continued
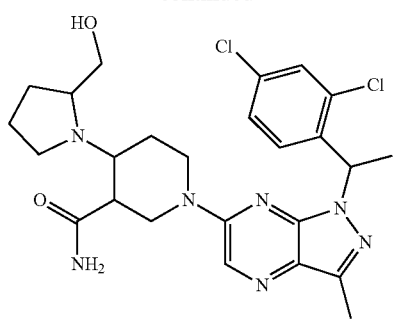
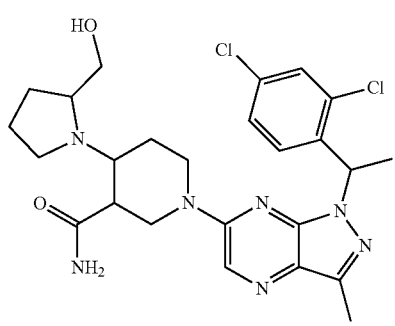
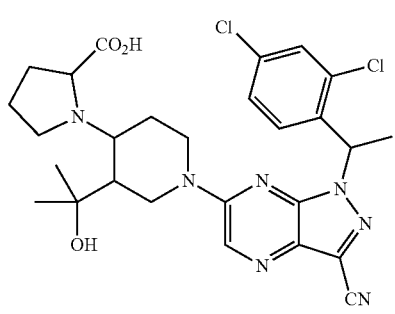
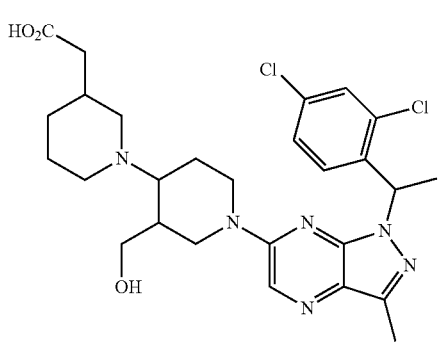
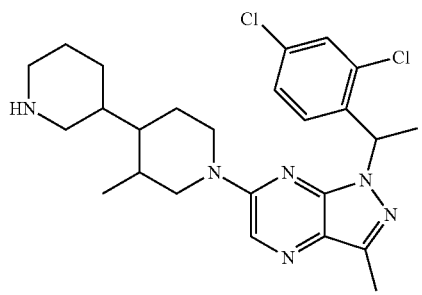
498
-continued
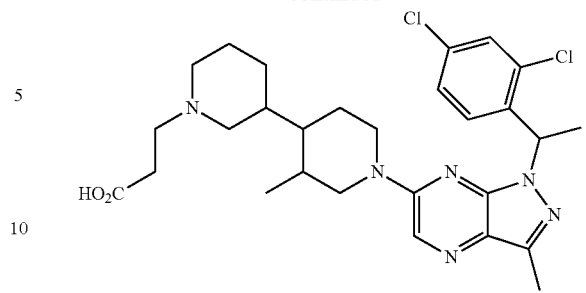
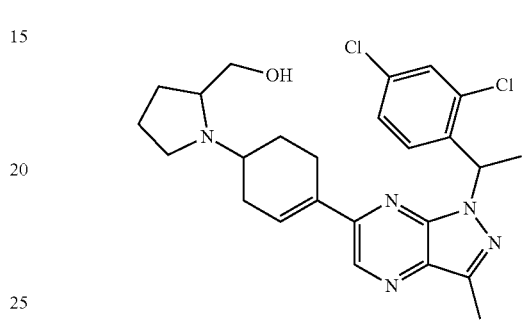
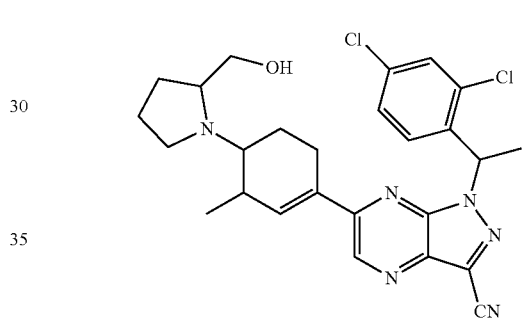
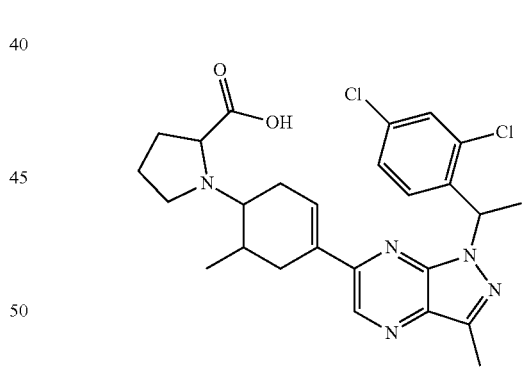
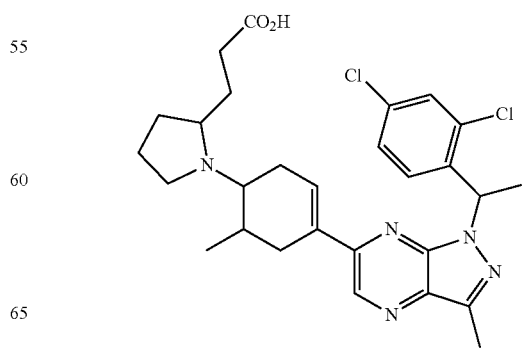

499
-continued
500
-continued
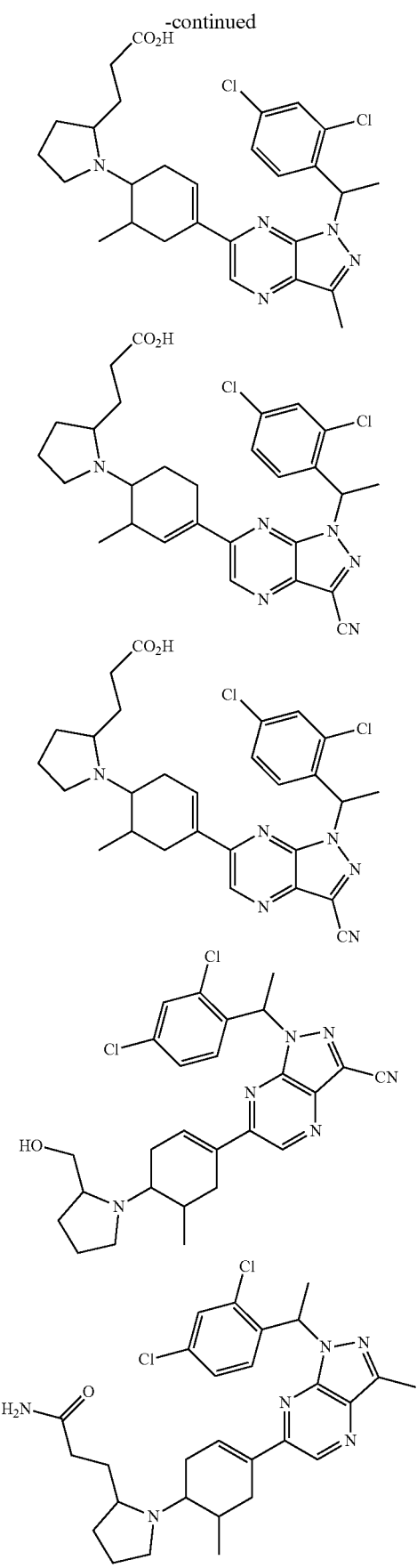
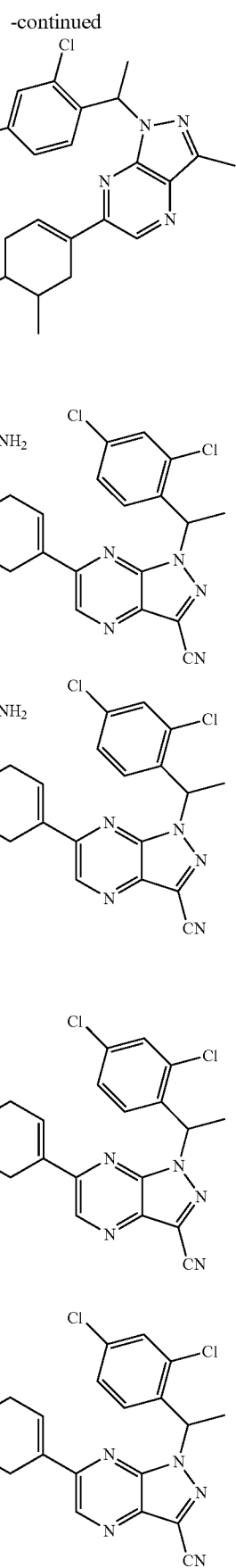

501
-continued

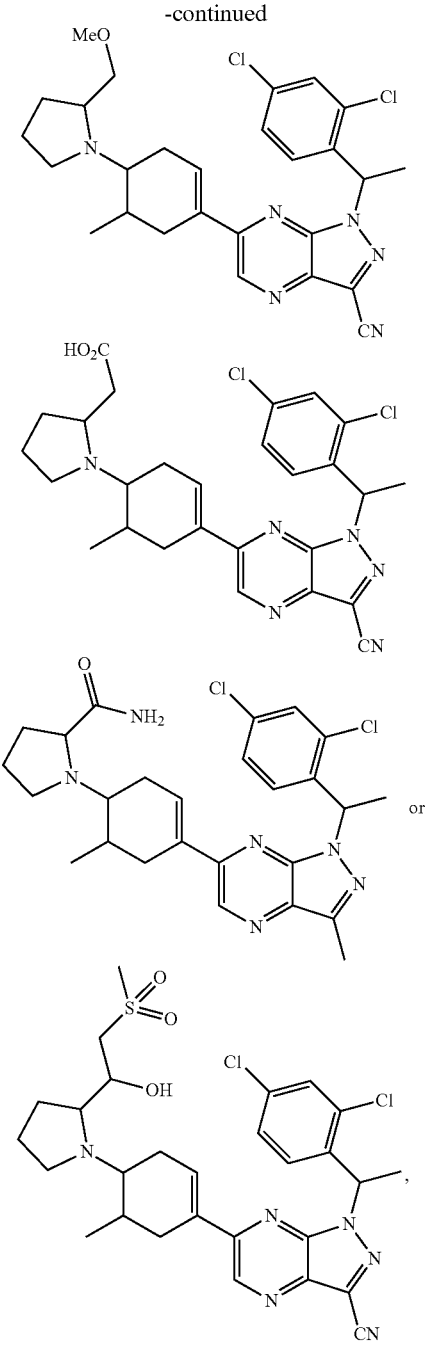

or a pharmaceutically acceptable salt thereof.

Embodiment PI74 A pharmaceutical composition, comprising a compound of embodiment PI1 and a pharmaceutically acceptable excipient.

Embodiment PI75 A method of inhibiting C—C chemokine receptor type 4 (CCR4), the method comprising contacting CCR4 with a compound of embodiment PI1.

Embodiment PI76 A method of treating or preventing a disease or disorder mediated by CCR4, comprising administering to a subject in need thereof a therapeutically effective amount of a compound of embodiment PI1 or a pharmaceutically acceptable salt thereof.

Embodiment PI77 The method of embodiment PI76, wherein the disease or disorder is an immune or inflammatory disease or disorder.

502

Embodiment PI78 The method of embodiment PI76, wherein the disease or disorder is a cardiovascular or metabolic disease or disorder.

Embodiment PI79 The method of embodiment PI76, wherein the disease or disorder is cancer.

PII EMBODIMENTS

Embodiment PII1 A compound having structural Formula (I):

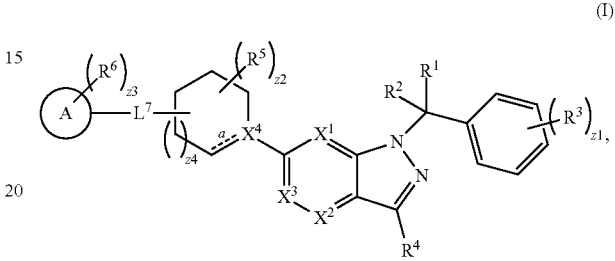

(I)

or a pharmaceutically acceptable salt thereof, wherein:
A is a substituted or unsubstituted heterocycloalkyl;
$X^1$ is $CR^8$ or N;
$X^2$ is $CR^9$ or N;
$X^3$ is $CR^{10}$ or N;
$X^4$ is C, $CR^{11}$ or N;
n1 is an integer from 0 to 4;
m1 and v1 are independently 1 or 2;
z1 is an integer from 0 to 5;
z2 is an integer from 0 to 13;
z3 is an integer from 0 to 12;
z4 is an integer from 0 to 3;
═ is a single bond or double bond, wherein if ═ is a single bond, then $X^4$ is $CR^{11}$ or N, and if ═ is a double bond, then $X^4$ is C;
$L^7$ is a bond, —O—, —S—, —$NR^{7B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —NHC(O)$NHNR^{1B}R^{1C}$, —NHC(O)$NR^{1B}R^{1C}$, —N(O)$_{m1}$, —$NR^{1B}R^{1C}$, —C(O)$R^{1D}$, —C(O)O$R^{1D}$, —C(O)$NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, halogen, —$CX^{2.1}_3$, —$CHX^{2.1}_2$, —$CH_2X^{2.1}$, —CN, —$SO_{n1}R^{2A}$, —$SO_{v1}NR^{2B}R^{2C}$, —$NHNR^{2B}R^{2C}$, —$ONR^{2B}R^{2C}$, —NHC(O)$NHNR^{2B}R^{2C}$, —NHC(O)$NR^{2B}R^{2C}$, —N(O)$_{m1}$, —$NR^{2B}R^{2C}$, —C(O)$R^{2D}$, —C(O)O$R^{2D}$, —C(O)$NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-CX^{3.1}{}_3$, $-CHX^{3.1}{}_2$, $-CH_2X^{3.1}$, $-CN$, $-SO_{n1}R^{3A}$, $-SO_{v1}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m1}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^{3.1}{}_3$, $-OCHX^{3.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, $-CX^{4.1}{}_3$, $-CHX^{4.1}{}_2$, $-CH_2X^{4.1}$, $-CN$, $-SO_{n1}R^{4A}$, $-SO_{v1}NR^{4B}R^{4C}$, $-NHNR^{4B}R^{4C}$, $-ONR^{4B}R^{4C}$, $-NHC(O)NHNR^{4B}R^{4C}$, $-NHC(O)NR^{4B}R^{4C}$, $-N(O)_{m1}$, $-NR^{4B}R^{4C}$, $-C(O)R^{4D}$, $-C(O)OR^{4D}$, $-C(O)NR^{4B}R^{4C}$, $-OR^{4A}$, $-NR^{4B}SO_2R^{4A}$, $-NR^{4B}C(O)R^{4D}$, $-NR^{4B}C(O)OR^{4D}$, $-NR^{4B}OR^{4D}$, $-OCX^{4.1}{}_3$, $-OCHX^{4.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is hydrogen, halogen, oxo, $-CX^{5.1}{}_3$, $-CHX^{5.1}{}_2$, $-CH_2{}^{5.1}$, $-CN$, $-SO_{n1}R^{5A}$, $-SO_{v1}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m1}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^{5.1}{}_3$, $-OCHX^{5.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is hydrogen, halogen, oxo, $-CX^{6.1}{}_3$, $-CHX^{6.1}{}_2$, $-CH_2X^{6.1}$, $-CN$, $-SO_{n1}R^{6A}$, $-SO_{v1}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m1}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}{}_3$, $-OCHX^{6.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^8$ is hydrogen, halogen, $-CX^{8.1}{}_3$, $-CHX^{8.1}{}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}{}_3$, $-OCHX^{8.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $-CX^{9.1}{}_3$, $-CHX^{9.1}{}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}{}_3$, $-OCHX^{9.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $-CX^{10.1}{}_3$, $-CHX^{10.1}{}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}{}_3$, $-OCHX^{10.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $-CX^{11.1}{}_3$, $-CHX^{11.1}{}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}{}_3$, $-OCHX^{11.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7B}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$ and $R^{11D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{8B}$ and $R^{8C}$, $R^{9B}$ and $R^{9C}$, $R^{10B}$ and $R^{10C}$, $R^{11B}$ and $R^{11C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$ are independently $-Cl$, $-Br$, $-I$ or $-F$, wherein at least one of $X^1$, $X^2$ and $X^3$ is N.

Embodiment PII2 The compound of embodiment PII, wherein the substituted or unsubstituted heterocycloalkyl is a 4-membered to 8-membered ring.

Embodiment PII3 The compound of embodiment PII1, wherein the compound has structural Formula (Ia):

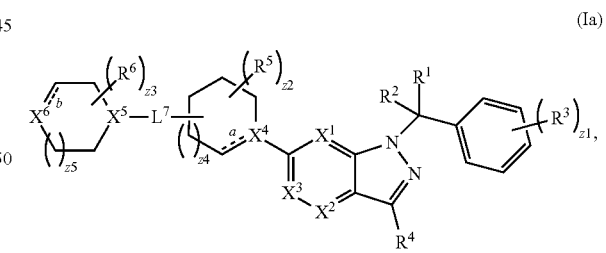

(Ia)

or a pharmaceutically acceptable salt thereof, wherein:
$X^5$ is $CR^{12}$ or N;
$X^6$ is $CR^{13}$, $CR^{13}R^{14}$, N or $NR^{15}$;
z3 is an integer from 0 to 12;
z5 is an integer from 0 to 3;
$R^{12}$ is hydrogen, halogen, $-CX^{12.1}{}_3$, $-CHX^{12.1}{}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}{}_3$, $-OCHX^{12.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_vNR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$ and $R^{15D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12B}$ and $R^{12C}$, $R^{13B}$ and $R^{13C}$, $R^{14B}$ and $R^{14C}$ and $R^{15B}$ and $R^{15C}$ substituents bonded to the same nitrogen atom may optionally be joined to form a substituted or unsubstituted heterocycloalkyl or substituted or unsubstituted heteroaryl;

⸺ is a single bond or double bond, wherein if ⸺ is a single bond, then $X^4$ is $CR^{13}R^{14}$ or $NR^{15}$, and if ⸺ is a double bond, then $X^4$ is N or $CR^{13}$; and $X^{12.1}$, $X^{13.1}$, $X^{14.1}$ and $X^{15.1}$ are independently $-Cl$, $-Br$, $-I$ or $-F$.

Embodiment PII4 The compound of embodiment PII1, wherein:
z1 is 2; and
z4 is 1.

Embodiment PII5 The compound of embodiment PII1, wherein $R^1$ and $R^2$ are independently hydrogen, substituted or unsubstituted alkyl or substituted or unsubstituted heteroalkyl.

Embodiment PII6 The compound of embodiment PII1, wherein $L^7$ is a bond.

Embodiment PII7 The compound of embodiment PII3, wherein the compound has structural Formula (II):

(II)

or a pharmaceutically acceptable salt thereof, wherein:
$R^4$ is hydrogen, $-CX^{4.1}_3$, $-CN$, $-C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.2}$ is hydrogen, halogen, $-CX^{3.2}_3$, $-CHX^{3.2}_2$, $-CH_2X^{3.2}$, $-CN$, $-SO_{n1}R^{3.2A}$, $-SO_{v1}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m1}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.3}$ is hydrogen, halogen, $-CX^{3.3}_3$, $-CHX^{3.3}_2$, $-CH_2X^{3.3}$, $-CN$, $-SO_{n1}R^{3.3A}$, $-SO_{v1}NR^{3.3B}R^{3.3C}$, $-NHNR^{3.3B}R^{3.3C}$, $-ONR^{3.3B}R^{3.3C}$, $-NHC(O)NHNR^{3.3B}R^{3.3C}$, $-NHC(O)NR^{3.3B}R^{3.3C}$, $-N(O)_{m1}$, $-NR^{3.3B}R^{3.3C}$, $-C(O)R^{3.3D}$, $-C(O)OR^{3.3D}$, $-C(O)NR^{3.3B}R^{3.3C}$, $-OR^{3.3A}$, $-NR^{3.3B}SO_2R^{3.3A}$, $-NR^{3.3B}C(O)R^{3.3D}$, $-NR^{3.3B}C(O)OR^{3.3D}$, $-NR^{3.3B}OR^{3.3D}$, $-OCX^{3.3}_3$, $-OCHX^{3.3}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.2A}$, $R^{3.2B}$, $R^{3.2C}$, $R^{3.2D}$, $R^{3.3A}$, $R^{3.3B}$, $R^{3.3C}$ and $R^{3.3D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.2B}$, $R^{3.2C}$, $R^{3.3B}$ and $R^{3.3C}$ substituents bonded to the same nitrogen atom may optionally be joined to form a substituted or unsubstituted heterocycloalkyl or substituted or unsubstituted heteroaryl; and $X^{3.2}$ and $X^{3.3}$ are independently $-Cl$, $-Br$, $-I$ or $-F$.

Embodiment PII8 The compound of embodiment PII3, wherein the compound has structural Formula (III):

(III)

or a pharmaceutically acceptable salt thereof.

Embodiment PII9 The compound of embodiment PII3, wherein the compound has structural Formula (IIIa):

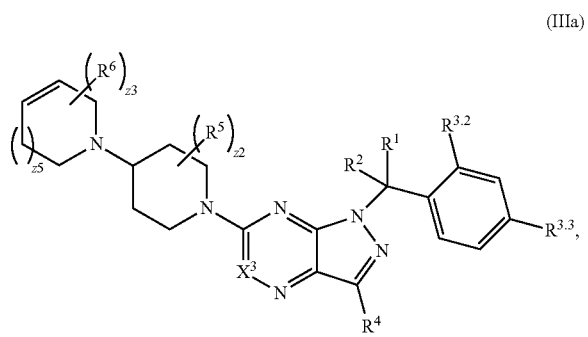

or a pharmaceutically acceptable salt thereof.

Embodiment PII10 The compound of embodiment PII3, wherein the compound has structural Formula (IIIb):

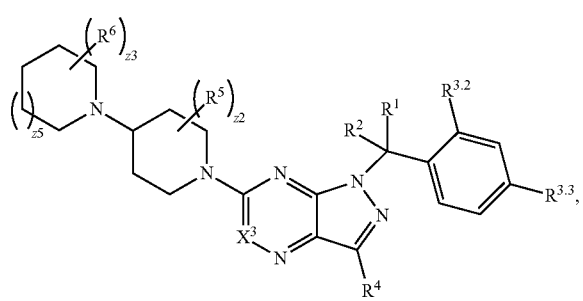

or a pharmaceutically acceptable salt thereof.

Embodiment PII11 The compound of embodiment PII3, wherein the compound has structural Formula (IV):

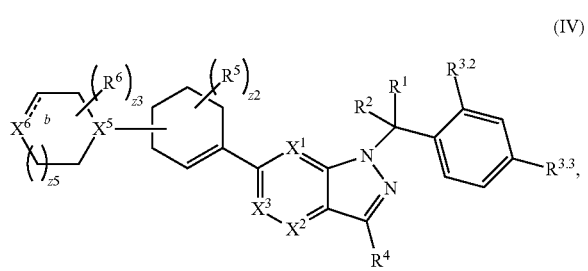

or a pharmaceutically acceptable salt thereof.

Embodiment PII12 The compound of embodiment PII3, wherein the compound has structural Formula (V):

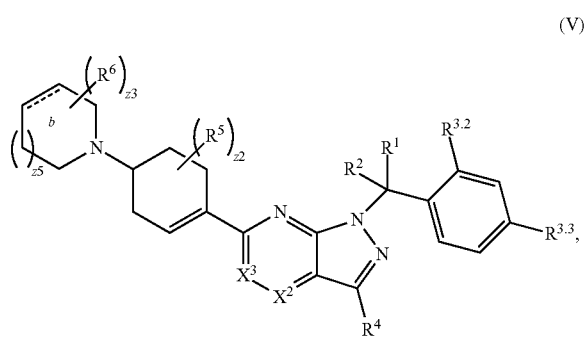

or a pharmaceutically acceptable salt thereof.

Embodiment PII13 The compound of embodiment PII3, wherein the compound has structural Formula (Va):

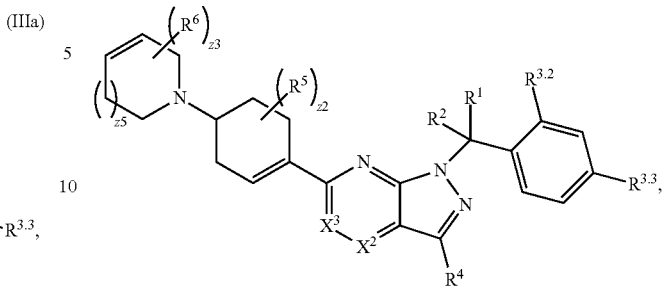

or a pharmaceutically acceptable salt thereof.

Embodiment PII14 The compound of embodiment PII3, wherein the compound has structural Formula (Vb):

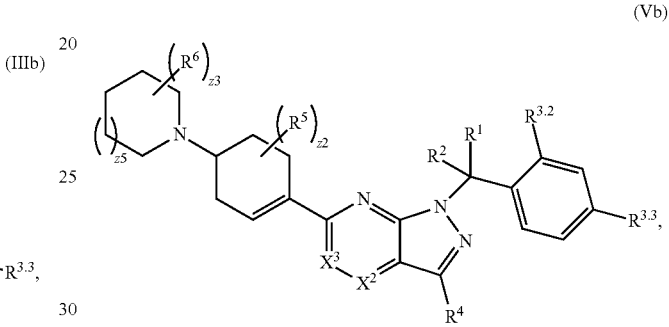

or a pharmaceutically acceptable salt thereof.

Embodiment PII15 The compound of any one of embodiments PII1 to PII14, wherein $R^4$ is hydrogen, —CN, —$CX^{4.1}_3$, —$C(O)R^{4D}$, —$C(O)OR^{4D}$, —$C(O)NR^{4B}R^{4C}$, substituted or unsubstituted alkyl or substituted or unsubstituted heteroalkyl.

Embodiment PII16 The compound of embodiment PII15, wherein $R^4$ is —CN, —$CF_3$, —$C(O)NH_2$, —$CH_3$ or —$C(CH_3)_2OH$.

Embodiment PII17 The compound of any one of embodiments PII7 to PII14, wherein $R^{3.2}$ and $R^{3.3}$ are independently halogen, —CN, $CF_3$ or unsubstituted alkyl.

Embodiment PII18 The compound of embodiment PII17, wherein the halogen is chlorine or fluorine.

Embodiment PII19 The compound of embodiment PII17, wherein the unsubstituted alkyl is —$CH_3$.

Embodiment PII20 The compound of any one of embodiments PII1 to PII14, wherein $R^1$ and $R^2$ are independently hydrogen or unsubstituted alkyl.

Embodiment PII21 The compound of embodiment PII20, wherein $R^1$ is —$CH_3$ or —$CH_2CH_3$.

Embodiment PII22 The compound of embodiment PII20, wherein $R^2$ is —$CH_3$ or —$CH_2CH_3$.

Embodiment PII23 The compound of any one of embodiments PII1 to PII14, wherein $R^1$ is hydrogen.

Embodiment PII24 The compound of any one of embodiments PII1 to PII14, wherein $R^2$ is hydrogen.

Embodiment PII25 The compound of any one of embodiments PII1 to PII14, wherein $X^2$ is N.

Embodiment PII26 The compound of any one of embodiments PII1 to PII14, wherein $X^3$ is N.

Embodiment PII27 The compound of any one of embodiments PII1 to PII14, wherein z2 and z3 are independently an integer from 0 to 2.

Embodiment PII28 The compound of any one of embodiments PII1 to PII14, wherein $R^5$ is hydrogen, fluorine, —CN, —$CH_3$, —$CF_3$, —$(CH_2)_2OH$, —$CO_2NH_2$ or —$CO_2CH_2CH_3$.

Embodiment PII29 The compound of any one of embodiments PII1 to PII14, wherein $R^6$ is hydrogen, —OH, —CH$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H,

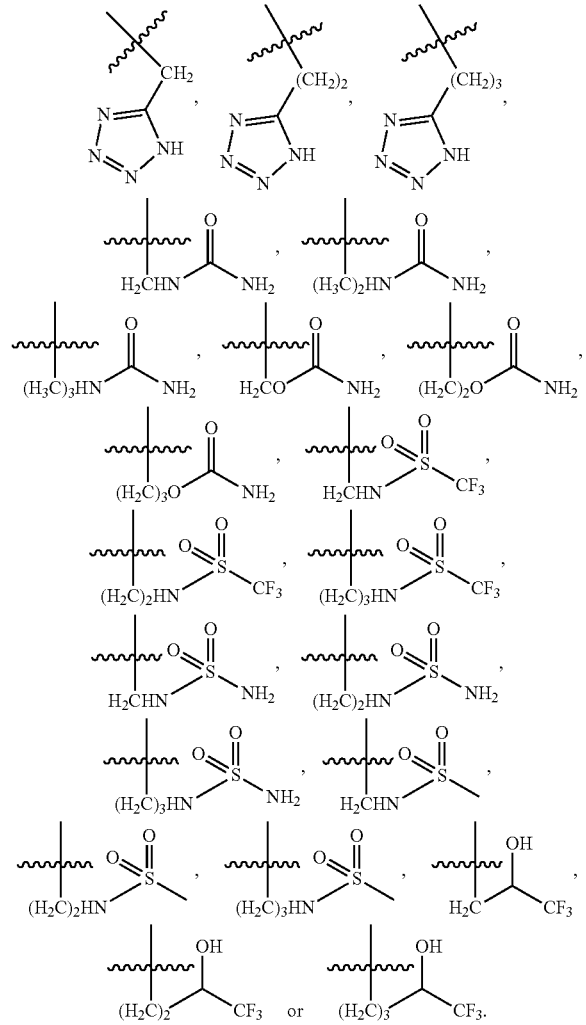

Embodiment PII30 The compound of embodiment PII3, wherein the compound has structural Formula (VI):

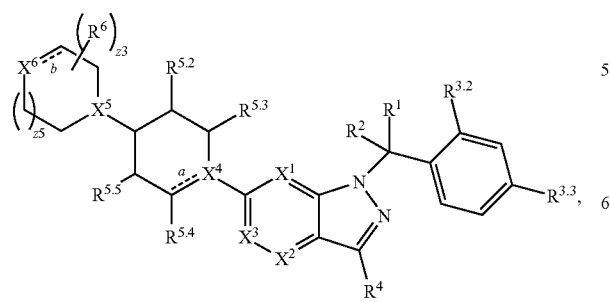

(VI)

or a pharmaceutically acceptable salt thereof, wherein:
$R^{5.2}$ is hydrogen, halogen, —CX$^{5.6}_3$, —CHX$^{5.6}_2$, —CH$_2$X$^{5.6}$, —CN, —SO$_{n1}$R$^{5.6A}$, SO$_{v1}$NR$^{5.6B}$R$^{5.6C}$, —NHNR$^{5.6B}$R$^{5.6C}$, —ONR$^{5.6B}$R$^{5.6C}$, —NHC(O)NHNR$^{5.6B}$R$^{5.6C}$, —NHC(O)NR$^{5.6B}$R$^{5.6C}$, —N(O)$_{m1}$, —NR$^{5.6B}$R$^{5.6C}$, —C(O)R$^{5.6D}$, —C(O)OR$^{5.6D}$, —C(O)NR$^{5.6B}$R$^{5.6C}$, OR$^{5.6A}$, —NR$^{5.6B}$SO$_2$R$^{5.6A}$, —NR$^{5.6B}$C(O)R$^{5.6D}$, —NR$^{5.6B}$C(O)OR$^{5.6D}$, —NR$^{5.6B}$OR$^{5.6D}$, —OCX$^{5.6}_3$, —OCHX$^{5.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5.3}$ is hydrogen, halogen, —CX$^{5.7}_3$, —CHX$^{5.7}_2$, —CH$_2$X$^{5.7}$, —CN, —SO$_{n1}$R$^{5.7A}$, —SO$_{v1}$NR$^{5.7B}$R$^{5.7C}$, —NHNR$^{5.7B}$R$^{5.7C}$, —ONR$^{5.7B}$R$^{5.7C}$, —NHC(O)NHNR$^{5.7B}$R$^{5.7C}$, —NHC(O)NR$^{5.7B}$R$^{5.7C}$, —N(O)$_{m1}$, —NR$^{5.7B}$R$^{5.7C}$, —C(O)R$^{5.7D}$, —C(O)OR$^{5.7D}$, —C(O)NR$^{5.7B}$R$^{5.7}$, —OR$^{5.7A}$, —NR$^{5.7B}$SO$_2$R$^{5.7A}$, —NR$^{5.7B}$C(O)R$^{5.7D}$, —NR$^{5.7B}$C(O)OR$^{5.7D}$, —NR$^{5.7B}$OR$^{5.7D}$, —OCX$^{5.7}_3$, —OCHX$^{5.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5.4}$ is hydrogen, halogen, —CX$^{5.8}_3$, —CHX$^{5.8}_2$, —CH$_2$X$^{5.8}$, —CN, —SO$_{n1}$R$^{5.8A}$, —SO$_{v1}$NR$^{5.8B}$R$^{5.8C}$, —NHNR$^{5.8B}$R$^{5.8C}$, —ONR$^{5.8B}$R$^{5.8C}$, —NHC(O)NHNR$^{5.8B}$R$^{5.8C}$, —NHC(O)NR$^{5.8B}$R$^{5.8C}$, —N(O)$_{m1}$, —NR$^{5.8B}$R$^{5.8C}$, —C(O)R$^{5.8D}$, —C(O)OR$^{5.8D}$, —C(O)NR$^{5.8B}$R$^{5.8C}$, OR$^{5.8A}$, —NR$^{5.8B}$SO$_2$R$^{5.8A}$, —NR$^{5.8B}$C(O)R$^{5.8D}$, —NR$^{5.8B}$C(O)OR$^{5.8D}$, —NR$^{5.8B}$OR$^{5.8D}$, —OCX$^{5.8}_3$, —OCHX$^{5.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5.5}$ is hydrogen, halogen, —CX$^{5.9}_3$, —CHX$^{5.9}_2$, —CH$_2$X$^{5.9}$, —CN, —SO$_{n1}$R$^{5.9A}$, —SO$_{v1}$NR$^{5.9B}$R$^{5.9C}$, —NHNR$^{5.9B}$R$^{5.9C}$, —ONR$^{5.9B}$R$^{5.9C}$, —NHC(O)NHNR$^{5.9B}$R$^{5.9C}$, —NHC(O)NR$^{5.9B}$R$^{5.9C}$, —N(O)$_{m1}$, —NR$^{5.9B}$R$^{5.9C}$, —C(O)R$^{5.9D}$, —C(O)OR$^{5.9D}$, —C(O)NR$^{5.9B}$R$^{5.9C}$, —OR$^{5.9A}$, —NR$^{5.9B}$SO$_2$R$^{5.9A}$, —NR$^{5.9B}$C(O)R$^{5.9D}$, —NR$^{5.9B}$C(O)OR$^{5.9D}$, —NR$^{5.9B}$OR$^{5.9D}$, —OCX$^{5.9}_3$, —OCHX$^{5.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5.6A}$, $R^{5.6B}$, $R^{5.6C}$, $R^{5.6D}$, $R^{5.7A}$, $R^{5.7B}$, $R^{5.7C}$, $R^{5.7D}$, $R^{5.8A}$, $R^{5.8B}$, $R^{5.8C}$, $R^{5.8D}$, $R^{5.9A}$, $R^{5.9B}$, $R^{5.9C}$ and $R^{5.9D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5.6B}$ and $R^{5.6C}$, $R^{5.7B}$ and $R^{5.7C}$, $R^{5.8B}$ and $R^{5.8C}$, $R^{5.9B}$ and $R^{5.9C}$ substituents bonded to the same nitrogen atom may optionally be joined to form a substituted or unsubstituted heterocycloalkyl or substituted or unsubstituted heteroaryl; and $X^{5.6}$, $X^{5.7}$, $X^{5.8}$ and $X^{5.9}$ are independently —Cl, —Br, —I or —F.

Embodiment PII31 The compound of embodiment PII30, wherein the compound has structural Formula (VII):

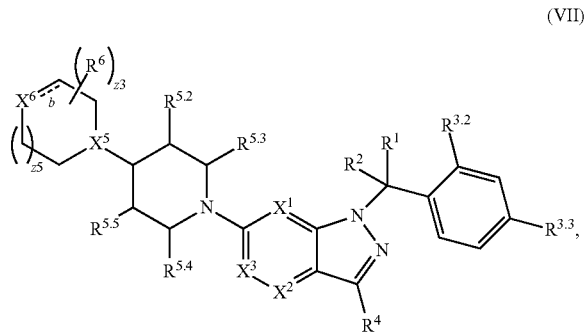

(VII)

or a pharmaceutically acceptable salt thereof.

Embodiment PII32 The compound of embodiment PII30, wherein the compound has structural Formula (VIIa):

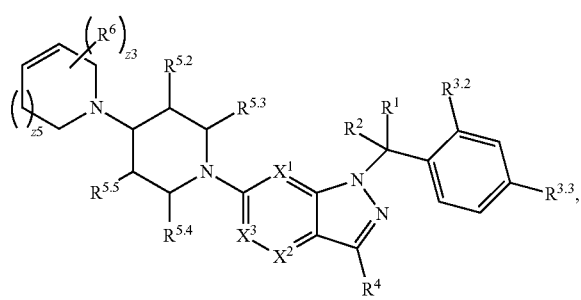

(VIIa)

or a pharmaceutically acceptable salt thereof.

Embodiment PII33 The compound of embodiment PII30, wherein the compound has structural Formula (VIIb):

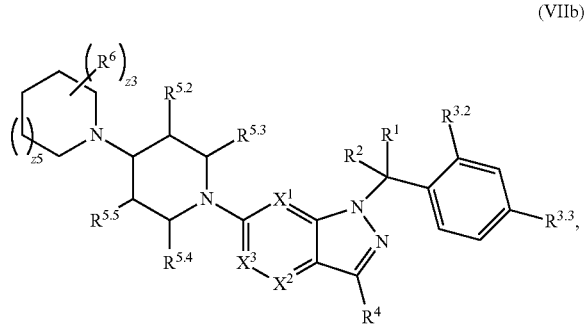

(VIIb)

or a pharmaceutically acceptable salt thereof.

Embodiment PII34 The compound of embodiment PII30, wherein the compound has structural Formula (VIII):

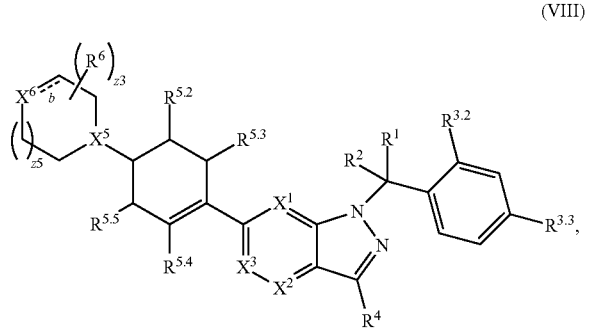

(VIII)

or a pharmaceutically acceptable salt thereof.

Embodiment PII35 The compound of embodiment PII34, wherein the compound has structural Formula (VIIIa):

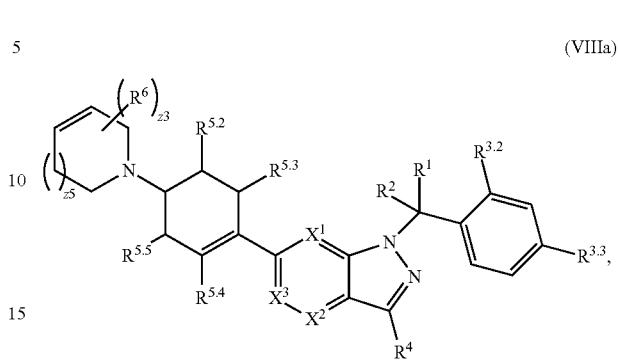

(VIIIa)

or a pharmaceutically acceptable salt thereof.

Embodiment PII36 The compound of embodiment PII34, wherein the compound has structural Formula (VIIIb):

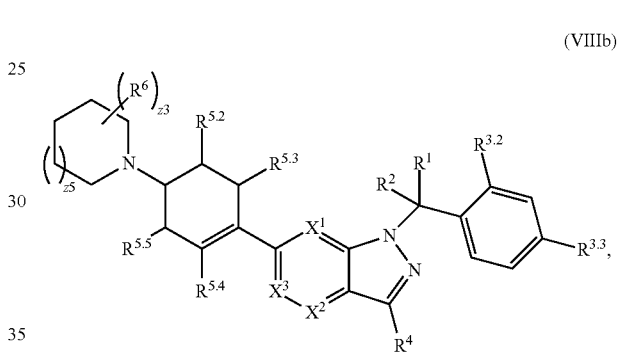

(VIIIb)

or a pharmaceutically acceptable salt thereof.

Embodiment PII37 The compound of any one of embodiments PII30 to PII36, wherein $X^1$ and $X^3$ are independently N.

Embodiment PII38 The compound of any one of embodiments PII30 to PII36, wherein $X^1$ and $X^2$ are independently N.

Embodiment PII39 The compound of any one of embodiments PII30 to PII36, wherein $R^4$ is —CN, —C(O)NH$_2$, —CF$_3$, —CH$_3$ or —C(CH$_3$)$_2$OH.

Embodiment PII40 The compound of any one of embodiments PII30 to PII36, wherein $R^{3.2}$ and $R^{3.3}$ are independently halogen, —CN, CF$_3$ or unsubstituted alkyl.

Embodiment PII41 The compound of embodiment PII40, wherein the halogen is chlorine or fluorine.

Embodiment PII42 The compound of embodiment PII40, wherein the unsubstituted alkyl is —CH$_3$.

Embodiment PII43 The compound of any one of embodiments PII30 to PII36, wherein $R^1$ and $R^2$ are independently hydrogen or unsubstituted alkyl.

Embodiment PII44 The compound of embodiment PII43, wherein $R^1$ is —CH$_3$ or —CH$_2$CH$_3$.

Embodiment PII45 The compound of embodiment PII43, wherein $R^2$ is —CH$_3$ or —CH$_2$CH$_3$.

Embodiment PII46 The compound of any one of embodiments PII30 to PII36, wherein $R^1$ is hydrogen.

Embodiment PII47 The compound of any one of embodiments PII30 to PII36, wherein $R^2$ is hydrogen.

Embodiment PII48 The compound of any one of embodiments PII30 to PII36, wherein z3 is an integer from 0 to 2.

Embodiment PII49 The compound of any one of embodiments PII30 to PII36, wherein $R^5$ is hydrogen, fluorine, —CN, —$CH_3$, —$CF_3$, —$(CH_2)_2OH$, —$CO_2NH_2$ or —$CO_2CH_2CH_3$.

Embodiment PII50 The compound of any one of embodiments PII30 to PII36, wherein $R^6$ is hydrogen, —OH, —$CH_3$, —$CH_2OH$, —$(CH_2)_2OH$, —$(CH_2)_3OH$, —$CH_2NH_2$, —$(CH_2)_2NH_2$, —$(CH_2)_3NH_2$, —$CH_2CO_2CH_2CH_3$, —$(CH_2)_2CO_2CH_2CH_3$, —$(CH_2)_3CO_2CH_2CH_3$, —$CH_2CO_2H$, —$(CH_2)_2CO_2H$, —$(CH_2)_3CO_2H$, —$(CH_2)CO_2NH_2$, —$(CH_2)_2CONH_2$, —$(CH_2)_3CO_2NH_2$, —$(CH_2)CHFCO_2H$, —$(CH_2)_2CHFCO_2H$, —$(CH_2)CF_2CO_2H$, —$(CH_2)_2CF_2CO_2H$,

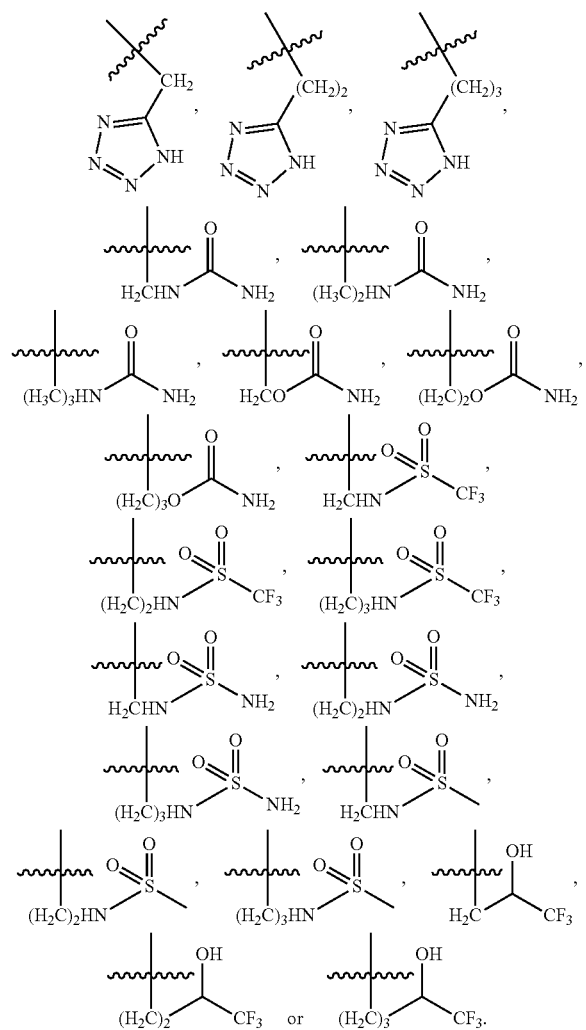

Embodiment PII51 The compound of any one of embodiments PII30 to PII36, wherein z5 is 1.

Embodiment PII52 The compound of any one of embodiments PII30 to PII36, wherein z5 is 0.

Embodiment PII53 The compound of embodiment PII36, wherein z3 and z5 are independently 1.

Embodiment PII54 The compound of embodiment PII36, wherein $R^6$ is halogen, substituted or unsubstituted alkyl or substituted or unsubstituted heteroalkyl.

Embodiment PII55 The compound of embodiment PII30, wherein the compound has structural Formula (IX):

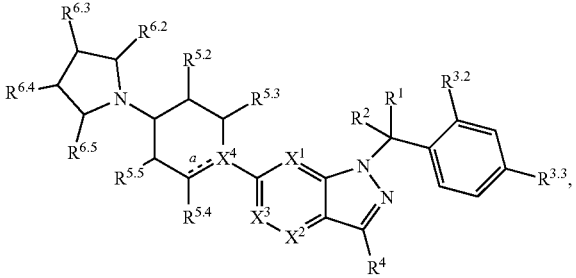

(IX)

or a pharmaceutically acceptable salt thereof, wherein:

$R^{6.2}$ is hydrogen, halogen, —$CX^{6.6}_3$, —$CHX^{6.6}_2$, —$CH_2X^{6.6}$, —CN, —$SO_{n1}R^{6.6A}$, —$SO_{v1}NR^{6.6B}R^{6.6C}$, —$NHNR^{6.6B}R^{6.6C}$, —$ONR^{6.6B}R^{6.6C}$, NHC(O)NHNR$^{6.6B}R^{6.6C}$, NHC(O)NR$^{6.6B}R^{6.6C}$, —$N(O)_{m1}$, —$NR^{6.6B}R^{6.6C}$=c, —$C(O)R^{6.6D}$, —$C(O)OR^{6.6D}$, —$C(O)NR^{6.6B}R^{6.6C}$, —$OR^{6.6A}$, —$NR^{6.6B}SO_2R^{6.6A}$, —$NR^{6.6B}C(O)R^{6.6D}$, —$NR^{6.6B}C(O)OR^{6.6D}$, —$NR^{6.6B}OR^{6.6D}$, —$OCX^{6.6}_3$, —$OCHX^{6.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6.3}$ is hydrogen, halogen, —$CX^{6.7}_3$, —$CHX^{6.7}_2$, —$CH_2X^{6.7}$, —CN, —$SO_{n1}R^{6.7A}$, —$SO_{v1}NR^{6.7B}R^{6.7C}$, —$NHNR^{6.7B}R^{6.7C}$, —$ONR^{6.7B}R^{6.7C}$, NHC(O)NHNR$^{6.7B}R^{6.7C}$, NHC(O)NR$^{6.7B}R^{6.7C}$, —$N(O)_{m1}$, —$NR^{6.7B}R^{6.7C}$, —$C(O)R^{6.7D}$, —$C(O)OR^{6.7D}$, —$C(O)NR^{6.7B}R^{6.7C}$, $OR^{6.7A}$, —$NR^{6.7B}SO_2R^{6.7A}$, —$NR^{6.7B}C(O)R^{6.7D}$, —$NR^{6.7B}C(O)OR^{6.7D}$, —$NR^{6.7B}OR^{6.7D}$, —$OCX^{6.7}_3$, —$OCHX^{6.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6.4}$ is hydrogen, halogen, —$CX^{6.8}_3$, —$CHX^{6.8}_2$, —$CH_2X^{6.8}$, —CN, —$SO_{n1}R^{6.8A}$, —$SO_{v1}NR^{6.8B}R^{6.8C}$, —$NHNR^{6.8B}R^{6.8C}$, —$ONR^{6.8B}R^{6.8C}$, —NHC(O)NHNR$^{6.8B}R^{6.8C}$, —NHC(O)NR$^{6.8B}R^{6.8C}$, —$N(O)_{m1}$, —$NR^{6.8B}R^{6.8C}$, —$C(O)R^{6.8D}$, —$C(O)OR^{6.8D}$, —$C(O)NR^{6.8B}R^{6.8C}$, $OR^{6.8A}$, —$NR^{6.8B}SO_2R^{6.8A}$, —$NR^{6.8B}C(O)R^{6.8D}$, —$NR^{6.8B}C(O)OR^{6.8D}$, —$NR^{6.8B}OR^{6.8D}$, —$OCX^{6.8}_3$, —$OCHX^{6.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6.5}$ is hydrogen, halogen, —$CX^{6.9}_3$, —$CHX^{6.9}_2$, —$CH_2X^{6.9}$, —CN, —$SO_{n1}R^{6.9A}$, —$SO_{v1}NR^{6.9B}R^{6.9C}$, —$NHNR^{6.9B}R^{6.9C}$, —$ONR^{6.9B}R^{6.9C}$, NHC(O)NHNR$^{6.9B}R^{6.9C}$, NHC(O)NR$^{6.9B}R^{6.9C}$, —$N(O)_{m1}$, —$NR^{6.9B}R^{6.9C}$, —$C(O)R^{6.9D}$, —$C(O)OR^{6.9D}$, —$C(O)NR^{6.9B}R^{6.9C}$, —$OR^{6.9A}$, —$NR^{6.9B}SO_2R^{6.9A}$, —$NR^{6.9B}C(O)R^{6.9D}$, —$NR^{6.9B}C(O)OR^{6.9D}$, —$NR^{6.9B}OR^{6.9D}$, —$OCX^{6.9}_3$, —$OCHX^{6.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{6.6A}$, $R^{6.6B}$, $R^{6.6C}$, $R^{6.6D}$, $R^{6.7A}$, $R^{6.7B}$, $R^{6.7C}$, $R^{6.7D}$, $R^{6.8A}$, $R^{6.8B}$, $R^{6.8C}$, $R^{6.8D}$, $R^{6.9A}$, $R^{6.9B}$, $R^{6.9C}$ and $R^{6.9D}$ are independently hydrogen, halogen, —$CF_3$, —$CCl_3$, —$CBr_3$, —Cl$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{6.6B}$ and R$^{6.6C}$, R$^{6.7B}$ and R$^{6.7C}$, R$^{6.8B}$ and R$^{6.8C}$, R$^{6.9B}$ and R$^{6.9C}$ substituents bonded to the same nitrogen atom may optionally be joined to form a substituted or unsubstituted heterocycloalkyl or substituted or unsubstituted heteroaryl; and X$^{6.6}$, X$^{6.7}$, X$^{6.8}$ and X$^{6.9}$ are independently —Cl, —Br, —I or —F.

Embodiment PII56

The compound of embodiment PII55, wherein the compound has structural Formula (IXa):

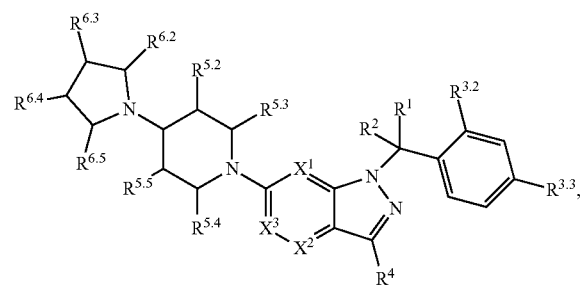

(IXa)

or a pharmaceutically acceptable salt thereof.

Embodiment PII57 The compound of embodiment PII56, wherein X$^1$ and X$^2$ are independently N.

Embodiment PII58 The compound of embodiment PII56, wherein R$^1$ and R$^2$ are independently hydrogen or unsubstituted alkyl.

Embodiment PII59 The compound of embodiment PII56, wherein R$^{3.2}$ and R$^{3.3}$ are independently halogen, —CN, CF$_3$ or unsubstituted alkyl.

Embodiment PII60 The compound of embodiment PII56, wherein R$^4$ is —CN, —C(O)NH$_2$, —CF$_3$, —CH$_3$ or —C(CH$_3$)$_2$OH.

Embodiment PII61 The compound of embodiment PII56, wherein R$^{5.4}$ and R$^{5.5}$ are independently hydrogen, fluorine, —CN, —CH$_3$, —CH$_2$CH$_3$, —CF$_3$, —(CH$_2$)OH, —(CH$_2$)$_2$OH, —(CH$_3$)$_2$OH, —CO$_2$H, —CO$_2$NH$_2$ or —CO$_2$CH$_2$CH$_3$.

Embodiment PII62 The compound of embodiment PII56, wherein R$^{6.2}$ is hydrogen, —CH$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H,

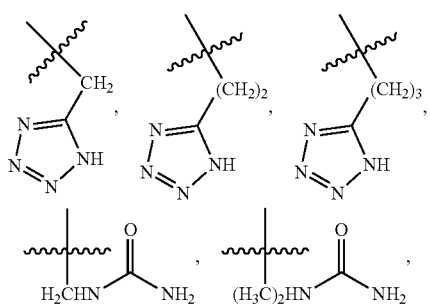

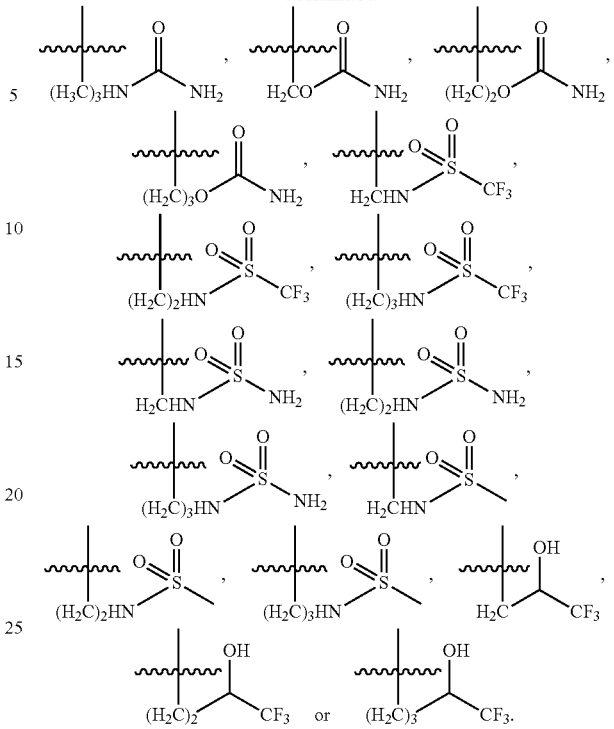

Embodiment PII63 The compound of embodiment PII55, wherein the compound has structural Formula (IXb):

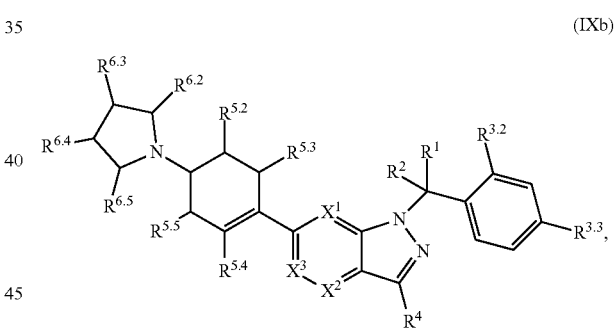

(IXb)

or a pharmaceutically acceptable salt thereof.

Embodiment PII64 The compound of embodiment PII63, wherein X$^1$ and X$^2$ are independently N.

Embodiment PII65 The compound of embodiment PII63, wherein R$^1$ and R$^2$ are independently hydrogen or unsubstituted alkyl.

Embodiment PII66 The compound of embodiment PII63, wherein R$^{3.2}$ and R$^{3.3}$ are independently halogen, —CN, CF$_3$ or unsubstituted alkyl.

Embodiment PII67 The compound of embodiment PII63, wherein R$^4$ is —CN, —C(O)NH$_2$, —CF$_3$, —CH$_3$ or —C(CH$_3$)$_2$OH.

Embodiment PII68 The compound of embodiment PII63, wherein R$^{5.2}$ and R$^{5.5}$ are independently hydrogen, fluorine, —CN, —CH$_3$, —CH$_2$CH$_3$, —CF$_3$, —(CH$_2$)OH, —(CH$_2$)$_2$OH, —(CH$_3$)$_2$OH, —CO$_2$H, —CO$_2$NH$_2$ or —CO$_2$CH$_2$CH$_3$.

Embodiment PII69 The compound of embodiment PII63, wherein R$^{6.2}$ is hydrogen, —OH, —CH$_3$, —CH$_2$OH, —(CH$_2$)$_2$OH, —(CH$_2$)$_3$OH, —CH$_2$NH$_2$, —(CH$_2$)$_2$NH$_2$,

517

—(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H,

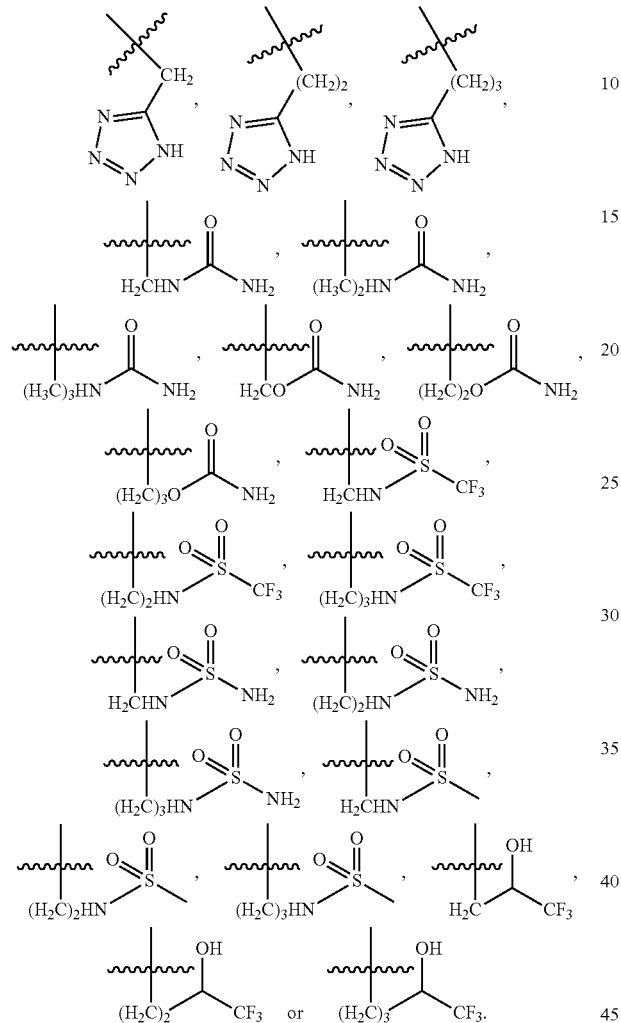

Embodiment PII70 The compound of embodiment PII3, wherein the compound has structural Formula (X):

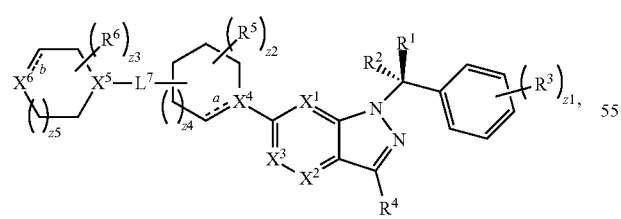

or a pharmaceutically acceptable salt thereof.

Embodiment PII71 The compound of embodiment PII70, wherein R$^1$ is hydrogen.

Embodiment PII72 The compound of embodiment PII70, wherein R$^2$ is hydrogen.

Embodiment PII73 The compound of embodiment PII1, wherein the compound is:

518

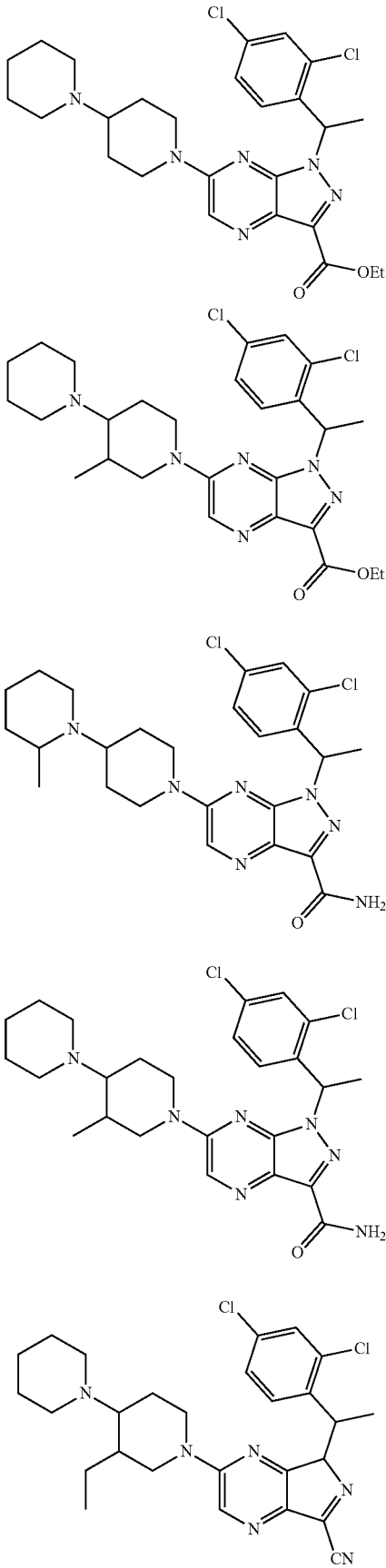

519
-continued
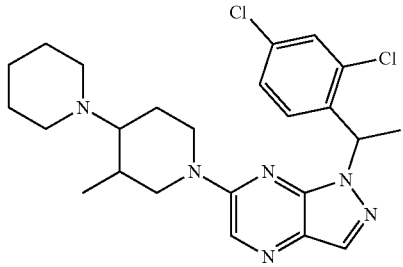
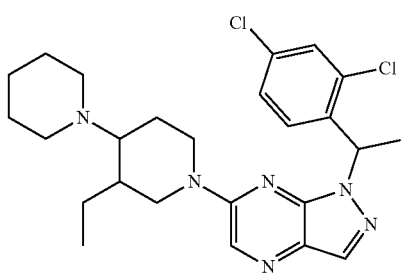
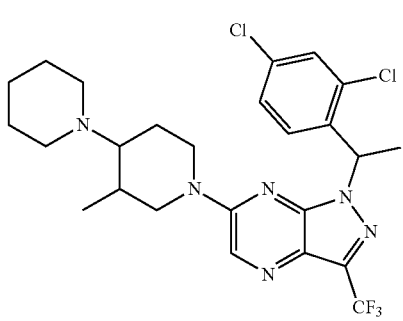
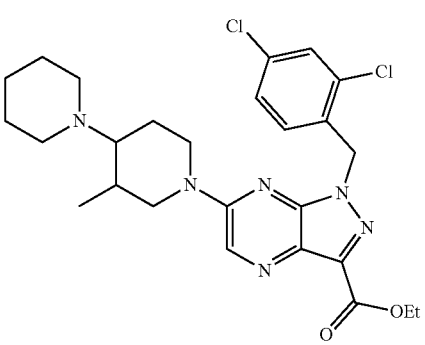
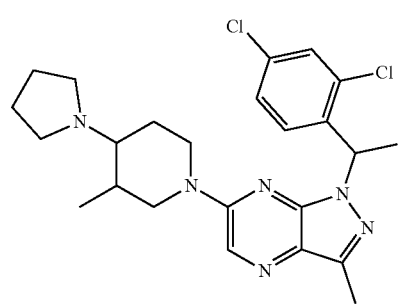
520
-continued
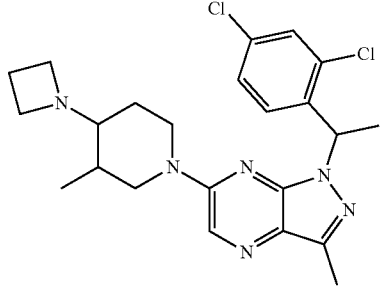
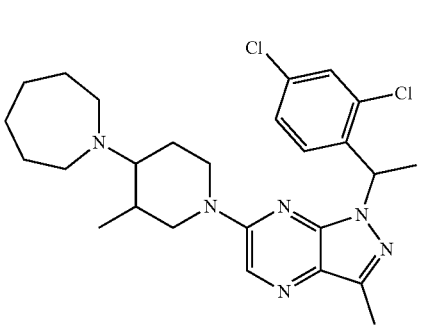
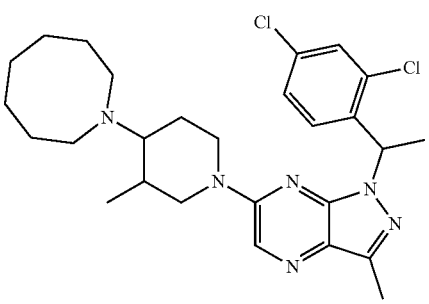
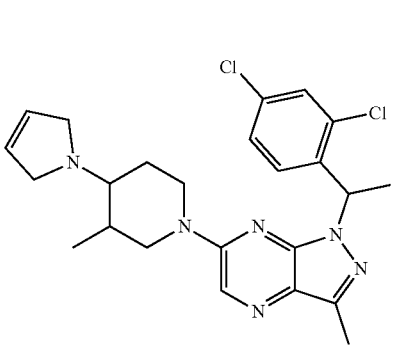
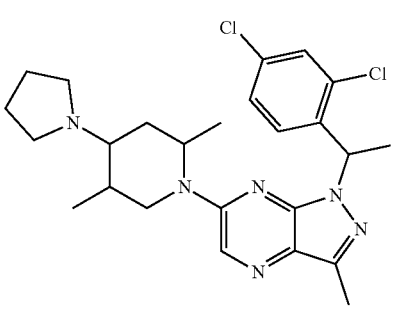

521
-continued
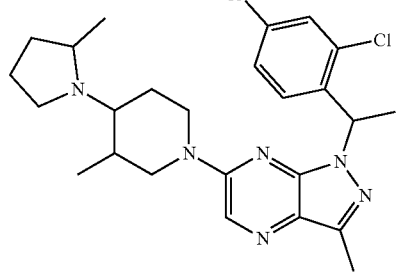
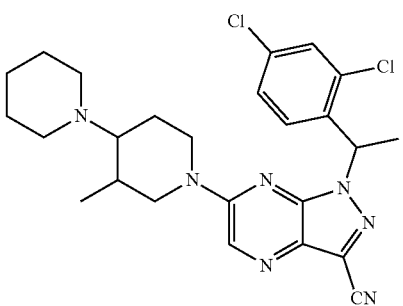
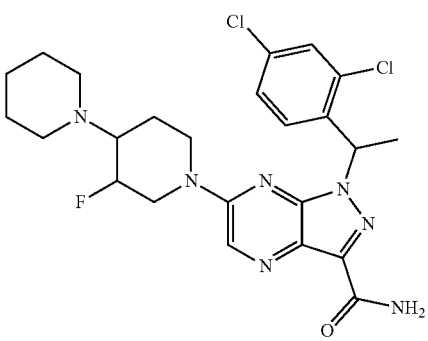
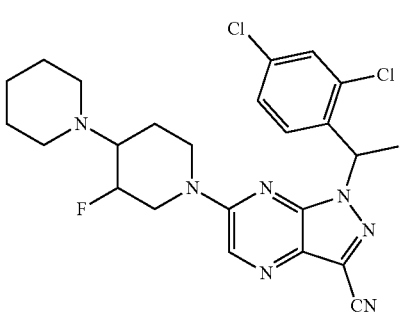
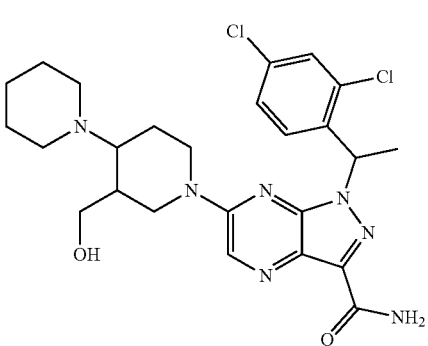
522
-continued
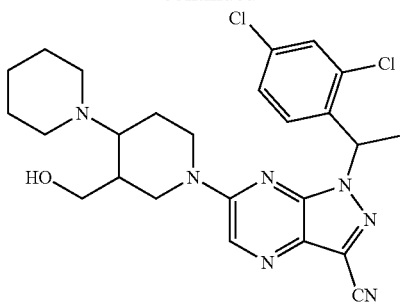
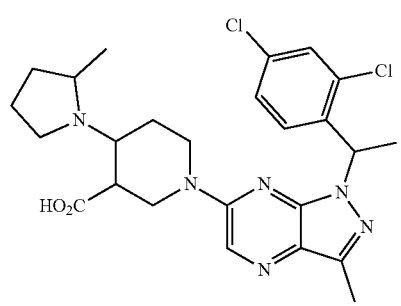
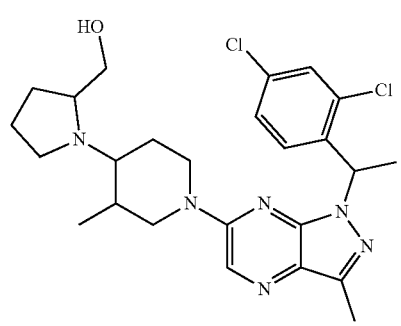
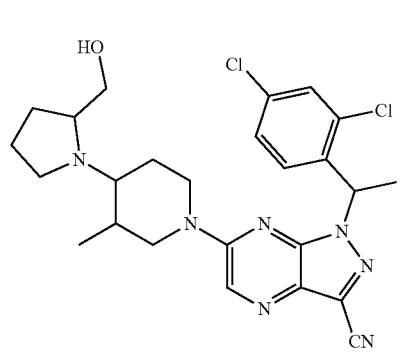
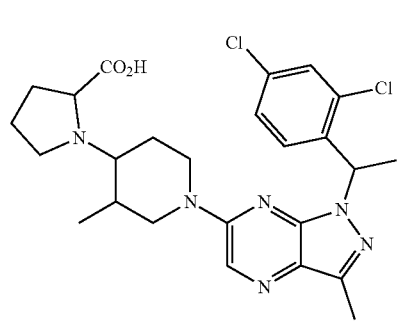

523
-continued
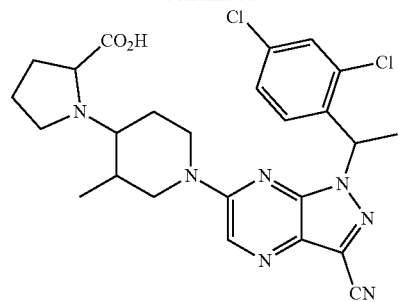
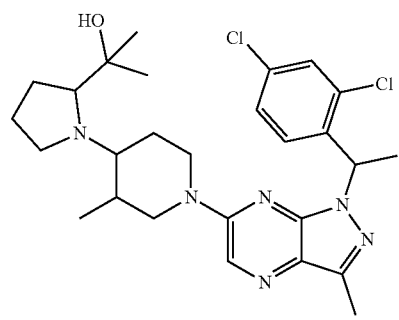
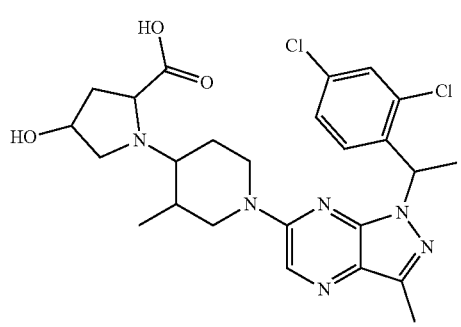
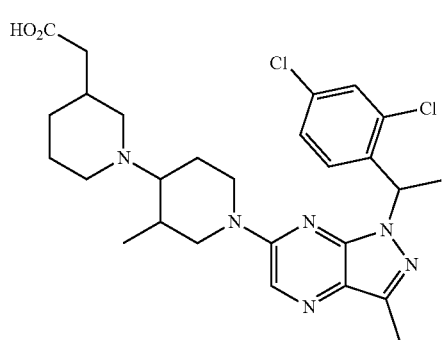
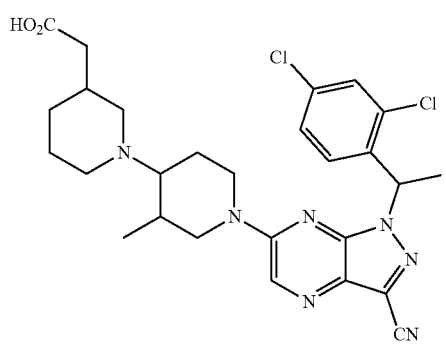
524
-continued
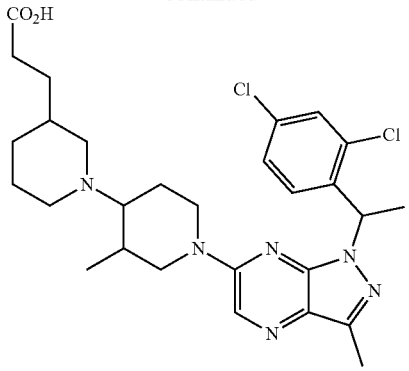
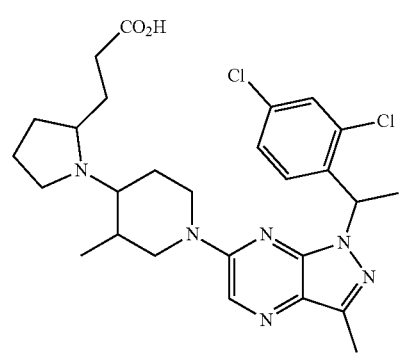
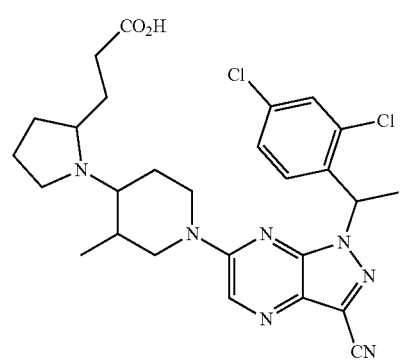
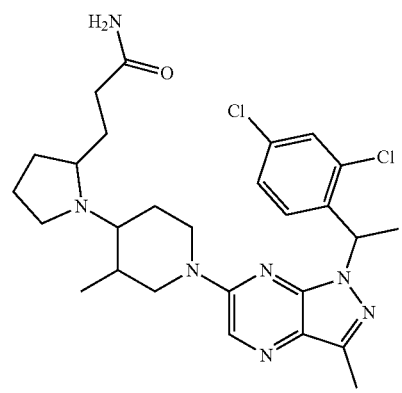

525
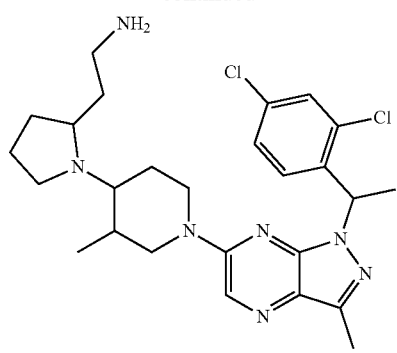
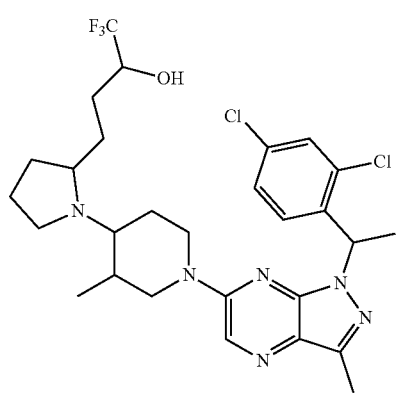
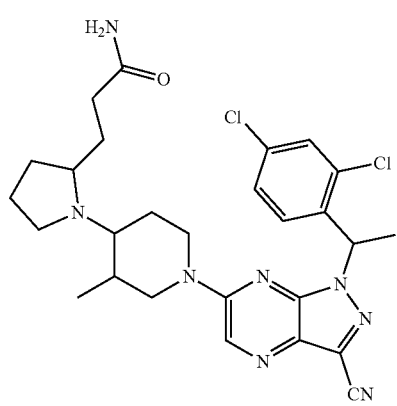
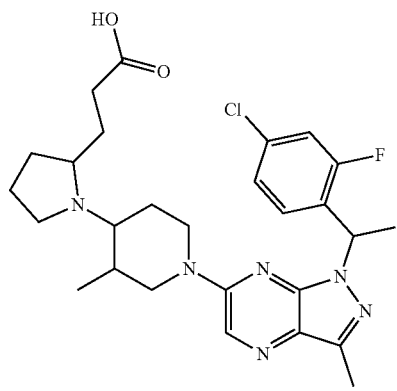
526
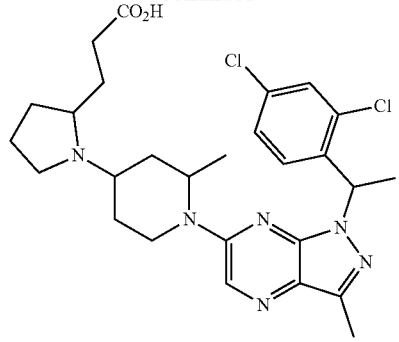
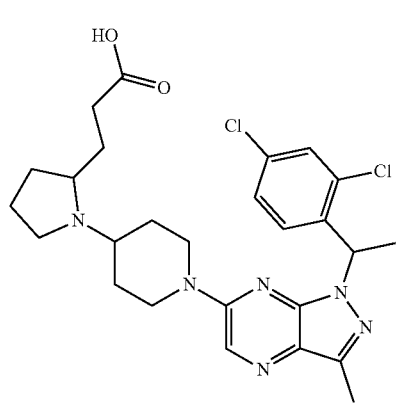
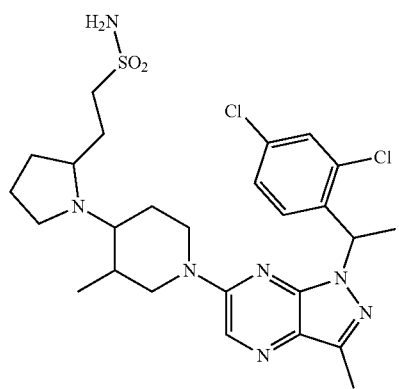

527
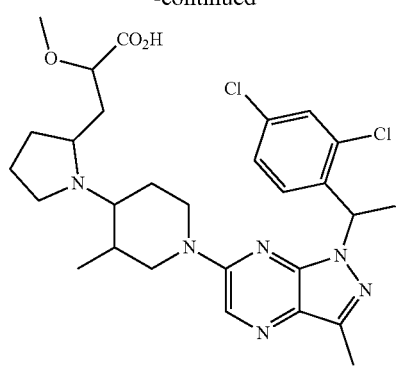
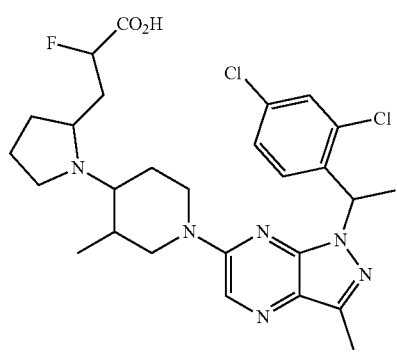
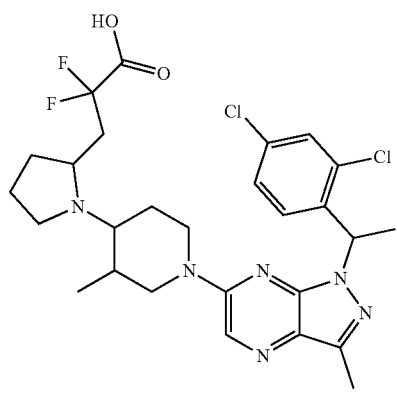
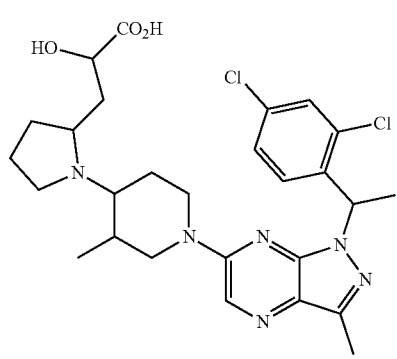
528
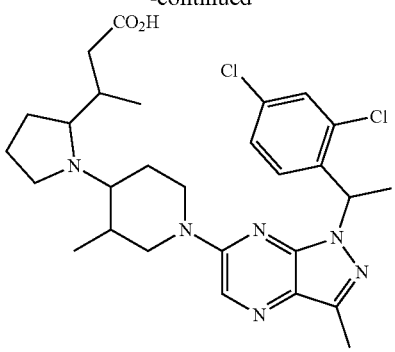
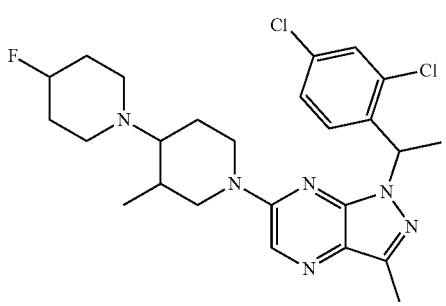
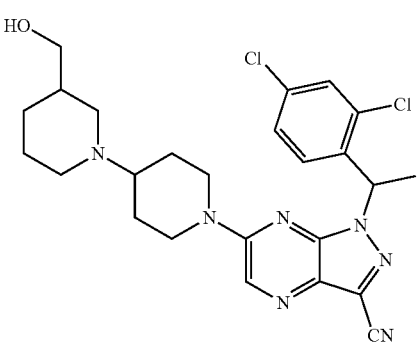
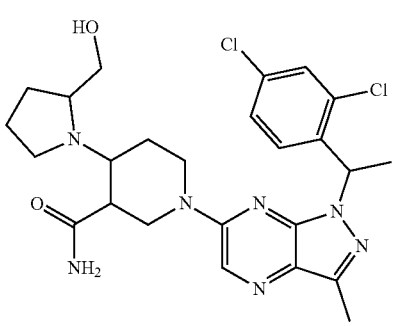
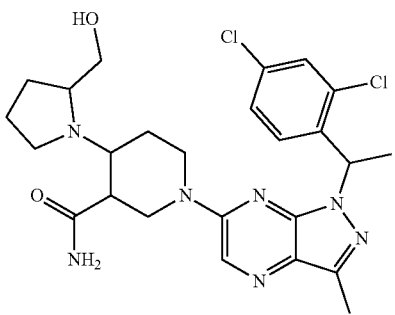

529
-continued
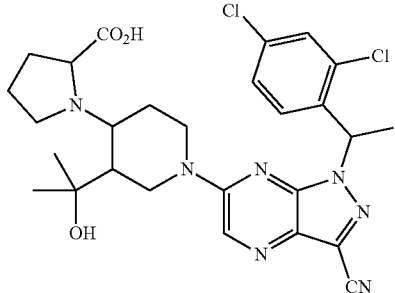
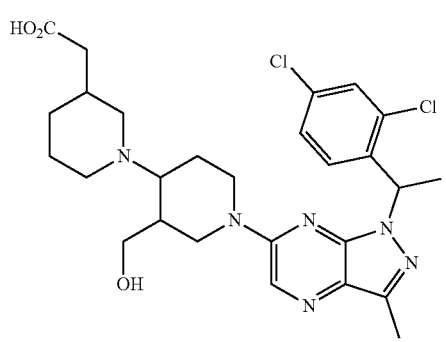
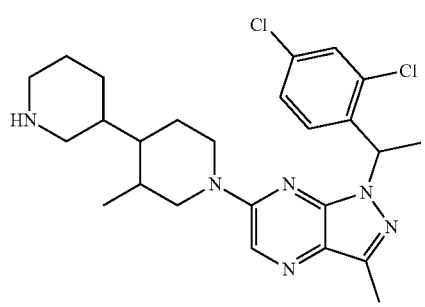
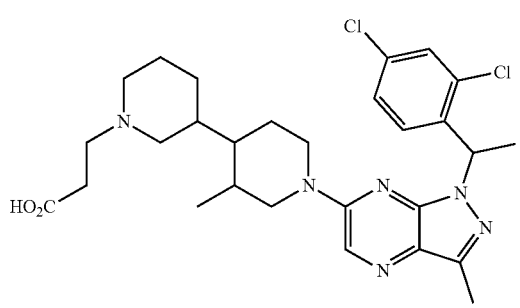
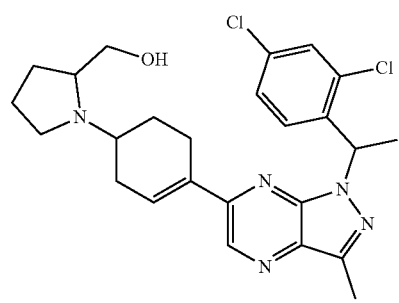
530
-continued
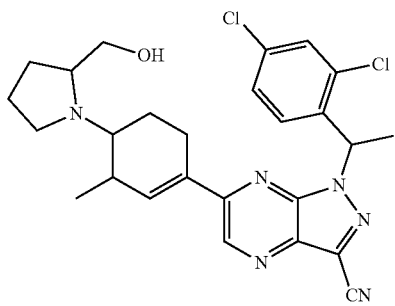
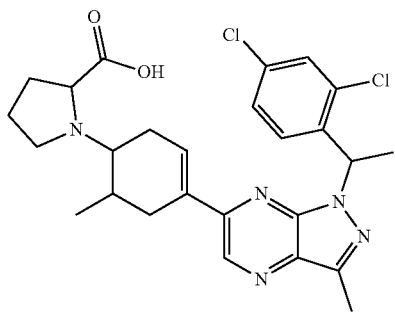
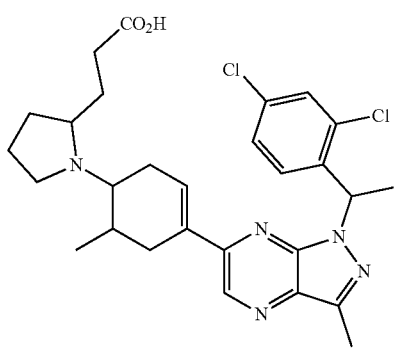
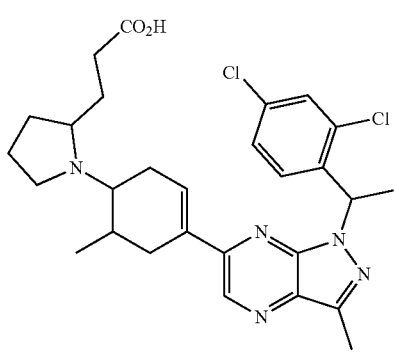
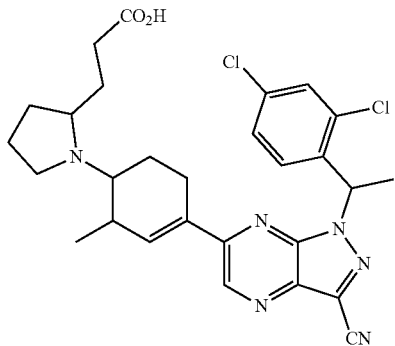

531
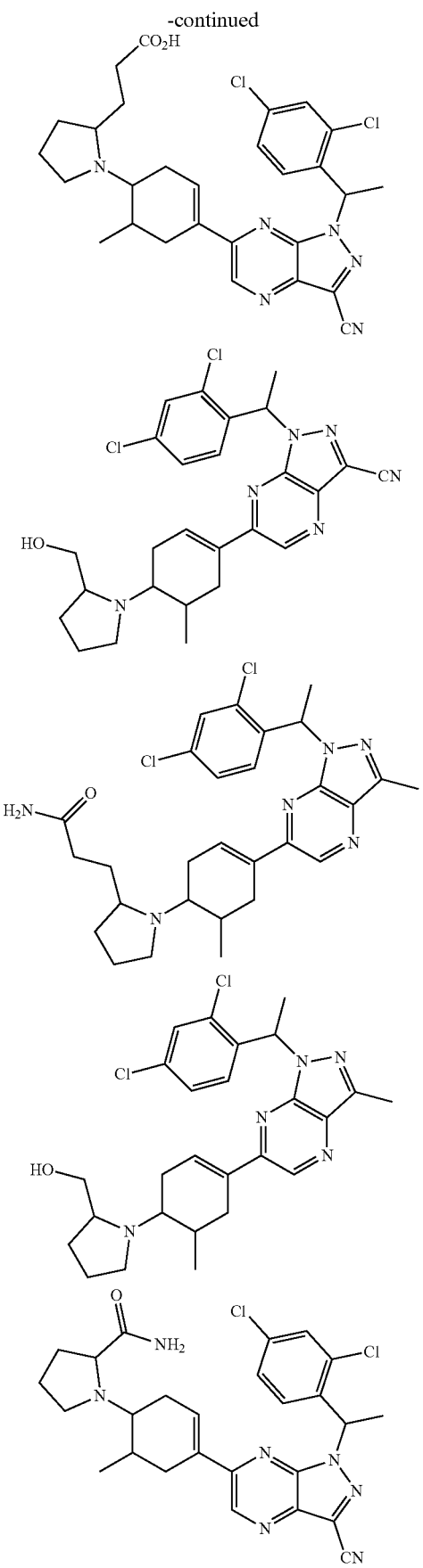
532
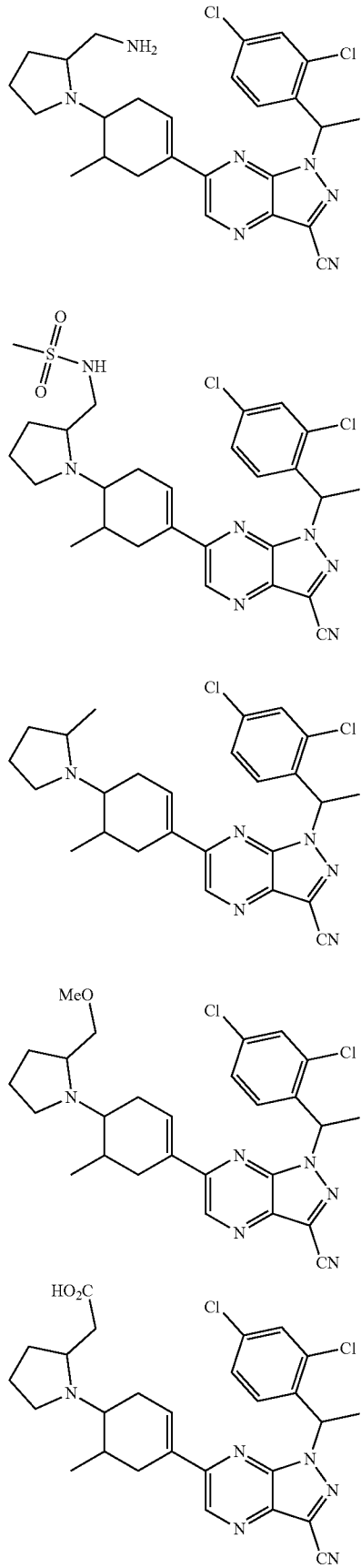

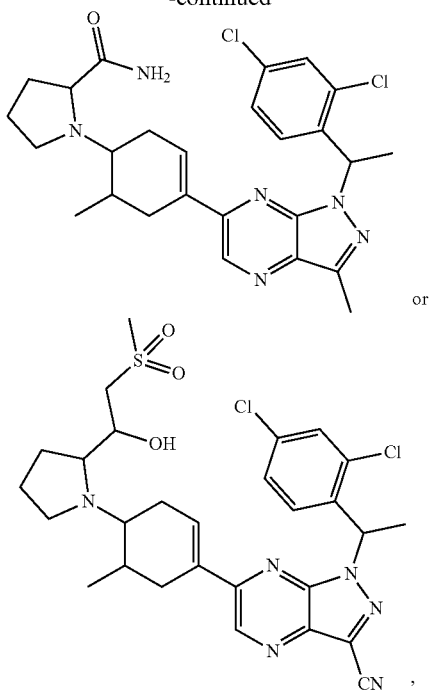

or a pharmaceutically acceptable salt thereof.

Embodiment PII74 A pharmaceutical composition, comprising a compound of embodiment PII1 and a pharmaceutically acceptable excipient.

Embodiment PII75 A method of inhibiting C—C chemokine receptor type 4 (CCR4), the method comprising contacting CCR4 with a compound of embodiment PII1.

Embodiment PII76 A method of treating or preventing a disease or disorder mediated by CCR4, comprising administering to a subject in need thereof a therapeutically effective amount of a compound of embodiment PII or a pharmaceutically acceptable salt thereof.

Embodiment PII77 The method of embodiment PII76, wherein the disease or disorder is an immune or inflammatory disease or disorder.

Embodiment PII78 The method of embodiment PII77, further comprising co-administering an anti-inflammatory agent in combination with a compound of structural Formula (I).

Embodiment PII79 The method of embodiment PII78, wherein the anti-inflammatory is thalidomide or a derivative thereof, a retinoid, dithranol or calcipotriol, a non-steroidal anti-inflammatory agent (NSAID), cyclo-oxygenase inhibiting nitric oxide donors (CINODs), glucocorticosteroids, methotrexate, leflunomide, hydroxychloroquine, d-penicillamine, auranofin, analgesics; diacerein, hyaluronic acid derivatives or nutritional supplements.

Embodiment PII80 The method of embodiment PII76, wherein the disease or disorder is a cardiovascular or metabolic disease or disorder.

Embodiment PII81 The method of embodiment PII80, further comprising co-administering a cardiovascular agent or a metabolic disorder agent in combination with a compound of structural Formula (I).

Embodiment PII82 The method of embodiment PII81, wherein the cardiovascular agent is a calcium channel blocker, a beta-adrenoceptor blocker, an angiotensin-converting enzyme (ACE) inhibitor, an angiotensin-2 receptor antagonist, a lipid lowering agent, a modulator of blood cell morphology, a thrombolytic or an anticoagulant.

Embodiment PII83 The method of embodiment PII76, wherein the disease or disorder is cancer.

Embodiment PII84 The method of embodiment PII83, further comprising co-administering a chemotherapeutic agent or anticancer agent in combination with a compound of structural Formula (I).

Embodiment PII85 The method of embodiment PII84, wherein the chemotherapeutic agent or anticancer agent is an antiproliferative/antineoplastic drug, an antimetabolite, an antitumour antibiotic, an antimitotic agent, a topoisomerase inhibitor, a cytostatic agent, an oestrogen receptor down regulator, an antiandrogen, a LHRH antagonist or LHRH agonist, a progestogen, an aromatase inhibitor, an inhibitor of 5.alpha.-reductase, an agent which inhibits cancer cell invasion, an inhibitor of growth factor function, a farnesyl transferase inhibitor, a tyrosine kinase inhibitor, a serine/threonine kinase inhibitor, an inhibitor of the epidermal growth factor family, an inhibitor of the platelet-derived growth factor family, an inhibitor of the hepatocyte growth factor family; an antiangiogenic agent, a vascular damaging agent, an agent used in antisense therapy, an anti-ras antisense, an agent used in a gene therapy, an immunotherapeutic agent, or an antibody.

Embodiment PII86 The method of embodiment PII83, further comprising co-administering a therapeutically effective amount of at least two of: a CCR4 inhibitor, an inhibitor of the PD-L1/PD-1 pathway, an inhibitor of CTLA-4, an agonistic antibody of CD137 (4-1BB) are co-administered.

Embodiment PII87 The method of embodiment PII83, further comprising co-administering a therapeutically effective amount of at least two of: a CCR4 inhibitor, an agent that may be an immune modulator or an agent from Table 1 are co-administered.

Embodiment PII88 The method of any one of embodiments PII83 to PII87, wherein the cancer is colon cancer or pancreatic cancer.

PIII EMBODIMENTS

Embodiment PIII1 A compound having structural Formula (I):

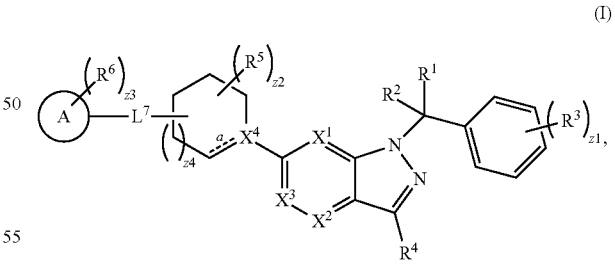

(I)

or a pharmaceutically acceptable salt thereof, wherein: A is a substituted or unsubstituted heterocycloalkyl; $X^1$ is $CR^8$ or N; $X^2$ is $CR^9$ or N; $X^3$ is $CR^{10}$ or N; $X^4$ is C, $CR^{11}$ or N; n1 is an integer from 0 to 4; m1 and v1 are independently 1 or 2; z1 is an integer from 0 to 5; z2 is an integer from 0 to 13; z3 is an integer from 0 to 12; z4 is an integer from 0 to 3; ⚌ is a single bond or double bond, wherein if ⚌ is a single bond, then $X^4$ is $CR^{11}$ or N, and if ⚌ is a double bond, then $X^4$ is C; $L^7$ is a bond, —O—, —S—, —NR$^{7B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is hydrogen, halogen, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}_3$, $-OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, $-CX^{2.1}_3$, $-CHX^{2.1}_2$, $-CH_2X^{2.1}$, $-CN$, $-SO_{n1}R^{2A}$, $-SO_{v1}NR^{2B}R^{2C}$, $-NHNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m1}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^{2B}C(O)R^{2D}$, $-NR^{2B}C(O)OR^{2D}$, $-NR^{2B}OR^{2D}$, $-OCX^{2.1}_3$, $-OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, $-CX^{3.1}_3$, $-CHX^{3.1}_2$, $-CH_2X^{3.1}$, $-CN$, $-SO_{n1}R^{3A}$, $-SO_{v1}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m1}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^{3.1}_3$, $-OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^4$ is hydrogen, halogen, $-CX^{4.1}_3$, $-CHX^{4.1}_2$, $-CH_2X^{4.1}$, $-CN$, $-SO_{n1}R^{4A}$, $-SO_{v1}NR^{4B}R^{4C}$, $-NHNR^{4B}R^{4C}$, $-ONR^{4B}R^{4C}$, $-NHC(O)NHNR^{4B}R^{4C}$, $-NHC(O)NR^{4B}R^{4C}$, $-N(O)_{m1}$, $-NR^{4B}R^{4C}$, $-C(O)R^{4D}$, $-C(O)OR^{4D}$, $-C(O)NR^{4B}R^{4C}$, $-OR^{4A}$, $-NR^{4B}SO_2R^{4A}$, $-NR^{4B}C(O)R^{4D}$, $-NR^{4B}C(O)OR^{4D}$, $-NR^{4B}OR^{4D}$, $-OCX^{4.1}_3$, $-OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^5$ is hydrogen, halogen, oxo, $-CX^{5.1}_3$, $-CHX^{5.1}_2$, $-CH_2X^{5.1}$, $-CN$, $-SO_{n1}R^{5A}$, $-SO_{v1}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m1}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^{5.1}_3$, $-OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^6$ is hydrogen, halogen, oxo, $-CX^{6.1}_3$, $-CHX^{6.1}_2$, $-CH_2X^{6.1}$, $-CN$, $-SO_{n1}R^{6A}$, $-SO_{v1}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m1}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ is hydrogen, halogen, $-CX^{11.1}_3$, $-CHX^{11.1}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7B}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$ and $R^{11D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{8B}$ and $R^{8C}$, $R^{9B}$ and $R^{9C}$, $R^{10B}$ and $R^{10C}$, $R^{11B}$ and $R^{11C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$ are independently $-Cl$, $-Br$, $-I$ or $-F$, wherein at least one of $X^1$, $X^2$ and $X^3$ is N.

Embodiment PIII2 The compound of embodiment PIII1, wherein the substituted or unsubstituted heterocycloalkyl is a 4-membered to 8-membered ring.

Embodiment PIII3 The compound of embodiment PIII1, wherein the compound has structural Formula (Ia):

(Ia)

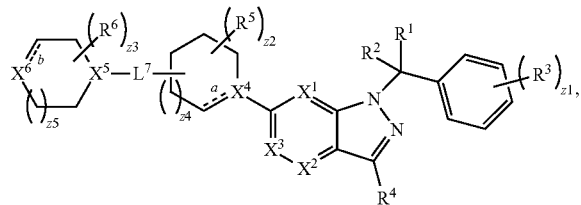

or a pharmaceutically acceptable salt thereof, wherein: $X^5$ is $CR^{12}$ or N; $X^6$ is $CR^{13}$, $CR^{13}R^{14}$, N or $NR^{15}$; z3 is an integer from 0 to 12; z5 is an integer from 0 to 3; $R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, $-CX^{15.3}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$ and $R^{15D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12B}$ and $R^{12C}$, $R^{13B}$ and $R^{13C}$, $R^{14B}$ and $R^{14C}$ and $R^{15B}$ and $R^{15C}$ substituents bonded to the same nitrogen atom may optionally be joined to form a substituted or unsubstituted heterocycloalkyl or substituted or unsubstituted heteroaryl; $\doublebond$ is a single bond or double bond, wherein if $\doublebond$ is a single bond, then $X^4$ is $CR^{13}R^{14}$ or $NR^{15}$, and if $\doublebond$ is a double bond, then $X^4$ is N or $CR^{13}$; and $X^{12.1}$, $X^{13.1}$, $X^{14.1}$ and $X^{15.1}$ are independently $-Cl$, $-Br$, $-I$ or $-F$.

Embodiment PIII4 The compound of embodiment PIII1, wherein: z1 is 2; and z4 is 1.

Embodiment PIII5 The compound of embodiment PIII1, wherein $R^1$ and $R^2$ are independently hydrogen, substituted or unsubstituted alkyl or substituted or unsubstituted heteroalkyl.

Embodiment PIII6 The compound of embodiment PIII1, wherein $L^7$ is a bond.

Embodiment PIII7 The compound of embodiment PIII3, wherein the compound has structural Formula (II):

(II)

or a pharmaceutically acceptable salt thereof, wherein: $R^4$ is hydrogen, $-CX^{4.1}_3$, $-CN$, $-C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.2}$ is hydrogen, halogen, $-CX^{3.2}_3$, $-CHX^{3.2}_2$, $-CH_2X^{3.2}$, $-CN$, $-SO_{n1}R^{3.2A}$, $-SO_{v1}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m1}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}_3$, $-OCHX^{3.2}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.3}$ is hydrogen, halogen, $-CX^{3.3}_3$, $-CHX^{3.3}_2$, $-CH_2X^{3.3}$, $-CN$, $-SO_{n1}R^{3.3A}$, $-SO_{v1}NR^{3.3B}R^{3.3C}$, $-NHNR^{3.3B}R^{3.3C}$, $-ONR^{3.3B}R^{3.3C}$, $-NHC(O)NHNR^{3.3B}R^{3.3c}$, $-NHC(O)NR^{3.3B}R^{3.3c}$, $-N(O)_{m1}$, $-NR^{3.3B}R^{3.3C}$, $-C(O)R^{3.3D}$, $-C(O)OR^{3.3D}$, $-C(O)NR^{3.3B}R^{3.3C}$, $-OR^{3.3A}$, $-NR^{3.3B}SO_2R^{3.3A}$, $-NR^{3.3B}C(O)R^{3.3D}$, $-NR^{3.3B}C(O)OR^{3.3D}$, $-NR^{3.3B}OR^{3.3D}$, $-OCX^{3.3}_3$, $-OCHX^{3.3}_2$, substituted or unsubstituted alkyl, substituted or unsubstituted heteroalkyl, substituted or unsubstituted heterocycloalkyl, substituted or unsubstituted aryl, or substituted or unsubstituted heteroaryl; $R^{3.2A}$, $R^{3.2B}$, $R^{3.2C}$, $R^{3.2D}$, $R^{3.3A}$, $R^{3.3B}$, $R^{3.3C}$ and $R^{3.3D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.2B}$, $R^{3.2C}$, $R^{3.3B}$ and $R^{3.3C}$ substituents bonded to the same nitrogen atom may optionally be joined to form a substituted or unsubstituted heterocycloalkyl or substituted or unsubstituted heteroaryl; and $X^{3.2}$ and $X^{3.3}$ are independently —Cl, —Br, —I or —F.

Embodiment PIII8 The compound of embodiment PIII3, wherein the compound has structural Formula (III):

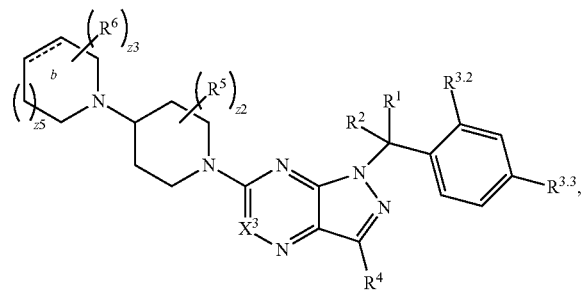

(III)

or a pharmaceutically acceptable salt thereof.

Embodiment PIII9 The compound of embodiment PIII3, wherein the compound has structural Formula (IIIa):

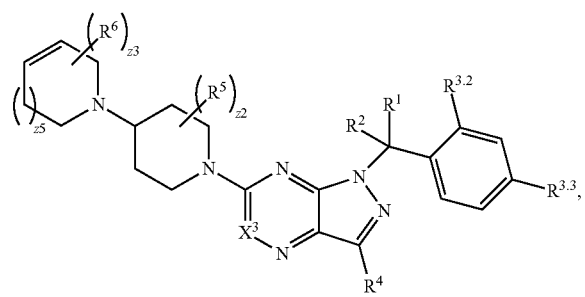

(IIIa)

or a pharmaceutically acceptable salt thereof.

Embodiment PIII10 The compound of embodiment PIII3, wherein the compound has structural Formula (IIIb):

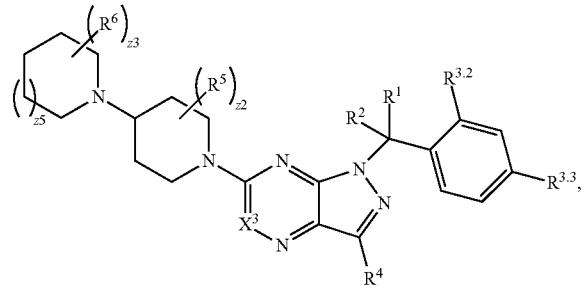

(IIIb)

or a pharmaceutically acceptable salt thereof.

Embodiment PIII11 The compound of embodiment PIII3, wherein the compound has structural Formula (IV):

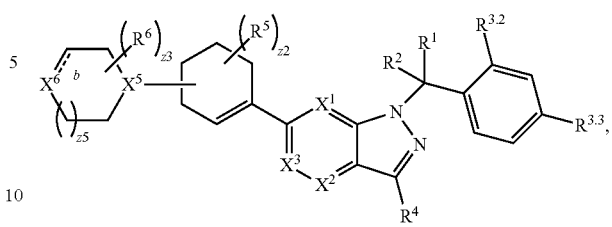

(IV)

or a pharmaceutically acceptable salt thereof.

Embodiment PIII12 The compound of embodiment PIII3, wherein the compound has structural Formula (V):

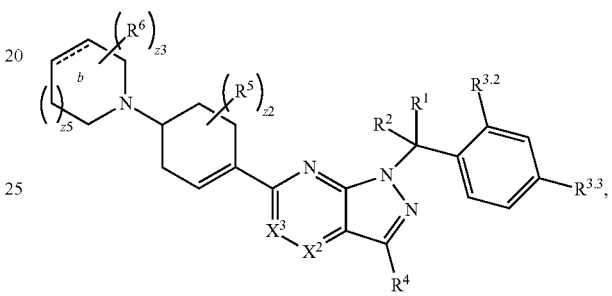

(V)

or a pharmaceutically acceptable salt thereof.

Embodiment PIII13 The compound of embodiment PIII3, wherein the compound has structural Formula (Va):

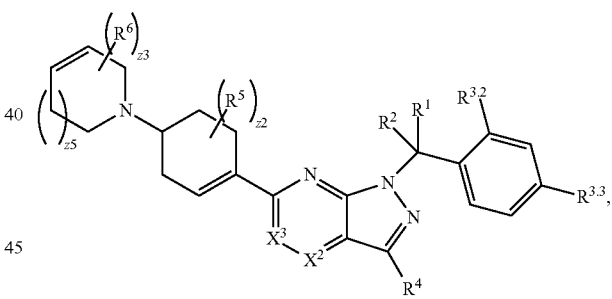

(Va)

or a pharmaceutically acceptable salt thereof.

Embodiment PIII14 The compound of embodiment PIII3, wherein the compound has structural Formula (Vb):

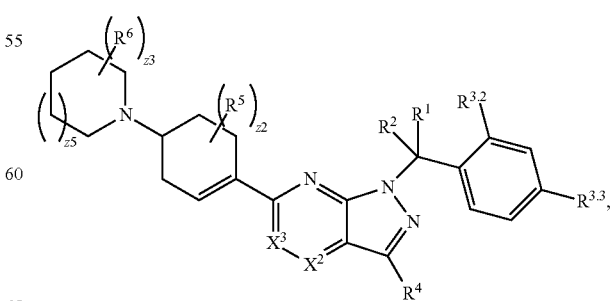

(Vb)

or a pharmaceutically acceptable salt thereof.

Embodiment PIII15 The compound of any one of embodiments PIII1 to PIII14, wherein $R^4$ is hydrogen, —CN, —$CX^{4.1}_3$, —C(O)$R^{4D}$, —C(O)O$R^{4D}$, —C(O)N$R^{4B}R^{4C}$, substituted or unsubstituted alkyl or substituted or unsubstituted heteroalkyl.

Embodiment PIII16 The compound of embodiment PIII15, wherein $R^4$ is —CN, —$CF_3$, —C(O)$NH_2$, —$CH_3$ or —C($CH_3$)$_2$OH.

Embodiment PIII17 The compound of any one of embodiments PIII7 to PIII14, wherein $R^{3.2}$ and $R^{3.3}$ are independently halogen, —CN, $CF_3$ or unsubstituted alkyl.

Embodiment PIII18 The compound of embodiment PIII17, wherein the halogen is chlorine or fluorine.

Embodiment PIII19 The compound of embodiment PIII17, wherein the unsubstituted alkyl is —$CH_3$.

Embodiment PIII20 The compound of any one of embodiments PIII1 to PIII14, wherein $R^1$ and $R^2$ are independently hydrogen or unsubstituted alkyl.

Embodiment PIII21 The compound of embodiment PIII20, wherein $R^1$ is —$CH_3$ or —$CH_2CH_3$.

Embodiment PIII22 The compound of embodiment PIII20, wherein $R^2$ is —$CH_3$ or —$CH_2CH_3$.

Embodiment PIII23 The compound of any one of embodiments PIII1 to PIII14, wherein $R^1$ is hydrogen.

Embodiment PIII24 The compound of any one of embodiments PIII1 to PIII14, wherein $R^2$ is hydrogen.

Embodiment PIII25 The compound of any one of embodiments PIII1 to PIII14, wherein $X^2$ is N.

Embodiment PIII26 The compound of any one of embodiments PIII1 to PIII14, wherein $X^3$ is N.

Embodiment PIII27 The compound of any one of embodiments PIII1 to PIII14, wherein z2 and z3 are independently an integer from 0 to 2.

Embodiment PIII28 The compound of any one of embodiments PIII1 to PIII14, wherein $R^5$ is hydrogen, fluorine, —CN, —$CH_3$, —$CF_3$, —($CH_2$)$_2$OH, —$CO_2NH_2$ or —$CO_2CH_2CH_3$.

Embodiment PIII29 The compound of any one of embodiments PIII1 to PIII14, wherein $R^6$ is hydrogen, —OH, —$CH_3$, —$CH_2$OH, —($CH_2$)$_2$OH, —($CH_2$)$_3$OH, —$CH_2NH_2$, —($CH_2$)$_2NH_2$, —($CH_2$)$_3NH_2$, —$CH_2CO_2CH_2CH_3$, —($CH_2$)$_2CO_2CH_2CH_3$, —($CH_2$)$_3CO_2CH_2CH_3$, —$CH_2CO_2H$, —($CH_2$)$_2CO_2H$, —($CH_2$)$_3CO_2H$, —($CH_2$)$CO_2NH_2$, —($CH_2$)$_2CONH_2$, —($CH_2$)$_3CO_2NH_2$, —($CH_2$)CHF$CO_2$H, —($CH_2$)$_2$CHF$CO_2$H, —($CH_2$)$CF_2CO_2$H, —($CH_2$)$_2CF_2CO_2$H,

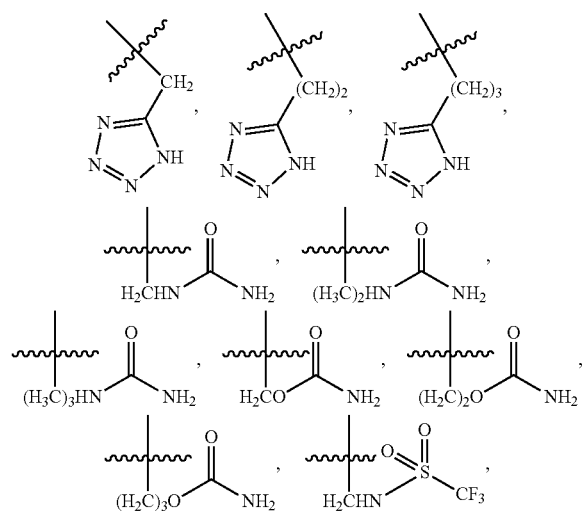

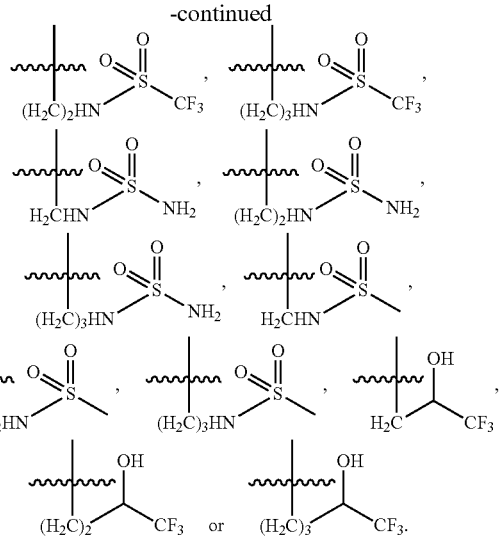

Embodiment PIII30 The compound of embodiment PIII3, wherein the compound has structural Formula (VI):

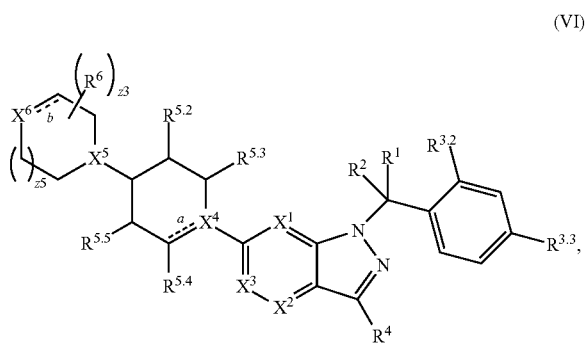

(VI)

or a pharmaceutically acceptable salt thereof, wherein: $R^{5.2}$ is hydrogen, halogen, —$CX^{5.6}_3$, —$CHX^{5.6}_2$, —$CH_2X^{5.6}$, —CN, —$SO_{n1}R^{5.6A}$, —$SO_{v1}NR^{5.6B}R^{5.6C}$, —NHN$R^{5.6B}R^{5.6C}$, —ON$R^{5.6B}R^{5.6C}$, —NHC(O)NHN$R^{5.6B}R^{5.6C}$, —NHC(O)N$R^{5.6B}R^{5.6C}$, —N(O)$_{m1}$, —N$R^{5.6B}R^{5.6C}$, —C(O)$R^{5.6D}$, —C(O)O$R^{5.6D}$, —C(O)N$R^{5.6B}R^{5.6C}$, —O$R^{5.6A}$, —N$R^{5.6B}SO_2R^{5.6A}$, —N$R^{5.6B}$C(O)$R^{5.6D}$, —N$R^{5.6B}$C(O)O$R^{5.6D}$, —N$R^{5.6B}$O$R^{5.6D}$, —OC$X^{5.6}_3$, —OCH$X^{5.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5.3}$ is hydrogen, halogen, —$CX^{5.7}_3$, —$CHX^{5.7}_2$, —$CH_2X^{5.7}$, —CN, —$SO_{n1}R^{5.7A}$, —$SO_{v1}NR^{5.7B}R^{5.7C}$, —NHN$R^{5.7B}R^{5.7C}$, —ON$R^{5.7B}R^{5.7C}$, —NHC(O)NHN$R^{5.7B}R^{5.7C}$, —NHC(O)N$R^{5.7B}R^{5.7C}$, —N(O)$_{m1}$, —N$R^{5.7B}R^{5.7C}$, —C(O)$R^{5.7D}$, —C(O)O$R^{5.7D}$, —C(O)N$R^{5.7B}R^{5.7C}$, —O$R^{5.7A}$, —N$R^{5.7B}SO_2R^{5.7A}$, —N$R^{5.7B}$C(O)$R^{5.7D}$, —N$R^{5.7B}$C(O)O$R^{5.7D}$, —N$R^{5.7B}$O$R^{5.7D}$, —OC$X^{5.7}_3$, —OCH$X^{5.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5.4}$ is hydrogen, halogen, —$CX^{5.8}_3$, —$CHX^{5.8}_2$, —$CH_2X^{5.8}$, —CN, —$SO_{n1}R^{5.8A}$, —$SO_{v1}NR^{5.8B}R^{5.8C}$, —NHN$R^{5.8B}R^{5.8C}$, ON$R^{5.8B}R^{5.8C}$, NHC(O)NHN$R^{5.8B}R^{5.8C}$, NHC(O)N$R^{5.8B}R^{5.8C}$, —N(O)$_{m1}$, —N$R^{5.8B}R^{5.8C}$, —C(O)$R^{5.8D}$, —C(O)O$R^{5.8D}$, —C(O)N$R^{5.8B}R^{5.8C}$, —O$R^{5.8A}$, —NR$^{5.8B}$SO$_2$R$^{5.8A}$, —NR$^{5.8B}$C(O)R$^{5.8D}$, —NR$^{5.8B}$C(O)OR$^{5.8D}$, —NR$^{5.8B}$OR$^{5.8D}$, —OCX$^{5.8}_3$, —OCHX$^{5.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{5.5}$ is hydrogen, halogen, —CX$^{5.9}_3$, —CHX$^{5.9}_2$, —CH$_2$X$^{5.9}$, —CN, —SO$_{n1}$R$^{5.9A}$, —SO$_{v1}$NR$^{5.9B}$R$^{5.9C}$, NHNR$^{5.9B}$R$^{5.9C}$, —ONR$^{5.9B}$R$^{5.9C}$, NHC(O)NHNR$^{5.9B}$R$^{5.9C}$, —NHC(O)NR$^{5.9B}$R$^{5.9}$c, —N(O)$_{m1}$, —NR$^{5.9B}$R$^{5.9C}$, —C(O)R$^{5.9D}$, —C(O)OR$^{5.9D}$, —C(O)NR$^{5.9B}$R$^{5.9C}$, —OR$^{5.9A}$, —NR$^{5.9B}$SO$_2$R$^{5.9A}$, —NR$^{5.9B}$C(O)R$^{5.9D}$, —NR$^{5.9B}$C(O)OR$^{5.9D}$, —NR$^{5.9B}$OR$^{5.9D}$, —OCX$^{5.9}_3$, —OCHX$^{5.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{5.6A}$, R$^{5.6B}$, R$^{5.6C}$, R$^{5.6D}$, R$^{5.7A}$, R$^{5.7B}$, R$^{5.7C}$, R$^{5.7D}$, R$^{5.8A}$, R$^{5.8B}$, R$^{5.8C}$, R$^{5.8D}$, R$^{5.9A}$, R$^{5.9B}$, R$^{5.9C}$ and R$^{5.9D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{5.6B}$ and R$^{5.6C}$, R$^{5.7B}$ and R$^{5.7C}$, R$^{5.8B}$ and R$^{5.8C}$, R$^{5.9B}$ and R$^{5.9C}$ substituents bonded to the same nitrogen atom may optionally be joined to form a substituted or unsubstituted heterocycloalkyl or substituted or unsubstituted heteroaryl; and X$^{5.6}$, X$^{5.7}$, X$^{5.8}$ and X$^{5.9}$ are independently —Cl, —Br, —I or —F.

Embodiment PIII31 The compound of embodiment PIII30, wherein the compound has structural Formula (VII):

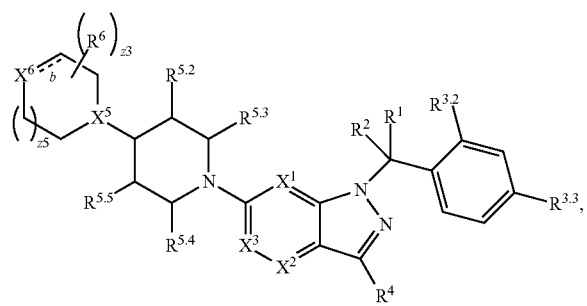

(VII)

or a pharmaceutically acceptable salt thereof.

Embodiment PIII32 The compound of embodiment PIII30, wherein the compound has structural Formula (VIIa):

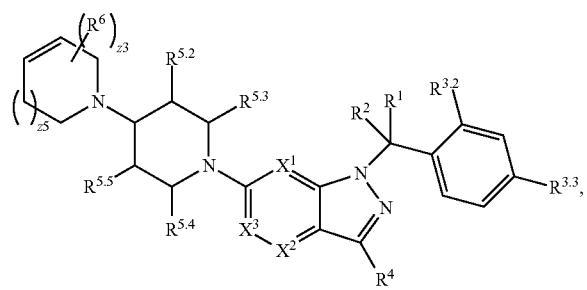

(VIIa)

or a pharmaceutically acceptable salt thereof.

Embodiment PIII33 The compound of embodiment PIII30, wherein the compound has structural Formula (VIIb):

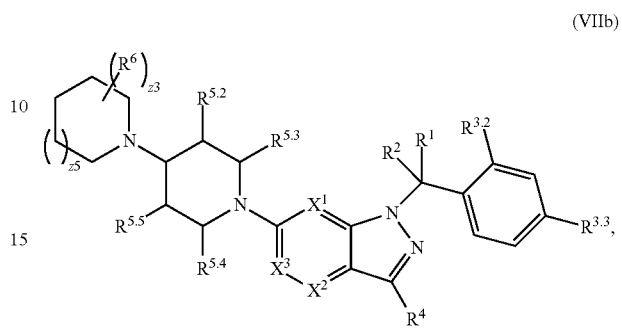

(VIIb)

or a pharmaceutically acceptable salt thereof.

Embodiment PIII34 The compound of embodiment PIII30, wherein the compound has structural Formula (VIII):

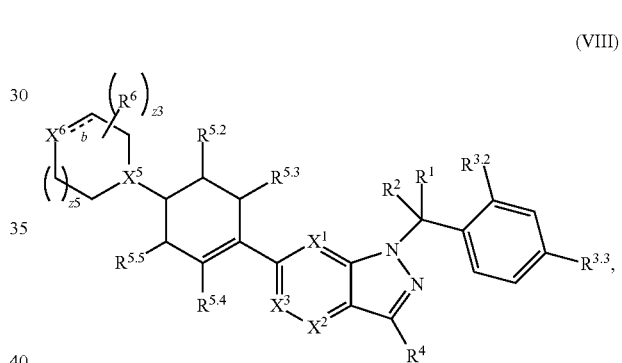

(VIII)

or a pharmaceutically acceptable salt thereof.

Embodiment PIII35 The compound of embodiment PIII34, wherein the compound has structural Formula (VIIIa):

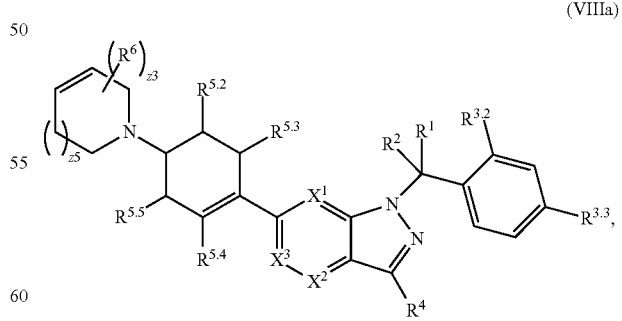

(VIIIa)

or a pharmaceutically acceptable salt thereof.

Embodiment PIII36 The compound of embodiment PIII34, wherein the compound has structural Formula (VIIIb):

(VIIIb)

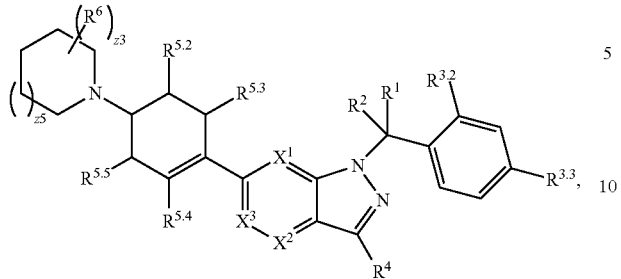

or a pharmaceutically acceptable salt thereof.

Embodiment PIII37 The compound of any one of embodiments PIII30 to PIII36, wherein $X^1$ and $X^3$ are independently N.

Embodiment PIII38 The compound of any one of embodiments PIII30 to PIII36, wherein $X^1$ and $X^2$ are independently N.

Embodiment PIII39 The compound of any one of embodiments PIII30 to PIII36, wherein $R^4$ is —CN, —C(O)NH$_2$, —CF$_3$, —CH$_3$ or —C(CH$_3$)$_2$OH.

Embodiment PIII40 The compound of any one of embodiments PIII30 to PIII36, wherein $R^{3.2}$ and $R^{3.3}$ are independently halogen, —CN, CF$_3$ or unsubstituted alkyl.

Embodiment PIII41 The compound of embodiment PIII40, wherein the halogen is chlorine or fluorine.

Embodiment PIII42 The compound of embodiment PIII40, wherein the unsubstituted alkyl is —CH$_3$.

Embodiment PIII43 The compound of any one of embodiments PIII30 to PIII36, wherein $R^1$ and $R^2$ are independently hydrogen or unsubstituted alkyl.

Embodiment PIII44 The compound of embodiment PIII43, wherein $R^1$ is —CH$_3$ or —CH$_2$CH$_3$.

Embodiment PIII45 The compound of embodiment PIII43, wherein $R^2$ is —CH$_3$ or —CH$_2$CH$_3$.

Embodiment PIII46 The compound of any one of embodiments PIII30 to PIII36, wherein $R^1$ is hydrogen.

Embodiment PIII47 The compound of any one of embodiments PIII30 to PIII36, wherein $R^2$ is hydrogen.

Embodiment PIII48 The compound of any one of embodiments PIII30 to PIII36, wherein z3 is an integer from 0 to 2.

Embodiment PIII49 The compound of any one of embodiments PIII30 to PIII36, wherein $R^5$ is hydrogen, fluorine, —CN, —CH$_3$, —CF$_3$, —(CH$_2$)$_2$OH, —CO$_2$NH$_2$ or —CO$_2$CH$_2$CH$_3$.

Embodiment PIII50 The compound of any one of embodiments PIII30 to PIII36, wherein $R^6$ is hydrogen, —OH, —CH$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H,

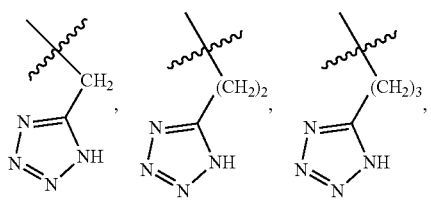

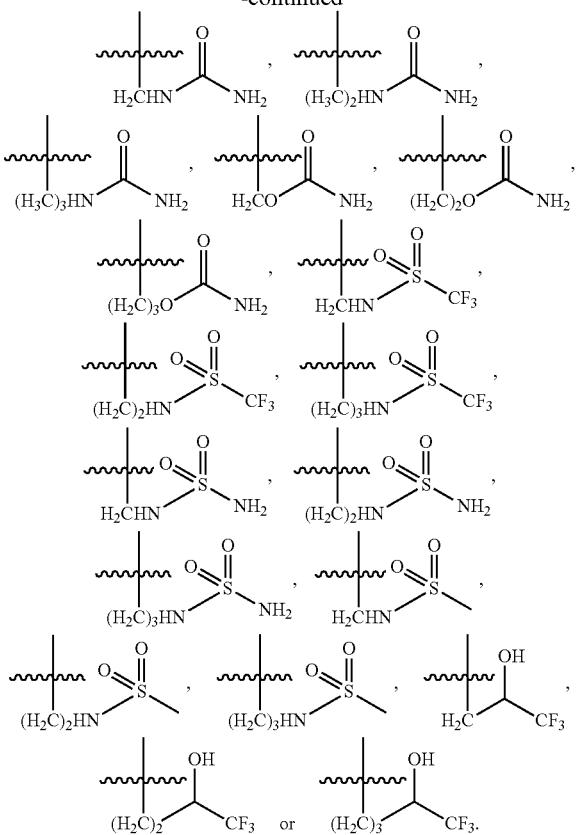

Embodiment PIII51 The compound of any one of embodiments PIII30 to PIII36, wherein z5 is 1.

Embodiment PIII52 The compound of any one of embodiments PIII30 to PIII36, wherein z5 is 0.

Embodiment PIII53 The compound of embodiment PIII36, wherein z3 and z5 are independently 1.

Embodiment PIII54 The compound of embodiment PIII36, wherein $R^6$ is halogen, substituted or unsubstituted alkyl or substituted or unsubstituted heteroalkyl.

Embodiment PIII55 The compound of embodiment PIII30, wherein the compound has structural Formula (IX):

(IX)

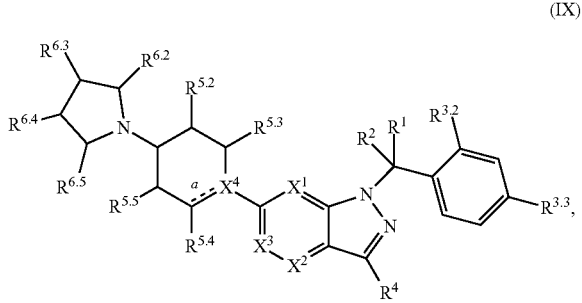

or a pharmaceutically acceptable salt thereof, wherein: $R^{6.2}$ is hydrogen, halogen, —CX$^{6.6}_3$, —CHX$^{6.6}_2$, —CH$_2$X$^{6.6}$, —CN, —SO$_{n1}$R$^{6.6A}$, —SO$_{v1}$NR$^{6.6B}$R$^{6.6C}$, NHNR$^{6.6B}$R$^{6.6C}$, ONR$^{6.6B}$R$^{6.6C}$, NHC(O)NHNR$^{6.6B}$R$^{6.6C}$, —NHC(O)NR$^{6.6B}$R$^{6.6C}$, —N(O)$_{m1}$, —NR$^{6.6B}$R$^{6.6C}$, —C(O)R$^{6.6D}$, —C(O)OR$^{6.6D}$, —C(O)NR$^{6.6B}$R$^{6.6C}$, —OR$^{6.6A}$, —NR$^{6.6B}$SO$_2$R$^{6.6A}$, —NR$^{6.6B}$C(O)R$^{6.6D}$, —NR$^{6.6B}$C(O)

$OR^{6.6D}$, $-NR^{6.6B}OR^{6.6D}$, $-OCX^{6.6}_3$, $-OCHX^{6.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6.3}$ is hydrogen, halogen, $-CX^{6.7}_3$, $-CHX^{6.7}_2$, $-CH_2X^{6.7}$, $-CN$, $-SO_{n1}R^{6.7A}$, $-SO_{v1}NR^{6.7B}R^{6.7C}$, $-NHNR^{6.7B}R^{6.7C}$, $-ONR^{6.7B}R^{6.7C}$, $-NHC(O)NHNR^{6.7B}R^{6.7C}$, $-NHC(O)NR^{6.7B}R^{6.7C}$, $-N(O)_{m1}$, $-NR^{6.7B}R^{6.7C}$, $-C(O)R^{6.7D}$, $-C(O)OR^{6.7D}$, $-C(O)NR^{6.7B}R^{6.7C}$, $-OR^{6.7A}$, $-NR^{6.7B}SO_2R^{6.7A}$, $-NR^{6.7B}C(O)R^{6.7D}$, $-NR^{6.7B}C(O)OR^{6.7D}$, $-NR^{6.7B}OR^{6.7D}$, $-OCX^{6.7}_3$, $-OCHX^{6.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6.4}$ is hydrogen, halogen, $-CX^{6.8}_3$, $-CHX^{6.8}_2$, $-CH_2X^{6.8}$, $-CN$, $-SO_{n1}R^{6.8A}$, $-SO_{v1}NR^{6.8B}R^{6.8C}$, $-NHNR^{6.8B}R^{6.8C}$, $-ONR^{6.8B}R^{6.8C}$, $-NHC(O)NHNR^{6.8B}R^{6.8C}$, $-NHC(O)NR^{6.8B}R^{6.8C}$, $-N(O)_{m1}$, $-NR^{6.8B}R^{6.8C}$, $-C(O)R^{6.8D}$, $-C(O)OR^{6.8D}$, $C(O)NR^{6.8B}R^{6.8C}$, $-OR^{6.8A}$, $-NR^{6.8B}SO_2R^{6.8A}$, $-NR^{6.8B}C(O)R^{6.8D}$, $-NR^{6.8B}C(O)OR^{6.8D}$, $-NR^{6.8B}OR^{6.8D}$, $-OCX^{6.8}_3$, $-OCHX^{6.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6.5}$ is hydrogen, halogen, $-CX^{6.9}_3$, $-CHX^{6.9}_2$, $-CH_2X^{6.9}$, $-CN$, $-SO_{n1}R^{6.9A}$, $-SO_{v1}NR^{6.9B}R^{6.9C}$, $-NHNR^{6.9B}R^{6.9C}$, $-ONR^{6.9B}R^{6.9C}$, $-NHC(O)NHNR^{6.9B}R^{6.9C}$, $-NHC(O)NR^{6.9B}R^{6.9C}$, $-N(O)_{m1}$, $-NR^{6.9B}R^{6.9C}$, $-C(O)R^{6.9D}$, $-C(O)OR^{6.9D}$, $-C(O)NR^{6.9B}R^{6.9C}$, $-OR^{6.9A}$, $-NR^{6.9B}SO_2R^{6.9A}$, $-NR^{6.9B}C(O)R^{6.9D}$, $-NR^{6.9B}C(O)OR^{6.9D}$, $-NR^{6.9B}OR^{6.9D}$, $-OCX^{6.9}_3$, $-OCHX^{6.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6.6A}$, $R^{6.6B}$, $R^{6.6C}$, $R^{6.6D}$, $R^{6.7A}$, $R^{6.7B}$, $R^{6.7C}$, $R^{6.7D}$, $R^{6.8A}$, $R^{6.8B}$, $R^{6.8C}$, $R^{6.8D}$, $R^{6.9A}$, $R^{6.9B}$, $R^{6.9C}$ and $R^{6.9D}$ are independently hydrogen, halogen, $-CF_3$, $-CCl_3$, $-CBr_3$, $-Cl_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6.6B}$ and $R^{6.6C}$, $R^{6.7B}$ and $R^{6.7C}$, $R^{6.8B}$ and $R^{6.8C}$, $R^{6.9B}$ and $R^{6.9C}$ substituents bonded to the same nitrogen atom may optionally be joined to form a substituted or unsubstituted heterocycloalkyl or substituted or unsubstituted heteroaryl; and $X^{6.6}$, $X^{6.7}$, $X^{6.8}$ and $X^{6.9}$ are independently $-Cl$, $-Br$, $-I$ or $-F$.

Embodiment PIII56 The compound of embodiment PIII55, wherein the compound has structural Formula (IXa):

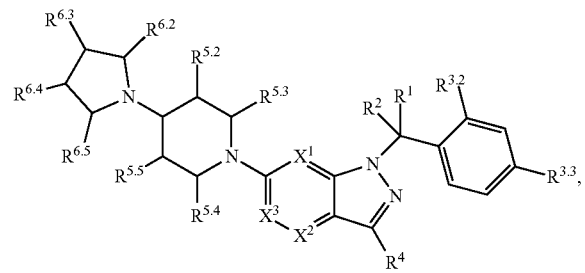

(IXa)

or a pharmaceutically acceptable salt thereof.

Embodiment PIII57 The compound of embodiment PIII56, wherein $X^1$ and $X^2$ are independently N.

Embodiment PIII58 The compound of embodiment PIII56, wherein $R^1$ and $R^2$ are independently hydrogen or unsubstituted alkyl.

Embodiment PIII59 The compound of embodiment PIII56, wherein $R^{3.2}$ and $R^{33}$ are independently halogen, $-CN$, $CF_3$ or unsubstituted alkyl.

Embodiment PIII60 The compound of embodiment PIII56, wherein $R^4$ is $-CN$, $-C(O)NH_2$, $-CF_3$, $-CH_3$ or $-C(CH_3)_2OH$.

Embodiment PIII61 The compound of embodiment PIII56, wherein $R^{5.4}$ and $R^{5.5}$ are independently hydrogen, fluorine, $-CN$, $-CH_3$, $-CH_2CH_3$, $-CF_3$, $-(CH_2)OH$, $-(CH_2)_2OH$, $-(CH_3)_2OH$, $-CO_2H$, $-CO_2NH_2$ or $-CO_2CH_2CH_3$.

Embodiment PIII62 The compound of embodiment PIII56, wherein $R^{6.2}$ is hydrogen, $-CH_3$, $-CH_2OH$, $-(CH_2)_2OH$, $-(CH_2)_3OH$, $-CH_2NH_2$, $-(CH_2)_2NH_2$, $-(CH_2)_3NH_2$, $-CH_2CO_2CH_2CH_3$, $-(CH_2)_2CO_2CH_2CH_3$, $-(CH_2)_3CO_2CH_2CH_3$, $-CH_2CO_2H$, $-(CH_2)_2CO_2H$, $-(CH_2)_3CO_2H$, $-(CH_2)CO_2NH_2$, $-(CH_2)_2CONH_2$, $-(CH_2)_3CO_2NH_2$, $-(CH_2)CHFCO_2H$, $-(CH_2)_2CHFCO_2H$, $-(CH_2)CF_2CO_2H$, $-(CH_2)_2CF_2CO_2H$,

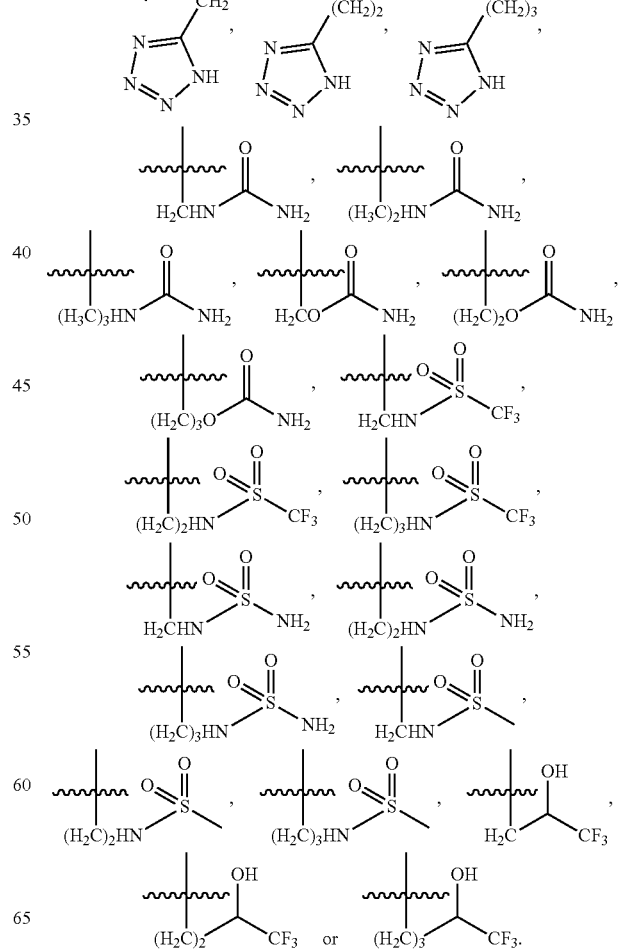

Embodiment PIII63 The compound of embodiment PIII55, wherein the compound has structural Formula (IXb):

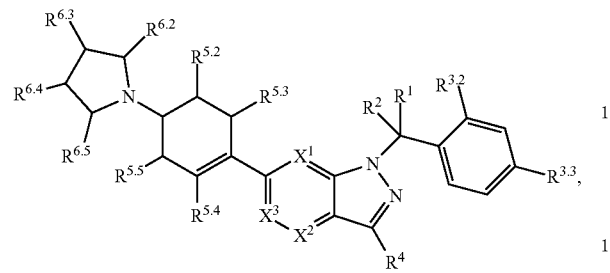

(IXb)

or a pharmaceutically acceptable salt thereof.

Embodiment PIII64 The compound of embodiment PIII63, wherein $X^1$ and $X^2$ are independently N.

Embodiment PIII65 The compound of embodiment PIII63, wherein $R^1$ and $R^2$ are independently hydrogen or unsubstituted alkyl.

Embodiment PIII66 The compound of embodiment PIII63, wherein $R^{3.2}$ and $R^{3.3}$ are independently halogen, —CN, $CF_3$ or unsubstituted alkyl.

Embodiment PIII67 The compound of embodiment PIII63, wherein $R^4$ is —CN, —C(O)NH$_2$, —CF$_3$, —CH$_3$ or —C(CH$_3$)$_2$OH.

Embodiment PIII68 The compound of embodiment PIII63, wherein $R^{5.2}$ and $R^{5.5}$ are independently hydrogen, fluorine, —CN, —CH$_3$, —CH$_2$CH$_3$, —CF$_3$, —(CH$_2$)OH, —(CH$_2$)$_2$OH, —(CH$_3$)$_2$OH, —CO$_2$H, —CO$_2$NH$_2$ or —CO$_2$CH$_2$CH$_3$.

Embodiment PIII69 The compound of embodiment PIII63, wherein $R^{6.2}$ is hydrogen, —OH, —CH$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H,

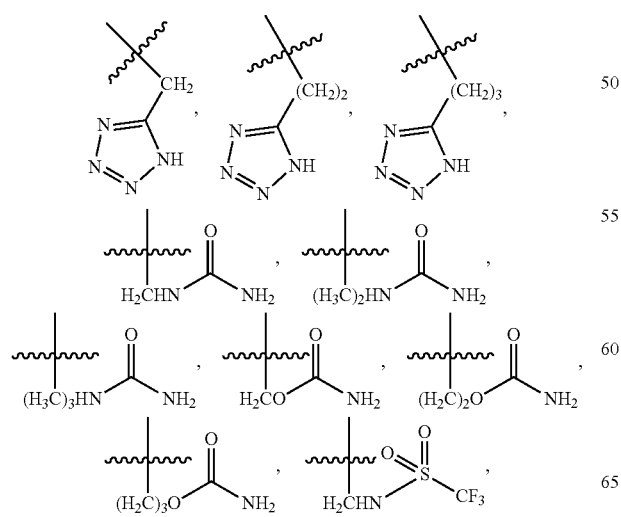

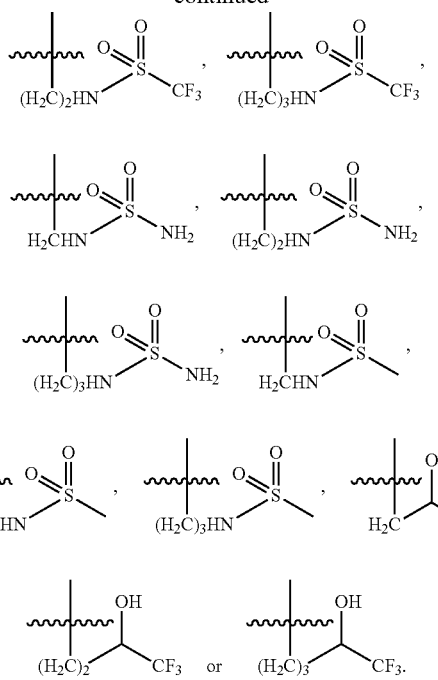

Embodiment PIII70 The compound of embodiment PIII3, wherein the compound has structural Formula (X):

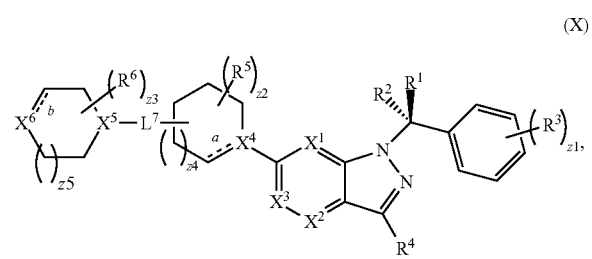

(X)

or a pharmaceutically acceptable salt thereof.

Embodiment PIII71 The compound of embodiment PIII70, wherein $R^1$ is hydrogen.

Embodiment PIII72 The compound of embodiment PIII70, wherein $R^2$ is hydrogen.

Embodiment PIII73 The compound of embodiment PIII1, wherein the compound is:

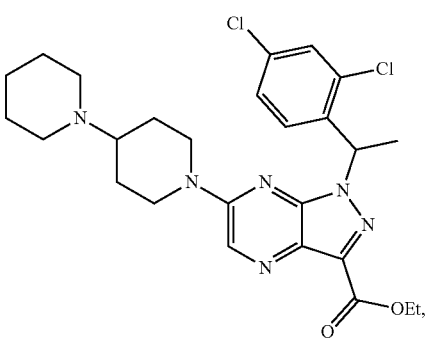

551
-continued
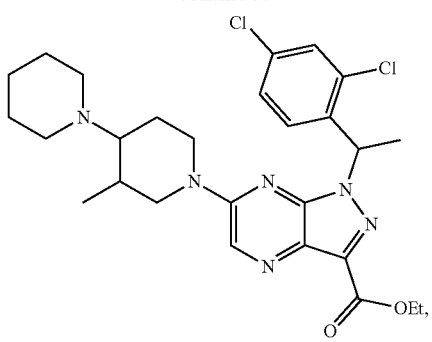
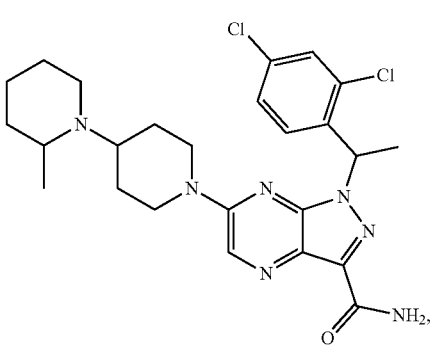
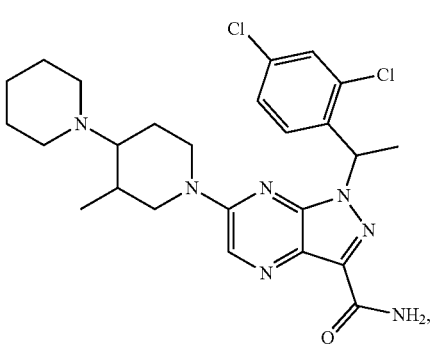
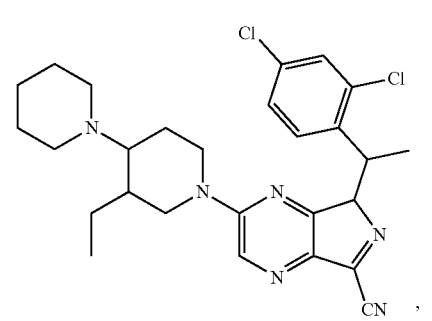
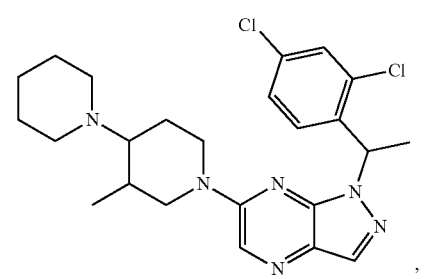
552
-continued
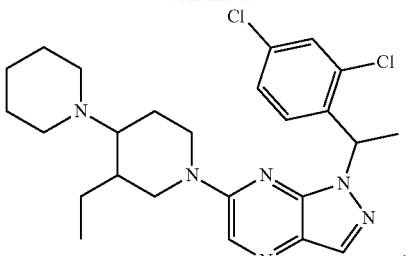
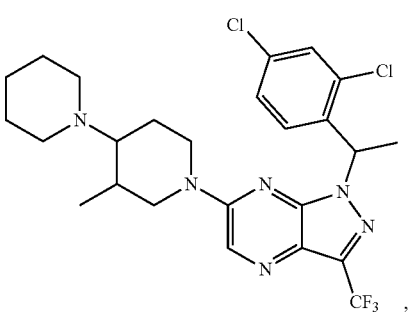
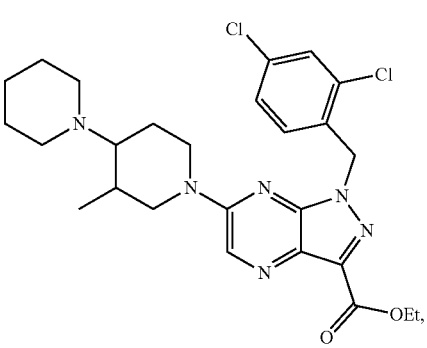
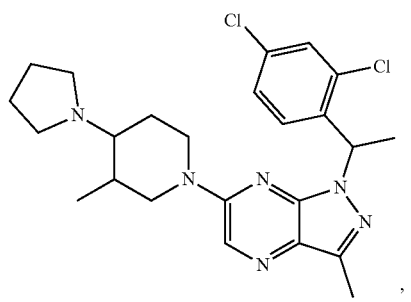
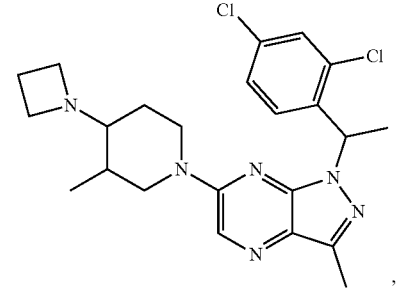

553
-continued
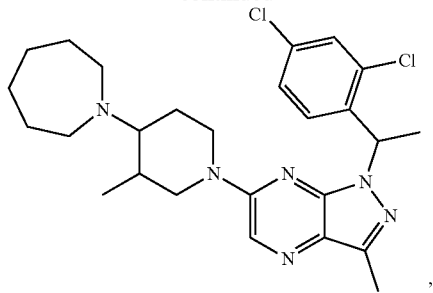
,
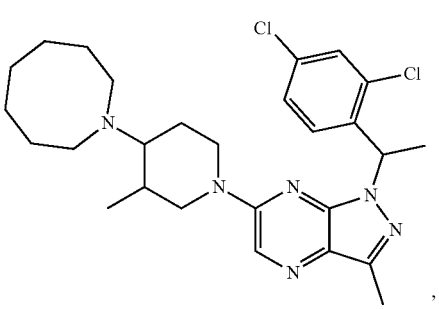
,
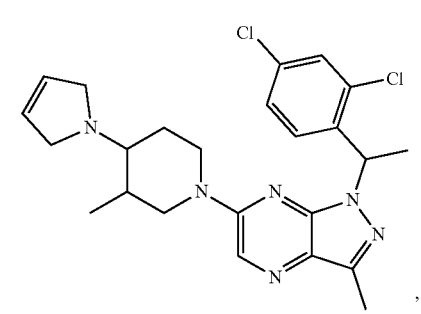
,
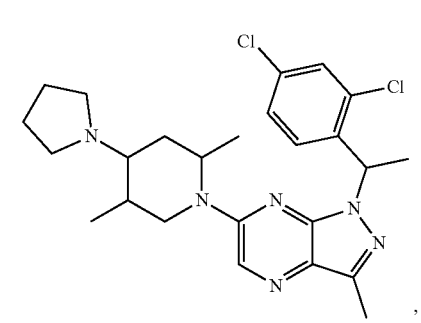
,
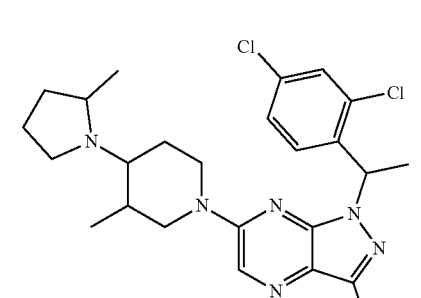
,
554
-continued
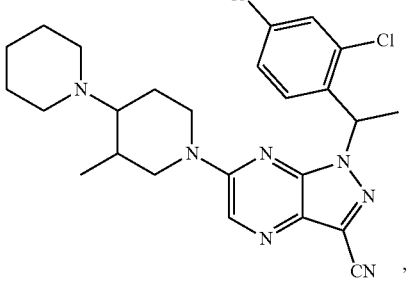
,
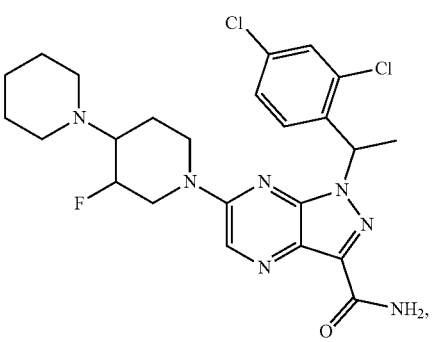
,
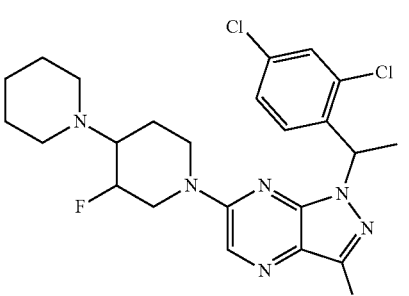
,
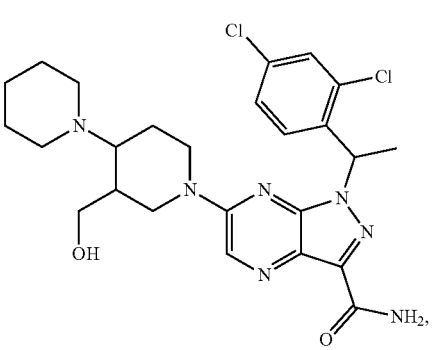
,
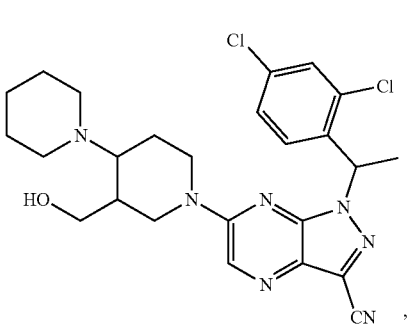
, 555
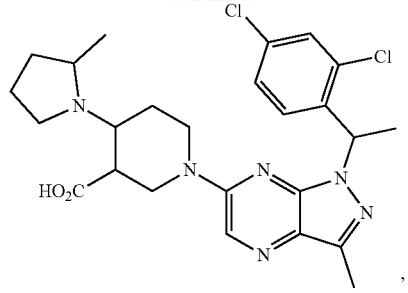
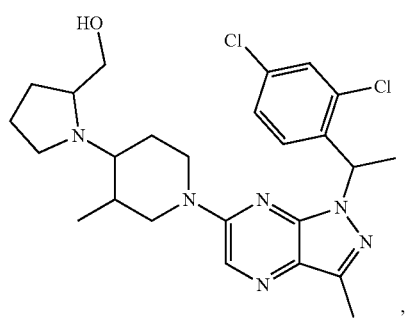
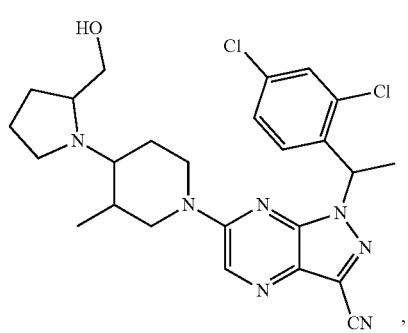
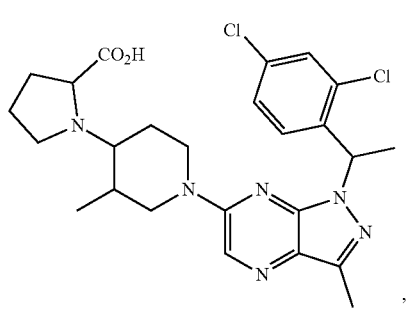
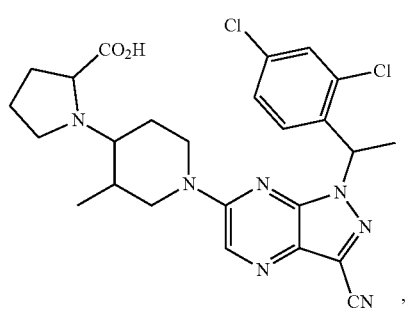
556
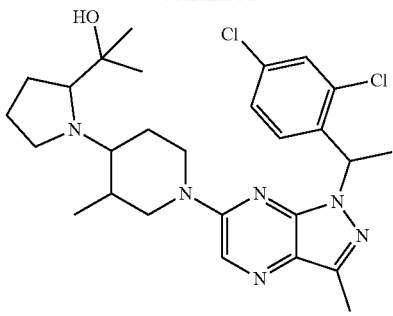
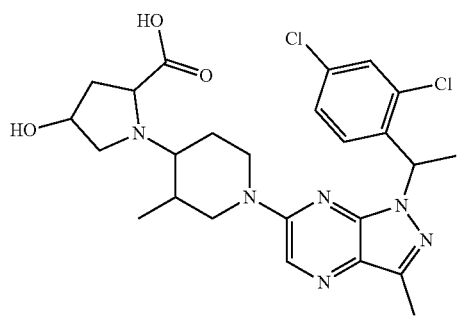
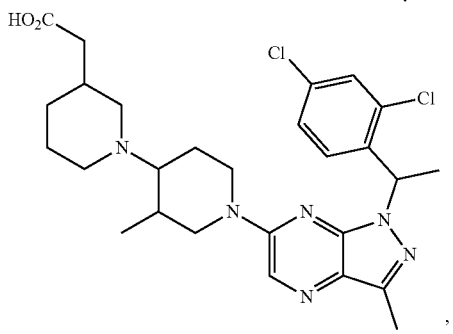
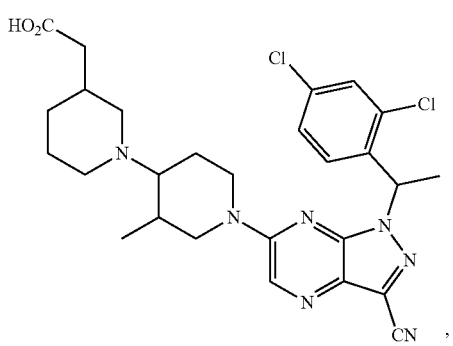
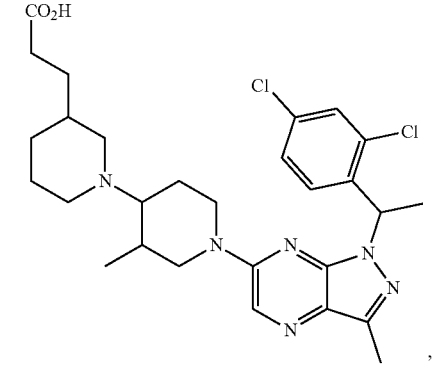

557
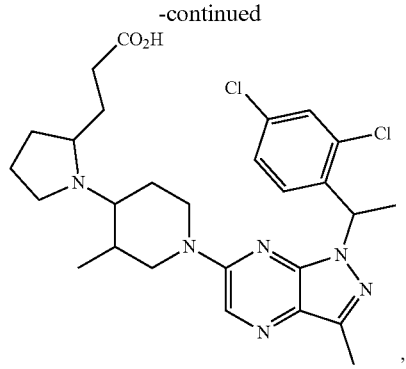
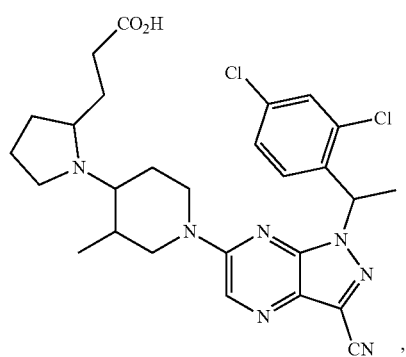
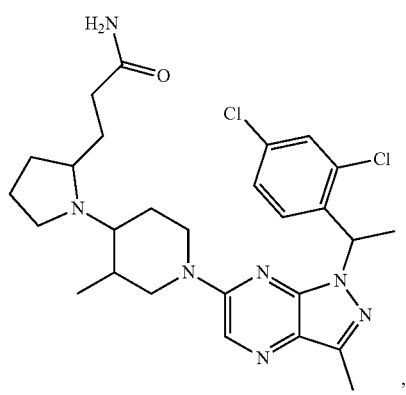
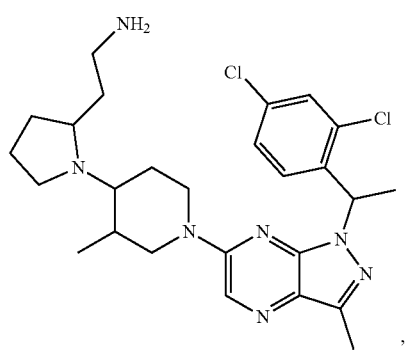
558
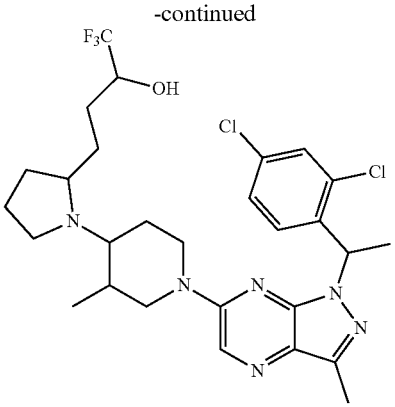
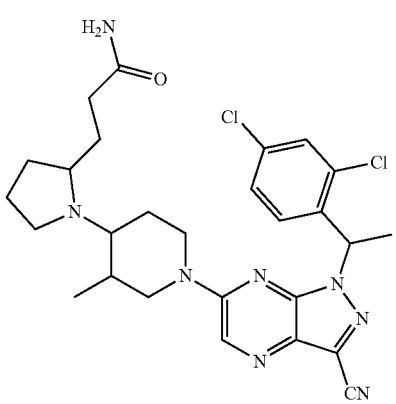
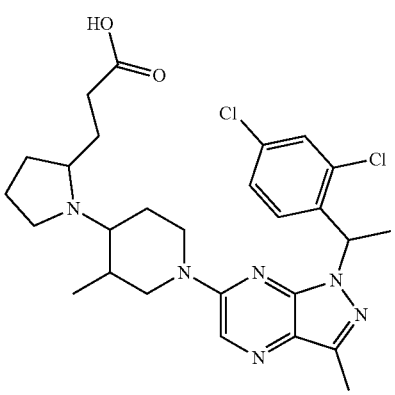
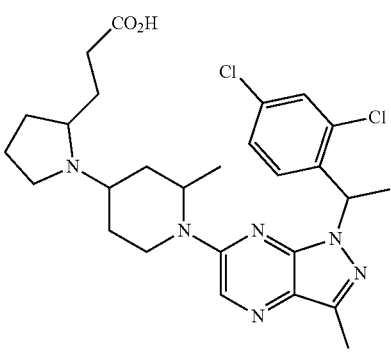

559
-continued
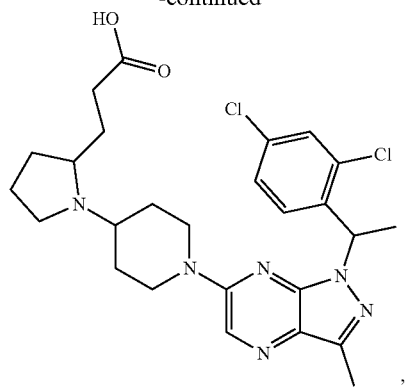
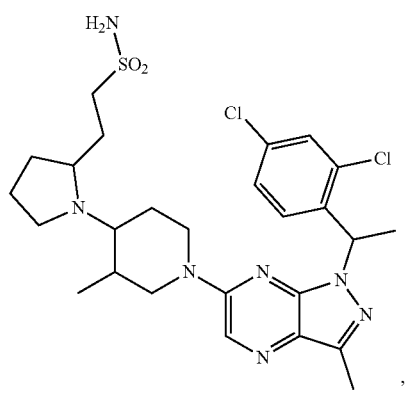
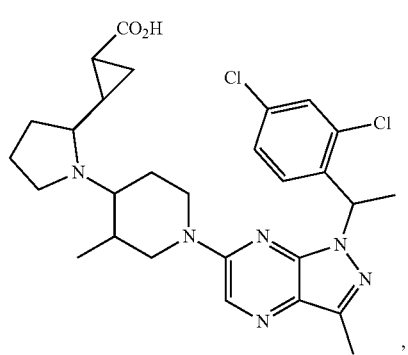
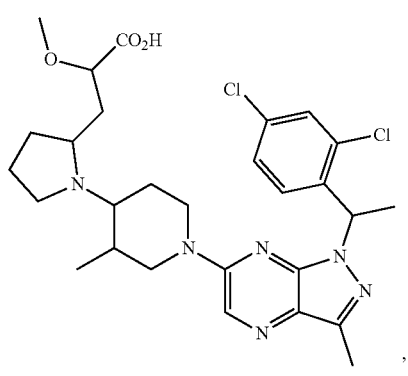
560
-continued
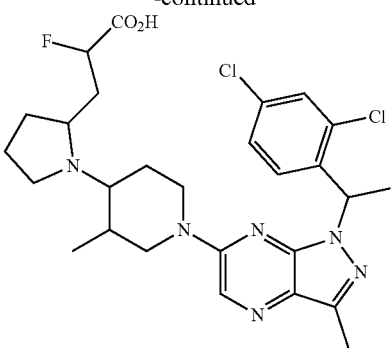
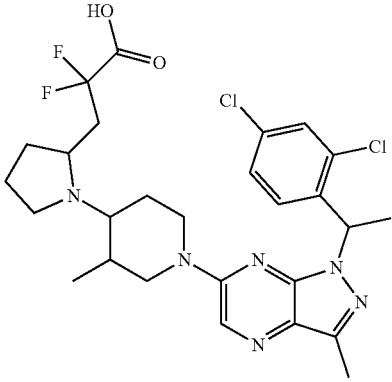
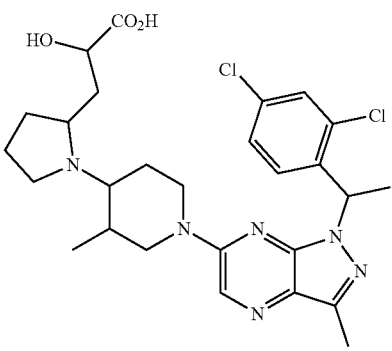
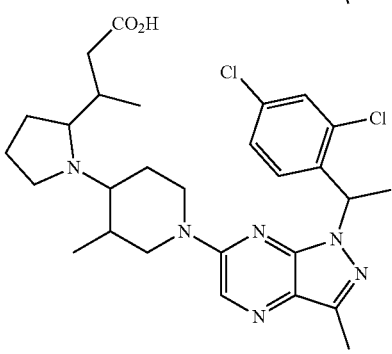
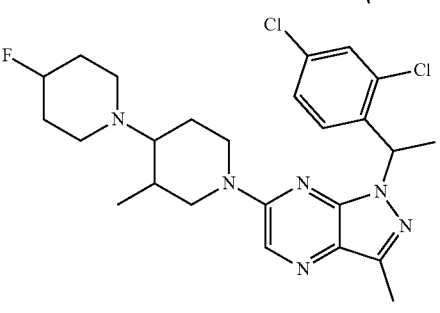

561
-continued
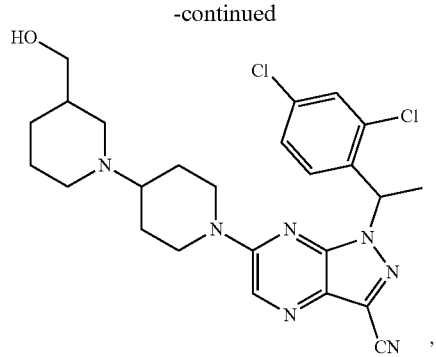
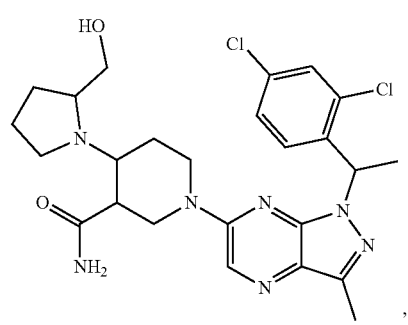
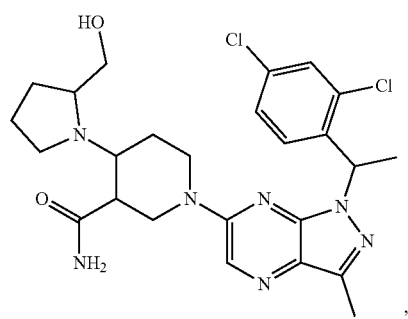
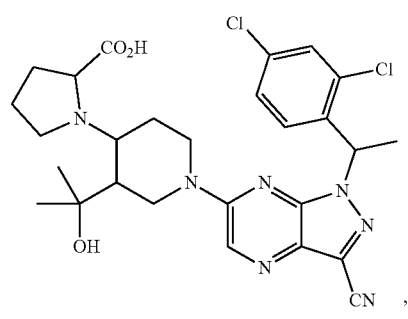
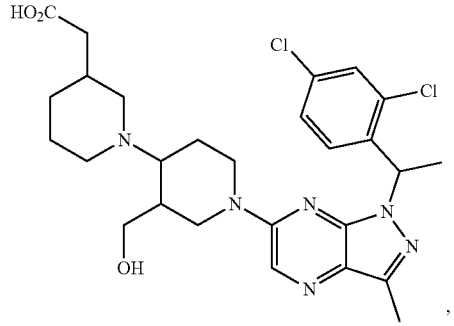
562
-continued
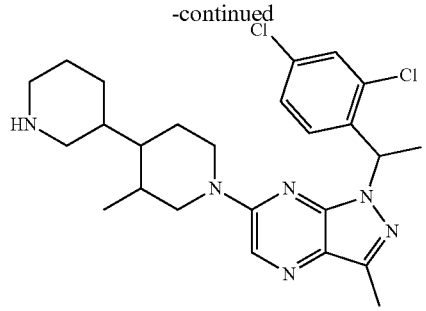
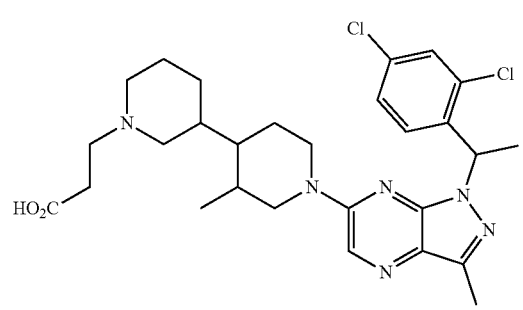
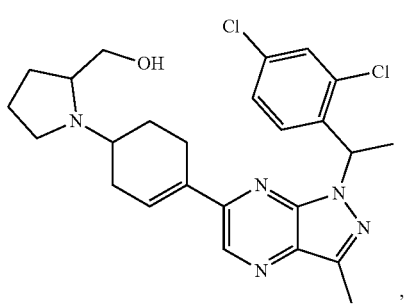
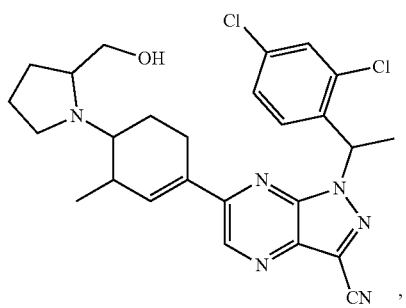
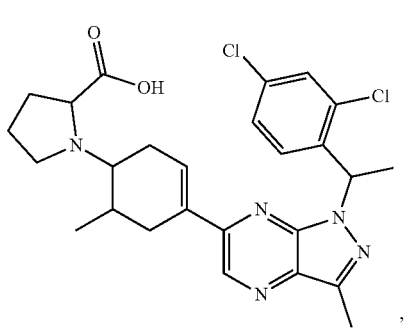

563
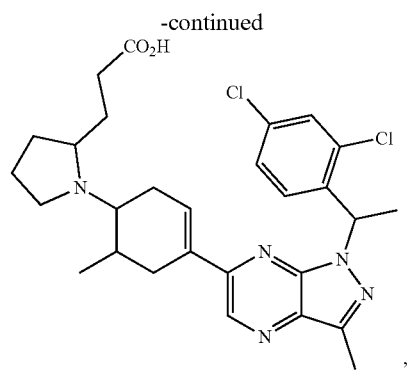
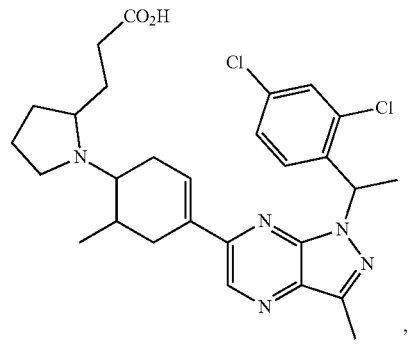
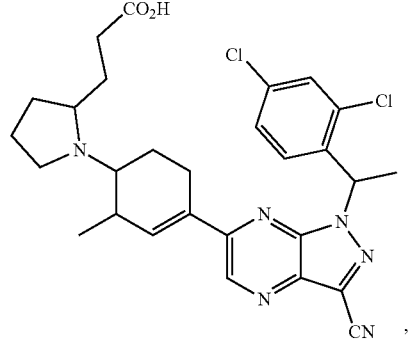
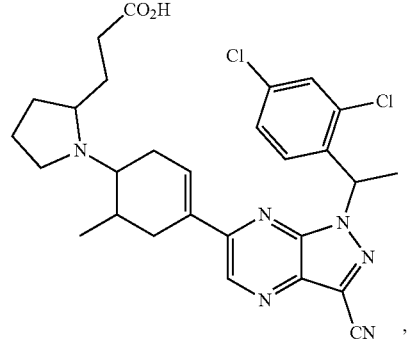
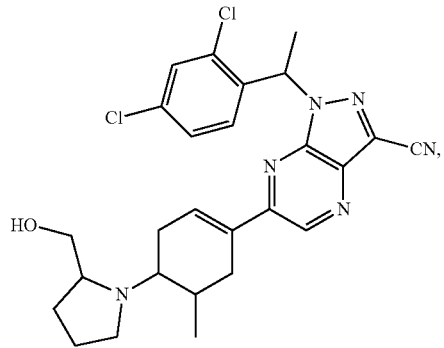
564
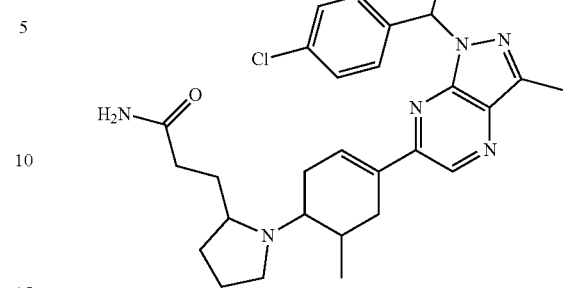
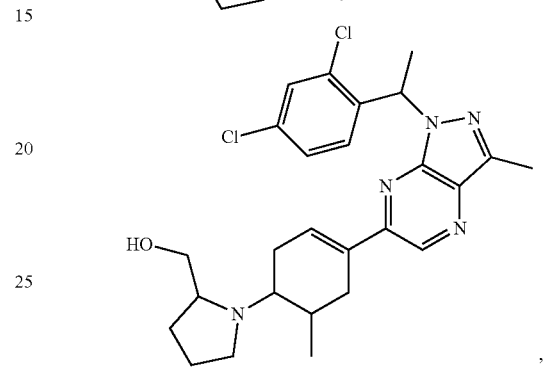
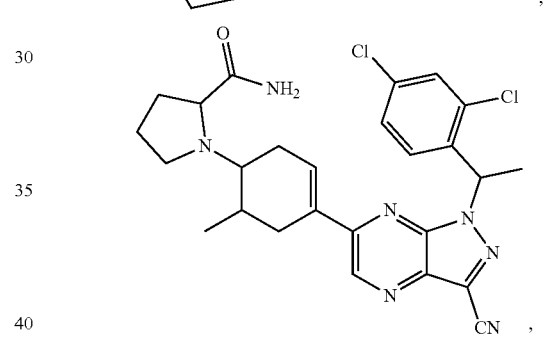
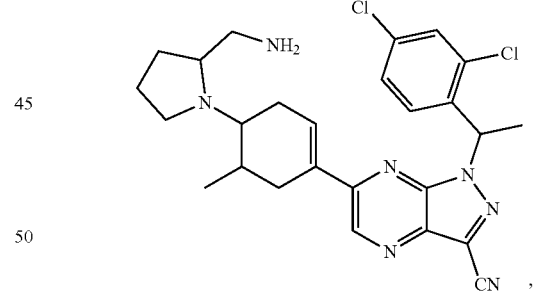
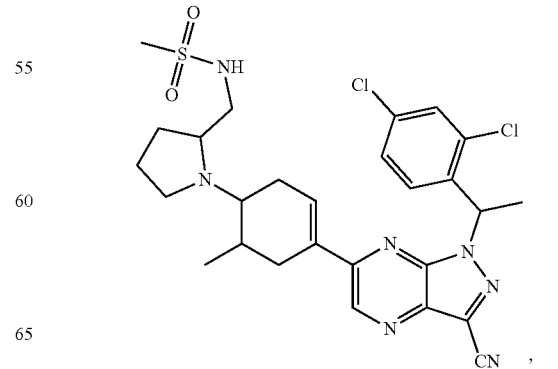

565
-continued
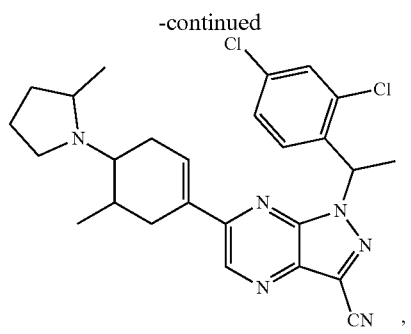
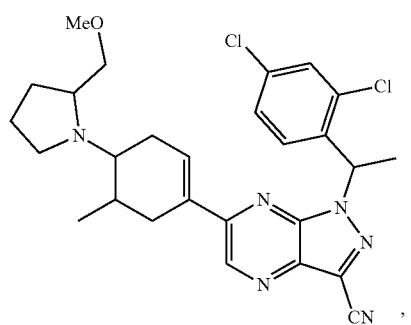
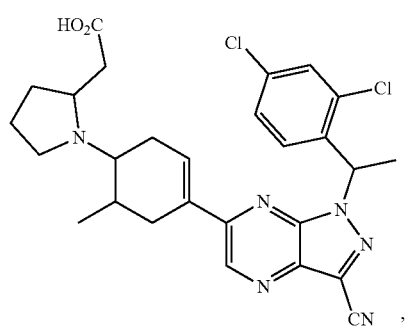
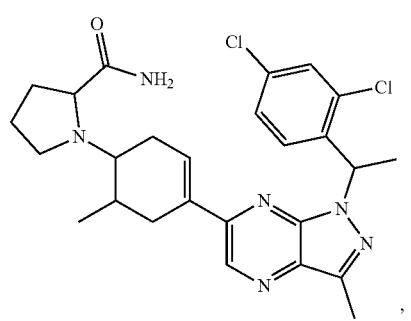
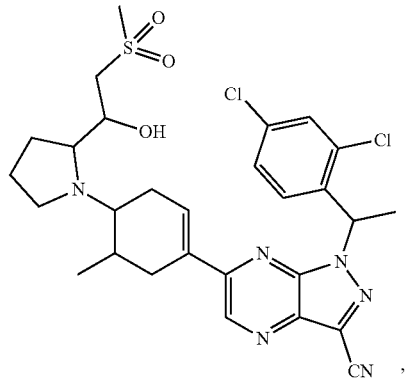
566
-continued
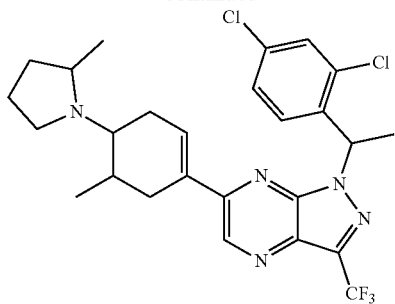
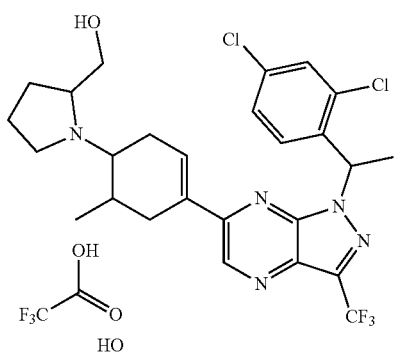
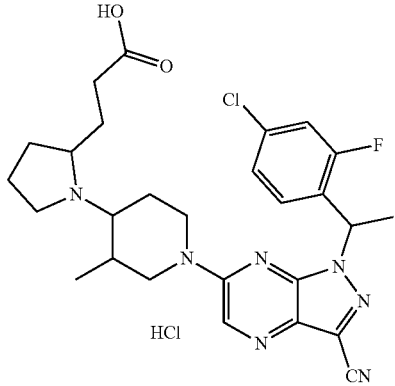
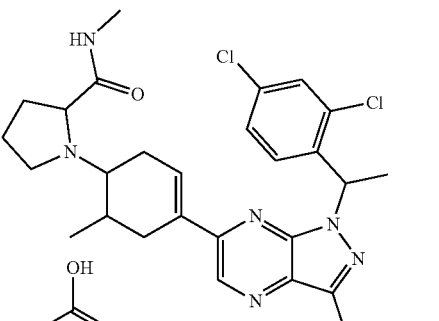
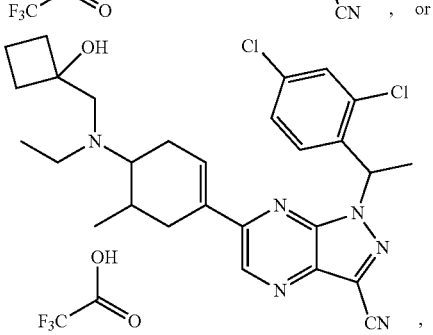
or a pharmaceutically acceptable salt thereof.

Embodiment PIII74 A pharmaceutical composition, comprising a compound of embodiment PIII1 and a pharmaceutically acceptable excipient.

Embodiment PIII75 A method of inhibiting C—C chemokine receptor type 4 (CCR4), the method comprising contacting CCR4 with a compound of embodiment PIII1.

Embodiment PIII76 A method of treating or preventing a disease or disorder mediated by CCR4, comprising administering to a subject in need thereof a therapeutically effective amount of a compound of embodiment PIII1 or a pharmaceutically acceptable salt thereof.

Embodiment PIII77 The method of embodiment PIII76, wherein the disease or disorder is an immune or inflammatory disease or disorder.

Embodiment PIII78 The method of embodiment PIII77, further comprising co-administering an anti-inflammatory agent in combination with a compound of structural Formula (I).

Embodiment PIII79 The method of embodiment PIII78, wherein the anti-inflammatory is thalidomide or a derivative thereof, a retinoid, dithranol or calcipotriol, a non-steroidal anti-inflammatory agent (NSAID), cyclo-oxygenase inhibiting nitric oxide donors (CINODs), glucocorticosteroids, methotrexate, leflunomide, hydroxychloroquine, d-penicillamine, auranofin, analgesics; diacerein, hyaluronic acid derivatives or nutritional supplements.

Embodiment PIII80 The method of embodiment PIII76, wherein the disease or disorder is a cardiovascular or metabolic disease or disorder.

Embodiment PIII81 The method of embodiment PIII80, further comprising co-administering a cardiovascular agent or a metabolic disorder agent in combination with a compound of structural Formula (I).

Embodiment PIII82 The method of embodiment PIII81, wherein the cardiovascular agent is a calcium channel blocker, a beta-adrenoceptor blocker, an angiotensin-converting enzyme (ACE) inhibitor, an angiotensin-2 receptor antagonist, a lipid lowering agent, a modulator of blood cell morphology, a thrombolytic or an anticoagulant.

Embodiment PIII83. The method of embodiment PIII76, wherein the disease or disorder is cancer.

Embodiment PIII84. The method of embodiment PIII83, further comprising co-administering a chemotherapeutic agent or anticancer agent in combination with a compound of structural Formula (I).

Embodiment PIII85. The method of embodiment PIII84, wherein the chemotherapeutic agent or anticancer agent is an antiproliferative/antineoplastic drug, an antimetabolite, an antitumor antibiotic, an antimitotic agent, a topoisomerase inhibitor, a cytostatic agent, an oestrogen receptor down regulator, an antiandrogen, a LHRH antagonist or LHRH agonist, a progestogen, an aromatase inhibitor, an inhibitor of 5.alpha.-reductase, an agent which inhibits cancer cell invasion, an inhibitor of growth factor function, a farnesyl transferase inhibitor, a tyrosine kinase inhibitor, a serine/threonine kinase inhibitor, an inhibitor of the epidermal growth factor family, an inhibitor of the platelet-derived growth factor family, an inhibitor of the hepatocyte growth factor family; an antiangiogenic agent, a vascular damaging agent, an agent used in antisense therapy, an anti-ras antisense, an agent used in a gene therapy, an immunotherapeutic agent, or an antibody.

Embodiment PIII86. The method of embodiment PIII83, further comprising co-administering a therapeutically effective amount of at least two of: a CCR4 inhibitor, an inhibitor of the PD-L1/PD-1 pathway, an inhibitor of CTLA-4, or an agonistic antibody of CD137 (4-1BB).

Embodiment PIII87. The method of embodiment PIII83, further comprising co-administering a therapeutically effective amount of at least two of: a CCR4 inhibitor, an immune modulator agent or an agent from Table 1.

Embodiment PIII88. The method of any one of embodiments PIII83 to PIII87, wherein the cancer is colon cancer or pancreatic cancer.

EMBODIMENTS

Embodiment 1. A compound having structural Formula (I):

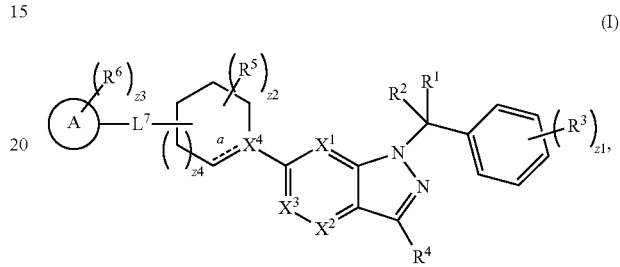

or a pharmaceutically acceptable salt thereof, wherein:
A is a substituted or unsubstituted heterocycloalkyl;
$X^1$ is $CR^8$ or N;
$X^2$ is $CR^9$ or N;
$X^3$ is $CR^{10}$ or N;
$X^4$ is C, $CR^{11}$ or N;
z1 is an integer from 0 to 5;
z2 is an integer from 0 to 13;
z3 is an integer from 0 to 12;
z4 is an integer from 0 to 3;
⸺ is a single bond or double bond, wherein if ⸺ is a single bond, then $X^4$ is $CR^{11}$ or N, and if ⸺ is a double bond, then $X^4$ is C;
$L^7$ is a bond, —O—, —S—, —$NR^{7B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, halogen, —$CX^{2.1}_3$, —$CHX^{2.1}_2$, —$CH_2X^{2.1}$, —CN, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently hydrogen, halogen, —$CX^{3.1}_3$, —$CHX^{3.1}_2$, —$CH_2X^{3.1}$, —CN, —$SO_{n3}R^{3A}$, —$SO_{v3}NR^{3B}R^{3C}$, —$NHNR^{3B}R^{3C}$, —$ONR^{3B}R^{3C}$, —$NHC(O)NHNR^{3B}R^{3C}$, —$NHC(O)NR^{3B}R^{3C}$, —$N(O)_{m3}$, —$NR^{3B}R^{3C}$, —$C(O)R^{3D}$, —$C(O)OR^{3D}$, —$C(O)NR^{3B}R^{3C}$, —$OR^{3A}$, —$NR^{3B}SO_2R^{3A}$, —$NR^{3B}C(O)R^{3D}$, —$NR^{3B}C(O)OR^{3D}$, —$NR^{3B}OR^{3D}$, —$OCX^{3.1}_3$, —$OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^4$ is hydrogen, halogen, —$CX^{4.1}_3$, —$CHX^{4.1}_2$, —$CH_2X^{4.1}$, —CN, —$SO_{n4}R^{4A}$, —$SO_{v4}NR^{4B}R^{4C}$, —$NHNR^{4B}R^{4C}$, —$ONR^{4B}R^{4C}$, —$NHC(O)NHNR^{4B}R^{4C}$, —$NHC(O)NR^{4B}R^{4C}$, —$N(O)_{m4}$, —$NR^{4B}R^{4C}$, —$C(O)R^{4D}$, —$C(O)OR^{4D}$, —$C(O)NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is independently hydrogen, halogen, oxo, —$CX^{5.1}_3$, —$CHX^{5.1}_2$, —$CH_2X^{5.1}$, —CN, —$SO_{n5}R^{5A}$, —$SO_{v5}NR^{5B}R^{5C}$, —$NHNR^{5B}R^{5C}$, —$ONR^{5B}R^{5C}$, —$NHC(O)NHNR^{5B}R^{5C}$, —$NHC(O)NR^{5B}R^{5C}$, —$N(O)_{m5}$, —$NR^{5B}R^{5C}$, —$C(O)R^{5D}$, —$C(O)OR^{5D}$, —$C(O)NR^{5B}R^{5C}$, —$OR^{5A}$, —$NR^{5B}SO_2R^{5A}$, —$NR^{5B}C(O)R^{5D}$, —$NR^{5B}C(O)OR^{5D}$, —$NR^{5B}OR^{5D}$, —$OCX^{5.1}_3$, —$OCHX^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^6$ is independently hydrogen, halogen, oxo, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —$NHC(O)NHNR^{6B}R^{6C}$, —$NHC(O)NR^{6B}R^{6C}$, —$N(O)_{m6}$, —$NR^{6B}R^{6C}$, —$C(O)R^{6D}$, —$C(O)OR^{6D}$, —$C(O)NR^{6B}R^{6C}$, —$OR^{6A}$, —$NR^{6B}SO_2R^{6A}$, —$NR^{6B}C(O)R^{6D}$, —$NR^{6B}C(O)OR^{6D}$, —$NR^{6B}OR^{6D}$, —$OCX^{6.1}_3$, —$OCHX^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^8$ is hydrogen, halogen, —$CX^{8.1}_3$, —$CHX^{8.1}_2$, —$CH_2X^{8.1}$, —CN, —$SO_{n8}R^{8A}$, —$SO_{v8}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m8}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$CX^{9.1}_3$, —$CHX^{9.1}_2$, —$CH_2X^{9.1}$, —CN, —$SO_{n9}R^{9A}$, —$SO_{v9}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m9}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^{10}$ is hydrogen, halogen, —$CX^{10.1}_3$, —$CHX^{10.1}_2$, —$CH_2X^{10.1}$, —CN, —$SO_{n10}R^{10A}$, —$SO_{v10}NR^{10B}R^{10C}$, —$NHNR^{10B}R^{10C}$, —$ONR^{10B}R^{10C}$, —$NHC(O)NHNR^{10B}R^{10C}$, —$NHC(O)NR^{10B}R^{10C}$, —$N(O)_{m10}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, —$CX^{11.1}_3$, —$CHX^{11.1}_2$, —$CH_2X^{11.1}$, —CN, —$SO_{n11}R^{11A}$, —$SO_{v11}NR^{11B}R^{11C}$, —$NHNR^{11B}R^{11C}$, —$ONR^{11B}R^{11C}$, —$NHC(O)NHNR^{11B}R^{11C}$, —$NHC(O)NR^{11B}R^{11C}$, —$N(O)_{m11}$, —$NR^{11B}R^{11C}$, —$C(O)R^{11D}$, —$C(O)OR^{11D}$, —$C(O)NR^{11B}R^{11C}$, —$OR^{11A}$, —$NR^{11B}SO_2R^{11A}$, —$NR^{11B}C(O)R^{11D}$, —$NR^{11B}C(O)OR^{11D}$, —$NR^{11B}OR^{11D}$, —$OCX^{11.1}_3$, —$OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7B}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$ and $R^{11D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{8B}$ and $R^{8C}$, $R^{9B}$ and $R^{9C}$, $R^{10B}$ and $R^{10C}$, $R^{11B}$ and $R^{11C}$ substituents bonded to the same nitrogen atom may optionally be joined to form a substituted or unsubstituted heterocycloalkyl or substituted or unsubstituted heteroaryl;

n1, n2, n3, n4, n5, n6, n8, n9, n10 and n11 are independently an integer from 0 to 4;

m1, m2, m3, m4, m5, m6, m8, m9, m10, m11, v1, v2, v3, v4, v5, v6, v8, v9, v10, and v11 are independently 1 or 2; and $X^{1.1}$, $X^{2.1}$, $X^{3.1}$, $X^{4.1}$, $X^{5.1}$, $X^{6.1}$, $X^{8.1}$, $X^{9.1}$, $X^{10.1}$, and $X^{11.1}$ are independently —Cl, —Br, —I or —F, wherein at least one of $X^1$, $X^2$, and $X^3$ is N.

Embodiment 2. The compound of embodiment 1, or a pharmaceutically acceptable salt thereof, wherein A is a 4-membered to 8-membered substituted or unsubstituted heterocycloalkyl.

Embodiment 3. The compound of one of embodiments 1 to 2, or a pharmaceutically acceptable salt thereof, wherein the compound has structural Formula (Ia):

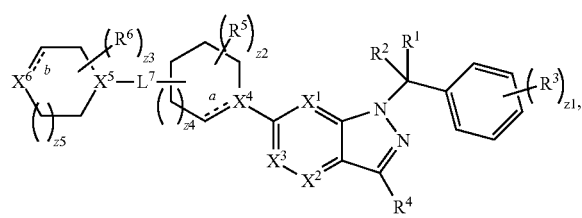

(Ia)

or a pharmaceutically acceptable salt thereof, wherein:
$X^5$ is —$CR^{12}$ or —N;
$X^6$ is —$CR^{13}$, —$CR^{13}R^{14}$, —N or —$NR^{15}$;
z3 is an integer from 0 to 12;
z5 is an integer from 0 to 3;
$R^{12}$ is hydrogen, halogen, —$CX^{12.1}_3$, —$CHX^{12.1}_2$, —$CH_2X^{12.1}$, —CN, —$SO_{n12}R^{12A}$, —$SO_{v12}NR^{12B}R^{12C}$, —NHNR$^{12B}$R$^{12C}$, —ONR$^{12B}$R$^{12C}$, —NHC(O)NHNR$^{12B}$R$^{12C}$, —NHC(O)NR$^{12B}$R$^{12C}$, —N(O)$_{m12}$, —NR$^{12B}$R$^{12C}$, —C(O)R$^{12D}$, —C(O)OR$^{12D}$, —C(O)NR$^{12B}$R$^{12C}$, —OR$^{12A}$, —NR$^{12B}$SO$_2$R$^{12A}$, —NR$^{12B}$C(O)R$^{12D}$, —NR$^{12B}$C(O)OR$^{12D}$, —NR$^{12B}$OR$^{12D}$, —OCX$^{12.1}_3$, —OCHX$^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, halogen, —CX$^{13.1}_3$, —CHX$^{13.1}_2$, —CH$_2$X$^{13.1}$, —CN, —SO$_{n13}$R$^{13A}$, —SO$_{v13}$NR$^{13B}$R$^{13C}$, —NHNR$^{13B}$R$^{13C}$, —ONR$^{13B}$R$^{13C}$, —NHC(O)NHNR$^{13B}$R$^{13C}$, —NHC(O)NR$^{13B}$R$^{13C}$, —N(O)$_{m13}$, —NR$^{13B}$R$^{13C}$, —C(O)R$^{13D}$, —C(O)OR$^{13D}$, —C(O)NR$^{13B}$R$^{13C}$, —OR$^{13A}$, —NR$^{13B}$SO$_2$R$^{13A}$, —NR$^{13B}$C(O)R$^{13D}$, —NR$^{13B}$C(O)OR$^{13D}$, —NR$^{13B}$OR$^{13D}$, —OCX$^{13.1}_3$, —OCHX$^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{14}$ is hydrogen, halogen, —CX$^{14.1}_3$, —CHX$^{14.1}_2$, —CH$_2$X$^{14.1}$, —CN, —SO$_{n14}$R$^{14A}$, —SO$_{v14}$NR$^{14B}$R$^{14C}$, —NHNR$^{14B}$R$^{14C}$, —ONR$^{14B}$R$^{14C}$, —NHC(O)NHNR$^{14B}$R$^{14C}$, —NHC(O)NR$^{14B}$R$^{14C}$, —N(O)$_{m14}$, —NR$^{14B}$R$^{14C}$, —C(O)R$^{14D}$, —C(O)OR$^{14D}$, —C(O)NR$^{14B}$R$^{14C}$, —OR$^{14A}$, —NR$^{14B}$SO$_2$R$^{14A}$, —NR$^{14B}$C(O)R$^{14D}$, —NR$^{14B}$C(O)OR$^{14D}$, —NR$^{14B}$OR$^{14D}$, —OCX$^{14.1}_3$, —OCHX$^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{15}$ is hydrogen, halogen, —CX$^{15.1}_3$, —CHX$^{15.1}_2$, —CH$_2$X$^{15.1}$, —CN, —SO$_{n15}$R$^{15A}$, —SO$_{v15}$NR$^{15B}$R$^{15C}$, —NHNR$^{15B}$R$^{15C}$, —ONR$^{15B}$R$^{15C}$, —NHC(O)NHNR$^{15B}$R$^{15C}$, —NHC(O)NR$^{15B}$R$^{15C}$, —N(O)$_{m15}$, —NR$^{15B}$R$^{15C}$, —C(O)R$^{15D}$, —C(O)OR$^{15D}$, —C(O)NR$^{15B}$R$^{15C}$, —OR$^{15A}$, —NR$^{15B}$SO$_2$R$^{15A}$, —NR$^{15B}$C(O)R$^{15D}$, —NR$^{15B}$C(O)OR$^{15D}$, —NR$^{15B}$OR$^{15D}$, —OCX$^{15.1}_3$, —OCHX$^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{12A}$, R$^{12B}$, R$^{12C}$, R$^{12D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$ and R$^{15D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{12B}$ and R$^{12C}$, R$^{13B}$ and R$^{13C}$, R$^{14B}$ and R$^{14C}$ and R$^{15B}$ and R$^{15C}$ substituents bonded to the same nitrogen atom may optionally be joined to form a substituted or unsubstituted heterocycloalkyl or substituted or unsubstituted heteroaryl;

n12, n13, n14, and n15 are independently an integer from 0 to 4;

m12, m13, m14, m15, v12, v13, v14, and v15 are independently 1 or 2;

═ is a single bond or double bond, wherein if ═ is a single bond, then X$^6$ is CR$^{13}$R$^{14}$ or NR$^{15}$, and if ═ is a double bond, then X$^6$ is N or CR$^{13}$; and X$^{12.1}$, X$^{13.1}$, X$^{14.1}$ and X$^{15.1}$ are independently —Cl, —Br, —I or —F.

Embodiment 4. The compound of one of embodiments 1 to 3, or a pharmaceutically acceptable salt thereof, wherein:
z1 is 2; and
z4 is 1.

Embodiment 5. The compound of one of embodiments 1 to 4, or a pharmaceutically acceptable salt thereof, wherein R$^1$ and R$^2$ are independently hydrogen, substituted or unsubstituted alkyl or substituted or unsubstituted heteroalkyl.

Embodiment 6. The compound of one of embodiments 1 to 5, or a pharmaceutically acceptable salt thereof, wherein L$^7$ is a bond.

Embodiment 7. The compound of embodiment 3, or a pharmaceutically acceptable salt thereof, wherein the compound has structural Formula (II):

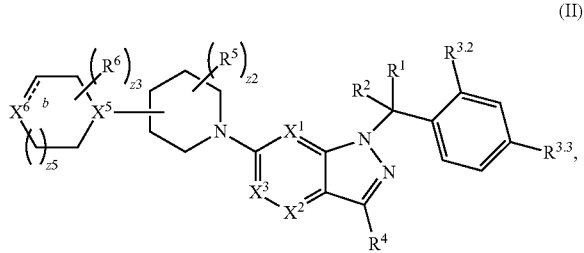

(II)

or a pharmaceutically acceptable salt thereof, wherein:

R$^4$ is hydrogen, —CX$^{4.1}_3$, —CN, —C(O)R$^{4D}$, —C(O)OR$^{4D}$, —C(O)NR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{3.2}$ is hydrogen, halogen, —CX$^{3.2}_3$, —CHX$^{3.2}_2$, —CH$_2$X$^{3.2}$, —CN, —SO$_{n3.2}$R$^{3.2A}$, —SO$_{v3.2}$NR$^{3.2B}$R$^{3.2C}$, —NHNR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}_3$, —OCHX$^{3.2}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{3.3}$ is hydrogen, halogen, —CX$^{3.3}_3$, —CHX$^{3.3}_2$, —CH$_2$X$^{3.3}$, —CN, —SO$_{n3.3}$R$^{3.3A}$, —SO$_{v3.3}$NR$^{3.3B}$R$^{3.3C}$, —NHNR$^{3.3B}$R$^{3.3C}$, —ONR$^{3.3B}$R$^{3.3C}$, —NHC(O)NHNR$^{3.3B}$R$^{3.3C}$, —NHC(O)NR$^{3.3B}$R$^{3.3C}$, —N(O)$_{m3.3}$, —NR$^{3.3B}$R$^{3.3C}$, —C(O)R$^{3.3D}$, —C(O)OR$^{3.3D}$, —C(O)NR$^{3.3B}$R$^{3.3C}$, —OR$^{3.3A}$, —NR$^{3.3B}$SO$_2$R$^{3.3A}$, —NR$^{3.3B}$C(O)R$^{3.3D}$, —NR$^{3.3B}$C(O)OR$^{3.3D}$, —NR$^{3.3B}$OR$^{3.3D}$, —OCX$^{3.3}_3$, —OCHX$^{3.3}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{3.2A}$, R$^{3.2B}$, R$^{3.2C}$, R$^{3.2D}$, R$^{3.3A}$, R$^{3.3B}$, R$^{3.3C}$ and R$^{3.3D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.2B}$ and $R^{3.2C}$, $R^{3.3B}$ and $R^{3.3C}$ substituents bonded to the same nitrogen atom may optionally be joined to form a substituted or unsubstituted heterocycloalkyl or substituted or unsubstituted heteroaryl;

n3.2 and n3.3 are independently an integer from 0 to 4; m3.2, m3.3, v3.2, and v3.3 are independently 1 or 2; and $X^{3.2}$ and $X^{3.3}$ are independently —Cl, —Br, —I or —F.

Embodiment 8. The compound of embodiment 7, or a pharmaceutically acceptable salt thereof, wherein the compound has structural Formula (III):

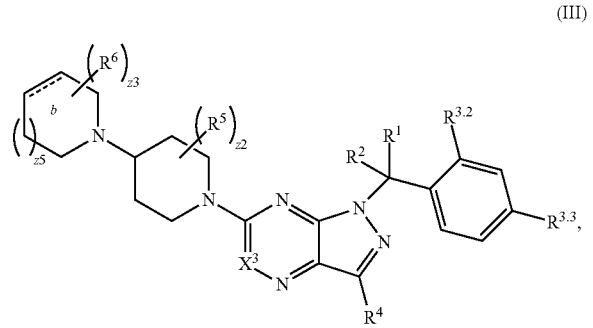

(III)

or a pharmaceutically acceptable salt thereof.

Embodiment 9. The compound of one of embodiments 7 to 8, or a pharmaceutically acceptable salt thereof, wherein the compound has structural Formula (IIIa):

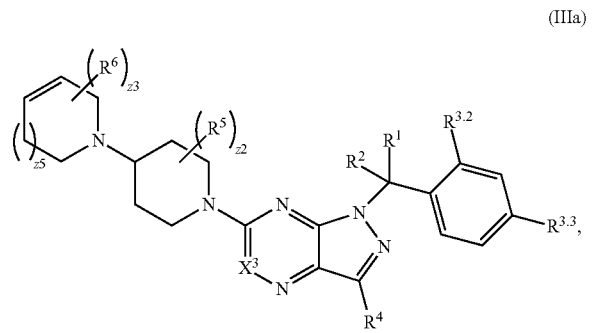

(IIIa)

or a pharmaceutically acceptable salt thereof.

Embodiment 10. The compound of one of embodiments 7 to 8, or a pharmaceutically acceptable salt thereof, wherein the compound has structural Formula (IIIb):

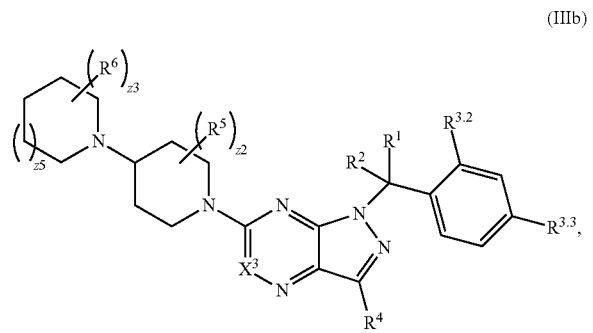

(IIIb)

or a pharmaceutically acceptable salt thereof.

Embodiment 11. The compound of embodiment 3, or a pharmaceutically acceptable salt thereof, wherein the compound has structural Formula (IV):

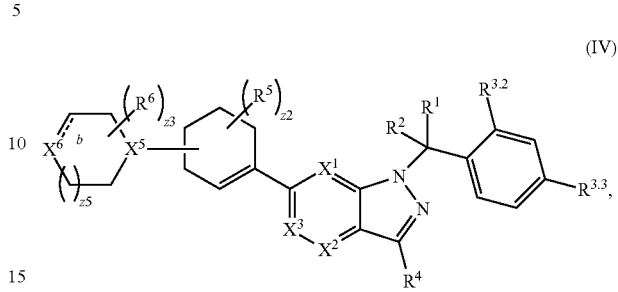

(IV)

or a pharmaceutically acceptable salt thereof, wherein:

$R^{3.2}$ is hydrogen, halogen, —$CX^{3.2}_3$, —$CHX^{3.2}_2$, —$CH_2X^{3.2}$, —CN, —$SO_{n3.2}R^{3.2A}$, —$SO_{v3.2}NR^{3.2B}R^{3.2C}$, —$NHNR^{3.2B}R^{3.2C}$, —$ONR^{3.2B}R^{3.2C}$, —NHC(O)NHNR$^{3.2B}R^{3.2C}$, —NHC(O)NR$^{3.2B}R^{3.2C}$, —N(O)$_{m3.2}$, —NR$^{3.2B}R^{3.2C}$, —C(O)R$^{3.2D}$, —C(O)OR$^{3.2D}$, —C(O)NR$^{3.2B}R^{3.2C}$, —OR$^{3.2A}$, —NR$^{3.2B}SO_2R^{3.2A}$, —NR$^{3.2B}C(O)R^{3.2D}$, —NR$^{3.2B}C(O)OR^{3.2D}$, —NR$^{3.2B}OR^{3.2D}$, —OCX$^{3.2}_3$, —OCHX$^{3.2}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.3}$ is hydrogen, halogen, —$CX^{3.3}_3$, —$CHX^{3.3}_2$, —$CH_2X^{3.3}$, —CN, —$SO_{n3.3}R^{3.3A}$, —$SO_{v3.3}NR^{3.3B}R^{3.3}c$, —$NHNR^{3.3B}R^{3.3C}$, —$ONR^{3.3B}R^{3.3}c$, —NHC(O)NHNR$^{3.3B}R^{3.3C}$, —NHC(O)NR$^{3.3B}R^{3.3C}$, —N(O)$_{m3.3}$, —NR$^{3.3B}R^{3.3C}$, —C(O)R$^{3.3D}$, —C(O)OR$^{3.3D}$, —C(O)NR$^{3.3B}R^{3.3C}$, —OR$^{3.3A}$, —NR$^{3.3B}SO_2R^{3.3A}$, —NR$^{3.3B}C(O)R^{3.3D}$, —NR$^{3.3B}C(O)OR^{3.3D}$, —NR$^{3.3B}OR^{3.3D}$, —OCX$^{3.3}_3$, —OCHX$^{3.3}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.2A}$, $R^{3.2B}$, $R^{3.2C}$, $R^{3.2D}$, $R^{3.3A}$, $R^{3.3B}$, $R^{3.3C}$ and $R^{3.3D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.2B}$ and $R^{3.2C}$, $R^{3.3B}$ and $R^{3.3C}$ substituents bonded to the same nitrogen atom may optionally be joined to form a substituted or unsubstituted heterocycloalkyl or substituted or unsubstituted heteroaryl;

n3.2 and n3.3 are independently an integer from 0 to 4; m3.2, m3.3, v3.2, and v3.3 are independently 1 or 2; and $X^{3.2}$ and $X^{3.3}$ are independently —Cl, —Br, —I or —F.

Embodiment 12. The compound of embodiment 11, or a pharmaceutically acceptable salt thereof, wherein the compound has structural Formula (V):

(V)

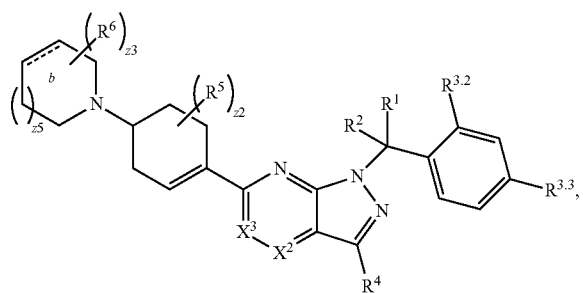

or a pharmaceutically acceptable salt thereof.

Embodiment 13. The compound of one of embodiments 11 to 12, or a pharmaceutically acceptable salt thereof, wherein the compound has structural Formula (Va):

(Va)

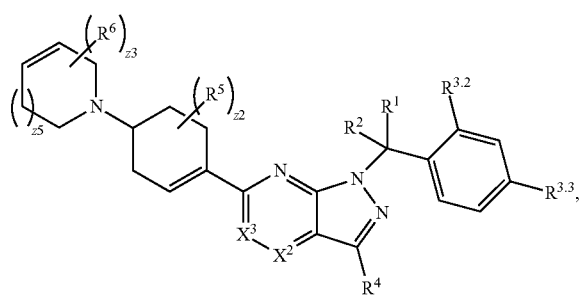

or a pharmaceutically acceptable salt thereof.

Embodiment 14. The compound of one of embodiments 11 to 12, or a pharmaceutically acceptable salt thereof, wherein the compound has structural Formula (Vb):

(Vb)

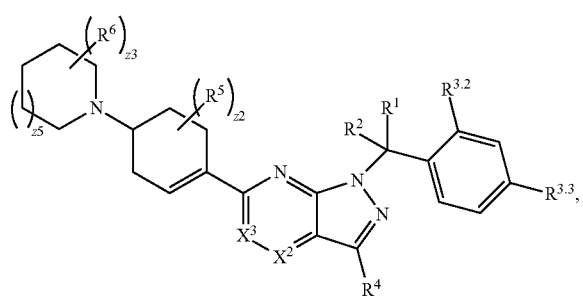

or a pharmaceutically acceptable salt thereof.

Embodiment 15. The compound of any one of embodiments 1 to 14, or a pharmaceutically acceptable salt thereof, wherein $R^4$ is hydrogen, —CN, —$CX^{4.1}_3$, —C(O)$R^{4D}$, —C(O)O$R^{4D}$, —C(O)N$R^{4B}R^{4C}$, substituted or unsubstituted alkyl or substituted or unsubstituted heteroalkyl.

Embodiment 16. The compound of one of embodiments 1 to 15, or a pharmaceutically acceptable salt thereof, wherein $R^4$ is —CN, —$CF_3$, —C(O)$NH_2$, —$CH_3$ or —C($CH_3$)$_2$OH.

Embodiment 17. The compound of any one of embodiments 7 to 15, or a pharmaceutically acceptable salt thereof, wherein $R^{3.2}$ and $R^{3.3}$ are independently halogen, —CN, —$CF_3$ or unsubstituted alkyl.

Embodiment 18. The compound of one of embodiments 7 to 17, or a pharmaceutically acceptable salt thereof, wherein $R^{3.2}$ and $R^{3.3}$ are independently —F, —Cl, —CN, —$CF_3$ or unsubstituted alkyl.

Embodiment 19. The compound of one of embodiments 7 to 17, or a pharmaceutically acceptable salt thereof, wherein $R^{3.2}$ and $R^{3.3}$ are independently halogen, —CN, —$CF_3$ or —$CH_3$.

Embodiment 20. The compound of any one of embodiments 1 to 19, or a pharmaceutically acceptable salt thereof, wherein $R^1$ and $R^2$ are independently hydrogen or unsubstituted alkyl.

Embodiment 21. The compound of one of embodiments 1 to 20, or a pharmaceutically acceptable salt thereof, wherein $R^1$ is —$CH_3$ or —$CH_2CH_3$.

Embodiment 22. The compound of one of embodiments 1 to 21, or a pharmaceutically acceptable salt thereof, wherein $R^2$ is —$CH_3$ or —$CH_2CH_3$.

Embodiment 23. The compound of any one of embodiments 1 to 20 or 22, or a pharmaceutically acceptable salt thereof, wherein $R^1$ is hydrogen.

Embodiment 24. The compound of any one of embodiments 1 to 21 or 23, or a pharmaceutically acceptable salt thereof, wherein $R^2$ is hydrogen.

Embodiment 25. The compound of any one of embodiments 1 to 7 or 11 to 24, or a pharmaceutically acceptable salt thereof, wherein $X^2$ is N.

Embodiment 26. The compound of any one of embodiments 1 to 25, or a pharmaceutically acceptable salt thereof, wherein $X^3$ is N.

Embodiment 27. The compound of any one of embodiments 1 to 26, or a pharmaceutically acceptable salt thereof, wherein z2 and z3 are independently an integer from 0 to 2.

Embodiment 28. The compound of any one of embodiments 1 to 27, or a pharmaceutically acceptable salt thereof, wherein $R^5$ is hydrogen, —F, —CN, —$CH_3$, —$CF_3$, —$(CH_2)_2OH$, —$CO_2NH_2$ or —$CO_2CH_2CH_3$.

Embodiment 29. The compound of any one of embodiments 1 to 28, or a pharmaceutically acceptable salt thereof, wherein $R^6$ is hydrogen, —OH, —$CH_3$, —$CH_2OH$, —$(CH_2)_2OH$, —$(CH_2)_3OH$, —$CH_2NH_2$, —$(CH_2)_2NH_2$, —$(CH_2)_3NH_2$, —$CH_2CO_2CH_2CH_3$, —$(CH_2)_2CO_2CH_2CH_3$, —$(CH_2)_3CO_2CH_2CH_3$, —$CH_2CO_2H$, —$(CH_2)_2CO_2H$, —$(CH_2)_3CO_2H$, —$(CH_2)CO_2NH_2$, —$(CH_2)_2CONH_2$, —$(CH_2)_3CO_2NH_2$, —$(CH_2)CHFCO_2H$, —$(CH_2)_2CHFCO_2H$, —$(CH_2)CF_2CO_2H$, —$(CH_2)_2CF_2CO_2H$,

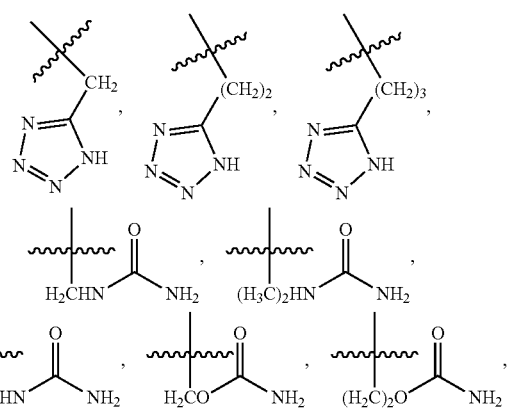

-continued

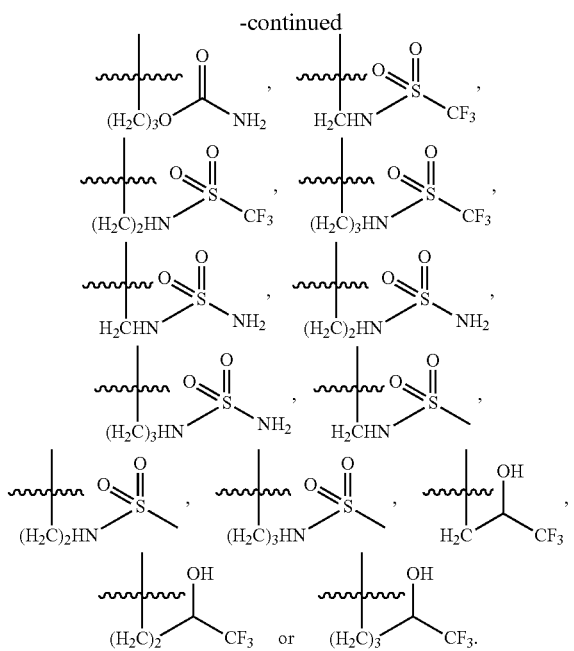

Embodiment 30. The compound of embodiment 3, or a pharmaceutically acceptable salt thereof, wherein the compound has structural Formula (VI):

(VI)

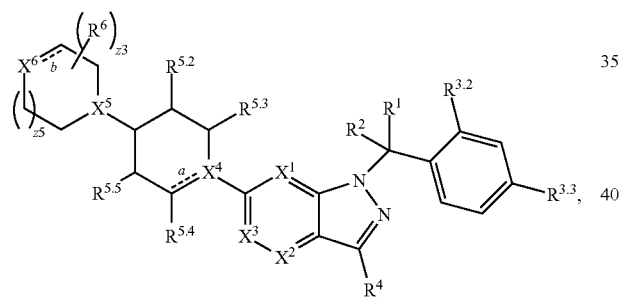

or a pharmaceutically acceptable salt thereof, wherein:
$R^{3.2}$ is hydrogen, halogen, $-CX^{3.2}{}_3$, $-CHX^{3.2}{}_2$, $-CH_2X^{3.2}$, $-CN$, $-SO_{n3.2}R^{3.2A}$, $-SO_{v3.2}NR^{3.2B}R^{3.2C}$, $-NHNR^{3.2B}R^{3.2C}$, $-ONR^{3.2B}R^{3.2C}$, $-NHC(O)NHNR^{3.2B}R^{3.2C}$, $-NHC(O)NR^{3.2B}R^{3.2C}$, $-N(O)_{m3.2}$, $-NR^{3.2B}R^{3.2C}$, $-C(O)R^{3.2D}$, $-C(O)OR^{3.2D}$, $-C(O)NR^{3.2B}R^{3.2C}$, $-OR^{3.2A}$, $-NR^{3.2B}SO_2R^{3.2A}$, $-NR^{3.2B}C(O)R^{3.2D}$, $-NR^{3.2B}C(O)OR^{3.2D}$, $-NR^{3.2B}OR^{3.2D}$, $-OCX^{3.2}{}_3$, $-OCHX^{3.2}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{3.3}$ is hydrogen, halogen, $-CX^{3.3}{}_3$, $-CHX^{3.3}{}_2$, $-CH_2X^{3.3}$, $-CN$, $-SO_{n3.3}R^{3.3A}$, $-SO_{v3.3}NR^{3.3B}R^{3.3C}$, $-NHNR^{3.3B}R^{3.3C}$, $-ONR^{3.3B}R^{3.3C}$, $-NHC(O)NHNR^{3.3B}R^{3.3C}$, $-NHC(O)NR^{3.3B}R^{3.3}c$, $-N(O)_{m3.3}$, $-NR^{3.3B}R^{3.3C}$, $-C(O)R^{3.3D}$, $-C(O)OR^{3.3D}$, $-C(O)NR^{3.3B}R^{3.3C}$, $-OR^{3.3A}$, $-NR^{3.3B}SO_2R^{3.3A}$, $-NR^{3.3B}C(O)R^{3.3D}$, $-NR^{3.3B}C(O)OR^{3.3D}$, $-NR^{3.3B}OR^{3.3D}$, $-OCX^{3.3}{}_3$, $-OCHX^{3.3}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{3.2A}$, $R^{3.2B}$, $R^{3.2C}$, $R^{3.2D}$, $R^{3.3A}$, $R^{3.3B}$, $R^{3.3C}$ and $R^{3.3D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3.2B}$ and $R^{3.2C}$, $R^{3.3B}$ and $R^{3.3C}$ substituents bonded to the same nitrogen atom may optionally be joined to form a substituted or unsubstituted heterocycloalkyl or substituted or unsubstituted heteroaryl;
n3.2 and n3.3 are independently an integer from 0 to 4;
m3.2, m3.3, v3.2, and v3.3 are independently 1 or 2;
$X^{3.2}$ and $X^{3.3}$ are independently $-Cl$, $-Br$, $-I$ or $-F$;
$R^{5.2}$ is hydrogen, halogen, $-CX^{5.6}{}_3$, $-CHX^{5.6}{}_2$, $-CH_2X^{5.6}$, $-CN$, $-SO_{n5.2}R^{5.6A}$, $-SO_{v5.2}NR^{5.6B}R^{5.6C}$, $-NHNR^{5.6B}R^{5.6C}$, $-ONR^{5.6B}R^{5.6C}$, $-NHC(O)NHNR^{5.6B}R^{5.6C}$, $-NHC(O)NR^{5.6B}R^{5.6C}$, $-N(O)_{m5.2}$, $-NR^{5.6B}R^{5.6C}$, $-C(O)R^{5.6D}$, $-C(O)OR^{5.6D}$, $-C(O)NR^{5.6B}R^{5.6C}$, $-OR^{5.6A}$, $-NR^{5.6B}SO_2R^{5.6A}$, $-NR^{5.6B}C(O)R^{5.6D}$, $-NR^{5.6B}C(O)OR^{5.6D}$, $-NR^{5.6B}OR^{5.6D}$, $-OCX^{5.6}{}_3$, $-OCHX^{5.6}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{5.3}$ is hydrogen, halogen, $-CX^{5.7}{}_3$, $-CHX^{5.7}{}_2$, $-CH_2X^{5.7}$, $-CN$, $-SO_{n5.3}R^{5.7A}$, $-SO_{v5.3}NR^{5.7B}R^{5.7C}$, $-NHNR^{5.7B}R^{5.7C}$, $-ONR^{5.7B}R^{5.7C}$, $-NHC(O)NHNR^{5.7B}R^{5.7C}$, $-NHC(O)NR^{5.7B}R^{5.7C}$, $-N(O)_{m5.3}$, $-NR^{5.7B}R^{5.7C}$, $-C(O)R^{5.7D}$, $-C(O)OR^{5.7D}$, $-C(O)NR^{5.7B}R^{5.7C}$, $-OR^{5.7A}$, $-NR^{5.7B}SO_2R^{5.7A}$, $-NR^{5.7B}C(O)R^{5.7D}$, $-NR^{5.7B}C(O)OR^{5.7D}$, $-NR^{5.7B}OR^{5.7D}$, $-OCX^{5.7}{}_3$, $-OCHX^{5.7}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{5.4}$ is hydrogen, halogen, $-CX^{5.8}{}_3$, $-CHX^{5.8}{}_2$, $-CH_2X^{5.8}$, $-CN$, $-SO_{n5.4}R^{5.8A}$, $-SO_{v5.4}NR^{5.8B}R^{5.8C}$, $-NHNR^{5.8B}R^{5.8C}$, $-ONR^{5.8B}R^{5.8C}$, $-NHC(O)NHNR^{5.8B}R^{5.8C}$, $-NHC(O)NR^{5.8B}R^{5.8C}$, $-N(O)_{m5.4}$, $-NR^{5.8B}R^{5.8C}$, $-C(O)R^{5.8D}$, $-C(O)OR^{5.8D}$, $-C(O)NR^{5.8B}R^{5.8C}$, $-OR^{5.8A}$, $-NR^{5.8B}SO_2R^{5.8A}$, $-NR^{5.8B}C(O)R^{5.8D}$, $-NR^{5.8B}C(O)OR^{5.8D}$, $-NR^{5.8B}OR^{5.8D}$, $-OCX^{5.8}{}_3$, $-OCHX^{5.8}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{5.5}$ is hydrogen, halogen, $-CX^{5.9}{}_3$, $-CHX^{5.9}{}_2$, $-CH_2X^{5.9}$, $-CN$, $-SO_{n5.5}R^{5.9A}$, $-SO_{v5.5}NR^{5.9B}R^{5.9C}$, $-NHNR^{5.9B}R^{5.9C}$, $-ONR^{5.9B}R^{5.9C}$, $-NHC(O)NHNR^{5.9B}R^{5.9C}$, $-NHC(O)NR^{5.9B}R^{5.9}c$, $-N(O)_{m5.5}$, $-NR^{5.9B}R^{5.9}c$, $-C(O)R^{5.9D}$, $-C(O)OR^{5.9D}$, $-C(O)NR^{5.9B}R^{5.9C}$, $-OR^{5.9A}$, $-NR^{5.9B}SO_2R^{5.9A}$, $-NR^{5.9B}C(O)R^{5.9D}$, $-NR^{5.9B}C(O)OR^{5.9D}$, $-NR^{5.9B}OR^{5.9D}$, $-OCX^{5.9}{}_3$, $-OCHX^{5.9}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5.6A}$, $R^{5.6B}$, $R^{5.6C}$, $R^{5.6D}$, $R^{5.7A}$, $R^{5.7B}$, $R^{5.7C}$, $R^{5.7D}$, $R^{5.8A}$, $R^{5.8B}$, $R^{5.8C}$, $R^{5.8D}$, $R^{5.9A}$, $R^{5.9B}$, $R^{5.9C}$ and $R^{5.9D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5.6B}$ and $R^{5.6C}$, $R^{5.7B}$ and $R^{5.7C}$, $R^{5.8B}$ and $R^{5.8C}$, $R^{5.9B}$ and $R^{5.9C}$ substituents bonded to the same nitrogen atom may optionally be joined to form a substituted or unsubstituted heterocycloalkyl or substituted or unsubstituted heteroaryl;

n5.2, n5.3, n5.4, and n5.5 are independently an integer from 0 to 4;

m5.2, m5.3, m5.4, m5.5, v5.2, v5.3, v5.4, and v5.5 are independently are independently 1 or 2; and $X^{5.6}$, $X^{5.7}$, $X^{5.8}$ and $X^{5.9}$ are independently —Cl, —Br, —I or —F.

Embodiment 31. The compound of embodiment 30, or a pharmaceutically acceptable salt thereof, wherein the compound has structural Formula (VII):

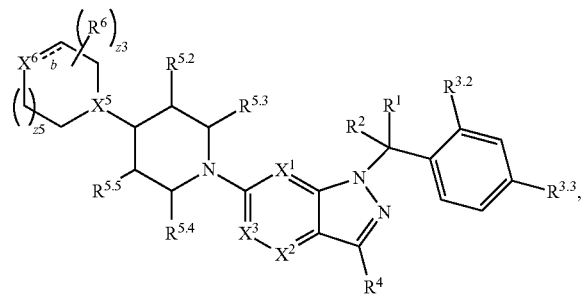
(VII)

or a pharmaceutically acceptable salt thereof.

Embodiment 32. The compound of one of embodiments 30 to 31, or a pharmaceutically acceptable salt thereof, wherein the compound has structural Formula (VIIa):

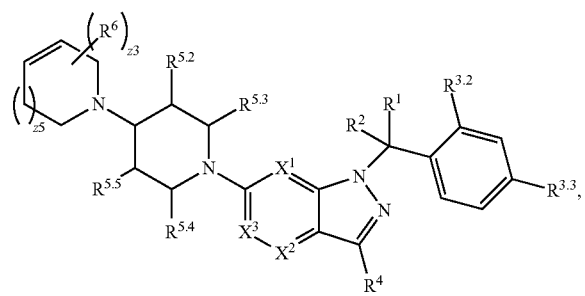
(VIIa)

or a pharmaceutically acceptable salt thereof.

Embodiment 33. The compound of one of embodiments 30 to 31, or a pharmaceutically acceptable salt thereof, wherein the compound has structural Formula (VIIb):

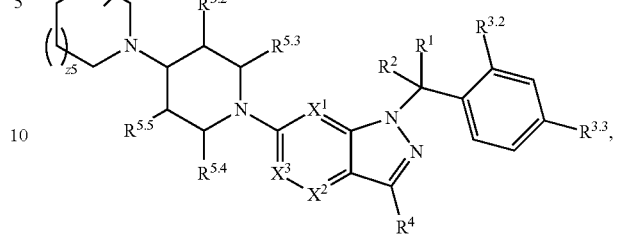
(VIIb)

or a pharmaceutically acceptable salt thereof.

Embodiment 34. The compound of embodiment 30, or a pharmaceutically acceptable salt thereof, wherein the compound has structural Formula (VIII):

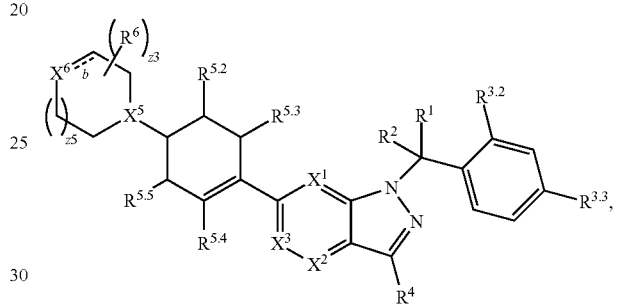
(VIII)

or a pharmaceutically acceptable salt thereof.

Embodiment 35. The compound of one of embodiments 30 or 34, or a pharmaceutically acceptable salt thereof, wherein the compound has structural Formula (VIIIa):

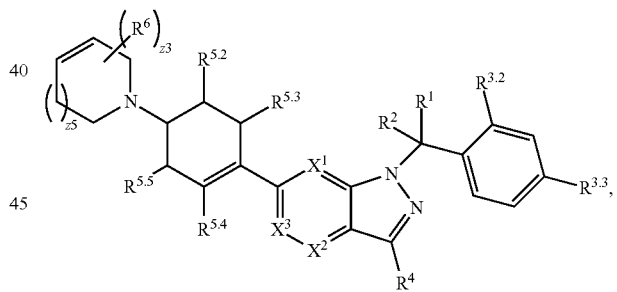
(VIIIa)

or a pharmaceutically acceptable salt thereof.

Embodiment 36. The compound of one of embodiments 30 or 34, or a pharmaceutically acceptable salt thereof, wherein the compound has structural Formula (VIIIb):

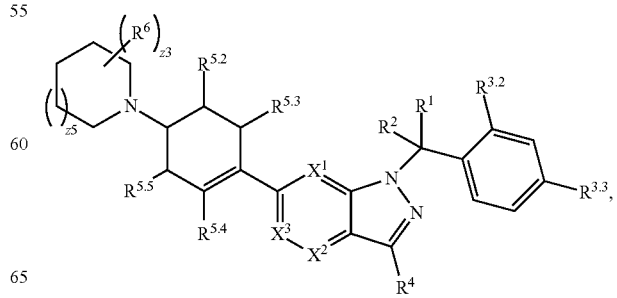
(VIIIb)

or a pharmaceutically acceptable salt thereof.

Embodiment 37. The compound of any one of embodiments 30 to 36, or a pharmaceutically acceptable salt thereof, wherein $X^1$ and $X^3$ are independently N.

Embodiment 38. The compound of any one of embodiments 30 to 37, or a pharmaceutically acceptable salt thereof, wherein $X^1$ and $X^2$ are independently N.

Embodiment 39. The compound of any one of embodiments 30 to 38, or a pharmaceutically acceptable salt thereof, wherein $R^4$ is —CN, —C(O)NH$_2$, —CF$_3$, —CH$_3$ or —C(CH$_3$)$_2$OH.

Embodiment 40. The compound of any one of embodiments 30 to 39, or a pharmaceutically acceptable salt thereof, wherein $R^{3.2}$ and $R^{3.3}$ are independently halogen, —CN, —CF$_3$ or unsubstituted alkyl.

Embodiment 41. The compound of one of embodiments 30 to 40, or a pharmaceutically acceptable salt thereof, wherein $R^{3.2}$ and $R^{3.3}$ are independently —F, —Cl, —CN, —CF$_3$ or unsubstituted alkyl.

Embodiment 42. The compound of one of embodiments 30 to 40, or a pharmaceutically acceptable salt thereof, wherein $R^{3.2}$ and $R^{3.3}$ are independently halogen, —CN, —CF$_3$ or —CH$_3$.

Embodiment 43. The compound of any one of embodiments 30 to 42, or a pharmaceutically acceptable salt thereof, wherein $R^1$ and $R^2$ are independently hydrogen or unsubstituted alkyl.

Embodiment 44. The compound of one of embodiments 30 to 43, or a pharmaceutically acceptable salt thereof, wherein $R^1$ is —CH$_3$ or —CH$_2$CH$_3$.

Embodiment 45. The compound of one of embodiments 30 to 44, or a pharmaceutically acceptable salt thereof, wherein $R^2$ is —CH$_3$ or —CH$_2$CH$_3$.

Embodiment 46. The compound of any one of embodiments 30 to 43 or 45, or a pharmaceutically acceptable salt thereof, wherein $R^1$ is hydrogen.

Embodiment 47. The compound of any one of embodiments 30 to 44 or 46, or a pharmaceutically acceptable salt thereof, wherein $R^2$ is hydrogen.

Embodiment 48. The compound of any one of embodiments 30 to 47, or a pharmaceutically acceptable salt thereof, wherein z3 is an integer from 0 to 2.

Embodiment 49. The compound of any one of embodiments 30 to 48, or a pharmaceutically acceptable salt thereof, wherein $R^{5.2}$, $R^{5.3}$, $R^{5.4}$, $R^{5.5}$ are independently hydrogen, —F, —CN, —CH$_3$, —CF$_3$, —(CH$_2$)$_2$OH, —CO$_2$NH$_2$ or —CO$_2$CH$_2$CH$_3$.

Embodiment 50. The compound of any one of embodiments 30 to 49, or a pharmaceutically acceptable salt thereof, wherein $R^6$ is hydrogen, —OH, —CH$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H,

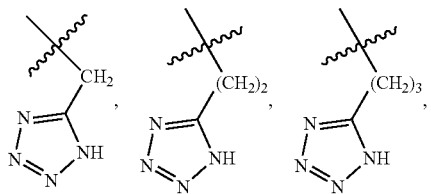

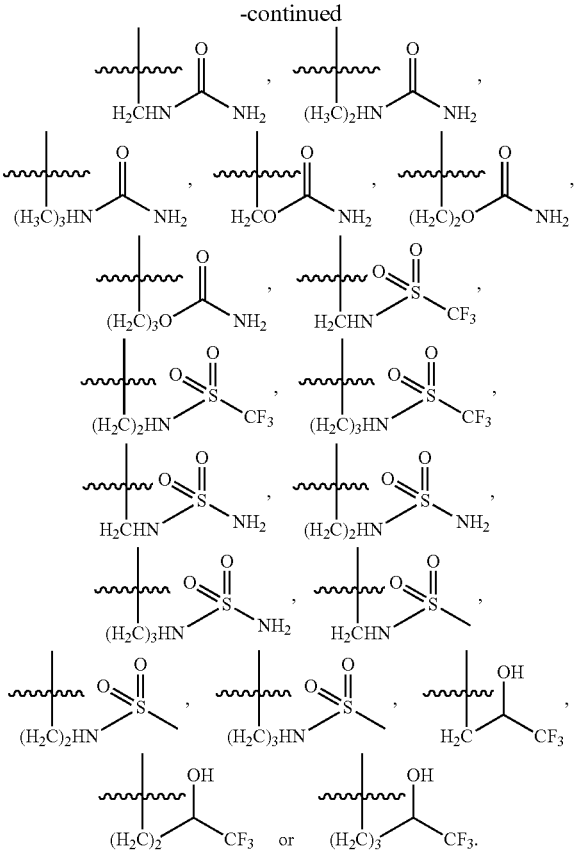

Embodiment 51. The compound of any one of embodiments 30 to 50, or a pharmaceutically acceptable salt thereof, wherein z5 is 1.

Embodiment 52. The compound of any one of embodiments 30 to 50, or a pharmaceutically acceptable salt thereof, wherein z5 is 0.

Embodiment 53. The compound of one of embodiments 30 to 51, or a pharmaceutically acceptable salt thereof, wherein z3 and z5 are independently 1.

Embodiment 54. The compound of one of embodiments 30 to 49 or 51 to 53, or a pharmaceutically acceptable salt thereof, wherein $R^6$ is halogen, substituted or unsubstituted alkyl or substituted or unsubstituted heteroalkyl.

Embodiment 55. The compound of embodiment 30, or a pharmaceutically acceptable salt thereof, wherein the compound has structural Formula (IX):

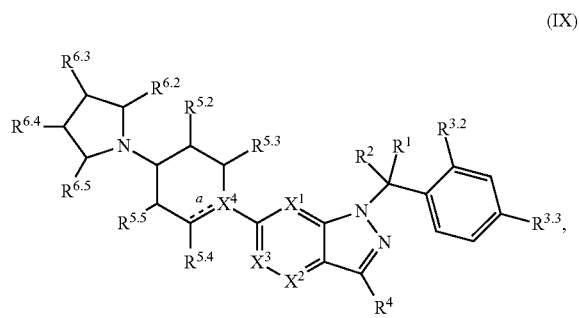

(IX)

or a pharmaceutically acceptable salt thereof, wherein:
$R^{6.2}$ is hydrogen, halogen, —CX$^{6.6}_3$, —CHX$^{6.6}_2$, —CH$_2$X$^{6.6}$, —CN, —SO$_{n6.2}$R$^{6.6A}$, —SO$_{v6.2}$NR$^{6.6B}$R$^{6.6C}$, —NHNR$^{6.6B}$R$^{6.6C}$, —ONR$^{6.6B}$R$^{6.6C}$, —NHC(O)NHNR$^{6.6B}$R$^{6.6C}$, —NHC(O)NR$^{6.6B}$R$^{6.6C}$, —N(O)$_{m6.2}$, —NR$^{6.6B}$R$^{6.6C}$, —C(O)R$^{6.6D}$, —C(O)OR$^{6.6D}$, —C(O)NR$^{6.6B}$R$^{6.6C}$, —OR$^{6.6A}$, —NR$^{6.6B}$SO$_2$R$^{6.6A}$, —NR$^{6.6B}$C(O)R$^{6.6D}$, —NR$^{6.6B}$C(O)OR$^{6.6D}$, —NR$^{6.6B}$OR$^{6.6D}$, —OCX$^{6.6}_3$, —OCHX$^{6.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{6.3}$ is hydrogen, halogen, —CX$^{6.7}_3$, —CHX$^{6.7}_2$, —CH$_2$X$^{6.7}$, —CN, —SO$_{n6.3}$R$^{6.7A}$, —SO$_{v6.3}$NR$^{6.7B}$R$^{6.7C}$, —NHNR$^{6.7B}$R$^{6.7C}$, —ONR$^{6.7B}$R$^{6.7C}$, —NHC(O)NHNR$^{6.7B}$R$^{6.7C}$, —NHC(O)NR$^{6.7B}$R$^{6.7C}$, —N(O)$_{m6.3}$, —NR$^{6.7B}$R$^{6.7C}$, —C(O)R$^{6.7D}$, —C(O)OR$^{6.7D}$, —C(O)NR$^{6.7B}$R$^{6.7C}$, —OR$^{6.7A}$, —NR$^{6.7B}$SO$_2$R$^{6.7A}$, —NR$^{6.7B}$C(O)R$^{6.7D}$, —NR$^{6.7B}$C(O)OR$^{6.7D}$, —NR$^{6.7B}$OR$^{6.7D}$, —OCX$^{6.7}_3$, —OCHX$^{6.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{6.4}$ is hydrogen, halogen, —CX$^{6.8}_3$, —CHX$^{6.8}_2$, —CH$_2$X$^{6.8}$, —CN, —SO$_{n6.4}$R$^{6.8A}$, —SO$_{v6.4}$NR$^{6.8B}$R$^{6.8C}$, —NHNR$^{6.8B}$R$^{6.8C}$, —ONR$^{6.8B}$R$^{6.8C}$, —NHC(O)NHNR$^{6.8B}$R$^{6.8C}$, —NHC(O)NR$^{6.8B}$R$^{6.8C}$, —N(O)$_{m6.4}$, —NR$^{6.8B}$R$^{6.8C}$, —C(O)R$^{6.8D}$, —C(O)OR$^{6.8D}$, —C(O)NR$^{6.8B}$R$^{6.8C}$, —OR$^{6.8A}$, —NR$^{6.8B}$SO$_2$R$^{6.8A}$, —NR$^{6.8B}$C(O)R$^{6.8D}$, —NR$^{6.8B}$C(O)OR$^{6.8D}$, —NR$^{6.8B}$OR$^{6.8D}$, —OCX$^{6.8}_3$, —OCHX$^{6.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{6.5}$ is hydrogen, halogen, —CX$^{6.9}_3$, —CHX$^{6.9}_2$, —CH$_2$X$^{6.9}$, —CN, —SO$_{n6.5}$R$^{6.9A}$, —SO$_{v6.5}$NR$^{6.9B}$R$^{6.9C}$, —NHNR$^{6.9B}$R$^{6.9C}$, —ONR$^{6.9B}$R$^{6.9C}$, —NHC(O)NHNR$^{6.9B}$R$^{6.9C}$, —NHC(O)NR$^{6.9B}$R$^{6.9C}$, —N(O)$_{m6.5}$, —NR$^{6.9B}$R$^{6.9C}$, —C(O)R$^{6.9D}$, —C(O)OR$^{6.9D}$, —C(O)NR$^{6.9B}$R$^{6.9C}$, —OR$^{6.9A}$, —NR$^{6.9B}$SO$_2$R$^{6.9A}$, —NR$^{6.9B}$C(O)R$^{6.9D}$, —NR$^{6.9B}$C(O)OR$^{6.9D}$, —NR$^{6.9B}$OR$^{6.9D}$, —OCX$^{6.9}_3$, —OCHX$^{6.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{6.6A}$, R$^{6.6B}$, R$^{6.6C}$, R$^{6.6D}$, R$^{6.7A}$, R$^{6.7B}$, R$^{6.7C}$, R$^{6.7D}$, R$^{6.8A}$, R$^{6.8B}$, R$^{6.8C}$, R$^{6.8D}$, R$^{6.9A}$, R$^{6.9B}$, R$^{6.9C}$ and R$^{6.9D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{6.6B}$ and R$^{6.6C}$, R$^{6.7B}$ and R$^{6.7C}$, R$^{6.8B}$ and R$^{6.8C}$, R$^{6.9B}$ and R$^{6.9C}$ substituents bonded to the same nitrogen atom may optionally be joined to form a substituted or unsubstituted heterocycloalkyl or substituted or unsubstituted heteroaryl;

n6.2, n6.3, n6.4, and n6.5 are independently an integer from 0 to 4;

m6.2, m6.3, m6.4, m6.5, v6.2, v6.3, v6.4, and v6.5 are independently 1 or 2; and X$^{6.6}$, X$^{6.7}$, X$^{6.8}$ and X$^{6.9}$ are independently —Cl, —Br, —I or —F.

Embodiment 56. The compound of embodiment 55, or a pharmaceutically acceptable salt thereof, wherein the compound has structural Formula (IXa):

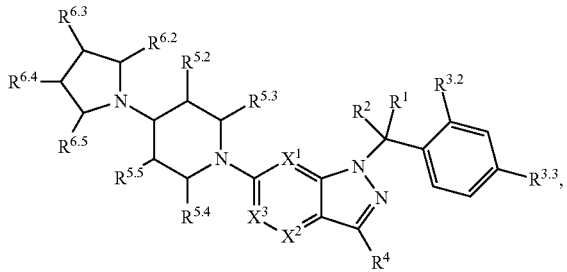

(IXa)

or a pharmaceutically acceptable salt thereof.

Embodiment 57. The compound of one of embodiments 55 to 56, or a pharmaceutically acceptable salt thereof, wherein X$^1$ and X$^2$ are independently N.

Embodiment 58. The compound of one of embodiments 55 to 57, or a pharmaceutically acceptable salt thereof, wherein R$^1$ and R$^2$ are independently hydrogen or unsubstituted alkyl.

Embodiment 59. The compound of one of embodiments 55 to 58, or a pharmaceutically acceptable salt thereof, wherein R$^{3.2}$ and R$^{3.3}$ are independently halogen, —CN, —CF$_3$ or unsubstituted alkyl.

Embodiment 60. The compound of one of embodiments 55 to 59, or a pharmaceutically acceptable salt thereof, wherein R$^4$ is —CN, —C(O)NH$_2$, —CF$_3$, —CH$_3$ or —C(CH$_3$)$_2$OH.

Embodiment 61. The compound of one of embodiments 55 to 60, or a pharmaceutically acceptable salt thereof, wherein R$^{5.4}$ and R$^{5.5}$ are independently hydrogen, fluorine, —CN, —CH$_3$, —CH$_2$CH$_3$, —CF$_3$, —(CH$_2$)OH, —(CH$_2$)$_2$OH, —(CH$_3$)$_2$OH, —CO$_2$H, —CO$_2$NH$_2$ or —CO$_2$CH$_2$CH$_3$.

Embodiment 62. The compound of one of embodiments s 55 to 61, or a pharmaceutically acceptable salt thereof, wherein R$^{6.2}$ is hydrogen, —CH$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H,

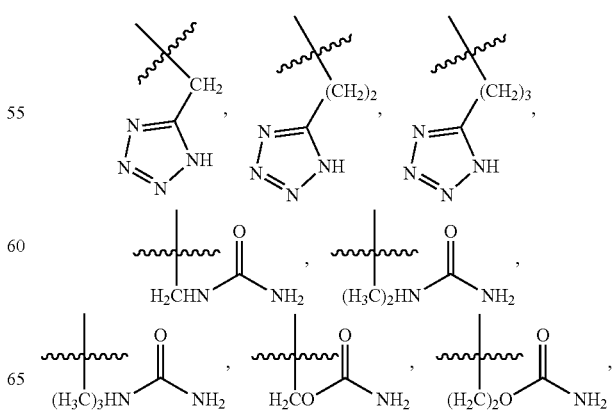

-continued

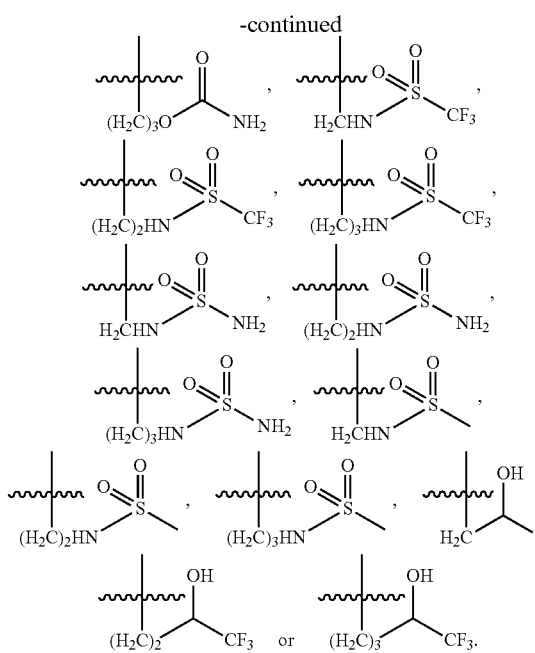

Embodiment 63. The compound of embodiment 55, or a pharmaceutically acceptable salt thereof, wherein the compound has structural Formula (IXb):

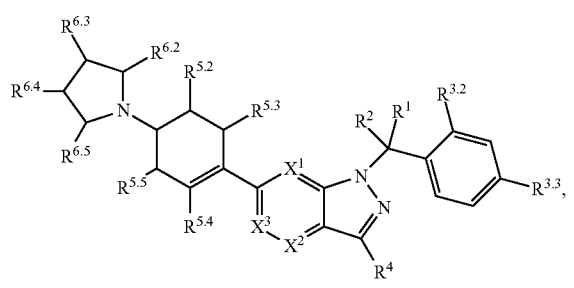

or a pharmaceutically acceptable salt thereof.

Embodiment 64. The compound of embodiment 63, or a pharmaceutically acceptable salt thereof, wherein $X^1$ and $X^2$ are independently N.

Embodiment 65. The compound of one of embodiments 63 to 64, or a pharmaceutically acceptable salt thereof, wherein $R^1$ and $R^2$ are independently hydrogen or unsubstituted alkyl.

66. The compound of one of embodiments 63 to 65, or a pharmaceutically acceptable salt thereof, wherein $R^{3.2}$ and $R^{3.3}$ are independently halogen, —CN, —$CF_3$ or unsubstituted alkyl.

Embodiment 67. The compound of one of embodiments 63 to 66, or a pharmaceutically acceptable salt thereof, wherein $R^4$ is —CN, —C(O)$NH_2$, —$CF_3$, —$CH_3$ or —C($CH_3$)$_2$OH.

Embodiment 68. The compound of one of embodiments 63 to 67, or a pharmaceutically acceptable salt thereof, wherein $R^{5.2}$ and $R^{5.5}$ are independently hydrogen, fluorine, —CN, —$CH_3$, —$CH_2CH_3$, —$CF_3$, —($CH_2$)OH, —($CH_2$)$_2$OH, —($CH_3$)$_2$OH, —$CO_2H$, —$CO_2NH_2$ or —$CO_2CH_2CH_3$.

Embodiment 69. The compound of one of embodiments 63 to 68, or a pharmaceutically acceptable salt thereof, wherein $R^{6.2}$ is hydrogen, —OH, —$CH_3$, —$CH_2OH$, —($CH_2$)$_2$OH, —($CH_2$)$_3$OH, —$CH_2NH_2$, —($CH_2$)$_2NH_2$, —($CH_2$)$_3NH_2$, —$CH_2CO_2CH_2CH_3$, —($CH_2$)$_2$CO$_2$CH$_2$CH$_3$, —($CH_2$)$_3$CO$_2$CH$_2$CH$_3$, —$CH_2CO_2H$, —($CH_2$)$_2$CO$_2$H, —($CH_2$)$_3$CO$_2$H, —($CH_2$)CO$_2$NH$_2$, —($CH_2$)$_2$CONH$_2$, —($CH_2$)$_3$CO$_2$NH$_2$, —($CH_2$)CHFCO$_2$H, —($CH_2$)$_2$CHFCO$_2$H, —($CH_2$)CF$_2$CO$_2$H, —($CH_2$)$_2$CF$_2$CO$_2$H,

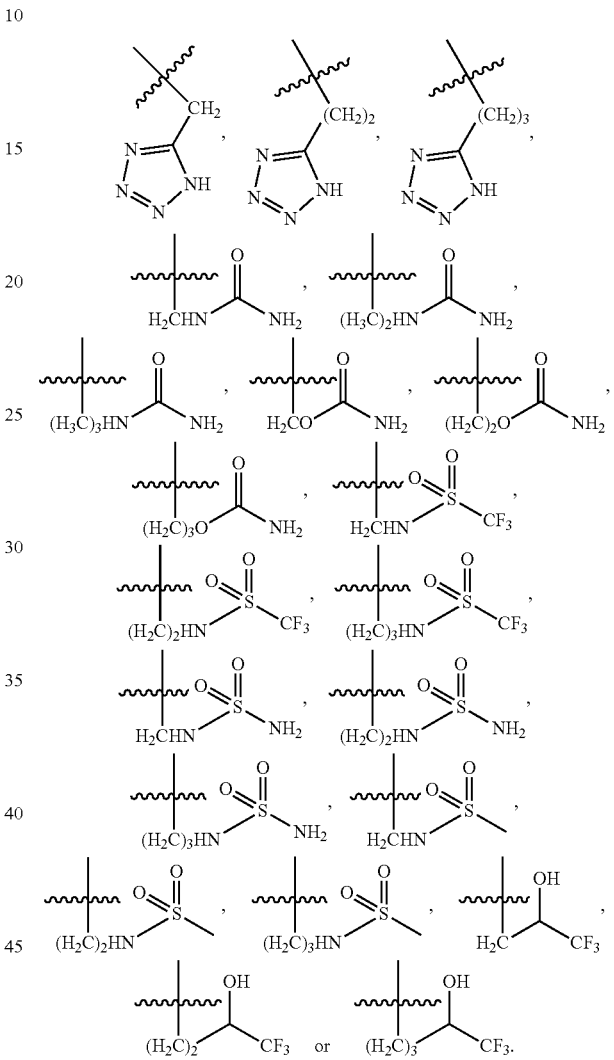

Embodiment 70. The compound of embodiment 3, or a pharmaceutically acceptable salt thereof, wherein the compound has structural Formula (X):

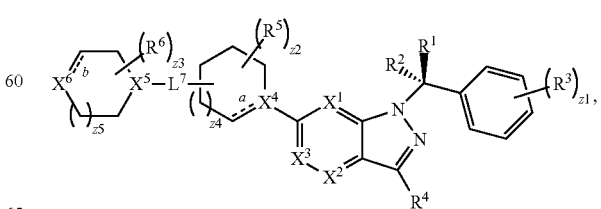

or a pharmaceutically acceptable salt thereof.

Embodiment 71. The compound of embodiment 70, or a pharmaceutically acceptable salt thereof, wherein R¹ is hydrogen.
Embodiment 72. The compound of one of embodiments 70 to 71, or a pharmaceutically acceptable salt thereof, wherein R² is hydrogen.
Embodiment 73. The compound of embodiment 1, or a pharmaceutically acceptable salt thereof, wherein the compound is:
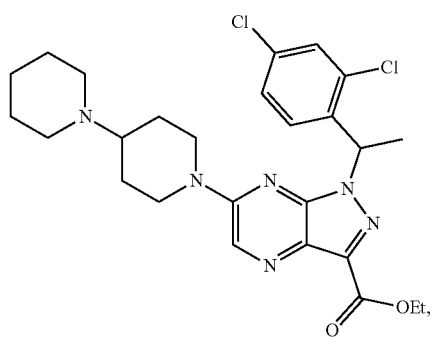
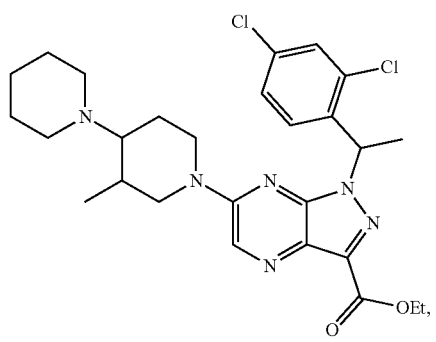
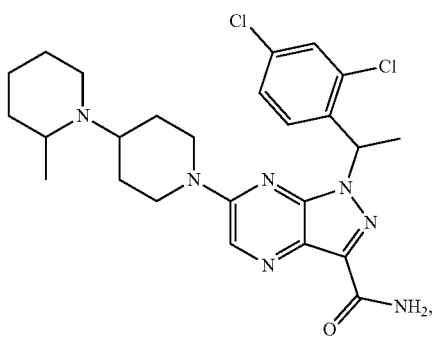
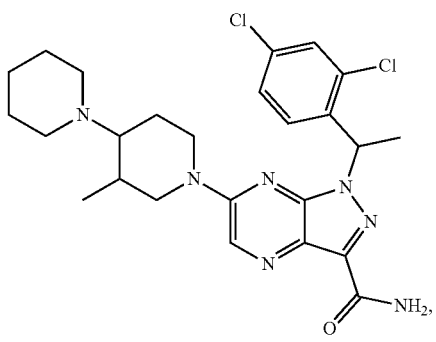
-continued
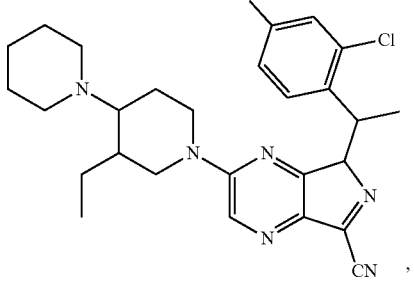
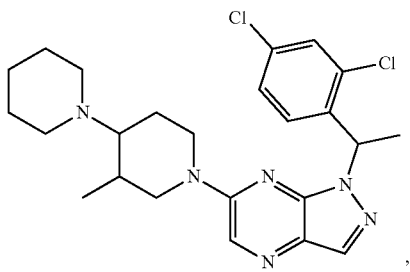
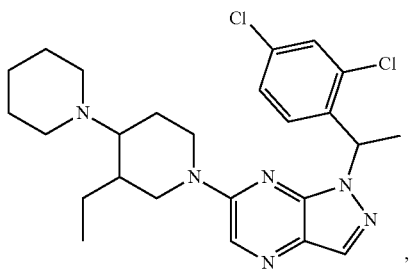
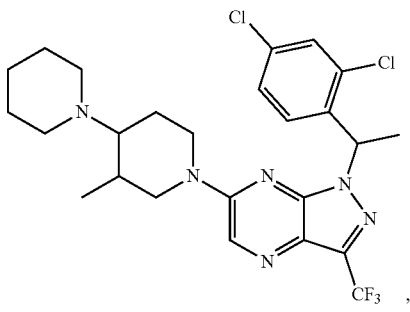
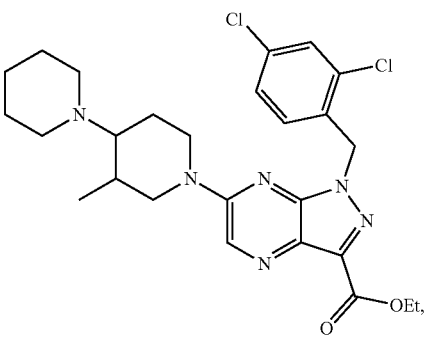

589
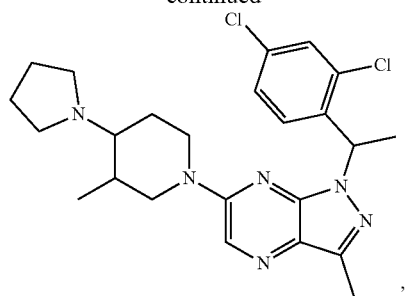
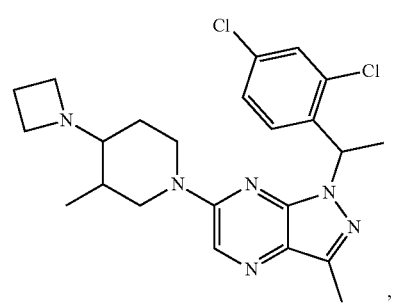
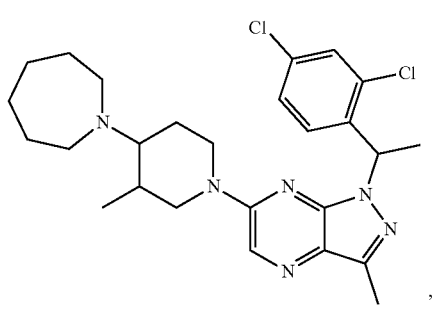
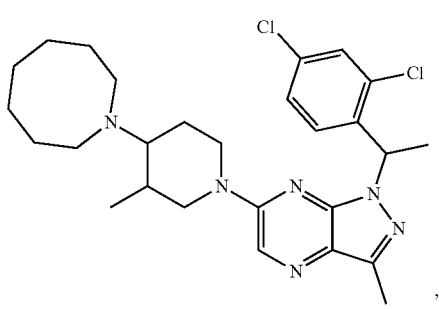
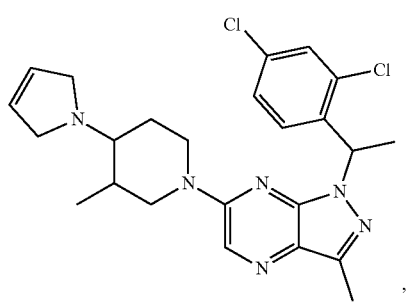
590
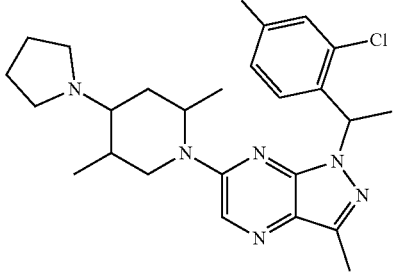
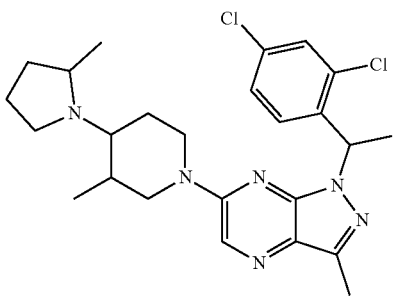
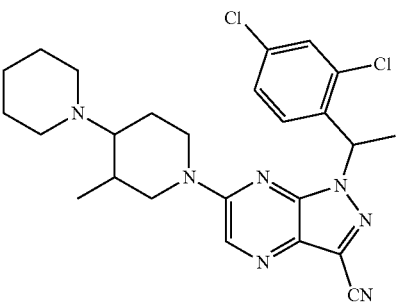
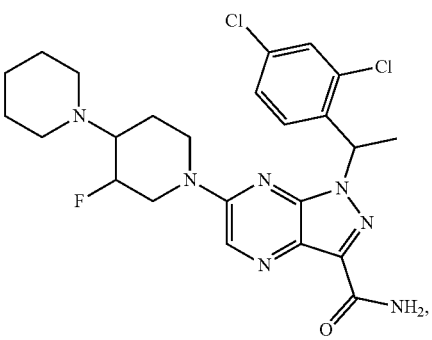
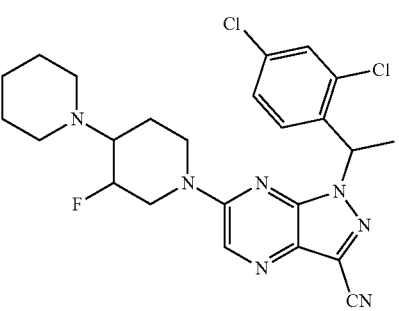

591
-continued
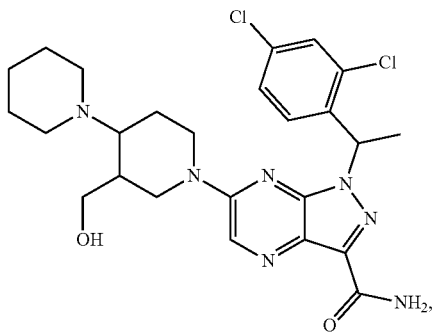
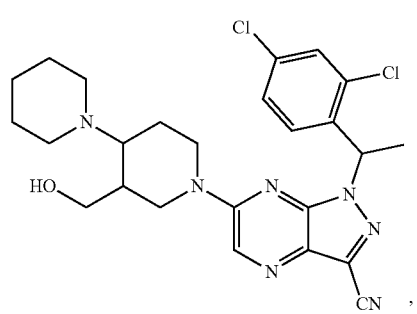
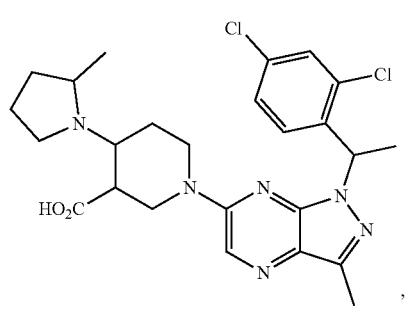
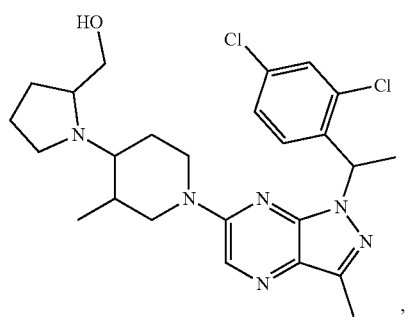
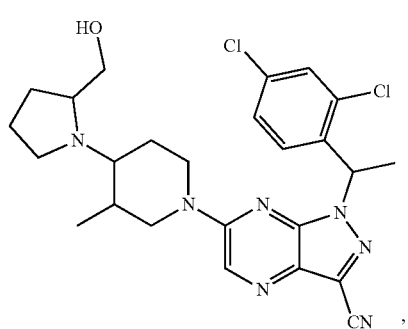
592
-continued
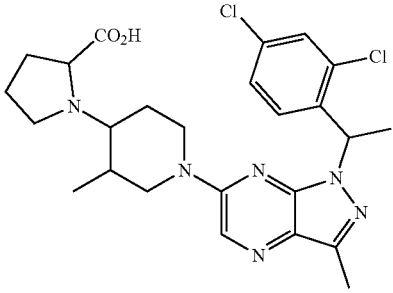
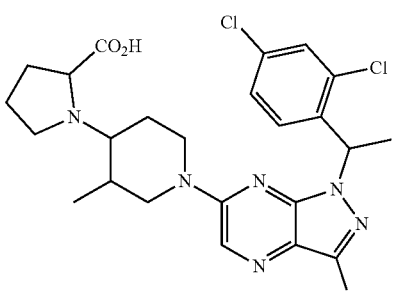
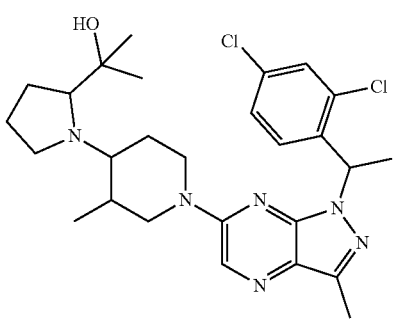
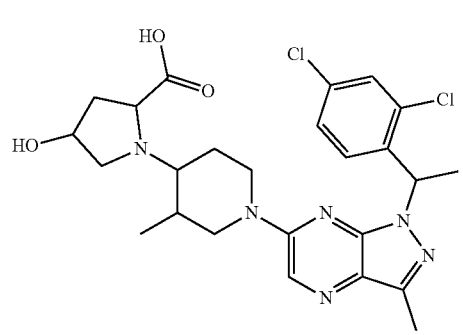
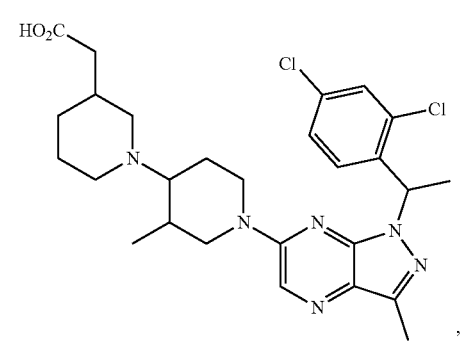

593
-continued
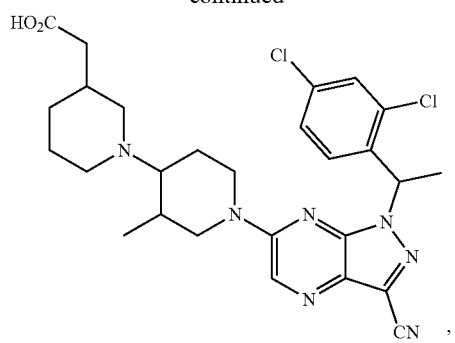
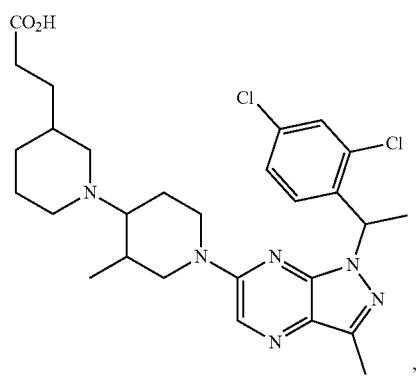
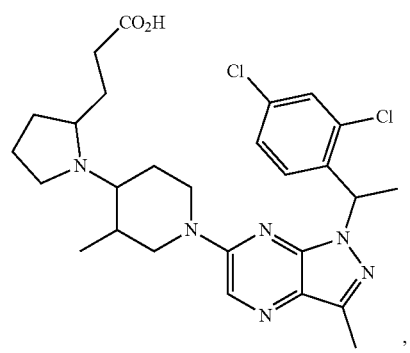
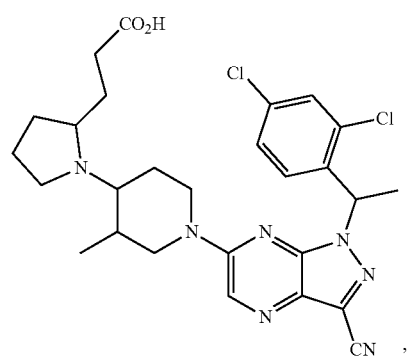
594
-continued
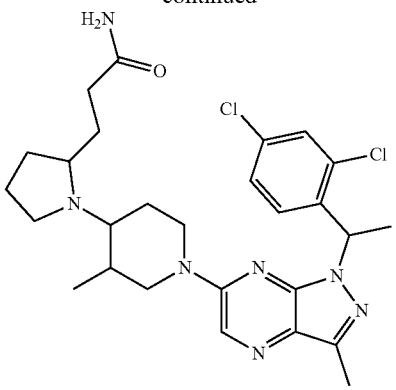
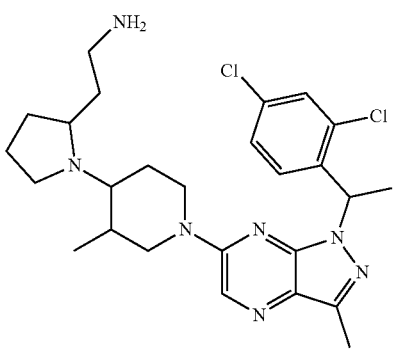
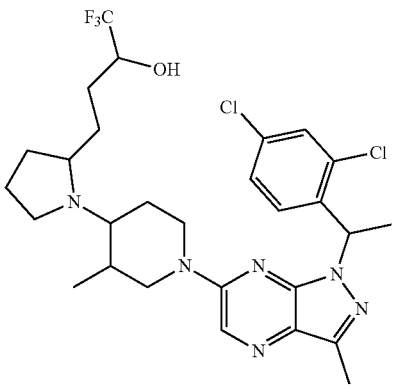
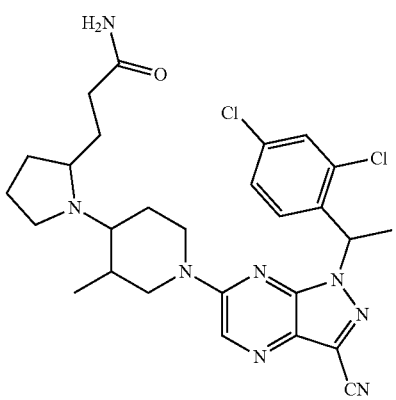

595
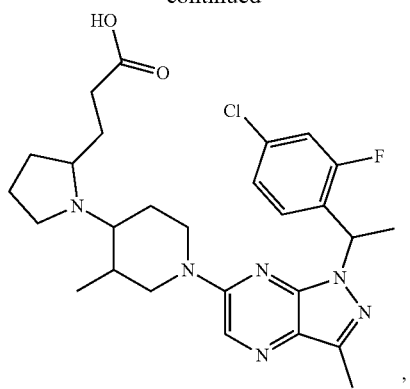
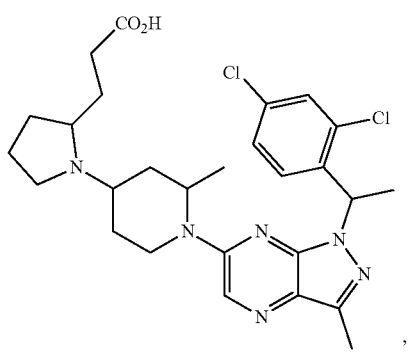
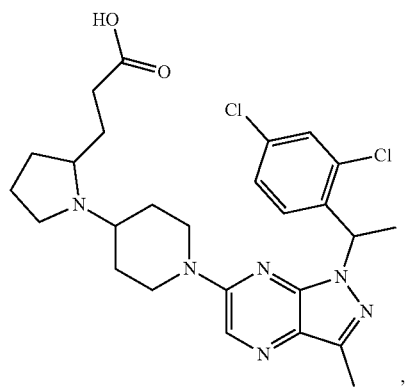
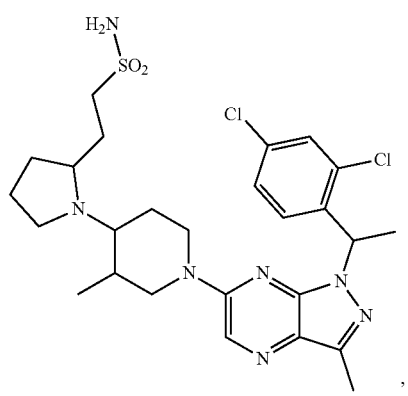
596
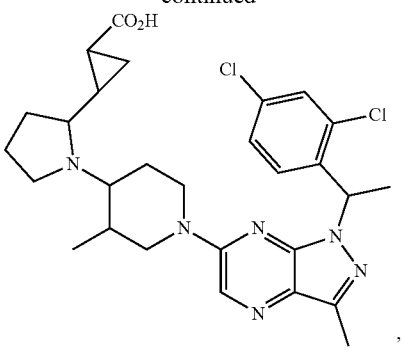
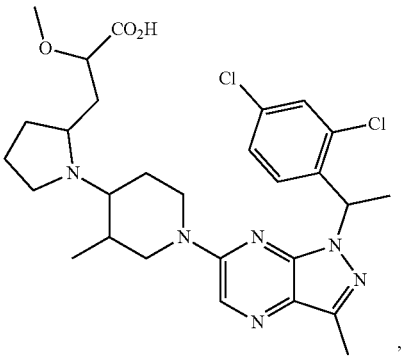
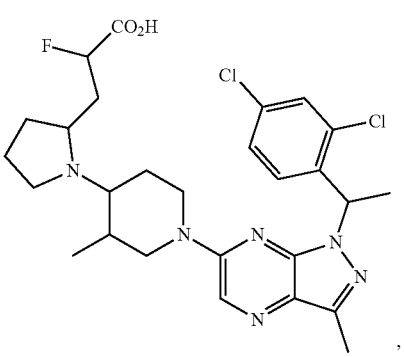
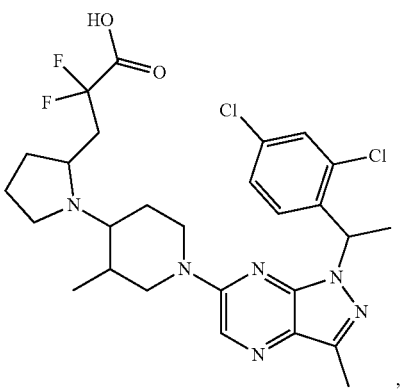

597
-continued
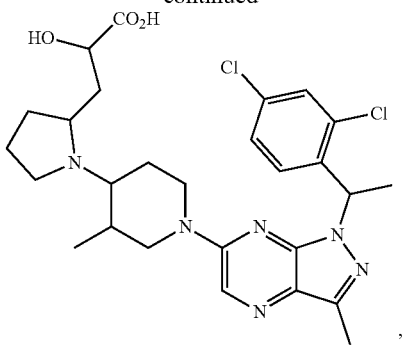
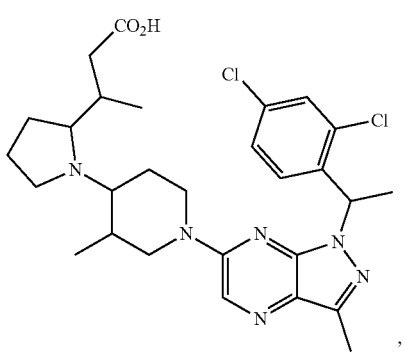
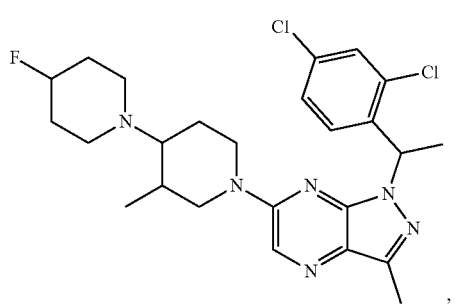
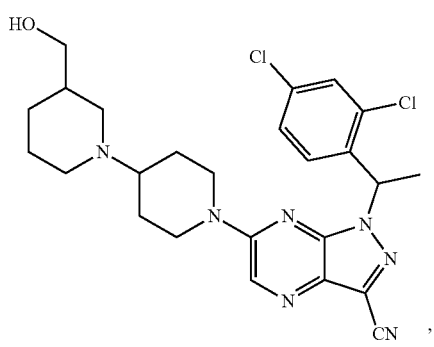
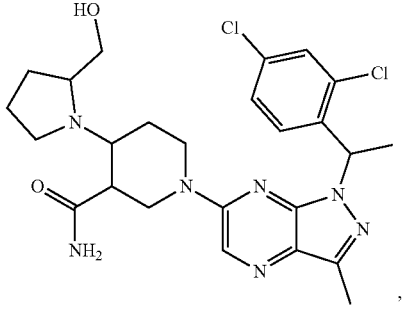
598
-continued
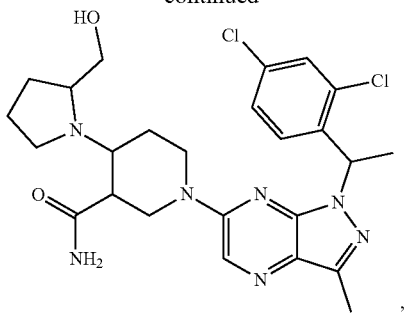
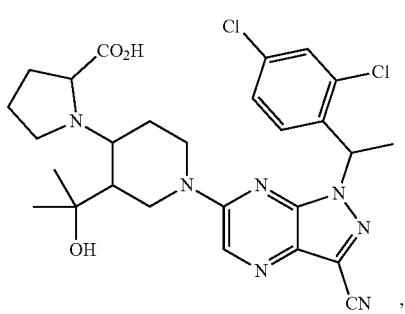
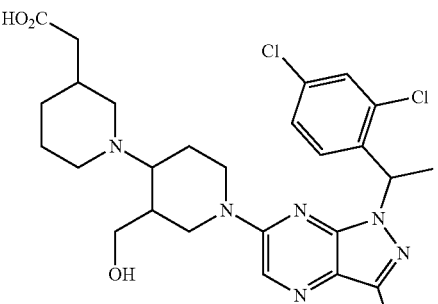
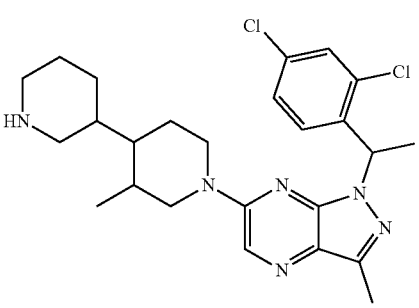
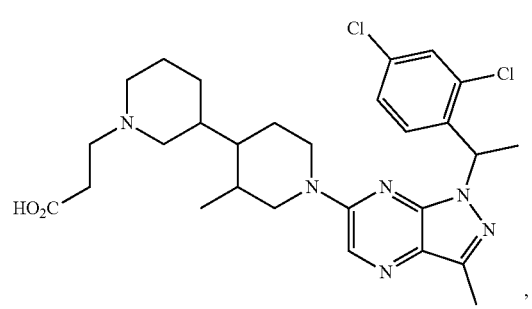

599
-continued
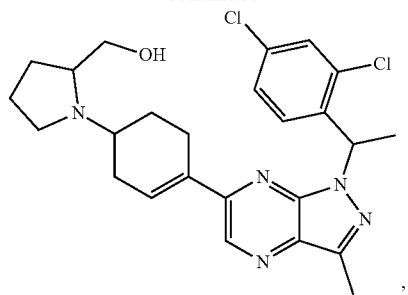
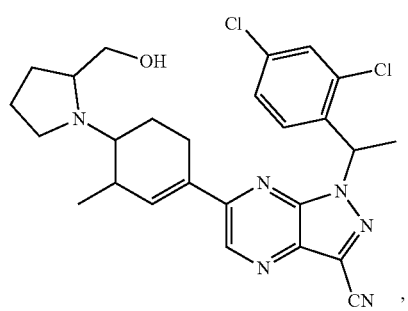
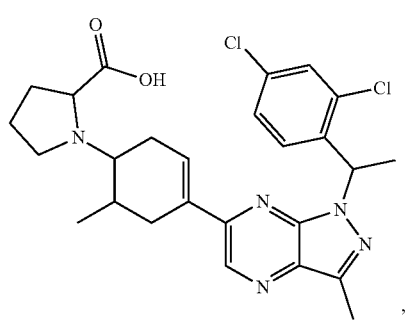
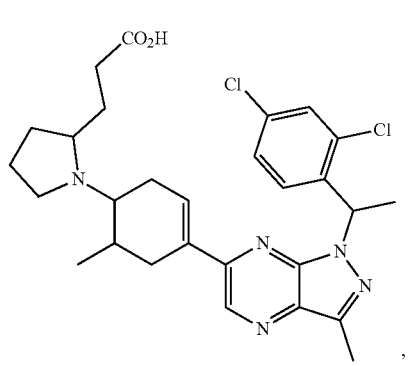
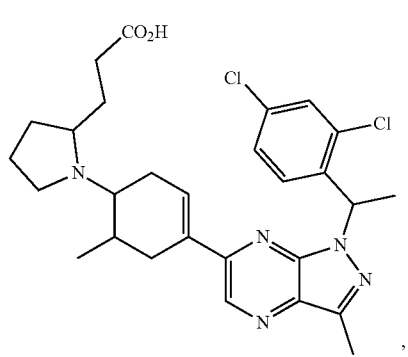
600
-continued
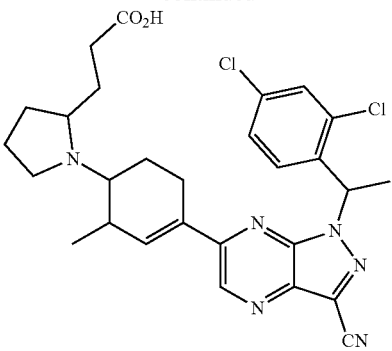
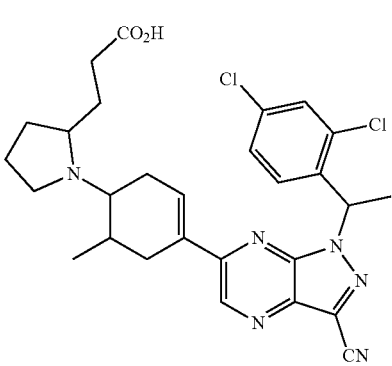
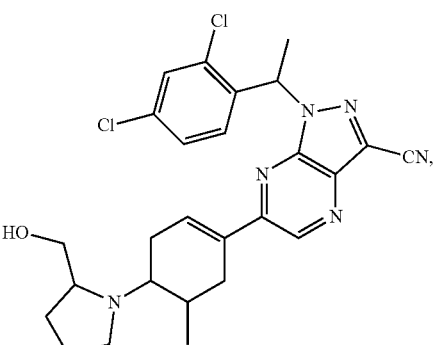
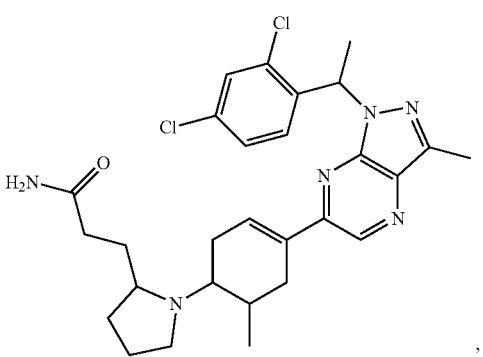

601
-continued
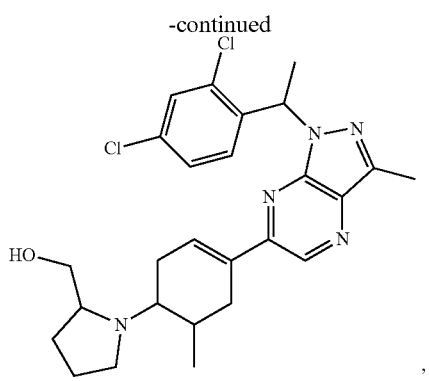
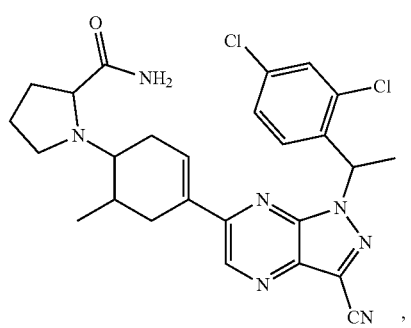
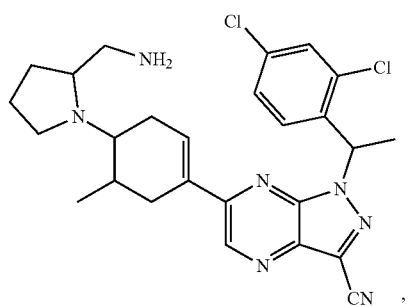
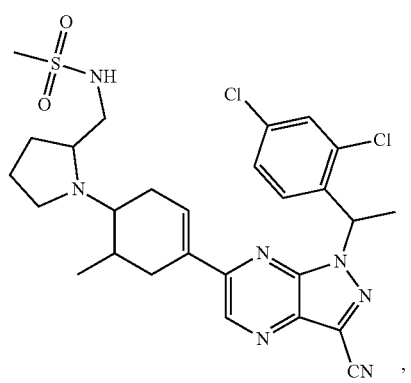
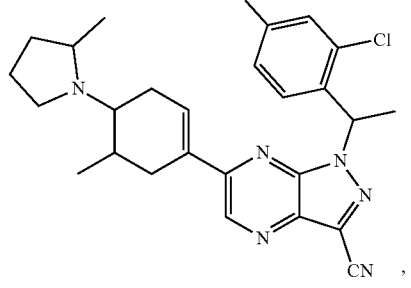
602
-continued
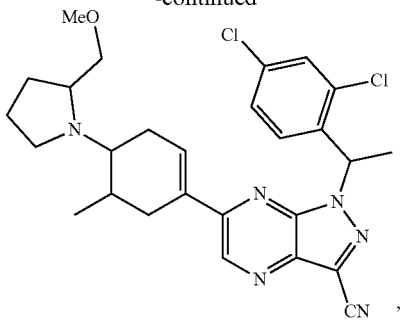
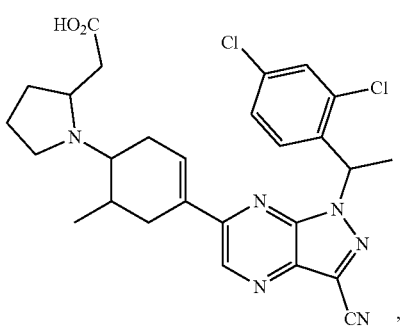
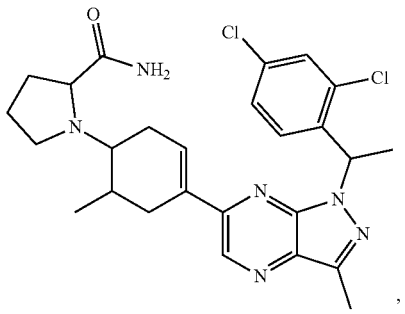
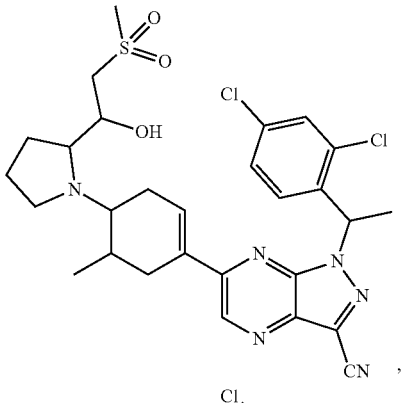
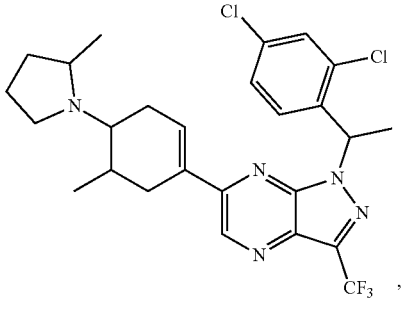

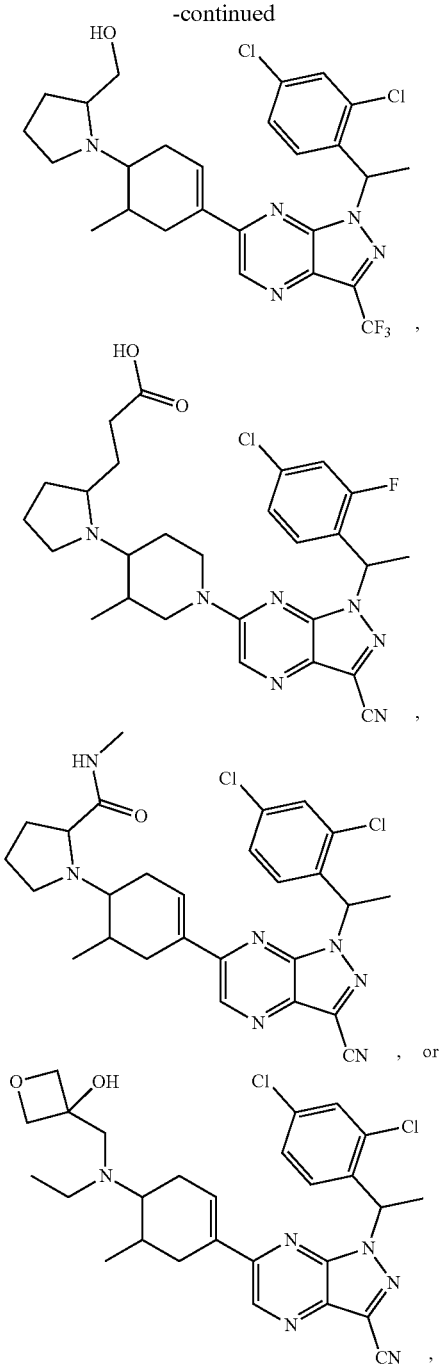

or a pharmaceutically acceptable salt thereof.

Embodiment 74. A pharmaceutical composition, comprising a compound of one of embodiments 1 to 73 and a pharmaceutically acceptable excipient.

Embodiment 75. A method of inhibiting C—C chemokine receptor type 4 (CCR4), the method comprising contacting CCR4 with a compound of one of embodiments 1 to 73.

Embodiment 76. A method of treating or preventing a disease or disorder mediated by CCR4, comprising administering to a subject in need thereof a therapeutically effective amount of a compound of one of embodiments 1 to 73 or a pharmaceutically acceptable salt thereof.

Embodiment 77. The method of embodiment 76, wherein the disease or disorder is an immune or inflammatory disease or disorder.

Embodiment 78. The method of one of embodiments 76 to 77, further comprising co-administering an anti-inflammatory agent to a subject in need thereof.

Embodiment 79. The method of one of embodiments 76 to 78, wherein the anti-inflammatory is thalidomide or a derivative thereof, a retinoid, dithranol or calcipotriol, a non-steroidal anti-inflammatory agent (NSAID), cyclo-oxygenase inhibiting nitric oxide donors (CINODs), glucocorticosteroids, methotrexate, leflunomide, hydroxychloroquine, d-penicillamine, auranofin, analgesics; diacerein, hyaluronic acid derivatives or nutritional supplements.

Embodiment 80. The method of embodiment 76, wherein the disease or disorder is a cardiovascular or metabolic disease or disorder.

Embodiment 81. The method of one of embodiments 76 or 80, further comprising co-administering a cardiovascular agent or a metabolic disorder agent to a subject in need thereof.

Embodiment 82. The method of embodiment 81, wherein the cardiovascular agent is a calcium channel blocker, a beta-adrenoceptor blocker, an angiotensin-converting enzyme (ACE) inhibitor, an angiotensin-2 receptor antagonist, a lipid lowering agent, a modulator of blood cell morphology, a thrombolytic or an anticoagulant.

Embodiment 83. The method of embodiment 76, wherein the disease or disorder is cancer.

Embodiment 84. The method of one of embodiments 76 or 83, further comprising co-administering a chemotherapeutic agent or anticancer agent to a subject in need thereof.

Embodiment 85. The method of one of embodiments 76, 83, or 84, wherein the chemotherapeutic agent or anticancer agent is an antiproliferative/antineoplastic drug, an antimetabolite, an antitumor antibiotic, an antimitotic agent, a topoisomerase inhibitor, a cytostatic agent, an oestrogen receptor down regulator, an antiandrogen, a LHRH antagonist or LHRH agonist, a progestogen, an aromatase inhibitor, an inhibitor of 5.alpha.-reductase, an agent which inhibits cancer cell invasion, an inhibitor of growth factor function, a farnesyl transferase inhibitor, a tyrosine kinase inhibitor, a serine/threonine kinase inhibitor, an inhibitor of the epidermal growth factor family, an inhibitor of the platelet-derived growth factor family, an inhibitor of the hepatocyte growth factor family; an antiangiogenic agent, a vascular damaging agent, an agent used in antisense therapy, an anti-ras antisense, an agent used in a gene therapy, an immunotherapeutic agent, or an antibody.

Embodiment 86. The method of one of embodiments 76 or 83, further comprising co-administering a therapeutically effective amount of an inhibitor of the PD-L1/PD-1 pathway, an inhibitor of CTLA-4, or an agonistic antibody of CD137 (4-1BB).

Embodiment 87. The method of one of embodiments 76 or 83, further comprising co-administering a therapeutically effective amount of an immune modulator agent or an agent of Table 1.

Embodiment 88. The method of any one of embodiments 76 or 83 to 87, wherein the cancer is colon cancer or pancreatic cancer.

What is claimed is:
1. A compound having structural Formula (I):

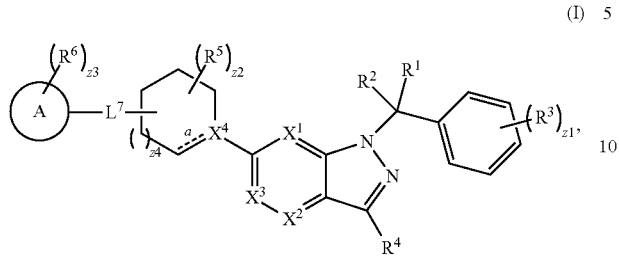

or a pharmaceutically acceptable salt thereof, wherein:
A is a substituted or unsubstituted heterocycloalkyl;
$X^1$ is N;
$X^2$ is N;
$X^3$ is $CR^{10}$;
$X^4$ is C, $CR^{11}$ or N;
z1 is an integer from 0 to 5;
z2 is an integer from 0 to 13;
z3 is an integer from 0 to 12;
z4 is an integer from 0 to 3;
⚌ is a single bond or double bond, wherein if ⚌ is a single bond, then $X^4$ is $CR^{11}$ or N, and if ⚌ is a double bond, then $X^4$ is C;
$L^7$ is a bond, —O—, —S—, —$NR^{7B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein each substituted alkylene, substituted heteroalkylene, substituted cycoalkylene, substituted heterocycloalkylene, substituted arylene, or substituted heteroarylene is substituted with at least one substituent group;
$R^1$ is hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;
$R^2$ is hydrogen, halogen, —$CX^{2.1}_3$, —$CHX^{2.1}_2$, —$CH_2X^{2.1}$, —CN, —$SO_{n2}R^{2A}$, —$SO_{v2}NR^{2B}R^{2C}$, —$NHNR^{2B}R^{2C}$, —$ONR^{2B}R^{2C}$, —NHC(O)NHNR$^{2B}$R$^{2C}$, —NHC(O)NR$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^{2.1}_3$, —OCHX$^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocloalkyl, substituted aryl, or substituted heteroaryl is substituted with at least one substituent group;
$R^3$ is independently hydrogen, halogen, —$CX^{3.1}_3$, —$CHX^{3.1}_2$, —$CH_2X^{3.1}$, —CN, —$SO_{n3}R^{3A}$, —$SO_{v3}NR^{3B}R^{3C}$, —$NHNR^{3B}R^{3C}$, —$ONR^{3B}R^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^{3.1}_3$, —OCHX$^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; wherein each substituted alkyl, substituted heteroalkyl, substituted cycloalkyl, substituted heterocycloalkyl, substituted aryl, or substituted heteroaryl is substituted with at least on substituent group;
$R^4$ is hydrogen, halogen, —$CX^{4.1}_3$, —$CHX^{4.1}_2$, —$CH_2X^{4.1}$, —CN, —$SO_{n4}R^{4A}$, —$SO_{v4}NR^{4B}R^{4C}$, —$NHNR^{4B}R^{4C}$, —$ONR^{4B}R^{4C}$, —NHC(O)NHNR$^{4B}$R$^{4C}$, —NHC(O)NR$^{4B}$R$^{4C}$, —N(O)$_{m4}$, —NR$^{4B}$R$^{4C}$, —C(O)R$^{4D}$, —C(O)OR$^{4D}$, —C(O)NR$^{4B}$R$^{4C}$, —OR$^{4A}$, —NR$^{4B}$SO$_2$R$^{4A}$, —NR$^{4B}$C(O)R$^{4D}$, —NR$^{4B}$C(O)OR$^{4D}$, —NR$^{4B}$OR$^{4D}$, —OCX$^{4.1}_3$, —OCHX$^{4.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;
$R^5$ is independently hydrogen, halogen, oxo, —$CX^{5.1}_3$, —$CHX^{5.1}_2$, —$CH_2X^{5.1}$, —CN, —$SO_{n5}R^{5A}$, —$SO_{v5}NR^{5B}R^{5C}$, —$NHNR^{5B}R^{5C}$, —$ONR^{5B}R^{5C}$, —NHC(O)NHNR$^{5B}$R$^{5C}$, —NHC(O)NR$^{5B}$R$^{5C}$, —N(O)$_{m5}$, —NR$^{5B}$R$^{5C}$, —C(O)R$^{5D}$, —C(O)OR$^{5D}$, —C(O)NR$^{5B}$R$^{5C}$, —OR$^{5A}$, —NR$^{5B}$SO$_2$R$^{5A}$, —NR$^{5B}$C(O)R$^{5D}$, —NR$^{5B}$C(O)OR$^{5D}$, —NR$^{5B}$OR$^{5D}$, —OCX$^{5.1}_3$, —OCHX$^{5.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; wherein each substituted alkyl, substituted heteroalkyl, substituted cycloalkyl, substituted hetercycloalkyl, substituted aryl, or substituted heteroaryl is substituted with at least one substituent group;
$R^6$ is independently hydrogen, halogen, oxo, —$CX^{6.1}_3$, —$CHX^{6.1}_2$, —$CH_2X^{6.1}$, —CN, —$SO_{n6}R^{6A}$, —$SO_{v6}NR^{6B}R^{6C}$, —$NHNR^{6B}R^{6C}$, —$ONR^{6B}R^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

$R^{10}$ is hydrogen, halogen, $-CX^{10.1}{}_3$, $-CHX^{10.1}{}_2$, $-CH_2X^{10.1}$, $-CN$, $-SO_{n10}R^{10A}$, $-SO_{v10}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m10}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}{}_3$, $-OCHX^{10.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

$R^{11}$ is hydrogen, halogen, $-CX^{11.1}{}_3$, $-CHX^{11.1}{}_2$, $-CH_2X^{11.1}$, $-CN$, $-SO_{n11}R^{11A}$, $-SO_{v11}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m11}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}{}_3$, $-OCHX^{11.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7B}$, $R^{10A}$, $R^{10B}$, $R^{10C}$, $R^{10D}$, $R^{11A}$, $R^{11B}$, $R^{11C}$ and $R^{11D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ and $R^{1C}$, $R^{2B}$ and $R^{2C}$, $R^{3B}$ and $R^{3C}$, $R^{4B}$ and $R^{4C}$, $R^{5B}$ and $R^{5C}$, $R^{6B}$ and $R^{6C}$, $R^{10B}$ and $R^{10C}$, $R^{11B}$ and $R^{11C}$ substituents bonded to the same nitrogen atom may optionally be joined to form a substituted or unsubstituted heterocycloalkyl or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

n1, n2, n3, n4, n5, n6, n10 and n11 are independently an integer from 0 to 4;

m1, m2, m3, m4, m5, m6, m10, m11, v1, v2, v3, v4, v5, v6, v10, and v11 are independently 1 or 2; and $X^{1.1}$, $X^{2.1}$, $X^{3.1}$, $X^{4.1}$, $X^{5.1}$, $X^{6.1}$, $X^{10.1}$, and $X^{11.1}$ are independently $-Cl$, $-Br$, $-I$ or $-F$.

2. The compound of claim 1, wherein the compound has structural Formula (Ia):

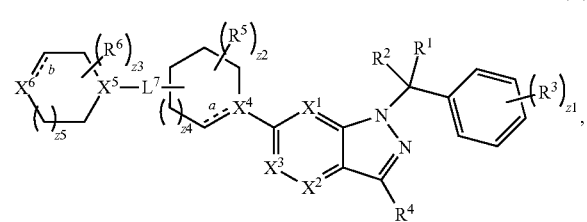

(Ia)

or a pharmaceutically acceptable salt thereof, wherein:

$X^5$ is $-CR^{12}$ or $-N$;

$X^6$ is $-CR^{13}$, $-CR^{13}R^{14}$, $-N$ or $-NR^{15}$;

z3 is an integer from 0 to 12;

z5 is an integer from 0 to 3;

$R^{12}$ is hydrogen, halogen, $-CX^{12.1}{}_3$, $-CHX^{12.1}{}_2$, $-CH_2X^{12.1}$, $-CN$, $-SO_{n12}R^{12A}$, $-SO_{v12}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m12}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}{}_3$, $-OCHX^{12.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; herein each substituted alkyl, substituted heteroalkyl, substituted cycloalkyl, substituted heterocycloalkyl, substituted aryl, or substituted heteroaryl is substituted with at least one substituent group;

$R^{13}$ is hydrogen, halogen, $-CX^{13.1}{}_3$, $-CHX^{13.1}{}_2$, $-CH_2X^{13.1}$, $-CN$, $-SO_{n13}R^{13A}$, $-SO_{v13}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m13}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}{}_3$, $-OCHX^{13.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycoloalkyl, substituted heterocycloalkyl, substituted aryl, or substituted heteroaryl is substituted with at least one substituent group;

$R^{14}$ is hydrogen, halogen, $-CX^{14.1}{}_3$, $-CHX^{14.1}{}_2$, $-CH_2X^{14.1}$, $-CN$, $-SO_{n14}R^{14A}$, $-SO_{v14}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m14}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}{}_3$, $-OCHX^{14.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, ort substituted heteroaryl is substituted with at least one substituent group;

$R^{15}$ is hydrogen, halogen, —$CX^{15.1}{}_3$, —$CHX^{15.1}{}_2$, —$CH_2X^{15.1}$, —CN, —$SO_{n15}R^{15A}$, —$SO_{v15}NR^{15B}R^{15C}$, —$NHNR^{15B}R^{15C}$, —$ONR^{15B}R^{15C}$, —$NHC(O)NHNR^{15B}R^{15C}$, —$NHC(O)NR^{15B}R^{15C}$, —$N(O)_{m15}$, —$NR^{15B}R^{15C}$, —$C(O)R^{15D}$, —$C(O)OR^{15D}$, —$C(O)NR^{15B}R^{15C}$, —$OR^{15A}$, —$NR^{15B}SO_2R^{15A}$, —$NR^{15B}C(O)R^{15D}$, —$NR^{15B}C(O)OR^{15D}$, —$NR^{15B}OR^{15D}$, —$OCX^{15.1}{}_3$, —$OCHX^{15.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

$R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$ and $R^{15D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12B}$ and $R^{12C}$, $R^{13B}$ and $R^{13C}$, $R^{14B}$ and $R^{14C}$ and $R^{15B}$ and $R^{15C}$ substituents bonded to the same nitrogen atom may optionally be joined to form a substituted or unsubstituted heterocycloalkyl or substituted or unsubstituted heteroaryl; wherein each substituted alkyl, substituted heteroalkyl, substituted cycloalkyl, substituted heterocycloalkyl, substituted aryl, or subsituted heteroaryl is substituted with at least on substituent group;

n12, n13, n14, and n15 are independently an integer from 0 to 4;

m12, m13, m14, m15, v12, v13, v14, and v15 are independently 1 or 2;

═ is a single bond or double bond, wherein if ═ is a single bond, then $X^6$ is $CR^{13}R^{14}$ or $NR^{15}$, and if ═ is a double bond, then $X^6$ is N or $CR^{13}$; and $X^{12.1}$, $X^{13.1}$, $X^{14.1}$ and $X^{15.1}$ are independently —Cl, —Br, —I or —F.

3. The compound of claim 2, wherein the compound has structural Formula (II):

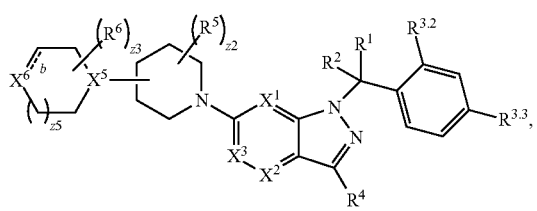

(II)

or a pharmaceutically acceptable salt thereof, wherein:

$R^4$ is hydrogen, —$CX^{4.1}{}_3$, —CN, —$C(O)R^{4D}$, —$C(O)OR^{4D}$, —$C(O)NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3.2}$ is hydrogen, halogen, —$CX^{3.2}{}_3$, —$CHX^{3.2}{}_2$, —$CH_2X^{3.2}$, —CN, —$SO_{n3.2}R^{3.2A}$, —$SO_{v3.2}NR^{3.2B}R^{3.2C}$, —$NHNR^{3.2B}R^{3.2C}$, —$ONR^{3.2B}R^{3.2C}$, —$NHC(O)NHNR^{3.2B}R^{3.2C}$, —$NHC(O)NR^{3.2B}R^{3.2C}$, —$N(O)_{m3.2}$, —$NR^{3.2B}R^{3.2C}$, —$C(O)R^{3.2D}$, —$C(O)OR^{3.2D}$, —$C(O)NR^{3.2B}R^{3.2C}$, —$OR^{3.2A}$, —$NR^{3.2B}SO_2R^{3.2A}$, —$NR^{3.2B}C(O)R^{3.2D}$, —$NR^{3.2B}C(O)OR^{3.2D}$, —$NR^{3.2B}OR^{3.2D}$, —$OCX^{3.2}{}_3$, —$OCHX^{3.2}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

$R^{3.3}$ is hydrogen, halogen, —$CX^{3.3}{}_3$, —$CHX^{3.3}{}_2$, —$CH_2X^{3.3}$, —CN, —$SO_{n3.3}R^{3.3A}$, —$SO_{v3.3}NR^{3.3B}R^{3.3C}$, —$NHNR^{3.3B}R^{3.3C}$, —$ONR^{3.3B}R^{33C}$, —$NHC(O)NHNR^{3.3B}R^{3.3C}$, —$NHC(O)NR^{3.3B}R^{3.3}c$, —$N(O)_{m3.3}$, —$NR^{3.3B}R^{3.3C}$, —$C(O)R^{3.3D}$, —$C(O)OR^{3.3D}$, —$C(O)NR^{3.3B}R^{3.3C}$, —$OR^{3.3A}$, —$NR^{3.3B}SO_2R^{3.3A}$, —$NR^{3.3B}C(O)R^{3.3D}$, —$NR^{3.3B}C(O)OR^{3.3D}$, —$NR^{3.3B}OR^{3.3D}$, —$OCX^{3.3}{}_3$, —$OCHX^{3.3}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one subtituent group;

$R^{3.2A}$, $R^{3.2B}$, $R^{3.2C}$, $R^{3.2D}$, $R^{3.3B}$ and $R^{3.3D}$ are independently hydrogen, halogen, —$CF_3$, —$CCl_3$, —$CBr_3$, —$CI_3$, —COOH, —$CONH_2$, substituted or unsubstituted alkyl, substituted or unsubtituted heteroalkyl, substituted or unsubstituted cycloalkyl, substituted or unsubstituted heterocycloalkyl, substituted or unsubstituted aryl, or substituted or unsubstituted heteroaryl; $R^{3.2B}$ and $R^{3.2C}$, $R^{3.3B}$ and $R^{3.3C}$ substituents bonded to the same nitrogen atom may optionally be joined to form a substituted or unsubstituted heterocycloalkyl or substituted or unsusbtituted heteroaryl; wherein each substituted alkyl, substituted heteroalkyl, substititued cycloalkyl, substituted heterocycloalkyl, substituted aryl, or substituted heteroaryl is substituted with at least one substituent group;

n3.2 and n3.3 are independently an integer from 0 to 4;

m3.2, m3.3, v3.2, and v3.3 are independently 1 or 2; and $X^{3.2}$ and $X^{3.3}$ are independently —Cl, —Br, —I or —F.

4. The compound of claim 3, wherein the compound has structural Formula (IV):

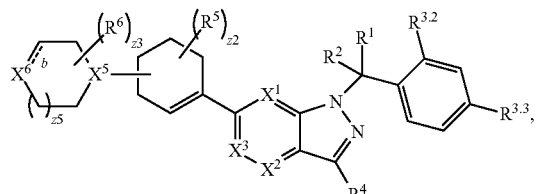

(IV)

or a pharmaceutically acceptable salt thereof.

5. The compound of claim 3, wherein the compound has structural Formula (VI):

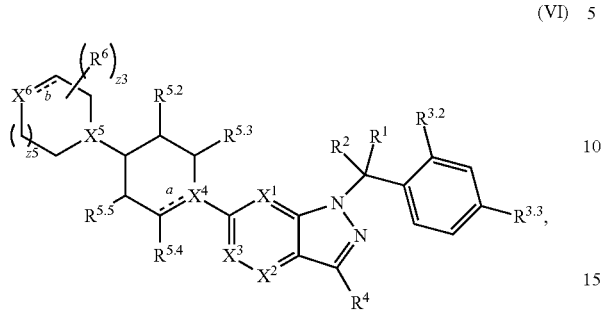

(VI)

or a pharmaceutically acceptable salt thereof, wherein:

$R^{5.2}$ is hydrogen, halogen, $-CX^{5.6}_3$, $-CHX^{5.6}_2$, $-CH_2X^{5.6}$, $-CN$, $-SO_{n5.2}R^{5.6A}$, $-SO_{v5.2}NR^{5.6B}R^{5.6C}$, $NHNR^{5.6B}R^{5.6C}$, $-ONR^{5.6B}R^{5.6C}$, $NHC(O)NHNR^{5.6B}R^{5.6C}$, $-NHC(O)NR^{5.6B}R^{5.6C}$, $-N(O)_{m5.2}$, $-NR^{5.6B}R^{5.6C}$, $-C(O)R^{5.6D}$, $-C(O)OR^{5.6D}$, $-C(O)NR^{5.6B}R^{5.6C}$, $-OR^{5.6A}$, $-NR^{5.6B}SO_2R^{5.6A}$, $-NR^{5.6B}C(O)R^{5.6D}$, $-NR^{5.6B}C(O)OR^{5.6D}$, $-NR^{5.6B}OR^{5.6D}$, $-OCX^{5.6}_3$, $-OCHX^{5.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

$R^{5.3}$ is hydrogen, halogen, $-CX^{5.7}_3$, $-CHX^{5.7}_2$, $-CH_2X^{5.7}$, $-CN$, $-SO_{n5.3}R^{5.7A}$, $-SO_{v5.3}NR^{5.7B}R^{5.7C}$, $-NHNR^{5.7B}R^{5.7C}$, $-ONR^{5.7B}R^{5.7C}$, $-NHC(O)NHNR^{5.7B}R^{5.7C}$, $-NHC(O)NR^{5.7B}R^{5.7C}$, $-N(O)_{m5.3}$, $-NR^{5.7B}R^{5.7C}$, $-C(O)R^{5.7D}$, $-C(O)OR^{5.7D}$, $-C(O)NR^{5.7B}R^{5.7C}$, $-OR^{5.7A}$, $-NR^{5.7B}SO_2R^{5.7A}$, $-NR^{5.7B}C(O)R^{5.7D}$, $-NR^{5.7B}C(O)OR^{5.7D}$, $-NR^{5.7B}OR^{5.7D}$, $-OCX^{5.7}_3$, $-OCHX^{5.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

$R^{5.4}$ is hydrogen, halogen, $-CX^{5.8}_3$, $-CHX^{5.8}_2$, $-CH_2X^{5.8}$, $-CN$, $-SO_{n5.4}R^{5.8A}$, $-SO_{v5.4}NR^{5.8B}R^{5.8C}$, $-NHNR^{5.8B}R^{5.8C}$, $-ONR^{5.8B}R^{5.8C}$, $NHC(O)NHNR^{5.8B}R^{5.8C}$, $-NHC(O)NR^{5.8B}R^{5.8C}$, $-N(O)_{m5.4}$, $-NR^{5.8B}R^{5.8C}$, $-C(O)R^{5.8D}$, $-C(O)OR^{5.8D}$, $-C(O)NR^{5.8B}R^{5.8C}$, $-OR^{5.8A}$, $-NR^{5.8B}SO_2R^{5.8A}$, $-NR^{5.8B}C(O)R^{5.8D}$, $-NR^{5.8B}C(O)OR^{5.8D}$, $-NR^{5.8B}OR^{5.8D}$, $-OCX^{5.8}_3$, $-OCHX^{5.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalykl, substituted cycloalkyl, substituted heterocycloalkyl, substituted aryl, or substituted heteroaryl is substituted with at least one substituent group;

$R^{5.5}$ is hydrogen, halogen, $-CX^{5.9}_3$, $-CHX^{5.9}_2$, $-CH_2X^{5.9}$, $-CN$, $-SO_{n5.5}R^{5.9A}$, $-SO_{v5.5}NR^{5.9B}R^{5.9C}$, $NHNR^{5.9B}R^{5.9C}$, $-ONR^{5.9B}R^{5.9C}$, $NHC(O)NHNR^{5.9B}R^{5.9C}$, $-NHC(O)NR^{5.9B}R^{5.9C}$, $-N(O)_{m5.5}$, $-NR^{5.9B}R^{5.9C}$, $-C(O)R^{5.9D}$, $-C(O)OR^{5.9D}$, $-C(O)NR^{5.9B}R^{5.9C}$, $-OR^{5.9A}$, $-NR^{5.9B}SO_2R^{5.9A}$, $-NR^{5.9B}C(O)R^{5.9D}$, $-NR^{5.9B}C(O)OR^{5.9D}$, $-NR^{5.9B}OR^{5.9D}$, $-OCX^{5.9}_3$, $-OCHX^{5.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

$R^{5.6A}$, $R^{5.6B}$, $R^{5.6C}$, $R^{5.6D}$, $R^{5.7A}$, $R^{5.7B}$, $R^{5.7C}$, $R^{5.7D}$, $R^{5.8A}$, $R^{5.8B}$, $R^{5.8C}$, $R^{5.8D}$, $R^{5.9A}$, $R^{5.9B}$, $R^{5.9C}$ and $R^{5.9D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5.6B}$ and $R^{5.6C}$, $R^{5.7B}$ and $R^{5.7C}$, $R^{5.8B}$ and $R^{5.8C}$, $R^{5.9B}$ and $R^{5.9C}$ substituents bonded to the same nitrogen atom may optionally be joined to form a substituted or unsubstituted heterocycloalkyl or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

n5.2, n5.3, n5.4, and n5.5 are independently an integer from 0 to 4;

m5.2, m5.3, m5.4, m5.5, v5.2, v5.3, v5.4, and v5.5 are independently are independently 1 or 2; and $X^{5.6}$, $X^{5.7}$, $X^{5.8}$ and $X^{5.9}$ are independently $-Cl$, $-Br$, $-I$ or $-F$.

6. The compound of claim 5 wherein the compound has structural Formula (VII):

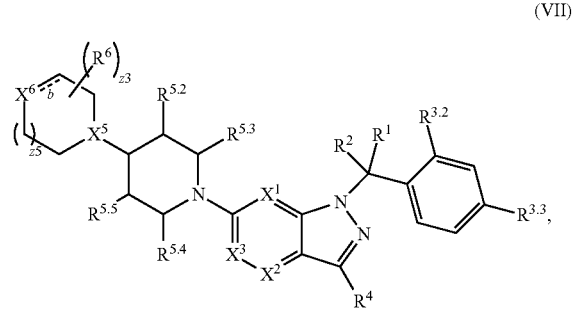

(VII)

or a pharmaceutically acceptable salt thereof.

7. The compound of claim 5, wherein the compound has structural Formula (VIII):

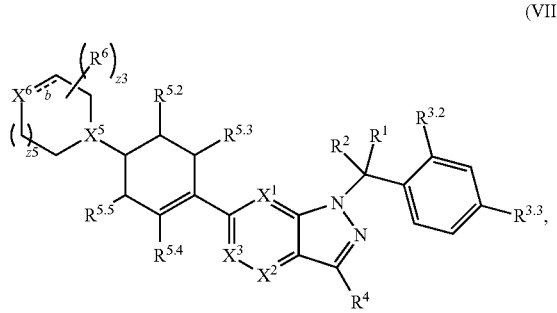

(VIII)

or a pharmaceutically acceptable salt thereof.

8. The compound of claim 5, wherein the compound has structural Formula (VIIIa):

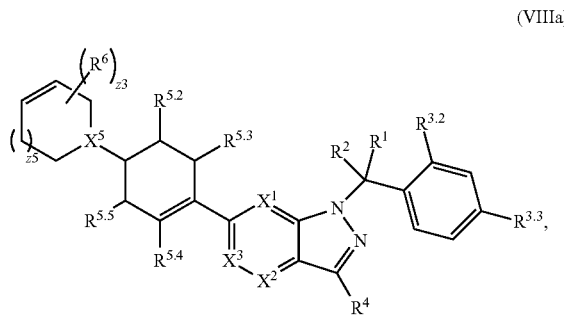

(VIIIa)

or a pharmaceutically acceptable salt thereof.

9. The compound of claim 5, wherein the compound has structural Formula (VIIIb):

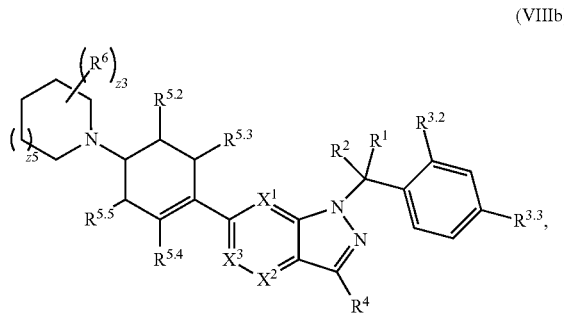

(VIIIb)

or a pharmaceutically acceptable salt thereof.

10. The compound of claim 5, wherein the compound has structural Formula (IX):

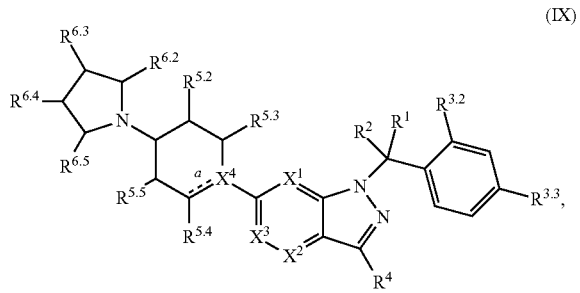

(IX)

or a pharmaceutically acceptable salt thereof, wherein:
$R^{6.2}$ is hydrogen, halogen, —$CX^{6.6}_3$, —$CHX^{6.6}_2$, —$CH_2X^{6.6}$, —CN, —$SO_{n6.2}R^{6.6A}$, —$SO_{v6.2}NR^{6.6B}R^{6.6C}$, —$NHNR^{6.6B}R^{6.6C}$, —$ONR^{6.6B}R^{6.6C}$, —$NHC(O)NHNR^{6.6B}R^{6.6C}$, —$NHC(O)NR^{6.6B}R^{6.6C}$, —$N(O)_{m6.2}$, —$NR^{6.6B}R^{6.6C}$, —$C(O)R^{6.6D}$, —$C(O)OR^{6.6D}$, —$C(O)NR^{6.6B}R^{6.6C}$, —$OR^{6.6A}$, —$NR^{6.6B}SO_2R^{6.6A}$, —$NR^{6.6B}C(O)R^{6.6D}$, —$NR^{6.6B}C(O)OR^{6.6D}$, —$NR^{6.6B}OR^{6.6D}$, —$OCX^{6.6}_3$, —$OCHX^{6.6}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

$R^{6.3}$ is hydrogen, halogen, —$CX^{6.7}_3$, —$CHX^{6.7}_2$, —$CH_2X^{6.7}$, —CN, —$SO_{n6.3}R^{6.7A}$, —$SO_{v6.3}NR^{6.7B}R^{6.7C}$, —$NHNR^{6.7B}R^{6.7C}$, —$ONR^{6.7B}R^{6.7C}$, —$NHC(O)NHNR^{6.7B}R^{6.7C}$, —$NHC(O)NR^{6.7B}R^{6.7C}$, —$N(O)_{m6.3}$, —$NR^{6.7B}R^{6.7C}$, —$C(O)R^{6.7D}$, —$C(O)OR^{6.7D}$, —$C(O)NR^{6.7B}R^{6.7C}$, —$OR^{6.7A}$, —$NR^{6.7B}SO_2R^{6.7A}$, —$NR^{6.7B}C(O)R^{6.7D}$, —$NR^{6.7B}C(O)OR^{6.7D}$, —$NR^{6.7B}OR^{6.7D}$, —$OCX^{6.7}_3$, —$OCHX^{6.7}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

$R^{6.4}$ is hydrogen, halogen, —$CX^{6.8}_3$, —$CHX^{6.8}_2$, —$CH_2X^{6.8}$, —CN, —$SO_{n6.4}R^{6.8A}$, —$SO_{v6.4}NR^{6.8B}R^{6.8C}$, —$NHNR^{6.8B}R^{6.8C}$, —$ONR^{6.8B}R^{6.8C}$, —$NHC(O)NHNR^{6.8B}R^{6.8C}$, —$NHC(O)NR^{6.8B}R^{6.8C}$, —$N(O)_{m6.4}$, —$NR^{6.8B}R^{6.8C}$, —$C(O)R^{6.8D}$, —$C(O)OR^{6.8D}$, —$C(O)NR^{6.8B}R^{6.8C}$, —$OR^{6.8A}$, —$NR^{6.8B}SO_2R^{6.8A}$, —$NR^{6.8B}C(O)R^{6.8D}$, —$NR^{6.8B}C(O)OR^{6.8D}$, —$NR^{6.8B}OR^{6.8D}$, —$OCX^{6.8}_3$, —$OCHX^{6.8}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituded heteroalkyl, substituted cycloalkyl, substituted heterocycloalkyl, substituted aryl, or substituded heteroaryl is substituted with at least one substituent group;

$R^{6.5}$ is hydrogen, halogen, —$CX^{6.9}_3$, —$CHX^{6.9}_2$, —$CH_2X^{6.9}$, —CN, —$SO_{n6.5}R^{6.9A}$, —$SO_{v6.5}NR^{6.9B}R^{6.9C}$, —$NHNR^{6.9B}R^{6.9C}$, —$ONR^{6.9B}R^{6.9C}$, —$NHC(O)NHNR^{6.9B}R^{6.9C}$, —$NHC(O)NR^{6.9B}R^{6.9C}$, —$N(O)_{m6.5}$, —$NR^{6.9B}R^{6.9C}$, —$C(O)R^{6.9D}$, —$C(O)OR^{6.9D}$, —$C(O)NR^{6.9B}R^{6.9C}$, —$OR^{6.9A}$, —$NR^{6.9B}SO_2R^{6.9A}$, —$NR^{6.9B}C(O)R^{6.9D}$, —$NR^{6.9B}C(O)OR^{6.9D}$, —$NR^{6.9B}OR^{6.9D}$, —$OCX^{6.9}_3$, —$OCHX^{6.9}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

$R^{6.6A}$, $R^{6.6B}$, $R^{6.6C}$, $R^{6.6D}$, $R^{6.7A}$, $R^{6.7B}$, $R^{6.7C}$, $R^{6.7D}$, $R^{6.8A}$, $R^{6.8B}$, $R^{6.8C}$, $R^{6.8D}$, $R^{6.9A}$, $R^{6.9B}$, $R^{6.9C}$ and $R^{6.9D}$ are independently hydrogen, halogen, —CF₃, —CCl₃, —CBr₃, —Cl₃, —COOH, —CONH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{6.6B}$ and $R^{6.6C}$, $R^{6.7B}$ and $R^{6.7C}$, $R^{6.8B}$ and $R^{6.8C}$, $R^{6.9B}$ and $R^{6.9C}$ substituents bonded to the same nitrogen atom may optionally be joined to form a substituted or unsubstituted heterocycloalkyl or substituted or unsubstituted heteroaryl; wherein each substituted alkyl, substituted heteroalkyl, substituted cycloalkyl, substituted heterocycloalkyl, substituted aryl, or substituted heteroaryl is substituted with at least one substituent group;

n6.2, n6.3, n6.4, and n6.5 are independently an integer from 0 to 4;

m6.2, m6.3, m6.4, m6.5, v6.2, v6.3, v6.4, and v6.5 are independently 1 or 2; and $X^{6.6}$, $X^{6.7}$, $X^{6.8}$ and $X^{6.9}$ are independently —Cl, —Br, —I or —F.

11. The compound of claim 2, wherein the compound has structural Formula (X):

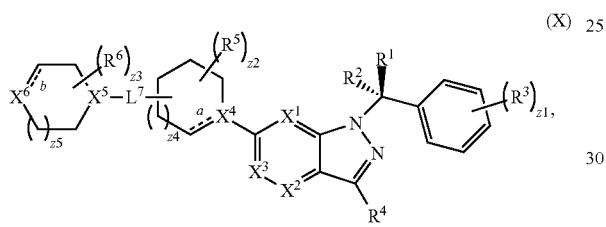

or a pharmaceutically acceptable salt thereof.

12. The compound of claim 11, or a pharmaceutically acceptable salt thereof, wherein $R^1$ is hydrogen.

13. The compound of claim 11, or a pharmaceutically acceptable salt thereof, wherein $R^2$ is hydrogen.

14. The compound of claim 1, wherein the compound is:

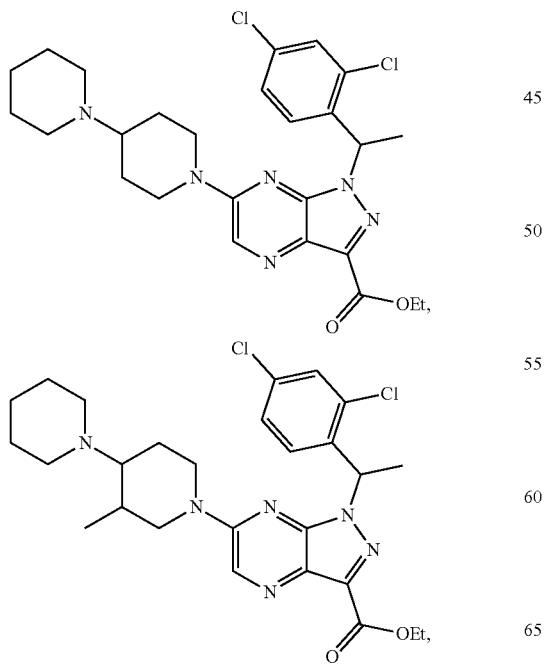

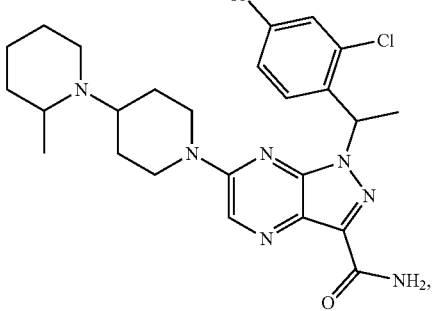

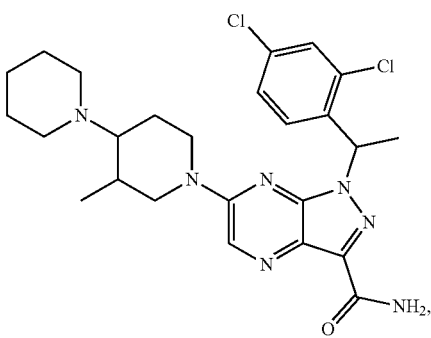

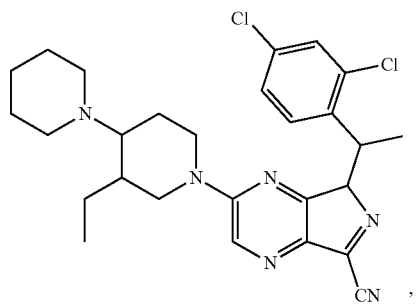

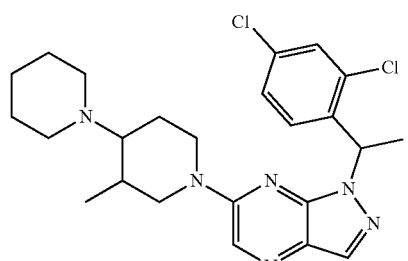

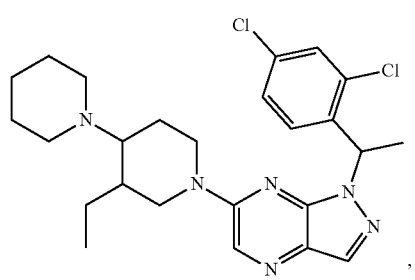

617
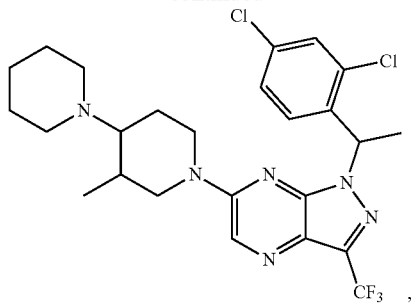
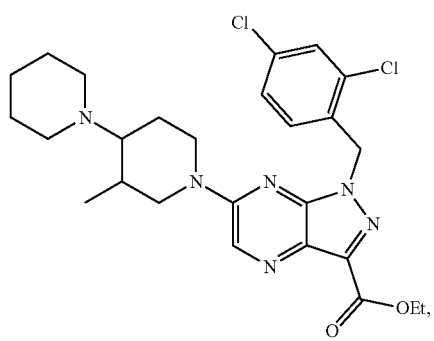
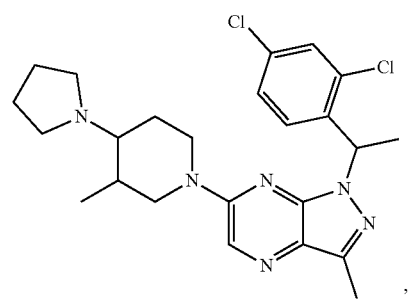
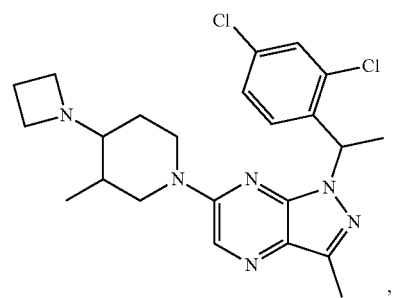
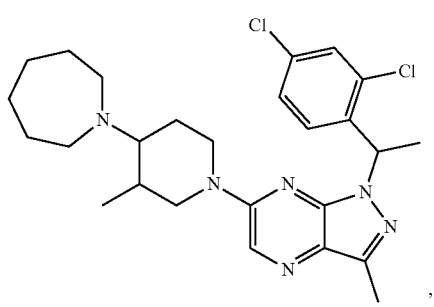
618
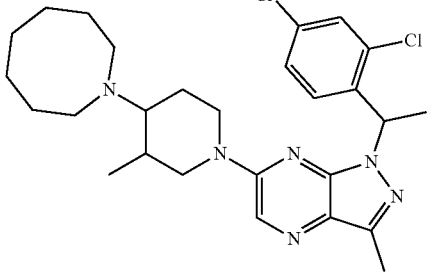
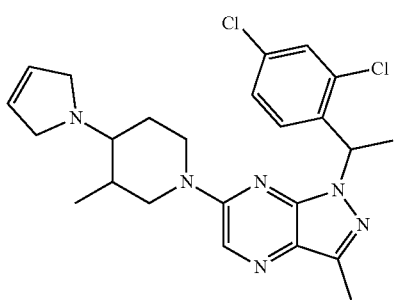
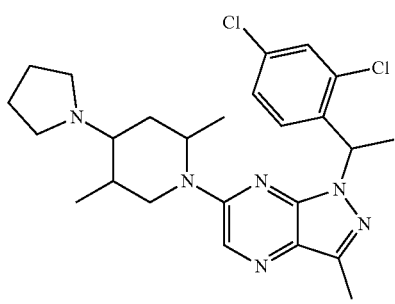
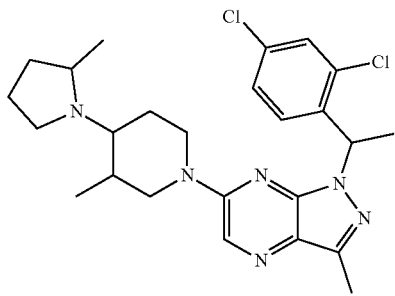
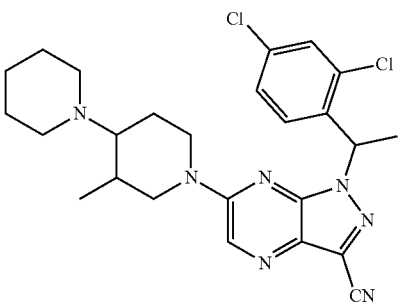

619
-continued
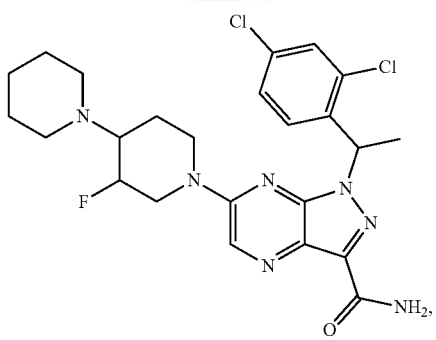
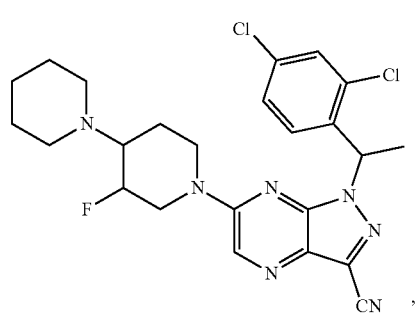
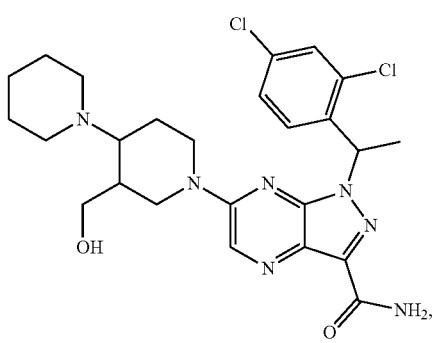
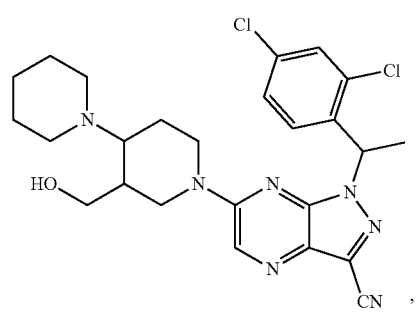
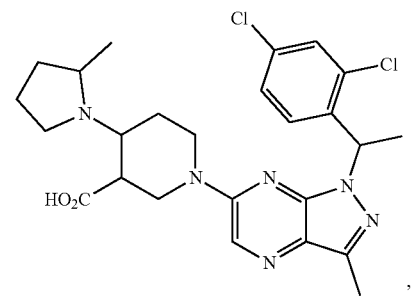
620
-continued
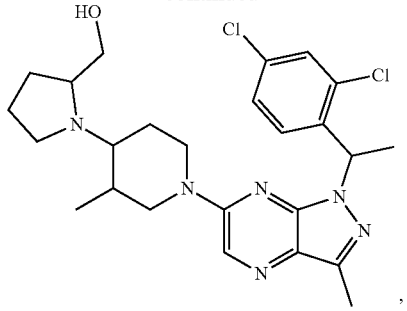
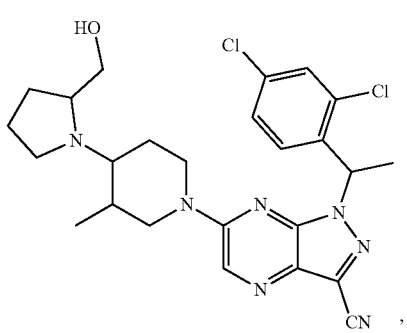
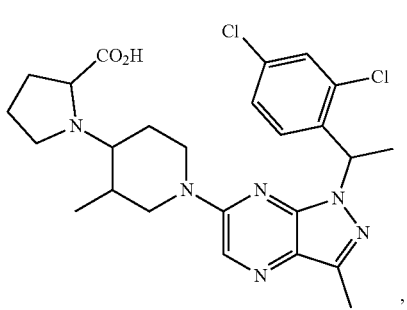
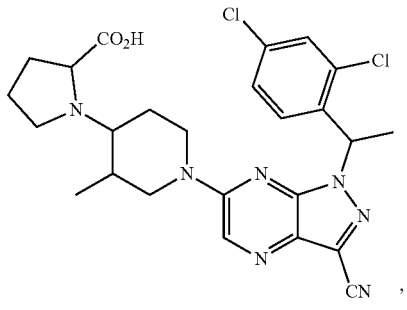
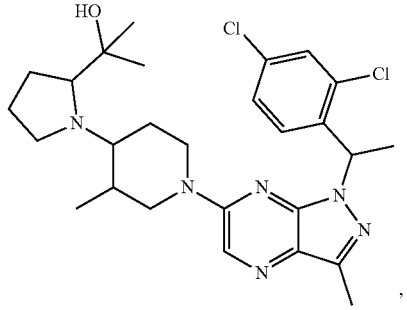

621
-continued
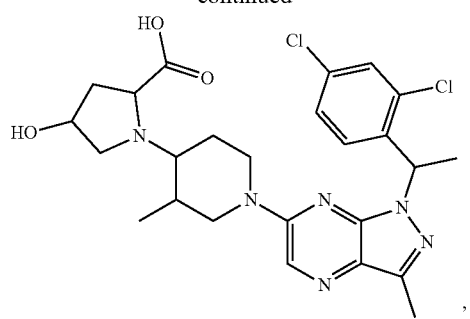
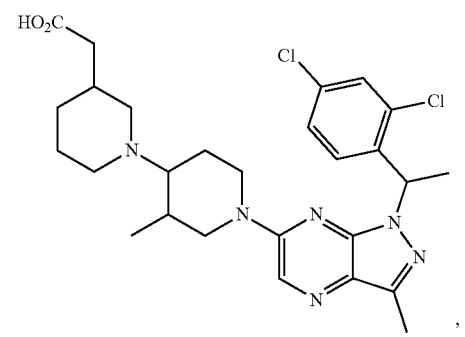
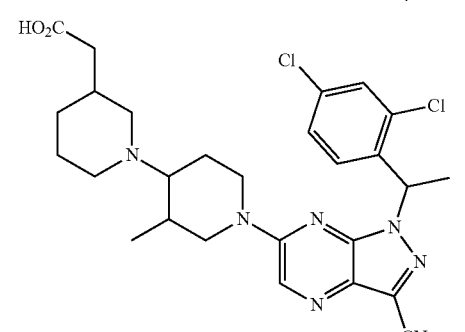
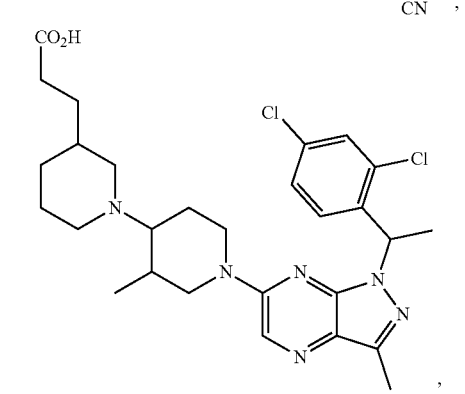
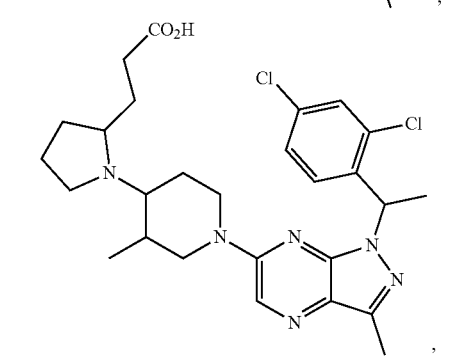
622
-continued
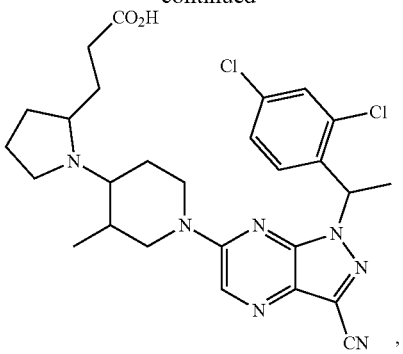
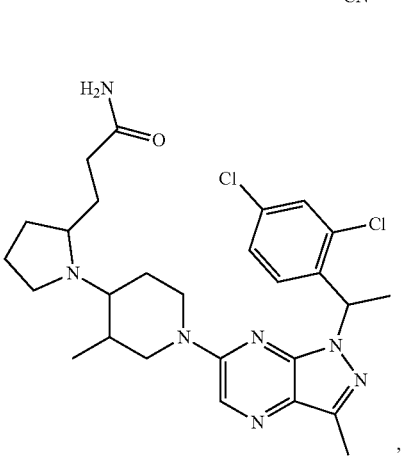
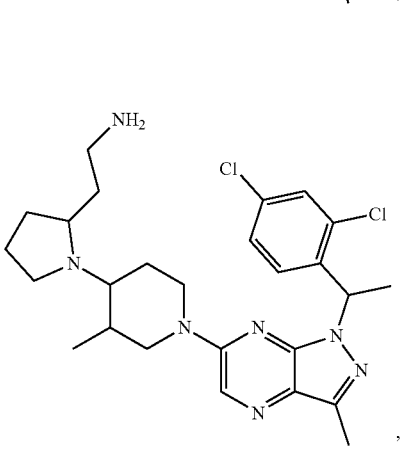
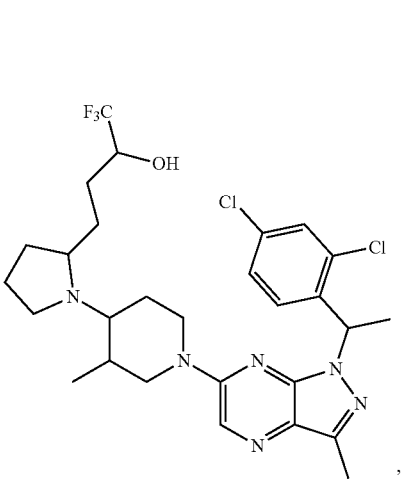

623
-continued
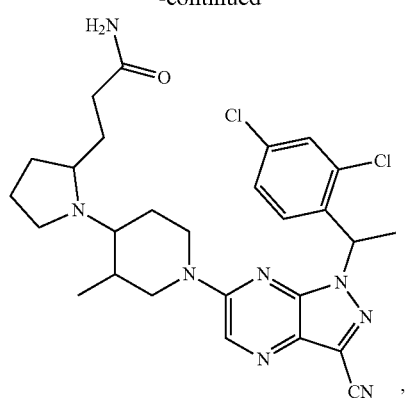
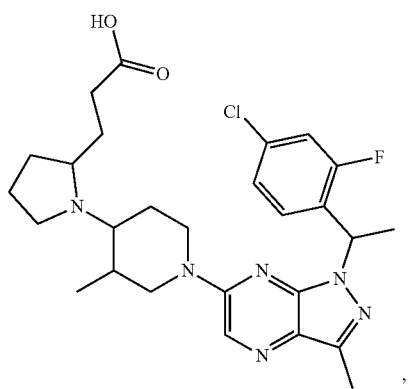
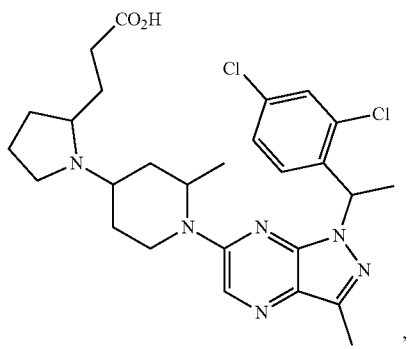
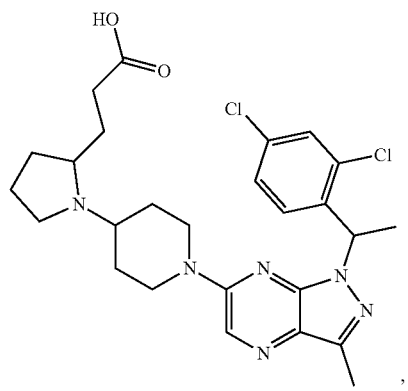
624
-continued
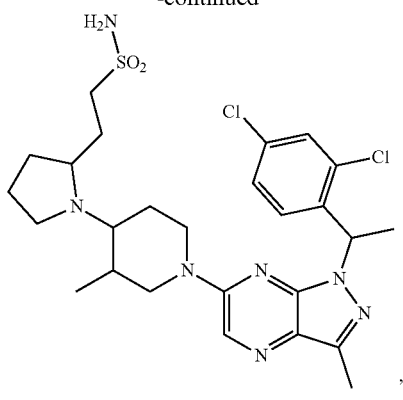
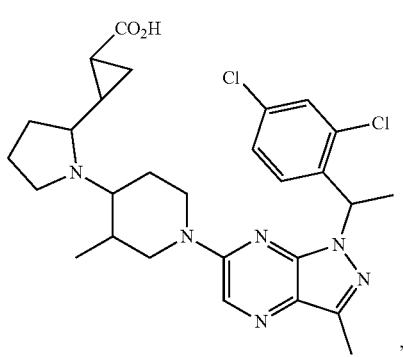
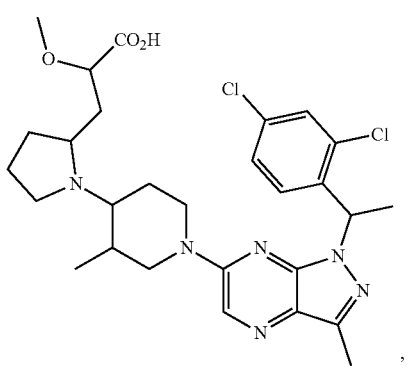
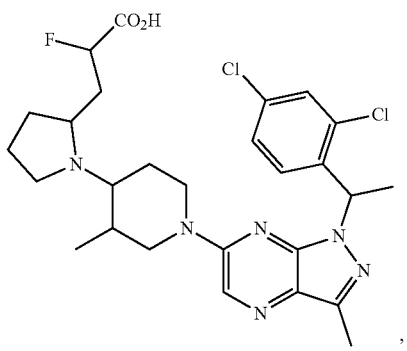

625
-continued
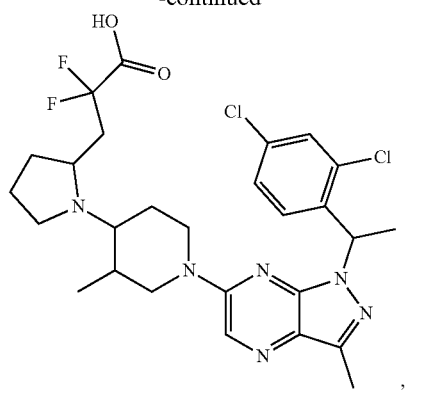
,
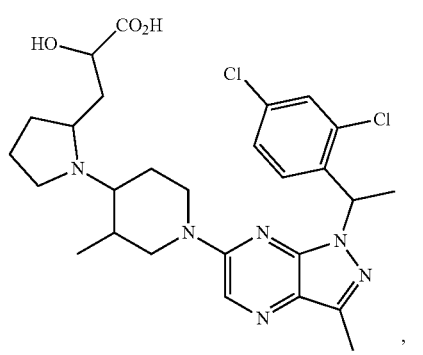
,
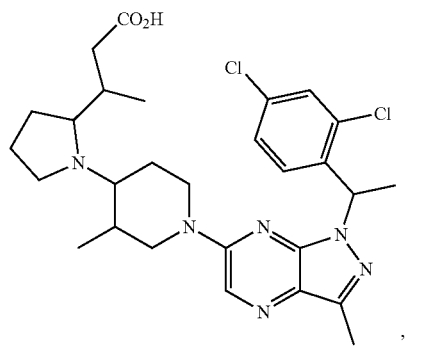
,
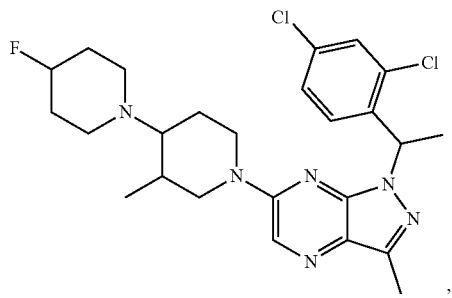
,
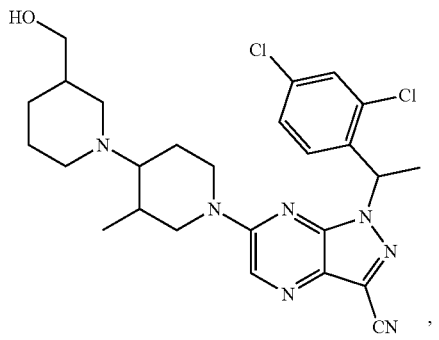
,
626
-continued
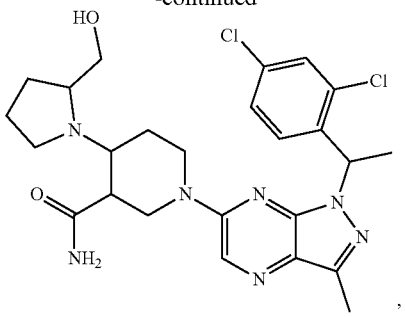
,
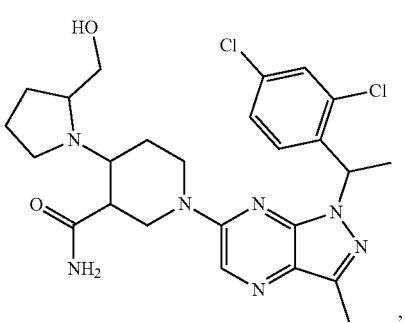
,
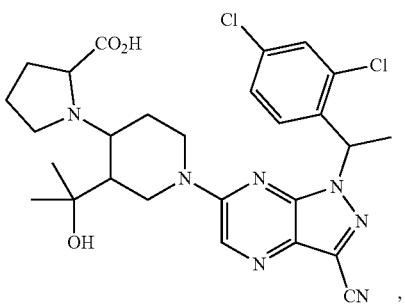
,
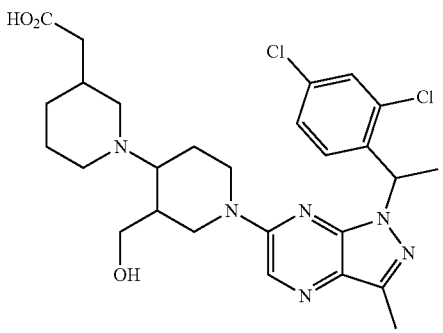
,
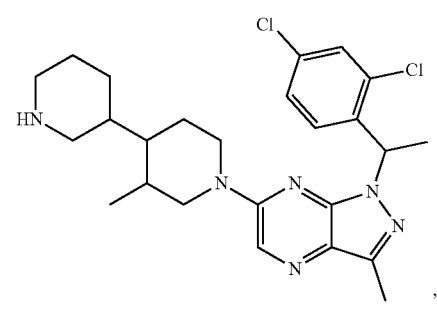
, 627
-continued
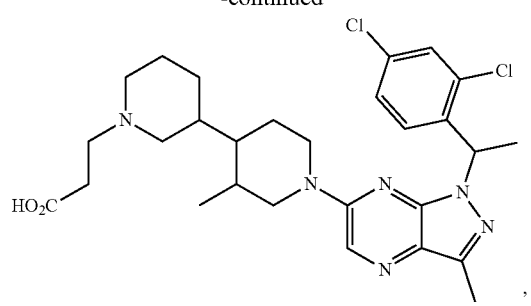
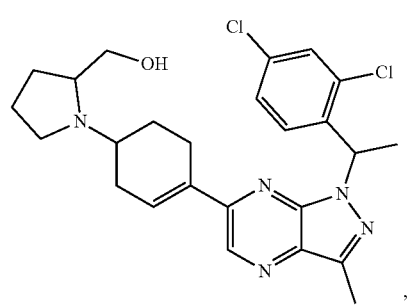
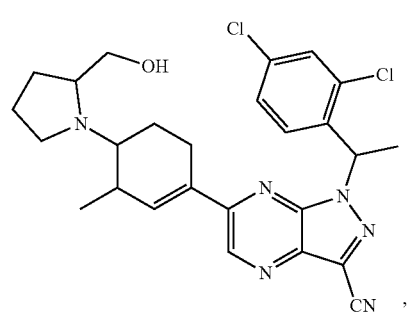
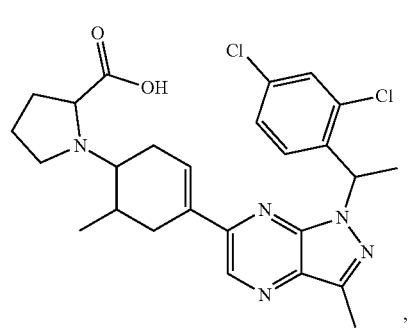
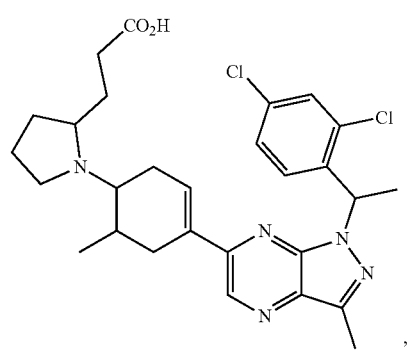
628
-continued
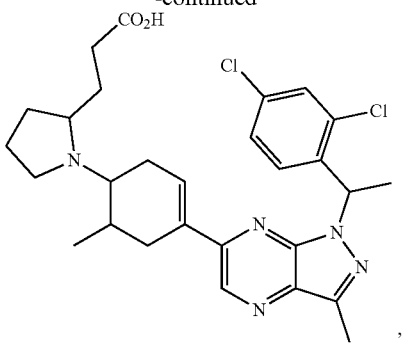
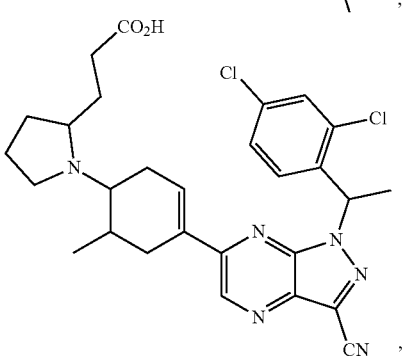
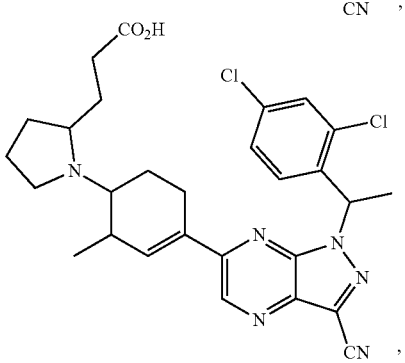
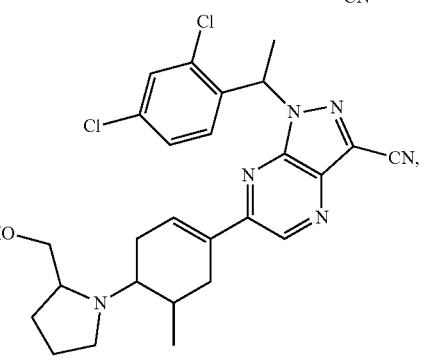
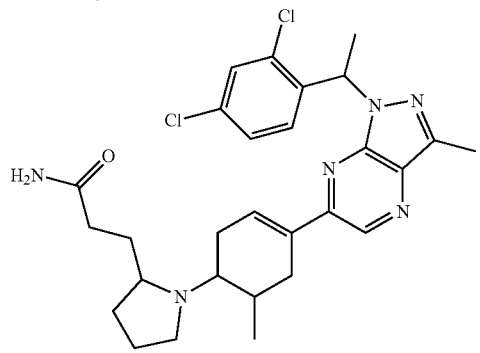

629
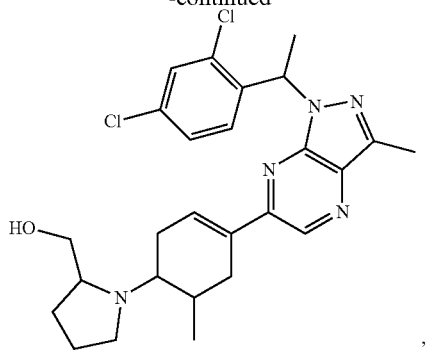
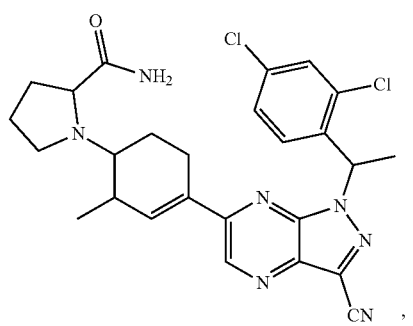
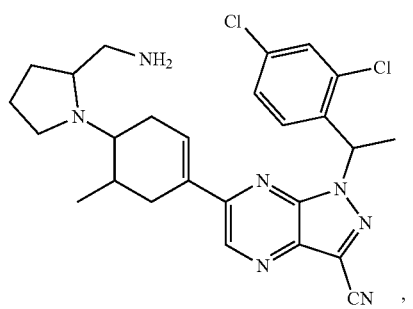
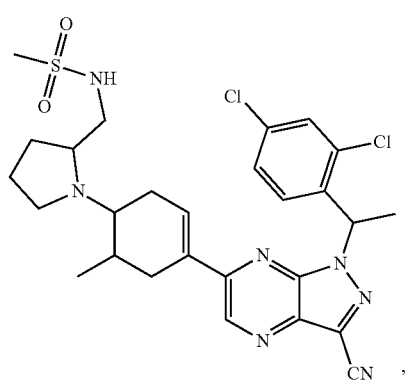
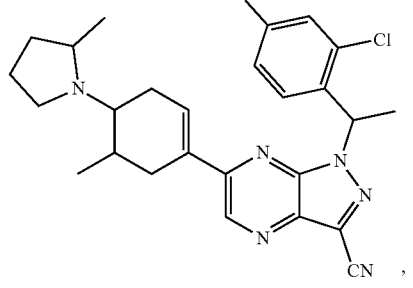
630
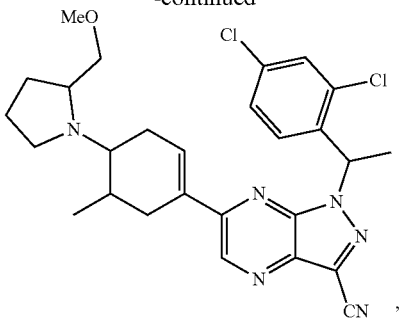
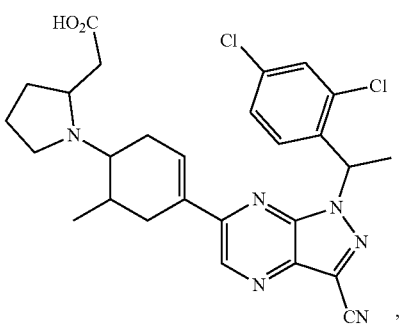
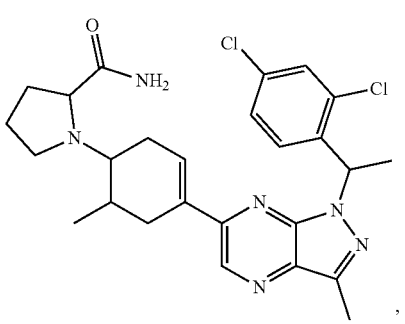
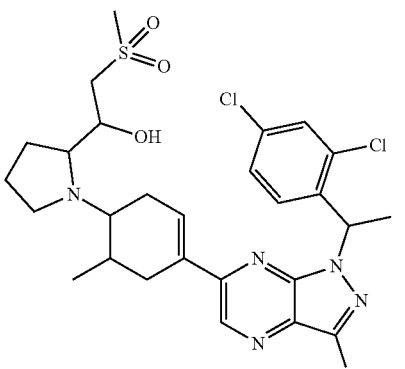
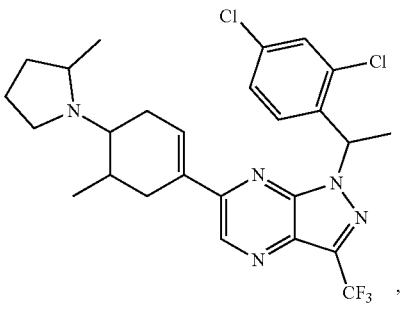

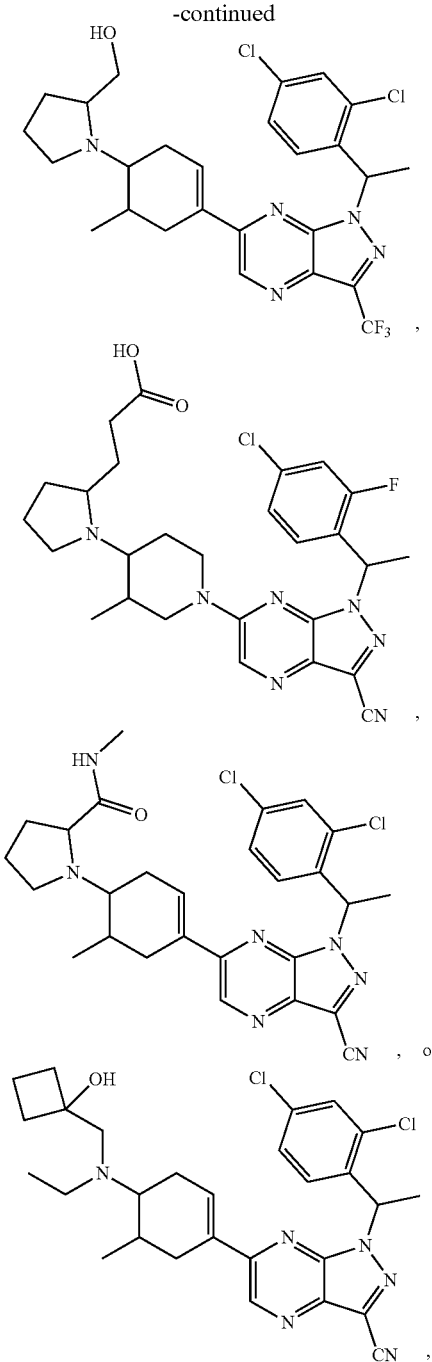

or a pharmaceutically acceptable salt thereof.

15. A pharmaceutical composition, comprising a compound of claim 1 and a pharmaceutically acceptable excipient.

16. A method of treating a disease or disorder mediated by CCR4, comprising administering to a subject in need thereof a therapeutically effective amount of a compound of claim 1 or a pharmaceutically acceptable salt thereof, wherein the CCR4 mediated disease or disorder is cancer, an immune disease or disorder, or an imflammatory disease or disorder.

17. The method of claim 16, wherein the disease or disorder is an immune or inflammatory disease or disorder selected from asthma, dermatitis, infection, chronic inflammation, rheumatoid arthritis, and systemic Lupus Erythematosus.

18. The method of claim 16, wherein the disease or disorder is cancer selected from carcinoma, sarcoma, adenocarcinoma, lymphoma, leukemia, solid cancer and lymphoid cancer.

19. The compound of claim 1, or a pharmaceutically acceptable salt thereof, wherein A is a 4-membered to 8-membered substituted or unsubstituted heterocycloalkyl.

20. The compound of claim 2, or a pharmaceutically acceptable salt thereof, wherein:
z1 is 2; and
z4 is 1.

21. The compound of claim 2, or a pharmaceutically acceptable salt thereof, wherein $R^1$ and $R^2$ are independently hydrogen, substituted or unsubstituted alkyl or substituted or unsubstituted heteroalkyl.

22. The compound of claim 3, wherein the compound has structural Formula (III):

(III)

or a pharmaceutically acceptable salt thereof.

23. The compound of claim 22, wherein the compound has structural Formula (IIIa):

(IIIa)

or a pharmaceutically acceptable salt thereof.

24. The compound of claims 22, wherein the compound has structural Formula (IIIb):

(IIIb)

or a pharmaceutically acceptable salt thereof.

25. The compound of claim 4, wherein the compound has structural Formula (V):

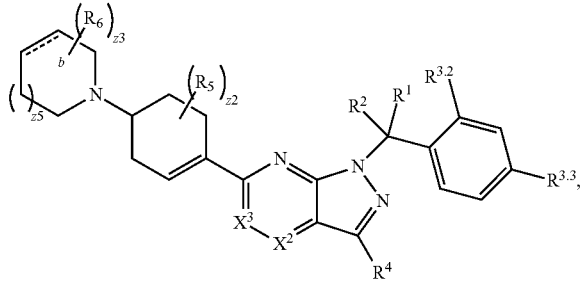

(V)

or a pharmaceutically acceptable salt thereof.

26. The compound of claim 25, wherein the compound has structural Formula (Va):

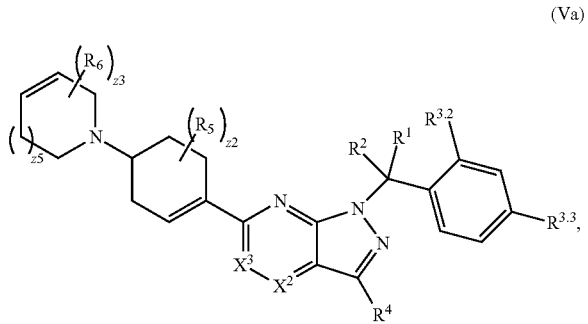

(Va)

or a pharmaceutically acceptable salt thereof.

27. The compound of claim 25, wherein the compound has structural Formula (Vb):

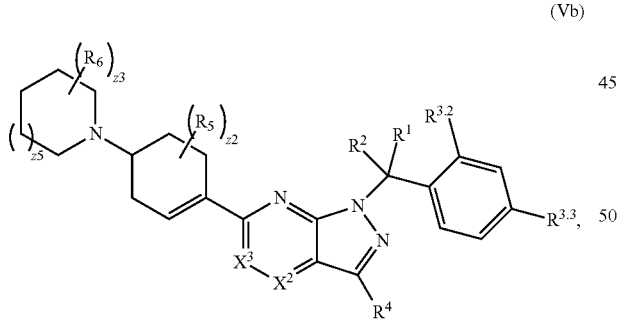

(Vb)

or a pharmaceutically acceptable salt thereof.

28. The compound of claim 1, or a pharmaceutically acceptable salt thereof, wherein $R^4$ is hydrogen, —CN, —$CX^{4.1}_3$, —C(O)$R^{4D}$, —C(O)O$R^{4D}$, —C(O)N$R^{4B}R^{4C}$, substituted or unsubstituted alkyl or substituted or unsubstituted heteroalkyl.

29. The compound of claim 28, or a pharmaceutically acceptable salt thereof, wherein $R^4$ is —CN, —$CF_3$, —C(O)$NH_2$, —$CH_3$ or —C($CH_3$)$_2$OH.

30. The compound of claim 3, or a pharmaceutically acceptable salt thereof, wherein $R^{3.2}$ and $R^{3.3}$ are independently halogen, —CN, —$CF_3$ or unsubstituted alkyl.

31. The compound of claim 30, or a pharmaceutically acceptable salt thereof, wherein $R^{3.2}$ and $R^{3.3}$ are independently —F, —Cl, —CN, —$CF_3$ or unsubstituted alkyl.

32. The compound of claim 30, or a pharmaceutically acceptable salt thereof, wherein $R^{3.2}$ and $R^{3.3}$ are independently halogen, —CN, —$CF_3$ or —$CH_3$.

33. The compound of claim 1, or a pharmaceutically acceptable salt thereof, wherein $R^1$ and $R^2$ are independently hydrogen or unsubstituted alkyl.

34. The compound of claim 33, or a pharmaceutically acceptable salt thereof, wherein $R^1$ is —$CH_3$ or —$CH_2CH_3$.

35. The compound of claim 33, or a pharmaceutically acceptable salt thereof, wherein $R^2$ is —$CH_3$ or —$CH_2CH_3$.

36. The compound of claim 33, or a pharmaceutically acceptable salt thereof, wherein $R^1$ is hydrogen.

37. The compound of claim 33, or a pharmaceutically acceptable salt thereof, wherein $R^2$ is hydrogen.

38. The compound of claim 1, or a pharmaceutically acceptable salt thereof, wherein $X^2$ is N.

39. The compound of claim 1, or a pharmaceutically acceptable salt thereof, wherein $X^3$ is N.

40. The compound of claim 1, or a pharmaceutically acceptable salt thereof, wherein z2 and z3 are independently an integer from 0 to 2.

41. The compound of claim 1, or a pharmaceutically acceptable salt thereof, wherein $R^5$ is hydrogen, —F, —CN, —$CH_3$, —$CF_3$, —($CH_2$)$_2$OH, —$CO_2NH_2$ or —$CO_2CH_2CH_3$.

42. The compound of claim 1, or a pharmaceutically acceptable salt thereof, wherein $R^6$ is hydrogen, —OH, —$CH_3$, —$CH_2$OH, —($CH_2$)$_2$OH, —($CH_2$)$_3$OH, —$CH_2NH_2$, —($CH_2$)$_2NH_2$, —($CH_2$)$_3NH_2$, —$CH_2CO_2CH_2CH_3$, —($CH_2$)$_2CO_2CH_2CH_3$, —($CH_2$)$_3CO_2CH_2CH_3$, —$CH_2CO_2H$, —($CH_2$)$_2CO_2H$, —($CH_2$)$_3CO_2H$, —($CH_2$)$CO_2NH_2$, —($CH_2$)$_2CONH_2$, —($CH_2$)$_3CO_2NH_2$, —($CH_2$)CHF$CO_2$H, —($CH_2$)$_2$CHF$CO_2$H, —($CH_2$)$CF_2CO_2$H, —($CH_2$)$_2CF_2CO_2$H,

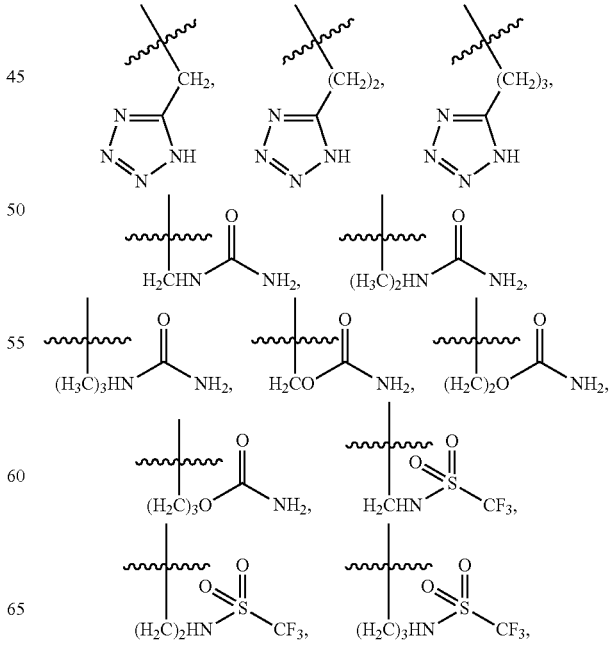

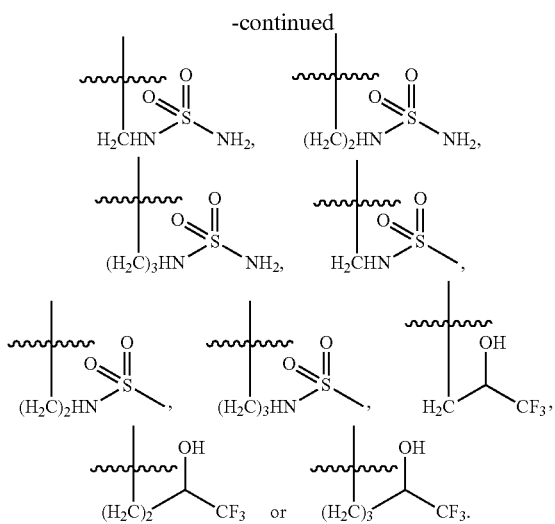

43. The compound of claim 6, wherein the compound has structural Formula (VIIa):

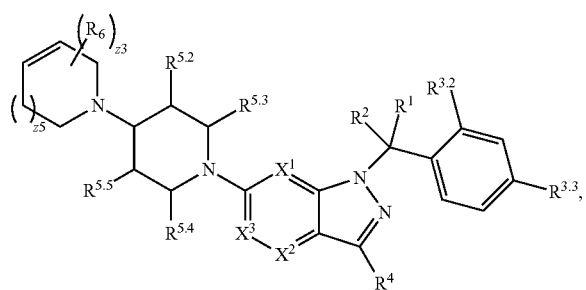

(VIIa)

or a pharmaceutically acceptable salt thereof.

44. The compound of claim 6, wherein the compound has structural Formula (VIIb):

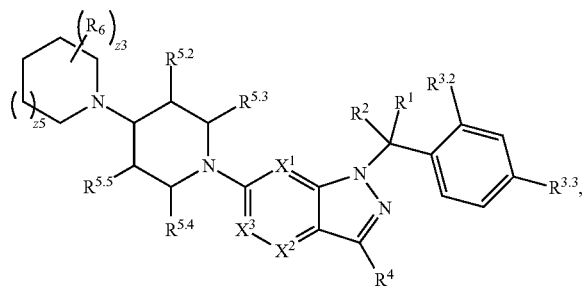

(VIIb)

or a pharmaceutically acceptable salt thereof.

45. The compound of claim 5, or a pharmaceutically acceptable salt thereof, wherein $X^1$ and $X^3$ are independently N.

46. The compound of claim 5, or a pharmaceutically acceptable salt thereof, wherein $X^1$ and $X^2$ are independently N.

47. The compound of claim 5, or a pharmaceutically acceptable salt thereof, wherein $R^4$ is —CN, —C(O)NH$_2$, —CF$_3$, —CH$_3$ or —C(CH$_3$)$_2$OH.

48. The compound of claim 5, or a pharmaceutically acceptable salt thereof, wherein $R^{3.2}$ and $R^{3.3}$ are independently halogen, —CN, —CF$_3$ or unsubstituted alkyl.

49. The compound of claim 48, or a pharmaceutically acceptable salt thereof, wherein $R^{3.2}$ and $R^{3.3}$ are independently —F, —Cl, —CN, —CF$_3$ or unsubstituted alkyl.

50. The compound of claim 48, or a pharmaceutically acceptable salt thereof, wherein $R^{3.2}$ and $R^{3.3}$ are independently halogen, —CN, —CF$_3$ or —CH$_3$.

51. The compound of claim 5, or a pharmaceutically acceptable salt thereof, wherein $R^1$ and $R^2$ are independently hydrogen or unsubstituted alkyl.

52. The compound of claim 51, or a pharmaceutically acceptable salt thereof, wherein $R^1$ is —CH$_3$ or —CH$_2$CH$_3$.

53. The compound of claim 51, or a pharmaceutically acceptable salt thereof, wherein $R^2$ is —CH$_3$ or —CH$_2$CH$_3$.

54. The compound of claim 5, or a pharmaceutically acceptable salt thereof, wherein $R^1$ is hydrogen.

55. The compound of claim 5, or a pharmaceutically acceptable salt thereof, wherein $R^2$ is hydrogen.

56. The compound of claim 5, or a pharmaceutically acceptable salt thereof, wherein z3 is an integer from 0 to 2.

57. The compound of claim 5, or a pharmaceutically acceptable salt thereof, wherein $R^{5.2}, R^{5.3}, R^{5.4}, R^{5.5}$ are independently hydrogen, —F, —CN, —CF$_3$, —(CH$_2$)$_2$OH, —CO$_2$NH$_2$ or —CO$_2$CH$_2$CH$_3$.

58. The compound of claim 5, or a pharmaceutically acceptable salt thereof, wherein $R^6$ is hydrogen, —OH, —CH$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, —CH$_2$CO$_2$CH$_2$CH$_3$, —(CH$_2$)$_2$CO$_2$CH$_2$CH$_3$, —(CH$_2$)$_3$CO$_2$CH$_2$CH$_3$, —CH$_2$CO$_2$H, —(CH$_2$)$_2$CO$_2$H, —(CH$_2$)$_3$CO$_2$H, —(CH$_2$)CO$_2$NH$_2$, —(CH$_2$)$_2$CONH$_2$, —(CH$_2$)$_3$CO$_2$NH$_2$, —(CH$_2$)CHFCO$_2$H, —(CH$_2$)$_2$CHFCO$_2$H, —(CH$_2$)CF$_2$CO$_2$H, —(CH$_2$)$_2$CF$_2$CO$_2$H,

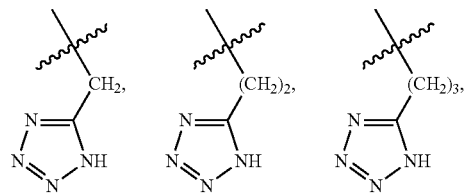

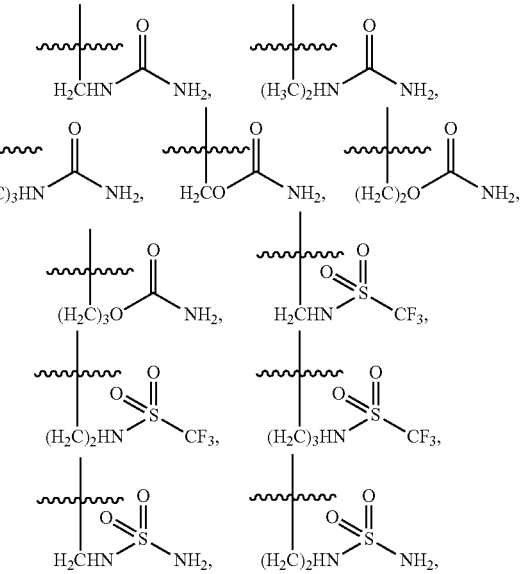

-continued

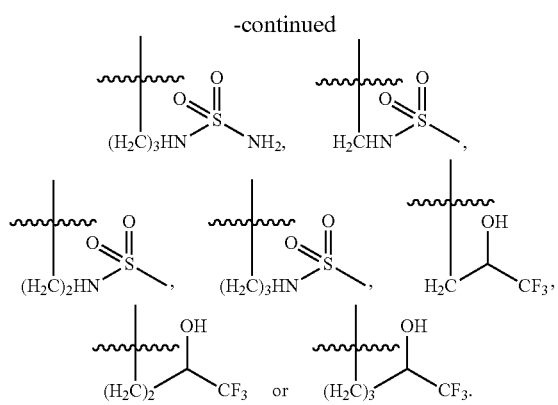

59. The compound of claim 5, or a pharmaceutically acceptable salt thereof, wherein z5 is 1.

60. The compound of claim 5, or a pharmaceutically acceptable salt thereof, wherein z5 is 0.

61. The compound of claim 54, or a pharmaceutically acceptable salt thereof, wherein z3 and z5 are independently 1.

62. The compound of claim 54, or a pharmaceutically acceptable salt thereof, wherein $R^6$ is halogen, substituted or unsubstituted alkyl or substituted or unsubstituted heteroalkyl.

63. The compound of claim 10, wherein the compound has structural Formula (IXa):

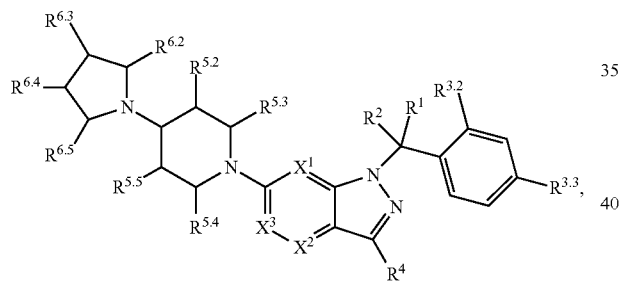

or a pharmaceutically acceptable salt thereof.

64. The compound of claim 10, or a pharmaceutically acceptable salt thereof, wherein $X^1$ and $X^2$ are independently N.

65. The compound of claim 10, or a pharmaceutically acceptable salt thereof, wherein $R^1$ and $R^2$ are independently hydrogen or unsubstituted alkyl.

66. The compound of claim 10, or a pharmaceutically acceptable salt thereof, wherein $R^{3.2}$ and $R^{3.3}$ are independently halogen, —CN, —$CF_3$ or unsubstituted alkyl.

67. The compound of claim 10, or a pharmaceutically acceptable salt thereof, wherein $R^4$ is —CN, —C(O)$NH_2$, —$CF_3$, —$CH_3$ or —C($CH_3$)$_2$OH.

68. The compound of claim 10, or a pharmaceutically acceptable salt thereof, wherein $R^{5.4}$ and $R^{5.5}$ are independently hydrogen, fluorine, —CN, —$CH_3$, —$CH_2CH_3$, —$CF_3$, —($CH_2$)OH, —($CH_2$)$_2$OH, —($CH_3$)$_2$OH, —$CO_2$H, —$CO_2NH_2$ or —$CO_2CH_2CH_3$.

69. The compound of claim 10, or a pharmaceutically acceptable salt thereof, wherein $R^{6.2}$ is hydrogen, —$CH_3$, —$CH_2OH$, —($CH_2$)$_2$OH, —($CH_2$)$_3$OH, —$CH_2NH_2$, —($CH_2$)$_2NH_2$, —($CH_2$)$_3NH_2$, —$CH_2CO_2CH_2CH_3$, —($CH_2$)$_2CO_2CH_2CH_3$, —($CH_2$)$_3CO_2CH_2CH_3$, —$CH_2CO_2H$, —($CH_2$)$_2CO_2H$, —($CH_2$)$_3CO_2H$, —($CH_2$)$CO_2NH_2$, —($CH_2$)$_2CONH_2$, —($CH_2$)$_3CO_2NH_2$, —($CH_2$)CHFCO$_2$H, —($CH_2$)$_2$CHFCO$_2$H, —($CH_2$)CF$_2$CO$_2$H, —($CH_2$)$_2$CF$_2$CO$_2$H,

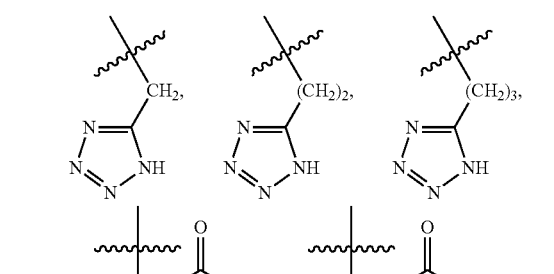

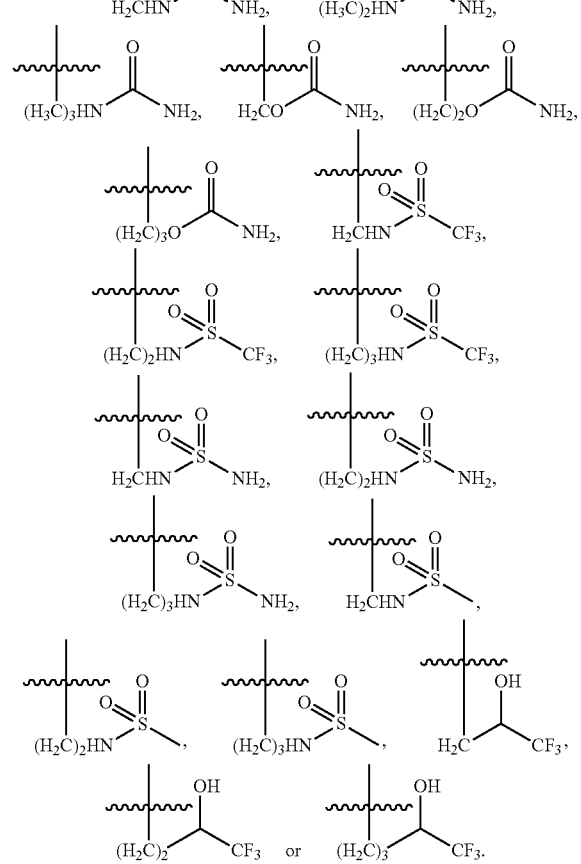

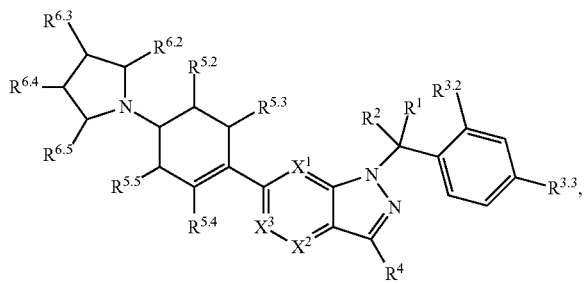

70. The compound of claim 10, wherein the compound has structural Formula (IXb):

(IXb)

or a pharmaceutically acceptable salt thereof.

71. The compound of claim 70, or a pharmaceutically acceptable salt thereof, wherein $X^1$ and $X^2$ are independently N.

72. The compound of claim 70, or a pharmaceutically acceptable salt thereof, wherein $R^1$ and $R^2$ are independently hydrogen or unsubstituted alkyl.

73. The compound of claim 70, or a pharmaceutically acceptable salt thereof, wherein $R^{3.2}$ and $R^{3.3}$ are independently halogen, —CN, —$CF_3$ or unsubstituted alkyl.

74. The compound of claim 70, or a pharmaceutically acceptable salt thereof, wherein $R^4$ is —CN, —$C(O)NH_2$, —$CF_3$, —$CH_3$ or —$C(CH_3)_2OH$.

75. The compound of claim 70, or a pharmaceutically acceptable salt thereof, wherein $R^{5.2}$ and $R^{5.5}$ are independently hydrogen, fluorine, —CN, —$CH_3$, —$CH_2CH_3$, —$CF_3$, —$(CH_2)OH$, —$(CH_2)_2OH$, —$(CH_3)_2OH$, —$CO_2H$, —$CO_2NH_2$ or —$CO_2CH_2CH_3$.

76. The compound of claim 70, or a pharmaceutically acceptable salt thereof, wherein $R^{6.2}$ is hydrogen, —OH, —$CH_3$, —$CH_2OH$, —$(CH_2)_2OH$, —$(CH_2)_3OH$, —$CH_2NH_2$, —$(CH_2)_2NH_2$, —$(CH_2)_3NH_2$, —$CH_2CO_2CH_2CH_3$, —$(CH_2)_2CO_2CH_2CH_3$, —$(CH_2)_3CO_2CH_2CH_3$, —$CH_2CO_2H$, —$(CH_2)_2CO_2H$, —$(CH_2)_3CO_2H$, —$(CH_2)CO_2NH_2$, —$(CH_2)_2CONH_2$, —$(CH_2)_3CO_2NH_2$, —$(CH_2)CHFCO_2H$, —$(CH_2)_2CHFCO_2H$, —$(CH_2)CF_2CO_2H$, —$(CH_2)_2CF_2CO_2H$,

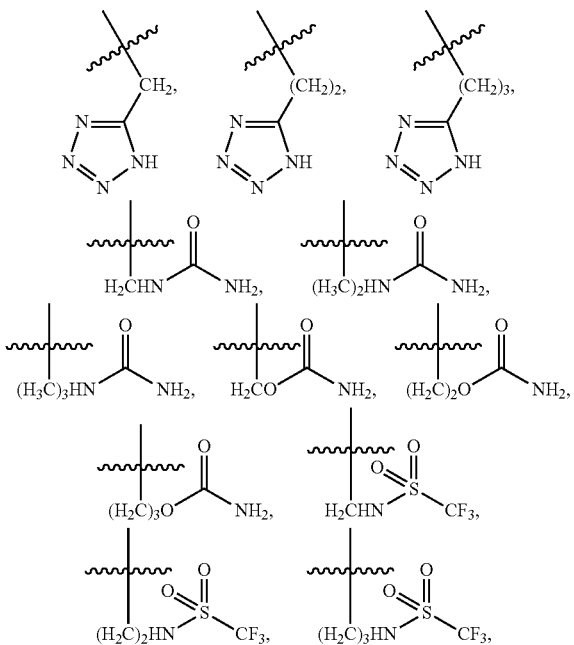
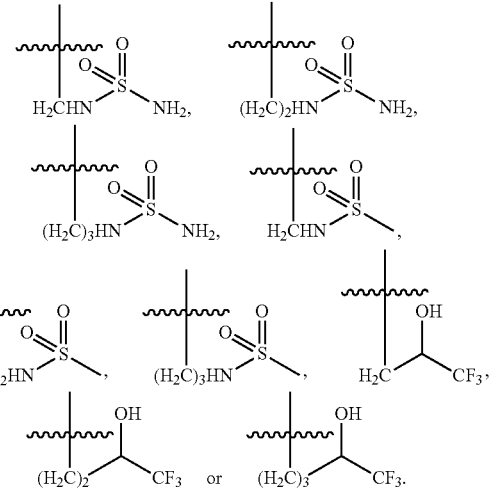

77. The method of claim 18, wherein the cancer is kidney cancer, breast cancer, lung cancer, bladder cancer, colon cancer, ovarian cancer, prostate cancer, pancreatic cancer, stomach cancer, brain cancer, head and neck cancer, skin cancer, uterine cancer, testicular cancer, glioma, esophagus cancer, liver cancer, hepatocarcinoma, B-acute lymphoblastic lymphoma, non-Hodgkin's lymphomas, Burkitt's, Small Cell, and Large Cell lymphomas, Hodgkin's lymphoma, MDS, AML, ALL, ATLL, CML, multiple myeloma, glioblastoma, neuroblastoma, colorectal cancer, cervical cancer, gastric cancer, cancer of the thyroid, cancer of the endocrine system, non-small cell lung cancer, melanoma, mesothelioma, Medulloblastoma, colorectal cancer, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioblastoma multiforme, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

* * * * *